US011565979B2

(12) United States Patent
Temme et al.

(10) Patent No.: US 11,565,979 B2
(45) Date of Patent: Jan. 31, 2023

(54) METHODS AND COMPOSITIONS FOR IMPROVING PLANT TRAITS

(71) Applicant: Pivot Bio, Inc., Berkeley, CA (US)

(72) Inventors: Karsten Temme, Oakland, CA (US); Alvin Tamsir, San Francisco, CA (US); Sarah Bloch, Emeryville, CA (US); Rosemary Clark, El Cerrito, CA (US); Emily Tung, Milbrae, CA (US); Kevin Hammill, Danville, CA (US); Douglas Higgins, Berkeley, CA (US); Austin Davis-Richardson, San Francisco, CA (US)

(73) Assignee: Pivot Bio, Inc., Berkeley, CA (US)

( * ) Notice: Subject to any disclaimer, the term of this patent is extended or adjusted under 35 U.S.C. 154(b) by 0 days.

(21) Appl. No.: 16/192,738

(22) Filed: Nov. 15, 2018

(65) Prior Publication Data

US 2019/0144352 A1 May 16, 2019

Related U.S. Application Data

(63) Continuation of application No. PCT/US2018/013671, filed on Jan. 12, 2018.

(60) Provisional application No. 62/577,147, filed on Oct. 25, 2017, provisional application No. 62/566,199, filed on Sep. 29, 2017, provisional application No. 62/467,032, filed on Mar. 3, 2017, provisional application No. 62/447,889, filed on Jan. 18, 2017, provisional application No. 62/445,557, filed on Jan. 12, 2017, provisional application No. 62/445,570, filed on Jan. 12, 2017.

(51) Int. Cl.
| | | |
|---|---|---|
| C05F 11/08 | (2006.01) | |
| C12N 1/20 | (2006.01) | |
| A01H 3/00 | (2006.01) | |
| A01N 63/20 | (2020.01) | |
| A01H 6/46 | (2018.01) | |
| C12N 1/04 | (2006.01) | |
| C12N 15/11 | (2006.01) | |
| C12N 15/52 | (2006.01) | |
| C12N 15/74 | (2006.01) | |
| C12N 15/70 | (2006.01) | |
| C12R 1/01 | (2006.01) | |
| C12R 1/07 | (2006.01) | |
| C12R 1/22 | (2006.01) | |
| C12R 1/025 | (2006.01) | |
| C12R 1/065 | (2006.01) | |

(52) U.S. Cl.
CPC ............... *C05F 11/08* (2013.01); *A01H 3/00* (2013.01); *A01H 6/4684* (2018.05); *A01N 63/20* (2020.01); *C12N 1/04* (2013.01); *C12N 1/20* (2013.01); *C12N 1/205* (2021.05); *C12N 15/111* (2013.01); *C12N 15/52* (2013.01); *C12N 15/70* (2013.01); *C12N 15/743* (2013.01); *C12R 2001/01* (2021.05); *C12R 2001/025* (2021.05); *C12R 2001/065* (2021.05); *C12R 2001/07* (2021.05); *C12R 2001/22* (2021.05)

(58) Field of Classification Search
CPC .............. A01C 7/00; A01C 5/00; C05F 11/08
See application file for complete search history.

(56) References Cited

U.S. PATENT DOCUMENTS

| | | |
|---|---|---|
| 1,520,545 A | 12/1924 | Murphy |
| 4,782,022 A | 11/1988 | Puhler et al. |
| 4,832,728 A | 5/1989 | Allan et al. |
| 5,071,743 A | 12/1991 | Slilaty et al. |
| 5,116,506 A | 5/1992 | Williamson et al. |
| 5,188,960 A | 2/1993 | Payne et al. |
| 5,229,291 A | 7/1993 | Nielsen et al. |
| 5,354,670 A | 10/1994 | Nickoloff et al. |
| 5,427,785 A | 6/1995 | Ronson et al. |
| 5,610,044 A | 3/1997 | Lam et al. |
| 5,780,270 A | 7/1998 | Lesley |
| 5,789,166 A | 8/1998 | Bauer et al. |
| 5,877,012 A | 3/1999 | Estruch et al. |
| 5,880,275 A | 3/1999 | Fischhoff et al. |
| 5,916,029 A | 6/1999 | Smith et al. |
| 6,033,861 A | 3/2000 | Schafer et al. |
| 6,033,874 A | 3/2000 | Baum et al. |
| 6,083,499 A | 7/2000 | Narva et al. |
| 6,107,279 A | 8/2000 | Estruch et al. |
| 6,127,180 A | 10/2000 | Narva et al. |
| 6,137,033 A | 10/2000 | Estruch et al. |
| 6,218,188 B1 | 4/2001 | Cardineau et al. |
| 6,248,535 B1 | 6/2001 | Danenberg et al. |
| 6,326,351 B1 | 12/2001 | Donovan et al. |

(Continued)

FOREIGN PATENT DOCUMENTS

| | | |
|---|---|---|
| AU | 636565 | 5/1993 |
| CA | 2051071 A1 | 3/1993 |

(Continued)

OTHER PUBLICATIONS

Mus et al. (Appl. Environ. Microbiol. 82.13 (2016): 3698-3710) (Year: 2016).*
Buddrus-Schiemann et al. (Microb Ecol (2010) 60:381-393) (Year: 2010).*
Okubo et al. (Microbes Environ. vol. 29, No. 2,184-190, 2014) (Year: 2014).*

(Continued)

*Primary Examiner* — Micah Paul Young
(74) *Attorney, Agent, or Firm* — Fish & Richardson P.C.

(57) ABSTRACT

Methods and systems are provided for generating and utilizing a bacterial composition that comprises at least one genetically engineered bacterial strain that fixes atmospheric nitrogen in an agricultural system that has been fertilized with more than 20 lbs of Nitrogen per acre.

14 Claims, 44 Drawing Sheets

Specification includes a Sequence Listing.

(56) References Cited

U.S. PATENT DOCUMENTS

| | | |
|---|---|---|
| 6,340,593 B1 | 1/2002 | Cardineau et al. |
| 6,391,548 B1 | 5/2002 | Bauer et al. |
| 6,399,330 B1 | 6/2002 | Donovan et al. |
| 6,548,289 B1 | 4/2003 | Beynon et al. |
| 6,548,291 B1 | 4/2003 | Narva et al. |
| 6,596,509 B1 | 7/2003 | Bauer et al. |
| 6,624,145 B1 | 9/2003 | Narva et al. |
| 6,673,610 B2 | 1/2004 | Miyawaki et al. |
| 6,713,063 B1 | 3/2004 | Malvar et al. |
| 6,713,285 B2 | 3/2004 | Bauer et al. |
| 6,773,900 B2 | 8/2004 | Short et al. |
| 6,841,358 B1 | 1/2005 | Locht et al. |
| 6,949,626 B2 | 9/2005 | Donovan et al. |
| 6,962,705 B2 | 11/2005 | Malvar et al. |
| 7,064,249 B2 | 6/2006 | Corbin et al. |
| 7,070,982 B2 | 7/2006 | Malvar et al. |
| 7,084,331 B2 | 8/2006 | Isawa et al. |
| 7,105,332 B2 | 9/2006 | Abad et al. |
| 7,132,265 B2 | 11/2006 | Bauer et al. |
| 7,244,820 B2 | 7/2007 | Miles et al. |
| 7,329,736 B2 | 2/2008 | Abad et al. |
| 7,378,499 B2 | 5/2008 | Abad et al. |
| 7,385,107 B2 | 6/2008 | Donovan et al. |
| 7,449,552 B2 | 11/2008 | Abad et al. |
| 7,462,760 B2 | 12/2008 | Abad et al. |
| 7,470,427 B2 | 12/2008 | Cocking |
| 7,476,781 B2 | 1/2009 | Abad et al. |
| 7,485,451 B2 | 2/2009 | Vandergheynst et al. |
| 7,491,698 B2 | 2/2009 | Hey et al. |
| 7,491,869 B2 | 2/2009 | Abad et al. |
| 7,504,229 B2 | 3/2009 | Donovan et al. |
| 7,615,686 B2 | 11/2009 | Miles et al. |
| 7,803,943 B2 | 9/2010 | Mao et al. |
| 7,858,849 B2 | 12/2010 | Cerf et al. |
| 7,923,602 B2 | 4/2011 | Carozzi et al. |
| 8,076,142 B2 | 12/2011 | Huang et al. |
| 8,084,416 B2 | 12/2011 | Sampson et al. |
| 8,084,418 B2 | 12/2011 | Hey et al. |
| 8,137,665 B2 | 3/2012 | Cocking |
| 8,236,757 B2 | 8/2012 | Carozzi et al. |
| 8,237,020 B2 | 8/2012 | Miles et al. |
| 8,268,584 B1 | 9/2012 | Harwood et al. |
| 8,304,604 B2 | 11/2012 | Lira et al. |
| 8,304,605 B2 | 11/2012 | Lira et al. |
| 8,319,019 B2 | 11/2012 | Abad et al. |
| 8,334,366 B1 | 12/2012 | Hughes et al. |
| 8,334,431 B2 | 12/2012 | Sampson et al. |
| 8,377,671 B2 | 2/2013 | Cournac et al. |
| 8,481,026 B1 | 7/2013 | Woodruff et al. |
| 8,513,494 B2 | 8/2013 | Wu et al. |
| 8,530,411 B2 | 9/2013 | Cerf et al. |
| 8,575,433 B2 | 11/2013 | Cerf et al. |
| 8,686,233 B2 | 4/2014 | Cerf et al. |
| 8,759,619 B2 | 6/2014 | Sampson et al. |
| 8,795,965 B2 | 8/2014 | Zhang |
| 8,802,933 B2 | 8/2014 | Abad et al. |
| 8,802,934 B2 | 8/2014 | Abad et al. |
| 9,150,851 B2 | 10/2015 | Wigley et al. |
| 9,321,697 B2 | 4/2016 | Das et al. |
| 9,487,451 B2 | 11/2016 | Doty et al. |
| 9,512,431 B2 | 12/2016 | Mirsky et al. |
| 9,657,298 B2 | 5/2017 | Soto, Sr. et al. |
| 9,796,957 B2 | 10/2017 | Barney et al. |
| 9,957,509 B2 | 5/2018 | Mirsky et al. |
| 9,975,817 B2 | 5/2018 | Temme et al. |
| 9,994,557 B2 | 6/2018 | Davidson et al. |
| 10,384,983 B2 | 8/2019 | Temme et al. |
| 10,525,318 B2 | 1/2020 | Dougherty |
| 10,556,839 B2 | 2/2020 | Temme et al. |
| 10,662,432 B2 | 5/2020 | Mirsky et al. |
| 10,919,814 B2 | 2/2021 | Temme et al. |
| 10,934,226 B2 | 3/2021 | Temme et al. |
| 10,968,446 B2 | 4/2021 | Zhao et al. |
| 2004/0197916 A1 | 10/2004 | Carozzi et al. |
| 2004/0197917 A1 | 10/2004 | Carozzi et al. |
| 2004/0210964 A1 | 10/2004 | Carozzi et al. |
| 2004/0210965 A1 | 10/2004 | Carozzi et al. |
| 2004/0216186 A1 | 10/2004 | Carozzi et al. |
| 2004/0235663 A1 | 11/2004 | Cocking |
| 2004/0241847 A1 | 12/2004 | Okuyama et al. |
| 2004/0250311 A1 | 12/2004 | Carozzi et al. |
| 2005/0081262 A1 | 4/2005 | Cook et al. |
| 2005/0266541 A1 | 12/2005 | Dillon |
| 2006/0033867 A1 | 2/2006 | Krisko et al. |
| 2006/0096918 A1 | 5/2006 | Semmens |
| 2006/0112447 A1 | 5/2006 | Bogdanova et al. |
| 2006/0127988 A1 | 6/2006 | Wood et al. |
| 2006/0191034 A1 | 8/2006 | Baum |
| 2006/0243011 A1 | 11/2006 | Someus |
| 2007/0249018 A1 | 10/2007 | Vemuri et al. |
| 2008/0295207 A1 | 11/2008 | Baum et al. |
| 2008/0311632 A1 | 12/2008 | Figge et al. |
| 2009/0105076 A1 | 4/2009 | Stewart et al. |
| 2009/0137390 A1* | 5/2009 | Triplett .................. A01N 63/00 504/117 |
| 2009/0144852 A1 | 6/2009 | Tomso et al. |
| 2009/0152195 A1 | 6/2009 | Rodgers et al. |
| 2009/0162477 A1 | 6/2009 | Nadel |
| 2009/0258404 A1 | 10/2009 | Mikkelsen et al. |
| 2009/0308121 A1* | 12/2009 | Reddy .................. C05F 11/08 71/6 |
| 2010/0005543 A1 | 1/2010 | Sampson et al. |
| 2010/0017914 A1 | 1/2010 | Hart et al. |
| 2010/0028870 A1 | 2/2010 | Welch et al. |
| 2010/0184038 A1 | 7/2010 | Boddy et al. |
| 2010/0197592 A1 | 8/2010 | Heinrichs |
| 2010/0267147 A1 | 10/2010 | Qiao |
| 2010/0298211 A1 | 11/2010 | Carozzi et al. |
| 2011/0023184 A1 | 1/2011 | Desai et al. |
| 2011/0064710 A1 | 3/2011 | Benson et al. |
| 2011/0104690 A1 | 5/2011 | Yu et al. |
| 2011/0263488 A1 | 10/2011 | Carozzi et al. |
| 2012/0015806 A1 | 1/2012 | Paikray et al. |
| 2012/0107889 A1 | 5/2012 | Doty et al. |
| 2012/0192605 A1 | 8/2012 | Mcspadden |
| 2012/0266332 A1 | 10/2012 | Kuykendall |
| 2012/0278954 A1 | 11/2012 | Bowen et al. |
| 2012/0284813 A1 | 11/2012 | Olivier et al. |
| 2012/0311745 A1 | 12/2012 | Meade et al. |
| 2012/0311746 A1 | 12/2012 | Meade et al. |
| 2012/0317681 A1 | 12/2012 | Meade et al. |
| 2012/0317682 A1 | 12/2012 | Meade et al. |
| 2012/0324605 A1 | 12/2012 | Meade et al. |
| 2012/0324606 A1 | 12/2012 | Meade et al. |
| 2012/0331589 A1 | 12/2012 | Meade et al. |
| 2012/0331590 A1 | 12/2012 | Meade et al. |
| 2013/0116170 A1 | 5/2013 | Graser et al. |
| 2013/0126428 A1 | 5/2013 | Jones et al. |
| 2013/0167268 A1 | 6/2013 | Narva et al. |
| 2013/0167269 A1 | 6/2013 | Narva et al. |
| 2014/0011261 A1 | 1/2014 | Wang et al. |
| 2014/0155283 A1 | 6/2014 | Venkateswaran et al. |
| 2014/0182018 A1 | 6/2014 | Lang et al. |
| 2014/0223598 A1 | 8/2014 | Sampson et al. |
| 2014/0223599 A1 | 8/2014 | Sampson et al. |
| 2014/0230504 A1 | 8/2014 | Finlayson et al. |
| 2014/0273226 A1 | 9/2014 | Wu et al. |
| 2014/0301990 A1 | 10/2014 | Gregory et al. |
| 2014/0329326 A1 | 11/2014 | Mirsky et al. |
| 2014/0336050 A1 | 11/2014 | Soto, Sr. et al. |
| 2015/0080261 A1 | 3/2015 | Wigley et al. |
| 2015/0101373 A1 | 4/2015 | Munusamy et al. |
| 2015/0128670 A1* | 5/2015 | Das .................. C05F 11/08 71/7 |
| 2015/0237807 A1 | 8/2015 | Valiquette |
| 2015/0239789 A1 | 8/2015 | Kang et al. |
| 2015/0315570 A1 | 11/2015 | Zhao et al. |
| 2016/0174570 A1 | 6/2016 | Vujanovic et al. |
| 2016/0264929 A1 | 9/2016 | Barney et al. |
| 2016/0292355 A1 | 10/2016 | Lou et al. |
| 2016/0295868 A1 | 10/2016 | Jones et al. |
| 2016/0304842 A1 | 10/2016 | Donovan et al. |
| 2017/0086402 A1 | 3/2017 | Meadows-Smith et al. |
| 2017/0107160 A1 | 4/2017 | Newman et al. |

(56) References Cited

U.S. PATENT DOCUMENTS

| | | |
|---|---|---|
| 2017/0119690 A1 | 5/2017 | Hansen et al. |
| 2017/0152519 A1 | 6/2017 | Mirsky et al. |
| 2017/0267997 A1 | 9/2017 | Nicol et al. |
| 2017/0367349 A1 | 12/2017 | Gruver et al. |
| 2018/0002243 A1 | 1/2018 | Temme et al. |
| 2018/0020671 A1 | 1/2018 | Bioconsortia |
| 2018/0065896 A1 | 3/2018 | Ibema et al. |
| 2018/0073028 A1 | 3/2018 | Mirsky et al. |
| 2018/0273437 A1 | 9/2018 | Temme et al. |
| 2018/0290942 A1 | 10/2018 | Voigt et al. |
| 2018/0297905 A1 | 10/2018 | Temme et al. |
| 2018/0297906 A1 | 10/2018 | Temme et al. |
| 2019/0039964 A1 | 2/2019 | Temme et al. |
| 2020/0087221 A1 | 3/2020 | Temme et al. |
| 2020/0115715 A1 | 4/2020 | Mirsky et al. |
| 2020/0299637 A1 | 9/2020 | Voigt et al. |
| 2020/0308594 A1 | 10/2020 | Tamsir et al. |
| 2020/0331820 A1 | 10/2020 | Tamsir et al. |
| 2021/0009483 A1 | 1/2021 | Temme et al. |
| 2021/0163374 A1 | 6/2021 | Bioch et al. |
| 2021/0214282 A1 | 7/2021 | Temme et al. |
| 2021/0315212 A1 | 10/2021 | Rezaei et al. |
| 2022/0017911 A1 | 1/2022 | Temme et al. |
| 2022/0079163 A1 | 3/2022 | Reisinger et al. |
| 2022/0127627 A1 | 4/2022 | Bloch et al. |
| 2022/0211048 A1 | 7/2022 | Temme et al. |

FOREIGN PATENT DOCUMENTS

| | | | |
|---|---|---|---|
| CN | 1289852 | 4/2001 | |
| CN | 1500801 | 6/2004 | |
| CN | 1552846 A | 12/2004 | |
| CN | 1746304 | 3/2006 | |
| CN | 101328477 | 12/2008 | |
| CN | 101880676 | 11/2010 | |
| CN | 101899430 | 12/2010 | |
| CN | 102041241 | 5/2011 | |
| CN | 102417882 | 4/2012 | |
| CN | 102690808 | 9/2012 | |
| CN | 103451130 A | 12/2013 | |
| CN | 104136599 | 11/2014 | |
| CN | 104204211 | 12/2014 | |
| CN | 106086042 | 11/2016 | |
| EA | 002757 | 8/2002 | |
| EP | 0256889 | 2/1988 | |
| EP | 0292984 | 11/1988 | |
| EP | 0339830 | 11/1989 | |
| EP | 0339830 A2 * | 11/1989 | ............ C12N 15/90 |
| EP | 0339830 A2 * | 12/1989 | ............ C12N 15/00 |
| EP | 1535913 | 6/2005 | |
| EP | 2186890 | 5/2010 | |
| EP | 3322679 A1 | 5/2018 | |
| FR | 2910230 | 6/2008 | |
| JP | S63-501924 | 8/1988 | |
| JP | H01225483 A | 9/1989 | |
| JP | H02-131581 | 5/1990 | |
| JP | H07-501201 | 2/1995 | |
| JP | 2009-232721 | 10/2009 | |
| JP | 2014096996 A | 5/2014 | |
| JP | 2015037385 A | 2/2015 | |
| JP | 2015042633 A | 3/2015 | |
| JP | 2015-518023 | 6/2015 | |
| JP | 2015113274 A | 6/2015 | |
| JP | 2015-519352 | 7/2015 | |
| WO | WO 1987/004182 | 7/1987 | |
| WO | WO-9305154 A1 | 3/1993 | |
| WO | WO-9810088 A1 | 3/1998 | |
| WO | WO-9909834 A2 * | 3/1999 | ............ A01N 63/00 |
| WO | WO-0057183 A1 | 9/2000 | |
| WO | WO-0107567 A1 | 2/2001 | |
| WO | WO 2004/074462 | 9/2004 | |
| WO | WO 2005/021585 | 3/2005 | |
| WO | WO 2005/038032 | 4/2005 | |
| WO | WO-2006005100 A1 | 1/2006 | |
| WO | WO 2006/083891 | 8/2006 | |
| WO | WO 2006/098225 | 9/2006 | |
| WO | WO 2006/119457 | 11/2006 | |
| WO | WO 2007/027776 | 3/2007 | |
| WO | WO-2009060012 A2 | 5/2009 | |
| WO | WO-2009091557 A1 | 7/2009 | |
| WO | WO 2010/080184 | 7/2010 | |
| WO | WO 2011/103247 | 8/2011 | |
| WO | WO 2011/103248 | 8/2011 | |
| WO | WO-2011099019 A1 | 8/2011 | |
| WO | WO-2011099024 A1 | 8/2011 | |
| WO | WO-2011154960 A1 | 12/2011 | |
| WO | WO 2012/139004 | 10/2012 | |
| WO | WO 2012/154651 | 11/2012 | |
| WO | WO-2012174271 A2 | 12/2012 | |
| WO | WO-2013076687 A2 | 5/2013 | |
| WO | WO-2013132518 A1 | 9/2013 | |
| WO | WO-2014042517 A2 | 3/2014 | |
| WO | WO-2014071182 A1 | 5/2014 | |
| WO | WO-2014201044 A2 | 12/2014 | |
| WO | WO-2016016629 A1 | 2/2016 | |
| WO | WO-2016016630 A1 | 2/2016 | |
| WO | WO-2016100727 A1 | 6/2016 | |
| WO | WO-2016146955 A1 | 9/2016 | |
| WO | WO 2016/181228 | 11/2016 | |
| WO | WO-2016178580 A2 | 11/2016 | |
| WO | WO-2016179046 A1 | 11/2016 | |
| WO | WO-2016191828 A1 | 12/2016 | |
| WO | WO-2017011602 A1 | 1/2017 | |
| WO | WO-2017042833 A1 | 3/2017 | |
| WO | WO-2017062412 A1 | 4/2017 | |
| WO | WO-2017069717 A1 | 4/2017 | |
| WO | WO 2017/112827 | 6/2017 | |
| WO | WO 2017/203440 | 11/2017 | |
| WO | WO 2018/081543 | 5/2018 | |
| WO | WO 2018/133774 | 7/2018 | |
| WO | WO-2018132774 A1 | 7/2018 | |
| WO | WO-2019032926 A1 | 2/2019 | |
| WO | WO-2019084342 A1 | 5/2019 | |
| WO | WO 2019/140125 | 7/2019 | |
| WO | WO 2020/006064 | 1/2020 | |
| WO | WO 2020/006246 | 1/2020 | |
| WO | WO 2020/014498 | 1/2020 | |
| WO | WO 2020/023630 | 1/2020 | |
| WO | WO 2020/061363 | 3/2020 | |
| WO | WO 2020/092940 | 5/2020 | |
| WO | WO 2020/146372 | 7/2020 | |
| WO | WO 2020/163251 | 8/2020 | |
| WO | WO 2020/190363 | 9/2020 | |
| WO | WO 2020/191201 | 9/2020 | |
| WO | WO 2020/219893 | 10/2020 | |
| WO | WO 2020/219932 | 10/2020 | |
| WO | WO 2021/113352 | 6/2021 | |
| WO | WO 2021/146209 | 7/2021 | |

OTHER PUBLICATIONS

Gibson (Australian Journal of Biological Sciences 16.1 (1963): 28-42) (Year: 1963).*
Andersen et al. (Journal of General Microbiology (1977), 103, 107-122) (Year: 1977).*
A. Romina Fox et al (Major cereal crops benefit from biological nitrogen fixation when inoculated with the nitrogen-fixing bacterium Pseudomonas protegens Pf-5 X940; Environmental Microbiology 2016) (Year: 2016).*
Wu et al (Effects of biofertilizer containing N-fixer, P and K solubilizer and AM fungi on maize growth: a greenhouse trial; Geoderma, 125, 2005, 155-166) (Year: 2005).*
Of A. Romina Fox etal (Major cereal crops benefit from biological nitrogen fixation when inoculated with the nitrogen-fixing bacterium Pseudomonas protegens Pf-5 X940; Environmental Microbiology 2016) (Year: 2016).*
40 CFR 725.3 U.S. Government Publishing Office (Jul. 1, 2010) http://www.gpo.gov/fdsys/pkg/CFR-2010-title40-vol30/pdf/CFR-2010-title40-vol30-sec725-3.pdf.
Arsene, et al., Modulation of NifA activity by PII in Azospirillum brasilense: Evidence for a Regulatory role of the NifA N-Terminal Domain. Journal of Bacteriology, Aug. 1996, p. 4830-4838.

(56) References Cited

OTHER PUBLICATIONS

Bali, et al., Excretion of Ammonium by a nifL Mutant of Azotobacter vinelandii fixing Nitrogen. Applied and Environmental Microbiology, May 1992, p. 1711-1718.
Barney, et al., Gene deletions resulting in increased nitrogen release by azotobacter vinelandii: application of a novel nitrogen biosensor. Appl. Environ. Microbiol. 2015; 81(13):4316-4328.
Barney, et al., Transcriptional analysis of an Ammonium-excreting stain of azotobacter vinelandii deregulated for nitrogen fixation. Appl. Environ. Microbiol. 2017; 83(20): 1-22.
Barrangou, R., Exploiting CRISPR-Cas immune systems for genome editing in bacteria. Curr. Opin. Biotechnol. 2016; 37:61-68.
Beringer, et al., Genetic engineering and nitrogen fixation. Biotech. Gen. Eng. Rev. 1984; 1(1):65-88.
BLAST. Basic local alignment search tool. Available at http://blast.ncbi.nlm.nih.gov/Blast.cgi. Accessed on Oct. 10, 2016.
Brewin, et al., The Basis of Ammonium release in nifL Mutants of Azotobacter vinelandii. Journal of Bacteriology, Dec. 1999; 181(23): p. 7356-7362.
Chen, et al., Complete genome sequence of Kosakonia sacchari type strain SP1T. Stand Genomic Sci. Jun. 15, 2014; 9(3): 1311-1318.
Chiang, et al., Mutagenic Oligonucleotide-directed PCR Amplification (Mod-PCR): An Efficient Method for Generating Random Base Substitution Mutations in a DNA sequence element. PCR methods and applications. 1993; 2:210-217.
Cohen, J.D., In vitro Tomato Fruit Cultures Demonstrate a Role for Indole-3-acetic Acid in Regulating Fruit Ripening. J. Amer. Soc. Hort. Sci. 121(3):520-524. 1996.
Colnaghi, R. et al., Strategies for increased ammonium production in free-living or plant associated nitrogen fixing bacteria. Plant and Soil, 1997; 194: 145-154.
Conniff, R., Microbes help grow better crops. Scientific american. http://www.scientificamerican.com/article/microbes-help-grow-better-crops/ Sep. 2013.
Co-pending U.S. Appl. No. 15/950,534, filed Apr. 11, 2018.
Co-pending U.S. Appl. No. 15/954,557, filed Apr. 16, 2018.
Co-pending U.S. Appl. No. 15/954,558, filed Apr. 16, 2018.
Co-pending U.S. Appl. No. 16/159,542, filed Oct. 12, 2018.
Curatti, et al., Genes required for rapid expression of nitrogenase activity in Azotobacter vinelandii. PNAS 2005; 102(18): 6291-6296.
Datsenko, K.A. and Wanner, B.L., One-step inactivation of chromosomal genes in *Escherichia coli* K-12 using PCR products. PNAS. Jun. 6, 2000; 97(12): 6640-6645.
DeBruijn, F.J., et al., The Cloning and characterization of the glnF (ntrA) Gene of Klebsiella pneumoniae: Role of glnF (ntrA) in the Regulation of Nitrogen Fixation (nif) and other Nitrogen assimilation genes. Mol. Genet. 1983; 192:342-353.
Delaux, et al., Tracing the evolutionary path to nitrogen-fixing crops. Curr. Opin. Plant Biol. 2015; 26:95-99.
Dent, et al., Establishing symbiotic nitrogen fixation in cereals and other non-legume crops: The greener nitrogen revolution. Agric & Food Secur 2017; 6(7): 1-9.
Desnoues, N. et al., Nitrogen fixation genetics and regulation in a Pseudomonas stutzeri strain associated with rice. Microbiology, 2003; 149:2251-2262.
Dixon, R. and Kahn, D., Genetic regulation of biological nitrogen fixation. Nature Reviews 2004; 2:621-631.
Dos; Santos., "Dos Santos, P.C. et al., Distribution of nitrogen fixation and nitrogenase-like sequences amongst microbial genomes. BMC Genomics, 2012; (13)162: 1-12".
Egener, et al., Identification of NifL-like protein in a diazotroph of the b-subgroup of the proteobacteria, *azoarcus* sp. strain BH72, Microbiology 2002; 148: 3203-3212.
Emboss. Emboss Needle: Pairwise Sequence Alignment (NUCLEOTIDE). Available at http://www.ebi.ac.uk/Tools/psa/emboss_needle/nucleotide.html. Accessed on Oct. 10, 2016.
Emboss. Emboss Water: Pairwise Sequence Alignment (NUCLEOTIDE). Available at http://www.ebi.ac.uk/Tools/psa/emboss_water/nucleotide.html. Accessed on Oct. 10, 2016.

Fox, et al., Major cereal crops benefit from biological nitrogen fixation when inoculated with the nitrogen-fixing bacterium Pseudomonas protegens Pf-5 X940. Environmental Microbiology 2016; 18(10):3522-3534.
Geddes, B.A., Use of plant colonizing bacteria as chassis for transfer of N2-fixation to cereals. Curr. Opin. Biotechnol. 2015; 32:216-222.
Hale, et al., An efficient stress-free strategy to displace stable bacterial plasmids. BioTechniques 2010; 48:223-228.
Hunter, P., "Genetically Modified Lite" placates public but not activists. EMBO Reports 2014; 15(2): 138-141.
Iniguez, et al., Nitrogen Fixation in Wheat Provided by Klebsiella pneumoniae 342. MPMI vol. 17, No. 10, 2004, pp. 1078-1085.
International Search report dated Dec. 2, 2016 for International Application No. PCT/US2016/042170.
Kant, et al., Understanding plant response to nitrogen limitation for the improvement of crop nitrogen use efficiency. Journal of Experimental Botany, 2011; vol. 62, No. 4, pp. 1499-1509.
Kurzweil, A. Plant Bacteria breakthrough enables crops worldwide to take nitrogen from the air. Aug. 1, 2013. http://www.kurzweilai.net/plant-bacteria-breakthrough-enables-crops-worldwide-to-take-nitrogen-from-the-air. 4 Pages.
Lauritsen, et al., A versatile one-step CRISPR-Cas9 based approach to plasmid-curing. Microb Cell Fact 2017; 16(135): 1-10.
Masepohl, et al., Organization and regulation of genes encoding the molybdenum nitrogenase and the alternative nitrogenase in Rhodobacter capsulatus. Arch. Microbiol. 1996;165:80-90.
Mengel, D., Roots, growth and nutrient uptake. Dept. of Agronomy publication #AGRY-95-08 (Rev. May 1995).
Mus, et al., Symbiotic nitrogen fixation and the challenges to its extension nonlegumes. Appl. Environ. Microbiol. 2016; 82(13): 3698-3710.
Rogers, et al., Synthetic biology approaches to engineering the nitrogen symbiosis in cereals. Journal of Experimental Botany, 2014; 65(8):1939-1946.
Nelissen, et al., Translational research:from pot to plot. Plant Biotechnology Journal 2014; 12: 277-285.
Nestmann, E.R., Mutagenesis by nitrosoguanidine, ethyl methanesulfonate, and mutator gene mutH in continuous cultures of *Escherichia coli*. Science Direct. Jun. 1975; 28(3): 323-330.
Nielsen, K.M., Transgenic organisms—time for conceptual diversification? Nature Biotechnology 2003; 21: 227-228.
Ortiz-Marquez, et al., Association with an Ammonium-excreting bacterium allows diazotrophic culture of oil-rich Eukaryotic microalgae. Appl. Microbiol. 2012; 78(7): 2345-2352.
PCT/US2018/013671 International Search Report and Written Opinion dated Mar. 22, 2018.
Roncato-Maccari, et al., Endophytic Herbaspirillum seropedicae expresses nif genes in gramineous plants. FEMS Microbiology Ecology. 2003; 45: 39-47.
Saikia, et al., Biological nitrogen fixation with non-legumes: An achievable target or a dogma? Curr. Sci. 2007; 92(3): 317-322.
Santi, et al., Biological nitrogen fixation in non-legume plants. Annals of Botany 2013; 111: 743-767.
Schouten, et al., Do cisgenic plants warrant less stringent oversight? Nature Biotechnology 2006;24: 753.
Service, R. Genetically engineered microbes make their own fertilizer, could feed the world's poorest. Science Apr. 2017: doi:l0.1126/science.aal1000.
Setten, et al., Engineering Pseudomonas protegens Pf-5 for Nitrogen Fixation and its application to improve plant growth under nitrogen-deficient conditions, PLOS One 2013; 8(5): 1-14.
Shamseldin, A. The rold of different genes involved in symbiotic nitrogen fixation—review. Global Journal of Biotechnology & Biochemistry 8 (4): 84-94, 2013.
Siddavattam, et al., Regulation of nif Gene expression in Enterobacter agglomerans: Nucleotide sequence of the nifLA operon and influence of temperature and ammonium on its transcription. Molecular and general genetics. Dec. 20, 1995; 249(6): 629-636.
Souza, et al., The N-Terminus of the NIFA protein of herbaspirillum seropedicae is probably involved in sensing of ammonia. In Tikhonovich

(56) References Cited

OTHER PUBLICATIONS et al. (Eds.) Proceedings of the 10th International Congress on Nitrogen Fixation, St. Petersburg, Russia, May 28-Jun. 3, 1995 (p. 260) Dordrecht: Kluwer.
Steenhoudt, et al., Azospirillum, a free-living nitrogen-fixing bacterium closely associated with grasses: genetic, biochemical and ecological aspects. FEMS Microbial. Rev. 2000; 24: 487-506.
Stemmer, W.P.C., DNA shuffling by random fragmentation and reassembly: In vitro recombination for molecular evolution. Oct. 1994. Proc. Natl. Acad. Sci. USA vol. 91, pp. 10747-10751.
Stemple, D.L., Tilling—a high-throughput harvest for functional genomics. Nature Reviews Genetics 5, 145-150 (Feb. 2004) | doi:10.1038/nrg1273.
Swain, et al., Nitrogen fixation and its improvement through genetic engineering. J. Global Biosciences 2013; 2(5): 98-112.
Temme, et al., Refactoring the nitrogen fixation gene cluster from Klebsiella oxytoca. PNAS, May 1, 2012; 109(18):7085-7090.
Triplett, E.W. Diazotrophic endophytes: progress and prospects for nitrogen fixation in monocots. Plant and Soil 1996; 186: 29-38.
Tritt, et al., An Integrated Pipeline for de Novo Assembly of Microbial Genomes. Sep. 13, 2012. PLOS one. https://doi.org/10.1371/journal.pone.0042304.
Ueda, et al., Remarkable N2-Fixing Bacterial Diversity Detected in Rice Roots by Molecular Evolutionary Analysis of nifH Gene Sequences. Journal of Bacteriology, Mar. 1995, p. 1414-1417.
U.S. Appl. No. 15/636,595 Notice of Allowance dated Mar. 30, 2018.
U.S. Appl. No. 15/636,595 Office Action dated Dec. 18, 2017.
U.S. Appl. No. 15/950,534 Office Action dated Aug. 10, 2018.
Vernon, et al., Analysis of 16S rRNA gene sequences and circulating cell-free DNA from plasma of chronic fatigue syndrome and non-fatigued subjects. BMC Microbiology 2002; 2:39.
Villa, et al., Azotobacter vinelandii siderophore can provide nitrogen to support the culture of the green algae neochloris oleoabundans and scenedesmus. FEMS Microbial. Lett. 2014; 351(1): 70-77.
Wang, et al., A minimal nitrogen fixation gene cluster from *paenibacillus* sp. WLY78 enables expression of active nitrogenase in *Escheichia coli*. Plos Genetics. Oct. 17, 2013; 9(10): 1-11; DOI:10.1371/journal.pgen.1003865.
Wang, et al., Using Synthetic biology to distinguish and overcome regulatory and functional barriers related to nitrogen fixation. PLOS One 2013; 8(7): 1-11.
Yoshida, T. and Yoneyama, T., Atmospheric dinitrogen fixation in the flooded rice rhizosphere as determined by the N-15 isotope technique. Soil Science and Plant Nutrition, 26:4, 551-559, DOI: 10.1080/00380768.1980.10431242.
Young, C. and Pratt-Szeliga, A., Ceres Trust. 2012. https://cerestrust.org/wp-content/uploads/NitrogenFixingBacteriaCorn.pdf. 9 Pages.
Zhang, et al., Involvement of the ammonium transporter AmtB in nitrogenase regulation and ammonium excretion in Pseudomonas stutzeri A1501. Res. Microbial. 2012; 163: 332-339.
An et al. Constitutive expression of the nifA gene activates associative nitrogen fixation of Enterobacter gergoviae 57-7, an opportunistic endophytic diazotroph. Journal of Applied Microbiology 103(3):613-620 (Sep. 1, 2007). First published Feb. 7, 2007.
Andersen, et al. Energetics of biological nitrogen fixation: determination of the ratio of formation of H2 to NH4+ catalysed by nitrogenase of Klebsiella pneumoniae in vivo. J Gen Microbiol. Nov. 1977;103(1):107-22.
Andrews et al. Use of Nitrogen Fixing Bacteria Inoculants as a Substitute for Nitrogen Fertiliser for Dryland Graminaceous Crops: Progress Made, Mechanisms of Action and Future Potential. Symbiosis 34 (2003). 21 pages.
Blanco, et al. Sequence and molecular analysis of the nifL gene of Azotobacter vinelandii. Mol Microbiol. Aug. 1993;9(4):869-79.
Bosworth, et al. Alfalfa yield response to inoculation with recombinant strains of Rhizobium meliloti with an extra copy of dctABD and/or modified nifA expression. Appl Environ Microbiol. Oct. 1994;60(10):3815-32.
Buchanan-Wollaston, et al. Role of the nifA gene product in the regulation of nif expression in Klebsiella pneumoniae. Nature. Dec. 24, 1981;294(5843):776-8.
Buddrus-Schiemann, et al. Root colonization by *Pseudomonas* sp. DSMZ 13134 and impact on the indigenous rhizosphere bacterial community of barley. Microb Ecol. Aug. 2010;60(2):381-93. doi: 10.1007/s00248-010-9720-8. Epub Jul. 20, 2010.
Contreras, et al. The product of the nitrogen fixation regulatory gene nfrX of Azotobacter vinelandii is functionally and structurally homologous to the uridylyltransferase encoded by glnD in enteric bacteria. J Bacteriol. Dec. 1991; 173(24): 7741-7749.
Gibson, A. H. Physical Environment and Symbiotic Nitrogen Fixation. Australian Journal of Biological Sciences. 1963; 16, 28-42.
Govantes, et al. Mechanism of coordinated synthesis of the antagonistic regulatory proteins NifL and NifA of Klebsiella pneumoniae. J Bacteriol. Dec. 1996; 178(23): 6817-6823.
Hidaka, et al. Promotion of the Growth of Rice by Inoculation of Nitrogen-Fixing-Activity-Enhanced Bacteria to the Rhizosphere. In Nitrogen Fixation: From Molecules to Crop Productivity (Part of the Current Plant Science and Biotechnology in Agriculture book series (PSBA, vol. 38)), pp. 445; 1999.
Kerby, et al. Photoproduction of ammonium by immobilized mutant strains of Anabaena variabilis.Applied Microbiology and Biotechnology. Apr. 1986, vol. 24, Issue 1, pp. 42-46.
Kim, et al. Constitutive expression of nitrogenase system in Klebsiella oxytoca by gene targeting mutation to the chromosomal nifLA operon. Journal of Biotechnology. vol. 10, Issues 3-4, Jun. 1989, pp. 293-301.
Macneil, et al. Fine-structure mapping and complementation analysis of nif (nitrogen fixation) genes in Klebsiella pneumoniae. J Bacteriol. Oct. 1978; 136(1): 253-266.
Macneil, et al. Mutations in nif genes that cause Klebsiella pneumoniae to be derepressed for nitrogenase synthesis in the presence of ammonium. J Bacteriol. Nov. 1980; 144(2): 744-751.
Mitra, Ranjana. Regulation of nifLA operon in Azotobacter vinelandii. Thesis submitted to the Jawaharlal Nehru University, New Delhi, for the degree of doctor of philosophy. 2000.
Mus, et al. Symbiotic Nitrogen Fixation and the Challenges to Its Extension to Nonlegumes. Appl Environ Microbiol. Jul. 1, 2016; 82(13): 3698-3710.Published online Jun. 13, 2016.Prepublished online Apr. 15, 2016.doi: 10.1128/AEM.01055-16.
Nassar, et al. Promotion of plant growth by an auxin-producing isolate of the yeast Williopsis saturnus endophytic in maize (*Zea mays* L.) roots. Biology and Fertility of Soils; 2005; 42: 97-108.
Nichkawade, Anuradha. Studies on upstream regulatory sequence of the nifLA promoter of Klebsiella pnuemoniae. Thesis submitted to the Jawaharlal Nehru University, New Delhi, for the degree of doctor of philosophy. 1996.
Okubo, et al. Effects of Elevated Carbon Dioxide, Elevated Temperature, and Rice Growth Stage on the Community Structure of Rice Root-Associated Bacteria. Microbes Environ. Jun. 2014; 29(2): 184-190.Published online May 31, 2014.doi: 10.1264/jsme2.ME14011.
Qiu, et al. Construction of genetically engineered strains of Enterobacter cloacae (nifL~(-)A~(c)). Acta Phytophysiologica Sinica. [Jan. 1, 1999, 25(3):269-273].
Roberts, et al. Regulation and characterization of protein products coded by the nif (nitrogen fixation) genes of Klebsiella pneumoniae. J Bacteriol. Oct. 1978; 136(1): 267-279.
Rosenblueth et al. Nitrogen Fixation in Cereals. Frontiers in Microbiology, vol. 9, Article 1794. (Aug. 9, 2018). 13 pages.
Schmitz, et al. Iron is required to relieve inhibitory effects on NifL on transcriptional activation by NifA in Klebsiella pneumoniae. J Bacteriol. Aug. 1996; 178(15): 4679-4687.
Sibold et al. A nif mutant of Klebsiella pneumoniae fixing nitrogen in the presence of ammonia. FEMS Microbiology Letters 10(1):37-41 (Jan. 1, 1981).
Sibold, et al. Constitutive expression of nitrogen fixation (nif) genes of Klebsiella pneumoniae due to a DNA duplication. EMBO J. 1982;1(12):1551-8.
Singh, et al. An L-methionine-D,L-sulfoximine-resistant mutant of the cyanobacterium Nostoc muscorum showing inhibitor-resistant γ-glutamyl-transferase, defective glutamine synthetase and produc-

(56) References Cited

OTHER PUBLICATIONS ing extracellular ammonia during N2 fixation.FEBS Letters. vol. 154, Issue 1, Apr. 5, 1983, pp. 10-14.
EP16825147.8 Partial Supplementary European Search Report dated Mar. 4, 2019.
U.S. Appl. No. 15/954,558 Office Action dated May 2, 2019.
Spiller, et al. Isolation and characterization of nitrogenase-derepressed mutant strains of cyanobacterium Anabaena variabilis. J Bacteriol. Feb. 1986; 165(2): 412-419.
Thomas, et al. Ammonium Excretion by an l-Methionine-dl-Sulfoximine-Resistant Mutant of the Rice Field Cyanobacterium Anabaena siamensis.Appl Environ Microbiol. Nov. 1990; 56(11): 3499-3504.
U.S. Appl. No. 15/950,534 Notice of Allowance dated May 2, 2019.
U.S. Appl. No. 15/954,557 Office Action dated Mar. 4, 2019.
U.S. Appl. No. 16/159,542 Office Action dated Mar. 8, 2019.
Zehr, et al. New Nitrogen-Fixing Microorganisms Detected in Oligotrophic Oceans by Amplification of Nitrogenase (nifH) Genes. Appl Environ Microbiol. Sep. 1998; 64(9): 3444-3450.
Alper et al., Tuning genetic control through promoter engineering. Proc Natl Acad Sci U S A. Sep. 6, 2005;102(36):12678-83. Epub Aug. 25, 2005. Erratum in: Proc Natl Acad Sci U S A. Feb. 21, 2006;103(8):3006.
Altschul et al. Basic local alignment search tool. J Mol Biol 215(3):403-410 (1990).
Altschul, et al. Gapped BLAST and PSI-BLAST: a new generation of protein database search programs. Nucleic Acids Res 25:3389-3402 (1977).
Andersen, et al. Herpesvirus-mediated gene delivery into the rat brain: specificity and efficiency of the neuron-specific enolase promoter.Cell. Mol. Neurobiol. 13:503-15 (1993).
Arbuthnot, et al. In vitro and in vivo hepatoma cell-specific expression of a gene transferred with an adenoviral vector. Hum Gene Ther. Aug. 20, 1996;7(13):1503-14.
Austin, et al. Characterisation of the Klebsiella pneumoniae nitrogen-fixation regulatory proteins NIFA and NIFL in vitro. Eur J Biochem. Jan. 26, 1990;187(2):353-60.
Bageshwar, et al. An Environmentally Friendly Engineered Azotobacter Strain That Replaces a Substantial Amount of Urea Fertilizer while Sustaining the Same Wheat Yield.Appl Environ Microbiol. Aug. 1, 2017; 83(15): e00590-17.
Batista, et al. Manipulating nitrogen regulation in diazotrophic bacteria for agronomic benefit. Biochem Soc Trans. Apr. 30, 2019;47(2):603-614.
Bikard et al., The synthetic integron: an in vivo genetic shuffling device. Nucleic Acids Res. Aug. 2010;38(15):e153. doi:10.1093/nar/gkq511. Epub Jun. 9, 2010.
Bilitchenko et al., Eugene—a domain specific language for specifying and constraining synthetic biological parts, devices, and systems. PLoS One. Apr. 29, 2011;6(4):e18882. doi: 10.1371/journal.pone.0018882.
Bonde, et al.MODEST: a web-based design tool for oligonucleotide-mediated genome engineering and recombineering. Nucleic Acids Res. Jul. 1, 2014; 42(Web Server issue): W408-W415.
Boshart, et al. A very strong enhancer is located upstream of an immediate early gene of human cytomegalovirus. Cell. Jun. 1985;41(2):521-30.
Boyle, et al. Tools for genome-wide strain design and construction. Curr Opin Biotechnol. Oct. 2012;23(5):666-71. doi: 10.1016/j.copbio.2012.01.012. Epub Feb. 20, 2012.
Brandl, et al. *Salmonella* interactions with plants and their associated microhiota. Phytopathology 103, 316-325 (2013).
Carr, et al. Enhanced multiplex genome engineering through co-operative oligonucleotide co-selection. Nucleic Acids Res. Sep. 1, 2012;40(17):e132. Epub May 25, 2012.
Chan et al., "Refactoring bacteriophage T7," Molecular Systems Biology, 2005, vol. 1, No. 1, pp. E1-E10 (doi:10.1038/msb4100025).
Chen, et al. Expression of rat bone sialoprotein promoter in transgenic mice. J Bone Miner Res. May 1996;11(5):654-64.

Choi, et al. A Tn7-based broad-range bacterial cloning and expression system. Nat Methods. Jun. 2005;2(6):443-8.
Choudhary, et al. Interactions of *Bacillus* spp. and Plants—With Special Reference to Induced Systemic Resistance (ISR). Microbiological Research. 2009, vol. 164, No. 5; pp. 493-513; p. 501, first column first paragraph; DOI: 10.1016/j.micres.2008.08.007.
Clancy, et al. The domains carrying the opposing activities in adenylyltransferase are separated by a central regulatory domain. FEBS J. Jun. 2007;274(11):2865-77. Epub May 4, 2007.
Cobb et al., Directed evolution: an evolving and enabling synthetic biology tool. Curr Opin Chem Biol. Aug. 2012;16(3-4):285-91. doi:10.1016/j.cbpa.2012.05.186. Epub Jun. 4, 2012.
Colebatch, et al. Symbiotic nitrogen fixation research in the postgenomics era. (2002). New Phytologist. 2020; 153(1), 37-42. doi:10.1046/j.0028-646X.2001,00304.x.
Colnaghi, et al. Lethality of glnD null mutations in Azotobacter vinelandii is suppressible by prevention of glutamine synthetase adenylylation. Microbiology. May 2001;147(Pt 5):1267-76.
Co-pending U.S. Appl. No. 16/671,036, filed Oct. 31, 2019.
Co-pending U.S. Appl. No. 16/685,997, filed Nov. 15, 2019.
The Extended European Search Report from EP Appl. No. 12800054.4, dated Dec. 19, 2014.
The International Search Report and Written Opinion from PCT/US2012/042502, dated Jan. 31, 2013.
Dong, et al. Kinetics and Strain Specificity of Rhizosphere and Endophytic Colonization by Enteric Bacteria on Seedlings of Medicago sativa and Medicago truncatula.Appl Environ Microbiol. Mar. 2003; 69(3): 1783-1790.doi: 10.1128/AEM.69.3.1783-1790.2003.
Du et al., Customized optimization of metabolic pathways by combinatorial transcriptional engineering. Nucleic Acids Res. Oct. 2012;40(18):e142. doi: 10.1093/nar/gks549. Epub Jun. 19, 2012.
Easter, et al. Role of the parCBA Operon of the Broad-Host-Range Plasmid RK2 in Stable Plasmid Maintenance. Journal Of Bacteriology. Nov. 1998, vol. 180, No. 2 2; pp. 6023-6030.
Engler, et al. A one pot, one step, precision cloning method with high throughput capability. PLoS One. 2008;3(11):e3647. doi: 10.1371/journal.pone.0003647. Epub Nov. 5, 2008.
Engler, et al. Golden gate shuffling: a one-pot DNA shuffling method based on type IIs restriction enzymes. PLoS One. 2009;4(5):e5553. doi: 10.1371/journal.pone.0005553. Epub May 14, 2009.
EP16825147.8 The Extended European Search Report dated Jun. 6, 2019.
EP16854192.8 The Extended European Search Report dated Feb. 20, 2019.
Feher, et al. In the fast lane: large-scale bacterial genome engineering. J Biotechnol. Jul. 31, 2012;160(1-2):72-9. doi: 10.1016/j.jbiotec.2012.02.012. Epub Mar. 1, 2012.
Ferrieres, et al. The yjbEFGH locus in *Escherichia coli* K-12 is an operon encoding proteins involved in exopolysaccharide production. Microbiology. Apr. 2007;153(Pt 4):1070-80.
Fischbach et al., "Prokaryotic gene clusters: A rich toolbox for synthetic biology," Biotechnology Journal, 2010, 15(12): 1277-1296.
Frasch et al., Design-based re-engineering of biosynthetic gene clusters: plug-and-play in practice. CurrOpin Biotechnol. Dec. 2013;24(6):1144-50. doi: 10.1016/j.copbio.2013.03.006. Epub Mar. 27, 2013.
Gamer, et al. A T7 RNA polymerase-dependent gene expression system for Bacillus megaterium. Appl Microbiol Biotechnol. Apr. 2009;82(6):1195-203. doi: 10.1007/S00253-009-1952-5. Epub Mar. 24, 2009.
Gebeyehu, G., et al., "Novel biotinylated nucleotide-analogs for labeling and colorimetric detection of DNA," Nucl. Acids Res. 15:4513 (1987).
Gossen et al. Tight control of gene expression in mammalian cells by tetracycline-responsive promoters. PNAS USA 89.12 (1992): 5547-5551.
Gossen et al. Transcriptional activation by tetracyclines in mammalian cells. Science 268(5218):1766-1769 (1995).
Guo et al., Discovery of Reactive Microbiota-Derived Metabolites that Inhibit Host Proteases. Cell. Jan. 26, 2017;168(3):517-526.e18. doi:10.1016/j.cell.2016.12.021. Epub Jan. 19, 2017.

(56) References Cited

OTHER PUBLICATIONS

Haapalainen, M., van Gestel, K., Pirhonen, M. & Taira, S. Soluble plant cell signals induce the expression of the type III secretion system of Pseudomonas syringae and upregulate the production of pilus protein HrpA. Mol. Plant Microbe Interact. 22, 282-290 (2009).
Hansal, et al. Cutting Edge: Induction of antigen-specific hyporesponsiveness by transplantation of hemopoietic cells containing an MHC class I transgene regulated by a lymphocyte-specific promoter. J Immunol. Aug. 1, 1998;161(3):1063-8.
Harvey, et al. Inducible control of gene expression: prospects for gene therapy. Curr Opin Chem Biol. Aug. 1998;2(4):512-8.
Herlache, et al. Characterization of the Agrobacterium vitis pehA gene and comparison of the encoded polygalacturonase with the homologous enzymes from Erwinia carotovora and Ralstonia solanacearum. Appl Environ Microbiol. Jan. 1997; 63(1): 338-346.
Holden, et al. Colonization outwith the colon: plants as an alternative environmental reservoir for human pathogenic enterobacteria. FEMS Microbiol. Rev. 33, 689-703 (2009).
International Preliminary Report on Patentability dated May 14, 2015 in connection with Application No. PCT/US2013/068055.
International Search Report and Written Opinion dated Feb. 18, 2014 in connection with Application No. PCT/US2013/068055.
Jaschke, et al. A fully decompressed synthetic bacteriophage øX174 genome assembled and archived in yeast. Virology 434, 278-284 (2012).
Karlin, et al. Applications and statistics for multiple high-scoring segments in molecular sequences. Proc Natl Acad Sci U S A. Jun. 15, 1993;90(12):5873-7.
Karlin, et al. Methods for assessing the statistical significance of molecular sequence features by using general scoring schemes. Proc Natl Acad Sci U S A. Mar. 1990;87(6):2264-8.
Kornberg, A., DNA Replication, pp. 75-77, W.H. Freeman & Co., San Francisco, 1980.
Kutter, et al. Colonization of barley (*Hordeum vulgare*) with *Salmonella enterica* and *Listeria* spp. FEMS Microbiol. Ecol. 56, 262-271 (2006).
Leang, et al. Genome-wide analysis of the RpoN regulon in Geobacter sulfurreducens. BMC Genomics. Jul. 22, 2009;10:331. doi: 10.1186/1471-2164-10-331.
Liang et al., Minimal effect of gene clustering on expression in *Escherichia coli*. Genetics. Feb. 2013;193(2):453-65. doi:10.1534/genetics.112.147199. Epub Dec. 5, 2012.
Lim, et al. Fundamental relationship between operon organization and gene expression. Proc Natl Acad Sci U S A. Jun. 28, 2011;108(26):10626-31. doi: 10.1073/pnas.1105692108. Epub Jun. 13, 2011.
Liu, et al. Whole genome analysis of halotolerant and alkalotolerant plant growth-promoting *rhizobacterium Klebsiella* sp. D5A. Sci Rep. May 24, 2016; 6: 1-10.
Magari, et al. Pharmacologic control of a humanized gene therapy system implanted into nude mice. J Clin Invest. Dec. 1, 1997; 100(11): 2865-2872.
Marroqui, et al. Enhanced Symbiotic Performance by Rhizobium tropici Glycogen Synthase Mutants. J Bacteriol. Feb. 2001; 183(3): 854-864.
Martinez-Noel et al., NifB and NifEN protein levels are regulated by ClpX2 under nitrogen fixation conditions in Azotobacter vinelandii. Mol Microbiol. Mar. 2011;79(5):1182-93. doi: 10.1111/j.1365-2958.2011.07540.x. Epub Jan. 25, 2011.
Marx, et al. Broad-host-range cre-lox system for antibiotic marker recycling in gram-negative bacteria. Biotechniques. Nov. 2002;33(5):1062-7.
Matsubayashi, et al. Peptide hormones in plants. Annu Rev Plant Biol. 2006;57:649-74.
Medema et al., Computational tools for the synthetic design of biochemical pathways. Nat Rev Microbiol. Jan. 23, 2012;10(3):191-202. doi: 10.1038/nrmicro2717.
Mirsky, Ethan M., Refactoring the *Salmonella* Type III Secretion System. (Doctoral Dissertation) Apr. 12, 2012 Retrieved from web at Proquest site (media.proquest.com/media/pq/classic/doc/2644519781/fmUaijrep/NPDF?hl=&cit:auth=Mirsky).
Moon et al., Genetic programs constructed from layered logic gates in single cells. Nature. Nov. 8, 2012;491(7423):249-53. doi: 10.1038/nature11516. Epub Oct. 7, 2012.
Mueller, et al. Closing yield gaps through nutrient and water management. Nature 490, 254-257 (2012).
No, et al., "Ecdysone-inducible gene expression in mammalian cells and transgenic mice" Proc. Natl. Acad. Sci. USA vol. 93, Issue 8, pp. 3346-3351, Apr. 1996.
PCT/US18/57613 International Search Report dated Mar. 5, 2019.
PCT/US2018/046148 International Search Report dated Dec. 3, 2018.
PCTUS2016/055429 International Search Report and Written Opinion dated Dec. 30, 2016.
Pfleger, et al. Combinatorial engineering of intergenic regions in operons tunes expression of multiple genes. Nat Biotechnol. Aug. 2006;24(8):1027-32. Epub Jul. 16, 2006.
Piccioli, et al. Neuroantibodies: ectopic expression of a recombinant anti-substance P antibody in the central nervous system of transgenic mice. Neuron. Aug. 1995;15(2):373-84.
Piccioli, et al. Neuroantibodies: molecular cloning of a monoclonal antibody against substance P for expression in the central nervous system. Proc Natl Acad Sci U S A. Jul. 1, 1991; 88(13): 5611-5615.
Plotnikova, et a. Pathogenesis of the human opportunistic pathogen Pseudomonas aeruginosa PA14 in *Arabidopsis*. Plant Physiol. 124, 1766-1774 (2000).
Ran et al., Genome erosion in a nitrogen-fixing vertically transmitted endosymbiotic multicellular cyanobacterium. PLoS One. Jul. 8, 2010;5(7):e11486. doi: 10.1371/journal.pone.0011486. Erratum in: PLoS One. 2010;5(9) doi: 10.1371/annotation/835c5766-5128-41c4-b636-adfe0c503103.
Resendis-Antonio, et al. Systems biology of bacterial nitrogen fixation: High-throughput technology and its integrative description with constraint-based modeling. BMC Syst Biol. 2011; 5: 120.
Rommens, et al. Intergeneric transfer and functional expression of the tomato disease resistance gene Pto. Plant Cell. Oct. 1995; 7(10): 1537-1544.
Rosenblueth, et al. Bacterial endophytes and their interactions with hosts. Mol Plant Microbe Interact. Aug. 2006;19(8):827-37.
Sandig, et al. HBV-derived promoters direct liver-specific expression of an adenovirally transduced LDL receptor gene. Gene Ther. Nov. 1996;3(11):1002-9.
Sandoval, et al. Strategy for directing combinatorial genome engineering in *Escherichia coli*. Proc Natl Acad Sci U S A. Jun. 26, 2012;109(26):10540-5. doi: 10.1073/pnas.1206299109. Epub Jun. 11, 2012.
Sleight et al.; "Designing and engineering evolutionary robust genetic circuits" Biological Engineering; 4:12, 2010 (20 pages).
Smanski et al., Synthetic biology to access and expand nature's chemical diversity. Nat Rev Microbiol. Mar. 2016;14(3):135-49. doi: 10.1038/nrmicro.2015.24.
Smanski, et al. Functional optimization of gene clusters by combinatorial design and assembly. Nat Biotechnol. Dec. 2014;32(12):1241-9. doi: 10.1038/nbt.3063. Epub Nov. 24, 2014.
Stein, et al. The osteocalcin gene: a model for multiple parameters of skeletal-specific transcriptional control. Mol Biol Rep. Aug. 1997;24(3):185-96.
Stephanopoulos. Challenges in engineering microbes for biofuels production. Science. Feb. 9, 2007;315(5813):801-4.
Subtil, et al. Secretion of Predicted Inc Proteins of Chlamydia pneumoniae by a Heterologous Type III Machinery. Molecular Microbiology. Feb. 2001, vol. 39, No. 3; pp. 792-800; abstract; DOI: 10.1046/j.1365-2958.2001.02272.x.
T7 RNA Polymerase Expression System for Bacillus megaterium ; T7 RNAP Expression System Handbook, Jan. 2010, © MoBiTec GmbH, 18 pages.
Temme et al., Modular control of multiple pathways using engineered orthogonal T7 polymerases. Nucleic Acids Res. Sep. 1, 2012;40(17):8773-81. Epub Jun. 28, 2012.
Temme, Karsten Louis. Designing and Engineering Complex Behavior in Living Machines. (Doctoral Dissertation) Oct. 1, 2011. Retrieved from the web at escholarship.org/uc/item/1r41x99s.

(56) References Cited

OTHER PUBLICATIONS

Tilman, et al. Global food demand and the sustainable intensification of agriculture. PNAS 108, 20260-20264 (2011).
U.S. Appl. No. 14/440,183 Office Action dated Feb. 5, 2018.
U.S. Appl. No. 14/440,183 Office Action dated Jul. 20, 2017.
U.S. Appl. No. 14/440,183 Office Action dated May 2, 2019.
U.S. Appl. No. 14/440,183 Office Action dated Nov. 13, 2019.
U.S. Appl. No. 15/706,353 Notice of Allowance dated Aug. 7, 2019.
U.S. Appl. No. 15/706,353 Office Action dated Jan. 25, 2019.
U.S. Appl. No. 15/954,557 Notice of Allowance dated Oct. 11, 2019.
U.S. Appl. No. 15/954,557 Office Action dated Jun. 28, 2019.
U.S. Appl. No. 15/954,558 Office Action dated October/, 2019.
U.S. Appl. No. 16/159,542 Office Action dated Jul. 25, 2019.
Voigt et al., "Genetic parts to program bacteria, "Current Opinion in Biotechnology, 2006, 17(5):548-557.
Voigt, C., "Gaining Access: Rebuilding Genetics from the Ground Up". Institute of Medicine Board on Global Health Forum on Microbial Threats. Mar. 14, 2011. Retrieved from the web at iom.edu/-/media/Files/ActivityFiles/PublicHealth/MicrobiaiThreats/2011-MAR- 14Noigt.pdf.
Wang et al., Positive and negative regulation of gene expression in eukaryotic cells with an inducible transcriptional regulator. Gene Ther., 4.5 (May 1997): 432-441.
Wang, et al. Ligand-inducible and liver-specific target gene expression in transgenic mice. Nat Biotechnol. Mar. 1997;15(3):239-43.
Wang, et al. Programming cells by multiplex genome engineering and accelerated evolution. Nature. Aug. 13, 2009;460(7257):894-8. doi: 10.1038/nature08187. Epub Jul. 26, 2009.
Watanabe et al., Chapter 15. Plasmid-borne gene cluster assemblage and heterologous biosynthesis of nonribosomal peptides in *Escherichia coli*. Methods Enzymol. 2009;458:379-99. doi: 10.1016/80076-6879(09)04815-0.
Weber, et al. A modular cloning system for standardized assembly of multigene constructs. PLoS One. Feb. 18, 2011;6(2):e16765. doi: 10.1371/journal.pone.0016765.
Welch, et al., 2009, Design Parameters to Control Synthetic Gene Expression in *Escherichia coli*, PLoS One, 4(9): e7002.
Werner et al., Fast track assembly of multigene constructs using Golden Gate cloning and the MoClo system. Bioeng Bugs. Jan. 1, 2012;3(1):38-43. doi: 10.1371/journal.pone.0016765. Epub Jan. 1, 2012.
Widmaier, et al. Engineering the *Salmonella* type III secretion system to export spider silk monomers. Mol. Syst. Biol. 5, 309 (2009).
Wootton, et al. Statistics of local complexity in amino acid sequences and sequence databases. Computers & Chemistry. vol. 17, Issue 2, Jun. 1993, pp. 149-163.
Zhang, et al. GlnD Is Essential for NifA Activation, NtrB/NtrC-Regulated Gene Expression, and Posttranslational Regulation of Nitrogenase Activity in the Photosynthetic, Nitrogen-Fixing Bacterium Rhodospirillum rubrum. J Bacteriol. Feb. 2005; 187(4): 1254-1265.
Zhang, et al. Influence of different factors on the nitrogenase activity of the engineered *Escherichia coli* 78-7. World J Microbiol Biotechnol. Jun. 2015;31(6):921-7.
International Preliminary Report on Patentability dated Jul. 16. 2019 in connection with Application No. PCT/US2018/013671, 6 pages.
Yarza, et al. "Uniting the classification of cultured and uncultured bacteria and archaea using 16S rRNA gene sequences," Nature Rev. Micro., 2014 12:635-345.
Klose er al., "Glutamate at the site of phosphorylation of nitorgen-regulatory protein NTRC mimics aspartyl-phosphate and activates the protein," J Mol Biol., Jul. 1993, 232(1):67-78.
Kranz et al., "Ammonia-constitutive nitrogen fixation mutants of Rhodobacter capsulatus," Gene, Nov. 1988, 71(1):65-74.
Mus et al., "Diazotrophic Growth Allows Azotobacter vinelandii to Overcome the Deleterious Effects of a glnE Deletion," Appl Environ Microbiol., Jun. 2017, 83(13):e00808-17.

PCT International Search Report and Written Opinion in International Appln. No. PCT/US2020/031201, dated Mar. 9, 2021, 28 pages.
Baum et al., "Control of coleopteran insect pests through RNA interference," Nature Biotechnology, Nov. 2007, 25(11):1322-1326.
Bosmans et al., "Sea anemone venom as a source of insecticidal peptides acting on voltage-gated Na+ channels." Toxicon. Mar. 2007, 49(4):550-560.
Chakroun et al., "Bacterial Vegetative Insecticidal Proteins (Vip) from Entomopathogenic Bacteria," Microbiol Mol Biol Rev., Mar. 2016, 80(2):329-50.
Compant et al., "A review on the plant microbiome: Ecology, functions, and emerging trends in microbial application," Journal of Advanced Research. Sep. 2019, 19:29-37.
Crickmore et al., "Revision of the Nomenclature for the Bacillus thuringiensis Pesticidal Crystal Proteins." Microbiol Mol Biol Rev., Sep. 1998, 62(3):807-813.
EP Partial Supplementary European Search Report in European Appln. No. 18843845.1, dated Apr. 12, 2021, 17 pages.
Eyraud et al., "Expression and Biological Activity of the Cystine Knot Bioinsecticide PA1b (Pea Albumin 1 Subunit b)," PLOS One, Dec. 2013, 8(12):e81619, 9 pages.
Forner et al., "Treatment of hepatocellular carcinoma," Crit Rev Oncol Hematol., Nov. 2006, 60(2):89-98.
Janczarek et al., "Multiple copies of rosR and pssA genes enhance exopolysaccharide production, symbiotic competitiveness and clover nodulation in Rhizobium leguminosarum bv. *trifolii*," Antonie Van Leeuwenhoek, Nov. 2009, 96(4):471-86.
King et al., "Spider-Venom Peptides: Structure. Pharmacology, and Potential for Control of Insect Pests," Annu. Rev. Entomol., 2013, 58:475-96.
Lifesci.sussex.ac.uk, [online]. "Bacillus thuringiensis Toxin Nomenclature," 2016, retrieved on Mar. 25, 2021, retrieved from URL<www.lifesci.sussex.ac.uk/home/Neil_Crickmore/Bt/< 1 page.
Lin et al., "PC, a Novel Oral Insecticidal Toxin from Bacillus bombysepticus Involved in Host Lethality via APN and BtR-175," Scientific Reports, Jun. 2015, 5:11101, 14 pages.
Martinelli et al., "Structure-function studies on jaburetox, a recombinant insecticidal peptide derived from jack bean (Canavalia ensiformis) urease," Biochimica et Biophysica Acta. Mar. 2014. 1840(3):935-44.
Naimov et al., "Solubilization. Activation, and insecticidal Activity of Bacillus thuringiensis Serovar thompsoni HD542 Crystal Proteins," Applied and Environmental Microbiology, Dec. 2008, 74(23):7145-7151.
Nature.com, [online], "Transcription Unit." 2005. retrieved on Apr. 15. 2021, retrieved from URL<https://www.nature.com/scitable/definition/transcription-unit-260>, 2 pages.
Parker et al., "Pore-forming protein toxins: from structure to function," Progress in Biophysics & Molecular Biology, 2005, 88:91-142.
PCT International Preliminary Report on Patentability in International Appln. No. PCT/US2019/041429, dated Jan. 12, 2021, 11 pages.
PCT International Search Report and Written Opinion in International Appl. No. PCT/US2019/039528, dated Nov. 6, 2019, 19 pages.
PCT International Search Report and Written Opinion in International Appln. No. PCT/US2018/057613, dated Mar. 5, 2019, 11 pages.
PCT Written Opinion in International Appln. No. PCT/US2018/057174, dated Jan. 4, 2019, 3 pages.
Purcell et al., "Cholesterol oxidase: a potent insecticidal protein active against boll weevil larvae," Biochem Biophys Res Commun. Nov. 1993. 196(3): 1406-13.
Qaim et al., "Yield Effects of Genetically Modified Crops in Developing Countries," Science, Feb. 2003, 299(5608):900-2.
Robledo et al., "Rhizobium cellulase CelC2 is essential for primary symbiotic infection of legume host roots," Proc Natl Acad Sci USA, May 2008, 105(19):7064-9.
Robledo et al., "Role of Rhizobium endoglucanase CelC2 in cellulose biosynthesis and biofilm formation on plant roots and abiotic surface," Microb Cell Fact., Sep. 2012, 11:125, 12 pages.

(56) References Cited

OTHER PUBLICATIONS

Sanahuja et al.. "Bacillus thuringiensis: a century of research, development and commercial applications," Plant Biotechnology Journal, Apr. 2011, 9(3):283-300.
Sanyal et al., "The etiology of hepatocellular carcinoma and consequences for treatment," Oncologist, 2010, 15(Suppl 4):14-22.
Schuler et al., "Insect-resistant transgenic plants," Trends in Biotechnology. Apr. 1998, 16(4):168-175.
Tijssen, "Laboratory Techniques In Biochemistry and Molecular Biology," Elsevier, 1993, 24:65 pages.
Woolbright et al., "Novel insight into mechanisms of cholestatic liver injury," World J Gastroenterol., Sep. 2012, 18(36):4985-93.
Dash et al., "Functionalities of Phosphate-Solubilizing Bacteria of Rice Rhizosphere: Techniques and Perspectives," Recent Advances in Applied Microbiology, 2017, 151-163.
Intechopen.com, [online], "*Escherichia coli* as a Model Organism and Its Application in Biotechnology, IntechOpen," 2020, retrieved on Mar. 31, 2020, retrieved from URL<https://www.intechopen.com/books/-i-escherichia-coli-i-recent-advances-on-physiology-pathogenesis-and-biotechnological-applications/-i-escherichi%E2%80%A6>, 15 pages.
Lenski et al., "Effects of Segregation and Selection on Instability of Plasmid pACYC184 in *Escherichia coli* B," Journal of Bacteriology, Nov. 1987, 169(11):5314-5316.
Parts.igem.org, [online], "Registry of Standard Biological Parts," 2017, retrieved on Apr. 8, 2021, retrieved from URL <parts.igem.org/Catalog>, 4 pages.
PCT International Preliminary Report on Patentability in International Appln. No. PCT/US2019/052003, dated Mar. 23, 2021, 10 pages.
Poliner et al., "Nontransgenic Marker-Free Gene Disruption by an Episomal CRISPR System in the Oleaginous Microalga, Nannochloropsis oceanica CCMP1779," ACS Synth. Biol., 2018, 7(4):962-968.
Pyne et al., "Coupling the CRISPR/Cas9 System with Lambda Red Recombineering Enables Simplified Chromosomal Gene Replacement in *Escherichia coli*," Applied and Environmental Microboloy, Aug. 2015, 81(15):5103-5144.
Suzuki et al., "Immune-mediated motor polyneuropathy after hematopoietic stem cell transplantation," Bone Marrow Transplant., Aug. 2007, 40(3):289-91.
Vick et al., "Optimized compatible set of BioBrick™ vectors for metabolic pathway engineering," Appl Microbiol Biotechnol., Dec. 2011, 92(6):1275-86.
Adhikary et al., "Artificial citrate operon confers mineral phosphate solubilization ability to diverse fluorescent pseudomonads," PLoS One, Sep. 2014, 9(9):e107554, 12 pages.
Ambrosio et al., "Metabolic engineering of a diazotrophic bacterium improves ammonium release and biofertilization of plants and microalgae," Metab Eng., Mar. 2017, 40:59-68.
EP Extended European Search Report in European Appln. No. 18739050.5, dated Feb. 1, 2021, 22 pages.
Jayaraman et al., "Strain Improvement of Phosphate Solubilizing Fungal Strains," Journal of Ecobiotechnology, Dec. 2010, 2(5):65-70.
Kumar et al., "Establishment of phosphate-solubilizing strains of *Azotobacter chroococcum* in the rhizosphere and their effect on wheat cultivars under green house conditions," Microbiol Res., 2001, 156(1):87-93.
Liu et al., "Development of an engineered soil bacterium enabling to convert both insoluble inorganic and organic phosphate into plant available phosphate and its use as a biofertilizer," Mol Biotechnol., May 2015, 57(5):419-29.
Miller et al., "Biochemical and genomic comparison of inorganic phosphate solubilization in Pseudomonas species," Environ Microbiol Rep., Jun. 2010, 2(3):403-11.
Murphy et al., "A modified single solution method for the determination of phosphate in natural waters," Analytica Chimica Acta, 1962, 27:31-36.

PCT International Search Report and Written Opinion in International Appln. No. PCT/US2019/052003, dated Dec. 19, 2019, 15 pages.
Rajput et al., "Derepression of Mineral Phosphate Solubilization Phenotype by Insertional Inactivation of iclR in Klebsiella pneumoniae," PLoS One, Sep. 2015, 10(9):e0138235, 15 pages.
Ramirez et al., "Burkholderia and Paraburkholderia are Predominant Soybean Rhizobial Genera in Venezuelan Soils in Different Climatic and Topographical Regions," Microbes and Environments, Mar. 2019, 34(1):43-58.
Reyes et al., "Characteristics of phosphate solubilization by an isolate of a tropical Penicillium rugulosum and two UV-induced mutants," FEMS Microbiology Ecology, Mar. 1999, 28(3):291-295.
Rodriguez et al., "Genetics of phosphate solubilization and its potential applications for improving plant growth-promoting bacteria," Plant and Soil, Sep. 2006, 287(1-2):15-21.
Shulse et al., "Engineered Root Bacteria Release Plant—Available Phosphate from Phytate," Appl Environ Microbiol., Aug. 2019, 85(18):e01210-19.
Wagh et al., "Heterologous expression of pvrroloquinoline quinone (pqq) gene cluster confers mineral phosphate solubilization ability to Herbaspirillum seropedicae Z67," Appl. Microbiol Biotechnol., Jun. 2014, 98(11):5117-29.
Werra et al., "Role of gluconic acid production in the regulation of biocontrol traits of Pseudomonas fluorescens CHAo," Appl Environ Microbiol., Jun. 2009, 75(12):4162-74.
Xie et al., "Interaction between NifL and NifA in the nitrogen-fixing Pseudomonas stutzeri A1501," Microbiology (Reading), Dec. 2006, 152(Pt 12):3535-3542.
Ausubel, et al. Glutamine Synthetase Mutations Which Affect Expression of Nitrogen Fixation Genes in Klebsiella pneumoniae. J Bacteriol 1979, 140(2):597.606.
Bender, et al. Regulatory mutations in the Klebsiella aerogenes structural gene for glutamine synthetase. J Bacteriol. Oct. 1977, vol. 132, No. 1, pp. 100-105.
PCT International Search Report and Written Opinion in International Appln. No. PCT/2020/29831, dated Nov. 16, 2020, 19 pages.
Muse et al., "The nac (Nitrogen Assimilation Control) Gene from *Escherichia coli*," Journal of Bacteriology, Mar. 1998, 180(5):1166-1173.
PCT International Preliminary Report on Patentability in International Appln. No. PCT/US2020/029894, dated Nov. 4, 2021, 13 pages.
PCT International Search Report and Written Opinion in International Appln. No. PCT/US2020/029894, dated Aug. 31, 2020, 19 pages.
Robson et al., "Azotobacter Genomes: The Genome of Azotobacter chroococcum NCIMB 8003 (ATCC 4412)," PLOS ONE, Jun. 2015, 35 pages.
Saleh et al., "Involvement of gacS and rpoS in enhancement of the plant growth-promoting capabilities of Enterobacter cloacae CAL2 and UW4," Canadian Journal of Microbiology, Aug. 2001, 47(8):698-705.
EP Extended European Search Report in European Appln. No. 18843845.1, dated Jul. 22, 2021, 20 pages.
EP Extended European Search Report in European Appln. No. 18870346.6, dated Jul. 22, 2021, 5 pages.
EP Partial Supplementary European Search Report in European Appln. No. 18870036.3, dated Aug. 19, 2021, 19 pages.
Kim et al., "A 20 nucleotide upstream element is essential for the nopaline synthase (nos) promoter activity," Plant Mol Biol., Jan. 1994, 24(1):105-17.
Li et al., "Human Enhancers Are Fragile and Prone to Deactivating Mutations," Mol Biol Evol., Aug. 2015, 32(8):2161-80.
Pakula et al., "Genetic analysis of protein stability and function," Annu Rev Genet, 1989, 23:289-310.
PCT International Preliminary Report on Patentability in International Appln. No. PCT/US2019/068152, dated Jul. 1, 2021, 12 pages.
Singer et al., "Genes and Genomes," Moscow: Mir, 1998, 1:33, 4 pages (with machine translation).

(56) References Cited

OTHER PUBLICATIONS

Wang et al., "Roles of poly-3-hydroxybutyrate (PHB) and glycogen in symbiosis of Sinorhizobium meliloti with *Medicago* sp.," Microbiology, Feb. 2007, 153(2):388-398.
Witkowski et al., "Conversion of a β-Ketoacyl synthase to a malonyl decarboxylase by replacement of the active-site cysteine with glutamine," Biochemistry, Sep. 1999, 38(36): 11643-50.
Zhang et al., "Mutagenesis and functional characterization of the four domains of GlnD, a bifunctional nitrogen sensor protein," Journal of Bacteriology, Jun. 2010, 192(11):2711-2721.
Bittner et al., "RpoS and RpoN are involved in the growth-dependent regulation of rfaH transcription and O antigen expression in *Salmonella enterica* serovar typhi," Microbial Pathogenesis, Jan. 2004, 36(1):19-24.
Extended European Search Report in European Appln. No. 18870036.3, dated Dec. 14, 2021, 28 pages.
Kumar et al., "Metabolic regulation of *Escherichia coli* and its gdhA, glnL, gltB, D mutants under different carbon and nitrogen limitations in the continuous culture," Microbial Cell Factories, Jan. 2010, 9(8):1-17.
Liu et al., "Phenazine-1-carboxylic acid biosynthesis in Pseudomonas Chlororaphis GP72 is positively regulated by the sigma factor RpoN," World Journal of Microbiology and Biotechnology, Jan. 2008, 24(9):1961-1966.
Yan et al., "Global transcriptional analysis of nitrogen fixation and ammonium repression in root-associated Pseudomonas stutzeri A1501," BMC Genomics, Jan. 2010, 11(11):1-13.
Zhang et al., "Mutagenesis and Functional Characterization of the glnB, glnA, and nifA Genes from the Photosynthetic Bacterium Rhodospirillum rubrum," Journal of Bacteriology, Feb. 2000, 182(4):983-992.
US 8,476,226, 11/1999, Koenck
"New Plant Breeding Techniques," Science Council of Japan, retrieved from URL <http://www.scj.go.jp/ja/info/kohyo/pdf/kohyo-22-h140826.pdf>, Aug. 26, 2014, 88 pages (partial English translation).
Aita, T., Husimi, Y. "Adaptive walks by the fittest among finite random mutants on a Mt. Fugi-type fitness landscape," J. Theor, Biol, 193:383-405 (1998).
Amalraj et al., "Effect of Polymeric Additives, Adjuvants, Surfactants on Survival, Stability and Plant Growth Promoting Ability of Liquid Bioinoculants," J. Plant Physiol. Pathol., 2013, 1:2, 6 pages.
Anderson et al., "BglBricks: A flexible standard for biological part assembly," Journal of Biological Engineering, 2010, 4:1, 12 pages.
Andrianantoandro et al., "Synthetic biology: new engineering rules for an emerging discipline," Mol. Syst. Biol., 2006, 2:2006.0028, 14 pages.
Arnold et al., "Nucleotide sequence of a 24,206-base-pair DNA fragment carrying the entire nitrogen fixation gene cluster of *Klebsiella pneumoniae*," J. Mol. Biol., 1988, 203(3):715-738.
Arriel-Elias et al., "Shelf life enhancement of plant growth promoting rhizobacteria using a simple formulation screening method," African Journal of Microbiology Research, Feb. 2018, 12(5):115-126.
Batzer et al., "Enhanced evolutionary PCR using oligonucleotides with inosine at the 3'-termins," Nucleic Acid Res., 1991, 19:5081, 1 page.
Bayer et al., "Synthesis of Methyl Halides from Biomass Using Engineered Microbes," J. Am. Chem. Soc., 2009, 131(18):6508-6515.
Berninger et al., "Maintenance and assessment of cell viability in formulation of non-sporulating bacterial inoculants," Microb. Biotechnol., Mar. 2018, 11(2):277-301 (2018); doi: 10.1111/1751-7915.12880.
Beynon et al., "The nif promoters of Klebsiella pneumoniae have a characteristic primary structure," Cell, 1983, 34(2):665-671.
Biggins et al., "Metabolites from the induced expression of crypic single operons found in the genome of Burkolderia pseudomallei," JACS, 2011, 133:163 8-1641.

Bloch et al., "Biological nitrogen fixation in maize: optimizing nitrogenase expression in a root-associated diazotroph," Journal of Experimental Botany, Jul. 2020, 71(15):4591-4603.
Buck et al., "Frameshifts close to the Klebsiella pneumoniae nifH promoter prevent multicopy inhibition by hybrid nifH plasmids," Mo.l Gen. Genet., 1987, 207(2-3):492-498.
Buckley Lab NifH database, retrieved via WayBack Machine from URL <http://www.css.cornell.edu/faculty/buckley/nifh.htm>, available on or before Jan. 10, 2018, 2 pages.
Burris et al., "Nitrogenases," J. Biol. Chem., 1991, 266(15):9339-9342.
Cardinale et al., "Contextualizing context for synthetic biology identifying causes of failure of synthetic biological systems," Biotechnol. J., 2012, 7:856-866.
cera-gmc.org [online], "GM Crop Database," Center for Environmental Risk Assessment (CERA), 2010, retrieved from URL <http://ucbiotech.org/biotech_info/PDFs/Center_for_Environmental_Risk_Assessment_CERA_2011_GM_Crop_Database.pdf>, 1 page.
Chen et al., "Characterization of 582 natural and synthetic terminators and quantification of their design constraints," Nat. Methods, 2013, 10:659-664.
Chin, "Programming and engineering biological networks," Curr. Opin. Struct. Biol., 2006, 16:551-556.
Colby, "Calculating Synergistic and Antagonistic Responses of Herbicide Combinations," Weeds, Jan. 1967, 15(1):20-22, 4 pages.
Cornelis et al., "The type III secretion injectisome," Nature Reviews Microbiology, 2006, 4(11):811-825.
Costerton et al., "Microbial Biofilms," Annu. Rev. Microbial., Oct. 1995, 49:711-745.
Crameri et al., "Molecular evolution of an arsenate detoxification pathway by DNA shuffling," Nat. Biotechnol., 1997, 15:436-438.
Crook et al., "Re-engineering multicloning sites for function and convenience," Nucl. Acids Res., 2011, 39:e92, 10 pages.
Czar et al., "Gene synthesis demystified," Trends Biotechnol, 2009, 27(2):63-72.
Da Silva et al., "Survival of endophytic bacteria in polymer-based inoculants and efficiency of their application to sugarcane," Plant Soil, May 2012, 356:231-243.
Dandekar et al., "Conservation of gene order: a fingerprint of proteins that physically interact," Trends Biochem. Sci., 1998, 23:324-328.
Das et al., "Microbial assay of N2 fixation rate, a simple alternate for acetylene reduction assay," MethodsX, 2018, 5:909-914.
Davin-Regli et al., "Enterobacter aerogenes and Enterobacter cloacae; versatile bacterial pathogens confronting antibiotic treatment," Front. Microbiol., 2015, 6:392, 10 pages.
De Freitas, "Yield and N assimilation of winter wheat (*Triticum aestivum* L., var. *Norstar*) inoculated with rhizobacteria," Pedobiologia, Jan. 2000, 44(2):97-104.
De Raad et al., "A solid-phase platform for combinatorial and scarless multipart gene assembly," ACS Synth. Biol., 2013, 2:316-326.
Dixon et al., "Genetic transfer of nitrogen fixation from Klebsiella pneumoniae to *Escherichia coli*," Nature, 1972, 237(5350):102-103.
Dykxhoorn et al., "A set of compatible tac promoter expression vectors," Gene, 1996, 177(1-2):133-136.
Endy et al., "Foundations for engineering biology," Nature, 2005, 438:449-453.
Enkh-Amgalan et al., "Molecular evolution of the nif gene cluster carrying nifl 1 and nifl2 genes in the Gram-positive phototrophic bacterium Heliobacterium chlorum," International Journal of Systematic and Evolutionary Microbiology, 2006, 56:65-74.
EP Extended European Search Report in European Appln. No. 19186353.9, dated Nov. 13, 2019, 9 pages.
EP Partial Supplementary European Search Report Appln. No. 19826654.6 dated Mar. 17, 2022, 11 pages.
EP Supplementary Partial European Search Report in International Appln. No. 18739050.5, dated Oct. 27, 2020, 18 pages.
Estrem et al., "Identification of an UP element consensus sequence for bacterial promoters," PNAS, 1998, 95(11):9761-9766.

(56) References Cited

OTHER PUBLICATIONS

Fani et al., "Molecular evolution of nitrogen fixation: the evolutionary history of the niID, nifK, nifE, and nifN gene," J. Mol. Evol., 2000, 51(1):1-11.
Fischbach et al., "The evolution of gene collectives: how natural selection drives chemical innovation," Proc. Natl. Acad. Sci. USA, 2008, 105:4601-4608.
Fontana et al., "RNA folding and combinatory landscapes," Phys. Rev. E., 1993, 47:2083-2099.
Gaby et al., "A comprehensive aligned nifH gene database: a multipurpose tool for studies of nitrogen-fixing bacteria," Database, 2014, 2014:bau001, 8 pages.
GenBank Accession No. CP007215.3, "Kosakonia sacchari SP1 chromosome, complete genome," Sep. 19, 2017, 729 pages.
GenBank Accession No. CP016337.1 "Kosakonia sacchari strain BO-1 chromosome, complete genome," Jul. 11, 2016, 1119 pages.
Georg et al., "cis-antisense RNA, another level of gene regulation in bacteria," Microbiol. Mol. Biol. Rev., 2011, 75(2):286-300.
Gibson et al., "Chemical synthesis of the mouse mitochondrial genome," Nat. Methods, 2010, 7:901-903.
Gibson et al., "Enzymatic assembly of DNA molecules up to several hundred kilobases," Nat Methods, 2009, 6(5):343-345.
Gosink et al., "The product of the Klebsiella pneumoniae nifX gene is a negative regulator of the nitrogen fixation (nif) regulon," J Bacteriology, 1990, 172(3): 1441-1447.
Gottelt et al., "Deletion of a regulatory gene within the cpk gene cluster reveals novel antibacterial activity in Streptomyces coelicolor A3(2)," Microbiology, 2010, 156:2343-2353.
Guell et al., "Bacterial transcriptomics: what is beyond the RNA horiz-ome?," Nature Reviews Microbiology, 2011, 9(9):658-669.
Guell et al., "Transcriptome complexity in a genome-reduced bacterium," Science, 2009, 326:1268-1271.
Hernandez et al., "Biochemical analysis of the recombinant Fur (ferric uptake regulator) protein from Anabaena PCC 7119: factors affecting its oligomerization state," Biochem. J., 2002, 366:315-322.
Hoeschle-Zeledon et al., "Regulatory challenges for biological control," The CGIAR Systemwide Program on Integrated Pest Management, Jan. 2013, SP-IPM Secretariat, International Institute of Tropical Agriculture (IITA), Ibadan, Nigeria, 53 pages.
Hu et al., "Assembly of nitrogenase MoFe protein," Biochemistry, 2008, 47(13):3973-3981.
Huynen et al., "Smoothness within ruggedness: the role of neutrality in adaptation," Proc. Natl. Acad. Sci. USA, 1996, 93:3 97-401.
Iber, "A quantitative study of the benefits of co-regulation using the spoIIA operon as an example," Mol. Sys. Biol., 2006, 2:1-6.
Idalia et al., "*Escherichia coli* as a model organism and its application in biotechnology," Recent Advances on Physiology, Pathogenesis, and Biotechnological Applications, Chapter 13, 2017, pp. 253-274.
International Preliminary Report on Patentability in International Appln. No. PCT/US2019/039528, dated Jan. 7, 2021, 15 pages.
International Preliminary Report on Patentability in International Appln. No. PCT/US2020/029831, dated Nov. 4, 2021, 8 pages.
International Search Report and Written Opinion in International Appln. No. PCT/US2019/064782, dated Apr. 16, 2020, 14 pages.
International Search Report and Written Opinion in International Appln. No. PCT/US2020/014083, dated Jul. 20, 2020, 24 pages.
International Search Report and Written Opinion in International Appln. No. PCT/US2021/029993, dated Sep. 15, 2021, 12 pages.
International Search Report and Written Opinion in International Appln. No. PCT/US2021/055858, dated Mar. 25, 2022, 12 pages.
Invitation to Pay Additional Fees in International Appln. No. PCT/US2020/014083, dated May 28, 2020, 20 pages.
Ishihama, "Prokaryotic genome regulation: multifactor promoters, multitarget regulators and hierarchic networks," FEMS Microbial Rev., 2010, 34(5):628-645.
Ivanova et al., "Artificial Regulation of Genes, of the coding proteins of the nitrogenase complex Rhizobial bacteria," Natural Sciences, 2014, 13(174):36-39 (Machine Translation).
Izquierdo et al., "Distribution of Extensive nifH Gene Diversity Across Physical Soil Microenvironments," Microbial Ecology, 2006, 51(4):441-452.
Jacob et al., "Solid-state NMR studies of Klebsiella pneumoniae grown under nitrogen-fixing conditions," J. Biol, Chem., 1987, 262(1):254-259.
Jacoby et al., "The Role of Soil Microorganisms in Plant Mineral Nutrition-Current Knowledge and Future Directions," Frontiers in Plant Science, 2017, 8(19):1-19.
Jahn et al., "Extraction of Extracellular Polymeric Substances (EPS) from Biofilms Using a Cation Exchange Resin," Wat. Sci. Tech., 1995, 32(8):157-164.
Jensen, "The *Escherichia coli* K-12 "wild types" W3110 and MG1655 have an rph frameshift mutation that leads to pyrimidine starvation due to low pyre expression levels," J. Bacteriol., 1993, 175:3401-3407.
Johnson et al., "Properties of overlapping genes are conserved across microbial genomes," Genome Res., 2004, 14(11):2268-2272.
Joseph et al., "Recent developments of the synthetic biology toolkit for Clostridum," Frontiers in Microbiology, 2018, 9(154):1-13.
Kabaluk et al., "The use and regulation of microbial pesticides in representative jurisdictions worldwide," IOBC Global, 2010, 99 pages.
Kalir et al., "Ordering genes in a flagella pathway by analysis of expression kinetics from living bacteria," Science, 2001, 292(5524):2080-2083.
Kaneko et al., "Complete genomic structure of the cultivated rice endophyte *Azospirillum* sp. B510," DNA Res., 2010, 17:37-50.
Katsnelson, "Engineered bacteria could boost corn yields: Gene-edited microbe offer continuous nitrogen fixation," Chemical & Engineering News, Dec. 28, 2021, retrieved from URL <https://cen.acs.org/food/agriculture/Engineered-bacteria-boost-corn-yields/99/web/2021/12>, 3 pages.
Kececiglu et al., "Of mice and men: Algorithms for evolutionary distances between genomes with translocation," SODA: Proceedings of the sixth annual ACM-SIAM symposium on Discrete algorithms, 1995, 10 pages.
Kelly et al., "Measuring the activity of BioBrick promoters using an in vivo reference standard," J. Biol. Eng., 2009, 3:4, 13 pages.
Kent et al., "A Transposable Partitioning Locus Used To Stabilize Plasmid-Borne Hydrogen Oxidation and Trifolitoxin Production Genes in a Sinorhizobium Strain," Appl. Environ. Microbiol., 1998, 64(5):1657-1662.
Kingsford et al., "Rapid, accurate, computational discovery of Rho-independent transcription terminators illuminates their relationship to DNA uptake," Genome Bio. 2007, 8(2):R22, 12 pages.
Kitano, "Systems biology: a brief overview," Science, 2002, 295(5560): 1662-1664.
Knight, "Idempotent Vector Design for Standard Assembly of Biobricks," MIT Artificial Intelligence Laboratory, The TTL Data Book for Design Engineers, 2003, 11 pages.
Kovacs et al., "Stochasticity in protein levels drives colinearity of gene order in metabolic operons of *Escherichia coli*," PLoS Biol., 2009, 7(5):e1000115, 9 pages.
Lee et al., "The class IId bacteriocin thuricin-17 increases plant growth," Planta, 2009, 229:747-755.
Levican et al., "Comparative genomic analysis of carbon and nitrogen assimilation mechanisms in three indigenous bioleaching bacteria: predictions and validations," BMC Genomics, 2008, 9:581, 19 pages.
Levin-Karp et al., "Quantifying translational coupling in *E. coli* synthetic operons using RBS modulation and fluorescent reporters," ACS Synth. Biol., 2013, 2:327-336.
Lombo et al., "The mithramycin gene cluster of Streptomyces argillaceus contains a positive regulatory gene and two repeated DNA sequences that are located at both ends of the cluster," J. Bacterial., 1999, 181:642-647.
Lowman et al., "Strategies for enhancement of switchgrass (*Panicum virgatum* L.) performance under limited nitrogen supply based on utilization of N-fixing bacterial endophytes," Plant and Soil, Aug. 2016, 405(1):47-63, 17 pages.
Lucks et al., "Toward scalable parts families for predictable design of biological circuits," Curr. Opin. Microbiol., 2008, 11:567-573.

(56) References Cited

OTHER PUBLICATIONS

Ma et al., "Effect of nicotine from tobacco root exudates on chemotaxis, growth, biocontrol efficiency, and colonization by *Pseudomonas aeruginosa* NXHG29," Antonie van Leeuwenhoek, 2018, 111(7):1237-1257.
Mabrouk et al., "Chapter 6: Potential of Rhizobia in Improving Nitrogen Fixation and Yields of Legumes," Symbiosis, May 30, 2018, IntechOpen, pp. 1-16, retrieved on Jan. 12, 2021, retrieved from URL<https://www.intechopen.com/books/symbiosis/potential-of-rhizobia-in-improving- B351nitrogen-fixation-and-yields-of-legumes> 2 pages, Abstract.
Maduro, "Random DNA Generator," retrieved from URL <http://www.faculty.ucr.edu/~mmaduro/random.htm>, 2011, 1 page.
Magasanik, "Genetic control of nitrogen assimilation in bacteria," Ann. Rev. Genet, 1982, 16:135-68.
Mandal et al., "Gene regulation by riboswitches," Nat. Rev. Mol. Cell Biol., 2004, 5(6):451-463.
Mao et al., "Silencing a cotton bollworm P450 monooxygenase gene by plant-mediated RNAi impairs larval tolerance of gossypol," Nature Biotechnology, Nov. 2007, 25(11): 1307-1313.
Mason et al., "Cryptic Growth in Klebsiella-Pneumoniae," Appl. Microbiol. Biot., 1987, 25(6):577-584.
Medema et al., "Exploiting plug-and-play synthetic biology for drug discovery and production in microorganisms," Nat. Rev. Microbiol., 2011, 9:131-137.
Medema et al., "Synthetic biology in Streptomyces bacteria," Methods Enzymol., 2011, 497:485-502.
Merriam-webster.com, [online], "Merriam-Webster Originate," 2020, Retrieved on Jun. 7, 2020, retrieved from URL<https://www.merriam-webster.com/dictionary/originate?utm_campaign=sd&utm_medium=serp&utm_source=jsonld>, 13 pages.
Mirzahoseini et al., "Heterologous Proteins Production in *Escherichia coli*: An Investigation on the Effect of Codon Usage and Expression Host Optimization," Cell Journal (Yakhteh), Dec. 2011, 12(4):453, 7 pages.
Miyazaki, "Creating random mutagenesis libraries by megaprimer PCR of whole plasmid (MEGA WHOP)," Methods Mol. Biol., 2003, 231:23-28.
Mutalik et al., "Quantitative estimation of activity and quality for collections of functional genetic elements," Nat. Methods, 2013, 10:347-353.
Nagy et al., "Nanofibrous solid dosage form of living bacteria prepared by electrospinning," eXPRESS Polymer Letters, 2014, 8(5):352-361.
Nielsen et al., "Conceptual model for production and composition of exopolymers in biofilms," Wat. Sci. Tech., 1997, 36(1): 11-19.
Nielsen et al., "Extraction of EPS," Wingender et al. (eds.), Microbial Extracellular Polymeric Substances, 1999, 24 pages.
Noskov et al., "Assembly of large, high G+C bacterial DNA fragments in yeast," ACS Synth, Biol., 2012, 1:267-273.
Oh et al., "Organization of nif gene cluster in *Frankia* sp. EuIK1 strain, a symbiont of Elaeagnus umbellata," Arch. Microbiol., 2012, 194:29-34.
Ohta et al., "Associative N2-fixation of Rice with Soil and Microorganisms," 1985, 27:17-27 (Abstract Only).
Ohtsuka et al., "An alternative approach to deoxyoligonucleotides as hybridization probes by insertion of deoxyinosine at ambiguous codon positions," J. Biol. Chem., 1985, 260:2605-2608.
Orme-Johnson, "Molecular basis of biological nitrogen fixation," Annu. Rev. Biophys. Biophys. Chem., 1985, 14:419-459.
Patil et al., "Liquid formulations of Acetobacter diazotrophicus L1 and Herbaspirillum seropedicae J24 and their field trials on wheat," International Journal of Environmental Science, 2012, 3(3):1116-1129, 4 pages (Abstract Only).
PCT International Preliminary Report on Patentability in International Appln. No. PCT/US2012/042502, dated Dec. 17, 2013, 8 pages.
PCT International Preliminary Report on Patentability in International Appln. No. PCT/US2016/042170, dated Jan. 16, 2018, 19 pages.

PCT International Preliminary Report on Patentability in International Appln. No. PCT/US2016/055429, dated Apr. 10, 2018, 12 pages.
PCT International Preliminary Report on Patentability in International Appln. No. PCT/US2018/046148, dated Feb. 11, 2020, 10 pages.
PCT International Preliminary Report on Patentability in International Appln. No. PCT/US2018/057174, dated Apr. 28, 2020, 4 pages.
PCT International Preliminary Report on Patentability in International Appln. No. PCT/US2018/057613, dated Apr. 28, 2020, 7 pages.
PCT International Search Report and Written Opinion in International Appln. No. PCT/US2019/041429, dated Dec. 3, 2019, 18 pages.
PCT International Search Report and Written Opinion in International Appln. No. PCT/US2019/059450, dated Mar. 10, 2020, 20 pages.
PCT International Search Report and Written Opinion in International Appln. No. PCT/US2019/068152, dated Jun. 25, 2020, 21 pages.
PCT International Search Report and Written Opinion in International Appln. No. PCT/US2019/39217, dated Nov. 19, 2019, 13 pages.
Philippe et al., "Improvement of pCVD442, a suicide plasmid for gene allele exchange in bacteria," Plasmid, 2004, 51(3):246-255.
Pickens et al., "Metabolic engineering for the production of natural products," Annu. Rev. Chem. Biomol. Eng., 2011, 2:211-236.
Price et al., "Operon formation is driven by co-regulation and not by horizontal gene transfer," Genome Res., 2005, 15:809-819.
Price et al., "The life-cycle of operons," PLoS Genet., 2006, 2:e96, 15 pages.
Purnick et al., "The second wave of synthetic biology: from modules to systems," Nat. Rev. Mol. Cell Biol., 2009, 10(6):410-422.
Rakhee et al., "Extracellular polymeric substances of the marine fouling diatom Amphora rostrata Wm.Sm," Biofouling, 2001, 17(2):117-127, 12 pages.
Ramon et al., "Single-step linker-based combinatorial assembly of promoter and gene cassettes for pathway engineering," Biotechnol. Lett., 2011, 33:549-555.
Riedel et al., "Nitrogen fixation by Klebsiella pneumoniae is inhibited by certain multicopy hybrid nif plasmids," J. Bacterial, 1983, 153(1):45-56.
Rojas-Tapias et al., "Preservation of Azotobacter chroococcum vegetative cells in dry polymers," Univ. Sci., 2015, 20(2):201-207.
Rong et al., "Promoter specificity determinants of T7 RNA polymerase," Proc. Natl. Acad. Sci. USA, 1998, 95(2):515-519.
Rossolini et al., "Use of Deoxyinosine-Containing Primers vs Degenerate Primers for Polymerase Chain Reaction Based on Ambiguous Sequence Information," Mol. Cell. Probes, 1994, 8:91-98.
Rubio et al., "Maturation of Nitrogenase: a Biochemical Puzzle," J. Bacteriology, 2005, 187(2):405-414.
Ryu et al., "Control of nitrogen fixation in bacteria that associate with cereals," Nat. Microbiol., Feb. 2020, 5(2):314-330, 31 pages.
Salis et al., "Automated design of synthetic ribosome binding sites to control protein expression," Nat. Biotechnol., 2009, 27(10):946-950.
Sanjuan et al., "Multicopy plasmids carrying the Klebsiella pneumoniae nifA gene enhance Rhizobium meliloti nodulation competitiveness on alfalfa," Molecular Plant-Microbe Interactions, 1991, 4(4):365-369.
Schmidt-Dannert et al., "Molecular breeding of carotenoid biosynthetic pathways," Nat. Biotechnol., 2000, 18:750-753.
Schuler et al., "Potential side effects of insect-resistant transgenic plants on arthropod natural enemies," Trends Biotechnol., May 1999, 17(5):210-216.
Search Report in AP Appln, No. AP/P/2020/012401, dated Feb. 8, 2022, 4 pages.
Search Report in AP Appln. No. AP/P/2020/012402, dated Feb. 15, 2022, 5 pages.

(56) References Cited

OTHER PUBLICATIONS

Shetty et al., "Engineering BioBrick vectors from BioBrick parts," J. Biol. Eng., 2008, 2:5, 12 pages.
Simon et al., "Perturbation of nifT expression in Klebsiella pneumoniae has limited effect on nitrogen fixation," J. Bacteriol., 1996, 178(10):2975-2977.
Sivaraman et al., "Codon choice in genes depends on flanking sequence information—implications for theoretical reverse translation," Nucleic Acids Res., 2008, 36(3):e16, 8 pages.
Sleight et al., "Randomized BioBrick assembly: a novel DNA assembly method for randomizing and optimizing genetic circuits and metabolic pathways," ACS Synth. Biol., 2013, 2(9):506-518.
Smanski et al., "Engineered Streptomyces platensis strains that overproduce antibiotics platensimycin and platencin," Antimicrob. Agents Chemother., 2009, 53:1299-12304.
Sorek et al., "Prokaryotic transcriptomics: a new view on regulation, physiology, and pathogenicity," Nat. Rev. Genet., 2010, 11:9-16.
Staron et al., "The Third Pillar of Bacterial Signal Transduction: Classification of the Extracytoplasmic Function (ECF) Sigma Factor Protein Family," Mol. Microbiol., 2009, 14(3): 557-81.
Stewart et al., "In situ studies on nitrogen fixation with the acetylene reduction technique," Science, 1967, 158(3800):536.
Stucken et al., "The smallest known genomes of multicellular and toxic cyanobacteria: comparison, minimal gene sets for linked traits and the evolutionary implications," PLoS ONE, 2010, 5:e9235, 15 pages.
Suh et al., "Functional expression of the FeMo-cofactor-specific biosynthetic genes nifEN as a NifE-N fusion protein synthesizing unit in Azotobacter vinelandii," Biochem, Biophys. Res. Comm., 2002, 299:233-240.
Tamsir et al., "Robust multicellular computing using genetically encoded NOR gates and chemical 'wires'," Nature, 2011, 469(7329):212-215.
Tan, "A synthetic biology challenge: making cells compute," Mol. Biosyst., 2007, 3:343-353.
Temme et al., "Induction and relaxation dynamics of the regulatory network controlling the type III secretion system encoded within Salmonella pathogenicity island 1," J. Mol. Biol., 2008, 377(1):47-61.
Thiel et al., "Characterization of genes for a second Mo-dependent nitrogenase in the cyanobacterium Anabaena variabilis," J. Bact., 1997, 179:5222-5225.
Uozumi et al., "Cloning and Expression of the nifA Gene of Klebsiella oxytoca in K. pneumoniae and Azospirillum lipoferum," Agricultural and Biological Chemistry, 1986, 50(6):1539-1544.
Van Dongen, "Performance criteria for graph clustering and Markov cluster experiments," CWI, 2000, 36 pages.
Van Heeswijk et al., "Nitrogen Assimilation in *Escherichia coli*: Putting Molecular Data into a Systems Perspective," Microbiology and Molecular Biology Reviews, Dec. 2013, 77(4):628-695.
Villalobos et al., "Gene Designer: a synthetic biology tool for constructing artificial DNA segments," BMC Bioinformatics, 2006, 7:285, 8 pages.
Wang et al., "Biofilm formation enables free-living nitrogen-fixing rhizobacteria to fix nitrogen under aerobic conditions," The ISME Journal, Jul. 2017, 11:1602-1613.
Watanabe et al., "Total biosynthesis of antitumor nonribosomal peptides in *Escherichia coli*," Nature Chemical Biology, 2006, 2:423-428.
Wei et al., "Endophytic nitrogen-fixing Klebsiella variicola strain DX120E promotes sugarcane growth," Biology and fertility of soils, 2014, 50:657-666.
Wells, "Additivity of mutational effects in proteins," Biochemistry, 1990, 29:8509-8517.
Wen et al., "Enabling Biological Nitrogen Fixation for Cereal Crops in Fertilized Fields," ACS Synth. Biol., Dec. 2021, 10(12):3264-3277.
Wenzel et al., "Recent developments towards the heterologous expression of complex bacterial natural product biosynthetic pathways," Curr. Opin. Biotechnol., 2005, 16(6):594-606.
Wimpenny et al., "Community structure and co-operation in biofilms," 59th Symposium of the Society for General Microbiology, Allison et al. (eds.), Sep. 2000, 23 pages.
Wu et al., "Multivariate modular metabolic engineering of *Escherichia coli* to produce resveratrol from L-tyrosine," J. Biotechnol., 2013, 167:404-411.
Wu et al., "Root exudates from two tobacco cultivars affect colonization of Ralstonia solanacearum and the disease index," European Journal of Plant Pathology, 2014, 141(4):667-677.
Xu et al., "ePathBrick: a synthetic biology platform for engineering metabolic pathways in *E. coli*.," ACS Synth. Biol., 2012, 1:256-266.
Yao et al., "Complementation analysis of heterologous nifA genes to nifA mutants of Sinorhizobium pallida," Chinese Science Bulletin, Oct. 2006, 51(19):2258-2264, 2 pages (English abstract only).
Ye et al., "Primer-BLAST: a tool to design target-specific primers for polymerase chain reaction," BMC Bioinformatics., Jun. 2012, 13(134): 1-11.
Yokobayashi et al., "Directed evolution of a genetic circuit," Proc. Natl. Acad. Sci. USA, 2002, 99(26): 16587-16591.
Yu et al., "Recombineering Pseudomonas protegens CHA0: An innovative approach that improves nitrogen fixation with impressive bactericidal potency," Microbiological Research, Jan. 2019, 218:58-65.
Zaslaver et al., "Optimal gene partition into operons correlates with gene functional order," Phys. Biol., 2006, 3(3):183-189.
Zazopoulos et al., "A genomics-guided approach for discovering and expressing cryptic metabolic pathways," Nat. Biotechnol., 2003, 21(2): 187-190.
Zehr Lab NifH database, retrieved from URL <https://wwwzehr.pmc.ucsc.edu/nifH_Database Public/>, Apr. 4, 2014, 1 page.
Zhao et al., "Evidence for nifU and nifS participation in the biosynthesis of the iron-molybdenum cofactor of nitrogenase," J. Biol, Chem., 2007, 282(51):37016-37025.
Zomer, "PPP: Perform Promoter Prediction," retrieved from URL <http://bioinformatics.biol.rug.nl/websoftware/ppp/ppp_start.php>, 2011, 2 pages.
Search Report in Russian Appln. No. 2020116764, dated Apr. 28, 2022, 15 pages (with English translation).
Extended European Search Report in European Appln. No. 19833252.0, dated Mar. 14, 2022, 7 pages.
Duca et al., "Indole-3-acetic acid in plant-microbe interactions," Antonie van Leeuwenhoek, Jan. 2014, 106(1):85-125, 41 pages.
Extended European Search Report in European Appln. No. 19826654.6, dated Jul. 4, 2022, 16 pages.
Schluter et al., "Global mapping of transcription start sites and promoter motifs in the symbiotic α-proteobacterium *Sinorhizobium meliloti*," BMC Genomics, Mar. 2013, 14(1):156, 21 pages.
Lugtenberg et al., "Molecular Determinants of Rhizosphere Colonization by *Pseudomonas*," Annu. Rev. Phytopathol., Sep. 2001, 39(1):461-490, 31 pages.
Machado et al., "Excretion of ammonium by *Azospirillum brasilense* mutants resistant to ethylenediamine," Can. J. Microbiol., Jul. 1991, 37(7): 549-553, 2 pages (Abstract Only).
Pankievicz et al., "Robust biological-nitrogen fixation in a model grass—bacterial association," The Plant Journal, 81(6), Mar. 2015, 907-919.

* cited by examiner

|       | no glutamine | 1mM glutamine | 10 mM glutamine |         |
|-------|--------------|---------------|-----------------|---------|
| amtB  | 716462       | 175150        | 1045            |         |
| galK  | 15           | 405           | 814             |         |
| glnB  | 8025         | 10275         | 7493            |         |
| glnK  | 752360       | 183994        | 320             |         |
| nifA  | 306663       | 92963         | 194             | 0% air  |
| nifH  | 12387186     | 3599183       | 161             |         |
| nifL  | 226368       | 42825         | 123             |         |
| ntrB  | 50439        | 25236         | 1081            |         |
| ntrC  | 78056        | 35760         | 1216            |         |
| amtB  | 241247       | 139599        | 1207            |         |
| galK  | 404          | 770           | 1012            |         |
| glnB  | 8296         | 6899          | 9376            |         |
| glnK  | 241645       | 158973        | 288             |         |
| nifA  | 237483       | 115545        | 197             | 10% air |
| nifH  | 4702957      | 2448758       | 108             |         |
| nifL  | 173765       | 66818         | 75              |         |
| ntrB  | 25676        | 19630         | 1118            |         |
| ntrC  | 40312        | 30703         | 1295            |         |
| amtB  | 160293       | 167736        | 1353            |         |
| galK  | 1311         | 976           | 1200            |         |
| glnB  | 8522         | 8185          | 9445            |         |
| glnK  | 166653       | 191992        | 366             |         |
| nifA  | 200774       | 164973        | 198             | 20% air |
| nifH  | 862984       | 2337297       | 80              |         |
| nifL  | 129054       | 99096         | 80              |         |
| ntrB  | 17326        | 21370         | 1146            |         |
| ntrC  | 24115        | 31446         | 1370            |         |

FIG. 5

Colonization Sampling

For older roots, the entire root is not necessary as long as it fits the requirements listed below.

Sample size: 5 grams of tissue with roughly the same number and size (smaller ok) of lateral roots. The samples do not have to be cleaned of soil.

For transcriptomics, sample size is required to be packed in a solution and shipped on dry ice

| Strain Name | Activity (mmol N / Microbe hr) | Peak Colonization (CFU / g fw) |
|---|---|---|
| CI006 | 4.45E-16 | 2.55E+05 |
| CM038 | 3.26E-13 | 7.39E+05 |
| CM014 | 2.72E-13 | 7.39E+05 |
| CM093 | 4.27E-13 | 7.39E+05 |
| CM094 | 5.49E-13 | 7.39E+05 |
| CM029 | 2.95E-13 | 7.39E+05 |
| CI019 | 4.32E-17 | 2.89E+07 |
| CM011 | 2.95E-15 | 3.49E+07 |
| CM067 | 2.30E-17 | 3.49E+07 |
| CM069 | 3.10E-17 | 3.49E+07 |
| CM081 | 8.63E-16 | 3.49E+07 |
| 19-715 | 1.28E-15 | 3.49E+07 |
| 19-714 | 1.57E-15 | 3.49E+07 |
| 19-594 | 3.31E-15 | 3.49E+07 |
| 19-590 | 1.14E-14 | 3.49E+07 |
| 19-713 | 1.96E-14 | 3.49E+07 |
| 19-724 | 2.41E-14 | 3.49E+07 |
| CI911 | 3.48E-17 | 1.24E+07 |
| CI730 | 5.64E-17 | 2.89E+07 |

FIG. 28A
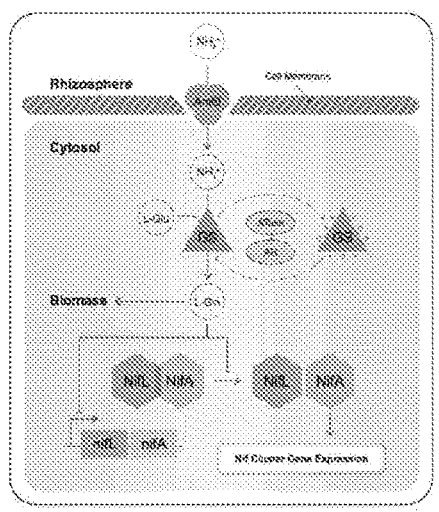
FIG. 28B
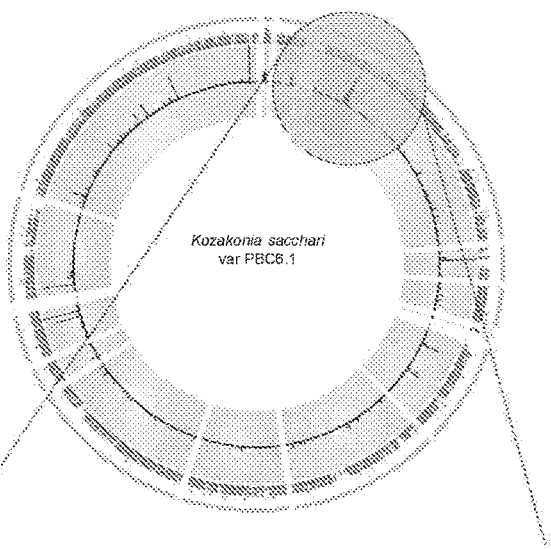
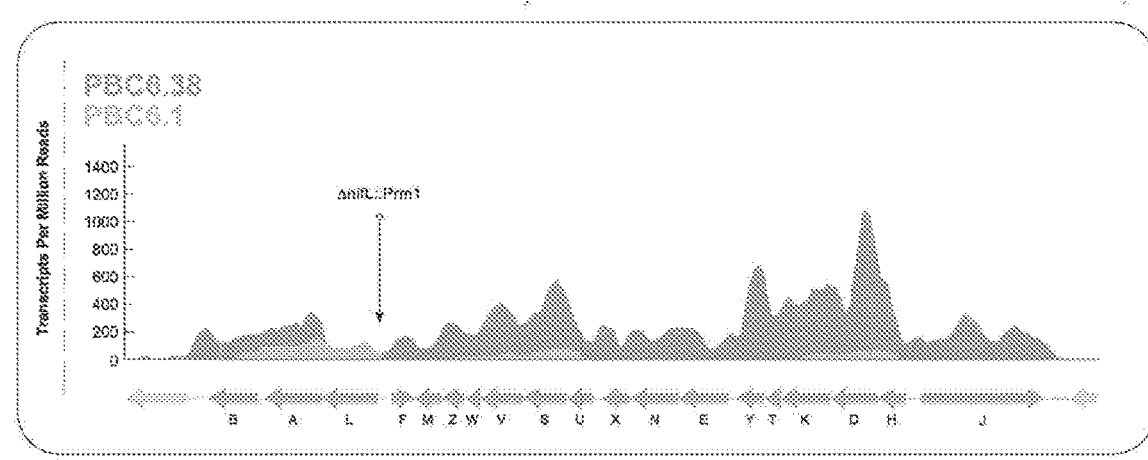
FIG. 28C
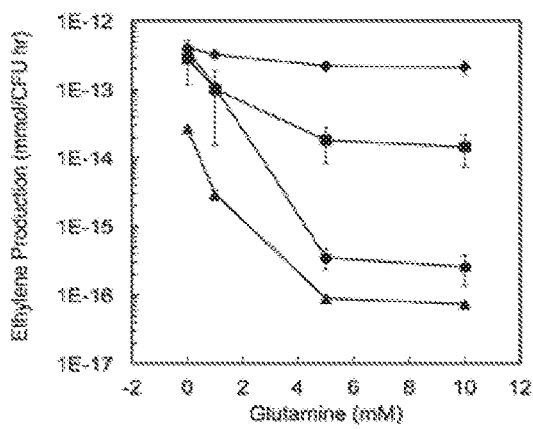
FIG. 28D
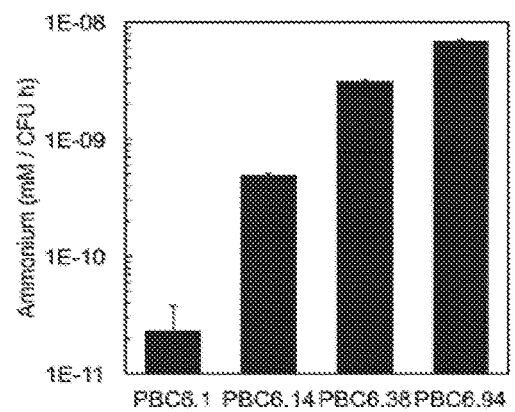
FIG. 28E

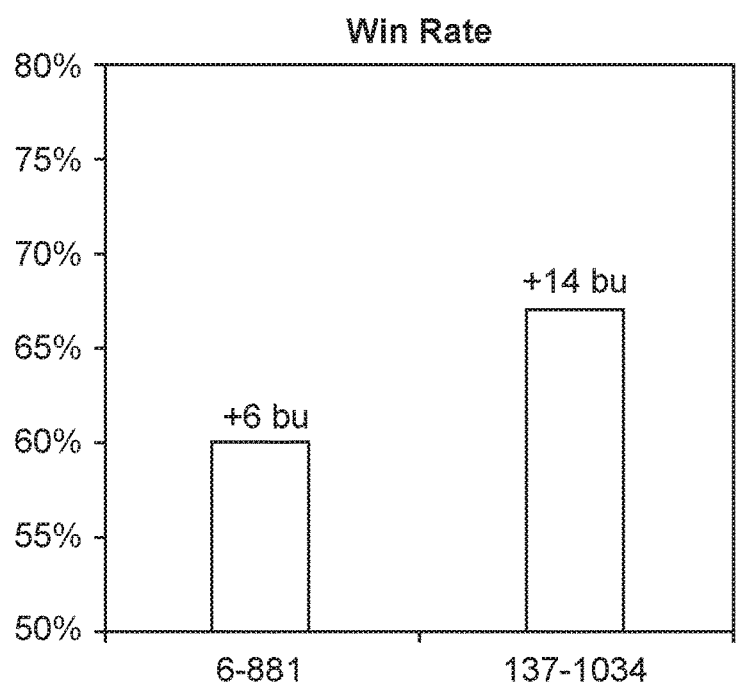
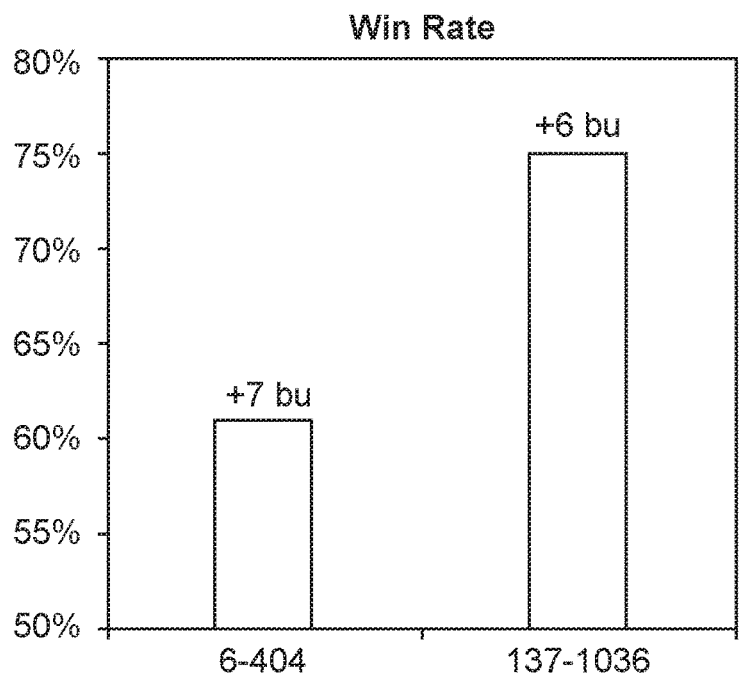
FIG. 33

METHODS AND COMPOSITIONS FOR IMPROVING PLANT TRAITS

CROSS-REFERENCE

This application claims the benefit of U.S. Provisional Application No. 62/445,570, filed Jan. 12, 2017; U.S. Provisional Application No. 62/445,557, filed Jan. 12, 2017; U.S. Provisional Application No. 62/447,889, filed Jan. 18, 2017; U.S. Provisional Application No. 62/467,032, filed Mar. 3, 2017; U.S. Provisional Application No. 62/566,199, filed Sep. 29, 2017; and U.S. Provisional Application No. 62/577,147, filed Oct. 25, 2017, which applications are incorporated herein by reference.

STATEMENT AS TO FEDERALLY SPONSORED RESEARCH

This invention was made with the support of the United States government under SBIR grant 1520545 awarded by the National Science Foundation. The government has certain rights in the disclosed subject matter.

STATEMENT REGARDING SEQUENCE LISTING

The instant application contains a Sequence Listing which has been submitted electronically in ASCII format and is hereby incorporated by reference in its entirety. Said ASCII copy, created on Jan. 3, 2018, is named 47736-707_601_SL.txt and is ≈599 kb in size.

BACKGROUND OF THE INVENTION

Plants are linked to the microbiome via a shared metabolome. A multidimensional relationship between a particular crop trait and the underlying metabolome is characterized by a landscape with numerous local maxima. Optimizing from an inferior local maximum to another representing a better trait by altering the influence of the microbiome on the metabolome may be desirable for a variety of reasons, such as for crop optimization. Economically-, environmentally-, and socially-sustainable approaches to agriculture and food production are required to meet the needs of a growing global population. By 2050 the United Nations' Food and Agriculture Organization projects that total food production must increase by 70% to meet the needs of the growing population, a challenge that is exacerbated by numerous factors, including diminishing freshwater resources, increasing competition for arable land, rising energy prices, increasing input costs, and the likely need for crops to adapt to the pressures of a drier, hotter, and more extreme global climate.

One area of interest is in the improvement of nitrogen fixation. Nitrogen gas ($N_2$) is a major component of the atmosphere of Earth. In addition, elemental nitrogen (N) is an important component of many chemical compounds which make up living organisms. However, many organisms cannot use $N_2$ directly to synthesize the chemicals used in physiological processes, such as growth and reproduction. In order to utilize the $N_2$, the $N_2$ must be combined with hydrogen. The combining of hydrogen with $N_2$ is referred to as nitrogen fixation. Nitrogen fixation, whether accomplished chemically or biologically, requires an investment of large amounts of energy. In biological systems, an enzyme known as nitrogenase catalyzes the reaction which results in nitrogen fixation. An important goal of nitrogen fixation research is the extension of this phenotype to non-leguminous plants, particularly to important agronomic grasses such as wheat, rice, and maize. Despite enormous progress in understanding the development of the nitrogen-fixing symbiosis between rhizobia and legumes, the path to use that knowledge to induce nitrogen-fixing nodules on non-leguminous crops is still not clear. Meanwhile, the challenge of providing sufficient supplemental sources of nitrogen, such as in fertilizer, will continue to increase with the growing need for increased food production.

SUMMARY OF THE INVENTION

An aspect of the invention provides a bacterial composition that comprises at least one genetically engineered bacterial strain that fixes atmospheric nitrogen in an agricultural system that has been fertilized with more than 20 lbs of Nitrogen per acre.

Another aspect of the invention provides a bacterial composition that comprises at least one bacterial strain that has been bred to fix atmospheric nitrogen in an agricultural system that has been fertilized with more than 20 lbs of Nitrogen per acre.

An additional aspect of the invention provides a bacterial composition that comprises at least one genetically engineered bacterial strain that fixes atmospheric nitrogen, the at least one genetically engineered bacterial strain comprising exogenously added DNA wherein said exogenously added DNA shares at least 80% identity to a corresponding native bacterial strain.

A further aspect of the invention provides a seed composition comprising a seed of a plant that is inoculated with a bacterial composition.

Another aspect of the invention provides a method of growing a crop using a plurality of seeds having a seed composition that is inoculated with a bacterial composition.

An additional aspect of the invention provides a method of applying a bacterial composition to a field.

A further aspect of the invention provides a fertilizer composition comprising a bacterial composition.

Another aspect of the invention provides a method of maintaining soil nitrogen levels. The method comprises planting, in soil of a field, a crop inoculated by a genetically engineered bacterium that fixes atmospheric nitrogen. The method also comprises harvesting said crop, wherein no more than 90% of a nitrogen dose required for producing said crop is administered to said soil of said field between planting and harvesting.

An additional aspect of the invention provides a method of delivering a probiotic supplement to a crop plant. The method comprises coating a crop seed with a seed coating, seed treatment, or seed dressing. Said seed coating, seed dressing, or seed treatment comprises living representatives of said probiotic. Additionally, the method comprises applying, in soil of a field, said crop seeds.

In a further aspect of the invention, the genetically engineered bacterial strain is a genetically engineered Gram-positive bacterial strain. In some cases, the genetically engineered Gram-positive bacterial strain has an altered expression level of a regulator of a Nif cluster. In some cases, the genetically engineered Gram-positive bacterial strain expresses a decreased amount of a negative regulator of a Nif cluster. In some cases, the genetically engineered bacterial strain expresses a decreased amount of GlnR. In some cases, the genome of the genetically engineered bacterial strain encodes a polypeptide with at least 75% identity to a sequence from the Zehr lab NifH database. In some cases, the genome of the genetically engineered bacterial strain encodes a polypeptide with at least 85% identity to a sequence from the Zehr lab NifH database. In some cases, the genome of the genetically engineered bacterial strain encodes a polypeptide with at least 75% identity to a sequence from the Buckley lab NifH database. In some cases, the genome of the genetically engineered bacterial strain encodes a polypeptide with at least 85% identity to a sequence from the Buckley lab NifH database.

Another aspect of the invention provides a method of increasing nitrogen fixation in a non-leguminous plant. The method comprises applying to the plant a plurality of non-intergeneric bacteria, said plurality comprising non-intergeneric bacteria that (i) have an average colonization ability per unit of plant root tissue of at least about $1.0 \times 10^4$ bacterial cells per gram of fresh weight of plant root tissue and (ii) produce fixed N of at least about $1 \times 10^{-17}$ mmol N per bacterial cell per hour. Additionally, the plurality of non-intergeneric bacteria, in planta, produce 1% or more of the fixed nitrogen in the plant. Further, each member of the plurality of non-intergeneric bacteria comprises at least one genetic variation introduced into at least one gene, or non-coding polynucleotide, of the nitrogen fixation or assimilation genetic regulatory network, such that the non-intergeneric bacteria are capable of fixing atmospheric nitrogen in the presence of exogenous nitrogen.

An additional aspect of the invention provides a method of increasing nitrogen fixation in a non-leguminous plant. The method comprises applying to the plant a plurality of non-intergeneric bacteria, said plurality comprising non-intergeneric bacteria that (i) have an average colonization ability per unit of plant root tissue of at least about $1.0 \times 10^4$ bacterial cells per gram of fresh weight of plant root tissue and/or (ii) produce fixed N of at least about $1 \times 10^{-17}$ mmol N per bacterial cell per hour. Additionally, the plurality of non-intergeneric bacteria, in planta, produce 1% or more of the fixed nitrogen in the plant. Further, each member of the plurality of non-intergeneric bacteria comprises at least one genetic variation introduced into at least one gene, or non-coding polynucleotide, of the nitrogen fixation or assimilation genetic regulatory network, such that the non-intergeneric bacteria are capable of fixing atmospheric nitrogen in the presence of exogenous nitrogen.

A further aspect of the invention provides a method of breeding microbial strains to improve specific traits of agronomic relevance. The method comprises providing a plurality of microbial strains that have the ability to colonize a desired crop. The method also comprises improving regulatory networks influencing the trait through intragenomic rearrangement. Further, the method comprises assessing microbial strains within the plurality of microbial strains to determine a measure of the trait. Additionally, the method comprises selecting one or more microbial strains of the plurality of microbial strains that generate an improvement in the trait in the presence of the desired crop.

Another aspect of the invention provides a method of breeding microbial strains to improve specific traits of agronomic relevance. The method comprises providing a plurality of microbial strains that have the ability to colonize a desired crop. The method also comprises introducing genetic diversity into the plurality of microbial strains. Additionally, the method comprises assessing microbial strains within the plurality of microbial strains to determine a measure of the trait. Further, the method comprises selecting one or more microbial strains of the plurality of microbial strains that generate an improvement in the trait in the presence of the desired crop.

Another aspect of the invention provides a method of increasing the amount of atmospheric derived nitrogen in a non-leguminous plant. The method comprises exposing said non-leguminous plant to engineered non-intergeneric microbes, said engineered non-intergeneric microbes comprising at least one genetic variation introduced into a nitrogen fixation genetic regulatory network or at least one genetic variation introduced into a nitrogen assimilation genetic regulatory network.

A further aspect of the invention provides a method of increasing an amount of atmospheric derived nitrogen in a corn plant. The method comprises exposing said corn plant to engineered non-intergeneric microbes comprising engineered genetic variations within at least two genes selected from the group consisting of nifL, glnB, glnE, and amtB.

Another aspect of the invention provides a method of increasing an amount of atmospheric derived nitrogen in a corn plant. The method comprises exposing said corn plant to engineered non-intergeneric microbes comprising at least one genetic variation introduced into a nitrogen fixation genetic regulatory network and at least one genetic variation introduced into a nitrogen assimilation genetic regulatory network, wherein said engineered non-intergeneric microbes, in planta, produce at least 5% of fixed nitrogen in said corn plant as measured by dilution of 15N in crops grown in fields treated with fertilizer containing 1.2% 15N.

An additional aspect of the invention provides a method of increasing nitrogen fixation in a non-leguminous plant. The method comprises applying to the plant a plurality of non-intergeneric bacteria, said plurality comprising non-intergeneric bacteria that (i) have an average colonization ability per unit of plant root tissue of at least about $1.0 \times 10^4$ bacterial cells per gram of fresh weight of plant root tissue and (ii) produce fixed N of at least about $1 \times 10^{-17}$ mmol N per bacterial cell per hour. Additionally, the product of (i) the average colonization ability per unit of plant root tissue and (ii) produced fixed N per bacterial cell per hour, is at least about $2.5 \times 10^{-8}$ mmol N per gram of fresh weight of plant root tissue per hour. Further, the plurality of non-intergeneric bacteria, in planta, produce 1% or more of the fixed nitrogen in the plant. Additionally, each member of the plurality of non-intergeneric bacteria comprises at least one genetic variation introduced into at least one gene, or non-coding polynucleotide, of the nitrogen fixation or assimilation genetic regulatory network, such that the non-intergeneric bacteria are capable of fixing atmospheric nitrogen in the presence of exogenous nitrogen.

Another aspect of the invention provides a method of increasing nitrogen fixation in a non-leguminous plant. The method comprises applying to the plant a plurality of bacteria, said plurality comprising bacteria that (i) have an average colonization ability per unit of plant root tissue of at least about $1.0 \times 10^4$ bacterial cells per gram of fresh weight of plant root tissue and/or (ii) produce fixed N of at least about $1 \times 10^{-17}$ mmol N per bacterial cell per hour. Additionally, the plurality of bacteria, in planta, produce 1% or more of the fixed nitrogen in the plant.

An additional aspect of the invention provides a non-intergeneric bacterial population capable of increasing nitrogen fixation in a non-leguminous plant, comprising a plurality of non-intergeneric bacteria that (i) have an average colonization ability per unit of plant root tissue of at least about $1.0 \times 10^4$ bacterial cells per gram of fresh weight of plant root tissue and/or (ii) produce fixed N of at least about $1 \times 10^{-17}$ mmol N per bacterial cell per hour. Additionally, the plurality of non-intergeneric bacteria, in planta, produce 1% or more of the fixed nitrogen in a plant grown in the presence of the plurality of non-intergeneric bacteria. Further, each member of the plurality of non-intergeneric bacteria comprises at least one genetic variation introduced into at least one gene, or non-coding polynucleotide, of the nitrogen fixation or assimilation genetic regulatory network, such that the non-intergeneric bacteria are capable of fixing atmospheric nitrogen in the presence of exogenous nitrogen.

A further aspect of the invention provides a bacterial population capable of increasing nitrogen fixation in a non-leguminous plant, the bacterial population comprising a plurality of bacteria that (i) have an average colonization ability per unit of plant root tissue of at least about $1.0 \times 10^4$ bacterial cells per gram of fresh weight of plant root tissue; and/or (ii) produce fixed N of at least about $1 \times 10^{-17}$ mmol N per bacterial cell per hour. Additionally, the plurality of bacteria, in planta, produce 1% or more of the fixed nitrogen in the plant.

In another aspect of the invention, a bacterium is provided that (i) has an average colonization ability per unit of plant root tissue of at least about $1.0 \times 10^4$ bacterial cells per gram of fresh weight of plant root tissue and/or (ii) produces fixed N of at least about $1 \times 10^{-17}$ mmol N per bacterial cell per hour.

In a further aspect of the invention, a non-intergeneric bacterium is provided that comprises at least one genetic variation introduced into at least one gene, or non-coding polynucleotide, of the nitrogen fixation or assimilation genetic regulatory network, such that the non-intergeneric bacterium is capable of fixing atmospheric nitrogen in the presence of exogenous nitrogen, and wherein said bacterium (i) has an average colonization ability per unit of plant root tissue of at least about $1.0 \times 10^4$ bacterial cells per gram of fresh weight of plant root tissue and/or (ii) produces fixed N of at least about $1 \times 10^{-17}$ mmol N per bacterial cell per hour.

In an additional aspect of the invention provides a method for increasing nitrogen fixation in a plant, comprising administering to the plant an effective amount of a composition that comprises a purified population of bacteria that comprises bacteria with a 16S nucleic acid sequence that is at least about 97% identical to a nucleic acid sequence selected from SEQ ID NOs: 85, 96, 111, 121, 122, 123, 124, 136, 149, 157, 167, 261, 262, 269, 277-283; a purified population of bacteria that comprises bacteria with a nucleic acid sequence that is at least about 90% identical to a nucleic acid sequence selected from SEQ ID NOs: 86-95, 97-110, 112-120, 125-135, 137-148, 150-156, 158-166, 168-176, 263-268, 270-274, 275, 276, 284-295; and/or a purified population of bacteria that comprises bacteria with a nucleic acid sequence that is at least about 90% identical to a nucleic acid sequence selected from SEQ ID NOs: 177-260, 296-303; and wherein the plant administered the effective amount of the composition exhibits an increase in nitrogen fixation, as compared to a plant not having been administered the composition.

A further aspect of the invention provides an isolated bacteria comprising a 16S nucleic acid sequence that is at least about 97% identical to a nucleic acid sequence selected from SEQ ID NOs: 85, 96, 111, 121, 122, 123, 124, 136, 149, 157, 167, 261, 262, 269, 277-283; a nucleic acid sequence that is at least about 90% identical to a nucleic acid sequence selected from SEQ ID NOs: 86-95, 97-110, 112-120, 125-135, 137-148, 150-156, 158-166, 168-176, 263-268, 270-274, 275, 276, 284-295; and/or a nucleic acid sequence that is at least about 90% identical to a nucleic acid sequence selected from SEQ ID NOs: 177-260, 296-303.

Another aspect of the invention provides a method of detecting a non-native junction sequence, comprising: amplifying a nucleotide sequence that shares at least about 70%, 71%, 72%, 73%, 74%, 75%, 76%, 77%, 78%, 79%, 80%, 81%, 82%, 83%, 84%, 85%, 86%, 87%6, 88%, 89%, 90%, 91%, 92%, 93%, 94%, 95%, 96%, 97%, 98%, 99%, or 100% sequence identity to SEQ ID NOs: 372-405.

An additional aspect of the invention provides a method of detecting a non-native junction sequence, comprising: amplifying a nucleotide sequence that shares at least about 70%, 71%, 72%, 73%, 74%, 75%, 76%, 77%, 78%, 79%, 80%, 81%, 82%, 830%, 84%, 85%, 86%, 87%, 88%, 89%, 90%, 91%, 92%, 93%, 94%, 95%, 96%, 97%, 98%, 99%, or 100% sequence identity to at least a 10 contiguous base pair fragment contained in SEQ ID NOs: 372-405, said contiguous base pair fragment being comprised of nucleotides at the intersection of: an upstream sequence comprising SEQ ID NOs: 304-337 and downstream sequence comprising SEQ ID NOs: 338-371.

A further aspect of the invention provides a non-native junction sequence comprising a nucleotide sequence that shares at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NOs: 372-405.

An additional aspect of the invention provides a non-native junction sequence comprising a nucleotide sequence that shares at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to at least a 10 contiguous base pair fragment contained in SEQ ID NOs: 372-405, said contiguous base pair fragment being comprised of nucleotides at the intersection of: an upstream sequence comprising SEQ ID NOs: 304-337 and downstream sequence comprising SEQ ID NOs: 338-371.

A further aspect of the invention provides a bacterial composition comprising at least one remodeled bacterial strain that fixes atmospheric nitrogen, the at least one remodeled bacterial strain comprising exogenously added DNA wherein said exogenously added DNA shares at least 80% identity to a corresponding native bacterial strain.

An additional aspect of the invention provides a method of maintaining soil nitrogen levels. The method comprises planting, in soil of a field, a crop inoculated by a remodeled bacterium that fixes atmospheric nitrogen. The method also comprises harvesting said crop, wherein no more than 90% of a nitrogen dose required for producing said crop is administered to said soil of said field between planting and harvesting.

Another aspect of the invention provides a method of delivering a probiotic supplement to a crop plant. The method comprises coating a crop seed with a seed coating, seed treatment, or seed dressing, wherein said seed coating, seed dressing, or seed treatment comprise living representatives of said probiotic. The method also comprises applying said crop seeds in soil of a field.

An additional aspect of the invention provides a method of increasing the amount of atmospheric derived nitrogen in a non-leguminous plant. The method comprises exposing said non-leguminous plant to remodeled non-intergeneric microbes, said remodeled non-intergeneric microbes comprising at least one genetic variation introduced into a nitrogen fixation genetic regulatory network or at least one genetic variation introduced into a nitrogen assimilation genetic regulatory network.

A further aspect of the invention provides a method of increasing an amount of atmospheric derived nitrogen in a corn plant. The method comprises exposing said corn plant to remodeled non-intergeneric microbes comprising remodeled genetic variations within at least two genes selected from the group consisting of nifL, glnB, glnE, and amtB.

Another aspect of the invention provides a method of increasing an amount of atmospheric derived nitrogen in a corn plant. The method comprises exposing said corn plant to remodeled non-intergeneric microbes comprising at least one genetic variation introduced into a nitrogen fixation genetic regulatory network and at least one genetic variation introduced into a nitrogen assimilation genetic regulatory network, wherein said remodeled non-intergeneric microbes, in planta, produce at least 5% of fixed nitrogen in said corn plant as measured by dilution of 15N in crops grown in fields treated with fertilizer containing 1.2% 15N.

Additional aspects of the invention provide genus of microbes that are evolved and optimized for in planta nitrogen fixation in non-leguminous crops. In particular, methods of increasing nitrogen fixation in a non-leguminous plant are disclosed. The methods can comprise exposing the plant to a plurality of bacteria. Each member of the plurality comprises one or more genetic variations introduced into one or more genes of non-coding polynucleotides of the bacteria's nitrogen fixation or assimilation genetic regulatory network, such that the bacteria are capable of fixing atmospheric nitrogen in the presence of exogenous nitrogen. The bacteria are not intergeneric microorganisms. Additionally, the bacteria, in planta, produce 1% or more of the fixed nitrogen in the plant.

Further aspects of the invention provide beneficial isolated microbes and microbial compositions. In particular, isolated and biologically pure microorganisms that have applications, inter alia, in increasing nitrogen fixation in a crop are provided. The disclosed microorganism can be utilized in their isolated and biologically pure states, as well as being formulated into compositions. Furthermore, the disclosure provides microbial compositions containing at least two members of the disclosed microorganisms, as well as methods of utilizing said microbial compositions.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 5 depicts in culture expression profile of 9 different genes in strains CI006 involved in diazaotrophic nitrogen fixation. Numbers represent counts of each transcript. Various conditions (0, 1, 10 mM Glutamine and 0%, 10%, 20% atmospheric air in N2) are indicated.

FIGS. 28A-28E illustrate derivative microbes that fix and excrete nitrogen in vitro under conditions similar to high nitrate agricultural soils. FIG. 28A illustrates the regulatory network controlling nitrogen fixation and assimilation in PBC6.1 is shown, including the key nodes NifL, NifA, GS, GlnE depicted as the two-domain ATase-AR enzyme, and AmtB. FIG. 28B illustrates the genome of *Kosakonia sacchari* isolate PBC6.1 is shown. The three tracks circumscribing the genome convey transcription data from PBC6.1, PBC6.38, and the differential expression between the strains respectively. FIG. 28C illustrates the nitrogen fixation gene cluster and transcription data is expanded for finer detail. FIG. 28D illustrates nitrogenase activity under varying concentrations of exogenous nitrogen is measured with the acetylene reduction assay. The wild type strain exhibits repression of nitrogenase activity as glutamine concentrations increase, while derivative strains show varying degrees of robustness. Error bars represent standard error of the mean of at least three biological replicates. FIG. 28E illustrates temporal excretion of ammonia by derivative strains is observed at mM concentrations. Wild type strains are not observed to excrete fixed nitrogen, and negligible ammonia accumulates in the media. Error bars represent standard error of the mean.

FIG. 29A illustrates microbe colonization six weeks after inoculation of corn plants by PBC6.1 derivative strains. Error bars show standard error of the mean of at least eight biological replicates. FIG. 29B illustrates in planta transcription of nifH measured by extraction of total RNA from roots and subsequent Nanostring analysis. Only derivative strains show nifH transcription in the root environment. Error bars show standard error of the mean of at least 3 biological replicates. FIG. 29C illustrates microbial nitrogen fixation measured by the dilution of isotopic tracer in plant tissues. Derivative microbes exhibit substantial transfer of fixed nitrogen to the plant. Error bars show standard error of the mean of at least ten biological replicates.

FIG. 33 illustrates results from a summer 2017 field testing experiment. The yield results obtained demonstrate that the microbes of the disclosure perform consistently across locations. Furthermore, the yield results demonstrate that the microbes of the disclosure perform well in both a nitrogen stressed environment, as well as an environment that has sufficient supplies of nitrogen. The microbe "6-881" (also known as CM094, PBC6.94), and which is a progeny mutant *Kosakonia sacchari* strain from CI006 WT, was deposited as NCMA 201708002 and can be found in Table A. The microbe "137-1034," which is a progeny mutant *Klebsiella variicola* strain from CI137 WT, was deposited as NCMA 201712001 and can be found in Table A. The microbe "137-1036," which is a progeny mutant *Klebsiella variicola* strain from CI137 WT, was deposited as NCMA 201712002 and can be found in Table A. The microbe "6-404" (also known as CM38, PBC6.38), and which is a progeny mutant *Kosakonia sacchari* strain from CI006 WT, was deposited as NCMA 201708003 and can be found in Table A. The "Nutrient Stress" condition corresponds to the 0% nitrogen regime. The "Sufficient Fertilizer" condition corresponds to the 100% nitrogen regime.

DETAILED DESCRIPTION OF THE INVENTION

Figure 1A:
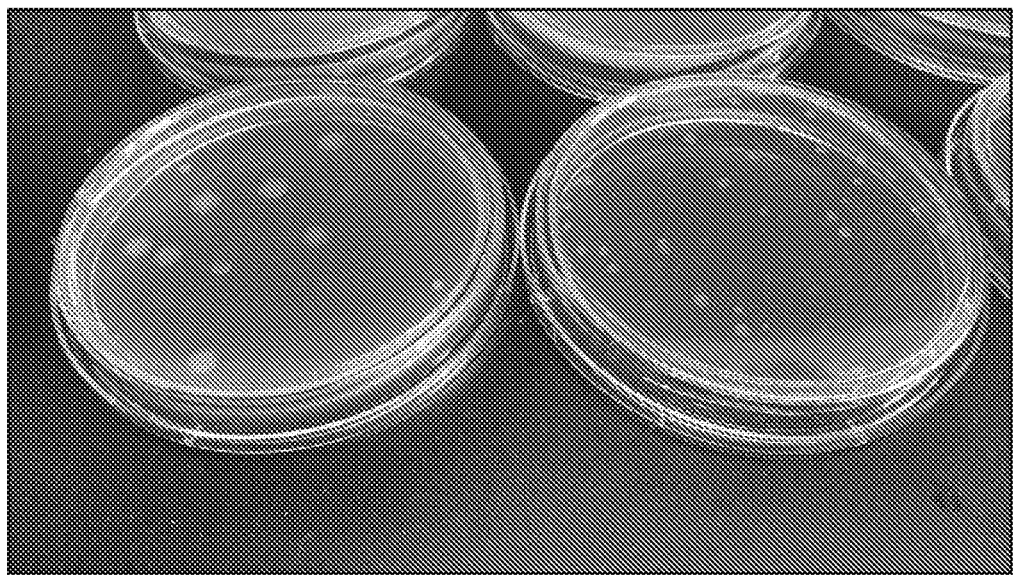
FIGS. 1A-B depict enrichment and isolation of nitrogen fixing bacteria. (A) Nfb agar plate was used to isolate single colonies of nitrogen fixing bacteria. (B) Semi-solid Nfb agar casted in Balch tube. The arrow points to pellicle of enriched nitrogen fixing bacteria.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Increased fertilizer utilization brings with it environmental concerns and is also likely not possible for many economically stressed regions of the globe. Furthermore, many industry players in the microbial arena are focused on creating intergeneric microbes. However, there is a heavy regulatory burden placed on engineered microbes that are characterized/classified as intergeneric. These intergeneric microbes face not only a higher regulatory burden, which makes widespread adoption and implementation difficult, but they also face a great deal of public perception scrutiny.

Currently, there are no engineered microbes on the market that are non-intergeneric and that are capable of increasing nitrogen fixation in non-leguminous crops. This dearth of such a microbe is a missing element in helping to usher in a truly environmentally friendly and more sustainable $21^{st}$ century agricultural system.

The present disclosure solves the aforementioned problems and provides a non-intergeneric microbe that has been engineered to readily fix nitrogen in crops. These microbes are not characterized/classified as intergeneric microbes and thus will not face the steep regulatory burdens of such. Further, the taught non-intergeneric microbes will serve to help $21^{st}$ century farmers become less dependent upon utilizing ever increasing amounts of exogenous nitrogen fertilizer.

Definitions

The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA (tRNA), ribosomal RNA (rRNA), short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

"Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner according to base complementarity. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the enzymatic cleavage of a polynucleotide by an endonuclease. A second sequence that is complementary to a first sequence is referred to as the "complement" of the first sequence. The term "hybridizable" as applied to a polynucleotide refers to the ability of the polynucleotide to form a complex that is stabilized via hydrogen bonding between the bases of the nucleotide residues in a hybridization reaction.

"Complementarity" refers to the ability of a nucleic acid to form hydrogen bond(s) with another nucleic acid sequence by either traditional Watson-Crick or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary, respectively). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions. Sequence identity, such as for the purpose of assessing percent complementarity, may be measured by any suitable alignment algorithm, including but not limited to the Needleman-Wunsch algorithm (see e.g. the EMBOSS Needle aligner available at www.ebi.ac.uk/Tools/psa/emboss_needle/nucleotide.html, optionally with default settings), the BLAST algorithm (see e.g. the BLAST alignment tool available at blast.ncbi.nlm.nih.gov/Blast.cgi, optionally with default settings), or the Smith-Waterman algorithm (see e.g. the EMBOSS Water aligner available at www.ebi.ac.uk/Tools/psa/emboss_water/nucleotide.html, optionally with default settings). Optimal alignment may be assessed using any suitable parameters of a chosen algorithm, including default parameters.

In general, "stringent conditions" for hybridization refer to conditions under which a nucleic acid having complementarity to a target sequence predominantly hybridizes with a target sequence, and substantially does not hybridize to non-target sequences. Stringent conditions are generally sequence-dependent and vary depending on a number of factors. In general, the longer the sequence, the higher the temperature at which the sequence specifically hybridizes to its target sequence. Non-limiting examples of stringent conditions are described in detail in Tijssen (1993), Laboratory Techniques In Biochemistry And Molecular Biology-Hybridization With Nucleic Acid Probes Part I, Second Chapter "Overview of principles of hybridization and the strategy of nucleic acid probe assay", Elsevier, N.Y.

As used herein, "expression" refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

The terms "polypeptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" includes natural and/or unnatural or synthetic amino acids, including glycine and both the D or L optical isomers, and amino acid analogs and peptidomimetics.

As used herein, the term "about" is used synonymously with the term "approximately." Illustratively, the use of the term "about" with regard to an amount indicates that values slightly outside the cited values, e.g., plus or minus 0.1% to 10%.

The term "biologically pure culture" or "substantially pure culture" refers to a culture of a bacterial species described herein containing no other bacterial species in quantities sufficient to interfere with the replication of the culture or be detected by normal bacteriological techniques.

"Plant productivity" refers generally to any aspect of growth or development of a plant that is a reason for which the plant is grown. For food crops, such as grains or vegetables, "plant productivity" can refer to the yield of grain or fruit harvested from a particular crop. As used herein, improved plant productivity refers broadly to improvements in yield of grain, fruit, flowers, or other plant parts harvested for various purposes, improvements in growth of plant parts, including stems, leaves and roots, promotion of plant growth, maintenance of high chlorophyll content in leaves, increasing fruit or seed numbers, increasing fruit or seed unit weight, reducing $NO_2$ emission due to reduced nitrogen fertilizer usage and similar improvements of the growth and development of plants.

Microbes in and around food crops can influence the traits of those crops. Plant traits that may be influenced by microbes include: yield (e.g., grain production, biomass generation, fruit development, flower set); nutrition (e.g., nitrogen, phosphorus, potassium, iron, micronutrient acquisition); abiotic stress management (e.g., drought tolerance, salt tolerance, heat tolerance); and biotic stress management (e.g., pest, weeds, insects, fungi, and bacteria). Strategies for altering crop traits include: increasing key metabolite concentrations; changing temporal dynamics of microbe influence on key metabolites; linking microbial metabolite production/degradation to new environmental cues; reducing negative metabolites; and improving the balance of metabolites or underlying proteins.

As used herein, a "control sequence" refers to an operator, promoter, silencer, or terminator.

As used herein, "in planta" refers to in the plant, and wherein the plant further comprises plant parts, tissue, leaves, roots, stems, seed, ovules, pollen, flowers, fruit, etc.

In some embodiments, native or endogenous control sequences of genes of the present disclosure are replaced with one or more intrageneric control sequences.

As used herein, "introduced" refers to the introduction by means of modern biotechnology, and not a naturally occurring introduction.

In some embodiments, the bacteria of the present disclosure have been modified such that they are not naturally occurring bacteria.

In some embodiments, the bacteria of the present disclosure are present in the plant in an amount of at least $10^3$ cfu, 10 cfu, 10 cfu, $10^6$ cfu, $10^7$ cfu, $10^8$ cfu, $10^9$ cfu, $10^{10}$ cfu, $10^{11}$ cfu, or $10^{12}$ cfu per gram of fresh or dry weight of the plant. In some embodiments, the bacteria of the present disclosure are present in the plant in an amount of at least about $10^3$ cfu, about $10^4$ cfu, about $10^5$ cfu, about $10^6$ cfu, about $10^7$ cfu, about $10^8$ cfu, about $10^9$ cfu, about $10^{10}$ cfu, about $10^{11}$ cfu, or about $10^{12}$ cfu per gram of fresh or dry weight of the plant. In some embodiments, the bacteria of the present disclosure are present in the plant in an amount of at least $10^3$ to $10^9$, $10^3$ to $10^7$, $10^3$ to $10^5$, $10^5$ to $10^9$, $10^5$ to $10^7$, $10^6$ to $10^{10}$, $10^6$ to $10^7$ cfu per gram of fresh or dry weight of the plant.

Fertilizers and exogenous nitrogen of the present disclosure may comprise the following nitrogen-containing molecules: ammonium, nitrate, nitrite, ammonia, glutamine, etc. Nitrogen sources of the present disclosure may include anhydrous ammonia, ammonia sulfate, urea, diammonium phosphate, urea-form, monoammonium phosphate, ammonium nitrate, nitrogen solutions, calcium nitrate, potassium nitrate, sodium nitrate, etc.

As used herein, "exogenous nitrogen" refers to non-atmospheric nitrogen readily available in the soil, field, or growth medium that is present under non-nitrogen limiting conditions, including ammonia, ammonium, nitrate, nitrite, urea, uric acid, ammonium acids, etc.

As used herein, "non-nitrogen limiting conditions" refers to non-atmospheric nitrogen available in the soil, field, media at concentrations greater than about 4 mM nitrogen, as disclosed by Kant el al. (2010. J. Exp. Biol. 62(4): 1499-1509), which is incorporated herein by reference.

As used herein, an "intergeneric microorganism" is a microorganism that is formed by the deliberate combination of genetic material originally isolated from organisms of different taxonomic genera. An "intergeneric mutant" can be used interchangeably with "intergeneric microorganism". An exemplary "intergeneric microorganism" includes a microorganism containing a mobile genetic element which was first identified in a microorganism in a genus different from the recipient microorganism. Further explanation can be found, inter alia, in 40 C.F.R. § 725.3.

In aspects, microbes taught herein are "non-intergeneric," which means that the microbes are not intergeneric.

As used herein, an "intrageneric microorganism" is a microorganism that is formed by the deliberate combination of genetic material originally isolated from organisms of the same taxonomic genera. An "intrageneric mutant" can be used interchangeably with "intrageneric microorganism".

As used herein, "introduced genetic material" means genetic material that is added to, and remains as a component of, the genome of the recipient.

In some embodiments, the nitrogen fixation and assimilation genetic regulatory network comprises polynucleotides encoding genes and non-coding sequences that direct, modulate, and/or regulate microbial nitrogen fixation and/or assimilation and can comprise polynucleotide sequences of the nif cluster (e.g., nifA, nifB, nifC, . . . , nifZ), polynucleotides encoding nitrogen regulatory protein C, polynucleotides encoding nitrogen regulatory protein B, polynucleotide sequences of the gin cluster (e.g., glnA and glnD), draT, and ammonia transporters/permeases. In some cases, the Nif cluster may comprise NifB, NifH, NifD, NifK, NifE, NifN, NifX, hesa, and NifV. In some cases, the Nif cluster may comprise a subset of NifB, NifH, NifD, NifK, NifE, NifN, NifX, hesa, and NifV.

In some embodiments, fertilizer of the present disclosure comprises at least 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% nitrogen by weight.

In some embodiments, fertilizer of the present disclosure comprises at least about 5%, about 6%, about 7%, about 8%, about 90%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% nitrogen by weight.

In some embodiments, fertilizer of the present disclosure comprises about 5% to 50%, about 5% to 75%, about 10% to 50%, about 10% to 75%, about 15% to 50%, about 15% to 75%, about 20% to 50%, about 20% to 75%, about 25% to 50%, about 25% to 75%, about 30% to 50%, about 30% to 75%, about 35% to 50%, about 35% to 75%, about 40% to 50%, about 40% to 75%, about 45% to 50%, about 45% to 75%, or about 50% to 75% nitrogen by weight.

In some embodiments, the increase of nitrogen fixation and/or the production of 1% or more of the nitrogen in the plant are measured relative to control plants, which have not been exposed to the bacteria of the present disclosure. All increases or decreases in bacteria are measured relative to control bacteria. All increases or decreases in plants are measured relative to control plants.

As used herein, a "constitutive promoter" is a promoter, which is active under most conditions and/or during most development stages. There are several advantages to using constitutive promoters in expression vectors used in biotechnology, such as: high level of production of proteins used to select transgenic cells or organisms; high level of expression of reporter proteins or scorable markers, allowing easy detection and quantification; high level of production of a transcription factor that is part of a regulatory transcription system; production of compounds that requires ubiquitous activity in the organism; and production of compounds that are required during all stages of development. Non-limiting exemplary constitutive promoters include, CaMV 35S promoter, opine promoters, ubiquitin promoter, alcohol dehydrogenase promoter, etc.

As used herein, a "non-constitutive promoter" is a promoter which is active under certain conditions, in certain types of cells, and/or during certain development stages. For example, tissue specific, tissue preferred, cell type specific, cell type preferred, inducible promoters, and promoters under development control are non-constitutive promoters. Examples of promoters under developmental control include promoters that preferentially initiate transcription in certain tissues.

As used herein, "inducible" or "repressible" promoter is a promoter which is under chemical or environmental factors control. Examples of environmental conditions that may affect transcription by inducible promoters include anaerobic conditions, certain chemicals, the presence of light, acidic or basic conditions, etc.

As used herein, a "tissue specific" promoter is a promoter that initiates transcription only in certain tissues. Unlike constitutive expression of genes, tissue-specific expression is the result of several interacting levels of gene regulation. As such, in the art sometimes it is preferable to use promoters from homologous or closely related species to achieve efficient and reliable expression of transgenes in particular tissues. This is one of the main reasons for the large amount of tissue-specific promoters isolated from particular tissues found in both scientific and patent literature.

As used herein, the term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation. In another example, the complementary RNA regions of the disclosure can be operably linked, either directly or indirectly, 5' to the target mRNA, or 3' to the target mRNA, or within the target mRNA, or a first complementary region is 5' and its complement is 3' to the target mRNA.

In aspects, "applying to the plant a plurality of non-intergeneric bacteria," includes any means by which the plant (including plant parts such as a seed, root, stem, tissue, etc.) is made to come into contact (i.e. exposed) with said bacteria at any stage of the plant's life cycle. Consequently, "applying to the plant a plurality of non-intergeneric bacteria," includes any of the following means of exposing the plant (including plant parts such as a seed, root, stem, tissue, etc.) to said bacteria: spraying onto plant, dripping onto plant, applying as a seed coat, applying to a field that will then be planted with seed, applying to a field already planted with seed, applying to a field with adult plants, etc.

As used herein "MRTN" is an acronym for maximum return to nitrogen and is utilized as an experimental treatment in the Examples. MRTN was developed by Iowa State University and information can be found at: http://cnrc.agron.iastate.edu/ The MRTN is the nitrogen rate where the economic net return to nitrogen application is maximized. The approach to calculating the MRTN is a regional approach for developing corn nitrogen rate guidelines in individual states. The nitrogen rate trial data was evaluated for Illinois, Iowa, Michigan, Minnesota, Ohio, and Wisconsin where an adequate number of research trials were available for corn plantings following soybean and corn plantings following corn. The trials were conducted with spring, sidedress, or split preplant/sidedress applied nitrogen, and sites were not irrigated except for those that were indicated for irrigated sands in Wisconsin. MRTN was developed by Iowa State University due to apparent differences in methods for determining suggested nitrogen rates required for corn production, misperceptions pertaining to nitrogen rate guidelines, and concerns about application rates. By calculating the MRTN, practitioners can determine the following: (1) the nitrogen rate where the economic net return to nitrogen application is maximized, (2) the economic optimum nitrogen rate, which is the point where the last increment of nitrogen returns a yield increase large enough to pay for the additional nitrogen, (3) the value of corn grain increase attributed to nitrogen application, and the maximum yield, which is the yield where application of more nitrogen does not result in a corn yield increase. Thus the MRTN calculations provide practitioners with the means to maximize corn crops in different regions while maximizing financial gains from nitrogen applications.

The term mmol is an abbreviation for millimole, which is a thousandth ($10^{-3}$) of a mole, abbreviated herein as mol.

As used herein the terms "microorganism" or "microbe" should be taken broadly. These terms, used interchangeably, include but are not limited to, the two prokaryotic domains, Bacteria and Archaea. The term may also encompass eukaryotic fungi and protists.

The term "microbial consortia" or "microbial consortium" refers to a subset of a microbial community of individual microbial species, or strains of a species, which can be described as carrying out a common function, or can be described as participating in, or leading to, or correlating with, a recognizable parameter, such as a phenotypic trait of interest.

The term "microbial community" means a group of microbes comprising two or more species or strains. Unlike microbial consortia, a microbial community does not have to be carrying out a common function, or does not have to be participating in, or leading to, or correlating with, a recognizable parameter, such as a phenotypic trait of interest.

As used herein, "isolate," "isolated," "isolated microbe," and like terms, are intended to mean that the one or more microorganisms has been separated from at least one of the materials with which it is associated in a particular environment (for example soil, water, plant tissue, etc.). Thus, an "isolated microbe" does not exist in its naturally occurring environment, rather, it is through the various techniques described herein that the microbe has been removed from its natural setting and placed into a non-naturally occurring state of existence. Thus, the isolated strain or isolated microbe may exist as, for example, a biologically pure culture, or as spores (or other forms of the strain). In aspects, the isolated microbe may be in association with an acceptable carrier, which may be an agriculturally acceptable carrier.

In certain aspects of the disclosure, the isolated microbes exist as "isolated and biologically pure cultures." It will be appreciated by one of skill in the art, that an isolated and biologically pure culture of a particular microbe, denotes that said culture is substantially free of other living organisms and contains only the individual microbe in question. The culture can contain varying concentrations of said microbe. The present disclosure notes that isolated and biologically pure microbes often "necessarily differ from less pure or impure materials." See. e.g. In re *Bergstrom*, 427 F.2d 1394, (CCPA 1970)(discussing purified prostaglandins), see also, In re *Bergy*, 596 F.2d 952 (CCPA 1979)

(discussing purified microbes), see also, *Parke-Davis & Co. v. H.K. Mulford & Co.*, 189 F. 95 (S.D.N.Y. 1911) (Learned Hand discussing purified adrenaline), aff'd in part, rev'd in part, 196 F. 496 (2d Cir. 1912), each of which are incorporated herein by reference. Furthermore, in some aspects, the disclosure provides for certain quantitative measures of the concentration, or purity limitations, that must be found within an isolated and biologically pure microbial culture. The presence of these purity values, in certain embodiments, is a further attribute that distinguishes the presently disclosed microbes from those microbes existing in a natural state. See, e.g., *Merck & Co. v. Olin Mathieson Chemical Corp.*, 253 F.2d 156 (4th Cir. 1958) (discussing purity limitations for vitamin B12 produced by microbes), incorporated herein by reference.

As used herein, "individual isolates" should be taken to mean a composition, or culture, comprising a predominance of a single genera, species, or strain, of microorganism, following separation from one or more other microorganisms.

Microbes of the present disclosure may include spores and/or vegetative cells. In some embodiments, microbes of the present disclosure include microbes in a viable but non-culturable (VBNC) state. As used herein, "spore" or "spores" refer to structures produced by bacteria and fungi that are adapted for survival and dispersal. Spores are generally characterized as dormant structures; however, spores are capable of differentiation through the process of germination. Germination is the differentiation of spores into vegetative cells that are capable of metabolic activity, growth, and reproduction. The germination of a single spore results in a single fungal or bacterial vegetative cell. Fungal spores are units of asexual reproduction, and in some cases are necessary structures in fungal life cycles. Bacterial spores are structures for surviving conditions that may ordinarily be nonconducive to the survival or growth of vegetative cells.

As used herein, "microbial composition" refers to a composition comprising one or more microbes of the present disclosure. In some embodiments, a microbial composition is administered to plants (including various plant parts) and/or in agricultural fields.

As used herein, "carrier," "acceptable carrier," or "agriculturally acceptable carrier" refers to a diluent, adjuvant, excipient, or vehicle with which the microbe can be administered, which does not detrimentally effect the microbe.

Regulation of Nitrogen Fixation

In some cases, nitrogen fixation pathway may act as a target for genetic engineering and optimization. One trait that may be targeted for regulation by the methods described herein is nitrogen fixation. Nitrogen fertilizer is the largest operational expense on a farm and the biggest driver of higher yields in row crops like corn and wheat. Described herein are microbial products that can deliver renewable forms of nitrogen in non-leguminous crops. While some endophytes have the genetics necessary for fixing nitrogen in pure culture, the fundamental technical challenge is that wild-type endophytes of cereals and grasses stop fixing nitrogen in fertilized fields. The application of chemical fertilizers and residual nitrogen levels in field soils signal the microbe to shut down the biochemical pathway for nitrogen fixation.

Changes to the transcriptional and post-translational levels of components of the nitrogen fixation regulatory network may be beneficial to the development of a microbe capable of fixing and transferring nitrogen to corn in the presence of fertilizer. To that end, described herein is Host-Microbe Evolution (HoME) technology to precisely evolve regulatory networks and elicit novel phenotypes. Also described herein are unique, proprietary libraries of nitrogen-fixing endophytes isolated from corn, paired with extensive omics data surrounding the interaction of microbes and host plant under different environmental conditions like nitrogen stress and excess. In some embodiments, this technology enables precision evolution of the genetic regulatory network of endophytes to produce microbes that actively fix nitrogen even in the presence of fertilizer in the field. Also described herein are evaluations of the technical potential of evolving microbes that colonize corn root tissues and produce nitrogen for fertilized plants and evaluations of the compatibility of endophytes with standard formulation practices and diverse soils to determine feasibility of integrating the microbes into modern nitrogen management strategies.

In order to utilize elemental nitrogen (N) for chemical synthesis, life forms combine nitrogen gas ($N_2$) available in the atmosphere with hydrogen in a process known as nitrogen fixation. Because of the energy-intensive nature of biological nitrogen fixation, diazotrophs (bacteria and archaea that fix atmospheric nitrogen gas) have evolved sophisticated and tight regulation of the nif gene cluster in response to environmental oxygen and available nitrogen. Nif genes encode enzymes involved in nitrogen fixation (such as the nitrogenase complex) and proteins that regulate nitrogen fixation. Shamseldin (2013. Global J. Biotechnol. Biochem. 8(4):84-94) discloses detailed descriptions of nif genes and their products, and is incorporated herein by reference. Described herein are methods of producing a plant with an improved trait comprising isolating bacteria from a first plant, introducing a genetic variation into a gene of the isolated bacteria to increase nitrogen fixation, exposing a second plant to the variant bacteria, isolating bacteria from the second plant having an improved trait relative to the first plant, and repeating the steps with bacteria isolated from the second plant.

In Proteobacteria, regulation of nitrogen fixation centers around the $\sigma_{54}$-dependent enhancer-binding protein NifA, the positive transcriptional regulator of the nif cluster. Intracellular levels of active NifA are controlled by two key factors: transcription of the nifLA operon, and inhibition of NifA activity by protein-protein interaction with NifL. Both of these processes are responsive to intracelluar glutamine levels via the PII protein signaling cascade. This cascade is mediated by GlnD, which directly senses glutamine and catalyzes the uridylylation or deuridylylation of two PII regulatory proteins—GlnB and GlnK—in response the absence or presence, respectively, of bound glutamine. Under conditions of nitrogen excess, unmodified GlnB signals the deactivation of the nifLA promoter. However, under conditions of nitrogen limitation, GlnB is post-translationally modified, which inhibits its activity and leads to transcription of the nifLA operon. In this way, nifLA transcription is tightly controlled in response to environmental nitrogen via the PII protein signaling cascade. On the post-translational level of NifA regulation, GlnK inhibits the NifL/NifA interaction in a matter dependent on the overall level of free GlnK within the cell.

NifA is transcribed from the nifLA operon, whose promoter is activated by phosphorylated NtrC, another $\sigma_{54}$-dependent regulator. The phosphorylation state of NtrC is mediated by the histidine kinase NtrB, which interacts with deuridylylated GlnB but not uridylylated GlnB. Under conditions of nitrogen excess, a high intracellular level of glutamine leads to deuridylylation of GlnB, which then interacts with NtrB to deactivate its phosphorylation activity and activate its phosphatase activity, resulting in dephosphorylation of NtrC and the deactivation of the nifLA promoter. However, under conditions of nitrogen limitation, a low level of intracellular glutamine results in uridylylation of GlnB, which inhibits its interaction with NtrB and allows the phosphorylation of NtrC and transcription of the nifLA operon. In this way, nifLA expression is tightly controlled in response to environmental nitrogen via the PII protein signaling cascade, nifA, ntrB, ntrC, and glnB, are all genes that can be mutated in the methods described herein. These processes may also be responsive to intracellular or extracellular levels of ammonia, urea or nitrates.

The activity of NifA is also regulated post-translationally in response to environmental nitrogen, most typically through NifL-mediated inhibition of NifA activity. In general, the interaction of NifL and NifA is influenced by the PII protein signaling cascade via GlnK, although the nature of the interactions between GlnK and NifL/NifA varies significantly between diazotrophs. In *Klebsiella pneumoniae*, both forms of GlnK inhibit the NifL/NifA interaction, and the interaction between GlnK and NifL/NifA is determined by the overall level of free GlnK within the cell. Under nitrogen-excess conditions, deuridylylated GlnK interacts with the ammonium transporter AmtB, which serves to both block ammonium uptake by AmtB and sequester GlnK to the membrane, allowing inhibition of NifA by NifL. On the other hand, in *Azotobacter vinelandii*, interaction with deuridylylated GlnK is required for the NifL/NifA interaction and NifA inhibition, while uridylylation of GlnK inhibits its interaction with NifL. In diazotrophs lacking the nifL gene, there is evidence that NifA activity is inhibited directly by interaction with the deuridylylated forms of both GlnK and GlnB under nitrogen-excess conditions. In some bacteria the Nif cluster may be regulated by glnR, and further in some cases this may comprise negative regulation. Regardless of the mechanism, post-translational inhibition of NifA is an important regulator of the if cluster in most known diazotrophs. Additionally, nifL, amtB, glnK, and glnR are genes that can be mutated in the methods described herein.

In addition to regulating the transcription of the nif gene cluster, many diazotrophs have evolved a mechanism for the direct post-translational modification and inhibition of the nitrogenase enzyme itself, known as nitrogenase shutoff. This is mediated by ADP-ribosylation of the Fe protein (NifH) under nitrogen-excess conditions, which disrupts its interaction with the MoFe protein complex (NifDK) and abolishes nitrogenase activity. DraT catalyzes the ADP-ribosylation of the Fe protein and shutoff of nitrogenase, while DraG catalyzes the removal of ADP-ribose and reactivation of nitrogenase. As with nifLA transcription and NifA inhibition, nitrogenase shutoff is also regulated via the PII protein signaling cascade. Under nitrogen-excess conditions, deuridylylated GlnB interacts with and activates DraT, while deuridylylated GlnK interacts with both DraG and AmtB to form a complex, sequestering DraG to the membrane. Under nitrogen-limiting conditions, the uridylylated forms of GlnB and GlnK do not interact with DraT and DraG, respectively, leading to the inactivation of DraT and the diffusion of DraG to the Fe protein, where it removes the ADP-ribose and activates nitrogenase. The methods described herein also contemplate introducing genetic variation into the nifH, nifD, nifK, and draT genes.

Although some endophytes have the ability to fix nitrogen in vitro, often the genetics are silenced in the field by high levels of exogenous chemical fertilizers. One can decouple the sensing of exogenous nitrogen from expression of the nitrogenase enzyme to facilitate field-based nitrogen fixation. Improving the integral of nitrogenase activity across time further serves to augment the production of nitrogen for utilization by the crop. Specific targets for genetic variation to facilitate field-based nitrogen fixation using the methods described herein include one or more genes selected from the group consisting of nifA, nifL, ntrB, ntrC glnA, glnB, glnK, draT, amtB, glnD, glnE, nifJ, nifH, nifD, nifK, nifY, nifE, nifN, nifU, nifS, nifV, nifW, nifZ, nifM, nifF, nifB, and nifQ.

An additional target for genetic variation to facilitate field-based nitrogen fixation using the methods described herein is the NifA protein. The NifA protein is typically the activator for expression of nitrogen fixation genes. Increasing the production of NifA (either constitutively or during high ammonia condition) circumvents the native ammonia-sensing pathway. In addition, reducing the production of NifL proteins, a known inhibitor of NifA, also leads to an increased level of freely active NifA. In addition, increasing the transcription level of the nifAL operon (either constitutively or during high ammonia condition) also leads to an overall higher level of NifA proteins. Elevated level of nifAL expression is achieved by altering the promoter itself or by reducing the expression of NtrB (part of ntrB and ntrC signaling cascade that originally would result in the shutoff of nifAL operon during high nitrogen condition). High level of NifA achieved by these or any other methods described herein increases the nitrogen fixation activity of the endophytes.

Another target for genetic variation to facilitate field-based nitrogen fixation using the methods described herein is the GlnD/GlnB/GlnK PII signaling cascade. The intracellular glutamine level is sensed through the GlnD/GlnB/GlnK PII signaling cascade. Active site mutations in GlnD that abolish the uridylyl-removing activity of GlnD disrupt the nitrogen-sensing cascade. In addition, reduction of the GlnB concentration short circuits the glutamine-sensing cascade. These mutations "trick" the cells into perceiving a nitrogen-limited state, thereby increasing the nitrogen fixation level activity. These processes may also be responsive to intracellular or extracellular levels of ammonia, urea or nitrates.

The amtB protein is also a target for genetic variation to facilitate field-based nitrogen fixation using the methods described herein. Ammonia uptake from the environment can be reduced by decreasing the expression level of amtB protein. Without intracellular ammonia, the endophyte is not able to sense the high level of ammonia, preventing the down-regulation of nitrogen fixation genes. Any ammonia that manages to get into the intracellular compartment is converted into glutamine. Intracellular glutamine level is the major currency of nitrogen sensing. Decreasing the intracellular glutamine level prevents the cells from sensing high ammonium levels in the environment. This effect can be achieved by increasing the expression level of glutaminase, an enzyme that converts glutamine into glutamate. In addition, intracellular glutamine can also be reduced by decreasing glutamine synthase (an enzyme that converts ammonia into glutamine). In diazotrophs, fixed ammonia is quickly assimilated into glutamine and glutamate to be used for cellular processes. Disruptions to ammonia assimilation may enable diversion of fixed nitrogen to be exported from the cell as ammonia. The fixed ammonia is predominantly assimilated into glutamine by glutamine synthetase (GS), encoded by glnA, and subsequently into glutamine by glutamine oxoglutarate aminotransferase (GOGAT). In some examples, glnS encodes a glutamine synthetase. GS is regulated post-translationally by GS adenylyl transferase (GlnE), a bi-functional enzyme encoded by glnE that catalyzes both the adenylylation and deadenylylation of GS through activity of its adenylyl-transferase (AT) and adenylyl-removing (AR) domains, respectively. Under nitrogen limiting conditions, glnA is expressed, and GlnE's AR domain de-adynylylates GS, allowing it to be active. Under conditions of nitrogen excess, glnA expression is turned off, and GlnE's AT domain is activated allosterically by glutamine, causing the adenylylation and deactivation of GS.

Furthermore, the draT gene may also be a target for genetic variation to facilitate field-based nitrogen fixation using the methods described herein. Once nitrogen fixing enzymes are produced by the cell, nitrogenase shut-off represents another level in which cell downregulates fixation activity in high nitrogen condition. This shut-off could be removed by decreasing the expression level of DraT.

Methods for imparting new microbial phenotypes can be performed at the transcriptional, translational, and post-translational levels. The transcriptional level includes changes at the promoter (such as changing sigma factor affinity or binding sites for transcription factors, including deletion of all or a portion of the promoter) or changing transcription terminators and attenuators. The translational level includes changes at the ribosome binding sites and changing mRNA degradation signals. The post-translational level includes mutating an enzyme's active site and changing protein-protein interactions. These changes can be achieved in a multitude of ways. Reduction of expression level (or complete abolishment) can be achieved by swapping the native ribosome binding site (RBS) or promoter with another with lower strength/efficiency. ATG start sites can be swapped to a GTG, TTG, or CTG start codon, which results in reduction in translational activity of the coding region. Complete abolishment of expression can be done by knocking out (deleting) the coding region of a gene. Frame-shifting the open reading frame (ORF) likely will result in a premature stop codon along the ORF, thereby creating a non-functional truncated product. Insertion of in-frame stop codons will also similarly create a non-functional truncated product. Addition of a degradation tag at the N or C terminal can also be done to reduce the effective concentration of a particular gene.

Conversely, expression level of the genes described herein can be achieved by using a stronger promoter. To ensure high promoter activity during high nitrogen level condition (or any other condition), a transcription profile of the whole genome in a high nitrogen level condition could be obtained and active promoters with a desired transcription level can be chosen from that dataset to replace the weak promoter. Weak start codons can be swapped out with an ATG start codon for better translation initiation efficiency. Weak ribosomal binding sites (RBS) can also be swapped out with a different RBS with higher translation initiation efficiency. In addition, site specific mutagenesis can also be performed to alter the activity of an enzyme.

Increasing the level of nitrogen fixation that occurs in a plant can lead to a reduction in the amount of chemical fertilizer needed for crop production and reduce greenhouse gas emissions (e.g., nitrous oxide).

Generation of Bacterial Populations
Isolation of Bacteria

Microbes useful in methods and compositions disclosed herein can be obtained by extracting microbes from surfaces or tissues of native plants. Microbes can be obtained by grinding seeds to isolate microbes. Microbes can be obtained by planting seeds in diverse soil samples and recovering microbes from tissues. Additionally, microbes can be obtained by inoculating plants with exogenous microbes and determining which microbes appear in plant tissues. Non-limiting examples of plant tissues may include a seed, seedling, leaf, cutting, plant, bulb, or tuber.

A method of obtaining microbes may be through the isolation of bacteria from soils. Bacteria may be collected from various soil types. In some example, the soil can be characterized by traits such as high or low fertility, levels of moisture, levels of minerals, and various cropping practices. For example, the soil may be involved in a crop rotation where different crops are planted in the same soil in successive planting seasons. The sequential growth of different crops on the same soil may prevent disproportionate depletion of certain minerals. The bacteria can be isolated from the plants growing in the selected soils. The seedling plants can be harvested at 2-6 weeks of growth. For example, at least 400 isolates can be collected in a round of harvest. Soil and plant types reveal the plant phenotype as well as the conditions, which allow for the downstream enrichment of certain phenotypes.

Microbes can be isolated from plant tissues to assess microbial traits. The parameters for processing tissue samples may be varied to isolate different types of associative microbes, such as rhizopheric bacteria, epiphytes, or endophytes. The isolates can be cultured in nitrogen-free media to enrich for bacteria that perform nitrogen fixation. Alternatively, microbes can be obtained from global strain banks.

In planta analytics are performed to assess microbial traits. In some embodiments, the plant tissue can be processed for screening by high throughput processing for DNA and RNA. Additionally, non-invasive measurements can be used to assess plant characteristics, such as colonization. Measurements on wild microbes can be obtained on a plant-by-plant basis. Measurements on wild microbes can also be obtained in the field using medium throughput methods. Measurements can be done successively over time. Model plant system can be used including, but not limited to, *Setaria*.

Microbes in a plant system can be screened via transcriptional profiling of a microbe in a plant system. Examples of screening through transcriptional profiling are using methods of quantitative polymerase chain reaction (qPCR), molecular barcodes for transcript detection, Next Generation Sequencing, and microbe tagging with fluorescent markers. Impact factors can be measured to assess colonization in the greenhouse including, but not limited to, microbiome, abiotic factors, soil conditions, oxygen, moisture, temperature, inoculum conditions, and root localization. Nitrogen fixation can be assessed in bacteria by measuring 15N gas/fertilizer (dilution) with IRMS or NanoSIMS as described herein NanoSIMS is high-resolution secondary ion mass spectrometry. The NanoSIMS technique is a way to investigate chemical activity from biological samples. The catalysis of reduction of oxidation reactions that drive the metabolism of microorganisms can be investigated at the cellular, subcellular, molecular and elemental level. NanoSIMS can provide high spatial resolution of greater than 0.1 μm. NanoSIMS can detect the use of isotope tracers such as $^{13}C$, $^{15}N$, and $^{18}O$. Therefore, NanoSIMS can be used to the chemical activity nitrogen in the cell.

Automated greenhouses can be used for planta analytics. Plant metrics in response to microbial exposure include, but are not limited to, biomass, chloroplast analysis, CCD camera, volumetric tomography measurements.

One way of enriching a microbe population is according to genotype. For example, a polymerase chain reaction (PCR) assay with a targeted primer or specific primer. Primers designed for the nifH gene can be used to identity diazotrophs because diazotrophs express the nifH gene in the process of nitrogen fixation. A microbial population can also be enriched via single-cell culture-independent approaches and chemotaxis-guided isolation approaches. Alternatively, targeted isolation of microbes can be performed by culturing the microbes on selection media. Premeditated approaches to enriching microbial populations for desired traits can be guided by bioinformatics data and are described herein.

Enriching for Microbes with Nitrogen Fixation Capabilities Using Bioinformatics

Bioinformatic tools can be used to identify and isolate plant growth promoting *rhizobacteria* (PGPRs), which are selected based on their ability to perform nitrogen fixation. Microbes with high nitrogen fixing ability can promote favorable traits in plants. Bioinformatic modes of analysis for the identification of PGPRs include, but are not limited to, genomics, metagenomics, targeted isolation, gene sequencing, transcriptome sequencing, and modeling.

Genomics analysis can be used to identify PGPRs and confirm the presence of mutations with methods of Next Generation Sequencing as described herein and microbe version control.

Metagenomics can be used to identify and isolate PGPR using a prediction algorithm for colonization. Metadata can also be used to identify the presence of an engineered strain in environmental and greenhouse samples.

Transcriptomic sequencing can be used to predict genotypes leading to PGPR phenotypes. Additionally, transcriptomic data is used to identify promoters for altering gene expression. Transcriptomic data can be analyzed in conjunction with the Whole Genome Sequence (WGS) to generate models of metabolism and gene regulatory networks.

Domestication of Microbes

Microbes isolated from nature can undergo a domestication process wherein the microbes are converted to a form that is genetically trackable and identifiable. One way to domesticate a microbe is to engineer it with antibiotic resistance. The process of engineering antibiotic resistance can begin by determining the antibiotic sensitivity in the wild type microbial strain. If the bacteria are sensitive to the antibiotic, then the antibiotic can be a good candidate for antibiotic resistance engineering. Subsequently, an antibiotic resistant gene or a counterselectable suicide vector can be incorporated into the genome of a microbe using recombineering methods. A counterselectable suicide vector may consist of a deletion of the gene of interest, a selectable marker, and the counterselectable marker sacB. Counterselection can be used to exchange native microbial DNA sequences with antibiotic resistant genes. A medium throughput method can be used to evaluate multiple microbes simultaneously allowing for parallel domestication. Alternative methods of domestication include the use of homing nucleases to prevent the suicide vector sequences from looping out or from obtaining intervening vector sequences.

DNA vectors can be introduced into bacteria via several methods including electroporation and chemical transformations. A standard library of vectors can be used for transformations. An example of a method of gene editing is CRISPR preceded by Cas9 testing to ensure activity of Cas9 in the microbes.

Non-Transgenic Engineering of Microbes

A microbial population with favorable traits can be obtained via directed evolution. Direct evolution is an approach wherein the process of natural selection is mimicked to evolve proteins or nucleic acids towards a user-defined goal. An example of direct evolution is when random mutations are introduced into a microbial population, the microbes with the most favorable traits are selected, and the growth of the selected microbes is continued. The most favorable traits in growth promoting *rhizobacteria* (PGPRs) may be in nitrogen fixation. The method of directed evolution may be iterative and adaptive based on the selection process after each iteration.

Plant growth promoting *rhizobacteria* (PGPRs) with high capability of nitrogen fixation can be generated. The evolution of PGPRs can be carried out via the introduction of genetic variation. Genetic variation can be introduced via polymerase chain reaction mutagenesis, oligonucleotide-directed mutagenesis, saturation mutagenesis, fragment shuffling mutagenesis, homologous recombination, CRISPR/Cas9 systems, chemical mutagenesis, and combinations thereof. These approaches can introduce random mutations into the microbial population. For example, mutants can be generated using synthetic DNA or RNA via oligonucleotide-directed mutagenesis. Mutants can be generated using tools contained on plasmids, which are later cured. Genes of interest can be identified using libraries from other species with improved traits including, but not limited to, improved PGPR properties, improved colonization of cereals, increased oxygen sensitivity, increased nitrogen fixation, and increased ammonia excretion. Intrageneric genes can be designed based on these libraries using software such as Geneious or Platypus design software. Mutations can be designed with the aid of machine learning. Mutations can be designed with the aid of a metabolic model. Automated design of the mutation can be done using a la Platypus and will guide RNAs for Cas-directed mutagenesis.

The intra-generic genes can be transferred into the host microbe. Additionally, reporter systems can also be transferred to the microbe. The reporter systems characterize promoters, determine the transformation success, screen mutants, and act as negative screening tools.

The microbes carrying the mutation can be cultured via serial passaging. A microbial colony contains a single variant of the microbe. Microbial colonies are screened with the aid of an automated colony picker and liquid handler. Mutants with gene duplication and increased copy number express a higher genotype of the desired trait.

Selection of Plant Growth Promoting Microbess Based on Nitrogen Fixation

The microbial colonies can be screened using various assays to assess nitrogen fixation. One way to measure nitrogen fixation is via a single fermentative assay, which measures nitrogen excretion. An alternative method is the acetylene reduction assay (ARA) with in-line sampling over time. ARA can be performed in high throughput plates of microtube arrays. ARA can be performed with live plants and plant tissues. The media formulation and media oxygen concentration can be varied in ARA assays. Another method of screening microbial variants is by using biosensors. The use of NanoSIMS and Raman microspectroscopy can be used to investigate the activity of the microbes. In some cases, bacteria can also be cultured and expanded using methods of fermentation in bioreactors. The bioreactors are designed to improve robustness of bacteria growth and to decrease the sensitivity of bacteria to oxygen. Medium to high TP plate-based microfermentors are used to evaluate oxygen sensitivity, nutritional needs, nitrogen fixation, and nitrogen excretion. The bacteria can also be co-cultured with competitive or beneficial microbes to elucidate cryptic pathways. Flow cytometry can be used to screen for bacteria that produce high levels of nitrogen using chemical, colorimetric, or fluorescent indicators. The bacteria may be cultured in the presence or absence of a nitrogen source. For example, the bacteria may be cultured with glutamine, ammonia, urea or nitrates.

Microbe Breeding

Figure 17A:
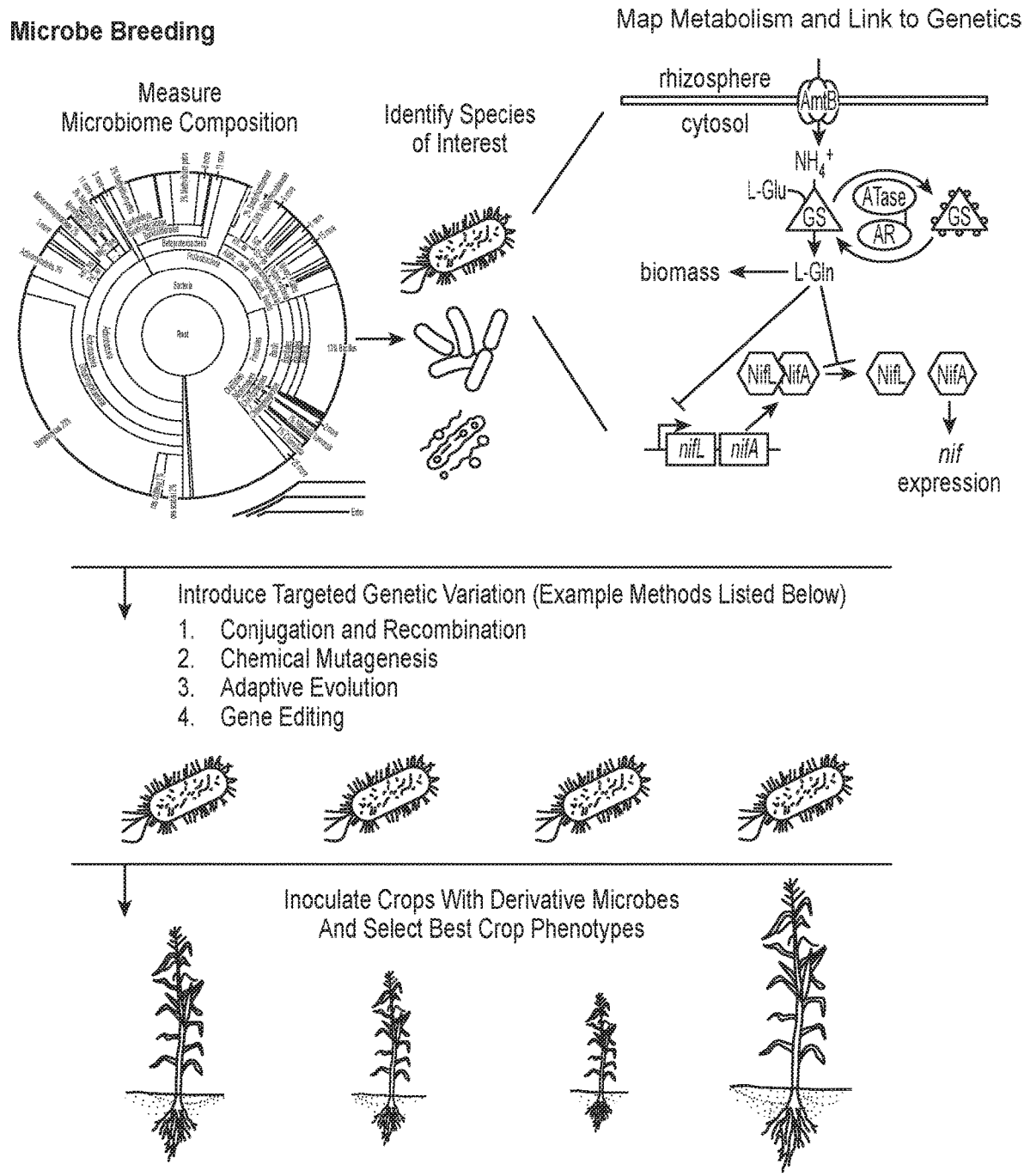
FIG. 17A depicts a schematic of microbe breeding, in accordance with embodiments.

Microbe breeding is a method to systematically identify and improve the role of species within the crop microbiome. The method comprises three steps: 1) selection of candidate species by mapping plant-microbe interactions and predicting regulatory networks linked to a particular phenotype, 2) pragmatic and predictable improvement of microbial phenotypes through intra-species crossing of regulatory networks and gene clusters, and 3) screening and selection of new microbial genotypes that produce desired crop phenotypes. To systematically assess the improvement of strains, a model is created that links colonization dynamics of the microbial community to genetic activity by key species. The model is used to predict genetic targets breeding and improve the frequency of selecting improvements in microbiome-encoded traits of agronomic relevance. See, FIG. 17A for a graphical representation of an embodiment of the process. In particular, FIG. 17A depicts a schematic of microbe breeding, in accordance with embodiments. As illustrated in FIG. 17A, rational improvement of the crop microbiome may be used to increase soil biodiversity, tune impact of keystone species, and/or alter timing and expression of important metabolic pathways. To this end, the inventors have developed a microbe breeding pipeline to identify and improve the role of strains within the crop microbiome. The method comprises three steps: i) selection of candidate species by mapping plant-microbe interactions and predicting regulatory networks linked to a particular phenotype, 2) pragmatic and predictable improvement of microbial phenotypes through intragenomic crossing of gene regulatory networks and gene clusters, and 3) screening and selection of new microbial genotypes that produce desired crop phenotypes. To systematically assess the improvement of strains, the inventors employ a model that links colonization dynamics of the microbial community to genetic activity by key species. This process represents a methodology for breeding and selecting improvements in microbiome-encoded traits of agronomic relevance.

Production of bacteria to improve plant traits (e.g., nitrogen fixation) can be achieved through serial passage. The production of this bacteria can be done by selecting plants, which have a particular improved trait that is influenced by the microbial flora, in addition to identifying bacteria and/or compositions that are capable of imparting one or more improved traits to one or more plants. One method of producing a bacteria to improve a plant trait includes the steps of: (a) isolating bacteria from tissue or soil of a first plant; (b) introducing a genetic variation into one or more of the bacteria to produce one or more variant bacteria; (c) exposing a plurality of plants to the variant bacteria; (d) isolating bacteria from tissue or soil of one of the plurality of plants, wherein the plant from which the bacteria is isolated has an improved trait relative to other plants in the plurality of plants; and (e) repeating steps (b) to (d) with bacteria isolated from the plant with an improved trait (step (d)). Steps (b) to (d) can be repeated any number of times (e.g., once, twice, three times, four times, five times, ten times, or more) until the improved trait in a plant reaches a desired level. Further, the plurality of plants can be more than two plants, such as 10 to 20 plants, or 20 or more, 50 or more, 100 or more, 300 or more, 500 or more, or 1000 or more plants.

In addition to obtaining a plant with an improved trait, a bacterial population comprising bacteria comprising one or more genetic variations introduced into one or more genes (e.g., genes regulating nitrogen fixation) is obtained. By repeating the steps described above, a population of bacteria can be obtained that include the most appropriate members of the population that correlate with a plant trait of interest. The bacteria in this population can be identified and their beneficial properties determined, such as by genetic and/or phenotypic analysis. Genetic analysis may occur of isolated bacteria in step (a). Phenotypic and/or genotypic information may be obtained using techniques including: high through-put screening of chemical components of plant origin, sequencing techniques including high throughput sequencing of genetic material, differential display techniques (including DDRT-PCR, and DD-PCR), nucleic acid microarray techniques, RNA-sequencing (Whole Transcriptome Shotgun Sequencing), and qRT-PCR (quantitative real time PCR). Information gained can be used to obtain community profiling information on the identity and activity of bacteria present, such as phylogenetic analysis or microarray-based screening of nucleic acids coding for components of rRNA operons or other taxonomically informative loci. Examples of taxonomically informative loci include 16S rRNA gene, 23S rRNA gene, 5S rRNA gene, 5.8S rRNA gene, 12S rRNA gene, 18S rRNA gene, 28S rRNA gene, gyrB gene, rpoB gene, fusA gene, recA gene, coxl gene, nifD gene. Example processes of taxonomic profiling to determine taxa present in a population are described in US20140155283. Bacterial identification may comprise characterizing activity of one or more genes or one or more signaling pathways, such as genes associated with the nitrogen fixation pathway. Synergistic interactions (where two components, by virtue of their combination, increase a desired effect by more than an additive amount) between different bacterial species may also be present in the bacterial populations.

Genetic Variation—Locations and Sources of Genomic Alteration

The genetic variation may be a gene selected from the group consisting of: nifA, nifL, ntrB, ntrC, glnA, glnB, glnK, draT, amtB, glnD, glnE, nifJ, nifH, nifD, nifK, nifY, nifE, nifN, nifU, nifS, nifV, nifW, nifZ, nifM, nifF, nifB, and nifQ. The genetic variation may be a variation in a gene encoding a protein with functionality selected from the group consisting of: glutamine synthetase, glutaminase, glutamine synthetase adenylyltransferase, transcriptional activator, anti-transcriptional activator, pyruvate flavodoxin oxidoreductase, flavodoxin, or NAD+-dinitrogen-reductase aDP-D-ribosyltransferase. The genetic variation may be a mutation that results in one or more of: increased expression or activity of NifA or glutaminase; decreased expression or activity of NifL, NtrB, glutamine synthetase, GlnB, GlnK, DraT, AmtB; decreased adenylyl-removing activity of GlnE; or decreased uridylyl-removing activity of GlnD. Introducing a genetic variation may comprise insertion and/or deletion of one or more nucleotides at a target site, such as 1, 2, 3, 4, 5, 10, 25, 50, 100, 250, 500, or more nucleotides. The genetic variation introduced into one or more bacteria of the methods disclosed herein may be a knock-out mutation (e.g. deletion of a promoter, insertion or deletion to produce a premature stop codon, deletion of an entire gene), or it may be elimination or abolishment of activity of a protein domain (e.g. point mutation affecting an active site, or deletion of a portion of a gene encoding the relevant portion of the protein product), or it may alter or abolish a regulatory sequence of a target gene. One or more regulatory sequences may also be inserted, including heterologous regulatory sequences and regulatory sequences found within a genome of a bacterial species or genus corresponding to the bacteria into which the genetic variation is introduced. Moreover, regulatory sequences may be selected based on the expression level of a gene in a bacterial culture or within a plant tissue. The genetic variation may be a pre-determined genetic variation that is specifically introduced to a target site. The genetic variation may be a random mutation within the target site. The genetic variation may be an insertion or deletion of one or more nucleotides. In some cases, a plurality of different genetic variations (e.g. 2, 3, 4, 5, 10, or more) are introduced into one or more of the isolated bacteria before exposing the bacteria to plants for assessing trait improvement. The plurality of genetic variations can be any of the above types, the same or different types, and in any combination. In some cases, a plurality of different genetic variations are introduced serially, introducing a first genetic variation after a first isolation step, a second genetic variation after a second isolation step, and so forth so as to accumulate a plurality of genetic variations in bacteria imparting progressively improved traits on the associated plants.

Genetic Variation—Methods of Introducing Genomic Alteration

In general, the term "genetic variation" refers to any change introduced into a polynucleotide sequence relative to a reference polynucleotide, such as a reference genome or portion thereof, or reference gene or portion thereof. A genetic variation may be referred to as a "mutation," and a sequence or organism comprising a genetic variation may be referred to as a "genetic variant" or "mutant". Genetic variations can have any number of effects, such as the increase or decrease of some biological activity, including gene expression, metabolism, and cell signaling. Genetic variations can be specifically introduced to a target site, or introduced randomly. A variety of molecular tools and methods are available for introducing genetic variation. For example, genetic variation can be introduced via polymerase chain reaction mutagenesis, oligonucleotide-directed mutagenesis, saturation mutagenesis, fragment shuffling mutagenesis, homologous recombination, recombineering, lambda red mediated recombination, CRISPR/Cas9 systems, chemical mutagenesis, and combinations thereof. Chemical methods of introducing genetic variation include exposure of DNA to a chemical mutagen, e.g., ethyl methanesulfonate (EMS), methyl methanesulfonate (MMS), N-nitrosourea (EN U), N-methyl-N-nitro-N'-nitrosoguanidine, 4-nitroquinoline N-oxide, diethylsulfate, benzopyrene, cyclophosphamide, bleomycin, triethylmelamine, acrylamide monomer, nitrogen mustard, vincristine, diepoxyalkanes (for example, diepoxybutane), ICR-170, formaldehyde, procarbazine hydrochloride, ethylene oxide, dimethylnitrosamine, 7,12 dimethylbenz(a)anthracene, chlorambucil, hexamethylphosphoramide, bisulfan, and the like. Radiation mutation-inducing agents include ultraviolet radiation, γ-irradiation, X-rays, and fast neutron bombardment. Genetic variation can also be introduced into a nucleic acid using, e.g., trimethylpsoralen with ultraviolet light. Random or targeted insertion of a mobile DNA element, e.g., a transposable element, is another suitable method for generating genetic variation. Genetic variations can be introduced into a nucleic acid during amplification in a cell-free in vitro system, e.g., using a polymerase chain reaction (PCR) technique such as error-prone PCR. Genetic variations can be introduced into a nucleic acid in vitro using DNA shuffling techniques (e.g., exon shuffling, domain swapping, and the like). Genetic variations can also be introduced into a nucleic acid as a result of a deficiency in a DNA repair enzyme in a cell, e.g., the presence in a cell of a mutant gene encoding a mutant DNA repair enzyme is expected to generate a high frequency of mutations (i.e., about 1 mutation/100 genes-1 mutation/10,000 genes) in the genome of the cell. Examples of genes encoding DNA repair enzymes include but are not limited to Mut H, Mut S, Mut L, and Mut U, and the homologs thereof in other species (e.g., MSH 1 6, PMS 1 2, MLH 1, GTBP, ERCC-1, and the like). Example descriptions of various methods for introducing genetic variations are provided in e.g., Stemple (2004) Nature 5:1-7; Chiang et al. (1993) PCR Methods Appl 2(3): 210-217; Stemmer (1994) Proc. Natl. Acad. Sci. USA 91:10747-10751; and U.S. Pat. Nos. 6,033,861, and 6,773,900.

Genetic variations introduced into microbes may be classified as transgenic, cisgenic, intragenomic, intrageneric, intergeneric, synthetic, evolved, rearranged, or SNPs.

Genetic variation may be introduced into numerous metabolic pathways within microbes to elicit improvements in the traits described above. Representative pathways include sulfur uptake pathways, glycogen biosynthesis, the glutamine regulation pathway, the molybdenum uptake pathway, the nitrogen fixation pathway, ammonia assimilation, ammonia excretion or secretion, Nitrogen uptake, glutamine biosynthesis, annamox, phosphate solubilization, organic acid transport, organic acid production, agglutinins production, reactive oxygen radical scavenging genes, Indole Acetic Acid biosynthesis, trehalose biosynthesis, plant cell wall degrading enzymes or pathways, root attachment genes, exopolysaccharide secretion, glutamate synthase pathway, iron uptake pathways, siderophore pathway, chitinase pathway, ACC deaminase, glutathione biosynthesis, phosphorous signaling genes, quorum quenching pathway, cytochrome pathways, hemoglobin pathway, bacterial hemoglobin-like pathway, small RNA rsmZ, rhizobitoxine biosynthesis, lapA adhesion protein, AHL quorum sensing pathway, phenazine biosynthesis, cyclic lipopeptide biosynthesis, and antibiotic production.

CRISPR/Cas9 (Clustered regularly interspaced short palindromic repeats)/CRISPR-associated (Cas) systems can be used to introduce desired mutations. CRISPR/Cas9 provide bacteria and archaea with adaptive immunity against viruses and plasmids by using CRISPR RNAs (crRNAs) to guide the silencing of invading nucleic acids. The Cas9 protein (or functional equivalent and/or variant thereof, i.e., Cas9-like protein) naturally contains DNA endonuclease activity that depends on the association of the protein with two naturally occurring or synthetic RNA molecules called crRNA and tracrRNA (also called guide RNAs). In some cases, the two molecules are covalently link to form a single molecule (also called a single guide RNA ("sgRNA"). Thus, the Cas9 or Cas9-like protein associates with a DNA-targeting RNA (which term encompasses both the two-molecule guide RNA configuration and the single-molecule guide RNA configuration), which activates the Cas9 or Cas9-like protein and guides the protein to a target nucleic acid sequence. If the Cas9 or Cas9-like protein retains its natural enzymatic function, it will cleave target DNA to create a double-stranded break, which can lead to genome alteration (i.e., editing: deletion, insertion (when a donor polynucleotide is present), replacement, etc.), thereby altering gene expression. Some variants of Cas9 (which variants are encompassed by the term Cas9-like) have been altered such that they have a decreased DNA cleaving activity (in some cases, they cleave a single strand instead of both strands of the target DNA, while in other cases, they have severely reduced to no DNA cleavage activity). Further exemplary descriptions of CRISPR systems for introducing genetic variation can be found in, e.g. U.S. Pat. No. 8,795,965.

As a cyclic amplification technique, polymerase chain reaction (PCR) mutagenesis uses mutagenic primers to introduce desired mutations. PCR is performed by cycles of denaturation, annealing, and extension. After amplification by PCR, selection of mutated DNA and removal of parental plasmid DNA can be accomplished by: 1) replacement of dCTP by hydroxymethylated-dCTP during PCR, followed by digestion with restriction enzymes to remove non-hydroxymethylated parent DNA only; 2) simultaneous mutagenesis of both an antibiotic resistance gene and the studied gene changing the plasmid to a different antibiotic resistance, the new antibiotic resistance facilitating the selection of the desired mutation thereafter; 3) after introducing a desired mutation, digestion of the parent methylated template DNA by restriction enzyme DpnI which cleaves only methylated DNA, by which the mutagenized unmethylated chains are recovered; or 4) circularization of the mutated PCR products in an additional ligation reaction to increase the transformation efficiency of mutated DNA. Further description of exemplary methods can be found in e.g. U.S. Pat. Nos. 7,132,265, 6,713,285, 6,673,610, 6,391,548, 5,789,166, 5,780,270, 5,354,670, 5,071,743, and US20100267147.

Oligonucleotide-directed mutagenesis, also called site-directed mutagenesis, typically utilizes a synthetic DNA primer. This synthetic primer contains the desired mutation and is complementary to the template DNA around the mutation site so that it can hybridize with the DNA in the gene of interest. The mutation may be a single base change (a point mutation), multiple base changes, deletion, or insertion, or a combination of these. The single-strand primer is then extended using a DNA polymerase, which copies the rest of the gene. The gene thus copied contains the mutated site, and may then be introduced into a host cell as a vector and cloned. Finally, mutants can be selected by DNA sequencing to check that they contain the desired mutation.

Genetic variations can be introduced using error-prone PCR. In this technique the gene of interest is amplified using a DNA polymerase under conditions that are deficient in the fidelity of replication of sequence. The result is that the amplification products contain at least one error in the sequence. When a gene is amplified and the resulting product(s) of the reaction contain one or more alterations in sequence when compared to the template molecule, the resulting products are mutagenized as compared to the template. Another means of introducing random mutations is exposing cells to a chemical mutagen, such as nitrosoguanidine or ethyl methanesulfonate (Nestmann, Mutat Res 1975 June; 28(3):323-30), and the vector containing the gene is then isolated from the host.

Saturation mutagenesis is another form of random mutagenesis, in which one tries to generate all or nearly all possible mutations at a specific site, or narrow region of a gene. In a general sense, saturation mutagenesis is comprised of mutagenizing a complete set of mutagenic cassettes (wherein each cassette is, for example, 1-500 bases in length) in defined polynucleotide sequence to be mutagenized (wherein the sequence to be mutagenized is, for example, from 15 to 100, 000 bases in length). Therefore, a group of mutations (e.g. ranging from 1 to 100 mutations) is introduced into each cassette to be mutagenized. A grouping of mutations to be introduced into one cassette can be different or the same from a second grouping of mutations to be introduced into a second cassette during the application of one round of saturation mutagenesis. Such groupings are exemplified by deletions, additions, groupings of particular codons, and groupings of particular nucleotide cassettes.

Fragment shuffling mutagenesis, also called DNA shuffling, is a way to rapidly propagate beneficial mutations. In an example of a shuffling process, DNAse is used to fragment a set of parent genes into pieces of e.g. about 50-100 bp in length. This is then followed by a polymerase chain reaction (PCR) without primers—DNA fragments with sufficient overlapping homologous sequence will anneal to each other and are then be extended by DNA polymerase. Several rounds of this PCR extension are allowed to occur, after some of the DNA molecules reach the size of the parental genes. These genes can then be amplified with another PCR, this time with the addition of primers that are designed to complement the ends of the strands. The primers may have additional sequences added to their 5' ends, such as sequences for restriction enzyme recognition sites needed for ligation into a cloning vector. Further examples of shuffling techniques are provided in US20050266541.

Homologous recombination mutagenesis involves recombination between an exogenous DNA fragment and the targeted polynucleotide sequence. After a double-stranded break occurs, sections of DNA around the 5' ends of the break are cut away in a process called resection. In the strand invasion step that follows, an overhanging 3' end of the broken DNA molecule then "invades" a similar or identical DNA molecule that is not broken. The method can be used to delete a gene, remove exons, add a gene, and introduce point mutations. Homologous recombination mutagenesis can be permanent or conditional. Typically, a recombination template is also provided. A recombination template may be a component of another vector, contained in a separate vector, or provided as a separate polynucleotide. In some embodiments, a recombination template is designed to serve as a template in homologous recombination, such as within or near a target sequence nicked or cleaved by a site-specific nuclease. A template polynucleotide may be of any suitable length, such as about or more than about 10, 15, 20, 25, 50, 75, 100, 150, 200, 500, 1000, or more nucleotides in length. In some embodiments, the template polynucleotide is complementary to a portion of a polynucleotide comprising the target sequence. When optimally aligned, a template polynucleotide might overlap with one or more nucleotides of a target sequences (e.g. about or more than about 1, 5, 10, 15, 20, 25, 30, 35, 40, 45, 50, 60, 70, 80, 90, 100 or more nucleotides). In some embodiments, when a template sequence and a polynucleotide comprising a target sequence are optimally aligned, the nearest nucleotide of the template polynucleotide is within about 1, 5, 10, 15, 20, 25, 50, 75, 100, 200, 300, 400, 500, 1000, 5000, 10000, or more nucleotides from the target sequence. Non-limiting examples of site-directed nucleases useful in methods of homologous recombination include zinc finger nucleases, CRISPR nucleases, TALE nucleases, and meganuclease. For a further description of the use of such nucleases, see e.g. U.S. Pat. No. 8,795,965 and US20140301990.

Mutagens that create primarily point mutations and short deletions, insertions, transversions, and/or transitions, including chemical mutagens or radiation, may be used to create genetic variations. Mutagens include, but are not limited to, ethyl methanesulfonate, methylmethane sulfonate, N-ethyl-N-nitrosurea, triethylmelamine, N-methyl-N-nitrosourea, procarbazine, chlorambucil, cyclophosphamide, diethyl sulfate, acrylamide monomer, melphalan, nitrogen mustard, vincristine, dimethylnitrosamine, N-methyl-N'-nitro-Nitrosoguanidine, nitrosoguanidine, 2-aminopurine, 7,12 dimethyl-benz(a)anthracene, ethylene oxide, hexamethylphosphoramide, bisulfan, diepoxyalkanes (diepoxyoctane, diepoxybutane, and the like), 2-methoxy-6-chloro-9[3-(ethyl-2-chloro-ethyl)aminopropylamino]acridine dihydrochloride and formaldehyde.

Introducing genetic variation may be an incomplete process, such that some bacteria in a treated population of bacteria carry a desired mutation while others do not. In some cases, it is desirable to apply a selection pressure so as to enrich for bacteria carrying a desired genetic variation. Traditionally, selection for successful genetic variants involved selection for or against some functionality imparted or abolished by the genetic variation, such as in the case of inserting antibiotic resistance gene or abolishing a metabolic activity capable of converting a non-lethal compound into a lethal metabolite. It is also possible to apply a selection pressure based on a polynucleotide sequence itself, such that only a desired genetic variation need be introduced (e.g. without also requiring a selectable marker). In this case, the selection pressure can comprise cleaving genomes lacking the genetic variation introduced to a target site, such that selection is effectively directed against the reference sequence into which the genetic variation is sought to be introduced. Typically, cleavage occurs within 100 nucleotides of the target site (e.g. within 75, 50, 25, 10, or fewer nucleotides from the target site, including cleavage at or within the target site). Cleaving may be directed by a site-specific nuclease selected from the group consisting of a Zinc Finger nuclease, a CRISPR nuclease, a TALE nuclease (TALEN), or a meganuclease. Such a process is similar to processes for enhancing homologous recombination at a target site, except that no template for homologous recombination is provided. As a result, bacteria lacking the desired genetic variation are more likely to undergo cleavage that, left unrepaired, results in cell death. Bacteria surviving selection may then be isolated for use in exposing to plants for assessing conferral of an improved trait.

A CRISPR nuclease may be used as the site-specific nuclease to direct cleavage to a target site. An improved selection of mutated microbes can be obtained by using Cas9 to kill non-mutated cells. Plants are then inoculated with the mutated microbes to re-confirm symbiosis and create evolutionary pressure to select for efficient symbionts. Microbes can then be re-isolated from plant tissues. CRISPR nuclease systems employed for selection against non-variants can employ similar elements to those described above with respect to introducing genetic variation, except that no template for homologous recombination is provided. Cleavage directed to the target site thus enhances death of affected cells.

Other options for specifically inducing cleavage at a target site are available, such as zinc finger nucleases, TALE nuclease (TALEN) systems, and meganuclease. Zinc-finger nucleases (ZFNs) are artificial DNA endonucleases generated by fusing a zinc finger DNA binding domain to a DNA cleavage domain. ZFNs can be engineered to target desired DNA sequences and this enables zinc-finger nucleases to cleave unique target sequences. When introduced into a cell, ZFNs can be used to edit target DNA in the cell (e.g., the cell's genome) by inducing double stranded breaks. Transcription activator-like effector nucleases (TALENs) are artificial DNA endonucleases generated by fusing a TAL (Transcription activator-like) effector DNA binding domain to a DNA cleavage domain. TALENS can be quickly engineered to bind practically any desired DNA sequence and when introduced into a cell, TALENs can be used to edit target DNA in the cell (e.g., the cell's genome) by inducing double strand breaks. Meganucleases (homing endonuclease) are endodeoxyribonucleases characterized by a large recognition site (double-stranded DNA sequences of 12 to 40 base pairs. Meganucleases can be used to replace, eliminate or modify sequences in a highly targeted way. By modifying their recognition sequence through protein engineering, the targeted sequence can be changed. Meganucleases can be used to modify all genome types, whether bacterial, plant or animal and are commonly grouped into four families: the LAGLIDADG family (SEQ ID NO: 1), the GIY-YIG family, the His-Cyst box family and the HNH family. Exemplary homing endonucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII.

Genetic Variation—Methods of Identification

The microbes of the present disclosure may be identified by one or more genetic modifications or alterations, which have been introduced into said microbe. One method by which said genetic modification or alteration can be identified is via reference to a SEQ ID NO that contains a portion of the microbe's genomic sequence that is sufficient to identify the genetic modification or alteration.

Further, in the case of microbes that have not had a genetic modification or alteration (e.g. a wild type, WT) introduced into their genomes, the disclosure can utilize 16S nucleic acid sequences to identify said microbes. A 16S nucleic acid sequence is an example of a "molecular marker" or "genetic marker," which refers to an indicator that is used in methods for visualizing differences in characteristics of nucleic acid sequences. Examples of other such indicators are restriction fragment length polymorphism (RFLP) markers, amplified fragment length polymorphism (AFLP) markers, single nucleotide polymorphisms (SNPs), insertion mutations, microsatellite markers (SSRs), sequence-characterized amplified regions (SCARs), cleaved amplified polymorphic sequence (CAPS) markers or isozyme markers or combinations of the markers described herein which defines a specific genetic and chromosomal location. Markers further include polynucleotide sequences encoding 16S or 18S rRNA, and internal transcribed spacer (ITS) sequences, which are sequences found between small-subunit and large-subunit rRNA genes that have proven to be especially useful in elucidating relationships or distinctions when compared against one another. Furthermore, the disclosure utilizes unique sequences found in genes of interest (e.g., nif H,D,K,L,A, glnE, amtB, etc.) to identify microbes disclosed herein.

The primary structure of major rRNA subunit 16S comprise a particular combination of conserved, variable, and hypervariable regions that evolve at different rates and enable the resolution of both very ancient lineages such as domains, and more modern lineages such as genera. The secondary structure of the 16S subunit include approximately 50 helices which result in base pairing of about 67% of the residues. These highly conserved secondary structural features are of great functional importance and can be used to ensure positional homology in multiple sequence alignments and phylogenetic analysis. Over the previous few decades, the 16S rRNA gene has become the most sequenced taxonomic marker and is the cornerstone for the current systematic classification of bacteria and archaea (Yarza et al. 2014. *Nature Rev. Micro.* 12:635-45).

Thus, in certain aspects, the disclosure provides for a sequence, which shares at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to any sequence in Tables E, F, G, or H.

Thus, in certain aspects, the disclosure provides for a microbe that comprises a sequence, which shares at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NOs: 62-303. These sequences and their associated descriptions can be found in Tables F, G, and H.

In some aspects, the disclosure provides for a microbe that comprises a 16S nucleic acid sequence, which shares at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NOs: 85, 96, 111, 121, 122, 123, 124, 136, 149, 157, 167, 261, 262, 269, 277-283. These sequences and their associated descriptions can be found in Tables G and H.

In some aspects, the disclosure provides for a microbe that comprises a nucleic acid sequence, which shares at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NOs: 86-95, 97-110, 112-120, 125-135, 137-148, 150-156, 158-166, 168-176, 263-268, 270-274, 275, 276, 284-295. These sequences and their associated descriptions can be found in Tables G and H.

In some aspects, the disclosure provides for a microbe that comprises a nucleic acid sequence, which shares at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NOs: 177-260, 296-303. These sequences and their associated descriptions can be found in Tables G and H.

In some aspects, the disclosure provides for a microbe that comprises, or primer that comprises, or probe that comprises, or non-native junction sequence that comprises, a nucleic acid sequence, which shares at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NOs: 304-424. These sequences and their associated descriptions can be found in Table E.

In some aspects, the disclosure provides for a microbe that comprises a non-native junction sequence that shares at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NOs: 372-405. These sequences and their associated descriptions can be found in Table E.

In some aspects, the disclosure provides for a microbe that comprises an amino acid sequence, which shares at least about 70%, 71%, 72%, 73%, 74%, 75%, 76%, 77%, 78%, 79%, 800% a, 81%, 82%, 83%, 84%, 85%, 86%, 87%6, 88%, 89%, 90%, 91%, 92%, 93%, 94%, 95%, 96%, 97%, 98%, 99%, or 100% sequence identity to SEQ ID NOs: 77, 78, 81, 82, or 83. These sequences and their associated descriptions can be found in Tables F and H.

Genetic Variation—Methods of Detection: Primers, Probes, and Assays

The present disclosure teaches primers, probes, and assays that are useful for detecting the microbes taught herein. In some aspects, the disclosure provides for methods of detecting the WT parental strains. In other aspects, the disclosure provides for methods of detecting the non-intergeneric engineered microbes derived from the WT strains. In aspects, the present disclosure provides methods of identifying non-intergeneric genetic alterations in a microbe.

In aspects, the genomic engineering methods of the present disclosure lead to the creation of non-natural nucleotide "junction" sequences in the derived non-intergeneric microbes. These non-naturally occurring nucleotide junctions can be used as a type of diagnostic that is indicative of the presence of a particular genetic alteration in a microbe taught herein.

The present techniques are able to detect these non-naturally occurring nucleotide junctions via the utilization of specialized quantitative PCR methods, including uniquely designed primers and probes. In some aspects, the probes of the disclosure bind to the non-naturally occurring nucleotide junction sequences. In some aspects, traditional PCR is utilized. In other aspects, real-time PCR is utilized. In some aspects, quantitative PCR (qPCR) is utilized.

Thus, the disclosure can cover the utilization of two common methods for the detection of PCR products in real-time: (1) non-specific fluorescent dyes that intercalate with any double-stranded DNA, and (2) sequence-specific DNA probes consisting of oligonucleotides that are labelled with a fluorescent reporter which permits detection only after hybridization of the probe with its complementary sequence. In some aspects, only the non-naturally occurring nucleotide junction will be amplified via the taught primers, and consequently can be detected via either a non-specific dye, or via the utilization of a specific hybridization probe. In other aspects, the primers of the disclosure are chosen such that the primers flank either side of a junction sequence, such that if an amplification reaction occurs, then said junction sequence is present.

Aspects of the disclosure involve non-naturally occurring nucleotide junction sequence molecules per se, along with other nucleotide molecules that are capable of binding to said non-naturally occurring nucleotide junction sequences under mild to stringent hybridization conditions. In some aspects, the nucleotide molecules that are capable of binding to said non-naturally occurring nucleotide junction sequences under mild to stringent hybridization conditions are termed "nucleotide probes."

In aspects, genomic DNA can be extracted from samples and used to quantify the presence of microbes of the disclosure by using qPCR. The primers utilized in the qPCR reaction can be primers designed by Primer Blast (https://www.ncbi.nlm.nih.gov/tools/primer-blast/) to amplify unique regions of the wild-type genome or unique regions of the engineered non-intergeneric mutant strains. The qPCR reaction can be carried out using the SYBR GreenER qPCR SuperMix Universal (Thermo Fisher P/N 11762100) kit, using only forward and reverse amplification primers; alternatively, the Kapa Probe Force kit (Kapa Biosystems P/N KK4301) can be used with amplification primers and a TaqMan probe containing a FAM dye label at the 5' end, an internal ZEN quencher, and a minor groove binder and fluorescent quencher at the 3' end (Integrated DNA Technologies).

Certain primer, probe, and non-native junction sequences are listed in Table E. qPCR reaction efficiency can be measured using a standard curve generated from a known quantity of gDNA from the target genome. Data can be normalized to genome copies per g fresh weight using the tissue weight and extraction volume.

Quantitative polymerase chain reaction (qPCR) is a method of quantifying, in real time, the amplification of one or more nucleic acid sequences. The real time quantification of the PCR assay permits determination of the quantity of nucleic acids being generated by the PCR amplification steps by comparing the amplifying nucleic acids of interest and an appropriate control nucleic acid sequence, which may act as a calibration standard.

TaqMan probes are often utilized in qPCR assays that require an increased specificity for quantifying target nucleic acid sequences. TaqMan probes comprise a oligonucleotide probe with a fluorophore attached to the 5' end and a quencher attached to the 3' end of the probe. When the TaqMan probes remain as is with the 5' and 3' ends of the probe in close contact with each other, the quencher prevents fluorescent signal transmission from the fluorophore. TaqMan probes are designed to anneal within a nucleic acid region amplified by a specific set of primers. As the Taq polymerase extends the primer and synthesizes the nascent strand, the 5' to 3' exonuclease activity of the Taq polymerase degrades the probe that annealed to the template. This probe degradation releases the fluorophore, thus breaking the close proximity to the quencher and allowing fluorescence of the fluorophore. Fluorescence detected in the qPCR assay is directly proportional to the fluorophore released and the amount of DNA template present in the reaction.

The features of qPCR allow the practitioner to eliminate the labor-intensive post-amplification step of gel electrophoresis preparation, which is generally required for observation of the amplified products of traditional PCR assays. The benefits of qPCR over conventional PCR are considerable, and include increased speed, ease of use, reproducibility, and quantitative ability Improvement of Traits Methods of the present disclosure may be employed to introduce or improve one or more of a variety of desirable traits. Examples of traits that may introduced or improved include: root biomass, root length, height, shoot length, leaf number, water use efficiency, overall biomass, yield, fruit size, grain size, photosynthesis rate, tolerance to drought, heat tolerance, salt tolerance, resistance to nematode stress, resistance to a fungal pathogen, resistance to a bacterial pathogen, resistance to a viral pathogen, level of a metabolite, and proteome expression. The desirable traits, including height, overall biomass, root and/or shoot biomass, seed germination, seedling survival, photosynthetic efficiency, transpiration rate, seed/fruit number or mass, plant grain or fruit yield, leaf chlorophyll content, photosynthetic rate, root length, or any combination thereof, can be used to measure growth, and compared with the growth rate of reference agricultural plants (e.g., plants without the improved traits) grown under identical conditions.

A preferred trait to be introduced or improved is nitrogen fixation, as described herein. In some cases, a plant resulting from the methods described herein exhibits a difference in the trait that is at least about 5% greater, for example at least about 5%, at least about 8%, at least about 10%, at least about 15%, at least about 20%, at least about 25%, at least about 30%, at least about 40%, at least about 50%, at least about 60%, at least about 75%, at least about 80%, at least about 80%, at least about 90%, or at least about 100%, at least about 200%, at least about 300%, at least about 400% or greater than a reference agricultural plant grown under the same conditions in the soil. In additional examples, a plant resulting from the methods described herein exhibits a difference in the trait that is at least about 5% greater, for example at least about 5%, at least about 8%, at least about 10%, at least about 15%, at least about 20%, at least about 25%, at least about 30%, at least about 40%, at least about 50%, at least about 60%, at least about 75%, at least about 80%, at least about 80%, at least about 90%, or at least about 100%, at least about 200%, at least about 300%, at least about 400% or greater than a reference agricultural plant grown under similar conditions in the soil.

The trait to be improved may be assessed under conditions including the application of one or more biotic or abiotic stressors. Examples of stressors include abiotic stresses (such as heat stress, salt stress, drought stress, cold stress, and low nutrient stress) and biotic stresses (such as nematode stress, insect herbivory stress, fungal pathogen stress, bacterial pathogen stress, and viral pathogen stress).

The trait improved by methods and compositions of the present disclosure may be nitrogen fixation, including in a plant not previously capable of nitrogen fixation. In some cases, bacteria isolated according to a method described herein produce 1% or more (e.g. 2%, 3%, 4%, 5%, 6%, 7%, 8%, 9%, 10%, 15%, 20%, or more) of a plant's nitrogen, which may represent an increase in nitrogen fixation capability of at least 2-fold (e.g. 3-fold, 4-fold, 5-fold, 6-fold, 7-fold, 8-fold, 9-fold, 10-fold, 20-fold, 50-fold, 100-fold, 1000-fold, or more) as compared to bacteria isolated from the first plant before introducing any genetic variation. In some cases, the bacteria produce 5% or more of a plant's nitrogen. The desired level of nitrogen fixation may be achieved after repeating the steps of introducing genetic variation, exposure to a plurality of plants, and isolating bacteria from plants with an improved trait one or more times (e.g. 1, 2, 3, 4, 5, 10, 15, 25, or more times). In some cases, enhanced levels of nitrogen fixation are achieved in the presence of fertilizer supplemented with glutamine, ammonia, or other chemical source of nitrogen. Methods for assessing degree of nitrogen fixation are known, examples of which are described herein.

Microbe breeding is a method to systematically identify and improve the role of species within the crop microbiome. The method comprises three steps: 1) selection of candidate species by mapping plant-microbe interactions and predicting regulatory networks linked to a particular phenotype, 2) pragmatic and predictable improvement of microbial phenotypes through intra-species crossing of regulatory networks and gene clusters, and 3) screening and selection of new microbial genotypes that produce desired crop phenotypes. To systematically assess the improvement of strains, a model is created that links colonization dynamics of the microbial community to genetic activity by key species. The model is used to predict genetic targets breeding and improve the frequency of selecting improvements in microbiome-encoded traits of agronomic relevance.

Measuring Nitrogen Delivered in an Agriculturally Relevant Field Context

In the field, the amount of nitrogen delivered can be determined by the function of colonization multiplied by the activity.

$$\text{Nitrogen delivered} = \int_{Time\&Space} \text{Colonization} \times \text{Activity}$$

The above equation requires (1) the average colonization per unit of plant tissue, and (2) the activity as either the amount of nitrogen fixed or the amount of ammonia excreted by each microbial cell. To convert to pounds of nitrogen per acre, corn growth physiology is tracked over time, e.g., size of the plant and associated root system throughout the maturity stages.

The pounds of nitrogen delivered to a crop per acre-season can be calculated by the following equation:

$$\text{Nitrogen delivered} = \int \text{Plant Tissue}(t) \times \text{Colonization}(t) \times \text{Activity}(t) \, dt$$

The Plant Tissue(t) is the fresh weight of corn plant tissue over the growing time (t). Values for reasonably making the calculation are described in detail in the publication entitled Roots, Growth and Nutrient Uptake (Mengel. Dept. of Agronomy Pub. #AGRY-95-08 (Rev. May-95. p. 1-8.).

The Colonization (t) is the amount of the microbes of interest found within the plant tissue, per gram fresh weight of plant tissue, at any particular time, t, during the growing season. In the instance of only a single timepoint available, the single timepoint is normalized as the peak colonization rate over the season, and the colonization rate of the remaining timepoints are adjusted accordingly.

Activity(t) is the rate of which N is fixed by the microbes of interest per unit time, at any particular time, t, during the growing season. In the embodiments disclosed herein, this activity rate is approximated by in vitro acetylene reduction assay (ARA) in ARA media in the presence of 5 mM glutamine or Ammonium excretion assay in ARA media in the presence of 5 mM ammonium ions.

The Nitrogen delivered amount is then calculated by numerically integrating the above function. In cases where the values of the variables described above are discretely measured at set timepoints, the values in between those timepoints are approximated by performing linear interpolation.

Nitrogen Fixation

Described herein are methods of increasing nitrogen fixation in a plant, comprising exposing the plant to bacteria comprising one or more genetic variations introduced into one or more genes regulating nitrogen fixation, wherein the bacteria produce 1% or more of nitrogen in the plant (e.g. 2%, 5%, 10%, or more), which may represent a nitrogen-fixation capability of at least 2-fold as compared to the plant in the absence of the bacteria. The bacteria may produce the nitrogen in the presence of fertilizer supplemented with glutamine, urea, nitrates or ammonia. Genetic variations can be any genetic variation described herein, including examples provided above, in any number and any combination. The genetic variation may be introduced into a gene selected from the group consisting of nifA, nifL, ntrB, ntrC, glutamine synthetase, glnA, glnB, glnK, draT, amtB, glutaminase, glnD, glnE, nifJ, nifH, nifD, nifK, nifY, nifE, nifN, nifU, nifS, nifV, nifW, nifZ, nifM, nifF, nifB, and nifQ. The genetic variation may be a mutation that results in one or more of: increased expression or activity of nifA or glutaminase; decreased expression or activity of nifL, ntrB, glutamine synthetase, glnB, glnK, draT, amtB; decreased adenylyl-removing activity of GlnE; or decreased uridylyl-removing activity of GlnD. The genetic variation introduced into one or more bacteria of the methods disclosed herein may be a knock-out mutation or it may abolish a regulatory sequence of a target gene, or it may comprise insertion of a heterologous regulatory sequence, for example, insertion of a regulatory sequence found within the genome of the same bacterial species or genus. The regulatory sequence can be chosen based on the expression level of a gene in a bacterial culture or within plant tissue. The genetic variation may be produced by chemical mutagenesis. The plants grown in step (c) may be exposed to biotic or abiotic stressors.

The amount of nitrogen fixation that occurs in the plants described herein may be measured in several ways, for example by an acetylene-reduction (AR) assay. An acetylene-reduction assay can be performed in vitro or in vivo. Evidence that a particular bacterium is providing fixed nitrogen to a plant can include: 1) total plant N significantly increases upon inoculation, preferably with a concomitant increase in N concentration in the plant; 2) nitrogen deficiency symptoms are relieved under N-limiting conditions upon inoculation (which should include an increase in dry matter); 3) $N_2$ fixation is documented through the use of an $^{15}N$ approach (which can be isotope dilution experiments, $^{15}N_2$ reduction assays, or $^{15}N$ natural abundance assays); 4) fixed N is incorporated into a plant protein or metabolite; and 5) all of these effects are not be seen in non-inoculated plants or in plants inoculated with a mutant of the inoculum strain.

The wild-type nitrogen fixation regulatory cascade can be represented as a digital logic circuit where the inputs $O_2$ and $NH_4^+$ pass through a NOR gate, the output of which enters an AND gate in addition to ATP. In some embodiments, the methods disclosed herein disrupt the influence of $NH_4^+$ on this circuit, at multiple points in the regulatory cascade, so that microbes can produce nitrogen even in fertilized fields. However, the methods disclosed herein also envision altering the impact of ATP or $O_2$ on the circuitry, or replacing the circuitry with other regulatory cascades in the cell, or altering genetic circuits other than nitrogen fixation. Gene clusters can be re-engineered to generate functional products under the control of a heterologous regulatory system. By eliminating native regulatory elements outside of, and within, coding sequences of gene clusters, and replacing them with alternative regulatory systems, the functional products of complex genetic operons and other gene clusters can be controlled and/or moved to heterologous cells, including cells of different species other than the species from which the native genes were derived. Once re-engineered, the synthetic gene clusters can be controlled by genetic circuits or other inducible regulatory systems, thereby controlling the products' expression as desired. The expression cassettes can be designed to act as logic gates, pulse generators, oscillators, switches, or memory devices. The controlling expression cassette can be linked to a promoter such that the expression cassette functions as an environmental sensor, such as an oxygen, temperature, touch, osmotic stress, membrane stress, or redox sensor.

As an example, the nifL, nifA, nifT, and nifX genes can be eliminated from the nif gene cluster. Synthetic genes can be designed by codon randomizing the DNA encoding each amino acid sequence. Codon selection is performed, specifying that codon usage be as divergent as possible from the codon usage in the native gene. Proposed sequences are scanned for any undesired features, such as restriction enzyme recognition sites, transposon recognition sites, repetitive sequences, sigma 54 and sigma 70 promoters, cryptic ribosome binding sites, and rho independent terminators. Synthetic ribosome binding sites are chosen to match the strength of each corresponding native ribosome binding site, such as by constructing a fluorescent reporter plasmid in which the 150 bp surrounding a gene's start codon (from −60 to +90) is fused to a fluorescent gene. This chimera can be expressed under control of the Ptac promoter, and fluorescence measured via flow cytometry. To generate synthetic ribosome binding sites, a library of reporter plasmids using 150 bp (−60 to +90) of a synthetic expression cassette is generated. Briefly, a synthetic expression cassette can consist of a random DNA spacer, a degenerate sequence encoding an RBS library, and the coding sequence for each synthetic gene. Multiple clones are screened to identify the synthetic ribosome binding site that best matched the native ribosome binding site. Synthetic operons that consist of the same genes as the native operons are thus constructed and tested for functional complementation. A further exemplary description of synthetic operons is provided in US20140329326.

Bacterial Species

Microbes useful in the methods and compositions disclosed herein may be obtained from any source. In some cases, microbes may be bacteria, archaea, protozoa or fungi. The microbes of this disclosure may be nitrogen fixing microbes, for example a nitrogen fixing bacteria, nitrogen fixing archaea, nitrogen fixing fungi, nitrogen fixing yeast, or nitrogen fixing protozoa. Microbes useful in the methods and compositions disclosed herein may be spore forming microbes, for example spore forming bacteria. In some cases, bacteria useful in the methods and compositions disclosed herein may be Gram positive bacteria or Gram negative bacteria. In some cases, the bacteria may be an endospore forming bacteria of the Firmicute phylum. In some cases, the bacteria may be a diazatroph. In some cases, the bacteria may not be a diazotroph.

The methods and compositions of this disclosure may be used with an archaea, such as, for example, *Methanothermobacter thermoautotrophicus*.

In some cases, bacteria which may be useful include, but are not limited to, *Agrobacterium radiobacter, Bacillus acidocaldarius, Bacillus acidoterrestris, Bacillus agri, Bacillus aizawai, Bacillus albolactis, Bacillus alcalophilus, Bacillus alvei, Bacillus aminoglucosidicus, Bacillus aminovorans, Bacillus anylolyticus* (also known as *Paenibacillus amylolyticus*) *Bacillus amyloliquefaciens, Bacillus aneurinolyticus, Bacillus atrophaeus, Bacillus azoloformans, Bacillus badius, Bacillus cereus* (synonyms: *Bacillus enduorhythmos, Bacillus medusa*), *Bacillus chitinosporus, Bacillus circulans, Bacillus coaxgulans, Bacillus endoparasiticus Bacillus fastidiosus, Bacillus firmus, Bacillus kurstaki, Bacillus lacticola, Bacillus lactimorbus, Bacillus lactis, Bacillus laterosporus* (also known as *Brevibacillus laterosporus*), *Bacillus lautus, Bacillus lentimorbus, Bacillus lentus, Bacillus licheniformis, Bacillus maroccanus, Bacillus megaterium, Bacillus metiens, Bacillus mycoides, Bacillus natto, Bacillus nematocida, Bacillus nigrificans, Bacillus nigrum, Bacillus panlothenticus, Bacillus popillae, Bacillus psvchrosaccharolvticus, Bacillus pumlus, Bacillus siamensis, Bacillus smithii, Bacillus sphaericus, Bacillus subtlis, Bacillus thuringiensis, Bacillus uniflagellalus, Bradyrhizobium japonicum, Brevibacillus brevis Brevibacillus laterosporus* (formerly *Bacillus laterosporus*), *Chromobacterium subtsugae, Delftia acidovorans, Lactobacillus acidophilus, Lysobacter antibioticus, Lysobacter enzyrmogenes, Paenibacillus alvei, Paenibacllus xpolymvxa, Paenibacillus popilliae* (formerly *Bacillus popilliae*), *Pantoea agglomerans, Pasteuria penetrans* (formerly *Bacillus penetrans*), *Pasteuria usgae, Pectobacterium carotovorum* (formerly *Erwinia carotovora*), *Pseudomonas aeruginosa, Pseudomonas aureofaciens, Pseudomonas cepacia* (formerly known as *Burkholderia cepacia*), *Pseudomonas chlororaphis, Pseudomonas fluorescens, Pseudomonas proradix, Pseudomonas putida, Pseudmronas syringae, Serratia entomophila, Serratia marcescens, Streptomvyces colombiensis, Streptomyvces galbus, Streptomrnyces goshikiensis, Streptomyces griseoviridis, Streptomyces lavendulae, Streptomyces prasinus, Streptomyces saraceticus, Streptomyces venezuelae, Xanthomonas campestris, Xenorhabdus luminescens, Xenorhabdus nematophila, Rhodococcus globerulus* AQ719 (NRRL Accession No. B-21663), *Bacillus* sp. AQ175 (ATCC Accession No. 55608), *Bacillus* sp. AQ 177 (ATCC Accession No. 55609), *Bacillus* sp. AQ178 (ATCC Accession No. 53522), and *Streptomyces* sp. strain NRRL Accession No. B-30145. In some cases the bacterium may be *Azotobacter chroococcum, Methanosarcina barkeri, Klesiella pneumoniae, Azolobacter vinelandii, Rhodobacter spharoides, Rhodobacter capsulatus, Rhodobcter palustris, Rhodosporillum rubrum, Rhizobium leguminosarum* or *Rhizobium etli*.

In some cases the bacterium may be a species of *Clostridium*, for example *Clostridium pasteuriamum, Clostridium beijerinckii, Clostridium perfringens, Clostridium tetani, Clostridium acetobutylicum*.

In some cases, bacteria used with the methods and compositions of the present disclosure may be cyanobacteria. Examples of cyanobacterial genuses include *Anabaena* (for example *Anagaena* sp. PCC7120), *Nostoc* (for example *Nostoc punctiforme*), or *Synechocystis* (for example *Synechocystis* sp. PCC6803).

In some cases, bacteria used with the methods and compositions of the present disclosure may belong to the phylum Chlorobi, for example *Chlorobium tepidum*.

In some cases, microbes used with the methods and compositions of the present disclosure may comprise a gene homologous to a known NifH gene. Sequences of known NifH genes may be found in, for example, the Zehr lab NifH database, (https://wwwzehr.pmc.ucsc.edu/nifH_Database_Public/, Apr. 4, 2014), or the Buckley lab NifH database (http://www.css.cornell.edu/faculty/buckley/nifh.htm, and Gaby, John Christian, and Daniel H. Buckley. "A comprehensive aligned nifH gene database: a multipurpose tool for studies of nitrogen-fixing bacteria." *Database* 2014 (2014): bau001.). In some cases, microbes used with the methods and compositions of the present disclosure may comprise a sequence which encodes a polypeptide with at least 60%, 70%, 80%, 85%, 90%, 95%, 96%, 96%, 98%, 99% or more than 99% sequence identity to a sequence from the Zehr lab NifH database, (https://wwwzehr.pmc.ucsc.edu/nifH_Database_Public/, Apr. 4, 2014). In some cases, microbes used with the methods and compositions of the present disclosure may comprise a sequence which encodes a polypeptide with at least 60%, 70%, 80%, 85%, 90%, 95%, 96%, 96%, 98%, 99% or more than 99% sequence identity to a sequence from the Buckley lab NifH database, (Gaby, John Christian, and Daniel H. Buckley. "A comprehensive aligned nifH gene database: a multipurpose tool for studies of nitrogen-fixing bacteria." *Database* 2014 (2014): bau001.).

Microbes useful in the methods and compositions disclosed herein can be obtained by extracting microbes from surfaces or tissues of native plants; grinding seeds to isolate microbes; planting seeds in diverse soil samples and recovering microbes from tissues; or inoculating plants with exogenous microbes and determining which microbes appear in plant tissues. Non-limiting examples of plant tissues include a seed, seedling, leaf, cutting, plant, bulb or tuber. In some cases, bacteria are isolated from a seed. The parameters for processing samples may be varied to isolate different types of associative microbes, such as rhizospheric, epiphytes, or endophytes. Bacteria may also be sourced from a repository, such as environmental strain collections, instead of initially isolating from a first plant. The microbes can be genotyped and phenotyped, via sequencing the genomes of isolated microbes; profiling the composition of communities in planta; characterizing the transcriptomic functionality of communities or isolated microbes; or screening microbial features using selective or phenotypic media (e.g., nitrogen fixation or phosphate solubilization phenotypes). Selected candidate strains or populations can be obtained via sequence data; phenotype data; plant data (e.g., genome, phenotype, and/or yield data); soil data (e.g., pH, N/P/K content, and/or bulk soil biotic communities); or any combination of these.

The bacteria and methods of producing bacteria described herein may apply to bacteria able to self-propagate efficiently on the leaf surface, root surface, or inside plant tissues without inducing a damaging plant defense reaction, or bacteria that are resistant to plant defense responses. The bacteria described herein may be isolated by culturing a plant tissue extract or leaf surface wash in a medium with no added nitrogen. However, the bacteria may be unculturable, that is, not known to be culturable or difficult to culture using standard methods known in the art. The bacteria described herein may be an endophyte or an epiphyte or a bacterium inhabiting the plant rhizosphere (rhizospheric bacteria). The bacteria obtained after repeating the steps of introducing genetic variation, exposure to a plurality of plants, and isolating bacteria from plants with an improved trait one or more times (e.g. 1, 2, 3, 4, 5, 10, 15, 25, or more times) may be endophytic, epiphytic, or rhizospheric. Endophytes are organisms that enter the interior of plants without causing disease symptoms or eliciting the formation of symbiotic structures, and are of agronomic interest because they can enhance plant growth and improve the nutrition of plants (e.g., through nitrogen fixation). The bacteria can be a seed-borne endophyte. Seed-borne endophytes include bacteria associated with or derived from the seed of a grass or plant, such as a seed-borne bacterial endophyte found in mature, dry, undamaged (e.g., no cracks, visible fungal infection, or prematurely germinated) seeds. The seed-borne bacterial endophyte can be associated with or derived from the surface of the seed; alternatively, or in addition, it can be associated with or derived from the interior seed compartment (e.g., of a surface-sterilized seed). In some cases, a seed-borne bacterial endophyte is capable of replicating within the plant tissue, for example, the interior of the seed. Also, in some cases, the seed-borne bacterial endophyte is capable of surviving desiccation.

The bacterial isolated according to methods of the disclosure, or used in methods or compositions of the disclosure, can comprise a plurality of different bacterial taxa in combination. By way of example, the bacteria may include Proteobacteria (such as *Pseudomonas, Enterobacter, Stenotrophomonas, Burkholderia, Rhizobium, Herbaspirillum, Pantoea, Serratia, Rahnella, Azospirillum, Azorhizobium, Azotobacter, Duganella, Delftia, Bradyrhizobiun, Sinorhizobium* and *Halomonas*). Firmicutes (such as *Bacillus, Paenibacillus, Lactobacillus, Mycoplasma*, and *Acetabacterium*), and Actinobacteria (such as *Streptomyces, Rhodacoccus, Microbacterium*, and *Curtobacterium*). The bacteria used in methods and compositions of this disclosure may include nitrogen fixing bacterial consortia of two or more species. In some cases, one or more bacterial species of the bacterial consortia may be capable of fixing nitrogen. In some cases, one or more species of the bacterial consortia may facilitate or enhance the ability of other bacteria to fix nitrogen. The bacteria which fix nitrogen and the bacteria which enhance the ability of other bacteria to fix nitrogen may be the same or different. In some examples, a bacterial strain may be able to fix nitrogen when in combination with a different bacterial strain, or in a certain bacterial consortia, but may be unable to fix nitrogen in a monoculture. Examples of bacterial genuses which may be found in a nitrogen fixing bacterial consortia include, but are not limited to, *Herbaspirillum, Azospirillum, Enterobacter*, and *Bacillus*.

Bacteria that can be produced by the methods disclosed herein include *Azotobacter* sp., *Bradyrhizobium* sp., *Klebsiella* sp., and *Sinorhizobium* sp. In some cases, the bacteria may be selected from the group consisting of: *Azotobacter vinelandii, Bradyrhizobium japonicum, Klebsiella pneumoniae*, and *Sinorhizobium meliloti*. In some cases, the bacteria may be of the genus *Enterobacter* or *Rahnella*. In some cases, the bacteria may be of the genus *Frankia*, or *Clostridium*. Examples of bacteria of the genus *Clostridium* include, but are not limited to, *Clostridium acetobutilicum, Clostridium pasteurianum, Clostridium beijerinckii, Clostridium perfringens*, and *Clostridium tetani*. In some cases, the bacteria may be of the genus *Paenibacillus*, for example *Paenibacillus azotofixans, Paembacillus borealis, Paenibacillus durus, Paenibacillus macerans, Paenibacillus polymyxa, Paenibacillus alvei, Paenibacillus amylolyticus, Paenibacillus campinasensis, Paenibacillus chibensis, Paenibacillus glucanolyticus, Paenibacillus illinoisensis, Paenibacillus larvae* subsp. *Larvae, Paenibacillus larvae* subsp. *Pulvifaciens, Paenibacillus lautus, Paenibacillus macerans, Paenibacillus macquariensis, Paenibacillus macquariensis, Paenibacillus pabuli, Paenibacillus peoriae*, or *Paenibacillus polymyxa*.

In some examples, bacteria isolated according to methods of the disclosure can be a member of one or more of the following taxa: *Achromobacter, Acidithiobacillus, Acidovorax, Acidovoraz, Acinetobacter, Actinoplanes, Adlercreutzia, Aerococcus, Aeromonas, Afipia, Agromyces, Ancylobacter, Arthrobacter, Atopostipes, Azospirillum, Bacillus, Bdellovibrio, Beijerinckia, Bosea, Bradyrhizobium, Brevibacillus, Brevundimonas, Burkholderia, Candidatus Haloredivivus, Caulobacter, Cellulomonas, Cellvibrio, Chryseobacterium, Citrobacter, Clostridium, Coraliomargarita, Corynebacterium, Cupriavidus, Curtobacterium, Curvibacter, Deinococcus, Delftia, Desemzia, Devosia, Dokdonella, Dyella, Enhydrobacter, Enterobacter, Enterococcus, Erwinia, Escherichia, Escherichia/Shigella, Exiguobacterium, Ferroglobus, Filimonas, Finegoldia, Flavisolibacter, Flavobacterium, Frigoribacterium, Gluconacetobacter, Hafnia, Halobaculum, Halomonas, Halosimplex, Herbaspirillum, Hymenobacter, Klebsiella, Kocuria, Kosakonia, Lactobacillus, Leclercia, Lentzea, Luteibacter, Luteimonas, Massilia, Mesorhizobium, Methylobacterium, Microbacterium, Micrococcus, Microvirga, Mycobacterium, Neisseria, Nocardia, Oceanibaculum, Ochrobactrum, Okibacterium, Oligotropha, Oryzihumus, Oxalophagus, Paenibacillus, Panteoa, Pantoea, Pelomonas, Perlucidibaca, Plantibacter, Polynucleobacter, Propionibacterium, Propioniciclava, Pseudoclavibacter, Pseudomonas, Pseudonocardia, Pseudoxanthomonas, Psychrobacter, Rahnella, Ralstonia, Rheinheimera, Rhizobium, Rhodococcus, Rhodopseudomonas, Roseateles, Ruminococcus, Sebaldella, Sediminibacillus, Sediminibacterium, Serratia, Shigella, Shinella, Sinorhizobium, Sinosporangium, Sphingobacterium, Sphingomonas, Sphingopyxis, Sphingosinicella, Staphylococcus, Stenotrophomonas, Strenotrophomonas, Streptococcus, Streptomyces, Stygiolobus, Sulfurisphaera, Tatumella, Tepidimonas, Thermomonas, Thiobacillus, Variovorax*, WPS-2 genera incertae sedis, *Xanthomonas*, and *Zimmermannella*.

In some cases, a bacterial species selected from at least one of the following genera are utilized: *Enterobacter, Klebsiella, Kosakonia*, and *Rahnella*. In some cases, a combination of bacterial species from the following genera are utilized: *Enterobacter. Klebsiella, Kosakonia*, and *Rahnella*. In some cases, the species utilized can be one or more of: *Enterobacter sacchari, Klebsiella variicola, Kosakonia sacchari*, and *Rahnella aquatilis*.

In some cases, a Gram positive microbe may have a Molybdenum-Iron nitrogenase system comprising: nifH, nifD, nifK, nifB, nifE, nifN, nif, hesA, nifV, nifW, nifU, nifS, nifI1, and nifI2. In some cases, a Gram positive microbe may have a vanadium nitrogenase system comprising: vnfDG, vnfK, vnfE, vnfN, vupC, vupB, vupA, vnfV, vnfR1, vnfH, vnfR2, vnfA (transcriptional regulator). In some cases, a Gram positive microbe may have an iron-only nitrogenase system comprising: anfK, anfG, anfD, anfH, anfA (transcriptional regulator). In some cases a Gram positive microbe may have a nitrogenase system comprising glnB, and glnK (nitrogen signaling proteins). Some examples of enzymes involved in nitrogen metabolism in Gram positive microbes include glnA (glutamine synthetase), gdh (glutamate dehydrogenase), bdh (3-hydroxybutyrate dehydrogenase), glutaminase, gltAB/gltB/gltS (glutamate synthase), asnA/asnB (aspartate-ammonia ligase/asparagine synthetase), and ansA/ansZ (asparaginase). Some examples of proteins involved in nitrogen transport in Gram positive microbes include amtB (ammonium transporter), glnK (regulator of ammonium transport), glnPHQ/glnQHMP (ATP-dependent glutamine/glutamate transporters), glnT/alsT/yrbD/yflA (glutamine-like proton symport transporters), and gltP/gltT/yhcl/nqt (glutamate-like proton symport transporters).

Examples of Gram positive microbes which may be of particular interest include *Paenibacillus polymixa, Paenibacillus riograndensis, Paenibacillus* sp., *Frankia* sp., *Heliobacterium* sp., *Heliobacterium chlorum, Heliobacillus* sp., *Heliophilum* sp., *Heliorestis* sp., *Clostridium acetobutylicum, Clostridium* sp., *Mycobacterium flaum, Mycobacterium* sp., *Arthrobacter* sp., *Agromyces* sp., *Corynebacterium autitrophicum, Corynebacterium* sp., *Micromonspora* sp., *Propionibacteria* sp., *Streptomyces* sp., and *Microbacterium* sp.

Some examples of genetic alterations which may be make in Gram positive microbes include: deleting glnR to remove negative regulation of BNF in the presence of environmental nitrogen, inserting different promoters directly upstream of the nif cluster to eliminate regulation by GlnR in response to environmental nitrogen, mutating glnA to reduce the rate of ammonium assimilation by the GS-GOGAT pathway, deleting amtB to reduce uptake of ammonium from the media, mutating glnA so it is constitutively in the feedback-inhibited (FBI-GS) state, to reduce ammonium assimilation by the GS-GOGAT pathway.

In some cases, glnR is the main regulator of N metabolism and fixation in *Paenibacillus* species. In some cases, the genome of a *Paenibacillus* species may not contain a gene to produce glnR. In some cases, the genome of a *Paenibacillus* species may not contain a gene to produce glnE or glnD. In some cases, the genome of a *Paenibacillus* species may contain a gene to produce glnB or glnK. For example *Paenibacillus* sp. WLY78 doesn't contain a gene for glnB, or its homologs found in the archaeon *Methanococcus maripaludis*, nifI1 and nifI2. In some cases, the genomes of *Paenibacillus* species may be variable. For example, *Paenibacillus* polymixa E681 lacks glnK and gdh, has several nitrogen compound transporters, but only amtB appears to be controlled by GlnR. In another example, *Paenibacillus* sp. JDR2 has glnK, gdh and most other central nitrogen metabolism genes, has many fewer nitrogen compound transporters, but does have glnPHQ controlled by GlnR. *Paenibacillus riograndensis* SBR5 contains a standard glnRA operon, an fdx gene, a main nif operon, a secondary nif operon, and an anf operon (encoding iron-only nitrogenase). Putative glnR/tnrA sites were found upstream of each of these operons. GlnR may regulate all of the above operons, except the anf operon. GlnR may bind to each of these regulatory sequences as a dimer.

*Paenibacillus* N-fixing strains may fall into two subgroups: Subgroup I, which contains only a minimal nif gene cluster and subgroup II, which contains a minimal cluster, plus an uncharacterized gene between nifX and hesA, and often other clusters duplicating some of the nif genes, such as nifH, nifHDK, nifBEN, or clusters encoding vanadaium nitrogenase (vnf) or iron-only nitrogenase (anf) genes.

In some cases, the genome of a *Paenibacillus* species may not contain a gene to produce glnB or glnK. In some cases, the genome of a *Paenibacillus* species may contain a minimal nif cluster with 9 genes transcribed from a sigma-70 promoter. In some cases a *Paenibacillus* nif cluster may be negatively regulated by nitrogen or oxygen. In some cases, the genome of a *Paenibacillus* species may not contain a gene to produce sigma-54. For example, *Paenibacillus* sp. WLY78 does not contain a gene for sigma-54. In some cases, a nif cluster may be regulated by glnR, and/or TnrA. In some cases, activity of a nif cluster may be altered by altering activity of glnR, and/or TnrA.

In Bacilli, glutamine synthetase (GS) is feedback-inhibited by high concentrations of intracellular glutamine, causing a shift in confirmation (referred to as FBI-GS). Nif clusters contain distinct binding sites for the regulators GlnR and TnrA in several Bacilli species. GlnR binds and represses gene expression in the presence of excess intracellular glutamine and AMP. A role of GlnR may be to prevent the influx and intracellular production of glutamine and ammonium under conditions of high nitrogen availability. TnrA may bind and/or activate (or repress) gene expression in the presence of limiting intracellular glutamine, and/or in the presence of FBI-GS. In some cases the activity of a Bacilli nif cluster may be altered by altering the activity of GlnR.

Feedback-inhibited glutamine synthetase (FBI-GS) may bind GlnR and stabilize binding of GlnR to recognition sequences. Several bacterial species have a GlnR/TnrA binding site upstream of the nif cluster. Altering the binding of FBI-GS and GlnR may alter the activity of the nif pathway.

Sources of Microbes

The bacteria (or any microbe according to the disclosure) may be obtained from any general terrestrial environment, including its soils, plants, fungi, animals (including invertebrates) and other biota, including the sediments, water and biota of lakes and rivers; from the marine environment, its biota and sediments (for example, sea water, marine muds, marine plants, marine invertebrates (for example, sponges), marine vertebrates (for example, fish)); the terrestrial and marine geosphere (regolith and rock, for example, crushed subterranean rocks, sand and clays); the cryosphere and its meltwater: the atmosphere (for example, filtered aerial dusts, cloud and rain droplets); urban, industrial and other manmade environments (for example, accumulated organic and mineral matter on concrete, roadside gutters, roof surfaces, and road surfaces).

The plants from which the bacteria (or any microbe according to the disclosure) are obtained may be a plant having one or more desirable traits, for example a plant which naturally grows in a particular environment or under certain conditions of interest. By way of example, a certain plant may naturally grow in sandy soil or sand of high salinity, or under extreme temperatures, or with little water, or it may be resistant to certain pests or disease present in the environment, and it may be desirable for a commercial crop to be grown in such conditions, particularly if they are, for example, the only conditions available in a particular geographic location. By way of further example, the bacteria may be collected from commercial crops grown in such environments, or more specifically from individual crop plants best displaying a trait of interest amongst a crop grown in any specific environment: for example the fastest-growing plants amongst a crop grown in saline-limiting soils, or the least damaged plants in crops exposed to severe insect damage or disease epidemic, or plants having desired quantities of certain metabolites and other compounds, including fiber content, oil content, and the like, or plants displaying desirable colors, taste or smell. The bacteria may be collected from a plant of interest or any material occurring in the environment of interest, including fungi and other animal and plant biota, soil, water, sediments, and other elements of the environment as referred to previously.

The bacteria (or any microbe according to the disclosure) may be isolated from plant tissue. This isolation can occur from any appropriate tissue in the plant, including for example root, stem and leaves, and plant reproductive tissues. By way of example, conventional methods for isolation from plants typically include the sterile excision of the plant material of interest (e.g. root or stem lengths, leaves), surface sterilization with an appropriate solution (e.g. 2% sodium hypochlorite), after which the plant material is placed on nutrient medium for microbial growth. Alternatively, the surface-sterilized plant material can be crushed in a sterile liquid (usually water) and the liquid suspension, including small pieces of the crushed plant material spread over the surface of a suitable solid agar medium, or media, which may or may not be selective (e.g. contain only phytic acid as a source of phosphorus). This approach is especially useful for bacteria which form isolated colonies and can be picked off individually to separate plates of nutrient medium, and further purified to a single species by well-known methods. Alternatively, the plant root or foliage samples may not be surface sterilized but only washed gently thus including surface-dwelling epiphytic microorganisms in the isolation process, or the epiphytic microbes can be isolated separately, by imprinting and lifting off pieces of plant roots, stem or leaves onto the surface of an agar medium and then isolating individual colonies as above. This approach is especially useful for bacteria, for example. Alternatively, the roots may be processed without washing off small quantities of soil attached to the roots, thus including microbes that colonize the plant rhizosphere. Otherwise, soil adhering to the roots can be removed, diluted and spread out onto agar of suitable selective and non-selective media to isolate individual colonies of rhizospheric bacteria.

Budapest Treaty on the International Recognition of the Deposit of Microorganisms for the Purpose of Patent Procedures The microbial deposits of the present disclosure were made under the provisions of the Budapest Treaty on the International Recognition of the Deposit of Microorganisms for the Purpose of Patent Procedure (Budapest Treaty).

Applicants state that pursuant to 37 C.F.R. § 1.808(a)(2) "all restrictions imposed by the depositor on the availability to the public of the deposited material will be irrevocably removed upon the granting of the patent." This statement is subject to paragraph (b) of this section (i.e. 37 C.F.R. § 1.808(b)).

Biologically pure cultures of *Rahnella aquatilis* and *Enterobacter sacchari* were deposited on Jul. 14, 2015 with the American Type Culture Collection (ATCC; an International Depositary Authority), 10801 University Blvd., Manassas, Va. 20110, USA, and assigned ATTC Patent Deposit Designation numbers PTA-122293 and PTA-122294, respectively. The applicable deposit information is found below in Table A.

The *Enterobacter sacchari* has now been reclassified as *Kosakonia sacchari*, the name for the organism may be used interchangeably throughout the manuscript.

Figure 18:
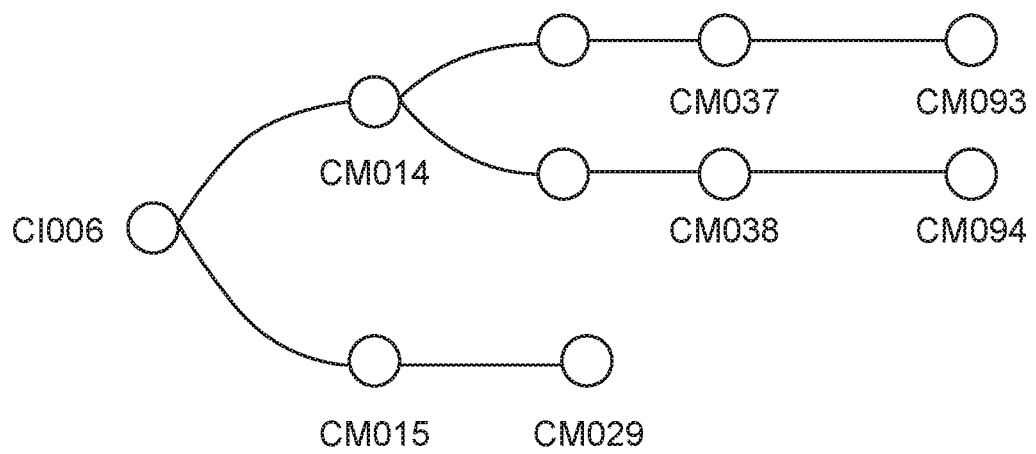
FIG. 18 depicts the lineage of modified strains that were derived from strain CI006.
Figure 19:
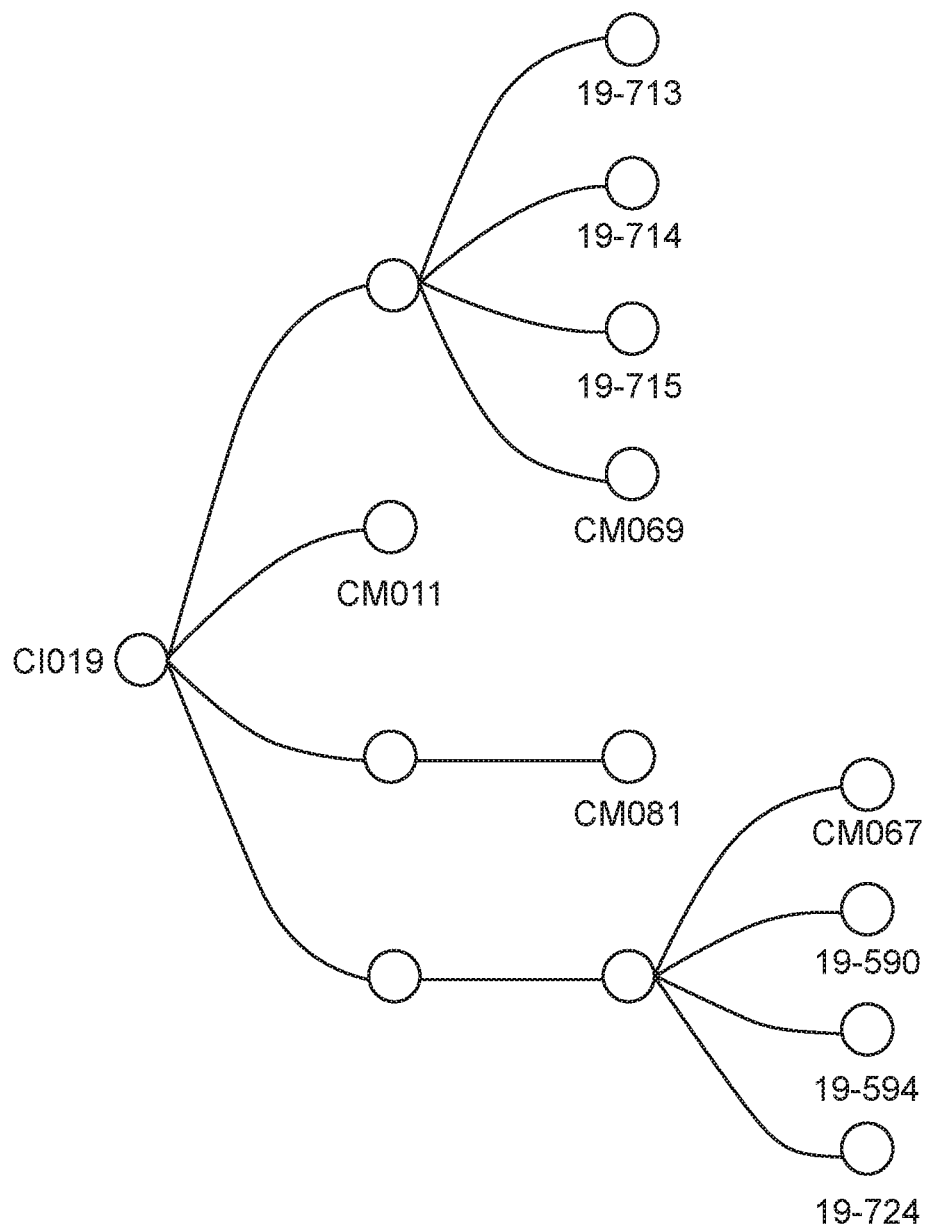
FIG. 19 depicts the lineage of modified strains that were derived from strain CI019.

Many microbes of the present disclosure are derived from two wild-type strains, as depicted in FIG. 18 and FIG. 19. Strain CI006 is a bacterial species previously classified in the genus *Enterobacter* (see aforementioned reclassification into *Kosakonia*), and FIG. 19 identifies the lineage of the mutants that have been derived from CI006. Strain CI019 is a bacterial species classified in the genus *Rahnella*, and FIG. 19 identifies the lineage of the mutants that have been derived from CI019. With regard to FIG. 18 and FIG. 19, it is noted that strains comprising CM in the name are mutants of the strains depicted immediately to the left of said CM strain. The deposit information for the CI006 *Kosakonia* wild type (WT) and CI019 *Rahnella* WT are found in the below Table A.

Some microorganisms described in this application were deposited on Jan. 6, 2017 or Aug. 11, 2017 with the Bigelow National Center for Marine Algae and Microbiota (NCMA), located at 60 Bigelow Drive, East Boothbay, Me. 04544, USA. As aforementioned, all deposits were made under the terms of the Budapest Treaty on the International Recognition of the Deposit of Microorganisms for the Purposes of Patent Procedure. The Bigelow National Center for Marine Algae and Microbiota accession numbers and dates of deposit for the aforementioned Budapest Treaty deposits are provided in Table A.

Biologically pure cultures of *Kosakonia sacchari* (WI), *Rahnella aquatilis* (WI), and a variant *Kosakonia sacchari* strain were deposited on Jan. 6, 2017 with the Bigelow National Center for Marine Algae and Microbiota (NCMA), located at 60 Bigelow Drive, East Boothbay, Me. 04544, USA, and assigned NCMA Patent Deposit Designation numbers 201701001, 201701003, and 201701002, respectively. The applicable deposit information is found below in Table A.

Biologically pure cultures of variant *Kosakonia sacchari* strains were deposited on Aug. 11, 2017 with the Bigelow National Center for Marine Algae and Microbiota (NCMA), located at 60 Bigelow Drive, East Boothbay, Me. 04544, USA, and assigned NCMA Patent Deposit Designation numbers 201708004, 201708003, and 201708002, respectively. The applicable deposit information is found below in Table A.

A biologically pure culture of *Klebsiella variicola* (W) was deposited on Aug. 11, 2017 with the Bigelow National Center for Marine Algae and Microbiota (NCMA), located at 60 Bigelow Drive, East Boothbay, Me. 04544, USA, and assigned NCMA Patent Deposit Designation number 201708001. Biologically pure cultures of two *Klebsiella variicola* variants were deposited on Dec. 20, 2017 with the Bigelow National Center for Marine Algae and Microbiota (NCMA), located at 60 Bigelow Drive, East Boothbay, Me. 04544, USA, and assigned NCMA Patent Deposit Designation numbers 201712001 and 201712002, respectively. The applicable deposit information is found below in Table A.

TABLE A

Microorganisms Deposited under the Budapest Treaty

| Depository | Pivot Strain Designation (some strains have multiple designations) | Taxonomy | Accession Number | Date of Deposit |
|---|---|---|---|---|
| ATCC | | *Rahnella aquatilis* | PTA-122293 | Jul. 14, 2015 |
| ATCC | | *Enterobacter sacchari* (taxonomically reclassified after deposit as *Kosakonia sacchari*) | PTA-122294 | Jul. 14, 2015 |
| NCMA | CI006, PBC6.1, 6 | *Kosakonia sacchari* (WT) | 201701001 | Jan. 6, 2017 |
| NCMA | CI019, 19 | *Rahnella aquatilis* (WT) | 201701003 | Jan. 6, 2017 |
| NCMA | CM029, 6-412 | *Kosakonia sacchari* | 201701002 | Jan. 6, 2017 |
| NCMA | 6-403 CM037 | *Kosakonia sacchari* | 201708004 | Aug. 11, 2017 |
| NCMA | 6-404, CM38, PBC6.38 | *Kosakonia sacchari* | 201708003 | Aug. 11, 2017 |
| NCMA | CM094, 6-881, PBC6.94 | *Kosakonia sacchari* | 201708002 | Aug. 11, 2017 |
| NCMA | CI137, 137, PB137 | *Klebsiella variicola* (WT) | 201708001 | Aug. 11, 2017 |
| NCMA | 137-1034 | *Klebsiella variicola* | 201712001 | Dec. 20, 2017 |
| NCMA | 137-1036 | *Klebsiella variicola* | 201712002 | Dec. 20, 2017 |

Isolated and Biologically Pure Microorganisms

The present disclosure, in certain embodiments, provides isolated and biologically pure microorganisms that have applications, inter alia, in agriculture. The disclosed microorganisms can be utilized in their isolated and biologically pure states, as well as being formulated into compositions (see below section for exemplary composition descriptions). Furthermore, the disclosure provides microbial compositions containing at least two members of the disclosed isolated and biologically pure microorganisms, as well as methods of utilizing said microbial compositions. Furthermore, the disclosure provides for methods of modulating nitrogen fixation in plants via the utilization of the disclosed isolated and biologically pure microbes.

In some aspects, the isolated and biologically pure microorganisms of the disclosure are those from Table A. In other aspects, the isolated and biologically pure microorganisms of the disclosure are derived from a microorganism of Table A. For example, a strain, child, mutant, or derivative, of a microorganism from Table A are provided herein. The disclosure contemplates all possible combinations of microbes listed in Table A, said combinations sometimes forming a microbial consortia. The microbes from Table A, either individually or in any combination, can be combined with any plant, active (synthetic, organic, etc.), adjuvant, carrier, supplement, or biological, mentioned in the disclosure.

Compositions

Compositions comprising bacteria or bacterial populations produced according to methods described herein and/or having characteristics as described herein can be in the form of a liquid, a foam, or a dry product. Compositions comprising bacteria or bacterial populations produced according to methods described herein and/or having characteristics as described herein may also be used to improve plant traits. In some examples, a composition comprising bacterial populations may be in the form of a dry powder, a slurry of powder and water, or a flowable seed treatment. The compositions comprising bacterial populations may be coated on a surface of a seed, and may be in liquid form.

The composition can be fabricated in bioreactors such as continuous stirred tank reactors, batch reactors, and on the farm. In some examples, compositions can be stored in a container, such as a jug or in mini bulk. In some examples, compositions may be stored within an object selected from the group consisting of a bottle, jar, ampule, package, vessel, bag, box, bin, envelope, carton, container, silo, shipping container, truck bed, and/or case.

Compositions may also be used to improve plant traits. In some examples, one or more compositions may be coated onto a seed. In some examples, one or more compositions may be coated onto a seedling. In some examples, one or more compositions may be coated onto a surface of a seed. In some examples, one or more compositions may be coated as a layer above a surface of a seed. In some examples, a composition that is coated onto a seed may be in liquid form, in dry product form, in foam form, in a form of a slurry of powder and water, or in a flowable seed treatment. In some examples, one or more compositions may be applied to a seed and/or seedling by spraying, immersing, coating, encapsulating, and/or dusting the seed and/or seedling with the one or more compositions. In some examples, multiple bacteria or bacterial populations can be coated onto a seed and/or a seedling of the plant. In some examples, at least two, at least three, at least four, at least five, at least six, at least seven, at least eight, at least nine, at least ten, or more than ten bacteria of a bacterial combination can be selected from one of the following genera: *Acidovorax, Agrobacterium, Bacillus, Burkholderia, Chryseobacterium, Curtobacterium, Enterobacter, Escherichia, Methylobacterium, Paenibacillus, Pantoea, Pseudomonas, Ralstonia, Saccharibacillus, Sphingomonas,* and *Stenotrophomonas.*

In some examples, at least two, at least three, at least four, at least five, at least six, at least seven, at least eight, at least nine, at least ten, or more than ten bacteria and bacterial populations of an endophytic combination are selected from one of the following families: Bacillaceae, Burkholderiaceae, Comamonadaceae, Enterobacteriaceae, Flavobacteriaceae, Methylobacteriaceae, Microbacteriaceae, Paenibacillileae, Pseudomonnaceae, Rhizobiaceae, Sphingomonadaceae, Xanthomonadaceae, Cladosporiaceae, Gnomoniaceae, Incertae sedis, Lasiosphaeriaceae, Netriaceae, and Pleosporaceae.

In some examples, at least two, at least three, at least four, at least five, at least six, at least seven, at least eight, at least night, at least ten, or more than ten bacteria and bacterial populations of an endophytic combination are selected from one of the following families: Bacillaceae, Burkholderiaceae, Comamonadaceae, Enterobacteriaceae, Flavobacteriaceae, Methylobacteriaceae, Microbacteriaceae, Paenibacillileae, Pseudomonnaceae, Rhizobiaceae, Sphingomonadaceae, Xanthomonadaceae, Cladosporiaceae, Gnomoniaceae, Incertae sedis, Lasiosphaeriaceae, Netriaceae, Pleosporaceae.

Examples of compositions may include seed coatings for commercially important agricultural crops, for example, sorghum, canola, tomato, strawberry, barley, rice, maize, and wheat. Examples of compositions can also include seed coatings for corn, soybean, canola, sorghum, potato, rice, vegetables, cereals, and oilseeds. Seeds as provided herein can be genetically modified organisms (GMO), non-GMO, organic, or conventional. In some examples, compositions may be sprayed on the plant aerial parts, or applied to the roots by inserting into furrows in which the plant seeds are planted, watering to the soil, or dipping the roots in a suspension of the composition. In some examples, compositions may be dehydrated in a suitable manner that maintains cell viability and the ability to artificially inoculate and colonize host plants. The bacterial species may be present in compositions at a concentration of between $10^8$ to $10^{10}$ CFU/ml. In some examples, compositions may be supplemented with trace metal ions, such as molybdenum ions, iron ions, manganese ions, or combinations of these ions. The concentration of ions in examples of compositions as described herein may between about 0.1 mM and about 50 mM. Some examples of compositions may also be formulated with a carrier, such as beta-glucan, carboxylmethyl cellulose (CMC), bacterial extracellular polymeric substance (EPS), sugar, animal milk, or other suitable carriers. In some examples, peat or planting materials can be used as a carrier, or biopolymers in which a composition is entrapped in the biopolymer can be used as a carrier. The compositions comprising the bacterial populations described herein can improve plant traits, such as promoting plant growth, maintaining high chlorophyll content in leaves, increasing fruit or seed numbers, and increasing fruit or seed unit weight.

The compositions comprising the bacterial populations described herein may be coated onto the surface of a seed. As such, compositions comprising a seed coated with one or more bacteria described herein are also contemplated. The seed coating can be formed by mixing the bacterial population with a porous, chemically inert granular carrier. Alternatively, the compositions may be inserted directly into the furrows into which the seed is planted or sprayed onto the plant leaves or applied by dipping the roots into a suspension of the composition. An effective amount of the composition can be used to populate the sub-soil region adjacent to the roots of the plant with viable bacterial growth, or populate the leaves of the plant with viable bacterial growth. In general, an effective amount is an amount sufficient to result in plants with improved traits (e.g. a desired level of nitrogen fixation).

Bacterial compositions described herein can be formulated using an agriculturally acceptable carrier. The formulation useful for these embodiments may include at least one member selected from the group consisting of a tackifier, a microbial stabilizer, a fungicide, an antibacterial agent, a preservative, a stabilizer, a surfactant, an anti-complex agent, an herbicide, a nematicide, an insecticide, a plant growth regulator, a fertilizer, a rodenticide, a desiccant, a bactericide, a nutrient, or any combination thereof. In some examples, compositions may be shelf-stable. For example, any of the compositions described herein can include an agriculturally acceptable carrier (e.g., one or more of a fertilizer such as a non-naturally occurring fertilizer, an adhesion agent such as a non-naturally occurring adhesion agent, and a pesticide such as a non-naturally occurring pesticide). A non-naturally occurring adhesion agent can be, for example, a polymer, copolymer, or synthetic wax. For example, any of the coated seeds, seedlings, or plants described herein can contain such an agriculturally acceptable carrier in the seed coating. In any of the compositions or methods described herein, an agriculturally acceptable carrier can be or can include a non-naturally occurring compound (e.g., a non-naturally occurring fertilizer, a non-naturally occurring adhesion agent such as a polymer, copolymer, or synthetic wax, or a non-naturally occurring pesticide). Non-limiting examples of agriculturally acceptable carriers are described below. Additional examples of agriculturally acceptable carriers are known in the art.

In some cases, bacteria are mixed with an agriculturally acceptable carrier. The carrier can be a solid carrier or liquid carrier, and in various forms including microspheres, powders, emulsions and the like. The carrier may be any one or more of a number of carriers that confer a variety of properties, such as increased stability, wettability, or dispersability. Wetting agents such as natural or synthetic surfactants, which can be nonionic or ionic surfactants, or a combination thereof can be included in the composition. Water-in-oil emulsions can also be used to formulate a composition that includes the isolated bacteria (see, for example, U.S. Pat. No. 7,485,451). Suitable formulations that may be prepared include wettable powders, granules, gels, agar strips or pellets, thickeners, and the like, microencapsulated particles, and the like, liquids such as aqueous flowables, aqueous suspensions, water-in-oil emulsions, etc. The formulation may include grain or legume products, for example, ground grain or beans, broth or flour derived from grain or beans, starch, sugar, or oil.

In some embodiments, the agricultural carrier may be soil or a plant growth medium. Other agricultural carriers that may be used include water, fertilizers, plant-based oils, humectants, or combinations thereof. Alternatively, the agricultural carrier may be a solid, such as diatomaceous earth, loam, silica, alginate, clay, bentonite, vermiculite, seed cases, other plant and animal products, or combinations, including granules, pellets, or suspensions. Mixtures of any of the aforementioned ingredients are also contemplated as carriers, such as but not limited to, pesta (flour and kaolin clay), agar or flour-based pellets in loam, sand, or clay, etc. Formulations may include food sources for the bacteria, such as barley, rice, or other biological materials such as seed, plant parts, sugar cane bagasse, hulls or stalks from grain processing, ground plant material or wood from building site refuse, sawdust or small fibers from recycling of paper, fabric, or wood.

For example, a fertilizer can be used to help promote the growth or provide nutrients to a seed, seedling, or plant. Non-limiting examples of fertilizers include nitrogen, phosphorous, potassium, calcium, sulfur, magnesium, boron, chloride, manganese, iron, zinc, copper, molybdenum, and selenium (or a salt thereof). Additional examples of fertilizers include one or more amino acids, salts, carbohydrates, vitamins, glucose, NaCl, yeast extract, $NH_4H_2PO_4$, $(NH_4)_2SO_4$, glycerol, valine, L-leucine, lactic acid, propionic acid, succinic acid, malic acid, citric acid, KH tartrate, xylose, lyxose, and lecithin. In one embodiment, the formulation can include a tackifier or adherent (referred to as an adhesive agent) to help bind other active agents to a substance (e.g., a surface of a seed). Such agents are useful for combining bacteria with carriers that can contain other compounds (e.g., control agents that are not biologic), to yield a coating composition. Such compositions help create coatings around the plant or seed to maintain contact between the microbe and other agents with the plant or plant part. In one embodiment, adhesives are selected from the group consisting of: alginate, gums, starches, lecithins, formononetin, polyvinyl alcohol, alkali formononetinate, hesperetin, polyvinyl acetate, cephalins, Gum Arabic, Xanthan Gum, Mineral Oil, Polyethylene Glycol (PEG), Polyvinyl pyrrolidone (PVP), Arabino-galactan, Methyl Cellulose, PEG 400, Chitosan, Polyacrylamide, Polyacrylate, Polyacrylonitrile, Glycerol, Triethylene glycol, Vinyl Acetate, Gellan Gum, Polystyrene, Polyvinyl, Carboxymethyl cellulose, Gum Ghatti, and polyoxyethylene-polyoxybutylene block copolymers.

In some embodiments, the adhesives can be, e.g. a wax such as carnauba wax, beeswax, Chinese wax, shellac wax, spermaceti wax, candelilla wax, castor wax, ouricury wax, and rice bran wax, a polysaccharide (e.g., starch, dextrins, maltodextrins, alginate, and chitosans), a fat, oil, a protein (e.g., gelatin and zeins), gum arables, and shellacs. Adhesive agents can be non-naturally occurring compounds, e.g., polymers, copolymers, and waxes. For example, non-limiting examples of polymers that can be used as an adhesive agent include: polyvinyl acetates, polyvinyl acetate copolymers, ethylene vinyl acetate (EVA) copolymers, polyvinyl alcohols, polyvinyl alcohol copolymers, celluloses (e.g., ethylcelluloses, methylcelluloses, hydroxymethylcelluloses, hydroxypropylcelluloses, and carboxymethylcelluloses), polyvinylpyrolidones, vinyl chloride, vinylidene chloride copolymers, calcium lignosulfonates, acrylic copolymers, polyvinylacrylates, polyethylene oxide, acylamide polymers and copolymers, polyhydroxyethyl acrylate, methylacrylamide monomers, and polychloroprene.

In some examples, one or more of the adhesion agents, anti-fungal agents, growth regulation agents, and pesticides (e.g., insecticide) are non-naturally occurring compounds (e.g., in any combination). Additional examples of agriculturally acceptable carriers include dispersants (e.g., polyvinylpyrrolidone/vinyl acetate PVPIVA S-630), surfactants, binders, and filler agents.

The formulation can also contain a surfactant. Non-limiting examples of surfactants include nitrogen-surfactant blends such as Prefer 28 (Cenex), Surf-N (US), Inhance (Brandt), P-28 (Wilfarm) and Patrol (Helena); esterified seed oils include Sun-It II (AmCy), MSO (UAP), Scoil (Agsco), Hasten (Wilfarm) and Mes-100 (Drexel); and organo-silicone surfactants include Silwet L77 (UAP), Silikin (Terra), Dyne-Amic (Helena), Kinetic (Helena), Sylgard 309 (Wilbur-Ellis) and Century (Precision). In one embodiment, the surfactant is present at a concentration of between 0.01% v/v to 10% v/v. In another embodiment, the surfactant is present at a concentration of between 0.1% v/v to 1% v/v.

In certain cases, the formulation includes a microbial stabilizer. Such an agent can include a desiccant, which can include any compound or mixture of compounds that can be classified as a desiccant regardless of whether the compound or compounds are used in such concentrations that they in fact have a desiccating effect on a liquid inoculant. Such desiccants are ideally compatible with the bacterial population used, and should promote the ability of the microbial population to survive application on the seeds and to survive desiccation. Examples of suitable desiccants include one or more of trehalose, sucrose, glycerol, and Methylene glycol. Other suitable desiccants include, but are not limited to, non reducing sugars and sugar alcohols (e.g., mannitol or sorbitol). The amount of desiccant introduced into the formulation can range from about 5% to about 50% by weight/volume, for example, between about 10% to about 40%, between about 15% to about 35%, or between about 20%, to about 30%. In some cases, it is advantageous for the formulation to contain agents such as a fungicide, an antibacterial agent, an herbicide, a nematicide, an insecticide, a plant growth regulator, a rodenticide, bactericide, or a nutrient. In some examples, agents may include protectants that provide protection against seed surface-borne pathogens. In some examples, protectants may provide some level of control of soil-borne pathogens. In some examples, protectants may be effective predominantly on a seed surface.

In some examples, a fungicide may include a compound or agent, whether chemical or biological, that can inhibit the growth of a fungus or kill a fungus. In some examples, a fungicide may include compounds that may be fungistatic or fungicidal. In some examples, fungicide can be a protectant, or agents that are effective predominantly on the seed surface, providing protection against seed surface-borne pathogens and providing some level of control of soil-borne pathogens. Non-limiting examples of protectant fungicides include captan, maneb, thiram, or fludioxonil.

In some examples, fungicide can be a systemic fungicide, which can be absorbed into the emerging seedling and inhibit or kill the fungus inside host plant tissues. Systemic fungicides used for seed treatment include, but are not limited to the following: azoxystrobin, carboxin, mefenoxam, metalaxyl, thiabendazole, trifloxystrobin, and various triazole fungicides, including difenoconazole, ipconazole, tebuconazole, and triticonazole. Mefenoxam and metalaxyl are primarily used to target the water mold fungi *Pythium* and *Phytophthora*. Some fungicides are preferred over others, depending on the plant species, either because of subtle differences in sensitivity of the pathogenic fungal species, or because of the differences in the fungicide distribution or sensitivity of the plants. In some examples, fungicide can be a biological control agent, such as a bacterium or fungus. Such organisms may be parasitic to the pathogenic fungi, or secrete toxins or other substances which can kill or otherwise prevent the growth of fungi. Any type of fungicide, particularly ones that are commonly used on plants, can be used as a control agent in a seed composition.

In some examples, the seed coating composition comprises a control agent which has antibacterial properties. In one embodiment, the control agent with antibacterial properties is selected from the compounds described herein elsewhere. In another embodiment, the compound is Streptomycin, oxytetracycline, oxolinic acid, or gentamicin. Other examples of antibacterial compounds which can be used as part of a seed coating composition include those based on dichlorophene and benzylalcohol hemi formal (Proxel® from ICI or Acticide® RS from Thor Chemie and Kathon® MK 25 from Rohm & Haas) and isothiazolinone derivatives such as alkylisothiazolinones and benzisothiazolinones (Acticide® MBS from Thor Chemie).

In some examples, growth regulator is selected from the group consisting of: Abscisic acid, amidochlor, ancymidol, 6-benzylaminopurine, brassinolide, butralin, chlormequat (chlormequat chloride), choline chloride, cyclanilide, daminozide, dikegulac, dimethipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat (mepiquat chloride), naphthaleneacetic acid, N-6-benzyladenine, paclobutrazol, prohexadione phosphorotrithioate, 2,3,5-tri-iodobenzoic acid, trinexapac-ethyl and uniconazole. Additional non-limiting examples of growth regulators include brassinosteroids, cytokinines (e.g., kinetin and zeatin), auxins (e.g., indolylacetic acid and indolylacetyl aspartate), flavonoids and isoflavanoids (e.g., formononetin and diosmetin), phytoaixins (e.g., glyceolline), and phytoalexin-inducing oligosaccharides (e.g., pectin, chitin, chitosan, polygalacuronic acid, and oligogalacturonic acid), and gibellerins. Such agents are ideally compatible with the agricultural seed or seedling onto which the formulation is applied (e.g., it should not be deleterious to the growth or health of the plant). Furthermore, the agent is ideally one which does not cause safety concerns for human, animal or industrial use (e.g., no safety issues, or the compound is sufficiently labile that the commodity plant product derived from the plant contains negligible amounts of the compound).

Some examples of nematode-antagonistic biocontrol agents include ARF18; 30 *Arthrobotrys* spp.; *Chaetomium* spp.; *Cylindrocarpon* spp.; *Exophilia* spp.; *Fusarium* spp.; *Gliocladium* spp.; *Hirsutella* spp.; *Lecanicillium* spp.; *Monacrosporium* spp.; *Myrothecium* spp.; *Neocosmospora* spp.; *Paecilomyces* spp.; *Pochonia* spp.; *Stagonospora* spp.; vesicular-arbuscular mycorrhizal fungi, *Burkholderia* spp.; *Pasteuria* spp., *Brevibacillus* spp.; *Pseudomonas* spp.; and *Rhizobacteria*. Particularly preferred nematode-antagonistic biocontrol agents include ARF18, *Arthrobotrys oligospora, Arthrobotrys dactyloides, Chaetomium globosum, Cylindrocarpon heteronema, Exophilia jeanselmei, Exophilia pisciphila, Fusarium aspergilus, Fusarium solani, Gliocladium catenulatum, Gliocladium roseum, Gliocladium vixens, Hirsutella rhossiliensis, Hirsutella minnesotensis, Lecanicillium lecanii, Monacrosporium drechsleri, Monacrosporium gephyropagum, Myrotehcium verrucaria, Neocosmospora vasinfecta, Paecilomyces lilacinus, Pochonia chlamydosporia, Stagonospora heteroderae, Stagonospora phaseoli*, vesicular-arbuscular mycorrhizal fungi, *Burkholderia cepacia, Pasteuria penetrans, Pasteuria thornei, Pasteuria nishizawae, Pasteuria ramosa, Pastrueia usage, Brevibacillus laterosporus* strain G4, *Pseudomonas fluorescens* and *Rhizobacteria*.

Some examples of nutrients can be selected from the group consisting of a nitrogen fertilizer including, but not limited to Urea, Ammonium nitrate, Ammonium sulfate, Non-pressure nitrogen solutions, Aqua ammonia, Anhydrous ammonia, Ammonium thiosulfate, Sulfur-coated urea, Urea-formaldehydes, IBDU, Polymer-coated urea, Calcium nitrate, Ureaform, and Methylene urea, phosphorous fertilizers such as Diammonium phosphate, Monoammonium phosphate, Ammonium polyphosphate, Concentrated superphosphate and Triple superphosphate, and potassium fertilizers such as Potassium chloride, Potassium sulfate, Potassium-magnesium sulfate, Potassium nitrate. Such compositions can exist as free salts or ions within the seed coat composition. Alternatively, nutrients/fertilizers can be complexed or chelated to provide sustained release over time.

Some examples of rodenticides may include selected from the group of substances consisting of 2-isovalerylindan-1, 3-dione, 4-(quinoxalin-2-ylamino) benzenesulfonamide, alpha-chlorohydrin, aluminum phosphide, antu, arsenous oxide, barium carbonate, bisthiosemi, brodifacoum, bromadiolone, bromethalin, calcium cyanide, chloralose, chlorophacinone, cholecalciferol, coumachlor, coumafuryl, coumatetralyl, crimidine, difenacoum, difethialone, diphacinone, ergocalciferol, flocoumafen, fluoroacetamide, flupropadine, flupropadine hydrochloride, hydrogen cyanide, iodomethane, lindane, magnesium phosphide, methyl bromide, norbormide, phosacetim, phosphine, phosphorus, pindone, potassium arsenite, pyrinuron, scilliroside, sodium arsenite, sodium cyanide, sodium fluoroacetate, strychnine, thallium sulfate, warfarin and zinc phosphide.

In the liquid form, for example, solutions or suspensions, bacterial populations can be mixed or suspended in water or in aqueous solutions. Suitable liquid diluents or carriers include water, aqueous solutions, petroleum distillates, or other liquid carriers.

Solid compositions can be prepared by dispersing the bacterial populations in and on an appropriately divided solid carrier, such as peat, wheat, bran, vermiculite, clay, talc, bentonite, diatomaceous earth, fuller's earth, pasteurized soil, and the like. When such formulations are used as wettable powders, biologically compatible dispersing agents such as non-ionic, anionic, amphoteric, or cationic dispersing and emulsifying agents can be used.

The solid carriers used upon formulation include, for example, mineral carriers such as kaolin clay, pyrophyllite, bentonite, montmorillonite, diatomaceous earth, acid white soil, vermiculite, and pearlite, and inorganic salts such as ammonium sulfate, ammonium phosphate, ammonium nitrate, urea, ammonium chloride, and calcium carbonate. Also, organic fine powders such as wheat flour, wheat bran, and rice bran may be used. The liquid carriers include vegetable oils such as soybean oil and cottonseed oil, glycerol, ethylene glycol, polyethylene glycol, propylene glycol, polypropylene glycol, etc.

Application of Bacterial Populations on Crops

The composition of the bacteria or bacterial population described herein can be applied in furrow, in talc, or as seed treatment. The composition can be applied to a seed package in bulk, mini bulk, in a bag, or in talc.

The planter can plant the treated seed and grows the crop according to conventional ways, twin row, or ways that do not require tilling. The seeds can be distributed using a control hopper or an individual hopper. Seeds can also be distributed using pressurized air or manually. Seed placement can be performed using variable rate technologies. Additionally, application of the bacteria or bacterial population described herein may be applied using variable rate technologies. In some examples, the bacteria can be applied to seeds of corn, soybean, canola, sorghum, potato, rice, vegetables, cereals, pseudocereals, and oilseeds. Examples of cereals may include barley, fonio, oats, palmer's grass, rye, pearl millet, sorghum, spelt, teff, triticale, and wheat. Examples of pseudocereals may include breadnut, buckwheat, cattail, chia, flax, grain amaranth, hanza, quinoa, and sesame. In some examples, seeds can be genetically modified organisms (GMO), non-GMO, organic or conventional.

Additives such as micro-fertilizer, PGR, herbicide, insecticide, and fungicide can be used additionally to treat the crops. Examples of additives include crop protectants such as insecticides, nematicides, fungicide, enhancement agents such as colorants, polymers, pelleting, priming, and disinfectants, and other agents such as inoculant, PGR, softener, and micronutrients. PGRs can be natural or synthetic plant hormones that affect root growth, flowering, or stem elongation. PGRs can include auxins, gibberellins, cytokinins, ethylene, and abscisic acid (ABA).

The composition can be applied in furrow in combination with liquid fertilizer. In some examples, the liquid fertilizer may be held in tanks. NPK fertilizers contain macronutrients of sodium, phosphorous, and potassium.

The composition may improve plant traits, such as promoting plant growth, maintaining high chlorophyll content in leaves, increasing fruit or seed numbers, and increasing fruit or seed unit weight. Methods of the present disclosure may be employed to introduce or improve one or more of a variety of desirable traits. Examples of traits that may introduced or improved include: root biomass, root length, height, shoot length, leaf number, water use efficiency, overall biomass, yield, fruit size, grain size, photosynthesis rate, tolerance to drought, heat tolerance, salt tolerance, tolerance to low nitrogen stress, nitrogen use efficiency, resistance to nematode stress, resistance to a fungal pathogen, resistance to a bacterial pathogen, resistance to a viral pathogen, level of a metabolite, modulation in level of a metabolite, proteome expression. The desirable traits, including height, overall biomass, root and/or shoot biomass, seed germination, seedling survival, photosynthetic efficiency, transpiration rate, seed/fruit number or mass, plant grain or fruit yield, leaf chlorophyll content, photosynthetic rate, root length, or any combination thereof, can be used to measure growth, and compared with the growth rate of reference agricultural plants (e.g., plants without the introduced and/or improved traits) grown under identical conditions. In some examples, the desirable traits, including height, overall biomass, root and/or shoot biomass, seed germination, seedling survival, photosynthetic efficiency, transpiration rate, seed/fruit number or mass, plant grain or fruit yield, leaf chlorophyll content, photosynthetic rate, root length, or any combination thereof, can be used to measure growth, and compared with the growth rate of reference agricultural plants (e.g., plants without the introduced and/or improved traits) grown under similar conditions.

An agronomic trait to a host plant may include, but is not limited to, the following: altered oil content, altered protein content, altered seed carbohydrate composition, altered seed oil composition, and altered seed protein composition, chemical tolerance, cold tolerance, delayed senescence, disease resistance, drought tolerance, ear weight, growth improvement, health enhancement, heat tolerance, herbicide tolerance, herbivore resistance improved nitrogen fixation, improved nitrogen utilization, improved root architecture, improved water use efficiency, increased biomass, increased root length, increased seed weight, increased shoot length, increased yield, increased yield under water-limited conditions, kernel mass, kernel moisture content, metal tolerance, number of ears, number of kernels per ear, number of pods, nutrition enhancement, pathogen resistance, pest resistance, photosynthetic capability improvement, salinity tolerance, stay-green, vigor improvement, increased dry weight of mature seeds, increased fresh weight of mature seeds, increased number of mature seeds per plant, increased chlorophyll content, increased number of pods per plant, increased length of pods per plant, reduced number of wilted leaves per plant, reduced number of severely wilted leaves per plant, and increased number of non-wilted leaves per plant, a detectable modulation in the level of a metabolite, a detectable modulation in the level of a transcript, and a detectable modulation in the proteome, compared to an isoline plant grown from a seed without said seed treatment formulation.

In some cases, plants are inoculated with bacteria or bacterial populations that are isolated from the same species of plant as the plant element of the inoculated plant. For example, an bacteria or bacterial population that is normally found in one variety of *Zea mays* (corn) is associated with a plant element of a plant of another variety of *Zea mays* that in its natural state lacks said bacteria and bacterial populations. In one embodiment, the bacteria and bacterial populations is derived from a plant of a related species of plant as the plant element of the inoculated plant. For example, an bacteria and bacterial populations that is normally found in *Zea diploperennis* Iltis et al., (diploperennial teosinte) is applied to a *Zea mays* (corn), or vice versa. In some cases, plants are inoculated with bacteria and bacterial populations that are heterologous to the plant element of the inoculated plant. In one embodiment, the bacteria and bacterial populations is derived from a plant of another species. For example, an bacteria and bacterial populations that is normally found in dicots is applied to a monocot plant (e.g., inoculating corn with a soybean-derived bacteria and bacterial populations), or vice versa. In other cases, the bacteria and bacterial populations to be inoculated onto a plant is derived from a related species of the plant that is being inoculated. In one embodiment, the bacteria and bacterial populations is derived from a related taxon, for example, from a related species. The plant of another species can be an agricultural plant. In another embodiment, the bacteria and bacterial populations is part of a designed composition inoculated into any host plant element.

In some examples, the bacteria or bacterial population is exogenous wherein the bacteria and bacterial population is isolated from a different plant than the inoculated plant. For example, in one embodiment, the bacteria or bacterial population can be isolated from a different plant of the same species as the inoculated plant. In some cases, the bacteria or bacterial population can be isolated from a species related to the inoculated plant.

In some examples, the bacteria and bacterial populations described herein are capable of moving from one tissue type to another. For example, the present invention's detection and isolation of bacteria and bacterial populations within the mature tissues of plants after coating on the exterior of a seed demonstrates their ability to move from seed exterior into the vegetative tissues of a maturing plant. Therefore, in one embodiment, the population of bacteria and bacterial populations is capable of moving from the seed exterior into the vegetative tissues of a plant. In one embodiment, the bacteria and bacterial populations that is coated onto the seed of a plant is capable, upon germination of the seed into a vegetative state, of localizing to a different tissue of the plant. For example, bacteria and bacterial populations can be capable of localizing to any one of the tissues in the plant, including: the root, adventitious root, seminal 5 root, root hair, shoot, leaf, flower, bud, tassel, meristem, pollen, pistil, ovaries, stamen, fruit, stolon, rhizome, nodule, tuber, trichome, guard cells, hydathode, petal, sepal, glume, rachis, vascular cambium, phloem, and xylem. In one embodiment, the bacteria and bacterial populations is capable of localizing to the root and/or the root hair of the plant. In another embodiment, the bacteria and bacterial populations is capable of localizing to the photosynthetic tissues, for example, leaves and shoots of the plant. In other cases, the bacteria and bacterial populations is localized to the vascular tissues of the plant, for example, in the xylem and phloem. In still another embodiment, the bacteria and bacterial populations is capable of localizing to the reproductive tissues (flower, pollen, pistil, ovaries, stamen, fruit) of the plant. In another embodiment, the bacteria and bacterial populations is capable of localizing to the root, shoots, leaves and reproductive tissues of the plant. In still another embodiment, the bacteria and bacterial populations colonizes a fruit or seed tissue of the plant. In still another embodiment, the bacteria and bacterial populations is able to colonize the plant such that it is present in the surface of the plant (i.e., its presence is detectably present on the plant exterior, or the episphere of the plant). In still other embodiments, the bacteria and bacterial populations is capable of localizing to substantially all, or all, tissues of the plant. In certain embodiments, the bacteria and bacterial populations is not localized to the root of a plant. In other cases, the bacteria and bacterial populations is not localized to the photosynthetic tissues of the plant.

The effectiveness of the compositions can also be assessed by measuring the relative maturity of the crop or the crop heating unit (CHU). For example, the bacterial population can be applied to corn, and corn growth can be assessed according to the relative maturity of the corn kernel or the time at which the corn kernel is at maximum weight. The crop heating unit (CHU) can also be used to predict the maturation of the corn crop. The CHU determines the amount of heat accumulation by measuring the daily maximum temperatures on crop growth.

In examples, bacterial may localize to any one of the tissues in the plant, including: the root, adventitious root, seminal root, root hair, shoot, leaf, flower, bud tassel, meristem, pollen, pistil, ovaries, stamen, fruit, stolon, rhizome, nodule, tuber, trichome, guard cells, hydathode, petal, sepal, glume, rachis, vascular cambium, phloem, and xylem. In another embodiment, the bacteria or bacterial population is capable of localizing to the photosynthetic tissues, for example, leaves and shoots of the plant. In other cases, the bacteria and bacterial populations is localized to the vascular tissues of the plant, for example, in the xylem and phloem. In another embodiment, the bacteria or bacterial population is capable of localizing to reproductive tissues (flower, pollen, pistil, ovaries, stamen, or fruit) of the plant. In another embodiment, the bacteria and bacterial populations is capable of localizing to the root, shoots, leaves and reproductive tissues of the plant. In another embodiment, the bacteria or bacterial population colonizes a fruit or seed tissue of the plant. In still another embodiment, the bacteria or bacterial population is able to colonize the plant such that it is present in the surface of the plant. In another embodiment, the bacteria or bacterial population is capable of localizing to substantially all, or all, tissues of the plant. In certain embodiments, the bacteria or bacterial population is not localized to the root of a plant. In other cases, the bacteria and bacterial populations is not localized to the photosynthetic tissues of the plant.

The effectiveness of the bacterial compositions applied to crops can be assessed by measuring various features of crop growth including, but not limited to, planting rate, seeding vigor, root strength, drought tolerance, plant height, dry down, and test weight.

Plant Species

The methods and bacteria described herein are suitable for any of a variety of plants, such as plants in the genera *Hordeum*, *Oryza*, *Zea*, and *Triticeae*. Other non-limiting examples of suitable plants include mosses, lichens, and algae. In some cases, the plants have economic, social and/or environmental value, such as food crops, fiber crops, oil crops, plants in the forestry or pulp and paper industries, feedstock for biofuel production and/or ornamental plants. In some examples, plants may be used to produce economically valuable products such as a grain, a flour, a starch, a syrup, a meal, an oil, a film, a packaging, a nutraceutical product, a pulp, an animal feed, a fish fodder, a bulk material for industrial chemicals, a cereal product, a processed human-food product, a sugar, an alcohol, and/or a protein. Non-limiting examples of crop plants include maize, rice, wheat, barley, *sorghum*, millet, oats, rye triticale, buckwheat, sweet corn, sugar cane, onions, tomatoes, strawberries, and asparagus.

In some examples, plants that may be obtained or improved using the methods and composition disclosed herein may include plants that are important or interesting for agriculture, horticulture, biomass for the production of biofuel molecules and other chemicals, and/or forestry. Some examples of these plants may include pineapple, banana, coconut, lily, grasspeas and grass; and dicotyledonous plants, such as, for example, peas, alfalfa, tomatillo, melon, chickpea, chicory, clover, kale, lentil, soybean, tobacco, potato, sweet potato, radish, cabbage, rape, apple trees, grape, cotton, sunflower, thale cress, canola, citrus (including orange, mandarin, kumquat, lemon, lime, grapefruit, tangerine, tangelo, citron, and pomelo), pepper, bean, lettuce, *Panicum virgatum* (switch), *Sorghum bicolor* (*sorghum, sudan*), *Miscanthus giganteus* (*miscanthus*), *Saccharum* sp. (energycane), *Populus balsamifera* (poplar), *Zea mays* (corn), *Glycine max* (soybean), *Brassica napus* (canola), *Triticum aestivum* (wheat), *Gossypium hirsutum* (cotton), *Oryza sativa* (rice), *Helianthus annuus* (sunflower), *Medicago sativa* (alfalfa), *Beta vulgaris* (sugarbeet), *Pennisetum glaucum* (pearl millet), *Panicum* spp. *Sorghum* spp., *Miscanthus* spp., *Saccharum* spp., *Erianthus* spp., *Populus* spp., *Secale cereale* (rye), *Salix* spp. (willow), *Eucalyptus* spp. (*eucalyptus*), *Triticosecale* spp. (*triticum*-25 wheat X rye), Bamboo, *Carthamus tinctorius* (safflower), *Jatropha curcas* (*Jatropha*), *Ricinus communis* (castor), *Elaeis guineensis* (oil palm), *Phoenix dactylifera* (date palm), *Archontophoenix cunninghamiana* (king palm), *Syagrus romanzoffiana* (queen palm), *Linum usitatissimum* (flax), *Brassica juncea*, *Manihot esculenta* (cassaya), *Lycopersicon esculentum* (tomato), *Lactuca saliva* (lettuce), *Musa paradisiaca* (banana), *Solanum tuberosum* (potato), *Brassica oleracea* (broccoli, cauliflower, brussel sprouts), *Camellia sinensis* (tea), *Fragaria ananassa* (strawberry), *Theobroma cacao* (cocoa), *Coffea arabica* (coffee), *Vitis vinifera* (grape), *Ananas comosus* (pineapple), *Capsicum annum* (hot & sweet pepper), *Allium cepa* (onion), *Cucumis melo* (melon), *Cucumis sativus* (cucumber), *Cucurbita maxima* (squash), *Cucurbita moschata* (squash), *Spinacea oleracea* (spinach), *Citrullus lanatus* (watermelon), *Abelmoschus esculentus* (okra), *Solanum melongena* (eggplant), *Papaver somniferum* (opium poppy), *Papaver orientale*, *Taxus baccata*, *Taxus brevifolia*, *Artemisia annua*, *Cannabis saliva*, *Camptotheca acuminate*, *Catharanthus roseus*, *Vinca rosea*, *Cinchona officinalis*, *Coichicum autumnale*, *Veratrum californica*, *Digitalis lanata*, *Digitalis purpurea*, *Dioscorea* 5 spp., *Andrographis paniculata*, *Atropa belladonna*, *Datura stomonium*, *Berberis* spp., *Cephalotaxus* spp., *Ephedra sinica*, *Ephedra* spp., *Erythroxylum coca*, *Galanthus wornorii*, *Scopolia* spp., *Lycopodium serratum* (*Huperzia serrata*), *Lycopodium* spp., *Rauwolfia serpentina*, *Rauwolfia* spp., *Sanguinaria canadensis*, *Hyoscyamus* spp., *Calendula officinalis*, *Chrysanthemum parthenium*, *Coleus forskohlii*, *Tanacetum parthenium*, *Parthenium argentatum* (guayule), *Hevea* spp. (rubber), *Mentha spicata* (mint), *Mentha piperita* (mint), *Bixa orellana*, *Alstroemeria* spp., *Rosa* spp. (rose), *Dianthus caryophyllus* (carnation), *Petunia* spp. (*petunia*), *Poinsettia pulcherrima* (poinsettia), *Nicotiana tabacum* (tobacco), *Lupinus albus* (lupin), *Uniola paniculata* (oats), *Hordeum vulgare* (barley), and *Lolium* spp. (rye).

In some examples, a monocotyledonous plant may be used. Monocotyledonous plants belong to the orders of the Alismatales, Arales, Arecales, Bromeliales, Commelinales, Cyclanthales, Cyperales, Eriocaulales, Hydrocharitales, Juncales, Lilliales, Najadales. Orchidales, Pandanales, Poales, Restionales, Triuridales, Typhales, and Zingiberales. Plants belonging to the class of the Gymnospermae are Cycadales, Ginkgoales, Gnetales, and Pinales. In some examples, the monocotyledonous plant can be selected from the group consisting of a maize, rice, wheat, barley, and sugarcane.

In some examples, a dicotyledonous plant may be used, including those belonging to the orders of the Aristochiales, Asterales, Batales, Campanulales, Capparales, Caryophyllales, Casuarinales, Celastrales, Cornales, Diapensales, Dilleniales, Dipsacales, Ebenales, Ericales, Eucomiales, Euphorbiales, Fabales, Fagales, Gentianales, Geraniales, Haloragales, Hamamelidales, Middles, Juglandales, Lamiales, Laurales, Lecythidales, Leitneriales, Magniolales, Malvales, Myricales, Myrtales, Nymphaeales, Papeverales, Piperales, Plantaginales, Plumb aginales, Podostemales, Polemoniales, Polygalales, Polygonales, Primulales, Proteales, Rafflesiales, Ranunculales, Rhamnales, Rosales, Rubiales, Salicales, Santales, Sapindales, Sarraceniaceae, Scrophulariales, Theales, Trochodendrales, Umbellales, Urticales, and Violates. In some examples, the dicotyledonous plant can be selected from the group consisting of cotton, soybean, pepper, and tomato.

In some cases, the plant to be improved is not readily amenable to experimental conditions. For example, a crop plant may take too long to grow enough to practically assess an improved trait serially over multiple iterations. Accordingly, a first plant from which bacteria are initially isolated, and/or the plurality of plants to which genetically manipulated bacteria are applied may be a model plant, such as a plant more amenable to evaluation under desired conditions. Non-limiting examples of model plants include *Setaria, Brachypodium,* and *Arabidopsis.* Ability of bacteria isolated according to a method of the disclosure using a model plant may then be applied to a plant of another type (e.g. a crop plant) to confirm conferral of the improved trait.

Traits that may be improved by the methods disclosed herein include any observable characteristic of the plant, including, for example, growth rate, height, weight, color, taste, smell, changes in the production of one or more compounds by the plant (including for example, metabolites, proteins, drugs, carbohydrates, oils, and any other compounds). Selecting plants based on genotypic information is also envisaged (for example, including the pattern of plant gene expression in response to the bacteria, or identifying the presence of genetic markers, such as those associated with increased nitrogen fixation). Plants may also be selected based on the absence, suppression or inhibition of a certain feature or trait (such as an undesirable feature or trait) as opposed to the presence of a certain feature or trait (such as a desirable feature or trait).

Concentrations and Rates of Application of Agricultural Compositions

As aforementioned, the agricultural compositions of the present disclosure, which comprise a taught microbe, can be applied to plants in a multitude of ways. In two particular aspects, the disclosure contemplates an in-furrow treatment or a seed treatment For seed treatment embodiments, the microbes of the disclosure can be present on the seed in a variety of concentrations. For example, the microbes can be found in a seed treatment at a cfu concentration, per seed of: $1 \times 10^1$, $1 \times 10^2$, $1 \times 10^3$, $1 \times 10^4$, $1 \times 10^5$, $1 \times 10^6$, $1 \times 10^7$, $1 \times 10^8$, $1 \times 10^9$, $1 \times 10^{10}$, or more. In particular aspects, the seed treatment compositions comprise about $1 \times 10^4$ to about $1 \times 10^8$ cfu per seed. In other particular aspects, the seed treatment compositions comprise about $1 \times 10^5$ to about $1 \times 10^7$ cfu per seed. In other aspects, the seed treatment compositions comprise about $1 \times 10^6$ cfu per seed.

In the United States, about 10% of corn acreage is planted at a seed density of above about 36,000 seeds per acre; ⅓ of the corn acreage is planted at a seed density of between about 33,000 to 36,000 seeds per acre; ⅓ of the corn acreage is planted at a seed density of between about 30,000 to 33,000 seeds per acre, and the remainder of the acreage is variable. See, "Corn Seeding Rate Considerations," written by Steve Butzen, available at: https://www.pioneer.com/home/site/us/agronomy/library/corn-seeding-rate-considerations/

Table B below utilizes various cfu concentrations per seed in a contemplated seed treatment embodiment (rows across) and various seed acreage planting densities ($1^{st}$ column: 15K-41K) to calculate the total amount of cfu per acre, which would be utilized in various agricultural scenarios (i.e. seed treatment concentration per seed×seed density planted per acre). Thus, if one were to utilize a seed treatment with $1 \times 10^6$ cfu per seed and plant 30,000 seeds per acre, then the total cfu content per acre would be $3 \times 10^{10}$ (i.e. 30K*$1 \times 10^6$).

TABLE B

Total CFU Per Acre Calculation for Seed Treatment Embodiments

| Corn Population (i.e. seeds per acre) | 1.00E+02 | 1.00E+03 | 1.00E+04 | 1.00E+05 | 1.00E+06 | 1.00E+07 | 1.00E+08 | 1.00E+09 |
|---|---|---|---|---|---|---|---|---|
| 15,000 | 1.50E+06 | 1.50E+07 | 1.50E+08 | 1.50E+09 | 1.50E+10 | 1.50E+11 | 1.50E+12 | 1.50E+13 |
| 16,000 | 1.60E+06 | 1.60E+07 | 1.60E+08 | 1.60E+09 | 1.60E+10 | 1.60E+11 | 1.60E+12 | 1.60E+13 |
| 17,000 | 1.70E+06 | 1.70E+07 | 1.70E+08 | 1.70E+09 | 1.70E+10 | 1.70E+11 | 1.70E+12 | 1.70E+13 |
| 18,000 | 1.80E+06 | 1.80E+07 | 1.80E+08 | 1.80E+09 | 1.80E+10 | 1.80E+11 | 1.80E+12 | 1.80E+13 |
| 19,000 | 1.90E+06 | 1.90E+07 | 1.90E+08 | 1.90E+09 | 1.90E+10 | 1.90E+11 | 1.90E+12 | 1.90E+13 |
| 20,000 | 2.00E+06 | 2.00E+07 | 2.00E+08 | 2.00E+09 | 2.00E+10 | 2.00E+11 | 2.00E+12 | 2.00E+13 |
| 21,000 | 2.10E+06 | 2.10E+07 | 2.10E+08 | 2.10E+09 | 2.10E+10 | 2.10E+11 | 2.10E+12 | 2.10E+13 |
| 22,000 | 2.20E+06 | 2.20E+07 | 2.20E+08 | 2.20E+09 | 2.20E+10 | 2.20E+11 | 2.20E+12 | 2.20E+13 |
| 23,000 | 2.30E+06 | 2.30E+07 | 2.30E+08 | 2.30E+09 | 2.30E+10 | 2.30E+11 | 2.30E+12 | 2.30E+13 |
| 24,000 | 2.40E+06 | 2.40E+07 | 2.40E+08 | 2.40E+09 | 2.40E+10 | 2.40E+11 | 2.40E+12 | 2.40E+13 |
| 25,000 | 2.50E+06 | 2.50E+07 | 2.50E+08 | 2.50E+09 | 2.50E+10 | 2.50E+11 | 2.50E+12 | 2.50E+13 |
| 26,000 | 2.60E+06 | 2.60E+07 | 2.60E+08 | 2.60E+09 | 2.60E+10 | 2.60E+11 | 2.60E+12 | 2.64E+13 |
| 27,000 | 2.70E+06 | 2.70E+07 | 2.70E+08 | 2.70E+09 | 2.70E+10 | 2.70E+11 | 2.70E+12 | 2.70E+13 |
| 28,000 | 2.80E+06 | 2.80E+07 | 2.80E+08 | 2.80E+09 | 2.80E+10 | 2.80E+11 | 2.80E+12 | 2.80E+13 |

TABLE B-continued

Total CFU Per Acre Calculation for Seed Treatment Embodiments

| Corn Population (i.e. seeds per acre) | 1.00E+02 | 1.00E+03 | 1.00E+04 | 1.00E+05 | 1.00E+06 | 1.00E+07 | 1.00E+08 | 1.00E+09 |
|---|---|---|---|---|---|---|---|---|
| 29,000 | 2.90E+06 | 2.90E+07 | 2.90E+08 | 2.90E+09 | 2.90E+10 | 2.90E+11 | 2.90E+12 | 2.90E+13 |
| 30,000 | 3.00E+06 | 3.00E+07 | 3.00E+08 | 3.00E+09 | 3.00E+10 | 3.00E+11 | 3.00E+12 | 3.00E+13 |
| 31,000 | 3.10E+06 | 3.10E+07 | 3.10E+08 | 3.10E+09 | 3.10E+10 | 3.10E+11 | 3.10E+12 | 3.10E+13 |
| 32,000 | 3.20E+06 | 3.20E+07 | 3.20E+08 | 3.20E+09 | 3.20E+10 | 3.20E+11 | 3.20E+12 | 3.20E+13 |
| 33,000 | 3.30E+06 | 3.30E+07 | 3.30E+08 | 3.30E+09 | 3.30E+10 | 3.30E+11 | 3.30E+12 | 3.30E+13 |
| 34,000 | 3.40E+06 | 3.40E+07 | 3.40E+08 | 3.40E+09 | 3.40E+10 | 3.40E+11 | 3.40E+12 | 3.40E+13 |
| 35,000 | 3.50E+06 | 3.50E+07 | 3.50E+08 | 3.50E+09 | 3.50E+10 | 3.50E+11 | 3.50E+12 | 3.50E+13 |
| 36,000 | 3.60E+06 | 3.60E+07 | 3.60E+08 | 3.60E+09 | 3.60E+10 | 3.60E+11 | 3.60E+12 | 3.60E+13 |
| 37,000 | 3.70E+06 | 3.70E+07 | 3.70E+08 | 3.70E+09 | 3.70E+10 | 3.70E+11 | 3.70E+12 | 3.70E+13 |
| 38,000 | 3.80E+06 | 3.80E+07 | 3.80E+08 | 3.80E+09 | 3.80E+10 | 3.80E+11 | 3.80E+12 | 3.80E+13 |
| 39,000 | 3.90E+06 | 3.90E+07 | 3.90E+08 | 3.90E+09 | 3.90E+10 | 3.90E+11 | 3.90E+12 | 3.90E+13 |
| 40,000 | 4.00E+06 | 4.00E+07 | 4.00E+08 | 4.00E+09 | 4.00E+10 | 4.00E+11 | 4.00E+12 | 4.00E+13 |
| 41,000 | 4.10E+06 | 4.10E+07 | 4.10E+08 | 4.10E+09 | 4.10E+10 | 4.10E+11 | 4.10E+12 | 4.10E+13 |

For in-furrow embodiments, the microbes of the disclosure can be applied at a cfu concentration per acre of: $1\times10^6$, $3.20\times10^{10}$, $1.60\times10^{11}$, $3.20\times10^{11}$, $8.0\times10^{11}$, $1.6\times10^{12}$, $3.20\times10^{12}$, or more. Therefore, in aspects, the liquid in-furrow compositions can be applied at a concentration of between about $1\times10^6$ to about $3\times10^{12}$ cfu per acre.

In some aspects, the in-furrow compositions are contained in a liquid formulation. In the liquid in-furrow embodiments, the microbes can be present at a cfu concentration per milliliter of: $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, or more. In certain aspects, the liquid in-furrow compositions comprise microbes at a concentration of about $1\times10^6$ to about $1\times10^{11}$ cfu per milliliter. In other aspects, the liquid in-furrow compositions comprise microbes at a concentration of about $1\times10^7$ to about $1\times10^{10}$ cfu per milliliter. In other aspects, the liquid in-furrow compositions comprise microbes at a concentration of about $1\times10^8$ to about $1\times10^9$ cfu per milliliter. In other aspects, the liquid in-furrow compositions comprise microbes at a concentration of up to about $1\times10^{13}$ cfu per milliliter.

EXAMPLES

The examples provided herein describe methods of bacterial isolation, bacterial and plant analysis, and plant trait improvement. The examples are for illustrative purposes only and are not to be construed as limiting in any way.

Example 1: Isolation of Microbes from Plant Tissue

Topsoil was obtained from various agricultural areas in central California. Twenty soils with diverse texture characteristics were collected, including heavy clay, peaty clay loam, silty clay, and sandy loam. Seeds of various field corn, sweet corn, heritage corn and tomato were planted into each soil, as shown in Table 1.

TABLE 1

Crop Type and Varieties planted into soil with diverse characteristics

| Crop Type | Field Corn | Sweet Corn | Heritage Corn | Tomato |
|---|---|---|---|---|
| Varieties | Mo17 | Ferry-Morse 'Golden Cross Bantam T-51' | Victory Seeds 'Moseby Prolific' | Ferry-Morse Roma VF |
| | B73 | Ferry-Morse 'Silver Queen Hybrid' | Victory Seeds 'Reid's Yellow Dent' | Stover Roma |
| | DKC 66-40 | Ferry-Morse 'Sugar Dots' | Victory Seeds 'Hickory King' | Totally Tomatoes 'Micro Tom Hybrid' |
| | DKC 67-07 | | | Heinz 1015 |
| | DKC 70-01 | | | Heinz 2401 |
| | | | | Heinz 3402 |
| | | | | Heinz 5508 |
| | | | | Heinz 5608 |
| | | | | Heinz 8504 |

Plants were uprooted after 2-4 weeks of growth and excess soil on root surfaces was removed with deionized water. Following soil removal, plants were surface sterilized with bleach and rinsed vigorously in sterile water. A cleaned, 1 cm section of root was excised from the plant and placed in a phosphate buffered saline solution containing 3 mm steel beads. A slurry was generated by vigorous shaking of the solution with a Qiagen TissueLyser II.

Figure 1B:
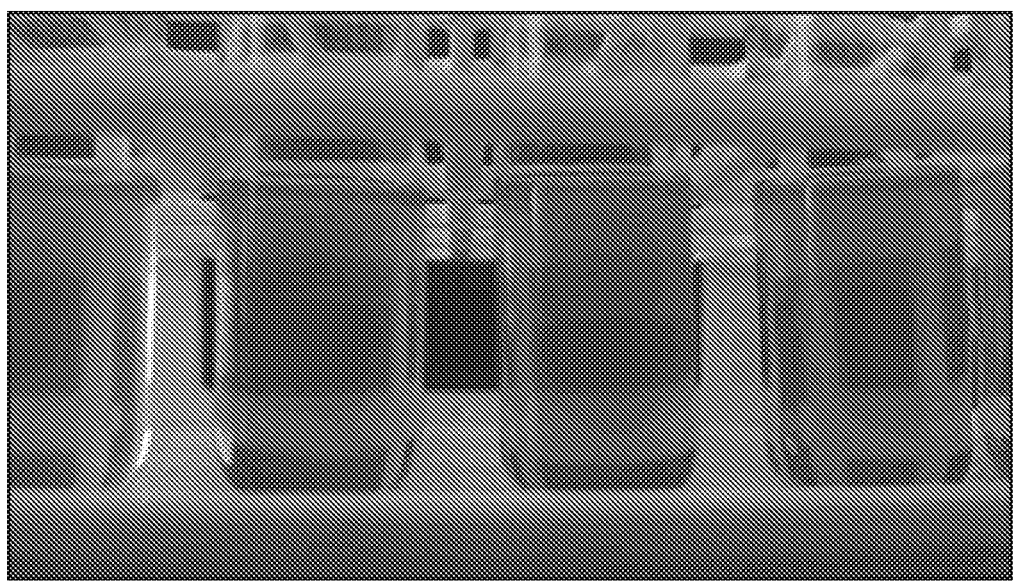

The root and saline slurry was diluted and inoculated onto various types of growth media to isolate rhizospheric, endophytic, epiphytic, and other plant-associated microbes. R2A and Nfb agar media were used to obtain single colonies, and semisolid Nfb media slants were used to obtain populations of nitrogen fixing bacteria. After 2-4 weeks incubation in semi-solid Nfb media slants, microbial populations were collected and streaked to obtain single colonies on R2A agar, as shown in FIG. 1A-B. Single colonies were resuspended in a mixture of R2A and glycerol, subjected to PCR analysis, and frozen at −80° C. for later analysis. Approximately 1,000 single colonies were obtained and designated "isolated microbes."

Figure 2:
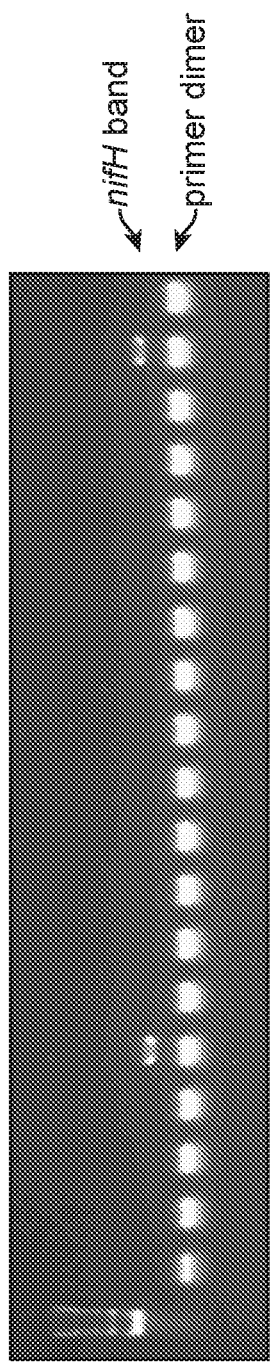
FIG. 2 depicts a representative if-H PCR screen. Positive bands were observed at ~350 bp for two colonies in this screen. Lower bands represent primer-dimers.

Isolates were then subjected to a colony PCR screen to detect the presence of the nifH gene in order to identify diazotrophs. The previously-described primer set Ueda 19F/388R, which has been shown to detect over 90% of diazotrophs in screens, was used to probe the presence of the nif cluster in each isolate (Ueda et al. 1995; J. Bacteriol. 177: 1414-1417). Single colonies of purified isolates were picked, resuspended in PBS, and used as a template for colony PCR, as shown in FIG. 2. Colonies of isolates that gave positive PCR bands were re-streaked, and the colony PCR and re-streaking process was repeated twice to prevent false positive identification of diazotrophs. Purified isolates were then designated "candidate microbes."

Example 2: Characterization of Isolated Microbes

Sequencing, Analysis and Phylogenetic Characterization

Sequencing of 16S rDNA with the 515f-806r primer set was used to generate preliminary phylogenetic identities for isolated and candidate microbes (see e.g. Vernon et al.; BMC Microbiol. 2002 Dec. 23; 2:39.). The microbes comprise diverse genera including: *Enterobacter, Burkholderia, Klebsiella, Bradyrhizobium, Rahnella, Xanthomonas, Raoultella, Pantoea, Pseudomonas, Brevundimonas, Agrobacterium*, and *Paenibacillus*, as shown in Table 2.

TABLE 2

Diversity of microbes isolated from tomato plants as determined by deep 16S rDNA sequencing.

| Genus | Isolates |
|---|---|
| *Achromobacter* | 7 |
| *Agrobacterium* | 117 |
| *Agromyces* | 1 |
| *Alicyclobacillus* | 1 |
| *Asticcacaulis* | 6 |
| *Bacillus* | 131 |
| *Bradyrhizobium* | 2 |
| *Brevibacillus* | 2 |
| *Burkholderia* | 2 |
| *Caulobacter* | 17 |
| *Chryseobacterium* | 42 |
| *Comamonas* | 1 |
| *Dyadobacter* | 2 |
| *Flavobacterium* | 46 |
| *Halomonas* | 3 |
| *Leptothrix* | 3 |
| *Lysobacter* | 2 |
| *Neisseria* | 13 |
| *Paenibacillus* | 1 |
| *Paenisporosarcina* | 3 |
| *Pantoea* | 14 |
| *Pedobacter* | 16 |
| *Pimelobacter* | 2 |
| *Pseudomonas* | 212 |
| *Rhizobium* | 4 |
| *Rhodoferax* | 1 |
| *Sphingobacterium* | 13 |
| *Sphingobium* | 23 |
| *Sphingomonas* | 3 |
| *Sphingopyxis* | 1 |

TABLE 2-continued

Diversity of microbes isolated from tomato plants as determined by deep 16S rDNA sequencing.

| Genus | Isolates |
|---|---|
| *Stenotrophomonas* | 59 |
| *Streptococcus* | 3 |
| *Variovorax* | 37 |
| *Xylanimicrobium* | 1 |
| unidentified | 75 |

Subsequently, the genomes of 39 candidate microbes were sequenced using Illumina Miseq platform. Genomic DNA from pure cultures was extracted using the QIAmp DNA mini kit (QIAGEN), and total DNA libraries for sequencing were prepared through a third party vendor (SeqMatic, Hayward). Genome assembly was then carried out via the A5 pipeline (Tritt et al. 2012; PLoS One 7(9):e42304). Genes were identified and annotated, and those related to regulation and expression of nitrogen fixation were noted as targets for mutagenesis.

Transcriptomic Profiling of Candidate Microbes

Transcriptomic profiling of strain CI010 was performed to identify promoters that are active in the presence of environmental nitrogen. Strain CI010 was cultured in a defined, nitrogen-free media supplemented with 10 mM glutamine. Total RNA was extracted from these cultures (QIAGEN RNeasy kit) and subjected to RNAseq sequencing via Illumina HiSeq (SeqMatic, Fremont Calif.). Sequencing reads were mapped to CI010 genome data using Geneious, and highly expressed genes under control of proximal transcriptional promoters were identified.

Tables 3A-C lists genes and their relative expression level as measured through RNASeq sequencing of total RNA. Sequences of the proximal promoters were recorded for use in mutagenesis of nif pathways, nitrogen utilization related pathways, or other genes with a desired expression level.

TABLE 3A

| Name | Minimum | Maximum | Length | Direction |
|---|---|---|---|---|
| murein lipoprotein CDS | 2,929,898 | 2,930,134 | 237 | forward |
| membrane protein CDS | 5,217,517 | 5,217,843 | 327 | forward |
| zinc/cadmium-binding protein CDS | 3,479,979 | 3,480,626 | 648 | forward |
| acyl carrier protein CDS | 4,563,344 | 4,563,580 | 237 | reverse |
| ompX CDS | 4,251,002 | 4,251,514 | 513 | forward |
| DNA-binding protein HU-beta CDS | 375,156 | 375,428 | 273 | forward |
| sspA CDS | 629,998 | 630,636 | 639 | reverse |
| tatE CDS | 3,199,435 | 3,199,638 | 204 | reverse |
| LexA repressor CDS | 1,850,457 | 1,851,065 | 609 | forward |
| hisS CDS | <3999979 | 4,001,223 | >1245 | forward |

TABLE 3B

| Name | Differential Expression Absolute Confidence | Differential Expression Ratio | RNASeq_nifL - Raw Read Count | RNASeq_nifLp - Raw Transcript Count | RNASeq_WT - Raw Read Count | RNASeq_WT - Raw Transcript Count |
|---|---|---|---|---|---|---|
| murein lipoprotein CDS | 1000 | −1.8 | 12950.5 | 10078.9 | 5151.5 | 4106.8 |
| membrane protein CDS | 1000 | −1.3 | 9522.5 | 5371.3 | 5400 | 3120 |
| zinc/cadmium-binding protein CDS | 3.3 | 1.1 | 6461 | 1839.1 | 5318 | 1550.6 |

TABLE 3B-continued

| Name | Differential Expression Absolute Confidence | Differential Expression Ratio | RNASeq_nifL - Raw Read Count | RNASeq_nifLp - Raw Transcript Count | RNASeq_WT - Raw Read Count | RNASeq_WT - Raw Transcript Count |
|---|---|---|---|---|---|---|
| acyl carrier protein CDS | 25.6 | 1.6 | 1230.5 | 957.6 | 1473.5 | 1174.7 |
| ompX CDS | 1.7 | 1.1 | 2042 | 734.2 | 1687.5 | 621.5 |
| DNA-binding protein HU-beta CDS | 6.9 | −1.3 | 1305 | 881.7 | 725 | 501.8 |
| sspA CDS | 0.2 | 1 | 654 | 188.8 | 504.5 | 149.2 |
| tatE CDS | 1.4 | 1.3 | 131 | 118.4 | 125 | 115.8 |
| LexA repressor CDS | 0.1 | −1.1 | 248 | 75.1 | 164 | 50.9 |
| hisS CDS | 0 | −1.1 | 467 | 69.2 | 325 | 49.3 |

TABLE 3C

| Name | Prm (In Forward direction, −250 to +10 region) | SEQ ID NO: | Expressed Sequence | SEQ ID NO: | Neighbor Sequence | SEQ ID NO: |
|---|---|---|---|---|---|---|
| murein lipoprotein CDS | GCCTCTCGGGGC GCTTTTTTTATT CCGGCACTAGCC GCTATTAATAAA AATGCAAATCGG AATTTACTATTTA ACGCGAGATTAT CTAAGATGAATC CGATGGAAGCGC GCTGTTTTCACTC GCCTTTTTAAAGT TACGTGATGATTT CGATGCTTCTTTG AGCGAACGATCA AAAATAAGCGTA TTCAGGTAAAAA AATATTCTCATCA CAAAAAAGTTTG TGTAATACTTGTA ACGCT--- ACATGGAGATTA ACTC | 3 | ATGAATCGTACT AAACTGGTACTG GGCGCGGTAATC CTGGGTTCTACTC TGCTGGCTGGTT GCTCCAGCAATG CTAAAATCGATC AGCTGTCTTCTGA CGTTCAGACTCT GAACGCTAAAGT TGACCAGCTGAG CAACGACGTGAA CGCAATGCGTTC CGACGTTCAGGC TGCTAAAGATGA CGCAGCTCGCGC TAACCAGCGTCT GGACAACGCAGC TACTAAATACCG TAAGTAA | 13 | ATGAAAAAGACC AAAATTGTTTGC ACCATCGGTCCG AAAACCGAATCC GAAGAGATGTTG ACCAAAATGCTG GACGCGGGCATG AACGTTATGCGT CTGAACTTCTCTC ACGGTGACTATG CGGAACACGGTC AGCGCATCCAGA ATCTGCGCAATG TGATGAGTAAAA CCGGTAAGAAAG CGGCAATCCTGC TGGACACCAAAG GTCCGGAAATCC GTACCATTAAGC TGGAAGGCGGCA ACGACGTCTCCC TGAAAGCGGGCC AGACCTTCACCTT CACCACCGATAA ATCCGTTGTCGGT AATAACGAAATC GTTGCGGTGACC TATGAAGGCTTC ACCAGCGACCTG AGCGTTGGCAAC ACGGTACTGGTT GACGATGGTCTG ATCGGTATGGAA GTGACCGCTATC GAAGGCAACAAA GTTGTTTGTAAA GTGCTGAACAAC GGCGACCTCGGC GAGAACAAAGGC GTTAACCTGCCG GGCGTATCTATC GCGCTGCCGGCG CTGGCTGAAAAA GACAAACAGGAT CTGATCTTCGGTT GCGAACAGGGCG TTGACTTTGTTGC GGCATCCTTTATC CGTAAGCGTTCT GACGTTGTTGAA ATCCGTGAGCAC CTGAAAGCCCAC GGCGGCGAGAAG | 23 |

TABLE 3C-continued

| Name | Prm (In Forward direction, -250 to +10 region) | SEQ ID NO: | Expressed Sequence | SEQ ID NO: | Neighbor Sequence | SEQ ID NO: |
|---|---|---|---|---|---|---|
| | | | ATCCAGATCATC | | | |
| | | | TCCAAAATCGAA | | | |
| | | | AACCAGGAAGGC | | | |
| | | | CTGAACAACTTC | | | |
| | | | GACGAAATCCTC | | | |
| | | | GAAGCCTCTGAC | | | |
| | | | GGCATCATGGTA | | | |
| | | | GCCCGTGGCGAC | | | |
| | | | CTGGGCGTTGAA | | | |
| | | | ATCCCGGTTGAA | | | |
| | | | GAAGTTATCTTC | | | |
| | | | GCGCAGAAGATG | | | |
| | | | ATGATCGAGAAA | | | |
| | | | TGTATCCGCGCG | | | |
| | | | CGTAAAGTCGTT | | | |
| | | | ATCACCGCGACC | | | |
| | | | CAGATGCTGGAT | | | |
| | | | TCCATGATCAAA | | | |
| | | | AACCCGCGTCCG | | | |
| | | | ACCCGTGCGGAA | | | |
| | | | GCAGGCGACGTG | | | |
| | | | GCCAACGCCATC | | | |
| | | | CTCGACGGCACC | | | |
| | | | GACGCAGTTATG | | | |
| | | | CTGTCCGGCGAA | | | |
| | | | TCCGCGAAAGGT | | | |
| | | | AAATACCCGCTG | | | |
| | | | GAAGCGGTCACC | | | |
| | | | ATCATGGCGACC | | | |
| | | | ATCTGCGAACGT | | | |
| | | | ACCGACCGCGTC | | | |
| | | | ATGACCAGCCGT | | | |
| | | | CTTGAGTACAAC | | | |
| | | | AACGACAACCGT | | | |
| | | | AAGCTGCGCATC | | | |
| | | | ACCGAAGCGGTG | | | |
| | | | TGCCGCGGTGCG | | | |
| | | | GTAGAAACGGCT | | | |
| | | | GAAAAACTGGAA | | | |
| | | | GCGCCGCTGATC | | | |
| | | | GTTGTGGCAACC | | | |
| | | | CAGGGCGGTAAA | | | |
| | | | TCCGCGCGCGCC | | | |
| | | | GTACGTAAATAC | | | |
| | | | TTCCCGGATGCC | | | |
| | | | ACTATCCTGGCG | | | |
| | | | CTGACCACCAAC | | | |
| | | | GAAACCACCGCG | | | |
| | | | CGTCAGCTGGTG | | | |
| | | | CTGAGCAAAGGC | | | |
| | | | GTTGTGGCACAG | | | |
| | | | CTGGTTGAAGAT | | | |
| | | | ATCTCCTCTACCG | | | |
| | | | ATGCGTTCTACAT | | | |
| | | | CCAGGGTAAAGA | | | |
| | | | ACTGGCGCTGCA | | | |
| | | | GAGCGGTCTGGC | | | |
| | | | GCGTAAAGGCGA | | | |
| | | | CGTGGTTGTTATG | | | |
| | | | GTTTCCGGCGCG | | | |
| | | | TTAGTCCCGAGC | | | |
| | | | GGAACCACCAAT | | | |
| | | | ACCGCTTCCGTG | | | |
| | | | CACGTGCTGTAA | | | |
| membrane protein CDS | GGTTCACATAAA CATAATTATCGC CACGGCGATAGC CGTACGCTTTTG CGTCACAACATC CATGGTGAAGCC GGCTTTTTCAAG AACACGCGCCAC CTCATCGGGTCTT AAATACATACTC ATTCCTCATTATC | 4 | ATGGCCAACCGA GCAAACCGCAAC AACGTAGAAGAG AGCGCTGAAGAT ATCCATAACGAT GTCAGCCAATTA GCGGATACGCTG GAAGAGGTGCTG AAATCGTGGGGC AGCGACGCCAAA GACGAAGCGGAG | 14 | ATGTATTTAAGA CCCGATGAGGTG GCGCGTGTTCTTG AAAAAGCCGGCT TCACCATGGATG TTGTGACGCAAA AAGCGTACGGCT ATCGCCGTGGCG ATAATTATGTTTA TGTGAACCGTGA AGCTCGTATGGG | 24 |

TABLE 3C-continued

| Name | Prm (In Forward direction, -250 to +10 region) | SEQ ID NO: | Expressed Sequence | SEQ ID NO: | Neighbor Sequence | SEQ ID NO: |
|---|---|---|---|---|---|---|
| | TTTTACCGCACGT TAACCTTACCTTA TTCATTAAAGGC AACGCTTTCGGA ATATTCCATAAA GGGCTATTTACA GCATAATTCAAA ATCTTGTCCTACA CTTATAGACTCA ATGGAATTAAGG GA | | GCCGCGCGCAAA AAAGCGCAGGCG CTGCTGAAAGAG ACCCGCGCCCGG CTTAACGGCAAC AACCGCGTCCAG CAGGCGGCGTGC GACGCCATGGGC TGCGCTGACAGC TACGTGCGCGAC AAACCGTGGCAA AGCGTCGGCGCC GCAGCAGCCGTT GGGGTATTTATT GGCGTATTACTG AATTTACGTCGA TAA | | GCGTACCGCGTT AATTATTCATCCG GCTTTAAAAGAG CGCAGCACAACG CTTGCGGAGCCC GCGTCGGATATC AAAACCTGCGAT CATTATGAGCAG TTCCCGCTCTATT TAGCGCTGGGATG CTCAACACTCATT ATGGTATTCCAC ACGGGTTCAGTT CGCGAATGGCGC TTGAGCGTTTTCT GAGTGGCCTGTT TGGCGAAACGCA GTATAGCTGA | |
| zinc/cadmium- binding protein CDS | GCGCGGAAAATC GACGCATAGCGC ATTCTCAGAAGC CGGCCTGGTCTC GGTGGAAAAGCG AATCTTTCCCACG ACCGCCGGGCCT TTAACAAAAGAA TCAATGACCTGA TTAATGTCGCTAT CCATTCTCTCTCC GCGTAATGCGAT CTTTTTTCATCAT ACCTAACAAACT GGCAGAGGGAAA AGCCGCGCGGTT TTTCTGCGAAGT GTATTGTAAGAT TTGTTTGATATGT TATATCGTAACA TATTATTGCAAA CAT | 5 | ATGACCAAAAAG ATTTCCGCCCTAG CGTTTGGCATTG GCATGGTAATGG CGAGCAGCCAGG CTTTTGCCCACGG TCACCATAGTCA TGGCCCGGCGCT GACCGAAGCGGA ACAAAAGGCGAG TGAAGGCATTTTT GCTGACCAGGAC CTTAAAGGACAGG GCGCTGAGCGAC TGGGAGGGGATC TGGCAGTCGGTT AACCCCTATCTG CTGAACGGGGAT TTAGATCCGGTTC TGGAGCAGAAGG CCAAAAAGGCCG GTAAAAGCGTGG CGGAATATCGGG AATATTATAAGA AGGGCTACGCTA CCGATGTCGACC AGATTGGTATCG AGGATAACGTCA TGGAGTTTCACG TCGGGAAAACCG TCAACGCCTGTA AGTACAGCTATT CCGGTTACAAAA TTCTGACCTACGC ATCCGGTAAAAA AGGCGTGCGCTA CCTGTTCGAATG CCAGCAGGCGGA TTCAAAAGCGCC GAAGTTTGTTCA GTTTAGCGATCA CACCATCGCGCC ACGCAAGTCCCA GCATTTCCACATC TTTATGGGCAAT GAGTCCCAGGAA GCGCTGCTGAAA GAGATGGATAAC TGGCCAACCTAC TATCCTTATGCGC TGCATAAAGAGC AGATTGTCGACG AAATGCTGCACC ACTAA | 15 | ATGGATAGCGAC ATTAATCAGGTC ATTGATTCTTTTG TTAAAGGCCCGG CGGTCGTGGGAA AGATTCGCTTTTC CACCGAGACCAG GCCGGCTTCTGA GAATGCGCTATG CGTCGATTTTCCG CGCCTCGAAATC ATGCTTGCGGGT CAGCTTCACGAT CCGGCGATTAAA GCCGATCGCGCC CAGCTCATGCCG CACGATGTGCTG TATATTCCGCTG GCGGATGGAATG ACCCGCAATGGC TGGCGCCCTCCA CTCTGCTCACTAT CTTATTTGGTAAA CAGCAGCTGGAA TTCGTCCTGCGCC ACTGGGACGGCA GCGCGCTTAACG TGCTGGATAAAC AGCAGGTTCCGC GCCGCGGTCCCC GGGTCGGCTCTTT TCTGCTGCAGGC GCTGAATGAAAT GCAGATGCAGCC GCGGGAGCAGCA CACGGCCCGCTT TATTGTCACCAG CCTGCTCAGCCA CTGTGCCGATCT GCTGGGCAGCCA GGTACAAACCTC ATCGCGCAGCCA GGCGCTTTTTGA AGCGATTCGTAA GCATATTGACGC CCACTTTGCCGA CCCGTTAACCCG GGAGTCGGTGGC GCAGGCGTTTTA CCTCTCGCCAAA CTATCTATCCCAC CTGTTCCAGAAA TGCGGGCCAATG GGCTTTAACGAG TATCTGAATCAC ATCCGCCTGGAG CAGGCCAGAATG | 25 |

TABLE 3C-continued

| Name | Prm (In Forward direction, -250 to +10 region) | SEQ ID NO: | Expressed Sequence | SEQ ID NO: | Neighbor Sequence | SEQ ID NO: |
|---|---|---|---|---|---|---|
| | | | | | CTGTTAAAAGGC CACGATATGAAA GTGAAAGATATC GCCCACGCCTGC GGTTTCGCCGAC AGCAACTACTTC TGCCGCCTGTTTC GCAAAAACACCG AACGCTCGCCGT CGGAGTATCGCC GTCAATATCACA GCCAGCTGACGG AAAAAACAGCCC CGGCAAAAAACT AG | |
| acyl carrier protein CDS | CTGACGAAGCGA GTTACATCACCG GTGAAACTCTGC ACGTCAACGGCG GAATGTATATGG TCTGACCGAGAT TTGCGCAAAACG CTCAGGAACCGC GCAGTCTGTGCG GTTCACTGTAAT GTTTTGTACAAA ATGATTTGCGTTA TGAGGGCAAACA GCCGCAAAATAG CGTAAAATCGTG GTAAGACCTGCC GGGATTTAGTTG CAAATTTTTCAAC ATTTTATACACTA CGAAAACCATCG CGAAAGCGAGTT TTGA | 6 | ATGAGCACTATC GAAGAACGCGTT AAGAAAATTATC GGCGAACAGCTG GGCGTTAAGCAG GAAGAAGTTACC AACAATGCTTCC TTCGTTGAAGAC CTGGGCGCTGAT TCTCTTGACACCG TTGAGCTGGTAA TGGCTCTGGAAG AAGAGTTTGATA CTGAGATTCCGG ACGAAGAAGCTG AGAAAATCACTA CTGTTCAGGCTG CCATTGATTACAT CAACGGCCACCA GGCGTAA | 16 | ATGAGTTTTGAA GGAAAAATCGCG CTGGTTACCGGT GCAAGTCGCGGG ATTGGCCGCGCA ATCGCTGAAACG CTCGTTGCCCGTG GCGCGAAAGTTA TCGGGACTGCGA CCAGCGAAAGCG GCGCGCAGGCGA TCAGCGATTATTT AGGTGCTAACGG TAAAGGTCTGCT GCTGAATGTGAC CGATCCTGCATCT ATTGAATCTGTTC TGGGAAATATTC GCGCAGAATTTG GTGAAGTTGATA TCCTGGTGAACA ATGCCGGGATCA CTCGTGATAACC TGTTAATGCGCA TGAAAGATGATG AGTGGAACGATA TTATCGAAACCA ACCTGTCATCTGT TTTCCGTCTGTCA AAAGCGGTAATG CGCGCTATGATG AAAAAGCGTCAT GGACGTATTATC ACTATCGGTTCTG TGGTTGGTACCA TGGGAAATGCGG GTCAGGCCAACT ACGCTGCGGCGA AAGCGGGTCTGA TTGGCTTCAGTA AATCACTGGCTC GCGAAGTTGCGT CCCGCGGTATTA CTGTAAACGTTG TTGCTCCGGGCTT TATTGAAACGGA CATGACGCGTGC GCTGACCGATGA GCAGCGTGCGGG TACGCTGGCGGC AGTTCCTGCGGG GCGCCTCGGCTC TCCAAATGAAAT CGCCAGTGCGGT GGCATTTTTAGCC TCTGACGAAGCG AGTTACATCACC GGTGAAACTCTG | 26 |

TABLE 3C-continued

| Name | Prm (In Forward direction, -250 to +10 region) | SEQ ID NO: | Expressed Sequence | SEQ ID NO: | Neighbor Sequence | SEQ ID NO: |
| --- | --- | --- | --- | --- | --- | --- |
| | | | | | CACGTCAACGGC GGAATGTATATG GTCTGA | |
| ompX CDS | ACGCCTGGGGCG CCGACCAGCGGG AAGAGTGATTTG GCCAACGAGGCG CCGCTCTGAATG GAAATCATGGCG ATTAAAATAACC AGTATCGGCAAC CATGCCGGTACC TTACGAGACGAG CCGGGCATCCTTT CTCCTGTCAATTT TGTCAAATGCGG TAAAGGTTCCAG TGTAATTGAATT ACCCCGCGCCGG TTGAGCTAATGTT GAAAAAAAGGGT CTTAAAAGCAGT ACAATAGGGCGG GTCTGAAGATAA TTTCA | 7 | ATGAATAAAATT GCACGTTTTTCAG CACTGGCCGTTG TTCTGGCTGCATC CGTAGGTACCAC TGCTTTCGCTGCG ACTTCTACCGTTA CCGGTGGCTACG CGCAGAGCGACA TGCAGGGTGAAG CGAACAAAGCTG GCGGTTTCAACC TGAAGTACCGCT ACGAGCAAGACA ACAACCCGCTGG GTGTTATCGGTTC TTTCACCTACACC GAAAAAGATCGT TCTGAATCTGGC GTTTACAAAAAA GGCCAGTACTAC GGCATCACCGCA GGTCCGGCTTAC CGTCTGAACGAC TGGGCTAGCATC TACGGCGTAGTG GGTGTTGGTTAC GGTAAATTCCAG GACAACAGCTAC CCGAACAAATCT GATATGAGCGAC TACGGTTTCTCTT ACGGCGCTGGTC TGCAGTTCAACC CGATCGAAAACG TTGCCCTGGACTT CTCCTACGAGCA GTCTCGCATTCGT AACGTTGACGTT GGCACCTGGATT GCTGGCGTAGGT TACCGCTTCTAA | 17 | ATGCCCGGCTCG TCTCGTAAGGTA CCGGCATGGTTG CCGATACTGGTT ATTTTAATCGCCA TGATTTCCAT | 27 |
| DNA-binding protein HU-beta CDS | TCTGATTCCTGAT GAAAATAAACGC GACCTTGAAGAA ATTCCGGATAAC GTTATCGCCGATT TAGATATCCATC CGGTGAAACGAA TCGAGGAAGTTC TGGCACTTGCGC TACAGAACGAAC CGTTTGGAATGG AAGTCGTCACGG CAAAATAGTGAT TTCGCGCAAATA GCGCTAAGAAAA ATAGGGCTGGTA AGTAAATTCGTA CTTGCCAGCCTTT TTTTGTGTAGCTA ACTTAGATCGCT GGCAGGGGGGTC AATT | 8 | GTGAATAAATCT CAACTGATTGAC AAAATTGCTGCC GGTGCGGACATT TCTAAAGCCGCA GCTGGACGTGCG TTAGATGCTTTAA TCGCTTCTGTTAC TGAATCTCTGCA GGCTGGAGATGA CGTTGCGCTGGT AGGGTTTGGTAC TTTTGCTGTTAAA GAGCGCGCTGCC CGTACTGGTCGC AATCCGCAAACA GGCAAAGAAATC ACCATTGCTGCT GCTAAAGTTCCG GGTTTCCGCGCA GGTAAAGCGCTG AAAGACGCGGTA AACTGA | 18 | ATGAATCCTGAG CGTTCTGAACGC ATTGAAATCCCC GTATTGCCGTTGC GCGATGTGGTGG TTTATCCGCACAT GGTCATACCCCT GTTTGTAGGGCG GGAAAAATCTAT CCGTTGTCTCGA AGCAGCCATGGA CCATGATAAAAA AATCATGCTGGT TGCGCAGAAAGA AGCCTCGACGGA TGAGCCGGGTGT AAACGATCTTTTC ACCGTCGGGACC GTGGCGTCTATTT TGCAAATGCTGA AGCTACCGGACG GTACTGTTAAAG TGCTGGTCGAAG GTTTGCAGCGCG CGCGCATCTCTG CGCTGTCTGATA ATGGCGAACATT TTTCGGCGAAGG CGGAATACCTTG | 28 |

TABLE 3C-continued

| Name | Prm (In Forward direction, -250 to +10 region) | SEQ ID NO: | Expressed Sequence | SEQ ID NO: | Neighbor Sequence | SEQ ID NO: |
|---|---|---|---|---|---|---|
| | | | AATCGCCGGCGA | | | |
| | | | TTGACGAACGCG | | | |
| | | | AGCAGGAAGTGC | | | |
| | | | TGGTTCGTACCG | | | |
| | | | CTATCAGCCAGT | | | |
| | | | TTGAAGGCTACA | | | |
| | | | TCAAGCTGAACA | | | |
| | | | AAAAAATCCCTC | | | |
| | | | CGGAAGTGCTGA | | | |
| | | | CGTCGCTGAATA | | | |
| | | | GCATCGACGATC | | | |
| | | | CGGCGCGTCTGG | | | |
| | | | CGGATACCATCG | | | |
| | | | CTGCGCATATGC | | | |
| | | | CGCTGAAGCTGG | | | |
| | | | CGGACAAACAGT | | | |
| | | | CCGTGCTGGAGA | | | |
| | | | TGTCCGACGTTA | | | |
| | | | ACGAGCGTCTGG | | | |
| | | | AATATCTGATGG | | | |
| | | | CGATGATGGAGT | | | |
| | | | CGGAAATCGATC | | | |
| | | | TGCTGCAGGTGG | | | |
| | | | AGAAGCGTATTC | | | |
| | | | GCAACCGCGTGA | | | |
| | | | AAAAGCAGATGG | | | |
| | | | AGAAATCTCAGC | | | |
| | | | GCGAGTACTATC | | | |
| | | | TGAATGAGCAAA | | | |
| | | | TGAAAGCCATTC | | | |
| | | | AAAAAGAGCTCG | | | |
| | | | GCGAGATGGACG | | | |
| | | | ACGCCCCGGACG | | | |
| | | | AGAACGAAGCGC | | | |
| | | | TGAAGCGTAAGA | | | |
| | | | TCGACGCGGCGA | | | |
| | | | AAATGCCGAAAG | | | |
| | | | AGGCAAAAGAGA | | | |
| | | | AAACCGAAGCGG | | | |
| | | | AACTGCAAAAAC | | | |
| | | | TGAAAATGATGT | | | |
| | | | CCCCGATGTCGG | | | |
| | | | CGGAAGCGACCG | | | |
| | | | TCGTTCGCGGCT | | | |
| | | | ACATCGACTGGA | | | |
| | | | TGGTGCAGGTAC | | | |
| | | | CGTGGAACGCTC | | | |
| | | | GCAGCAAGGTTA | | | |
| | | | AAAAAGACCTGC | | | |
| | | | GTCAGGCTCAGG | | | |
| | | | AGATCCTCGATA | | | |
| | | | CCGATCACTACG | | | |
| | | | GCCTTGAGCGCG | | | |
| | | | TGAAGGATCGCA | | | |
| | | | TTCTTGAGTACCT | | | |
| | | | CGCGGTGCAGAG | | | |
| | | | CCGTGTTAACAA | | | |
| | | | GCTCAAAGGGCC | | | |
| | | | GATCCTGTGCCT | | | |
| | | | GGTTGGGCCTCC | | | |
| | | | GGGGGTAGGTAA | | | |
| | | | AACCTCTCTCGG | | | |
| | | | CCAATCCATCGC | | | |
| | | | CAAAGCAACTGG | | | |
| | | | ACGCAAATATGT | | | |
| | | | GCGTATGGCGCT | | | |
| | | | GGGCGGCGTGCG | | | |
| | | | TGATGAAGCGGA | | | |
| | | | AATCCGCGGTCA | | | |
| | | | CCGCCGTACCTA | | | |
| | | | TATTGGCTCAAT | | | |
| | | | GCCGGGCAAACT | | | |
| | | | GATCCAGAAAAT | | | |
| | | | GGCTAAAGTGGG | | | |
| | | | CGTTAAAAACCC | | | |
| | | | GCTGTTCTTGCTG | | | |

TABLE 3C-continued

| Name | Prm (In Forward direction, -250 to +10 region) | SEQ ID NO: | Expressed Sequence | SEQ ID NO: | Neighbor Sequence | SEQ ID NO: |
|------|-----|-----|-----|-----|-----|-----|
| | | | GATGAGATCGAC | | | |
| | | | AAGATGTCTTCT | | | |
| | | | GACATGCGCGGC | | | |
| | | | GATCCGGCCTCG | | | |
| | | | GCGCTGCTGGAG | | | |
| | | | GTGTTGGATCCG | | | |
| | | | GAACAGAACGTG | | | |
| | | | GCCTTTAACGAC | | | |
| | | | CACTATCTGGAA | | | |
| | | | GTGGATTACGAT | | | |
| | | | CTCAGCGACGTG | | | |
| | | | ATGTTCGTTGCG | | | |
| | | | ACCTCTAACTCC | | | |
| | | | ATGAACATCCCG | | | |
| | | | GCGCCGCTGCTG | | | |
| | | | GATCGTATGGAA | | | |
| | | | GTGATCCGCCTCT | | | |
| | | | CCGGCTATACCG | | | |
| | | | AAGATGAGAAGC | | | |
| | | | TAAACATCGCCA | | | |
| | | | AACGCCATCTGC | | | |
| | | | TGTCAAAACAGA | | | |
| | | | TTGAGCGTAACG | | | |
| | | | CGCTCAAGAAAG | | | |
| | | | GCGAGCTGACGG | | | |
| | | | TGGATGACAGCG | | | |
| | | | CGATTATCGGCA | | | |
| | | | TCATTCGCTACTA | | | |
| | | | CACCCGTGAAGC | | | |
| | | | AGGCGTGCGTGG | | | |
| | | | TCTGGAGCGTGA | | | |
| | | | AATCTCGAAACT | | | |
| | | | GTGCCGCAAAGC | | | |
| | | | GGTGAAACAGCT | | | |
| | | | GCTGCTGGATAA | | | |
| | | | GTCGCTGAAACA | | | |
| | | | CATCGAGATTAA | | | |
| | | | CGGCGACAACCT | | | |
| | | | GCACGATTTCCTT | | | |
| | | | GGCGTGCAGCGC | | | |
| | | | TACGACTATGGT | | | |
| | | | CGTGCGGATAGC | | | |
| | | | GAAAACCGCGTA | | | |
| | | | GGTCAGGTGACC | | | |
| | | | GGACTGGCGTGG | | | |
| | | | ACGGAAGTGGGC | | | |
| | | | GGCGATCTGCTG | | | |
| | | | ACCATTGAAACC | | | |
| | | | GCCTGCGTTCCG | | | |
| | | | GGTAAAGGCAAA | | | |
| | | | CTGACCTACACC | | | |
| | | | GGTTCACTGGGT | | | |
| | | | GAAGTCATGCAG | | | |
| | | | GAATCCATCCAG | | | |
| | | | GCGGCGCTGACG | | | |
| | | | GTGGTTCGTTCAC | | | |
| | | | GTGCGGATAAGC | | | |
| | | | TGGGTATTAACT | | | |
| | | | CAGACTTTTACG | | | |
| | | | AAAAACGTGATA | | | |
| | | | TTCACGTTCACGT | | | |
| | | | GCCGGAAGGCGC | | | |
| | | | GACGCCGAAGGA | | | |
| | | | TGGTCCAAGCGC | | | |
| | | | CGGTATCGCGAT | | | |
| | | | GTGCACCGCGCT | | | |
| | | | GGTTTCCTGTCTG | | | |
| | | | ACGGGTAATCCG | | | |
| | | | GTACGCGCCGAC | | | |
| | | | GTGGCGATGACC | | | |
| | | | GGTGAGATTACC | | | |
| | | | CTCCGTGGCCAG | | | |
| | | | GTATTGCCGATT | | | |
| | | | GGTGGTCTGAAG | | | |
| | | | GAAAAACTGTTG | | | |
| | | | GCCGCGCATCGC | | | |

TABLE 3C-continued

| Name | Prm (In Forward direction, -250 to +10 region) | SEQ ID NO: | Expressed Sequence | SEQ ID NO: | Neighbor Sequence | SEQ ID NO: |
|---|---|---|---|---|---|---|
| | | | | | GGCGGCATTAAG ACTGTTCTGATTC CTGATGAAAATA AACGCGACCTTG AAGAAATTCCGG ATAACGTTATCG CCGATTTAGATA TCCATCCGGTGA AACGAATCGAGG AAGTTCTGGCAC TTGCGCTACAGA ACGAACCGTTTG GAATGGAAGTCG TCACGGCAAAAT AG | |
| sspA CDS | GTAAGAAAGTCG GCCTGCGTAAAG CACGTCGTCGTC CTCAGTTCTCCAA ACGTTAATTGTTT TCTGCTCACGCA GAACAATTTGCG AAAAAACCCGCT TCGGCGGGTTTTT TTATGGATAAAT TTGCCATTTTCCC TCTACAAACGCC CCATTGTTACCAC TTTTTCAGCATTT CCAGAATCCCCT CACCACAACGTC TTCAAAATCTGG TAAACTATCATC CAATTTTCTGCCC AAATGCAGGTGA TTGTTCATTTTT | 9 | ATGGCTGTCGCT GCCAACAAACGT TCGGTAATGACG CTGTTTTCTGGTC CTACTGACATCT ATAGCCATCAGG TCCGCATCGTGCT GGCCGAAAAAGG TGTTAGTTTTGAG ATAGAGCACGTG GAGAAGGACAAC CCGCCTCAGGAT CTGATTGACCTC AACCCGAATCAA AGCGTACCGACG CTTGTGGATCGT GAGCTCACTCTG TGGGAATCTCGC ATCATTATGGAA TATCTGGATGAG CGTTTCCCGCATC CGCCGCTCATGC CGGTTTACCCGG TGGCGCGTGGGG AAAGCCGTCTGT ATATGCAGCGTA TCGAAAAGGACT GGTATTCGTTGAT GAATACCATTCA GACCGGTACCGC TGCGCAGGCTGA TACTGCGCGTAA GCAGCTGCGTGA AGAACTACAGGC GATTGCGCCAGT TTTCACCCAGAA GCCCTACTTCCTG AGCGATGAGTTC AGCCTGGTGGAC TGCTACCTGGCA CCACTGCTGTGG CGTCTGCCGGTTC TCGGCGTAGAGC TGGTCGGCGCTG GCGCGAAAGAGC TTAAAGGCTATA TGACTCGCGTATT TGAGCGCGACTC TTTCCTCGCTTCT TTAACTGAAGCC GAACGTGAAATG CGTCTCGGTCGG GGCTAA | 19 | ATGGCTGAAAAT CAATACTACGGC ACCGGTCGCCGC AAAAGTTCCGCA GCTCGCGTTTTCA TCAAACCGGGCA ACGGTAAAATCG TTATCAACCAGC GTTCTCTGGAAC AGTACTTCGGTC GTGAAACTGCCC GCATGGTAGTTC GTCAGCCGCTGG AACTGGTCGACA TGGTTGAGAAAT TAGATCTGTACA TCACCGTTAAAG GTGGTGGTATCT CTGGTCAGGCTG GTGCGATCCGTC ACGGTATCACCC GCGCTCTGATGG AGTACGACGAGT CCCTGCGTGGCG AACTGCGTAAAG CTGGTTTCGTTAC TCGTGATGCTCGT CAGGTTGAACGT AAGAAAGTCGGC CTGCGTAAAGCA CGTCGTCGTCCTC AGTTCTCCAAAC GTTAA | 29 |
| tatE CDS | GTCAAAGCCGTA TTATCGACCCCTT AGGGACAACGCT TGCCGGGGCGGG AGAGCGGCCGCA GTTGATTTTTGCC | 10 | ATGGGTGAGATT AGTATTACCAAA CTGCTGGTAGTC GCAGCGCTGATT ATCCTGGTGTTTG GTACCAAAAAGT | 20 | ATGTTTGTTGCTG CCGGACAATTTG CCGTAACGCCGG ACTGGACGGGAA ACGCGCAGACCT GCGTCAGCATGA | 30 |

TABLE 3C-continued

| Name | Prm (In Forward direction, −250 to +10 region) | SEQ ID NO: | Expressed Sequence | SEQ ID NO: | Neighbor Sequence | SEQ ID NO: |
|---|---|---|---|---|---|---|
| | GAACTTTCAGCT GATTATATTCAG CAGGTACGCGAG CGCCTGCCGGTG TTGCGCAATCGC CGCTTTGCGCCA CCGCAATTATTAT GACGTTTTTTAA ACAAGGCTTGAT TCACCTTGTTACA GATTGCTATTGTG TCCGCGCGTCAA ATAGCCGTTAAT TGTATGCGTGTAT GATGGCGTATTCG | | TACGCACGCTGG GTGGAGACCTGG GCTCGGCTATCA AAGGCTTTAAAA AAGCCATGAGCG ATGACGATGACA GTGCGAAGAAGA CCAGTGCTGAAG AAGCGCCGGCAC AGAAGCTCTCTC ATAAAGAGTAA | | TGCGCCAGGCCG CGGAGCGGGGGG CGTCGCTTCTGGT TCTGCCTGAGGC GTTGCTGGCGCG AGACGATAACGA TGCGGATTTATC GGTTAAATCCGC CCAGCAGCTGGA TGGCGGCTTCTTA CAGCTCTTGCTG GCGGAGAGCGAA AACAGCGCTTTG ACGACGGTGCTG ACCCTGCATATC CCTTCCGGCGAA GGTCGAGCGACG AATACGCTGGTG GCCCTGCGTCAG GGGAAGATTGTG GCGCAATATCAG AAACTGCATCTC TATGATGCGTTC AATATCCAGGAA TCCAGGCTGGTC GATGCCGGGCGG CAAATTCCGCCG CTGATCGAAGTC GACGGGATGCGC GTCGGGCTGATG ACCTGCTACGAT TTACGTTTCCCTG AGCTGGCGCTGT CGTTAGCGCTCA GCGGCGCGCAGC TCATAGTGTTGCC TGCCGCGTGGGT AAAAGGGCCGCT GAAGGAACATCA CTGGGCGACGCT GCTGGCGGCGCG GGCGCTGGATAC AACCTGCTATATT GTCGCCGCAGGA GAGTGCGGGACG CGTAATATCGGT CAAAGCCGTATT ATCGACCCCTTA GGGACAACGCTT GCCGGGGCGGGA GAGCGGCCGCAG TTGATTTTTGCCG AACTTTCAGCTG ATTATATTCAGC AGGTACGCGAGC GCCTGCCGGTGT TGCGCAATCGCC GCTTTGCGCCAC CGCAATTATTAT GA | |
| LexA repressor CDS | GAGGCGGTGGTT GACCGTATCGGT CCCGAGCATCAT GAGCTTTCGGGG CGAGCGAAAGAT ATGGGATCGGCG GCGGTACTGCTG GCGATTATCATC GCGCTGATCGCG TGGGGAACGCTG CTGTGGGCGAAC TACCGCTAAGTC TTGTCGTAGCTGC TCGCAAAACGGA AAGAAACTCCTG | 11 | ATGAAAGCGTTA ACGACCAGGCAG CAAGAGGTGTTT GATCTCATTCGG GATCATATCAGC CAGACGGGCATG CCGCCGACGCGT GCGGAGATTGCT CAGCGCTTGGGG TTTCGCTCCCAA ACGCGGCGGAAG AGCATCTGAAAG CGCTGGCGCGTA AAGGCGCAATCG AGATCGTTTCCG | 21 | ATGGCCAATAAT ACCACTGGGTTA ACCCGAATTATT AAAGCGGCCGGG TATTCCTGGAAA GGATTCCGTGCG GCGTGGGTCAAT GAGGCCGCATTT CGTCAGGAAGGC ATCGCGCCGTT ATTGCCGTGGCG ATCGCCTGCTGG TTGGACGTCGAT GCCATCACGCGG GTGCTGCTCATTA | 31 |

TABLE 3C-continued

| Name | Prm (In Forward direction, -250 to +10 region) | SEQ ID NO: | Expressed Sequence | SEQ ID NO: | Neighbor Sequence | SEQ ID NO: |
|---|---|---|---|---|---|---|
| | ATTTTTGTGTGAA ATGTGGTTCCAA AATCACCGTTAG CTGTATATACTCA CAGCATAACTGT ATATACACCCAG GGGGC | | GCGCCTCCCGCG GTATTCGTCTGCT GACGGAAGAAGA AACCGGTCTGCC GCTTATTGGCCG CGTCGCGGCAGG TGAGCCGCTGCT AGCGCAGCAGCA CATTGAAGGCCA CTACCAGGTGGA CCCGGCCATGTTT AAGCCGAACGCC GATTTCTGCTGC GTGTTAGCGGTA TGTCGATGAAGG ATATCGGTATTCT CGATGGCGACCT GCTGGCTGTCCA TAAAACGCAGGA TGTGCGCAATGG TCAGGTGGTTGT GGCGCGTATCGA CGAAGAAGTGAC CGTGAAGCGTCT GAAAAAACAGGG TAACGTCGTGGA ATTGCTGCCGGA AAACAGCGAATT CTCGCCGATCGT GGTCGACCTTCG CGAACAAAGCTT TACTATTGAAGG CCTGGCCGTCGG CGTTATCCGCAA CGGCAACTGGCA ATAA | | GCTCGGTCCTGTT AGTGATGATAGT TGAAATTATCAA TAGCGCGATTGA GGCGGTGGTTGA CCGTATCGCTCC CGAGCATCATGA GCTTTCGGGGCG AGCGAAAGATAT GGGATCGGCGGC GGTACTGCTGGC GATTATCATCGC GCTGATCGCGTG GGGAACGCTGCT GTGGGCGAACTA CCGCTAA | |
| hisS CDS | TAAGAAAAGCGG CCTGTACGAAGA CGGCGTACGTAA AGACACTGCTGGA TAACGACGATAT GATCGATCAGCT GGAAGCGCGTAT TCGCGCTAAAGC ATCGATGCTGGA TGAGGCGCGTCG TATCGATATCCA GCAGGTTGAAGC GAAATAACGTGT TGCTGAAGCGATA CGCTTCCCGTGTA TGATTGAACCTG CGGGCGCGAGGC GCCGGGGTTCAT TTTTGTATATATA AAGAGAATAAAC GTGGCAAAGAAC ATTCAA | 12 | ...ATGAACGATTA TCTGCCGGGCGA AACCGCTCTCTG GCAGCGCATTGA AGGCTCACTGAA GCAGGTGCTTGG TAGCTACGGTTA CAGCGAAATCCG TTTGCCGATTGTA GAGCAGACCCCG TTATTCAAACGC GCTATCGGCGAA GTGACCGACGTG GTTGAAAAAGAG ATGTACACCTTTG AGGACCGTAACG GCGATAGCCTGA CTCTACGTCCGG AAGGCACGGCTG GCTGCGTACGCG CCGGTATCGAAC ATGGTCTCCTGTA CAATCAAGAACA GCGCCTGTGGTA CATTGGGCCGAT GTTCCGCCACGA ACGTCCGCAAAA AGGCCGCTACCG TCAGTTCCACCA GATTGGCGCCGA AGCGTTTGGCCT GCAGGGGCCGGA TATCGATGCCGA GCTGATTATGCT GACCGCCCGCTG GTGGCGCGAGCT GGGCATCTCCGG CCACGTTGCGCT GGAGCTGAACTC | 22 | ATGCATAACCAG GCTCCGATTCAA CGTAGAAAATCA AAACGAATTTAC GTTGGGAATGTG CCGATTGGCGAT GGCGCCCCCATC GCCGTACAGTCG ATGACAAACACG CGCACCACCGAT GTGGCGGCGACG GTAAATCAAATT AAAGCCCTCGAG CGCGTTGGCGCG GATATCGTGCGC GTTTCGGTGCCG ACGATGGATGCG GCGGAAGCGTTC AAACTTATCAAA CAGCAGGTTAAC GTCCCGCTGGTT GCCGATATCCAC TTCGATTACCGC ATTGCGCTGAAG GTAGCGGAATAC GGCGTTGATTGC CTGCGTATTAAC CCGGGCAATATC GGCAACGAAGAG CGTATCCGCATG GTGGTGGACTGC GCTCGCGATAAA AATATTCCTATCC GTATCGGGGTAA ACGCCGGTTCTCT GGAAAAAGATCT CCAGGAAAAATA CGGCGAACCGAC TCCGCAGGCGCT | 32 |

TABLE 3C-continued

| Name | Prm (In Forward direction, -250 to +10 region) | SEQ ID NO: | Expressed Sequence | SEQ ID NO: | Neighbor Sequence | SEQ ID NO: |
|---|---|---|---|---|---|---|
| | | | TATCGGTTCGCTG | | GCTGGAATCGGC | |
| | | | GAGGCTCGCGCT | | AATGCGCCATGT | |
| | | | AACTATCGCGAC | | TGATCATCTCGAT | |
| | | | GCGCTGGTGGCC | | CGTCTCAACTTCG | |
| | | | TATCTTGAGCAG | | ATCAGTTTAAAG | |
| | | | TTTAAAGATAAG | | TCAGCGTAAAAG | |
| | | | CTGGACGAAGAC | | CCTCCGATGTGTT | |
| | | | TGCAAACGCCGC | | CCTCGCGGTTGA | |
| | | | ATGTACACCAAC | | ATCCTATCGCCTG | |
| | | | CCGCTGCGCGTG | | TTGGCGAAACAG | |
| | | | CTGGATTCTAAA | | ATCGATCAGCCT | |
| | | | AACCCGGACGTC | | CTGCACCTCGGG | |
| | | | CAGGCGCTGCTG | | ATCACCGAAGCG | |
| | | | AACGACGCCCCG | | GGCGGCGCGCGC | |
| | | | ACGCTGGGCGAC | | AGCGGCGCGGTG | |
| | | | TATCTTGATGAA | | AAGTCCGCGATC | |
| | | | GAGTCCAAAACG | | GGCCTCGGCCTG | |
| | | | CATTTTGCCGGG | | CTGCTGTCTGAA | |
| | | | CTGTGCGCGCTG | | GGGATTGGCGAT | |
| | | | CTGGATGATGCC | | ACGCTGCGCGTC | |
| | | | GGTATTCGCTAT | | TCTCTGGCGGCG | |
| | | | ACCGTGAATCAG | | GATCCCGTTGAA | |
| | | | CGTCTGGTACGC | | GAGATCAAAGTG | |
| | | | GGTCTCGACTAC | | GGCTTCGATATTC | |
| | | | TACAACCGCACC | | TCAAGTCGCTGC | |
| | | | GTGTTTGAGTGG | | GTATTCGCTCTCG | |
| | | | GTCACCACCAGC | | CGGGATCAACTT | |
| | | | CTCGGTTCCCAG | | TATTGCCTGCCCG | |
| | | | GGCACCGTCTGC | | ACCTGTTCACGTC | |
| | | | GCCGGAGGCCGT | | AGGAGTTTGACG | |
| | | | TACGATGGTCTG | | TTATCGGTACCGT | |
| | | | GTTGAGCAGCTT | | TAACGCGCTGGA | |
| | | | GGCGGTCGCGCT | | GCAGCGCCTGGA | |
| | | | ACCCCTGGCGTC | | AGATATCATTAC | |
| | | | GGCTTTGCGATG | | GCCGATGGATAT | |
| | | | GGGCTGGAACGT | | TTCGATCATTGGC | |
| | | | CTTGTTTTACTGG | | TGCGTGGTAAAC | |
| | | | TTCAGGCAGTGA | | GGTCCCGGCGAG | |
| | | | ATCCGGAATTTA | | GCGCTGGTTTCC | |
| | | | AAGCCGATCCTG | | ACCCTCGGCGTA | |
| | | | TTGTCGATATATA | | ACCGGCGGCAAT | |
| | | | CCTGGTAGCCTC | | AAGAAAAGCGGC | |
| | | | CGGAACTGACAC | | CTGTACGAAGAC | |
| | | | CCAGTCCGCAGC | | GGCGTACGTAAA | |
| | | | AATGCGTCTGGC | | GACAGGCTGGAT | |
| | | | TGAACAGGTACG | | AACGACGATATG | |
| | | | CGATGCGTTACC | | ATCGATCAGCTG | |
| | | | CGGCGTTAAGCT | | GAAGCGCGTATT | |
| | | | GATGACCAACCA | | CGCGCTAAAGCA | |
| | | | TGGCGGCGGCAA | | TCGATGCTGGAT | |
| | | | CTTTAAGAAGCA | | GAGGCGCGTCGT | |
| | | | GTTTGCGCGCGC | | ATCGATATCCAG | |
| | | | TGATAAATGGGG | | CAGGTTGAAGCG | |
| | | | CGCTCGCGTTGC | | AAATAA | |
| | | | GCTGGTGCTGGG | | | |
| | | | CGAATCAGAAAT | | | |
| | | | CGCCGACGGAAA | | | |
| | | | CGTGGTAGTGAA | | | |
| | | | AGATTTACGCTC | | | |
| | | | AGGTGAGCAAAC | | | |
| | | | TACCGTAACGCA | | | |
| | | | GGATAGCGTTGC | | | |
| | | | TGCGCATTTGCG | | | |
| | | | CACACTTCTGGG | | | |
| | | | TTAA | | | |

Table of Strains

Figure 4A:
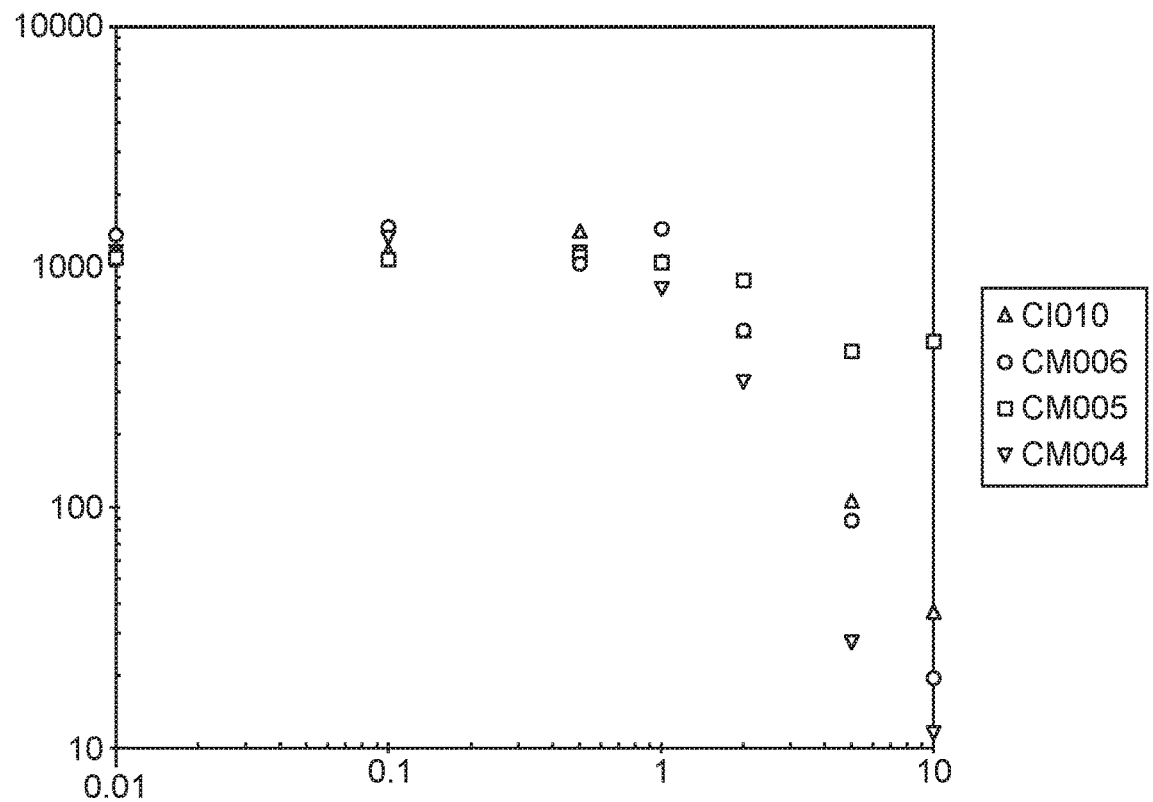
FIGS. 4A-D depict in vitro phenotypes of various strains. The Acetylene Reduction Assay (ARA) activities of mutants of strain CI010 (FIG. 4A) and mutants of strain CI006 (FIG. 4B) grown in nitrogen fixation media supplemented with 0 to 10 mM glutamine. ARA activities of additional strains are shown in FIG. 4C, and the ammonium excretion profile across time of two strains is shown in FIG. 4D.
Figure 4B:
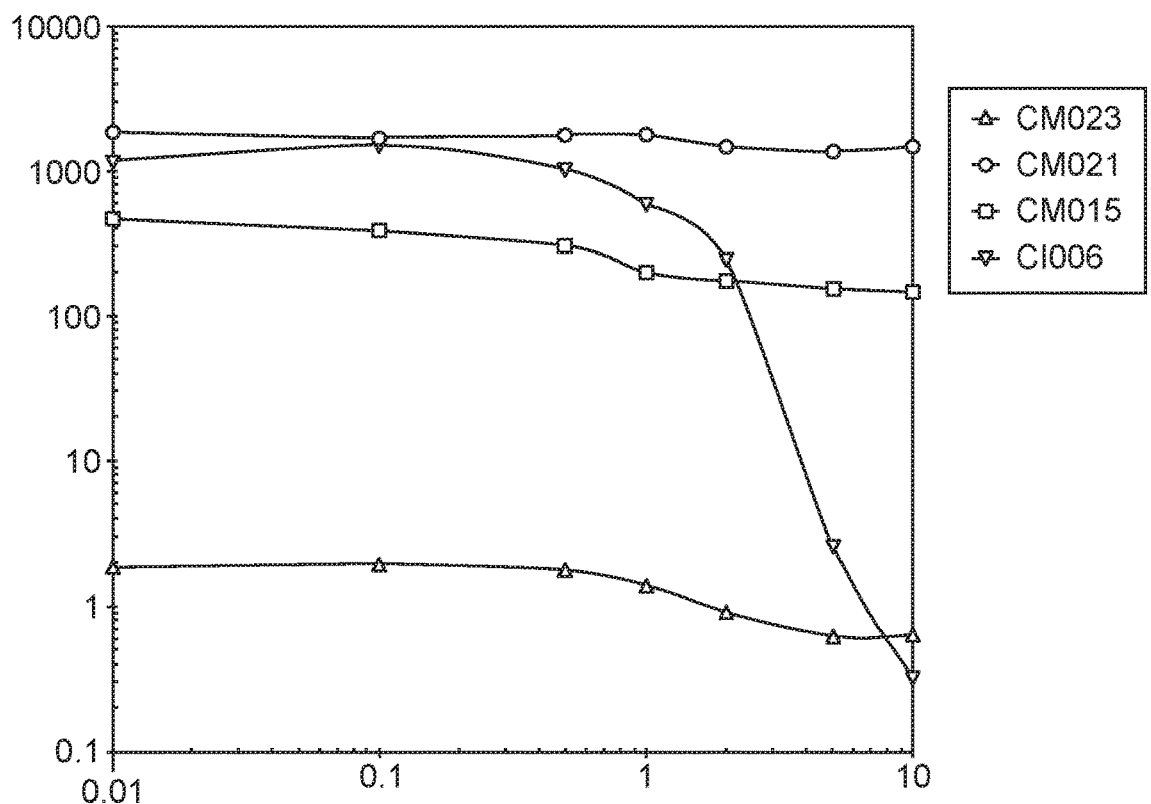

| Sort | First Reference | Current Name | Universal Name | Lineage | Mutagenic DNA Description | Genotype | Gene 1 mutation | Gene 2 mutation |
|---|---|---|---|---|---|---|---|---|
| 1 | Application text | CI006 | CI006 | Isolated strain from *Enterobacter* genera | None | WT | | |
| 2 | Application text | CI008 | CI008 | Isolated strain from *Burkholderia* genera | None | WT | | |
| 3 | Application text | CI010 | CI010 | Isolated strain from *Klebsiella* genera | None | WT | | |
| 4 | Application text | CI019 | CI019 | Isolated strain from *Rahnella* genera | None | WT | | |
| 5 | Application text | CI028 | CI028 | Isolated strain from *Enterobacter* genera | None | WT | | |
| 6 | Application text | CI050 | CI050 | Isolated strain from *Klebsiella* genera | None | WT | | |
| 7 | Application text | CM002 | CM002 | Mutant of CI050 | Disruption of nifL gene with a kanamycin resistance expression cassette (KanR) encoding the aminoglycoside O-phosphotransferase gene aph1 inserted. | ΔnifL::KanR | SEQ ID NO: 33 | |
| 8 | Application text | CM011 | CM011 | Mutant of CI019 | Disruption of nifL gene with a spectinomycin resistance expression cassette (SpecR) encoding the streptomycin 3"-O-adenylyltransferase gene aadA inserted. | ΔnifL::SpecR | SEQ ID NO: 34 | |
| 9 | Application text | CM013 | CM013 | Mutant of CI006 | Disruption of nifL gene with a kanamycin resistance expression cassette (KanR) encoding the aminoglycoside O-phosphotransferase gene aph1 inserted. | ΔnifL::KanR | SEQ ID NO: 35 | |
| 10 | FIG. 4A | CM004 | CM004 | Mutant of CI010 | Disruption of amtB gene with a kanamycin resistance expression cassette (KanR) encoding the aminoglycoside O-phosphotransferase gene aph1 inserted. | ΔamtB::KanR | SEQ ID NO: 36 | |
| 11 | FIG. 4A | CM005 | CM005 | Mutant of CI010 | Disruption of nifL gene with a kanamycin resistance expression cassette (KanR) encoding the aminoglycoside O-phosphotransferase gene aph1 inserted. | ΔnifL::KanR | SEQ ID NO: 37 | |
| 12 | FIG. 4B | CM015 | CM015 | Mutant of CI006 | Disruption of nifL gene with a fragment of the region upstream of the ompX gene inserted (Prm5). | ΔnifL::Prm5 | SEQ ID NO: 38 | |
| 13 | FIG. 4B | CM021 | CM021 | Mutant of CI006 | Disruption of nifL gene with a fragment of the region upstream of an unanotated gene and | ΔnifL::Prm2 | SEQ ID NO: 39 | |

Table of Strains

Figure 10A:
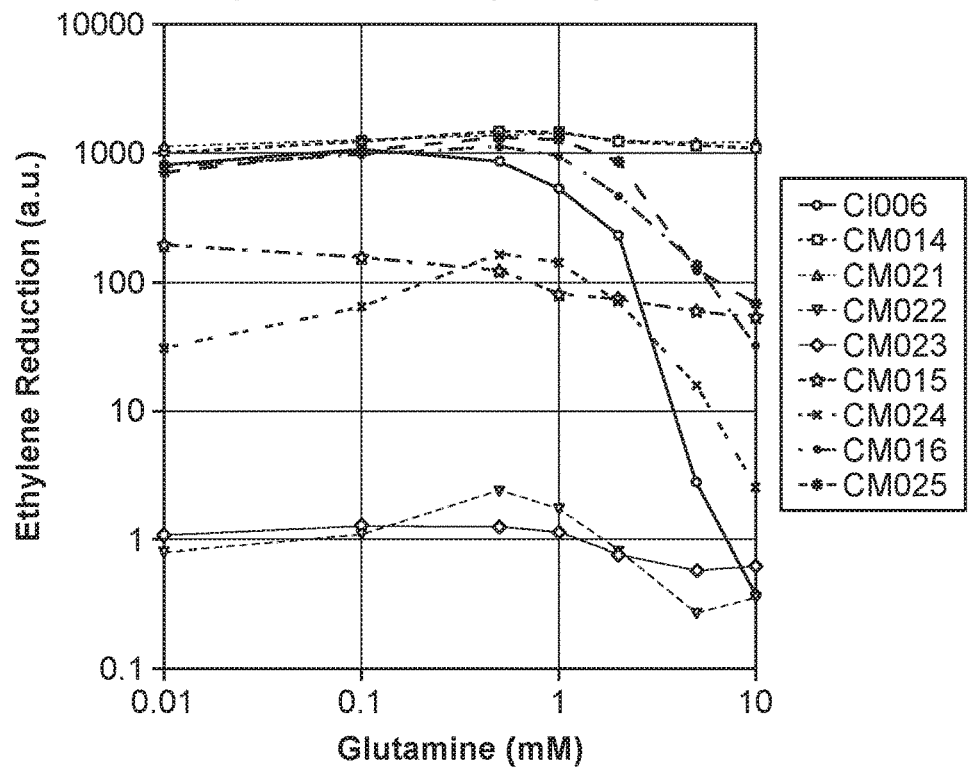
FIGS. 10A-C depict additional results for ARA activities of candidate microbes and counterpart candidate mutants grown in nitrogen fixation media supplemented with 0 to 10 mM glutamine.
Figure 10B:
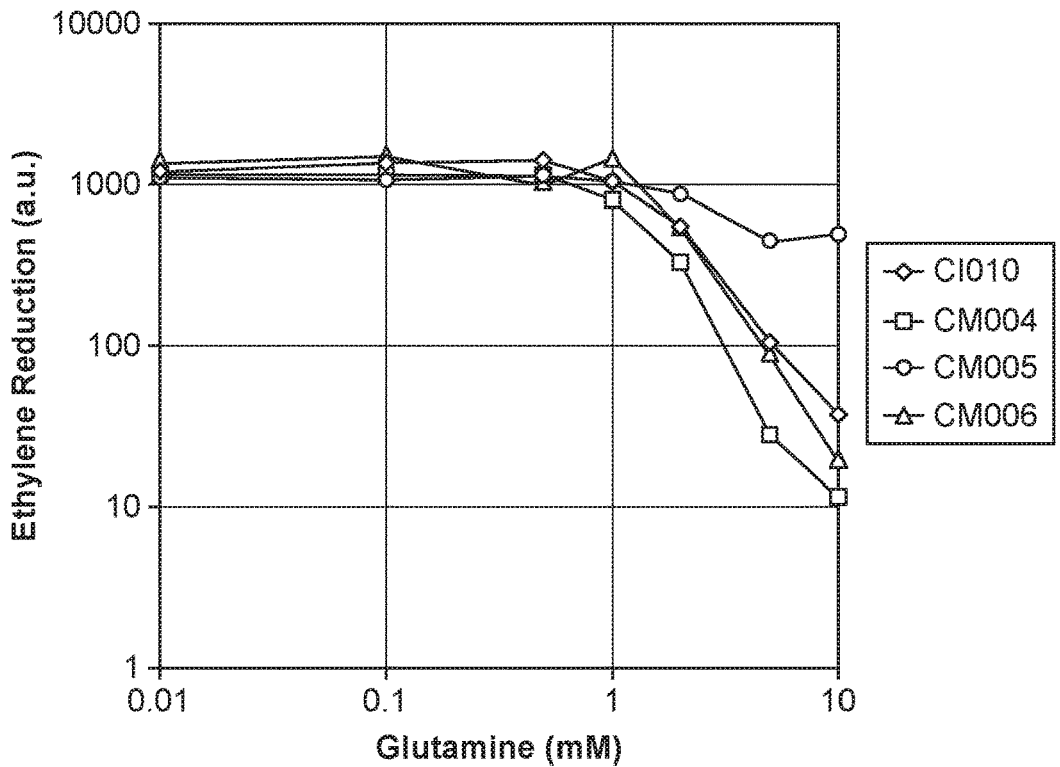

| Sort | First Reference | Current Name | Universal Name | Lineage | Mutagenic DNA Description | Genotype | Gene 1 mutation | Gene 2 mutation |
|---|---|---|---|---|---|---|---|---|
| 14 | FIG. 4B | CM023 | CM023 | Mutant of CI006 | the first 73bp of that gene inserted (Prm2). Disruption of nifL gene with a fragment of the region upstream of the acpP gene and the first 121bp of the acpP gene inserted (Prm4). | ΔnifL::Prm4 | SEQ ID NO: 40 | |
| 15 | FIG. 10A | CM014 | CM014 | Mutant of CI006 | Disruption of nifL gene with a fragment of the region upstream of the lpp gene and the first 29bp of the lpp gene inserted (Prm1). | ΔnifL::Prm1 | SEQ ID NO: 41 | |
| 16 | FIG. 10A | CM016 | CM016 | Mutant of CI006 | Disruption of nifL gene with a fragment of the region upstream of the lexA 3 gene and the first 21bp of the lexA 3 gene inserted (Prm9). | ΔnifL:Prm9 | SEQ ID NO: 42 | |
| 17 | FIG. 10A | CM022 | CM022 | Mutant of CI006 | Disruption of nifL gene with a fragment of the region upstream of the mntP 1 gene and the first 53bp of the mntP 1 gene inserted (Prm3). | ΔnifL::Prm3 | SEQ ID NO: 43 | |
| 18 | FIG. 10A | CM024 | CM024 | Mutant of CI006 | Disruption of nifL gene with a fragment of the region upstream of the sspA gene inserted (Prm7). | ΔnifL::Prm7 | SEQ ID NO: 44 | |
| 19 | FIG. 10A | CM025 | CM025 | Mutant of CI006 | Disruption of nifL gene with a fragment of the region upstream of the hisS gene and the first 52bp of the hisS gene inserted (Prm10). | ΔnifL::Prm10 | SEQ ID NO: 45 | |
| 20 | FIG. 10B | CM006 | CM006 | Mutant of CI010 | Disruption of glnB gene with a kanamycin resistance expression cassette (KanR) encoding the aminoglycoside O-phosphotransferase gene aph1 inserted. | ΔglnB::KanR | SEQ ID NO: 46 | |
| 21 | FIG. 10C | CI028 nifL:KanR | CM017 | Mutant of CI028 | Disruption of nifL gene with a kanamycin resistance expression cassette (KanR) encoding the aminoglycoside O-phosphotransferase gene aph1 inserted. | ΔnifL::KanR | SEQ ID NO: 47 | |
| 22 | FIG. 10C | CI019 nifL:SpecR | CM011 | Mutant of CI019 | Disruption of nifL gene with a spectinomycin resistance expression cassette (SpecR) encoding the streptomycin 3''-O-adenylyltransferase gene aadA inserted. | ΔnifL::SpecR | SEQ ID NO: 48 | |
| 23 | FIG. 10C | CI006 nifL:KanR | CM013 | Mutant of CI006 | Disruption of nifL gene with a kanamycin resistance expression cassette (KanR) encoding the | ΔnifL::KanR | SEQ ID NO: 49 | |

Table of Strains

Figure 10C:
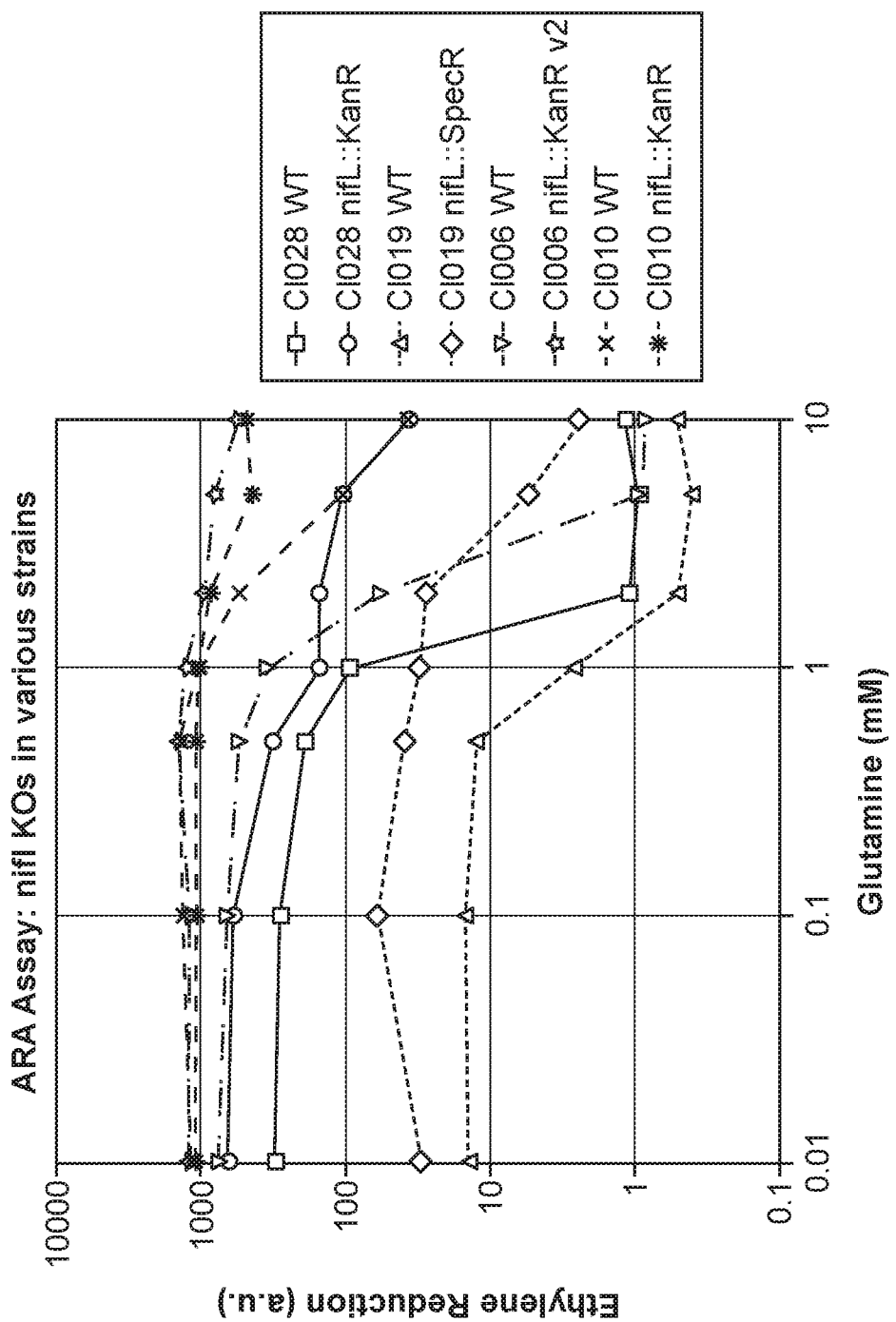

| Sort | First Reference | Current Name | Universal Name | Lineage | Mutagenic DNA Description | Genotype | Gene 1 mutation | Gene 2 mutation |
|---|---|---|---|---|---|---|---|---|
| 24 | FIG. 10C | CI010 nifL:KanR | CM005 | Mutant of CI010 | aminoglycoside O-phosphotransferase gene aph1 inserted. Disruption of nifL gene with a kanamycin resistance expression cassette (KanR) encoding the aminoglycoside O-phosphotransferase gene aph1 inserted. | ΔnifL::KanR | SEQ ID NO: 50 | |
| 25 | FIG. 4C | Strain 2 | CI006 | Isolated strain from *Enterobacter* genera | None | WT | | |
| 26 | FIG. 4C | Strain 4 | CI010 | Isolated strain from *Kiebsiella* genera | None | WT | | |
| 27 | FIG. 4C | Strain 1 | CI019 | Isolated strain from *Rahnella* genera | None | WT | | |
| 28 | FIG. 4C | Strain 3 | CI028 | Isolated strain from *Enterobacter* genera | None | WT | | |
| 29 | FIG. 4B | Strain 2 | CI006 | Isolated strain from *Enterobacter* genera | None | WT | | |
| 30 | FIG. 4B | High | CM014 | Mutant of CI006 | Disruption of nifL gene with a fragment of the region upstream of the lpp gene and the first 29bp of the lpp gene inserted (Prm1). | ΔnifL::Prm1 | SEQ ID NO: 51 | |
| 31 | FIG. 4B | Med | CM015 | Mutant of CI006 | Disruption of nifL gene with a fragment of the region upstream of the ompX gene inserted (Prm5). | ΔnifL::Prm5 | SEQ ID NO: 52 | |
| 32 | FIG. 4B | Low | CM023 | Mutant of CI006 | Disruption of nifL gene with a fragment of the region upstream of the acpP gene and the first 121bp of the acpP gene inserted (Prm4). | ΔnifL::Prm4 | SEQ ID NO: 53 | |
| 33 | FIG. 4D | Strain 2 | CI006 | Isolated strain from *Enterobacter* genera | None | WT | | |
| 34 | FIG. 4D | Evolved | CM029 | Mutant of CI006 | Disruption of nifL gene with a fragment of the region upstream of the ompX gene inserted (Prm5) and deletion of the 1287bp after the start codon of the glnE gene containing the adenylyl-removing domain of glutamate-ammonia-ligase adenylyltransferase (ΔglnE-AR_KO1). | ΔnifL::Prm5 ΔglnE-AR_KO1 | SEQ ID NO: 54 | SEQ ID NO: 61 |
| 35 | FIG. 14C | Wild | CI006 | Isolated strain from *Enterobacter* genera | None | WT | | |

Table of Strains

Figure 14A:
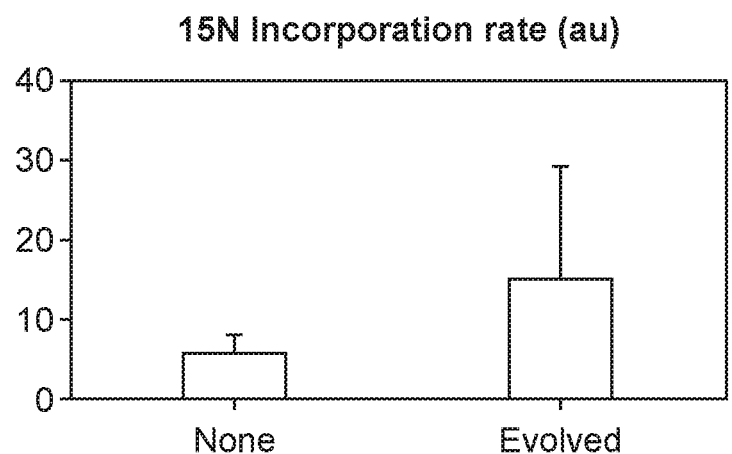
FIG. 14A depicts rate of incorporation of 15N gas. Plants inoculated with evolved strain showed increase in 15N gas incorporation compared to uninoculated plants.
Figure 14B:
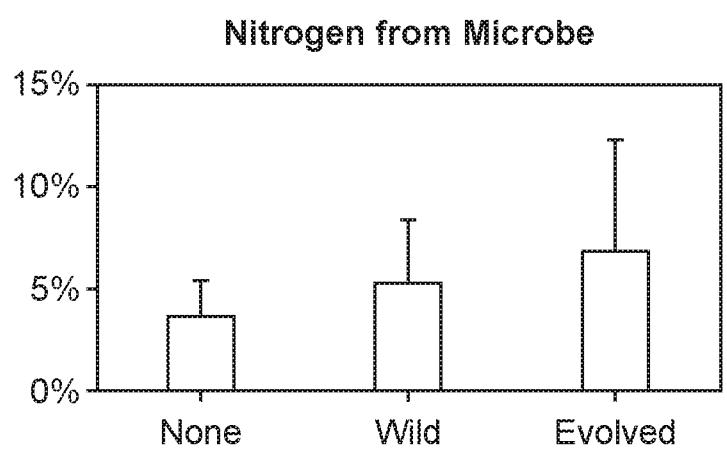
FIG. 14B depicts 4 weeks after planting, up to 7/o of the nitrogen in plants inoculated with an evolved strain is derived from microbially fixed nitrogen.
Figure 14C:
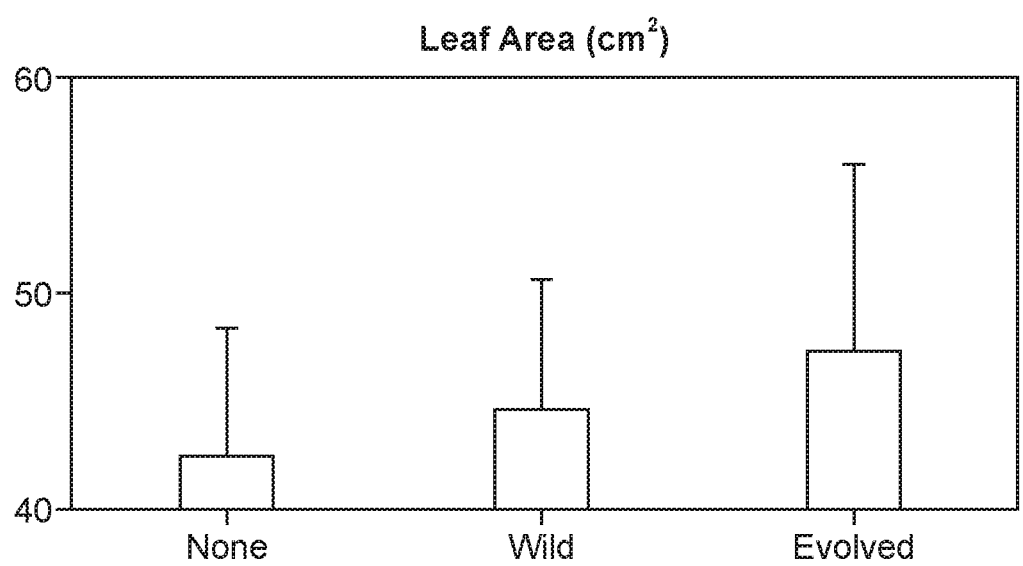
FIG. 14C depicts leaf area (and other biomass measurement, data not shown) is increased in plants inoculated with an evolved strain when compared to uninoculated or wild type inoculated plants.
Figure 15A:
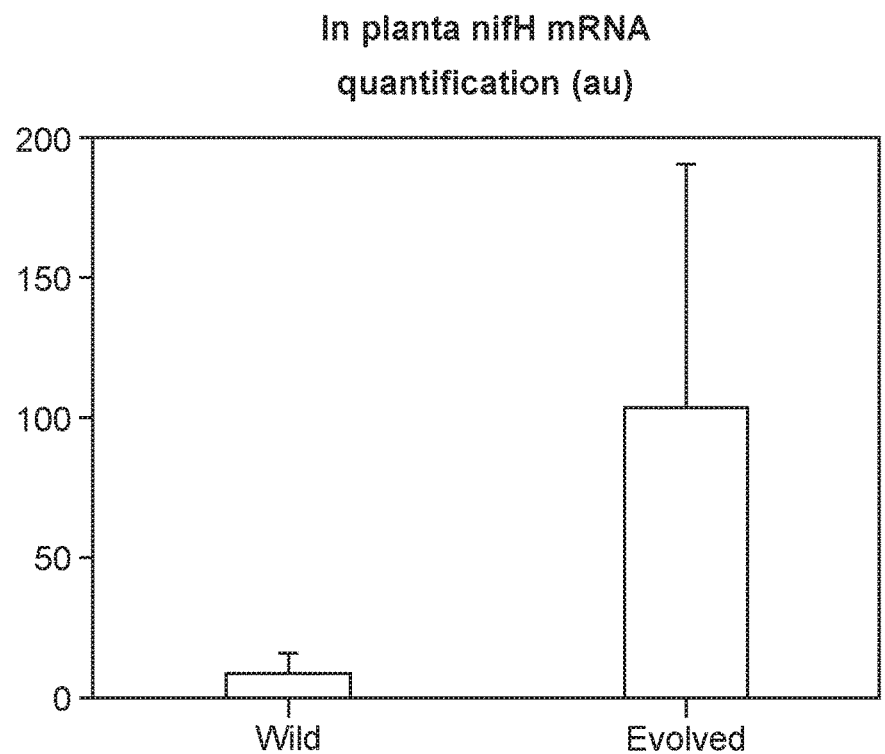
FIG. 15A depicts evolved strains that show significantly higher nifH production in the root tissue, as measured by in planta transcriptomic study.
Figure 15B:
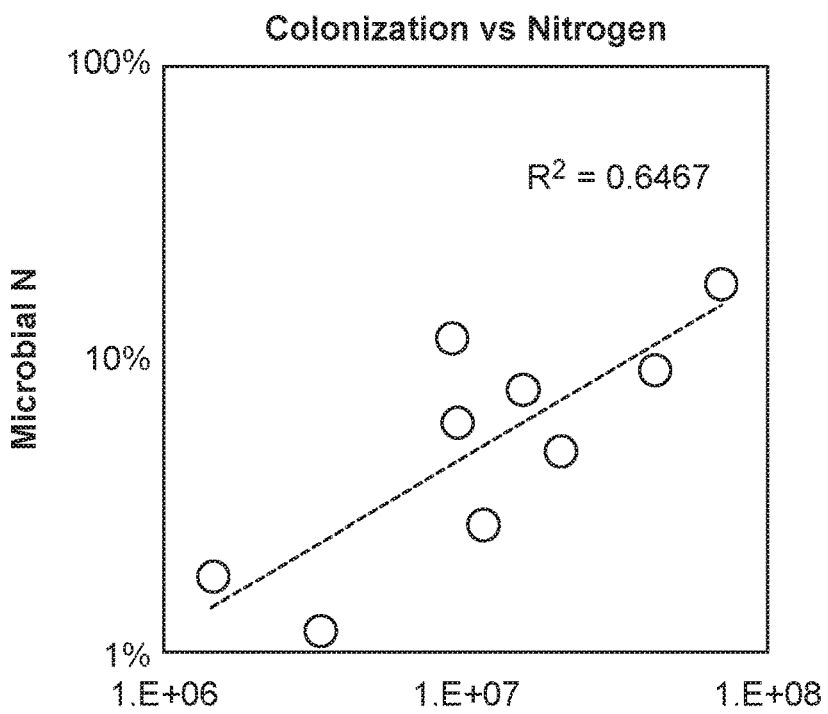
FIG. 15B depicts that rate of fixed nitrogen found in plant tissue is correlated with the rate in which that particular plant is colonized by HoME optimized strain.
Figures 16A, 16B:
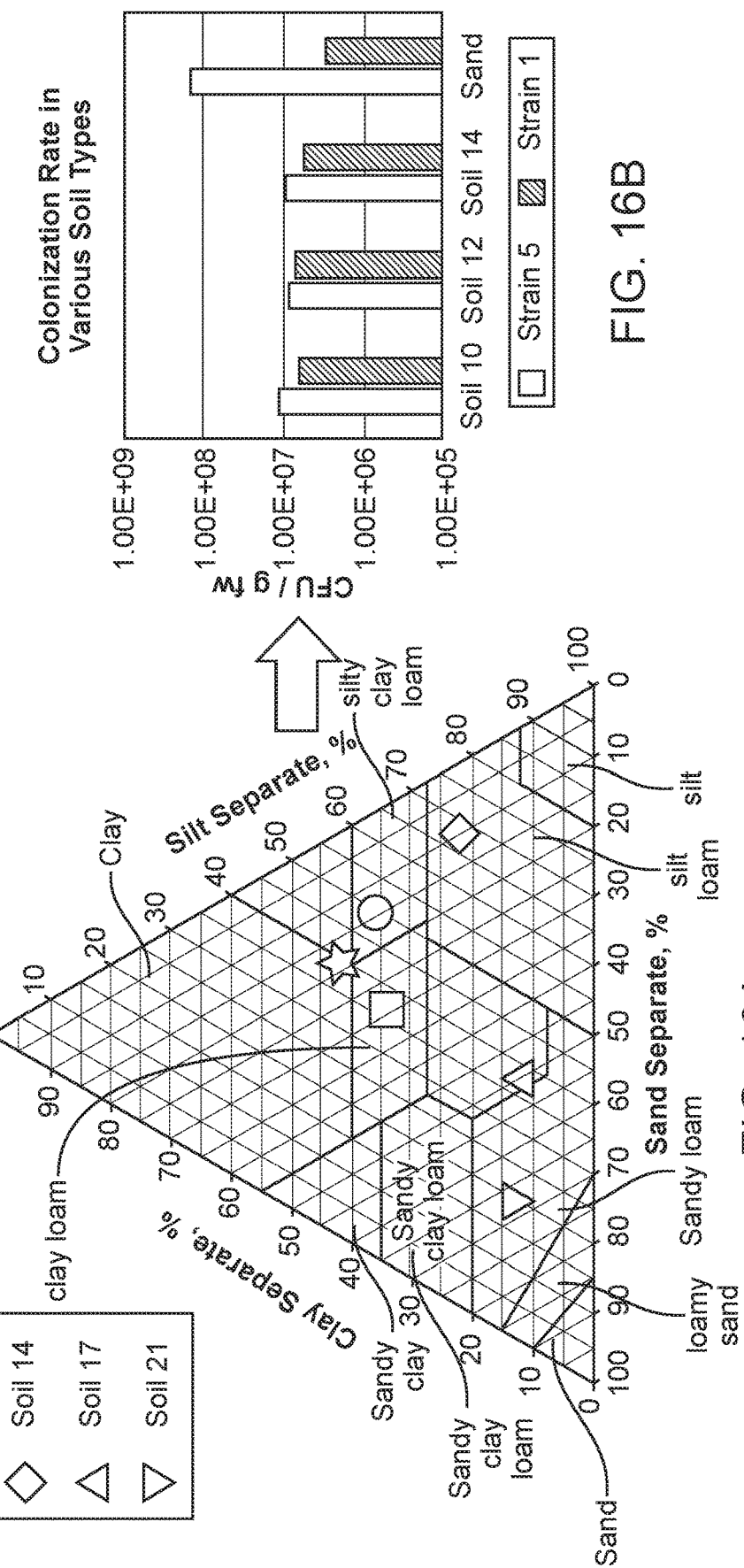
FIG. 16A depicts a soil texture map of various field soils tested for colonization. Soils in which a few microbes were originally source from are indicated as stars.
FIG. 16B depicts the colonization rate of Strain 1 and Strain 5 that are tested across four different soil types (circles). Both strains showed relatively robust colonization profile across diverse soil types.

| Sort | First Reference | Current Name | Universal Name | Lineage | Mutagenic DNA Description | Genotype | Gene 1 mutation | Gene 2 mutation |
|---|---|---|---|---|---|---|---|---|
| 36 | FIG. 14C | Evolved | CM014 | Mutant of CI006 | Disruption of nifL gene with a fragment of the region upstream of the lpp gene and the first 29bp of the lpp gene inserted (Prm1). | ΔnifL::Prm1 | SEQ ID NO: 55 | |
| 37 | FIG. 14B | Wild | CI019 | Isolated strain from *Rahnella* genera | None | WT | | |
| 38 | FIG. 14B | Evolved | CM011 | Mutant of CI019 | Disruption of nifL gene with a spectinomycin resistance expression cassette (SpecR) encoding the streptomycin 3"-O-adenylyltransferase gene aadA inserted. | ΔnifL::SpecR | SEQ ID NO: 56 | |
| 39 | FIG. 14A | Evolved | CM011 | Mutant of CI019 | Disruption of nifL gene with a spectinomycin resistance expression cassette (SpecR) encoding the streptomycin 3"-O-adenylyltransferase gene aadA inserted. | ΔnifL:SpecR | SEQ ID NO: 57 | |
| 40 | FIG. 15A | Wild | CI006 | Isolated strain from *Enterobacter* genera | None | WT | | |
| 41 | FIG. 15A | Evolved | CM013 | Mutant of CI006 | Disruption of nifL gene with a kanamycin resistance expression cassette (KanR) encoding the aminoglycoside O-phosphotransferase gene aph1 inserted. | ΔnifL::KanR | SEQ ID NO: 58 | |
| 42 | FIG. 15B | No name | CM011 | Mutant of CI019 | Disruption of nifL gene with a spectinomycin resistance expression cassette (SpecR) encoding the streptomycin 3"-O-adenylyltransferase gene aadA inserted. | ΔnifL::SpecR | SEQ ID NO: 59 | |
| 43 | FIG. 16B | Strain 5 | CI008 | Isolated strain from *Burkholderia* genera | None | WT | | |
| 44 | FIG. 16B | Strain 1 | CM011 | Mutant of CI019 | Disruption of nifL gene with a spectinomycin resistance expression cassette (SpecR) encoding the streptomycin 3"-O-adenylyltransferase gene aadA inserted. | ΔnifL::SpecR | SEQ ID NO: 60 | |

Table of Strains Sequences

| SEQ ID NO: | Sequence |
|---|---|
| 33 | ATGAGCCATATTCAACGGGAAACGTCTTGCTCCAGGCCGCGATTAAATT CCAACATGGATGCTGATTTATATGGGTATAAATGGGCTCGCGATAATGT CGGGCAATCAGGTGCGACAATCTATCGATTGTATGGGAAGCCCGATGCG |

Table of Strains Sequences

| SEQ ID NO: | Sequence |
|---|---|
|  | CCAGAGTTGTTTCTGAAACATGGCAAAGGTAGCGTTGCCAATGATGTTA<br>CAGATGAGATGGTCAGACTAAACTGGCTGACGGAATTTATGCCTCTTCC<br>GACCATCAAGCATTTTATCCGTACTCCTGATGATGCATGGTTACTCACCA<br>CTGCGATCCCCGGGAAAACAGCATTCCAGGTATTAGAAGAATATCCTGA<br>TTCAGGTGAAAATATTGTTGATGCGCTGGCAGTGTTCCTGCGCCGGTTGC<br>ATTCGATTCCTGTTTGTAATTGTCCTTTTAACAGCGATCGCGTATTTCGTC<br>TCGCTCAGGCGCAATCACGAATGAATAACGGTTTGGTTGATGCGAGTGA<br>TTTTGATGACGAGCGTAATGGCTGGCCTGTTGAACAAGTCTGGAAAGAA<br>ATGCATAAGCTTTTGCCATTCTCACCGGATTCAGTCGTCACTCATGGTGA<br>TTTCTCACTTGATAACCTTATTTTTGACGAGGGGAAATTAATAGGTTGTA<br>TTGATGTTGGACGAGTCGGAATCGCAGACCGATACCAGGATCTTGCCAT<br>CCTATGGAACTGCCTCGGTGAGTTTTCTCCTTCATTACAGAAACGGCTTT<br>TTCAAAAATATGGTATTGATAATCCTGATATGAATAAATTGCAGTTTCAT<br>TTGATGCTCGATGAGTTTTTCTAATAAGCCTGCCTGGTTCTGCGTTTCCC<br>GCTCTTTAATACCCTGACCGGAGGTGAGCAATGA |
| 34 | ATGAGCATCACGGCGTTATCAGCATCATTTCCTGAGGGGAATATCGCCA<br>GCCGCTTGTCGCTGCAACATCCTTCACTGTTTTATACCGTGGTTGAACAA<br>TCTTCGGTGGCGAGCGTGTTGAGTCATCCTGACTAGCTGAGATGAGGGC<br>TCGCCCCCTCGTCCCGACACTTCCAGATCGCCATAGCGCACAGCGCCTC<br>GAGCGGTGGTAACGGCGCAGTGGCGGTTTTCATGGCTTGTTATGACTGT<br>TTTTTTGGGGTACAGTCTATGCCTCGGGCATCCAAGCAGCAAGCGCGTT<br>ACGCCGTGGGTCGATGTTTGATGTTATGGAGCAGCAACGATGTTACGCA<br>GCAGGGCAGTCGCCCTAAAACAAAGTTAAACATCATGAGGGAAGCGGT<br>GATCGCCGAAGTATCGACTCAACTATCAGAGGTAGTTGGCGTCATCGAG<br>CGCCATCTCGAACCGACGTTGCTGGCCGTACATTTGTACGGCTCCGCAG<br>TGGATGGCGGCCTGAAGCCACACAGTGATATTGATTTGCTGGTTACGGT<br>GACCGTAAGGCTTGATGAAACAACGCGGCGAGCTTTGATCAACGACCTT<br>TTGGAAACTTCGGCTTCCCCTGGAGAGAGCGAGATTCTCCGCGCTGTAG<br>AAGTCACCATTGTTGTGCACGACGACATCATTCCGTGGCGTTATCCAGCT<br>AAGCGCGAACTGCAATTTGGAGAATGGCAGCGCAATGACATTCTTGCAG<br>GTATCTTCGAGCCAGCCACGATCGACATTGATCTGGCTATCTTGCTGACA<br>AAAGCAAGAGAACATAGCGTTGCCTTGGTAGGTCCAGCGGCGGAGGAA<br>CTCTTTGATCCGGTTCCTGAACAGGATCTATTTGAGGCGCTAAATGAAA<br>CCTTAACGCTATGGAACTCGCCGCCCGACTGGGCTGGCGATGAGCGAAA<br>TGTAGTGCTTACGTTGTCCCGCATTTGGTACAGCGCAGTAACCGGCAAA<br>ATCGCGCCGAAGGATGTCGCTGCCGACTGGGCAATGGAGCGCCTGCCGG<br>CCCAGTATCAGCCCGTCATACTTGAAGCTAGACAGGCTTATCTTGGACA<br>AGAAGAAGATCGCTTGGCCTCGCGCGCAGATCAGTTGGAAGAATTTGTC<br>CACTACGTGAAAGGCGAGATCACCAAGGTAGTCGGCAAATAATGTCTA<br>ACAATTCGTTCAAGCCGACGCCGCTTCGCGGCGCGGCTTAACTCAAGCG<br>TTAGATGCACTAAGCACATAATTGCTCACAGCCAAACTATCAGGTCAAG<br>TCTGCTTTTATTATTTTTAAGCGTGCATAATAAGCCCTACACAAATGGTA<br>CCCGACCGGTGGTGAATTTAATCTCGCTGACGTGTAGACATTCCCTTATC<br>CAGACGCTGATCGCCCATCATCGCGGTTCTTTAGATCTCTCGGTCCGCCC<br>TGATGGCGGCACCTTGCTGACGTTACGCCTGCCGGTACAGCAGGTTATC<br>ACCGGAGGCTTAAAATGA |
| 35 | CTGATCCTTCAACTCAGCAAAAGTTCGATTTATTCAACAAAGCCACGTT<br>GTGTCTCAAAATCTCTGATGTTACATTGCACAAGATAAAAATATATCAT<br>CATGAACAATAAAACTGTCTGCTTACATAAACAGTAATACAAGGGGTGT<br>TATGAGCCATATTCAACGGGAAACGTCTTGCTCCAGGCCGCGATTAAAT<br>TCCAACATGGATGCTGATTTATATGGGTATAAATGGGCTCGCGATAATG<br>TCGGGCAATCAGGTGCGACAATCTATCGATTGTATGGGAAGCCCGATGC<br>GCCAGAGTTGTTTCTGAAACATGGCAAAGGTAGCGTTGCCAATGATGTT<br>ACAGATGAGATGGTCAGACTAAACTGGCTGACGGAATTTATGCCTCTTC<br>CGACCATCAAGCATTTTATCCGTACTCCTGATGATGCATGGTTACTCACC<br>ACTGCGATCCCCGGGAAAACAGCATTCCAGGTATTAGAAGAATATCCTG<br>ATTCAGGTGAAAATATTGTTGATGCGCTGGCAGTGTTCCTGCGCCGGTT<br>GCATTCGATTCCTGTTTGTAATTGTCCTTTTAACAGCGATCGCGTATTTC<br>GTCTCGCTCAGGCGCAATCACGAATGAATAACGGTTTGGTTGATGCGAG<br>TGATTTTGATGACGAGCGTAATGGCTGGCCTGTTGAACAAGTCTGGAAA<br>GAAATGCATAAGCTTTTGCCATTCTCACCGGATTCAGTCGTCACTCATGG<br>TGATTTCTCACTTGATAACCTTATTTTTGACGAGGGGAAATTAATAGGTT<br>GTATTGATGTTGGACGAGTCGGAATCGCAGACCGATACCAGGATCTTGC<br>CATCCTATGGAACTGCCTCGGTGAGTTTTCTCCTTCATTACAGAAACGGC<br>TTTTTCAAAAATATGGTATTGATAATCCTGATATGAATAAATTGCAGTTT<br>CATTTGATGCTCGATGAGTTTTTCTAATAAGCCTTGACCCTACGATTCCC<br>GCTATTTCATTCACTGACCGGAGGTTCAAAATGA |
| 36 | ATGAAGATAGCAACAATGAAAACAGGTCTGGGAGCGTTGGCTCTTCTTC<br>CCTGATCCTTCAACTCAGCAAAAGTTCGATTTATTCAACAAAGCCACGTT<br>GTGTCTCAAAATCTCTGATGTTACATTGCACAAGATAAAAATATATCAT<br>CATGAACAATAAAACTGTCTGCTTACATAAACAGTAATACAAGGGGTGT<br>TATGAGCCATATTCAACGGGAAACGTCTTGCTCCCGTCCGCGCTTAAAC |

| SEQ ID NO: | Sequence |
|---|---|
|  | TCCAACATGGACGCTGATTTATATGGGTATAAATGGGCTCGCGATAATG<br>TCGGGCAATCAGGTGCGACAATCTATCGCTTGTATGGGAAGCCCGATGC<br>GCCAGAGTTGTTTCTGAAACATGGCAAAGGTAGCGTTGCCAATGATGTT<br>ACAGATGAGATGGTCCGTCTCAACTGGCTGACGGAGTTTATGCCTCTCC<br>CGACCATCAAGCATTTTATCCGTACTCCTGATGATGCGTGGTTACTCACC<br>ACCGCGATTCCTGGGAAAACAGCCTTCCAGGTATTAGAAGAATATCCTG<br>ATTCAGGTGAAAATATTGTTGATGCGCTGGCCGTGTTCCTGCGCCGGTTA<br>CATTCGATTCCTGTTTGTAATTGTCCTTTTAACAGCGATCGTGTATTTCGT<br>CTTGCTCAGGCGCAATCACGCATGAATAACGGTTTGGTTGATGCGAGTG<br>ATTTTGATGACGAGCGTAATGGCTGGCCTGTTGAACAAGTCTGGAAAGA<br>AATGCACAAGCTCTTGCCATTCTCACCGGATTCAGTCGTCACTCATGGTG<br>ATTTCTCACTTGATAACCTTATTTTTGACGAGGGGAAATTAATAGGTTGT<br>ATTGATGTTGGACGGGTCGGAATCGCAGACCGTTACCAGGACCTTGCCA<br>TTCTTTGGAACTGCCTCGGTGAGTTTTCTCCTTCATTACAGAAACGGCTT<br>TTTCAAAAATATGGTATTGATAATCCTGATATGAATAAATTGCAGTTTCA<br>TTTGATGCTCGATGAGTTTTTCTAATAAGCCTGTGAAGGGCTGGACGTA<br>AACAGCCACGGCGAAAACGCCTACAACGCCTGA |
| 37 | ATGACCCTGAATATGATGCTCGATAACGCCGTACCCGAGGCGATTGCCG<br>GCTGATCCTTCAACTCAGCAAAAGTTCGATTTATTCAACAAAGCCACGT<br>TGTGTCTCAAAATCTCTGATGTTACATTGCACAAGATAAAAATATATCAT<br>CATGAACAATAAAACTGTCTGCTTACATAAACAGTAATACAAGGGGTGT<br>TATGAGCCATATTCAACGGGAAACGTCTTGCTCCCGTCCGCGCTTAAAC<br>TCCAACATGGACGCTGATTTATATGGGTATAAATGGGCTCGCGATAATG<br>TCGGGCAATCAGGTGCGACAATCTATCGCTTGTATGGGAAGCCCGATGC<br>GCCAGAGTTGTTTCTGAAACATGGCAAAGGTAGCGTTGCCAATGATGTT<br>ACAGATGAGATGGTCCGTCTCAACTGGCTGACGGAGTTTATGCCTCTCC<br>CGACCATCAAGCATTTTATCCGTACTCCTGATGATGCGTGGTTACTCACC<br>ACCGCGATTCCTGGGAAAACAGCCTTCCAGGTATTAGAAGAATATCCTG<br>ATTCAGGTGAAAATATTGTTGATGCGCTGGCCGTGTTCCTGCGCCGGTTA<br>CATTCGATTCCTGTTTGTAATTGTCCTTTTAACAGCGATCGTGTATTTCGT<br>CTTGCTCAGGCGCAATCACGCATGAATAACGGTTTGGTTGATGCGAGTG<br>ATTTTGATGACGAGCGTAATGGCTGGCCTGTTGAACAAGTCTGGAAAGA<br>AATGCACAAGCTCTTGCCATTCTCACCGGATTCAGTCGTCACTCATGGTG<br>ATTTCTCACTTGATAACCTTATTTTTGACGAGGGGAAATTAATAGGTTGT<br>ATTGATGTTGGACGGGTCGGAATCGCAGACCGTTACCAGGACCTTGCCA<br>TTCTTTGGAACTGCCTCGGTGAGTTTTCTCCTTCATTACAGAAACGGCTT<br>TTTCAAAAATATGGTATTGATAATCCTGATATGAATAAATTGCAGTTTCA<br>TTTGATGCTCGATGAGTTTTTCTAATAAGCCTTGGTTCTGCGTTTCCCGCT<br>CTTTAATACCCTGACCGGAGGTGAGCAATGA |
| 38 | ATGACCCTGAATATGATGATGGATGCCGGCGACATCATCGCGACAAAC<br>AATATTAATACCGGCAACCACACCGGCAATTTACGAGACTGCGCAGGCA<br>TCCTTTCTCCCGTCAATTTCTGTCAAATAAAGTAAAAGAGGCAGTCTACT<br>TGAATTACCCCCGGCTGGTTGAGCGTTTGTTGAAAAAAAGTAACTGAAA<br>AATCCGTAGAATAGCGCCACTCTGATGGTTAATTAACCTATTCAATTAA<br>GAATTATCTGGATGAATGTGCCATTAAATGCGCAGCATAATGGTGCGTT<br>GTGCGGGAAAACTGCTTTTTTTTGAAAGGGTTGGTCAGTAGCGGAAACA<br>ACTCACTTCACACCCCGAAGGGGGAAGTTGCCTGACCCTACGATTCCCG<br>CTATTTCATTCACTGACCGGAGGTTCAAAATGA |
| 39 | ATGACCCTGAATATGATGATGGATGCCGGCTCACCACGGCGATAACCAT<br>AGGTTTTCGGCGTGGCCACATCCATGGTGAATCCCACTTTTTCCAGCACG<br>CGCGCCACTTCATCGGGTCTTAAATACATAGATTTTCCTCGTCATCTTTC<br>CAAAGCCTCGCCACCTTACATGACTGAGCATGGACCGTGACTCAGAAAA<br>TTCCACAAACGAACCTGAAAGGCGTGATTGCCGTCTGGCCTTAAAAATT<br>ATGGTCTAAACTAAAATTTACATCGAAAACGAGGGAGGATCCTATGTTT<br>AACAAACCGAATCGCCGTGACGTAGATGAAGGTGTTGAGGATATTAACC<br>ACGATGTTAACCAGCTCGAACTCACTTCACACCCCGAAGGGGGAAGTTG<br>CCTGACCCTACGATTCCCGCTATTTCATTCACTGACCGGAGGTTCAAAAT<br>GA |
| 40 | ATGACCCTGAATATGATGATGGATGCCGGCTGACGAGGCAGGTTACATC<br>ACTGGTGAAACCCTGCACGTCAATGGCGGAATGTATATGGTTTAACCAC<br>GATGAAAATTATTTGCGTTATTAGGGCGAAAGGCCTCAAAATAGCGTAA<br>AATCGTGGTAAGAACTGCCGGGATTTAGTTGCAAATTTTTCAACATTTTA<br>TACACTACGAAAACCATCGCGAAAGCGAGTTTTGATAGGAAATTTAAGA<br>GTATGAGCACTATCGAAGAACGCGTTAAGAAAATTATCGGCGAACAGCT<br>GGGCGTTAAGCAGGAAGAAGTTACCAACAATGCTTCCTTCGTTGAAGAC<br>CTGGGCGCTGATTCTCTTGACACCGAACTCACTTCACACCCCGAAGGGG<br>GAAGTTGCCTGACCCTACGATTCCCGCTATTTCATTCACTGACCGGAGGT<br>TCAAAATGA |
| 41 | ATGACCCTGAATATGATGATGGATGCCGGCCGTCCTGTAATAATAACCG<br>GACAATTCGGACTGATTAAAAAAGCGCCCTTGTGGCGCTTTTTTTATATT |

Table of Strains Sequences

| SEQ ID NO: | Sequence |
|---|---|
|  | CCCGCCTCCATTTAAAATAAAAAATCCAATCGGATTTCACTATTTAAACT<br>GGCCATTATCTAAGATGAATCCGATGGAAGCTCGCTGTTTTAACACGCG<br>TTTTTTAACCTTTTATTGAAAGTCGGTGCTTCTTTGAGCGAACGATCAAA<br>TTTAAGTGGATTCCCATCAAAAAAATATTCTCAACCTAAAAAAGTTTGT<br>GTAATACTTGTAACGCTACATGGAGATTAACTCAATCTAGAGGGTATTA<br>ATAATGAATCGTACTAAACTGGTACTGGGCGCAACTCACTTCACACCCC<br>GAAGGGGGAAGTTGCCTGACCCTACGATTCCCGCTATTTCATTCACTGA<br>CCGGAGGTTCAAAATGA |
| 42 | ATGACCCTGAATATGATGATGGATGCCGGCATATTGACACCATGACGCG<br>CGTAATGCTGATTGGTTCTGTGACGCTGGTAATGATTGTCGAAATTCTGA<br>ACAGTGCCATCGAAGCCGTAGTAGACCGTATTGGTGCAGAATTCCATGA<br>ACTTTCCGGGCGGGCGAAGGATATGGGGTCGGCGGCGGTGCTTGATGTCC<br>ATCCTGCTGGCGATGTTTACCTGGATCGCATTACTCTGGTCACATTTTCG<br>ATAACGCTTCCAGAATTCGATAACGCCCTGGTTTTTTGCTTAAATTTGGT<br>TCCAAAATCGCCTTTAGCTGTATATACTCACAGCATAACTGTATATACAC<br>CCAGGGGGCGGGATGAAAGCATTAACGGCCAGGAACTCACTTCACACC<br>CCGAAGGGGGAAGTTGCCTGACCCTACGATTCCCGCTATTTCATTCACT<br>GACCGGAGGTTCAAAATGA |
| 43 | ATGACCCTGAATATGATGATGGATGCCGGCATCATATTGCGCTCCCTGG<br>TTATCATTTGTTACTAAATGAAATGTTATAATATAACAATTATAAATACC<br>ACATCGCTTTCAATTCACCAGCCAAATGAGAGGAGCGCCGTCTGACATA<br>GCCAGCGCTATAAAACATAGCATTATCTATATGTTTATGATTAATAACTG<br>ATTTTTGCGTTTTGGATTTGGCTGTGGCATCCTTGCCGCTCTTTTCGCAGC<br>GTCTGCGTTTTTGCCCTCCGGTCAGGGCATTTAAGGGTCAGCAATGAGTT<br>TTTACGCAATTACGATTCTTGCCTTCGGCATGTCGATGGATGCTTTAACT<br>CACTTCACACCCCGAAGGGGGAAGTTGCCTGACCCTACGATTCCCGCTA<br>TTTCATTCACTGACCGGAGGTTCAAAATGA |
| 44 | ATGACCCTGAATATGATGATGGATGCCGGCCGCGTCAGGTTGAACGTAA<br>AAAAGTCGGTCTGCGCAAAGCACGTCGTCGTCCGCAGTTCTCCAAACGT<br>TAATTGGTTTCTGCTTCGGCAGAACGATTGGCGAAAAAACCCGGTGCGA<br>ACCGGGTTTTTTTATGGATAAAGATCGTGTTATCCACAGCAATCCATTGA<br>TTATCTCTTCTTTTTCAGCATTTCCAGAATCCCCTCACCACAAAGCCCGC<br>AAAATCTGGTAAACTATCATCCAATTTTCTGCCCAAATGGCTGGGATTGT<br>TCATTTTTTGTTTGCCTTACAACGAGAGTGACAGTACGCGCGGGTAGTTA<br>ACTCAACATCTGACCGGTCGATAACTCACTTCACACCCCGAAGGGGGAA<br>GTTGCCTGACCCTACGATTCCCGCTATTTCATTCACTGACCGGAGGTTCA<br>AAATGA |
| 45 | ATGACCCTGAATATGATGATGGATGCCGGCCCTGTATGAAGATGGCGTG<br>CGCAAAGATCGCCTGGATAACAGCGATATGATTAGCCAGCTTGAAGCCC<br>GCATTCGCGCGAAAGCGTCAATGCTGGACGAAGCGCGTCGTATCGATGT<br>GCAACAGGTAGAAAAATAAGGTTGCTGGGAAGCGGCAGGCTTCCCGTG<br>TATGATGAACCCGCCCGGCGCGACCCGTTGTTCGTCGCGGCCCCGAGGG<br>TTCATTTTTTGTATTAATAAAGAGAATAAACGTGGCAAAAAATATTCAA<br>GCCATTCGCGGCATGAACGATTATCTGCCTGGCGAACTCACTTCACACC<br>CCGAAGGGGGAAGTTGCCTGACCCTACGATTCCCGCTATTTCATTCACT<br>GACCGGAGGTTCAAAATGA |
| 46 | ATGAAAAAGATTGATGCGATTATTAAACCTTTCAAACTGGATGACGTGC<br>GCTGATCCTTCAACTCAGCAAAAGTTCGATTTATTCAACAAAGCCACGT<br>TGTGTCTCAAAATCTCTGATGTTACATTGCACAAGATAAAAATATATCAT<br>CATGAACAATAAAACTGTCTGCTTACATAAACAGTAATACAAGGGGTGT<br>TATGAGCCATATTCAACGGGAAACGTCTTGCTCCCGTCCGCGCTTAAAC<br>TCCAACATGGACGCTGATTTATATGGGTATAAATGGGCTCGCGATAATG<br>TCGGGCAATCAGGTGCGACAATCTATCGCTTGTATGGGAAGCCCGATGC<br>GCCAGAGTTGTTTCTGAAACATGGCAAAGGTAGCGTTGCCAATGATGTT<br>ACAGATGAGATGGTCCGTCTCAACTGGCTGACGGAGTTTATGCCTCTCC<br>CGACCATCAAGCATTTTATCCGTACTCCTGATGATGCGTGGTTACTCACC<br>ACCGCGATTCCTGGGAAAACAGCCTTCCAGGTATTAGAAGAATATCCTG<br>ATTCAGGTGAAAATATTGTTGATGCGCTGGCCGTGTTCCTGCGCCGGTTA<br>CATTCGATTCCTGTTTGTAATTGTCCTTTTAACAGCGATCGTGTATTTCGT<br>CTTGCTCAGGCGCAATCACGCATGAATAACGGTTTGGTTGATGCGAGTG<br>ATTTTGATGACGAGCGTAATGGCTGGCCTGTTGAACAAGTCTGGAAAGA<br>AATGCACAAGCTCTTGCCATTCTCACCGGATTCAGTCGTCACTCATGGTG<br>ATTTCTCACTTGATAACCTTATTTTTGACGAGGGGAAATTAATAGGTTGT<br>ATTGATGTTGGACGGGTCGGAATCGCAGACCGTTACCAGGACCTTGCCA<br>TTCTTTGGAACTGCCTCGGTGAGTTTTCTCCTTCATTACAGAAACGGCTT<br>TTTCAAAAATATGGTATTGATAATCCTGATATGAATAAAATTGCAGTTTCA<br>TTTGATGCTCGATGAGTTTTTCTAATAAGCCTCGCGCGTGATTCGTATCC<br>GCACCGGCGAAGAAGACGACGCGGCGATTTAA |

Table of Strains Sequences

| SEQ ID NO: | Sequence |
|---|---|
| 47 | ATGACCATGAACCTGATGACGGATGTCGTCTCAGCCACCGGGATCGCCG<br>GGTTGCTTTCACGACAACACCCGACGCTGTTTTTTACACTAATTGAACAG<br>GCCCCCGTGGCGATCACGCTGACGGATACCGCTGCCCGCATTGTCTATG<br>CCAACCCGGGCGTGTTGAGTCATCCTGACTAGCTGAGATGAGGGCTCGC<br>CTGATCCTTCAACTCAGCAAAAGTTCGATTTATTCAACAAAGCCACGTT<br>GTGTCTCAAAATCTCTGATGTTACATTGCACAAGATAAAAATATATCAT<br>CATGAACAATAAAACTGTCTGCTTACATAAACAGTAATACAAGGGGTGT<br>TATGAGCCATATTCAACGGGAAACGTCTTGCTCCAGGCCGCGATTAAAT<br>TCCAACATGGATGCTGATTTATATGGGTATAAATGGGCTCGCGATAATG<br>TCGGGCAATCAGGTGCGACAATCTATCGATTGTATGGGAAGCCCGATGC<br>GCCAGAGTTGTTTCTGAAACATGGCAAAGGTAGCGTTGCCAATGATGTT<br>ACAGATGAGATGGTCAGACTAAACTGGCTGACGGAATTTATGCCTCTTC<br>CGACCATCAAGCATTTTATCCGTACTCCTGATGATGCATGGTTACTCACC<br>ACTGCGATCCCCGGGAAAACAGCATTCCAGGTATTAGAAGAATATCCTG<br>ATTCAGGTGAAAATATTGTTGATGCGCTGGCAGTGTTCCTGCGCCGGTT<br>GCATTCGATTCCTGTTTGTAATTGTCCTTTTAACAGCGATCGCGTATTTC<br>GTCTCGCTCAGGCGCAATCACGAATGAATAACGGTTTGGTTGATGCGAG<br>TGATTTTGATGACGAGCGTAATGGCTGGCCTGTTGAACAAGTCTGGAAA<br>GAAATGCATAAGCTTTTGCCATTCTCACCGGATTCAGTCGTCACTCATGG<br>TGATTTCTCACTTGATAACCTTATTTTTGACGAGGGGAAATTAATAGGTT<br>GTATTGATGTTGGACGAGTCGGAATCGCAGACCGATACCAGGATCTTGC<br>CATCCTATGGAACTGCCTCGGTGAGTTTTCTCCTTCATTACAGAAACGGC<br>TTTTTCAAAAATATGGTATTGATAATCCTGATATGAATAAATTGCAGTTT<br>CATTTGATGCTCGATGAGTTTTTCTAATAAGCCTGACCGGTGGTGAATTT<br>AATCTCGCTGACGTGTAGACATTCATCGATCTGCATCCACGGTCCGGCG<br>GCGGTACCTGCCTGACGCTACGTTTACCGCTCTTTTATGAACTGACCGGA<br>GGCCCAAGATGA |
| 48 | ATGAGCATCACGGCGTTATCAGCATCATTTCCTGAGGGGAATATCGCCA<br>GCCGCTTGTCGCTGCAACATCCTTCACTGTTTTATACCGTGGTTGAACAA<br>TCTTCGGTGGCGAGCGTGTTGAGTCATCCTGACTAGCTGAGATGAGGGC<br>TCGCCCCCTCGTCCCGACACTTCCAGATCGCCATAGCGCACAGCGCCTC<br>GAGCGGTGGTAACGGCGCAGTGGCGGTTTTCATGGCTTGTTATGACTGT<br>TTTTTTGGGGTACAGTCTATGCCTCGGGCATCCAAGCAGCAAGCGCGTT<br>ACGCCGTGGGTCGATGTTTGATGTTATGGAGCAGCAACGATGTTACGCA<br>GCAGGGCAGTCGCCCTAAAACAAAGTTAAACATCATGAGGGAAGCGGT<br>GATCGCCGAAGTATCGACTCAACTATCAGAGGTAGTTGGCGTCATCGAG<br>CGCCATCTCGAACCGACGTTGCTGGCCGTACATTTGTACGGCTCCGCAG<br>TGGATGGCGGCCTGAAGCCACACAGTGATATTGATTTGCTGGTTACGGT<br>GACCGTAAGGCTTGATGAAACAACGCGGCGAGCTTTGATCAACGACCTT<br>TTGGAAACTTCGGCTTCCCCTGGAGAGAGCGAGATTCTCCGCGCTGTAG<br>AAGTCACCATTGTTGTGCACGACGACATCATTCCGTGGCGTTATCCAGCT<br>AAGCGCGAACTGCAATTTGGAGAATGGCAGCGCAATGACATTCTTGCAG<br>GTATCTTCGAGCCAGCCACGATCGACATTGATCTGGCTATCTTGCTGACA<br>AAAGCAAGAGAACATAGCGTTGCCTTGGTAGGTCCAGCGGCGGAGGAA<br>CTCTTTGATCCGGTTCCTGAACAGGATCTATTTGAGGCGCTAAATGAAA<br>CCTTAACGCTATGGAACTCGCCGCCCGACTGGGCTGGCGATGAGCGAAA<br>TGTAGTGCTTACGTTGTCCCGCATTTGGTACAGCGCAGTAACCGGCAAA<br>ATCGCGCCGAAGGATGTCGCTGCCGACTGGGCAATGGAGCGCCTGCCGG<br>CCCAGTATCAGCCCGTCATACTTGAAGCTAGACAGGCTTATCTTGGACA<br>AGAAGAAGATCGCTTGGCCTCGCGCGCAGATCAGTTGGAAGAATTTGTC<br>CACTACGTGAAAGGCGAGATCACCAAGGTAGTCGGCAAATAATGTCTA<br>ACAATTCGTTCAAGCCGACGCCGCTTCGCGGCGCGGCTTAACTCAAGCG<br>TTAGATGCACTAAGCACATAATTGCTCACAGCCAAACTATCAGGTCAAG<br>TCTGCTTTTATTATTTTTAAGCGTGCATAATAAGCCCTACACAAATGGTA<br>CCCGACCGGTGGTGAATTTAATCTCGCTGACGTGTAGACATTCCCTTATC<br>CAGACGCTGATCGCCCATCATCGCGGTTCTTTAGATCTCTCGGTCCGCCC<br>TGATGGCGGCACCTTGCTGACGTTACGCCTGCCGGTACAGCAGGTTATC<br>ACCGGAGGCTTAAAATGA |
| 49 | CTGATCCTTCAACTCAGCAAAAGTTCGATTTATTCAACAAAGCCACGTT<br>GTGTCTCAAAATCTCTGATGTTACATTGCACAAGATAAAAATATATCAT<br>CATGAACAATAAAACTGTCTGCTTACATAAACAGTAATACAAGGGGTGT<br>TATGAGCCATATTCAACGGGAAACGTCTTGCTCCAGGCCGCGATTAAAT<br>TCCAACATGGATGCTGATTTATATGGGTATAAATGGGCTCGCGATAATG<br>TCGGGCAATCAGGTGCGACAATCTATCGATTGTATGGGAAGCCCGATGC<br>GCCAGAGTTGTTTCTGAAACATGGCAAAGGTAGCGTTGCCAATGATGTT<br>ACAGATGAGATGGTCAGACTAAACTGGCTGACGGAATTTATGCCTCTTC<br>CGACCATCAAGCATTTTATCCGTACTCCTGATGATGCATGGTTACTCACC<br>ACTGCGATCCCCGGGAAAACAGCATTCCAGGTATTAGAAGAATATCCTG<br>ATTCAGGTGAAAATATTGTTGATGCGCTGGCAGTGTTCCTGCGCCGGTTA<br>GCATTCGATTCCTGTTTGTAATTGTCCTTTTAACAGCGATCGCGTATTTC<br>GTCTCGCTCAGGCGCAATCACGAATGAATAACGGTTTGGTTGATGCGAG<br>TGATTTTGATGACGAGCGTAATGGCTGGCCTGTTGAACAAGTCTGGAAA |

| SEQ ID NO: | Sequence |
|---|---|
| | GAAATGCATAAGCTTTTGCCATTCTCACCGGATTCAGTCGTCACTCATGG<br>TGATTTCTCACTTGATAACCTTATTTTTGACGAGGGGAAATTAATAGGTT<br>GTATTGATGTTGGACGAGTCGGAATCGCAGACCGATACCAGGATCTTGC<br>CATCCTATGGAACTGCCTCGGTGAGTTTTCTCCTTCATTACAGAAACGGC<br>TTTTTCAAAAATATGGTATTGATAATCCTGATATGAATAAATTGCAGTTT<br>CATTTGATGCTCGATGAGTTTTTCTAATAAGCCTTGACCCTACGATTCCC<br>GCTATTTCATTCACTGACCGGAGGTTCAAAATGA |
| 50 | ATGACCCTGAATATGATGCTCGATAACGCCGTACCCGAGGCGATTGCCG<br>GCTGATCCTTCAACTCAGCAAAAGTTCGATTTATTCAACAAAGCCACGT<br>TGTGTCTCAAAATCTCTGATGTTACATTGCACAAGATAAAAATATATCAT<br>CATGAACAATAAAACTGTCTGCTTACATAAACAGTAATACAAGGGGTGT<br>TATGAGCCATATTCAACGGGAAACGTCTTGCTCCCGTCCGCGCTTAAAC<br>TCCAACATGGACGCTGATTTATATGGGTATAAATGGGCTCGCGATAATG<br>TCGGGCAATCAGGTGCGACAATCTATCGCTTGTATGGGAAGCCCGATGC<br>GCCAGAGTTGTTTCTGAAACATGGCAAAGGTAGCGTTGCCAATGATGTT<br>ACAGATGAGATGGTCCGTCTCAACTGGCTGACGGAGTTTATGCCTCTCC<br>CGACCATCAAGCATTTTATCCGTACTCCTGATGATGCGTGGTTACTCACC<br>ACCGCGATTCCTGGGAAAACAGCCTTCCAGGTATTAGAAGAATATCCTG<br>ATTCAGGTGAAAATATTGTTGATGCGCTGGCCGTGTTCCTGCGCCGGTTA<br>CATTCGATTCCTGTTTGTAATTGTCCTTTTAACAGCGATCGTGTATTTCGT<br>CTTGCTCAGGCGCAATCACGCATGAATAACGGTTTGGTTGATGCGAGTG<br>ATTTTGATGACGAGCGTAATGGCTGGCCTGTTGAACAAGTCTGGAAAGA<br>AATGCACAAGCTCTTGCCATTCTCACCGGATTCAGTCGTCACTCATGGTG<br>ATTTCTCACTTGATAACCTTATTTTTGACGAGGGGAAATTAATAGGTTGT<br>ATTGATGTTGGACGGGTCGGAATCGCAGACCGTTACCAGGACCTTGCCA<br>TTCTTTGGAACTGCCTCGGTGAGTTTTCTCCTTCATTACAGAAACGGCTT<br>TTTCAAAAATATGGTATTGATAATCCTGATATGAATAAATTGCAGTTTCA<br>TTTGATGCTCGATGAGTTTTTCTAATAAGCCTTGGTTCTGCGTTTCCCGCT<br>CTTTAATACCCTGACCGGAGGTGAGCAATGA |
| 51 | ATGACCCTGAATATGATGATGGATGCCGGCCGTCCTGTAATAATAACCG<br>GACAATTCGGACTGATTAAAAAAGCGCCCTTGTGGCGCTTTTTTTATATT<br>CCCGCCTCCATTTAAAATAAAAAATCCAATCGGATTTCACTATTTAAACT<br>GGCCATTATCTAAGATGAATCCGATGGAAGCTCGCTGTTTTAACACGCG<br>TTTTTTAACCTTTTATTGAAAGTCGGTGCTTCTTTGAGCGAACGATCAAA<br>TTTAAGTGGATTCCCATCAAAAAAATATTCTCAACCTAAAAAAGTTTGT<br>GTAATACTTGTAACGCTACATGGAGATTAACTCAATCTAGAGGGTATTA<br>ATAATGAATCGTACTAAACTGGTACTGGGCGCAACTCACTTCACACCCC<br>GAAGGGGGAAGTTGCCTGACCCTACGATTCCCGCTATTTCATTCACTGA<br>CCGGAGGTTCAAAATGA |
| 52 | ATGACCCTGAATATGATGATGGATGCCGGCGGACATCATCGCGACAAAC<br>AATATTAATACCGGCAACCACACCGGCAATTTACGAGACTGCGCAGGCA<br>TCCTTTCTCCCGTCAATTTCTGTCAAATAAAGTAAAAGAGGCAGTCTACT<br>TGAATTACCCCCGGCTGGTTGAGCGTTTGTTGAAAAAAAGTAACTGAAA<br>AATCCGTAGAATAGCGCCACTCTGATGGTTAATTAACCTATTCAATTAA<br>GAATTATCTGGATGAATGTGCCATTAAATGCGCAGCATAATGGTGCGTT<br>GTGCGGGAAAACTGCTTTTTTTTGAAAGGGTTGGTCAGTAGCGGAAACA<br>ACTCACTTCACACCCCGAAGGGGGAAGTTGCCTGACCCTACGATTCCCG<br>CTATTTCATTCACTGACCGGAGGTTCAAAATGA |
| 53 | ATGACCCTGAATATGATGATGGATGCCGGCTGACGAGGCAGGTTACATC<br>ACTGGTGAAACCCTGCACGTCAATGGCGGAATGTATATGGTTTAACCAC<br>GATGAAAATTATTTGCGTTATTAGGGCGAAAGGCCTCAAAATAGCGTAA<br>AATCGTGGTAAGAACTGCCGGGATTTAGTTGCAAATTTTTCAACATTTTA<br>TACACTACGAAAACCATCGCGAAAGCGAGTTTTGATAGGAAATTTAAGA<br>GTATGAGCACTATCGAAGAACGCGTTAAGAAAATTATCGGCGAACAGCT<br>GGGCGTTAAGCAGGAAGAAGTTACCAACAATGCTTCCTTCGTTGAAGAC<br>CTGGGCGCTGATTCTCTTGACACCGAACTCACTTCACACCCCGAAGGGG<br>GAAGTTGCCTGACCCTACGATTCCCGCTATTTCATTCACTGACCGGAGGT<br>TCAAAATGA |
| 54 | ATGACCCTGAATATGATGATGGATGCCGGCGGACATCATCGCGACAAAC<br>AATATTAATACCGGCAACCACACCGGCAATTTACGAGACTGCGCAGGCA<br>TCCTTTCTCCCGTCAATTTCTGTCAAATAAAGTAAAAGAGGCAGTCTACT<br>TGAATTACCCCCGGCTGGTTGAGCGTTTGTTGAAAAAAAGTAACTGAAA<br>AATCCGTAGAATAGCGCCACTCTGATGGTTAATTAACCTATTCAATTAA<br>GAATTATCTGGATGAATGTGCCATTAAATGCGCAGCATAATGGTGCGTT<br>GTGCGGGAAAACTGCTTTTTTTTGAAAGGGTTGGTCAGTAGCGGAAACA<br>ACTCACTTCACACCCCGAAGGGGGAAGTTGCCTGACCCTACGATTCCCG<br>CTATTTCATTCACTGACCGGAGGTTCAAAATGA |
| 55 | ATGACCCTGAATATGATGATGGATGCCGGCCGTCCTGTAATAATAACCG<br>GACAATTCGGACTGATTAAAAAAGCGCCCTTGTGGCGCTTTTTTTATATT |

Table of Strains Sequences

| SEQ ID NO: | Sequence |
|---|---|
| | CCCGCCTCCATTTAAAATAAAAAATCCAATCGGATTTCACTATTTAAACT<br>GGCCATTATCTAAGATGAATCCGATGGAAGCTCGCTGTTTTAACACGCG<br>TTTTTTAACCTTTTATTGAAAGTCGGTGCTTCTTTGAGCGAACGATCAAA<br>TTTAAGTGGATTCCCATCAAAAAAATATTCTCAACCTAAAAAAGTTTGT<br>GTAATACTTGTAACGCTACATGGAGATTAACTCAATCTAGAGGGTATTA<br>ATAATGAATCGTACTAAACTGGTACTGGGCGCAACTCACTTCACACCCC<br>GAAGGGGGAAGTTGCCTGACCCTACGATTCCCGCTATTTCATTCACTGA<br>CCGGAGGTTCAAAATGA |
| 56 | ATGAGCATCACGGCGTTATCAGCATCATTTCCTGAGGGGAATATCGCCA<br>GCCGCTTGTCGCTGCAACATCCTTCACTGTTTTATACCGTGGTTGAACAA<br>TCTTCGGTGGCGAGCGTGTTGAGTCATCCTGACTAGCTGAGATGAGGGC<br>TCGCCCCCTCGTCCCGACACTTCCAGATCGCCATAGCGCACAGCGCCTC<br>GAGCGGTGGTAACGGCGCAGTGGCGGTTTTCATGGCTTGTTATGACTGT<br>TTTTTTGGGGTACAGTCTATGCCTCGGGCATCCAAGCAGCAAGCGCGTT<br>ACGCCGTGGGTCGATGTTTGATGTTATGGAGCAGCAACGATGTTACGCA<br>GCAGGGCAGTCGCCCTAAAACAAAGTTAAACATCATGAGGGAAGCGGT<br>GATCGCCGAAGTATCGACTCAACTATCAGAGGTAGTTGGCGTCATCGAG<br>CGCCATCTCGAACCGACGTTGCTGGCCGTACATTTGTACGGCTCCGCAG<br>TGGATGGCGGCCTGAAGCCACACAGTGATATTGATTTGCTGGTTACGGT<br>GACCGTAAGGCTTGATGAAACAACGCGGCGAGCTTTGATCAACGACCTT<br>TTGGAAACTTCGGCTTCCCCTGGAGAGAGCGAGATTCTCCGCGCTGTAG<br>AAGTCACCATTGTTGTGCACGACGACATCATTCCGTGGCGTTATCCAGCT<br>AAGCGCGAACTGCAATTTGGAGAATGGCAGCGCAATGACATTCTTGCAG<br>GTATCTTCGAGCCAGCCACGATCGACATTGATCTGGCTATCTTGCTGACA<br>AAAGCAAGAGAACATAGCGTTGCCTTGGTAGGTCCAGCGGCGGAGGAA<br>CTCTTTGATCCGGTTCCTGAACAGGATCTATTTGAGGCGCTAAATGAAA<br>CCTTAACGCTATGGAACTCGCCGCCCGACTGGGCTGGCGATGAGCGAAA<br>TGTAGTGCTTACGTTGTCCCGCATTTGGTACAGCGCAGTAACCGGCAAA<br>ATCGCGCCGAAGGATGTCGCTGCCGACTGGGCAATGGAGCGCCTGCCGG<br>CCCAGTATCAGCCCGTCATACTTGAAGCTAGACAGGCTTATCTTGGACA<br>AGAAGAAGATCGCTTGGCCTCGCGCGCAGATCAGTTGGAAGAATTTGTC<br>CACTACGTGAAAGGCGAGATCACCAAGGTAGTCGGCAAATAATGTCTA<br>ACAATTCGTTCAAGCCGACGCCGCTTCGCGGCGCGGCTTAACTCAAGCG<br>TTAGATGCACTAAGCACATAATTGCTCACAGCCAAACTATCAGGTCAAG<br>TCTGCTTTTATTATTTTTAAGCGTGCATAATAAGCCCTACACAAATGGTA<br>CCCGACCGGTGGTGAATTTAATCTCGCTGACGTGTAGACATTCCCTTATC<br>CAGACGCTGATCGCCCATCATCGCGGTTCTTTAGATCTCTCGGTCCGCCC<br>TGATGGCGGCACCTTGCTGACGTTACGCCTGCCGGTACAGCAGGTTATC<br>ACCGGAGGCTTAAAATGA |
| 57 | ATGAGCATCACGGCGTTATCAGCATCATTTCCTGAGGGGAATATCGCCA<br>GCCGCTTGTCGCTGCAACATCCTTCACTGTTTTATACCGTGGTTGAACAA<br>TCTTCGGTGGCGAGCGTGTTGAGTCATCCTGACTAGCTGAGATGAGGGC<br>TCGCCCCCTCGTCCCGACACTTCCAGATCGCCATAGCGCACAGCGCCTC<br>GAGCGGTGGTAACGGCGCAGTGGCGGTTTTCATGGCTTGTTATGACTGT<br>TTTTTTGGGGTACAGTCTATGCCTCGGGCATCCAAGCAGCAAGCGCGTT<br>ACGCCGTGGGTCGATGTTTGATGTTATGGAGCAGCAACGATGTTACGCA<br>GCAGGGCAGTCGCCCTAAAACAAAGTTAAACATCATGAGGGAAGCGGT<br>GATCGCCGAAGTATCGACTCAACTATCAGAGGTAGTTGGCGTCATCGAG<br>CGCCATCTCGAACCGACGTTGCTGGCCGTACATTTGTACGGCTCCGCAG<br>TGGATGGCGGCCTGAAGCCACACAGTGATATTGATTTGCTGGTTACGGT<br>GACCGTAAGGCTTGATGAAACAACGCGGCGAGCTTTGATCAACGACCTT<br>TTGGAAACTTCGGCTTCCCCTGGAGAGAGCGAGATTCTCCGCGCTGTAG<br>AAGTCACCATTGTTGTGCACGACGACATCATTCCGTGGCGTTATCCAGCT<br>AAGCGCGAACTGCAATTTGGAGAATGGCAGCGCAATGACATTCTTGCAG<br>GTATCTTCGAGCCAGCCACGATCGACATTGATCTGGCTATCTTGCTGACA<br>AAAGCAAGAGAACATAGCGTTGCCTTGGTAGGTCCAGCGGCGGAGGAA<br>CTCTTTGATCCGGTTCCTGAACAGGATCTATTTGAGGCGCTAAATGAAA<br>CCTTAACGCTATGGAACTCGCCGCCCGACTGGGCTGGCGATGAGCGAAA<br>TGTAGTGCTTACGTTGTCCCGCATTTGGTACAGCGCAGTAACCGGCAAA<br>ATCGCGCCGAAGGATGTCGCTGCCGACTGGGCAATGGAGCGCCTGCCGG<br>CCCAGTATCAGCCCGTCATACTTGAAGCTAGACAGGCTTATCTTGGACA<br>AGAAGAAGATCGCTTGGCCTCGCGCGCAGATCAGTTGGAAGAATTTGTC<br>CACTACGTGAAAGGCGAGATCACCAAGGTAGTCGGCAAATAATGTCTA<br>ACAATTCGTTCAAGCCGACGCCGCTTCGCGGCGCGGCTTAACTCAAGCG<br>TTAGATGCACTAAGCACATAATTGCTCACAGCCAAACTATCAGGTCAAG<br>TCTGCTTTTATTATTTTTAAGCGTGCATAATAAGCCCTACACAAATGGTA<br>CCCGACCGGTGGTGAATTTAATCTCGCTGACGTGTAGACATTCCCTTATC<br>CAGACGCTGATCGCCCATCATCGCGGTTCTTTAGATCTCTCGGTCCGCCC<br>TGATGGCGGCACCTTGCTGACGTTACGCCTGCCGGTACAGCAGGTTATC<br>ACCGGAGGCTTAAAATGA |
| 58 | CTGATCCTTCAACTCAGCAAAAGTTCGATTTATTCAACAAAGCCACGTT<br>GTGTCTCAAAATCTCTGATGTTACATTGCACAAGATAAAAATATATCAT |

| SEQ ID NO: | Sequence |
|---|---|
| | CATGAACAATAAAACTGTCTGCTTACATAAACAGTAATACAAGGGGTGT<br>TATGAGCCATATTCAACGGGAAACGTCTTGCTCCAGGCCGCGATTAAAT<br>TCCAACATGGATGCTGATTTATATGGGTATAAATGGGCTCGCGATAATG<br>TCGGGCAATCAGGTGCGACAATCTATCGATTGTATGGGAAGCCCGATGC<br>GCCAGAGTTGTTTCTGAAACATGGCAAAGGTAGCGTTGCCAATGATGTT<br>ACAGATGAGATGGTCAGACTAAACTGGCTGACGGAATTTATGCCTCTTC<br>CGACCATCAAGCATTTTATCCGTACTCCTGATGATGCATGGTTACTCACC<br>ACTGCGATCCCCGGGAAAACAGCATTCCAGGTATTAGAAGAATATCCTG<br>ATTCAGGTGAAAATATTGTTGATGCGCTGGCAGTGTTCCTGCGCCGGTT<br>GCATTCGATTCCTGTTTGTAATTGTCCTTTTAACAGCGATCGCGTATTTC<br>GTCTCGCTCAGGCGCAATCACGAATGAATAACGGTTTGGTTGATGCGAG<br>TGATTTTGATGACGAGCGTAATGGCTGGCCTGTTGAACAAGTCTGGAAA<br>GAAATGCATAAGCTTTTGCCATTCTCACCGGATTCAGTCGTCACTCATGG<br>TGATTTCTCACTTGATAACCTTATTTTTGACGAGGGGAAATTAATAGGTT<br>GTATTGATGTTGGACGAGTCGGAATCGCAGACCGATACCAGGATCTTGC<br>CATCCTATGGAACTGCCTCGGTGAGTTTTCTCCTTCATTACAGAAACGGC<br>TTTTTCAAAAATATGGTATTGATAATCCTGATATGAATAAATTGCAGTTT<br>CATTTGATGCTCGATGAGTTTTTCTAATAAGCCTTGACCCTACGATTCCC<br>GCTATTTCATTCACTGACCGGAGGTCAAAATGA |
| 59 | ATGAGCATCACGGCGTTATCAGCATCATTTCCTGAGGGGAATATCGCCA<br>GCCGCTTGTCGCTGCAACATCCTTCACTGTTTTATACCGTGGTTGAACAA<br>TCTTCGGTGGCGAGCGTGTTGAGTCATCCTGACTAGCTGAGATGAGGGC<br>TCGCCCCCTCGTCCCGACACTTCCAGATCGCCATAGCGCACAGCGCCTC<br>GAGCGGTGGTAACGGCGCAGTGGCGGTTTTCATGGCTTGTTATGACTGT<br>TTTTTTGGGGTACAGTCTATGCCTCGGGCATCCAAGCAGCAAGCGCGTT<br>ACGCCGTGGGTCGATGTTTGATGTTATGGAGCAGCAACGATGTTACGCA<br>GCAGGGCAGTCGCCCTAAAACAAAGTTAAACATCATGAGGGAAGCGGT<br>GATCGCCGAAGTATCGACTCAACTATCAGAGGTAGTTGGCGTCATCGAG<br>CGCCATCTCGAACCGACGTTGCTGGCCGTACATTTGTACGGCTCCGCAG<br>TGGATGGCGGCCTGAAGCCACACAGTGATATTGATTTGCTGGTTACGGT<br>GACCGTAAGGCTTGATGAAACAACGCGGCGAGCTTTGATCAACGACCTT<br>TTGGAAACTTCGGCTTCCCCTGGAGAGAGCGAGATTCTCCGCGCTGTAG<br>AAGTCACCATTGTTGTGCACGACGACATCATTCCGTGGCGTTATCCAGCT<br>AAGCGCGAACTGCAATTTGGAGAATGGCAGCGCAATGACATTCTTGCAG<br>GTATCTTCGAGCCAGCCACGATCGACATTGATCTGGCTATCTTGCTGACA<br>AAAGCAAGAGAACATAGCGTTGCCTTGGTAGGTCCAGCGGCGGAGGAA<br>CTCTTTGATCCGGTTCCTGAACAGGATCTATTTGAGGCGCTAAATGAAA<br>CCTTAACGCTATGGAACTCGCCGCCCGACTGGGCTGGCGATGAGCGAAA<br>TGTAGTGCTTACGTTGTCCCGCATTTGGTACAGCGCAGTAACCGGCAAA<br>ATCGCGCCGAAGGATGTCGCTGCCGACTGGGCAATGGAGCGCCTGCCGG<br>CCCAGTATCAGCCCGTCATACTTGAAGCTAGACAGGCTTATCTTGGACA<br>AGAAGAAGATCGCTTGGCCTCGCGCGCAGATCAGTTGGAAGAATTTGTC<br>CACTACGTGAAAGGCGAGATCACCAAGGTAGTCGGCAAATAATGTCTA<br>ACAATTCGTTCAAGCCGACGCCGCTTCGCGGCGCGGCTTAACTCAAGCG<br>TTAGATGCACTAAGCACATAATTGCTCACAGCCAAACTATCAGGTCAAG<br>TCTGCTTTTATTATTTTTAAGCGTGCATAATAAGCCCTACACAAATGTA<br>CCCGACCGGTGGTGAATTTAATCTCGCTGACGTGTAGACATTCCCTTATC<br>CAGACGCTGATCGCCCATCATCGCGGTTCTTTAGATCTCTCGGTCCGCCC<br>TGATGGCGGCACCTTGCTGACGTTACGCCTGCCGGTACAGCAGGTTATC<br>ACCGGAGGCTTAAAATGA |
| 60 | ATGAGCATCACGGCGTTATCAGCATCATTTCCTGAGGGGAATATCGCCA<br>GCCGCTTGTCGCTGCAACATCCTTCACTGTTTTATACCGTGGTTGAACAA<br>TCTTCGGTGGCGAGCGTGTTGAGTCATCCTGACTAGCTGAGATGAGGGC<br>TCGCCCCCTCGTCCCGACACTTCCAGATCGCCATAGCGCACAGCGCCTC<br>GAGCGGTGGTAACGGCGCAGTGGCGGTTTTCATGGCTTGTTATGACTGT<br>TTTTTTGGGGTACAGTCTATGCCTCGGGCATCCAAGCAGCAAGCGCGTT<br>ACGCCGTGGGTCGATGTTTGATGTTATGGAGCAGCAACGATGTTACGCA<br>GCAGGGCAGTCGCCCTAAAACAAAGTTAAACATCATGAGGGAAGCGGT<br>GATCGCCGAAGTATCGACTCAACTATCAGAGGTAGTTGGCGTCATCGAG<br>CGCCATCTCGAACCGACGTTGCTGGCCGTACATTTGTACGGCTCCGCAG<br>TGGATGGCGGCCTGAAGCCACACAGTGATATTGATTTGCTGGTTACGGT<br>GACCGTAAGGCTTGATGAAACAACGCGGCGAGCTTTGATCAACGACCTT<br>TTGGAAACTTCGGCTTCCCCTGGAGAGAGCGAGATTCTCCGCGCTGTAG<br>AAGTCACCATTGTTGTGCACGACGACATCATTCCGTGGCGTTATCCAGCT<br>AAGCGCGAACTGCAATTTGGAGAATGGCAGCGCAATGACATTCTTGCAG<br>GTATCTTCGAGCCAGCCACGATCGACATTGATCTGGCTATCTTGCTGACA<br>AAAGCAAGAGAACATAGCGTTGCCTTGGTAGGTCCAGCGGCGGAGGAA<br>CTCTTTGATCCGGTTCCTGAACAGGATCTATTTGAGGCGCTAAATGAAA<br>CCTTAACGCTATGGAACTCGCCGCCCGACTGGGCTGGCGATGAGCGAAA<br>TGTAGTGCTTACGTTGTCCCGCATTTGGTACAGCGCAGTAACCGGCAAA<br>ATCGCGCCGAAGGATGTCGCTGCCGACTGGGCAATGGAGCGCCTGCCGG<br>CCCAGTATCAGCCCGTCATACTTGAAGCTAGACAGGCTTATCTTGGACA<br>AGAAGAAGATCGCTTGGCCTCGCGCGCAGATCAGTTGGAAGAATTTGTC |

Table of Strains Sequences

| SEQ ID NO: | Sequence |
|---|---|
| | CACTACGTGAAAGGCGAGATCACCAAGGTAGTCGGCAAATAATGTCTA<br>ACAATTCGTTCAAGCCGACGCCGCTTCGCGGCGCGGCTTAACTCAAGCG<br>TTAGATGCACTAAGCACATAATTGCTCACAGCCAAACTATCAGGTCAAG<br>TCTGCTTTTATTATTTTTAAGCGTGCATAATAAGCCCTACACAAATGGTA<br>CCCGACCGGTGGTGAATTTAATCTCGCTGACGTGTAGACATTCCCTTATC<br>CAGACGCTGATCGCCCATCATCGCGGTTCTTTAGATCTCTCGGTCCGCCC<br>TGATGGCGGCACCTTGCTGACGTTACGCCTGCCGGTACAGCAGGTTATC<br>ACCGGAGGCTTAAAATGA |
| 61 | ATGTTTAACGATCTGATTGGCGATGATGAAACGGATTCGCCGGAAGATG<br>CGCTTTCTGAGAGCTGGCGCGAATTGTGGCAGGATGCGTTGCAGGAGGA<br>GGATTCCACGCCCGTGCTGGCGCATCTCTCAGAGGACGATCGCCGCCGC<br>GTGGTGGCGCTGATTGCCGATTTTCGCAAAGAGTTGGATAAACGCACCA<br>TTGGCCCGCGAGGGCGGCAGGTACTCGATCACTTAATGCCGCATCTGCT<br>CAGCGATGTATGCTCGCGCGACGATGCGCCAGTACCGCTGTCACGCCTG<br>ACGCCGCTGCTCACCGGAATTATTACCCGCACCACTTACCTTGAGCTGCT<br>AAGTGAATTTCCCGGCGCACTGAAACACCTCATTTCCCTGTGTGCCGCGT<br>CGCCGATGGTTGCCAGTCAGCTGGCGCGCTACCCGATCCTGCTTGATGA<br>ATTGCTCGACCCGAATACGCTCTATCAACCGACGGCGATGAATGCCTAT<br>CGCGATGAGCTGCGCAATACCTGCTGCGCGTGCCGGAAGATGATGAAG<br>AGCAACAGCTTGAGGCGCTGCGGCAGTTTAAGCAGGCGCAGTTGCTGCG<br>CGTGGCGGCGGCGGATATTGCCGGTACGTTGCCAGTAATGAAAGTGAGC<br>GATCACTTAACCTGGCTGGCGGAAGCGATTATTGATGCGGTGGTGCAGC<br>AAGCCTGGGGGCAGATGGTGGCGCGTTATGGCCAGCCAACGCATCTGCA<br>CGATCGCGAAGGGCGCGGTTTTGCGGTGGTCGGTTATGGCAAGCTGGGC<br>GGCTGGGAGCTGGGTTACAGCTCCGATCTGGATCTGGTATTCCTGCACG<br>ACTGCCCGATGGATGTGATGACCGATGGCGAGCGTGAAATCGATGGTCG<br>CCAGTTCTATTTGCGTCTCGCGCAGCGCGTGATGCACCTGTTTAGCACGC<br>GCACGTCGTCCGGCATCCTTTATGAAGTTGATGCGCGTCTGCGTCCATCT<br>GGCGCTGCGGGGATGCTGGTCACTACTACGGAATCGTTCGCCGATTACC<br>AGCAAAACGAAGCCTGGACGTGGGAACATCAGGCGCTGGCCCGTGCGC<br>GCGTGGTGTACGGCGATCCGCAACTGACCGCCGAATTTGACGCCATTCG<br>CCGCGATATTCTGATGACGCCTCGCGACGGCGCAACGCTGCAAACCGAC<br>GTGCGAGAAATGCGCGAGAAAATGCGTGCCCATCTTGGCAACAAGCAT<br>AAAGACCGCTTCGATCTGAAAGCCGATGAAGGCGGTATCACCGACATCG<br>AGTTTATCGCCCAATATCTGGTGCTGCGCTTTGCCCATGACAAGCCGAA<br>ACTGACGCGCTGGTCGGATAATGTGCGCATTCTCGAAGGGCTGGCGCAA<br>AACGGCATCATGGAGGAGCAGGAAGCGCAGGCATTGACGCTGGCGTAC<br>ACCACATTGCGTGATGAGCTGCACCACCTGGCGCTGCAAGAGTTGCCGG<br>GACATGTGGCGCTCTCCTGTTTTGTCGCCGAGCGTGCGCTTATTAAAACC<br>AGCTGGGACAAGTGGCTGGTGGAACCGTGCGCCCCGGCGTAA |

Assessment of Genetic Tractability

Candidate microbes were characterized based on transformability and genetic tractability. First, optimal carbon source utilization was determined by growth on a small panel of relevant media as well as a growth curve in both nitrogen-free and rich media. Second, the natural antibiotic resistance of each strain was determined through spot-plating and growth in liquid culture containing a panel of antibiotics used as selective markers for mutagenesis. Third, each strain was tested for its transformability through electroporation of a collection of plasmids. The plasmid collection comprises the combinatorial expansion of seven origins of replication, i.e., p15a, pSC101, CloDF, colA, RK2, pBBR1, and pRO1600 and four antibiotic resistance markers. i.e., CmR, KmR, SpecR, and TetR This systematic evaluation of origin and resistance marker compatibility was used to identify vectors for plasmid-based mutagenesis in candidate microbes.

Example 3: Mutagenesis of Candidate Microbes

Lambda-Red Mediated Knockouts

Several mutants of candidate microbes were generated using the plasmid pKD46 or a derivative containing a kanamycin resistance marker (Datsenko et al. 2000; PNAS 97(12): 6640-6645). Knockout cassettes were designed with 250 bp homology flanking the target gene and generated via overlap extension PCR. Candidate microbes were transformed with pKD46, cultured in the presence of arabinose to induce Lambda-Red machinery expression, prepped for electroporation, and transformed with the knockout cassettes to produce candidate mutant strains. Four candidate microbes and one laboratory strain, *Klebsiella oxytoca* M5A1, were used to generate thirteen candidate mutants of the nitrogen fixation regulatory genes nifL, glnB, and amtB, as shown in Table 4.

TABLE 4

List of single knockout mutants created through Lambda-red mutagenesis

| Strain | nifL | glnB | amtB |
|---|---|---|---|
| M5A1 | X | X | X |
| CI006 | X | X | X |
| CI010 | X | X | X |
| CI019 | X | X | |
| CI028 | X | X | |

Oligo-Directed Mutagenesis with Cas9 Selection

Oligo-directed mutagenesis was used to target genomic changes to the rpoB gene in *E. coli* DH10B, and mutants were selected with a CRISPR-Cas system. A mutagenic oligo (ss1283: "G*T*T*G*ATCAGACCGATGTTCGGA-CCTTCcaagGTTTCGATCGGACATACGCGAC CGTAGTGGGTCGGGTGTACGTCTCGAACTT-CAAAGCC" (SEQ ID NO: 2), where * denotes phosphorothioate bond) was designed to confer rifampicin resistance through a 4-bp mutation to the rpoB gene. Cells containing a plasmid encoding Cas9 were induced for Cas9 expression, prepped for electroporation, and then electroporated with both the mutagenic oligo and a plasmid encoding constitutive expression of a guide RNA (gRNA) that targets Cas9 cleavage of the WT rpoB sequence. Electroporated cells were recovered in nonselective media overnight to allow sufficient segregation of the resulting mutant chromosomes. After plating on selection for the gRNA-encoding plasmid, two out of ten colonies screened were shown to contain the desired mutation, while the rest were shown to be escape mutants generated through protospacer mutation in the gRNA plasmid or Cas9 plasmid loss.

Lambda-Red Mutagenesis with Cas9 Selection

Figure 3:
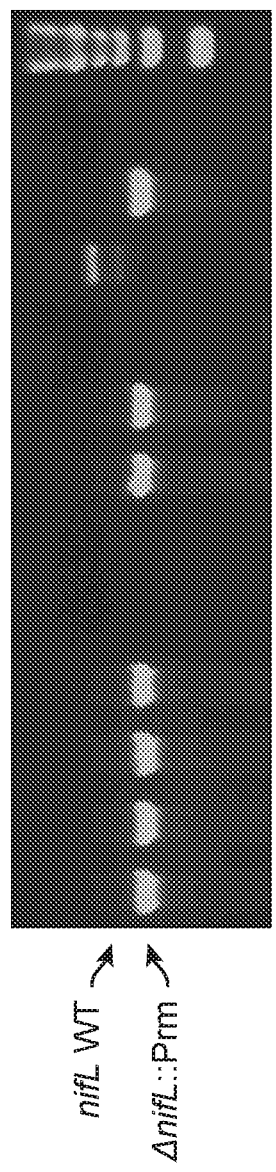
FIG. 3 depicts an example of a PCR screen of colonies from CRISPR-Cas-selected mutagenesis. CI006 colonies were screened with primers specific for the nifL locus. The wild type PCR product is expected at ~2.2 kb, whereas the mutant is expected at ~1.1 kb. Seven of ten colonies screened unambiguously show the desired deletion.

Mutants of candidate microbes CI006 and CI010 were generated via lambda-red mutagenesis with selection by CRISPR-Cas. Knockout cassettes contained an endogenous promoter identified through transcriptional profiling (as described in Example 2 and depicted in Tables 3A-C) and ~250 bp homology regions flanking the deletion target. CI006 and CI010 were transformed with plasmids encoding the Lambda-red recombination system (exo, beta, gam genes) under control of an arabinose inducible promoter and Cas9 under control of an IPTG inducible promoter. The Red recombination and Cas9 systems were induced in resulting transformants, and strains were prepared for electroporation. Knockout cassettes and a plasmid-encoded selection gRNA were subsequently transformed into the competent cells. After plating on antibiotics selective for both the Cas9 plasmid and the gRNA plasmid, 7 of the 10 colonies screened showed the intended knockout mutation, as shown in FIG. 3.

Example 4: In Vitro Phenotyping of Candidate Molecules

The impact of exogenous nitrogen on nitrogenase biosynthesis and activity in various mutants was assessed. The Acetylene Reduction Assay (ARA) (Temme et. al. 2012; 109(18): 7085-7090) was used to measure nitrogenase activity in pure culture conditions. Strains were grown in air-tight test tubes, and reduction of acetylene to ethylene was quantified with an Agilent 6890 gas chromatograph. ARA activities of candidate microbes and counterpart candidate mutants grown in nitrogen fixation media supplemented with 0 to 10 mM glutamine are shown in FIGS. 4A-B and FIGS. 10A-C.

Figure 4C:
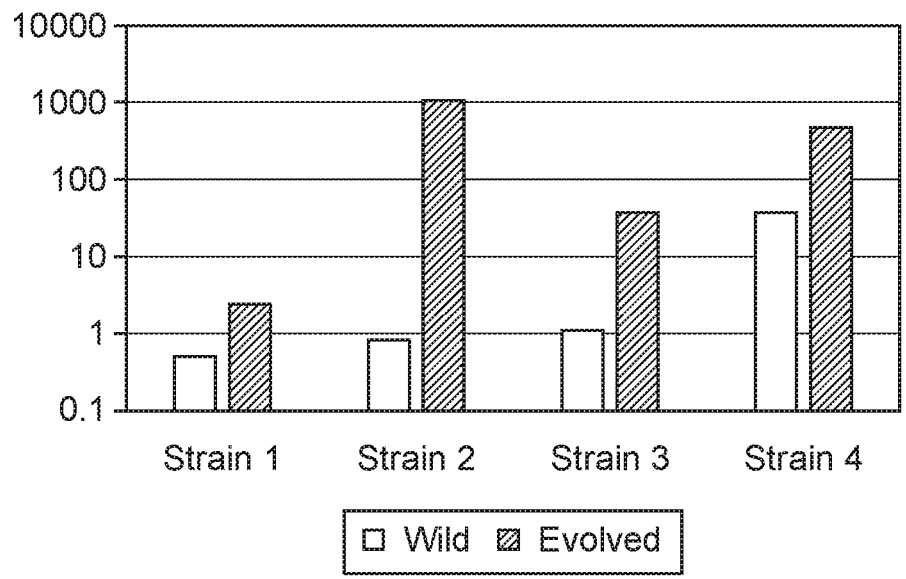
Figure 4D:
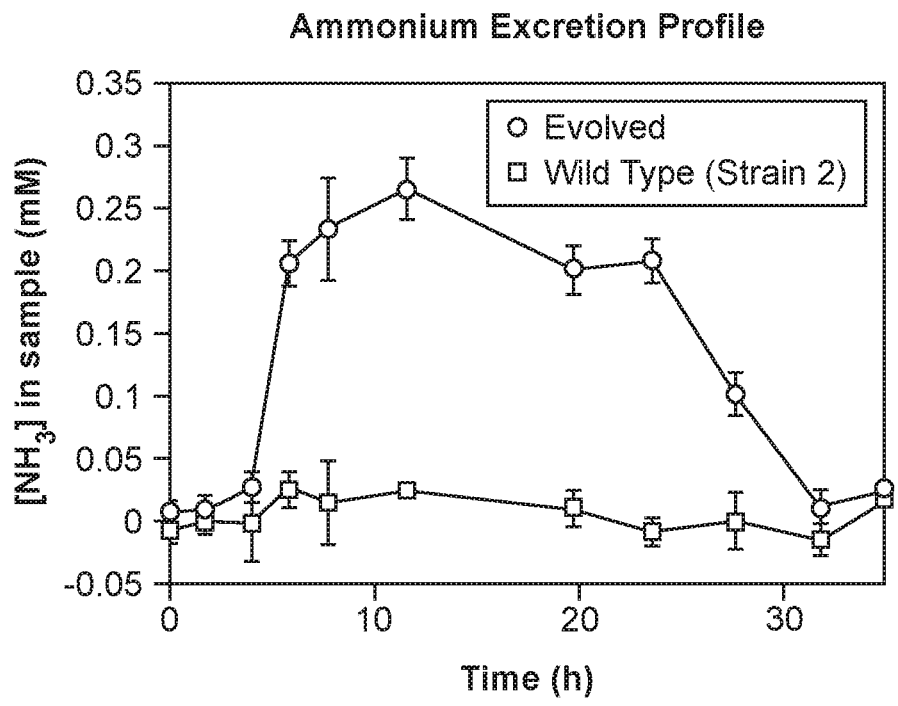
Figure 11:
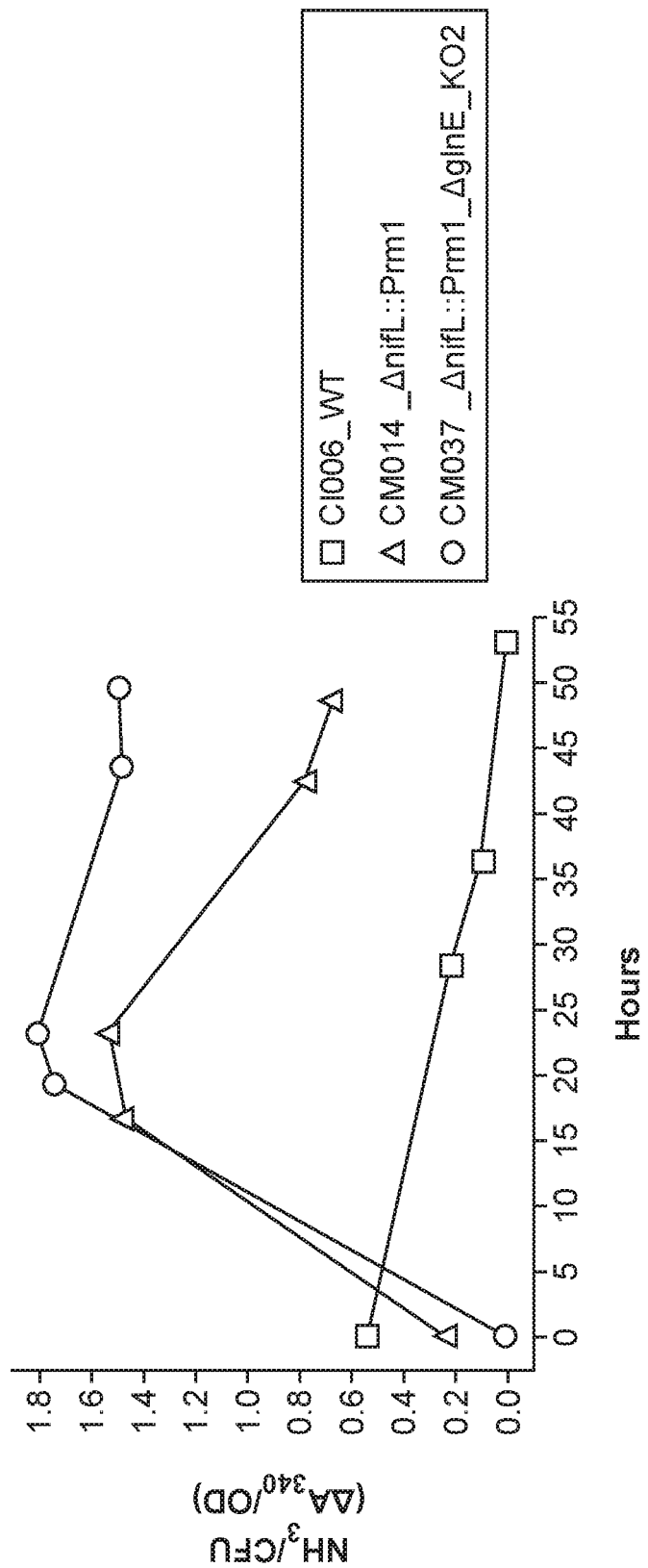
FIG. 11 depicts a double mutant that exhibits higher ammonia excretion than the single mutant from which it was derived.

Under anaerobic culture conditions, a range of glutamine and ammonia concentrations was tested to quantify impact on nitrogen fixation activity. In wild-type cells, activity quickly diminished as glutamine concentrations increased. However, in a series of initial knock-out mutations, a class of mutation was validated enabling expression of nitrogen fixation genes under concentrations of glutamine that would otherwise shut off activity in wild type. This profile was generated in four different species of diazotrophs, as seen in FIG. 4C. In addition, by rewiring the regulatory network using genetic parts that have been identified, the nitrogen fixation activity level was tuned predictably. This is seen in FIG. 4B, which illustrates strains CM023, CM021, CM015, and CI006. Strain CM023 is an evolved strain low; strain CM021 is an evolved strain high; strain CM015 is an evolved strain mid; strain CI006 is a wild-type (strain 2). Ammonia excreted into culture supernatants was tested using a enzymatic-based assay (MEGAZYME). The assay measures the amount of NADPH consumed in the absorbance of 340 nm. The assay was conducted on bacterial cultures grown in nitrogen-free, anaerobic environment with a starting density of 1E9 CFU/ml. Across a panel of six evolved strains, one strain excreted up to 100 µM of ammonia over a course of a 48 hour period, as seen in FIG. 4D. Further, a double mutant exhibited higher ammonia excretion than the single mutant from which it was derived, as seen in FIG. 11. This demonstrates a microbial capacity to produce ammonia in excess of its physiological needs.

Transcription Profiling of Pure Cultures

Transcriptional activity of CI006 was measured using the Nanostring Elements platform. Cells were grown in nitrogen-free media and 10E8 cells were collected after 4 hours incubation. Total RNA was extracted using the Qiagen RNeasy kit. Purified RNA was submitted to Core Diagnostics in Palo Alto, Calif., for probe hybridization and Digital Analyzer analysis, as shown in FIG. 5.

Example 5: In Planta Phenotyping of Candidate Microbes

Colonization of Plants by Candidate Microbes

Figure 6:
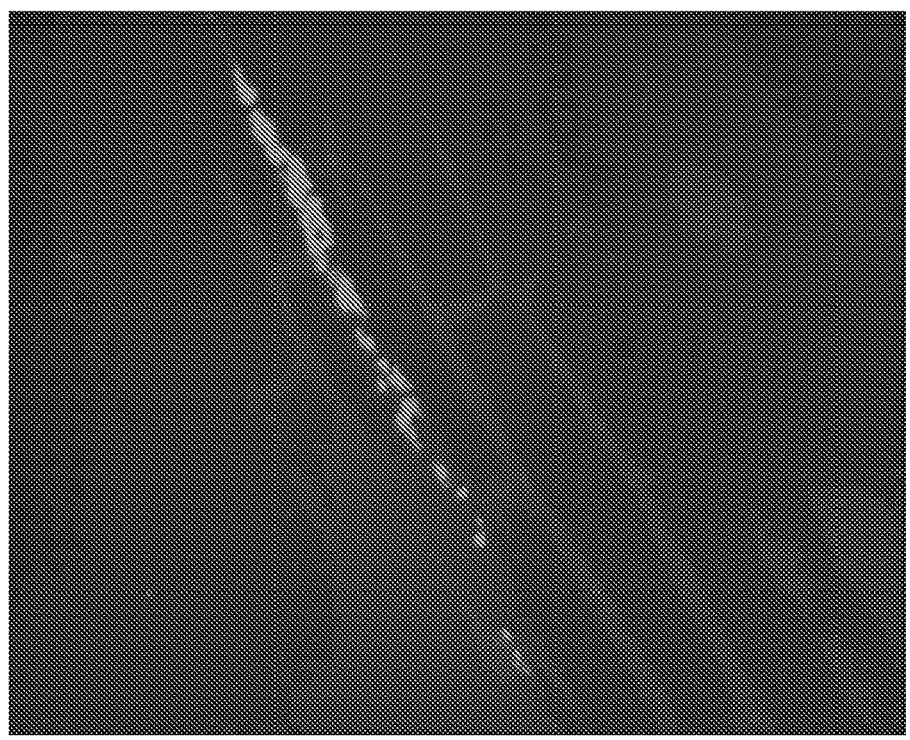
FIG. 6 depicts CI006 colonization of corn roots. Corn seedlings were inoculated with CI006 harboring an RFP expression plasmid. After two weeks of growth and plasmid maintenance through watering with the appropriate antibiotic, roots were harvested and imaged through fluorescence microscopy. Colonization of the root intercellular space is observed.

Colonization of desired host plants by a candidate microbe was quantified through short-term plant growth experiments. Corn plants were inoculated with strains expressing RFP either from a plasmid or from a Tn5-integrated RFP expression cassette. Plants were grown in both sterilized sand and nonsterile peat medium, and inoculation was performed by pipetting 1 mL of cell culture directly over the emerging plant coleoptile three days post-germination. Plasmids were maintained by watering plants with a solution containing the appropriate antibiotic. After three weeks, plant roots were collected, rinsed three times in sterile water to remove visible soil, and split into two samples. One root sample was analyzed via fluorescence microscopy to identify localization patterns of candidate microbes. Microscopy was performed on 10 mm lengths of the finest intact plant roots, as shown in FIG. 6.

A second quantitative method for assessing colonization was developed. A quantitative PCR assay was performed on whole DNA preparations from the roots of plants inoculated with the endophytes. Seeds of corn (Dekalb DKC-66-40) were germinated in previously autoclaved sand in a 2.5 inch by 2.5 inch by 10 inch pot. One day after planting, 1 ml of endophyte overnight culture (SOB media) was drenched right at the spot of where the seed was located. 1 mL of this overnight culture is roughly equivalent to about 10^9 cfu, varying within 3-fold of each other, depending on which strain is being used. Each seedling was fertilized 3× weekly with 50 mL modified Hoagland's solution supplemented with either 2.5 mM or 0.25 mM ammonium nitrate. At four weeks after planting, root samples were collected for DNA extraction. Soil debris were washed away using pressurized water spray. These tissue samples were then homogenized using QIAGEN Tissuelyzer and the DNA was then extracted using QIAmp DNA Mini Kit (QIAGEN) according to the recommended protocol. qPCR assay was performed using Stratagene Mx3005P RT-PCR on these DNA extracts using primers that were designed (using NCBI's Primer BLAST) to be specific to a loci in each of the endophyte's genome. The presence of the genome copies of the endophytes was quantified. To further confirm the identity of the endophytes, the PCR amplification products were sequenced and are confirmed to have the correct sequence. The summary of the colonization profile of strain CI006 and CI008 from candidate microbes are presented in Table 5. Colonization rate as high as $10^7\times$ cfu/g fw of root was demonstrated in strain CI008.

TABLE 5

Colonization of corn as measured by qPCR

| Strain | Colonization Rate (CFU/g fw) |
|---|---|
| CI006 | $1.45 \times 10^5$ |
| CI008 | $1.24 \times 10^7$ |

In Planta RNA Profiling

Biosynthesis of nif pathway components in planta was estimated by measuring the transcription of nif genes. Total RNA was obtained from root plant tissue of CI006 inoculated plants (planting methods as described previously). RNA extraction was performed using RNEasy Mini Kit according to the recommended protocol (QIAGEN). Total RNA from these plant tissues was then assayed using Nanostring Elements kits (NanoString Technologies, Inc.) using probes that were specific to the nif genes in the genome of strain CI006. The data of nif gene expression in planta is summarized in Table 6. Expression of nifH genes was detected in plants inoculated by CM013 strains whereas nifH expression was not detectable in CI006 inoculated plants. Strain CM013 is a derivative of strain CI006 in which the nifL gene has been knocked out.

Highly expressed genes of CM011, ranked by transcripts per kilobase million (TPM), were measured in planta under fertilized condition. The promoters controlling expression of some of these highly expressed genes were used as templates for homologous recombination into targeted nitrogen fixation and assimilation loci. RNA samples from greenhouse grown CM011 inoculated plant were extracted, rRNA removed using Ribo-Zero kit, sequenced using Illumina's Truseq platform and mapped back to the genome of CM011. Highly expressed genes from CM011 are listed in Table 7.

TABLE 6

Expression of nifH in planta

| Strains | Relative Transcript Expression |
|---|---|
| CI006 | 9.4 |
| CM013 | 103.25 |

TABLE 7

| Gene Name | Gene Location | Direction | Raw Read Count | TPM (Transcripts Per Kilobase Million) |
|---|---|---|---|---|
| rpsH CDS | 18196-18588 | reverse | 4841.5 | 27206.4 |
| rplQ CDS | 11650-12039 | reverse | 4333 | 24536.2 |
| rpsJ CDS | 25013-25324 | reverse | 3423 | 24229 |
| rplV CDS | 21946-22278 | reverse | 3367.5 | 22333 |
| rpsN CDS | 18622-18927 | reverse | 2792 | 20150.1 |
| rplN CDS | 19820-20191 | reverse | 3317 | 19691.8 |
| rplF CDS | 17649-18182 | reverse | 4504.5 | 18628.9 |
| rpsD CDS | 13095-13715 | reverse | 5091.5 | 18106.6 |
| rpmF CDS | 8326-8493 | forward | 1363.5 | 17923.8 |
| rplW CDS | 23429-23731 | reverse | 2252 | 16413.8 |
| rpsM CDS | 14153-14509 | reverse | 2269 | 14036.2 |
| rplR CDS | 17286-17639 | reverse | 2243.5 | 13996.1 |

TABLE 7-continued

| Gene Name | Gene Location | Direction | Raw Read Count | TPM (Transcripts Per Kilobase Million) |
|---|---|---|---|---|
| rplC CDS | 24350-24979 | reverse | 3985 | 13969.2 |
| rplK CDS | 25526-25954 | reverse | 2648.5 | 13634.1 |
| rplP CDS | 20807-21217 | reverse | 2423 | 13019.5 |
| rplX CDS | 19495-19809 | reverse | 1824 | 12787.8 |
| rpsQ CDS | 20362-20616 | reverse | 1460.5 | 12648.7 |
| bhsA 3 CDS | 79720-79977 | reverse | 1464 | 12531.5 |
| rpmC CDS | 20616-20807 | reverse | 998.5 | 11485 |
| rpoA CDS | 12080-13069 | reverse | 4855 | 10830.2 |
| rplD CDS | 23728-24333 | reverse | 2916.5 | 10628.5 |
| bhsA 1 CDS | 78883-79140 | reverse | 1068 | 9141.9 |
| rpsS CDS | 22293-22571 | reverse | 1138.5 | 9011.8 |
| rpmA CDS | 2210-2467 | forward | 1028.5 | 8803.7 |
| rpmD CDS | 16585-16764 | reverse | 694.5 | 8520.8 |
| rplB CDS | 22586-23410 | reverse | 3132 | 8384 |
| rpsC CDS | 21230-21928 | reverse | 2574.5 | 8133.9 |
| rplE CDS | 18941-19480 | reverse | 1972.5 | 8066.9 |
| rplO CDS | 16147-16581 | reverse | 1551 | 7874.2 |
| preprotein translocase subunit SecY CDS | 14808-16139 | reverse | 4657 | 7721.2 |
| rpsE CDS | 16771-17271 | reverse | 1671.5 | 7368 |
| rpsK CDS | 13746-14135 | reverse | 1223.5 | 6928.2 |
| tufA CDS | 27318-28229 | reverse | 2850 | 6901.3 |
| rpmI CDS | 38574-38771 | forward | 615 | 6859.5 |
| rplU CDS | 1880-2191 | forward | 935.5 | 6621.7 |
| rplT CDS | 38814-39170 | forward | 1045 | 6464.4 |
| bhsA 2 CDS | 79293-79550 | reverse | 754 | 6454.1 |
| rpmB CDS | 8391-8627 | reverse | 682 | 6355.1 |
| rplJ CDS | 23983-24480 | reverse | 1408 | 6243.9 |
| fusA 2 CDS | 481-2595 | reverse | 5832 | 6089.6 |
| rpsA CDS | 25062-26771 | reverse | 4613 | 5957.6 |
| rpmJ CDS | 14658-14774 | reverse | 314 | 5926.9 |
| rpsR CDS | 52990-53217 | forward | 603 | 5840.7 |
| rpsG CDS | 2692-3162 | reverse | 1243 | 5828.2 |
| rpsI CDS | 11354-11746 | reverse | 980.5 | 5509.8 |
| cspC 1 CDS | 8091-8300 | reverse | 509 | 5352.8 |
| rpsF CDS | 52270-52662 | forward | 916 | 5147.4 |
| rpsT CDS | 55208-55471 | reverse | 602 | 5035.9 |
| infC CDS | 38128-38478 | forward | 755 | 4750.3 |
| cspG CDS | 30148-30360 | forward | 446 | 4624.2 |

$^{15}$N Assay

The primary method for demonstrating fixation uses the nitrogen isotope 15N, which is found in the atmosphere at a set rate relative to 14N. By supplementing either fertilizer or atmosphere with enriched levels of 15N, one can observe fixation either directly, in heightened amounts of 15N fixed from an atmosphere supplemented with 15N2 gas (Yoshida 1980), or inversely, through dilution of enriched fertilizer by atmospheric N2 gas in plant tissues (Iniguez 2004). The dilution method allows for the observation of cumulative fixed nitrogen over the course of plant growth, while the $15N_2$ gas method is restricted to measuring the fixation that occurs over the short interval that a plant can be grown in a contained atmosphere (rate measurement). Therefore, the gas method is superior in specificity (as any elevated $15N_2$ levels in the plant above the atmospheric rate can be attributed unambiguously to fixation) but cannot show cumulative activity.

Figure 7:
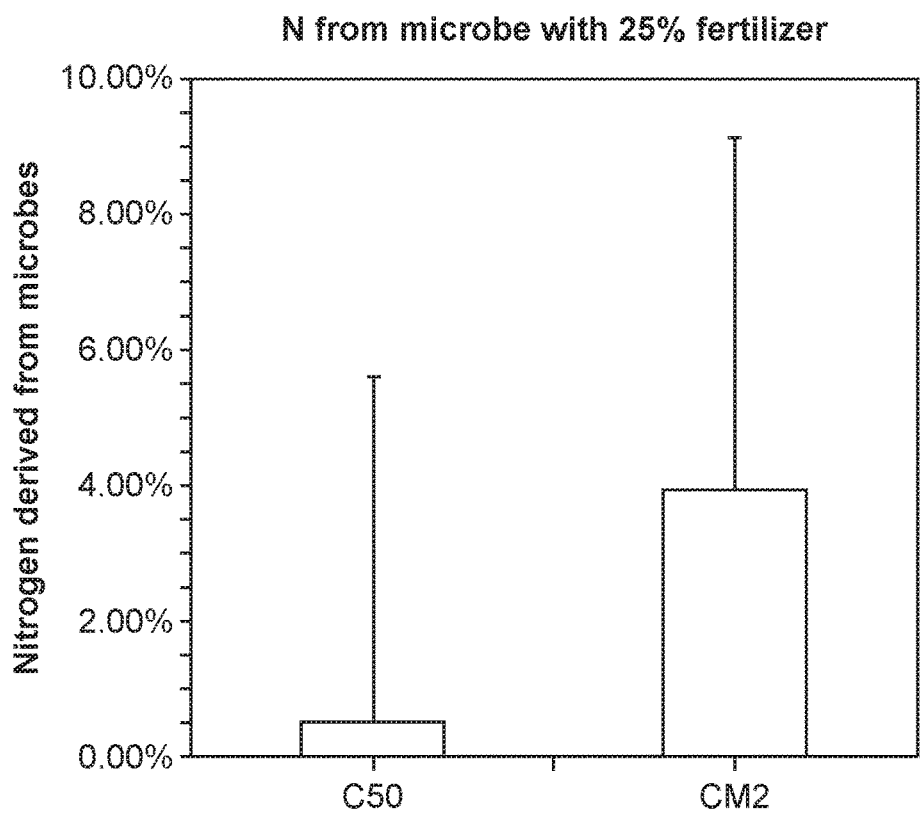
FIG. 7 depicts nitrogen derived from microbe level in WT (CI050) and optimized (CM002) strain.
Figure 12:
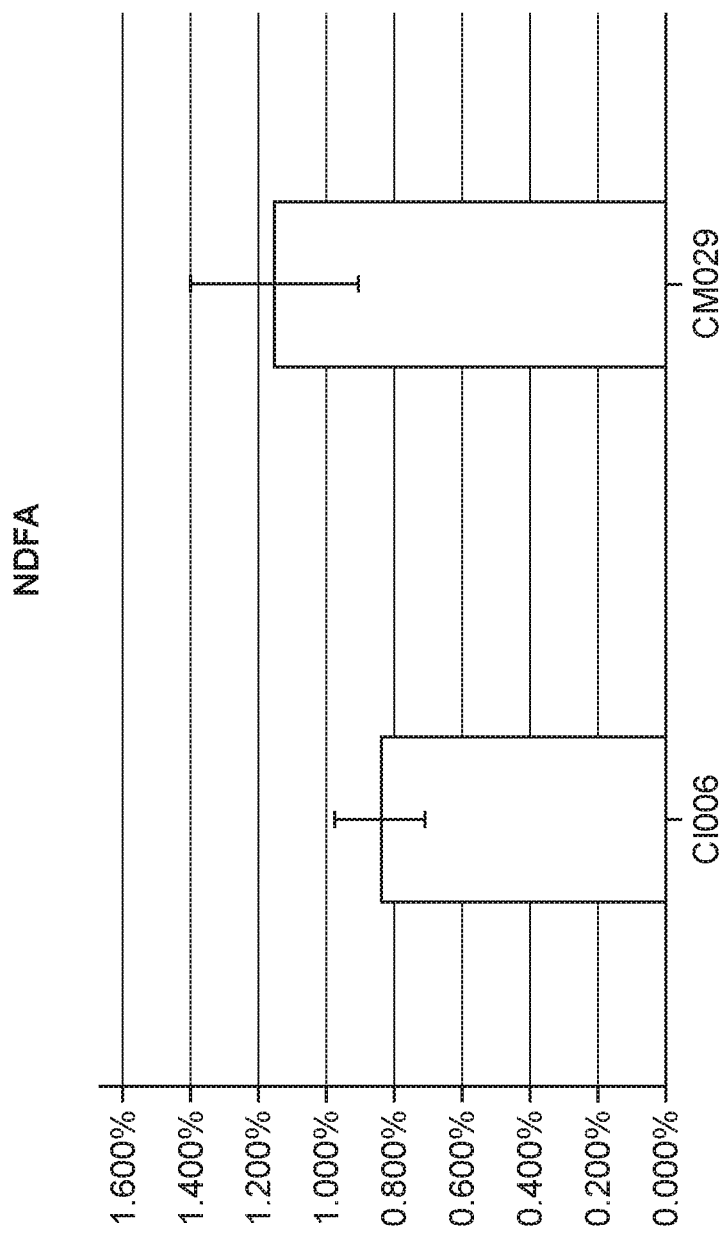
FIG. 12 depicts NDFA obtained from 15N Gas Uptake experiment (extrapolated back using days exposed) to measure NDFA in Corn plants in fertilized condition.
Figure 13:
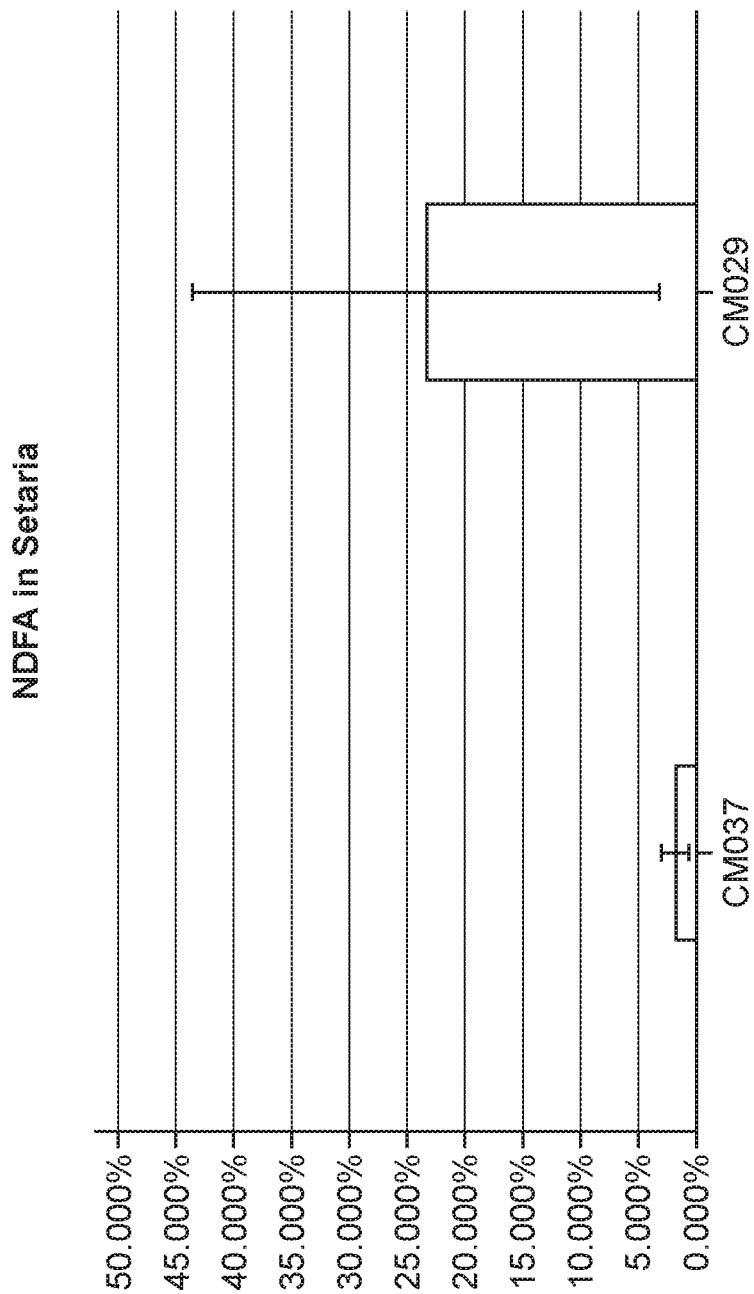
FIG. 13 depicts NDFA value obtained from 15N Gas Uptake experiment (extrapolated back using days exposed) to measure NDFA in Setaria plants in fertilized condition.

Both types of assay has been performed to measure fixation activity of improved strains relative to wild-type and uninoculated corn plants, and elevated fixation rates were observed in planta for several of the improved strains (FIG. 12, FIG. 14A, and FIG. 14B). These assays are instrumental in demonstrating that the activity of the strains observed in vitro translates to in vivo results. Furthermore, these assays allow measurement of the impact of fertilizer on strain activity, suggesting suitable functionality in an agricultural setting. Similar results were observed when *setaria* plants were inoculated with wild-type and improved strains (FIG. 13). In planta fixation activity shown in FIGS. 14A-14C is further backed up by transcriptomic data. Evolved strains exhibit increased nifH transcript level relative to wild-type counterparts. Furthermore, the microbe derived nitrogen level in planta is also correlated with the colonization level on a plant by plant basis. These results (FIG. 12, FIG. 13, FIGS. 14A-14C, FIG. 15A, and FIG. 15B) support the hypothesis that the microbe, through the improved regulation of the nif gene cluster, is the likely reason for the increase in atmospheric derived nitrogen seen in the plant tissue. In addition to measuring fixation directly, the impact of inoculating plants with the improved strains in a nitrogen-stressed plant biomass assay was measured. While plant biomass may be related to many possible microbe interactions with the plant, one would expect that the addition of fixed nitrogen would impact the plant phenotype when nitrogen is limited. Inoculated plants were grown in the complete absence of nitrogen, and significant increases in leaf area, shoot fresh and dry weight, and root fresh and dry weight in inoculated plants relative to untreated controls was observed (FIG. 14C). Although these differences cannot be attributed to nitrogen fixation exclusively, they support the conclusion that the improved strains are actively providing nitrogen to the plant. Corn and *setaria* plants were grown and inoculated as described above. Fertilizer comprising 1.2% $^{15}$N was regularly supplied to plants via watering. Nitrogen fixation by microbes was quantified by measuring the $^{15}$N level in the plant tissue. Fourth leaf tissue was collected and dried at 4 weeks after planting. Dried leaf samples were homogenized using beads (QIAGEN Tissue-lyzer) and aliquoted out into tin capsules for IRMS (MBL Stable Isotope Laboratory at The Ecosystems Center, Woods Hole, Mass.). Nitrogen derived from the atmosphere (NDFA) was calculated, and nitrogen production by CI050 and CM002 are shown in FIG. 7.

Phytohormone Production Assay

Figure 8:
FIG. 8 shows an experimental setup for a Micro-Tom fruiting mass assay.
Figure 9:
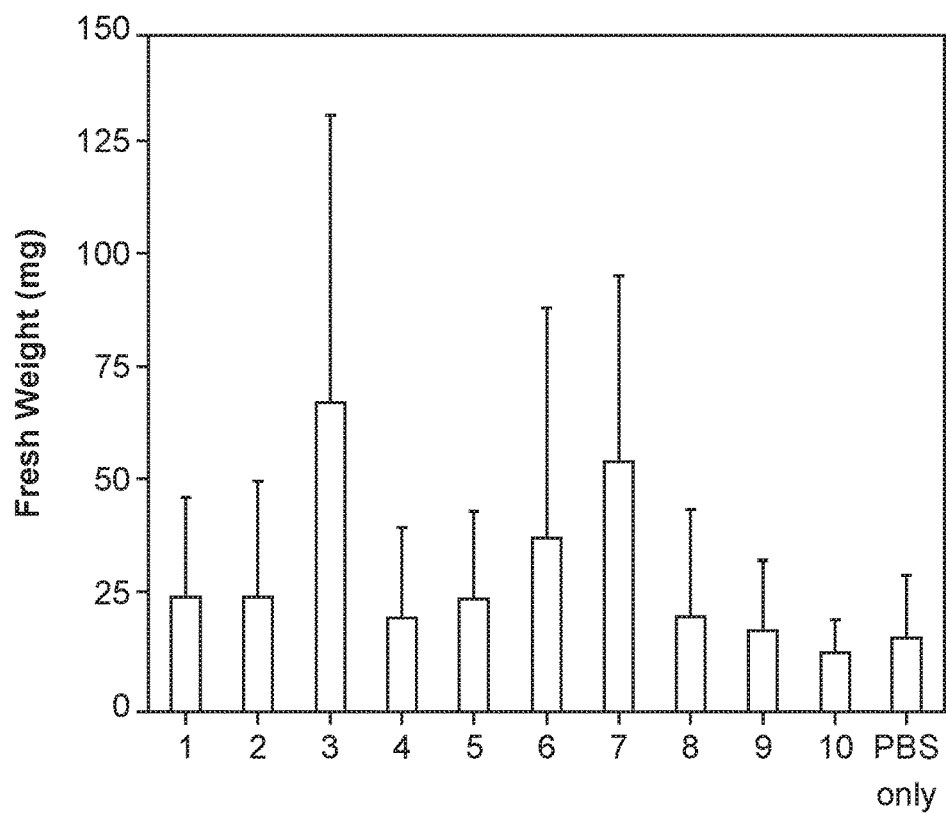
FIG. 9 shows a screen of 10 strains for increase in Micro-Tom plant fruit mass. Results for six replicates are presented. For column 3, p=0.07. For column 7, p=0.05.

The dwarf tomato (*Solanum lycopersicum*) cultivar 'Micro-Tom' has previously been used to study the influence of indole-3-acetic acid on fruit ripening through an in vitro assay (Cohen 1996; J Am Soc Hortic Sci 121: 520-524). To evaluate phytohormone production and secretion by candidate microbes, a plate-based screening assay using immature Micro-Tom fruit was developed. Twelve-well tissue culture test plates were prepared by filling wells with agar medium, allowing it to solidify, and spotting 10 uL of overnight microbial cultures onto the agar surface, as shown in FIG. 8. Wells with agar containing increasing amounts of gibberellic acid (GA) but no bacterial culture were used as a positive control and standards. Flowers one day post-anthesis abscised from growing Micro-Tom plants were inserted, stem-first, into the agar at the point of the bacterial spot culture. These flowers were monitored for 2-3 weeks, after which the fruits were harvested and weighed. An increase in plant fruit mass across several replicates indicates production of plant hormone by the inoculant microbe, as shown in FIG. 9.

Example 6: Cyclical Host-Microbe Evolution

Corn plants were inoculated with CM013 and grown 4 weeks to approximately the V5 growth stage. Those demonstrating improved nitrogen accumulation from microbial sources via $^{15}$N analysis were uprooted, and roots were washed using pressurized water to remove bulk soil. A 0.25 g section of root was cut and rinsed in PBS solution to remove fine soil particles and non-adherent microbes. Tissue samples were homogenized using 3 mm steel beads in QIAGEN TissueLyser II. The homogenate was diluted and plated on SOB agar media. Single colonies were resuspended in liquid media and subjected to PCR analysis of 16s rDNA and mutations unique to the inoculating strain. The process of microbe isolation, mutagenesis, inoculation, and re-isolation can be repeated iteratively to improve microbial traits, plant traits, and the colonization capability of the microbe.

Example 7: Compatibility Across Geography

The ability of the improved microbes to colonize an inoculated plant is critical to the success of the plant under field conditions. While the described isolation methods are designed to select from soil microbes that may have a close relationship with crop plants such as corn, many strains may not colonize effectively across a range of plant genotypes, environments, soil types, or inoculation conditions. Since colonization is a complex process requiring a range of interactions between a microbial strain and host plant, screening for colonization competence has become a central method for selecting priority strains for further development. Early efforts to assess colonization used fluorescent tagging of strains, which was effective but time-consuming and not scalable on a per-strain basis. As colonization activity is not amenable to straightforward improvement, it is imperative that potential product candidates are selected from strains that are natural colonizers.

An assay was designed to test for robust colonization of the wild-type strains in any given host plant using qPCR and primers designed to be strain-specific in a community sample. This assay is intended to rapidly measure the colonization rate of the microbes from corn tissue samples. Initial tests using strains assessed as probable colonizers using fluorescence microscopy and plate-based techniques indicated that a qPCR approach would be both quantitative and scalable.

A typical assay is performed as follows: Plants, mostly varieties of maize and wheat, are grown in a peat potting mix in the greenhouse in replicates of six per strain. At four or five days after planting, a 1 mL drench of early stationary phase cultures of bacteria diluted to an OD590 of 0.6-1.0 (approximately 5E+08 CFU/mL) is pipetted over the emerging coleoptile. The plants are watered with tap water only and allowed to grow for four weeks before sampling, at which time, the plants are uprooted and the roots washed thoroughly to remove most peat residues. Samples of clean root are excised and homogenized to create a slurry of plant cell debris and associated bacterial cells. We developed a high-throughput DNA extraction protocol that effectively produced a mixture of plant and bacterial DNA to use as template for qPCR. Based on bacterial cell spike-in experiments, this DNA extraction process provides a quantitative bacterial DNA sample relative to the fresh weight of the roots. Each strain is assessed using strain-specific primers designed using Primer BLAST (Ye 2012) and compared to background amplification from uninoculated plants. Since some primers exhibit off-target amplification in uninoculated plants, colonization is determined either by presence of amplification or elevated amplification of the correct product compared to the background level.

This assay was used to measure the compatibility of the microbial product across different soil geography. Field soil qualities and field conditions can have a huge influence on the effect of a microbial product. Soil pH, water retention capacity, and competitive microbes are only a few examples of factors in soil that can affect inoculum survival and colonization ability. A colonization assay was performed using three diverse soil types sampled from agricultural fields in California as the plant growth medium (FIG. 16A). An intermediate inoculation density was used to approximate realistic agricultural conditions. Within 3 weeks, Strain 5 colonized all plants at 1E+06 to 1E+07 CFU/g FW. After 7 weeks of plant growth, an evolved version of Strain 1 exhibited high colonization rates (1E+06 CFU/g FW) in all soil types. (FIG. 16B).

Figure 16C:
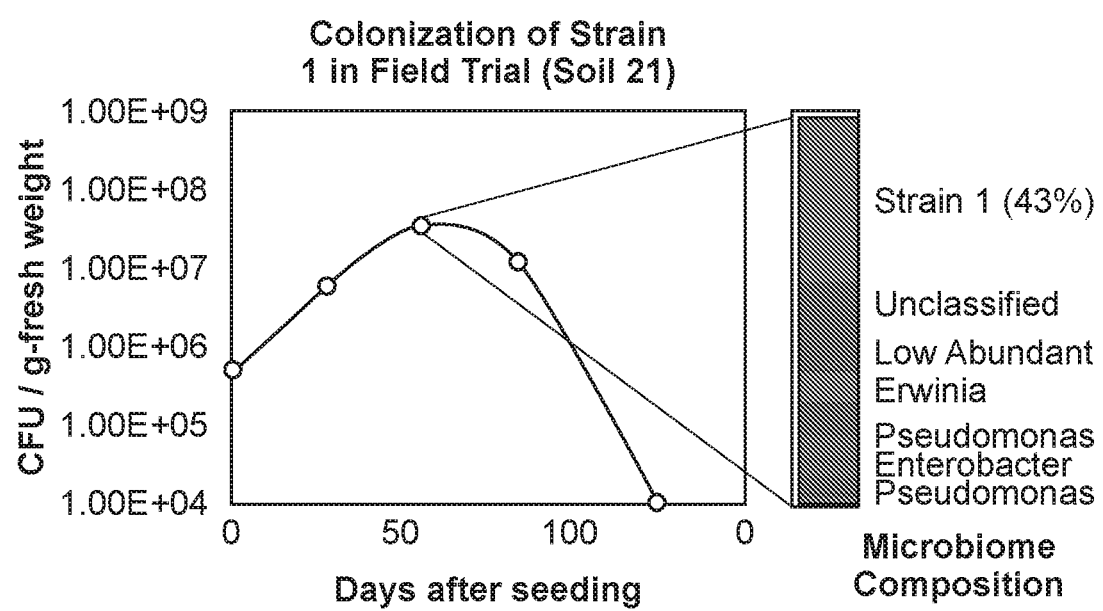
FIG. 16C depicts colonization of Strain 1 as tested in a field trial over the span of a growing season. Strain 1 persists in the corn tissue up to week 12 after planting and starts to show decline in colonization after that time.

Additionally, to assess colonization in the complexity of field conditions, a 1-acre field trial in San Luis Obispo in June of 2015 was initiated to assess the impacts and colonization of seven of the wild-type strains in two varieties of field corn. Agronomic design and execution of the trial was performed by a contract field research organization, Pacific Ag Research. For inoculation, the same peat culture seed coating technique tested in the inoculation methods experiment was employed. During the course of the growing season, plant samples were collected to assess for colonization in the root and stem interior. Samples were collected from three replicate plots of each treatment at four and eight weeks after planting, and from all six reps of each treatment shortly before harvest at 16 weeks. Additional samples were collected from all six replicate plots of treatments inoculated with Strain 1 and Strain 2, as well as untreated controls, at 12 weeks. Numbers of cells per gram fresh weight of washed roots were assessed as with other colonization assays with qPCR and strain-specific primers. Two strains, Strain 1 and Strain 2, showed consistent and widespread root colonization that peaked at 12 weeks and then declined precipitously (FIG. 16C). While Strain 2 appeared to be present in numbers an order of magnitude lower than Strain 1, it was found in more consistent numbers from plant to plant. No strains appeared to effectively colonize the stem interior. In support of the qPCR colonization data, both strains were successfully re-isolated from the root samples using plating and 16S sequencing to identify isolates of matching sequence.

Example 8: Microbe Breeding

Examples of microbe breeding can be summarized in the schematic of FIG. 17A. FIG. 17A depicts microbe breeding wherein the composition of the microbiome can be first measured and a species of interest is identified. The metabolism of the microbiome can be mapped and linked to genetics. Afterwards, a targeted genetic variation can be introduced using methods including, but not limited to, conjugation and recombination, chemical mutagenesis, adaptive evolution, and gene editing. Derivative microbes are used to inoculate crops. In some examples, the crops with the best phenotypes are selected.

Figure 17B:
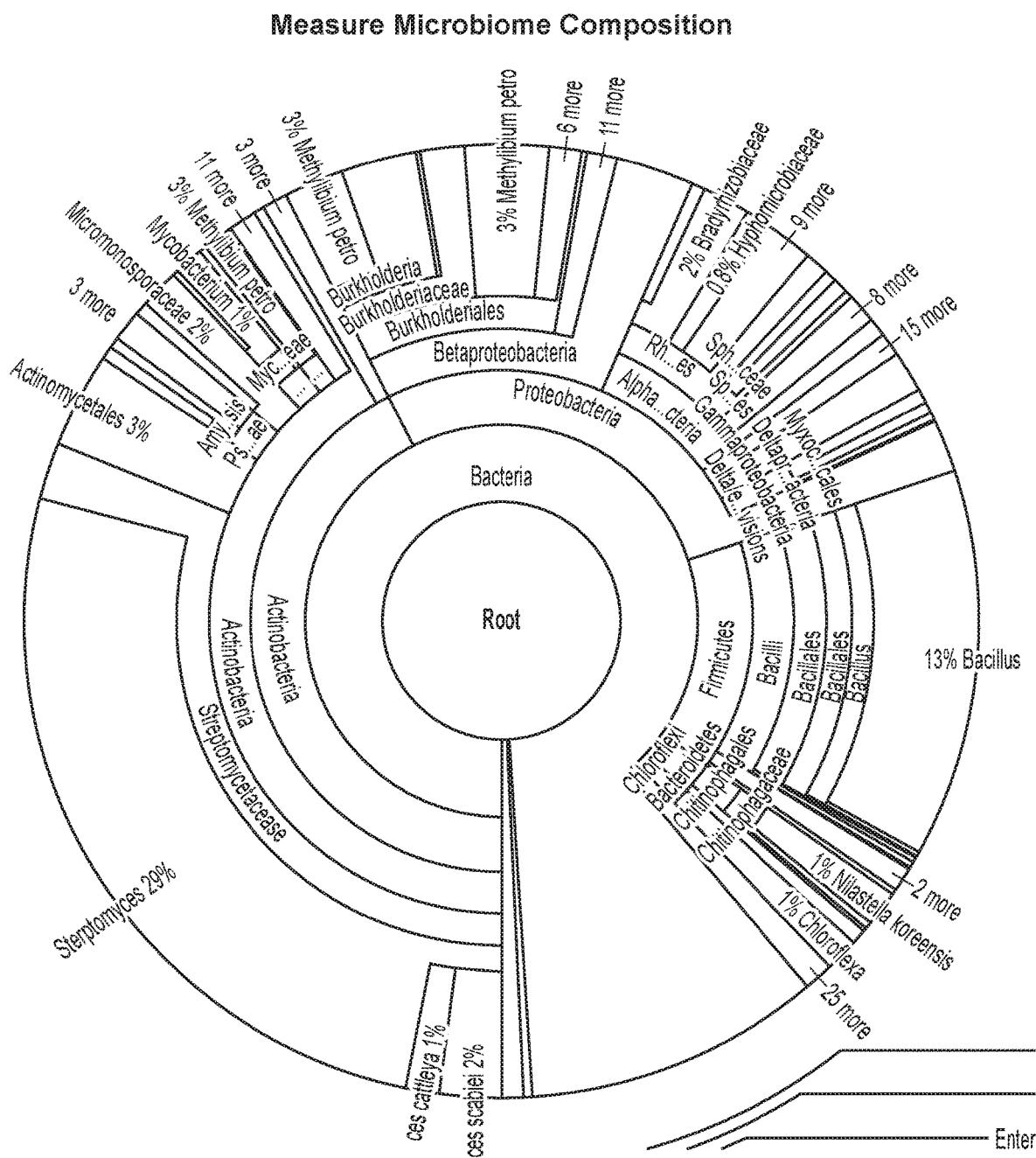
FIG. 17B depicts an expanded view of the measurement of microbiome composition as shown in FIG. 17A.

As provided in FIG. 17A, the composition of the microbiome can be first measured and a species of interest is identified. FIG. 17B depicts an expanded view of the measurement of the microbiome step. The metabolism of the microbiome can be mapped and linked to genetics. The metabolism of nitrogen can involve the entrance of ammonia ($NH_4$) from the rhizosphere into the cytosol of the bacteria via the AmtB transporter. Ammonia and L-glutamate (L-Glu) are catalyzed by glutamine synthetase and ATP into glutamine. Glutamine can lead to the formation of biomass (plant growth), and it can also inhibit expression of the nif operon. Afterwards, a targeted genetic variation can be introduced using methods including, but not limited to, conjugation and recombination, chemical mutagenesis, adaptive evolution, and gene editing. Derivative microbes are used to inoculate crops. The crops with the best phenotypes are selected.

Example 9: Field Trials with Microbes of the Disclosure—Summer 2016

In order to evaluate the efficacy of strains of the present disclosure on corn growth and productivity under varying nitrogen regimes, field trials were conducted.

Trials were conducted with (1) seven subplot treatments of six strains plus the control—four main plots comprised 0, 15, 85, and 100% of maximum return to nitrogen (MRTN) with local verification. The control (UTC only) was conducted with 10 100% MRTN plus, 5, 10, or 15 pounds. Treatments had four replications.

Plots of corn (minimum) were 4 rows of 30 feet in length, with 124 plots per location. All observations were taken from the center two rows of the plots, and all destructive sampling was taken from the outside rows. Seed samples were refrigerated until 1.5 to 2 hours prior to use.

Local Agricultural Practice:

The seed was a commercial corn without conventional fungicide and insecticide treatment. All seed treatments were applied by a single seed treatment specialist to assure uniformity. Planting date, seeding rate, weed/insect management, etc. were left to local agricultural practices. With the exception of fungicide applications, standard management practices were followed.

Soil Characterization:

Soil texture and soil fertility were evaluated. Soil samples were pre-planted for each replicate to insure residual nitrate levels lower than 50 lbs/Ac. Soil cores were taken from 0 cm to 30 cm. The soil was further characterized for pH, CEC, total K and P.

Assessments:

The initial plant population was assessed 14 days after planting (DAP)/acre, and were further assessed for: (1) vigor (1 to 10 scale, w/10=excellent) 14 DAP & V10; (2) recordation of disease ratings any time symptoms are evident in the plots; (3) record any differences in lodging if lodging occurs in the plots; (4) yield (Bu/acre), adjusted to standard moisture pct; (5) test weight; and (6) grain moisture percentage.

Sampling Requirements:

The soil was sampled at three timepoints (prior to trial initiation, V10-VT, 1 week post-harvest). All six locations and all plots were sampled at 10 grams per sample (124 plots×3 timepoints×6 locations).

Figure 17C:
FIG. 17C depicts sampling of roots utilized in Example 7.

Colonization Sampling:

Colonization samples were collected at two timepoints (V10 and VT) for five locations and six timepoints (V4, V8, V10, VT, R5, and Post-Harvest). Samples were collected as follows: (1) from 0% and 100% MRTN, 60 plots per location; (2) 4 plants per plot randomly selected from the outside rows; (3) 5 grams of root, 8 inches of stalk, and top three leaves-bagged and IDed each separately—12/bags per plot; (4) five locations (60 plots×2 timepoints×12 bags/plot); and one location (60 plots×6 timepoints×12 bags/plot. See, FIG. 17C illustrating colonization sampling.

Normalized difference vegetation index (NDVI) determination was made using a Greenseeker instrument at two timepoints (V4-V6 and VT). Assessed each plot at all six locations (124 plots×2 timepoints×6 locations).

Root analysis was performed with Win Rhizo from one location that best illustrated treatment differentiation. Ten plants per plot were randomly sampled (5 adjacent from each outside row; V3-V4 stage plants were preferred) and gently washed to remove as much dirt as reasonable. Ten roots were placed in a plastic bag and labelled. Analyzed with WinRhizo Root Analysis.

Stalk Characteristics were measured at all six locations between R2 and R5. The stalk diameter of ten plants per plot at the 6" height were recorded, as was the length of the first internode above the 6" mark. Ten plants were monitored; five consecutive plants from the center of the two inside rows. Six locations were evaluated (124 plots×2 measures×6 locations).

The tissue nitrates were analyzed from all plots and all locations. An 8" segment of stalk beginning 6" above the soil when the corn is between one and three weeks after black layer formation; leaf sheaths were removed. All locations and plots were evaluated (6 locations×124 plots).

The following weather data was recorded for all locations from planting to harvest: daily maximum and minimum temperatures, soil temperature at seeding, daily rainfall plus irrigation (if applied), and any unusual weather events such as excessive rain, wind, cold, or heat.

Yield data across all six locations is presented in Table 8. Nitrogen rate had a significant impact on yield, but strains across nitrogen rates did not. However, at the lowest nitrogen rate, strains CI006, CM029, and CI019 numerically out-yielded the UTC by 4 to 6 bu/acre. Yield was also numerically increased 2 to 4 bu/acre by strains CM029, CI019, and CM081 at 15% MRTN.

TABLE 8

Yield data across all six locations

| | YLD (bu) | Vigor_E | Vigor_L | Stalk Diameter (mm) | Internode Length (in) | NDVI_Veg | NDVI_Rep |
|---|---|---|---|---|---|---|---|
| MRTN % | | | | | | | |
| 0 | 143.9 | 7.0 | 5.7 | 18.87 | 7.18 | 64.0 | 70.6 |
| 15 | 165.9 | 7.2 | 6.3 | 19.27 | 7.28 | 65.8 | 72.5 |
| 85 | 196.6 | 7.1 | 7.1 | 20.00 | 7.31 | 67.1 | 74.3 |
| 100 | 197.3 | 7.2 | 7.2 | 20.23 | 7.37 | 66.3 | 72.4 |
| Strain | | | | | | | |
| CI006 (1) | 176.6 | 7.2 | 6.6 | 19.56 | 18.78 | 66.1 | 72.3 |
| CM029 (2) | 176.5 | 7.1 | 6.5 | 19.54 | 18.61 | 65.4 | 71.9 |
| CM038 (3) | 175.5 | 7.2 | 6.5 | 19.58 | 18.69 | 65.7 | 72.8 |
| CI019 (4) | 176.0 | 7.1 | 6.6 | 19.51 | 18.69 | 65.5 | 72.9 |
| CM081 (5) | 176.2 | 7.1 | 6.6 | 19.57 | 18.69 | 65.8 | 73.1 |
| CM029/CM081 (6) | 174.3 | 7.1 | 6.6 | 19.83 | 18.79 | 66.2 | 72.5 |
| UTC (7) | 176.4 | 7.1 | 6.6 | 19.54 | 18.71 | 65.9 | 71.7 |
| MRTN/Strain | | | | | | | |
| 0 1 | 145.6 | 7.0 | 5.6 | 19.07 | 7.12 | 63.5 | 70.3 |
| 0 2 | 147.0 | 7.0 | 5.5 | 18.74 | 7.16 | 64.4 | 70.4 |
| 0 3 | 143.9 | 7.0 | 5.5 | 18.83 | 7.37 | 64.6 | 70.5 |
| 0 4 | 146.0 | 6.9 | 5.7 | 18.86 | 7.15 | 63.4 | 70.7 |
| 0 5 | 141.7 | 7.0 | 5.8 | 18.82 | 7.05 | 63.6 | 70.9 |
| 0 6 | 142.2 | 7.2 | 5.8 | 19.12 | 7.09 | 64.7 | 69.9 |
| 0 7 | 141.2 | 7.0 | 5.8 | 18.64 | 7.32 | 64.0 | 71.4 |
| 15 1 | 164.2 | 7.3 | 6.1 | 19.09 | 7.21 | 66.1 | 71.5 |
| 15 2 | 167.3 | 7.2 | 6.3 | 19.32 | 7.29 | 65.5 | 72.7 |
| 15 3 | 165.6 | 7.3 | 6.3 | 19.36 | 7.23 | 64.8 | 72.5 |
| 15 4 | 167.9 | 7.3 | 6.4 | 19.31 | 7.51 | 66.1 | 72.3 |
| 15 5 | 169.3 | 7.2 | 6.2 | 19.05 | 7.32 | 66.0 | 72.8 |
| 15 6 | 161.9 | 7.1 | 6.3 | 19.45 | 7.20 | 66.2 | 72.2 |
| 15 7 | 165.1 | 7.3 | 6.4 | 19.30 | 7.18 | 66.0 | 73.3 |
| 85 1 | 199.4 | 7.3 | 7.2 | 19.70 | 7.32 | 67.2 | 74.0 |
| 85 2 | 195.1 | 7.1 | 7.2 | 19.99 | 7.09 | 66.5 | 74.4 |
| 85 3 | 195.0 | 7.0 | 7.0 | 20.05 | 7.26 | 67.3 | 74.6 |
| 85 4 | 195.6 | 7.2 | 7.1 | 20.04 | 7.29 | 66.4 | 74.4 |
| 85 5 | 196.4 | 7.2 | 7.0 | 19.87 | 7.39 | 67.3 | 74.5 |
| 85 6 | 195.1 | 7.0 | 6.9 | 20.35 | 7.34 | 67.4 | 74.4 |
| 85 7 | 199.5 | 6.9 | 7.2 | 19.97 | 7.48 | 67.4 | 74.1 |
| 100 1 | 197.1 | 7.2 | 7.3 | 20.38 | 7.68 | 67.5 | 73.4 |
| 100 2 | 196.5 | 7.0 | 7.1 | 20.11 | 7.21 | 65.3 | 70.2 |
| 100 3 | 197.6 | 7.5 | 7.3 | 20.08 | 7.42 | 66.3 | 73.4 |
| 100 4 | 194.6 | 7.1 | 7.1 | 19.83 | 7.40 | 66.1 | 74.1 |
| 100 5 | 197.4 | 7.2 | 7.3 | 20.53 | 7.36 | 66.2 | 74.3 |
| 100 6 | 198.1 | 7.2 | 7.4 | 20.40 | 7.16 | 66.6 | 73.6 |
| 100 7 | 199.9 | 7.2 | 7.2 | 20.26 | 7.32 | 66.2 | 68.1 |

Another analysis approach is presented in Table 9. The table comprises the four locations where the response to nitrogen was the greatest which suggests that available residual nitrogen was lowest. This approach does not alter the assessment that the nitrogen rate significantly impacted yield, which strains did not when averaged across all nitrogen rates. However, the numerical yield advantage at the lowest N rate is more pronounced for all strains, particularly CI006, CM029, and CM029/CM081 where yields were increased from 8 to 10 bu/acre. At 15% MRTN, strain CM081 out yielded UTC by 5 bu.

TABLE 9

Yield data across four locations 4 Location Average - SGS, AgIdea, Bennett, RFR

| Table 16 MRTN % | YLD (bu) | Vigor_E | Vigor_L | Stalk Diameter (mm) | Internode Length (in) |
|---|---|---|---|---|---|
| 0 | 137.8 | 7.3 | 5.84 | 18.10 | 5.36 |
| 15 | 162.1 | 7.5 | 6.63 | 18.75 | 5.40 |
| 85 | 199.2 | 7.4 | 7.93 | 19.58 | 5.62 |
| 100 | 203.5 | 7.5 | 8.14 | 19.83 | 5.65 |

| Strain | YLD (bu) | Vigor_E | Vigor_L | Stalk Diameter (mm) | Internode Length (in) |
|---|---|---|---|---|---|
| CI006 (1) | 175.4 | 7.5 | 7.08 | 19.03 | 5.59 |
| CM029 (2) | 176.1 | 7.4 | 7.08 | 19.09 | 5.39 |
| CM038 (3) | 175.3 | 7.5 | 7.05 | 19.01 | 5.59 |
| CI019 (4) | 174.8 | 7.5 | 7.16 | 19.02 | 5.45 |
| CM081 (5) | 176.7 | 7.4 | 7.16 | 19.00 | 5.53 |
| CM029/CM081 (6) | 175.1 | 7.4 | 7.17 | 19.33 | 5.46 |
| UTC (7) | 176.0 | 7.3 | 7.27 | 18.98 | 5.55 |

| MRTN/ Strain | | YLD (bu) | Vigor_E | Vigor_L | Stalk Diameter (mm) | Internode Length (in) |
|---|---|---|---|---|---|---|
| 0 | 1 | 140.0 | 7.3 | 5.69 | 18.32 | 5.28 |
| 0 | 2 | 140.7 | 7.4 | 5.69 | 18.19 | 5.23 |
| 0 | 3 | 135.5 | 7.3 | 5.63 | 17.95 | 5.50 |
| 0 | 4 | 138.8 | 7.3 | 5.81 | 17.99 | 5.36 |
| 0 | 5 | 136.3 | 7.3 | 6.06 | 18.05 | 5.34 |
| 0 | 6 | 141.4 | 7.5 | 6.00 | 18.43 | 5.30 |
| 0 | 7 | 131.9 | 7.3 | 6.00 | 17.75 | 5.48 |
| 15 | 1 | 158.0 | 7.6 | 6.44 | 18.53 | 5.34 |
| 15 | 2 | 164.1 | 7.5 | 6.56 | 19.13 | 5.42 |
| 15 | 3 | 164.3 | 7.6 | 6.63 | 18.68 | 5.51 |
| 15 | 4 | 163.5 | 7.6 | 6.81 | 18.84 | 5.34 |
| 15 | 5 | 166.8 | 7.5 | 6.63 | 18.60 | 5.39 |
| 15 | 6 | 156.6 | 7.4 | 6.56 | 18.86 | 5.41 |
| 15 | 7 | 161.3 | 7.5 | 6.81 | 18.62 | 5.42 |
| 85 | 1 | 199.4 | 7.6 | 8.00 | 19.15 | 5.63 |
| 85 | 9 | 199.0 | 7.4 | 8.09 | 19.49 | 5.46 |
| 85 | 3 | 198.2 | 7.4 | 7.75 | 19.88 | 5.69 |
| 85 | 4 | 196.8 | 7.4 | 8.00 | 19.65 | 5.60 |
| 85 | 5 | 199.5 | 7.4 | 7.75 | 19.26 | 5.70 |
| 85 | 6 | 198.7 | 7.3 | 7.81 | 19.99 | 5.61 |
| 85 | 7 | 202.8 | 7.2 | 8.13 | 19.66 | 5.65 |
| 100 | 1 | 204.3 | 7.4 | 8.19 | 20.11 | 6.10 |
| 100 | 2 | 200.6 | 7.3 | 8.00 | 19.53 | 5.46 |
| 100 | 3 | 203.3 | 7.7 | 8.19 | 19.55 | 5.67 |
| 100 | 4 | 200.2 | 7.6 | 8.00 | 19.59 | 5.49 |
| 100 | 5 | 203.9 | 7.4 | 8.19 | 20.08 | 5.68 |
| 100 | 6 | 203.8 | 7.5 | 8.31 | 20.05 | 5.52 |
| 100 | 7 | 208.1 | 7.4 | 8.13 | 19.90 | 5.63 |

The results from the field trial are also illustrated in FIGS. 21-27. The results indicate that the microbes of the disclosure are able to increase plant yield, which points to the ability of the taught microbes to increase nitrogen fixation in an important agricultural crop, i.e. corn.

The field based results further validate the disclosed methods of non-intergenerially modifying the genome of selected microbial strains, in order to bring about agriculturally relevant results in a field setting when applying said engineered strains to a crop.

FIG. 18 depicts the lineage of modified strains that were derived from strain CI006 (WT *Kosakonia sacchari*). The field data demonstrates that an engineered derivative of the CI006 WT strain, i.e. CM029, is able to bring about numerically relevant results in a field setting. For example, Table 8 illustrates that at 0% MRTN CM029 yielded 147.0 bu/acre compared to untreated control at 141.2 bu/acre (an increase of 5.8 bu/acre). Table 8 also illustrates that at 15% MRTN CM029 yielded 167.3 bu/acre compared to untreated control at 165.1 bu/acre (an increase of 2.2 bu/acre). Table 9 is supportive of these conclusions and illustrates that at 0% MRTN CM029 yielded 140.7 bu/acre compared to untreated control at 131.9 bu/acre (an increase of 8.8 bu/acre). Table 9 also illustrates that at 15% MRTN CM029 yielded 164.1 bu/acre compared to untreated control at 161.3 bu/acre (an increase of 2.8 bu/acre).

FIG. 19 depicts the lineage of modified strains that were derived from strain CI019 (WT *Rahnella aquatilis*). The field data demonstrates that an engineered derivative of the CI019 WT strain, i.e. CM081, is able to bring about numerically relevant results in a field setting. For example, Table 8 illustrates that at 15% MRTN CM081 yielded 169.3 bu/acre compared to untreated control at 165.1 bu/acre (an increase of 4.2 bu/acre). Table 9 is supportive of these conclusions and illustrates that at 0% MRTN CM081 yielded 136.3 bu/acre compared to untreated control at 131.9 bu/acre (an increase of 4.4 bu/acre). Table 9 also illustrates that at 15% MRTN CM081 yielded 166.8 bu/acre compared to untreated control at 161.3 bu/acre (an increase of 5.5 bu/acre).

Further, one can see in Table 9 that the combination of CM029/CM081 at 0% MRTN yielded 141.4 bu/acre compared to untreated control at 131.9 bu/acre (an increase of 9.5 bu/acre).

Example 10: Field Trials with Microbes of the Disclosure

A diversity of nitrogen fixing bacteria can be found in nature, including in agricultural soils. However, the potential of a microbe to provide sufficient nitrogen to crops to allow decreased fertilizer use may be limited by repression of nitrogenase genes in fertilized soils as well as low abundance in close association with crop roots. Identification, isolation and breeding of microbes that closely associate with key commercial crops might disrupt and improve the regulatory networks linking nitrogen sensing and nitrogen fixation and unlock significant nitrogen contributions by crop-associated microbes. To this end, nitrogen fixing microbes that associate with and colonize the root system of corn were identified.

Figure 30:
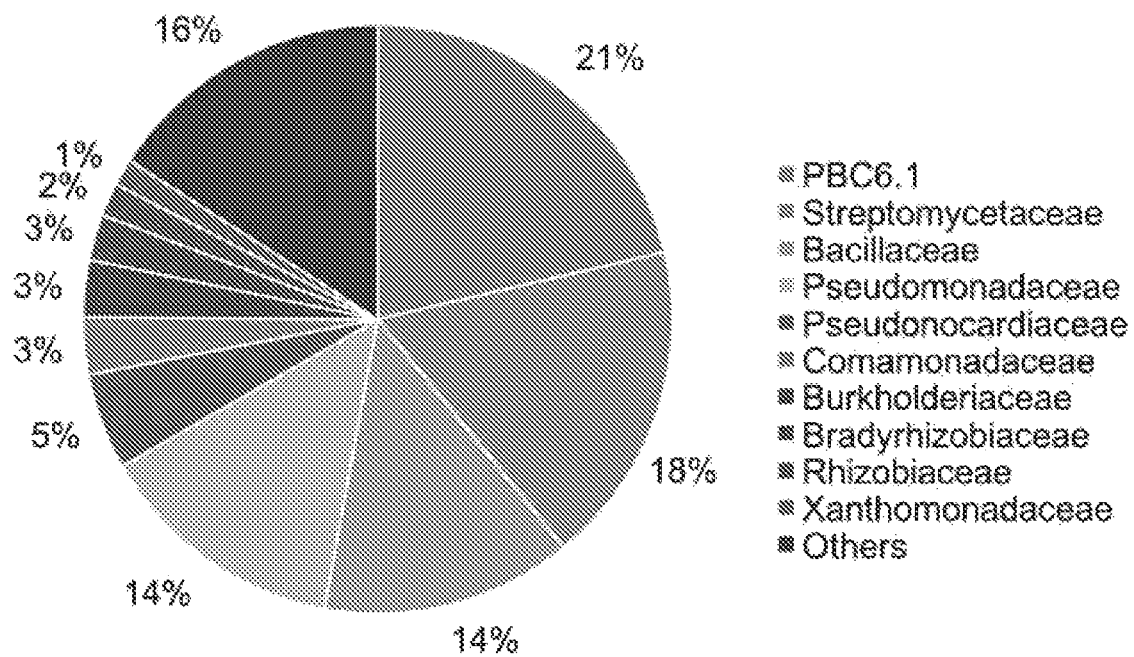
FIG. 30 illustrates PBC6.1 colonization to nearly 21% abundance of the root-associated microbiota in corn roots. Abundance data is based on 16S amplicon sequencing of the rhizosphere and endosphere of corn plants inoculated with PBC6.1 and grown in greenhouse conditions.

Root samples from corn plants grown in agronomically relevant soils were collected, and microbial populations extracted from the rhizosphere and endosphere. Genomic DNA from these samples was extracted, followed by 16S amplicon sequencing to profile the community composition. A *Kosakonia sacchari* microbe (strain PBC6.1) was isolated and classified through 16S rRNA and whole genome sequencing. This is a particularly interesting nitrogen fixer capable of colonizing to nearly 21% abundance of the root-associated microbiota (FIG. 30). To assess strain sensitivity to exogenous nitrogen, nitrogen fixation rates in pure culture were measured with the classical acetylene reduction assay (ARA) and varying levels of glutamine supplementation. The species exhibited a high level of nitrogen fixing activity in nitrogen-free media, yet exogenous fixed nitrogen repressed nif gene expression and nitrogenase activity (Strain PBC6.1, FIGS. 28C and 28D). Additionally, when released ammonia was measured in the supernatant of PBC6.1 grown in nitrogen-fixing conditions, very little release of fixed nitrogen could be detected (FIG. 28E).

We hypothesized that PBC6.1 could be a significant contributor of fixed nitrogen in fertilized fields if regulatory networks controlling nitrogen metabolism were rewired to allow optimal nitrogenase expression and ammonia release in the presence of fixed nitrogen. Sufficient genetic diversity should exist within the PBC6.1 genome to enable broad phenotypic remodeling without the insertion of transgenes or synthetic regulatory elements. The isolated strain has a genome of at least 5.4 Mbp and a canonical nitrogen fixation gene cluster. Related nitrogen metabolism pathways in PBC6.1 are similar to those of the model organism for nitrogen fixation, *Klebsiella oxytoca* m5al.

Several gene regulatory network nodes were identified which may augment nitrogen fixation and subsequent transfer to a host plant, particularly in high exogenous concentrations of fixed nitrogen (FIG. 28A). The nifLA operon directly regulates the rest of the nif cluster through transcriptional activation by NifA and nitrogen- and oxygen-dependent repression of NifA by NifL. Disruption of nifL can abolish inhibition of NifA and improve nif expression in the presence of both oxygen and exogenous fixed nitrogen. Furthermore, expressing nifA under the control of a nitrogen-independent promoter may decouple nitrogenase biosynthesis from regulation by the NtrB/NtrC nitrogen sensing complex. The assimilation of fixed nitrogen by the microbe to glutamine by glutamine synthetase (GS) is reversibly regulated by the two-domain adenylyltransferase (ATase) enzyme GlnE through the adenylylation and deadenylylation of GS to attenuate and restore activity, respectively. Truncation of the GlnE protein to delete its adenylyl-removing (AR) domain may lead to constitutively adenylated glutamine synthetase, limiting ammonia assimilation by the microbe and increasing intra- and extracellular ammonia. Finally, reducing expression of AmtB, the transporter responsible for uptake of ammonia, could lead to greater extracellular ammonia. To generate rationally designed microbial phenotypes without the use of transgenes, two approaches were employed: creating markerless deletions of genomic sequences encoding protein domains or whole genes, and rewiring regulatory networks by intragenomic promoter rearrangement. Through an iterative mutagenesis process, several non-transgenic derivative strains of PBC6.1 were generated (Table 10).

TABLE 10

List of isolated and derivative *K. sacchari* strains used in this work. Prm, promoter sequence derived from the PBC6.1 genome; ΔglnE$_{AR}$1 and ΔglnE$_{AR}$2, different truncated versions of glnE gene removing the adenylyl-removing domain sequence.

| Strain ID | Genotype |
|---|---|
| PBC6.1 | WT |
| PBC6.14 | ΔnifL::Prm1 |
| PBC6.15 | ΔnifL::Prm5 |
| PBC6.22 | ΔnifL::Prm3 |
| PBC6.37 | ΔnifL::Prm1 ΔglnE$_{AR}$2 |
| PBC6.38 | ΔnifL::Prm1 ΔglnE$_{AR}$1 |
| PBC6.93 | ΔnifL::Prm1 ΔglnE$_{AR}$2 ΔamtB |
| PBC6.94 | ΔnifL::Prm1 ΔglnE$_{AR}$1 ΔamtB |

Figure 31:
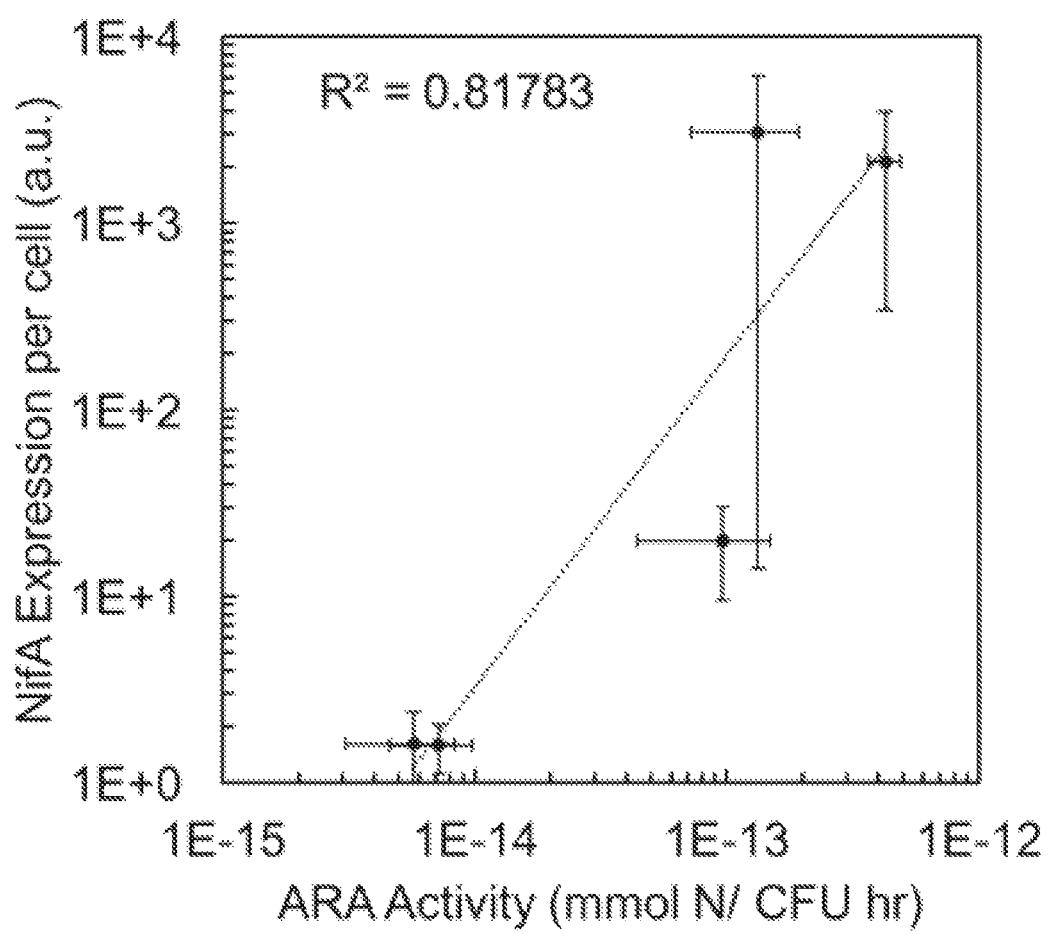
FIG. 31 illustrates transcriptional rates of nifA in derivative strains of PBC6.1 correlated with acetylene reduction rates. An ARA assay was performed as described in the Methods, after which cultures were sampled and subjected to qPCR analysis to determine nifA transcript levels. Error bars show standard error of the mean of at least three biological replicates in each measure.

Several in vitro assays were performed to characterize specific phenotypes of the derivative strains. The ARA was used to assess strain sensitivity to exogenous nitrogen, in which PBC6.1 exhibited repression of nitrogenase activity at high glutamine concentrations (FIG. 28D). In contrast, most derivative strains showed a derepressed phenotype with varying levels of acetylene reduction observed at high glutamine concentrations. Transcriptional rates of nifA in samples analyzed by qPCR correlated well with acetylene reduction rates (FIG. 31), supporting the hypothesis that nifL disruption and insertion of a nitrogen-independent promoter to drive nifA can lead to nif cluster derepression. Strains with altered GlnE or AmtB activity showed markedly increased ammonium excretion rates compared to wild type or derivative strains without these mutations (FIG. 28E), illustrating the effect of these genotypes on ammonia assimilation and reuptake.

Figure 29A:
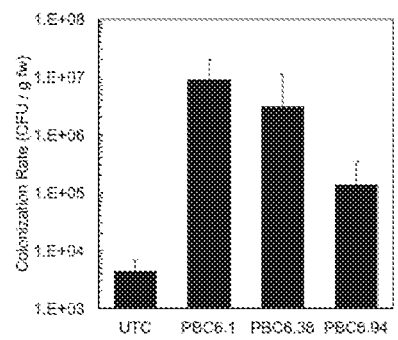
FIGS. 29A-29C illustrate greenhouse experiments demonstrate microbial nitrogen fixation in corn.
Figure 29B:
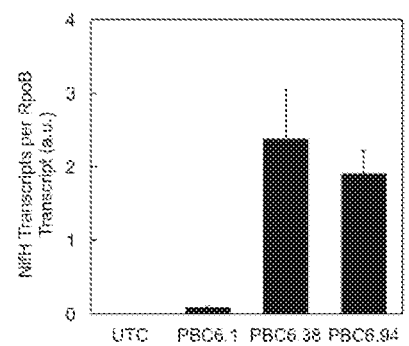
Figure 29C:
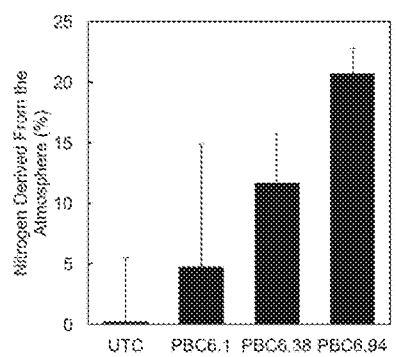

Two experiments were performed to study the interaction of PBC6.1 derivatives with corn plants and quantify incorporation of fixed nitrogen into plant tissues. First, rates of microbial nitrogen fixation were quantified in a greenhouse study using isotopic tracers. Briefly, plants are grown with 15N labeled fertilizer, and diluted concentrations of 15N in plant tissues indicate contributions of fixed nitrogen from microbes. Corn seedlings were inoculated with selected microbial strains, and plants were grown to the V6 growth stage. Plants were subsequently deconstructed to enable measurement of microbial colonization and gene expression as well as measurement of 15N/14N ratios in plant tissues by isotope ratio mass spectrometry (IRMS). Analysis of the aerial tissue showed a small, nonsignificant contribution by PBC6.38 to plant nitrogen levels, and a significant contribution by PBC6.94 (p=0.011). Approximately 20% of the nitrogen found in above-ground corn leaves was produced by PBC6.94, with the remainder coming from the seed, potting mix, or "background" fixation by other soilborne microbes (FIG. 29C). This illustrates that our microbial breeding pipeline can generate strains capable of making significant nitrogen contributions to plants in the presence of nitrogen fertilizer. Microbial transcription within plant tissues was measured, and expression of the nif gene cluster was observed in derivative strains but not the wild type strain (FIG. 29B), showing the importance of nif derepression for contribution of BNF to crops in fertilized conditions. Root colonization measured by qPCR demonstrated that colonization density is different for each of the strains tested (FIG. 29A). A 50 fold difference in colonization was observed between PBC6.38 and PBC6.94. This difference could be an indication that PBC6.94 has reduced fitness in the rhizosphere relative to PBC6.38 as a result of high levels of fixation and excretion.

Methods

Media

Minimal medium contains (per liter) 25 g Na$_2$HPO$_4$, 0.1 g CaCL$_2$-2H$_2$O, 3 g KH$_2$PO$_4$, 0.25 g MgSO$_4$.7H$_2$O, 1 g NaCl, 2.9 mg FeCl$_3$, 0.25 mg Na$_2$MoO$_4$.2H$_2$O, and 20 g sucrose. Growth medium is defined as minimal medium supplemented with 50 ml of 200 mM glutamine per liter.

Isolation of Diazotrophs

Corn seedlings were grown from seed (DKC 66-40, DeKalb, Ill.) for two weeks in a greenhouse environment controlled from 22° C. (night) to 26° C. (day) and exposed to 16 hour light cycles in soil collected from San Joaquin County, Calif. Roots were harvested and washed with sterile deionized water to remove bulk soil. Root tissues were homogenized with 2 mm stainless steel beads in a tissue lyser (TissueLyser II, Qiagen P/N 85300) for three minutes at setting 30, and the samples were centrifuged for 1 minute at 13,000 rpm to separate tissue from root-associated bacteria. Supernatants were split into two fractions, and one was used to characterize the microbiome through 16S rRNA amplicon sequencing and the remaining fraction was diluted and plated on Nitrogen-free Broth (NfB) media supplemented with 1.5% agar. Plates were incubated at 30° C. for 5-7 days. Colonies that emerged were tested for the presence of the nifH gene by colony PCR with primers Ueda19f and Ueda406r. Genomic DNA from strains with a positive nifH colony PCR was isolated (QIAamp DNA Mini Kit, Cat No. 51306, QIAGEN, Germany) and sequenced (Illumina MiSeq v3, SeqMatic, Fremont, Calif.). Following sequence assembly and annotation, the isolates containing nitrogen fixation gene clusters were utilized in downstream research.

Microbiome Profiling of Isolation Seedlings

Genomic DNA was isolated from root-associated bacteria using the ZR-96 Genomic DNA I Kit (Zymo Research P/N D3011), and 16S rRNA amplicons were generated using nextera-barcoded primers targeting 799f and 1114r. The amplicon libraries were purified and sequenced with the Illumina MiSeq v3 platform (SeqMatic, Fremont, Calif.). Reads were taxonomically classified using Kraken using the minikraken database (FIG. 30).

Acetylene Reduction Assay (ARA)

A modified version of the Acetylene Reduction Assay was used to measure nitrogenase activity in pure culture conditions. Strains were propagated from single colony in SOB (RPI, P/N S25040-1000) at 30° C. with shaking at 200 RPM for 24 hours and then subcultured 1:25 into growth medium and grown aerobically for 24 hours (30° C., 200 RPM). 1 ml of the minimal media culture was then added to 4 ml of minimal media supplemented with 0 to 10 mM glutamine in air-tight Hungate tubes and grown anaerobically for 4 hours (30° C., 200 RPM). 10% headspace was removed then replaced by an equal volume of acetylene by injection, and incubation continued for 1 hr. Subsequently, 2 ml of headspace was removed via gas tight syringe for quantification of ethylene production using an Agilent 6850 gas chromatograph equipped with a flame ionization detector (FID).

Ammonium Excretion Assay

Excretion of fixed nitrogen in the form of ammonia was measured using batch fermentation in anaerobic bioreactors. Strains were propagated from single colony in 1 ml/well of SOB in a 96 well DeepWell plate. The plate was incubated at 30° C. with shaking at 200 RPM for 24 hours and then diluted 1:25 into a fresh plate containing 1 ml/well of growth medium. Cells were incubated for 24 hours (30° C., 200 RPM) and then diluted 1:10 into a fresh plate containing minimal medium. The plate was transferred to an anaerobic chamber with a gas mixture of >98.5% nitrogen, 1.2-1.5% hydrogen and <30 ppM oxygen and incubated at 1350 RPM, room temperature for 66-70 hrs. Initial culture biomass was compared to ending biomass by measuring optical density at 590 nm. Cells were then separated by centrifugation, and supernatant from the reactor broth was assayed for free ammonia using the Megazyme Ammonia Assay kit (P/N K-AMIAR) normalized to biomass at each timepoint.

Extraction of Root-Associated Microbiome

Roots were shaken gently to remove loose particles, and root systems were separated and soaked in a RNA stabilization solution (Thermo Fisher P/N AM7021) for 30 minutes. The roots were then briefly rinsed with sterile deionized water. Samples were homogenized using bead beating with ½-inch stainless steel ball bearings in a tissue lyser (TissueLyser II, Qiagen P/N 85300) in 2 ml of lysis buffer (Qiagen P/N 79216). Genomic DNA extraction was performed with ZR-96 Quick-gDNA kit (Zymo Research P/N D3010), and RNA extraction using the RNeasy kit (Qiagen P/N 74104).

Root Colonization Assay

Four days after planting, 1 ml of a bacterial overnight culture (approximately $10^9$ cfu) was applied to the soil above the planted seed. Seedlings were fertilized three times weekly with 25 ml modified Hoagland's solution supplemented with 0.5 mM ammonium nitrate. Four weeks after planting, root samples were collected and the total genomic DNA (gDNA) was extracted. Root colonization was quantified using qPCR with primers designed to amplify unique regions of either the wild type or derivative strain genome. QPCR reaction efficiency was measured using a standard curve generated from a known quantity of gDNA from the target genome. Data was normalized to genome copies per g fresh weight using the tissue weight and extraction volume. For each experiment, the colonization numbers were compared to untreated control seedlings.

In Planta Transcriptomics

Transcriptional profiling of root-associated microbes was measured in seedlings grown and processed as described in the Root Colonization Assay. Purified RNA was sequenced using the Illumina NextSeq platform (SeqMatic, Fremont, Calif.). Reads were mapped to the genome of the inoculated strain using bowtie2 using '--very-sensitive-local' parameters and a minimum alignment score of 30. Coverage across the genome was calculated using samtools. Differential coverage was normalized to housekeeping gene expression and visualized across the genome using Circos and across the nif gene cluster using DNAplotlib. Additionally, the in planta transcriptional profile was quantified via targeted Nanostring analysis. Purified RNA was processed on an nCounter Sprint (Core Diagnostics, Hayward, Calif.).

15N Dilution Greenhouse Study

A 15N fertilizer dilution experiment was performed to assess optimized strain activity in planta. A planting medium containing minimal background N was prepared using a mixture of vermiculite and washed sand (5 rinses in DI $H_2O$). The sand mixture was autoclaved for 1 hour at 122° C. and approximately 600 g measured out into 40 cubic inch (656 mL) pots, which were saturated with sterile DI $H_2O$ and allowed to drain 24 hours before planting. Corn seeds (DKC 66-40) were surface sterilized in 0.625% sodium hypochlorite for 10 minutes, then rinsed five times in sterile distilled water and planted 1 cm deep. The plants were maintained under fluorescent lamps for four weeks with 16-hour day length at room temperatures averaging 22° C. (night) to 26° C. (day).

Five days after planting, seedlings were inoculated with a 1 ml suspension of cells drenched directly over the emerging coleoptile. Inoculum was prepared from 5 ml overnight cultures in SOB, which were spun down and resuspended twice in 5 ml PBS to remove residual SOB before final dilution to OD of 1.0 (approximately $10^9$ CFU/ml). Control plants were treated with sterile PBS, and each treatment was applied to ten replicate plants.

Plants were fertilized with 25 ml fertilizer solution containing 2% 15N-enriched 2 mM $KNO_3$ on 5, 9, 14, and 19 days after planting, and the same solution without $KNO_3$ on 7, 12, 16, and 18 days after planting. The fertilizer solution contained (per liter) 3 mmol $CaCl_2$, 0.5 mmol $KH_2PO_4$, 2 mmol $MgSO_4$, 17.9 μmol $FeSO_4$, 2.86 mg $H_3BO_3$, 1.81 mg $MnCl_2*4H_2O$, 0.22 mg $ZnSO_4.7H_2O$, 51 μg $CuSO_4.5H_2O$, 0.12 mg $Na_2MoO_4.2H_2O$, and 0.14 nmol $NiCl_2$. All pots were watered with sterile DI $H_2O$ as needed to maintain consistent soil moisture without runoff.

At four weeks, plants were harvested and separated at the lowest node into samples for root gDNA and RNA extraction and aerial tissue for IRMS. Aerial tissues were wiped as needed to remove sand, placed whole into paper bags and dried for at least 72 hours at 60° C. Once completely dry, total aerial tissue was homogenized by bead beating and 5-7 mg samples were analyzed by isotope ratio mass spectrometry (IRMS) for δ15N by the MBL Stable Isotope Laboratory (The Ecosystems Center, Woods Hole, Mass.). Percent NDFA was calculated using the following formula: % NDFA=(δ15N of UTC average−δ15N of sample)/(δ15N of UTC average)×100.

Example 11: Field Trials with Microbes of the Disclosure—Summer 2017

In order to evaluate the efficacy of strains of the present disclosure on corn growth and productivity under varying nitrogen regimes, field trials were conducted. The below field data demonstrates that the non-intergeneric microbes of the disclosure are able to fix atmospheric nitrogen and deliver said nitrogen to a plant—resulting in increased yields—in both a nitrogen limiting environment, as well as a non-nitrogen limiting environment.

Trials were conducted at seven locations across the United states with six geographically diverse Midwestern locations. Five nitrogen regimes were used for fertilizer treatments: 100% of standard agricultural practice of the site/region, 100% minus 25 pounds, 100% minus 50 pounds, 100% minus 75 pounds, and 0%; all per acre. The pounds of nitrogen per acre for the 100% regime depended upon the standard agricultural practices of the site/region. The aforementioned nitrogen regimes ranged from about 153 pounds per acre to about 180 pounds per acre, with an average of about 164 pounds of nitrogen per acre.

Within each fertilizer regime there were 14 treatments. Each regime had six replications, and a split plot design was utilized. The 14 treatments included: 12 different microbes, 1 UTC with the same fertilizer rate as the main plot, and 1 UTC with 100% nitrogen. In the 100% nitrogen regime the $2^{nd}$ UTC is 100 plus 25 pounds.

Plots of corn, at a minimum, were 4 rows of 30 feet in length (30 inches between rows) with 420 plots per location. All observations, unless otherwise noted, were taken from the center two rows of the plants, and all destructive sampling was taken from the outside rows. Seed samples were refrigerated until 1.5 to 2 hours prior to use.

Local Agricultural Practice:

The seed was a commercial corn applied with a commercial seed treatment with no biological co-application. The seeding rate, planting date, weed/insect management, harvest times, and other standard management practices were left to the norms of local agricultural practices for the regions, with the exception of fungicide application (if required).

Microbe Application:

The microbes were applied to the seed in a seed treatment over seeds that had already received a normal chemical treatment. The seed were coated with fermentation broth comprising the microbes.

Soil Characterization:

Soil texture and soil fertility were evaluated. Standard soil sampling procedures were utilized, which included soil cores of depths from 0-30 cm and 30-60 cm. The standard soil sampling included a determination of nitrate nitrogen, ammonium nitrogen, total nitrogen, organic matter, and CEC. Standard soil sampling further included a determination of pH, total potassium, and total phosphorous. To determine the nitrogen fertilizer levels, preplant soil samples from each location were taken to ensure that the 0-12" and potentially the 12" to 24" soil regions for nitrate nitrogen.

Prior to planting and fertilization, 2 ml soil samples were collected from 0 to 6-12" from the UTC. One sample per replicate per nitrogen region was collected using the middle of the row. (5 fertilizer regimes×6 replicates=thirty soil samples).

Post-planting (V4-V6), 2 ml soil samples were collected from 0 to 6-12" from the UTC. One sample per replicate per nitrogen region was collected using the middle of the row. (5 fertilizer regimes×6 replicates=thirty soil samples).

Post-harvest (V4-V6), 2 ml soil samples were collected from 0 to 6-12" from the UTC. One sample per replicate per nitrogen region was collected using the middle of the row. Additional post-harvest soil sample collected at 0-12" from the UTC and potentially 12-24" from the UTC (5 fertilizer regimes×6 replicates=thirty soil samples).

A V6-V10 soil sample from each fertilizer regime (excluding the treatment of 100% and 100%+25 lbs [in the 100% block] for all fertilizer regimes at 0-12" and 12-24". (5 fertilizer regimes×2 depths=10 samples per location).

Post-harvest soil sample from each fertilizer regime (excluding the treatment of 100% and 100%+25 lbs [in the 100% block] for all fertilizer regimes at 0-12" and 12-24". (5 fertilizer regimes×2 depths=10 samples per location).

Assessments:

The initial plant population was assessed at ~50% UTC and the final plant population was assessed prior to harvest. Assessment included (1) potentially temperature (temperature probe); (2) vigor (1-10 scale with 10=excellent) at V4 and V8-V10; (3) plant height at V8-V10 and V14; (4) yield (bushels/acre) adjusted to standard moisture percentage; (5) test weight; (6) grain moisture percentage; (7) stalk nitrate tests at black layer (420 plots×7 locations); (8) colonization with 1 plant per plot in zip lock bag at 0% and 100% fertilizer at V4-V6 (1 plant×14 treatments×6 replicates×2 fertilizer regimes=168 plants); (9) transcriptomics with 1 plant per plot in zip lock bag at 0% and 100% fertilizer at V4-V6 (1 plant×14 treatments×6 replicates×2 fertilizer regimes=168 plants); (10) Normalized difference vegetative index (NDVI) or normalized difference red edge (NDRE) determination using a Greenseeker instrument at two time points (V4-V6 and VT) to assess each plot at all 7 locations (420 plots×2 time points×7 locations=5,880 data points); (11) stalk characteristics measured at all 7 locations between R2 and R5 by recording the stalk diameter of 10 plants/plot at 6" height, record length of first internode above the 6" mark, 10 plants monitored (5 consecutive plants from center of two inside rows) (420 plots×10 plants×7 locations=29, 400 data points).

Monitoring Schedule:

Practitioners visited all trials at V3-V4 stage to assess early-season response to treatments and during reproductive growth stage to monitor maturity. Local cooperator visited research trial on an on-going basis.

Weather Information:

Weather data spanning from planting to harvest was collected and consisted of daily minimum and maximum temperatures, soil temperature at seeding, daily rainfall plus irrigation (if applied), and unusual weather events such as excessive wind, rain, cold, heat.

Data Reporting:

Including the data indicated above, the field trials generated data points including soil textures; row spacing; plot sizes; irrigation; tillage; previous crop; seeding rate; plant population; seasonal fertilizer inputs including source, rate, timing, and placement; harvest area dimensions, method of harvest, such as by hand or machine and measurement tools used (scales, yield monitor, etc.)

Figure 32:
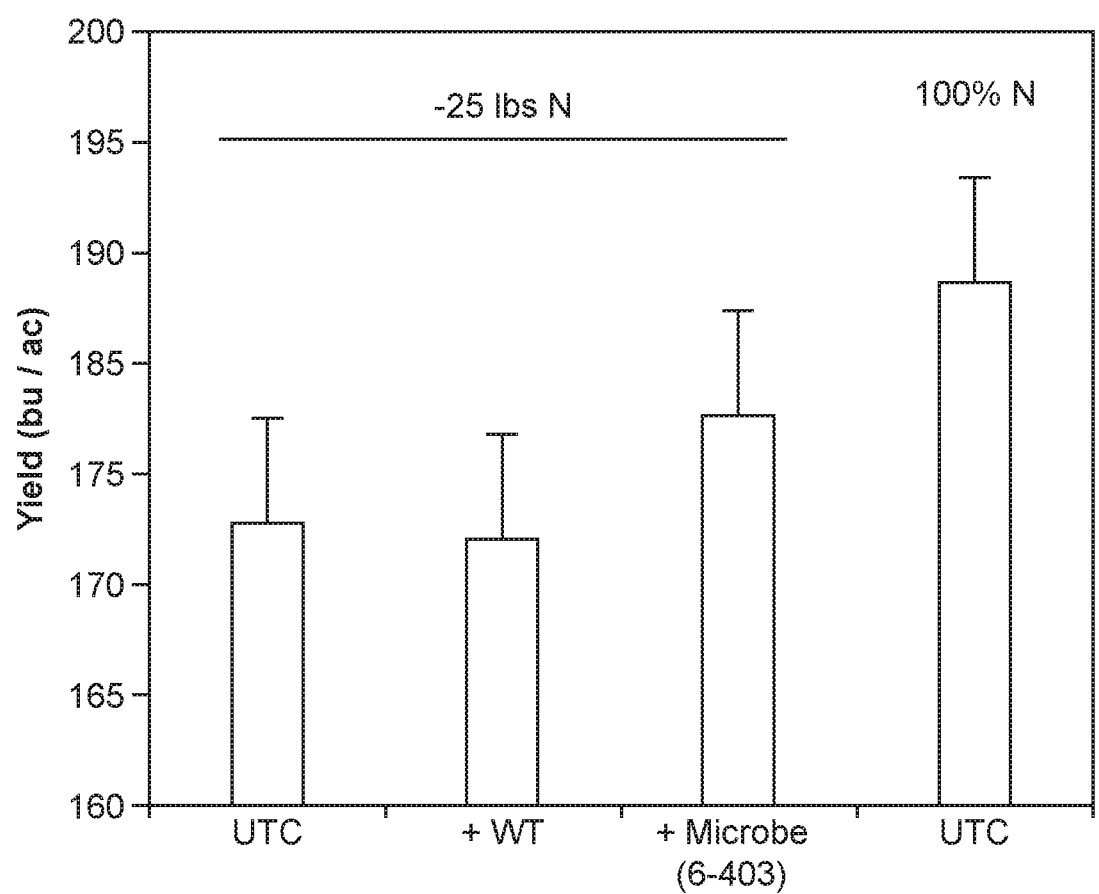
FIG. 32 illustrates results from a summer 2017 field testing experiment. The yield results obtained demonstrate that the microbes of the disclosure can serve as a potential fertilizer replacement. For instance, the utilization of a microbe of the disclosure (i.e. 6-403) resulted in a higher yield than the wild type strain (WT) and a higher yield than the untreated control (UTC). The "−25 lbs N" treatment utilizes 25 lbs less N per acre than standard agricultural practices of the region. The "100% N" UTC treatment is meant to depict standard agricultural practices of the region, in which 100% of the standard utilization of N is deployed by the farmer. The microbe "6-403" was deposited as NCMA 201708004 and can be found in Table A. This is a mutant *Kosakonia sacchari* (also called CM037) and is a progeny mutant strain from CI006 WT.
Figure 34:
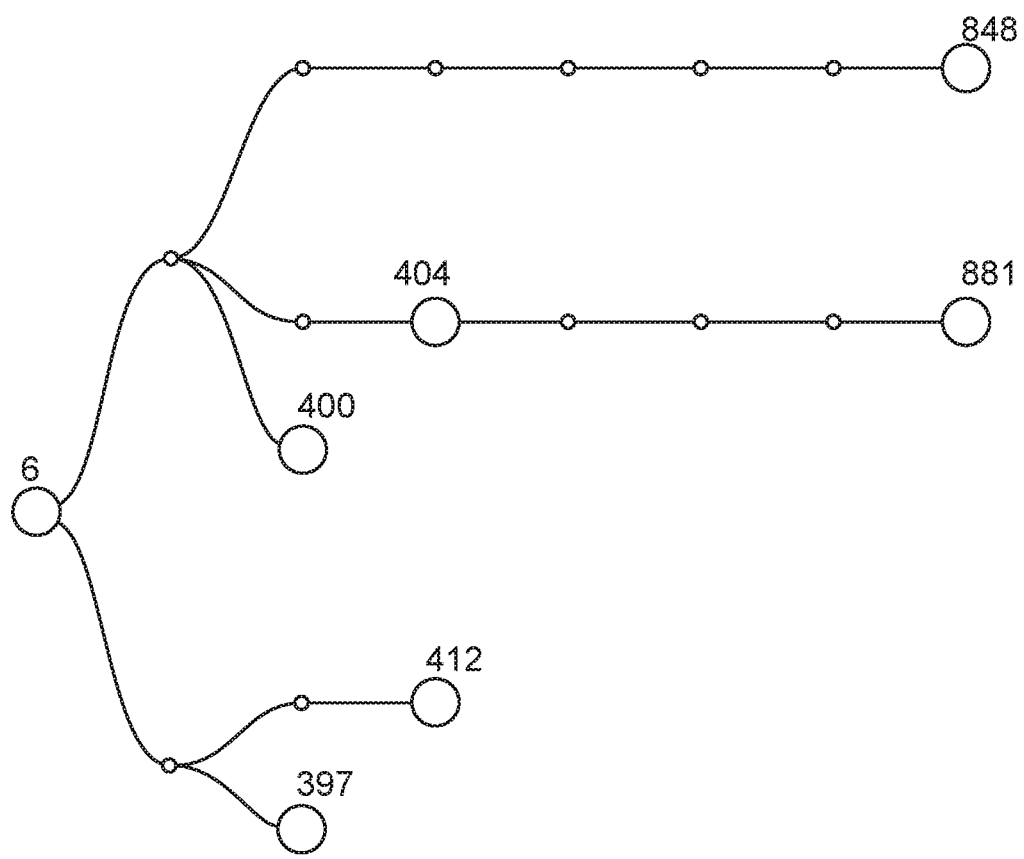
FIG. 34 depicts the lineage of modified strains that were derived from strain CI006 (also termed "6", *Kosakonia sacchari* WT).
Figure 35:
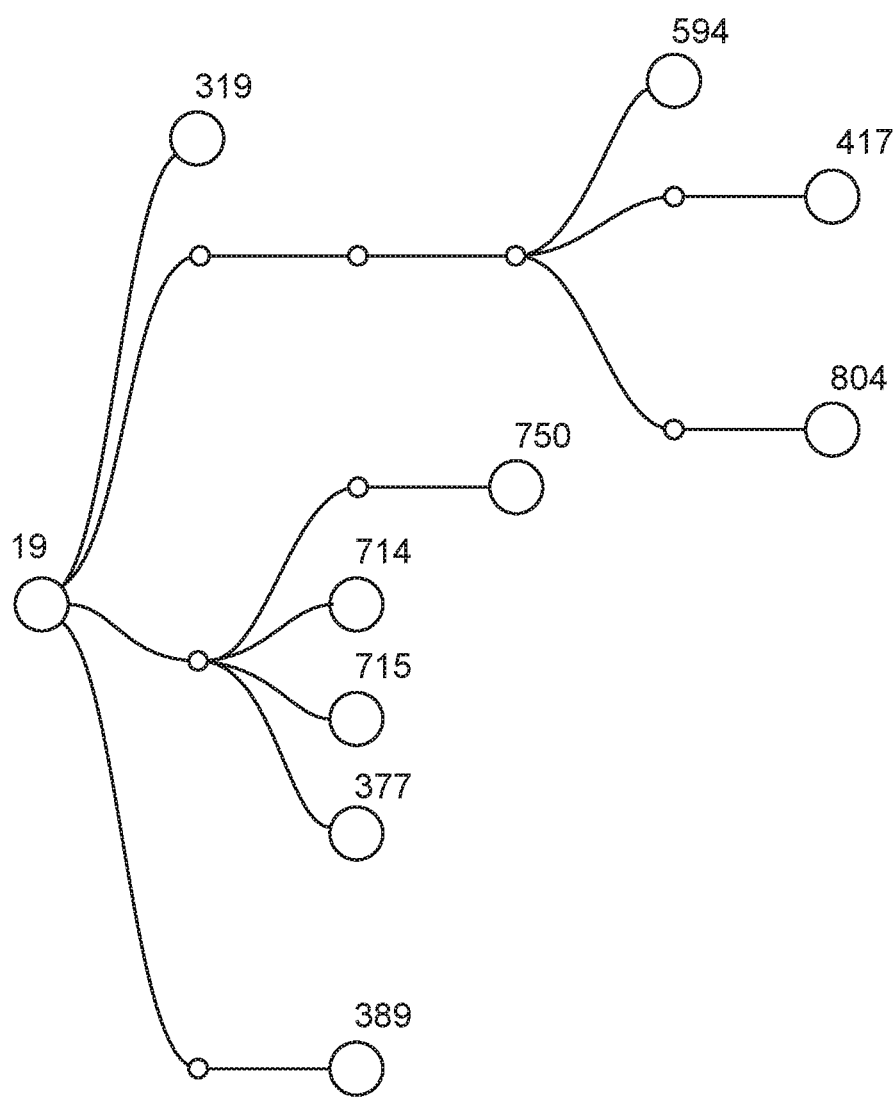
FIG. 35 depicts the lineage of modified strains that were derived from strain CI019 (also termed "19", *Rahnella aquatilis* WT).
Figure 36:
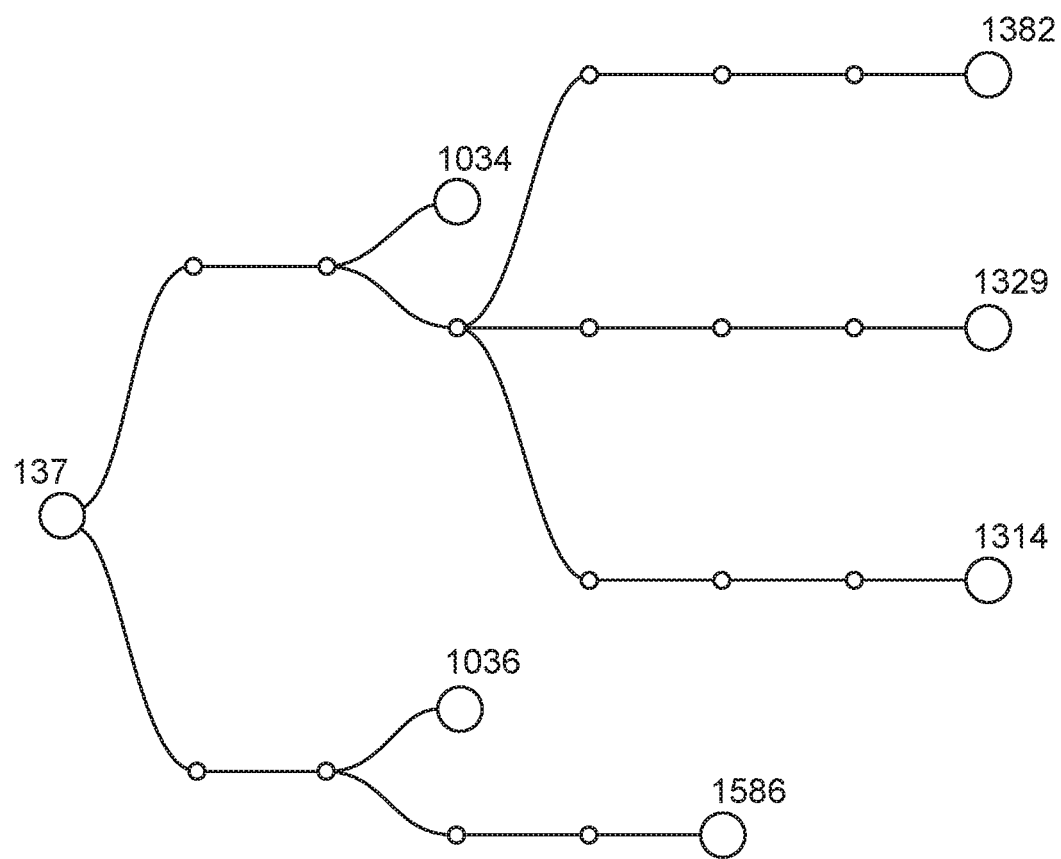
FIG. 36 depicts the lineage of modified strains that were derived from strain CI137 (also termed ("137", *Klebsiella variicola* WT).
Figure 37:
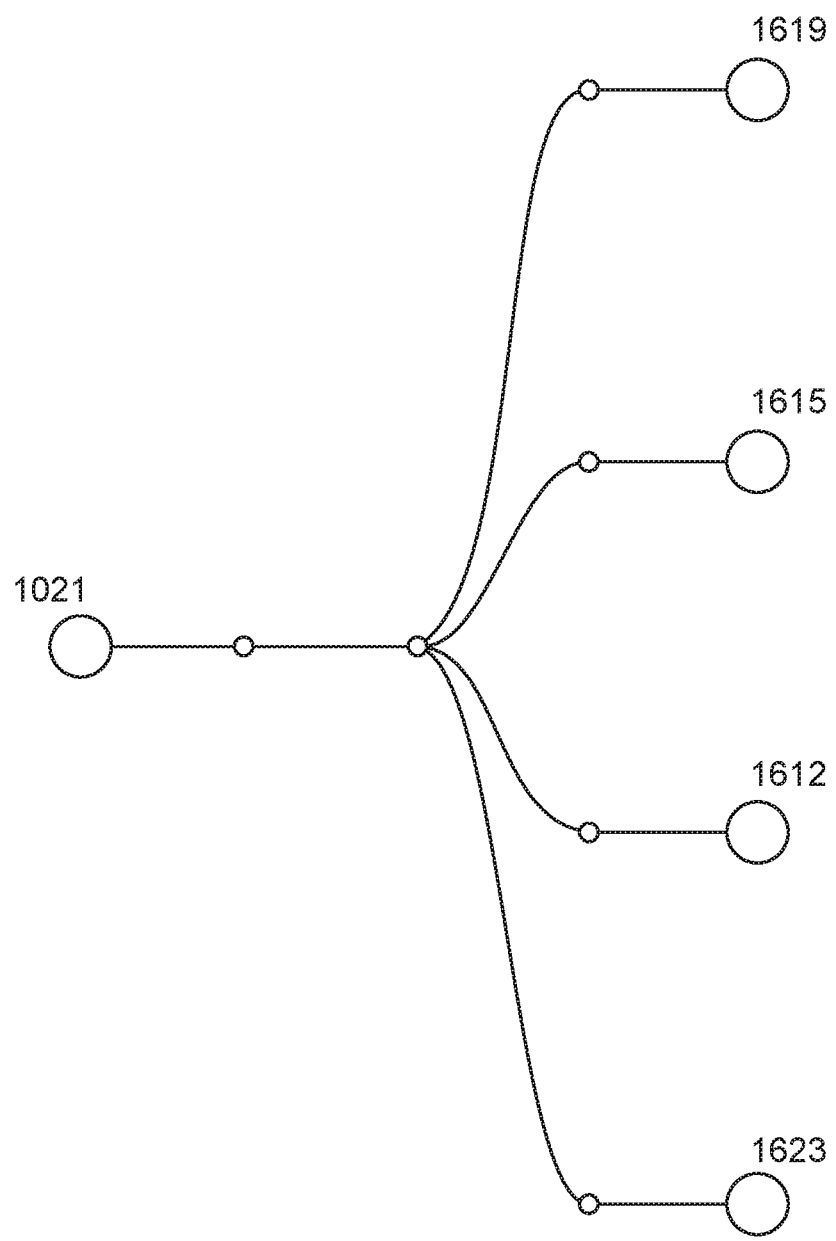
FIG. 37 depicts the lineage of modified strains that were derived from strain 1021 (*Kosakonia pseudosacchari* WT).
Figure 38:
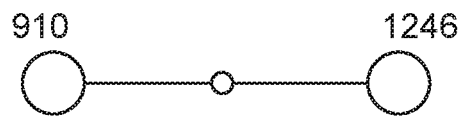
FIG. 38 depicts the lineage of modified strains that were derived from strain 910 (*Kluyvera intermedia* WT).
Figure 39:
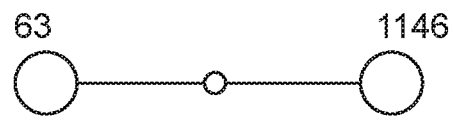
FIG. 39 depicts the lineage of modified strains that were derived from strain 63 (*Rahnella aquatilis* WT).

Results:

Select results from the aforementioned field trial are reported in FIG. 32 and FIG. 33.

In FIG. 32, it can be seen that a microbe of the disclosure (i.e. 6-403) resulted in a higher yield than the wild type strain (WT) and a higher yield than the untreated control (UTC). The "−25 lbs N" treatment utilizes 25 lbs less N per acre than standard agricultural practices of the region. The "100% N" UTC treatment is meant to depict standard agricultural practices of the region, in which 100% of the standard utilization of N is deployed by the farmer. The microbe "6-403" was deposited as NCMA 201708004 and can be found in Table A. This is a mutant *Kosakonia sacchari* (also called CM037) and is a progeny mutant strain from CI006 WT.

In FIG. 33, the yield results obtained demonstrate that the microbes of the disclosure perform consistently across locations. Furthermore, the yield results demonstrate that the microbes of the disclosure perform well in both a nitrogen stressed environment (i.e. a nitrogen limiting environment), as well as an environment that has sufficient supplies of nitrogen (i.e. a non-nitrogen-limiting condition). The microbe "6-881" (also known as CM094, PBC6.94), and which is a progeny mutant *Kosakonia sacchari* strain from CI006 WT, was deposited as NCMA 201708002 and can be found in Table A. The microbe "137-1034," which is a progeny mutant *Klebsiella variicola* strain from CI137 WT, was deposited as NCMA 201712001 and can be found in Table A. The microbe "137-1036," which is a progeny mutant *Klebsiella variicola* strain from CI137 WT, was deposited as NCMA 201712002 and can be found in Table A. The microbe "6-404" (also known as CM38, PBC6.38), and which is a progeny mutant *Kosakonia sacchari* strain from CI006 WT, was deposited as NCMA 201708003 and can be found in Table A.

Example 12: Genus of Non-Intergeneric Microbes Beneficial for Agricultural Systems The microbes of the present disclosure were evaluated and compared against one another for the production of nitrogen produced in an acre across a season. See FIG. 20, FIG. 40, and FIG. 41

It is hypothesized by the inventors that in order for a population of engineered non-intergeneric microbes to be beneficial in a modern row crop agricultural system, then the population of microbes needs to produce at least one pound or more of nitrogen per acre per season.

Figure 20:
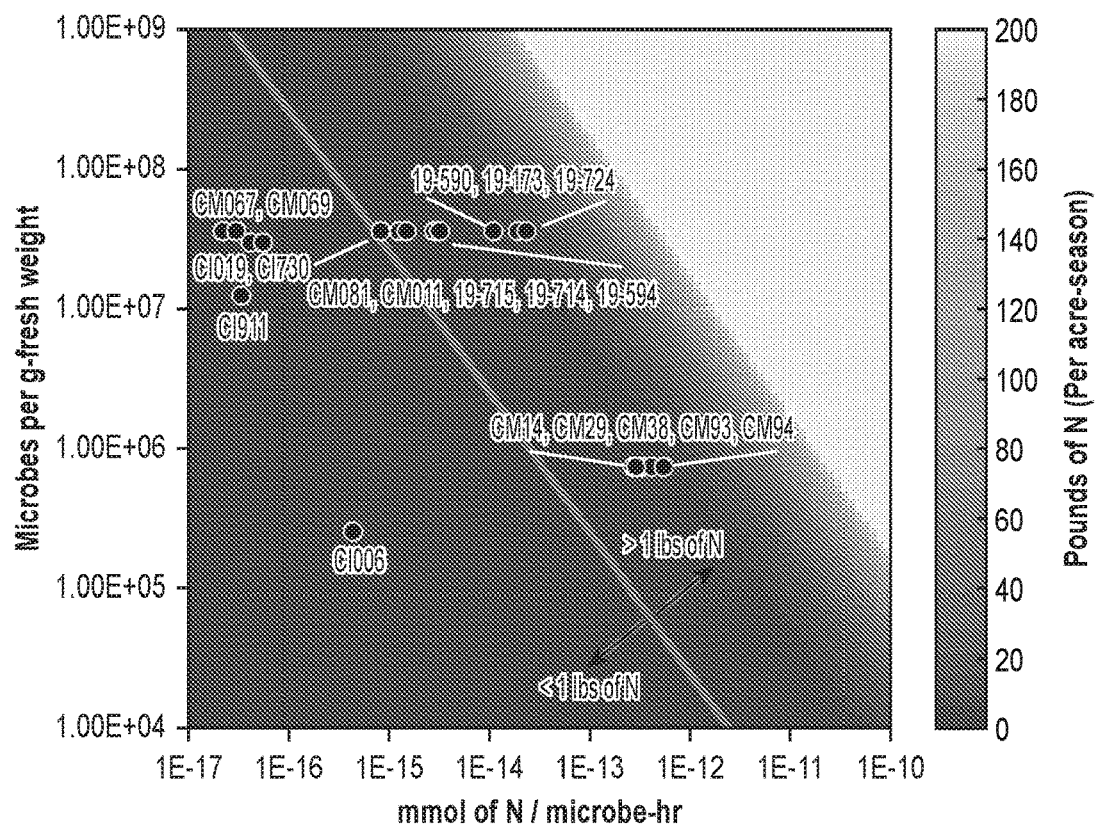
FIG. 20 depicts a heatmap of the pounds of nitrogen delivered per acre-season by microbes of the present disclosure recorded as a function of microbes per g-fresh weight by mmol of nitrogen/microbe-hr. Below the thin line that transects the larger image are the microbes that deliver less than one pound of nitrogen per acre-season, and above the line are the microbes that deliver greater than one pound of nitrogen per acre-season. The table below the heatmap gives the precise value of mmol N produced per microbe per hour (mmol N/Microbe hr) along with the precise CFU per gram of fresh weight (CFU/g fw) for each microbe shown in the heatmap. The microbes utilized in the heatmap were assayed for N production in corn. For the WT strains CI006 and CI019, corn root colonization data was taken from a single field site. For the remaining strains, colonization was assumed to be the same as the WT field level. N-fixation activity was determined using an in vitro ARA assay at 5 mM glutamine.
Figure 21:
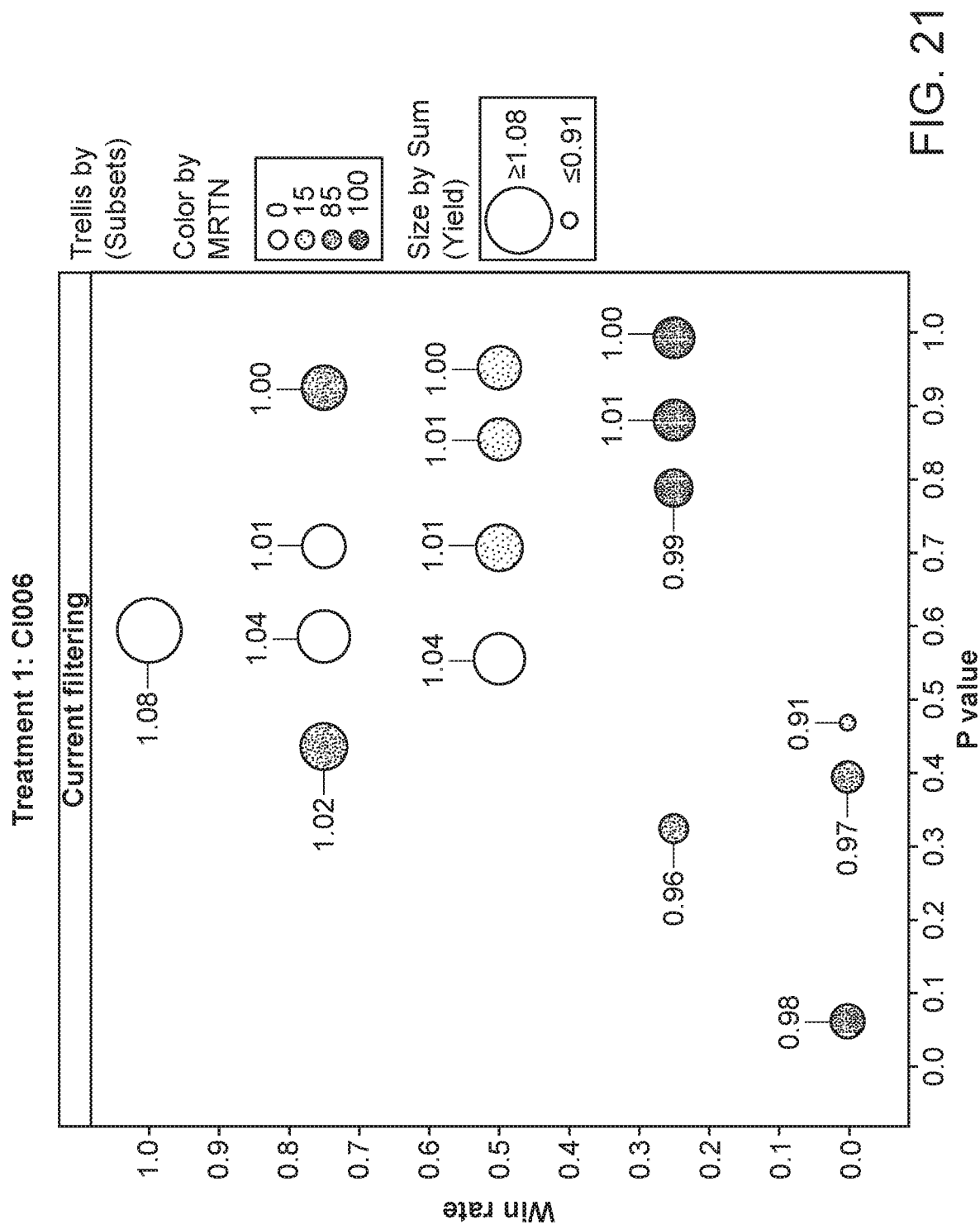
FIG. 21 depicts the plant yield of plants having been exposed to strain CI006. The area of the circles corresponds to the relative yield, while the shading corresponds to the particular MRTN treatment. The x-axis is the p value and the y-axis is the win rate.
Figure 22:
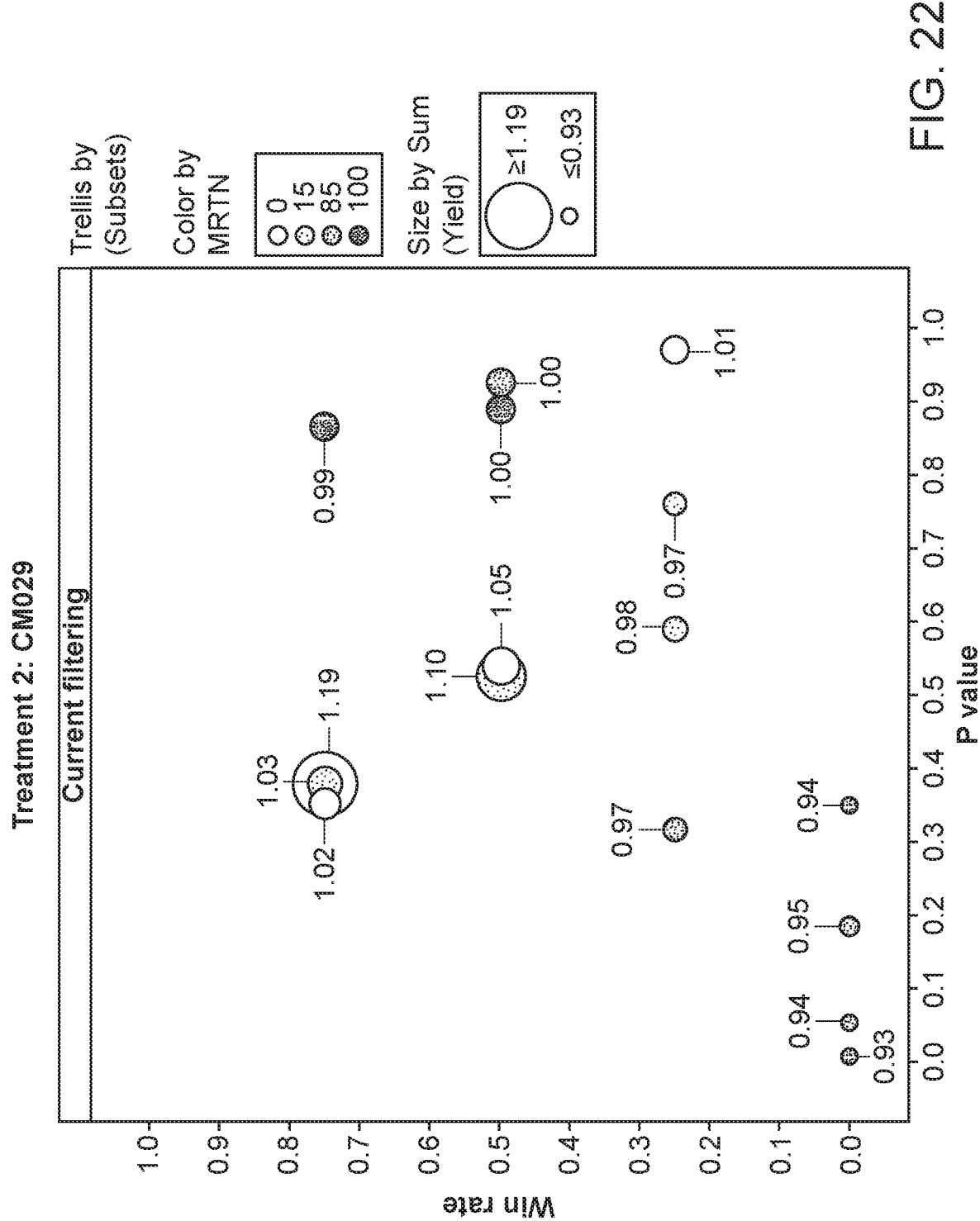
FIG. 22 depicts the plant yield of plants having been exposed to strain CM029. The area of the circles corresponds to the relative yield, while the shading corresponds to the particular MRTN treatment. The x-axis is the p value and the y-axis is the win rate.
Figure 23:
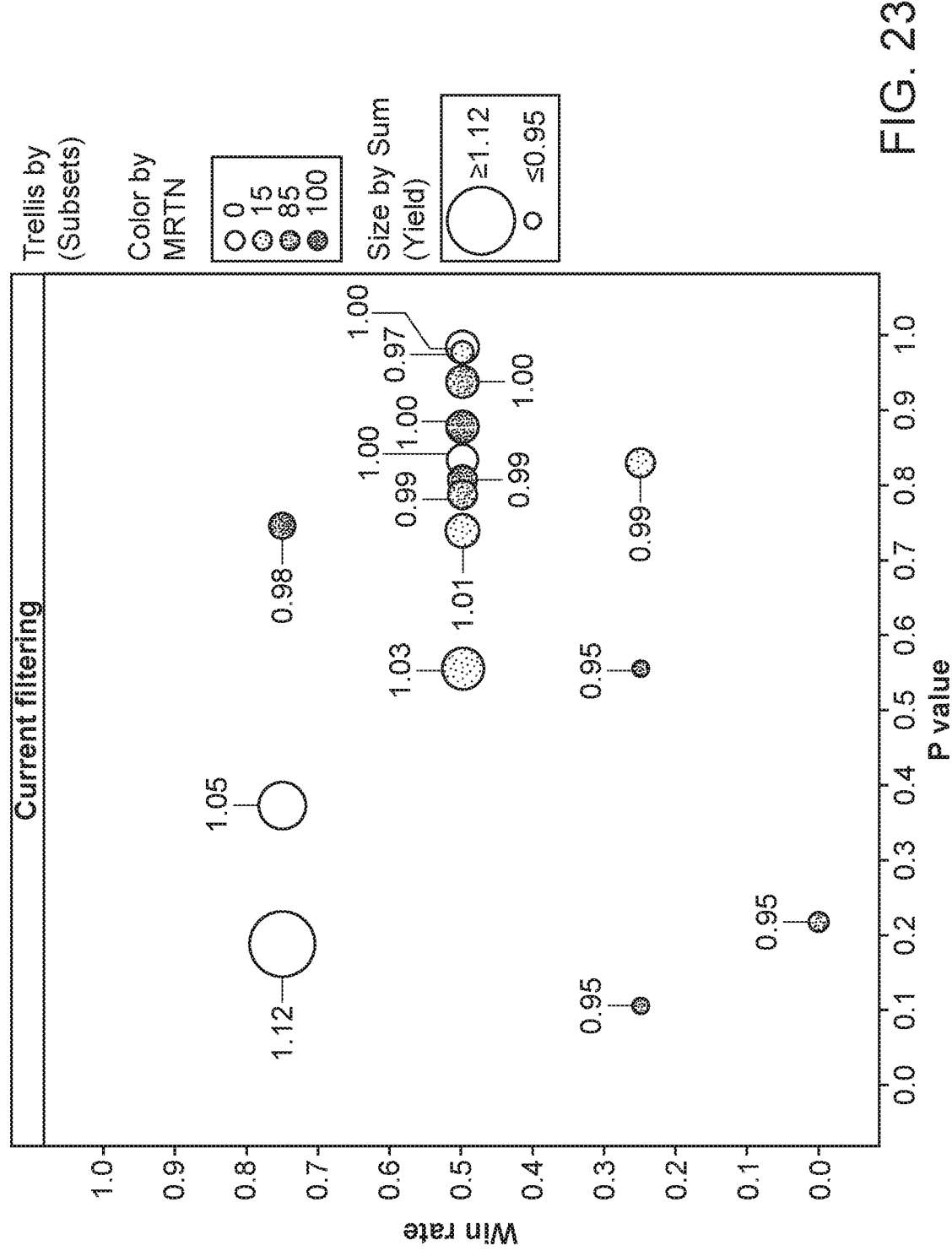
FIG. 23 depicts the plant yield of plants having been exposed to strain CM038. The area of the circles corresponds to the relative yield, while the shading corresponds to the particular MRTN treatment. The x-axis is the p value and the y-axis is the win rate.
Figure 24:
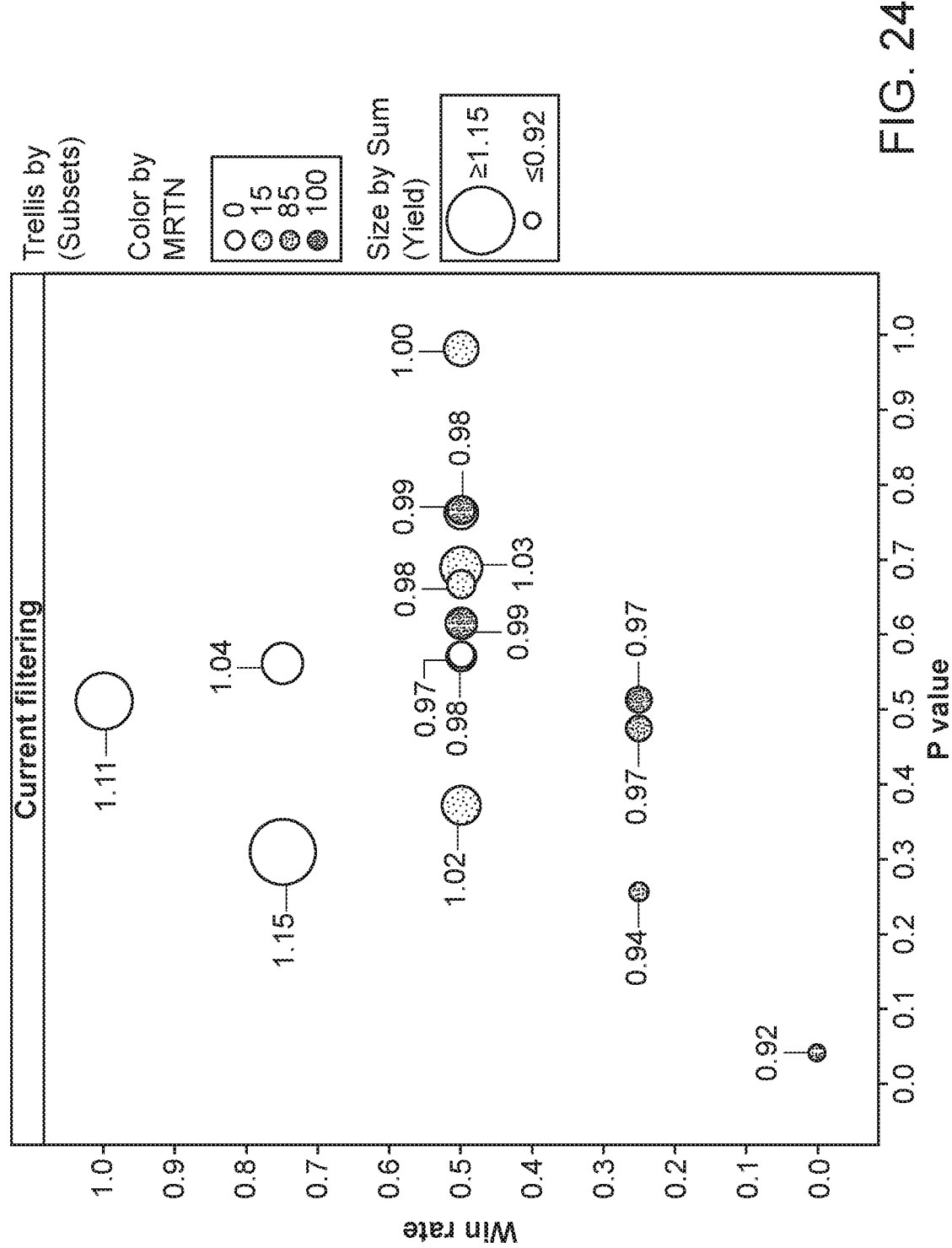
FIG. 24 depicts the plant yield of plants having been exposed to strain CI019. The area of the circles corresponds to the relative yield, while the shading corresponds to the particular MRTN treatment. The x-axis is the p value and the y-axis is the win rate.
Figure 25:
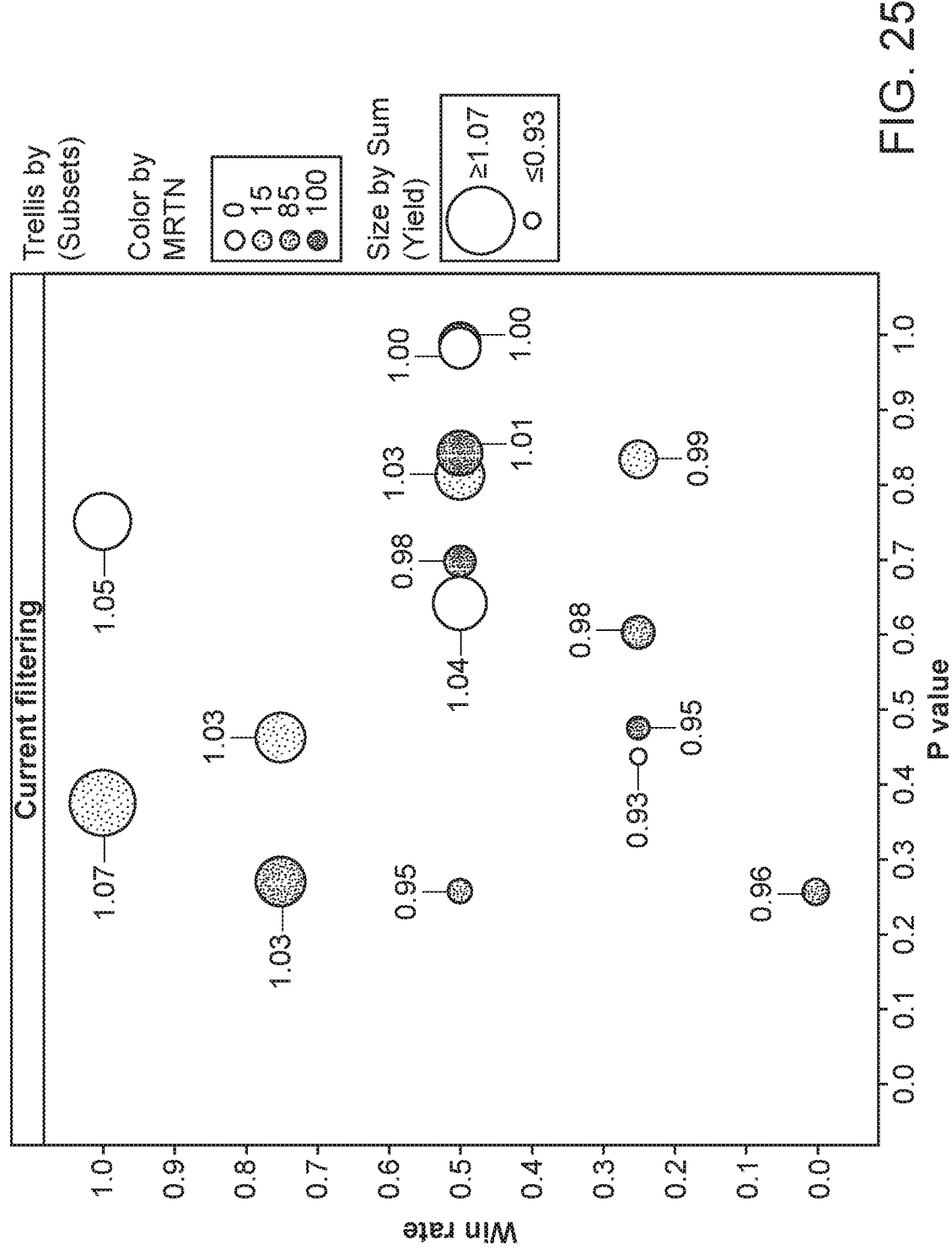
FIG. 25 depicts the plant yield of plants having been exposed to strain CM081. The area of the circles corresponds to the relative yield, while the shading corresponds to the particular MRTN treatment. The x-axis is the p value and the y-axis is the win rate.
Figure 26:
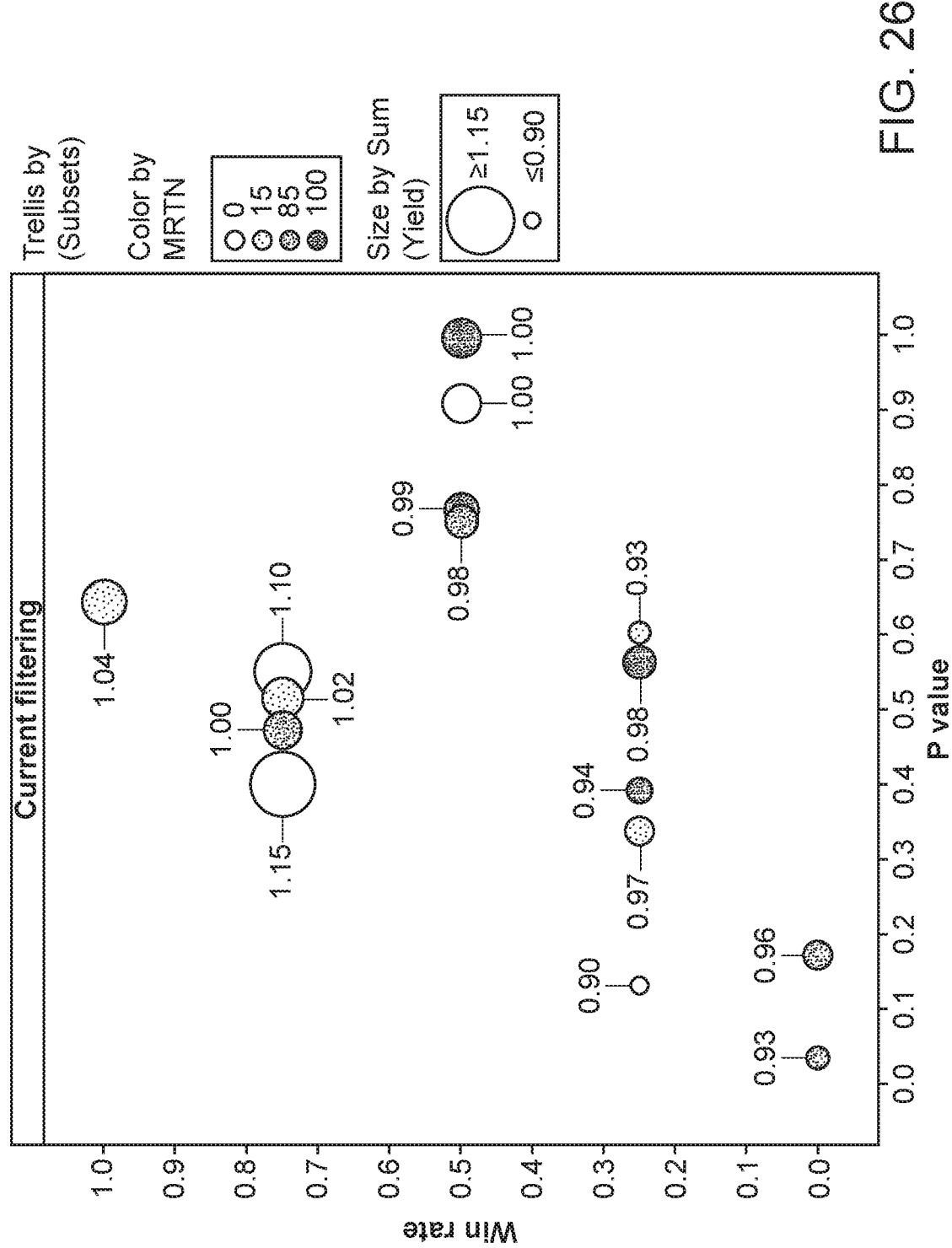
FIG. 26 depicts the plant yield of plants having been exposed to strains CM029 and CM081. The area of the circles corresponds to the relative yield, while the shading corresponds to the particular MRTN treatment. The x-axis is the p value and the y-axis is the win rate.
Figure 27:
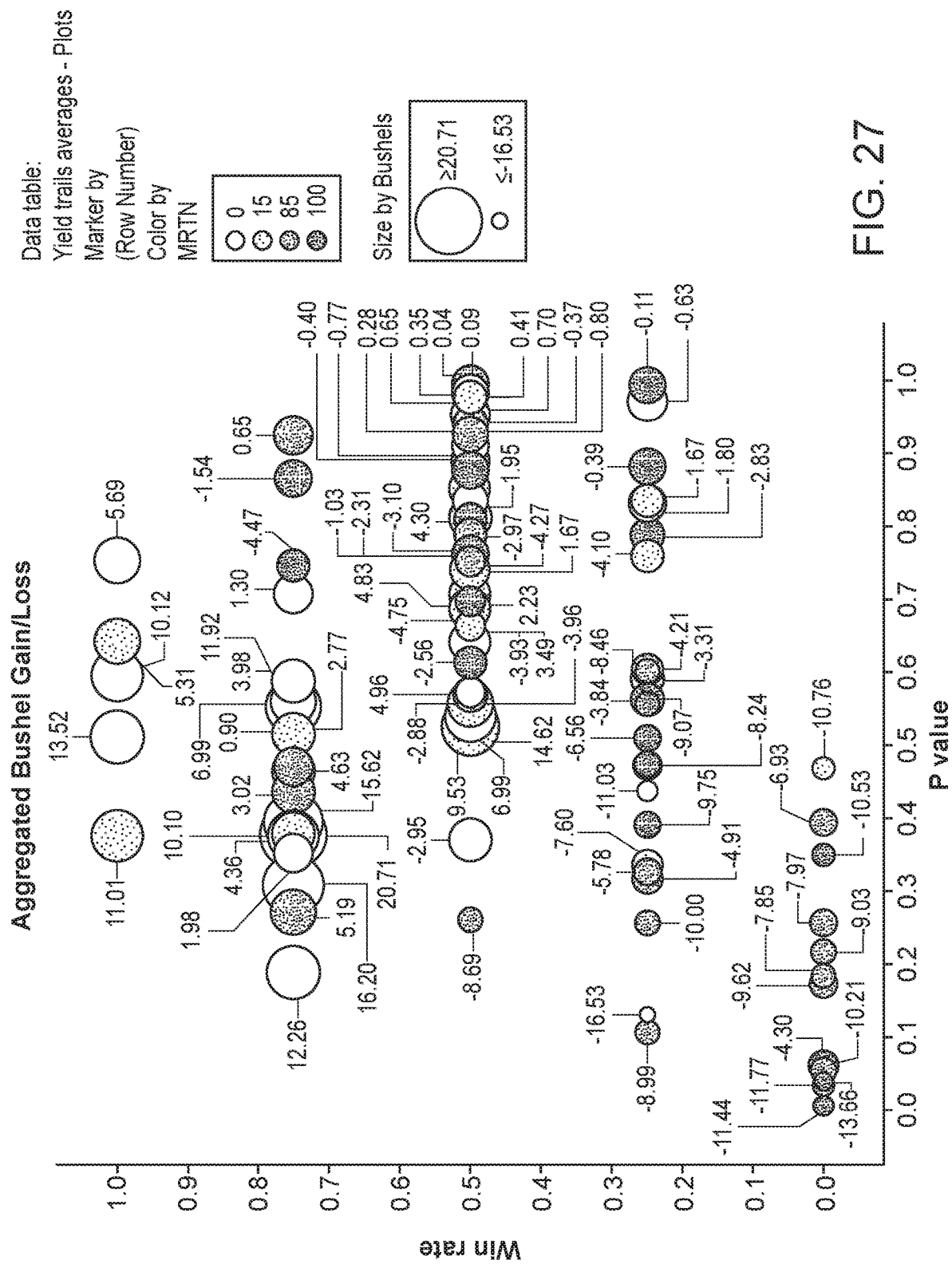
FIG. 27 depicts the plant yield of plants as the aggregated bushel gain/loss. The area of the circles corresponds to the relative yield, while the shading corresponds to the particular MRTN treatment. The x-axis is the p value and the y-axis is the win rate.
Figure 40:
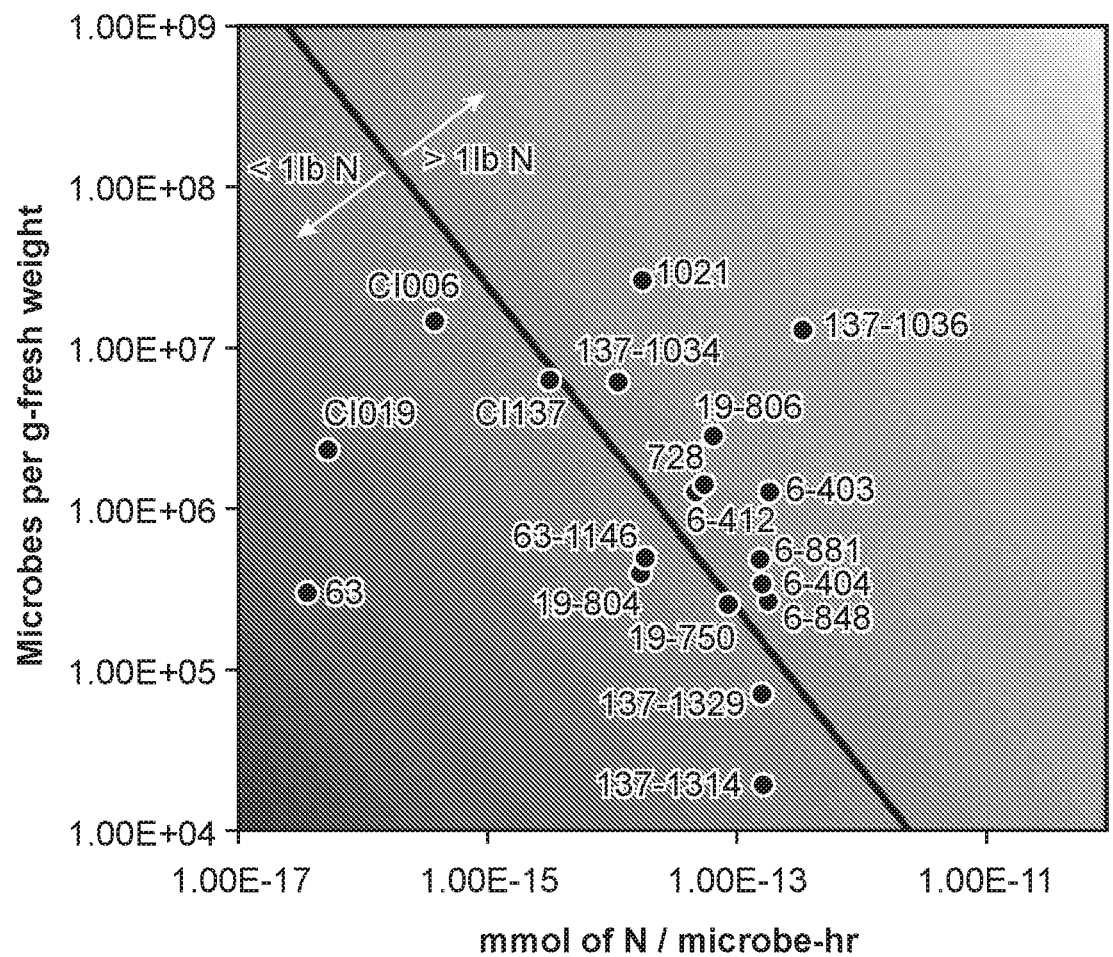
FIG. 40 depicts a heatmap of the pounds of nitrogen delivered per acre-season by microbes of the present disclosure recorded as a function of microbes per g-fresh weight by mmol of nitrogen/microbe-hr. Below the thin line that transects the larger image are the microbes that deliver less than one pound of nitrogen per acre-season, and above the line are the microbes that deliver greater than one pound of nitrogen per acre-season. The Table C in Example 12 gives the precise value of mmol N produced per microbe per hour (mmol N/Microbe hr) along with the precise CFU per gram of fresh weight (CFU/g fw) for each microbe shown in the heatmap. The data in FIG. 40 is derived from microbial strains assayed for N production in corn in field conditions. Each point represents lb N/acre produced by a microbe using corn root colonization data from a single field site. N-fixation activity was determined using in vitro ARA assay at 5 mM N in the form of glutamine or ammonium phosphate.
Figure 41:
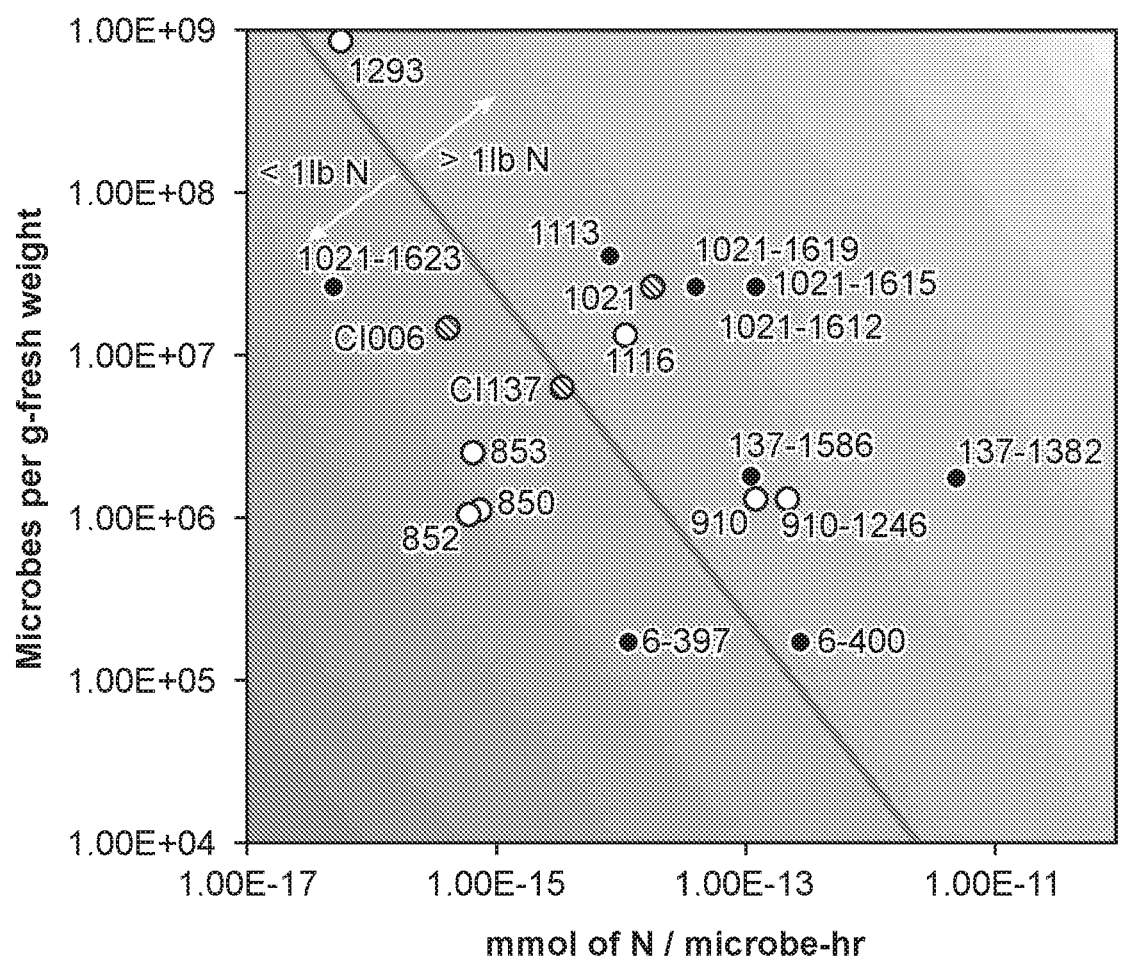
FIG. 41 depicts a heatmap of the pounds of nitrogen delivered per acre-season by microbes of the present disclosure recorded as a function of microbes per g-fresh weight by mmol of nitrogen/microbe-hr. Below the thin line that transects the larger image are the microbes that deliver less than one pound of nitrogen per acre-season, and above the line are the microbes that deliver greater than one pound of nitrogen per acre-season. The Table D in Example 12 gives the precise value of mmol N produced per microbe per hour (mmol N/Microbe hr) along with the precise CFU per gram of fresh weight (CFU/g fw) for each microbe shown in the heatmap. The data in FIG. 41 is derived from microbial strains assayed for N production in corn in laboratory and greenhouse conditions. Each point represents lb N/acre produced by a single strain. White points represent strains in which corn root colonization data was gathered in greenhouse conditions. Black points represent mutant strains for which corn root colonization levels are derived from average field corn root colonization levels of the wild-type parent strain. Hatched points represent the wild type parent strains at their average field corn root colonization levels. In all cases, N-fixation activity was determined by in vitro ARA assay at 5 mM N in the form of glutamine or ammonium phosphate.

To that end, the inventors have surprisingly discovered a functional genus of microbes that are able to contribute, inter alia, to: increasing yields in non-leguminous crops; and/or lessening a farmer's dependence upon exogenous nitrogen application; and/or the ability to produce at least one pound of nitrogen per acre per season, even in non-nitrogen-limiting environments, said genus being defined by the product of colonization ability×mmol of N produced per microbe per hour (i.e. the line partitioning FIGS. 20, 40, and 41).

With respect to FIGS. 20, 40, and 41, certain data utilizing microbes of the disclosure was aggregated, in order to depict a heatmap of the pounds of nitrogen delivered per acre-season by microbes of the disclosure, which are recorded as a function of microbes per g-fresh weight by mmol of nitrogen/microbe-hr. Below the thin line that transects the larger images are the microbes that deliver less than one pound of nitrogen per acre-season, and above the line are the microbes that deliver greater than one pound of nitrogen per acre-season.

Field Data & Wild Type Colonization Heatmap:

The microbes utilized in the FIG. 20 heatmap were assayed for N production in corn. For the WT strains CI006 and CI019, corn root colonization data was taken from a single field site. For the remaining strains, colonization was assumed to be the same as the WT field level. N-fixation activity was determined using an in vitro ARA assay at 5 mM glutamine. The table below the heatmap in FIG. 20 gives the precise value of mmol N produced per microbe per hour (mmol N/Microbe hr) along with the precise CFU per gram of fresh weight (CFU/g fw) for each microbe shown in the heatmap.

Field Data Heatmap:

The data utilized in the FIG. 40 heatmap is derived from microbial strains assayed for N production in corn in field conditions. Each point represents lb N/acre produced by a microbe using corn root colonization data from a single field site. N-fixation activity was determined using in vitro ARA assay at 5 mM N in the form of glutamine or ammonium phosphate. The below Table C gives the precise value of mmol N produced per microbe per hour (mmol N/Microbe hr) along with the precise CFU per gram of fresh weight (CFU/g fw) for each microbe shown in the heatmap of FIG. 40.

Greenhouse & Laboratory Data Heatmap:

The data utilized in the FIG. 41 heatmap is derived from microbial strains assayed for N production in corn in laboratory and greenhouse conditions. Each point represents lb N/acre produced by a single strain. White points represent strains in which corn root colonization data was gathered in greenhouse conditions. Black points represent mutant strains for which corn root colonization levels are derived from average field corn root colonization levels of the wild-type parent strain. Hatched points represent the wild type parent strains at their average field corn root colonization levels. In all cases, N-fixation activity was determined by in vitro ARA assay at 5 mM N in the form of glutamine or ammonium phosphate. The below Table D gives the precise value of mmol N produced per microbe per hour (mmol N/Microbe hr) along with the precise CFU per gram of fresh weight (CFU/g fw) for each microbe shown in the heatmap of FIG. 41.

TABLE C

FIG. 40 - Field Data Heatmap

| Strain Name | Activity (mmol N/ Microbe hr) | Peak Colonization (CFU/g fw) | N Produced/ acre season | Taxonomic Designation |
|---|---|---|---|---|
| CI006 | 3.88E−16 | 1.50E+07 | 0.24 | *Kosakonia sacchari* |
| 6-404 | 1.61E−13 | 3.50E+05 | 2.28 | *Kosakonia sacchari* |
| 6-848 | 1.80E−13 | 2.70E+05 | 1.97 | *Kosakonia sacchari* |
| 6-881 | 1.58E−13 | 5.00E+05 | 3.20 | *Kosakonia sacchari* |
| 6-412 | 4.80E−14 | 1.30E+06 | 2.53 | *Kosakonia sacchari* |
| 6-403 | 1.90E−13 | 1.30E+06 | 10.00 | *Kosakonia sacchari* |
| CI019 | 5.33E−17 | 2.40E+06 | 0.01 | *Rahnella aquatilis* |
| 19-806 | 6.65E−14 | 2.90E+06 | 7.80 | *Rahnella aquatilis* |
| 19-750 | 8.90E−14 | 2.60E+05 | 0.94 | *Rahnella aquatilis* |
| 19-804 | 1.72E−14 | 4.10E+05 | 0.29 | *Rahnella aquatilis* |
| CI137 | 3.24E−15 | 6.50E+06 | 0.85 | *Klebsiella variicola* |

TABLE C-continued

FIG. 40 - Field Data Heatmap

| Strain Name | Activity (mmol N/ Microbe hr) | Peak Colonization (CFU/g fw) | N Produced/ acre season | Taxonomic Designation |
|---|---|---|---|---|
| 137-1034 | 1.16E−14 | 6.30E+06 | 2.96 | Klebsiella variicola |
| 137-1036 | 3.47E−13 | 1.30E+07 | 182.56 | Klebsiella variicola |
| 137-1314 | 1.70E−13 | 1.99E+04 | 0.14 | Klebsiella variicola |
| 137-1329 | 1.65E−13 | 7.25E+04 | 0.48 | Klebsiella variicola |
| 63 | 3.60E−17 | 3.11E+05 | 0.00 | Rahnella aquatilis |
| 63-1146 | 1.90E−14 | 5.10E+05 | 0.39 | Rahnella aquaiilis |
| 1021 | 1.77E−14 | 2.69E+07 | 19.25 | Kosakonia pseudosacchari |
| 728 | 5.56E−14 | 1445240.09 | 3.25 | Klebsiella variicola |

TABLE D

FIG. 41 - Greenhouse & Laboratory Data Heatmap

| Strain Name | Activity (mmol N/ Microbe hr) | Peak Colonization (CFU/g fw) | N Produced/ acre season | Taxonomic Designation |
|---|---|---|---|---|
| CI006 | 3.88E−16 | 1.50E+07 | 0.24 | Kosakonia sacchari |
| 6-400 | 2.72E−13 | 1.79E+05 | 1.97 | Kosakonia sacchari |
| 6-397 | 1.14E−14 | 1.79E+05 | 0.08 | Kosakonia sacchari |
| CI137 | 3.24E−15 | 6.50E+06 | 0.85 | Klebsiella variicola |
| 137-1586 | 1.10E−13 | 1.82E+06 | 8.10 | Klebsiella variicola |
| 137-1382 | 4.81E−12 | 1.82E+06 | 354.60 | Klebsiella variicola |
| 1021 | 1.77E−14 | 2.69E+07 | 19.25 | Kosakonia pseudosacchari |
| 1021-1615 | 1.20E−13 | 2.69E+07 | 130.75 | Kosakonia pseudosacchari |
| 1021-1619 | 3.93E−14 | 2.69E+07 | 42.86 | Kosakonia pseudosacchari |
| 1021-1612 | 1.20E−13 | 2.69E+07 | 130.75 | Kosakonia pseudosacchari |
| 1021-1623 | 4.73E−17 | 2.69E+07 | 0.05 | Kosakonia pseudosacchari |
| 1293 | 5.44E−17 | 8.70E+08 | 1.92 | Azospirillum lipoferum |
| 1116 | 1.05E−14 | 1.371+07 | 5.79 | Enterobacter sp. |
| 1113 | 8.05E−15 | 4.13E+07 | 13.45 | Enterobacter sp. |
| 910 | 1.19E−13 | 1.34E+06 | 6.46 | Kluyvera intermedia |
| 910-1246 | 2.16E−13 | 1.34E+06 | 11.69 | Kluyvera intermedia |
| 850 | 7.2301E−16 | 1.17E+06 | 0.03 | Achromobacter spiritinus |
| 852 | 5.96E−16 | 1.07E+06 | 0.03 | Achromobacter marplatensis |
| 853 | 6.42E−16 | 2.55E+06 | 0.07 | Microbacterium murale |

Conclusions:

The data in FIGS. 20, 40, 41, and Tables C and D, illustrates more than a dozen representative members of the described genus (i.e. microbes to the right of the line in the figures). Further, these numerous representative members come from a diverse array of taxonomic genera, which can be found in the above Tables C and D. Further still, the inventors have discovered numerous genetic attributes that depict a structure/function relationship that is found in many of the microbes. These genetic relationships can be found in the numerous tables of the disclosure setting forth the genetic modifications introduced by the inventors, which include introducing at least one genetic variation into at least one gene, or non-coding polynucleotide, of the nitrogen fixation or assimilation genetic regulatory network.

Consequently, the newly discovered genus is supported by: (1) a robust dataset, (2) over a dozen representative members, (3) members from diverse taxonomic genera, and (4) classes of genetic modifications that define a structure/function relationship, in the underlying genetic architecture of the genus members.

Example 13: Methods and Assays for Detection of Non-Intergeneric Engineered Microbes The present disclosure teaches primers, probes, and assays that are useful for detecting the microbes utilized in the various aforementioned Examples. The assays are able to detect the non-natural nucleotide "junction" sequences in the derived/mutant non-intergeneric microbes. These non-naturally occurring nucleotide junctions can be used as a type of diagnostic that is indicative of the presence of a particular genetic alteration in a microbe.

The present techniques are able to detect these non-naturally occurring nucleotide junctions via the utilization of specialized quantitative PCR methods, including uniquely designed primers and probes. The probes can bind to the non-naturally occurring nucleotide junction sequences. That is, sequence-specific DNA probes consisting of oligonucleotides that are labelled with a fluorescent reporter, which permits detection only after hybridization of the probe with its complementary sequence can be used. The quantitative methods can ensure that only the non-naturally occurring nucleotide junction will be amplified via the taught primers, and consequently can be detected via either a non-specific dye, or via the utilization of a specific hybridization probe. Another aspect of the method is to choose primers such that the primers flank either side of a junction sequence, such that if an amplification reaction occurs, then said junction sequence is present.

Consequently, genomic DNA can be extracted from samples and used to quantify the presence of microbes of the disclosure by using qPCR. The primers utilized in the qPCR reaction can be primers designed by Primer Blast (https://www.ncbi.nlm.nih.gov/tools/primer-blast/) to amplify unique regions of the wild-type genome or unique regions of the engineered non-intergeneric mutant strains. The qPCR reaction can be carried out using the SYBR GreenER qPCR SuperMix Universal (Thermo Fisher P/N 11762100) kit, using only forward and reverse amplification primers; alternatively, the Kapa Probe Force kit (Kapa Biosystems P/N KK4301) can be used with amplification primers and a TaqMan probe containing a FAM dye label at the 5' end, an internal ZEN quencher, and a minor groove binder and fluorescent quencher at the 3' end (Integrated DNA Technologies).

Certain primer, probe, and non-native junction sequences—which can be used in the qPCR methods—are listed in the below Table E. Specifically, the non-native junction sequences can be found in SEQ ID NOs: 372-405.

TABLE E

Microbial Detection

| base CI | Junction Name | up/down stream junction | SEQ ID NO | 100 bp upstream of junction | SEQ ID NO | 100 bp downstream of junction | SEQ ID NO | Junction SEQ "/" indicating junction | Junction des. | F primer SEQ | R primer SEQ | Probe SEQ |
|---|---|---|---|---|---|---|---|---|---|---|---|---|
| 1021 | ds1131 | up | 304 | TGGTGTCCGGGCGAACGTCGCCAGGTGGCACAAATTGTCAGAACTACGACACGACTAACCGACCGCAGGAGTGTGCGATGACCCTGAATATGATGATGGA | 338 | TTCTTGGTTCTCTGGAGCGCTTTATCGGCATCCTGACTGAAGAATTTGCAGGCTTCTTCCCAACCTGGCTTGCACCCGTGCAGGTAGTTGTGATGAACAT | 372 | 5'-TGGTGTCCGGGCGAACGTCGCCAGGTGGCACAAATTGTCAGAACTACGACACGACTAACCGACCGCAGGAGTGTGCGATGACCCTGAATATGATGATGGA/TTCTTGGTTCTCTGGAGCGCTTTATCGGCATCCTGACTGAAGAATTTGCAGGCTTCTTCCCAACCTGGCTTGCACCCGTGCAGGTAGTTGTGATGAACAT-3' | disrupted nifL gene/PinfC | N/A | N/A | N/A |
| 1021 | ds1131 | down | 305 | CGGAAAACGAGTTCAAACGGCGCGTCCCAATCGTATTAATGGCGAGATTCGCGCCACGGAAGTTCGCTTAACAGGTCTGGAAGGCGAGCACCTTGGTATT | 339 | GCGATAGAACTCACTTCACGCCCCGAAGGGGGAAGCTGCCTGACCCTACGATTCCCGCTATTCATTCACTGACCGGAGGTTCAAAATGACCCAGCGAAC | 373 | 5'-CGGAAAACGAGTTCAAACGGCGCGTCCCAATCGTATTAATGGCGAGATTCGCGCCACGGAAGTTCGTTAACAGGTCTGGAAGGCGAGCAGCTTGGTATT/GCGATAGAACTCACTTCACGCCCCGAAGGGGGAAGCTGCCTGACCCTACGATTCCCGCTATTTCATTCACTGACGGAGGTTCAAAATGACCCAGCGAAC-3' | PinfC/disrupted nifL gene | N/A | N/A | N/A |
| 1021 | ds1133 | N/A | 306 | CGCCAGAGAGTTGAAATCGAACATTTCCGTAATACCGCCATTACCCAGGAGCCGTTCTGGTTGCACAGCGGAAACGTTAACGAAAGGATATTTCGCATG | 340 | TCCCTGTGCGCCGCGTCGCCGATGGTGGCCAGCCAACTGGCGCGCTACCCGATCCTGCTCGATGAACTGCTCGACCCGAACACGCTCTATCAACCGACGG | 374 | 5'-CGCCAGAGAGTTGAAATCGAACATTTCCGTAATACCGCCATTACCCAGGAGCCGTTCTGGTTGCACAGCGGAAAACGTTAACGAAAGGATATTTCGCATG/TCCCTGTGCGCCGCGTCGCCGATGGTGGCCAGCCAACTGGCGCGCTACCCGATCCTGCTCGATGAACTGCTCGACCCGAACACGCTCTATCAACCGACGG-3' | 5' UTR and ATG/truncated glnE gene | N/A | N/A | N/A |
| 1021 | ds1145 | up | 307 | CGGGCGAACGTCGCCAGGTGGCACAAATTGTCAGAACTACGACACGACTAACCGACCGCAGGAGTGTGCGATGACCCTGAATATGATGATGGATGCCAGC | 341 | CGTTCTGTAATAATAACCGGACAATTCGGACTGATTAAAAAAGCGCCCTCGCGGCGCTTTTTTTATATTCTGACTCCATTTAAAATAAAAAATCCAATC | 375 | 5'-CGGGCGAACGTCGCCAGGTGGCACAAATTGTCAGAACTACGACACGACTAACCGACCGCAGGAGTGTGCGATGACCCTGAATATGATGATGGATGCCAGC/CGTTCTGTAATAATAACCGGACAA | disrupted nifL gene/Prm1 | N/A | N/A | N/A |

TABLE E-continued

Microbial Detection

| base CI | Junction Name | up/down stream junction | SEQ ID NO | 100 bp upstream of junction | SEQ ID NO | 100 bp downstream of junction | SEQ ID NO | Junction SEQ "/" indicating junction | Junction des. | F primer SEQ | R primer SEQ | Probe SEQ |
|---|---|---|---|---|---|---|---|---|---|---|---|---|
| | | | | | | | | TTCGGACTGATT AAAAAAGCGCCC TCGCGGCGCTTTT TTTATATTCTCGA CTCCATTTAAAAT AAAAAAATCCAAT C-3' | | | | |
| 1021 | ds1145 | down | 308 | TCAACCTAAAAA AGTTTGTGTAATA CTTGTAACGCTAC ATGGAGATTAAC TCAATCTAGAGG GTATTAATAATG AATCGTACTAAA CTGGTACTGGGC GC | 342 | AACTCACTTCAC GCCCCGAAGGGG GAAGCTGCCTGA CCCTACGATTCCC GCTATTTCATTCA CTGACCGGAGGT TCAAAATGACCC AGCGAACCGAGT CG | 376 | 5'-TCAACCTAAAAA AGTTTGTGTAAT ACTTGTAACGCT ACATGGAGATTA ACTCAATCTAGA GGGTATTAATAA TGAATCGTACTA AACTGGTACTGG GCGC/ AACTCACTTCAC GCCCCGAAGGGG GAAGCTGCCTGA CCCTACGATTCCC GCTATTTCATTCA CTGACCGGAGGT TCAAAATGACCC AGCGAACCGAGT CG-3' | Prm1/ disrupted nifL gene | N/A | N/A | N/A |
| 1021 | ds1148 | up | 309 | CGGGCGAACGTC GCCAGGTGGCAC AAATTGTCAGAA CTACGACACGAC TAACCGACCGCA GGAGTGTGCGAT GACCCTGAATAT GATGATGGATGC CAGC | 343 | CGCGTCAGGTTG AACGTAAAAAAG TCGGTCTGCGCA AAGCACGTCGTC GTCCGCAGTTCTC CAAACGTTAATT GGTTTCTGCTTCG GCAGAACGATTG GC | 377 | 5'-CGGGCGAACGTC GCCAGGTGGCAC AAATTGTCAGAA CTACGACACGAC TAACCGACCGCA GGAGTGTGCGAT GACCCTGAATAT GATGATGGATGC CAGC/ CGCGTCAGGTTG AACGTAAAAAAG TCGGTCTGCGCA AAGCACGTCGTC GTCCGCAGTTCTC CAAACGTTAATT GGTTTCTGCTTCG GCAGAACGATTG GC-3' | disrupted nifL gene/ Prm7 | N/A | N/A | N/A |
| 1021 | ds1148 | down | 310 | AATTTTCTGCCCA AATGGCTGGGAT TGTTCATTTTTTG TTTGCCTTACAAC GAGAGTGACAGT ACGCGCGGGTAG TTAACTCAACATC TGACCGGTCGAT | 344 | AACTCACTTCAC GCCCCGAAGGGG GAAGCTGCCTGA CCCTACGATTCCC GCTATTTCATTCA CTGACCGGAGGT TCAAAATGACCC AGCGAACCGAGT CG | 378 | 5'-AATTTTCTGCCCA AATGGCTGGGAT TGTTCATTTTTTG TTTGCCTTACAAC GAGAGTGACAGT ACGCGCGGGTAG TTAACTCAACAT CTGACCGGTCGA T/ AACTCACTTCAC GCCCCGAAGGGG GAAGCTGCCTGA CCCTACGATTCCC GCTATTTCATTCA CTGACCGGAGGT TCAAAATGACCC AGCGAACCGAGT CG-3' | Prm4/ disrupted nifL gene | N/A | N/A | N/A |
| CI006 | ds126 | N/A | 311 | GTAACCAATAAA GGCCACCACGCC AGACCACACGAT AGTGATGGCAAC | 345 | CCGATCCCCATC ACTGTGTGTCTTG TATTACAGTGCC GCTTCGTCGGCTT | 379 | 5'-GTAACCAATAAA GGCCACCACGCC AGACCACACGAT | 5' UTR up to ATG-4bp of amtB gene/ | N/A | N/A | N/A |

TABLE E-continued

Microbial Detection

| base CI | Junction Name | up/down stream junction | SEQ ID NO | 100 bp upstream of junction | SEQ ID NO | 100 bp downstream of junction | SEQ ID NO | Junction SEQ "/" indicating junction | Junction des. | F primer SEQ | R primer SEQ | Probe SEQ |
|---|---|---|---|---|---|---|---|---|---|---|---|---|
| | | | | ACTTTCCAGCTGC ACCAGCACCTGA TGGCCCATGGTC ACACCTTCAGCG AAA | | CGCCGGTACGAA TACGAATGACGC GTTGCAGCTCAG CAACGAAAATTT TG | | AGTGATGGCAAC ACTTTCCAGCTGC ACCAGCACCTGA TGGCCCATGGTC ACACCTTCAGCG AAA/ CCGATCCCCATC ACTGTGTGTCTTG TATTACAGTGCC GCTTCGTCGGCTT CGCCGGTACGAA TACGAATGACGC GTTGCAGCTCAG CAACGAAAATTT TG-3' | disrupted amtB gene | | | |
| CI019 | ds172 | down | 312 | TGGTATTGTCAGT CTGAATGAAGCT CTTGAAAAAGCT GAGGAAGCGGGC GTCGATTTAGTAG AAATCAGTCCGA ATGCCGAGCCGC CAGTTTGTCGAATC | 346 | CCGTCTCTGAAG CTCTCGGTGAAC ATTGTTGCGAGG CAGGATGCGAGC TGGTTGTGTTTTG ACATTACCGATA ATGTGCCGCGTG AACGGGTGCGTT ATG | 380 | 5'-TGGTATTGTCAGT CTGAATGAAGCT CTTGAAAAAGCT GAGGAAGCGGGC GTCGATTTAGTA GAAATCAGTCCG AATGCCGAGCCG CCAGTTTGTCGA ATC/ CCGTCTCTGAAG CTCTCGGTGAAC ATTGTTGCGAGG CAGGATGCGAGC TGGTTGTGTTTTG ACATTACCGATA ATGTGCCGCGTG AACGGGTGCGTT ATG-3' | Prm1.2/ disrupted nifL gene | SEQ ID NO: 406 CAAG AAGT TCGC CTCA CAGG | SEQ ID NO: 407 TGCC TCGC AACA ATGT TCAC | N/A |
| CI019 | ds172 | up | 313 | ACCGATCCGCAG GCGCGCATTTGTT ATGCCAATCCGG CATTCTGCCGCCA GACGGGTTTTGC ACTTGAGACACTT TTGGGCGAGAAC CACCGTCTGCTGG | 347 | TGAACATCACTG ATGCACAAGCTA CCTATGTCGAAG AATTAACTAAAA AACTGCAAGATG CAGGCATTCGCG TTAAAGCCGACT TGAGAAATGAGA AGAT | 381 | 5'-ACCGATCCGCAG GCGCGCATTTGTT ATGCCAATCCGG CATTCTGCCGCC AGACGGGTTTTG CACTTGAGACAC TTTTGGGCGAGA ACCACCGTCTGC TGG/ TGAACATCACTG ATGCACAAGCTA CCTATGTCGAAG AATTAACTAAAA AACTGCAAGATG CAGGCATTCGCG TTAAAGCCGACT TGAGAAATGAGA AGAT-3' | disrupted nifL gene/ Prm1.2 | N/A | N/A | N/A |
| CI019 | ds175 | down | 314 | CGGGAACCGGTG TTATAATGCCGCG CCCTCATATTGTG GGGATTTCTTAAT GACCTATCCTGG GTCCTAAAGTTGT AGTTGACATTAG CGGAGCACTAAC | 348 | CCGTCTCTGAAG CTCTCGGTGAAC ATTGTTGCGAGG CAGGATGCGAGC TGGTTGTGTTTTG ACATTACCGATA ATGTGCCGCGTG AACGGGTGCGTT ATG | 382 | 5'-CGGGAACCGGTG TTATAATGCCGCG CCCTCATATTGT GGGGATTTCTTA ATGACCTATCCT GGGTCCTAAAGT TGTAGTTGACATT AGCGGAGCACTA AC/ CCGTCTCTGAAG CTCTCGGTGAAC ATTGTTGCGAGG CAGGATGCGAGC TGGTTGTGTTTTG ACATTACCGATA | Prm3.1/ disrupted nifL gene | SEQ ID NO: 408 CGCC CTCA TATT GTGG GGAT | SEQ ID NO: 409 GGCA TAAC GCAC CCGT TCA | SEQ ID NO: 410/ 56-FAM/ ACC CGT C/ZE N/T CTG AAG CTC TCG GT/3I |

TABLE E-continued

Microbial Detection

| base CI | Junction Name | up/down stream junction | SEQ ID NO | 100 bp upstream of junction | SEQ ID NO | 100 bp downstream of junction | SEQ ID NO | Junction SEQ "/" indicating junction | Junction des. | F primer SEQ | R primer SEQ | Probe SEQ |
|---|---|---|---|---|---|---|---|---|---|---|---|---|
| CI019 | ds175 | up | 315 | ACCGATCCGCAGGCGCGCATTTGTTATGCCAATCCGGCATTCTGCCGCCAGACGGGTTTTGCACTTGAGACACTTTTTGGGCGAGAACCACCGTCTGCTGG | 349 | TACAGTAGCGCCTCTCAAAAATAGATAAACGGCTCATGTACGTGGGCCGTTTATTTTTTCTACCCATAATCGGGAACCGGTGTTATAATGCCGCGCCCTC | 383 | 5'-ACCGATCCGCAGGCGCGCATTTGTTATGCCAATCCGGCATTCTGCCGCCAGACGGGTTTTGCACTTGAGACACTTTTTGGGCGAGAACCACCGTCTGCTGG/TACAGTAGCGCCTCTCAAAAATAGATAAACGGCTCATGTACGTGGGCCGTTTATTTTTTCTACCCATAATCGGGAACCGGTGTTATAATGCCGCGCCCTC-3' | disrupted nifL gene/ Prm3.1 | N/A | N/A | N/A |
| CI006 | ds20 | down | 316 | TCAACCTAAAAAAGTTTGTGTAATACTTGTAACGCTACATGGAGATTAACTCAATCTAGAGGGTATTAATAATGAATCGTACTAAACTGGTACTGGGCGC | 350 | AACTCACTTCACACCCCGAAGGGGGAAGTTGCCTGACCCTACGATTCCCGCTATTTCATTCACTGACCGGAGGTTCAAAATGACCCAGCGAACCGAGTCG | 384 | 5'-TCAACCTAAAAAAGTTTGTGTAATACTTGTAACGCTACATGGAGATTAACTCAATCTAGAGGGTATTAATAATGAATCGTACTAAACTGGTACTGGGCGC/AACTCACTTCACACCCCGAAGGGGGAAGTTGCCTGACCCTACGATTCCCGCTATTTCATTCACTGACCGGAGGTTCAAAATGACCCAGCGAACCGAGTCG-3' | Prm1/ disrupted nifL gene | SEQ ID NO: 411 TAAACTGGTACTGGGCGCAACT | SEQ ID NO: 412 CAAATCGATAGCGCCAGACGGTAT | SEQ ID NO: 413/ 56-FAM/AAGTTGCT/ZEN/GACCCTACGATTCCC/3IABkFQ/ |
| CI006 | ds20 | up | 317 | GGGCGACAAACGGCCTGGTGGCACAAATTGTCAGAACTACGACACGACTAACTGACCGCAGGAGTGTGCGATGACCCTGAATATGATGATGGATGCCGGC | 351 | CGTCCTGTAATAATAACCGGACAATTCGGACTGATTAAAAAAGCGCCCTTGTGGCGCTTTTTTTATATTCCCGCCTCCATTTAAAATAAAAAATCCAATC | 385 | 5'-GGGCGACAAACGGCCTGGTGGCACAAATTGTCAGAACTACGACACGACTAACTGACCGCAGGAGTGTGCGATGACCCTGAATATGATGATGGATGCCGGC/CGTCCTGTAATAATAACCGGACAATTCGGACTGATTAAAAAAGCGCCCTTGTGGCGCTTTTTTTATATTCCCGCCTCCATTTAAAATAAAAAATCCAATC-3' | disrupted nifL gene/ Prm1 | N/A | N/A | N/A |
| CI006 | ds24 | up | 318 | GGGCGACAAACGGCCTGGTGGCACAAATTGTCAGAACTACGACACGACTAACTGACCGCAGGAGTGTGCGATGACCCTGAATAT | 352 | GGACATCATCGCGACAAACAATATTAATACCGGCAACCACACCGGCAATTTACGAGACTGCGCAGGCATCCTTTCTCCCGTCAAT | 386 | 5'-GGGCGACAAACGGCCTGGTGGCACAAATTGTCAGAACTACGACACGACTAACTGACCGCAGGAGTGTGCGATGACCCTGAATAT | disrupted nifL gene/ Prm5 | SEQ ID NO: 414 GGTGCACTCTTT | SEQ ID NO: 415 GCGCAGTCTCGT | SEQ ID NO: 416/ 56-FAM/CA |

TABLE E-continued

Microbial Detection

| base CI | Junction Name | up/down stream junction | SEQ ID NO | 100 bp upstream of junction | SEQ ID NO | 100 bp downstream of junction | SEQ ID NO | Junction SEQ "/" indicating junction | Junction des. | F primer SEQ | R primer SEQ | Probe SEQ |
|---|---|---|---|---|---|---|---|---|---|---|---|---|
| | | | | GATGATGGATGCCGGC | | TTCTGTCAAATAAAG | | 5'-GACCCTGAATATGATGATGGATGCCGGC/GGACATCATCGCGACAAACAATATTAATACCGGCAACCACACCGGCAATTTACGAGACTGCGCAGGCATCCTTTCTCCCGTCAATTTCTGTCAAATAAAG-3' | | GCATGGTT | AAATTGCC | GGAGTGT/ZEN/GCGATGACCCTGAT/3IABkFQ |
| CI006 | ds24 | down | 319 | TAAGAATTATCTGGATGAATGTGCCATTAAATGCGCAGCATAATGGTGCGTTGTGCGGGAAAACTGCTTTTTTTGAAAGGGTTGGTCAGTAGCGGAAAC | 353 | AACTCACTTCACACCCCGAAGGGGGAAGTTGCCTGACCCTACGATTCCCGCTATTTCATTCACTGACCGGAGGTTCAAAATGACCCAGCGAACCGAGTCG | 387 | 5'-TAAGAATTATCTGGATGAATGTGCCATTAAATGCGCAGCATAATGGTGCGTTGTGCGGGAAAACTGCTTTTTTTGAAAGGGTTGGTCAGTAGCGGAAAC/AACTCACTTCACACCCCGAAGGGGGAAGTTGCCTGACCCTACGATTCCCGCTATTTCATTCACTGACCGGAGGTTCAAAATGACCCAGCGAACCGAGTCG-3' | Prm5/disrupted nifL gene | N/A | N/A | N/A |
| CI006 | ds30 | N/A | 320 | CGCCAGAGAGTCGAAATCGAACATTTCCGTAATACCGCGATTACCCAGGAGCCGTTCTGGTTGCACAGCGGAAAACGTTAACGAAAGGATATTTCGCATG | 354 | TTTAACGATCTGATTGGCGATGATGAAACGGATTCGCCGGAAGATGCGCTTTTCTGAGAGCTGGCGCGAATTGTGGCAGGATGCGTTGCAGGAGGAGGATT | 388 | 5'-CGCCAGAGAGTCGAAATCGAACATTTCCGTAATACCGCGATTACCCAGGAGCCGTTCTGGTTGCACAGCGGAAAACGTTAACGAAAGGATATTTCGCATG/TTTAACGATCTGATTGGCGATGATGAAACGGATTCGCCGGAAGATGCGCTTTTCTGAGAGCTGGCGCGAATTGTGGCAGGATGCGTTGCAGGAGGAGGATT-3' | 5' UTR and ATG/truncated glnE gene | N/A | N/A | N/A |
| CI006 | ds31 | N/A | 321 | CGCCAGAGAGTCGAAATCGAACATTTCCGTAATACCGCGATTACCCAGGAGCCGTTCTGGTTGCACAGCGGAAAACGTTAACGAAAGGATATTTCGCATG | 355 | GCACTGAAACACCTCATTTCCCTGTGTGCCGCGTCGCCGATGGTTGCCAGTCAGCTGGCGCGCTACCCGATCCTGCTTGATGAATTGCTCGACCCGAATA | 389 | 5'-CGCCAGAGAGTCGAAATCGAACATTTCCGTAATACCGCGATTACCCAGGAGCCGTTCTGGTTGCACAGCGGAAAACGTTAACGAAAGGATATTTCGCATG/GCACTGAAACACCTCATTTCCCTGTGTGCCGCGTCGCCGATGGTTGCCAGTCAGCTGGCGCGCTACCCGATCCTGCTTGATGAATTGCTCGACCCGAATA-3' | 5' UTR and ATG/truncated glnE gene | N/A | N/A | N/A |

TABLE E-continued

Microbial Detection

| base CI | Junction Name | up/down stream junction | SEQ ID NO | 100 bp upstream of junction | SEQ ID NO | 100 bp downstream of junction | SEQ ID NO | Junction SEQ indicating junction | Junction des. | F primer SEQ | R primer SEQ | Probe SEQ |
|---|---|---|---|---|---|---|---|---|---|---|---|---|
| CI019 | ds34 | N/A | 322 | GATGATGGATGCTTTCTGGTTAAACGGGCAACCTCGTTAACTGACTGACTAGCCTGGGCAAACTGCCCGGGCTTTTTTTTGCAAGGAATCTGATTTCATG | 356 | GCGCTCAAACAGTTAATCCGTCTGTGTGCCGCCTCGCCGATGGTCGCGACACAACTTGCACGTCATCCTTTATTGCTCGATGAACTGCTCGACCCGCGCA | 390 | 5'-GATGATGGATGCTTTCTGGTTAAACGGGCAACCTCGTTAACTGACTGACTAGCCTGGGCAAACTGCCCGGGCTTTTTTTGCAAGGAATCTGATTTCATG/GCGCTCAAACAGTTAATCCGTCTGTGTGCCGCCTCGCCGATGGTCGCGACACAACTTGCACGTCATCCTTTATTGCTCGATGAACTGCTCGACCCGCGCA-3' | 5' UTR and ATG/truncated glnE gene | N/A | N/A | N/A |
| CI019 | ds70 | up | 323 | ACCGATCCGCAGGCGCGCATTTGTTATGCCAATCCGGCATTCTGCCGCCAGACGGGTTTTGCACTTGAGACACTTTTGGGCGAGAACCACCGTCTGCTGG | 357 | AGTCTGAACTCATCCTGCGGCAGTCGGTGAGACGTATTTTTGACCAAAGAGTGATCTACATCACGGAATTTTGTGGTTGTTGCTGCTTAAAAGGGCAAAT | 391 | 5'-ACCGATCCGCAGGCGCGCATTTGTTATGCCAATCCGGCATTCTGCCGCCAGACGGGTTTTGCACTTGAGACACTTTTGGGCGAGAACCACCGTCTGCTGG/AGTCTGAACTCATCCTGCGGCAGTCGGTGAGACGTATTTTTGACCAAAGAGTGATCTACATCACGGAATTTTGTGGTTGTTGCTGCTTAAAAGGGCAAAT-3' | disrupted nifL gene/Prm4 | N/A | N/A | N/A |
| CI019 | ds70 | down | 324 | CATCGGACACCACCAGCTTACAAATTGCCTGATTGCGGCCCCGATGGCCGGTATCACTGACCGACCATTTCGTGCCTTATGTCATGCGATGGGGGCTGGG | 358 | CCGTCTCTGAAGCTCTCGGTGAACATTGTTGCGAGGCAGGATGCGAGCTGGTTGTGTTTTGACATTACCGATAATGTGCCGCGTGAACGGGTGCGTTATG | 392 | 5'-CATCGGACACCACCAGCTTACAAATTGCCTGATTGCGGCCCCGATGGCCGGTATCACTGACCGACCATTTCGTGCCTTATGTCATGCGATGGGGGCTGGG/CCGTCTCTGAAGCTCTCGGTGAACATTGTTGCGAGGCAGGATGCGAGCTGGTTGTGTTTTGACATTACCGATAATGTGCCGCGTGAACGGGTGCGTTATG-3' | Prm4/disrupted nifL gene | N/A | N/A | N/A |
| 137 | ds799 | down | 325 | TCTTCAACAACTGGAGGAATAAGGTATTAAAGGCGGAAAACGAGTTCAAACGGCACGTCCGAATCGTATCAATGGCGAGATTCGCGCCCTGGAAGTTCGC | 359 | GCCATTGAGCTGGCTTCCCGACCGCAGGGCGGCACCTGCCTGACCCTGCGTTTCCCGCTGTTTAACACCCTGACCGGAGGTGAAGCATGATCCCTGAATC | 393 | 5'-TCTTCAACAACTGGAGGAATAAGGTATTAAAGGCGGAAAACGAGTTCAAACGGCACGTCCGAATCGTATCAATGGCGAGATTCGCGCCCTGGAAGTTCGC/GCCATTGAGCTGGCTTCCCGACCGCAGGGCGGCACC | PinfC/disrupted nifL gene | SEQ ID NO: 417 CTCGGCAGCATGGACGTAA | SEQ ID NO: 418 AGGGTGTTAAACAGCGGGAAA | SEQ ID NO: 419 56-FAM/AACGGCACG/ZEN/T |

TABLE E-continued

Microbial Detection

| base CI | Junction Name | up/down stream junction | SEQ ID NO | 100 bp upstream of junction | SEQ ID NO | 100 bp downstream of junction | SEQ ID NO | Junction SEQ "/" indicating junction | Junction des. | F primer SEQ | R primer SEQ | Probe SEQ |
|---|---|---|---|---|---|---|---|---|---|---|---|---|
| | | | | | | | | GCTTCCCGACCG CAGGGCGGCACC TGCCTGACCCTG CGTTTCCCGCTGT TAACACCCTGA CCGGAGGTGAAG CATGATCCCTGA ATC-3' | | | | CCG AAT CGT ATC AA/3I ABkF Q/ |
| 137 | ds799 | up | 326 | TCCGGGTTCGGCT TACCCCGCCGCGT TTTGCGCACGGTG TCGGACAATTTGT CATAACTGCGAC ACAGGAGTTTGC GATGACCCTGAA TATGATGCTCGA | 360 | AGCGTCAGGTAC CGGTCATGATTC ACCGTGCGATTCT CGGTTCCCTGGA GCGCTTCATTGGC ATCCTGACCGAA GAGTTCGCTGGC TTCTTCCCAACCTG | 394 | 5'-TCCGGGTTCGGC TTACCCCGCCGC GTTTTGCGCACG GTGTCGGACAAT TTGTCATAACTGC GACACAGGAGTT TGCGATGACCCT GAATATGATGCT CGA/ AGCGTCAGGTAC CGGTCATGATTC ACCGTGCGATTC TCGGTTCCCTGG AGCGCTTCATTG GCATCCTGACCG AAGAGTTCGCTG GCTTCTTCCCAAC CTG-3' | disrupted nifL gene/ PinfC | N/A | N/A | N/A |
| 137 | ds809 | N/A | 327 | ATCGCAGCGTCTT TGAATATTTCCGT CGCCAGGCGCTG GCTGCCGAGCCG TTCTGGCTGCATA GTGGAAAACGAT AATTTCAGGCCA GGGAGCCCTTATG | 361 | GCGCTGAAGCAC CTGATCACGCTCT GCGCGGCGTCGC CGATGGTCGCCA GCCAGCTGGCGC GCCACCCGCTGC TGCTGGATGAGC TGCTGGATCCCA ACA | 395 | 5'-ATCGCAGCGTCT TTGAATATTTCCG TCGCCAGGCGCT GGCTGCCGAGCC GTTCTGGCTGCAT AGTGGAAAACGA TAATTTCAGGCC AGGGAGCCCTTA TG/ GCGCTGAAGCAC CTGATCACGCTCT GCGCGGCGTCGC CGATGGTCGCCA GCCAGCTGGCGC GCCACCCGCTGC TGCTGGATGAGC TGCTGGATCCCA ACA-3' | 5' UTR and ATG/ truncated glnE gene | SEQ ID NO: 420 GAGC CGTT CTGG CTGC ATAG | SEQ ID NO: 421 GCCG TCGG CTGA TAGA GG | SEQ ID NO: 422/ 56-FAM/ TTAT GGC GC/Z EN/T GAA GCA CCTG ATC A/3IA BkFQ/ |
| 137 | ds843 | up | 328 | TCCGGGTTCGGCT TACCCCGCCGCGT TTTGCGCACGGTG TCGGACAATTTGT CATAACTGCGAC ACAGGAGTTTGC GATGACCCTGAA TATGATGCTCGA | 362 | GCCCGCTGACCG ACCAGAACTTCC ACCTTGGACTCG GCTATACCCTTGG CGTGACGGCGCG CGATAACTGGGA CTACATCCCCATT CCGGTGATCTTACC | 396 | 5'-TCCGGGTTCGGC TTACCCCGCCGC GTTTTGCGCACG GTGTCGGACAAT TTGTCATAACTGC GACACAGGAGTT TGCGATGACCCT GAATATGATGCT CGA/ GCCCGCTGACCG ACCAGAACTTCC ACCTTGGACTCG GCTATACCCTTG GCGTGACGGCGC GCGATAACTGGG ACTACATCCCCA TTCCGGTGATCTT ACC-3' | disrupted nifL gene/ Prm1.2 | N/A | N/A | N/A |
| 137 | ds843 | down | 329 | TCACTTTTTAGCA AAGTTGCACTGG ACAAAAGGTACC | 363 | GCCATTGAGCTG GCTTCCCGACCG CAGGGCGGCACC | 397 | 5'-TCACTTTTCAGCA AAGTTGCACTGG | Prm1.2/ disrupted nifL gene | N/A | N/A | N/A |

TABLE E-continued

Microbial Detection

| base CI | Junction Name | up/down stream junction | SEQ ID NO | 100 bp upstream of junction | SEQ ID NO | 100 bp downstream of junction | SEQ ID NO | Junction SEQ "/" indicating junction | Junction des. | F primer SEQ | R primer SEQ | Probe SEQ |
|---|---|---|---|---|---|---|---|---|---|---|---|---|
| | | | | ACAATTGGTGTACTGATACTCGACACAGCATTAGTGTCGATTTTTCATATAAAGGTAATTTTG | | TGCCTGACCCTGCGTTTCCCGCTGTTTAACACCCTGACCGGAGGTGAAGCATGATCCCTGAATC | | 5'-ACAAAAGGTACCACAATTGGTGTACTGATACTCGACACAGCATTAGTGTCGATTTTTCATATAAAGGTAATTTTG/GCCATTGAGCTGCTTCCCGACCGCAGGGCGGCACCTGCCTGACCCTGCGTTTCCCGCTGTTTAACACCCTGACCGGAGGTGAAGCATGATCCCTGAATC-3' | | | | |
| 137 | ds853 | up | 330 | TCCGGGTTCGGCTTACCCCGCCGCGTTTTGCGCACGGTGTCGGACAATTTGTCATAACTGCGACACAGGAGTTTGCGATGACCCTGAATATGATGCTCGA | 364 | GCTAAAGTTCTCGGCTAATCGCTGATAACATTGACGCAATGCGCAATAAAAGGGCATCATTTGATGCCCTTTTTGCACGCTTTCATACCAGAACCTGGC | 398 | 5'-TCCGGGTTCGGCTTACCCCGCCGCGTTTTGCGCACGGTGTCGGACAATTTGTCATAACTGCGACACAGGAGTTTGCGATGACCCTGAATATGATGCTCGA/GCTAAAGTTCTCGGCTAATCGCTGATAACATTDGACGCAATGCGCAATAAAAGGGCATCATTTGATGCCCTTTTTGCACGCTTTCATACCAGAACCTGGC-3' | disrupted nifL gene/ Prm6.2 | N/A | N/A | N/A |
| 137 | ds853 | down | 331 | GTTCTCCTTTGCAATAGCAGGGAAGAGGCGCCAGAACCGCCAGCGTTGAAGCAGTTTGAACGCGTTCAGTGTATAATCCGAAACTTAATTTCGGTTTGGA | 365 | GCCATTGAGCTGCTTCCCGACCGCAGGGCGGCACCTGCCTGACCCTGCGTTTCCCGCTGTTTAACACCCTGACCGGAGGTGAAGCATGATCCCTGAATC | 399 | 5'-GTTCTCCTTTGCAATAGCAGGGAAGAGGCGCCAGAACCGCCAGCGTTGAAGCAGTTTGAACGCGTTCAGTGTATAATCCGAAACTTAATTTCGGTTTGGA/GCCATTGAGCTGCTTCCCGACCGCAGGGCGGCACCTGCCTGACCCTGCGTTTCCCGCTGTTTAACACCCTGACCGGAGGTGAAGCATGATCCCTGAATC-3' | Prm6.2/ disrupted nifL gene | N/A | N/A | N/A |
| 137 | ds857 | up | 332 | TCCGGGTTCGGCTTACCCCGCCGCGTTTTGCGCACGGTGTCGGACAATTTGTCATAACTGCGACACAGGAGTTTGCGATGACCCTGAATATGATGCTCGA | 366 | CGCCGTCCTCGCAGTACCATTGCAACCGACTTTACAGCAAGAAGTGATTCTGGCACGCATGGAACAAATTCTTGCCAGTCGGGCTTTATCCGATGACGAA | 400 | 5'-TCCGGGTTCGGCTTACCCCGCCGCGTTTTGCGCACGGTGTCGGACAATTTGTCATAACTGCGACACAGGAGTTTGCGATGACCCTGAATATGATGCTCGA/CGCCGTCCTCGCACTACCATTGCAACCGACTTTACAGCAAGAAGTGATTCTGGCACGCAT | disrupted nifL gene/ Prm8.2 | N/A | N/A | N/A |

TABLE E-continued

Microbial Detection

| base CI | Junction Name | up/down stream junction | SEQ ID NO | 100 bp upstream of junction | SEQ ID NO | 100 bp downstream of junction | SEQ ID NO | Junction SEQ "/" indicating junction | Junction des. | F primer SEQ | R primer SEQ | Probe SEQ |
|---|---|---|---|---|---|---|---|---|---|---|---|---|
| | | | | | | | | GGAACAAATTCT TGCCAGTCGGGC TTTATCCGATGAC GAA-3' | | | | |
| 137 | ds857 | down | 333 | GATATGCCTGAA GTATTCAATTACT TAGGCATTTACTT AACGCAGGCAGG CAATTTTGATGCT GCCTATGAAGCG TTTGATTCTGTAC TTGAGCTTGATC | 367 | GCCATTGAGCTG GCTTCCCGACCG CAGGGCGGCACC TGCCTGACCCTGC GTTTCCCGCTGTT TAACACCCTGAC CGGAGGTGAAGC ATGATCCCTGAA TC | 401 | 5'-GATATGCCTGAA GTATTCAATTACT TAGGCATTTACTT AACGCAGGCAGG CAATTTTGATGCT GCCTATGAAGCG TTTGATTCTGTAC TTGAGCTTGATC/ GCCATTGAGCTG GCTTCCCGACCG CAGGGCGGCACC TGCCTGACCCTG CGTTTCCCGCTGT TAACACCCTGA CCGGAGGTGAAG CATGATCCCTGA ATC-3' | Prm8.2/ disrupted nifL gene | N/A | N/A | N/A |
| 63 | ds908 | down | 334 | TGGTATTGTCAGT CTGAATGAAGCT CTTGAAAAAGCT GAGGAAGCGGGC GTCGATTTAGTAG AAATCAGTCCGA ATGCCGAGCCGC CAGTTTGTCGAATC | 368 | TCTTTAGATCTCT CGGTCCGCCCTG ATGGCGGCACCT GCTGACGTTAC GCCTGCCGGTAC AGCAGGTTATCA CCGGAGGCTTAA AATGACCCAGTT ACC | 402 | 5'-TGGTATTGTCAGT CTGAATGAAGCT CTTGAAAAAGCT GAGGAAGCGGGC GTCGATTTAGTA GAAATCAGTCCG AATGCCGAGCCG CCAGTTTGTCGA ATC/ TCTTTAGATCTCT CGGTCCGCCCTG ATGGCGGCACCT GCTGACGTTAC GCCTGCCGGTAC AGCAGGTTATCA CCGGAGGCTTAA AATGACCCAGTT ACC-3' | PinfC/ disrupted nifL gene | SEQ ID NO: 423 GGAA AACG AGTT CAAC CGGC | SEQ ID NO: 424 GGGC GGAC CGAG AGAT CTAA | N/A |
| 63 | ds908 | up | 335 | TGCAAATTGCAC GGTTATTCCGGGT GAGTATATGTGT GATTTGGGTTCCG GCATTGCGCAAT AAAGGGGAGAAA GACATGAGCATC ACGGCGTTATCA GC | 369 | TGAATATCACTG ACTCACAAGCTA CCTATGTCGAAG AATTAACTAAAA AACTGCAAGATG CAGGCATTCGCG TTAAAGCCGACT TGAGAAATGAGA AGAT | 403 | 5'-TGCAAATTGCAC GGTFATTCCGGG TGAGTATATGTG TGATTTGGGTTCC GGCATTGCGCAA TAAAGGGGAGAA AGACATGAGCAT CACGGCGTTATC AGC/ TGAATATCACTG ACTCACAAGCTA CCTATGTCGAAG AATTAACTAAAA AACTGCAAGATG CAGGCATTCGCG TTAAAGCCGACT TGAGAAATGAGA AGAT-3' | disrupted nifL gene/ PinfC | N/A | N/A | N/A |
| 910 | ds960 | up | 336 | TCAGGGCTGCGG ATGTCGGGCGTTT CACAACACAAAA TGTTGTAAATGCG ACACAGCCGGGC CTGAAACCAGGA GCGTGTGATGAC | 370 | CTGGGGTCACTG GAGCGCTTTATC GGCATCCTGACC GAAGAATTTGCC GGTTTCTTCCCGA CCTGGCTGGCCC CTGTTCAGGTTGT | 404 | 5'-TCAGGGCTGCGG ATGTCGGGCGTT TCACAACACAAA ATGTTGTAAATG CGACACAGCCGG GCCTGAAACCAG | disrupted nifL gene/ PinfC | N/A | N/A | N/A |

TABLE E-continued

Microbial Detection

| base CI | Junction Name | up/down stream junction | SEQ ID NO | 100 bp upstream of junction | SEQ ID NO | 100 bp downstream of junction | SEQ ID NO | Junction SEQ "/" indicating junction | Junction des. | F primer SEQ | R primer SEQ | Probe SEQ |
|---|---|---|---|---|---|---|---|---|---|---|---|---|
| | | | | CTTTAATATGATGC | | GGTGATGAATAT CA | | GAGCGTGTGATG ACCTTTAATATG ATGC/ CTGGGGTCACTG GAGCGCTTTATC GGCATCCTGACC GAAGAATTTGCC GGTTTCTTCCCGA CCTGGCTGGCCC CTGTTCAGGTTGT GGTGATGAATAT CA-3' | | | | |
| 910 | ds960 | down | 337 | CGGAAAACGAGT TCAAACGGCACG TCCGAATCGTATC AATGGCGAGATT CGCGCCCAGGAA GTTCGCTTAACTG GTCTGGAAGGTG AGCAGCTGGGTA TT | 371 | GCAATAGAACTA ACTACCCGCCCT GAAGGCGGTACC TGCCTGACCCTGC GATTCCCGTTATT TCATTCACTGACC GGAGGCCCACGA TGACCCAGCGACC | 405 | 5'-CGGAAAACGAGT TCAAACGGCACG TCCGAATCGTAT CAATGGCGAGAT TCGCGCCCAGGA AGTTCGCTTAACT GGTCTGGAAGGT GAGCAGCTGGGT ATT/ GCAATAGAACTA ACTACCCGCCCT GAAGGCGGTACC TGCCTGACCCTG CGATTCCCGTTAT TTCATTCACTGAC CGGAGGCCCACG ATGACCCAGCGA CC-3' | PinfC/ disrupted nifL gene | N/A | N/A | N/A |

TABLE F

Engineered Non-intergeneric Microbes

| Strain Name | Genotype | SEQ ID NO |
|---|---|---|
| CI006 | 16S rDNA - contig 5 | 62 |
| CI006 | 16S rDNA - contig 8 | 63 |
| CI019 | 16S rDNA | 64 |
| CI006 | nifH | 65 |
| CI006 | nifD | 66 |
| CI006 | nifK | 67 |
| CI006 | nifL | 68 |
| CI006 | nifA | 69 |
| CI019 | nifH | 70 |
| CI019 | nifD | 71 |
| CI019 | nifK | 72 |
| CI019 | nifL | 73 |
| CI019 | nifA | 74 |
| CI006 | Prm5 with 500 bp flanking regions | 75 |
| CI006 | nifLA operon - upstream intergenic region plus nifL and nifA CDSs | 76 |
| CI006 | nifL (Amino Acid) | 77 |
| CI006 | nifA (Amino Acid) | 78 |
| CI006 | glnE | 79 |
| CI006 | glnE_KO1 | 80 |
| CI006 | glnE (Amino Acid) | 81 |
| CI006 | glnE_KO1 (Amino Acid) | 82 |
| CI006 | GlnE ATase domain (Amino Acid) | 83 |
| CM029 | Prm5 inserted into nifL region | 84 |

TABLE G

Engineered Non-intergeneric Microbes

| Strain | Strain ID | SEQ ID NO | Genotype | Description | Associated Novel Junction If Applicable |
|---|---|---|---|---|---|
| CI63; CI063 | 63 | SEQ ID NO 85 | 16S | N/A | N/A |
| CI63; CI063 | 63 | SEQ ID NO 86 | nifH | N/A | N/A |

TABLE G-continued

Engineered Non-intergeneric Microbes

| Strain | Strain ID | SEQ ID NO | Genotype | Description | Associated Novel Junction If Applicable |
|---|---|---|---|---|---|
| CI63; CI063 | 63 | SEQ ID NO 87 | nifD1 | 1 of 2 unique genes annotated as nifD in 63 genome | N/A |
| CI63; CI063 | 63 | SEQ ID NO 88 | nifD2 | 2 of 2 unique genes annotated as nifD in 63 genome | N/A |
| CI63; CI063 | 63 | SEQ ID NO 89 | nifK1 | 1 of 2 unique genes annotated as nifK in 63 genome | N/A |
| CI63; CI063 | 63 | SEQ ID NO 90 | nifK2 | 2 of 2 unique genes annotated as nifK in 63 genome | N/A |
| CI63; CI063 | 63 | SEQ ID NO 91 | nifL | N/A | N/A |
| CI63; CI063 | 63 | SEQ ID NO 92 | nifA | N/A | N/A |
| CI63; CI063 | 63 | SEQ ID NO 93 | glnE | N/A | N/A |
| CI63; CI063 | 63 | SEQ ID NO 94 | amtB | N/A | N/A |
| CI63; CI063 | 63 | SEQ ID NO 95 | PinfC | 500 bp immediately upstrea of the ATG start codon of the infC gene | N/A |
| CI137 | 137 | SEQ ID NO 96 | 16S | N/A | N/A |
| CI137 | 137 | SEQ ID NO 97 | nifH1 | 1 of 2 unique genes annotated as nifH in 137 genome | N/A |
| CI137 | 137 | SEQ ID NO 98 | nifH2 | 2 of 2 unique genes annotated as nifH in 137 genome | N/A |
| CI137 | 137 | SEQ ID NO 99 | nifD1 | 1 of 2 unique genes annotated as nifD in 137 genome | N/A |
| CI137 | 137 | SEQ ID NO 100 | nifD2 | 2 of 2 unique genes annotated as nifD in 137 genome | N/A |
| CI137 | 137 | SEQ ID NO 101 | nifK1 | 1 of 2 unique genes annotated as nifK in 137 genome | N/A |
| CI137 | 137 | SEQ ID NO 102 | nifK2 | 2 of 2 unique genes annotated as nifK in 137 genome | N/A |
| CI137 | 137 | SEQ ID NO 103 | nifL | N/A | N/A |
| CI137 | 137 | SEQ ID NO 104 | nifA | N/A | N/A |
| CI137 | 137 | SEQ ID NO 105 | glnE | N/A | N/A |
| CI137 | 137 | SEQ ID NO 106 | PinfC | 500 bp immediately upstream of the TTG start codon of infC | N/A |
| CI137 | 137 | SEQ ID NO 107 | amtB | N/A | N/A |
| CI137 | 137 | SEQ ID NO 108 | Prm8.2 | internal promoter located in nfpI gene; 299 bp starting at 81 bp after the A of the ATG of the nlpI gene | N/A |
| CI137 | 137 | SEQ ID NO 109 | Prm6.2 | 300 bp upstream of the secE gene starting at 57 bp upstream of the A of the ATG of secE | N/A |

TABLE G-continued

Engineered Non-intergeneric Microbes

| Strain | Strain ID | SEQ ID NO | Genotype | Description | Associated Novel Junction If Applicable |
|---|---|---|---|---|---|
| CI137 | 137 | SEQ ID No 110 | Prm1.2 | 400 bp immediately upstream of the ATG of cspE gene | N/A |
| none | 728 | SEQ ID No 111 | 16S | N/A | N/A |
| none | 728 | SEQ ID NO 112 | nifH | N/A | N/A |
| none | 728 | SEQ ID NO 113 | nifD1 | 1 of 2 unique genes annotated as nifD in 728 genome | N/A |
| none | 728 | SEQ ID NO 114 | nifD2 | 2 of 2 unique genes annotated as nifD in 728 genome | N/A |
| none | 728 | SEQ ID NO 115 | nifK1 | 1 of 2 unique genes annotated as nifK in 728 genome | N/A |
| none | 728 | SEQ ID NO 116 | nifK2 | 2 of 2 unique genes annotated as nifK in 728 genome | N/A |
| none | 728 | SEQ ID NO 117 | nifL | N/A | N/A |
| none | 728 | SEQ ID NO 118 | nifA | N/A | N/A |
| none | 728 | SEQ ID NO 119 | glnE | N/A | N/A |
| none | 728 | SEQ ID NO 120 | amtB | N/A | N/A |
| none | 850 | SEQ ID NO 121 | 16S | N/A | N/A |
| none | 852 | SEQ ID NO 122 | 16S | N/A | N/A |
| none | 853 | SEQ ID NO 123 | 16S | N/A | N/A |
| none | 910 | SEQ ID NO 124 | 16S | N/A | N/A |
| none | 910 | SEQ ID NO 125 | nifH | N/A | N/A |
| none | 910 | SEQ ID NO 126 | Dinitrogenase iron-molybdenum cofactor CDS | N/A | N/A |
| none | 910 | SEQ ID NO 127 | nifD1 | N/A | N/A |
| none | 910 | SEQ ID NO 128 | nifD2 | N/A | N/A |
| none | 910 | SEQ ID NO 129 | nifK1 | N/A | N/A |
| none | 910 | SEQ ID NO 130 | nifK2 | N/A | N/A |
| none | 910 | SEQ ID NO 131 | nifL | N/A | N/A |
| none | 910 | SEQ ID NO 132 | nifA | N/A | N/A |
| none | 910 | SEQ ID NO 133 | glnE | N/A | N/A |

TABLE G-continued

Engineered Non-intergeneric Microbes

| Strain | Strain ID | SEQ ID NO | Genotype | Description | Associated Novel Junction If Applicable |
|---|---|---|---|---|---|
| none | 910 | SEQ ID NO 134 | amtB | N/A | N/A |
| none | 910 | SEQ ID NO 135 | PinfC | 498 bp immediately upstream of the ATG of the infC gene | N/A |
| none | 1021 | SEQ ID NO 136 | 16S | N/A | N/A |
| none | 1021 | SEQ ID NO 137 | nifH | N/A | N/A |
| none | 1021 | SEQ ID NO 138 | nifD1 | 1 of 2 unique genes annotated as nifD in 910 genome | N/A |
| none | 1021 | SEQ ID NO 139 | nifD2 | 2 of 2 unique genes annotated as nifD in 910 genome | N/A |
| none | 1021 | SEQ ID NO 140 | nifK1 | 1 of 2 unique genes annotated as nifK in 910 genome | N/A |
| none | 1021 | SEQ ID NO 141 | nifK2 | 2 of 2 unique genes annotated as nifK in 910 genome | N/A |
| none | 1021 | SEQ ID NO 142 | nifL | N/A | N/A |
| none | 1021 | SEQ ID NO 143 | nifA | N/A | N/A |
| none | 1021 | SEQ ID NO 144 | glnE | N/A | N/A |
| none | 1021 | SEQ ID NO 145 | amtB | N/A | N/A |
| none | 1021 | SEQ ID NO 146 | PinfC | 500 bp immediately upstream of the ATG start codon of the infC gene | N/A |
| none | 1021 | SEQ ID NO 147 | Prm1 | 348 bp includes the 319 bp immediately upstream of the ATG start codon of the lpp gene and the first 29 bp of the lpp gene | N/A |
| none | 1021 | SEQ ID NO 148 | Prm7 | 339 bp upstream of the sspA gene, ending at 46 bp upstream of the ATG of the sspA gene | N/A |
| none | 1113 | SEQ ID NO 149 | 16S | N/A | N/A |
| none | 1113 | SEQ ID NO 150 | nifH | N/A | N/A |
| none | 1113 | SEQ ID NO 151 | nifD1 | 1 of 2 unique genes annotated as nifD in 1113 genome | N/A |
| none | 1113 | SEQ ID NO 152 | nifD2 | 2 of 2 unique genes annotated as nifD in 1113 genome | N/A |
| none | 1113 | SEQ ID NO 153 | nifK | N/A | N/A |
| none | 1113 | SEQ ID NO 154 | nifL | N/A | N/A |
| none | 1113 | SEQ ID NO 155 | nifA partial gene | due to a gap in the sequence assembly, we can only identify a partial gene from the 1113 genome | N/A |
| none | 1113 | SEQ ID NO 156 | glnE | N/A | N/A |

TABLE G-continued

Engineered Non-intergeneric Microbes

| Strain | Strain ID | SEQ ID NO | Genotype | Description | Associated Novel Junction If Applicable |
|---|---|---|---|---|---|
| none | 1116 | SEQ ID NO 157 | 16S | | N/A |
| none | 1116 | SEQ ID NO 158 | nifH | | N/A |
| none | 1116 | SEQ ID NO 159 | nifD1 | 1 of 2 unique genes annotated as nifD in 1116 genome | N/A |
| none | 1116 | SEQ ID NO 160 | nifD2 | 2 of 2 unique genes annotated as nifD in 1116 genome | N/A |
| none | 1116 | SEQ ID NO 161 | nifK1 | 1 of 2 unique genes annotated as nifK in 1116 genome | N/A |
| none | 1116 | SEQ ID NO 162 | nifK2 | 2 of 2 unique genes annotated as nifK in 1116 genome | N/A |
| none | 1116 | SEQ ID NO 163 | nifL | N/A | N/A |
| none | 1116 | SEQ ID NO 164 | nifA | N/A | N/A |
| none | 1116 | SEQ ID NO 165 | glnE | N/A | N/A |
| none | 1116 | SEQ ID NO 166 | amtB | N/A | N/A |
| none | 1293 | SEQ ID NO 167 | 16S | N/A | N/A |
| none | 1293 | SEQ ID NO 168 | nifH | N/A | N/A |
| none | 1293 | SEQ ID NO 169 | nifD1 | 1 of 2 unique genes annotated as nifD in 1293 genome | N/A |
| none | 1293 | SEQ ID NO 170 | nifD2 | 2 of 2 unique genes annotated as nifD in 1293 genome | N/A |
| none | 1293 | SEQ ID NO 171 | nifK | 1 of 2 unique genes annotated as nifK in 1293 genome | N/A |
| none | 1293 | SEQ ID NO 172 | nifK1 | 2 of 2 unique genes annotated as nifK in 1293 genome | N/A |
| none | 1293 | SEQ ID NO 173 | nifA | N/A | N/A |
| none | 1293 | SEQ ID NO 174 | glnE | N/A | N/A |
| none | 1293 | SEQ ID NO 175 | amtB1 | 1 of 2 unique genes annotated as amtB in 1293 genome | N/A |
| none | 1293 | SEQ ID NO 176 | amtB2 | 2 of 2 unique genes annotated as amtB in 1293 genome | N/A |
| none | 1021-1612 | SEQ ID NO 177 | ΔnifL::PinfC | starting at 24 bp after the A of the ATG start codon, 1375 bp of nifL, have been deleted and replaced with the 1021 PinfC promoter sequence | ds1131 |
| none | 1021-1612 | SEQ ID NO 178 | ΔnifL::PinfC with 500 bp flank | starting at 24 bp after the A of the ATG start codon, 1375 bp of nifL, have been deleted and replaced with the 1021 PinfC promoter sequence; 500 bp flanking the nifL gene upstream and downstream are included | ds1131 |

TABLE G-continued

Engineered Non-intergeneric Microbes

| Strain | Strain ID | SEQ ID NO | Genotype | Description | Associated Novel Junction If Applicable |
|---|---|---|---|---|---|
| none | 1021-1612 | SEQ ID NO 179 | glnEΔAR-2 | glnE gene with 1673 bp immediately downstream of the ATG start codon deleted, resulting in a truncated glnE protein lacking the adenylyl-removing (AR) domain | ds1133 |
| none | 1021-1612 | SEQ ID NO 180 | glnEΔAR-2 with 500 bp flank | glnE gene with 1673 bp immediately downstream of the ATG start codon deleted, resulting in a truncated glnE protein lacking the adenylyl-removing (AR) domain; 500 bp flanking the glnE gene upstream and downstream are included | ds1133 |
| none | 1021-1615 | SEQ ID NO 181 | ΔnifL::Prm1 | starting at 24 bp after the A of the ATG start codon, 1375 bp of nifL have been deleted and replaced with the 1021 Prm1 promoter sequence | ds1145 |
| none | 1021-1615 | SEQ ID NO 182 | ΔnifL:Prm1 with 500 bp flank | starting at 24 bp after the A of the ATG start codon, 1375 bp of nifL have been deleted and replaced with the 1021 rm1 promoter sequence; 500 bp flanking the nifL gene upstream and downstream are included | ds1145 |
| none | 1021-1615 | SEQ ID NO 183 | glnEΔAR-2 | glnE gene with 1673 bp immediately downstream of the ATG start codon deleted, resulting in a truncated glnE protein lacking the adenylyl-removing (AR) domain | ds1133 |
| none | 1021-1615 | SEQ ID NO 184 | glnEΔAR-2 with 500 bp flank | glnE gene with 1673 bp immediately downstream of the ATG start codon deleted, resulting in a truncated glnE protein lacking the adenylyl-removing (AR) domain; 500 bp flanking the glnE gene upstream and downstream are included | ds1133 |
| none | 1021-1619 | SEQ ID NO 185 | ΔnifL::Prm1 | starting at 24 bp after the A of the ATG start codon, 1375 bp of nifL have been deleted and replaced with the 1021 Prm1 promoter sequence | ds1145 |
| none | 1021-1619 | SEQ ID NO 186 | ΔnifL::Prm1 with 500 bp flank | starting at 24 bp after the A of the ATG start codon, 1375 bp of nifL have been deleted and replaced with the 1021 rm1 promoter sequence; 500 bp flanking the nifL gene upstream and downstream are included | ds1145 |
| none | 1021-1623 | SEQ ID NO 187 | glnEΔAR-2 | glnE gene with 1673 bp immediately downstream of the ATG start codon deleted, resulting in a truncated glnE, protein lacking the adenylyl-removing (AR) domain | ds1133 |
| none | 1021-1623 | SEQ ID NO 188 | glnEΔAR-2 with 500 bp flank | glnE gene with 1673 bp immediately downstream of the ATG start codon deleted, resulting in a truncated glnE protein lacking the adenylyl-removing (AR) domain; 500 bp flanking the glnE gene upstream and downstream are included | ds1133 |
| none | 1021-1623 | SEQ ID NO 189 | ΔnifL::Prm7 | starting at 24 bp after the A of the ATG start codon, 1375 bp of nifL have been deleted and replaced with the 1021 Prm7 promoter sequence | ds1148 |
| none | 1021-1623 | SEQ ID NO 190 | ΔnifL::Prm7 with 500 bp flank | starting at 24 bp after the A of the ATG start codon, 1375 bp of nifL have been | ds1148 |

TABLE G-continued

Engineered Non-intergeneric Microbes

| Strain | Strain ID | SEQ ID NO | Genotype | Description | Associated Novel Junction If Applicable |
|---|---|---|---|---|---|
| | | | | deleted and replaced with the 1021 rm7 promoter sequence; 500 bp flanking the nifL gene upstream and downstream are included | |
| none | 137-1034 | SEQ ID NO 191 | glnEΔAR-2 | glnE gene with 1290 bp immediately downstream of the ATG start codon deleted, resulting in a truncated glnE protein lacking the adenylyl-removing (AR) domain | ds809 |
| none | 137-1034 | SEQ ID NO 192 | glnEΔAR-2 with 500 bp flank | glnE gene with 1290 bp immediately downstream of the ATG start codon deleted, resulting in a truncated glnE protein lacking the adenylyl-removing (AR) domain; 500 bp flanking the glnE gene upstream and downstream are included | ds809 |
| none | 137-1036 | SEQ ID NO 193 | ΔnifL::PinfC | starting at 24 bp after the A of the ATG start codon, 1372 bp of nifL have been deleted and replaced with the 137 PinfC promoter sequence | ds799 |
| none | 137-1036 | SEQ ID NO 194 | ΔnifL::PinfC with 500 bp flank | starting at 24 bp after the A of the ATG start codon, 1372 bp of nifL have been deleted and replaced with the 137 PinfC promoter sequence; 500 bp flanking the nifL gene upstream and downstream are included | ds799 |
| none | 137-1314 | SEQ ID NO 195 | glnEΔAR-2 36 bp deletion | glnE gene with 1290 bp immediately downstream of the ATG start codon deleted AND 36 bp deleted beginning at 1472 bp downstream of the start codon, resulting in a truncated glnE protein lacking the adenylyl-removing (AR) domain | none |
| none | 137-1314 | SEQ ID NO 196 | glnEΔAR-2 36 bp deletion | glnE gene with 1290 bp immediately downstream of the ATG start codon deleted AND 36 bp deleted beginning at 1472 bp downstream of the start codon, resulting in a truncated glnE protein lacking the adenylyl-removing (AR) domain; 500 bp flanking the nifL gene upstream and downstream are included | none |
| none | 137-1314 | SEQ ID NO 197 | ΔnifL::Prm8.2 | starting at 24 bp after the A of the ATG start codon, 1372 bp of nifL have been deleted and replaced with the 137 Prm8.2 promotor sequence | ds857 |
| none | 137-1314 | SEQ ID NO 198 | ΔnifL::Prm8.2 with 500 bp flank | starting at 24 bp after the A of the ATG start codon, 1372 bp of nifL have been deleted and replaced with the 137 Prm8.2 promoter sequence; 500 bp flanking the nifL gene upstream and downstream are included | ds857 |
| none | 137-1329 | SEQ ID NO 199 | glnEΔAR-2 36 bp deletion | glnE gene with 1290 bp immediately downstream of the ATG start codon deleted AND 36 bp deleted beginning at 1472 bp downstream of the start codon. resulting in a truncated gluE protein lacking the adenylyl-removing (AR) domain | none |
| none | 137-1329 | SEQ ID NO 200 | glnEΔAR-2 36 bp deletion | glnE gene with 1290 bp immediately downstream of the ATG start codon deleted AND 36 bp deleted beginning at 1472 bp downstream of the start codon, resulting in a truncated glnE protein | none |

TABLE G-continued

Engineered Non-intergeneric Microbes

| Strain | Strain ID | SEQ ID NO | Genotype | Description | Associated Novel Junction If Applicable |
|---|---|---|---|---|---|
| | | | | lacking the adenylyl-removing (AR) domain; 500 bp flanking the nifL gene upstream and downstream are included | |
| none | 137-1329 | SEQ ID NO 201 | ΔnifL::Prm6.2 | starting at 24 bp after the A of the ATG start codon, 1372 bp of nifL have been deleted and replaced with the 137 Prm6.2 promoter sequence | ds853 |
| none | 137-1329 | SEQ ID NO 202 | ΔnifL::Prm6.2 500 bp flank | starting at 24 bp after the A of the ATG start codon, 1372 bp of nifL have been deleted and replaced with the 137 Prm6.2 promoter sequence; 500 bp flanking the nifL gene upstream and downstream are included | ds853 |
| none | 137-1382 | SEQ ID NO 203 | ΔnifL::Prm1.2 | starting at 24 bp after the A of the ATG start codon, 1372 bp of nifL have been deleted and replaced with the 137 Prm1.2 promoter sequence | ds843 |
| none | 137-1382 | SEQ ID NO 204 | ΔnifL::Prm1.2 with 500 bp flank | starting at 24 bp after the A of the ATG start codon, 1372 bp of nifL have been deleted and replaced with the 137 Prm1.2 promoter sequence; 500 bp flanking the nifL gene upstream and downstream are included | ds843 |
| none | 137-1382 | SEQ ID NO 205 | glnEΔAR-2 36 bp deletion | glnE gene with 1290 bp immediately downstream of the ATG start codon deleted AND 36 bp deleted beginning at 1472 bp downstream of the start codon, resulting in a truncated glnE protein lacking the adenylyl-removing (AR) domain | none |
| none | 137-1382 | SEQ ID NO 206 | glnEΔAR-2 36 bp deletion | glnE gene with 1290 bp immediately downstream of the ATG start codon deleted AND 36 bp deleted beginning at 1472 bp downstream of the start codon, resulting in a truncated glnE protein lacking the adenylyl-removing (AR) domain; 500 bp flanking the nifL gene upstream and downstream are included | none |
| none | 137-1586 | SEQ ID NO 207 | ΔnifL::PinfC | starting at 24 bp after the A of the ATG start codon, 1372 bp of nifL have been deleted and replaced with the 137 PinfC promoter sequence | ds799 |
| none | 137-1586 | SEQ ID NO 208 | ΔnifL::PinfC with 500 bp flank | starting at 24 bp after the A of the ATG start codon, 1372 bp of nifL have been deleted and replaced with the 137 PinfC promoter sequence; 500 bp flanking the nifL gene upstream and downstream are included | ds799 |
| none | 137-1586 | SEQ ID NO 209 | glnEΔAR-2 | glnE gene with 1290 bp immediately downstream of the ATG start codon deleted, resulting in a truncated glnE protein lacking the adenylyl-removing (AR) domain | ds809 |
| none | 137-1586 | SEQ ID NO 210 | glnEΔAR-2 with 500 bp flank | glnE gene with 1290 bp immediately downstream of the ATG start codon deleted, resulting in a truncated glnE protein lacking the adenylyl-removing (AR) domain; 500 bp flanking the glnE gene upstream and downstream are included | ds809 |
| none | 19-594 | SEQ ID NO 211 | glnEΔAR-2 | glnE gene with 1650 bp immediately downstream of the ATG start codon | ds34 |

TABLE G-continued

Engineered Non-intergeneric Microbes

| Strain | Strain ID | SEQ ID NO | Genotype | Description | Associated Novel Junction If Applicable |
|---|---|---|---|---|---|
| | | | | deleted, resulting in a truncated glnE protein lacking the adenylyl-removing (AR) domain | |
| none | 19-594 | SEQ ID NO 212 | glnEΔAR-2 with 500 bp flank | glnE gene with 1650 bp immediately downstream of the ATG start codon deleted, resulting in a truncated glnE protein lacking the adenylyl-removing (AR) domain; 500 bp flanking the glnE gene upstream and downstream are included | ds34 |
| none | 19-594 | SEQ ID NO 213 | ΔnifL::Prm6.1 | starting at 221 bp after the A of the ATG start codon, 845 bp of nifL have been deleted and replaced with the CI019 Prm6.1 promoter sequence | ds180 |
| none | 19-594 | SEQ ID NO 214 | ΔnifL::Prm6.1 with 500 bp flank | starting at 221 bp after the A of the ATG start codon, 845 bp of nifL have been deleted and replaced with the CI019 Prm6.1 promoter sequence; 500 bp flanking the nifL gene upstream and downstream are included | ds180 |
| none | 19-714 | SEQ ID NO 215 | ΔnifL::Prm6.1 | starting at 221 bp after the A of the ATG start codon, 845 bp of nifL have been deleted and replaced with the CI019 Prm6.1 promoter sequence | ds180 |
| none | 19-714 | SEQ ID NO 216 | ΔnifL::Prm6.1 with 500 bp flank | starting at 221 bp after the A of the ATG start codon, 845 bp of nifL have been deleted and replaced with the CI019 Prm6.1promoter sequence; 500 bp flanking the nifL gene upstream and downstream are included | ds180 |
| none | 19-715 | SEQ ID NO 217 | ΔnifL::Prm7.1 | starting at 221 bp after the A of the ATG start codon, 845 bp of nifL have been deleted and replaced with the CI019 Prm7.1 promoter sequence | ds181 |
| none | 19-715 | SEQ ID NO 218 | ΔnifL::Prm7.1 with 500 bp flank | starting at 221 bp after the A of the ATG start codon, 845 bp of nifL have been deleted and replaced with the CI019 Prm76.1promoter sequence; 500 bp flanking the nifL gene upstream and downstream are included | ds181 |
| 19-713 | 19-750 | SEQ ID NO 219 | ΔnifL::Prm1.2 | starting at 221 bp after the A of the ATG start codon, 845 bp of nifL have been deleted and replaced with the CI019 Prm1.2 promoter sequence | ds172 |
| 19-713 | 19-750 | SEQ ID NO 220 | ΔnifL::Prm1.2 with 500 bp flank | starting at 221 bp after the A of the ATG start codon, 845 bp of nifL have been deleted and replaced with the CI019 Prm1.2 promoter sequence; 500 bp flanking the nifL gene upstream and downstream are included | ds172 |
| 17-724 | 19-804 | SEQ ID NO 221 | ΔnifL::Prm1.2 | starting at 221 bp after the A of the ATG start codon, 845 bp of nifL have been deleted and replaced with the CI019 Prm1.2 promoter sequence | ds172 |
| 17-724 | 19-804 | SEQ ID NO 222 | ΔnifL::Prm1.2 with 500 bp flank | starting at 221 bp after the A of the ATG start codon, 845 bp of nifL have been deleted and replaced with the CI019 Prm1.2 promoter sequence; 500 bp flanking the nifL gene upstream and downstream are included | ds172 |

TABLE G-continued

Engineered Non-intergeneric Microbes

| Strain | Strain ID | SEQ ID NO | Genotype | Description | Associated Novel Junction If Applicable |
|---|---|---|---|---|---|
| 17-724 | 19-804 | SEQ ID NO 223 | glnEΔAR-2 | glnE gene with 1650 bp immediately downstream of the ATG start codon deleted, resulting in a truncated glnE protein lacking the adenylyl-removing (AR) domain | ds34 |
| 17-724 | 19-804 | SEQ ID NO 224 | glnEΔAR-2 with 500 bp flank | glnE gene with 1650 bp immediately downstream of the ATG start codon deleted, resulting in a truncated glnE protein lacking the adenylyl-removing (AR) domain; 500 bp flanking the glnE gene upstream and downstream are included | ds34 |
| 19-590 | 19-806 | SEQ ID NO 225 | ΔnifL::Prm3.1 | starting at 221 bp after the A of the ATG start codon, 845 bp of nifL have been deleted and replaced with the CI019 Prm3.1 promoter sequence | ds175 |
| 19-590 | 19-806 | SEQ ID NO 226 | ΔnifL::Prm3.1 with 500 bp flank | starting at 221 bp after the A of the ATG start codon, 845 bp of nifL have been deleted and replaced with the CI019 Prm3.1 promoter sequence; 500 bp flanking the nifL gene upstream and downstream are included | ds175 |
| 19-590 | 19-806 | SEQ ID NO 227 | glnEΔAR-2 | glnE gene with 1650 bp immediately downstream of the ATG start codon deleted, resulting in a truncated glnE protein lacking the adenylyl-removing (AR) domain | ds34 |
| 19-590 | 19-806 | SEQ ID NO 228 | glnEΔAR-2 with 500 bp flank | glnE gene with 1650 bp immediately downstream of the ATG start codon deleted, resulting in a truncated glnE protein lacking the adenylyl-removing (AR) domain; 500 bp flanking the glnE gene upstream and downstream are included | ds34 |
| none | 63-1146 | SEQ ID NO 229 | ΔnifL::PinfC | starting at 24 bp after the A of the ATG start codon, 1375 bp of nifL have been deleted and replaced with the 63 PinfC promoter sequence | ds908 |
| none | 63-1146 | SEQ ID NO 230 | ΔnifL::PinfC with 500 bp flank | starting at 24 bp after the A of the ATG start codon, 1375 bp of nifL have been deleted and replaced with the 63 PinfC promoter sequence; 500 bp flanking the nifL gene upstream and downstream are included | ds908 |
| CM015; PBC6.15 | 6-397 | SEQ ID NO 231 | ΔnifL::Prm5 | starting at 31 bp after the A of the ATG start codon, 1375 bp of nifL have been deleted and replaced with the CI006 Prm5 promoter sequence | ds24 |
| CM015; PBC6.15 | 6-397 | SEQ ID NO 232 | ΔnifL::Prm5 with 500 bp flank | starting at 31 bp after the A of the ATG start codon, 1375 bp of nifL have been deleted and replaced with the CI006 Prm5 promoter sequence; 500 bp flanking the nifL gene upstream and downstream are included | ds24 |
| CM014 | 6-400 | SEQ ID NO 233 | ΔnifL::Prm1 | starting at 31 bp after the A of the ATG start codon, 1375 bp of nifL have been deleted and replaced with the CI006 Prm1 promoter sequence | ds20 |
| CM014 | 6-400 | SEQ ID NO 234 | ΔnifL::Prm1 with 500 bp flank | starting at 31 bp after the A of the ATG start codon, 1375 bp of nifL have been deleted and replaced with the CI006 | ds20 |

TABLE G-continued

Engineered Non-intergeneric Microbes

| Strain | Strain ID | SEQ ID NO | Genotype | Description | Associated Novel Junction If Applicable |
|---|---|---|---|---|---|
| | | | | Prm1 promoter sequence; 500 bp flanking the nifL gene upstream and downstream are included | |
| CM037; PBC6.37 | 6-403 | SEQ ID NO 235 | ΔnifL::Prm1 | starting at 31 bp after the A of the ATG start codon, 1375 bp of nifL have been deleted and replaced with the CI006 Prm1 promoter sequence | ds20 |
| CM037; PBC6.38 | 6-403 | SEQ ID NO 236 | ΔnifL::Prm1 with 500 bp flank | starting at 31 bp after the A of the ATG start codon, 1375 bp of nifL have been deleted and replaced with the CI006 Prm1 promoter sequence: 500 bp flanking the nifL gene upstream and downstream are included | ds20 |
| CM037; PBC6.39 | 6-403 | SEQ ID NO 237 | glnEΔAR-2 | glnE gene with 1644 bp immediately downstream of the ATG start codon deleted, resulting in a truncated glnE protein lacking the adenylyl-removing (AR) domain | ds31 |
| CM037; PBC6.40 | 6-403 | SEQ ID NO 238 | glnEΔAR-2 with 500 bp flank | glnE gene with 1644 bp immediately downstream of the ATG start codon deleted, resulting in a truncated glnE protein lacking the adenylyl-removing (AR) domain; 500 bp flanking the glnE gene upstream and downstream are included | ds31 |
| CM038; PBC6.38 | 6-404 | SEQ ID NO 239 | glnEΔAR-1 | glnE gene with 1287 bp immediately downstream of the ATG start codon deleted, resulting in a truncated glnE protein lacking the adenylyl-removing (AR) domain | ds30 |
| CM038; PBC6.38 | 6-404 | SEQ ID NO 240 | ΔnifL::Prm1 | starting at 31 bp after the A of the ATG start codon, 1375 bp of nifL have been deleted and replaced with the CI006 Prm1 promoter sequence | ds20 |
| CM038; PBC6.38 | 6-404 | SEQ ID NO 241 | ΔnifL:Prm1 with 500 bp flank | starting at 31 bp after the A of the ATG start codon, 1375 bp of nifL have been deleted and replaced with the CI006 Prm1 promoter sequence; 500 bp flanking the nifL gene upstream and downstream are included | ds20 |
| CM038; PBC6.38 | 6-404 | SEQ ID NO 242 | glnEΔAR-1 with 500 bp flank | glnE gene with 1287 bp immediately downstream of the ATG start codon deleted, resulting in a truncated glnE protein lacking the adenylyl-removing (AR) domain; 500 bp flanking the glnE gene upstream and downstream are included | ds30 |
| CM029; PBC6.29 | 6-412 | SEQ ID No 243 | glnEΔAR-1 | glnE gene with 1287 bp immediately downstream of the ATG start codon deleted, resulting in a truncated glnE protein lacking the adenylyl-removing (AR) domain | ds30 |
| CM029; PBC6.29 | 6-412 | SEQ ID NO 244 | glnEΔAR-1 with 500 bp flank | glnE gene with 1287 bp immediately downstream of the ATG start codon deleted, resulting in a truncated glnE protein lacking the adenylyl-removing (AR) domain; 500 bp flanking the glnE gene upstream and downstream are included | ds30 |

TABLE G-continued

Engineered Non-intergeneric Microbes

| Strain | Strain ID | SEQ ID NO | Genotype | Description | Associated Novel Junction If Applicable |
|---|---|---|---|---|---|
| CM029; PBC6.29 | 6-412 | SEQ ID NO 245 | ΔnifL::Prm5 | starting at 31 bp after the A of the ATG start codon, 1375 bp of nifL have been deleted and replaced with the CI006 Prm5 promoter sequence | ds24 |
| CM029; PBC6.29 | 6-412 | SEQ ID NO 246 | ΔnifL::Prm5 with 500 bp flank | starting at 31 bp after the A of the ATG start codon, 1375 bp of nifL have been deleted and replaced with the CI006 Prm5 promoter sequence; 500 bp flanking the nifL gene upstream and downstream are included | ds24 |
| CM093; PBC6.93 | 6-848 | SEQ ID NO 247 | ΔnifL::Prm1 | starting at 31 bp after the A of the ATG start codon, 1375 bp of nifL have been deleted and replaced with the CI006 Prm1 promoter sequence | ds20 |
| CM093; PBC6.93 | 6-848 | SEQ ID NO 248 | ΔnifL::Prm1 with 500 bp flank | starting at 31 bp after the A of the ATG start codon, 1375 bp of nifL have been deleted and replaced with the CI006 Prm1 promoter sequence; 500 bp flanking the nifL gene upstream and downstream are included | ds20 |
| CM093; PBC6.93 | 6-848 | SEQ ID NO 249 | glnEΔAR-2 | glnE gene with 1644 bp immediately downstream of the ATG start codon deleted, resulting in a truncated glnE protein lacking the adenylyl-removing (AR) domain | ds31 |
| CM093; PBC6.93 | 6-848 | SEQ ID NO 250 | glnEΔAR-2 with 500 bp flank | glnE gene with 1644 bp immediately downstream of the ATG start codon deleted, resulting in a truncated glnE protein lacking the adenylyl-removing (AR) domain; 500 bp flanking the glnE gene upstream and downstream are included | ds31 |
| CM093; PBC6.93 | 6-848 | SEQ ID NO 251 | ΔamtB | First 1088 bp of amtB gene and 4 bp upstream of start codon deleted; 199 bp of gene remaining lacks a start codon; no amtB protein is translated | ds126 |
| CM093; PBC6.93 | 6-848 | SEQ ID NO 252 | ΔamtB with 500 bp flank | First 1088 bp of amtB gene and 4 bp upstream of start codon deleted; 199 bp of gene remaining lacks a start codon; no amtB protein is translated | ds126 |
| CM094; PBC6.94 | 6-881 | SEQ ID NO 253 | glnEΔAR-1 | glnE gene with 1287 bp immediately downstream of the ATG start codon deleted, resulting in a truncated glnE protein lacking the adenylyl-removing (AR) domain | ds30 |
| CM094; PBC6.94 | 6-881 | SEQ ID NO 254 | glnEΔAR-1 with 500 bp flank | glnE gene with 1287 bp immediately downstream of the ATG start codon deleted, resulting in a truncated glnE protein lacking the adenylyl-removing (AR) domain; 500 bp flanking the glnE gene upstream and downstream are included | ds30 |
| CM094; PBC6.94 | 6-881 | SEQ ID NO 255 | ΔnifL::Prm1 | starting at 31 bp after the A of the ATG start codon, 1375 bp of nifL have been deleted and replaced with the CI006 Prm1 promoter sequence | ds20 |
| CM094; PBC6.94 | 6-881 | SEQ ID NO 256 | ΔnifL::Prm1 with 500 bp flank | starting at 31 bp after the A of the ATG start codon, 1375 bp of nifL have been deleted and replaced with the CI006 Prm1 promoter sequence; 500 bp | ds20 |

TABLE G-continued

Engineered Non-intergeneric Microbes

| Strain | Strain ID | SEQ ID NO | Genotype | Description | Associated Novel Junction If Applicable |
|---|---|---|---|---|---|
| | | | | flanking the nifL gene upstream and downstream are included | |
| CM094; PBC6.94 | 6-881 | SEQ ID NO 257 | ΔamtB | First 1088 bp of amtB gene and 4 bp upstream of start codon deleted; 199 bp of gene remaining lacks a start codon; no amtB protein is translated | ds126 |
| CM094; PBC6.94 | 6-881 | SEQ ID NO 258 | ΔamtB with 500 bp flank | First 1088 bp of amtB gene and 4 bp upstream of start codon deleted; 199 bp of gene remaining lacks a start codon; no amtB protein is translated | ds126 |
| none | 910-1246 | SEQ ID NO 259 | ΔnifL::PinfC | starting at 20 bp after the A of the ATG start codon, 1379 bp of nifL have been deleted and replaced with the 910 PinfC promoter sequence | ds960 |
| none | 910-1246 | SEQ ID NO 260 | ΔnifL::PinfC with 500 bp flank | starting at 20 bp after the A of the ATG start codon, 1379 bp of nifL have been deleted and replaced with the 910 PinfC promoter sequence; 500 bp flanking the nifL gene upstream and downstream are included | ds960 |
| PBC6.1, 6, CI6 | CI006 | SEQ ID NO 261 | 16S-1 | 1 of 3 unique 16S rDNA genes in the CI006 genome | N/A |
| PBC6.1, 6, CI6 | CI006 | SEQ ID NO 262 | 16S-2 | 2 of 3 unique 16S rDNA genes in the CI006 genome | N/A |
| PBC6.1, 6, CI6 | CI006 | SEQ ID NO 263 | nifH | N/A | N/A |
| PBC6.1, 6, CI6 | CI006 | SEQ ID NO 264 | nifD2 | 2 of 2 unique genes annotated as nifD in CI006 genome | N/A |
| PBC6.1, 6, CI6 | CI006 | SEQ ID NO 265 | nifK2 | 2 of 2 unique genes annotated as nifK in CI006 genome | N/A |
| PBC6.1, 6, CI6 | CI006 | SEQ ID NO 266 | nifL | N/A | N/A |
| PBC6.1, 6, CI6 | CI006 | SEQ ID NO 267 | nifA | N/A | N/A |
| PBC6.1, 6, CI6 | CI006 | SEQ ID NO 268 | glnE | N/A | N/A |
| PBC6.1, 6, CI6 | CI006 | SEQ ID NO 269 | 16S-3 | 3 of 3 unique 16S rDNA genes in the CI006 genome | N/A |
| PBC6.1, 6, CI6 | CI006 | SEQ ID NO 270 | nifD1 | 1 of 2 unique genes annotated as nifD in CI006 genome | N/A |
| PBC6.1, 6, CI6 | CI006 | SEQ ID NO 271 | nifK1 | 1 of 2 unique genes annotated as nifK in CI006 genome | N/A |
| PBC6.1, 6, CI6 | CI006 | SEQ ID NO 272 | amtB | N/A | N/A |
| PBC6.1, 6, CI6 | CI006 | SEQ ID NO 273 | Prm1 | 348 bp includes the 319 bp immediately upstream of the ATG start codon of the lpp gene and the first 29 bp of the lpp gene | N/A |
| PBC6.1, 6, CI6 | CI006 | SEQ ID NO 274 | Prm5 | 313 bp starting at 432 bp upstream of the ATG start codon of the ompX gene and ending 119 bp upstream of the ATG start codon of the ompX gene | N/A |
| 19, CI19 | CI019 | SEQ ID NO 275 | nifL | N/A | N/A |

TABLE G-continued

Engineered Non-intergeneric Microbes

| Strain | Strain ID | SEQ ID NO | Genotype | Description | Associated Novel Junction If Applicable |
|---|---|---|---|---|---|
| 19, CI19 | CI019 | SEQ ID NO 276 | nifA | N/A | N/A |
| 19, CI19 | CI019 | SEQ ID NO 277 | 16S-1 | 1 of 7 unique 16S rDNA genes in the CI019 genome | N/A |
| 19, CI19 | CI019 | SEQ ID NO 278 | 16S-2 | 2 of 7 unique 16S rDNA genes in the CI019 genome | N/A |
| 19, CI19 | CI019 | SEQ ID NO 279 | 16S-3 | 3 of 7 unique 16S rDNA genes in the CI019 genome | N/A |
| 19, CI19 | CI019 | SEQ ID NO 280 | 16S-4 | 4 of 7 unique 16S rDNA genes in the CI019 genome | N/A |
| 19, CI19 | CI019 | SEQ ID NO 281 | 16S-5 | 5 of 7 unique 16S rDNA genes in the CI019 genome | N/A |
| 19, CI19 | CI019 | SEQ ID NO 282 | 16S-6 | 6 of 7 unique 16S rDNA genes in the CI019 genome | N/A |
| 19, CI19 | CI019 | SEQ ID NO 283 | 16S-7 | 7 of 7 unique 16S rDNA genes in the CI019 genome | N/A |
| 19, CI19 | CI019 | SEQ ID NO 284 | nifH1 | 1 of 2 unique genes annotated as nifH in CI019 genome | N/A |
| 19, CI19 | CI019 | SEQ ID NO 285 | nifH2 | 2 of 2 unique genes annotated as nifH in CI019 genome | N/A |
| 19, CI19 | CI019 | SEQ ID NO 286 | nifD1 | 1 of 2 unique genes annotated as nifD in CI019 genome | N/A |
| 19, CI19 | CI019 | SEQ ID NO 287 | nifD2 | 2 of 2 unique genes annotated as nifD in CI019 genome | N/A |
| 19, CI19 | CI019 | SEQ ID NO 288 | nifK1 | 1 of 2 unique genes annotated as nifK in CI019 genome | N/A |
| 19, CI19 | CI019 | SEQ ID NO 289 | nifK2 | 2 of 2 unique genes annotated as nifK in CI019 genome | N/A |
| 19, CI19 | CI019 | SEQ ID NO 290 | glnE | N/A | N/A |
| 19, CI19 | CI019 | SEQ ID NO 291 | Prm4 | 449 bp immediately upstream of the ATG of the dscC 2 gene | N/A |
| 19, CI19 | CI019 | SEQ ID NO 292 | Prm1.2 | 500 bp immediately upstream of the TTG start codon of the infC gene | N/A |
| 19, CI19 | CI019 | SEQ ID NO 293 | Prm3.1 | 170 bp immediately upstream of the ATG start codon of the rplN gene | N/A |
| 19, CI20 | CI020 | SEQ ID NO 294 | Prm6.1 | 142 bp immediately upstream of the ATG of a highly-expressed hypothetical protein (annotated as PROKKA_00662 in CI019 assembly 82) | N/A |
| 19, CI21 | CI021 | SEQ ID NO 295 | Prm7.1 | 293 bp immediately upstream of the ATG of the lpp gene | N/A |
| 19-375, 19-417, CM067 | CM67 | SEQ ID NO 296 | glnEΔAR-2 | glnE gene with 1650 bp immediately downstream of the ATG start codon deleted, resulting in a truncated glnE protein lacking the adenylyl-removing (AR) domain | ds34 |
| 19-375, 19-417, CM067 | CM67 | SEQ ID NO 297 | glnEΔAR-2 with 500 bp flank | glnE gene with 1650 bp immediately downstream of the ATG start codon deleted, resulting in a truncated glnE | ds34 |

TABLE G-continued

Engineered Non-intergeneric Microbes

| Strain | Strain ID | SEQ ID NO | Genotype | Description | Associated Novel Junction If Applicable |
|---|---|---|---|---|---|
| | | | | protein lacking the adenylyl-removing (AR) domain; 500 bp flanking the glnE gene upstream and downstream are included | |
| 19-375, 19-417, CM067 | CM67 | SEQ ID NO 298 | ΔnifL::null-v1 | starting at 221 bp after the A of the ATG start codon, 845 bp of nifL have been deleted and replaced with the 31 bp sequence "GGAGTCTGAACTCATCCTGCGATGGGGGCTG" | none |
| 19-375, 19-417, CM067 | CM467 | SEQ ID NO 299 | ΔnifL::null-v1 with 500 bp flank | starting at 221 bp after the A of the ATG start codon, 845 bp of nifL have been deleted and replaced with the 31 bp sequence "GGAGTCTGAACTCATCCTGCGATGGGGGCTG"; 500 bp flanking the nifL gene upstream and downstream are included | none |
| 19-377, CM069 | CM69 | SEQ ID NO 300 | ΔnifL::null-v2 | starting at 221 bp after the A of the ATG start codon, 845 bp of nifL have been deleted and replaced with the 5 bp sequence "TTAAA" | none |
| 19-377 CM069 | CM69 | SEQ ID NO 301 | ΔnifL::null-v2 with 500 bp flank | starting at 221 bp after the A of the ATG start codon, 845 bp of nifL have been deleted and replaced with the 5 bp sequence "TTAAA"; 500 bp flanking the nifL gene upstream and downstream are included | none |
| 19-389, 19-418, CM081 | CM81 | SEQ ID NO 302 | ΔnifL::Prm4 | starting at 221 bp after the A of the ATG start codon, 845 bp of nifL have been deleted and replaced with the CI19 Prm4 sequence | ds70 |
| 19-389, 19-418, CM081 | CM81 | SEQ ID NO 303 | ΔnifL::Prm4 with 500 bp flank | starting at 221 bp after the A of the ATG start codon, 845 bp of nifL have been deleted and replaced with the CI19 Prm4 sequence; 500 bp flanking the nifL gene upstream and downstream are included | ds70 |

TABLE H

| SEQ ID NO: | Sequence |
|---|---|
| 61 | atgttttaacgatctgattggcgatgatgaaacggattcgccggaagatgcgctttctgagagctggcgcgaattgtggcaggatgcgttgcaggaggaggattccacgcccgtgctggcgcatctctcagaggacgatcgccgccgcgtggtggcgctgattgccgattttcgcaaagagttggataaacgcaccattggcccgcgaggcgcggcagtactcgatcacttaatgccgcatcggtatgctcgcgcgacgatgcgccagtaccgctgtcacgcctgacgccgctgctcaccggaattattacccgcaccacttaccttgagagctaagtgaatttcccggcgcactgaaacacctcatttccctgtgtgccgcgtcgccgatggttgccagtcagctggcgcgctacccgatcctgcttgatgaattgctcgaccgaatacgctctatcaaccgacggcgatgaatgccatcgcgatgagctgcgccaatacctgctgcgcgtgccggaagatgatgaagagcaacagcttgaggcgctgcggcagtttaagcaggcgcagttgctgcgcgtggcggcggcggatattgccggtacgttgccagtgagcgatcacttaacctggctggcggaagcgattattgatgcggtggtgcagcaagcctggggggcagatggttggcggttatgcggccagccaaccgcatctgcacgatcgcgaagggcgcggttttgcggtggtcggttatggcaagctgggcggctgggagctgggttacagctccgatctggatctggtattcctgcacgactgcccgatggatgtgatgaccgatggcgagcgtgaaatcgatggtcgccagttctatttgcgtctcgcgcagcgcgtgatgcacctgtttagcacgcgcacgtcgtccggcatccttatgaagttgatgcgcgtctgcgtccatctggcgctgcggggatgctggtcactactacggaatcgttcgccgattaccagcaaaacgaagcctggacgtggaacatcaggcgctggcccgtcgccgtgcgcgtggtgtacggccattaccaactgaccgccaatttgacgccattcgcccgcgatattctgatgacgcctcgcgacgcgcaacgctgcaaaccgactgtgcgagaaatgcgcgaaaaatgcgtgcccatcttggcaacaagcataaagaccgcttcgatctgaaagccgatgaaggcggtatcaccgacatcgagtttatcgcccaatatctggtgctgcgctttgcccatgacaagccgaaactgacgcgctggtcggataatgcgcattctcgaagggctggcgcaaaacgcatcatggaggagcaggaagcgcaggcattgacgctggcgtacaccacattgcgtgatgagctgcaccacctggcgtcgaagttgccgggacatgtggcgctctcctgttttgtcgccgagcgtgcgcttattaaaaccagctgggacaagtggctggtggaaccgtgcgcccggcgtaa |
| 62 | ttgaagagtttgatcatggctcagattgaacgctggcggcaggcctaacacatgcaagtcgaacggtagcacagagagcttgctctcgggtgacgagtggcggacgggtgagtaatgtctgggaaactgcctgatggaggggataactactggaaacggtagctaataccgcataacgtcgcaagaccaaa |

TABLE H-continued

| SEQ ID NO: | Sequence |
|---|---|
| | gaggggggaccttcgggcctcttgccatcagaggcccagatgggattagctagtaggtggggtaacggctcacctaggcgacgatccctagctggta gagaggatgaccagccacactggaactgagacacggtccagactcctacgggaggcagcagtggggaatattgcacaatgggcgcaagcctgatgc agccatgccgcgtgtgaagaaggccttcgggttgtaaagcactttcagcggggaggaagggagtaaggttaataaccttattcattgacgttacc cgcagaagaagcaccggctaactccgtgccagcagccgcggtaatacggagggtgcaagcgttaatcggaattactgggcgtaaagcgcacgcagg cggtctgtcaagtcggatgtgaaatccccgggctcaacctgggaactgcatccgaaactggcaggcttgagtctcgtagagggaggtagaattcca ggtgtagcggtgaaatgcgtagagatctggaggaataccggtggcgaaggcggcctcctggacgaagactgacgctcaggtgcgaaagcgtgggga gcaaacaggattagataccctggtagtccacgccgtaaacgatgtctatttggaggttgtgcccttgaggcgtggcttccggagctaacgcgttaa atagaccgcctgggagtacggccgcaaggttaaaactcaaatgaattgacggggcccgcacaagcggcgagcatgtggtttaattcgatgcaac gcgaagaaccttacctggtcttgacatccacagaacttttccagagatggattggtgccttcgggaactgtgagacaggtgctgcatggctgtcgtc agctcgtgttgtgaaatgttgggttaagtcccgcaacgagcgcaacccttatcctttgttgtccagcggttccggccgcgaactcaaaggagactgcc agtgataaactggaggaaggtggggatgacgtcaagtcatcatggcccttacgaccagggctacacacgtgctacaatggcgcatacaaagagaag cgacctcgcgagagtaagcggacctcataaagtgcgtcgtagtccggattggagtctgcaactcgactccatgaagtcggaatcgctagtaatcgt ggatcagaatgccacggtgaatacgttcccgggccttgtacacaccgcccgtcacaccatgggagtgggttgcaaaagaagtaggtagcttaacct tcgggagggcgcttaccactttgtgattcatgactggggtgaagtcgtaacaaggtaaccgtaggggaacctgcggttggatcacctcctt |
| 63 | ttgaagagtttgatcatggctcagattgaacgctggcggcaggcctaacacatgcaagtcgaacggtagcacagagagcttgctctcgggtgacga gtggcggacgggtgagtaatgtcgggaaactgcctgatggaggggataactactggaaacgtagctaataccgcataacgtcgcaagaccaaag aggggaccttcgggcctcttgccatcagatggtgcccagatggattagctagtaggtggggtaacggctcacctaggcgacgatccctagctggt ctgagaggatgaccagccacactggaactgagacacggtccagactcctacgggaggcagcagtggggaatattgcacaatgggcgcaagcctgat gcagccatgccgcgtgtgtgaagaaggccttcgggttgtaaagcactttcagcggggaggaggnantanggttaataacctgtgttnattgacgtt acccgcagaagaagcaccggctaactccgtgccagcagccgcggtaatacggagggtgcaagcgttaatcggaattactgggcgtaaagcgcacgc aggcggtctgtcaagtcggatgtgaaatccccgggctcaacctgggactgcatccgaaactgcaggcttgagtctcgtagagggaggtagaattc caggtgtagcggtgaaatgcgtagagatctggaggaataccggtggcgaaggcggcctcctggacgaagactgacgctcaggtgcgaaagcgtggg gagcaaacaggattagataccctggtagtccacgccgtaaacgatgtctatttggaggttgtgcccttgaggcgtggcttccggagctaacgcgtt aaatagaccgcctgggagtacggccgcaaggttaaaactcaaatgaattgacggggcccgcacaagcggtggagcatgtggtttaattcgatgc aacgcgaagaaccttacctggtcttgacatccacagaacttagcagagatgcttggtgccttcgggaactgtgagacaggtgctgcatggctgtc gtcagctcgtgttgtgaaatgttgggttaagtcccgcaacgagcgcaacccttatcctttgttgccagcggttaggccgcgaactcaaaggagact gccagtgataaactggaggaaggtggggatgacgtcaagtcatcatggcccttacgaccacggctacacacgtgctacaatggcgcatacaaagag aagcgacctcgcgagagtaagcggacctcataaagtgcgtcgtagtccggattggagtctgcaactcgactccatgaagtcggaatcgctagtaat cgtggatcagaatgccacggtgaatacgttcccgggccttgtacacaccgcccgtcacaccatgggagtgggttgcaaaagaagtaggtagcttaa ccttcgggagggcgcttaccactttgtgattcatgactggggtgaagtcgtaacaaggtaaccgtaggggaacctgcggttggatcacctcctt |
| 64 | attgaagagtttgatcatggctcagattgaacgctggcggcaggcctaacacatgcaagtcgagcggcancgggaagtagcttgctactttgccg gcgagcggcggacgggtgagtaatgtctgggaaactgcctgatggaggggataactactggaaacgtagctaataccgcatgacctcgaaagag caaagtgggatcttcggacctcacgccatccgatgtgcccagatggtagtaggtaggtaatggctnacctaggcgacgatccctagc tggtctgagaggatgaccagccacactggaactgagacacggtccagactcctacgggaggcagcagtggggaatattgcacaatgggcgcaagcc tgatgcagccatgccgcgtgtgtgaagaaggccttagggttgtaaagcactttcagcgaggaggaggcancanacttaatacgtgtgntgattgac gttactcgcagaagaagcaccggctaactccgtgccagcagccgcggtaatacggagggtgcaagcgttaatcggaattactgggcgtaaagcgca cgcaggcggttgttaagtcagatgtgaaatccccgagctcaacttcgggaactgcatttgaaactggcaagtctagagttcttagaggggtag aattccaggtgtagcggtgaaatgcgtagagatctggaggaataccggtggcgaaggcggccccctggacaaagactgacgctcaggtgcgaaagc gtggggagcaattcaggattagataccctggtagtccacgctgtaaacgatgtcgacttggaggttgtgcccttgaggcgtggcttccggagctaa cgcgttaagtcgaccgcctgggagtacggccgcaaggttaaaactcaaatgaattgacggggcccgcacaagcggtggagcatgtggtttaatt cgatgcaacgcgaagaaccttacctactcttgacatccagagaattgccagagatggcttcggttgttcatccggaacttgtgagacaggtgctgcatg gctgcgtcagctcgtgttgtgaaatgttgggttaagtcccgcaacgagcgcaacccttatcctttgttgccagcacgtnatggtgggaactcaaag gagactgccggtgataaaccggaggaaggtggggatgacgtcaagtcatcatggcccttacgagtagggctacacacgtgctacaatggcatatac aaagagaagcgaactcgcgagagcaagcggacctcataaagtatgtcgtagtccggattggagtagcaactcgactccatgaagtcggaatcgcta gtaacgtagatcagaatgctacggtgaatacgttccgggccttgtacacaccgcccgtcacaccatgggagtgggttgcaaaagaagtaggtagct taaccttcgggagggcgcttaccactttgtgattcatgactggggtgaagtcgtaacaaggtaaccgtaggggaacctgcggttggatcacctcctt |
| 65 | atgaccatgcgtcaatgcgccatttacggcaaaggtgggatcggcaaatcgaccaccacacagaacctggtcgccgcgctggcggagatgggtaaa aaagtcatgattgtcggctgtgacccgaaagccgattccacgcgtttgatcctgcatgcgaaagcgcagaacaccattatggagatggctgctgaa gtcggctccgtggaagacctggagttagaagacgtgctgcaaatcggttacggcgcgtgcgctgcgcaggctccggcggccccggagccaggcgtg ggctgtgccggtcgcggggtgataccgcgattaacttcctcgaagaagaaggcgcttacgtgccgatctcgattttgttttctacgacgtgctg ggcgacgtggtatgcggtggtttcgccatgccgattcgtgaaaacaaagcgcaggagatctacatcgtttgctctggcgaaatgatggcgatgtac gccgccaacaacatctccaaaggcatcgtgaaatacgccaaatccggtaaagtgcgcctcggcgggctgatttgtaactcgcgccagaccgaccgt gaagatgaactgattcattgcgctggcagaaaaactcggctggcagaaaactcacctttgttccccgcgacaacattgtgcagcgtgcggaaatccgcc gtatgacggttatcgaatatgaccgacctgcaatcaggcgaacgaatatcgcagccttgccagcaaaatcgtcaacaacaccaaaatggtggtgc ccaccccctgcaccatggatgaactggaagaactgctgatggagttcggcattatggatgtggaagacaccagcatcattggtaaaaccgccgccg aagaaaacgccgtctga |
| 66 | atgagcaatgcaacaggcgaacgcaacctggagataatcgagcaggtgctcgaggttttcccggaagacgcgcaaagaacgcagaaaacacatg atggtgacggacccggagcaggaaagcgtcggtaagtgcatcatctctaaccgcaaatcgcagccaggcgtgatgaccgtgcgcggctgctcgtat gccggttcgaaagggtggtatttgggccaatcaaggatatgcgcatatctcgcatggcccaatcggctgcggccaatactcccgcgccgggcgg cggactactacaccgcgctcagcggcgtggacagcttcgcacgctcaacttcacctccgattttcaggagcgacatcgtgtttggccgcgata aaaagctcgccaaactgattgaagagctggaagagctgttcccgctgaccaaaggcattcgattcagtcggaatgccggtcggcctgattggcg atgacattgaggccgtcgcgaacgccagccgcaaagccatcaacaaaccggttattccggtcgcgttgcgaaggcttcgcggcgtgtcgcaatccc tcggtcaccatattgccaacgatgtgatccgcgactgggtgctggataaccgcgaaggcaaaccgttcgaatccaccccttacgatgtggcgatca tcggcgattacaacctggccggcgatggtctgggttcgcagcattttgctcgaagagtgggcttcgggtggtggcacagtggtctggcgacggta cgctggtggagatggaaaacacgccgttcgtcaaactgaacctggtgcattgttaccgctcaatgaactacatctcgcgccatatggaggagaagc acggtattccgtggatgaatacaacttcttggtccgacgaaaatcgcggaatcgctcgcaaaatcgccgaccagtttgacgacaccattcgcgc caacgccgaagcggtgatcgccagataccaggcgcaaaacgacgccattatcgccaaatatcgcccgcgtctggaggggcgcaaagtgctgcttta tatgggcgggctgcgtccgcacatgtgattggcgcctatgaagacctgggaaatggagatcatcgctgccggttatgaaggctgcctttcggtcataacgatga ttacgaccgcaccttgccggatctgaaagagggcacgctgctgtttgatgatgccacagttatgagaggaggcgttcgtcaacgcgctgaaaccg gatctcatcggttccggcatcaaagagaagtacatctttcagaaaatgggcgtgccgtttcgcagatgcactcctgggattactccggcccgtac cacggctatgacggcttcgccatcttcgcccgcgatatggatatgacgctcaacaaccccgcgtggggccagttgaccgcgccgtggctgaaatcc gcctga |

TABLE H-continued

| SEQ ID NO: | Sequence |
| --- | --- |
| 67 | atgagccagactgctgagaaaatacagaattgccatccctgtttgaacaggatgcttaccagacgctgtttgccggtaaacgggcactcgaagag<br>gcgcactcgccggagcgggtgcaggagtgtttcaatggaccactaccccggaatatgaagcgctgaactttaaacgcgaagcgctgactatccacc<br>cggcaaaagcctgccagccgctgggcgcggtgctctgttcgctggggtttgccaatacctaccgtatgtgcacgcttcacaggttgcgtggccta<br>ttttccgcacgtactttaaccgccacttaaagaaccggtggcctgcgtgtcggattcaatgacggaagacgcggcggtgttcggcgggaataacaa<br>cctcaacaccggcttacaaaacgccagcgcgctgtataaaccggagattatcgccgtctctaccacctgtatggcggaagtgatcggtgatgattt<br>gcaggcctttatcgccaacgccaaaaaagatggttttctcgatgccgccatccccgtgcctacgcgcacaccccagttttatcggcagccatat<br>caccggctgggataacatgtttgaaggttttgcccggacctttacggagaccatgaagctcagcccggcaaactttcacgcatcaacctggtgacc<br>gggtttgaaacctatctcggcaatttccgcgtgctgaaacgcatgatggaacaaatggaggtgccggcagtggctctccgatccgtcggaagtgc<br>tgcatactcccgccaacgggcattaccagatgtacgcgggcgggacgacgcagcaagagatgcgcgaggcgccggatgctatcgacacccgttcc<br>tgcagccctggcaactggtgaaaagcaaaaagtggtgcaggagatgtggaatcagcccgccaccgaggtttctgttcccgttgggctggcaggaa<br>cacacgaactgttgatggcgattagccagttaaccggcaaggccattcccgattcactggcgctggagcgccgcggctggtcgatatgatgctcg<br>attcccacacctggttgcacggtaaaaaattcggcctgaggcgatccggattttgtcatgggattgacccgtttcctgctggagctgggctgcgaa<br>ccgaccgttatcctctgccacaacggtaacaaacgctggcagaaagcaatgaagaaaatgcttgacgcctcgccgtacggccaggagagcgaagtt<br>tatcaactgcgatttgtgcatttccgctgctgatgtttaccgccagccggattttatgattggcaactcgtacggcaagttcattcagcgcga<br>cacttagccaaaggcgagcagtttgaagttccgctgatccgcctcggttttccccttcgaccgccaccatctgcaccgccagaccacctgggct<br>acgagggcgccatgagcattctcactacccttgtgaatgcggtactggagaaagtggacaagagaccatcaagctcggcaaaaccgactacagct<br>tcgatcttatccgttaa |
| 68 | atgaccctgaatatgatgatggatgccggcgcgcccgaggcaatccccggtgcgctttcgcgacaccatcctgggctgttttttaccatcgttgaa<br>gaagcgcccgtcgccattcgctgactgatgccgacgcacgcattgtctatgccaacccggctttctgccgccagaccggctatgaactagaagcg<br>ttgttgcagcaaaatccccgcctgatgcaagtcgccaaaccccacgggaaatctatcaggatatgtggcacaccttgttacaacgccgaccgtggc<br>gcgggcaattgattaaccgccaccgcgacggcagcgcctgatctggtcgagatcgatatcaccccggtgattaaccgttggcgaactggaacacta<br>cctggcaatgcagcgcgatatcagcgccagttatgccgtcggagcagcggttgcccaatcacatgacgctgaccgaagcggtgctgaataacattcc<br>ggcggcggtggttgtagtggatgaacgcgatcatgtggttatggataaccttgcctacaaaacgttctgtgccgactgcggcggaaaagagctcct<br>gagcgaactcaatttttcagcccgaaaagcggagctggcaaacggccagctcttaccggtggtgctgcgcggtgaggtgcgctggttgtcggtgac<br>ctgctgggcgctgccgcgcgtcagcgaagaagccagcgctacttttattgataacaggctgacgcgcacgctgggtgatcaccgacgacacccaac<br>aacgccagcagcaggggcgacttgaccgccttaaacagcagatgaccaacggcaaactactggcagcgatccgcgaagcgcttgacgccg<br>cgctgatccagcttaactgccccatcaatatgctggcggcggcgcgacgtttaaacgcagtgataacaacaatgtggcgctcgacgccgcgtggc<br>gcgaaggtgaagaggcgatggcgcggctgaaacgttgccgcccgtcgctggaactggaaaggcggccgtctggccgctgcaacccattttgacgat<br>ctgcgcgcgctttatcttcaccgctacgagcagggggaaaaatttgcaggtcacgctggattcccatcatctggtgggatttggtcagcgtacgca<br>actgttagcctgcctgagtctgtggctcgatcgcaacgtcggtgatattgccgcgggctgggtgatttcaccgcgcaaacgcagatttacgccgcga<br>agaagagggctggctactttgtatatcactgacaatgtgccgagatcccgctgccacacccactcgccggatgcgcttaacgctccgggaaaag<br>gcatggagctgcgcctgatccagacgctggtggcacaccaccacgcgcaatagaactcacttcacaccccgaaggggggaagttgcctgaccctac<br>gattcccgctatttcattcactgaccgcaggttcaaaatga |
| 69 | atgacccagcgaaccgagtcgggtaataccgtctggcgatcgatttgtcccagcagttcactgcgatgcagcgcataaggtggtactcagccgggc<br>gaccgaggtcgatcagacgctccagcaagtgctgtgcgtattgcacaatgacgcctttttgcagcacggcatgatctgctgtacgacagccagcag<br>gcgattttgaatattgaagcgttgcaggaagccgatcagcagttaatccccggcagctcgcaaatccgctatcgtccgggcgaagggctggtcggg<br>acggtgctttcgcagggccaatcattaggctggcgcgcgtttgctgacgatcagcgctttcttgaccggctccgggttttgtattgattacaactgccgt<br>ttatcgccgtgccgctgataggggcagatgcgcagactttcggttgtgagacggcacaaccccatggcgcgttacgaagagcgattaccgcctgcac<br>ccgcttttctggaaacggtcgctaacctggtcgcgcaaaccgtgcgtttgatggcaccaccggcagtgcgccttccccgcgccgccataacaca<br>ggccgccagcccgattatcctgcacggcctcacgcgcatttggttttgaaaatatggtcggtaacagtccggcgatgcgccagaccatggagatta<br>tccgcaggttttcgcgctgggacaccaccgttctggtacgcggcgagagtggcaccggcaaggagctgattgccaacgccatccaccaccattcgcc<br>gcgtgccggtgcgccatttgtgaaattcaactgtgcggcgctgccggacacactgctggaaagcgaattgttcggtcacgagaaagggcatttac<br>cggcgcggtacgccagcgtaaaggccgttttgagctggccgatggcggcacgctgtttcttgacgagatcggcgagagtagcgcctcgtttcaggc<br>taagctgctgcgcattttgcaggaaggcgaagggaacgcgtcggcggcgacgagacattgcaagtgatttgtgcgcattattgccgcgacgaaccg<br>caatcttgaagatgaagtccggctggggcaacttttcgcgaagatctctattatcgcctgaatgtgatgcccatcgccctgccgccactacgcgaacg<br>ccaggaggacattgccggctggcgcactactggtgcgtaaaatcgcccataaccagagccgtacgctgcgcattagcgagggcgctatccgcctg<br>ctgatgagctacaactggccggtaatgtgcgcgaactggaaaactgcatgagcgctcagcggtgatgtcggagaacggtctgatcgatcgggatg<br>tgattttgtttaatcatcgcgaccagccagccaaaccgccagttatcaggtctcgcatgatgataactggctcgataacaaccttgacgagcgcca<br>gcggctgattgcggcgctggaaaaagcgggatgggtacaagccaaagccgcgcgcttgctggggatgacgccgcgccaggtcgcctatcgtattca<br>gacgatggatataaccctgccaaggctataa |
| 70 | atggcaatgcgtcaatgtgcaatctacgggaaggggtattggtaaatccaccactacccaaaaccttgtagcggctctggccgaaatgaataag<br>aaggtcatgatcgtcggctgtgaccctaaggctgattcaaccgactcattctgcatgcgaaagcacagaacaccatcatggaaatggccgctgaa<br>gtgggctccgtggtagatctggagctggagagatgtgatgcaaatcggctatggcggcgtgcgctggcggaatcaggcggccctgagcctggtgtgg<br>gttgtgccggacgcggggtgatcaccgccatcaacttcctgaagaagaaggcgcgtatgtgccggatcggattcgtgttttacgacgtattg<br>ggcgatgtggtctgtggcggtttcgcgatgccaattcgcgaaaacaaagcgcaggaaatctacatcgtatgctccggtgaaatgatgcgatgtat<br>gccgccaacaacatttccaaaggcatcgtgaaatacgcgaaatcgggcaaagttcgcctggccgggctgatctgtaactcccgccagacggatcgc<br>gaagatgaactgatcatcgcgaggctgaaaaacttggcacgcaaatgatccacttcgtgcccgctgacaacattgtgcaacgcgctgaaatccgcc<br>gcatgacggtcatcgaatacgaccccgacttgtgcgcaggcagatcagtcgtgcactggcgaacaaaatcgtcaacaacaccaaaatggtggtgccg<br>acaccggtcaccatggatgagctggaagccctgttaatggaatttggcattatggaagaagaagacctgaccatcgtcggtcgtaccgccgccgaa<br>gaggcgtga |
| 71 | atgaccagtgaaacacgcgaacgtaacgaggcattgatccaggaagtgctggagatcttcccgagaaggcgcttaaagatcgtaagaaacacatg<br>atgaccaccgaccgcgatggaatctgtcggcaaggtattgtctcaaaccgcaaatcacagccgggcgtgatgaccgtgcgaggctgcgcttacg<br>ccggttccaaaggcgtggtctttggcccgataaagacatggcgcatatctcccacgcccggttggttgcggccagtattctcgtgccggacgcc<br>gtaactattacaccggctcggaagggcgtgaacagctttggcaccctcaacttcaccagtgatttcaggaacgggacatcgtatttggcggcgataa<br>aaagctcgacaaactgatcgacgaactggagatgttgtcccgctgaccaaaggcatttcggtacgtcggaatgtccggtcggtctgatcggcgat<br>gacatttctgccgtcgccaaagccagcagcgccaaaatcggtaagccggtcgtgccggtacgctgcgagggtctccggtggtgtcgcaatcgctc<br>ggccatcacattgctaacgatgtcatccgcgactgggtgctggataaccgcgaaggcaatgaatttgaaaccacgcctttacgacgtggcgattatc<br>gcgactacaacatcggcggtgacgcctgggcctcacgtattctgctcgaaaatggggctgcgtgtggtgcgcagtggtccggcaggcgcacg<br>ctggtgggagatggaaaacaccccgaaagtcgcactcaatctgtgcactgctaccgctcgatgaactacatctcccgcatatggaagaaaaacg<br>gcattccgtggatggaatacaacttctttggcccgtccaaaattgcggaatctctgcgcgaaatcgcggcgcgttttgacgataccatccggaaaa<br>acgccgaagcggtgattgaaaaatatcaggcgcaaacgcaggcggtgatcgacaaataccgtccgcgtaggaaggcaaaaggtgctgttgtatct<br>cggcggtttacgtccgcgccacatcatcggggcgtatgaagatctgggaatggaaatcatcggtaccggctatgaattcggtcataacgatgatta<br>cgaccgcaccttaccgatgctcaaagaaggcacgttgcgtgttcgatgacctgtgcagttatgagctggaagcgttcgttaaagcgctgaaccgga |

TABLE H-continued

| SEQ ID NO: | Sequence |
|---|---|
| | tcttgtcgggtcaggcatcaaagaaaaatacattttccacaaaatgggcgtgccgttccgccagatgcactcctgggattattccggcccttatca cggctacgacggtttcggcattttttgcccgtgacatggacatgacgctgaacaatcccgggctggagtcagctgaccgcccccctggttgaaatcggc ctga |
| 72 | atgagtcaagatcttggcaccccaaaatcctgtttcccgctgacgagcaggatgaataccagagtatgtttacccacaaacgcgcgaggaagaagc acacggcgaggcgatagtgcgggaagtgtgtttgaatggaccaccacgcaggaatatcaggatctgaacttctcgcgtgaagcgctgaccgtcgaccc ggcgaaagcctgccagccgttaggcgcggtactttgcgcgctgggttttgccaacacgttgccgtatgtccacggttcacaaggctgtgtggcgta tttccgtaccatattttaatcctcatttcaaagagccggtggcctgtgtttccgactcaatgaccgaagatgccgccgttttggcggaaataacaa catgaatgtcggtctggaaaacgccagcgcgctgtacaagccggaaattattgctgtctccaccacctgtatggcggaagtgatcggtgatgacct gcaggcttttatcgccaacgccaaaaaaagacggatttttgtggatgccgggatgccaatcccgtatgccatacaccgagtttctgggcagtcatgtc accggctgggacaacatgtttgaaggcttcgcccgtacctttaccaccgacgccacgcgggaatatcagccgggcaaacttgccaaactgaacgtg gtgaccggttttgaaacttatctcggcaactaccggggtattcaccgcatgatgagccagatggggcgaatgcagcgtcttgtccgatccgtct gaagtgctcgacaccccggctgacggccaataccgcatgtatgccggcggcaccacgcaaaccgaaatgcgtgatgcaccggatgccatcgacacc ttgctgctgcaaccgtggcaattgcagaaaaccaaaaaaagtggtgatcagccgggcaccgaagtcagtgtaccgattggcctg gcggcgaccgatgccttgctgatgacggtaagcgaactgaccggcaaaccgatagctgacacgctggcgactgaacgtggccgtctggtggacatg atgctcgattcccacacctggctgcatggcaagcgtttcggtctctacggtgaccggattttgtgatgggcatgaccgcattcctgctggaactg ggctgtgaaccgaccaccattctcagccataacggcaacaaacgctggcagaaagccatgaagaaaatgctggctgattcgccttacgggcaggac agcgaagtgtattgtgaactgcgatctgtggcattccgctcgctgatgtttaccgtaaccggacttttatgatcggcaacctcaacgaaaattc attcagcgtgacacgctggccaaaggcgaacattcgaagtgccgctgatccgcatcggttttccgattttttgaccggcaccatttgcaccgtcag accacctggggatacgaaggggcgatgagcatactgacgcaactggtgaatgccgtacttgaacaactggatcgcgaaaccatgaagctcggcaaa accgactacaacttcgtcctgttccgctaa |
| 73 | atgagcatcacgcgcgttatcagcatcatttcctgaggggaatatcgccagccgcttgtcgctgcaacatccttcactgttttataccgtggttgaa caatcttcggtggcgatttcgctgaccgatccgcaggcgcgcatttgttatgccaatccggcaactgccgccagacgggttttgcacttgagacac ttttgggcgagaaccaccgtctgctggccagccagcagacgccgaaacatatctatgacgaaatgtggcgcactttgagcagggcaaatcctggaa cggccaactgatcaaccggcgtaataaccgttcgctttatctggcggatgtcactatcacgcctgttttaggcgggacggcaggtggagcattac ctcggcatgcacaaagatatcagcgagaaatacgcgctggaacagcggttgccgcaaccacatccacctttgttcacggagtgctgaacaatattcc gccgccgtggtggtggtggatgagcaggacaatgtggtgatggacaatctggcctacaaaaccctttgcgcggactgcggcggcaaagagctgctg gctgaaatgggctatccgcaactcaaagagatgctcaacagtggcgaaccggtgccggtttccatgcgcggcaacgtacgctggttttctttcggt caatggttattcagggcgttaatgattgaggccagccgctttttaccggcattaccgcgccgggaaaactgattgttctgaccgactgcaccgat cagcatcaccggcagcagggttatcttgaccggctttaagcaaaaactcaccaacggcaaattattggcggccatccgtgagtcgctcgatgcc gcgcttatccagctcaacgggccaatcaatatgctggcggctccgcgtcgtcttaacggcgaagaaggcaacaacatggcgctggaattcgctgg cgcaaggcgagcaggcggtgagtcgcttacaggcctgccgtccgtcgctggattttgagccgcaggcagaatggccggtcagtgaattctttgac gatctgagcgcgctgtacgacagccattttctcagtgacggtgaattgcgttacgtggtcatgccatctgatctgcacgctgtcgggcaacgaacg caaatccttaccgcgctgagcttatggattgatcacacgctgtcacaggcgcagccatgcctctctgaagctctcggtgaacattgcgcgaggc aggatgcgagctggttgtgttttgacattaccgataatgtgccgcgtgaacgggtgcgttatgcccgccggaagcggcgttttccgtccgggga atggcatggagctgcgccttatccagacgctgatcgcccatcatcgcggttctttagatctctcggtccgccctgatgcggcaccttgctgacgt tacgcctgccggtacagcaggttatcaccggaggcttaaatga |
| 74 | atgacccagttcctaccgcgggcccggttatccggcgctttgatatgtctgcccagtttacggcgcttatcgcatcagcgtggcgctgagtcagg aaagcaacaccgggcgcgcactggcggcgatcctcgaagtgcttcacgatcatgcatttatgcaatacggcatggtgtgtctgtttgataaagaac gcaatgcactcttttgtggaatccctgcatggcatcgacggcgaaaggaaaaaagagacccgccatgtccgttaccgcatgggggaaggcgtgatcg gcgcggtgatgagccagcgtcaggcgctgtggttaccgcgcattcagacgatcagcgttttctcgaccgcctgaatatttacgattacagccttc cgttgattggcgtgcccgatccccgctggcggataatcagccatcgggcgtgctggtggcacagccgatgcgtgcacgaagaccggctgactgcc agtacgcggttttagaaatggtcgccaatctcatcagccagccactgcgttctgccacgcccccggaatcattgcctgctcaaacgccggtccgg tgcagtgttccgcgcagtttggtttcgagcagatggtcgggaaagtcaggcgatgcgccagacgatggacatttacgcgcaggtttccaaatgg gataccacggttctggtgcgtggtggaaagcggccaccggcaaggaacttatcgccaatgccattcattacaactcacccctgccggccgcgccattt gtgaaattcaactgcgccgcgctgccggataacctgctggaaagcgaactgttcggtcatgaaaaaggggccttcaccggcgctatccgtacccgt aaaggccgctttgaactggcggacggggcacgttattcctcgatgaaatcggcgaatcgagcgcgtcgtttcaggccaaattgctgcgcattttg caggaaggtgaaatggaacgggtcggcggcgatccacgctgaaagttgatgtgcgcattattgctgccaccaaccgtaatcttgaagaggaagtg cgtgccgggaattttcgcgaagacctgtattatcgcctgaacgtgatgccggtttcgctgcctgcactgcgtgaaaggctggatgatcgccgat ctggcgccgttaggtcaattaagattgcgctgcgtcagggggcggaactgccgcatcagcgacggtgcgtctgctgatgacctacgactgg ccaggcaacgtgcgtgaactggaaaactgtctcgaacgggcgtcggtaatgaccgatgaaggctgatcgaccgcgacgtgatcctgttcaatcac catgaatccccggcgctgtccgtcaaacccggcctgccgctcgcgacagatgaaagctggctggatcaggaactcgacgaacgccagcgggtgatt gccgcactggagaaaaccggctgggtgcaggccaaagcggcccgactgctgggcatgacaccgcgccagattgcctaccgtatccagattatggac atcaacatgcaccgtatctga |
| 75 | aaaactaccgccgcaattaatgaacccaacgctactgttgccgggccatgctcttcccggcgcgctgccggaaaggatatagattgcccagcac gcgccagcaccaagcgcgaacgccgcgccagtgagatcaacatgtgaaacattttcgcccagcggcagcagatacaagaggccaagtaccgccagg atcacccagatgaaatcccagcgggcgtgaggcaaaaagcgccaccgccagcggtaaattccagcgccaccgcaacgccgagcggtatc gtctggatcgataaatagaacatatagttcatgcgccgagcgacaggccataaaacagcagtgcaggcgttgttcacggtaaatgtaaacgc cagggcttgaacactacgaccaaaataaggggtgccaagtgcgagacgcagcgcggtgacgccgggtgcgcaacaatcggaaacagtgatttcgcc agcgacgcgcctccctgaatggacatcatcgcgacaaacaatattaataccggcaaccacaccggcaatttacgagactgcgcaggcatcctttct cccgtcaatttctgtcaaataaagtaaaagaggcgtctacttgaattaccccggctggttgagcgttgttgaaaaaagtaactgaaaaatccg tagaatagcgccactctgatggttaattaacctattcaattaagaattatctggatgaatgtgccattaaatgcgcagcataatggtgcgttgtgc gggaaaactgctttttttttgaaagggttggtcagtagcggaaactttctgttacatcaaatggcgtttagacccaattcccgcaaagagtttct taactaattttgatatatttaaacgcgtaggacgtaggatttacttgaagcacatttgaggtggattatgaaaaaaattgcatgtctttcagcact ggccgcacttctggcggtttctgcaggttccgcagtagcaccaacttcaaccgtaactggcgctacggtacgctcaggagacgcgctcagggtattgctaa caaaaattaacggtttcaacctgaaatatcgctacgcaggacaaaacccgctgggtgttatcggttcctttacttacactgaaaagatcgcac cgaaagcagcgtttataacaaaaagcgcagtactacggcatcaccgcaggcccggcttaccgcatcaacgcatgggcgagcatctacggtgttgtggg tgtaggttacggtaaattccagcagattgtagacaccgctaaagtgtctgacaccagcgactacg |
| 76 | aacacacgctcctgttgaaaaagagatcccgccgggaaatgcggtgaacgtgtctgatattgcgaagagtgtgccagttttggcgcgggcaaaacc tgcaccagtttggtattaatgcaccagtctggcgctttttttcgcgagtttctcctcgctaatgcccgcaggcgcggcttggcgctgatagcgc gctgaatccgatctggatcaaggttttgtcgggttatcagccaaaaggtgcactcttcgatggttatacgtgcctgacatgttgtccgggcgac aaacgccctggtggcacaaattgtcagaactacgacacgactaactgaccgcaggagtgtgcgatgaccctgaatatgatgatggatgccggcgcg cccgaggcaatcgccggtgcgctttcgcgacaccatcctgggctgttttttaccatcgttgaagagcgcccgtcgccatttcgctgactgatgcc |

TABLE H-continued

| SEQ ID NO: | Sequence |
|---|---|
| | gacgcacgcattgtctatgccaacccggctttctgccgccagaccggctatgaactagaagcgttgttgcagcaaaatccccgcctgcttgcaagt<br>cgccaaaccccacgggaaatctatcaggatatgtggcacaccattgttacaacgccgaccgtggcgcgggcaattgattaaccgccaccgcgacgg<br>cagcctgtatctggtcgagatcgatatcaccccggtgattaacccgtttggcgaactggaacactacctggcaatgcagcgcgatatcagcgccag<br>ttatgcgctggagcagggttgcgcaatcacatgacgctgaccgaagcggtgctgaataacattccggcggcggtggttgtagtggataacgcgat<br>catgtggttatggataaccttgcctacaaaacgttctgtgccgactgcggcggaaaagagctcctgaggaactcaattttttcagcccgaaaaggga<br>gctggcaaacggccaggtcttaccggtggtgctgcgcggtgaggtgcgctggtgttgtcggtgacctgctggggcgctgccgggcgtcagcgaagaagc<br>cagttcgctactttattgataacaggctgacgcgcacgctggtggtgatcaccgacgacacccaacaacgccagcagcaggaacagggccgacttg<br>accgcctaaacagcagatgaccaacggcaaactactggcagcgatccgcgaagcgcttgacgccgcgctgatccagataactgccccatcaatat<br>gctggcggcggcgacgtttaaacggcagtgataacaacaatgtggcgctcgacgccgcgtggcgcgaaggtgaagtggcgatggcgcggctgaa<br>acgttgccgcccgtcgctggaactggaaagtgcggccgtctggccgctgcaacccttttttgacgatctgcgcgcgctttatcacaccgctacgag<br>cagggggaaaaatttgcaggtcacgctggattcccatcatctggtgggatttggtcagcgtacgcaactgttagcctgcctgagtctgtggctcgat<br>cgcacgctggatattgccgccgggctgggtgattt caccgcgcaaacgcagatttacgcccgcgaagaagagggctggctctcttttgtatatcact<br>gacaatgtgccgctgatcccgctgcgccacacccactcgccggatgcgcttaacgctccgggaaaaggcatgcacctgcgcctgatccagacgctg<br>gtggcacaccaccacggcgcaatagaactcacttcacaccccgaaggggggaactgtcgtgaccctacgattcccgctattcattcactgaccggag<br>gttcaaatgacccagcgaacccgagtcgggtaataccgtctggcgcttcgatttgtcccagcagttcactgcgatgcagcgcataagcgtggtactc<br>agcccgggcgaccgaggtcgatcagacgctccagcaagtgctgtgcgtattgcacaatgacgccttttttgcagcacggcatgatctgtctgtacgac<br>agccagcaggcgattttgaatattgaagcgttgcaggaagccgatcagcagttaatccccggcagctcgcaaatccgctatcgtccgggcgaaggg<br>ctggtcgggacggtgcttt cgcagggccaatcattagtcgccggctggtttgctgacgatcaggcttcttgaccggctcgggttgtatgattaca<br>acctgccgtttatcgccgtgccgctgatagggcagatgcgcagacttcggtgtgctgacggcacaacccatggcgcgttacgaagagcgattac<br>ccgcctgcacccgctttctggaaacggtcgctaacctggtcgcgcaaaccgtgcgtttgatggcaccaccggcagtgcgcccttccccgcgcgccg<br>ccataacacaggcgccagcccgaaatcctgcacggcctcacgcgcatttggttttgaaaatatggtcggtaacagtccggcgatgcgccagacca<br>tggagattatcgtcaggtttcgcgctgggacaccaccgttctgtggtacgcggcgagagtggcaccggcaaggagctgattgccaacgccatccacc<br>accattcgccgcgtgccggtgcgcctttgtgaaatt caactgtgcggcgctgccggacacactgctggaaagcgaattgttcggtcacgagaaag<br>gggcatttaccggcgcggtacgccagcgtaaaggccgtttgagctggccgatggcggcacgctgttt cttgacgagatcggcgagagtagcgcct<br>cgtttcaggctaagctgctgcgcattttgcaggaaggcgaaatggaacgcgtcggcggcgacgagacattgcaagtgaatgtgcgcattattgccg<br>cgacgaaccgcaatcttgaagatgaagtccggctggcgcacttt cgcgaagatctctattatcgcctgaatgtgatgcccatcgcctgccgccac<br>tacgcgaacgccaggaggacattgccgagctggcgcacttt ctggtgcgtaaaatcgcccataaccagagccgtacgctgcgcattagcgagggg<br>ctatccgcctgctgatgagctacaactggcccggtaatgtgcgcgaactggaaaactgccttgagcgctcagcggtgatgtcggagaacggtctga<br>tcgatcgggatgtgattttgtttaatcatcgcgaccagccagccaaaccgccagttatcagcgtctcgcatgatgataactggctcgataacaacc<br>ttgacgagcgccagggctgattgcgcgctggaaaaagggggatgggtacaagccaaagccgcgcgcttgctggggatgacgccgcgccaggtcgcc<br>tatcgtattcagacgatggatataaccctgccaaggctataa |
| 77 | MTLNMMMDAGAPEAIAGALSRHHPGLFFTIVEEAPVAISLTDADARIVYANPAFCRQTGYELEALLQQNPRLLASRQTPREIYQDMWHTLLQRRPW<br>RGQLINRHRDGSLYLVEIDITPVINPFGELEHYLAMQRDISASYALEQRLRNHMTLTEAVLNNIPAAVVVVDERDHVVMDNLAYKTFCADCGGKEL<br>LSELNFSARKAELANGQVLPVVLRGEVRWLSVTCWALPGVSEEASRYFIDNRLTRTLVVITDDTQDRQQQEQGRLDRLKQQMTNGKLLAAIREALD<br>AALIQLNCPINMLAAARRLNGSDNNNVALDAAWREGEEAMARLKRCRPSLELESAAVWPLQPFFDDLRALYHTRYEQGKNLQVTLDSHHLVGFGQR<br>TQLLACLSLWLDRTLDIAAGLGDFTAQTQIYAREEEGWLSLYITDNVPLIPLRHTHSPDALNAPGKGMELRLIQTLVAHHHGAIELTSHPEGGSCL<br>TLRFPLFHSLTGGSK |
| 78 | MTQRTESGNTVWRFDLSQQFTAMQRISVVLSRATEVDQTLQQVLCVLHNDAFLQHGMICLYDSQQAILNIEALQEADQQLIPGSSQIRYRPGEGLV<br>GTVLSQGQSLVLARVADDQRFLDRLGLYDYNLPFIAVPLIGPDAQTFGVLTAQPMARYEERLPACTRFLETVANLVAQTVRLMAPPAVRPSPRAAI<br>TQAASPKSCTASRAFGFENMVGNSPAMRQTMEIIRQVSRWDTTVLVRGESGTGKELIANAIHHHSPRAGAPFVKFNCAALPDTLLESELFGHEKGA<br>FTGAVRQRKGRFELADGGTLFLDEIGESSASFQAKLLRILQEGEMERVGGDETLQVNVRIIAATNRNLEDEVRLGHFREDLYYRLNVMPIALPPLR<br>ERQEDIAELAHFLVRKIAHNQSRTLRISEGAIRLLMSYNWPGNVRELENCLERSAVMSENGLIDRDVILFNHRDQPAKPPVISVSHDDNWLDNNLD<br>ERQRLIAALEKAGWVQAKAARLLGMTPRQVAYRIQTMDITLPRL |
| 79 | atgccgcaccacgcagcattgtcgcagcactggcaaacggtattttctcgtctgccggaatcgctcaccgcgcagccattgagcgcgcaggcgcag<br>tcagtgctcactttagtgattttgttcaggacagcatcatcgcgcatcctgagtggctggcagagcttgaaagcgcgccgccgcctgcgaacgaa<br>tggcaacactatgcgcaatggctgcaagcggcgctggatggcgtcaccgatgaagcctcgctgatgcgcgcgctcgggctgtttcgccgtcgcatc<br>atggtgcgcatcgcctggagccaggcgttacagttggtggcggaagaagatatcctgcaacagcttagcgtgctggcggaaacccgatcgtcgcc<br>gcgcgcgactggctttatgaggcctgctgccgtgagtggggaacgccgagcaatccacaaggcgtggcgcagccgatgctggtactcggcatggc<br>aaactgggtggcggcgaactcaatttctcatccgatatcgatttgattttgcctgccggaaaatggcgcaacgcgggtggacgccgtgagctg<br>gataacgcgcaattttttcactcgccttggtcaacggctcgattaaagtcctcgaccagccaaccgcaggatggctttgtctaccgcgtcgatatgcgc<br>ttgcgcccgtttggcgacagcgcccgctggtgctgagctttgccgcgctggaagattactaccaggagcaggggcgcgattgggaacgctacgcg<br>atggtgaaagcgcgcattatgggcgataacgacggcgaccatgcgcgggagttgcgcgcaatgctgcgcccgtttgttttccgccgtatatcgact<br>tcagcgtgaacagtccctgcgtaacatgaaaggcgtgattgcccgcgaaggtgcgtcgcgtggcctgaaggacaacattaagctcggcgcgggcg<br>ggatccgcgaaatagaatttatcgtccaggttttccagagatctcgcggcggtcgtcgagcctgcactgcaatcgcgcacactgttgccgacgcttgct<br>gccatagatcaactgcatctgctgccggatggcgacgcaacccggctgcgcaggcgtatttgtggctgcgacggctggagaacctgctgcaaagc<br>atcaatgacgaacagacacagacgctgccgggcgatgaactgaatcgcgcgcctcgcctggggaatgggcaaagatagctgggaagcgctctgc<br>gaaacgctggaagcgcatatgtcggcggtgcgtcagatatttaacgatctgattgccgatgatgaaacggattcgccggaagatgcgctttctgag<br>agctggcgcgaattgtggcaggatgcgttgcaggaggaggattccacgcccgtgctggcgcatctctcagaggacatcgccgccgcgtggtggcg<br>ctgattgccgattttcgcaaagagttggataaacgcaccattggcccgcagggcggcaggtactcgatcacttaatgccgcatctgacagcgatg<br>tatgctcgcgcgacgatgcgccagtaccgctgtcacgcctgaccgccgctgacaccggaattattacccgcaccacttaccttgagctgctaagtga<br>atttcccggcgcactgaaacacctcatttccctgtgtgccgcgtcgccgtgatggttgccagtcagctggcgcgctaccgatcctgcttgatgaatt<br>gctcgacccgaatacgctctatcaaccgacggcgatgaatgctatcgcgatgagagcgccaatacctgctgcgcgtgccggaagatgatgaagag<br>caacagcttgaggcgctgcgcagtttaagcaggcgcagttgctgcgcgtggcggcggcggatattgccggtacgttgccagtaatgaaagtgagc<br>gatcacttaacctggctggcggaagcgattattgatgcggtggtgcagcaagcctgggggcagatggtggcgcgttatggccagccaacgcatctg<br>cacgatcgcgaaggggcggtttttgcggtggtcggttatggcaagctgggcggctggggagctgggttacagctccgatctggatctggtattcctg<br>cacgactgcccgatgatgtgatgaccgatgcgagcgtgaaatcgatggtgccagttctattttgcgtctccgcagccgctgatgcacctgttt<br>agcacgcgcacgtcgtccggcatcctttatgaagttgatgcgcgtctgcgtccatctggcgctgcggggatgctggtcactactacggaatcgttc<br>gccgattaccagcaaaacgaagcctggacgtgggaacatcaggcgctggccgtgcgcgtggtgtacggcgatccgcaactgaccgccgaatttt<br>gacgccattcgccgcgatattctgatcacgcctcgccagcgcgacgccgaacccgacgtgcgagaaatgcgcgaaaaatgcgtgcccatctt<br>ggcaacaagcataaagaccgcttcgatctgaaagccgatgaaggcggttatcaccgacatcgagtttatcgcccaatataggtgagcttgcccat<br>gacaagccgaaactgacgcgcttggtcggataatgtgcgcattctcgaagggctggcgcaaaacgcatcatggaggaggaggaagcgaggcattg<br>acgctggcgtacaccacattgcgtgatgagctgcaccacctggcgctgcaagagttgccgggacatgtggcgctctcctgttttgtcgccgagcgt<br>gcgcttattaaaccagctgggacaagtggctggtggaaccgtgcgccccggcgtaa |

TABLE H-continued

| SEQ ID NO: | Sequence |
|---|---|
| 80 | atgtttaacgatctgattggcgatgatgaaacggattcgccggaagatgcgctttctgagagctggcgcgaattgtggcaggatgcgttgcaggag gaggattccacgcccgtgctggcgcatctctcagaggacgatcgccgccgcgtggtggcgctgattgccgattttcgcaaagagttggataaacgc accattggccccgcgagggcggcaggtactcgatcacttaatgccgcatctgctcagcgatgtatgctcgcgcgacgatgcgccagtaccgctgtca cgcctgacgccgctgctcaccggaattattacccgcaccacttaccttgagctgctaagtgaatttccccggcgcactgaaacacctcatttccctg tgtgccgcgtcgccgaggttgccagtcagctggcgcgctaccgatcctgcttgatgaattgctcgacccgaatacgctctatcaaccgacggcga tgaatgcctatcgcgatgagctgcgccaataccctgctgcgcgtgccggaagatgatgaagagcaacagcttgaggcgctgcggcagtttaagcagg cgcagttgctgcgcgtggcggcgggatattgccggtacgttgccagtaatgaaagtgagcgatcacttaacctggctggcggaagcgattattg atgcggtggtgcagcaagctggggcagatggtggcgcgttatggccagcaacgcatctgcacgatcgcgaagggcgcggttttgcggtggtcg gttatggcaagctgggcggctgggagctgggttacagctccgatctggatctggattcctgcacgactgcccgatggatgtgatgaccgatggcga gcgtgaaatcgatggtcgccagttctatttgcgtctccgccagcgcgtgatgcacctgtttagcacgcgcacgtcgtccggcatccttatgaagt tgatgcgcgtctgcgtccatctggcgctgcggggatgctggtcactactacggaatcgttcgccgattaccagcaaaacgaagcctggacgtggga acatcaggcgctggcccgtgcgcgcgtggtgtacggcgaccgcaactgaccgccgaatttgacgccattcgccgcgatattctgatgacgcctcgc gacggcgcaacgctgcaaaccgacgtgcgagaaatgcgcgagaaatgcgtgcccatcttggcaacaagcataaagaccgcttcgatctgaaagcc gatgaaggcggtatcaccgacatcgagtttatcgccaatatctggtgctggcgcttgcccatgacaaagccgaaactgacgcgctggtcggataat gtgcgcattctcgaaggcgtggccgcaaaacggcatcatggaggagcaggaagcgcaggcattcacgctggcgtacaccatgctgtgatgagctg caccacctggcgctgcaagagttgcccgggacatgtggcgctctcctgttttgtcgccgagcgtgcgcttattaaaccagctgggacaagtgcctg gtggaaccgtgcgccccggcgtaa |
| 81 | MPHHAGLSQHWQTVFSRLPESLTAQPLSAQAQSVLTFSDFVQDSIIAHPEWLAELESAPPPANEWQHYAQWLQAALDGVTDEASLMRALRLFRRRI MVRIAWSQALQLVAEEDILQQLSVLAETLIVAARDWLYEACCREWGTPSNPQGVAQPMLVLGMGKLGGGELNFSSDIDLIFAWPENGATRGGRREL DNAQFFTRLGQRLIKVLDQPTQDGFVYRVDMRLRPFGDSGPLVLSFAALEDYYQEQGRDWERYAMVKARIMGDNDGDHARELRAMLRPPFVFRRYID FSVIQSLRNMKGMIAREVRRRGLKDNIKLGAGGIREIEFIVQVFQLIRGGREPALQSRSLLPTLAAIDQLHLLPDGDATRLREAYLWLRRLENLLQ SINDEQTQTLPGDELNRARLAWGMGKDSWEALCETLEAHMSAVRQIFNDLIGDDETDSPEDALSESWRELWQDALQEEDSTPVLAHLSEDDRRRVV ALIADFRKELDKRTIGPRGRQVLDHLMPHLLSDVCSRDDAPVPLSRLTPLLTGIITRTTYLELLSEFPGALKHLISLCAASPMVASQLARYPILLD ELLDPNTLYQPTAMNAYRDELRQYLLRVPEDDEEQQLEALRQFKQAQLLRVAAADIAGTLPVMKVSDHLTWLAEAIIDAVVQQAWGQMVARYGQPT HLHDREGRGFAVVGYGKLGGWELGYSSDLDLVFLHDCPMDVMTDGEREIDGRQFYLRLAQRVMHLFSTRTSSGILYEVDARLRPSGAAGMLVTTTE SFADYQQNEAWTWEHQALARARVVYGDPQLTAEFDAIRRDILMTPRDGATLQTDVREMREKMRAHLGNKHKDRFDLKADEGGITTDIEFIAQYLVL RFAHDKPKLTRWSDNVRILEQLAQNGIMEEQEAQALTLAYTTLRDELHHLALQELPGHVALSCFVAERALIKTSWDKWLVEPCAPA |
| 82 | MFNDLIGDDETDSPEDALSESWRELWQDALQEEDSTPVLAHLSEDDRRRVVALIADFRKELDKRTIGPRGRQVLDHLMPHLLSDVCSRDDAPVPLS RLTPLLTGIITRTTYLELLSEFPGALKHLISLCAASPMVASQLARYPILLDELLDPNTLYQPTAMNAYRDELRQYLLRVPEDDEEQQLEALRQFKQ AQLLRVAAADIAGTLPVMKVSDHLTWLAEAIIDAVVQQAWGQMVARYGQPTHLHDREGRGFAVVGYGKLGGWELGYSSDLDLVFLHDCPMDVMTDG EREIDGRQFYLRLAQRVMHLFSTRTSSGILYEVDARLRPSGAAGMLVTTTESFADYQQNEAWTWEHQALARARVVYGDYQLTAEFDAIRRDILMTP RDGATLQTDVREMEREKMRAHLGNKHKDRFDLKADEGGITDIEFIAQYLVLRFAHDKPKLTRWSDNVRILEGLAQNGIMEEQEAQALTLAYTTLRD ELHHLALQELPGHVALSCFVAERALIKTSWDKWLVEPCAPA |
| 83 | EEQQLEALRQFKQAQLLRVAAADIAGTLPVMKVSDHLTWLAEAIIDAVVQQAWGQMVARYGQPTHLHDREGRGFAVVGYGKLGGWELGYSSDLDLV FLHDCPMDVMTDGEREIDGRQFYLRLAQRVMHLFSTRTSSGILYEVDARLRPSGAAGMLVTTTESFADYQQNEAWTWEHQALARARVVYGDPQLTA EFDAIRRDILMTPRDGATLQTDVREMREKMRAHLGNKHKDRFDLKADEGGITDIEFIAQYLVLRFAHDKPKLTRWSDNVRILEGLAQNGIMEEQEA QALTLAYTTLRDELHHLALQELPGHVALSCFVAERALIKTSWDKWLVEPCAPA |
| 84 | ccgagcgtcggggtgcctaatatcagcaccggatacgagagaaaagtgtctacatcggttcggttgatattgaccggcgcatccgccagcccgcc agtttctggtggatctgtttggcgattttgcgggtcgttgcgggtgccgaaaaaaataccaatattttgccataacacacgctcctgttgaa aaagagatcccgccggaaatgcggtgaacgtgtctgatattgcgaagaggtgccagttttatcgcgggcaaaacctgccaccagtttggttattaa tgccaccagtctggcgctttttttcgccgagttttctcctcgctaatgcccgccaggcgcggctttggcgctgatagcgcgctgaataccgatctgga tcaaggttttgtcggggttatcagccaaaaggtgcactctttgcatggttatacgtgcctgacatgttgtccgggcgacaaacggcctggtggcaca aattattgtcagaactacgacacgactaactgaccgcaggagtgtgcgatgaccctgaatatgatgatgcgccgggacatcatcgcgacaaa caatattaataccggcaaccacaccggcaatttacgagactgcgcaggcatcctttctccgtcaatttctgtcaaataaagtaaagaggcagtc tacttgaattaccccggctggttgagcgtttgttgaaaaaaagtaactgaaaaatccgtagaatagcgccactctgatggttaattaacctattc aattaagaattatctggatgaatgtgccattaaatgcgcagcataatggtgcgttgtgcgggaaaactgcttttttttgaaagggttggtcagtag cggaaacaactcacttcacaccccgaagggggaagtttgcctgaccctacgattcccgctatttcattcactgaccggaggttcaaaatgacccagc gaaccgagtcgggtaataccgtctggcgcttcgatttgtcccagcagttcactgcgatgcagcgcatcagcgtgctcagccgggcgaccgagg tcgatcagacgctccagcaagtgctgcgctattgcacaatgacgccttttgcagcacggcatgatctgtctgtacgacagccagcaggcgatttt tgaatattgaagcgttgcaggaagccgatcagcagttaatccccggcagctcgcaaatccgctatcgtccgggcgaagggctggtcgggacggtgc tttcgcagggccaatcattagtgctggcgcgcgttgctgacgatcagcgctttcttgaccggctcgggttgtatgattacaacctgccgtttatc |
| 85 | attgaagagtttgatcatggctcagattgaacgctggcggcaggcctaacacatgcaagtcgagcggcagcgggaagtagatgctactttgccggc gagcggcggacgggtgagtaatgtctgggtatctgcctgatgaggggataactactggaaacggtagctaataccgcatgacctcgaaagagca aagtgtggggatcttcggacctcacgccatcggatgtgcccagatgggattagctagtaggtgaggtaatggctcacctaggcgacgatccctagct ggtctgagaggatgaccagccacactggaactgagacacggtccagactcctacgggaggcagcagtggggaatattgcacaatgggcgcaagcct gatgcagccatgccgcgtgtgtgaagaaggccttagggttgtaaagcacttttcagcgaggaggaagcatcanacttggtcggattgacg ttactcgcagaagaagcaccggctaactccgtgccagcagccgcggtaatacggagggtgcaagcgttaatcggaattactgggcgtaaagcgcac gcaggcggtttgttaagtcagatgtgaaatcccgcgcttaacgtgggaactgcatttgaaactggcaagctagagtcttgagagggggtagaat tccaggtgtagcggtgaaatgcgtagagatctggaggaataccggtggcgaaggcgggccctggacaaagactgacgctcaggtgcgaaagcgtg gggagcaaacaggattagataccctggtagtccacgctgtaaacgatgtcgacttggaggttgtgcccttgaggcgtggcttccggagctaacgcg ttaagtcgaccgcctggggagtacggccgcaaggttaaaactcaaatgaattgacgggggcccgcacaagcggtggagcatgtggtttaattcgat gcaacgcgaagaaccttacctactcttgacatccacgcaattcgccagagatggcttagtgccttcgggaaccgtgacacaggtgctgcatggctg tcgtcagctcgtgttgtgaaatgttgggttaagtcccgcaacgagcgcaacccttatcctttgttgccagcnngtnatgnngggaactcaaaggag actgccggtgataaaccggaggaaggtggggatgacgtcaagtcatcatggcccttacgagtagggctacacacgtgctacaatggcatatacaaa cagaagcgaactcgcgagg |
| 86 | atggcaatgcgtcaatgcgcaatctacggggaaggggggtattgggaaatccaccactacccaaaaccttgtagcggctctggccgaaatgaataag aaggtcatgatcgtcggctgtgacctaaggctgattcaacccgcctcattctgcatgcgaaagcacagaacaccatcatggaaatggccgctgaa gtgggctccgtgaagatctggagctgaagatgtgatgcaaatcggtcatgcgcgtgcgctgtgcgaatcaggcggccctgagcctggtgtg ggttgtgccggacgcgggtgatcacgccatcaacttcctgaagaagaaggcgcgtatgtgccggatcggattttgtgttttacgacgtattg ggcgatggtctgtggcggtttcgcgatgccaattcgcgaaaacaaagcgcaggaaatctacatcgtgtgctccggtgaaatgatggcgatgtat gccgccaacaacatttccaaaggcatcgtgaaatacgcgaaatcgggcaaagttcgcctggccgggctgatctgtaactcccgccagacggatcgc |

TABLE H-continued

| SEQ ID NO: | Sequence |
|---|---|
| | gaagatgaactgatcatcgcgctggctgaaaaacttacacgcaatttgatccacttcgtgccgcgtgacaacattgtgcaacgcgctgaaatccgc cgcatgacggtcatcgaatacgacccgacttgtgcgcaggcagatcagtatcgtgcactggcgaacaaaatcgtcaacaacaccaaaatggtggtg ccgacaccggtcaccatggatgagctggaagccctgttaatggaatttggcattatggaagaagaagacctcgccatcgtcggtcgtaccgccgcc gaagaggcgtga |
| 87 | atgaaggcaaaagagattctggcgctgattgatgagccagcctgtgagcataaccacaagcagaagtcggggttgcagcctgccgaaacgggcgcg acggcaggcggttgtgcgtttgatggcgcgcagattgcgctgctgccggtcgcggacgtcgcgcatctggtgcacggcccgattggctgtaccggc agttcatgggacaaccgtggcagccgcagttccgggccttccatcaaccgcatgggcttcaccaccgacatgagcgagcaggatgtgattatgggg cgcggcgagcgacgcttatttcacgccgtgcagcacatcgtcagccattaccatccggtggcggtctttatttacaacacctgcgtacccgcgatg gaagggatgacgttgaagccgtgtgtcgcgccgcatcggccgctgccggtgtgccggttatttcagtcgatgccgccggtttctacggcagcaaa aatctcggtaaccgcattgccggggacgtgatggtcaaaaaggtgatcggccagcgcgaacccgcgcgtggccggaaaactcaccgatccccgcc ggacaccgccacagcatcagcctgattggcgaattcaatattgccggcgagttctggcacgttctgccgctgctcgatgagctcgggatccgcgtg ctgtgcagcctttccggggattcccgttttgctgaaatccagactatgaaccgtggcgaagccaacatgctggtgtgctcgcgggcgctgatcaac gtcgcccgaaaaatggaagagcgttaccagatcccacatggttgaaggcagttttttatggcctgcgttccatggctgattccctgcgcacgatcgc gtgctgctcaaagacccggatttacaggcgcgcacagaacgtctgattgagcgcgaggaggcggcgacacatcttgcgcttgcgccttaccgtgcg cggctcagcgggcgcaaggcgctgctgtataccggtggcgtgaaatcctggtcggtggtctcggcgttacaggatttaggcatcacggtggtggcg accggcacccgaaaatcaaccgaagaagacaagcagcgtattcgcgaactgatgggtgaagacgtgctgatgctcgacgaaggcaatgccagaacc ttgctcgacaccctctatcgtttcggcgcgacatcatgatcgccggggccgcaacatgtataccgcgtacaaagccgcctgccgttcctggata tcaatcaggagcgcgagcatgcgtttgccggatatcacgggctggtaaatctggccgaacagttgtgtatcaccctggaaagcccggtctgggcgc aggtcaaccgtctggcgccgtggcgctaa |
| 88 | atgaccagtgaaacacgcgaacgtaacgaggcattgatccaggaagtgctggagatcttccccgagaaggcgcttaaagatcgtaagaaacacatg atgaccaccgaccccggcgatggaatctgtcggcaagtgtattgtctcaaaccgcaaatcacagccgggcgtgatgaccgtgcgaggctgcgcttac gccggttccaaaggcgtggtctttggcccgatcaaagacatgcgcatatctcccacggccccggttggttgcggccagtattcccgtgccggacgc cgtaactattacaccggctggagcggcgtgaacagctttggcaccctcaacttcaccagtgattttcaggaacgggacatcgtatttggcggcgat aaaaagctcgacaaattgatcgatgaactggagatgttgttcccgcgtcgagcaaaggcatttcggtgcagtcggaatgtccggtcggtctgatcggc gatgacatttctgccgtcgccaaagccagcagcgccaaatcggatcggtaaggcgtcgtgccggtacgctgcgagggggttccgcggtgtgtcgcaatcg ctcggccatcacattgctaacgatgtcatccgcgactgggtgctggataaccgcgaaggcaatgaatttgaaaccacgccttacgacgtggcgatt atcggcgactacaacatcggcggtgacgcctggccctcacgtattctgctcgaagaaatggggctgcgcgtggtggcgcagtggtccggcgacggc acgctggtggagatggaaaacaccccgaaagtcgcgctcaatctggtcgactgctgctaccgctcgatgaactacatctcccgtcatatggaagaaaa cacggcattccgtggatggaatacaacttctttttggcccgaccaaaattgcggaatctctgcgcgaaatcgcggcggttttgacgataccatccga aaaacgccgaagcggtgattgaaaaatatcaggcgcaaacgcaggcggtgatcgacaaataccgtccgcgtctgaaggcaaaaaggtgctgttgt atctcggcggtttacgtccgcgccacatcatcggggcgtatgaagatctggaatggaaatcatcggtaccggctatgaattcggtcataacgatg attacgaccgcaccttaccgatgctcaaagaaggcacgttgctgttcgatgacctgagcagttatgagctggaagcgttcgttaaagcgctgaaac cggatcttgtcgggtcaggtatcaaagaaaaatacattttccagaaaatgggcgtgccgttccgccagatgcactcctgggattattccggccctt atcacgctacgacggtttcggcattttttgccgctgacatggacatgacgctgaacaatccggctggagtcagctgaccgcccccctggttgaaaa gcctga |
| 89 | atggctcaaattctgcgtaatgccaagccgcttgccaccacgcctgtcaaaagcgggcaaccgctcgcggcgatcctggccagtcaggggctggaa aattgcatcccgctggttcacgcggcaaggttgtagcgcgttcgccaaagtttttcttcatccagcatttcacgatccgatcccgttgcagtcca cggcgatggaatcgaccacgactatcatgggctcggatggcaacgtcagtactgcgttgaccacgttgtgtcagcgcagtaatccaaaagccattg tgattttgagcaccggactgtcagaagcgcagggcagtgatttgtcgatggcgctgcgtgagtttcgcgacaaagaaccgcgctttaatgccatcg ctattctgaccgttaacacgccggattttttacggctcgctggaaaacgcacagccgcgctgatggaaagcgtgatcactcagtgggtgccggaaa agccgccgaccggcatgcgtaacaagcgcgtgaacctgctggtgagccatctgctgacgccgggagatctgaattactgcgcagctatgtcgaag cctttggcctgcaaccggtgatcctgccggattatcacagtcgctggacggacatctggcgaatggcgatttcaatccggtcacgcagggcggca cgtcgcaacgccagattgaacaaatggggcagagcctgaccaccattaccattggcagttcgctcaactgcgccgccagtctgatggcgatgcga gccgtggcatggcgctgaacctgccgcacctgatgacgctggaaaacatgacagtctgatccgccatctgcatcaggtgtcaggccgcgaggtac cggcatggattgagcgccagcgcgggcaactgaggacgccatgatcgactgccatacctggctgcagtcacagtattgcgctggcggcagaagc ggatttgctggtggcggtgtgcgatttcgctcagagccagggaatgcgcgtcgggccggtgattgcgccggttaatcagcagtcactggccgggct gccggtcgaacaggtggtgatcggcgatctggaagatttacaaacccggctcgacagctaccggtttcactgctggtggcgaactcccacgctgc accactggcggaaaaaacggtatcgcgctggtacgtgccggtttcccgcttacgaccgtctcggggaatttcgccgcgtgcggcagggctatgc gggtattcgcgacaccttgttcgaactcgcgaactcgatgaggcgcgccatcacatgctgacggcgtatcactcaccgcttaggcaggtgttcggc ctgagcccggtaccggaggccagtcatgaggcggctaa |
| 90 | atgagtcaagatcttggcaccccaaaatcctgtttcccgctcttccagcaggatgaataccagaatatgtttacccacaaacgcgcgctggaagaa gcacacggcgaggcgaaagtgcgggaagtgtttgaatggaccaccacgcaggaatatcaggatctgaactctctcgcgtgaagcgctgaccgtcgac ccggcgaaagcctgccagccgttaggcgccgtactttgcgcgctgggttttaccaacacgttgccgtatgctccatggttcacaaggctgtgtggcc tatttccgtacctattttaatcgtcatttcaaagagccggtggcctgtgtttccgactcaatgaccgaagatgccgccgttttggcggaaataac aacatgaatgtcggtctggaaaacgccagcgcgctgtacaagccggaaattattgcggtctccaccacctgtatggcggaagtgatcggtgatgac ctgcaggcttttatcgccaaccgcaaaaaagacggatttgtggatgccgtatgccataccgtatgccatacaccggagtttttctgggcagtcatg tcaccggctgggacaacatgtttgaaggcttcgcccgtaccttaccaccgacgccacgcgggaatatcagccgggcaaacttgccaaactgaacg tggtgaccggttttgaaacttatctcggcaactaccgggttattcaccgcatgatgagccagatggggtcgaatgcagcgtcttgtccgatccgt ctgaagtgctcgacaccccggctgacggccaataccgcatgtatgccgacggcaccacgcaaaccgaaatgcgtgatgaccggatgccatcgacac cttgcgctgctgcaactggcaattacagaaaaccaaaaaggtggtgcagggcgactggaatcagccgggcacgaagtcagtgtaccgattggcct ggcggcgaccgatgcctgctgatgacggtaaggaactgaccggcaaaccgatagctgacgcgctggcgactgaactggccgtctggtggacatg atgctcgattctcacacctggctgcacggcaagcgtttcggtctctacggtgaccggattttgtgatgggcatgaccgcattcctgctggaactg ggctgtgaaccgaccaccattctcagccataacggcaacaaacgctggcagaaagccatgaagaaaatgctggctgattcgccttacggacaggac agcgaagtgtatgtgaactgcgatctgtgcattcccgctcgctgatgtttacccgtaaaccggacttttatgcggcaactatacggaaaattca ttcagcgtgacacgctggccaaaggcgaacagttcgaagtgccgctgatccgtatccggattcccgattttttgaccggcaccattgcaccgtcaga ccacctgggatacgagggcgcgatgagcatcctgacgcaactggtgaatgcggtgctcgaacagtcggatcgcgaaaccatgaagctcggcaaaa ccgactacaacttcgatctgatccgctaa |
| 91 | atgagcatcacgcgcgttatcagcatcatttcctgaggggaatatcgccagcgcttgtcgctgcaacatccttcactgttttataccgtggttgaac aatcatcggtggcgatttcgctgaccgatccgcaggcgcgcatttgttatgccaatccggcattctgccgccagacgggttttgcacttgagacac ttttgggcgagaaccaccgtctgctggccagccagcagacgccgaaacatatctatgacgaaatgtggcgcactttgttgcagggctaatcctgga acggccaactgatcaaccggcgtaataaccgttcgctttatctggcggatgtcactatcacgcctgttttaggcgcggacgggcaggtggagcatt acctcggcatgcacaaagatatcagcgagaaatacgcgctgcagcagggtgcgcaaccacatcaccttgttcacggaggtgctgaacattttattc |

TABLE H-continued

| SEQ ID NO: | Sequence |
|---|---|
| | ccgccgccgtggtggtggtggatgagaggacaatgtggtgatggacaatctggcctacaaaaccctgtgcgctgactgcggcgcaaaagagctgtt<br>ggccgaaatgggctatccgcaactcaaagagatgctcaacagtggcgaaccggtgccggtttccatgcgcggcaacgtacgctggttttcttcgg<br>tcagtggtcattgcagggcgttaatgaagaggccagccgcttttttaccggcattaccgcgccgggaaaactgattgttctcaccgactgaccgat<br>cagcatcaccggcagcagcagggttatcttgaccggctcaagcaaaaacttaccaacggcaaattgctggcagccatccgcgagtcgcttgatgcc<br>gcgctgattcagctcaacgggccattttaatatgctggcggctgcgcgtcgtcttaacggcgaagaaggcaacaacatggcgctggaattcgcctg<br>gcgcgaaggcgagcaggcggtgagtcgcttacaggcctgccgtccgtcgctggattttgagccgcaggcagaatggccggtcagtgaattcttcga<br>cgatctgagcgcgctgtacgacagccattttctcagtgacggtgaattgcgtacgtggtcatgccatctgatctgcacgctgtcgggcaacgaacg<br>caaatccttaccgcgctgagcttatgattgatcacacgctgtcacaggcgcaggccatgccgtctctgaagctctcggtgaacattgttgcgaag<br>caggatgcgagctggttgtgtgttttgacattaccgataatgtgccgcgtgaacgggtgcgttatgcccgcccggaagcggcgttttcccgtccgggc<br>aatggcatggagctgcgccttatccagacgctgatcgcccatcatcgcggttctttagatctctcggtccgccctgatggcggccacttgagacgt<br>tacgcctgccggtacagcaggttatcaccggaggcttaaaatga |
| 92 | atgacccagttacctaccgcggggcccggttatccggcgctttgatatgtntgcccagtttacggcgctttatcgcatcagcgtggcgctgagtcag<br>gaaagcaataccgcgcgcgcactggcggcgatcctcgaagtgctcacgatcatgcatttatgcaatacggcatggtgtgtcgttcgataaagaa<br>cgcaatgcactgtttgtggaatccctgcatggcatcgacggcgaaaggaaaaaagagacccgccatgtccgttaccgcatgggggaaggcgtgatc<br>ggcgcggtgatgagccagcgtcaggcgctggtgtaccgcgcatttcagacgatcagcgttttctcgaccgcctgaatatttacgattacagcctgc<br>cgatgattggtgtgccgatcccccggtgcggataatcagcctgcgggtggctggtggcacagccgatggcgttgcacgaagaccggctggctgccag<br>tacgcggttttttagaaatggcgccaatctcatcagccagccgtctgccacgccccccggaatcattgcctgctcaaacgccggtccggtgc<br>agtgttccgcgcagtttggttttgagcagatggtcgggaaagtcaggcgatgcgccagacgatggacattttacggcaggtttccaaatgggata<br>ccacggttctggtgcgtggtgaaagcggcaccggcaaggaacttatcgccaatgccattcattacaactcaccccgtgcggccgcgccatttgtga<br>aattcaactgcgccgcgctgccggataacctgctggaaagcgaactgttcggtcatgaaaaggggccttcaccggcgctatacgcacccgaaaag<br>gccgctttgaactggcggacggggcacgttattcctcgatgaaatcggcgaatgcgagcgcgtcgttcaggccaaattgctgcgcattttgcagg<br>aaggtgaaatgaaacggtcggcggcgatacccacgctgaaagtttgatgtgcgcattattgctgccaccaaccgtaatcttgaggaggaagtgcgtg<br>ccgggaattttcgcgaagacctgtattatcgcctcaacgtgatgccggtttcgctgcctgactgcgtgaaaggctggatgatatcgccgatctgg<br>cgccgtttctggtcaaaaagattgcgctgcgtcaggggcgggaactgcgcatcagtgatggtgcggtgcgtctgctgatgacctacgctggccag<br>gcaacgtgcgtgaactggaaaactgcctcgaacgggcgtcggtaatgaccgatgaagggctgatcgaccgcgacgtgatcctgttcaatcaccatg<br>agtccccggcgctgtccgtcaaaccccggtctgccgctcgcgacagatgaaagctggctggatcaggaactcgacgaacgccagcgggtgattgctg<br>cactggagaaaaccgctgggtgcaggccaaagcggcccgactgagggcatgacaccgcgcagattgcctaccgtatccagattatggacatcaa<br>catgcaccgtatctga |
| 93 | atgttgccactttcttctgttttgcaaagccacgcgcagagtttgcctgaacgctggcatgaacatcctgaaaacctgcccctccccgatgatgaa<br>cagctggctgtgctgagcagcagtgaattcatgacggacagtttgctggcttttccgcagtggtggcatgaaattgtccaaaatcccctcaggcg<br>caggagtggcaactttaccgtcagtggctggatgaatcactgacgcaggtgactgacgaagccgggttaatgaaagctttgcgtctgttccgccgc<br>cgtattctgaccccgcattgcgtggtcacagtccgcgcaaaccagcgaagcaaaagatacgcttcaccagctgagtgaactggcggaattattgatt<br>gtcagcgcccgtgactggctgtatgccgcttgctgtcgcggagttgagccggtcaatgccgcagggggaaccgcagggaaccgcagagaatgctgatcctcggg<br>atgggcaaactcggcggtggcgagctgaatttcatcggacatcgacctgacctgattttttgcttatccggaaaatggccagacacgcggcggtcgg<br>cgtgaactggataacgcacaattttcacccggctcggccagcgtctgatcaaagcgctggatcagcccactatcgacggttttgtctatcgcgtgg<br>acatgcgtttgcgtccgttcggcgacagtggcccgctggtgatgagcttcccggcactggaagattattatcaggaacaggggcgcgactgggaac<br>gctacgcaatggtgaaagcgcgtctgatgggcggcgctacgcgcggtatttaacagcaggaattgcgtaaaatgctgtaaaatgctgtttgtcttccgccgtta<br>tatcgatttcagtgtgatccagtccctgcgtaacatgaaaggcatgatcgcccgcgaagtacgccgcgtggtctgaaagacaacatcaaactcgg<br>cgcaggcggtattcgtgaaattgaatttatcgtgcaggtatttcagctgatccgtggcggtcgtgaaccggcattgcagcagcgtgcgttgttgcc<br>aacgcttcaggcgctggaaaatctggggctgctgccggtagagcaggtgttgcagttgcgtaacagctatctgttcctgcgacgtctggaaaacct<br>gttgcaggccattgctgacgagcaaacgcaaacctaccgtccgatgagctgaatcaggcgcgtctggcgtgggggatgaattacgctggctggcc<br>gcagcttaggatgcagtgaatgctcacatgcaggccgtacgcgcggtatttaacgatctgattggcgatgacacgccagatgccgaagatgacgtg<br>caactctcccggttcagcagttatggattgatacgcttgagcctgacgagctggctccgctggtgccgcaactgacgaaaatgcgcaacggcat<br>gttttacatcagattgctgattttcgccgtgacgtggataaacgcacgataggcacgtgggcgtgatcagttggatttgctgatgccgcgttta<br>ctggcccaggtctgcacctataaaaatgcggatgtgacgttacagcgcctgatgcagttgctgctcaatatcgtcacgcgcacgacgtatatcgag<br>ctgctggtggaatatcccggtgcgctcaaacagttaatacgtctgtgcgctgcctcgccgatggtggcgacgcaacttgcgcgtcatcctttattg<br>ctcgacgaactgctcgaccccgcgcacgctttaccagccgattgagccgggcgctaccgtagtgaactgcggcaatatctgatgcgggtgccaacc<br>gaagacgaagaacaacagcttgaagccgtgcgcagttcaaacaggcacagcatttacgtattgcggccggggatatttccggtgcgttgccggtg<br>atgaaagtcagtgaccatttaacctacccttgcggaggccattctgacgttgtggttgcaacaggcgtgggaacaaatggtcgtaaaatacggtcag<br>ccaacccatcttcagcaccgtaaagggcgcggttttgccgtggtgggtacggaaaaccggtggctgggagctgggttacagctcggatctggat<br>ctggtcttcctgctcgattgcgcgccggaagtcatgaccgacggcgaacgcagcattgacgggcgtcagttttatctgcggctggcgcagcgcatc<br>atgcatttattagcaccccgtacgtcgtcaggcattcttttatgaggttgaccccgcgtctgcggccttccggtgctcccggcatgctggtcagcacca<br>tcgaagcttttgcggattatcaggccaacgaagcctggacatgggagcatcaggcgctggttcgcgcgtgtggtttatggtgatccgcaactga<br>cgcagcaatttaatgccacgcgtcgcgacattcttttgccgccagcgcgatgccgacgcttgcgtaaggaagtccgtgaaatgcgcgagaaaatgt<br>atgccatctgggcagcaaaagagccgacgagtttgatctgaaagccgatccgggtggcataacggatattgaattcatcgcacaatatctggttc<br>tgcgtttcgcgcatgatgagccgaagagacccgctggtagataacgtgcggattttcgaactgatggcgcgacatgacatcatgccggaagaggaa<br>gcacgccatctgacgcaggcttacgtgacattgcgcgatgaaattcatcatctggcgtgcaggaacacagcggggaaagtggccgcagacagctttg<br>ccactgagcgcgcccaaatccgcgccagctgggcaaactggcttggctga |
| 94 | atgaaaaaacttttatccatgatggggcttggtgcagtggcttttgctaccttcgcttgccatggcagcaccaccagcagcggcaaacggtgctgat<br>aacgcctttatgatgatttgtaccgcgctggtattgttcatgaccgtacccggtgtggcgttgttctacggcggcttactgcgttctaaaaacgtt<br>ttgtccatgctgactcaggttattgttacctttgctctggtctgcgtcctgtggatcctctacggttacagcctgccttcagtgaaggtaacgcg<br>ttcttcggtggtttcagcaacgtaataatgaaaaggcattggcctgagtctgtgactggcaccttctcgcagatgatccacgttgcattccagtgt<br>tcatttgcctgcatcactgtagcgctgatcgtaggtggtattgctgaacgtgtgcgtttctcagcagttctgattttcactgtgctggctgact<br>ttctcttatattccgatggctcacatggtatgggcaggcggtttcctggctgctgacggtgcgctggactttgccggtggtaccgttgttcatatc<br>aatgccgcaattgctggcctggtaggggcttatctgctgggtaaacgcgccggttttggcaaagaagctttcaaaccacacaacctgccaatggtc<br>ttcactggcgcctcaatcctgtatgtgggctggttcggcttcaatgcgggttcagcaagtgccgcaagctctgttgccgcgctggctttcctgaac<br>actgtcattgctactgctgacgcatcctgtcctggacgctggttgagtggatggtgccggtaagccctcactgctgggcgcaagctccggtgct<br>atcgcaggtctggtggctatcacgcctgcagttgtacggtcggcgtaggtggtgctctgattatcgctgtaggcgtatcactgtctgtgg<br>ggggtgttacccctgaaaaaatggctgcgtgttgatgacacctgtgatgtgttcggtgttcatgcgtgtgcggtatcgtaggttgtctgctgacg<br>ggtgtattcacgtccagttcacttggcggcgtgggctacgcagaaggcgtgaccatgggccatcaggtttgggtgcagttcttcagcgtgtgcgta<br>acattggtctggtcaggcgttgttgccttcatcggttacaaagtggctgacatgatcgtaggtctgcgtgttcctgaagaacaagaacgcgaaggt<br>ctggacgttaacagccacggcgaaaacgcttacaaccaataa |

TABLE H-continued

| SEQ ID NO: | Sequence |
|---|---|
| 95 | tgaatatcactgactcacaagctacctatgtcgaagaattaactaaaaaactgcaagatgcaggcattcgcgttaaagccgacttgagaaatgaga<br>agattggctttaaaattcgcgaacacacgctacgccgtgttccttatatgttagtttgtggcgataaagaggtcgaagcaggcaaagttgctgttc<br>gtactcgtcgcggcaaagacttaggaagcatggatgttagcgaagtcgttgacaaactgctggcggaaatccgcagcagaagtcatcatcaactgg<br>aggaataaagtattaaaggcggaaaacgagttcaaccggcgtcctaatcgcattaacaaagagattcgcgcgcaagaagttcgcctcaccggcgtc<br>gatggcgagcagattggtattgtcagtctgaatgaagctcttgaaaaagctgaggaagcgggcgtcgatttagtagaaatcagtccgaatgccgag<br>ccgccagtttgtcgaatc |
| 96 | attgaagagtttgatcatggctcagattgaacgctggcggcaggcctaacacatgatagtcgagcggtagcacagagagcttgctctcgggtgacg<br>agcggcggaccggtgagtaatgtctgggaaactgcctgatggaggggggataactactggaaacggtagctaataccgcataacgtcgcaagaccaa<br>agtgggggaccttcgggcctcatgccatcagatgtgcccagatgggattagctagtaggtggggtaacggctcacctaggcgacgatccctagctg<br>gtctgagaggatgaccagccacactggaactgagacacggtccagactcctacgggaggcagcagtggggaatattgcacaatgggcgcaagcctg<br>atgcagccatgccgcgtgtgtgaagaaggccttcggggttgtaaagcactttcagcggggaggaaggcggtgaggttaataacctcaccgattgacg<br>ttacccgcagaagaagcaccggctaactccgtgccagcagccgcggtaatacggagggtgcaagcgttaatcggaattactgggcgtaaagcgcac<br>gcaggcggtctgtcaagtcggatgtgaaatccccgggctcaacctgggaactgcattcgaaactggcaggctagagtcttgtagaggggggtagaa<br>ttccaggtgtagggtgaaatgcgtagagatctggaggaataccggtggcgaaggcgggcccctggacaaagactgacgctcaggtgcgaaagcgtg<br>gggagcaaacaggattagataccctggtagtccacgctgtaaacgatgtcgatttggaggttgtgcccttgaggcgtggcttccggagctaacgcg<br>ttaaatcgaccgcctggggagtacggccgcaaggttaaaactcaaatgaattgacggggcccgcacaagcggtggagcatgtggtttaattcgat<br>gcaacgcgaagaaccttacctggtcttgacatccacagaactttccagagatggattggtgccttcgggaactgtgagacaggtgctgcatggctg<br>tcgtcagctcgtgttgtgaaatgttggg |
| 97 | atgaccatgcgtcaatgcgctatctacggtaaaggcggtatcggtaaatccaccaccacccagaatctcgtcgcggccctcgccgagatgggtaag<br>aaagtgatgatcgtcggctgcgatccgaaagcggattccaccgtctgatcctccacgctaaagcccagaacaccatcatggagatggcggcggaa<br>gtgggctcggtcgaggatctggagctcgaagacgttctgcaaatcggctatgtcgatgtccgttgcgccgaatccggcggcccggagccaggcgtc<br>ggctgcgccggacgcggggtgatcaccgccatcaacttcctcgaggaagaaggcgcctatgaagaagatttggatttcgtcttctatgacgtcctc<br>ggcgacgtcgtctgcggcggcttcgctatgccgatccgcgcgaaaacaaagcccaggagatctacatcgtctgctccggcgagatgatggcgatgtat<br>gccgccaacaatatctccaaagggatcgtgaagtacgccaaatccggcaaggtgcgcctcggcggcctgatctgtaactcgcaaaaccgaccggga<br>agacgaactgatcatcgccctggcggagaagcttggcacgcagatgatccacttcgttccccgcgacaacattgtgcagcgcgcggagatccgccg<br>gatgacggtgatcgagtacgacccgacctgtcagcaggcgaatgaatatcgtcaactggcgcagaagatcgtcaataacaccaaaaaagtggtgcc<br>gacgccgtgcaccatggacgagctggaatcgctgctgatggagttccgcatcatggaagaagaagacaccagcatcattggtaaaaccgccgctga<br>agaaaacgcggcctga |
| 98 | atggttaggaaaagtagaagtaaaaatacaaatatagaactaactgaacatgaccattttattaataagtcaaataaaaaagcttaaaacacaaac<br>cacttgctttttttaataataaaggaggggtttgggaagactacattagtagcaaatttaggagcagagctatcaataaactttagtgcaaaagttct<br>tattgtggatgccgaccctcaatgtaatctcacgcagtatgtatttagtgatgaagaaactcagattattgggcaagaaaatccagatagtat<br>ttatacagtaataagaccactatccttggtaaaggatatgaaagtgacctccctataaggcatgtagagaattcggttttgacataattgtcgg<br>tgaccctagacttgctttacaggaagaccttttagctggagactggcgagatgccaaaggcggtgggatgcgaggaattaggacaacttttgtatt<br>tgcagagttaattaagaaagctcgtgagctaaattatgattttgttttctttgacatgggaccatcattaggcgcaatcaacagggcagtattact<br>ggcaatggaattctttgtcgtcccaatgtcaatcgatgtattttcactatgggctattaaaaatattggctccacggtttcaatatggaaaaaga<br>attagacacagggattcggctctcagaggaacctagcgaattatcacaattatcacctcaaggaaaactaaagttttctcggttacgtcacccaaca<br>acataaagaacgctctggatacgatacaattcagcttgagaatactgaggaagaaataaaatcgaaacgtcgggtaaaggcgtatgaagacattgg<br>agaggtgtttccttctaaaattactgagcatctttctaaactttatgcatcaaaagatatgaacccacaccttggagatatacgtcatttaggtag<br>tttagctccgaaatcacaatcacaacacgttccgatgatatcagtgtctggtacaggaaattacaccagacttagaaaaagcgcgcgtgaacttta<br>tcgagatattgcaagaagatacttagagaacattcagactgctaatggcgagaaatag |
| 99 | atgaagggaaaggaaattctggcgctgctggacgaacccgcctgcgagcacaaccagaagcaaaaatccggctgcagcgcccctaagcccggcgc<br>taccgccggcggttgcgccttcgacggcgcgcagataacgctcctgcccatcgccgacgtcgcgcacctggtgcacggcccatcggctgcgcggg<br>cagctcgtgggataaccgcggcagcgtcagcgccggcccggccctcaaccggctcggctttaccaccgatcttaacgaacaggttgtgattatggg<br>ccgcggcgaacgccgcctgttccacgccgtgcgtcacatcgtcgaccgctatcatccggcggcggtctttatctacaacacctgcgtaccggcgat<br>ggagggcgatgacatcgaggcggtctgccaggccgcacagaccgccaccggcgtcccggtcatcgctattgacgccgccggtttctacggcagtaa<br>aaatcttggcaacgaatggcgggcgacgtgatgctcaggcaggtgattggccagcgcgaaccggccccgtggccagacaacacgcccttgcccc<br>ggcccagcgccagcgatatcggcctgattggcgaattcaatatcgccggcgagttctcggcaggtccagccgctgctcgacgagctggggatccgcgt<br>cctcggcagcctctccggcgacggccgctttgccgagatcagaccctgcaccgggcgcaggccaatatgctggtgtgctcgcgcgggcgctgatcaa<br>cgtcgcccggggctggagctgcgctacggcacgccgtggtttgaaggatgcttctacgggatccgcgccacctccgacgcctgcgccagctggc<br>gacgctgctggggatgacgacctgcgccgccgcaccgaggcgctgatcgcccgcgaagagcaggcggcggagcaggctcttgcgccgtggcgtga<br>gcagctccgcgggcgcaaagtgctgtctcatacccggcggcgtgaaatcctggtggtatcggccctgcaggatctcggcatgaccgtggtggc<br>caccggcacgcgcaaatccaccgaggaggacaaacagcggatccgtgagctgatgggcgacgaggcggtgatgcttgaggagggcaatgcccgcac<br>cctgctcgacgtggtgtaccgctatcaggccgacctgatgatcgccggcgacgcaatatgtacaccgctggaaagcccggctgccgttctcgat<br>atcaatcaggagcgcgagcacgcctacgccggctatcagggcatcatcaccctcgcccgccagctctgtctgaccctcgccagccccgtctggccg<br>caaacgcatacccgcgccccgtggcgctag |
| 100 | atgaccaacgcaacaggcgaacgtaaccttgcgctcatccaggaagtcctggaggtgtttcccgaaaccgcgcgcaaagagcgcagaaagcacatg<br>atgatcagcgatccgcagatggagagcgctcggcaagtgcattatctcgaaccgtaaatcgcagcccgggggtgatgaccgtgcgaggctgcgcctat<br>gcgggctcgaaaggggtggtgtttgggccaatcaaaagacatggccccatatctcgcacggcccccatcggctgcggccagtattcccgcgccgacgg<br>cgcaactactataccggcgtcagcggtcgacagcttcggcaccctgaacttcacctctgattttcaggagcgcgatattgttttcggcggcgat<br>aaaaagctgaccaaactgatcgaagagatggagctgctgttcccgctgaccaaaggggatcaccatccagtcggagtgcccgtgggcctgatcggc<br>gatgacatcagccgcgtagccaacgccagcagcaaggcgctggataaaccggtgatcccggtgcgctgcgaaggctttcgcggcgtatcgcaatcg<br>ctgggccaccatatcgccaacgacgtggtgcgcgactgggtgctgcaacaatcgcgaagggcagccgtttgccacaccccgtacgatgttgccatc<br>attggcgattacaacatcgccggcgacgcctgggcctcgcgcattctgctggaagagatgggcctgcgtagtggcgcagtggttccggcgacggc<br>accctggtggagatggagaacaccccattcgttaagcttaacctcgtccactgctaccgttcgatgaactatatcgcccgccatatgagagaaa<br>catcagatcccatggatggaatataacttcttcggcccgaccaaaatcgccgaatcgctgcgcaagatcgccgatcaatttgatgacaccattcgc<br>gccaatgcgaagcggtgatcgcataatatgaggggcagatggcggccatcatcgccaaatatcgcccgcggctggagggcgcaaagtgctgctg<br>tacatgggggggctgcggcgcacgtcatcggcgcctatgaggatctcggatggagatcatccgccgccggctacggagtttgcccataacgat<br>gattacgaccgcaccctgccggacctaaagagggcaccctgctgtttgacgatgccagcagctatgagctgtgaggccttcgtcaaagcgctgaaa<br>cctgacctcatcggctccgggatcaaagagaaatatatcttccagaaaatgggggtgccgttccgccagatgcactcctgggactattccggcccc<br>tatcacggctatgacggcttcgccatcttttgcccgcgatatggatatgaccctgaacaatccggcgtggaacgaactgactgccccgtggctgaag<br>tctgcgtga |

TABLE H-continued

| SEQ ID NO: | Sequence |
|---|---|
| 101 | atggcagatattatccgcagtgaaaaaccgctggcatgagcccgattaaaaccgggcaaccgctcggggcgatcctcgccagcctcgggctggccc<br>aggccatcccgctggtccacggcgcccagggctgcagcgccttcgccaaagttttctttattcagcatttccatgacccggtgccgctgcagtcga<br>cggccatggatccgaccgccacgatcatgggggccgacggcaatatcttcaccgcgctcgacaccctctgccagcgccacagcccgcaggccatcg<br>tgctgctcagcaccggtctggcggaagcgcagggcagcgatatcgcccgggtggtgcgccagtttcgcgaggcgcatccgcgccataacggcgtgg<br>cgatcctcaccgtcaatacccccggattttttttggctctatggaaaacggctacagcgcggtgatcgagagcgtgatcgagcagtgggtcgcgccga<br>cgccgcgtccggggcagcggccccggcgggtcaacctgctggtcagccacctctgttcgccagggggatatcgaatggctgggccgctgcgtggagg<br>cctttggcctgcagcccgtgatcctgccggacctctcgcagtcaatggatggccacctcggtgaaggggattttacgcccctgacccagggcggcg<br>cctcgctgcgccagattgcccagatgggccagagtctgggcagcttcgccattggcgtgtcgctccagcgggcggcatcgctcctgacccaacgca<br>gccgaggcgacgtgatcgccctgccgcatctgatgaccctcgaccattgcgataccttatccatcagctggcgaagatgtccggacgccgcgtac<br>cggcctggattgagcgccagcgtggccagctgcaggatgcgatgatcgactgccatatgtggcttcagggccagcgcatggcgatggcggccgagg<br>gcgacctgctggcggcgtggtgtgatttcgcccgcagccagggggatgcagcccggccgctggtcgccccaccagccaccccagcctgcgccagc<br>tgccggtcgagcaagtcgtgccggggggatcttgaggatctgcagcagctgctgagccaccaacccgccgatctgctggtggctaactctcacgccc<br>gcgatctggcggagcagtttgccctgccgctgatccgcgtcggttttcccctcttcgaccggctcggtgagtttcgtcgcgtccgccaggggtacg<br>ccggtatgcgagatacgctgtttgaactggccaatctgctgcgcgaccgccatcaccacaccgccctaccgctcgccgcttcgccagggcgccg<br>accccagccggcttcaggagacgcttatgccgccattaa |
| 102 | atgagccaaacgatcgataaaattcacagctgttatccgctgtttgaacaggatgaataccagacccgttccagaataaaaagaccttgaagag<br>gcgcacgacgcgcagcgtgtgcaggaggttttgcctggaccaccaccgccgagtatgaagcgctgaaatccagcgcgaggcgctgaccgtcgacc<br>cggccaaagcctgccagccgctcggcgccgtactctgcgcgctggggttcgccggcaccctgccctacgtgcacggctcccagggctgcgtcgcct<br>attttcgcacctactttaaccgccattttaaagagccggtcgcctgcgtctccgactccatgaccgaggacgcggcggtgttcggcggcaacaaca<br>acatgaatctgggcctgcagaatgccagcgcgctgtataaacccgagattatcgccgtctccaccacctgtatggccgaggtgatcggcgacgatc<br>tgcaggcgtttatcgccaacgccaaaaaagagggattgttgacgaccgcatcgccattccttacgcccatacccccagctttatcggcagccatg<br>tcaccggctgggacaatatgttcgaagggttcgcgaagacctttaccgctgactacgccgggcagccgggcaaacagcaaaagctcaatctggtga<br>ccggatttgagacctatctcggcaacttccgcgtgctgaagggatgatggcgcagatggatgtcccgtgcagcctgctctccgacccatcagaggt<br>gctcgacaccccgccgacggccattaccggatgtacgccggcggcaccagccagcaggagatcaaaaccgcgccggacgccattgacaccctgct<br>gctgcagccgtggcagctggtgaaaagcaaaaaggtggttcaggagatgtggaaccgcccgccaccgaggtggccgttccgctgggcctggccgc<br>caccgacgcgctgctgatgaccgtcagtcagctgaccggcaaaaccgatcgccgacgactgaccaggagcgcggccggctggtcgacatgatgctgg<br>attcccacacctggctgcatggcaaaaaattcggcctctacggcgatccggatttcgtgatgggcgtgacgcgcttcctgctggagctgggctgcg<br>agccgacggtgatcctcagtcataacgccaataaacgctggcaaaaagcgatgaagaaaatgctcgatgcctcgccgtacggtcaggaaagcgaag<br>tgttcatcaactgcgacctgtggcacttccggtcgctgatgttcacccgtcagccggactttatgctcggtaactcctacggcaagtttatccagg<br>cgatacccctggcaaagggcaaagcctcgaagtgccgctgatccgtctgggctttccgctgttcgaccgccatcatctgcaccgccagaccacctg<br>gggctatgaaggcgcaatgaacatcgtcacgacgctggtgaacgccgtgctggaaaaactggaccacgacaccagccagttgggcaaaaccgatta<br>cagcttcgacctcgttcgttaa |
| 103 | atgaccctgaatatgatgctcgataacgccgcgccggaggccatcgccggcgcgctgactcaacaacatccggggctgttttttaccatggtggaa<br>caggcctcggtgccatctccctcaccgatgccagcgccaggatcatttacgccaaccccggcgttttgccgccagaccggctattcgctggcgcaa<br>ttgttaaaccagaacccgcgcctgctggccagcagccagacgccgcgagatctatcaggagatgtggcataccctgctccagcgtcagccctgg<br>cgcggtcagctgcattaatcagcgtcgggacggcggcctgtacctggtggagattgacatcaccccggtgcttagccccgcaaggggaactggagcat<br>tatctggcgatgcagcgggatatcagcgtcagctacaccctcgaacagcggctgcgcaaccatatgaccctgatggaggcggtgctgaataatatc<br>cccgccgccgtggtagtggtggacgagcaggatcgggtggtgatggacaacctcgcctacaaaaccttctgcgctgactgcggcgggcgggagctg<br>ctcaccgagctgcaggtctcccctggccggatgacgcccggcgtggaggcgatcctgccggtggcgctgcgcggggccgcgcgctggctgtcggta<br>acctgctggccgttacccgccgtcagtgaagaggccagccgctacttttatcgacagcgcgctggcggaccctggtggtgatcgccgactgtacc<br>cagcagcgtcagcagcaggagcaaggcgccttgaccggtcgaagcagcaaatgaccgccggcaactgctggcggcgatccgcgagtcgctgaacg<br>ccgcgctgatccagctgaactgcccgattaatatgctggcggcagcccgtcggctgaacggcgagggaagcgggaatgtggcgctggaggccgcct<br>ggcgtgaaggggaagaggcgatggcgcggctccagcgctgtcgcccatcgctggaactcgaaaaccccgccgtctggccgctgcagccttttcg<br>acgatctgtcgcgccctctaccgtacacgcttcgatccccgacgggctgcaggtcgacatggcctcaccgcatctgatcggctttggccagcgcacc<br>cactgctggcgtcttaagcctgtggctcgatcgcaccctggccctcgccgcgcgaactccctccgtgccgctggcgatgcagctctacgccgagg<br>agaacgacggaggctgtcgctgtatctgactgacaacgtaccgctgctgcaggtcgctacgctcactcccccgacgcgctgaactcgccggcaa<br>aggcatggagctgcggctgatccagaccctggtggcgcaccatcgcgagccattgagctggcttcccgaccgcagggcggcacctgcctgaccctg<br>cgtttcccgctgtttaacaccctgaccggaggtgaagcatga |
| 104 | atgatccctgaatccgaccggacaccaccgtcagacgcttcgacctctctcagcagttcaccgccatgagcggataagcgtggtgctgagcggg<br>ccaccgaggcagcaaaacgctgcaggaggtgctcagcgtattacacaacgatgcctttatgcagcacgggatgatctgcctgtacgacagcgagc<br>aggagatcctcagtatcgaagcgctgcagcaaaccggccagcagcccctcccggcagcacgcagatccgctatcgcccggcgagggactggtgg<br>ggaccgtgctggccagggggcagtcgctggtgctgccccgggtcgccgacgatcagcgttttctcgaccgcctgagcactacgattacgatctgcc<br>gtttatcgccgtaccgttgatgggcccaacgcccggccaataggggtgctggcggcccagccgatggcgcgccaggaagagcggctgccggcctg<br>cacccgttttctcgaaaccgtcgccaacctcgtcgcccagaccatccggctgatgatccttccggcctcaccgccctgtcgagccgccagccgcc<br>gaaggtggaacgccgccggcctgctcgtcgtcgcgcggcgtgggccttgacaatatggtcggcaagagcccggcgatgcgccagatcgtggaggt<br>gatccgtcaggtttcgcgctggcgacaccgtgctggtacgcggccagaccgccgggaaaagctgatcgccaacgccatccatcaccattc<br>gccacgggctggccgccgcttcgtcaaatttaaactgcgcgcgctgccggacaccctgctggaaagcgaactgttcggccatgagaaaggcgcct<br>ttaccgagcggtgcgtcagcgtaaaggacgttttgagctggcggatgcggcaccctgttcctcgatgagattggtgaaagcagcgcctcgttcca<br>ggccaagctgctgcgatcctccaggaggggagatggagcgggtcggcggcgatgagaccctgcgggtgaatgtccgcatcatcgccgccaccaac<br>cgtcacctggaggaggaggtccggctgggccatttccggcaggatctctatcatcgctgaacgtgatgccatcgccctgccccccgagcgcgagcat<br>caggaggacatcgccgagctgcgcgcacttcctggtgcgcaaaatcggccagcatcaggggcgcacgctgcggatcagcgagggcgcgatccgcctg<br>ctgatggagtacagctgccgggtaacgttcgcgaactggagaactgcctcgaacgatcggcggtgatgcggagtggcctgatcgatcgcacg<br>tgatcctcttcactcaccaggatcgtcccgccaaagccctgcctgcctgcgggcagcggaagacagctggctggacaacagcctggacgaacgt<br>cagcgactgatcgccgcgctggaaaaagccggctggggtgcaggccaagccggcacggctgctggggatgacgccgcgcaggtcgcttatcggatc<br>cagatcatggatatcaccctgccgcgtctgtag |
| 105 | atgatgccgctttctccgcaattacagcagcactggcagacgtcgctgaccgtctgccagcggatttcccattgccgaactgagcccacaggcc<br>aggtccgtcatggcgtcatgcgattttgtcgaacagagtgtgatcgcccagcccggctggctgaatgagcttgcggactcctcgccggagcggaa<br>gagtggcggcattacgaggcctggctgcaggatcgcctgcaggcgttcactgacgaagcggggtttgatgcgagagctgcgtcttcttccgccgcag<br>atgatggtccgcatcgcctgggcgcaggcgctgtcgctggtgagcgaagaagagactctgcagcagctgagcgtcctggcggagaccctgattgtc<br>gccgcccgcgactggctgtacgccgcctgctgtaaggagtggggaacgccatgcaatgccgagggccagccgcagccgctgctgatcctcgggatg<br>ggaaaagctgggcggcggcgagctgaacttctcttccgatatcgatctgatctttgcctggcctgagcatggcgccaccgcggcggccgccgcga<br>gctggataacgcccaggcttacccgtctgggcagcggctgatcaaggcccttgaccagccgacgcaggacggctttgtctatcgggttgacatg |

TABLE H-continued

| SEQ ID NO: | Sequence |
|---|---|
| | cgcctgcggccgtttggcgacagtgggccgctggtactcagttttgcggcgctggaagattattaccaggagcagggtcgggactgggaacgctat gcgatggtgaaagcgcggatcatgggcgataacgacggcgtgtacgccagcgagttgcgcgcgatgctccgtccttcgtcttccgcgttatatc gacttcagcgtgatccagtcgctgcgtaacatgaaaggcatgatcgcccgcgaagtgcggcgtcgcgggctgaaagacaacatcaagctcggcgcc ggcgggatccgtgaaattgagtttatcgttcaggtcttccaactgatccgcggtggtcgcgaacctgcactgcagcaggcccctgctgccgacgc tggcggcgattgatgagctacatctgctgccggaaggcgacgcggcgctgctgcgcgaggcctatctgttcctgcgccggctggaaaacctgctgc aaagcatcaacgatgagcagaccagaccctgccgcaggatgaacttaaccgcgccaggctggcgtggggatgcataccgaagactgggagacgc tgagcgcgcagctggcgagccagatggccaacgtgcggcgagtgtttaatgaactgatcggcgatgatgaggatcagtccccggatgagcaactgg ccgagtactggcgcgagctgtggcaggatgcgctggaagaagatgacgccagcccggcgctggcgcatttaaacgataccgaccgccgtagcgtgc tggcgctgattgccgattttcgtaaagagctggatcggcgcaccatcggccccgcgggccgccaggtgctggatcagctgatgccgcatctgctgag cgaaatctgctcgcgccgatgcgccgctgcctctggcggatcacgcgcgtgttgaccgggatcgtcacccgtaccacctatcttgagctgctga gcgaattccccgcgcgctgaagcacctgatcacgctctgcgcggcgtcgccgatggtcgccagccagctggcgcgcacccgctgctgctggatg agctcgctggatcccaacaccctctatcagccgacggcgaccgatgcctatcgcgacgagctgcgccagtacctgctgcgcgtgccggaagaggat gaagagcagcagctggaggcgttgcgccagtttaagcaggcgcagcagagcatatcgcggcggcggatatcgctggtaccctgccggtgatgaagg tcagcgatcattttaacctggcttgccgaaacgatcctcgacgcggtgcagcaggcatgggggcagatggtcgctcgctacggccagccgaccc acctgcacgatcgccaggtcgcggcttcgccgtcgtcggctacggtaagcttggcgctgggagctgggctacagctccgatctcgatctggtgt tcctccatgactgcccggcggaggtgatgaccgacggcgagcgggagattgacggccgtcagttctacctgcggctggccagcggatcatgcacc tgttcagcacccgcacctcgccggtattctctacgaagtggacgcccggctgcgtccttctggcgcggcgggatgctggtcaccaccgccgacgc gtttgctgactatcagcagaacgaagcctggacgtgggaacatcaggcgctggtgcgccgcctggtctatgcgcgaccccggcgctgcaggcgcg cttttgacgccattcgtcgcgatatcctgaccacccccgcgggagggggatgaccctgcagaccgaggttcgcgagatgcgcgagaagatgcgcgccca ccttggcaacaaacatcccgatcgtttgatatcaaagccgatgccggcgggatcaccgatattgaatttattactcagtatctggtcctacgctat gccagtgacaagccgaagctgacccgctggtctgacaacgtgcgtattcttgagctgctggcgcagaagacatcatggacgaggaggaggcgcgcg cctaacgcatgcgtacaccaccttgcgtgatgcgctccatccctggccctgcaggagcagccgggacacgtggcgccagaggccttcagccggg agcgtcagcaggtcagcgccagctggcagaagtggctgatggcttaa |
| 106 | agcgtcaggtaccggtcatgattcaccgtgcgattctcggttccctggagcgcttcattggcatcctgaccgaagagttcgctggcttcttcccaa cctggattgcaccagtgcaggtagtggtcatgaatattaccgattctcaggctgaatacgttaacgaattgacgcgtaaactacaaaatgcgggca ttcgtgtaaaagcagactttgagaaatgagaagattggctttaaaatccgcagcacacttttacgtcgtgcccgtatatgttggtcgtgtggcgacaa agaagtcgaagccggcaaagtggccgtgcgcacccgtcgcgggaaagacctcggcagcatggacgtaagtgaagtgattgagaagctgcaacaaga gattcgcagccgcagtcttcaacaactggaggaataaggtattaaaggcggaaaacgagttcaaacggcacgtccgaatcgtatcaatggcgagat tcgcgccctggaagttcgc |
| 107 | atgaaaatggcaacaatgaaatcgggtctgggggcattagccccttcttccgggactggcaatggccgcgcccgcagtggcggacaaagccgataac gcgtttatgatgatttgcaccgcgctggttctgtttatgaccatcccgggatcgcgctgttttacggcggcctgatccgcggcaaaaacgtcctt tccatgctgactcaggtgattgtgaccctttggcctcgtctgcgtactgtgggtgatttatggctataccctggccttcggcaccggcggcagcttc ttcgctagttttgactgggtgatgctgaaaaatattgaactgaaaggcgctattgggcacctctctatcagtacatccacgtggcatccaggctcgt tcgcctgtatcaccgtcgggctgatcgtgcgggcgctggctgagcgtattcgttctccgccgtgctgattttttgtggtggtgtggatgacgctct cttatgttccgattgcgcacatggtctggggcggcggtctgctggcgaccacggcgcgctggacttcgcgggcggcaccgttgtacacatcaacg ccgcggttgccggctggtgggtgcgtacatgatgggcaaacgtggggcttcggcaaagaagcgttcaaaccgcacaatctgccgatggtgttcac cggaaccgccatcctctacgtgggctggttcggcttcaacggcggccagcgcagcgaacgaaattgccgcattggccttcgtcaacaccgt cgtcgccacagcggctgccatcctggcgttgggaccttggcgaatgggccctgcgcggtaaaccttcactgctgggcgcctgctccggggcgattgc cggtctggttggcgtcacaccagctgtgggtatatcggtgtcggtgggcgttgattgtgggatcgcatctggtctggcgggcatctgggcgta acggcgctgaaacgtggctgcgggttgatgaccctttgcgacgtcttcggcgtccacggcgtctgcggcatcgtcggctgtatcctgaccggtatc ttcgcggccacctctctgggcggcgtgggttatgcagaaggcgtcaccatgggccatcagctgctggtgcaactcgagagtatcgcggattaccatc gtctggtcgggcgttgtcgctttcattggctacaaagtggcggacatgaccgtggggctgcgcgtaccagaagagcaggagcgcgaaggactggac gtcaacagcggcatggcgaaaacgcctacaacgcctga |
| 108 | cgccgtcctcgcagtaccattgcaaccgactttacagcaagaagtgattctggcacgcatggaacaaattcttgccagtcgggctttatccgatga cgaacgcgcacagcttttatatgagcgcggagtgttgtatgatagtctcggtctgagggcattagcgcgaaatgattttttcacaagcgctggcaat ccgacccgatatgcctgaagtattcaattacttaggcatttacttaacgcaggcaggcaattttgatgctgcctatgaagcgtttgattctgtact tgagcttgatc |
| 109 | gctaaagttctcggctaatcgctgataacatttgacgcaatgcgcaataaaagggcatcatttgatgcccttttttgcacgctttcataccagaacc tggctcatcagtgatttttttgtcataatcattgctgagacaggctctgaagagggcgtttatacaccaaaccattcgagcggtagcgcgacggc aagtcagcgttctcctttgcaatagcagggaagaggcgccagaaccgccagcgttgaagcagtttgaacgcgttcagtgtataatccgaaacttaa tttcggtttgga |
| 110 | gcccgctgaccgaccagaacttccaccttggactcggctatacccttggcgtgacggcgcgcgataactgggactacatcccattccggtgatct taccattggcgtcaataggttacggtccggcgactttccagatgacctatattcccggcacctacaataacgttaacgtttacttcgcctgggctc gatacagttttaattcgctaagtcttagcaataaatgagataagcggtgtgtcttgtggaaaaacaaggactaaagcgttacccactaaaaaagat agcgacttttatcactttttagcaaagttgcactggacaaaaggtaccacaattggtgtactgatactcgacacagcattagtgtcgatttttcat ataaaggtaattttg |
| 111 | ttgaagagtttgatcatggctcagattgaacgctggcggcaggcctaacacatgcaagtcgagcggtagcacagagagcttgctctcgggtgacga gcggcggacgggtgagtaatgtagggaaactgcctgatggagggggataactactggaaacgtagctaataccgcataacgtcgcaagaccaaag tgggggaccttcgggcctcatgccatcagatgtgcccagatggattagctagtaggtggggtaacggctcacctaggcgacgatccctagctggt ctgagaggatgaccagccacactggaactgagacacggtccagactcctacgggaggcagcagtggggaatattgcacaatgggcgcaagcctgat gcagccatgccgcgtgtgtgaagaaggccttcgggttgtaaagcacttcagcggtgaggaaggcgntnaggttaataaccttgtcgattgacgtt acccgcagaagaagcaccggctaactccggcagcagccgcggtaatacggagggtgcaagcgttaatcggaattactgggcgtaaagcgcacgca ggcggtagtcaagtcggatgtgaaatcccccgggctcaacctgggaactgcattcgaaactggcaggctagagtcttgtagaggggggtagaattcc aggtgtagcggtgaaatgcgtagagatctggaggaataccggtggcgaaggcggccccctggacaaagactgacgctcaggtgcgaaagcgtgggga gcaaacaggattagataccctggtagtccacgctgtaaacgatgtctactgttgtggttccttgaggactttgtggccgtagctaacgcgttaaat agaccgcctggggagtacggccgcaaggttaaaactcaaatgaattgacgggggcccgcacaagcggtggagcatgtggtttaattcgatgcaacg cgaagaaccttacctggtcttgacatccacagaactttccagagatggattggtgccttcgggaactgtgagacaggtgctgcatggctgtcgtca gctcgtgttgtgaaatgttgggttaagtcccgcaacgagcgcaacccttatcctttgttgccagcggtnnggccgggaactcaaaggagactgcca gtgataaactggaggaaggtggggatgacgtcaagtcatcatggcccttacgaccagggctacacacgtgctacaatggcatatacaaagagaagc gacctcgcgagagcaagcggacctcataaagtatgtcgtagtccggattggagtctgcaactcgactccatgaagtcggaatcgctagtaatcgta |

TABLE H-continued

| SEQ ID NO: | Sequence |
|---|---|
| | gatcagaatgctacggtgaatacgttcccgggccttgtacacaccgcccgtacaccatgggagtgggttgcaaaagaagtaggtagcttaaccttc<br>ggggagggcgcttaccactttgtgattcatgactggggtgaagtcgtaacaaggtaaccgtaggggaacctgcggttggatcaccctcctt |
| 112 | atgaccatgcgtcaatgcgctatctacggtaaaggcggtatcggtaaatccaccaccacccagaatctcgtcgcggcctcgccgagatgggtaaga<br>aagtgatgatcgtcggctgcgatccgaaagcggactccacccgtctgatccttcacgctaaagcccagaacaccatcatggagatggcggcggaag<br>tgggctcggtcgaggatctggagctcgaagacgttctgcaaatcggctatgcgatgtccgttgcgccgaatccggcggccggagccaggcgtcg<br>gctcgccggacgcggggtgatcaccgccatcaacttcctcgaggaagaaggcgcctatgaggaagatttggatttcgtcttctatgacgtcctcg<br>gcgacgtagtctgcggcggcttcgccatgccgatccgcgaaaacaaagcccaggagatctacatcgtctgctccggcgagatgatggcgatgtatg<br>ccgccaacaatatctccaaggggatcgtgaagtacgcgaaatctggcaaggtgcgcctcggcggcctgatctgtaactcgcgcaaaaccgaccggg<br>aagacgaactgatcatccgccctggcggagaagcttggcacgcagatgatccacttcgttccccgcgacaacattgtgcagcgcgcggagatccgcc<br>ggatgacggtgatcgagtacgaccgacctgtcagcaggcgaatgaatatcgtcaactggcgcagaagatcgtcaataacaccaaaaaagtggtgc<br>caacgccgtgcaccatggacgagctggaatcgctgctgatggagttcggcatcatggaagaagaagacaccagcatcattggtaaaaccgccgctg<br>aagaaaacgcggcctga |
| 113 | atgaccaacgcaacaggcgaacgtaaccttgcgctcatccaggaagtcctggaggtgtttcccgaaaccgcgcgcaaagagcgcagaaagcacatg<br>atgatcagcgatccgcagatggagagcgtcggcaagtgcattatctcgaaccgtaaatcgcagcccggggtgatgaccgtgcgtggctgcgcctat<br>gcgggcttcgaaaggggtggtgtttgggccaatcaaagacatggcccatatctcgcacggccccatcggctgcggccagtactgcgcgccggacgg<br>cgcaactactataccggcgtcagcggtgtcgacagcttcggcaccctgaacttcacctctgattttcaggagcgcgatattgttttcggcggcgat<br>aaaaagctgaccaaactgatcgaagagatggagctgcttcccgctgctccaaagggatcaccatccaatcggagtgcccggtgggcctgatcggcg<br>atgacatcagcgccgtggccaacgccagcagcaaggcgctggataaaaccggtgatcccggtgcgctgcgaaggctttcgcggcgtatcgcaatcgc<br>tgggccaccatatcgccaacgacgtggtgcgcgactgggtgctgaacaatcgcgaagggcagccgtttgccagcacccgtatgatgttgccatca<br>ttggcgattacaacatcggcggcgacgcctgggcctcgcgcattctgctggaagagatggggcgtgcgcgtagtggcgcagtggttccggcgacggca<br>ccctggttgagatggagaacaccccattcgttaagcttaacctcgccactgctaccgacgatgaactatatcgcccgccatatggaggagaaacat<br>cagatcccgtggatggaatataacttcttcggcccgaccaaaatcgccgaatcgctgcgcaagatcgccgatcaatttgatgacaccattcgcgcc<br>aatgcggaagcggtgatcgccaaatatgaggggcagatggcggccatcatcgccaaatatcgcccgcggctggaggggcgcaaagtgctgctgtac<br>atggagggctgcggccgcgccacgtcatcggcgcctatgaggatctcggatggagatcatcgccgccggctacgagtttgcccataacgatgatt<br>acgaccgcaccctgcccgacctgaaagagggcacccctgctgtttgacgatgccagcagctatgagctggaggccttcgtcaaagcgctgaaacctg<br>acctcatcggctccgggatcaaagagaaatatatcttccagaaaatggggggtgccgttccgccagatgcactcctgggactattccgccctatc<br>acggctatgacggcttcgccatctttgcccgccatatggatatgaccctgaacaatccggcgtggaacgaactgactgccccgtggctgaagtctg<br>cgtga |
| 114 | atgaagggaaaggaaattaggcgctgctggacgaacccgcctgcgagcacaaccagaagcaaaaatccggctgcagcgctcctaagcccggcgcaa<br>ccgccggcggctgcgcttcgacgcgcgcagataacgctcctgcccatcgccgacgtcgcgcacctggtgcacggcccatcggctgcgcgggca<br>gctcgtgggataaccgcggcagcgtcagcgccggcccggccctcaaccggctcggcttaccaccgatcttaacgaacaggatgtgattatgggcc<br>gcggcgaacgccgcctgttccacgccgtccgtcactatcgtcgaccgctatcatccggcggcggtcttttatctacaacaacctgcgtaccggcgatgg<br>aggggatgacctggaggccgtctgccaggccgcacagaccgccaccggcgtcccggtcatcgccattgacgccgccggtttctacggcagtaaaa<br>atcttggcaaccgaatgcgggcgacgtgatgctcaggcaggtgattggcagcgcgaaccggcccgtggccagacaacacgcccttttgccccgg<br>cccagcgccacgatatcggcctgattggcgaattcaatatcgccggcgagttctggcaggtccagccgctgctcgacgagctggggatccgcgtcc<br>tcggcagcctctccggcgacggccgctttgccgagatccagaccctgcaccgggcgcaggccaatatgctggtgtgctcgcgcgcgctgatcaacg<br>tcgcccgggggctggagctgcgctacggcacgcgtggtttgaaggcagcttctacgggatccgcgcacctccgacgccttgcgccagctggcg<br>cgctgctgggaatgacgacctgtccgccgccaccgaggcgctgatcgcccgcgaagagcaggcggcggagcaggcgctggcgcctgtggcgcgagca<br>gctccgtgggcgcaaagtgttgctctacaccgcggcgtgaaatcctggtcggtggtatcagccctgcaggatctcggcatgaccgtggtggccac<br>cggcacgcggaaatccaccgaggaggacaaacaggatccgtgagctgatcgagcgacgaggcggtgatgcttgaggagggcaatgctcgcaccctg<br>ctcgacgtggtgaccgctatcaggccgacctgatgatcgccggcggacgcaatatgtacaccgcctggaaagccgctgccgtttctcgatatca<br>atcaggagcgcgagcacgcctacgccggctatcagggcatcatcaccctcgcccgccagactgtctgaccctcgccagtcccgtctggccgcaaac<br>gcatacccgcgccccgtggcgctag |
| 115 | atggcagacattatccgcagtgaaaaaccgctggcggtgagcccgattaaaaccgggcaaccgctcggggcgatcctcgccagcctcgggctggcc<br>caggccatcccgctggtccacgcgcccagggctgcagcgccttcgccaaagttttcttattcagcatttccatgacccggtgccgctgcagtcg<br>acggccatggatccgaccgccacgatcatgggggccgacggcaatatcttcaccgcgctcgacaccctctgccagcgccacagcccgcaggccatc<br>gtgctgctcagccaccggtctggcggaagcgcagggcagcgatatcgcccgggtggtgcgcagttttcgtgaggcgcatccgcgccataacggcgtg<br>gcgatcctcaccgtcaatacccggatttttttggctcgatggaaaacggctacagcgccggtgatcgagagcgtgatcgagcagtgggcgcgcga<br>cgccgcgtccggggcagcgccccggcgggtcaacctgctggtcagccaccctctgttcgcagggggatatcgaatggctgggccgctgcgtggagg<br>cctttggcctgcagccggtgatcctgccggaccctctcgcagtcaatggatggccaccctcggtgaaggggattttacgcccctgacccagggcggcg<br>cctcgctgcgccagattgcccagatgggccagagtctgggcagcttcgccattggcgtgtcgctccagcgggcggcatcgctcctgacccaacgca<br>gccgcggcgacgtgatcgccctgccgcatctgatgaccctcgaccattgcgataccttatccatcagctggcgaagatggccgacgccgcgtac<br>cggcctggattgagcgccagcgcgccagctgcaggatgcgatgatcgactgccatatgtggcttcagggccagcgcatggcgatggcggcggagg<br>gcgacctgaggcggcgtggtgtgatttcgcccgcagccaggggatgcagcccggcccgctggtcgccccaccagccaccccagcctgagcagct<br>gccggtcgatcaggtcgtgccggggatcttgaggatctgcagcagctgctgagccaccaacccgccgatctgctggtggctaactctcacgcccg<br>ctgatctggcggacagtttgcctgccgctgatccgcgtcggttttccctatcgaccggctcggtgagatcgtcgcgtccgccaggcgtacgcc<br>ggtatgcgagatacgctgtttgagctggccaatctgctgcgaccgccatcaccacaccgccctctaccgctcgccgcttcgccagggcgccgac<br>cccctgccggcttcaggagacgcttatgccgcccattaa |
| 116 | gtgccgctgatccgtctgggctttccgctgttcgaccgccatcatctgcaccgccagaccacctgggctatgaaggcgcaatgaacatcgtcacg<br>acgctggtgaacgccgtgctggaaaaactggaccacgacaccagttgggcaaaaccgattacagcttcgacctcgttcgttaa |
| 117 | atgaccctgaatatgatgctcgataacgccgcaccggaggccatcgccggcgcgctgactcaacaacatccggggctgttttttaccatggtggaa<br>caggcctcggtggccatatccctaccgatcgcacggcatcatttacgcgacccagctttgccgccagaccgctattcgctgcgcaat<br>tgttaaaccagaacccgcgcctgctggccagcagccagacgccgcgcgatctatcaggagatggcataccctgctccagctcagccctggc<br>gcgtcagctgattaatcagcgtcgggacggcggcctgtgcctggtggagattgacatcaccccggtgcttagcccgcaaggggaactggagcatt<br>atctggcgatgcagcgggatatcagcgtcagctacaccctcgaacaacggctgcgcaaccatatgaccctgatggaggcggtgctgaataatatcc<br>gccgccgtggtggtgtggacgagcaggatcggtggtgatggacaacctcgcctacataaccttctgcgctgactgcggcggccgggagctg<br>tcaccgactgcaggtctcccctggccggatgacgcccggcgtggaggcgatcctgccggtagcgctgccggggccgcgcctgctgtcggtaa<br>cctgctggccgttgccggcgtcagtgaagagggcagccgctacttatcgacagcgcgctgacgcggaccctggtggtgatcgcgactgtaccc<br>agcagcgtcagcagcaggagcaaggacgccttgaccggctgaagcagcaaatgaccgccggcaagctgctggcggcgatccgcgagtcgctggacg<br>ccgcgctgatccagctgaactgcccgattaatatgaggcggcagcccgtcggctgaacggcgagggaagcgggaatgtggcgctggaggccgcctg<br>gcgtgaagggcaagaggcgatggcgcggctccagcgctgtcgcccatcgctggaactcgaaaaccccgccgtctgccgctgcagcccttttcga |

TABLE H-continued

| SEQ ID NO: | Sequence |
|---|---|
| | cgatctgtgcgccctctaccgtacccgcttcgatcccgacgcgctgcaggtcgacatggcctcaccgcatctgatcggctttggccagcgcacccc gctgctgccgtgcttaagcctgtggctcgaccgcaccctggccctcgccgccgaattgccctccatgcgctggcgatgcagctctatgccgaggag aacgacggctggctgtcgctcgtacctgactgataacgtaccgctgttgcagggcgctacgccactccccgacgcgctgaactcgccgggtaaag gcatggagctgcgcctgatccagacccctggtggcgcaccatcgcggggccattgagctggcttcccgaccgcagggcggcacctgcctgaccctgc gtttcccgctgtttaacaccctgaccggaggtgaagcatga |
| 118 | atgatccctgaatccgaccccggacaccaccgtcagacgcttcgacctctacagcagttcaccgccatgcagcggataagcgtggtgctgagcggg ccaccgaggccagcaaaacgctgcaggaggtactcactgtattgcacaacgatgccatatgcagcacgggatgatctgctgtacgacagcgagca ggagatcctcagtatcgaagcgctgcagcaaaccggccagcagccctccccggcagcacgcagatccgctatcgccccggcgagggactggtggg gaccgtgctggcccaggggcagtcgctggtgctgccccgggtcgccgacgatcagcgttttctcgaccgcctgagcctctacgattacgatctgcc gtttatcgccgtaccgttgatggggccaacgcccggccaataggggtgctggcggccagccgatggcgcgcaggaagagcggctgccggcctg cacccgttttacgaaaccgtcgccaacacgtcgcccagaccatccggctgatgatcctccggcctcaccgccagtcgagccgccagccgccgaa ggtggaacggccgccggcctgctcgtcgtcgcgcgcgtgggccttgacaatatggtcggcaagagcccggcgatgcgccagatcgtggaggtgat ccgtcaggtttcgcgctgggacaccaccgtgctggtgcgcgtggaaagcggcaccgggaaagagctgatcgccaacgccatccatcaccattcgcc acggggctggccgccgcctcgtcaaatttaactgcggcgcgctgccggcacacccgtgctggaaagcgaactgttcggccatgagaaaggcgcctttac cggggcggtgcgtcagcgtaaaggacgttttgagctggccgatcgcggcaccctgttcctcgatgagattggtgaaagcagcgcctcgttccaggc caagctgctgcgtatcctccaggaggggagatggagcgggtcggcggcgatgagaccctgcgggtgaatgtccgcatcatcgccgccaccaaccg tcacctggaggaggaggtccgggctgggccattttccgcgaggatctctattatcgtctgaacgtgatgcccatcgccctgccccccgctgcgcgagcg tcaggaggacatcgccgagctggcgcacttcctggtgcgcaaaatcggccagcatcaggggcgcacgctgcggatcagcgagggcgcgatccgcct gctgatgagtacagctggccgggtaacgttcgcgaactggagaactgcctcgaacgatcggcggtgatgtcggagagtggcctgatcgatcgcga cgtgatcctcttcactcaccaggatcgtcccgccaaagccctgcctgccaggggcagcggaagacagctggctggacaacagcctggacgaacgt cagcgactgatcgcccgcgctggaaaaagccggctgggtgcaggccaaggcgccacggctgctggggatgacgccgcgccaggtcgcttaccggatc cagatcatggatatcaccctgccgcgtctgtag |
| 119 | atgatgccgctttctccgcaattacagcagcactggcagacggtcgctgaccgtctgccagcggattttcccattgcagaactgagcccacaggcc aggtcggtcatggcgttcagcgatttttgtcgaacagagtgtgatcgcccagccgggctggctgaatgagatgcggactcctcgccggaggcggaag agtggcggcattacggcctggctgcaggatcgcctgcaggccgtcactgacgaagcggggttgatgcgagagctgcgtctatccgccgccagat gatggtccgcatcgcagggcgcaggcgctcgctggtgagcgaagaagagaccctgagcagctgagcgccctgccggagaccctgattgtccgcg cccgcgactggctctacgccgcctgctgtaaggagtggggaacgccatgcaatgccgagggccagccgcagccgctgctgatcctcggatgggaa agctgggcggcggcgagctgaacttctatccgatatcgatagactctttgcctggcctgagcatggcgccaccgcggcggccgccgcagctggat aacgccagttcttaccgctctggggcagcggctgatcaaggccctgaccagccgacgcaggacggctttgtctatcgggttgacatgcgcctg cggccgttttggcgacagtgggccgctggtactcagctttgcggcactggaagattattaccaggagcagggtcgggactgggaacgctatgcgatg gtgtaagcgcggatcatgggcgataacgacggcgtgtacgccagcgagttgcgcgcgatgctccgtccttcgtcttccgccgttatatcgacttc agcgtgatccagtcgctgcgtaacatgaaaggcatgatcgcccgcgaagtgcggcgtcgcgggctgaaagacaacatcaagctcggcgccggcggg atccgtgaaattgagtttatcgttcaggtcttttcagctgatccaggttggtcgcgaacctgcactgcagcagccgccctgctgccgacgctggc gcgattgatgagctacatctgctgccggaaggcgacgcggcgctgctgcgcgaggcctatctgttcctgcgccggctggaaaacctgctgcaaagc atcaacgatgattcagacccagaccctgccgcaggatgaacttaaccgcgcaggctggcgtggggatgcataccgaagactgggagacgctgag cgcgcagctggcgagccagatgccaacgtgcggcgagtgttaatgaactgatcggcgatgatgaggatcagtcccccggatgagcaactggccga gtactggcgagctgtggcaggatgcgctggaagaagatgcgccggcgctggcgcatttaaacgataccgaccgcgtagcgtgctggc gctgattgccgattttcgtaaagagctggatcggcgcaccatcggcccgccggccgcaggtgctgatcagctgatgccgcatctgagagcgaa atctgctcgcgtgccgatgcgccgagcctctggccgcgatcaccgcgctgttgaccgggatcgtcacccgtaccacctatcttgagctgctgagcg aattcccccggcgcgctgaagcacctgatcacgctctgcgcggcgtcgccgatggtcgccagccagctggcgcgccaccccgctgctgctggatgagc tgctggatcccaaccacctctatcagccgacggcgaccgatgcctatcgccgacgagctgcgccagtaccttgctgcgcgtgccggaaggagcaag agcagcagctggaggcgtgcgccagtttaagcaggcgcagagctgcatatcgcggcggcgatatcctggtaccctgccggtgatgaaggtcagg atcacttaacctggcttgccgaagcgatcctcgacgcggttggtgcagcaggcatggggcgcagatggtcgctcgctacggtcagccgacccacctgc acgatcgccagggtcgcggatcgccgttgtcggctacggtaagctcggcgcctgggagctggactacagctccgatctcgatctggtgttcctcca tgactgcccggccgaggtgatgaccgacgcgagggggagattgacggccgtcagttctacctgcggcgtggccagcggatcatgcaccgttcagc acccgcacctcgtccggtattactacgaagtggacgccccggctcgtcatctgccgcaggttgctggtcaccaccgccgacgcgtttgctgac tatcagagaacgaagcctggacgtgggaacatcaggcgctggtgcgcgcccgcgtggtctatggcgacccggcgctgcaggcgcgctttgacgcca ttcgtcgcgatatcctgaccaccccgcggggagggacgaccctgcagaccgaggttcgcaagatgcgcgagaagatgcgcgcccaccttggcaaca aacatcccgatcgattgatatcaaagccgatgccggcgggatcaccgatattgaatttattactcagtatctggtcctacgctatgccagtgacaa gccgaagctgaccgctgtctgacaacgtgcgtattcttgagctgctggcgcaggacgacatcatggacgaggaggaggcgcgccttaacgca tgcatacaccaccttgcgtgatgcgctccatcacctggccctgcaggagcagccgggacacgtggcgccagaggccttcagccgggagcgtcagca ggtcagcgccagctggcagaagtggctgatggcttaa |
| 120 | atgaaaatggcaacaatgaaatcggtctgggggcattagcccttcttccgggactggcaatggccgcgcccgcagtggcggacaaagccgataac gcgtttatgatgatttgcaccgcgaggttctgtttatgaccatcccggggatcgcgctgattacggcggcctgatccgcggcaaaaacgtcctttc catgctgactcaggtgattgtgaccttggcctggtctgcgtactgtgggtgatttatggctatacccctggccttcggaaccggcggcagcttctt cggtagctttgactgggtgatgctgaaaaatattgaactgaaagcgctgatgggcaccttctatcagtacatccacgtggccttccagggctcgtt cgcctgtatcaccgtcgggctgatcgtgggggcgctggctgagcgatattcgtttctccgccgtcgtgattttcgtggtggtgatgacgctact tatgttccgattgcgcacatggtctgggcggcggtctgctggcgaccacgcgcgcgctggacttcgccggcgcaccgttgtacacatcaacgcc gcggttgccgggctggtgggtgcgtatatgatgggcaaacgtgtgggcttcggcaaagaagcgttcaaaccgcacaatctgccgatggtgttcacc ggaaccgccatcctctacgtgggctggttcggcttcaacgccggctccgcagcgcagcgaacgaaattgccgcactggctttcgtcaacaccgtc gtcgccacagcggcagccatcctggcctggaccttggcgaagttgcgcggaacctcactgctgggcgcctgctccgggggcgtct ggtctggttggcgtcacaccagcctgtgggatatccggtgtcggtgggggcgttgattgtgggatcgcatcggctcggcggcatctgggcgta acggcgctgaaacgctggctgcgggtgatgacccttgcgacgtcttcggcgtccacggcgtctgcggtcgtcggctgtatcctgaccggtatctt cgcggccacctctctgggcggcgtgggttatgcagaaggcgtcaccatgggccatcagctgctggtgcaactcgagagtatcgcgattaccatcgt ctggtcgggcgttgtcgattcattggctacaaagtggcggacatgaccgtggggctgcgcgtaccagaagagaggagcgcgaaggactggacgtca acagccatggcgaaaacgcctacaacgcctga |
| 121 | ctgaagagtttgatcctggctcagattgaacgctagcgggatgccttacacatgcaagtcgaacgcagcacggacttcggtctggtggcgagtgg cgaacgggtgagtaatgtatcggaacgtgcctagtagcgggggataactacgcgaaagcgtagctaataccgcatacgccctacggggggaaagcag gggatcgcaagaccttgcactattagagcggccgatatcggattagatagttggtgggtaanggctccaaggcgacgatcctagctggattg agaggacgaccagccacactgggactgagacacggcccagactcctacgggaggcagcagtggggaatttggacaatgggggaaaccctgatcca gccatcccgcgtgtgcgatgaaggccttcgggatgtaaagcacttttggcaggaaagaaacgtcatgggntaatacccgtgaaactgacggtacc tgcagaataagcaccggctaactacgtgccagcagccgcggtaatacgtagggtgcaagcgttaatcggaattactgggcgtaaagcgtgcgcagg cggttcggaaagaaagatgtgaaatcccagagcttaacttggaactgcatttttaactaccgggctagagtgtgtcagagggaggtggaattccg |

TABLE H-continued

| SEQ ID NO: | Sequence |
|---|---|
| | cgtgtagcagtgaaatgcgtagatatgcggaggaacaccgatggcgaaggcagcctcctgggataacactgacgctcatgcacgaaagcgtgggga<br>gcaaacaggattagataccctgctagtccacgccctaaacgatgtcaactagctgttggggccttcgggccttagtagcgcagataacgcgtgaag<br>ttgaccgcctggggagtacggtcgcaagattaaaactcaaaggaattgacggggacccgcacaagcggtggatgatgtggattaattcgatgcaac<br>gcgaaaaaccttacctacccttgacatgtctggaattctgaagagattcggaagtgctcgcaagagaaccggaacacaggtgctgcatggctgtcg<br>tatgatcgtgtcgtgagatgtttgggttaagtcccgcaacgagcgcaacccttgtcattagttgctacgaaagggcactctaatgagactgccggtg<br>acaaaccggaggaaggtggggatgacgtcaagtcctcatggcccttatgggtagggcttcacacgtcatacaatggtcgggacagagggtcgccaa<br>cccgcgaggggagccaatcccagaaacccgatcgtagtccggatcgcagtctgcaactcgactgcgtgaagtcggaatcgctagtaatcgcggat<br>cagcatgtcgcggtgaatacgttcccgggtcttgtacacaccgcccgtcacaccatgggagtgggttttaccagaagtagttagcctaacc |
| 122 | ctgaagagtttgatcctcgctcagattgaacgctaggggatgccttacacatgcaagtcgaacggcagcacggacttcggtctggtggcgagtggc<br>gaacgggtgagtaatgtatcggaacgtgcctagtagcggggataactacgcgaaagcgtagctaataccgcatacgccctacggggaaagcagg<br>ggatcgcaagaccttgcactattagagcggccgatatcggattagatagttggtggggtaaaggcctcaccaaggcgacgatccgtagatggttgga<br>gaggacgaccagccacactgggactgagacacggcccagactcctacgggaggcagcagtgggaattttggacaatgggcgaaaccctgatccag<br>ccatcccgcgtgtgcgatgaaggccttcgggttgtaaagcacttttgtgcaggaaaagaaacgtcatgggttaataccccgtgaaactgacgtacct<br>gcagaataagcaccggctaactacgtgccagcagccgcggtaatacgtagggtgcaagcgttaatcggaattactgggcgtaaagcgtgcgcaggc<br>ggttcggaaagaaagatgtgaaatcccagagcttaactttggaactgcattttttaactaccgggctagagtgtgtcagagggaggtggaattccgc<br>gtgtagcagtgaaatgcgtagatatgcggaggaacaccgatggcgaaggcagcctcctgagataacactgacgctcatgcacgaaagcgtggggag<br>caaacaggattagataccctggtagtccacgccctaaacgatgtcaactagctgttggggcttcggccttagtagcgcagctaacgcgtgaagtt<br>gaccgcctggggagtacggtcgcaagattaaaactcaaaggaattgacggggacccgcacaagcggtggatgatgtggattaattcgatgcaacg<br>gaaaaaccttacctacccttgacatgtctggaattcngaagagattnggaagtgctcgcaagagaaccggaacacaggtgctgcatggctgtcgtc<br>agctcgtgtcgtgagatgtttgggttaagtcccgcaacgagcgcaaccctttgtcattagttgatacgattagggcactctaatgagactgccggtga<br>caaaccggaggaaggtgggcatgacgtcaagtcctcatggcccttatgggtagggcttcacacgtcatacaatggtcgggacagagggtcgccaac<br>ccgcgaggggagccaatcccagaaacccgatcgtagtccggatcgcagtctgcaactcgactgcgtgaagtcggaatcgctagtaatcgcggatc<br>agcatgtcgcggtgaatacgttcccgggtcttgtacacaccgcccgtcacaccatgggagtgggttttaccagaagtagttagcctaaccgnaagg<br>ggggcgattaccacggtaggattcatgactggggtgaagtcgtaacaaggtagccgtatcggaaggtgaggctggatcacctcctttt |
| 123 | tacggagagtttgatcctggctcagatgaacgctcgcggcctgcttaacacatgcaagtcgaacggttgaacacggagcttgctctctgggatca<br>gtggcgaacgggtgagtaacacgtcagcaacctgcccctgactctgggataagcgctggaaacggcgtctaatactgatatgtgacgtggccgca<br>tggtctgcgtctggaaagaatttcggttggggatgggatcgcggcctatatgcttgttggtgaggtaatggctcaccaaggcgtcgacgggtagcc<br>ggcctgagagggtgaccggccacactgggactgagacacgcccagactcctacgggaggcagcagtgggaatattgcacaatgggcgcaagcct<br>gatgcagcaacgccgcgtgagggatgacggccttcgggagtaaacctctttttagcagggaagaaggaaagtgacggtacctgcagaaaaagcgccg<br>gctaactacgtgccagcagccgcggtaatacgtagggcgcaagcgttatccggaattattgggcgtaaagagctcgtaggcggtttgtcgcgtctg<br>ctgtgaaatccggaggctcaacctccggcctgcagtgggtacgggcagactagagtgcggtaggggagattggaattcctggtgtagcggtggaat<br>gcgcagatatcaggaggaacaccgatggcgaaggcagatctctgggccgtaactgacgctgaggagcgaaagggtggggagcaaacaggcttagat<br>accctggtagtccaccccgtaaacgttgggactagttgtggggtccattccacggattccgtgacgcagctaacgcattaagttcccgcctgggg<br>gagtacggccgcaaggctaaaactcaaaggaattgacgggaccccgcacaagcgacggagcatgcggattaattcgatgcaacgcgaagaaccttac<br>ccaaggcttgacatatacgagaacgggccagaaatggtcaactctttggacactcgtaaacaggtggtgcatggttgtcgtcagatcgtgtcgtga<br>gatgttgggttaagtcccgcaacgagcgcaaccctcgttctatgttgccagcacctaatggtgggaactcatgggatactgccggggtcaactcgg<br>aggaaggtggggatgacgtcaaatcatcatccccttatgtcttggcttcacgcatgcacaatggccgtacaatgggctgcaatacgcgcagg<br>tggaccgaatcccaaaaagccggtcccagttcggattgaggtctgcaactcgacctcatgaagtcggagtcgctagtaatcgcagatcagcaacgc<br>tgcggtgaatacgttcccgggtcttgtacacaccgcccgtcaagtcatgaaagtcggtaacacctgaagccggtggcctaaccctgtggagggag<br>ccgtcgaaggtgggatcggtaattaggactaagtcgtaacaaggtagccgtaccggaaggtgcggctggatcacctcctttt |
| 124 | attgaagagtttgatcatggctcagattgaacgctggcggcagccctaacacatgcaagtcgaacggtagcacagagagcttgctctcgggtgacg<br>agtggcggacgggtgagtaatgtctgggaaactgcccgatggaggggataactactggaaacggtagctaataccgcataatgtcgcaagaccaa<br>agagggggaccttcggccctcttgccatcggatgtgcccagatgggattagattgatggtgaggtaatggatcaccaaggcgacgatccctagatg<br>gtctgagaggatgaccagccacactggaactgagacacggtccagacacggcccagactcctacgggaggcagcagtggggaatattgcacaatgggcgcaagcctg<br>atgcagccatgccgcgtgtgtgaagaaggccttcgggttgtaaagcactttcagcggtgaggaaggcgatncggttaataaccgtgttgattgacg<br>ttacccgcagaagaagcaccggctaactccgtgccagcagccgcggtaatacgagggtgcaagcgttaatcggaattactgggcgtaaagcgcac<br>gcaggcggtctgtcaagtcggatgtgaaatcccggggctcaacctgggaactgcattcgaaactggcaggcttgagtcttgtagaggggggtagaa<br>ttccaggtgtagcggtgaaatgcgtagatatctggaggaataccgtggcgaaggcggccccctggacaaagactgacgctcaggtgcgaaagcgt<br>ggggagcaaacaggattagataccctggtagtccacgccgtaaacgatgtcgacttggaggttgtgccctcgaggcgtggcttccggagctaacgc<br>gttaagtcgaccgcctggggagtacggccgcaaggttaaaactcaaatgaattgacgggggcccgcacaagcggtggagcatgtggtttaattcga<br>tgcaacgcgaagaaccttacctggtcttgacatccacggaatttggcagagatgccttagtgccttcgggaaccgtgagacaggtgctgcatggct<br>gtcgtcagctcgtgttgtgaaatgttgggttaagtcccgcaacgagcgcaaccccttatcctttgttgccagcggtccggccgggaactcaaaggag<br>actgccagtgataaactggaggaaggtggggatgacgtcaagtcatcatggcccttacgaccagggctacacacgtgctacaatggcatatacaaa<br>gagaagcgacctcgcgagagcaagcggacctcataaagtatgtcgtagtccggattggagtctgcaactcgactccatgaagtcggaatcgctagt<br>aatcgtggatcagaatgccacggtgaatacgttcccgggccttgtacacaccgcccgtcacaccatgggagtgggttgcaaaagaagtaggtagct<br>taaccttcgggagggcgcttaccactttgtgattcatgactggggtgaagtcgtaacaaggtaaccgtaggggaacctgcggttggatcacctcct<br>t |
| 125 | atgaccatgcgtcaatgcgccatttatggcaaaggtgggatcggcaaatccaccaccacgcaaaacctcgtcgccgctctcgcggaaatgggtaaa<br>aaagtgatgatcgtcggctgcgacccgaaagggactccacccgtctgatcctgcatgcgaaagcacagaacaccattatggagatggccgccgaag<br>tgggttcagtggaagaccttgaactgtaaaggtgtgcaaatcggttacggcggcgtgcgtttgtcgcagaatccggcggccggcaggcgtgg<br>gttgtgcaggccgcggcgttattaccgccattaacttcctgaagaagaaggcgcctatgtcagcgacctcgactttgtcttctatgacgtcctcg<br>gtgacgtggtctgcgcgggttcgccatgccgattcgtgaaaacaaagcgcaagagatctatatcgtctgctccggggaaatgatggcgatgtatg<br>ccgctaacaacataccaaaggcatcgtgaaatacgctaaatccggcaaggtgcgcctgggcgggctgatttgtaactcccgtcagaccgaccgcga<br>agatgaactgatcatccgctggcagaaaaactgggcaccagattgattcactttgtgccacgcgacaacatcgtccagcgccgcgaaattcgcc<br>gtatgacggttatcgaatatgacccgaaatgcaaccaggccgacgaataccggccgctggcgaacaagatcgtcaacaacacccgatggtcgtcc<br>cgaccccttgcaccatgtgaactgaaaagagctgctgatggaattcggcattatggatgtggaagacgccagcatcatcggtaaaaccgccgccg<br>aagaaaacgcggcctga |
| 126 | atgaacgataacgatgtcctttttctggcgcatgctgccgctatttcagtgtctgccggaactgcaacccgcgcagatcctggcctggctgacagga<br>gaacgcgacgacgccttaaccccggcgtacctcgataagcttaacgtccgcgaactggaagcgacctteccgtctgaaacggcgatgatgtcgccc<br>gcacgctggagccgcgttaacgcgtgccttcacggtacgctgcccgcacacctgcaggtaaaaagcaccactcgtcagggcaattacgggtagcc<br>ttttgttcacaggatggattgctgatcaatggtcattttggtcaggggcggctgttttttatctacgcctttgatgaacagggcggatggctacac<br>gcgttacgccgtcttcccctcggccccgcaaacccaggagccgaatgaagttcgcgcgcagctcctgagtgattgccacctgctgtttttgtgaagcc |

TABLE H-continued

| SEQ ID NO: | Sequence |
|---|---|
| | attggcggccctgcggcggcccggctgattcgtcacaatatccacccgatgaaagtgtcgccagggatgtccattgccgcccagtgtgatgccatt<br>accgcactgctgagcggacgtctgccaccgtggctggcaaaacgtcttgagaaagccaacccgctggagaagggtgttttaa |
| 127 | atgaagggaaatgacattctcgcgctgctggatgaacccgcctgcgaacacaatcacaaacagaaatccggctgtagcgccctaaacccggtgcc<br>acggcgggcggttgcgcgttcgacggcgcgcaaatcacccctgttgccgctgtcggtagtggcgcacctggtccacggaccgattggctgcacggga<br>agctcctgggataaccggggcagtatgagctcccggccccagtctcaaccggctcggctttaccacccgaccctgaacgagcaggatgtcaaatgggc<br>gcggcgaacggcggcttttccacgcggtgcgtcatatcgtcaaccgttatcacccctgccgccgtgtttatctataacaccctgccgttccggcgatgg<br>agggtgatgatattgacgccgtctgtcaggcggcggaaaccgccaccggcgtgccagtgattgccgttcatgccgcccgggttctatggcagcaaaa<br>accttggcaaccgtctcgcgggtgaagtgatggttaacaaggtcattggacggcgcccgcccgccccctggccggacgataccccttcgcgccgg<br>aacaccgccacgatatcggcctgattggcgaatttaatatcgccgggagttctggcacgttcagccgctgctcgatgagctgggtattcgcgtgc<br>tgggcagcctttccggggatggccgttttagtgaaatccagaccctgccaccacgcgcaggtcaatatgctggtctgctcaagagcgctgatcaatg<br>ttgcccgcaccctggaacagcgctatggcaccccctgtttgagggcagttttacggcgtgcgcgctacctccgatgccctgcgtcaactggcat<br>ccctgcttggcgacagcgatctgattgccccaccgaagccgttattgcccgcgaagaagccacgcgcaaatcagccgctcgccccgtggcgcgaac<br>ggctacagggtcgcaaagtgctgctctataccggtggcgtgaatcaggtcggtgattctccgcattgcaggattagggatgaccctcgtgccgac<br>tggcacccgcaaatctaccgaagaagataagcagcgtattcgcgaattaatgggcgatgacgcgctaatgctggaagaaggcaacgcccgcaccct<br>gctggatgtggtgtaccgctatcaggcggatttgatgatcgctgggggggcgtaacatgtataccgcgtacaaagcgggctgccgtttctggatatc<br>aaccaggagcgtgaacacgcctttgcgggttatcgcggcatcgtcaccctcgcccaacagcttttgccagactattgaaagcccgtctggccgcaa<br>acacacgcccgcgcgccgtgccaataa |
| 128 | atgagcaatgcaacaggcgaacgtaatctggaaattatccaggaagtgctggagatctttcccgaaaaaacgcgcaaagaacgcagaaagcacatg<br>atggttaccgacccggagatggaaagcgtcgggaaatgcatcatctctaaccgcaaatcgcagccgggtgtgatgactgtccgcggctgacctacg<br>ccgggtcgaaaggcgtggtttttgggccgattaaagatatggccacatctcccacgccgccgatcggctgtgggcagtactcccgtgccgggcggc<br>gcaactactacaccggggtcagcgcgttgattccttcgggacgctgaactttacctctgattttcaggagcgcgatatcgtcttcggccgcgata<br>aaaagctcaccaaactgattgaggagatggaggaactgttcccgctgaccaaaggcatctccattcagtcggagtgcccggtaggtttaatcggtg<br>acgatatcgaagcggtggcgaatgccagtaaaaaagcgctcaacaagccggtgatcccggtgcgttgcgaaggcttcgcggcgtgtcgcagtcgc<br>tcggtcaccatatcgccaacgacgttatccgcgactgggtgctggataaccgcgaaggagccctcgaatctaccccctatgacgtggccatca<br>tcggcgattacaacatcggggggggatgcctgggcgtcgcgcattctgcttgaagagatggggttacgcgtggtggcgcagtggtcgggtgacggca<br>cgctggtagagatggtaaacaccccgttcgtcaagctgaacaggtgcactgctaccgctctatgaactacatctctcgcatatggaagagaaaca<br>cggtatcccgtggatggagtacaacttcttcggcccgaccaattatcgccgaatcgagcgtaagatcgccgatcaatttgacgacaccatccgcgc<br>caatgcggaagcggtgatcgccaaatatcaggcgcaaattcgatgcgattatcgcaaataccgcccgcgtctcgaaggccgcaaggtgctgctct<br>atatgggtggcctgcgtcctcgccacgtgattggcgcgtataggattgggcatggagattgtcgccgccgggtatgaatttgcccataacgacg<br>attacgaccgcacccctgccggacctcaaagagggcacgctgttgttcgacgatgcagcagttatgaactggaagccttcgtgaaggcgattaagc<br>cggacctcattggctcaggcatcaaggaaaaatacattttccagaaaatggggtaccgtttcgccagatgcactcctgggattactccggcccgt<br>atcacggctatgacggctttgccatctttgcccgcaatatggacatgacgctcaacaatcccgcctggggcgagttgaccgcaccctggctgaaat<br>cagcctga |
| 129 | atggcagatatcatccgtaatcagaaaccgctggcggtaagcccggtaaaaagcggccagccgttaggcgccattctggcgagcctcggctttgtg<br>cacagattccactggtgcacggtgcgcagggatgcagcgcgttcgccaaagtgttttttatccaacattttcatgaccctattccgctgcaatcca<br>cggcgatggaccccacctcaacggtcattgggggcgacggcaatatccttgccgcgctcaatacgctgtccgcgcattcaccccgaaagctatc<br>gtcctgttgagtaccggcctgtctgaggcgcagggcagggcagcgatatcagccgctggtacgtcagtttcgtgaggattttccccgccacaaaaatatc<br>gccctcctgacggtcaacaccccggattttttacggcacgctggagaacggctttagtgcggtggtggaaagcgtcatcgaacagtgggtgccggaa<br>agcctcagcatggcctgcgtaaccggcgggtcaacttgttgttaagtcacctgctgacgcccggtgatgttgagttgctgcgcagctacgtcgagg<br>cttttggcctgcaaccggtgatcgtgccggatcttttcacagtcgctggtggtgcacctggcaagcgtgattttttcgccggtcactcagggggaa<br>cgcccctgcgcattatcgaacagatgggacagaggcctgtgcacgtttgctattggcgtgtcgctgtcccgtgcggcatcgagctggcacagcgtag<br>ccgtggcgaggtgatcgtgcttccccatctgatgaccatggaacattgcgaccgttttattcatcaactgaagatcatttccgggcgcgaggttcc<br>cgcctggattgagcgccagcgcggacaattgcaggatgcgatgatcgattgtcatatgtggttgcaggataccgcgctgcgctggccgccgaggg<br>cgatctgctggcgggctggtgtgatttcgccgtagccagggcatgctcccggccccgctggtggcgccggtcagccagccgggcctgcgacagct<br>tcccgtgagaaagtggtcattggcgatctggaagatatgcaggatttactctgcgctataccctgctgacctgctggtcgccaactcccatgccg<br>agacctggccgaacaattctccatcccgctgatccgcgcccgggttccctatcttgacaggcttggcgaatttcgtcgcgtgcgtcagggataccc<br>cggcattcgcgacacgctgtttgagctggcgaacctgatgcgcaacgtcatcaccacctgcccgtctaccgctccccctgcgccagcaatttgc<br>ccaggacgctgacggaggccgctatgcaacatgttaa |
| 130 | atgagccaaactgctgagaaaattgtcacctgtcatccgctgtttgaacaggacgaataccagacgctgtttcgcaataagcgcggtctggaagag<br>gcgcacgacccgcagcgcgtgaagaggtttttgaatggaccaccacgcgcgagtatgaagcgctgaactttaagcgtgaagcgttaaccgtcgatc<br>cggcaaaggcctgccagcctttaggatcggtactctgctcgctgggttttgccaatacgctgccttagtgcacggttcccagggctgtgtggccta<br>tttccgcacctattttaaccgtcatttcaaagagccgatcgcttgccgctctatgacagaggatgcggtcttcggccgccggcaacaacaac<br>ctaacaccggggttgcaaaatgccagcgcctgacaaaccggaaattgtcgctgtgctccactacctgtatgcggaggtcatcggcgatgacctgc<br>aggcctttatcgccaacgccaaaaaggacgggtttattgatgccgccattccggtgccctacgccatacgcaagttttatcggtagccacatca<br>ccggctgggacaacatgtttgaaggttcgcccggggcatttaccgccgatcacgtggcgcaacgggcaaactggcgaagctaaacctggtgaccg<br>gttttgaaacctatctggcaattaccgcgtgctcaaacgcatgatgcccagatggaggtgccctgtagcctgctctgaccgtctgagggtt<br>agatacgccagccgacggccactatcgcatgtatgcgggcggcacaacgcaacaagagatgcgcgaccgcccccgatgctatcgacacccagctgct<br>gctgcaaccctggcatctggtgaagagtaaaaaagtggtgcaggagtcctgggggcagcccgcacagaagtgtccatcccaatgggactgaccgg<br>gaccgacgaactgctgatggcagtcagtcagttaaccggcaaaccggtggccgatgaactgacgctggagcgtgggcgcctggtggatatgattct<br>cgattcacacaccctgctgcacgtaagaaattcggtctctacggtgctcaaaacgcatgatggcccagctgggtcctgctgctctgctggaactggctgc<br>gagccgacggttatcctctgtcataacggtagcaagcgctggcagaaagcgatgaagaaaatgcttgaggcatcgccctacggtcaggagacggaa<br>gtgttcatcaactgcgatctgtggcatttccgctcgctgatgtttaccgcaaaccggactttatgatcggcaactcgtacgccaattcatccag<br>cgtgacacgctggcgaaaggcgaacagtttgaagttccgctgatccgtcttggcttcccgttgttcgaccgccaccacctgcatcgccagaccaca<br>tggggttatgaagggcgatgaatatcgtcaccaccctggtcaacgccgtgctggaaaaagtcgaccgcgataccatcaaactgggcaaaacggac<br>tacagcttccgaccttgtccgctaa |
| 131 | atgacctttaatatgatgctggagaccagcgcaccgcagcacattgcgggcaacctctcacttcaacatcccggactgttttccacgatggttgaa<br>caggtccgatcgcgatttcgctgaccgacccggacgcggagatttctgtacgctaatccggcctttttgtcgccgaccggttatagctcggaagag<br>ctgctcaaccagaaccatcgcatactgcaagccancagacgccgcagcatttatcaggaactgttgcaaacgctgctgcaacagatgcctgg<br>cgcggtcagctcatcaatgccgtcggatgcagcctttatctggctgaggtcgatatcaccccggtcgtcaacaaacaggcgaactggaacac<br>tacctcgccatgcaacgtgatatcagcgccagctatgcgctcgaacagcgattgcgcaatcacaccaccatgagcgaggcggtgctgaacaacatt<br>cctgccgcgtggtggtggtcaacgagcaggaccaggtagtcatggacaacctcgcctacaaaaccttctgtgccgactgcggtggcaaggagctg<br>ctcaccgaactggatttctcccggcgcaaaagcgatctctatgccgggcaaatactgcctgtggtgctgcgcggcgccgtgcgctggactctgtca |

TABLE H-continued

| SEQ ID NO: | Sequence |
|---|---|
| | cctgaggaccttgccggggtgagcgaagaagccagccgctactttattgataccgcgagccccgcaccctggtggtgatcaccgactgcacccag caacaacaacaggcccgaacagggccgtctcgatcgtctcaaacaggagatgaccaccgggaagctgctggccgcgatccgtgaatcgttggatgc cgcgctggttcagctaaactgccccatcaatatgctggcggcggcgcgacgtctcaacggtgaagataaccataacgtggcgctggatgccgcgtg gcgcgaggggaagaggcgctggcccgcctgcaacgctgccgcccttctctcgatctggaagagagcgcgctgtggcctctgcaaccgctgtttga cgacctgcgcgccctttaccataccgctataacaatggcgaaaatctgcacgttgaaatggcctctccgcatctggcggggtttggtcagcgcac gcagatccttgcctgctcagtttgtggctcgaccgtacgctggccctcgccgccgcgctaccggacagaacgctgcataccagcttacgcccgt gaagaagatggctggctgtgtccatttggctgacagataatggccgctcatccatgtgcgatacgcccactccccgatgcctgaacgcccccgg caaagggatggagctgcgattgattcaaaccctggttgcccatcatcgcggcgcaatagaactaactaccccgccagatggcggtacctgcctgacc ctgcgattcccgttatttcattcactgacccgaggcccacgatga |
| 132 | atgacccagccgacccgagtcgggcaccaccgtctggcgttttgatctctcacagcaatttaccgccatgcagcgcatcagcgtggtgttgagtcgc gcaaccgagataagcagacgctgcaggaggtgctgtgtgttctgcataatgacgcatttatgcaacacggcatgctgtgtctgtatgacaaccag caggaaattctgagtattgaagccttgcaggaggcagaccaacatctgatccccggcagctcgcaaattcgctatcgccctggcgaagggctggta ggagccgtactgtcccagggacaatctcttgtgctgccgcgtgtgccgacgatcaacgcttttctcgacaggcttggcatctatgattacacctgc cgtttatcgccgtcccccttaatggggcaggccgcgcagacgattggcgtgctcgccgcagccgatggcgcgtctggaggagcggcttccttctg tacgcgctttctggaaaccgtcgccaatctggtcgcacagacagtccggctgatgaccccgcctgccgccgccacaccggcgccgcgattgccca gaccgaacgccagcgcaactgtggcactcctcgccccttcggctttgagaatatggtgggcaaaagcccggccatgcagcagacaatggacattat ccgcaggtttcgcgctgggataccacggtactggtgcgcggcgaaagcggcaccggtaaagaacttatcgccaatgctattcatcacaactcccc tcgcgccgccgcgcccttttgtgaaatttaactgcgcggcgctaccggatacgctggagagagcgaattgttcggccatgaaaaaggggcgttcacc ggcgcggttcgccagcgtaaaggacgtttgaactggccgatggcggcacactgtttcttgatgaaattggcgaaagcagcgcctcgttccaggcca aactgctgcgtattttgcaggagggtgaaatggagcgcgttggcggcgacgaaaccctgcgcgtcaatgtgcgtatcatcgccgccaccaaccgga atctggaagaagaggtgcggatgggcaattccgcgaggatctctattatcgctcaacgtaatgcccatctccctgccccgctgcgtgaacgtc aggagacattgccgagctggcgcacttttctggtgcgcaaaatcgcccataaccagggggcgtacgctgcgcatcagtgatggcgccatccgtctgc tgatgggttacaactggcccggtaacgtgctgtgagctggaaaattgcctggaacgttcggcagtgatgtcagaaaaacggcctgatcgaccgcgat gtggtgctctttaaccaccgtgagaacacgccaaaactcgctatcgccgccgcgcaaaagaggtagctggcttgatcaaacgctggatgaacgt caacggctgattgccgcgctggaaaaagccggggtgggtgcaggccaaagcggcgcgtctgctgggtatgacgcccgtcaggtcgcctatcggata caaattatggatatcagcatgcccaggatgtga |
| 133 | atgatgccgcactctccacagctacagcagcactggcaaactgtactggcccgcttgcctgagtcattcagtgaaacaccgcttagtgaacaagcg cagttagtgcttacttctcagtgattttgtgcaggatagccttgccgcgcatcctgactggctggctgagctggaaagcgcaccgccacaggcggac gagtggaagcagtatgcgcaaacccttcgcgaatcgctggaaaggtgtgggagatgaggcatcattaatgcgtgcgcgtgccgcctgttccgtcgcca tatgatggtgcgcattgcctgggcgcagtcgctggcgctggtggcagaagatgagacgttgcagcagttgagcgtactggcggagaccctgatcgt cgctgcacgcgactggctttacgatgcctgctgtcgcgagtggggaacgccgtgcaatcagcaggggggaaccgcagccgttgctgatcctgggcat gggcaagctgggtggcggggagcttaacttttcgtccgatatcgatctgattttgcctggccggaaaacggttcaacgcgcggtgggcgacgcga acttgataacgcccagtttttactcgcttgggacagccgcctgatcaaagtgctcgaccagccgaccgcaggatggctttgtctatcgcgtggatat gcggctgcgcccgtttggcgacagcggttccgctggtgctgagttttgccgcgctggaagattattatcaggagcaggggcgcgactgggaacgtta tgcgatggtgaaagcccgcattatgggcgataaggacgatgtttacgctggcgaattacgggccatgctgcggccgttcgtcttccgtcgctatat cgatttcagcgttattcagtctctgcgtaacatgaaagggatgattgcccgcgaagtgcgccgccgtggtctgaaagataacattaagctgggcgc gggcgcatccgtgagattgagtttatcgttcaggtgttccagttatacgcggtggcgcgagccgtcgttgcagtcccgttcactgttaccgga gctgacgctatcgataagctgggttttgctgccgcctggcgatgcaccggcgcgttacgcaggcctatttgtatctgcgccgtctggaaaaacctgc tgcaaagcattaacgacgaacaaacgcagacgctgccgacagatgaactcaatcgcgcgcgtctgccctggggatgcgggtcgcagactgggaaa ccctgaccgctgagcttgaaaagcagatgtctgccgtacgagggatattcaacaccctgattggcgatgacgaagccgaagagcaggggatgcgc tctgcgggcaatggagtgagttgtggcaggatgcgtttcaggaagatgacagccgctgctggccgcaggatgatgcgccgccgg tggtcgcgatgattgctgattttcgcaaagagctggataaacgcaccattggccacgcgggcccaggtgctcgaccatctgatgccgcatctgt tgagtgatgtctgctcccgtgaggatgccctgtaccgttgtctcgcgtgacgccgctgttaacgggaattgtcacgcgtacgacgtatcttgagc tgctcagcgagtttcctggtgcgcgtaagcatctgatttcactctgtgccgcctcgccgatggtggccagtaagctggcgcgctatccgttattgc tggatgagttgctcgatccgaataccttcatcagccaccggcgatgaatgcctccaccgtaccgggatgagctacgtcagtatctgctgcgtgtgccggatg acgatgaagagcagcaactggaggcgttacgccagtttaaacaggctcaattgttgcgtgtggcggcagcagatctgcaggcacactcccccgtga tgaaagtgagcgatcacttaacatggctgccgaagccatcattgaagccgtggtacaacaggcgtggagcctgatggtatcgcgttatgggcagc cgaaacacttacgcgaccgtgaaggccgtgggtttgcagtggtcggttacggcaaactgggcggttgggagctgggctatagttccgatctggatt tgattttccttcatgactgtccggtggacgtgatgactgacggcgagcgggaaatcgatggccgccaattttatctgcgccgtttgcccagcgctga tgcacctgttcagtacgcgcacctcatccggagcatcctgtatgaggtagacgcgcgcttgcgccctccggtgcgggaatgctggtagacctcaa ccgaatccttgtgccgactaccagcgcaccgaagcctggacctgggaacaatcaggcgctggttcgcgccccgcgttgtctatggcgatccacaattaa acgcgcaatttgatgccatccgccgcgatatcaccatgaccgtgcgtaatggtgcaacgttacaaaccgaggtgcgcgagatgcgcgaaaaatgc gcgcccacttgagcaataagcacaaggatcgctttgatattaaagccgatgagggtggaattaccgatatcgaatttatcacccagtatctggtgc tgcgttatgccatgccaaaccgaaactgacgcgctggttcggacaatgtccgcattcttggaaggggctggcgcaaaacggcattatggaagagcagg aagcgcaggcacttaccaccgcctatacaacgtgcgtgatgagctgcatcacctggcgctcaggagctgccaggacatgttccggaggcatgtt ttgtcgctgaacgcgcgatggtgcgagcctgctggaacaagtggttggtgagccgtgcgaggacgcgtaa |
| 134 | atgaagaaagcactattaaaagcgggtctggcctcgctggcattactgccgtgtctggctatggcagccgatccggttgtcgtcgataaagccgac aatgcctttatgatgatttgcaccgcgctggtgctgtttatgtcaattccgggcatcgccctgttctatggtggtttaatccgcggtaaaaacgtc cttctctatgctgacacaggttgcggttacgttcgcactggtgtgcgtgctgtgggtggtttacggctactctctggcctttggcactggcggcagc ttcttcggtagcttcgactgggtgatgctgaaaatattgagctgaaagcgctgatgggcaccatctatcagtacattcacgttgcgttccaggcc tcgtttgcctgtattaccgtcgcgtgctgggcgtggcaacgtatccgttctccgcagtactgatttttcgtcgtggtatggctgacg ctgtcctacgtgccgatcgcacacatgtctggggcggcgtctgctgcaacccatggccgcatgattttgcgggcggtacagtcgttcacatc aacgcagccgttgcaggcctggtgggtcttacctgattggcaaacgtgtcggtttcggtaaagaagcgtttaaaccgcacaacctgccgatggtg tttaccggtacggcaatcctctacttgctggttcggattcaacgcgggttctgcaagcgcggcgaacgaaattgcgggtctggcttttgttaac accgtcgtggcaacgcgggtgcaatcctctcctgggtcttcggtgagtgggcgctgcgcgggcaaaccgtctcgttgggtgcctgttctgtgg attgtggcctcgtgggtatcacccgcgctgtgttacgttggtgtggggcgcgctgatcgtggcatcgttcaggcctggcgcggtctgtgg ggcgttaccgcgctgaaacgctggctgcgtgtttgacgaccgtgtgatgtcttcggtgttcacggcgtgtgcggtatcgtaggtgtatcatgaca ggtatcttcgcagccactcactggggcgtgggttatgccgaaggcgtgaccatgggccatcaggtctggtacaactggaaagtatcgcatt actgtctatggtctgtatcgtcgcctttatcggttacaaactggctgatatgacagtgggtctgcgtgttccggaagatcaggaacgcgaaggg ctggacgtcaacagccacggcgagaacgcctacaacgcctga |
| 135 | ctggggtcactggagcgctttatcggcatcctgaccgaagaatttgccggttttcttcccgacctggctggcccctgttcaggttgtggtgatgaat atcactgattctcaagctgaatatgtcaacgaattgacccgtaaattgcaaaatgcgggcattcgtgtaaaagcggacttgagaaacgagaagatt ggcctttaaaatccgcgagcacactttacgtcgtgtcccttatatgttggtctgtggtgataaagaggtggaagcaggcaaagtggccgttcgcacc |

TABLE H-continued

| SEQ ID NO: | Sequence |
|---|---|
| | cgccgcggtaaagacctgggcagcctggacgtaagtgaagtgattgagaagctgcaacaagagattcgcagccgcagtcttcaacaactggaggaa<br>taaggtattaaaggcggaaaacgagttcaaacggcacgtccgaatcgtatcaatggcgagattcgcgcccaggaagacgcttaactggtctggaag<br>gtgagcagctgggtatt |
| 136 | attgaagagtttcatcatggctcagattgaacgctggcggcaggcctaacacatgcaagtcgaacggtagcacagagagcttgctctcgggtgacg<br>agtggcggacgggtgagtaatgtctgggaaactgcctgctgatggaggggggataactactggaaacggtagctaataccgcataacgtcgcaagaccaa<br>agaggggaccttcgggcctcttgccatcagatgtgcccagatgggattagctagtaggtgggtaacggctcacctaggcgacgatccctagctg<br>gtctgagaggatgaccagccacactggaactgagacacggtccagactcctacgggaggcagcagtggggaatattgcacaatgggcgcaagcctg<br>atgcagccatgccgcgtgtatgaagaaggccttcgggttgtaaagtactttcagcggggaggaaggcganacggttaataaccgtgttgattgacg<br>ttacccgcagaagaagcaccggctaactccgtgccagcagccgcggtaatacggagggtgaagcgttaatcggaattactgggcgtaaagcgcacg<br>caggcggtctgtcaagtcggatgtgaaatcccgggctcaacctgggaactgcatccgaaactggcaggcttgagtacgtagagggaggtagaatt<br>ccaggtgtagcggtgaaatgcgtagagatctggaggaataccggtggcgaaggcggcctcctggacgaagactgacgctcaggtgcgaaagcgtgg<br>ggagcaaacaggattagataccctggtagtccacgccgtaaacgatgtctatttggaggttgtgcccttgaggcgtggcttccggagctaacgcgt<br>taaatagaccgcctggggagtacggccgcaggttaaaactcaaatgaattgacgggggcccgcacaagcggtggagcatgtggtttaattcgatgc<br>aacgcgaagaaccttacctggtcttgacatccacagaacttgccagagatggcttggtgccttcgggaactgtgagacaggtgctgcatggctgtc<br>gtcagctcgtgttgtgaaatgttgggttaagtcccgcaacgagcgcaacccttatcctttgttgccagcggtccggccgggaactcaaaggagact<br>gccagtgataaactggaggaaggtggggatgacgtcaagtcatcatggcccttacgaccagggctacacacgtgctacaatggcgcatacaaagaa<br>gcgacctcgcgagagcaagcggacctcataaagtgcgtcgtagtcccgattggagtctgcaactcgactccatgaagtcggaatcgctagtaatcg<br>tggatcagaatgccacggtgaatacgttcccgggccttgtacacaccgcccgtcacaccatgggagtgggttgcaaaagaagtaggtagcttaacc<br>ttcggagggcgcttaccactttgtgattcatgactggggtgaagtcgtaacaaggtaaccgtaggggaacctgcggttggatcacctcctt |
| 137 | atgaccatgcgtcaatgcgccatttacggcaaaggtgggatcggtaaatcgaccaccacacagaacctggtcgccgcgctggcggagatgggtaag<br>aaagtcatgatcgtcggctgcgatccgaaagccgactccacgcgtttgatcctgcatgcgaaagcgcagaacaccattatggagatggccgccgaa<br>gtcggctccgtcgaagacctggaattagaagacgtgctgcaaatcggttacggcggcgtgcgctgcgcggaatccggtggcccggagccaggtgtg<br>ggttgtgccggtcgtggcgtgatcaccgcgattaacttcctcgaagaagaaggcgcttacgtgccggatctggattttgttttctacgacgtgctg<br>ggcgacgtggtgcggtggtttcgccatgccgattcgtgaaaacaaagcgcaggagatctacatcgtttgctctggcgaaatgatgcggatgtac<br>gccgccaataacatctccaaaggcatcgtgaaaatgccaaatccggtaaagtgcgcctcggcgggctgatttgtaactcgccgcagaccgaccgc<br>gaagatgaactcatcattcgctgcggcgaaaaactcggcacgcaaatgatccactttgttccccgcgacaacattgtgcagcgtgcggaaatccgc<br>cgtatgacggttatcgaatatgacccgacctgcaatcaggccaacgaatatcgcagccttgccagcaaaatcgtcaacaacaccaaaatggtggta<br>ccaaccccctgcaccatggatgaactggaagaactgctgatggagttcggcattatggatgtggaagacgccagcatcattggtaaaaccgccgcc<br>gaagaaaacgccgtctga |
| 138 | atgagcaatgcaacaggcgaacgtaacctggaaatcatcgagcaggtgctggaggttttcccggaaaagacgcgcaaagagcgcagaaaacacatg<br>atggtgacggacccggagcaggagagctcggcaagtgcatcatctctaaccgcaaatcgcagccgggcgtgatgaccgtgcgtggctgctcgtat<br>gccggatcaaaaggggtgtatttgggccaatcaaagatatggcgcatatctcccacggcccgctgcgcggcgagtactcccgcgcgggcgg<br>cgtaactactataccggcgtcagcgcgctggacagtttcggcacgctcaacttcacctccgatttccaggagcgcgacatcgtgtttggcggcgac<br>aaaaagctcgccaaactgattgaagagctggaagaactgtttccgctgaccaaaggcatttcgattcagtcggaatgcccggtcggcctgattggc<br>gatgatattgaagccgtggcgaacgccagccgcaaagcgatcaacaaaccggttattccggtgcgttgcgaaggctttcgcggcgtgtcgcaatcc<br>ctcggtcaccatattgccaacgatgtgatccgcgactgggtactggatacgcgcgaaggcaaaccgtttgaatccaccccttacgatgtggcgatc<br>atcggcgattacaacatcggtggcgacgcctgggcctcgccgcattttgctcgaagagatgggggttcgggtggtcgccagtggtccggcgacata<br>cgctggtggagatggaaaacacgccgttcgtcaaactgaacctggtgcactgctaccgctcgatgaactacatctcgcgccatatggaggagaagc<br>acggtattccgtggatggaatacaacttctttggcccgacgaaaatcgcggaatcgctgcgcaaaatcgccgacctgttcgacgacaccattcgcg<br>ccaacgccgaagcggtgatcgccccgataccaggcgcagaacgaccgccattatcgccaaatatcgcccacgtctggagggtcgcaaagtgttgctct<br>atatgggcgggctgcgtccgccgcatgtgattggcgcctatgaagatcggaatggagatcatcgccgcggttatgagtttggtcataacgacg<br>attacgaccgcaccctgccggatctgaaagagggcacgctgctgtttgatgacgccagcagctatgagctggaggcgtttgtcaacgcgctgaaac<br>cggatctcatcggttccggcatcaaagagaagtacatctttcagaaaatgggcgtgccgtttcgccagatgcactcctgggattactccgccgcgt<br>accacggctatgacggcttcgccatcttcgcccgcgatatggatatgacgctcaacaaccccgcctggggtcagttgaccgcgccgtggcttaaat<br>ccgcctga |
| 139 | atgaaggggaacgacatcctggctctgctcgatgaaccagcctgcgagcataaccatgaaacagaaaaccggctgtagcgcgccaaacccggcgcca<br>ccgccggaggctgcgccttcgacggccacagatcaccctgctgccactttccgatgtggcgcatctggtacatgcccgattggctgcgccggca<br>gctcatgggataaccgtggcagcctgagttctggcccgctgattaaccgactcggattcaccactgatttgaacgaacaggatgtcatcatggggc<br>gcggcgagcggcggttgttttcacgcggtgcgccatattgtcgagcgctatcaccggcggcggtatttatttacaacacctgcgttccggctatgg<br>aaggcgatgacattgacgcggtctgccaggccgccgcgaccgccaccggtgtgcccgtgattgccgtagatgtggccggtttttttacggtagcaaa<br>aacctgggtaaccgcctcgcgggcgaggtgatggtgaaaaaagttatcggcgggcgcgaacccgcgccgtggccggacaatacaccttttgccccg<br>gcgcaccgccatgacataggccggttgtcgaattaacatggcgcattctggcatatccagccgctgcttgatggcgtgggtattcgcgtc<br>cttggctcccttttccggcgacgggcgcttgccgagatccagacgtgcaccgccgcaggtcaatatgctggtgtgctccaggcgcgcgtgattaat<br>gtcggcagatcgcttgaacaacgttatggcacaccctggtttgaaggcagttttatggcgttcgcgccacctccgatgccctgcgcagctggca<br>aacactcaccggcgatagcgatttaatggcgcgaaccgaacggctgatcgcacgtgaagagcaagccacagaacaggcgctagcaccgctgcgtgaa<br>cggttacacggccggaaagtgctgctctatacggtggcgtgaaatcctggtcggtggttcggcgctgcaggatctcggcatgacgctcgttgct<br>accggaacgcgcaaatccaccgaagaggatataaacaacgcatccgtgaactgatgggcgatgacgccatcatgctggatgaaggcaatgcccgcc<br>ttgctggatgtggtctatcgctacaaagcgacatgatgatcgcgggcgggcgcaacatgtacaccgcctataaagcgcgtctgccctttctggat<br>atcaaccaggagcgtgaacacgcgtttgccggttatcgcggcatcatcacgcttgccgaacaactttgtcagacgctggaaagcccggtctggccg<br>caaacacatgcccgcgccccgtggcaataa |
| 140 | atgagccagactgctgagaaaatacagaattgccatccctgtttgaacaggacgcctaccagacactatttgccggtaaacgggcactcgaagag<br>gctcactcgccggagcgggtgcaggaagtgtttcaatggaccaccaccccggaatacgaagcgctgaacttcaaacgcgaagcgctgactatcgac<br>ccggcaaaagcctgccagccgctggggggcggtgctgttcgctgggttgccaacacctgccgccgctatgtgcacggttcacaggggtgtgtggcct<br>atttccgtacgtactttaaccgccacttcaaagaaccggtggcctgcgtgtcggattcgatgacggaaagcgccgtgttcggcgggaataaca<br>acctcaacaccgattacaaaacgccagcgcactgtataaaacggtgattatcgccgtctctaccacctgtatggcggaagtgatcggtcgatgatttt<br>acaggcgtttatcgcaacgccaaaaagatggttttctcgatgccgccatccccgtgccctacgccacacccccagttttatcggtagccat<br>caccggctgggacaactgtttgaaggttttgccgtacctttaccgcaaaccatcagccacagccggtaaactttcacgcctgaacctggtgac<br>cgggtttgaaacctatctcggcaattccgcgtgagaaacgcatgatggaacaaatgaggtgcaggcggtgctctccgatcgctggaggtg<br>ctggacaccccgccaatggccattaccagatgtacgcggcggtacgacgcagcaagagatgcgcgaggcaccggatgccatcgacaccctgctg<br>ctgcaaccgtggcagctggtgaaaagcaaaaaagtggtgcaggagatgtgaatcagcccgccaccgaggttgccattcccgtcgggctggcaggc<br>acagacgaactgttgatggcgattagccagttaaccggcaaagccattcccgattcgctggcgctggagcgcgggcggctggtcgatatgatgctc<br>gactcccacacctggttacacggtaaaaaattcggtctgtttggcgatccggattttgtcatgggattgacccgcttcctgctggaactgggctgt |

TABLE H-continued

| SEQ ID NO: | Sequence |
|---|---|
| | gaacctgccgtcatcctctgccataacggtaacaaacgctggcaaaaagcgatgaagaaaatgctcgatgcttcaccgtacggccaggagagcgaa<br>gtgtttatcaactgcgacttgtggcatttccgctcgctgatgttcaccgccagccggattttatgattggcaactcgtacgccaagtttattcag<br>cgcgacaccttagccaagggcgaacagtttgaagtcccgctgatccgcctcggttttccgctgttcgaccgtcaccatctgcaccgccagaccacc<br>tggggctacgagggcgcgatgagcattctcacgacgctggtgaatgcggtactggagaaagtggacaaagagaccatcaagctcggcaaaaccgac<br>tacagcttcgatcttatccgttaa |
| 141 | atggctgatattgttcgtagtaaaaaaccgctggcggtgagcccgataaaaagcggccagccgctgggggcgatcctggcaagcctgggtttcgaa<br>cagtgcataccgctggtacacgcgctcaggggtgcagcgcgttcgcgaaagtgttctttattcaacattttcacgacccgatcccgctgcaatcg<br>acggcgatggacccgacttccaccattatgggcgccgatgaaaacatttttaccgcgctcaatgttctctgccagcgcaacgccgcgaaagccatc<br>gtgctgctcagcaccgggcgtgtcagaagcccaggggcagcgatatttcacgagtggtgcgccagtttcgtgatgacttccgcggcataaaaacgtg<br>gcgctgctcaccgtcaacaccccggatttctacggctcgctggaaaacggctacagccgcgtgctggaaagcatgattgaacagtgggtgcccgcg<br>cagcccgccgccagcctgcgcaaccgtcgcgtcaacctgctggtcagccatttactgacgccgggcgatatcgaactgttacgcagttatgtggaa<br>gcattcggtctgcaaccggtgattgtgccggatctatcgcagtcgctggacggacatctggccaacggtgattttcgcccgtcacccaggggga<br>acacgcctgcgcatgattgaacagatgggccaaaacctggccacttttgtgattggcgcactcgctggggcgggcggcggcgttactggcgcagcgc<br>agccgtggcgaggtgatcgccctgccgcatctgatgacgcttgatgcgtgcgacacctttatccatcgcctgaaaaccctctccgggcgcgacgtg<br>cccgcgtggattgagcgccagcgcgggcaagtgcaggatgcgatgatcgattgccatatgtggttgcagggcgcggcatcgccatgccgcagaa<br>ggcgatcacctggcggcatggtgcgatttcgcccgcagccagggcatgatcccggcccggttgtcgcgccggtcagccagccgggggttgcaaaat<br>ctgccggttgaaatggtggttcatcggcgatctggaagatatgcaggcttcggctttgcgcgacgcccgccgcgttactggtggcaattctcatg<br>ccgccgatctcgccacgcagtttgatatgtcgcttatccgcgccgttttccggtgtatgaccggctggggggaatttcgtcggctgcgccagggt<br>atagcggcattcgtgacacgtcgtttgagctggcgaatgtgatgcgcgaacgccattgcccgcttgcaacctaccgctcgccgctcgtcagcgct<br>tcggcgacaacgttacgccaggagatcggtatgccgcatgttaa |
| 142 | atgaccctgaatatgatgatggatgccagcgcgcccgaggccatcgccggtgcgctttcgcaacaacatcctgggctgttttttaccatcgttgaa<br>gaagcccgtcgctatttcactaaccgatgccgaggcacgtattgtctatgccaacccggcattctgccgccagaccggctatgagcttgaggagt<br>tgttcagcaaaatccccgcctgcttgccagtcagcagaccccacgggaaatctaccaggatatgtggcacaccctgttacaacgtcgaccatggc<br>gcgggcaattgatcaaccgccaccgtgacggcagccttttctggttgagatcgatatcaccccggtgattaaccgttggcgaactggaaact<br>acctggccatgcagccgcgatatcagcgccggttatgcgctggagcagcggttgcgtaatcacatggcgctgaccgaagcggtgctgaataacattc<br>cggccggtggtcgtggtcgatgaacgcgatcgtgtggttatgataacctcgcctataaaacttctgtgctgattgcggcggaaaagagctac<br>tgagcgaactccatttttcagcccgtaaagcggagctggcaaacggccaggtcttaccggtggtgctgcgcggcgggtgcgctggttgtcggtca<br>cctgctgggcgctgccaggcgtcagcgaagaagccagtcgctactttattgataatccttgacgcgcacgctggtggtcatcaccgacgacaccc<br>agcagccgcagcaagagcaagacggcttgaccgccttaaacagcagattgccggccagaggaccagcgcaaactgctggcggcgatccgcgaagcgcttgacg<br>ccgcgctgatccagcttaactgccccatcaatatgctggcggcgcgcggcgttaaacggcagtgataacagcaacgtagcgctggacgccgt<br>ggcgcgaaggtgaagaagcgatggcgcggctgaaacggtgccgcccgtcgctggagctggaaagtgccgccgtctggccgctgcaaccctttttg<br>acgacttcgcgcgctttatcacacccgctacgagcagggtaaaaatttgcaggtcacgctggattcgacgcatctggtgggatttggtcagcgaa<br>cccaactgctggcctgcctgagtctgtggctcgatcgcacgctggatattgccggctgcgtgatttcaccgcccaaacgcagattacgccc<br>gggaagaagcgggctggctctcgttgtatatcactgacaatgtgcgttgattccgctgcgccataccattcgccggcgcttaacgcaccgg<br>gaaaaggtatggagttgcggctgatccagacgctggtagcgcatcacaacggcgcgatagaactcacttcacgccccgaaggggggaagctgcctga<br>ccctacgattcccgctatttcattcactgaccggaggttcaaaatga |
| 143 | atgacccagcgaaccgagtcgggtaataccgtctggcgcttcgatttatcccagcagttcaccgcgatgagcggataagcgtggttctcagccggg<br>cgaccgaggttgaaacagacactccagcaggtgtgtgcgtattgcacaatgacgccttttttgcagcacggcatgatctgtctgtacgacagccagca<br>ggcgattttgactattgaagcgttgcaggaagccgatcagcagttgatccccggcagctcgcaaattcgctaccgtccgggtgaagggctggtcgg<br>gacggtgctttcgcaggggcaatcgttagtgctggcggcggtgacgatcacgccgctttcttgaccgcctgggacgtatgattacaacctgcc<br>gtttatcgccgtgccgctgatagggcgggatgcgcagactttggcgtgctgacggcgcaaccgatggcgcgttacgaagacggtttaccgcctg<br>cacccgctttctggaaacggtcgcgaatctggtggcgcagaccgtgcgtttgatgacgccgccggctgcacgcccttcccacgcgctgccatcac<br>gccaaccgccagcccgaaatcgtgcagtacttcacgcgcgttcggcttcgaaaatatggtcggcaacagcccggcaatgcgccagaccatggagat<br>tatccgtcaggtttcgcgctgggataccaccgttctggtgcgcggcgagagcggcaccggcaaggaactgattgccaacgccatccatcacaattc<br>gccgcgcgccagtgcgccatttgtgaaattcaactgtgcggcgctgccggacacattgcttgaaagcgaattatttggtcatgaaaaaggcgcctt<br>taccggcgcgtacgccagcgtaaaggccgttttgagctggccgatggcggcacgctgttcttgacgaaattggggaaagcagcgcctcgtttca<br>ggctaagctgctgcgtattttgcaggagggcgaaatgaacgcgtcggtggtgacgagacattgcaagtgaatgtgcgcatcattgccgcgacgaa<br>ccgcaaccttgaagatgaagtacgcctgggacattttcgcgaagatctctattaccgcctgaatgtgatgcccatcgccctgccgccgctgcgcga<br>acggccagaccacatccgcgaactggcacattttctggtgcgtaaaatcgcccacaaccagaaccgcacgctgcgcattagcgaggcgctatccg<br>cctgctgatgagctacagctggcccggcaatgtgcgcgaactggaaaaactgccttgagcgctctgcggtgatgtcggaaaacggtctgatcgatcg<br>ggacgtgatttatttaatcatcgcgaccagccagccaaaccgccggttatcagcgtcacgcccgacgataactggctcgataacacccttgacga<br>gcgccagcggctgattgccgcgctgaaaaaagcgggatgggtacaagccaaagccgcccgcttgctggggatgacgccgcgccaggtcgcttatcg<br>tattcagaccatggatatcaccctgccaaggctataa |
| 144 | atgccgcaccacgcaggattgtcgcagcactggcaaacggttttttctcgtctgccggaagcgctcaccgcgcaaccattgagcgcgcaggcgcag<br>tcagtgctcacttttagtgattttgttcaggacagcatcatcgtgcatcctgagtggctggcagagcttgaaagcgcaccgccgccagcgaacgag<br>tggcaacactacgcgcaatggctgcaagcggcgctggagggcgtcaccgatgaaacctcgctgatgcgcacgctgcggctgtttcgccgtcgcatt<br>atggtgcgcatcgcctggagtcaggcgctacagttggtggccgaagaggatatcctgcaacagtcagcgtgctggcggaaactctgatcgtcgcc<br>gcgcgcgactggctctatgacgcctgctgccgtgagtggggaacgccgtcaatccgcaaggcgtcgcgcagccgatgctggtgctcggcatgggc<br>aaactggcggcggcgaactcaatttctcatccgatatcgatttgattttgcctggccggaaaatggcaccacgcgcggcggacgccgtgaactg<br>gataacgcagtttttaccgcgcttggtcaacggctaattaaagtcctcgaccagccccacgcaggatggcttttgtctaccgcgtgatatgcgc<br>ttgctgtccctttggcgacaggcccgcctggtgctgagttttgccgcgctggaagattactaccaggagcaggggcgcgactggagttgaacgatacgcg<br>atggtgaaagcgcgcattatggggacaacgacggcgaccatgcgcgagagttgcgcgccatgctgcgcccgttcgttttccgccgctatatcgac<br>ttcagcgtgatccagtctctgcgcaacatgaaaggcatgattgcccgcgaagtgcggcgtcgcggcctgaaggacaacataaaactcggcgcgggc<br>ggtattcgcgaaatagagtttatcgtgcaggttttccagttgattcggcggtgcgagccctgcgctgcaatcgcgttcgctgttgccgacgttt<br>gctgccattgatcaactacatctgctgccagatggtgatgcacccccggcggcgcgcgaggcctgatttggctgcgacggctggaaaacttgctgaaa<br>gcattaatgacgaacagacagacgctgccggccgatgatttgaatcgcgcgcgcctcgcctgggaatgggcaaagagagctgggaagcgctct<br>gcgaaacgctggaagcgcatatgtcggcggtgggcagattttcaacgatctgattggcgatgatgaaacggattcgccggaagatgcgctttctga<br>ggctgagcgaatttgtcagcaggatcgcgtgcaggaagaggactctacgcccgtgctggcgcatcttccgaggacgatccgccgcgtggtggc<br>gctgattgctgatttcgcaaagagctggataaaacgcaccattggccgccgggcaacaggtactcgatcacttaatgccgcatctgctcagcga<br>tgtatgctcgcgtgacgatgcgccagtgccgctgtcgcgtctgacgccgctgctcaccggtattattacgcgcaccacttaccttgagctgctgag<br>tgaattccccggtgcgctgaaacacctcatttccctgtgcgccgcgtcgcgatggtggccagccaactggcgcgctacccgatcctgctcgatga<br>actgctcgacccgaacacgctctatcaaccgacggcgatgaacgcctatcgcgatgaactgcgacaatacctgttgcgcgtgccggaagaggatga<br>agagcagcaactggaggcgctacggcagtttaagcacgcgcagttgttgcgcgtagcggcggcggatatcgccggtacgttaccgtcatgaaagt |

TABLE H-continued

| SEQ ID NO: | Sequence |
|---|---|
|  | gagcgatcacttaacctggctggcggaagcgattatcgatgcggtggtcagcaagcctggaaccagatggtggcgcgttacggccagccgacgca tctgcacgatcgcgaagggcgcggtttcgccgtggtcggttacggcaaacttggcggctgggaattaggttacagctccgatctggatctggtgtt cctgcacgactgccccatggatgtgatgaccgatggcgagcgtgaaatcgatggccgccagttctatttgcgcctcgcgcagcgcgtcatgcacct gttcagcacgcgcacgtcgtccggcattctttatgaagtcgatgcgcgtttgcgcccgtccggcgcggccggaatgctggtgaccactgcggaagc gttcgccgattatcaaaaaaatgaagcctggacatgggagcatcaggcgctggcgcgtgcgcgcgtggtgtacggcgatccgcaactgaccgccga atttgacgccattcgccgcgatatcctgatgacctcccgcgatgccgctaccctgcaaaccgaagtgcgggaaatgcgtgagaaaatgcgcgccca tcttagtaacaagcacaaagaccgtttcgatctgaaagccgatgaaggcggtatcaccgatattgagtttatcgctcagtatctggtgctgcgctt tgcccatgagaagccgaaactgacgcgctggtcggataatgtgcgcatcctcgaagggctggcgcaaaacggcatcatggatgagcaggaagagca ggcattgacgctggcgtacaccacgttgcgtgatgagctgcaccacctggcgctgcaagagctgccaggacatgtggcgctctcctgttttgtcgc cgagcgtgcgcttatcaaaaccagctgggacaagtggctggtggaaccgtgcgccccggcgtaa |
|  145  | atgaaaaacacaacattaaaaacggctcttgctttcgctggcgttgctgccaggcctggcgatggcggctcccgctgtggcggataaagccgacaa cggctttatgatgatttgcaccgcgctggtgctgtttatgaccattccgggcattgcgagttctacggcggtttgatccgcggtaaaaacgtgctg tcgatgctgacgcaggttgccgtcaccttcgctctggtgtgcatccgtggtggttacggctactctctggcatttggcgagggcaacagcttc ttcggcagtttcaactgggcgatgttgaaaaacatcgaattgaaagccgtgatgggcagcatttatcagtacatccacgtggcgttccagggctcc tttgcttgtatcaccgttggcctgattgtcggtgcgctggctgagcgtattcgctctctgcggtgctgattttgtggtggtatggctgacgctt tcttatgtgccgattgcgcacatggtctgggggtggcggtctgctggcaacccacggcgcgctggatttcgcgcgcggtacggttgttcacatcaac gccgcgatcgcaggtctggtgggggcttacctgattggcaaaccgcgtgggctttggcaaagaaagcgttcaaaccgcataacctgccgatggtcttc accggcaccgcgatcctctatgttggctggtttggcttcaacgccggctctgcaagctcggcgaacgaaatcgctgcgctggcttcgtgaacacg gttgttgccactgcggccgctattctggcgtgggtatttggcgagtgggcaatgcgcggtaagccgtctctgctcggtgcctgttctggtgccatc gcgggtctggttggtatcaccctcggcgtgcggttatgtgggtgtcggcggcgcgctgattgtgggtctgattgccggtctggcagggctgtgggg cgttactgcactgaaacgtatgttggtgttgatgaccatgcgatgtcttcggtgtgcacggcgtgtgcggcatcgtgggttgtatcctgaccggt atcttcgcgtctacgtcgctgggcgcgtgtcggtttcgctgaagggtgaccatgggccatcaggtactggtacagctggaaagcgttgccatcact atcgtggtctggcgtggtggcctttatcggttacaaactggcggatatgacggtaggcctgcgcgtaccggaagagcaagagcgtgaagggctg gatgtgaacagccacggcgaaaatgcgtataacgcctga |
|  146  | ttcttggttctctggagcgctttatcggcatcctgactgaagaatttgcaggcttcttcccaacctggcttcacccgtgcaggtagttgtgatgaa catcactgattcgcaggctgaatacgttaacgaattgaccgtaaactgcaaaatgcgggcattcgtgtaaaagcagacttgagaaacgagaagat tggctttaaaatccgcgagcacactttacgtcgtgtccctatatgctggtttgtggtgacaaagaggtcgaagccggcaaagttgctgtgcgtac ccgtcgcggtaaagacctgggtagcctggacgtaaatgatgttatcgagaagctgcaacaagagattcgcagccgcagtcttcaacaactggagga ataaggtattaaaggcggaaaacgagttcaaacggcgcgtcccaatcgtattaatggcgagattcgcgccacggaagttcgcttaacaggtaggaa ggcgagcagcttggtatt |
|  147  | cgttctgtaataataaccggacaattcggactgattaaaaaagcgccctcgcggcgctttttttatattctcgactccatttaaaataaaaaatcc aatcggatttcactattttaaactggccattatctaagatgaatccgatggaagctcgctgttttaacacgcgttttttaaccattattgaaagtcg gtgcttctttgagcgaacgatcaaatttaagtcgattcccatcaaaaaaatattctcaacctaaaaaagtttgtgtaatacttgtaacgctacatg gagattaactcaatctagagggtattaataatgaatcgtactaaactggtactgggcgc |
|  148  | cgcgttcaggttgaacgtaaaaaagtcggtctgcgcaaagcacgtcgtcgtccgcagttctccaaacgttaattggtttctgcttcggcagaacgat tggcgaaaaaacccggtgcgaaccgggttttttatggataaagatcgtgttatccacagcaatccattgattatctcttcttttttcagcatttcc agaatcccctcaccacaaagcccgcaaaatctggtaaactatcatccaattttctgcccaaatggctgggattgttcatttttgtttgccttaca acgagagtgacagtacgcgcgggtagttaactcaacatctgaccggtcgat |
|  149  | ttgaagagtttgatcatggctcagattgaacgctggcggcaggcctaacacatgcaagtcgngcggaagcacaggagagcttgctctctgggtgac gagcggcggacgggtgagtaatgtctgggaaactgcctgatggaggggataactactggaaacggtagctaataccgcataacgtcgcaagacca agaggggggaccttcgggcctcttgccatcagatgtgcccagatgggattagctagtaggtgggtaacggcncacctaggcgacgatccctagct ggtctgagaggatgaccagccacactggaactgagacacggtcccagactcctacggaggcagcagtggggaatattgcacaatgggcgcaagcct gatgcagccatgccgcgtgtatgaagaaggcctt cgggttgtttaagtacttttcagcggggaggaagtgttgnggttaataaccncagcaattga cgttacccgcagaagaagcaccggctaactccgtgccagcagccgcggtaatacgagggntgcaagcgttanncgaatnantgggcgtaaagcgt ncgcaggcggtntgtnaagtcggatgtgaaatcccgggctcaacctgggaactgcattcgaaactggcaggctagagtnnngtagaggngggtag aattccnggtgtagcggtgaaatgcgtagagatcnggangaanaccngtggcgaaggcggccnnctggacaaagactgacgctnaggngcgaaagc ggggagcaaacaggattagataccctngtagtccacgccgtaaaacgatgtcgacttggaggttgtgcccttgaggcgtggcttccggagctaacg cgttaagtcgaccgcctggggagtacggccgcaaggtaaaactcaaatgaattgacggggcccgcacaagcggtggagcatgtggtttaattcg atgcaacgcgaagaaccttacctactcttgacatcagagaacttnncagagatgnnttggtgccttcgggaactctgagacaggtgctgcatggc tgtcgtcagctcgtgttgtgaaatgttgggttaagtcccgcaacgagcgcaacccttatccttttgtgccagcggtncggccgggaactcaaagga gactgccagtgataaactggaggaaggtggggatgacgtcaagtcatcatggcccttacgagtagggctacacacgtgctacaatggcatacaa agagaagcgacctcgcgagagcaagcggacctcataaagtgcgtcgtagtccggattggagtcgtcaactcgactccatgaagtcggaatcgctag taatcgtagatcagaatgctacggtgaatacgttcccgggccttgtacacaccgcccgtcacaccatgggagtgggttgcaaaagaagtaggtagc ttaaccttcgggagggcgcttaccactttgtgattcatgactggggtgaagtcgtaacaaggtaaccgtaggggaacctgcggttggatcacctcc tt |
|  150  | atgaccatgcgtcaatgtgccatttacggcaaaggtggtatcggtaaatccactaccacgcaaaacctggtcgccgcgctggcggagatgggcaag aaagtaatgatcgtcggctgcgacccgaaagcagactccactcgtctgatcctgcatgcgaaagcgcagaacaccattatggagatggcggctgaa gtccgctccgtggaagcctttgaactggaagatgtgctgcaaatcggttacggcgaatcgtacgtcgcgaatccgggcgccggaaccaggcgtt ggctgtgctggtcgcgggggtaattaccgccatcaacttcctgaagaagaaggcgcctatgttcccgacctcgattcgtctttacgacgtgttg ggcgacgtggtgtgcgggggggttcgccatgccgattcgcgaaaacaaagcgcaggagatctcatcgtctgctccggcgaaatgatgcgatgtac gccgccaacaacatctctaaaggcatcgtgaaatacgccaaatccggcaaaggcgccttggcgggctgatctgtaactcccgtcagaccgaccgcg aagtgagctgatcatgcgctggcggaaaactcggcacccagatgatccacttcgtgccgcgacaacatcgtcaacgcgctgaaatccgcc gtatgacggtgattgagtacgatccgaaatgcaaccaggccgatgaataaccgcacgctggcgaacaagatcgtcaacttacaccaaaatggtcgtg ccaacgcccatcaccatgacgaactggaagagctgttgatggaattcggcattatggatgtggaagacaccagcattatcggtaaaaccgccgca gaagaaaacgcggtttga |
|  151  | atgagcaatgcaacaggcgaacgtaataggagatcatccaggaagtgctggagatcttttccggaaaaaacgcgcaaagaacgcagaaagcacatga tggcgagcgaccggagatgaaagcgtcgggaaatgcatcatctccaaccgtaagtcgcagcccggcgtaatgaccgtcgcggttgctcttacg ccggttctaaaggggtggtattcgggccgatcaaagatatggcccatatttcccacgcccggtcggctgcggtcagtactccgcgccgggcggc gtaactactacaccgcgtcagcggtgtggatagcttcggtacgctcaactttacctccgattttcaggagcgcgatatcgtgtttggcggcgata aaaagctgaccaaaactgattgaagagatggagacgctgttcccgctgaccaaagggatctccattcagtccgaatgcccggtcggcctgattggcg |

TABLE H-continued

| SEQ ID NO: | Sequence |
|---|---|
| | acgacattgaagccgttgccaacgccagccgcaaagccatcaataaaccggtcattccggtgcgctgcgaaggttttcgcggcgtttcccagtcac<br>tcggtcaccacattgccaacgacgtgatccgcgactgggtactggataaccgcgaaggcaacgcgtttgaggccggtccttatgacgtggcgatca<br>tcgccgattacaacatcggcggcgatgcctgggcgtcgcgcatttgctcgaagagatgggcctgcgcgtggtggcgcagtggtccggcgacggca<br>cgctggttgagatggagaccacgccgttcgtcaaactcaaccttgtgcactgctaccgctcaatgaactatatctcccgcatatggaggagaaac<br>acggtattccgtggatggagtacaacttcttcggtccgaccaaagtcgccgaatcgttgcgcaaaatcgccgatatgtttgatgacaccattcgcg<br>ccaacgccgaagcggtgatcgccaaatatcaggcgcagaacgacgccatcatcgccaaataccgtccgcgtctggaaggccgcaaagtgctgctgt<br>atatgggcggtttacgtcctcgccatgtgattggcgcttatgaagatctgggaatggaaattatcgctgcgggttatgaattcgcccacaacgatg<br>actacgaccgcaccctgccggatctgaaagaaggcaccttgctgttcgacgatgccagcagttatgaactggaagcctttgtcaaagcgctgaagc<br>cggatctgatcggctccggcattaaagagaagtacatatccagaaaatgggcgtgccgtttcgccagatgcactcctgggattactccggcccta<br>tcacggttatgacggctttgccatcttcgcccgcgatatggatatgacgatcaacaaccccgcgtggggccagttgaccgcgccgtggctgaaatc<br>cgcctga |
| 152 | atgggacgcggcgagcgccgcctgttccatgccgtgcgccacatcgtcaaccgctaccacccggccgccgtctttatctataacacctgcgttccc<br>gcgatggagggcgacgatatcgaagccgtctgccaggcggcagaaaccgccatccgcgtaccggtgattgccgttgatcgccgggttttacggc<br>agcaaaaatctcggcaaccggttggccggtgaagtgatggtgaaaaaaggtgattggcgggcgtgaaccgccgtggccggaagatacccctt<br>tgccccggcgcaccgccacgatatcgggctgattggcgaattcaatattgccggagagttctggcatattcagccgctgctcgatgagctgggtat<br>tcgcgtgctcggcagcctctccggcgacgggcgcttcagtgaaatccagacgctgcaccgggcgcaggtcaatatgctggctcctccagggcgctg<br>atcaacgtcgccgctcgctggagcagcgctacggcacgccggtgtttgaaggcagttttatggtgttcgcgccacctctgacgccctgcgccaa<br>ctggcggcgctgaccggagaccgcgatctgatgcagcgcaccgattcagctcattgcccgcgaagagcagcaaacagagcaggcgctggccccgct<br>gcgcgagcgcctgcgcgggcgcaaagcgctgctctatccggcggcgtgaaatcctgacggtggtttcggcgcttcaggatctgggcatggaagt<br>ggtggcgaccggcacgcgcaaatccaccgaagaggataaacagcgcatccgcgaactgatgggcgccgacgcgctgatgcttgatgaaggtaacgc<br>ccgctcgctgctggacgggttttaccgctacaaggcggacatgatgatcgcgggggacgcaatatgtcaccgcctacaaagcgcggctgccgttcc<br>tcgatatcaatcaggagcgcgagcgccttttgccggctaccgcggcattgtcaccctggccgaacagctctgcctgaccatggaaagcccggtct<br>ggccgcaaacccattcccgcgcaccgtggcaataa |
| 153 | atgatggagcaaatggacgtgccgtccagcctgctttccgatccctccgaagtgctggataccccggctgacgggcattaccacatgtatgcgggg<br>cggtacgacccagcaggagatgcgcgaagcgcctgacgctatcgacaccctgctgctgcaaccctggcaactggtgtaaaccaaaaaagtggtgca<br>ggaaagctggaaccagcccgctaccgaggtgcaaatcccaatggggctggccggaaccgacgagctgctgatgacggtaagccagttaaccggcaa<br>agccattccggatagcttagcgctggaacgcggtcggctggtggatatgatgctcgactccacacctggctgcacggcaagaaattcggcctgtt<br>cggtgacccggattttgtcatgggggcttgacccgcttcctgctggaactgggctgcgaaccgacggtgattctgtgccataacggcagcaagcctg<br>gcagaaagcgatgaagaaaatgcttgaagcctcgccgccgtcgctggaactggaaagcccggcagtctggccgctccagccgttccttgacgatctgcgtgc<br>cctgtatcacacccgataacagggcgaaaacctgcaaattgagctggaatcccccgacctggtgggctttggccagcgaacacaactgcttgc<br>ctgcctgagcctgtggctcgacagaaccctggatattgccgcggagctacgtgatttcacggtacagactcaactttacgcccgcgaagagagcgg<br>ctggctgtcgttctatttaaacgacaatgtgccgctgattcaggtgcgctacacccattcacccgatgcactnaatgcgcccggtaaaggcatgga<br>gctgcggctgatccagacgctggtcgccaccatcgaggcgcaatagaactgacctcacgccctcagggaggcacctgtctgatcctgcgtttccc<br>attattttactcgctgacaggaggctcactatga |
| 154 | atgca<br>gcgcgacatcagcaccagctacgcgctggaacaacggctgcgcaatcatatgacgctgaccgaagccgtcttgaataacattccggcggcggtttgt<br>agtggtggatgaacgcgatcgggtggtgatggataaccctcgcctacaaaacctttgcgccgattgcgcggtaaagaactactcaccgaaatcaa<br>ccttttccgcccataaggcggagctggcgcagggcctggtactgccgtagtgctgcgcggcaccgtgcgctggttgtccgttacctgttgggcgt<br>gccgggcgtcagcgaagaagcaggccgctacttcttattgatagccgccgcgcgcacgctggtggtgatcaccgataatactcagcagcagcaaca<br>acaggagcaggggcgtcttgatcgtctgaagcagcagataaccagcggtaaattgctggcggcgatccgcgaatcgctggacgccgcgctggtaca<br>actcaattgcccaattaatatgctggccgccgcacgccgcttaaatggcgacgagcatagcaatctggcgctggatgccgcatggcgtgaaggcga<br>agaagcgatggcgccggttgcagcgctgccgcccgtcgctcggactggaaagccccggcagtctggccgctccagcgttccttgacgatctgcgtgc<br>cctgtatcacacccgataacagggcgaaaacctgcaaattgagctggaatccccgacctggtgggctttggccagcgaacacaactgcttgc<br>ctgcctgagcctgtggctcgacagaaccctggatattgccgcggagctacgtgatttcacggtacagactcaactttacgcccgcgaagagagcgg<br>ctggctgtcgttctatttaaacgacaatgtgccgctgattcaggtgcgctacacccattcacccgatgcactnaatgcgcccggtaaaggcatgga<br>gctgcggctgatccagacgctggtcgccaccatcgaggcgcaatagaactgacctcacgccctcagggaggcacctgtctgatcctgcgtttccc<br>attattttactcgctgacaggaggctcactatga |
| 155 | atgactcagcgaaccgagtcgggtacaaccgtctggcgctttgacctctcccaacagtttacagccatgcagcgtatcagtgtggtgttaagccgc<br>gcgacggagatcgggcagacgctacaggaagtgctgtgcgtgctgcacaacgatgcctttatgcagcacgggatgatctgtccgtacgcgcgggtg<br>cgcgtcttcgcgagcgtatggctttga |
| 156 | atgcgcgtggaagactggtcaacgctgaccgaacggctcgatgcccatatggcaggcgtgcgccgaatctttaacgaactgatcggtgatgacgaa<br>agtgagtcgcaggacgatgcgctctccgagcactggcgcgagctgtggcaggacgcgcttcaggaagatgacaccacgccggtgagacgcacttaa<br>ccgacgacgcgccatcgcgtggttggcgctgatcgctgcttgannttccgtcttgagagaacaaacgccgactcggcccgcgcgtngcgccaggtgctggat<br>cacctgatgccgcacctgagagcgaagtctgctcgcgtgcgcatgcgccggtgccgctgtcgcggatgatgcccctgagagggattatcaccgt<br>actacctaccttgaactcctgagcgagttccctggccgcgcttaagcacctgatttcactctgcgccgcgtcgccgatggtggccaacaagctggcg<br>cgttacccgctgctgctggatgagctgctcgatccgaataccctttatcaaccgacggcgaccgacgcctaccgggacgaactgcgtcagtatctg<br>ctgcgcgtgccggaagaagacgaagagcaacagctcggaggcgctgcgtttaagcaggcccagatgctgcgcggtgcgcgcagatattgc<br>cggaacgctgccggtgataaagtgagcgatcacttaacctggcttgcggaagcgattatcgacgcggtgggtgcatcaggcctggtcagatggt<br>ggcgcgctatggccagccgaaacatctggctgaccgtgatggtcgcggcttcgctggtggtgggttacggtaagctcggcggttgggagctgggct<br>atagctccgatctggattaatcttcctccacgactgcccggttgatgtgatgaccgacggcgagcgcgagattgacgggcgtcagttctacctgc<br>gcctggcgcagcgatcatgcaccctgttcagcaccgcacctcgtcgggcattttgtatgaagtggatgcccgtagcgcccgtccggcgcgggg<br>catgctggtcacctcgacggagtccttcgctgattaccagaagaatgaagcctggacgtggagcatcaggcgctggtgcgcgcccggtggtgtat<br>ggcgatccgctgctgaaaacgcagtttgacgtgattcgtaaggaagtcatgaccaccgtgcgcgatgcagcacgctgcaaacgaagtgcgcgaa<br>atgcgcgagaaaatgcgcgcgcacttaggcaataaacatcgcgatcgctttgatattaaagccgatgagggcggtattaccgatattgagtttatt<br>acccagtatctggtgttgctgcaccgcgacaagccgaagctgacgcgctggtcggataacgctgcgcattaggaactgctggcgcaaaacgaca<br>ttatggacgagcaggaggcaggccttaacccgtctatacaacgcttcgcgatgagctccatcatctggcgttgcaggagcagcngggncacg<br>tggcgctggactgtttcaccgctgaacgcgctcaggtaacggccagctggcagaagtggctggtggaaccgtcgctaacaaatcaagtgtga |
| 157 | agatgtgcccagatgggattagctagtaggtgggtaacggcncacctaggcgacgatccctagctggtctgagaggatgaccagccacactggaa<br>ctgagacacggtccagactcctacgggaggcagcagtggggaatattgcacaatgggcgcaagcctgatgcagccatgccgcgtgtatgaagaagg<br>ccttcgggttgtaaagtactttcagcggggaggaaggtgttgtggttaataaccncagcaattgacgttacccgcagaagaagcaccggctaactc<br>cgtgccagcagccgcggtaatacggagggtgcaagcgttaatcggaattactgggcgtaaagcgcacgcaggcggtctgtcaagtcggatgtgaaa<br>tccccgggctcaacctgggaactgcattcgaaactggcaggctagagtcttgtagaggggggtagaattccaggtgtagcggtgaaatgcgtagag<br>atctggaggaataccggtggcgaaggcggccccctggacaaagactgacgctcaggtgcgaaagcgtggggagcaaacaggattagataccctggt |

TABLE H-continued

| SEQ ID NO: | Sequence |
|---|---|
| | agtccacgccgtaaacgatgtcgacttggaggttgtgcccttgaggcgtggcttccggagctaacgcgttaagtcgaccgcctggggagtacggcc gcaaggttaaacctcaaatgaattgacgggggcccgcacaagcggtggagcatgtggttaattcgatgcaacgcgaagaaccttacctactcttg acatccagagaacttnncagagatgnnttggtgccttcgggaacctgagacaggtctgcatggctgtcgtcagctcgtgttgtgaaatgttgggtt aagtcccgcaacgagcgcaacccttatcctttgttgccagggtccggccgggaactcaaaggagactgccagtgataaactggaggaaggtgggga tgacgtcaagtcatcatggcccttacgagtagggctacacacgtgctacaatggcgcatacaaagagaagcgacctcgcgagagcaagggacctca taaagtgcgtcgtagtccggattggagtctgcaactcgactccatgaagtcggaatcgctagtaatcgtagatcagaatgctacggtgaatacgtt cccgggccttgtacacaccgcccgtcacaccatgggagtgggttgcaaaagaagtaggtagcttaaccttcgggagggcgcttaccactttgtgat tcatgactgggggtgaagtcgtaacaaggtaaccgtaggggaacctgcggttggatcacctccctt |
| 158 | atgaccatgcgcaatgtgccatttacggcaaaggtggtatcggtaaatccactaccacgcaaaacctggtcgccgcgctggcggagatgggcaaga aagtaatgatcgtcggctgcgaccgaaagcagactccactcgtctgatcctgcatgcgaaagcgcagaacaccattatggagatggcggctgaag tcggctccgtggaagaccttgaactggaagatgtgctgcaaatcggttacggcgacgtacgctgcgcagaatccggcggcccggaaccaggcgttg gagtgctggtcgcggggtaattaccgccatcaacttcctgaagaagaaggcgcctatgttcccgacctcgatttcgtcttttacgacgtgtttggg cgacgtggtgtgcggggggttcgccatgccgattcgcgaaaacaaagcgcaggagatctacatcgtctgctcccggcgaaatgatggcgatgtacgc cgccaacaacatctctaaaggcatcgtgaaatacgccaaatccggcaaagtgcgccttggcgggctgatctgtaactcccgtcagaccgaccgca agatgagctgatcatagcgctggcggaaaaactcggcacccagatgatccactcgtgccgcgcgacaacatcgtgcaacgcgctgaaatccgccg tatgacggtcgattgagtacgatccgaaatgcaaccaggccaatgaataccgcacgctggcgaacaagatcgtcaacaacaccaaaatggtcgtgcc aacgcccatcaccatggacgaactggaagagctgttgatgaattcggcattatggatgtggaagacaccagcattatcggtaaaaccgccgcaga agaaaacgcggtttga |
| 159 | atgagcaatgcaacaggcgaacgtaatctggagatcatccaggaagtgctggagatctttccggaaaaaacgcgcaaagaacgcagaaagcacatg atggtgagcgaccggagatggaaagcgtcgggaaatgcatcatctccaaccgtaagtcgcaacccggcgtaatgaccgtgcgcggttgctcttac gccggttctaaaggggtggtattcgggccgatcaaagatatggcccatatttcccacgcccggtcggctgcggcagtactcccgcgcgggcggg gtaactactacaccggcgtcagcggtgtggatagcttcggtacgctcaacttttacctccgattttcaggagcgcgatatcgtgtttggcggcgata aaaagctgaccaaactgattgaagtgatggagacgctgttcccgctgaccaaagggatctccattcagtccgaatgcccggtcggcctgattggcg acgacattgaagccgttgccaacgccagccgcaaagccatcaataaaccggtcattccggtgcgctgcgaaggttttcgcggcgtttcccagtcac tcggtcaccacattgccaacgacgtgatccgcgactgggtactgataaccgcggaaggcaagccgtttgaggccggtccttatgacgtggcgatca tcggcgattacaacatcggcggcgatgcctgggcgtcgcgcattttgctcgaagagatgggcctcgcgtgtggcgcagtggtccggcgacggca cgctggttgagatggagaacacgccgttcgtcaaactcaaccttgtgcactgctaccgctcaatgaactatatctcccgcatatggaggagaaac acggtattccgtggatggagtacaacttcttcggtccgaccaaagtcgccgaatcgttgcgcaaaatcgccgatatgtttgatgacaccattcgcg ccaacgccgaagcggtgatcgccaaatatcaggcgcagacgacgccatcatcgccaaataccgtccgcgtctggaaggccgcaaagtgctgctgt atatgggcggtttacgtcctcgccatgtgattggcgcttatgaagatctggggatggaaattatcgctgcgggttatgaattcgcccacaacgatg actacgaccgcaccctgccggatctgaaagaaggcaccttgctgttcgacgatgccagcagttatgaactggaagcctttgtcaaaggctgaagcc ggatctgatcggctccggcattaaagagaagtacatcttcagaaaatgggcgtgccgtttcgccagatgcactcctgggattactccggccccta tcacgggttatgacggctttgccatcttcgcccgcgatatggatatgacgatcaacaaccccgcgtggggccagttgaccgcgcgtggctgaaatc cgcctga |
| 160 | atgaaggggaacgagatcctggctttgctcgatgaacctgcctgcgagcacaaccatataaacagaaatccggctgcagcgcgccgaaacccggcgcg acagcgggcggctgcgccttgacggtgcgcagatcaccctgctgcactctcgatgttgcccacctggtacacggcccccattgttgtaccggt agctcatgggataaccgtggcagcttcagttccggcccgacgatcaaccggctgggttaccaccgatctgagcgaacaggatgtgatcatgggacg cggcgagcgccgcctgttccatgccgtgcgccacatcgtcaaccgctaccaccggccgccgtctttatctataacctgcgttcccgcgatgga gggcgacgatatcgaagccgtctgccaggcggcagaaaccgccatcggcgtaccggtgattgccgttgatgtcgccgggttttacggcagcaaaaa tctcggcaccggttggccggtgaagtgattggtgaaaaaggtgattggcggcgtgaacccgcgcgttggccggaagataccccctttttgccccgcg caccgccacgatatcgggctgattggcgaattcaatattgccggagagttctggcatattcagccgctgctcgatgagctgggtattcgcgtgctc ggcagcctctccggcgacgggcgcttcagtgaaatccagacgctgcaccgggcgcaggtcaatatgctggtctgctccagggcgctgatcaacgtc gcccgctcgctggagcagcgctacggcacgccgtggtttgaaggcagttttttatggtgttcgcgccacctctgacgccctgcgccaactggcggcg ctgaccggagaccgcgatctgatgcagcgcaccgaagacgcagcagcagcagcaaacagcagcaggcgctggcccccgctgcgcggcagcgc ctgcggggcgcaaagcgctgctctataccggcggcgtgaaatcaggtcggggtttcggcgcttcaggatctgggcatggaagtggtgcgaccggc acgcgcaaatccaccgaagaggataaaacagcgcatccgcgaactgatgggcgccgacgcgctgatgcttgatgaaggtaacgcccgctcgctgctg gacgtggtttaccgctacaaggcggacatgatgatcgccggggacgcaatatgtacaccgcctacaaagcgcggctgccgtcctcgatatcaatc aggagcgcgagcacgcctttgccggctaccgcggcattgtcacctggccgaacagctctgcctgaccatggaaagcccggtctgccgcaaaccc attcccgcgcaccgtggcaataa |
| 161 | atgagccaaagtgctgagaaaattcaaaactgtcatccgctgtttgaacaggatgcgtaccagatgctgataaagataaacggcaactggaagagg cccacgatccggcgcgcgtgcaggaggtcttcaatggaccaccaccgccgagtatgaagcgcttaactttcaacgcgaagcgctgactatcgatc cggcaaagcctgccagcgctgggtcggtactgtgctcgctgggcttccaataccctgccctatgttcacgactccacgggggagctgtgggccta tttccgcacctattttaaccgtcactttaaagagccgattgcctgtgtttctgactcgatgacggaagtgcggcagtattcggcggcaacaacaa cctgaacaccgggttgcagaacgccaggccctctacaagccggaaatcattgccgtctccaccacctgtatgcggaggtcatcggcgacgacctg caggcgtttattgctaacgccaaagaagacggctttatcgacgcggcgatcccggtgccttacgcgcacacgccaagctttatcggcagccatatc accggctgggacaatatgtttggaggtcgtcgccgtactcctttaccgccgattacagccgacaacgggcaaattaccgcgtatcaatctggtcagc ggatttgaaacctatctcggtaatttccgcgtgctgaaacgcatggtggagcaaatgacgtgccgtgcagcctgcttttccgatccctccgaagtg ctggataccccgctgacggcattaccacatgtatgcgggcggtacgacccagcaggagatgcgcgaagccgcctgacgctatcgacaccctgctg ctgcaaccctggcaactggttgaaaaccaaaaagtggtgcaggaaagctggaaccagcccgctaccgaggtgataatcccaatgggcttggccg gaaccgacgagagctgatgacggtaagcgcagttaaccgcaaaccattccggatagcttagcgaggaagcggtcggctggtggatatgatgctc gactcccacacccctggctgcacgcaagaaattcggcctgttcggtgacccggattttgtcatggggcgtgacccgcttcctgctgaactgggctgc gaaccgacggtgattctgtgccatagcggcagcaagcgaggcagaaagcgatgaagaaatgcttgaagcctcgccgtacgggaaagagagcgaag tctttatcaaagcgatttgtggcatttccgctcgctgatgtttacccgtcagccggactttatgatcggcaactcctacgccaagtttatccagcg cgatacgctcggcgaagggtgagcagtttgaagtgccgctgatccgctgggttcccgctgttcgatcgccaccatctgcaccgccagaccacctg gggttacgaagggcatgagtatcctcaccacgctggttaatgcggtgctggagaaagtcgacagagagaccatcaagctcggcaaaaccgacta cagcttcgatcttatccgttaa |
| 162 | atgccagaaattatccgctagttaaaaagccgctggccgtcagcccggtaaaaagtggccagccgctgggcgcgattctggcgagcatgggctttga acagagcattccgctggttcatggcgctcacgggtgcagcgccttcgcgaaggtctttttatccagcattttcacgatccgatcccgctgcaatc gacggcaatggacccgacatcgaccattatgggtgccgatgagaacatctttaccgcgtgaatgctgtgttcacgcaacaacccgaaagcgat tgttctgctgagcactggccttcgagcgcagggaagcgatattcgcgcgtggtgcgccagttccgcgatgaatatccgcgccataaaggggt ggcgctgctgaccgtcaacacgccgattttttacggcagcctggaaaacggctacagcgcggtgctggagagcatggttgaacagtgggtgccgga aaaaccgcagccgggcgtgcgcaatcgccgcgtgaacctgctgctcagccatttgcttacgccgggcgacattgagctgctgcgaagttatgtcga |

TABLE H-continued

| SEQ ID NO: | Sequence |
|---|---|
| | ggcatttggcctgcagccggtgatggtccggatctttcccagtcgctggatggccatctcgccagcggggatttctcgccaattacccagggcggc<br>agcagcctgcgcgctgattgaacagatgggacagagtcttggcacgttcgccattggcgtatccctctcccgccgcgcaattgctggcgcagcgc<br>agccatgcggaagtggtcaccctgccgcatctgatgaccatgagccagtcgcatacgtttattcatcaactgaagcgcctctccgggcgcgatgtt<br>ccggcgtggatcgaacgccagcgcgggcaactgcaggatgcgatgatcgattgtcatatgtggttgcagggcgcgcctgtcgcgctggccgccgag<br>ggcgatctgctcgccgcctggtgcgatttcgcctgcgatatgggcatggtgcccggcccggtggtggcgcggtgagccagaaagggttgcaggat<br>ctgccggtcgaaaagtcattatcggcgatcttggaggatatgcaggatctgttgtgtgaaacgcctgcatcgctgctcgtctctaattctcacgcc<br>gctgatttggccgggcagttcgacattccgctggtgcgcgccggtttcccctgttcgaccgtctgggcgagtttcgccgcgtgcgccagggttac<br>gccgggatgcgcgacaccttgtttgagctggcgaatgcgctgcgcgatcgccatcatcatcttgccgcttatcactcgccgctgcgccagcgtttt<br>tacgaacccgcatcttcgggaggtgactatgcaacatgttaa |
| 163 | atgaccctgaatatgatgatggacgccaccgcgcccgccgagatcgccggagcgctctcacaacagcatcccggattgttttcaccatggttgaa<br>caggcgcccgtcgcgatttcactgaccgatgccgatgcccacattctctacgccaaccccgcgttttgtcgccagtcggggtatgaactggaagag<br>ttgttgcagcaaaacccgcgcctgcttgccagtaagaagacgccgcgtgaaatctaccaggaaatgtggcacaccctgctgcaacaccgtccgtgg<br>cgcggacaaactgatcaaccgtcgccgcgacggcgcgtctgttctggatggaaatcgacatcaccccactgtttgatgcgttcggcaaactcgaacat<br>tacctggccatgagcgcgacatcagcaccagctacgcgctggaacaacggctgcgcaatcatatgacgctgaccgaagccgtcttgaataacattc<br>cggcggcggttgtagtggtggatgaacgcgatcgggtggtgatggataacctcgcctacaaaacctttgcgccgattgcggcggtaaagaactac<br>tcaccgaaatcaactttccgcccataaggcggagctggcgcagggcctggtactgccggtagtgctgcgggcaccgtgcgctggttgtccgttac<br>ctgttgggcgtgccgggcgtcagcgaagaagaggccgtctttattgatagcgccgtgccgcacgctggtggtgatcaccgataatactcag<br>cagcagcaacaacaggagcaggggcgtcttgatcgtctgaagcagagataaccagcggtaaattgctggcgcgatccgcgaatcgctggacgccg<br>cgctggtacaactcaattgcccaattaatatgctggccgccgcacgccgcttaaatggcgacgagcatagcaatctggcgctggatgccgcatggc<br>gtgaaggcgaagaagcgatggcgcggttgcagcgctgccgcccgtcgctggaactggaaagcccggcagtctggccgctccagccgttccttgacg<br>atctgcgtgccctgtatcacacccgatataaccagggcgaaaacctgcaaattgagctggaatcccccgacctggtgggctttggccagcgaacac<br>aactgcttgcctgcctgagcctgtggctcgacagaaacctggatattgccgcgagctacgtgatttcacggtacagactcaactttacgccgcg<br>aagagagcggctggctgtcgttctatttaaacgacaatgtgccgctgattcaggtgcgctacacccattcacccgatgcactcaatgcgcccggta<br>aaggcatggagctgcggctgatccagacgctggtcgcccaccatcgaggcgcaatagaactgacctcacgccctcagggaggcacctgtctgatcc<br>tgcgtttcccattattttactcgctgacaggaggctcactatga |
| 164 | atgactcagcgaaccgagtcggggacaaccgtctggcgctttgacctctcccaacagtttacagccatgcagcgtatcagtgtggtgttaaaccgc<br>gcgacggagatcgggcagacgctacaggaagtgctgtgcgtgctgcacaacgatgcctttatgcagcacgggatgatctgtctgtacgacagtaag<br>caagcgatccttttccattgaagccttgcatgaggccgatcagagttaattcccggcagttcacagattcgctaccgtccgggcgaagggctggtag<br>gcacggtgcttttcacagggacagtcgctggtactgccctgtgtctccgacgatcggcgttttctcgatcgcctgggattgtatgattacagcttgc<br>cgtttatcgccgtgccgctgatggggcaaactcgcagcctatcggcgtgctggccgccagcctatgcgcgttacgagagggcgtgcccgcctg<br>cacgcgttttcttgaaaccgtcgccaatctggtggcgcaaaccgttcgcctgatgacaccgccagcgtcgcgtctccacccgtgctgctgccgc<br>gcagattgccagccagcgcgggtgcgcgtcttcgcgagcgtatggctttgaaaacatggtcggtaaaagcgcggctatgcgtcagacgctggaaat<br>tattcgccaggtatcacgctgggacaccaccgtgctggtgcgtggcgaaagcggaaacggctaaagagttgatagccaacgctatccaccacaattc<br>accgcgcgccgccgcgcctttgtcaaattcaactgcgcggcgctgcccgatacgcgaggagagtgaactcttcggtcatgaaaaaggcgcgttt<br>accggcgcggtgcgccagcgcaaaggccgtttcgaactggcggatggcggtacgctgtttcttgatgagatcggcgaaagtagcgcctcgtttcag<br>gcgaaattgctgcgtatcttgcaggaaggcgaaatggaacgcgtcggcggcgacgaaacgctgcgggtgaatgtacggatcattgccgccaccaac<br>cgcaatctggaagaggaagtgcggctgggtaatttctcgcgaagatctctactatgcgctttaatgtgatgccgatctccctgccccccgctccgcgag<br>cgtcaggaggacatcgtcgagctggcattttctggtgcgcaaaatcgcgcaaaaccagaaccgcacgctgcgcatcagcgatggcgcgatccgt<br>ttgttgatgagctatagctggcctggaaacgtgcgtgagctggaaaactgccttgagcgatcggcggtgatgtcggaaaacgggcggatcgatcgc<br>gacgtgattttgtttcaccacagggaaaatctgcaaaaacgccacagaccagtgcgccgcgcaagagagctggctcgatcagaacctcgatgaggg<br>acaaagattgatcgccgcgctggagaaagccggttgggtacaggcaaaagccgcgcgcctgagggaatgaccccgcgccaggtggcctatcgtatt<br>cagacgatggacattgccatgccgagattgtag |
| 165 | atgccgcttcttcgcaggttacagcagcagtggcagaccgtttgcgaacgtctgcctgagtcattaccggcgtcatcgttaagcgagcaggcaaa<br>gagcgtgctcgtcttcagtgattttgtgcaggaaagtatcaccgccaacccgaactggctggcggaacttgagaacgcaccaccgcaggcagaaga<br>gtggcggcactatgctggctggctgcaaactgtactcgaagacgttacggatgaggccacgctgatgcgcgtcctgcgccagttccgtcgtcggct<br>gatggtgcgcattgcctgggctcaggcgctggaactggtaggcgaagagagtacgctgcagcagttaaggcgagtggcgcaaacgttgattgtcgc<br>cgcgcgagactggctctatgcctgctgtaaagagtggggcacgccgtgcagcgaggaagggggttcctcagccgctgttgattctgggcatgggaaa<br>gctggcggctgcgagctgaacttctcctctgatatcgacctgattttgcctggccggagaacggctccacgcgcggaggccgccgcgagctgaa<br>caacgcgcagttctttacccgtctcggccagcgcctgattaaagcgctggatcagcccacgcaggacggttttgtttaccgcgtggacatgcgcct<br>gcgtccgtttggcgacagcgggccgctggtgctgagctttgcggcgctggaagattattaccaggagcaaggtcgcgactgggagcgttacgcgat<br>ggtcaaagcgcggatcatgggcaacagcgacgacgtctatgccaacgagctgccgcccatgctgcgtcgtcgtgttccgtcgctatatgcgactt<br>cagcgtcatccagtccctgcgaaatatgaaaggggatgattgcccgcgaggtgcgccgccgtgggcgaaagacaatatcaagctcggtgcgggcgg<br>catccgcgaaatcgaatttatcgtccaggtcttccagcttattcgcggcggacgcgagccgtcgctgcagtccccgttccttattaccgacgctgag<br>cgccattgcgcagctgcatctcctgccggacgcgacgcgcaaaccctgcgcgaggcctatctttcctgcgtcgtctggaaaacctgctgcaaag<br>cattaatgacgaacagacccaaaccctgccgggcgacgaccttaaccgggcgcgtctggcctggggaatgcgcgtggaagactggtcaacgctgac<br>cgaacggctcgatgccatatggcaggcgtgcgcgaatctttaacgaacgtcatcggtgatgacgaaagtgagtgcaggacgatgcgctctccga<br>gcactgcgcgagctgtggcaggacgcgcttcaggaagatgacaccgccggtcgtgacgcacttaaccgacgacgcgcacatcgcgtggtgc<br>gctgatcgctgatttccgtcttgagctgaacaaacgcgccatcggcccgcgtggtcgccaggtctggatcacctgatgccgcacctgctgagcga<br>agtctgctcgcgtgccgatgcgccggtgccgctgtcgcggatgatgcccctgctgagggattatcacccgtactacctaccttgaactcctgagc<br>gagttccctggcgcgcttaagcacctgatttcactctgcgccgcgtcgccgatggtggccaacaagctggcgcgttacccgctgctgctggatgag<br>ctgccatcgatccgaataccctttatcaaccgacggcgaccgacgcctaccgggacgaactgcgtcagtatctgctgcgcgtgccggaagaagacga<br>gagcaacagctggaggcgctgcgtgaagcctggaacagccgacgacatcgctgcgcgtggcgcagatattgccggacgctgccggtgatgaaagtg<br>agcgatcacttaacctggctgcggaagcgattatcgacgcggtggtgcatcaggcctgggtgcagatggtggcgcgctatgccagccgaaacat<br>ctggctgaccgtgatggtcgcggcttcgcggtgtgggttacggtaagctcggcggttgggagctgggctatagctccgatctggatttaatcttc<br>ctccacgactgcccggttgatgtgatgaccgacggcgagcgcgagattgacgggcgtcagttctacctgcgcctggccgcagcgcatcatgcacctg<br>ttcagcacccgcacctcgtcgggcatttgtatgaagtggatgcccgtctgcgcccgtccggcgcggcgggcatgctggtcacctcgacggagtcc<br>ttcgctgattaccagaagataagcctggacgtgggtgcatcaggcgctggtgcgccgtgtggtgatggcgatcgctgctgaaacgcagt<br>ttgacgtgattcgtaaggaagtcatgaccaccgtgcgcgatgcagcacgctgaaacggaaggcgcgaaatgcgcgagaaaatgcgcgcgcactta<br>ggcaataaacatcgcgatcgctttgatattaaagccgatgaggcggtattaccgatattgagtttattaccccagtatctggtgttgctgcacgcg<br>catgacaagccgaagctgacgcgctggtcggataacgtgcgcattctggaactgctggcgcaaaacgacattatggacgagcaggaggcgcaggcc<br>ttaacccgtgcctatacaacgcttcgcgatgagctccatcatctggcgttgcaggagcagccgggacacgtggcgctggactgtttcaccgctgaa<br>cgcgctcaggtaacggccagctggcagaagtggctggtggaaccgtgcgtaacaaatcaagtgtga |

TABLE H-continued

| SEQ ID NO: | Sequence |
|---|---|
| 166 | atgaagatagcaacacttaaaacgggtctgggttcgctggcactgctgccgggcctggcgctggctgctgcacctgcggtggcagacaaagccgat<br>aacgcctttatgatgatcagcaccgcgctggtgctgttcatgtccattccgggcattgcgctgttctatggcggcctgatccgtggcaaaaacgtt<br>ctctccatgctgacgcaggttgccgtaacgttcgcgctggtctgcgtactgtgggtggtttacggttactcgctggctttcggcacgggcaacgcg<br>ttctttggtaacttcgactgggtgatgctgaaaaatattgaactgaccgcgctgatgggcagtttctaccagtatattcacgttgctttccagggc<br>tcgttcgcctgcattaccgtcgggctgattgtaggcgcgcttgccgagcgtattcgtttctctgcggtcctgatcttcgtggtggtctggctgacg<br>ctctcctatgtgccgattgcgcacatggtctggggtggcggctgctggcgacgcatggcgcgctggacttcgcgggcggtaccgttgtgcacatta<br>acgccgcatagcgggtctggttggcgcatacctgattggcaaacgcgtgggcttcggtaaagaagcgttcaaaccgcacaacctgccgatggtctt<br>caccggtaccgcgatcctctactttggctggttttggtttcaacgccggctcagcaagtgccgcgaacgaaatcgccgcctggccttcgtgaatac<br>cgttgtggcacggcaggtgcaatcctctcctgggtctttggcgagtgggctgtgcgcggtaaacctttctctgctgggtgcctgttcgggggcgat<br>tgctggtctggtcggtatcaccccagcatgtggttatgtcggtgtgggtggcgcgctgctggtcggcctggtgtcaggtctgcgggtctgtgggg<br>cgtgacggcgctgaaacgtattctgcgcgttgatgaccctgccgatgtgtttggcgtgcacggcgtgtgcggcatcgtcggctgtatcatgaccgg<br>tatcctttgcagcgaaatcgctgggtggcgtgggctacgcagaaggcgtcaccatggcccatcaggtgctggtgcagctggaaagtattgctgtcac<br>cgtggtggtctgccgttgtcgctttcattggctacaaactggcggacatgacggttggtctgcgcgtgccggaagagcaggaacgcgaaggtct<br>ggacgtcaacagccacggcgagaatgcgtataacgcatga |
| 167 | gccgagagaggggcccgcgtcggattaggtagttggtgaggtaatggctcaccaagccttcgatccgtagctggtctgagaggatgatcagccaca<br>ctgggactgagacacggcccagactcctacgggaggcagcagtggggaatattggacaatgggcgcaagcctgatccagcaatgccgcgtgagtga<br>tgaaggccttagggttgtaaagctctttcgcacgcgacgatgatgacggtagcgtgagaagaagccccggctaacttcgtgccagcagccgcggta<br>atacgnagggngcnagcgttnntcggaattactgggcgtaaagngcgcgtaggcggcntgttnagtcagaagtgaaagccccgggctcaacctggg<br>aatagcttttgatactggcaggcttgagttccggagaggatggtggaattcccngtgtagnggtgaaatncgtagatattgggangaacaccngtg<br>gcgaaggcggcnatctggacgganactgacgctgaggcgcgaaagcgtggggagcaaacaggattagataccctngtagtccacgccgtaaacgat<br>gaatgctagacgtcgggggtgcatgacttcggtgtcgccgctaacgcattaagcattccgcctggggagtacggccgcaaggttaaaactcaaagga<br>attgacggggccccgcacaaagcggtggagcatgtggtttaattcgaagcaacgcgcagaaccttaccaaccttgacatgtccactttgggctcga<br>gagatngggtccttcagttcggctgggtggaacacaggtgctgcatgctgtcgtcagctcgtgtcgtgagatgtggttaagtcccgcaacgag<br>cgcaaccctaccgtcagttgccatcattcagttgggcactcgtggtggaaccgccggtgacaagccggaggaaggcgggatgacgtcaagtcctc<br>atggcccttatgggttgggctacacacgtgctacaatggcggtgacagtgggaagcgaagtcgcgagatggagcaaatccccaaaagccgtctcag<br>ttcggatcgcactctgcaactcgagtgcgtgaagttggcaatcgctagtaatcgcggatcagcacgccggtgaatacgttcccgggccttgtac<br>acaccgcccgtcacaccatgggagttggttttacccgaaggtggtgcgctaaccgcaaggaggcagccaaccacggtaaggtcagcgactggggtg<br>aagtcgtaacaaggtagccgtagggcaacctgcggctggatcacctccttt |
| 168 | atggccaaagcgcctctgcgtcagatcgccttttacggcaagggcggtatcggcaagtccaccacctctcagaacacgctggccgcgctggtcgag<br>ctggatcagaggatcctgatcgtcggctgcgacccgaaggccgactcgacccgcctgatcctgcacgcaaaggcccaggacaccgtcctgcatctg<br>gccgccgaggccggctcggtcgaggatctggagctcgaggacgttctcaagatcggctacaagaacatcaagtgcgtcgagtccggcggtccggag<br>ccggggggtcggctgcgccggccgcggcgctcatcacctcgatcaacttcctggaagagaacggcgcctacgacgacgtggactatgtgtcctacgac<br>gtgctgggcgacgtggtctcgcggcggcttctccatgccgatccgcgagaacaaggccaggaaatctacatcgtcatgccggcgagatgatggcgc<br>tgtacgccgccaacaacatcgccaagggcatcctgaagtacgcgcacagcggcggcgtccgtctcggcggcctgatagcaacgagcgccagaccga<br>caaggaatgggatctggccgacgcgctggccaaccgcctgggctccaagctgatccacttcgtgccgcgcgacaacatcgtccagcacgccgagag<br>cgccgcatgacgctcatcgagtacgccccggacagcaagcaggccggcgaataccgcgcgctcgccaacaagatccatgcgaactccggccagggt<br>tgcatcccgaccccgatcaccatggaagagctggaagatgctgatggacttcggcatcatgaagaccgaggagcagcagctcgccgagctcgcc<br>gccaaggaagcggcgaaggccggcgcctga |
| 169 | atgagcctgtccgagaacaccacggtcgacgtcaagaacctcgtcaacgaagtcctcgaagcctatcccgaaaaatcccgcaagcgccgcgccaag<br>cacctgaacgtgctggaggccgaggccaaggaagggcgtcaagtcgaacgtcaagtccatccccggcgtcatgaccatccgcggctgcgcctatgc<br>cggctccaagggcgtggtgtggggtccgatcaaggacatgatccacatctcccacggtccggtcggctgcggctactactcaggtccggccgccgc<br>aactactacatcggcgacaccggtgtggacagctggggcacgatgcacttcacctccgacttccaggagaaggacatcgtcttcggcggcgacaag<br>aagctgacaaggtcatcgaggaaatcaacgagctgttcccgctggtgaacggcatctcgatccagtcggaaatgcccgatcggcgcctgatcggcgac<br>gacatcgaggctgtcgcccgcgccaagtcggcggaaatcggcaagccggtcatccccgtgcgctgcgaaggcttccgcggcgtgtccagtcgctg<br>ggccaccacatcgccaacgacgccatccgagactgggtgttcgagaagacggaacccaaggccggcttcgtctccaccccctatgacgtcaccatc<br>atcggcgactacaacatcggcggcgacgcaggtcgtcccgcatcctgctggaggagatcggcctgcgcgtgatcgcccagtggtcgggcgacggca<br>cgctcgccgaactggagaacgacgccgaaggccaaggtcaacctgatccactgctaccgctcgatgaactacatcgcgccgcacatggaagagaagt<br>tcaacattccttggatggaatacaacttcttcggcccgagccgatgccgaatccctgccgcaagatcgccgctctcttcgacgacaagatcaagg<br>agaacgccgagaaggtcatcgcccgctaccagccgatggtcgatgcggtcatcgccaagtacaagccgcggctcgaaggcaagaaggtcatgatct<br>acgtcggcggcctgcgtccccgccacgtcgtcgatgcctaccatgacctcggcatggagatcaccggcaccggctacgagttcgcccacaacgacg<br>actatcagcgcacgcagcactacgtgaaggaaggcacgctgatctacgacgacgtcaccgcgttcgaactggagaagttcgtcgaggcgatgcgtc<br>ccgacctcgtcgcgtcgggcatcaaggaaaagtacgtgttccagaagatgggccgtgccgttccgccagatgcacagctgggactactccggcccgt<br>accacggctatgacggcttcgcgatcttcgcccgcgacatggacctggccatcaacaaccgctctgggcgtgatgaaggccccgttctga |
| 170 | atgctccaggacaagatccaggatgtcttcaacgaaccgggctgcgcgaccaaccaagccaaatcggccaaggagaagaagaagggctgcaccaag<br>tcgctgaaaccggggcggcagccggcggcggcggcctatgacgggcgatgatcgtgctccagccgatcgccgacgccgccatctggtccatggc<br>cccatcgcctgcctcggaaacagttgggacaaccgcggctccaaatcctccgctcgcagctctaccgcaccggttcaccaccgatctgtcggaa<br>ctggacgtcatcggcggcggcgagaagaagctctaccgcgccatcaaggagatcgttcagcaatacgaccgcgccgtcttcgtctatcagacc<br>tgcgtgccgccatgaccggcgacgacatcgccgcattgcaagttcgccacgcagaagctgagcaagccggtgatcacggtggactcgccgggctt<br>cgtcgggtcgaagaatctcggcaacaagctcggccggcgaagccctgctggagcatgtcatcggcacggtcgaaccggactacaccaccccgaccga<br>cgtctgcatcatcggcgaatacaaccttgccggcgagctgtgcctggtcaagcgctgctggacgagatgcgatccgcctcctgtcctgcattc<br>cggcgacggccgctaccggaggtggccaggccaccgcgcccgcgtcaccatgatggtgtgcagccaggcgctggtgaatgtcgggcgcaagat<br>ggaggagcgctacggcatcctctatttcgaggggtccttctacggcgtgtccgacatgtcggcacccctgcgcaccatgacccgcatgctggtgga<br>gcgggccgcacaaggcgctgatcgaccgggaggcgtgatcgccggggaggaaagccgggtctggcgccggctggaaccctacaagccgcgc<br>ttcgacgcaagcgcgtcctttctcttcaccggcggctcaagagctggtcgatggtcagcgcgctggaggtgcgggcgtgaccatccggcacc<br>tccaccaagaaatcgaccaggcaggacaaggagcggcatcaagaagatgaagggcgaagagttccaccagtgggacgatttgaagccgcgcgacatc<br>tacaggatgctggccgacatcaggccgacatcatgatgtccggcggccgctcgcagttcatctcgctgaaggccaaggttccctggctcgacatc<br>aaccaggagcgccaccaggcctatgccggctatgacggcatcgtcaatcctgcgaggagatcgacaaaacgctgtcgaatccgatctggcgtcag<br>gtgcgtcagccggcaccgtgggagtccggcgcgtcctccacccttctggcttcctcgatggcggcggagtga |
| 171 | atgtcccacatccagcgcttcccctccgccgccaaggccgcctccaccaacccgctgaagatgagccagccgctgggtgcggctctggcctatctc<br>ggcgtcgaccgctgcctgccgctgttccatggctcgcagggctgcaccgccttcgggctggtcctgctggtgccgccatttccgcgaggcgatcccg<br>ctccagaccacggcgatggatcaggtcgccaccatcctcggcggctacgacaatctggagcaggcgatccgcaccatcgtcgagcgcaaccagccc |

TABLE H-continued

| SEQ ID NO: | Sequence |
|---|---|
| | gccatgatcgccgtcgccaccaccggcgtcaccgagaccaagggcgaggatatggccggacagtacacgctgttccgccagcgcaaccccgacttg<br>gccgacacggccctggtcttcgccaacaccccgacttcgccggcggcttcgaggacggcttcgccgccgcggtcaccgcgatggtcgagcggttg<br>gtcgaaccgtcgccggtgcgcatcccgacccaggtcaacgtgctggccggctgccatctgtccccggcgacgtggaggaactgcgcgacatcatc<br>gaaggcttcggcctgtcgccgatcttcctgaccgacctgtcgctgtcgatggcgggccgccagccggccgacttcaccgccacctcgctgggcggc<br>gtgaccgtcgatcagatccgcgccatgggcgcttcggccctcaccatcgtggtcggtgagcatatgcgggtggccggtaacgcgctggagctgaag<br>accgacgtgcccagccatttatcaaccgcctgaccgggcgtggaggcgacggacaagctggtccggctgctgatggagttgtcgggcaagcgggc<br>ccgccggctgcggcgccagcgcgaaagcctggtcgatgccatgctcgacgggcatttcttctacagcgcaagcgcatcgccgtcgcgctggagc<br>ccgacctgctctatgccgtcaccggcttcctcgccgacatggggggccgaggtgatcgccgcggtgtccccgacgcagagcccggtgctggagcggt<br>tgaaggccgccaccatcatggtcggcgatcattccgacgtggagacgctggccgcgacgccgacctgatcgctccaactcgcacgggcggcaggg<br>agccgccggatcggcggtggctctgcaccgcatgggcctgccgctgttcgaccggctggggggccggctgcgcgtccaggtcggctaccgaggcac<br>gcgggaactgctgtcgcacatcggcaacctgttcctcgcccgcgagatggaccacgagcacgggcacgagagccacgaccacggggaatcccacgg<br>ctgccgaggcggatcatgcggatgcaacgccgtctga |
| 172 | atgaccgacaagctttcgcagagcgccgacaaggtcctcgaccactacacccctcttccggcagcccgaatacgcggcgatgttcgagaagaagaag<br>accgagttcgagtacggccattcggacgaggaagtcgcccgcgtgtccgaatggaccaagtccgaggactacaaggcgaagaacttcgcccgtgaa<br>gcggtcgtcatcaacccgaccaaggcctgccagccgatcggcgcaatgttcgccgcccagggcttcgaaggcaccctgcccttcgtccacggctcc<br>cagggctgcgtcgcctattaccgcacccacctgacccgtcacttcaaggagccgaacagcgcggtctcctcgtcgagacggaggacgcggcggtgt<br>tcggcggcctgaacaacatgatcgacggcctggcgaacgcctatgcgctctacaaagccgaagatgatcgaggtgatgaccacctgcatggccgaag<br>tcatcggcgacgatttcagggcttcatcgccaatgcgaagaccaaggacaggtcccggccgacttcccggtccctacgcccacaccccggcctt<br>cgtcggcagccacatcgtcggctacgacaacatgatcaaggggatcctgaccaacttctggggtacgtcggagaatttcgacacacccaagaccga<br>gcagatcaacctgatcccgggattcgacggcttcgccgtcggcaacaaccgcgaactgaagcgcatcgccggcgaattcggcgtgaagctgcaaat<br>cctgtccgacgtgtccgacaattccgacacgccgatgaatggcgagtccgcatgtatgacggcggcaccaccatcgaggagaccaaggaggcct<br>gcacgccaaggccaccatctccatgcaggagtacaacacgaccccagaccctcgaattctgcaaggagaaggggtcaggaagtcgccaagttcaacta<br>cccgatgggcgtcaccggcaccgacgagctgctgctgaagctcgccgaactgtcgggcaagccggtcccggccagcctgaagctggagcggggccg<br>tctggtcgacgccatcgccgacagccacacccacatgcacggcaagcgcttcgccgtctatggcgacccggacttctgcctgggcatgtccaagtt<br>cctgctggagctgggtgcggagccggtgcacatcctgtcgacgtcgggtccaagaaggggagaagcaggtccagaaggtgctggacggctcgccc<br>ttcggcgcctcgggcaaggcccatggcggcaaggatctgtgtgcacctgcgttcgctgatcttcaccgacaaggtggactacatcatcggcaacagc<br>tacggcaagtatctggagcgcgacaccaaggttccgctgatccgcctgacctaccccgatcttcgaccgccaccaccaccaccgctaccgacctgg<br>ggctaccaggggcgcgctgaacgtgctggtacggatcctaaccggatcttcgaggacatcgacgccaacaccaacatcgtcggccagaccgactact<br>cgttcgacctgatccgctga |
| 173 | atgttgacctctgatattgttggcaaattgcgctgcatcgcagcagacccaaagcgggcatcgcaaggggcctcgacaccgggacgacgaagatc<br>ggtcccgtttggagggtgacgtgggcgacaccgtggatttcgaagcgctgcgccagcgggcggtccactccctgttcgaacatctggaatccatg<br>tgcgtcggcgccgtcgccgtcgaccacaccggccgcatcgcctggatggacgagaagtacaaggctctgctgggcgttcccgacgacccgcgcggc<br>cggcaggtggaggacgtcatccccaacagccagctgcgccgggtgatcgacagcgccagccgcagccgggatgcacatcatggagttcgacagccgg<br>tccttcgtggtgacgcgcatgccgctgttcggcaccgacggttcgatcatcggcgccatcggcttcgtgctgttcgaccgcgcgaatatctccgc<br>ccgctggtccgcaaatacgagaagatcgaggaggagctggcccgcacccagcaggagctggcgcatgagcgccgcgccaaatactccttctcgcag<br>ttcctgggcgccagcgaatcgatccgcgagatcaagcggctggggcgccgcgccgcccagatggattcgaccgtcctgctgctgggcgaaaccggg<br>accggccaaggagctgctggccccaggccatccattccgccagcccgcaggcgtccaagccctctcgtcggcgtcaatgctcgccgccattccggaaacc<br>ctgctggaggcggagtcttcggcgtcgcccccggcgccttcaccggcgccgaccgcgccaccgcgacgcaagttccagctcgccaacgcggc<br>accctgttcctcgacgagatcggcgacatgccgctgccggtgcaggccaagcttctgcgcgtgctgcaggagcgggagatcgagccgctcggctcc<br>aacaaggtggtgcgggtcgatgtccgcatcatcgccgccaccagccgtgacctgcacgccctggtgcgtgagaagcagttccgcgccgacctctat<br>taccgctgaatgtggtgccgatcaccctgccgccgctggcgcgaccggccggaggacatcgagagcatcgccgaccgcatcctggaacagctggcg<br>atccagcagggcacgccgccgcgagctgctggaatcggcggtgcaggtgctgcgcgactatgactggcccgcaatgtgcgcgagctttacaac<br>acgctggaacgggtggtggcgctgaccgatgcgccgatcctgaccgcgccgcacatccgcagcgtgctgcccggcagcatccggccggcgcgtcg<br>gccctgccgctgcggccggcgcgcggccgttgcaggaggtgctgacgccgccgagcgccacgccatcgccgcggcgcttgaggaggcgaacggcg<br>tcaaggcgcgggcggcgaagctgctgggcatttcgcgcgcgtcgctgtacgaacgcatggtgacgctgggggttgggggcgacgcagtag |
| 174 | atgccgagtcccatcgcgttctcaagccccttgccgaagccttttcgacagcgcgcaggcggcgctggggatggagcgctggcgccagcaggccgcc<br>gcggcggagccggagacccgcgcctgggcggaagccttcgccgattcggagaccggccggggcgctgatcggggcggtgtgcggcaacagcccgtat<br>ctccggcacagcctgacgcgggagttgccctcgtcgcccgtacagtgcaggacggcttcgacgacaccctcgccgcgctgatcgccgctctccat<br>gccgagcatggcgaggagaaatcgatggaccggctgatggccggcctgcgggtggcgaagcggcgggcgcggagctgatcgcgctggccgacatcg<br>ccgggcgtggccgctgttccgcgtcaccggcgccctgtcggagctggcggagacggggggtgcagctggccgcgaatttcctgctgccgcgcgccag<br>ggaggcggggacgctgacgctgccggatccgcagcgaaccgtgggtcggttcgggcctgatcgtttgggcatgggtaagcttggcgggcgcgaact<br>caactattccagcgacatcgacctgatcgtcctgtatgacgacgctgttgtgcagacgcccccagccggacaacctcgcgcgaaccttcatcaggct<br>cgcacgcgatcttgtccgcattatggatgaacggaccaaggacggctacgtcttccgcaccgaccttcggcttaggcccgatccccggccgcacgcc<br>gctggcggtttccgtctccgcagccgaaattttattacggcagcgtcggtcagaactgggaacgccgggcgatgatcaaggcccgtcccatcgccgg<br>cgatctgaggcgggcgcgcctcctttgtccgcttcctggagcccttcgtctggccgcaacctggatttcgccgccatccaggacatccattcg<br>atcaaacgccagatcaacgcccacaaggggccaccgcgaggtgacggtcaacgccacgacatcaaggtcggccgcggcggcatccgcgagatcgag<br>ttcttcgcccagaccagctgatcttcggcggggcgaccgccgctgcgaatcgctccgacctcagcgctggtcggctggcgatcgcgccgctaccgcgc<br>ggccgtgccgccgcagacggtggaagagcttgccggggcctatcatttcctgcgccgtgtcgaacatcgcatccagatgatcgacgaccagcag<br>acccatcgtattcccgccgacgatgccggggtggcgcatttggcgcacttcctcggctatgacgaccccgccgccttccgggcggaactgctggcg<br>acgctggggcaggtggaggaccgctatgccgagctgttcgaggaggcgccgtcgctttccggccccggcaatctggtcttcaccggcaccgaccccc<br>gatccgggcacgatggacgctgaaggcatcagctgatggcctcgccgatccggccgcgtcatcagcgtggtgctcggctggcatcgcgccgctaccgcgc<br>caccggtcgggccggcgcgggagctgctgacggagctgacgccgggcctgctgagtgcgctgaccaagacccggcccccgattcggcgctgat<br>gaacttcgacgatttcctcggcaagctgccggccggcgtcggtctgttctcgcgtgttcgtcgccaatccctggctcctggagctggtggcggagat<br>catgggcatcgcgccgcagatggcgcagacgctgtcgcgcaacccgtcgctgctcgacgccgtgctgtcgccggacttcttcgacccgctgccggg<br>caaggaggacgggctgcgacgacccgcgtgatggcgccgccccgcgatttcgaggatgcgctgacccctgtcggcgctggaccaacga<br>ccagcgcttccgcgccggggtgcatatcctgccggcatcaccgatggcgaccgctggcgccttcctggcgatctggccgacatcgtcgtccc<br>cgaccttgcccgccgggtggaggaggagtcgcccagcgccacggccatattccggcggcgccttgggtggtggtggcgatgggcaagtcggcagc<br>cggcagctgaccatcacgtccgacatcgacctgatcgtcatctacgatgtggcgcccggccaaggggcggggcggtccccgcttgtcggatggt<br>gccaagccgctgtcgccaacgagtattacatcaagtgactcagcgtctgaccaacgccattaccgcgccgattgcgcagcggcctctacgagg<br>tcgacatgcgggctgcgcccgtcgggcaacgccgggccgctcgccacctcgctggacgctttcctgaaatatcaggcgaccgatgcctgacctggg<br>agcatatgcgcctgacccgcgccgggtgatcgccggtgatgcggagctggccggggggtttcggcagcgatccgctcggtgctgacggcgccg<br>gcgatgccaccggctgctgtgggacgtggccgacatgcggcggcggatcgagaaggagttcgggacgaccaatgtctggaacgtcaaatacgccc<br>gcggcggcctgatcgacatcgagttcatcgcccagtacctgaactgcgccatggtcacgagcggccggacatcctgcacatcggcaccgccaaggc<br>gctgggctgcgccgccccggacggggcgcgctggcgccggaggtggcggaggatctgtcgagacgacgctgcggctgtggcggcgggtgcagggcttttct |

TABLE H-continued

| SEQ ID NO: | Sequence |
|---|---|
| | gcggttgaccaccgccggggtgctcgatcccaatcaggtgtcgcccagcctgctggccgggctggtccgcgccgcctttcctgctgactttcaggg<br>cgagcgtgagcctcgactgttgacttccccgaactggaccacaaaatccgtgccgtcgccgcccgcgcccatggtcatttcaagaccctggtcgag<br>gaaccggcgggccgtctggccccacccgccaccacgcctccagcctga |
| 175 | atgaaccgtctgttccaatggccgcaccgatgatggcggttgctctgggcgcggtcggcatgccggccgcagcccttgcccaggatccggcggctg<br>ccgccgctgccggctgcggctgcggctgccgccgctgctgccgcaccggcggctccggcgctgaatggcggcgacaccgcctggatgctcatct<br>ccaccgcgctggtgctgatgatgaccatccccggcctggcgctgttctacggcggcatggtccgcaagatgaacgtgctgtcgacggtgatgcaga<br>gcttcgccatcacctgcctgatcagcgtcctgtggtacgtcatcggctacagcctggccttcaccggcaccggtgcctatgtcggcggtctcgacc<br>ggctgttcctcaacgggctcgacttcacgaaggccttcgtgctgggcgaggcgaccgggtcgggcgtcccgacgaccatccccgagccggtcttca<br>tgatgttccagatgacctttgcgatcatcaccccggccctgatcaccggcgccttcgccgaccgatgaagttctcctccctgctggtcttcaccgc<br>gctgtggtcgatcgtggtctatgcgccgatcgcccactgggtctggtacccgtcgggcttcctgttcggcctagcgtgaggacttcgccggcggca<br>cggtcgtgcacatcaaccgccggcgtcgccggcctggtcgccgcgctggtgatcggcaagcgcaagggctacccgaaggaagccttcatgccgcac<br>aacctggtgctgtcgctgatcggcgcctcgctgctgtgggtcggctggttcggcttcaacgccggttcggccctgaccgccggtccgcgtgccggc<br>atggcgctggccgccacgcacatcgccaccgccggtgccgccatgggctcgtgttcggcggagtggatcgtcaagggcaagccgtcgatcctcggc<br>atcatctccggcgccgtcgccgcctggtcgggtgaccccgccgccggcttcgtcgaccccgacgggcgccatcgtcatcggcatcgtcgcccgcg<br>tggtctgcttctggtcggccaccagcctcaagcacatgctgggctatgacgacagcctggacgccttcggcgtgcacggcgtcggcggcctgatcg<br>gcgccatcctgaccgcgtcttcgccaagatgtcggtgtccaacagcgaaggcggcttcgcctccgtcctgcaggccgacccgaaggccacgctgg<br>gctgctggaaggcaacgccgccgcgtctggatccaggtccagggcgtcctctacaccatggtctggtcgccatcgccaccttcgtcctgctga<br>agatcgtcgatgtggtcatgggcctgcgcgtcgaagaggatgtggagcgcgacggtctcgacctcgccctgcatggcgagagcatccactaa |
| 176 | atggatgcggcaaagacgggtggcgacgtccttttcgtgctgatgggcgcggtgatggtgctggcgatgcattgcggcttcgccctgctggaggtc<br>gggacggtccggcgcaagaatcaggtcaacgcgctggtggaagatcctgtcggacttcgccatgtcgaccatcgcctattttttcgtcggttatgcc<br>gtggcctacggcatcgacttcttcgcgacgcccacacgctggtcggcaagggaagcggcgggttcgccgcctatggctacgatctggtgaagttc<br>ttcttcctggcgaccttcgccgccgcggtgccggccatcgtctcgggcggcatcgccgagcgtgctaggtctggccgcaggccgccgccacgctg<br>gcgctgatcgcgctgttctatccattgctggaaggcacggtctggggcaccccgcttcggcctgcaaagctggatggccgcgaccttcggccagcct<br>ttccacgacttcgccggatctgtggtggtgcatgccttcggcggctgggtggcgctgggtgccgtgctgaacctcggcaaccgccgcggccgctac<br>cgtccgaacggctcgctgatcgccattccgccgtcgaacatccccttcctggcgctgggcgcctgggtgctgtcgtggggtggttcggcttcaac<br>gtgatgagcgcccaggtgctggatggcgtgacgggtctggtggcgctgaactcgctgatgcgatggtcggccgcatcgtcacctcgctggtgatc<br>agccgcaccgatcccggcttcgtccacaacggcgcgctggccggtctggtggcggtctgcgccgggtccgacgtgatgcaccgctgggcgcgctg<br>gtcaccggcggcatcgccgggctgctgttcgtctgggccttcaacaaatgccagatcgactggaagatcgacgacgtgctgggcgtctggccgctg<br>cacggcctgtgcggcctgaccggcggcctgctggccggcgtcttcggggcaggaggcacctgggcgccttggcggcgtgtcgatcctcagccagatcg<br>tcggcacggcaagggcgccagcttcggattcgctacgggtctggcggtctaccgctgctggcgtcaccgtccgcatccgcctcgatcccgacc<br>aggagtacaaggcgccgacttgtcgttgcaccatatcaccgcgtacccggaagaggacgcgccgaccctgtaa |
| 177 | atgaccctgaatatgatgatggattcttggttctctggagcgctttatcggcatcctgactgaagatttgcaggcttcttcccaacctggcttgca<br>cccgtgcaggtagttgtgatgaacatcactgattcgcaggctgaatacgttaacgaattgacccgtaaactgcaaaatgcgggcattcgtgtaaaa<br>gcagacttgagaaacgagaagattggctttaaaatccgcgagcacactttacgtcgtgtcccttatatgctggtttgtggtgacaaagaggtcgaa<br>gccggcaaagttgctgtgcgtacccgtcgcggtaaagacctgggtagcctggacgtaaatgatgatcgagaagctgcaacaagagattcgcagccg<br>cagtcttcaacaactggaggaataaggtattaaaggcggaaaacgagttcaaacggcgcgtcccaacgtattaatggcgagattcgcgccacggaa<br>gttcgcttaacaggtctggaaggcagcttggtattgcgatagaactcacttcacgccccaagggggaagctgcctgaccctacgattcccg<br>ctatttcattcactgaccggaggttcaaaatga |
| 178 | accggataagagagaaaagtgtcgacgtcggtccggttgatattgaccggcgcatccgccagctcgcccagttttttggtggatctgtttggcgatt<br>ttgcgggtcttgccggtgtcggtgccgaaaaaaataccaatatttgccataacacacgctcctgttgaaaaagagatcccgcggggaaaatgcggt<br>gaacatgtcagctattgcgaagagtgtgccagttttgctcacgggcaaaagctgcaccagaatgggattaatgcaccagcctggcgctttttttcg<br>cggcacgtcccctcgctaatgcccgtctggcgcggctttgacgctgataaggcgctgaataccgatctggatcaaggtttgtcgggtatcgtcca<br>aaaggtgcactctttgcatggttataagtgcctgacatggtgtccgggcaaacgtcgccaggtggcacaaattgtcagaactacgacacgactaac<br>cgaccgcaggagtgtgcgatgacccttgaatatgatgatggattatggttctctggaacgcgttatcggcatcctgactgaagaatttgcaggcttc<br>ttcccaacctggcttgcacccgtgcaggtagttgtgatgaacatcactgattcggcaggctgaatacgttacgaattgacccgtaaactgcaaaatg<br>cgggcattcgtgtaaaagcagacttgagaaacgagaagattggctttaaaatccgcgagcacactttacgtcgtgtcccttatatgctggtttgtg<br>gtgacaaagaggtcgaagccggcaaagttgctgtgcgtacccgtcgcggtaaagacctgggtagcctggacgtaaatgatgatcgagaagctgc<br>aacaagagattcgcagccgcagtcttcaacaactggaggaataaggtattaaaggcggaaaacgagttcaaacggcgcgtcccaatcgtattaatg<br>gcgagattcgcgccacggaagttcgcttaacaggtctggaaggcgagcagcttggtattgcgataaactcacttcacgccccaagggggaagct<br>gcctgaccctacgattcccgctatttcattcactgaccggaggttcaaaatgacccagcgaaccgagtcgggtaataccgtctggcgcttcgattt<br>atcccagcagttcaccgcgatgcagcggataagcgtggttctcagccgggcgaccgaggttgaacagacactccagcaggtgctgtgcgtattgca<br>caatgacgccttttttgcagcacggcatgatctgtctgtacgacagccagcaggcgattttgactattgaagcgttgcaggaagccgatcagcagtt<br>gatccccggcagctcgcaaattcgctaccgtccggtgaagggctggtcgggacggtgcttcgcaggggcaatcgttagtgctggcgcgtgtggc<br>tgacgatcagcgctttcttgaccgcctgggactgtatgattacaacctgccgtttatcgccgtgccgctgatagggcgggatgcgcagacttttgg<br>cgtgctgacggcgcaaccgatggcgcgttacgaagagcggttacccgcctgcacccgctttctggaaacggtc |
| 179 | tccctgtgcgccgcgtcgccgatggtggccagccaactggcgcgctacccgatcctgctcgatgaactgctcgacccgaacacgtctatcaaccg<br>acggcgatgaacgcctatcgcgatgaactgcgacaatacctgttcgcgtgccggaagaggatgaagagcagcaactggaggcgctacggcagttt<br>aagcaggcgcagttgttgcgcgtagcggcggcggatatcgccggtacgttaccgtcatgaaagtgagcgatcacttaacctggctggcggaagcg<br>attatcgatgcggtggtgcagcaagcctggaaccagatggtggccgcgttacggccacgacgcagtcgtcgacgatcgccgaaggggcggtttcgcc<br>gtggtcggttacggcaaattggcggctgggaattaggtacagctccgatctggatctggtgttcctgcacgactccccatggatgtgatgacc<br>gatggcgagcgtgaaatcgatgcccccagttctatttgcgcctcgccgagcgcgtgatgcacctgttcagcacgcgcacgtcgtccggcattctt<br>tatgaagtcgatgcgcgtttgcgcccgtccggcgcggccggaatgctggtgaccactgcggaagcgttcgccgattatcaaaaaaatgaagcctgg<br>acatgggagcatcaggcgctggcgctgcgcgctggtgtacgatccgcaactgcgcgaatttgacgccattcgccgcgatatcctgatg<br>acctcccgcgatgccgctacccgcaaaccgaagtgcgggaaatgcgtgagaaatgcgcgcccatcttggtaacaagcacaaagaccgtttcgat<br>ctgaaagccgatgaaggcggatcaccgatattgagtttatcgctcagtatctggtgctgcgctttgcccatgagaagccgaaactgacgcgctggt<br>cggataatggcgcatcctcgaagggctggcgcaaaacggcatcatggatgagcaggaagcgcaggcattgacgctggcgtacaccacgttgcgtga<br>tgagctgcaccacctggcgctcaagagctgccaggacatgtggcgctctcctgttttgtcgccgagcgtgcgcttatcaaaaccagctgggacaa<br>gtggctggtgaaccgtgcgccccggcgtaa |
| 180 | taaagcgagcgctcacttacgtgatctgttgacgcagtccgaagcgaccattacttcagccgtttcagcagatacggcggtgtggagtgcgcaatc<br>agccctggcgaaactggtgctcaccgagtggttagtgacgcagggctggcgaaccttccttgatgaaaagcgcaggctaagtttgccgactcctt<br>taaacgctttgctgacgttcatctgtcacgcagcgccgccgagctgaaaaaagccttgcccagccgctgggcgacagctatcgcgaccagttacc |

TABLE H-continued

| SEQ ID NO: | Sequence |
|---|---|
| | gcggctggcgcgtgatatcgacagcgcgttattgctggccggacattacgatcgcgcgcgcgccgtggagtggctggaaaactggcaggggcttca<br>gcacgctattgaaacgcgccagagagttgaaatcgaacattccgtaataccgccattacccaggagccgttctggttgcacagggaaaacgttaa<br>cgaaaggatatttcgcatgtccctgtgcgccgcgtcgccgatggtggccagccaactggcgcgctacccgatcctgctcgatgaactgctcgaccc<br>gaacacgctctatcaaccgacggcgatgaacgcctatcgcgatgaactgcgacaatacctgttgcgcgtgccggaagaggatgaagagcagcaact<br>cgaggcgctacggcagttttaagcaggcgcagttgttgcgcgtagcggcggcggatatcgccggtacgttacccgtcatgaaagtgagcgatcactt<br>aacctggctggcggaagcgattatcgatgcggtggtgcagcaagcctggaaccagatggtggcgcgttacggccagccgacgcatctgcacgatcg<br>cgaagggcgcggtttcgccgtggtcggttacggcaaacttggcggctgggaattaggttacagctccgatctggatctggtgttcctgcacgactg<br>ccccatgatgtgatgaccgatggcgagcgtgaaatcgatggccgccagttctatttgcgcctcgcgcagcgcgtgatgcacctgttcagcacgcg<br>cacgtcgtccggcattctttatgaagtcgatgcgcgtttgcgcccgtccggcgcggccggaatgctggtgaccactgcggaagcgttcgccgatta<br>tcaaaaaaatgaagcctggacatgggagcatcaggcgctggcgcgtgcgcgcgtggtgtacggcgatccgcaactgaccgccgaatttgacgccat<br>tcgccgcagatatcctgatgacctcccgcgatgccgctaccctgcaaaccgaagtgcgggaaatgcgtgagaaaatgcgcgcccatcttggtaacaa<br>gcacaaagaccgtttcgatctgaaagccgatgaaggcggtatcaccgatattgagtttatcgctcagatctggtgctgcgctttgcccatgagaag<br>ccgaaactgacgcgctggtcggataatgtgcgcatcctcgaagggctggcgcaaaacggcatcatggatgagcaggaagcgcaggcattgacgctg<br>gcgtacaccacgttgcgtgatgagctgcaccacctggcgctgcaggagcgccaggacatgtggcgactctcctgttttgtcgccgagcgtgcgct<br>tatcaaaaccagctgggacaagtggctggtggaaccgtgcgccccggcgtaagtgtggatcatcgcgcgcaaattttgtatctctcaggagacag<br>gaatgaaagttacgctgccagagttcaatcaagccggtgtcatggtggtgggtgatgtgatgctggatcgctactggtacggcccaaccagccgca<br>tttctccggaagcgccagttccggttgttaaagtcgatactattgaagagcgaccgggcggtgcggcaaacgtggcgatgaacattgcctcgctgg<br>gcgcaacggcgcgtctggttggcctgactggcattgatgatgcggcgcgcgcgctgagcaaagcgctggcggatgttaatgttaaatgtgacttcg<br>tttctgttccgactcaccccaccatcactaagctgcgcgtgctgtcgcgtaaccagcaactgattcgc |
| 181 | atgaccctgaatatgatgatggatgccagccgttctgtaataataaccggacaattcggactgattaaaaagcgccctcgcggcgcttttttttat<br>attctgactccatttaaaataaaaaatccaatcggatttcactatttaaactggccattatctaagatgaatccgatggaagctcgctgttttaa<br>cacgcgtttttaaccttttattgaaagtcggtgcttctttgagcgaacgatcaaatttaagtggattcccatcaaaaaaatattctcaacctaaaa<br>aagtttgtgtaatacttgtaacgctacatggagtaactcaatctagagggtattaataatgaatcgtactaaactggtactgggcgcaactcac<br>ttcacgccccgaagggagaagctgcctgaccctacgattcccgctatttcattcactgaccggaggttcacaatga |
| 182 | accggataagagagaaaagtgtcgacgtcggtccggttgatattgaccggcgcatccgccagctcgcccagttttttggtggatctgtttggcgatt<br>ttgcgggtcttgccggtgtcggtgccgaaaaaataccaatatttgccataacacacgctcctgttgaaaaagagatcccgcggggaaatgcggt<br>gaacatgtcagctattgcgaagactgtgccagttttgctcacgggcaaaagctgcaccagaatgggtattaatgcaccagcctggcgcttttttttc<br>gcggcacgtccctcgctaatgcccgtctggcgcggctttgacgctgataaggcgctgaataccgatctggatcaaggttttgtcgggttatcgtc<br>caaaaggtgcactctttgcatggttataagtgcctgacatggtgtccgggcgaacgtcgccaggtgccacaaattgtcagaactacgacacgacta<br>accgaccgcaggagtgtgcgatgaccctgaatatgatgatggatgccagccgttctgtaataataccggacaattcggactgattaaaaagcgc<br>cctcgcggcgcttttttttatattctcgactccatttaaaataaaaatccaatcggatttcactatttaaactggccattatctaagatgaatccg<br>atggaagctcgctgttttaacacgcgttttttaaccttttattgaaagtcgggcttctttgagcgaacgatcaaatttaagtggattcccatcaaa<br>aaaatattctcaacctaaaaaagtttgtgtaatacttgtaacgctacattggagtaactcaatctagaggtattaataatgaatcgtactaaac<br>tggtactgggcgcaactcacttcacgccccgaaggggaagctgcctgaccctacgattcccgctatttcattcactgaccggaggttcaaaatga<br>cccagcgaaccgagtcgggtaataccgtctggcgcttcgatttatcccagcagttcaccgcgatgcagcgataagcgtggttctcagccggcca<br>ccgaggttgaacagacactccagcaggtgctgtgcgtattgcacaatgacgccttttgcagcacggcatgatctgtctgtacgacagccagcagg<br>cgattttgactattgaagcgttgcaggaagccgatcagcagttgatccccgcagctcgcaaattcgctaccgtccggggtgaagggctggtcggga<br>cggtgcttcgcaggggcaatctgtagtgctggccgcgtggtcgcgacgatcagcgcttcttgaccgcctgggactgtatgattacaacctgccgt<br>tatcgccgtgccgctgatagggccggatgcgcagacttttggcgtgctgacggcgcaaccgatggcgcgttacgaagagcggttacccgcctgca<br>cccgcttctggaaacggtc |
| 183 | tccctgtgcgccgcgtcgccgatggtggccagccaactggcgcgctacccgatcctgctcgatgaactgctcgacccgaacacgctctatcaaccg<br>acggcgatgaacgcctatcgcgatgaactgcgacaatacctgttgcgcgtgccggaagaggatgaagagcagcaactggaggcgctacggcagttt<br>aagcaggcgcagttgttgcgcgtagcggcggcggatatcgccggtacgttacccgtcatgaaagtgagcgatcacttaacctggctggcggaagcg<br>attatcgatgcggtggtgcagcaagcctggaaccagatggtggcgcgttacggccagccgacgcatctgcacgatcgcgaaggggcgcggtttcgcc<br>gtggtcggttacggcaaacttggcggctgggaattaggttacagctccgatctggatctggtgttcctgcacgactgccccatgatgtgatgacc<br>gatggcgagcgtgaaatcgatggcccccagttctatttgcgcctcgcgcagcgcgtgatgcacctgttcagcacgcgcacgtcgtccggcattctt<br>tatgaagtcgatgcgcgtttgcgcccgtccggcgggccggaatgctggtgaccactgggaagcgttcgccgattatcaaaaaaatgaagcctggac<br>atgggagcatcaggcgctggcgcgtgcgcgcgtggtgtacggcgatccgcaactgaccgccgaatttgacgccattcgccgcagatatcctgatgac<br>ctcccgcgatgccgctaccctgcaaaccgaagtgcgggaaatgcgtgagaaaatgcgcgcccatcttggtaacaagcacaaagaccgtttcgatct<br>gaaagccgatgaaggcggtatcaccgatattgagtttatcgctcagtatctgggctgcgctttgcccatgagaagccgaaactgacgcgctggtcg<br>gataatgtgcgcatcctcgaagggctggcgcaaaacggcatcatggatgagcagcaagcgcaggcattgacgctggcgctacaccacgttgcgtgat<br>gagctgcaccacctggcgctgcaagagctgccaggacatgtggcgctctcctgttttgtcgccgagcgtgcgcttatcaaaaccagctgggacaag<br>tggctggtggaaccgtgcgccccggcgtaa |
| 184 | taaagcgagcgctcacttacgtgatctgttgacgcagtccgaagcgaccattacttcagccgtttcagcagatacggcggtgtggagtgcgcaatc<br>agccctggcgaaactggtgctcaccgagtggttagtgacgcagggctggcgaaccttccttgatgaaaaagcgcaggctaagtttgccgactcctt<br>taaacgctttgctgacgttcatctgtcactcagcgccgccgagctgtaaaaagcctttgcccagccgctgggcgacagctattgcgaccagttacc<br>gcggctggcgcgtgatatcgacagcgcgttattgctggccggacattacgatcgcgcgcgcgccgtggagtggctggaaaactggcaggggcttca<br>gcacgctattgaaacgcgccagagagttgaaatcgaacattccgtaataccgccattacccaggagccgttctggttgcacagcggaaaacgtta<br>cgaaaggatatttcgcatgtccctgtgcgccgcgtcgccgatggtggccagccaactggcgcgctacccgatcctgctcgatgaactgctcgaccc<br>gaacacgctctatcaaccgacggcgatgaacgcctatcgcgatgaactgcgacaatacctgttgcgcgtgccggaagaggatgaagagcagcaact<br>ggaggcgctacggcagtttaagcaggcccagttgttgcgcgtagcggcggcggatatcgccggtacgttacccgtcatgaaagtgagcgatcactt<br>aacctggctggcggaagcgattatcgatgcggtggtgcagcaagcctggaaccagatggtggcgcgttacggccagccgacgcatctgcacgatcg<br>cgaagggcgcggtttcgccgtggtcggttacggcaaacttggcggctgggaattaggttacagctccgataggatctggtgttcctgcacgactgc<br>cccatgatgtgatgaccgatggcgagcgtgaaatcgatggccgccagttctatttgcgcctcgcgcagcgcgtgatgcacctgttcagcacgcga<br>cgtcgtccggcattctttatgaagtcgatgcgcgtttgcgcccgtccggcgcggccggaatgctggtgaccactgcggaagcgttcgccgattat<br>caaaaaaatgaagcctggacatgggagcatcaggcgctggcgcgtgcgcgcgtggtgtacggcgatccgcaactgaccgccgaatttgacgccatt<br>cgccgcagatatcctgatgacctcccgcgatgccgctaccctgcaaaccgaagtgcgggaaatgcgtgagaaaatgcgcgcccatcttggtaacaa<br>gcacaaagaccgtttcgatctgaaagccgatgaaggcggtatcaccgatattgagtttatcgctcagtatctggtgctgcgctttgcccatgagaa<br>ccgaaactgacgcgctggtcggataatgtgcgcatcctcgaagggctggcgcaaaacggcatcatggatgagcaggaagcgcaggcattgacgc<br>tggcgtacaccacgttgcgtgatgagctgcaccacctggcgctgcaagagctgccaggacatgtggcgctctcctgttttgtcgccgagcgtgcga<br>tatcaaaaccagctgggacaagtggctggtggaaccgtgcgccccggcgtaagtgtggatcatcgcgcgcaaattttgtatctctcaggagacag<br>gaatgaaagttacgctgccagagttcaatcaagccggtgtcatggtggtgggtgatgtgatgctggatcgctactatacgcccaaccagccgcat<br>ttctccggaagcgccagttccggttgttaaagtcgatactattgaagagcgaccgggcggtgcggcaaacgtggcgatgaacattgcctcgctggg |

TABLE H-continued

| SEQ ID NO: | Sequence |
|---|---|
| | cgcaacggcgcgtctggttggcctgactggcattgatgatgcggcgcgcgcgctgagcaaagcgctggcggagttaatgttaaatgtgacttcgtt<br>tctgttccgactcaccccaccatcactaagctgcgcgtgctgtcgcgtaaccagcaactgattcgc |
| 185 | atgaccctgaatatgatgatggatgccagccgttctgaataataaccggacaattcggactgattaaaaaagcgccctcgcggcgctttttttata<br>ttctcgactccatttaaaataaaaaatccaatcggatttcactatttaaactggccattatctaagatgaatccgatggaagacgctgattttaac<br>acgcgttttttaacctttttattgaaagtcggtgcttcttttgagcgaacgatcaaatttattgtggattcccatcaaaaaaatattctcaacctaaa<br>aaagtttgtgtaatacttgtaacgctacatggagattaactcaatctagagggtattaataatgaatcgtactaaactggtactgggcgcaactca<br>cttcacgccccgaagggggaagctgcctgaccctacgattcccgctatttcattcactgaccggaggttcaaaatga |
| 186 | accggataagagagaaaagtgtcgacgtcggtccggttgatattgaccggcgcatccgccagctcgcccagttttggtggatctgtttggcgatt<br>ttgcgggtcttgccggtgtcgctgccgaaaaaaataccaatatttgccataacacacgctcctgttgaaaaagagatcccgcggggaaatgcggt<br>gaacatgtcagctattgcgaagagtgtgccagttttgctcacgggcaaaagctgcaccagaatgggtattaatgcaccagcctggcgcttttttc<br>gcggcacgtcccctcgctaatgcccgtctggcgcggctttgacgctgataaggcgctgaataccgatctggatcaaggttttgtcgggttatcgtc<br>caaaaggtgcactcttttgcatggttataagtgcctgacatggtgtccgggcgaacgtcgccaggtggcacaaattgtcagaactacgacacgacta<br>accgaccgcaggagtgtgcgatgaccctgaatatgatgatggatgccagccgttctgtaataataaccggacaattcggactgattaaaaagcgc<br>cctcgcggcgcttttttatattctcgactccatttaaaataaaaaatccaatcggatttcactatttaaactggccattatctaagatgaatccgat<br>ggaagctcgctgtttaacacgcgttttttaaccttttattgaaagtcggtgcttctttgagcgaacgatcaaatttaagtggattcccatcaaaaa<br>aatattctcaacctaaaaaagtttgtgtaatacttgtaacgctacatggagattaactcaatctagaggtattaataatgaatcgtactaaactg<br>gtactgggcgcaactcacttcacgccccgaagggggaagctgcctgaccctacgattcccgctatttcattcactgaccggaggttcaaaatgacc<br>cagcgaaccgagtcgggtaataccgctctggcgcttcgatttatcccagcagttcaccgcgatgcagcggataagcgtggttctcagccgggcgacc<br>gaggttgaacagacactccagcaggtgctgtgcgtattgcacaatgacgcctttttgcagcacggcatgatctgtctgtacgacagccagcaggcg<br>attttgactattgaagcgttgcaggaagccgatcagcagttgatccccggcagctcgcaaattcgctaccgtccgggtgaagggctggtcgggacg<br>gtgctttcgcaggggcaatcgttagtgaggcgcgtgtggctgacgatcagcgctttcttgaccgcctgggactgtatgattacaacctgccgttta<br>tcgccgtgccgctgatagggccggatgcgcagactttttggcgtgctgacggcgcaaccgatggcgcgttacgaagagcggttacccgcctgcaccc<br>gctttctggaaacggtc |
| 187 | tccctgtgcgccgcgtcgccgatggtggccagccaactggcgcgctacccgatcctgctcgatgaactgctcgacccgaacacgctctatcaaccg<br>acggcgatgaacgcctatcgcgatgaactgcgacaatacctgttgcgcgtgccggaagaggatgaagagcagcaactggaggcgctacggcagttt<br>aagcaggcgcagttgttgcgcgtagcggcggcggatatcgccggtacgttacccgtcatgaaagtgagcgatcacttaacctggctggcggaagcg<br>attatcgatgcggtggtgcagcaagcctggaaccagatggtggcgcgttacggccagccgacgcatctgcacgatcgcgaagggcgcggtttcgcc<br>gtggtcggttacggcaaacttggcgcgtgggaattaggttacagctccgatctggatctggtgttcctgcacgactgccccatggatggatgaccg<br>atggcgagcgtgaaatcgatgccccccagttctatttgcgcctcgcgcagcgcgtgatgcacctgttcagcacgcgcacgtcgtccggcattcttt<br>atgaagtcgatgcgcgtttgcgcccgtccggcgcggccggaatgctggtgaccactgcggaagcgttcgccgattatcaaaaaaatgaagcctgga<br>catgggagcatcaggcgctggcgcgtcgcggtggtgtacggcgatccgcaactgaccgccgaatttgacgccattcgccgcgatatcctgatgacc<br>tcccgcgatgccgctaccctgcaaaccgaagtgcgggaaatgcgtgagaaaatgcgcgcccatcttggtaacaagcacaaagaccgtttcgatctg<br>aaagccgatgaaggcggtatcaccgatattgagtttatcgctcagtatctggtgctgcgctttgcccatgaagagcgaaactgacgcgctggtcg<br>gataatgtgcgcatcctcgaagggctggcgcaaaacggcatcatggatgagcaggaagcgcaggcattgacgctggcgtacaccacgttgcgtgat<br>gagctgcaccacctggcgctgcaagagagccaggacatgtggcgctctcctgttttgtcgccgagcgtgcgcttatcaaaccagctgggacaagt<br>ggctggtggaaccgtgcgccccggcgtaa |
| 188 | taaagcgagcgctcacttacgtgatctgttgacgcagtccgaagcgaccattacttcagccgtttcagcagatacggcggtgtggagtgcgcaatc<br>agccctggcgaaactggtgctcaccgagtggttagtgacgcagggctggcgaaccttccttgatgaaaagcgcaggctaagtttgccgactcctt<br>aaacgctttgctgacgttcatctgtcacgcagcgccgcgagctgaaaaaagcctttgcccagccgctgggcgacagctatcgcgaccagttaccg<br>cggctgcgcgtgatatcgacagcgcgttattgctggccgacattacgatcgcgcgcgccgctggagtggctggaaaactgcaggggcttcag<br>cacgctattgaaacgcgccagagagttgaaatcgaacatttccgtaataccgccattacccaggagccgttctggttgcacagcggaaaacgttaa<br>cgaaaggatatttcgcatgtccctgtgcgccgcgtcgccgatggtggccagccaactggcgcgctacccgatcctgctcgatgaactgctcgaccc<br>gaacacgctctatcaaccgacggcgatgaacgcctatcgcgatgaactgcgacaatacctgttgcgcgtgccggaagaggatgaagagcagcaact<br>ggaggcgctacggcagtttaagcaggcgcagttgttgcgcgtagcggcggcggatatcgccggtacgttacccgtcatgaaagtgagcgatcactt<br>aacctggctggcggaagcgattatcgatgcggtggtgcagcaagcctggaaccagatggtggcgcgttacggccagccgacgcatctgcacgatcg<br>cgaagggcgcggtttcgccgtggtcggttacggaaacttggcggctgggaattaggttacagctccgatctggatctggtgttcctgcacgactgc<br>cccatggatggatgaccgatggcgagcgtgaaatcgatgccgaccagttctatttgcgcctcgcgcagcgcgtgatgcacctgttcagcacgcgc<br>acgtcgtccggcattctttatgaagtcgatgcgcgtttgcgcccgtccggcgcggccggaatgctggtgaccactgcggaagcgttcgccgattatc<br>aaaaaaatgaagcctggacatgggagcatcaggcgctggcgcgtcgcggtggtgtacggcgatccgcaactgaccgccgaatttgacgccattc<br>gccgcgatatcctgatgacctcccgcgatgccgctaccctgcaaaccgaagtgcgggaaatgcgtgagaaaatgcgcgcccatcttggtaacaagc<br>acaaagaccgtttcgatctgaaagccgatgaaggcggtatcaccgatattgagtttatcgctcagtatctggtgctgcgctttgcccatgagaagc<br>gaaactgacgcgctggtcggataatgtgcgcatcctcgaagggctggcgcaaaacggcatcatggatgagcaggaagcgcaggcattgacgctggc<br>gacaccacgttgcgtgatgagctgcaccacctggcgctgcaagagagccaggacatgtggcgctctcctgttttgtcgccgagcgtgcgcttatcaa<br>accagctgggacaagtggctggtggaaccgtgcgccccggcgtaagtgtggtatcatcgcgcgcaaattttgtatctctcaggagacaggaatga<br>aagttacgctgccagagttcaatcaagccggtgtcatggtggtgggtgatgtgatgctggatcgctactggtacggcccaaccagccgcatttctc<br>cggaagcgccagttccggttgttaaagtcgatactattgaagagcgaccgggcgtgcggcaaacgtggcgatgaacattgcctgctgggcgcaa<br>cggcgcgtctggttggcctgactggcattgatgatgcggcgcgcgcgctgagcaaagcgctggcggatgttaatgtgaaatgtgacttcgtttctg<br>ttccgactcaccccaccatcactaagctgcgcgtgctgtcgcgtaaccagcaactgattcgc |
| 189 | atgaccctgaatatgatgatggatgccagccgcgtcaggttgaacgtaaaaaagtcggtctgcgcaaagcacgtcgtcgtccgcagttctccaaac<br>gttaattggtttctgcttcggcagaacgattggcgaaaaaacccggtgcgaacccgggtttttttatggataaagatcgtgttatccacagcaatcc<br>attgattatctcttcttttttcagcatttccagaatcccctcaccacaaagcccgcaaaatctggtaaactatcatccaattttctgcccaaatggc<br>tgggattgttcatttttttgtttgcatacaacgagagtgacagtacgcgcgggtagttaactcaacatctgaccggtcgataactcacttcacgccc<br>cgaagggggaagctgcctgaccctacgattcccgctatttcattcactgaccggaggttcaaaatga |
| 190 | accggataagagagaaaagtgtcgacgtcggtccggttgatattgaccggcgcatccgccagctcgcccagttttggtggatctgtttggcgatt<br>ttgcgggtcttgccggtgtcggtgccgaaaaaaataccaatatttgccataacacacgctcctgttgaaaaagagatcccgcggggaaatgcggg<br>aacatgtcagctattgcgaagagtgtgccagttttgctcacgggcaaaagctgcaccagaatgggtattaatgcaccagcctggcgcttttttcg<br>cggcacgtcccctcgctaatgcccgtctggcgcggctttgacgctgataaggcgctgaataccgatctggatcaaggttttgtcgggttatcgtcc<br>aaaaggtgcactcttttgcatggttataagtgcctgacatggtgtccgggcgaacgtcgccaggtggcacaaattgtcagaactacgacacgactaa<br>ccgaccgcaggagtgtgcgatgaccctgaatatgatgatggatgccagccgcgtcaggttgaacgtaaaaaagtcggtctgcgcaaagcacgtcgt<br>cgtccgcagttctccaaacgttaattggtttctgcttcggcagaacgattggcgaaaaaacccggtgcgaacccgggtttttttatggataaagatc<br>gtgttatccacagcaatccattgattatctcttcttttttcagcatttccagaatcccctcaccacaaagcccgcaaaatctggtaaactatcatcc |

TABLE H-continued

| SEQ ID NO: | Sequence |
|---|---|
| | aattttctgcccaaatggctgggattgttcattttttgtttgccttacaacgagagtgacagtacgcgcgggtagttaactcaacatctgaccggc<br>gataactcacttcacgccccgaagggggaagctgcctgacccctacgattcccgctatttcattcactgaccggaggttcaaaatgacccagcgaac<br>cgagtcgggtaataccgtctggcgcttcgatttatcccagcagttcaccgcgatgcagcggataagcgtggttctcagccgggcgaccgaggttga<br>acagacactccagcaggtgctgtgcgtattgcacaatgacgcctttttgcagcacggcatgatctgtctgtacgacagccagcaggcgattttgac<br>tattgaagcgttgcaggaagccgatcagcagttgatccccggcagctcgcaaattcgctaccgtccgggtgaagggctggtcgggacggtgctttc<br>gcaggggcaatcgttagtgctggcgcgtgtggctgacgatcagcgcttcttgaccgcctgggactgtatgattacaacctgccgtttatcgccgt<br>gccgctgataggggccggatgcgcagacttttggcgtgctgacggcgcaaccgatggcgcgttacgaagagcggttacccgcctgcacccgctttct<br>ggaaacggt |
| 191 | atggcgctgaagcacctgatcacgctctgcgcggcgtcgccgatggtcgccagccagctggcgcgccaccgctgctgctggatgagctgctggat<br>cccaacaccctctatcagccgacggcgaccgatgcctatcgcgacgagctgcgccagtacctgctgcgcgtgccggaagaggatgaagagcagcag<br>ctggaggcgttgcgcagtttaagcaggcgcagcagctgcatatcgcggcggcggatatcgctggtaccctgccggtgatgaaggtcagcgatcac<br>ttaacctggcttgccgaagcgatcctcgacgcggtggtgcagcaggcatggggcagatggtcgctcgctacggccagccgacccacctgcacgat<br>cgccagggtcgcggcttcgccgtcgtcggctacggtaagcttggcggctgggctacagctccgatctcgatctggtgttcctccatgac<br>tgcccggcggaggtgatgaccgacggcgagcgggagattgacggccgtcagttctacctgcggctggcccagcggatcatgcacctgttgcagcac<br>ccgcacctcgtccggtattctctacgaagtggacgcccggctgcgtcctctggcgcggcggggatgctgtggtcaccaccgccgacgcgtttgct<br>gactatcagcagaacgaagcctggacgtgggaacatcaggcgctggtgcgcgcccgcgtggtctatggcgacccggcgctgcaggcgcgctttgac<br>gccattcgtcgcgatatcctgaccaccccgcggggagggatgacccctgcagaccgaggttcgcgagatgcgcgagaagatgcgcgccaccttggc<br>aacaaacatcccgatcgttttgatatcaaagccgatgccggcgggatcaccgatattgaatttattactcagtatctggtcctacgctatgccagt<br>gacaagccgaagctgacccgctggtctgacaacgtgcgtattcttgagctgctggcgcagaacgacatcatgacgaggaggaggcgcgcgccta<br>acgcatgcgtacaccaccttgcgtgatgcgctccatcacctggccctgcaggaccagccgggacacgtggcgccagaggccttcagccgggagcgt<br>cagcaggtcagcgccagctggcagaagtggctgatggcttaa |
| 192 | cgtaaggcgaccaccagctccgcgcgttgctgaacgacgctgaagccgttctgctggccgcggacaccgccgacgaggcgttattccgcaccgag<br>gtcgtcggcgccaaactggccctgactgaatggctggtccagcgcggctggcgtccgttcctcaacgaggcaggagagaaaaatagccggatcgt<br>tcaaacggtttgccgatattaacctctcgcgggtggcggccgagctgcgcagcgccgtgcagcatctggcggttgaagatgccgcgaccagttgc<br>cgaagctgcccgcgacatcgacagcgtccagctgctggcgggcgccatgtgcgccgtcgcgccgtggctggagaactggcaggagcttcaccg<br>tgcaatagcacatgacgatcgcagcgtctttgaatatttccgtcgccaggcgctggctgccgagccgttctggctgcatagtggaaaacgataatt<br>tcaggccagggagcccttatggcgctgaagcacctgatcacgctctgcgcggcgtcgccgatggtcgccagccagctggcgcgccaccgctgctg<br>ctggatgagctgctggatcccaacaccctctatcagccgacggcgaccgatgcctatcgcgacgagctgcgccagtacctgctgcgcgtgccggaa<br>gaggatgaagagcagcagctggaggcgttgcgcagtttaagcaggcgcagcagctgcatatcgcggcggcggatatcgctggtaccctgccggtg<br>atgaaggtcagcgatcacttaacctggcttgccgaagcgatcctcgacgcggtggtgcagcaggcatggggcagatggtcgctcgctacggccag<br>ccgacccacctgcacgatcgccagggtcgcggcttcgccgtcgtcggctacggtaagcttggcggctgggagctgggctacagctccgatctcgat<br>ctggtgttcaccatgactgcccggcggaggtgatgaccgacggcgagcgggagattgacggccgcagttctacctgcggctggcccagcggatcat<br>gcacctgttcagcaccccgcacctcgtccggtattctctacgaagtggacgcccggctgcgtccttctggcgcggcggggatgctggtcaccaccgc<br>cgacgcgtttgctgactatcagcagaacgaagcctggacgtgggaacatcaggcgctggtgcgcgcccgcgtggtctatggcgacccggcgctgca<br>ggcgcgctttgacgccattcgtcgcgatatcctgaccaccccgcggggagggatgaccctgcagaccgaggttcgcgagatgcgcgagaagatgcg<br>cgcccaccttggcaacaaacatcccgatcgttttgatatcaaagccgatgccggcgggatcaccgatattgaatttattactcagtatctggtcct<br>acgctatgccagtgacaagccgaagctgacccgctggtctgacaacgtgcgtattcttgagctgctggcgcagaacgacatcatgacgaggaggag<br>gcgcgcgccttaacgcatgcgtacaccaccttgcgtgatgcgctccatcacctggccctgcaggacagccgggacacgtggcgccagaggcctt<br>cagccgggagcgtcagcaggtcagcgccagctggcagaagtggctgatggcttaactataaaatcgggtgtgctatatcgcgcgcaaagtttgcgt<br>ctcgcaggagagagtcatgaaagtaacgctgccggagtttgaacgtgcaggagtgttggtggtgggtgatgtgatgctggaccgctactggtacgg<br>ccccaccagtcgtatttcccggaaagccccgtgccggtggtgaaggtggaaaatatcgaagaacgtcctggcggcgcggcaaacgtagcgatgaac<br>atcgcctccctgggggcaacgtcgcgcctggtgggattgaccgggattgatgacgctgcccgcctgagccaggcgctggccaatgtgaatgtgaa<br>gtgcgacttcgtctccgtcccgactcacccgaccatcaccaagctgcgggtgctgtcgcgcaatcagcagctgatccgcctcgactttgaagaggg<br>cttctccggcgtggatccgcagccgatgcatgagcgcattcagcaggcgctgggagccattggcgcactgg |
| 193 | atgaccctgaatatgatgctagaagcgtcaggtaccggtcatgattcaccgtgcgattctcggttccctggagcgcttcattggcatcctgaccga<br>agagtcgctggcttcttcccaacctggattgcaccagtgcaggtagtggtcatgaatattaccgattctcaggctgaatacgttaacgaattgac<br>gcgtaaactacaaaatgcgggcattcgtgtaaaagcagacttgagaaatgagaagattggctttaaaatccgcgagcacactttacgtcgtgtccc<br>gtatatgttggtctgtggcgacaaagaagtcgaagccggcaaagtggccgtgccgcaccgtcgcgggaaagacctcggcagcatggacgtaagtga<br>agtgattgagaagctgcaacaagagattcgcagccgcagtcttcaacaactggaggaataaggtattaaaggcggaaaacgagttcaaacggcacg<br>tccgaatcgtatcaatggcgagattcgcgccctggaagttcgcgccattgagctggcttcccgaccgcagggcggcacagcctgaccctgcgtttc<br>ccgctgtttaacaccctgaccggaggtgaagcatga |
| 194 | ggccgtcgcccagcgtcggcgtccccaacagcagggcgggtaggccagcaggtccgcagcgtggcgcggttaatattgaccggggcggcggcggc<br>ctcccccagctgcttgtggatcatttcgcgatcttgcgggttttaccggtatcggtaccaaagaaaatgccaatgttcgccatagtacgctcct<br>gtcggaatggtgttgaaaaaaggaatgacgacagaggtattgcgaaggctgtgccaggttgccctgcaccgcgacggccatccctgccccatcag<br>gatcgcttcgcatcacgatgccgcgcgccaaaggcgcaccggcggggcgaaaggtaaaaatccgtgaattttcccctgtccggatcaatgtttcg<br>cgtggtcgttccgataaggcgcacactttgcatggttatccggcttcggcttaccccgccgagttttgcgcacggtgtcggacaatttgtcataa<br>ctgcgacacaggagtttgcgatgacccgtaatatgatgctagaagcgtcaggtaccggtcatgattcaccgtgcgattctcggttccctggagcct<br>tcattggcatcctgaccgaagagtcgctggcttcttcccaacctggattgcaccagtgcaggtagtggtcatgaatattaccgattctcaggctg<br>aatacgttaacgaattgacgcgtaaactacaaaatgcgggcattcgtgtaaaagcagacttgagaaatcagaagattggctttaaaatccgcgagc<br>acactttacgtcgtgtcccgtatatgttggtctgtggcgacaaagaagtcgaagccggcaaagtggccgtgccgcaccgtcgcgggaaagacctcg<br>gcagcatggacgtaagtgaagtgattgagaagctgcaaccagagattcgcagccgcagtcttcaacaactggaggaataaggtattaaaggcggaa<br>aacgagttcaaacggcacgtccgaatcgtatcaatggcgagattcgcgccctggaagttcgcgccattgagctggcttcccgaccgcagggcggca<br>cctgcctgaccctgcgtttcccgctgtttaacaccctgaccggaggtgaagcatgatccctgaatccgacccggacaccaccgtcagacgcttcga<br>cctctctcagcagttcaccgccatgcagcggataaggtgcgtgagagccgggcaccgaggccagcaaaacgctgcaggggtgctcagcgtattac<br>acaacgatgcctttatgcagcacggatgatctgcctctacgacagccagcaggagatcctcagtatgcgaagcgctgcagcaaaccggccagcag<br>ccctcccggcagcacgcagatccgctatcgcccggcgagggactggtggggaccgtgcgcccaggggcagtcgctggtgctgccccgggtcg<br>ccgacgatcagcgttttctcgaccgcctgagcctctacgattacgatctgccgtttatcgccgtaccgttgatggggcccaacgcccggccaatag<br>gggtgctggcggcccagccgatggcgcgccaggaagagcggctgccggcctgcacccgttttctcgaaaccgtc |
| 195 | atggcgctgaagcacctgatcacgctctgcgcggcgtcgccgatggtcgccagccagctggcgcgccaccgctgctgaggatgagctgctggatc<br>ccaacaccctctatcagccgacggcgaccgatgcctatcgcgacgagctgcgccagtacctgctgcgcgtgccggaagaggatgaagagcagcagc<br>tgcatatcgcggcggcggatatcgctggtaccctgccggtgatgaaggtcagcgatcacttaacctggcttgccgaagcgatcctcgacgcggtgg<br>tgcagcaggcatggggcagatggtcgctcgctacggccagccgacccacctgcacgatcgccagggtcgcggcttcgccgtcgtcggctacggta |

TABLE H-continued

| SEQ ID NO: | Sequence |
|---|---|
| | agcttggcggctgggagctgggctacagctccgatctcgatctggtgttcctccatgactgcccggcggaggtgatgaccgacggcgagcgggaga<br>ttgacggccgtcagttctacctgcggctggcccagcggatcatgcacctgttcagcacccgcacctcgtccggtattctctacgaagtggacgccc<br>ggctgcgtccttaggcgcggcgggatgctggtcaccaccgccgacgcgtttgctgactatcagcagaacgaagcctggacgtgggaacatcaggc<br>gctggtgcgcgcccgcgtggtctatggcgaccggcgctgcaggcgcgctttgacgccattcgtcgcgatatcctgaccacccgcgggaggggat<br>gaccctgcagaccgaggttcgcgagatgcgcgagaagatgcgcgcccaccttggcaacaaacatcccgatcgttttgatatcaaagccgatgccgg<br>cgggatcaccgatattgaatttattactcagtatctggtcctacgctatgccagtgacaagccgaagctgacccgctggtctgacaacgtgcgtat<br>tcttgagctgctggcgcagaacgacatcatggacgaggaggaggcgcgcgccttaacgcatgcgtacaccaccttgcgtgatgcgctccatcacct<br>ggccctgcaggagcagccgggacacgtggcgccagaggccttcagccgggagcgtcagcaggtcagcgccagctggcagaagtggctgatggctta<br>a |
| 196 | cgtaaggcgaccacccagctccgcgcgttgctgaacgacgctgaagccgttctgctaccgcggacaccgccgacgaggcgttattccgcaccgag<br>gtcgtcggcgccaaactggccctgactgaatggctggtccagcgcggctggcgtccgttcctcaacgaggcaggagagaaaaaaatagccggatcgt<br>tcaaacggtttgccgatattaacctctcgcgggtggcggccgagctgcgcagcgccgtgcagcatctggcggttgaagatgccgccgaccagttgc<br>cgaagctgtcccgcgacatcgacagcgtccagctgctggcgggcgctatggcgacgccgtcgccgtggctggagaactggcaggagcttcacc<br>gtgcaatagcacatgaccatcgcagcgtctttgaatatttccgtcgccaggcgctggctgccgagccgttctggctgcatagtggaaaacgataat<br>ttcaggccagggagcccttatggcgctgaagcacctgatcacgctctgcgcggcgtcgccgatggtcgccagccagctggcgcgccacccgctgct<br>gctggatgagctgctggatcccaacaccctctatcagccgacggcgaccgatgcctatcgcgacgagagcgccagtacctgctgcgcgtgccggaa<br>gaggatgaagagcaggctgcatatcgcggcgggcggatatcgctggtaccctgccggtgatgaaggtcagcgatcacttaacctggcttgccgaagc<br>gatcctcgacgcggtggtgcagcaggcatggggcagatggtcgctcgctacggccagccgaccacctgcacgatcgcagggtcgcggcttcgc<br>cgtcgtcggctacgtaagcttggcggctgggagctgggctacagctccgatctcgatctggtgttcctccatgactgcccggcggaggtgatgac<br>cgtcggcgagcgggagattgacggccgtcagttctacctgcggctggcccagcggatcatgcacctgttcagcacccgcacctcgtccggtattct<br>ctacgaagtggacgcccggctgcgtccttctggcgcggcggggatgctggtcaccaccgccgacgctttgagactatcagcagaacgaagcctg<br>gacgtgggaattcatcaggcgctggtgcgcgcccgcgtggtctatggcgaccggcgctgcaggcgcgctttgacgccattcgtcgcgatatcctga<br>ccacccgcgggaggggatgaccctgcagaccgaggttcgcgagatgcgcgagaagatgcgcgcccaccttggcaacaaacatcccgatcgttttga<br>tatcaaagccgatgccggcgggatcaccgatattgaatttattactcagtatctggtcctacgctatgccagtgacaagccgaagctgacccgctg<br>gtctgacaacgtgcgtattcttgagctgctggcgcagaacgacatcatggacgaggaggaggcgcgcgccttaacgcatgcgtacaccaccttgcg<br>tgatgcgctccatcacctggccctgcaggagcagccgggacacgtggcgcccagaggccttcagccgggagcgtcagcaggtcagcgccagctggca<br>gaagtggctgatggcttaactataaaatcgggtgtgctattatcgcgcgcaaagtttgcgtctcgcaggagagagtcatgaaagtaacgctgccgg<br>agtttgaacgtgcaggagtgttggtggtgggtgatgtgatgctggaccgctactggtacggccccaccagtcgtatttccccggaagcccggtgc<br>cggtggtgaaggtggtaaatatcgaagaacgtcctggcggcgcggcaaacgtagcgatgaacatgcctccctgggggcaacgtcgcgcctggtgg<br>gattgaccgggattgatgacgctgcccgcgcgctgagccaggcgctggccaatgtgaatgtgaagtgcgacttcgtctccgtcccgactcacccga<br>ccatcaccaagctgcgggtgctgtcgcgcaatcagcagctgatccgcctcgactttgaagagggcttctccggcgtggatccgcagccgatgcatg<br>agcgcattcagcaggcgctgggagccattggcgcactgg |
| 197 | atgaccctgaatataagctcgacgccgtcctcgcagtaccattgcaaccgactttacagcaagaagtgattctggcacgcatggaacaaattcttg<br>ccagtcgggctttatccgatgacgaacgcgcacagcttttatatgagcgcggagtgttgtatgatagtctcggtctgagggcattagcgcgaaatg<br>attttcacaagcgctggcaatccgacccgatatgcctgaagtattcaattacttaggcatttacttaacgcaggaggcaattttgatgctgcct<br>atgaagcgtttgattctgtacttgagcttgatcgccattgagctggcttcccgaccgcagggcggcacctgcctgaccctgcgtttcccgctgttt<br>aacaccctgaccggaggtgaagcatga |
| 198 | cccaacagcagggccgggtaggccagcaggtccgccagcgtggcgcggttaatattgaccggggcggcggcggcctccccagctgcttgtggatc<br>atttttcgcgatcttgcgggttttaccggtatcggtaccaaagaaaatgccaatgttcgccatagtacgctcctgtcggaatggtgttgaaaaaag<br>gaatgacgacagaggtattgcaaggcgctgtgcaggttgccctgcaccgcgaggcccatcctgcccatcaggatcgcttcgcatcacgatgccg<br>cgcgccaaaggcgcaccgtcggggggcgaaaggtaaaaatccgtgaattttcccccgtcggataatgatcgcgtggtcgttccgataagggcgca<br>cactttgcatggttatccgggttcggcttaccccgccgcgttttgcgcacggtgtcggacaatttgtcataactgcgacacaggagtttgcgatga<br>ccctgaatatgatgctcgacgccgtcctcgcagtaccattgcaaccgactttacagcaagaagtgattctggcacgcatggaacaaattcttgcca<br>gtcgggctttatccgatgacgaacgcgacagcattatatgagcgcggagtgttgtatgatagtctcggtctgagggcattagcgcgaaatgatttt<br>tcacaagcgctggcaatccgacccgatatgcctgaagtattcaattacttaggcatttacttaacgcaggaggcaattttgatgctgcctatgaa<br>gcgtttgattctgtacttgagcttgatcgccattgagaggcttcccgaccgcagggcggcacctgcctgaccctgcgtttcccgctgtttaacacc<br>ctgaccggaggtgaagcatgatccctgaatccgacccggacaccaccgtcagacgcttcgacctctctcagcagttcaccgccatgcagcggataa<br>gcgtggtgctgagccgggccaccgaggccgacaaaacgctgcaggaggtgctcagccgtattacacaacgatgcctttatgcagcacgggatgatct<br>gcctgtacgacagcgagcaggagatcctcagtatcgaagcgctgcagcaaaccggccagcagccccctccccggcagcacgcagatccgctatcgcc<br>ccggcgagggactggtggggaccgtgctggcccaggggcagtcgctggtgctgccccgggtcgccgacgatcagcgttttctcgaccgcctgagcc<br>tctacgattacgatctgccgtttatcgccgtaccgttgatggggcccaacgcccggccaataggggtgctggcggcccagccgatggcgcgccagg<br>aagagcggctgccggcctgcacccgttttctcgaaaccgtc |
| 199 | atggcgctgaagcacctgatcacgctctgcgcggcgtcgccgatggtcgccagccagctggcgcgccacccgctgctgctggatgagctgctggat<br>cccaacaccctctatcagccgacggcgaccgatgcctatcgcgacgagctgcgccagtacctgctgcgcgtgccgaagaggatgaagagcagcag<br>ctgcatatcgcggcggcggatatcgctggtaccctgccggtgatgaaggtcagcgatcacttaacctggcttgccgaagcgatcctcgacgcggtg<br>gtgcagcaggcatggggcagatggtcgctcgctacggccagccgaccacctgcacgatcgcagggtcgcggcttcgccgtcgtcggctacgtgt<br>aagcttggcggctgggagctgggctacagctccgatctcgatctggtgttcctccatgactgcccggcggaggtgatgaccgacggcgagcgggag<br>attgacggccgtcagttctacctgcggctggcccagcggatcatgcacctgttcagcacccgcacctcgtccggtattctctacgaagtggacgcc<br>cggctgcgtccttctggcgcggcggggatgctggtcaccaccgccgacgcgtttgctgactatcagcagaacgaagcctggacgtgggaacatcag<br>gcgctggtgcgcgcccgcgtggtctatggcgaccggcgctgcaggcgcgctttgacgccattcgtcgcgatatcctgaccacccgcgggagggga<br>tgaccctgcagaccgaggtcgcgagatgcgcgagaagatgcgcgcccaccttggcaacaaacatcccgatcgttttgatatcaaagccgatgcc<br>ggcgggatcaccgatattgaatttattactcagtatctggtcctacgctatgccagtgacaagccgaagctgacccgctggtctgacaacgtgcgt<br>attcttgagctgctggcgcagaacgacatcatggacgaggaggaggcgcgcgccttaacgcatgcgtacaccaccttgcgtgatgcgctccatcac<br>ctggccctgcaggagcagccgggacacgtggcgccagaggccttcagccgggagcgtcagcaggtcagcgccagctggcagaagtggctgatggct<br>taa |
| 200 | cgtaaggcgaccacccagctccgcgcgttgctgaacgacgctgaagccgttctgctggccgcggacaccgccgacgaggcgttattccgcaccgag<br>gtcgtcggcgccaaactggccctgactgaatggctggtccagcgcggctggcgtccgttcctcaacgaggcaggagagaaaaaaatagccggatcgt<br>tcaaacggtttgccgatattaacctctcgcgggtggcggccgagctgcgcagcgccgtgcagcatctggcggttgaagatgccgccgaccagttgc<br>cgaagctgtcccgcgacatcgacagctccagctgctggcgggcgctatgcgacgccgtcgccgtggctggagaactggcaggagcttcac<br>cgtgcaatagcacatgacgatcgcagcgtctttgaatatttccgtcgccaggcgctggctgccgagccgttctggctgcatagtggaaaacgata<br>atttcaggccagggagcccttatggcgctgaagcacctgatcacgctctgcgcggcgtcgccgatggtcgccagccagctggcgcgccacccgctg<br>ctgctggatgagctgctggatcccaacaccctctatcagccgacggcgaccgatgcctatcgcgacgagctgcgccagtacctgctgcgcgtgccg |

TABLE H-continued

| SEQ ID NO: | Sequence |
|---|---|
| | gaagaggatgaagagcagcagctgcatatcgcggcggcggatatcgctggtaccctgccggtgatgaaggtcagcgacacttaacctggcttgccg<br>aagcgatcctcgacgcggtggtgcagcaggcatgggggcagatggtcgctcgctacggccagccgacccacctgcacgatcgccagggtcgcggct<br>tcgccgtcgtcggctacggtaagcttggcggctgagagctgggctacagctccgatctcgatctggtgttcctccatgactgcccggcggaggtga<br>tgaccgacggcgagcgggagattgacggccgtcagttctacctccggctggcccagcggatcatgcacctgttcagcacccgcacctcgtccggta<br>ttctctacgaagtggacgcccggctgcgtccttctggcgcggcggggatgctggtcaccaccgccgacgcgtttgctgactatcagcagaacgaag<br>cctggacgtgggaacatcaggcgctggtgcgcgcccgcgtggtctatggcgaccgggcgctgcaggcggcgctttgacgccattcgtcgcgatatcc<br>tgaccaccccgcggggagggatgaccctgcagaccgaggttcgcgagatgcgcgagaagatgcgcgcccaccttggcaacaaacatcccgatcgtt<br>ttgatatcaaagccgatgccggcgggatcaccgatattgaatttattactcagtatctggtcctacgctatgccagtgacaagccgaagctgaccc<br>gctggtctgacaacgtgcgtattcttgagctgctggcgcagaacgacatcatggacgaggaggaggcgcgcgccttaacgcatgcgtacaccacct<br>tgcgtgatgcgctccatcacctggccctgcaggagcagccgggacacgtggcgccagaggccttcagccgggagcgtcagcaggtcagcgccagct<br>ggcagaagtggctgatggcttaactataaaatcgggtgtgctattatcgcgcgcaaagtttgcgtctcgcaggagagagtcatgaaactaacgctg<br>ccggagtttgaacgtgcaggagtgttggtggtgggtgatgtgatgctggaccgctactggtacggcccaccagtcgtatttcccgggaagcccg<br>gtgccggtggtgaaggtggaaaatatcgaagtacgtcctggcggcgcggcaaacgtagcgatgaacatcgcctccctgggggcaacgtcgcgcctg<br>gtggggattgaccgggattgatgacgctgcccgccgcgctgagccaggcgctggccaatgtgaatgtgaagtgcgacttcgtctccgtcccgactcac<br>ccgaccatcaccaagctgcgggtgctgtcgcgcaatcagcagctgatccgcctcgactttgaagagggcttctccggcgtggatccgcagccgatg<br>catgagcgcattcagcaggcgctgggagccattggcgcactgg |
| 201 | atgaccctgaatatgatgctcgagctaaagttctcggctaatcgctgattacatttgacgcaatgcgcaataaaagggcatcatttgatgccctt<br>ttgcacgctttcataccagaacctggctcatcagtgattttttttgtcataatcattgctgagacaggctctgaagagggcgtttatacaccaaac<br>cattcgagcggtagcgcgacggcaagtcagcgttctccttgcaatagcagggaagaggcgccagaaccgccagcgttgaagcagtttgaacgcgt<br>tcagtgtataatccgaaacttaatttcggtttggagccattgagctggcttcccgaccgcagggcggcacctgcctgaccctgcgtttcccgctgt<br>ttaacaccctgaccggaggtgaagcatga |
| 202 | ggccgtcgcccagcgtcggcgtccccaacagcagggccgggtaggccagcaggtccgccagcgtggcgcggttaatattgaccggggcggcggcgg<br>cctcccccagctgcttgtggatcattttcgcgatcttgcgggttttaccggtatcggtaccaaagaaaatgccaatgttcgccatagtacgctcct<br>gtcggaatggtgttgaaaaaaggaatgacgacagtggtattgcgaaggctgtgccaggttgccctgcaccgcgacggccatccctgcccatcag<br>gatcgcttcgcatcacgatgccgcgcgccaaaggcgcaccccggccggggcgaaaggtaaaaatccgtgaattttcccctgtcggatcaatgtttcg<br>cgtggtcgttccgataagggcgcacactttgcatggttatccgggttcggcttaccccgccgcgttttgcgcacggtgtcggacaatttgtcataa<br>ctgcgacacaggagtttgcgatgaccctgaatatgatgctcgagctaaagttctcggctaatcgctgataacatttgacgcaatgcgcaataaaag<br>ggcatcatttgatgccctttgcacgctttcataccagaacctggctcatcagtgattttttttgtcataatcattgctgagacaggctctgaaga<br>gggcgtttatacaccaaacattcgagcggtagcgcgacggcaagtcagcgttctccttgcaatagcagggaagaggcgccagaaccgccagcgt<br>tgaagcagtttgaacgcgttcagtgtataatccgaaacttaatttcggtttggagccattgagctggcttcccgaccgcagggcggcacctgcctg<br>accctgcgtttcccgctgtttaacaccctgaccggaggtgtagcatgatccctgaatccgacccagacaccaccgtcagacgcttcgacctctctc<br>agcagttcaccgccatgcagcggataagcgtggtgctgagccgggccaccgaggccagcaaaacgctgcaggaggtgctcagcgtattacacaacg<br>atgccttatgcagcacgggatgatctgcctgtacgacagcgagcaggagatcctcagtatcgaagcgctgcagcaaaccggccagcagcccc<br>ccggcagcacgcagatccgctatcgccccggcgaggactggtgggacgctgctggcccagggcagtcgctggtgctgcccgggtcgccg<br>atcagcgttttctccaccgcctgagcctctacgattacgatctgccgtttatcgccgtaccgttgatgggccccaacgcccggccaataggggtgc<br>tggcggcccagccgatggcgcgccaggaagagcggctgccggcctgcacccgtttctcgaaaccgtc |
| 203 | atgaccctgaatatgatgctcgagcccgctgaccgaccagaacttccacccttggactcggctataccctggcgtgacggcgcgcgataactggga<br>ctacatcccattccggtgatcttaccattggcgtcaataggttacggtccggcgactttccagatgacctatattcccggcacctacaataacgg<br>taacgtttacttcgcctgggctcgtatacagttttaattcgctaagtcttagcaataaatgagataagcggtgtgtcttgtgaaaaacaaggact<br>aaaagcgttacccactaaaaaagatagcgactttttatcacttttttagcaaagttgcactggacaaaaggtaccacaattggtgtactgatactcgac<br>acagcattagtgtcgatttttcatataaaggtaattttggccattgagctggcttcccgaccgcagggcggcacctgcctgaccctgcgtttcccg<br>ctgtttaacaccctgaccggaggtgaagcatga |
| 204 | ggccgtcgcccagcgtcggcgtccccaacagcagggccgggtaggccagcaggtccgccagcgtggcgcgcttaatattgaccggggcggcggcgg<br>cctcccccagctgcttgtggatcattttcgcgatcttgcgggttttaccggtatcggtaccaaagaaaatgccaatgttcgccatagtacgctcct<br>gtcggaatggtgttgaaaaaaggaatgacgacagaggattgcgaaggctgtgccaggttgccctgcaccgcgacggccatccctgccccatcagg<br>atcgcttcgcatcacgatgccgcgcgcaaaggcgcaccccggccggggcgaaaggtaaaaatccgtgaattttcccctgtcggatcaatgtttcgc<br>gtggtcgttccgataagggcgcacactttgcatggttatccgggttcggcttaccccgccgcgttttgcgcacggtgtcggacaatttgtcataac<br>tgcgacacaggagtttgcgatgaccctgaatatgatgctcgagcccgctgaccgaccagaacttccacccttggactcggctataccttggcgtga<br>cggcgcgcgataactgggactacatcccattccggtgatcttaccattggcgtcaataggttacggtccggcgactttccagatgacctatattc<br>ccggcacctacaataacggtaacgtttacttcgcctgggctcgtatacagttttaattcgctaagtcttagcaataaatgagataagcggtgtgtc<br>ttgtggaaaaacaaggactaaagcgttacccactaaaaaagatagcgactttttatcacttttttagcaaagttgcactggacaaaaggtaccacaat<br>tggtgtactgatactcgacacagcattagtgtcgatttttcatataaaggtaattttggccattgagctggcttcccgaccgcagggcggcacctg<br>cctgaccctgcgtttcccgctgtttaacaccctgaccggaggtgaagcatgatccctgaatccgacccggacaccaccgtcagacgatcgacctct<br>ctcagcagttcaccgccatgcagcggataagcgtggtgctgagccgggccaccgaggccagcaaaacgctgcaggaggtgctcagcgtattacaca<br>acgatgccttatgcagcacgggatgatctgcctgtacgacagcgagcaggagatcctcagtatcgaagcgctgcagcaaaccggccagcagcccc<br>tccccggcagcacgcagatccgctatcgccccggcgaggactggtgggacgctgctggcccagggcagtcgctggtgctgcccgggtcgccg<br>acgatcagcgttttctcgaccgcctgagcctctacgattacgatctgccgtttatcgccgtaccgttgatgggccccaacgcccggccaataggggg<br>tgctggcggcccagccgatggcgcgccaggaagagcggctgccggcctgcacccgtttctcgaaaccgtc |
| 205 | atggcgctgaagcacctgatcacgctctgcgcggcgtcgccgatggtcgccagccagctggcgcgccaccgctgctgctggatgagctgctggat<br>cccaacaccctctatcagccgacggcgaccgatgcctatcgcgacgagctgcgccagtacctgctgcgcgtgccggaagaggatgaagagcagcag<br>ctgcatatcgcggcggcggatatcgctggtaccctgccggtgatgaaggtcagcgatcacttaacctggcttgccgaagcgatcctcgacgcggtg<br>gtgcagcaggcatgggggcagatggtcgctcgctacggccagccgacccacctgcacgatcgccagggtcgcgccttcgccgtcgtcggctacggt<br>aagcttggcggctgggagagggctacagctccgatctcgatctggtgttcctccatgactgcccggcggaggtgatgaccgacggcgaggggagat<br>tgacggccgtcagttctacctgcggctggcccagcggatcatgcacctgttcagcacccgcacctcgtccggtattctctacgaagtggacgcccg<br>gctgcgtccttctggcgcggcggggatgctggtcaccaccgccgacgcgtttgctgactatcagcagaacgaagcctgggaacatcaggcgctggt<br>gcgcgcccgcgtggtctatggcgaccgggcgctgcaggcggcgctttgacgccattcgtcgcgatatcctgaccaccccgcggggagggat<br>gaccctgcagaccgaggttcgcgagatgcgcgagaagatgcgcgcccaccttggcaacaaacatcccgatcgttttgatatcaaagccgatgccgg<br>cgggatcaccgatattgaatttattactcagatctggtcctacgctatgccagtgacaagccgaagctgacccgctggtctgacaacgtgcgtatt<br>cttgagctgctggcgcagaacgacatcatggacgaggaggaggcgcgcgccttaacgcatgcgtacaccaccttgcgtgatgcgctccatcacctg<br>gccctgcaggagcagccgcgacacgtggcgccagaggccttcagccgggagcgtcagcaggtcagcgccagctggcagaagtggctgatggcttaa |

TABLE H-continued

| SEQ ID NO: | Sequence |
|---|---|
| 206 | cgtaaggcgaccacccagctccgcgcgttgctgaacgacgctgaagccgttctgctggccgcggacaccgccgacgaggcgttattccgcaccgag
gtcgtcggcgccaaactggccctgactgaatggctggtccagcgcggctggcgtccgttcctcaacgaggcaggagagaaaaaaatagccggatcg
ttcaacggtttgccgatattaacctctcgcaggtggcggccgagctgcgcagcgccgtgcagcatctggcggttgaagatgccgccgaccagttgc
cgaagctgtcccgcgacatcgacagcgtccagctgctggcgggcgcctatggcgacgccgtcgcgccgtggctggagaactggcaggagcttcacc
gtgcaatagcacatgacgatcgcagcgtctttgaatatttccgtcgccaggcgctggctgccgagccgttctggctgcatagggaaaacgataatt
tcaggccagggagcccttatggcgctgaagcacctgatcacgctctgccggcgtgccgatggtcgccagccagctggcgcgccacccgctgctg
ctggatgagctgctggatcccaacaccctctatcagccgacggcgaccgatgcctatcgcgacgagctgcgccagacctgctgcgcgtgccggaag
aggatgaagagcagcagctgcatatcgcggcggcggatatcgctggtaccctgccggtgatgaaggtcagcgatcacttaacctggcttgccgaag
cgatcctcgacgcggtggtgcagcatggggggcagatggtcgctcgctacggccagccgacccacctgcacgatcgccagggtcgcggcttcg
ccgtcgtcggctacggtaagcttggcggctgggagctgggctacagctccgatctcgatctggtgttcctccatgactgcccggcggaggtgatga
ccgacggcgaggggagattgacggccgcagttctacctgcggctggcccagcggatcatgcacctgttcagcacccgcacctcgccggtattctct
acgaagtggacgcccggctgcgtccttctggcgcggcgcggatgctggtcaccaccgccgacgcgtttgctgactatcagcagaacgaagcctgga
cgtgggaacatcaggcgctggtgcgcgcccgcggtctattgcgacccggcgatcgcgaggcgcgcttgacgccattcgtcgcgatatcctgacca
cccgcgggaggggatgaccctgcagaccgaggttcgcgagatgcgcgagaagatgcgcgcccaccttggcaacaaacatcccgatcgtttgata
tcaaagccgatgccggcgggatcaccgatattgaatttattactcagtatctggtcctacgctatgccagtgacaagccgaagctgacccgctggt
ctgacaacgtgcgtattcttgagctgctggcgcagaacgacatcatggacgaggaggaggcgcgcgccttaacgcatgcgtacaccaccttgcgtg
atgcgctccatcacctggccctgcaggagcagccgggacagcgcaggtaccggtcaggtcagcgaggtcagcgccagctggcaga
agtggctgatggcttaactataaaatcgggtgtgctattatcgcgcgcaaagtttgcgtctcgcaggagagagtcatgaaagtaacgctgccggag
tttgaacgtgcaggagttggtggtgggtgatgtgatgctggaccgctactggtacggcccaccagtcgtatttccccggaagccccggtgccggt
ggtgaaggtgaaaatatcgaagaacgtcctggcggcgcggcaaacgtagcgatgaacatcgcctccctggggcgaacgtcgcgcctggtgggatt
gaccgggattgatgacgctgcccgcgcgctgagccaggcgctggccaatgtgaatgtgaagtgcgacttcgtctccgtcccgactcacccgaccat
caccaagctgcgggtgctgtcgcgcaatcagcagctgatccgcctcgactttgaagagggcttctccggcgtggatccgcagccgatgcatgagcg
cattcagcaggcgctgggagccattggcgcactgg |
| 207 | atgacccctgaatatgatgctagaagcgtcaggtaccggtcatgattcaccgtgcgattctcggttccctggagcgcttcattggcatcctgaccga
agagttcgctggcttcttcccaacctggattgcaccagtgcaggtagtggtcatgaatattaccgattctcaggctgaatacgttaccgaattgac
gcgtaaactacaaaatgcgggcattcgtgtaaaagcagacttgagaaatgagaagattggcttaaatcggcgagcacactttacgtcgtgtccc
gtatatggtctgtggcgacaaagaagtcgaagccggcaaagtggccgtgcgcaccgtcgcgggaaagacctcggcagcatggacgtaagtgaa
gtgattgagaagctgcaacaagagattcgcagccgcagtcttcaacaactggaggaataaggtattaaaggcggaaaacgagttcaaacggcacgt
ccgaatcgtatcaatgccgagattcgcgccctcgaagttcgcgccattgagctggcttcccgaccgcagggcgccacctgcctgaccctgcgtttc
ccgctgtttaacaccctgaccggaggtgaagcatga |
| 208 | ggccgtcgcccagcgtcggcgtccccaacagcagggccgggtaggccagcaggccgccagcgtggccggttaatattgaccggggcggcggcggc
ctccccagagcttgtggatcattttcgcgatcttgcggttttaccggtatcgaaccaattgaaaatgccaatgttcgccatagtacgctcctgt
cggaatggtgttgaaaaaaggaatgacgacagaggtattgcgaaggctggccaggttgccctgcaccgcgacggcccatccctgcccatcaggat
cgcttcgcatcacgatgccgcgcgcaaaggcgcaccggcggggcgaaaggtaaaaatccgtgaattttcccctgtcggatcaatgtttcgcgt
ggtcgttccgataagggcgcacactttgcatggttatccgggttcggcttaccccgccgcgttttgcgcacgtgtcggacaatttgtcataactg
cgacacaggagtttgcgatgaccctgaatatgatgctagaagcgtcaggtaccgtgcatgattcaccgtgcgattctcggttcctggagcgatca
ttggcatcctgaccgaagagttcgctggcttcttcccaacctggattgcaccagtgcaggtagtggtcatgaatattaccgattctcaggctgaat
acgttaacgaattgacgcgtaaactacaaaatgcggcattcgtgtaaaagcagacttgagaaatgagaagattggctttaaaatccggcgagcacac
tttacgtcgtgtcccgtatatgttggtctgtggcgacaaagaagtcgaagccggcaaagtggccgtgcgcaccgtcgcgggaaagacctcggcag
catggacgtaagtgaagtgattgagaagctgcaacaagagattcgcagccgcagtcttcaacaactggaggaataaggtattaaaggcggaaaacg
agttcaaacggcacgtccgaatcgtatcaatgccgagattcgcgccctggaagttcgcgccattgagctggcttcccgaccgcagggcggcacctg
cctgaccctgcgtttcccgctgtttaacaccctgaccggaggtgaagcatgatccctgaatccgacccggacaccaccgtcagacgcttcgacctc
tctcagcagttcaccgccatgcagcggataagcgtggtgctgagccgggccaccgaggccagcaaaacgctgcaggtggtgctcagcgtattacac
aacgatgccttatgcagcacgggatgatctgcctgtacgacacggcagcaggagatcctcagtatcgaagcgctgcagcaaaccggccagcagccc
ctccccggcagcacgcagatccgctatcgccccgcgagggactggtggggacgtgctgctggccccagggcagtcgctggtgctgccccgggtcgcc
gacgatcagcgttttctcgaccgcctgagcctctacgattacgatctgccgtttatcgccgtaccgttgatgggccaacgcccggccaataggg
gtgctggcggcccagccgatggcgcgccaggaagagcggctgccggcctgcaccgttttctcgaaaccgtc |
| 209 | atggcgctgaagcacctgatcacgactgcgcggcgtcgccgatggtcgccagccagctcgcgcgccacccgctgctgctggatgagctgctggatc
ccaacaccctctatcagccgacggcgaccgatgcctatcgcgacgagctgcgccagtacctgctgcgcgtgccggaagaggatgaagagcagcagc
tggaggcgttgcgccagtttaagcaggcgcagcagctgcatatcgcggcggcggatatcgctggtaccctgccggtgatgaaggtcagcgatcact
taacctggcttgccgaagcgatcctcgacgcggtggtgcagcaggcatgggggcagatggtcgctcgctacggccagccgacccacctgcacgatc
gccagggtcgcggcttcgccgtcgtcggcttacggtaagcttggcggctgggagctgggctacagctccgatctcgatctggtgttcctccatgactg
cccggcggaggtgatgaccgacggcgagcgggagattgacggccgcagttctacctgcggctggcccagcggatcatgcacctgttcagcacccg
cacctcgtccggtattctctacgaagtggacgcccggctgcgtccttctggcgcggcggggatgctggtcaccaccgccgacgcgtttgctgacta
tcagcagaacgaagcctggacgtgggaacatcaggcgctggtgcgcgcccgcggtctatggcgacccggcgctgcaggcgcgctttgacgccattc
gtcgcgatatcctgaccacccgcggggaggggatgaccctgcagaccgaggttcgcgagatgcgcgagaagatgcgcgccaccttggcaacaaac
atcccgatcgtttgataatcaaagccgatgccggcgggatcaccgatattgaattattactcagtatctggtcctacgctatgccagtgacaagc
cgaagctgacccgctggtagacaacgtgcgtattcttgagctgctggcgcagaacgacatcatggacgaggaggaggcgcgcgccttaacgcatgc
gtacaccaccttgcgtcatgcgctccatcacctggccctgcaggagcagccgggacacgtggcgccagaggccttcagccgggagcgtcagcaggt
cagcgccagctggcagaagtggctgatggcttaa |
| 210 | cgtaaggcgaccacccagctccgcgcgttgctgaacgacgctgaagccgttctgctggccgcggacaccgccgacgaggcgttattccgcaccgag
gtcgtcggcgccaaactggccctgactgaatggctggtccagcgcggctggcgtccgttcctcaacgaggcaggagagaaaaaaatagccggatcg
ttcaacggtttgccgatattaacctctcgcaggtggcggccgagctgcgcagcgccgtgcagcatctggcggttgaagatgccgccgaccagttgc
cgaagctgtcccgcgacatcgacagcgtccagctgctggcgggcgcctatggcgacgccgtcgcgccgtggctggagaactggcaggagcttcacc
gtgcaatagcacatgacgatcgcagcgtctttgaatatttccgtcgccaggcgctggctgccgagccgttctggcttcatagtggaaaacgataatt
tcaggccagggagcccttatggcgctgaagcacctgatcacgctagcgcggcgtcgccgatggtcgccagccagctggcgcgccacccgctgctgc
tggatgagctgctggatcccaacaccctctatcagccgacggcgaccgatgcctatcgcgacgagctgcgccagacctgctgcgcgtgccggaag
aggatgaagagcagcagctggaggcgttgcgccagtttagcaggcgcagcagctgcatatcgcggcggcggatatcgctggtaccctgccggtgat
gaaggtcagcgatcacttaacctggcttgccgaagcgatcctcgacgcggtggtgcagcaggcatggggggcagatggtcgctcgctacggccagcc
gacccacctgcacgatcgccagcgtcgcggcttcgccgtcgtcggctacggtaagcttggcggctgggagctgggctacagctccgatctcgatct
ggtgttcctccatgtctgcccggcggaggtgatgaccgacggcgagcgggagattgacggccgcagttctacctgcggctggcccagcggatcat
gcacctgttcagcacccgcacctcgtccggtattctctacgaagtggacgcccggctgcgtccttctggcgcggcggggatgctggtcaccaccgc |

TABLE H-continued

| SEQ ID NO: | Sequence |
|---|---|
| | cgacgcgtttgctgactatcagcagaacgaagcctggacgtgggaacatcaggcgctggtgcgcgcccgcgtggtctatgccgacccggcgctgca<br>ggcgcgctttgacgccattcgtcgcgatatcctgaccaccccgcgggaggggatgaccctgcagaccgaggttcgcgagatgcgcgagaagatgcg<br>cgcccaccttggcaacaaacatcccgatcgtttgatatcaaagccgatgccggcgggatcaccgatattgaatttattactcagtatctggtcct<br>acgctatgccagtgacaagccgaagctgacccgctggtctgacaacgtgcgtattcttgagctgctggcgcagaacgacatcatgacgaggagga<br>ggcgcgcgccttaacgcatgcgtacaccaccttgcgtgatgcgctccatcacctggccctgcaggagcagccgggacacgtggcgccagaggcctt<br>cagccgggagcgtcagcaggtcagcgccagctggcagaaagtggctgatcgcttaactataaaatcgggtgtgctattatcgcgcgcaaagtttgcg<br>tctcgcaggagagagtcatgaaagtaacgctgccggagttgaacgtgcaggagtgttggtggtggggatgtgatgctggaccgctactggtacggc<br>cccaccagtcgtatttcccggaagcccggtgccggtggtgaaggtggaaaatatcgaagaacgtcctggcggcgcggcaaacgtagcgatgaac<br>atcgcctccctggggcaacgtcgcgcctggtgggattgaccgggattgatgacgctgcccgcgcgctgagccaggcgctggccaatggaatgtga<br>agtgcgactcgtctccgtcccgactcacccgaccatcaccaagctgcgggtgctgtcgcgcaatcagcagctgatccgcctcgactttgaagagg<br>gcttctccggcgtggatccgcagccgatgcatgagcgcattcagcaggcgctgggagccattggcgcactgg |
| 211 | atggcgctcaaacagttaatccgtctgtgtgccgcctcgccgatggtcgcgacaacttgcacgtcatcctttattgctcgatgaactgctcgaccc<br>gcgcacgctttaccagccgattgagccgggcgcttaccgcgacgaactgcgtcagtatagatgcgggtgccaacagaagacgaagaacagcagctt<br>gaagccgtgcgccagttcaaacaggcccagcatttgcgtatcgcagccggggatattccgggggcattgccggtgatgaaagtcagtgaccattta<br>acctaccttgccgaggccattctcgatgtcgtggtgcagcatgcgtgggaacaaatggtcgtaaaatacgggcagcccgcgcatcttcagcaccgt<br>gaggggcgcggttttgccgtggtcggttacgggaaactcggtggctgggagctgggttatagctcagatctggatctggtcttcctgctcgattgc<br>gcgccggcagttgatgacggacggcgaacgcagcatcgacggaccgtcagttttatatcggcgtggcgcagcgcattatgcacttattcagcaccgga<br>catcgtcaggcattctttacgaggttgatccgcgtagcgaccttccggcgcatccggcatgctggtcagtaccattgaagcgttgcagattatca<br>ggccaatgaagcctggacgtgggagcatcaggcgctggttcgcgcgcgcgtggtttacggggatccgcaactgacacagcaatttaacgccacgcg<br>tcgcgacattctttgccgccagcgcgatggcgacgccctgcgtaaggaggtccgtgaaatgcgcgagaaatgtatgcccatctggggagtaaaaa<br>agcccacgagtttgatctgaaagccgatccgggtggcatcacggatattgaattcattgcaccatacctggttctgcgtttcgcgcatgatgagcc<br>gaagctgacgcgctggtctgataacgtgcggattttttgaactgatggcacgatatgacatcatgccggaagaggaagcgcgccatctgacgcaggc<br>ttatgtgacgctgcgcgatgaaattcatcatctggcgttgcaggaacacagcgggaagtggccgcggacagctttgctactgagcgcgcgcagatc<br>cgtgccagctgggcaaagtggctcggctga |
| 212 | cggtactggaacagaaatcggcggatgcgtaggagatttgttatgacacggcctgtctgaagtgcaagtagtgcttacttcctggctggcaacctc<br>aggctggacgccgtttattgatgataaatctgcgaagaaactggacgcttccttcaaacgtttgctgacatcatgctcggtcgtaccgcagcgga<br>tctgaaagaagcctttgcgcagccactgacggaagaaggttatcgcgatcagctggcgcgcctgaaacgcagatcattaccttccatttgcttgc<br>cggtgcttaccctgaaaagacgtcgatgcgtatattgccggctgggtggacctgcaacaggccatcgttcagcagcaacacgcctgggaggattc<br>ggcccgttctcacgcggtgatgatggatgattctggttaaacgggcaacctcgtaactgactgactagcctgggcaaactgcccgggctttttttt<br>gcaaggaatctgatttcatggcgctcaaacagttaatccgtctgtgccgcctcgccgatggtcgcgacacaacttgcacgtcatcctttattgctc<br>gatgaactgctcgacccgcgcacgctttaccagccgattgagccgggcgcttaccgcgacgaactgcgtcagtatctgatgcgggtgccaacagaa<br>gacgaagaacagcagcttgaagccgtgcgccagttcaaacaggcccagcatttgcgtatcgcagccggggatattccgggggcattgccggtgatg<br>aaagtcagtgaccattaacctaccttgccgaggccattctcgatgtcgtggtgcagcatgcgtggtaaaatacgggcagccc<br>gcgcatcttcagcaccgtgaggggcgcggttttgccgtggtcggttacggggaaactcggtggctgggagctgggttatagctcagatctggatctg<br>gtcttcctgctcgattgcgcgccggaggtgatgacgacggcgaacgcagcatcgacggacgtcagttttatcttcggctggcgcagcgcattatg<br>cacttattcagcaccgacatcgtcaggcattctttacgaggttgatccgcgctgcgaccttccggcgcatccggcatgaggtcagtaccattga<br>agcgttgcagattatcaggccaatgaagcctggacgtgggagcatcaggcgggttcgcgcgcgcgtggtttacggggatccgcaactgacacag<br>caatttaacgccacgcgtcgcgacattctttgccgccagcgcgatggcgacgccctgcgtaaggaggtccgtgaaatgcgcgagaaatgtatgcc<br>catctggggagtaaaaaagcccacgagtttgatctgaaagccgatccgggtggcatcacggatattgaattcattgcacaatacctggttctgcgt<br>ttcgcgcatgatgagccgaagctgacgcgctggtctgataacgtgcggattttttgaactgatggcacgatatgacatcatgcccgaagaggaagcg<br>cgccatctgacgcaggcttatgtgacgctgcgcgatgaaattcatcatctggcgttgcaggaacacagcgggaaagtggccgcggacagctttgct<br>actgagcgcgcgcagatccgtgccagctgggcaaagtggctcggctgagggttttattcggctaacaggcgctcgtgatattatccggcgcattg<br>tatttacccgatttgatttatctcgtttggagtcttgggatgaaagtgactttgcctgattttcaccgcgcaggtgtgctggttgtcggtgacgta<br>atgttagaccgttactggtatggcccgaccaatcgtatttctccggaagctccggtgccggtggtgaaggtcagtaccattgaagagcggcctggc<br>ggtgagctaacgtggcagtgaagaacatttcatctctgggcgcctcttcctgtctgatcggcctgaccggcgtagacgacgctgcgtgccctcagtgag<br>cgtctggcagaagtgaaagaaactgcgattcgtcgcactatccacatcctaccatccacaaactgcgaattttgtcccgtaaccagcaactga<br>tccgcctcgactttgaggaaggttttgaaggcgttgatctcgagccgatgctgaccaaaataga |
| 213 | atgagcatcacggcgttatcagcatcatttcctgaggggaatatcgccagccgcttgtcgctgcaacatccttcactgttttataccgtggttgaa<br>caatcttcggtggcgatttcgctgaccgatccgcaggcgcgcatttgttatgccaatccggcattctgccgccagacgggttttgcacttgagaca<br>cttttgggcgagaaccaccgtctgctgaatttttttttcacaaagtgtagcgttattgaatcgcacattttaaactgttggccgctgtggaaggaat<br>attggtgaaaggtgcggttttaaggccttttctttgactctctgtcgttacaaagttaatatgcgcgccctccgtctctgaagctctcggtgaac<br>attgttgcgaggcaggatgcgagctggttgtgttttgacattaccgataatgtgccgcgtgaacgggtgcgttatgcccgcccggaagcggcgttt<br>tccgtccggggaatggcatggagctgcgccttatccagacgctgatcgcccatcatcgcggttctttagatctctcggtccgccctgatggcggc<br>accttgctgacgttacgcctgccggtacagcaggttatcaccggaggcttaaaatga |
| 214 | tgtttcgtctcgaggccgggcaactgagcggccccgttgaaaccgacctgggctggcatctgttgttgtgcgaacaaattcgcctgccgcaaccct<br>tgccgaaagccgaagccttaacgcggtgcgtcagcaactgattgcccgtgcaacagaaaacattatcagcgccagtggctgcaacaactgatcaacg<br>cctgagcctgttctccttcttgttgatgcagacagggttaatgcccgttttgacgaaaaatgcacataaattgcctgcgttgccttataacagcga<br>gggaaatcctgcctccggccttgtgccacaccgcgctttgcctggttttgtggtaaaaactggcccgctttgcatcctgatgcttaaaacacccgt<br>tcagatcaaccttggcagataagcccgcgaaaggcctgcaaattgcacggttattccgggtgagtatatgtgtgatttgggttccggcattgcg<br>caataaaggggagaaagacatgagcatcacggcgttatcagcatcattcctgaggggaatatcgccagccgcttgtcgctgcaacatccttcact<br>gttttataccgtggttgaacaatcttcggtggcgatttcgctgaccgatccgcaggcgcgcatttgttatgccaatccggcattctgccgccagac<br>gggttttgcacttgagacacttttgggcgagaaccaccgtctgctggaattttttttcacaaagtgtagcgttattgaatcgcacattttaaactg<br>ttggccgctgtggaagcgaatattggtgaaaggtgcggttttaaggccttttctttgactctctgtcgttacaaagttaatatgcgcgccctccg<br>tctctgaagctctcggtgaacattgttgcgaggcaggatgcgagctggttgtgttttgacattaccgataatgtgccgcgtgaacgggtgcgttat<br>gcccgcccggaagcggcgttttccgtccggggaatggcatggagctgcgccttatccagacgctgatcgcccatcatcgcggttctttagatctc<br>tcggtccgccctgatggcggcaccttgctgacgttacgcctgccggtacagcaggttatcaccggaggcttaaaatgacccagttacctaccgcgg<br>gcccggttatccggcgctttgatatgtctgcccagtttacggcgctttatcgcatcagcgtggcgctgagtcaggaaagcaacaccgggcgcgcac<br>tggccgcgatcctcaaggtgcttcacgatcatcgatttatgcaatacggcatggtgtgctgtttgataaagaaccgcaatgcactctttgtggaat<br>ccctgcatgcatcgacggcgaaagaaaaaaagaccccgccatgtccgtcggttaccgcattgaccgcatggggggaaggcgtgatcggcgcggtgatgagccaggcgtc<br>aggcgctggtgttaccgcgcattcagacgatcagcgttttctcgaccgcctgaatatttacgattacagcctgccgtgattggcgtgccgatcc<br>ccgtgcggataatcagccatcgggcgtgctggtggcacagccgatggcgttgcacgaagaccggctgactgccagtacgcggttttttagaaatgg<br>tc |

TABLE H-continued

| SEQ ID NO: | Sequence |
| --- | --- |
| 215 | atgagcatcacggcgttatcagcatcatttcctgaggggaatatcgccagccgcttgtcgctgcaacatccttcactgttttataccgtggttgaa<br>caatcttcggtggcgatttcgctgaccgatccgcaggcgcgcatttgttatgccaatccggcattctgccgccagacgggttttgcacttgagaca<br>cttttgggcgagaaccaccgtctgctggaattttttttcacaaagcgtagcgttattgaatcgcacattttgatgttggccgctgtggaagcgaat<br>attggtgaaaggtgcggttttaaggcctttttctttgactctctgtcgttacaaagttaatatgcgcgccctccgtctctgaagctctcggtgaac<br>attgttgcgaggcaggatgcgagctggttgtgttttgacattaccgataatgtgccgcgtgaacgggtgcgttatgcccgcccggttgcggcgttt<br>tcccgtccggggaatggcatggagctgcgccttatccagacgctgatcgcccatcatcgcggttctttagatctctcggtccgccctgatggcggc<br>accttgctgacgttacgcctgccggtacagcaggttatcaccggaggcttaaaatga |
| 216 | tgtttcgtctcgaggccgggcaactgagcggccccgttgaaaccgacctgggctggcatctgttgttgtgcgaacaaattcgcctgccgcaaccct<br>tgccgaaagccgaagccttaacgcgggtgcgtcagcaactgattgcccggcaacagaaacattatcagcgccagtggctggctgcaacaactgatcaacg<br>cctgagcctgttctccttcttgttgatgcagacgggttaatgcccgttttgcacgaaaaatgcacataaattgcctgcgttgccttataacagcgc<br>agggaaatcctgcctccggccttgtgccacaccgcgctttgcctggttttgtggtaaaaaactgccccgctttgcatcctgatgcttaaaacaccccg<br>ttcagatcaacctttgggcagataagcccgcgaaaggcctgcaaattgcacggttattccgggtgagtatatgtgtgatttgggttccggcattgc<br>gcaataaaggggagaaagacatgagcatcacggcgttatcagcatcatttcctgaggggaatatcgccagccgcttgtcgctgcaacatccttcac<br>tgttttataccgtggttgaacaatcttcggtggcgatttcgctgaccgatccgcaggcgcgcatttgttatgccaatccggcattctgccgccaga<br>cgggttttgcacttgagacacttttgggcgagaaccaccgtctgctggaattttttttcacaaagcgtagcgttattgaatcgcacattttaaact<br>gttggccgctgtggaagcgaatattggtgaaaggtgcggttttaaggcctttttctttgactctctgtcgttacaaagttaatatgcgcgccctcc<br>gtctctgaagctctcggtgacattgttgcgaggcaggatgcgagctggttgtgttttgacattaccgataatgtgccgcgtgaacgggtgcgtta<br>tgcccgcccggaagcggcgttttcccgtccggggaatggcatggagctgcgccttatccagacgctgatcgcccatcatcgcggttctttagatct<br>ctcggtccgccctgatggcggcaccttgctgacgttacgcctgccggtacagcaggttatcaccggaggcttaaaatgacccagttacctaccgcg<br>ggcccggttatcccgcgctttgatatgtctgcccagtttacggcgctttatcgcatcagcgtggcgctgagtcaggaaagcaacaccgggcgcgca<br>ctggcggcatcctcgaagtgcttcacgatcatgcatttatgcaatacggcatggtgtgtctgtttgataaagaacgcaatgcactcttttgtggaa<br>tccctgcatggcatcgacggcgaaaggaaaaaaagagacccgccatgtccgttacccgcatggggaaggcgtgatcggcgcggtgatgagccagcat<br>caggcgctggtgttaccgcgcatttcagacgatcagcgttttctcgaccgcctgaatatttacgattacagcctgccgttgtttggcgtgccgatc<br>cccggtgcggataatcagccatcggcgtgctggtggcacagccgatggcgttgcacgaagaccggctgactgccagtacgcggtttttagaaatg<br>gtc |
| 217 | atgagcatcacggcgttatcagcatcatttcctgaggggaatatcgccagccgcttgtcgctgcaacatccttcactgttttataccgtggttgaa<br>caatcttcggtggcgatttcgctgaccgatccgcaggcgcgcatttgttatgccaatccggcattctgccgccagacgggttttgcacttgagaca<br>cttttgggcgagaaccaccgtctgctggttaaaaacgtgaccacgagcattaataaacgccacgaaatgtggcgttatttattcaaaaagtatct<br>tctttcataaaaagtgctaaatgcagtagcagcaaaatgggataagtcccatggaatacggctgttttcgctgcaattttttaacttttcgtaaa<br>aaaagatgtttctttgagcgaacgatcaaaatataggttaaccggcaaaaaattattctcattagaaaatagtttgtgtaatacttgtaacgctac<br>atggagattaacttaatctagagggttttataccgtctctgaagctctacggtgaacattgttgcgaggcaggatgcgagctggttgtgttttgacat<br>taccgataatgtgccgcgtgaacgggtgcgttatgcccgcccggaagcggcgttttcccgtccggggaatggcatggagagcgccttatccagacg<br>ctgatcgcccatcatcgcggttctttagatctctcggtccgccctgatggcggcaccttgctgacgttacgcctgccggtacagcaggttatcacc<br>ggaggcttaaaatga |
| 218 | gtttcgtctcgaggccgggcaactgagcggccccgttgaaaccgacctgggctggcatctgttgttgtgcgaacaaattcgcctgccgcaacccctt<br>gccgaaagccgaagccttaacgcgggtgcgtcagcaactgattgcccggcaacagaaacattatcagcgccagtggctgcaacaactgatcaacgc<br>ctgagcctgttctccttatgttgatgcagacgggttaatgcccgttttgcacgaaaaatgcacataaattgcctgcgttgccttataacagcgcag<br>ggaaatcctgcctccggccttgtgccacaccgcgctttgcctggttttgtggtaaaaaactggcccgctttgcatcctgatgcttaaaacaccccgtt<br>cagatcaacctttgggcagataagcccgcgaaaggcctgcaaattgcacggttattccgggtgagtatatgtgtgatttgggttccggcattgcgc<br>aataaaggggagaaagacatgagcgttatcagcatcatttcctgaggggaatatcgccagccgcttgtcgctgcaacatccttcactg<br>ttttataccgtggttgaacaatcttcggtggcgatttcgctgaccgatccgcaggcgcgcatttgttatgccaatccggcattctgccgccagacg<br>ggttttgcacttgagacacttttgggcgagaaccaccgtctgctggttaaaaacgtgaccacgagcattaataaacgccacgaaatgtggcgttat<br>ttattcaaaaagtatctttcataaaaagtgctaaggcagtagcagcaaaatgggataagtcccatggaatacggctgtttcgctgcaattttt<br>taacttttcgtaaaaaaaagatgtttctttgagcgaacgatcaaaatatagcgttaaccggcaaaaaattattacattagaaaatagtttgtgtaa<br>tacttgtaacgctacatggagattaacttaatctagagggttttataccgtctctgaagctctcggtgaacattgttgcgaggcaggatgcgagag<br>gttgtgttttgacattaccgataatgtgccgcgtgaacgcgtgcgttatgcccgcccggaagcggcgttttcccgtccggggaatggcatggagct<br>gcgccttatccagacgctgatcgcccatcatcgcggttctttagatctctcggtccgccctgatggcggcaccttgctgacgttacgcctgccggt<br>acagcaggttatcaccggaggcttaaaatgacccagttacctaccgcgggcccggttatcccgcgctttgatatgtctgcccagtttacggcgcct<br>tatcgcatcagcgtggcgctgagtcaggaaagcaacaccgggcgcgcactggcggcgatcctcgaagtgcttcacgatcatgcatttatgcaatac<br>ggcatggtgtgtctgtttgataaagaacgcaatgcactcttttgtggaatccctgcatggcatcgacggcgaaaggaaaaaagagacccgccatgtc<br>cgttaccgcatggggaaggcgtgatcggcgcggtgatgagccagcgtcaggcgctggtgttaccgcgcatttcagacgatcagcgttttctcgac<br>cgcctgaatatttacgattacagcctgccgttgattggcgtgccgatccccggtgcggataatcagccatcggcgtgctggtggcacagccgatg<br>gcgttgcacgaagaccggctgactgccagtacgcgcttttagaaatggtcg |
| 219 | atgagcatcacggcgttatcagactcatttcctgagggaatatcgccagccgcttgtcgctgcaacatccttcactgttttataccgtggttgaac<br>aatcttcggtggcgatttcgctgaccgatccgcaggcgcgcatttgttatgccaatccggcattctgccgccagacgggttttgcacttgagacac<br>ttttgggcgagaaccaccgtctgctggtgaacatcactgatgcacaagctacctatgtcgaagaattaactaaaaactgaagatgcaggcattcg<br>cgttaaagccgacttggaaatgagaagattggctttaaaattcgcgaacacacgctacgccgtgttccttatatgttagtttgtggcgataaaga<br>ggtcgaagcaggcaaagttgctgttcgtaccccgccgcggcaaagacttaggaagcatggatgttagcgaagtcgttgacaaactgctggcggaaat<br>ccgcagcagaagtcttcatcaactggaggaataaagtattaaaggcggaaaacgagttcaaccggcgcgtcctaatcgcattaacaaagagattcg<br>cgcgcaagaagttcgcctcacaggcgtcgatggcgagcagattcgtgattgtcagtctgaatgaagctgtgaatgatgaggagcggggcgtcga<br>tttagtagaaatcagtccgagtgccgagccgccagtgtcgaatcccgtctagaagctctcggtgaacattgttgcgaggcaggatgcgagctgg<br>ttgtgttttgacattaccgataatgtgccgcgtgaacgggtgcgttatgcccgcccggaagcggcgttttcccgtccggggaatggcatggagctg<br>cgccttatccagacgctgatcgcccatcatcgcggttctttagatctctcggtccgccctgatggcggcaccttgctgacgttacgcctgccggta<br>cagcaggttatcaccggaggcttaaaatga |
| 220 | tgtttcgtctcgaggccgggcaactgagcggccccgttgaaaccgacctgggctggcatctgttgttgtgcgaacaaattcgcctgccgcaacccctt<br>gccgaaagccgaagccttaacgcgggtgcgtcagcaactgattgcccggcaacagaaacattatcagcgccagtggctgcaacaactgatcaacg<br>cctgagcctgttctccttcttgttgatgcagacgggttaatgcccgttttgcacgaaaaatgcacataaattgcctgcgttgccttataacagcgc<br>agggaaatcctgcctccggccttgtgccacaccgcgctttgcctggttttgtggtaaaaaactgccccgctttgcatcctgatgcttaaaacaccc<br>cgttcagatcaacctttgggcagataagcccgcgaaaggcctgcaaattgcacggttattccgggtgagtatatgtgtgatttgggttccggcat<br>tgcgcaataaaggggagaaagacatgagcatcacggcgttatcagcatcatttcctgaggggaatatcgccagccgcttgtcgctgcaacatcct<br>tcactgttttataccgtggttgaacaatcttcggtggcgatttcgctgaccgatccgcaggcgcgcatttgttatgccaatccggcattctgccg<br>ccagacgggttttgcacttgagacacttttgggcgagaaccaccgtctgctggtgaacatcactgatgcacaagctacctatgtcgaagaattaa |

TABLE H-continued

| SEQ ID NO: | Sequence |
|---|---|
| | ctaaaaaactgcaagatgcaggcattcgcgttaaagccgacttgagaaatgagaagattggctttaaaattcgcgaacacacgctacgccgtgtt<br>ccttatatgttagtttgtggcgataaagaggtcgaagcaggcaaagttgctgttcgtacccgccgcggcattagacttaggaagcatggatgtta<br>gcgaagtcgttgacaaactgctggcggaaatccgcagcagaagtcttcatcaactggaggaataaagtattaaaggcggaaaacgagttcaaccg<br>gcgcgtcctaatcgcattaacaaagagattcgcgcgcaagaagttcgcctcacaggcgtcgatggcgagcagattggtattgtcagtctgaatga<br>agctcttgaaaaagctgaggaagcgggcgtcgatttagtagaaatcagtccgaatgccgacccgccagtttgtcgaatcccgtctctgaagctct<br>cggtgaacattgttgcgaggcaggatgcgagctggttgtgttttgacattaccgataatgtgccgcgtgaacgggtgcgttatgcccgcccggag<br>ggcgtttcccgtccggggaatggcatggagctgcgccttatccagacgctgatcgcccatcatcgcggttctttagatctctcggtccgccctg<br>atggcggcaccttgctgacgttacgcctgccggtacagcaggttatcaccggaggcttaaaatgacccagttacctaccgcgggcccggttatcc<br>ggcgctttgatatgtctgcccagtttacggcgctttatcgcatcagctgtggcgctgagtcaggaaagcaacaccgggcgcactggcggcgatc<br>ctcgaagtgcttcacgatcatgcatttatgcaatacggcatggtgtgtctgtttgataaagaacgcaatgcactcttttgtggaatccctgcatgg<br>catcgacggcgaaaggaaaaaagagacccgccatgtccgttaccgcatggggaaggcgtgatcggcgcggtgatgagccagcgtcaggcgctgg<br>tgttaccgcgcatttcagacgatcagcgttttctcgaccgcctgaatatttacgattacagcctgccgttgattggcgtgccgatcccggtgcg<br>gataatcagccatcgggcgtgctggtggcacagccgatggcgttgcacgaagaccggctgactgccagtacgcggttttagaaatggtc |
| 221 | atgagcatcaccgcgttatcagcatcatttcctgaggggaatatcgccagccgcttgtcgctgcaacatccttcactgttttataccgtggttga<br>acaatcttcggtggcgatttcgctgaccgatccgcaggcgcgcattgttatgccaatccggcattctgccgccagacggtttgcacttgaga<br>cacttttgggcgagaaccaccgtctgctggtgaacatcactgatgcacaagctacctatgtcgaagaattaactaaaaaactgcaagatgcaggc<br>attcgcgttaaagccgacttgagaaatgagaagattggctttaaaattcgcgaacacacgctacgccgtgttccttatatgttagtggcgat<br>aaagaggtcgaagcaggcaaagttgctgttcgtacccgccgcggcaaagacttaggaagcatggatgttagcgaagtcgttgacaaactgctggc<br>ggaaatccgcagcagaagtcttcatcaactggaggaataaagtattaaaggcggaaaacgagttcaaccggcgcgtcctaatcgcattaacaaag<br>agattcgcgcgcaagaagttcgcctcacaggcgtcgatggcgagcagattggtattgtcagtctgaatgaagctcttgaaaaagctgaggaagcg<br>ggcgtcgatttagtagaaatcagtccgaatgccgagccgccagtttgtcgaatcccgtctctgaagctctcggtgaacattgttgcgaggcagga<br>tgcgagctggagtgttttgacattaccgataatgtgccgcgtgaacgggtgcgttatgcccccccggaagcgccgttttcccgtccggggaatgg<br>catggagctgcgccttatccagacgctgatcgcccatcatcgcggttctttagatctctcggtccgccctgatggcggcaccttgctgacgttac<br>gcctgccggtacagcaggttatcaccggacgcttaaaatga |
| 222 | tgtttcgtctcgaggccgggcaactgagcggcccgttgaaaccgacctgggctggcatctgttgttgtgcgaacaaattcgcctgccgcaaccc<br>ttgccgaaagccgaagcctttaacgcgggtcgctcagcaactgattgcccggcaacagaaacattatcagcgccagtggctgcaacaactgatcaa<br>cgcctgagcctgttctccttcttgttgatgcagacgggttaatgccgttttgcacgaaaaatgcacataaattgcctgcgttgccttataacagc<br>gcagggaaatcctgcctccggccttgtgccacaccgcgctttgcctggtttgtggtaaaaactggcccgctttgcatcctgatgcttaaaacacc<br>ccgttcagatcaaccttgggcagataagcccgcgaaaggcctgcaaattgcacggttattccgggtgagtatatgtgtgatttgggttccggca<br>ttgcgcaataaagggagaaagacatgagcatcacgcgttatcagcatcatttcctgaggggaatatcgccagccgcttgtcgctgcaacatcc<br>ttcactgttttataccgtggttgaacaatcttcggtggcgatttcgctgaccgatccgcaggcgcgcattgttatgccaatccggcattctgcc<br>gccagacgggttttgcacttgagacacttttgggcgagaaccaccgtctgctggtgaacatcactgatgcacaagctacctatgtcgaagaatta<br>actaaaaaactgcaagatgcaggcattcgcgttaaagccgacttgagaaatgagaagattggctttaaaattcgcgaacacacgctacgccgtgt<br>tccttatatgttagtttgtggcgataaagaggtcgaagcaggcaaagttgctgttcgtacccgccgcaaagacttaggaagcatggatgtta<br>gcgaagtcgttgacaaactgctggcggaaatccgcagcagaagtcttcatcaactggaggaataaagtattaaaggcggaaaacgagttcaaccg<br>gcgcgtcctaatcgcattaacaaagagattcgcgcgcaagaagttcgcctcacaggcgtcgatggcgagcagattggtattgtcagtctgaatga<br>agctcttgaaaaagctgaggaagcggcgtcgatttagtagaaatcagtccgaatgccgagccgccagtttgtcgaatcccgtctctgaagctctc<br>ggtgaacattgttgcgaggcaggatgcgagctggttgtgttttgacattaccgataatgtgccgcgtgaacgggtgcgttatgcccgcccggaag<br>ggcgtttcccgtccggggaatggcatggagctgcgccttatccagacgctgatcgcccatcatcgcggttctttagatctctcggtccgccctg<br>atggcggcaccttgctgacgttacgcctgccggtacagcaggttatcaccggaggcttaaaatgacccagttacctaccgcgggcccggttatcc<br>ggcgctttgatatgtctgcccagtttacggcgctttatcgcatcagctgtggcgctgagtcaggaaagcaacaccgggcgcactggcggcgatc<br>ctcgaagtgcttcacgatcatgcatttatgcaatacgcatggtgtgtctgtttgataaagaacgcaatgcactcttttgtggaatccctgcatgg<br>catcgacggcgaaaggaaaaaagagacccgccatgtccgttaccgcatggggaaggcgtgatcggcgcggtgatgagccaggcaggcgctggt<br>gttaccgcgcatttcagacgatcagcgttttctcgaccgcctgaatatttacgattacagcctgccgttgattggcgtgccgatcccggtgcgg<br>ataatcagccatcgggcgtgctggtggcacagccgatggcgttgcacgaagaccggctgactgccagtacgcggttttagaaatggtc |
| 223 | atggcgctcaaacagttaatccgtctgtgtgccgcctcgccgatggtcgcgacacaacttgcacgtcatcctttattgctcgatgaactgctcga<br>cccgcgcacgctttaccagccgattgagccgggcgcttaccgcgacgaactgcgtcagtatctgatgcgggtgccaacagaagacgaagaacagc<br>agcttgaagccgtgcgccagttcaaacaggcccagcatttgcgtatcgcagccgggatatttccggggcattgccggtgatgaaagtcagtgac<br>catttaacctaccttcccgaggccattctcgatgtcgtggtgcagcatgcgtgggaacaaatggtcgtaaaatacgggcagcccgcgcatcttca<br>gcaccgtgaggggcgcggttttgccgtggtcggttacgggaaactcggtggctgggagctggggtttatagctcagatctggatctggtcttcctgc<br>tcgattgcgcgccggaggtgatgacggacggcgaacgcagcatcgacggacgtcagttttatcttcggctggcgcagcgcattatgcacttattc<br>agcaccccggacatcgcaggcattctttacgaggttgatccgcgtctgcgaccttccggcgcatccggcatgctggtcagtaccattgaagcgttt<br>gcagattatcaggccaatgaagcctggacgtgggagcatcaggcgctggttcgcgcgcgtggtttacgggatccgcaactgacacagcaattt<br>aacgccacgcgtcgcgacattctttgccgccagcgcgatggcgacggcctgcgtaaggaggtccgtgaaatgcgcgagaaaatgtatgcccatc<br>ggggagtaaaaaagcccacgagtttgatctgaaagccgatccgggtggcatcacggatattgaattcattgcacaatacctggttctgcgtttcg<br>cgcatgatgagccgaagctgacgcgctggtctgataacgtgcggatttttgaactgatggcacgatatgacatcatgccggaagaggaagcgcgc<br>catctgacgcaggcttatgtgacgctgcgcgatgaaattcatcatctggcgttgcaggaacacagcggaaagtggcgcggacagctttgctact<br>gagcgcgcgcagatccgtgccagctgggcaaagtggctcggctga |
| 224 | cggtactggaacagaaatcggcggatgcgcaggaaatttgttatgacacggcctgtctgaagtgcaagttagtgcttacttcctggctggcaacc<br>tcaggctggacgccgtttattgatgataaatctgcgaagaaactggacgcttccttcaaacgttttgctgacatcatgctcggtcgtaccgcagg<br>gatctgaaagaagcctttgcgcagccactgacggaagaaggttatcgcgatcagctggcgcgctgaaacgcagatcattacctttccatttgct<br>tgccggtgcttacctgaaaaagacgtcgatgcgtatattgccggctgggtggacctgcaacaggccatcgttcagcagcaacacgcctgggagg<br>attcggccctcgttctcacgcgtgatgatggatgctttctggttaaacgggcaacctcgttaactgactgactagcctgggcaaactgcccgggct<br>ttttttgcaaggaatctgatttcatggcgctcaaacagttaatccgtctgtgtgccgcctcgccgatggtcgcgacacaacttgcacgtcatcc<br>tttattgctcgatgaactgctcgacccgcgcacgctttaccagccgattgagccgggcgcttaccgcgacgaactgcgtcagtatctgatgcggg<br>tgccaacagaagacgaagaacagcagcttgaagccgtgcgccagttcaaacaggcccagcatttgcgtatcgcagccggggatatttccggggca<br>ttgccggtgatgaaagtcagtgaccatttaacctaccttgccgaggccattctcgatgtcgtggtgcagcatgcgtgggaacaaatggtcgtaaa<br>atacgggcagcccgcgcatcttcagcaccgtgaggggcgcggttttgccgtggtcggttacgggagcctggttatagct<br>cagatctggatctggtcttcctgctcgattgcgcgccggaggtgatgacggacggcgaacgcagcatcgacggacgtcgtcagttttatcttcggctg<br>gcgcaggcattatgcacttattcagcaccccggacatcgcaggcattctttacgaggttgatccgcgtctgcgaccttccggcgcatccggcatg<br>ctggtcagtaccattgaaggtttgcagattatcaggccaatgaagcctggacgtgggagcatcaggcgctggttcgcgcgcgtggtttacggg<br>atccgcaactgacacagcaatttaacgccacgcgtcgcgacattctttgccgccagcgcgatggcgacggcctgcgtaaggaggtccgtgaaat<br>gcgcgagaaaatgtatgcccatctggggagtaaaaaagcccacgagtttgatctgaaagccgatccgggtggcatcacggatattgaattcattg |

TABLE H-continued

| SEQ ID NO: | Sequence |
|---|---|
| | acaatacctggttctgcgtttcgcgcatgatgagccgaagctgacgcgctggtctgataacgtgcggattttttgaactgatggcacgatatgaca<br>tcatgccggaagaggaagagcgccatctgacgcaggcttatgtgacgctgcgcgatgaaattcatcatctggcgttgcaggaacacagcgggaaa<br>gtggccgcggacagctttgctactgagcgcgcgcagatccgtgccagctgggcaaagtggctcggctgagggttttattcggctaacaggcgct<br>tgtgatattatccggcgcattgtatttacccgatttgatttatctgttttggagtcttgggatgaaagtgactttgcctgattttcaccgcgcag<br>gtgtgctggttgtcggtgacgtaatgttagaccgttactggtatggcccgaccaatcgtatttctccggaagctccggtgccggtggtgaagctc<br>agtaccattgaagagcggcctggcggtgcagctaacgtggcgatgaacattcatctctgggcgcctcttcctgtctgatcggcctgaccggcgt<br>agacgacgctgcgcgtgccctcagtgagcgtctggcagaagtgattagttaactgcgatttcgtcgcactatccacacatcctaccatcaccaaa<br>ctgcgaattttgtcccgtaaccagcaactgatccgcctcgactttgaggaaggttttgaaggcgttgatctcgagccgatgctgaccaaaataga |
| 225 | atgagcatcacggcgttatcagcatcatttcctgaggggaatatcgccagccgcttgtcgagcaacatccttcactgttttataccgtattgaac<br>aatcttcggtggcgatttcgctgaccgatccgcaggcgcgcatttgttatgccaatccggcattctgccgccagacgggttttgcacttgagaca<br>cttttgggcgagaaccaccgtctgctggtacagtagcgcctctcaaaaatagataaacggctcatgtacgtgggccgtttattttttctacccat<br>aatcgggaaccggtgttataatgccgcgccctcatattgtggggatttcttaatgacctatcctgggcctaaagttgtagttgacattagcggag<br>cactaacccgtctctgaagctctcggtgaacattgttgcgaggcaggatgcgagctggttgtgttttgacattaccgataatgtgccgcgtgaac<br>gggtgcgttatgcccgcccggaagcggcgttttccgtccggggaatggcatggagctgcgccttatccagacgctgatcgcccatcatcgcggt<br>tctttagatctctcggtccgccctgatggcggcaccttgctgacgttacgcctgccggtacagcaggttatcaccggaggcttaaaatga |
| 226 | tgtttcgtctcgaggccgggcaactgagcggcccgttaaaccgacctgggctggcatctgttgttgtgcgaacaaattcgcctgccgcaaccct<br>tgccgaaagccgaagccttaacgcgggtgcgtcagcaactgattgcccggcaacaggaatcattatcagcgcagtggctgcaacaactgatcaa<br>cgcctgagcctgttctccttcttgttgatgcagacgggttaatgcccgttttgcacgaaaaatgcacataaattgcctgcgttgccttataacag<br>cgcagggaaatcctgcctccggccttgtgccacaccgcgctttgcctggtttgtggtaaaaactggcccgctttgcatcctgatgataaaacacc<br>ccgtttcagatcaaccctttgggcagataagcccgcaaaggcctgcaaattgcacggttattccgggtgagtatatgtgtgatttgggttcaggc<br>attgcgcaataaaggggagaaagacatgagcatcacggcgttatcagcatcatttcctgaggggaatatcgccagccgcttgtcgctgcaacatc<br>cttcactgttttataccgtgcttgaacaatcttcggtggcgatttcgctgaccgatccgcaggcgcgcatttgttatgccaatccggcattctgc<br>cgccagacgggttttgcacttgagacacttttgggcgagaaccaccgtctgctggtacagtagcgcctctcaaaaatagataaacggctcatgta<br>cgtgggccgtttattttttctacccataatcgggaaccggtgttataatgccgcgccctcatattgtggggatttcttaatgacctatcctgggt<br>cctaaagttgtagttgacattagcggagcactaaccctgtctctgaagctctcggtgaacattgttgcgaggcaggatgcgagctggttgtgtttt<br>gacattaccgataatgtgccgcgtgaacgggtgcgttatgcccgcccggaagcggcgttttccctgtccggggaatggcatggagctgcgccttat<br>ccagacgctgatcgcccatcatcgcggttctttagatctctcggtccgccctgatggcggcaccttgctgacgttacgcctgccggtacagcagg<br>ttatcaccggaggcttaaaatgacccagttacctaccgcgggcccggttatccggcgctttgatatgtctgcccagtttacggcgctttatcgca<br>tcagcgtggcgctggctcaggaaagcaacaccgggcgcgcactggccggcgatcctcgaagtgcttcacgatcatgcatttatgcaatacgacatg<br>gtgtgtctgtttgataaaacgcaatgcactcttttgtggaatccctgcatggcatcgacggcgaaaggaaaaaagagacccgccatgtccgtta<br>ccgcatggggaaggcgtgatcggcgcggtgatgagccagcgtcaggcgctggtgttaccgcgcatttagacgatcagcgttttctcgaccgcc<br>tgaatatttacgattacagcctgccgttgattggcgtgccgatcccggtgcggataatcagccatcgggcgtgctggtggcacagccgatgcg<br>ttgcacgaagaccggctgactgccagtacgcggttttttagaaatggtc |
| 227 | atggcgctcaaacagttaatccgtctgtgtgccgcctcgccgatggtagcgacacaacttgcacgtcatccctttattgctcgatgaactgctcga<br>cccgcgcacgctttaccagccgattgagccgggcgcttaccgcgacgaactgcgtcagtatctgatgcgggtgccaacagaagacgaagaacagc<br>agcttgaagccgtgcgccagttcaaacaggccagcattttgcgtatcgcagccggggatatttccggggcatgcccgtgatgaaagtcagtgac<br>catttaacctaccttgccgaggccattctcgatgtcgtggtgcagcatgcgtgggaacaaatggtcgtaaaatacgggcagcccgcgcatcttca<br>gcaccgtgaggggcgcggttttgccgtggtcggtacgggaaactcggtggctgggagctgggtatagctcagatctggatctggtcttcagct<br>cgattgcgcgccggaggtgatgacgacggcgaacgcagcatcgacggacgtcagttttatcttcggctggcgcagccgcattatgcacttattca<br>gcacccggacatcgtcaggcatctttttacgaggttgatccgcgtctgcgaccttccggcgcatccggcatgctggtcagtaccattgaagcgttt<br>gcagattatcaggccaatgaagcctggacgtgggagcatcaggcgctggttcgcgcgcgcgtggtttacgggggatccgcaactgacacagcaatt<br>taacgccacgcgtcgcgacattctttgccgccagcgcgatggcgacggcctgcgtaaggaggtccgtgaaatgcgcgagaaaatgtatgcccatc<br>tggggagtaaaaaagcccacgagtttgatctgaaagccgatcccggtggcatcacggatattgaattcattgacaatacctggttctgcgtttcg<br>cgcatcatgagccgaagctgacgcgctggtctgataacgtgcggattttttgtactgatggcacgatatgacatcatgcggaagaggaagcgcgcc<br>atctgacgcaggcttatgtgacgctgcgcgatgaaattcatcatctggcgttgcacgaacacagcgggaaagtggccgcggacagctttgctact<br>gagcgcgcgcagatccgtgccagctgggcaaagtggctcggctga |
| 228 | cggtactggaacagaaatcggcggatgcgcaggaaatttgttatgacacggcctgtctgaagtgcaagttagtgcttacttcctggctggcaacc<br>tcaggctggacgccgtttattgatgataaatctgcgaagaaactggacgcttccttcaaacgttttgctgacatcatgctcggtcgtaccgcagc<br>ggatctgaaagaagcctttgcgcagccactgacggaagaaggttatcgcgatcagctggcgcgcctgaaacgccagatcattaccttccatttgc<br>ttgccggtgcttaccctgaaaaagacgtcgatgcgtatattgccggctgggtggacctgcaacaggccatcgttcagcagcaacacgcctgggag<br>gattcggcccgttctcacgcggttgatgatggatgctttctggttacgggcaacctcgttaactgactgactagcctgggcaaactgcccgggctt<br>ttttttgcaaggaatctgatttcatggcgctcaaacagttaatccgtctgtgtgccgcctcgccgatggtagcgacacaacttgcacgtcatcct<br>ttattgctcgatgaactgctcgaccccgcgcacgctttaccagccgattgagccgggcgcttaccgcgacgaactgcgtcagtatctgatgcgggt<br>gccaacagaagacgaagaacagcagcttgaagccgtgcgccagttcaaacaggccagcatttgcgtatcgcagccggggatatttccggggcat<br>gccgtgatgaaagtcagtgaccatttaacctaccttgccgaggccattctcgatgtcgtggtgcagaatgcgtgggaacaaatggtcgtaaaa<br>tacgggcagcccgcgcatcttcagcaccgtgaggggcgcggttttgccgtggtcggtacggggaaactcggtggctgggagctgggtatagctc<br>agatctggatctggtcttcctgctcgattgcgcgccggaggtgatgacgacggcgaacgcagcatcgacggacgtcagttttatcttcggaggcgc<br>agccgcattatgcacttattcagcacccggacatcgtcaggcatctttttacgaggttgatccgcgtctgcgaccttccggcgcatccggcatgctg<br>gtcagtaccattgaagcgtttgcagattatcaggccaatgaagcctggacgtgggagcatcaggcgctgtgtcgcgcgcgtggtttacgggga<br>tccgcaactgacacagcaatttaacgccacgcgtagcgacattctttgccgccagcgcgatggcgacggcctgcgtaaggaggtccgtgaaatgc<br>gcgagaaaatgtatgcccatctggggagtaaaaaagcccacgagtttgatctgaaagccgatcccggtggcatcacggatattgaattcattgca<br>caatacctggttctgcgtttcgcgcatgatgagccgaagctgacgcgctggtctgataacgtgcggattttttgaactgatggcacgatatgacat<br>catgccggaagaggaaggcgccatctgacgcaggcttatgtgacgctgcgcgatgaaattcatcatctggcgttgcaggaacacagcgggaaagt<br>ggccgcggacagctttgctactgagcgcgcgcagatccgtgccagctgggcaaagtggctcggctgagggttttattcggctaacaggcgcttg<br>tgatattatccggcgcattgtatttacccgatttgatttatctgttttggagtcttgggatgaaagtgactttgcctgattttcaccgcgcaggt<br>gtgctggttgtcggtgacgtaatgttagaccgttactggtatggcccgaccaatcgtatttctccggaagctccggtgccggtggtgaagctcag<br>taccattgaagagcggcctggcggtgcagctaacgtggcgatgaacattcatctctggacgcctcttcctgtctgatcggcctgaccggcgtaga<br>cgacgctgcgcgtgccctcagtgagcgtctggcagaagtgaaagttaactgcgatttcgtcgcactatccacacatcctaccatcaccaaactgc<br>gaattttgtcccgtaaccagcaactgatccgcctcgactttgaggaaggttttgaaggcgttgatctcgagccgatgctgaccaaaataga |
| 229 | atgagcatcacggcgttatcagctgaatatcactgactcacaagctacctatgtcgaagaattaactaaaaaactgcaagatgcaggcattcgcg<br>ttaaagcgacttgagaaatgagaagattggctttaaaattcgcgaacacacgctacgccgtgtcctatatgttagtttgtggcgataaagaggt<br>cgaagcaggcaaagttgctgttcgtactcgtcgcgggcaaagacttaggaagcatggatgttagcgaagtcgttgacaaactgctggcggaaatcc |

US 11,565,979 B2
251                                                                                                          252
TABLE H-continued

| SEQ ID NO: | Sequence |
|---|---|
| | gcagcagaagtcatcatcaactggaggaataaagtattaaaggcggaaaacgagttcaaccggcgcgtcctaatcgcattaacaaagagattcgc gcgcaagaagttcgcctcaccggcgtcgatggcgagcagattggtattgcagtctgaatgaagctcttgaaaaagctgaggaagcgggcgtcgat ttagtagaaatcagtccgaatgccgagccgccagtttgtcgaatctcttagatctctcggtccgccctgatggcggccttgctgacgttacg cctgccggtacagcaggttatcaccggaggcttaaaatga |
| 230 | tgtttcgtcgaagccgggcaactgagcagcccgttgaaaccgaactgggctggcatctgttgttgtgcgaacaaattcgcctgcgcaacccttg ccgaaagccgaggccttaacgcgggtgcgtcagcaactgattgcccggcaacagaatcattatcagcgccagtggctgcaacaactgatcaacgc ctgagcctgttctccttcttgttggtgcagacgggttaatgcccgttttgcacgaaaaatgcacataaactgccttcgctgccttataacagcgc atggaaatcctgcctcctgccttgtgccacgccgcgctttgcctggttttgtggtaaaaactggcccgctttgcatcctgatgtttaaaacacccc gttcagatcaacctttgggcagataagcccgcgaaaggcctgcaaattgcacggttattccgggtgagtatatatgtgatttgggttccggcatt gcgcaataaaggggagaaagacatgagcatcacgcgttatcagctgaatatcactgactcacaagctacctatgtcgaagaattaactaaaaaa ctgcaggatgcaggcattcgcgttaaagcgacttgagaaatgagaagattggctttaaaattcgcgaacacacgctacgccgtgttcttatat gttagtttgtggcgataaagaggtcgaagcaggcaaagtgctgttcgtactcgtcgcggcaaagacttaggaagcatggatgttagcgaagtcgt tgacaaactgctggcggagatccgcagcagaagtcatcatcaactggaggaataaagtattaaaggcggaaaacgagttcaaccggcgcgtccta atcgcattaacaaagagattcgcgcgcaagaagttcgcctcaccggcgtcgatggcgagcagattggtattgtcagtctgaatgaagacttgaaa aagctgaggaagcgggcgtcgatttagtagaaatcagtccgaatgccgagccgccagtttgtcgaatctcttagatctctcggtccgcctgat ggcggccttgctgacgttacgcctgccggtacagcaggttatcaccggaggcttaaaatgacccagttacctaccgcgggcccggttatccgg cgcttgatatgtctgcccagtttacggcgctttatcgcatcagcgtggcgctgagtcaggagagcaataccgcgcgcactggcggcgatcct cgaagtgcttcacgatcatgcatttatgcaatacgcatggtgtctgttcgataaaagaacgcaatgcactgtttgtgcaatccctgcatggca tcgacggcgaaaggaaaaaagaaacccgcatgtccgttaccgcatggggaaggcgtgatcggcgcggtgatgagccagcgtcaggcgtggtgt taccgcgcatttcagacgatcagcgttttctcgaccgcctgaatatttacgattacagcctgccgctgattggtgtgccgatcccggtgcggat aatcagcctgcgggtgtgctggtggcacagccgatggcgttgcacgaagaccggctggctgccactacgcgcttttagaaatggtc |
| 231 | atgaccctgaatatgatgatggatgccggcggacatcatcgcgacaaacaatattaataccggcaaccacaccggcaatttacgagactgcgcag gcatcctttacccgtcaatttctgtcaaataaagtaaaagaggcagtctacttgaattaccccggctggttgagcgtttgttgaaaaaagtaa ctgaaaatccgtagaatagcgccactctgatggttaattaacctattcaattaagaattatctggatgaatgtgccattaaatgcgcagcataat ggtgcgttgtgcgggaaaactgctttttttgaaagggttggtcagtagggaaacaactcacttcacaccccgaaggggaagttgcctgaccct acgattcccgctatttcattcactgaccggaggttcaaaatga |
| 232 | accggatacgagagaaaagtgtctacatttggttcggttgatattgaccggcgcatccgccagcccgcccagtttctggggatctgtttggcgat tttgcgggtcttgccggtgcggtgccgaaaaaaataccaatatttgccataacacacgctcctgttgaaaaagagatcccgccgggaaatgcgg tgaacgtgtctgatattgcgaagagtgtgccagttttggtcgcgggcaaaacctgcaccagtttggttattaatgcaccagtctggcgctttttt tcgccgagtttctcctcgctaatgcccgcaggcgcggctttggcgctgatagcgcgctgaataccgatctggatcaaggttttgtcgggttatc agccaaaaggtgcactctttgcatggttatacgtgcctgacatgttgtccgggcgacaaacggcctggtggcacaaattgtcagaactacgacac gactaactgaccgcaggagtgtgcgatgaccctgaatatgatggatgccggcggacctcatcgcgacaaacaatattaataccggcaaccac accggcaatttacgagactgcgcaggcatcctttctcccgtcaatttctgtcaaataaagtaaaagaggcagtctacttgaattaccccggctg gttgagcgtttgttgaaaaaagtaactgaaaatccgtagaatagcgccactctgatggttaattaacctattcaattaagaattatctggatg aatgtgccattaaatgcgcagattaatggtgcgttgtgcgggaaaactgctttttttgaaagggttggtcagtagcggaaacaactcacttcaca ccccgaaggggaagttgcctgaccctacgattcccgctatttcattcactgaccggaggttcaaaatgacccagcgaaccgagtcgggtaatac cgtctggcgcttcgatttgtcccagcagttcactgcgatgcagcgcataagcgtggtactcagccgggcgaccgaggtcgatcagacgctccagc aagtgctgtgcgtattgcacaatgacgccttttgcagcacggcatgatctgtctgtacgacagccagcaggcgattttgaatattgaagcgttg caggaagccgatcagcagttaatccccggcagctcgcaaatccgctatcgtccgggcgaagggctggtcgggacggtgctttcgcagggccaatc attagtgcttgcgcgcgttgctgacgatcagcgcttcttgaccggctcgggttgtatgattacaacctgccgtttatcgccgtgccgctgatag ggccagatgcgcagacttccggtggctgacggcacaacccatggcgcgttacgaagagcgattacccgcctgcacccgctttctggaaacggtc |
| 233 | atgaccctgaatatgatgatggatgccggccgtcctgtaataataaccggacaattcggactgattaaaaaagcgcccttgtggcgcttttttta tattcccgcctccatttaaaataaaaaatccaatcggatttcactatttaaactggccattatctaagatgaatccgatggaagctcgctgttttt aacacgcgttttttaacctttattgaaagtcggtgcttcttgagcgaacgatcaaatttaagtggattcccatcaaaaaaatattctcaacct aaaaaaagtttgtgtaatacttgtaacgctacatggagattaactcaatctagagggtattaataatgaatcgtactaaactggactgggcgcaac tcacttcacaccccgaaggggaagttgcctgaccctacgattcccgctatttcattcactgaccggaggttcaaaatga |
| 234 | accggatacgagagaaaagtgtctacatcggttcggttgatattgaccggcgcatccgccagcccgcccagtttctggtggatctgtttggcgat tttgcgggtcttgccggtgcggtgccgaaaaaaataccaatatttgccataacacacgctcctgttgaaaaagagatcccgccgggaaatgcggt gaacgtgtctgatattgcgaagagtgtgccagttttggtcgcgggcaaaacctgcaccagtttggttattaatgcaccagtctggcgctttttt cgccgagtttctcctcgctaatgcccgcaggcgcggctttggcgctgatagcgcgctgaataccgatctggatcaaggttttgtcgggttatca gccaaaaggtgcactctttgcatggttatacgtgcctgacatgttgtccgggcgacaaacggcctggtggcacaaattgtcagaactacgacacg actaactgaccgcaggagtgtgcgatgaccctgaatatgatgatggatgccggccgtcctgtaataataaccgcacaattcggactgattaaaaa agcgcccttgtggcgcttttttatattcccgcctccatttaaaataaaaaatccaatcggatttcactatttaaactggccattatctaagatg aatccgatggaagctcgctgttttaacacgcgttttttaaccttttattgaaagtcggtgcttcttgagcgaacgatcaaatttaagtggattc ccatcaaaaaaatattctcaacctaaaaaaagtttgtgtaatacttgtaacgctacatgtgagattaactcaatctagagggtattaataatgaatc gtactaaactggtactgggcgcaactcacttcacaccccgaaggggaagttgcctgaccctacgattcccgctatttcattcactgaccggagg ttcaaaatgacccagcgaaccgagtcgggtaataccgtctggcgcttcgatttgtcccagcagttcactgcgatgcagcgcataagcgtggtact cagccgggcgaccgaggtcgatcagacgctccagcaagtgctgtgcgtattgcacaatgacgccttttgcagcacggcatgatctgtctgtacg acagccagcaggcgattttgaattgaagcgttgcaggaagccgatcagcagttaatccccggcagctcgcaaatccgctatcgtccgggcgaa gggctggtcgggacggtgtttcgcagggcaatcattagtgctgcgcgcgttgctgacgatcagcgcttcttgaccggctcgggttgtatgatt acaacctgccgtttatcgccgtgccgctgatagggccagatgcgcagacttccggtggctgacggcacaacccatggcgcgttacgaagagcga ttacccgcctgcacccgctttctggaaacggtc |
| 235 | atgaccctgaatatgatgatggatgccggccgtcctgtaataataaccggacaattcggactgattaaaaaagcgcccttgtggcgcatttttttt attcccgcctccatttaaaataaaaaatccaatcggatttcactatttaaactggccattatctaagatgaatccgatggaagctcgctgtttta acacgcgttttttaaccttttattgaaagtcggtgcttcttgagcgaacgatcaaatttaagtggattcccatcaaaaaaatattctcaacctaa aaaaagtttgtgtaatacttgtaacgctacatggagattaactcaatctagagggtattaataatgaatcgtactaaactggtactgggcgcaact cacttcacaccccgaaggggaagttgcctgaccctacgattcccgctatttcattcactgaccggaggttcaaaatga |
| 236 | accggatacgagagaaaagtgtctacatcggttcggttgatattgaccggcgcatccgccagcccgcccagtttctggtggatctgtttggcgat tttgcgggtcttgccggtgtcggtgccgaaaaaaataccaatatttgccataacacacgctcctgttgaaaaagagatcccgccgggaaatgcgg tgaacgtgtctgatattgcgaagagtgtgccagttttggtcgcgggcaaaacctgcaccagtttggttattaatgcaccagtctggcgcttttttt |

TABLE H-continued

| SEQ ID NO: | Sequence |
|---|---|
| | tcgccgagtttctcctcgctaatgcccgccaggcgcggctttggcgctgatagcgcgctgaataccgatctggatcaaggttttgtcgggttatc<br>agccaaaaggtgcactctttgcatggttatacgtgcctgacatgttgtccgggcgacaaacggcctggtggcacaaattgtcagaactacgacac<br>gactaactgaccgcaggagtgtgcgatgaccctgaatatgatgatggatgccggccgtcctgtaataataaccggacaattcggactgattaaaa<br>aagcgcccttgtggcgcttttttatattcccgcctccatttaaaataaaaaatccaatcggatttcactatttaaactggccattatctaagat<br>gaatccgatggaagctcgctgttttaacacgcgttttttaaccttttattgaaagtcggtgcttctttgagcgaacgatcaaatttaagtggatt<br>cccatcaaaaaaatattctcaacctaaaaaagtttgtgtaatacttgtaacgctacatggagattaactcaatctagagggtattaataatgaat<br>cgtactaaactggtactgggcgcaactcacttcacaccccgaaggggaagttgcctgaccctacgattcccgctatttcattcactgaccggag<br>gttcaaaatgacccagcgaaccgagtcgggtaataccgtctggcgatcgatttgtcccagcagttcactgcgatgcagcgcataagcgtggtact<br>cagccgggcgaccgaggtcgatcagacgctccagcaagtgctgtgcgtattgcacaatgacgccttttgcagcacggcgatgatctgtctgtacg<br>acagccagcaggcgattttgaatattgaagcgttgcaggaagccgatcagcagttaatccccggcagctcgcaaatccgctatcgtccgggcgaa<br>gggctggtcgggacggtgctttcgcagggccaatcattagtgctggcgcgcgttgctgacgatcagcgctttcttgaccggctcgggttgtatga<br>ttacaacctgccgtttatcgccgtgccgctgatagggccagatgcgcagacttcggtgtgctgacggcacaacccatggcgcgttacgaagagc<br>gattaccccgcctgcacccgctttctggaaacggtc |
| 237 | atggcactgaaacacctcatttccctgtgtgccgcgtcgccgatggttgccagtcagctggcgcgctaccccgatcctgcttgatgaattgctcga<br>cccgaatacgctctatcaaccgacggcgatgaatgcctatcgcgatgagctgcgccaatacctgctgcgcgtgccggaagatgatgaagagcaac<br>agcttgaggcgctgcggcagtttaagcaggcgcagttgctgcgcgtggcggcggcggatattgccggtacgttgccagtaatgaaagtgagcgat<br>cacttaacctggctggccgaagcgattattgatgcggtggtgcagcaagcctggggggcagatggtggcgcgttatggccagccaacgcatctgca<br>cgatcgcgaagggcgggttttgcggtggtcggttatggcaagctgggcggctgggagctgggttacagctccgatctggatctggtattcctgca<br>cgactgcccgatggatgtgatgaccgatggcgagcgtgaaatcgatggtcgccagttctatttgcgtctcgcgcagcgcgtgatgcacctgttta<br>gcacgcgcacgtcgtccggcatcctttatgaagttgatgcgcgtctgcgtccatctggcgctgcggggatgctggtcactactacggaatcgttc<br>gccgattaccagcaaaacgaagcctggacgtgggaacatcaggcgcttggccccgtgcgcgtggtgtacggcgatccgcaactgaccgccgaatt<br>tgacgccattcgccgcgatattctgatgacgcctcgcgacggcgcaacgctgcaaaccgacgtgcgagaaatgcgcgagaaatgcgtgcccatc<br>ttggcaacaagcataaagaccgcttcgatctgaaagccgatgaaggcggtatcaccgacatcgagtttatcgcccaatatctggtgctgcgcttt<br>gcccatgacaagccgaaactgacgcgctggtcggataatgtgcgcattctcgaagggctggcgcaaaacggcatcatggaggagcaggaagcgca<br>ggcattgacgctggcgtacaccacattgcgtgatgagctgcaccacctggcgctgcaagagttgccggacatgtggcgctctcctgttttgtcg<br>ccgagcgtgcgcttattaaaaccagctgggacaagtggctggtggaa |
| 238 | gcgcaaagcgagtgctcacttacgtgatctgttgacacaatctgaagcgaccataacttctgccgtttcagcgaatacggcggtgtgagcgcac<br>aatcagccctggcgaagctggtgctcaccgagtggctagtgacgcagggctggcgaaccttccttgatgaaaaagcgcaggccaaattcgccgac<br>tccttaaacgctttgctgacatccatctgtcacgcagcgccgccgagctgaaaaaaggcctttgcccaaccgctggagcgacagctatcgccgacc<br>agttgccgcgcctggcgcgtgatatcgactgcgcgttactgctggccgggcattacgatcgcgcgcgcgtgaatggctggaaaactggcag<br>gggcttcagcacgccattgaaacgcgccagagagtcgaaatcgaacatttccgtaataccgcgattacccaggagccgttctggttgcacagcgg<br>aaaacgttaacgaaaggatatttcgcatggcactgaaacacctcatttccctgtgtgccgcgtcgccgatggttgccagtcagctggcgcgctac<br>ccgatcctgcttgatgaattgctcgacccgaatacgctctatcaaccgacggcgatgaatgcctatcgcgatgagctgcgccaatacctgctgcg<br>cgtgccggaagatgatgaagagcaacagcttgaggcgctgcggcagtttaagcaggcgcagttgctgcgcgtggcggcggcggatattgccggta<br>cgttgccagtaatgaaagtgagcgatcacttaacctggctggccgaagcgattattgatgcggtggtgcagcaagcctggggggcagatggtggcg<br>cgttatggccagccaacgcatctgcacgatcgcgaagggcgcggttttgcggtggtcggttatggcaagctgggcggctgggagctgggttacag<br>ctccgatctggatctggtattcctgcacgactgcccgatggatgtgatgaccgatggcgagcgtgaaatcgatggtcgccagttctatttgcgtc<br>tcgcgcagcgcgtgatgcacctgtttagcacgcgcacgtcgtccggcatcctttatgaagttgatgcgcgtctgcgtccatctggcgctgcgggg<br>atgctggtcactactacggaatcgttcgccgattaccagcaaaacgaagcctgcacgtgggaacatcaggcgcttggccccgtgcgcgtggtgta<br>cggcgatccgcaactgaccgccgaatttgacgccattcgccgcgatattctgatgacgcctcgcgacggcgcaacgctgcaaaccgacgtgcgag<br>aaatgcgcgagaaatgcgtgcccatcttggcaacaagcataaagaccgcttcgatctgaaagccgatgaaggcggtatcaccgacatcgagttt<br>atcgcccaatatctggtgctgcgctttgcccatgacaaaccgaaactgacgcgctggtcggataatgtgcgcattctcgaagggctggcgcaaaa<br>cggcatcatggaggagcaggaagcgcaggcattgacgctggcgtacaccacattgcgtgatgagctgcaccacctggcgctgcaagagttgccgg<br>gacatgtggcgctctcctgttttgtcgccgagcgtgcgcttattaaaaccagctgggacaagtggctggtggaaccgtgcgccccggcgtaagtg<br>tggtatcatcgcgcgcaaatttttgtatctctcaggagacaggaatgaagtgacgctgccagagtttaagcaagccggtgtaatggtggtgggtg<br>atgtgatgctggatcgttactggtatggccaaccagccgtatctctccggaagcgccagtcccggttgtttaaagtcgataccattgaagagcgt<br>cctggcggcgcggcaaacgtggcgatgaatatcgcctcactgggcgccacggcgcgtctggttggcctgactggcattgacgatgcggcgcgcgc<br>gctgagcaaagcgctggccgatgttaacgttaaatgtgacttcgtttctgttccgacgcatcccaccatcactaagctgcgcgtgctgtcgcgta<br>accagcagctgattcgcctggactttgaagaggggttttgaaggagtcgatccgcaaccgatgcatcgaacgcatcagccaggcgcttggtaatat<br>tggcgcgctggtgctgtcggatt |
| 239 | atgtttaacgatctgattggcgatgatgaaacggattcgccggaagatgcgctttctgagagctggcgcgaattgtggcaggatgcgttgcagga<br>ggaggattccacgcccgtgctggcgcatctctcagaggacgatcgccgccgcgtggtggcgctgattgccgattttcgcaaagagttggataaac<br>gcaccattggccgcgaggcggcaggtactcgatcactaatgccgcatctgctcagcgatgtatgctcgcggcgacgatgcgccagtaccgctg<br>tcacgcctgacgccgctgctcaccggaattattacccgcaccacttacctgagctgctaagtgaattccccggcgcactgaaacacctcatttc<br>cctgtgtgccgcgtcgccgatggttgccagtcagctggcgcgctaccccgatcctgcttgatgaattgctcgacccgaatacgctctatcaaccga<br>cggcgatgaatgcctatcgcgatgagctgcgccaatacctgctgcgcgtgccggaagatgatgaagagcaacagcttgaggcgctgcggcagttt<br>aagcaggcgcagttgctgcgcgtggcggcggcggatattgccggtacgttgccagtaatgaaagtgagcgatcacttaacctggctggccgaagc<br>gattattgatgcggtggtgcagcaagcctggggggcagatggtggcgcgttatggccagccaacgcatctgcacgatcgcgaagggcgcggttttg<br>cggtggtcggttatggcaagctgggcggctgggagctgggttacagctccgatctggatctggtattcctgcacgactgcccgatggatgtgatg<br>accgatggcgagcgtgaaatcgatggtcgccagttctatttgcgtctcgcgcagcgcgtgatgcacctgtttagcacgcgcacgtcgtccggcat<br>cctttatgaagttgatgcgcgtctgcgtccatctggcgctgcggggatgctggtcactactacggaatcgttcgccgattaccagcaaaacgaag<br>cctgacgtgggaacatcaggcgcttggccccgtgcacgcgtgggtacggcgatccgcaactgaccgccgaatttgacgccattcgccgcgatattc<br>tgatgacgcctcgcgacggcgcaacgctgcaaaccgacgtgcgagaaatgcgcgagaaatgcgtgcccatcttggcaacaagcataaagaccgc<br>ttcgatctgaaagccgatgaaggcggtatcaccgacatcgagtttatcgcccaatatctggtgctgcgctttgcccatgacaagccgaaactgac<br>gcgctggtcggataatgtgcgcattctcgaagggctggcgcaaaacggcatcatggaggagcaggaagcgcaggcattgacgctggcgtacaccac<br>attgcgtgatgagctgcaccacctggcgctgcaagagttgccgggacatgtggcgctctcctgttttgtcgccgagcgtgcgcttattaaaacca<br>gctgggacaagtggctggtggaaccgtgcgccccggcgtaa |
| 240 | atgaccctgaatatgatgatggatgccggccgtcctgtaataataaccggacaattcggactgattaaaaaagcgcccttgtggcgcttttttta<br>tattcccgcctccatttaaaataaaaaatccaatcggatttcactatttaaactggccattatctaagatgaatccgatggaagctcgctgttta<br>acacgcgttttttaaccttttattgaaagtcggtgcttctttgagcgaacgatcaaatttaagtggattcccatcaaaaaaatattctcaaccta<br>aaaaagtttgtgtaatacttgtaacgctacatggagattaactcaatctagagggtattaataatgaatcgtactaaactggtactgggcgcaac<br>tcacttcacaccccgaaggggaagttgcctgaccctacgattcccgctatttcattcactgaccggaggttcaaaatga |

TABLE H-continued

| SEQ ID NO: | Sequence |
|---|---|
| 241 | accggatacgagagaaaagtgtctacatcgatcggttgatattgaccggcgcatccgccagcccgcccagtttctggtggatctgtttggcgatt<br>ttgcgggtcttgccggtgtcggtgccgaaaaaaataccaatatttgccataacacacgctcctgttgaaaaagagatcccgccgggaaatgcggt<br>gaacgtgtctgatattgcgaagagtgtgccagttttggtcgcgggcaaaacctgcaccagtttggttattaatgcaccagtctggcgcttttttt<br>cgccgagtttctcctcgctaatgcccgccaggcgcggcttggcgctgatagcgcgctgaataccgatctggatcaaggttttgtcgggttatca<br>gccaaaaggtgcactctttgcatggttatacgtgcctgacatgttgtccggccgacaaacggcctggtggcacaaattgtcagaactacgacacg<br>actaactgaccgcaggagtgtgcgatgaccctgaatatgatgatggatgccggccgtcctgtaataataaccggacaattcggactgattaaaa<br>agcgcccttgtggcgcttttttttatattcccgcctccatttaaaataaaaaatccaatcggatttcactatttaaactggccattatctaagatg<br>aatccgatggaagctcgctgttttaacacgcgttttttaacctttt attgaaagtcggtgcttctttgagcgaacgatcaaatttaagtggattc<br>ccatcaaaaaaatattctcaacctaaaaaagtttgtgtaatacttgtaacgctacatggagattaactcaatctagagggtattaataatgaatc<br>gtactaaactggtactgggcgcaactcacttcacaccccgaaggggcaagttgcctgaccctacgattcccgctatttcattcactgaccggagg<br>ttcaaaatgacccagcgaaccgagtcgggtaataccgtctggcgcttcgatttgtcccagcagttcactgcgatgcagcgcataagcgtggtact<br>cagccgggcgaccgaggtcgatcagacgctccagcaagtgctgtgcgtattgcacaatgacgccttttt gcagcacggcatgatctgtctgtacg<br>acagccagcagccgattttgaatattgaagcgttgcaggaagccgatcagcagttaatccccggcagctcgcaaatccgtatcgtccgggcgaag<br>ggctggtcgggacggtgctttcgcaggggccaatcattagtgctggcgcgcgttgctgacgatcagcgcttt cttgaccggctcgggttgtatgat<br>tacaacctgccgtttatcgccgtgccgctgataggcgcagatgcgcagactttcggtgtgctgacggcacaacccatggcgcgttacgaagagcg<br>attacccgcctgcacccgctttctggaaacggtc |
| 242 | gcgcaaagcgagtgctcacttacgtgatctgttgacacaatctgaagcgaccataacttctgccgtttcagcgaatacgcggtgtggagcgcac<br>aatcagccctggcgaagctggtgctcaccgagtggctagtgacgcagggctggcgaaccttccttgatgaaaaagcgcaggccaaattcgccgac<br>tcctttaaaacgctttgctgacatccatctgtcacgcagcgccgccgagctgaaaaaagccttt gcccaaccgctgggcgacagctatcgcgacca<br>gttgccgcgcctggcgcgtgatatcgactgcgcgttactgctggccgggcattacgatcgcgcgcgcgccgtggaatggctggaaaactggcagg<br>ggcttcagcacgccattgaaacgcgccagagagtcgaaataccgcgattacccaggagccgttctggttgcacagcgga<br>aaacgttaacgaaaggatattctgcatgttttaacgatctgattggcgatgatgaaacggattcgccggaagatgcgctttctgagagctggccg<br>aattgtggcaggatgcgttgcaggaggaggattccacgcccgtgcgaggcgcatctctcaggacgatcgccgccgcgtggtggcgctgattgccg<br>atttttcgcaaagagttggataaacgcaccattggcccgcgagggcggcaggtactcgatcacttaatgccgcatctgctcagcgatgtatgacgc<br>gcgacgatgcgcagtaccgcgtgtcacgcctgacgccgctgacaccggaattattacccgcaccacttaccttgagctgctaagtgaatttcccg<br>gcgcactgaaacacctcatttccctgtgtgccgcgtcgccgatggttgccagtcagctggccgctcaccgatcctgcttgatgaattgctcgac<br>ccgaatacgctctatcaaccgacggcgatgaatgcctatcgcgatgagctgcgccaatacctgctgcgcgtgccggaagatgatgaagagcaaca<br>gcttgaggcgctgcggcagtttaagcaggcgcagttgctgcgcgtcgcggcggcggatattgccggtacgttgccagtaatgaaagtgagcgatc<br>acttaacctggctggcggaagcgattattgatgcggtggtgcagcaagcctgggggcagatggtggcgcgttatggccagccaacgcatctgcac<br>gatcgcgaagggcgcggttttcgcggtggtcggttatggcaagctgggcggctgggagctgggttacagctcccgatctggatctggtattcctgca<br>cgactgcccgatggatgtgatgaccgatggcgagcgtgaaatcgatggtcgccagtctatttgcgtctcgcgcagcgcgtgatgcacctgttta<br>gcacgcgcacgtcgccggcatcctttatgaagttgatgcgcgctgcgtccatctggcgctgcggggatgctggtcactactacggaatcgttcgc<br>cgattaccagcaaaacgaagcctggacgtgggaacatcaggcgctggcccgtgcgcgcgggtgtacggcgatccgcaactgaccgccgaatttga<br>cgccattcgccgcgatattctgatgacgcctcgcgacgggcgcaaccgtcgcgagaaatgcgcgagaaatgcgtgcccatcttg<br>gcaacaagcataaagaccgcttcgatctgaaagccgatgaaggcggtatcaccgacatcgagtttatcgcccaatatctggtgctgcgctttgcc<br>catgacaagccgaaactgacgcgctggtcggataatgtgcgcattctcgaagggctggcgcaaaacggcatcatggaggagcaggaagcgcaggc<br>attgacgctggcgtacaccacattgcgtgatgagctgcaccacctggcgctgcaagagttgccgggacatgtggcgctctcctgttttgtcgccg<br>agcgtgcgcttattaaaaccagctgggacaaagcggctggtggaaccgtgcgccccggcgtaagtggttgctatcatcgcgcgcaaattttgtatctc<br>tcaggagacaggaatgaaagtgacgctgccagagtttaagcaagccggtgtaatggtggtgggtgatgtgatgctggatcgttactggtatgcc<br>caaccagccgtatctctccggaagcgccagtcccggttgttaaagtcgataccattgaagagcgtcctggcgccgcggcaaacgtggcgatgaat<br>atcgcctcactgggcgccacggcgcgtctgttggcctgactggcattgacgatgcggcgcgcgctgagcaaagcgctggccgatgttaacgt<br>taaatgtgacttcgtttctgttccgacgcatcccaccatcactaagctgcgcgtgctgtcgcgtaaccagcagctgattcgcctggactttgaag<br>agggttttgaaggagtcgatccgcaaccgatgcatgaacgcatcagccaggcgcttggtaatattggcgcgctggtgctgtcggatt |
| 243 | atgtttaacgatctgattggcgatgatgaaacggattcgccggaagatgcgctttctgagagctggcgcgaattgtggcaggatgcgttgcagga<br>ggaggattccacgcccgtgctggcgcatctctcagaggacgatcgccgccgcgtggtggcgctgattgccgatttttcgcaaagagttggataaac<br>gcaccattggcccgcgagggcggcaggtactcgatcacttaatgccgcatctgctcagcgatgtatgctcgcgcgacgatgcgccagtaccgctg<br>cacgcctgacgccgctgctcaccggaattattacccgcaccacttaccttgagctgctaagtgaatttcccggcgcactgattacacctcatttc<br>cctgtgtgccgcgtcgccgatggttgccagtcagctggcgcgctacccgatcctgcttgatgaattgctcgacccgaatacgctctatcaaccga<br>cggcgatgaatgcctatcggatgagctgcgccaatacctgctgcgcgtgccggaagatgatgaagagcaacagcttgaggcgctgcggcagttta<br>agcaggcgcagttgctgcgcgtggcggcggcggatattgccggtacgttgccagtaatgaaagtgagcgatcacttaacctggctggcggaagcg<br>attattgatgcggtggtgcagcaagcctggggcagatggtggcgcgttatggccagccaacgcatctgacgatcgcgaagggcgcggttttgcgg<br>ggtcggttatggcaagctgggcggctgggagctgggtacagctccgatctggatctggtattcctgcacgactgcccgatggatgtgatgaccga<br>tggcgagcgtgaaatcgatggtcgccagtctatttgcgtctcgcgcagcgcgtgatgcacctgtttagcacgcgacgtcgtccggcatcctttat<br>gaagttgatgcgcgctgtcgtccatctggcgctgcggggatgctggtcactactacggaatcgttcgccgattaccagcaaaacgaagcctggac<br>gtgggaacatcaggcgctggcccgtgcgcgcgtgtacggcgatccgcaactgaccgccgaatttgacgccattcgccgcgatattctgatga<br>cgcctcgcgacggcgcaacgctgcaaaccgacgtgcgagaaatgcgcgagaaatgcgtgcccatcttggcaacaagcataaagaccgcttcgat<br>ctgaaagccgatgaaggcggtatcaccgacatcgagtttatcgcccaatatctggtgctgcgctttgcccatgacaagccgaaactgacgcgctg<br>gtcggataatgtgcgcattctcgaagggctggcgcaaaacggcatcatggaggagcaggaagcgcaggcattgacgctggcgtacaccacattgc<br>gtgatgagctgcaccacctggcgctgcaagagttgccgggacatgtggcgctctcctgttttgtcgccgagcgtgcgcttattaaaaccagctggga<br>caagtggctggtggaaccgtgcgccccggcgtaa |
| 244 | gcgcaaagcgagtgctcacttacgtgatctgttgacacaatctgaagcgaccataacttctgccgtttcagcgaatacgcggtgtggagcgcac<br>aatcagccctggcgaagctggtgctcaccgagtggctagtgacgcagggctggcgaaccttccttgatgaaaaagcgcaggccaaattcgccgac<br>tcctttaaaacgctttgctgacatccatctgtcacgcagcgccgccgagctgaaaaaagccttt gcccaaccgctgggcgacagctatcgcgacca<br>gttgccgcgcctggcgcgtgatatcgactgcgcgttactgctggccgggcattacgatcgcgcgcgcgccgtggaatggctggaaaactggcagg<br>ggcttcagcacgccattgaaacgcgccagagagtcgaaataccgcgattacccaggagccgttctggttgcacagcgga<br>aaacgttaacgaaaggatattctgcatgttttaacgatctgattggcgatgatgaaacggattcgccggaagatgcgctttctgagagctggcgc<br>aattgtggcaggatgcgttgcaggaggaggattccacgcccgtgctggcgcatctctcagaggacgatcgccgccgcgtggtggcgctgattgcc<br>gatttttcgcaaagagttggataaacgcaccattggcccgcgagggcggaaggtactcgatcacttaatgccgcatctgctcagcgatgtatgctc<br>gcgcgacgatgcgccagtaccgctgcacgcctgacgccgctgctcaccggaattattacccgcaccacttaccttgagctgctaagtgaatttc<br>ccggcgcactgaaacacctcatttccctgtgtgccgcgtcgccgatggttgccagtcagctggcgcgctacccgatcctgcttgatgaattgctc<br>gacccgaatacgctctatcaaccgacggcgatgaatgcctatcgcgatgagctgcgccaatacctgctgcgcgtgccggaagatgatgaagagca<br>acagcttgaggcgctgcggcagtttaagcaggcgcagttgctgcgcgtggcggcggcggatattgccggtacgttgccagtaatgaaagtgagcg<br>atcacttaacctggctggcggaagcgattattgatgcggtgggcagcaagcctgggggcagatggtggcgcgttatggccagccaacgcatagca<br>cgatcgcgaagggcgcggttttgcggtggtcggttatggcaagctgggcggctgggagctgggttacagctcccgatctggatctggtattcctga |

TABLE H-continued

| SEQ ID NO: | Sequence |
|---|---|
| | cgactgcccgatggatgtgatgaccgatggcgagcgtgaaatcgatggtcgccagttctatttgcgtctcgcgcagcgcgtgatgcacctgttta
gcacgcgcacgtcgtccggcatcctttatgaagttgatgcgcgtctgcgtccatctggcgctgcggggatgctggtcactactacgaatcgttc
gccgattaccagcaaaacgaagcctggacgtgggaacatcagccgctggcccgtgcgcgcgtggtgtacggcgatccgcaactgaccgccgaatt
tgacgccattcgccgcgatattctgatgacgcctcgcgacggcgcaacgctgcaaaccgacgtgcgagaaatgcgcgagagaaatgcgtgccca
tcttggcaacaagcataaagaccgcttcgatctgaaagccgatgaaggcggtatcaccgacatcgagtttatcgccaatatctgggctgcgctt
tgcccatgacaagccgaaactgacgcgctggcggataatgtgcgcattctcgaagggctggcgcaaaacggcatcatggaggagcaggaagcga
ggcattgacgctggcgtacaccacattgcgtgatgagctgcaccacctggcgctgcaagagttgccgggacatgtggcgctctcctgttttgtcg
ccgagcgtgcgcttattaaaaccagctgggacaagtggctggtggaacctgtgcgccccggcgtaagtgtggtatcatcgcgcgcaaattttgtat
ctctcaggagacagcaatgaaagtgacgctgccagagtttaagcaagccggtgtaatggtggtgggtgatgtgatgctggatcgttactggatg
gcccaaccagccgtatctctccggaagcgccagtcccggttgttaaagtcgataccattgaagagcgtcctggcggcgcggcaaacgtggcgatg
aatatcgcctcactgggcgcacggcgcgtctggttggcgtgactggcattgacgatgcggcgcgcgctgagcaaagcgctggccgatgttaa
cgtaaatgtgacttcgtttctgttccgacgcatcccaccatcactaagctgcgcgtgctgtcgcgtaaccagcagctgattcgcctggactttga
agagggttttgaaggagtcgatccgcaaccgatgcatgaacgcatcagccaggcgcttggtaatattggcgcgctggtgctgcggatt |
| 245 | atgaccctgaatatgatgatggatgccggcggacatcatcgcgacaaacaatattaataccggcaaccacaccggcaatttacgagactgcgcag
gcatcctttctcccgtcaatttctgtcaaataaagtaaaagaggcagtctacttgaattacccccggctggttcagcgtttgttgaaaaaaagta
actgaaaaatccgtagaatagcgccactctgatggtaattacctattcaattaagaattatctggatgaatgtgccattaaatgcgcagcataat
ggtggttgtgcgggaaaactgcttttttttgaaagggttggtcagtagcggaaacaactcacttcacaccccgaaggggggaagttgcctgaccct
acgattcccgctatttcattcactgaccggaggttcaaaatga |
| 246 | accggatacgagagaaaagtgtctacatcggttcggttgatattgaccggcgcatccgccagcccgcccagtttctggtggatctgtttggcgat
tttgcgggtcttgccggtgtcggtgccgaaaaaaataccaatatttgccataacacacgctcctgttgaaaaagagatcccgccgggaaatgcgg
tgaacgtgtctgatattgcgaagagtgtgccagttttggtcgcgggcaaacctgcaccagtttggttattaatgcaccagtctggcgcttttttt
cgccgagtttctcctcgctaatgcccgccaggcgcggctttggcgctgatagcgcgctgaataccgatctggatcaaggttttgtcgggttatca
gccaaaggtgcactctttgcatggtatacgtgcctgacatgttgtccgggcgacaaacggcctggtggcacaaattgtcagaactacgacacgac
taactgaccgcaggagtgtgcgatgaccctgaatatgatggatgccggccgtcctgtaataataaccggcaaccacaccggcaatttacgagactgcgcaggcat
cctttctcccgtcaatttctgtcaaataaagtaaaagaggcagtctacttgaattacccccggcgttgagcgtttgttgaaaaaaagtaactgaaaaa
tccgtagaatagcgccactctgatggtaattaacctattcaattaagaattatctggatgaatgtgccattaaatgcgcagcataatggtgcgttgtgcgggaaaactgcttttttttgaaagggttggtcagtagcggaaacaactcacttcacacccc
gaaggggaagttgcctgaccctacgattcccgctatttcattcactgaccggaggttcaaaatgacccagcgaaccgagtcgggtaataccgt
aggcgcttcgatttgtcccagcagttcactgcgatgcagcgcataagcgtggtactcagccgggcgaccgaggtcgatcagacgctccagcaagt
gctgtgcgtattgacaatgacgccttttgcagcacggcatgatctgctgtacgacagcaccaggcgattttgaatattgaagcgttgcaggaa
gccgatcagcagttaatcccggcagctcgcaaatccgctatcgtccgggcgaagggctggtcgggacggtgcttcgcagggccaatcattagt
gctggcgcgcgttgctgacgatcagcgctttcttgaccggctcggttgtatgattacaacctgccgtttatcgccgtgccgctgatagggccaga
tgcgcagactttcggtgtgctgacggcacaacccatggcgcgttacgaagagcgattacccgcctgcacccgctttctggaaacggtc |
| 247 | atgaccctgaatatgatgatggatgccggccgtcctgtaataataaccggacaattcggactgattaaaaaagcgcccttgtggcgcttttttta
tattcccgcctccatttaaaataaaaaatccaatcggattcactatttaaactggccattatctaagatgaatccgatggaagctcgctgttttta
acacgctttttaacctttattgaaagtcggtgcttctttgagcgaacgatcaaatttaagtggattccc
atcaaaaaatattctcaacctaaaaaagtttgtgtaatacttgtaacgctacatggagattaactcaatctagagggtattaataatgaatcgt
actaaactggtactgggcgcaactcacttcacaccccgaaggggaagttgcctgaccctacgattcccgctatttcattcactgaccggaggtt
caaaatga |
| 248 | accggatacgagagaaaagtgctacatcggttcggttgatattgaccggcgcatccgccagcccgcccagtttctggtggatctgtttggcgatt
tgcgggtcttgccggtgtcggtgccgaaaaaaataccaatatttgccataacacacgctcctgttgaaaaagagatcccgccgggaaatgcggt
gaacgtgtctgatattgcgaagagtgtgccagttttggtcgcgggcaaacctgcaccagtttggttattaatgcaccagtctggcgcttttttt
cgccgagtttctcctcgctaatgcccgccaggcgcggctttggcgctgatagcgcgctgaataccgatctggatcaaggtttgtcgggttatcag
ccaaaggtgcactctttgcatggttatacgtgcctgacatgttgtccgggcgacaaacggcctggtggcacaaattgtcagaactacgacacga
ctaactgaccgcaggagtgtcgatgaccctgaatatgatgatggatgccggccgtcctgtaataataaccggacaattcggactgattaaaaaa
gcgcccttgtggcgcttttttatatcccgcctccatttaaaataaaaaatccaatcggatttcactatttaaactggccattatctaagatga
atccgatggaagctcgctgttttaacacgcttttttaacctttattgaaagtcggtgcttctttgagcgaacgatcaaatttaagtggattccc
atcaaaaaatattctcaacctaaaaaagtttgtgtaatacttgtaacgctacatggagattaactcaatctagagggtattaataatgaatcgt
actaaactggtactgggcgcaactcacttcacaccccgaaggggaagttgcctgaccctacgattcccgctatttcattcactgaccggaggtt
caaaatgacccagcgaaccgagtcggggtaataccgtctggcgcttcgatttgtcccagcagttcactgcgatgcagcgcataagcgtggtactc
agccgggcgaccgaggtcgatcagacgctccagcaagtgctgtgcgtattgcacaatgacgccttttgcagcacggcatgatctgctgtacgac
agccagcaggcgattttgaatattgaagcgttgcaggaagccgatcagcagttaatcccggcagctcgcaaatccgctatcgtccgggcgaagg
gctggtcgggacggtgcttcgcagggccaatcattagtgctggcgcgcgttgctgacgatcagcgctttcttgaccggctcggttgatgatta
caacctgccgtttatcgccgtgccgctgatagggccagatgcgcagactttcggtgtgctgacggcacaacccatggcgcgttacgaagagcgat
tcccgcctgcacccgctttctggaaacggtc |
| 249 | atggcactgaaacacctccattccctgtgtgccgcgtcgccgatggttgccagtcagctggcgcgctaccgatcctgcttgatgaattgctcgac
ccgaatacgctctatcaaccgacggcgatgaatgcctatcgcgatgagagcgccaatacctgctgcgcgtgccggaagatgatgaagagcaacag
cttgaggcgctgcggcagtttaagcaggcgcagttgctgcgcgtggcggcggcggatattgccggtacgttgccagtaatgaaagtgagcgatca
cttaacctggctggcggaggcgattattgatgcggtggtgcagcaagcctggggcagatggtggcgcgttatggccagccaacgcatctgcacg
atgcgaagggcgcggttttgcggtggtcggttatggcaagctgggcggctgggacgtttgggttttacagctccgatctggatctggtattcctgcac
gactgcccgatggatgtgatgaccgatggcgagcgtgaaatcgatggtcaccagttctctatttgcgtctcgcgcagcgcgtgatgcacctgtttag
cacgcgcacgtcgtccggcatcctttatgaagttgatgcgcgtctgtccatctggcgctgcgcgatgctggtcactactacgaatcgttcgccga
ttaccagcaaaacgaagcctggacgtgggaacatcagccgctggcccgtgcgcgcgtggtgtacggcgatccgcaactgaccgccgaatttgacg
ccattcgccgcgatattctgatgacgcctcgcgacggcgcaacgctgcaaaccgacgtgcgagaaatgcgcgagagaaatgcgtgcccatcttgc
caacaagcataaagaccgcttcgatctgaaagccgatgaaggcggtatcaccgacatcgagtttatcgcccaatatctggtgctgcgctttgccca
tgacaagccgaaactgacgcgctggcggataatgtgcgcattctcgaagggctggcgcaaaacggcatcatggaggagcaggaagcgcaggcat
tgacgctggcgtacaccacattgcgtgatgagctgcaccacctggcgctgcaagagttgccgggacatgtggcgctctcctgttttgtcgccgag
cgtgcgcttattaaaaccagctgggacaagtggctggtggaa |
| 250 | gcgcaaagcgagtgctcacttacgtgatctgttgacacaatctgaagcgaccataactcgtgccgtttcagcgaatacggcggtgggagcgcac
aatcagccctggcgaagctggtgctcaccgagtggctagtgacgcagggctggcgaaccttccttgatgaaaaagcgcaggccaaattcgccgac
tcctttaaacgctttgctgacatccatctgtcacgcagcgccgccgagctgaaaaaagcctttgcccaaccgctgggcgacagtatcgcgacca
gttgccgcgcctggcgcgtgatatcgactgcgcgttactgctggccgggcattacgatcgcgcgcgccgtggaatggctggaaaactggcagg |

TABLE H-continued

| SEQ ID NO: | Sequence |
|---|---|
| | ggcttcagcacgccattgaaacgcgccagagagtcgaaatcgaacatttccgtaataccgcgattacccaggagccgttctggttgcacagcgga<br>aaacgttaacgaaaggatatttcgcatggcactgaaacacctcatttccctgtgtgccgcgtcgccgatggttgccagtcagctggcgcgctacc<br>cgatcctgcttgatgaattgctcgacccgaatacgctctatcaaccgacggcgatgaatgcctatcgcgatgagctgcgccaatacctgctgcgc<br>gtgccggaagatgatgaagagcaacagcttgaggcgctgcggcagtttaagcaggcgcagttgctgcgcgtggcggcgggatattgccggtacgt<br>tgccagtaatgaaagtgagcgatcacttaacctggctggcggaagcgattattgatgcggtggtgcagcaagcctgggggcagatggtggcgcgt<br>tatggccagccaacgcatctgcacgatcgcgaagggcgcggttttgcggtggtcggttatggcgaagaggggcggctgggagctgggttacagctcc<br>gatctggatctggtattcctgcacgactgcccgatggatgtgatgaccgatgcgagcgtgaaatcgatggtcgcagttctatttgcgtctcgcg<br>cagcgcgtgatgcacctgttagcacgcgcacgtcgtccggcatcctttatgaagttgatgcgcgtctgcgtccatctagcgctgcggggatgctg<br>gtcactactacggaatcgttcgccgattaccagcaaaacgaagcctggacgtgggaacatcaggcgctggcccgtgcgcgtggtgtacggcgatc<br>cgcaactgaccgccgaatttgacgccattcgccgcgatattctgatgacgcctcgcgacggcgcaacgctgcaaaccgacgtgcgagaaatgcgc<br>gagaaaatgcgtgcccatcttggcaacaagcataaagaccgcttcgatctgaaagccgatgaaggcggtatcaccgacatcgagtttatcgccca<br>atatctggtgctgcgctttgcccatgacaagccgaaactgacgcgctggtcggataatgtgcgcattctcgaacggctggcgcaaaacggcatca<br>tggaggagcaggaagcgcaggcattcacgctggcgtacaccacattgcgtgatgagctgcaccacctggcgctgcaagagttgccgggacatgtg<br>gcgctctcctgttttgtcgccgagcgtgcgctttattaaaaccagctgggacaagtggctggtggaaccgtgcgccccggcgtaagtgtggtatca<br>tcgcgcgcaaattttgtatctctcaggagacaggaatgaaagtgacgctgccagagtttaagcaagccggtgtaatggtggtgggtgatgtgatg<br>ctggatcgttactggtatggcccaaccagccgtatctctccggaaggccagtcccggttgttaaagtcgataccattgaagagcgtcctggcggc<br>gcggcaaacgtggcgatgaatatcgcctcactgggcgccacggcgcgcgtgttggcctgactggcattgacgatgcggcgcgcgcgctgagcaaa<br>gcgctggccgatgttaacgttaaatgtgacttcgtttctgttccgacgcatcccaccatcactaagctgcgcgtgctgtcggtaaccagcagctg<br>attcgcctggactttgaagagggttttgaaggagtcgatccgcaaccgatgcatgaacgcatcagccaggcgcttggtaatattggcgcgctggt<br>gctgtcggatt |
| 251 | tttcgctgaaggtgtgaccatgggccatcaggtgctggtgcagctggaaagtgttgccatcactatcgtgtggtctggcgtggtggcctttattg<br>gttacaaactggcggacatgacggtaggcctgcgcgtaccggaagaacaagaacgtgaagggctggatgaaacagccacggcgaaaacgcctata<br>acgcctga |
| 252 | tttcctttctgactctgcccgtccgggcgcactaacggcctgaaatactccctcttttcattcctggcacaacgattaaatgtagttgcgtgtta<br>gctgcggccattatcgaattcgactggaggggggatctatgaagctggttaccgtggtgattaagccattcaaacttgaagacgtgcgtgaagcgc<br>tttcttctattggtattcaagggttgaccgtaactgaagtgaaaggctttggccgtcagaagggtcacgctgagctgtaccgcggtgcggaatat<br>agcgttaaatttcctgccgaaagtgaaaattgatgtggcgatcgctgacgatcaactcgatgaagtaatcgatgtgatcagcaaagcggcctacac<br>cggaaaaattggcgacggcaaaattttcgttgctgagctgcaacgcgtcattcgtattcgtaccggcgaagccgacgaagcggcactgtaataca<br>agacacacagtgatggggatccggtttcgctgaaggtgtgaccatgggccatcaggtgctggtgcagctggaaagtgttgccatcactatcgtgtg<br>gtctggcgtggtggcctttattggttacaaactggcggacatgacggtaggcctgcgcgtaccggaagaacaagaacgtgaagggctggatgtaa<br>acagccacggcgaaaacgcctataacgcctgattgcgttgagttatctcctgagcataaaaaagcctccattcggaggcttttcttttttttaagt<br>ttaaaggcggttagttgcgattgcgcatgacgccttcctgcacgctggacgcgaccagcacaccctcttgcgtatagaactcgccgcgcacaaa<br>ccgcgagcgctggaggctgacgtgctttccacactgtagagcagccattcgttcattattaaacgggcgatggaaccacatgagtggtcaatggt<br>ggcaacctgcataccgcgctcaaggaagccacgccgtgcggctgaagtgcaaccggcaggaagttaaagtctgaggcatatccaagcagatatt<br>gatgtacgcgaaaatcgtccacaccgtgccgtttcgcgggatccataccttggcgggtgggatcggcaacgtggcctttcagcgggttatgaaact<br>caaccgggcggatctccagtggtttatcactaagaaacttctctttggcctgcgg |
| 253 | atgtttaacgatctgattggcgatgatgaaacggattcgccggaagatgcgctttctgagagctggcgcgaattgtggcaggatgcgttgcagga<br>ggaggattccacgcccgtgctggcgcatctctcagaggacgatcgccgccgcgtggtggcgctgattgccgattttcgcaaagagttggataaac<br>gcaccattggcccgcgagggcggcaggtactcgatcacttaatgccgcatctgctcagcgatgtatgctcgcgcgacgatgcgccagtaccgctg<br>tcacgcctgacgccgctgctcaccggaattattacccgcaccacttaccttgagctgctaagtgaattccccggcgcactgaaacacctcatttc<br>cctgtgtgccgcgtcgccgatggttgccagtcagctggcgcgctacccgatcctgcttgatgaattgctcgacccgaatacgctctatcaaccga<br>cggcgatgaatgcctatcgcgatgagctgcgccaatacctgctgcgcgtgccggaagatgatgaagagcaacagcttgaggcgctgcggcagttt<br>aagcaggcgcagttgctgcgcgggcggcggcggatattgccggtacgttgccagtaatgaaagtgagcgatcacttaacctggctggcggaagcg<br>attattgatgcggtggtgcagcaagcctgggggcagatggtggcgcgttatggccagccaacgcatctgcacgatcgcgaagggcgcggttttgc<br>ggtggtcggttatggcaagctgggcggctgggagctggttacagatccgatctggatctggtattcctgcacgactgcccgatggatgtgatga<br>ccgatgcgagcgtgaaatcgatggtcgcagttctatttgcgtctcccgcagcgcgtgatgcacctgtttagcacgcgcacgtcgtccggcatc<br>ctttatgaagttgatgcgcgtctgcgtccatctggcgctgcggggatgctggtcactactacggaatcgttcgccgattaccagcaaaacgaagc<br>ctggacgtgggaacatcaggcgctggcccgtgcgcgcgtggtgtacggcgatccgcaactgaccgccgaatttgacgccattcgccgcgatattc<br>tgatgacgcctcgcgacggcgcaacgctgcaaaccgacgtgcgagaaatgcgcgagaaaatgcgtgcccatcttggcaacaagcataaagaccgc<br>ttcgatctgaaagccgatgaaggcggtatcaccgacatcgagtttatcgcccaatatctggtgctgcgctttgcccatgacaagccgaaactgac<br>gcgctggtcggataatgtgcgcattctcgaagggctggcgcaaaacggcatcatggacgagcaggaagcgcaggcattgacgctggcgtacacca<br>cattgcgtgatgagctgcaccacctggcgctgcaagagttgccgggacatgggcgctctcctgttttgtcgccgagcgtgcgcttattaaaccag<br>ctgggacaagtggctggtggaaccgtgcgccccggcgtaa |
| 254 | gcgcaaagcgagtgctcacttacgtgatctgttgacacaatctgaaggaccataacttctgccgtttcagcgaatacggcggtgtggaggcacaa<br>tcagccctggcgaagctggtgctcaccgagtggctagtgacgcagggctggcgaaccttccttgatgaaaagcgcaggccaaattcgccgactc<br>ctttaaacgctttgctgacatccatctgtcacgcagcgccgccgagctgaaaaaagccttttgcccaaccgctgggcggcgacagctatcgcgaccagt<br>tgccgcgcctgccgcgtgatatcgactgcgcgttactgctggccgggcattacgatcgcgcgcgcgcgtgaattggctggaaaactggcagggg<br>cttcagcacgccattgaaacgcgccagagagtcgaaatcgaacatttccgtaataccgcgattacccaggagccgttctggttgcacagcggaaa<br>acgttaacgaaaggatatttcgcatgtttaacgatctgattggcgatgatgaaacggattcgccggaagatgcgctttctgagagctggcgcgaa<br>ttgtggcaggatgcgttgcaggaggaggattccacgcccgtgctggcgcatctctcagaggacgatcgccgccgcgtggtggcgctgattgccga<br>ttttcgcaaagagttggataaacgcaccattggcccgcgagggcggcaggtactcgatcacttaatgccgcatctgctcagcgatgtatgctcgc<br>gcgacgatgcgccagtaccgctgtcacgcctgacgccgctgctcaccggaattattacccgcaccacttaccttgagctgctaagtgaattccc<br>ggcgcactgaaacacctcatttccctgtgtgccgcgtcgccgatggttgccagtcagctggcgcgctacccgatcctgcttgatgaattgctcga<br>cccgaatacgctctatcaaccgacggcgatgaatgcctatcgcgatgagctgcgccaatacctgctgcgcgtgccggaagatgatgaagagcaac<br>agcttgaggcgctgcggcagtttaagcaggcgcagttgctgcgcgtggcggcgggatattgccggtacgttgccagtaatgaaagtgagcgatca<br>cttaacctggctggcggaagcgattattgatgcggtggtgcagcaagcctgggggcagatggtggcgcgttatggccagccaacgcatctgcacg<br>atcgcgaagggcgcggttttgcggtggtcggttatggcaagctgggcggctgggagctggttacagctccgatctggatctggtattcctgcac<br>gactgcccgatggatgtgatgaccgatgcgagcgtgaaatcgatggtcgcagttctatttgcgtctcgcgcagcgcgtgatgcacctgtttag<br>cacgcgcacgtcgtccggcatcctttatgaagttgatgcgcgtctgcgtccatctggcgctgcggggatgctggtcactactacggaatcgttcg<br>ccgattaccagcaaaacgaagcctggacgtgggaacatcaggcgctggcccgtgcgcgtggtgtacggcgatccgcaactgaccgccgaatttg<br>acgccattcgccgcgatattctgatgacgcctcgcgacggcgcaacgctgcaaaccgacgtgcgagaaatgcgcgagaaaatgcgtgcccatct<br>tggcaacaagcataaagaccgcttcgatctgaaagccgatgaaggcggtatcaccgacatcgagtttatcgcccaatatctggtgctgcgctttg<br>cccatgacaagccgaaactgacgcgctggtcggataatgtgcgcattctcgaagggctggcgcaaaacggcatcatggaggagcaggaagcgcag |

TABLE H-continued

| SEQ ID NO: | Sequence |
|---|---|
| | gcattgacgctggcgtacaccacattgcgtgatgagctgcaccacctggcgctgcaagagttgccgggacatgtggcgctctcctgttttgtcgc<br>cgagcgtgcgcttattaaaaccagctgggacaagtggctggtggaaccgtgcgccccggcgtaagtgtggtatcatcgcgcgcaaattttgtatc<br>tctcaggagacaggaatgaaagtgacgctgccagagtttaagcaagccggtgtaatggtggtgggtgatgtgatgctggatcgttactggtatgg<br>cccaaccagccgtatctctccggaagcgccagtcccggttgttaaagtcgataccattgaagagcgtcctggcggcgcggcaaacgtggcgatga<br>atatcgcctcactgggcgccacggcgcgtctggttggcctgactggcattgacgatgcggcgcgcgctgagcaaagcgctggccgatgttaac<br>gttaaatgtgacttcgtttctgttccgacgcatcccaccatcactaagctgcgcgtgctgtcgcgtaaccagcagctgattcgcctggacttga<br>agagggttttgaaggagtcgatccgcaaccgatgcatgaacgcatcagccaggcgcttggtaatattggcgcgctggtgctgtcggatt |
| 255 | atgaccctgaatatgatgatggatgccggccgtcctgtaataataaccggacaattggactgattaaaaaagcgcccttgtggcgatttttttata<br>ttcccgcctccatttaaaataaaaaatccaatcggatttcactatttaaactggccattatctaagatgaatccgatggaagctcgctgttttaa<br>cacgcgttttttaaccttttattgaaagtcggtgcttctttgagcgaacgatcaaattttaagtggattcccatcaaaaaaatattctcaacctaa<br>aaaaagtttgtgtaatacttgtaacgcttcatggagattaactcaatctagagggtattaataatgaatcgtactaaactggtactgggcgcaact<br>cacttcacaccccgaaggcgaagttgcctgaccctacgattcccgctatttcattcactgaccggaggttcaaaatga |
| 256 | accggatacgagagaaaagtgtctacatccggttcggttgatattgaccggcgcatccgccagcccgcccagtttctggtggatctgtttggcgat<br>tttgcgggtcttgccggtgtcggtgccgaaaaaaataccaatatttgccataacacacgctcctgttgaaaaagagatcccgccgggaaatgcgg<br>tgaacgtgtctgatattgcgaagagtgtgccagttttggtcgcgggcaaaacctgcaccagtttggttattaatgcaccagtctggcgcttttttt<br>tcgccgagtttctcctcgctaatgcccgccaggcgcggctttggcgctgatagcgcgctgaataccgatctggatcaaggttttgtcgggttatc<br>agccaaaaggtgcactctttgcatggttatacgtgcctgacatgttgtccggagcgacaaacggcctggtggcacaaattgtcagaactacgacac<br>gactaactgaccgcaggagtgtgcgatgaccctgaatatgatgatggatgccggccgtcctgtaataataaccggacaattcggactgattaaaa<br>aagcgcccttgtggcgctttttttatattcccgcctccatttaaaataaaaaatccaatcggatttcactatttaaactggccattatctaagat<br>gaatccgatggaagctcgctgttttaacacgcgttttttaaccttttattgaaagtcggtgcttctttgagcgaacgatcaaattttaagtggatt<br>cccatcaaaaaaatattcttcaacctaaaaaaagtttgtgtaatacttgtaacgctacatggagattaactcaatctagagggtattaataatgaa<br>tcgtactaaactggtactgggcgcaactcacttcacaccccgaaggggaagttgcctgaccctacgattcccgctatttcattcactgaccgga<br>ggttcaaaatgacccagcgaaccgagtcgggtaataccgtctggcgcttcgatttgtcccagcagttcactgcgatgcagcgcataagcgtggta<br>ctcagccgggcgaccgaggtcgatcagacgctccagcaagtgctgtgcgtattgcacaatgacgcctttttgcagcacggcatgatctgtctgta<br>cgacagccagcaggcgattttgaatattgaagcgttgcaggaagccgatcagcagttaatccccggcagctcgcaaatccgctatcgtccgggcg<br>aagggctggtcgggacggtgctttcgcagggccaatcattagtgctggcgcgcgtgctgacgatcagcgcttttcttgaccggctcgggttgtat<br>gattacaacctgccgtttatcgccgtgccgctgatagggccagatgcgcagactttcggtgtgctgacggcacaacccatggcgcgttacgaaga<br>gcgattacccgcctgcacccgctttctggaaacggtc |
| 257 | tttcgctgaaggtgtgaccatgggccatcaggtgctggtgcagctggaaagtgttgccatcactatcgtgtggtctggcgtggtggcctttattg<br>gttacaaactggcggacatgacggtaggcctgcgcgtaccggaagaacaagaacgtgaagggctggatgtaaacagccacggcgaaaacgcctat<br>aacgcctga |
| 258 | tttcctttctgactctgcccgtccgggcgcactaacggcctgaaatactccctcttttcattcctggcacaacgattgcaatgtctgttgcgtgt<br>tagctgcggccattatcgaattcgactggaggggatctatgaagctggttaccggtggtgattaagccattcaaacttgaagacgtcgtgaagc<br>gcttcttctattggtattcaagggttgaccgtaactgaagtgaaaggctttggccgtcagaagggtcacgctgagctgtaccgcggtgcggaat<br>atagcgttaatttcctgccgaaagtgaaaattgatgtggcgatcgctgacgatcaactcgatgaagtaatcgatgtgatcagcaaagcggcctac<br>accggaaaaattggcgacggcaaaattttcgttgctgagctgcaacgtcattcgtattcgtaccggcgaagccgacgaaggcactgtaatac<br>aagacacacagtgatggggatcggtttcgctgaaggtgtgaccatgggccatcaggtgctggtgcagctggaaagtgttgccatcactatcgtgt<br>ggtctggcgtggtggcctttattggttacaaactggcggacatgacggtaggcctgcgcgtaccggaagaacaagaacgtgaagggctggatgta<br>aacagccacggcgaaaacgcctataacgcctgattgcgttgagttatctcctgagcataaaaaagcctccattcggaggcttttctttttttaagt<br>ttaaagcgcggttagttgcgattgcgcatgacgccttcctgcacgctggacgcgaccagcacaccctcttgcgtatagaactgccgcgcacaaa<br>accgcgagcgctggaggctgacgtgctttccacactgtagagcagccattcgttcatattaaacgggcgatggaaccacatggagtggtcaatgg<br>tggcaacctgcataccgcgctcaaggaagcccacgccgtgcggctgaagtgcaaccggcaggaagttaaagtctgaggcatatccaagcagatat<br>tgatgtacgcgaaaatcgtccggcaccgtgccgtttgcgcggatccatacctggcgggtgggtcggcaacgtggcctttcagcgggttatgaaac<br>tcaaccgggcggatctccagtggtttatcactaagaaacttctcttttggcctgcgg |
| 259 | atgacctttaatatgatgcctggggtcactggagcgcttttatcggcatcctgaccgaagaatttgccggtttcttcccgacctggctggcccct<br>gttcaggttgtggtgataacactgattctcaagctgaatatgtcaacgaattgacccgtaaattgataaatgcgggcattcgtgtaaaagc<br>ggacttgagaaacgagaagattggctttaaaatccgcgagcacacttacgtcgtgtccctatatgttggtctgtggtgataaagaggtggaag<br>caggcaaagtggccgttcgcacccgccgcggtaaagacctgggcagcctggacgtaaggaagtgattgagaagctgcaacaacagattcgcagcc<br>gcagtcttcaacaactggaggaataaggtattaaaggcggaatacgagttcaaacggcacgtccgaatcgtatcaatggcgagattcgcgcccag<br>gaagttcgcttaactggtctggaaggtgagcagctgggtattgcaatagaactaactacccgcccgaaggcggtacctgcctgaccctgcgatt<br>cccgttatttcattcactgaccggaggcccacgatga |
| 260 | ggtacgacaaaaacgtctccagcgacgtgcggttaatattgactggcgcatccgccacatcccccagtttttgctggatcagtttggcgattttg<br>cggggttttttcccgtgtcactgccaaaaaaaataccaatgttagccatgtcgcgctcctgttgagaaagaataaggccgcctgcaaacggcggata<br>tccctttctcctgttgcgaaagcgtgtgccaggttttttttaaggccttctgtgtgcactgaaatgcgtgaaaaaatgactcttttttgtgcaggcaccg<br>tcctctctccgctatccagacctgcttttgaaggcctctgagggcaaatcagggcgcaaaacacgaatcacgatcaatgtttcggcggttacctg<br>ttcgaaaggtgcactctttgcatggttaatcacacccaatcagggctgcggatgtcggcgtttcacaacacaaaatgttgtaaatgcgacacag<br>ccgggcctgaaaccaggagcgtgtgatgaccttttaatatgatgcctggggtcactggagcgctttatcggcatcctgaccgaagaatttgccggt<br>ttcttcccgacctggctggcccctgttcaggttgtggtgataatcactgattctcaagctgaatatcaactcaagctgaatatgtcaacgaattgacccgtaaattgca<br>aaatgcgggcattcgtgtaaaagcggacttgagaaacgagaagattggctttaaaatccgcgagcacactttacgtcgtgtccctatatgttga<br>tctgtggtgataaagaggtggaagcaggcaaagtggccgttcgcacccgccgcggtaaagacctgggcagcctggacgtaagtgaagtgattgag<br>aagctgcaacaagagattcgcagccgcagtcttcaacaactggaggaataaggtattaaaggcggaaaacgagttcaaacggcacgtccgaatcg<br>tatcaatggcgagattcgcgcccaggaagttcgcttaactggtctggaaggtgagcagctgggtattgcaatagaactaactacccgccctgaag<br>gcggtacctgcctgaccctgcgattcccgttatttcattcactgaccggaggcccacgatgacccaccgaccgagtcgggcaccaccgtctggc<br>gttttgatctctcacagcaatttaccgccatgcagccgcatcagcgtggtgttgagtcgcgcaaccgagataagcagacgctgcaggaggtgctg<br>tgtgttctgcataatgacgcatttatgcaacacggcatgctgtgtctgatgacaaccagcaggaaattctgagtattgaagcttgcaggaggc<br>agaccaactgatccccgcagctcgcaaatctcgctatcgcctggcgaagggctggtaggagccgtactgtcccagggacaatctcttgtgc<br>tgccgcgtgtcgccgacgatcaacgcttttctcgacaggcttggcatctatgattacaacctgccgtttatcgccgtcccttaatggggcaggc<br>gcgcaaacgttggcgtctcgccgcgcagccgatggcgtctggaggagcgcgttccttcctgtacgcgctttctggaaaccgtc |
| 261 | ttgaagagtttgatcatggctcagattgaacgctggcggcaggcctaacacatgcaagtcgaacgtagcacagagagcttgctctcgggtgacg<br>agtggcggacgggtgagtaatgtctgggaaactgcctgatggaggggggataactactggaaacggtagctaataccgcataacgtcgcaagacca |

TABLE H-continued

| SEQ ID NO: | Sequence |
|---|---|
| | aagagggggaccttcgggcctcttgccatcagatgtgcccagatgggattagctagtaggtggggtaacggctcacctaggcgacgatccctagc<br>tggtctgagaggatgaccagccacactggaactgagacacggtccagactcctacgggaggcagcagtggggaatattgcacaatgggcgcaagc<br>ctgatgcagccatgccgcgtgtgtgaagaaggccttcggggttgtaaagcactttcagcggggaggaagggagtaaggttaataaccttattcatt<br>gacgttacccgcagaagaagcaccggctaactccgtgccagcagccgcggtaatacggagggtgcaagcgttaatcggaattactgggcgtaaac<br>cgcacgcaggcggtctgtcaagtcggatgtgaaatccccgggctcaacctgggaactgcatccgaaactggcaggcttgagtctcgtagagggag<br>gtagaattccaggtgtagcggtgaaatgcgtagagatctggaggaataccggtggcgaaggcggcctcctggacgaagactgacgctcaggtgcg<br>aaagcgtggggagcaaacaggattagataccctggtagtccacgccgtaaacgatgtctatttggaggttgtgcccttgaggcgtggcttccgga<br>gctaacgcgttaaatagaccgcctgggagtacggccgcaaggttaaaactcaaatgaattgacgggggcccgcacaagcggtggagcatgtggt<br>ttaattcgatgcaacgcgaagaaccttacctggtcttgacatccacagaacttttccagagatggattggtgccttcgggaactgtgagacaggtg<br>ctgcatggctgtcgtcagctcgtgttgtgaaatgttgggttaagtcccgcaacgagcgcaacccttatcctttgttgtccagcggtccggccggga<br>actcaaaggagactgccagtgataaactggaggaaggtggggatgacgtcaagtcatcatggcccttacgaccagggctacacacgtgctacaat<br>ggcgcatacaaagagaagcgacctcgcgagagtaagcggacctcataaagtcgtcgtagtccggattggagtctgcaactcgactccatgaagt<br>cggaatcgctagtaatcgtggatcagaatgccacggtgaatacgttcccgggccttgtacacaccgcccgtcacaccatgggagtgggttgcaaa<br>agaagtaggtagcttaaccttcggggagggcgcttaccactttgtgattcatgactggggtgaagtcgtaacaaggtaaccgtaggggaacctgcgg<br>gttggatcacctcctt |
| 262 | ttgagagtttgatcatggctcagattgaacgctggcggcaggcctaacacatgcaagtcgaacggtagcacagagagcttgctctcgggtgacga<br>gtggcggacgggtgagtaatgtctgggaaactgcctgatgagggggacgaactactggaaacggtagctaataccgcataacgtcgcaagaccaa<br>agagggggaccttcgggcctcttgccatcagatgtgcccagatgggattagctagtaggtggggtaacggctcacctaggcgacgatccctagct<br>ggtctgagaggatgaccagccacactggaactgagacacggtccagactcctacgggaggcagcagtggggaatattccacaatgggcgcaagcc<br>tgatgcagccatgccgcgtgtgtgaagaaggccttcggggttgtaaagcactttcagcggggaggaaggnantanggttaataaccttgtgttnatt<br>gacgttacccgcagaagaagcaccggctaactccgtgccagcagccgcggtaatacggagggtgcaagcgttaatcggaattactgggcgtaaag<br>cgcacgcaggcggtctgtcaagtcggatgtgaaatccccgggctcaacctgggaactgcatccgaaactggcaggcttgagtctcgtagagggag<br>gtagaattccaggtgtagcggtgaaatgcgtagagatctggaggaataccggtggcgaaggcggcctcctggacgaagactgacgctcaggtgcg<br>aaagcgtggggagcaaacaggattagataccctggtagtccacgccgtaaacgatgtctatttggaggttgtgcccttgaggcgtggcttccgga<br>gctaacgcgttaaatagaccgcctgggagtacggccgcaaggttaaaactcaaatgaattgacgggggcccgcacaagcggtggagcatgtggt<br>ttaattcgatgcaacgcgaagaaccttacctggtcttgacatccacagaacttagcagagatgcttttggtgccttcgggaactgtgagacaggtg<br>ctgcatggctgtcgtcagctcgtgttgtgaaatgttgggttaagtcccgcaacgagcgcaaccatatcctttgtgccagcggttaggccgggaa<br>ctcaaaggagactgccagtgataaactggaggaaggtggggatgacgtcaagtcatcatggcccttacgaccagggctacacacgtgctacaatg<br>gcgcatacaaagagaagcgacctcgcgagagtaagcggacctcataaagtccgtcgtagtccggattggagtctgcaactcgactccatgaagtc<br>ggaatcgctagtaatcgtggatcagaatgccacggtgaatacgttcccgggccttgtacacaccgcccgtcacaccatgggagtgggttgcaaaa<br>gaagtaggtagcttaaccttcggagggcgcttaccactttgtgattcatgactggggtgaagtcgtaacaaggtaaccgtaggggaacctgcgg<br>ttggatcacctcctt |
| 263 | atgaccatgcgtcaatgcgccatttacggcaaaggtgggatcggcaaatcgaccaccacacagaacctggtcgccgcgctggcggagatgggtaa<br>aaaagtcatgattgtcggctgtgacccgaaagccgattccacgcgtttgatcctgcatgcgaaagcgcagaacaccattatggagatggctgaga<br>agtcggctccgtggaagacctggagttagaagacgtgctgcaaatcggttacggcggcgtgcgctgcgcagagtccggcggcccggagccaggcg<br>tgggctgtgccggtcgccgggtgatcaccgcgattaacttcctcgaagaagaaggcgcttacgtgccggatctcgattttgttttctacgacgtg<br>ctgggcgacgtggtatgcggtgtttcgccatcccgattcgtgaaaacaaagcgcaggagatctacatcgtttgctctcgcgaaatgatgcgat<br>gtacgccgccaacaacatctccaaaggcatcgtgaaatacgccaaatccggtcaaagtgcgcctcggcgggctgatttgtaactcgcgccagaccg<br>accgtgaagatgaactgatcattgcgctggcagaaaaactcggcacgcagatgatccacttgttccccgcgacaacattgtgcagcgtgcggaa<br>atccgccgtatgacggttatcgaatatgacccgacctgcaatcaggcgaacgaatatcgcagccttgccagcaaaatcgtcaacaacaccaaaat<br>ggtggtgcccaccccctgcaccatggatgaactggaagaactgctgatggagtccggcattatggatgtgaaagacaccagcatcattggtaaaa<br>ccgccgccgaagaaaacgccgtctga |
| 264 | atgagcaatgcaacaggcgaacgcaacctggagataatcgagcaggtgctcgaggtttttcccggagaagacgcgcaaagaacgcagaaaacacat<br>gatggtgacggaccggagcaggaaaagcgtcggtaagtgcatcatctctaaccgcaaatcgcagccaggcgtgatgaccgtgcgcggctgctcgt<br>atgccggttcgaaaggggtggtatttgggccaatcaaggatatggcgcatatctcgcatgcccaatcgcgtgcggccaatactcccgcgccaag<br>cggcggaactactacaccggcgtcagcggcgtggacagcttcggcacgctcaacttcacctccgattttcaggagcgcagcatcgtgtttggcgg<br>cgataaaaagctcgccaaactgattgaagagctggaagagctgttcccgctgaccaaaggcatttcgattcagtcggaatgccggtcggcctga<br>ttggcgatgacattgaggccgtcgcgaacgccagccgcaaagccatcaacaaaccggttattccggtgcgttgcgaaggcttttgcgcggcgtgtcg<br>caatccctccggtcaacgatgtgtcaacgatgtgatccgcgactgggtgctggataaccgcgaaggcaaaccgttcgaatccaccccttacgatgt<br>ggcgatcatcggcgattacaacatcggcggcgatgcctggcttcgcgcattttgctcgaagagatgggctcgcgggggtggcacagtggtctgg<br>cgacggtacgctggtggagatggaaaacacgccgttcgtcaaactgaacctggtgcattgttaccgctcaatgaactacatctcgcgccatatgg<br>aggagaagcacggtattccgtggatggaatacaacttctttggtccgacgaaaatcgcggaatcgctgcgcaaaatcgccgaccagtttgacgac<br>accattcgcgcaacgccgaagcggtgatcgccagataccagccgcaaaacgccattatcgccaaatatcgcccgcgtctggagggggcgcaa<br>agtgctgctttatatggcgggctgcgtccgcgccatgtgattgccgctatgaagacctgggaatggagatcatcgtgccgctatgagttcgg<br>tcataacgatgattacgaccgcaccttgccggatctgaaagagggcacgctgctgtttgagatgccagcagttatgagctggaggcgttcgtcaa<br>cgcgctgaaaccggatctcatcggttccggcatcaaagagaagtacatctcttcagaaaatgggcgtgccgtttcgccagatgcactcctgggatt<br>actccggcccgtaccacggctatgacggcttcgccatcttcgcccgcgatatggatatgacgctcaacaacccgcgtggggccagttgaccgcg<br>ccgtggctgaaatccgcctga |
| 265 | atgagccagactgctgagaaaatacagaattgccatcccctgtttgaacaggatgcttaccagacgctgtttgccggtaaacgggcactcgaaga<br>ggcgcactcgccggacgggtgcaggaagtgtttcaatggcactactcccgtgaatatgaaggcgctgaacttttaaacgcgaagcgctgactatcg<br>acccgggcaaaagcctgccagccgctgggcgcggtgctctgttcgctggggttgccaatacctaccgtatgtgcacggttcacaggtgcgtg<br>gcctattccgcacgtactttaaccgccactttaaagaaccggtggctgcgtgtcggattcaatgacggaagacgcggccgtgttcggcgtgaa<br>taacaacctcaacaccggcttacaaaacgccagcgcgctgtataaaccggagattatcgccgtctctaccacctgtatggcggaagtgatcggtg<br>atgatttgcaggccttatcgccaaccgcaaaaaagatggttttcgtgccgccatccccgtgcctacgcgcacaccccagttttatcggc<br>agccatatcaccggctggataacatgtttgaaggttttgccccggacctttacggcagaccatgaagctcagccccgcaaacttttcacgcatcaa<br>cctggtgaccgggtttgaaacctatctcggcaatttccgcgtgctgaaacgcatgatggaacaaattgaggtgccggcgagtgtgctctccgatc<br>cgtcggaagtgctggatactcccgccaacgggcattaccagatgtacgcggcgggacgacgcagcaagagatgcgcgaggcgccggatgctatc<br>gacacccctgttgctgcagccctggcaactggtgaaaagcaaaaaagtggtgcaggagatgtggaatcagcccgccaccgaggtttctgttcccgt<br>tgggctggcaggaacagcgaactgttgatggcgattagccagttaaccgcgcaaggccattcccgattcactggcgtggagcgcggccggtggg<br>tcgatatgatgctcgattccacacccttgttgcacggtaaaaaattcggcctgtttggcgatccggattttgtcatgggattgacccgtttcctg<br>ctggagctgggctgcgaaccgaccgttatcctctgccacaacggtaacaaacgctggcagaaagcaatgaagaaaatgcttgacgcctcgccgta<br>cggccaggagagcgaagtgtttatcaactgcgatttgtggcattttccgctcgctgatgtttacccgccagccggatttttatgattggcaactcgt<br>acggcaagttcattcagcgcgacaccttagccaaaggcgagcagtttgaagttccgctgatccgcctcggttttcccctgttcgaccgccaccat |

TABLE H-continued

| SEQ ID NO: | Sequence |
|---|---|
| | ctgcaccgccagaccacctggggctacgagggcgccatgagcattctcactacccttgtgaatgcggtactggagagagtggacaaagagaccat<br>caagctcggcaaaaccgactacagcttcgatatcttatccgttaa |
| 266 | atgaccctgaatatgatgatggatgccggcgcgcccgaggcaatcgccggtgcgctttcgcgacaccatcctgggctgttttttaccatcgtgaa<br>gaagcgcccgtcgcatttcgctgactgatgccgacgcacgcattgtctatgccaacccggctttctgccgccagaccggctatgaactagaagc<br>gttgttgcagcaaaatccccgcctgcttgcaagtcgccaaacccacggggaaatctatcaggatatgtggcacaccttgttacaacgcgaccgt<br>ggcgcgggcaattgattaaccgccaccgcgacggcagcctgtatctggtcgagatcgatatcaccccggtgattaaccgtttggcgaactggaa<br>cactacctggcaatgcagcgcgatatcagcgccagttatgcgctggagcagcggttgcgcaatcacatgacgctgaccgaagcggtgctgaataa<br>cattccgccggcggtggttgtagtggataacgcgatcatgtggttatggataaccttgcctacaaaacgttctgtgccgactgcggcggaaaag<br>agctcctgagcgaacttcaattttttcagcccgaaaaagcggagctggcaaacggccaggtcttaccggtggtgctgcgcggtgaggtgcgtggttg<br>tcggtgacctgctgggcgctgccgcgcgtcagcgaagaagccagtcgctactttattgataacaggctgacgcgcacgctggtggtgatcaccga<br>cgacacccaacaacgccagcagcaggaacagggcgacttgaccgccttaaacagcagatgaccaacggcaaactactggcagcgatccgcgaag<br>gcttgacgccgcgctgatccagcttaactgccccatcaatatgctggcggcggcgcgacgtttaaacggcagtgataacaacaatgtggcgctcg<br>acgcgcgtacgcgaaggtgaagaggcgatggcgcggctgaaacgttgccgcccgtcgctggaactggaaagtgcggccgtctggccgctgcaac<br>cctttttttgacgatctgcgcgcgctttatcacacccgctacgagcagggaaaaatttgcaggtcacgctggattccatcatctggtgggattt<br>ggtcagcgtacgcaactgttagcctgcctgagtctgtggctcgatcgcacgctggatattgccgccgggctgggtgatttcaccgcgcaaacgca<br>gatttacgcccgcgaagaagagggctggctctcttttgtatatcactgacaatgtgccgctgatcccgctgcgccacacccactcgccggatgcgc<br>ttaacgctccgggaaaaggcatggagctgcgcctgatccagacgctggtggcacaccaccacggcgcaatagaactcacttcacaccccgaaggg<br>ggaagttgcctgaccctacgattcccgctatttcattcactgaccggaggttcaaaatga |
| 267 | atgacccagcgaaccgagtcggggtaataccgtctggcgatcgatttggcccagcagttcactgcgatgcagcgcataagcgtggtactcagccgg<br>gcgaccgaggtcgatcagacgctccagcaagtgctggcgtattgcacaatgacgccttttgcagcacggcatgatctgtctgtacgacagccag<br>caggcgattttgaatattgaagcgttgcaggaagccgatcagcagttaatccccggcagctcgcaaatccgctatcgtccgggcgaagggctggt<br>cgggacggtgctttcgcagggccaatcattagtgctggcgcgcgttgctgacgatcagcgcttcttgaccggctcgggttgtatgattacaacc<br>tgccgtttatcgccgtgccgctgatagggcagatgcgcagactttcggtgtgctgacggcacaacccatggcgcgttacgaagagcgattaccc<br>gcctgcaccgcttctggaaacggtcgctaacctggtcgcgcaaaccgtgcgtttgatggcaccaccggcagtgcgcccttccccgcgcgcgc<br>cataacacaggccgccagcccgaaatcctgcacggcctcacgcgcatttggttttgaaaatatggtcggtaacagtccggcgatgcgccagacca<br>tggagattatccgtcaggtttcgcgctgggacaccaccgttctggtacggcggagagtggcaccggcaagagctcgattgccaacgccatccac<br>caccattcgccgcgtgccggtgcgccatttgtgaaattcaactgtgcggcgctgccggacacactgctggaaagcgaattgttcggtcacgagaa<br>aggggcatttaccggcgcggtacgccagcgtaaaggccgttttgagctggccgatggcggcacgctgtttcttgacgagatcggcgagtgtagcg<br>cctcgttttcaggctaagctgctgcgcattttgcaggaaggcgaaatggaaacgctcggcgcgcgagcagcattgcaagtgaatgtgcgcattatt<br>gccgcgacgaaccgcaatcttgaagatgaagtccggctggggcactttcgcgaagatctctattatcgcctgaatgtgatgcccatcgccctgcc<br>gccactacgcgaacgccaggaggacattgccgagctggcactttctggtgcgtaaaatcgcccataacagagccgtacgctgcgcattagcg<br>agggcgctatccgcctgctgatgagctacaactggcccggtaatgtgcgcgaactggaaaactgccttgagcgctcagcggtgatgtcggagaac<br>ggtctgatcgatcgggatgtgattttgtttaatcatcgcgaccagccagccaaaccgccagttatcagcgtctcgcatgatgataactggctcga<br>taacaaccttgacgagcgccagcagctgtcctggaaaaagcgggatgggtacaagccaaagccgcgcgcttgctggggatgacgccgc<br>gccaggtcgcctatcgtattcagacgatggatataaccctgccaaggctataa |
| 268 | atgccgcaccacgcaggattgtcgcagcactggcaaacggtattttctcgtctgccggaatcgctcaccgcgcagccattgagcgcgcaggcgca<br>gtcagtgctcacttttagtgattttgttcaggacagcatcatcgcgcatcctgagtggctggcagagcttgaaagcgcgccgccgcctgcgaacg<br>aatggcaacactatgcgcaatggctgcaagcggcgctggatggcgtcaccgatgaagcctcgagatgcgcgcgctgcggctgtttcgccgtcgca<br>tcatggtgcgcatcgcctggagccaggcgttacagttggtggcggaagaagatatcctgcaacagcttagcgtgctggcggaaaccctgatcgtc<br>gccgcgcgcgactggctttatgaggcctgctgccgtgagtggggaagcgccgagcaatccacaaggcgtggcgcagccgatgctggtactcggcat<br>gggcaaactgggtggcggcgaactcaatttctcatccgatatcgatttgatttttcgcctgggacggaaaatggcgcaacgcgcggtggacgccgt<br>gagctggataacgcgcaattttttcactcgccttggtcaacggctgattaaagtcctcgaccagccaacgcaggatggctttgtctaccgcgtcga<br>tatgcgcttgcgcccgtttggcgacagcggcccgctggtgctgagctttgccgcgctggaagattactaccaggagcaggggcgcgattgggaac<br>gctacgcgatggtgaaagcgcgcattatgggcgataacgaccgcgaccatgcgcgggagttgcgccgcaatgctgcgccgtttgttttccgccgt<br>tatatcgacttcagcgtgattcagtccctgcgtaacatgaaaggcatgattgcccgcgaagtgcgtcgccgtggcctgaagacaacattaagctc<br>ggcgcgggcgggatccgcgaaatagaatttatcgtccaggttttccagctgattcgcggcggtcgcgagcctgcactgcaatcgcgttcactgtt<br>gccgacgcttgctgccatagatcaactgcatctgctgccggatggcgacgcaacccggctgcgcgaggcgtatttgtggctgcgacggctggaga<br>acctgctgcaaagcatcaatgacgaacagacacagacgctgccgggcgatgaatgaatcgcgcgcgctcgctcggggaatgggcaaagatagc<br>tgggaagcgctctgcgaaacgctcgaagcgcatatgtcggcggtcgtcagatatttaacgatctgattggcgatgatgaaacggattcgcgga<br>agatcgcttctgagagctggccgaattgtgccaggatgcgcagcaggaggaggattccacgcccgtgctggcgcatctctcagaggacgatcg<br>ccgccgcgtggtggcgctgattgccgattttcgcaaagagttggataaacgcaccattggcccgcgagggcggcaggtactcgatcacttaatgc<br>cgcatctgctcagcgatgtatgctcgcgcgacgatgcgccagtaccgctgtcacgcctgacgccgctgctcaccggaattattacccgcaccact<br>tacctttgagctgctaagtgaatttcccggcgcactgaaacacctcatttccctgtgtgccgcgtcgcgatggttgccagtcagaggcgcgctac<br>ccgatcctgcttgatgaattgctcgaccccgaatacgctctcaaccgacggcgatgaatgctatcgcgatgagctgcgcaatacctgctgcg<br>cgtgccggaagatgatgaagagcaacagcttgaggcgctcggcagtttaagcaggcgcagttgctgcgcgtggcggcggcggatattgccggta<br>cgttgccagtaatgaaagtgagcgatcacttaacctggctggcggaagcgattattgatgcggtggtgcagcaagcctgggggcagatggtggcg<br>cgttatgcgcagcaacgcatctgcacgatcgcgaagggcgcggttttgcgtggtcggttattggcggcggtggggagctgggtacag<br>ctccgatctggatctggtattcctgcacgactgcccgatggatgtgatgaccgatggcgagcgtgaaatcgatggtcgccagttctatttgcgtc<br>tcgcgcagcgcgtgatgcacctgtttagcacgcgcacgtcgtccggcatcctttatgaagttgatgcgcgtctgcgtccatctggcgctgcgggg<br>atgctggtcactactacggaatcgttcgccgattaccagcaaaacgaagcctggacgtgggaacatcaggcgctggcccgcggcgtggtgtacg<br>gcgatccgcaactgaccgccgaatttgacgccattcgccgcgatattcgtatcgacgcctcgcgacggcgcaacgctgcaaaccgacgtgcgagaa<br>atgcgcgagaaaatgcgtgcccatcttggcaacagcataaagaccgcttcgatctgaaagccgatgaaggcggtatcaccgacatcgagtttat<br>cgcccaatatctggtgctgcgctttgcccatgacaagccgaaactgacgcgctggtggataatgtgcgcattctcgaaggctggcgcaaaacg<br>gcatcatggaggagcaggaagcgcaggcattgacgctggcgtacaccacattgcgtgatgagctgcaccacctggcgctgcaagagttgccggga<br>catgtggcgctctcctgttttgtcgccgagcgtgcgcttattaaaaccagctgggacaagtggctggtggaaccgtgcgccccggcgtaa |
| 269 | attgaagagtttgatcatggctcagattgaacgctggcggcaggcctaacacatgcaagtcgaacggtagcacagagagcttgactctcgggttg<br>acgagtggcggacgggtgagtaatgtctgggaaactgcctgatggaggggataactactggaaacggtagctaataccgcataacgtcgcaaga<br>ccaaagagggggaccttcgggcctcttgccatcagatgtgcccagatggattagctagtaggtggggtaacggctcacctaggcgacgatccct<br>agctggtctgagaggatgaccagccacactggaactgagacacggtccagactcctacgggaggcagcagtggggaatattgcacaatgggcga<br>agcctgatgcagccatgccgcgtgtgtgaagaaggccttcgggttgtaaagcacttcagcggggaggaagggagtaaggttaataaccttgctc<br>attgacgttacccgcagaagaagcaccggctaactccgtgccagcagccgcggtaatacggagggtgcaagcgttaatcggaattactgggcgta<br>aagcgcacgcaggcggtctgtcaagtcggatgtgaaatccccgggctcaacctgggaactgcatccgaaactggcaggcttgagtctcgtagagg<br>ggggtagaattccaggtgtagcggtgaaatgcgtagagatctggaggaataccggtggcgaaggcggcctcctggacgaagactgacgctcaggt |

TABLE H-continued

| SEQ ID NO: | Sequence |
|---|---|
| | gcgaaagnnnnnnnnnnnaacaggattagatacccctggtagtccatgccgtaaacgatgtctactagccgttggggcctttgaggctttagtggc<br>gcagctaacgcgataagtagaccgcctggggagtacggtcgcaagactaaanctcaaatgaattgacggggcccgcacaagcggtggagcatgt<br>ggtttaattcgatgcaacgcgaagaaccttacctggccttgacatagtaagaattttccagagatggattggtgccttcgggaacttacatacag<br>gtgctgcatggctgtcgtcagctcgtgtcgtgagatgttgggttaagtcccgcaacgagcgcaaccttgtcattagttgctacatttagttggg<br>cactctaatgagactgccggtgacaaaccggaggaaggtggggatgacgtcaagtcctcatgcccttataggtggggctacacacgtcatacaa<br>tggctggtacaaagggttgccaacccgcgagggggagctaatcccataaaaccagtcgtagtccggatcgcagtctgcaactcgactgcgtgaag<br>tcggaatcgctagtaatcgtggatcagaatgtcacggtgaatacgttcccgggtcttgtacacaccgcccgtcacaccatgggagcgggttctgc<br>cagaagtagttagcttaaccgcaaggagggcgattaccacggcagggttcgtgactggggtgaagtcgtaacaaggtagccgtatcggaaggtgc<br>ggctgcatcacctccttt |
| 270 | atgaccatgcgtcaatgcgccatttacggcaaaggtgggatcggcaaatcgaccaccacacagaacctggtcgccgcgctggcggagatgggtaa<br>aaaagtcatgattgtcggctgtgacccgaaagccgattccacgcgtttgatcctgcatgcgaaagcgcagaacaccattatggagatggctgctg<br>aagtcggctccgtggaagacctggagttagaagacgtgctgcaaatcggttacggcggcgtgcgctgcgcagagtccggcggcccggagccaggc<br>gtgggctgtgccggtcgcggggtgatcaccgcgattaacttcctcgaagaagaaggcgcttacgtgccggatctcgattttgttttctacgacgt<br>gctgggcgacgtggtatgcgggtggtttcgccatgccgattcgtgaaaacaaagcgcaggagatctacatcgtttgctctggcgaaatgatggcga<br>tgtacgccgccaacaacatctccaaaggcatcgtgaaatacgccaaatccggtaaagtgcgcctcggcgggctgatttgtaactcgcgccagacc<br>gaccgtgaagatgaactgatcattgcgctggcagaaaaactcggcacgcagatgatccactttgttccccgcgacaacattgtgcagcgtgcgga<br>aatccgccgtatgacggttatcgaatatgacccgacctgcaatcaggcgaacgaatatcgcagccttgccagcaaaatcgtcaacaacaccatna<br>tggtggtgcccaccccctgcaccatggatgaactggaagaactgctgatggagttcggcattatggatgtggaagacaccagcatcattggtaaa<br>accgccgccgaagaaaacgccgtctga |
| 271 | atggccgaaattctgcgcagtaaaaaaccgctggcggtcagcccgataaaaagggccagccgctgggggcgatcctcgcaagcctgggtgtcgaa<br>cagtgcataccgctggtacacggcgcacagggatgtagcgcgttcgcgaaggtgttctttattctacattttcacgatccgatcccgctgcaatc<br>gacggcgatggatccgacttccaccattatgggcgccgatgaaaacatttttaccgcgctcaatgtgctctgccagcgcaacgccgcgaaagcca<br>ttgtgctgctcagcaccgggctttcagaagcccagggcagcgacatttcgcgggtggtgcgccagtttcgtgatgattttccccggcataaaggc<br>gttgcgctgctcaccgtcaacacacccgatttctacggctcgctggaaaacgatctacagccgcgtgctggaaagcatgattgaacagtgggtacc<br>cgcacagcccgccgccagcctgcgcaaccgccgtgtcaacctgctgtcagccattactgacaccaggcgatatcgaactgttgcgcagttatg<br>ttgaagccttcggcctgcaaccggtgattgtgccggatctgtcgctcgctggacgggcatctggcagacggtgattttttgcctgttacccaa<br>ggggaacatcgctgcgcatgattaacagatggggcaaaacctggccacctttgtgattggcgcctcgctgggccgtgcggcggcgttactggc<br>gcagcagccgtggcgaggtgatcgccctgccgcatctgatgacgcttgcagcctgcgacacgtttattcatcgactgaaaaccctctccgggc<br>gcgatgtccccgcgtggattgagcgccagcgcggccaagttcaggatgcgatgatcgattgccatatgtggctgcaggtgcggctatcgccatg<br>gcagcagaaggcgatcacctggcggcatggtgcgattcgcccgcagccagggcatgatccccggcccgattgtcgcaccgctcagccagccggg<br>gttgcaaaatctgccggttgaaaccgtggttatcggcgatctggaagatatgcaggatcggctttgcgcgacgcccgccgcgttactggtggcca<br>attctcatgccgccgatctcgccacgcagtttgatttgtcacttatccgcgccgggttcccggtgtataccggctggggaatttcgtcgcctg<br>cgccaggggtacagcggcattcgtgacacgctgtttgagctgggaatgtgatgcgcgagcgccatcacccgcttgcaacctaccgctcgccgctg<br>cgccagcacgccgacgacaacgttacgcctggagatctgtatgccgcatgttaa |
| 272 | atgaaaaacacaacattaaaaacagcgcttgcttcgctggcgttactgcctggcctggcgatggcggctcccgctgtggcggataaagccgacaa<br>cggctttatgatgatttgcaccgcgctggtgctgtttatgaccattccgggcgatctggcgcttctcacggcggtttgatccgcggtaaaaacgtgc<br>tgtcgatgctgacgcaggttgccgtcacctcgcactggttgcattcgtgggtggtgtatgctactcgctggcatttggcgagggcaacagc<br>ttcttcgggagttttaactgggcgatgttgaaaaacatcgaactgaaagccgtgatgggcagcatttatcagtatatccacgtggcgttccaggg<br>ttccttcgcctgtatcaccgttggcctgattgtcggtgcactggctgagcgtattcgcttactgcggtgctgattttgtggtggtatggctgac<br>gcttttcttacgtgccgattgcacacatggtgggggggcggcggtctgctggcaacccacggtgcgctggatttcgcaggcggtacggttgttcaca<br>tcaacgctgcgattgcaggtctggtgggggcttacctgattggcaaacgcggtggcttttggcaaagaagcattcaaaccgcataacctgccgatg<br>gtcttcactggcaccgctatcctgatgttggctggttttggtttcaacgccggctccgcaagctcggcgaacgaaattgctgcgctggccttcgtg<br>aacactgtcgttgccactgctgccgctattctggcgtgggtatttggcgaatgggcaatgcgcggcaagccgtctctgctcggtgcctgttctgg<br>tgccatcgcgggtctggttggtatcaccccgcctgtggttatgtgggtgtcggcggtgcgctgattgtgggtctgattgccggtctggctgggc<br>tgtggggcgttactgcgctgaaacgtatgttgcgtgtcgatgaccccgtgtgacgtattcggtgtgcacggcgtgtgcggcatcgtgggctgtatc<br>ctgacgggtatcttgcctctacgtcgctgggtggtcggttttcgctgaaggtgtgaccatgggccatcaggtgctggtgcagctggaaagtgt<br>tgccatcactcgtgtgctgcgctggtggtggccttattggttacaaactggcggacatgacggtaggcctgcgcgtaccggaagaacaagaac<br>gtgaagggctggatgtaaacagccacggcgaaaacgcctataacgcctga |
| 273 | cgtcctgtaataataaccggacaattcggactgattaaaaaagcgcccttgtggcgcttttttttatattcccgcctccatttaaaataaaaaatc<br>caatcggatttcactatttaaactggccattatctaagatgaatccgatggaagacgcgtgttttaacacgcgttttttaaccttttattgaaagt<br>cggtgcttcttttgagcgaacgatcaaatttaaatggattcccatcaaaaaaatattctcaacctaaaaaagtttgtgtaatacttgtaacgctac<br>atggagattaactcaatctagagggtattaataatgaatcgtactaaactggtactgggcgc |
| 274 | ggacatcatcgcgacaaacaatattaataccggcaaccacaccggcaatttacgagactgcgcaggcatccttctccccgtcaatttctgtcaaa<br>taaagtaaaagaggcagtctacttgaattaccccggctggttgagcgttttgttgaaaaaagtaactgaaaaatccgtagaatagcgccactct<br>gatggttaattaacctattcaattaagaattatctggatgaatgtgccattaaatgcgcagcataatggtgcgttgtgcgggaatactgctttt<br>tttgaaagggttagtcagtagcggaaac |
| 275 | atgaccctgaatatgatgctcgataacgccgcgccggacgccatcgccggcgcgctgactcaacaacatccggggagttttttaccatggtggaa<br>caggcctcggtggccatctccctcaccgatgccagcgcaggatcatttacgccaaccgcgtttgccgccagcacggctattcgctggcgca<br>attgttaaaccagaacccgctgctggccagcagccagacgcccgcgagatctatcaggagatggcataccctgaccagcgtcagccctg<br>gcgcgggtcagctgattaatcagcgtggcgcggcctgtacctggtggagattgacatcaccccggtgcttagcccgcaagggaactggagc<br>attatctggcgatgcagcgggatatcagcgtcagctacaccctcgaacagcggctgcgcaaccatatgaccctgatgagccggtgctgaataat<br>atccccgccgccgtggtagtggtggacgagcaggatcgggtggtgatggacaacctcgcctacaaaaccttctgcgctgactgcggcggccggga<br>gctgctcaccgagctgcaggtctccccctggcgtgaagtgacgcccggcgtggaggcgatcctgccggtggcgctgcgcggggccgcgcgctggctgt<br>cggtaacctgctggccgttgcccggccgcagtgaagaggccaagggcgccttgaccggctgaagcagcaaatgaccgccgcaagctgctggcggatcgcgagtc<br>gctggacgccgcgctgatccagctgaactgcccgattaatatgctggcggcagcccgtcggctgaacggcagggaagcgggaatggcgctgg<br>aggccgcctggcgtgaagggaagaggcgatggcgcggctccagcgctgtcgcccatcgctggaactcgaaaccccgccgtctggccgctgcag<br>ccctttttcgacgatctgtgcgccctctaccgtacacgcttcgatcccgacggctgcaggtcgacatggcctcaccgcatctgatcggctttgg<br>ccagcgcaccccactgctggcgtgccttaagcctgtggctcgatcgcaccctggccctcgccgccgaactccccctccgtgccgctggcgatgcagc |

TABLE H-continued

| SEQ ID NO: | Sequence |
|---|---|
| | tctacgccgaggagaacgacggctggctgtcgctgtatctgactgacaacgtaccgctgctgcagggcgctacgctcactccccgacgcgctga<br>actcgccgggcaaaggcatggagctgaggctgatccagaccctggtggcgcaccatcgcggggccattgagctggcttcccgaccgcagggcggc<br>acctgcctgaccctgcgtttcccgctgtttaacaccctgaccggaggtgaagcatga |
| 276 | atgatccctgaatccgaccggacaccaccgtcagacgcttcgacctctctcagcagttcaccgccatgcagcggataagcgtggtgctgagccg<br>ggccaccgaggccagcaaaacgctgcaggaggtgctcagcgtattacacaacgatgcctttatgcagcacgggatgatctgcctgtacgacagcg<br>agcaggagatcctcagtatcgaagcgctgcagcaaaccggccagcagcccctcccggcagcacgcagatccgctatcgcccggcgagcgactg<br>gtggggaccgtgctggccaggggcagtcgctggtgctgccccgggtcgccgacgatcagcgttttctcgaccgcctgagcctctacgattacga<br>tctgccgtttatcgccgaccgttgatgcggcccaacgcccggccaataggggtgctggcggcccagccgatgcgcgccaggaagagcggctgcc<br>ggcctgcacccgttttctcgaaaccgtcgccaacctcgtcgcccagaccatccggctgatgatccttccggcctcacccgccctgtcgagccgcc<br>agccgccgaaggtggaacgccgccggcctgctcgtcgtcgcgcggcgtgggccttgacaatatggtcggcaagacccggcgatgcgccagatc<br>gtggaggtgatccgtcaggtttcgcgctgggacaccaccgtgctggtacgcggcgaaagcggcaccgggaaagagctgatcgccaacgccatcca<br>tcaccattcgccacgggctggcgccgccttcgtcaaatttaactgcgcggcgctgccggacaccctgctgaaaagcgaactgttcggccatgaga<br>aaggcgccttaccggggcggtgcgtcagcgtaaaggacgttttgagctggcggatggcgcacccctgttcctcgatgagattggtgaaagcagc<br>gcctcgttccaggccaagagctgcgtatcctccaggaggggggagatggagcgggtcggcggcgatgagaccctgcgggtgaatgtccgcatcatc<br>gccgccaccaaccgtcacctggaggaggaggtccggctgggccatttccgcgaggatctctactatcgtctgaacgtgatgcccatcgccctgcc<br>ccgctgcgcgagcgtcaggaggacatcgccgagctggcgcacttcctggtgcgcaaaatcggccagcatcaggggcgcacgctgcggatcagcg<br>agggcgcgatccgcctgctgatggagtacagctggcgcgggtaacgttcgcgaactggagaactgcctcgaacgatcggcggtgatgtcggagagt<br>ggcctgatcgatcgcgacgtgatcctcttcactcaccaggatcgtcccgcaaagccctgcctgccagcgggccagcggaagacagctggctggac<br>aacagcctggacgaacgtcagcgactgatcgccgcgctggaaaaagcggctgggtgcaggcaaggcggcacggctgctggggatgacgccgcg<br>ccaggtcgcttatcggatccagatcatggatatcaccctgccgcgtctgtag |
| 277 | attgaagagtttgatcatggctcagattgaacgctggcggcaggcctaacacatgcaagtcgagcggcagcgggaagtagcttgctactttgccg<br>gcgagcggcggacgggtgagtaatgtctgggaaactgcctgatggaggggataactactggaaacggtagctaataccgcatgacctcgaaaga<br>gcaaagtgggggatcttcggacctcacgccatcggatgtgcccagatgggattagctagtaggtgaggtaatggctcacctaggcgacgatccct<br>agctggtctgagaggatgaccagccacactggaactgagacacggtccagactcctacgggaggcagcagtgggaatattgcacaatgggcgca<br>agcctgatgcagccatgccgcggtgtgaagaaggccttagggttgtaaagcactttcagcgaggaggaaggcatcatacttaatacgtgtggta<br>attgtcgttactcgcagaagaagcaccggctaactccgtgccagcagccgcggtaatacggagggtgcaagcgttaatcggaattactgggcgta<br>aagcgcacgcaggcggtttgttaagtcagatgtgaaatccccgagcttaacttgggaactgcatttgaaactggcaagctagagtcttgtagagg<br>ggggtagaattccaggtgtagcggtgaaatgcgtagagatctggaggaataccggtggcgaaggcggcccctggacaaagactgacgctcaggt<br>gcgaaagcgtggggagcaaacaggattagataccctggtagtccacgctgtaaacgatgtcgacttggaggttgtgcccttgaggcgtggcttcg<br>gagctaacgcgttaagtcgaccgcctggggagtacggccgcaagtttaaaactcaaatgaattgacgggggcccgcacaaagcggtggagcatgt<br>ggtttaattcgatgcaacgcgaagaaccttacctactcttgacatccagagaatttgccagagatggcgaagtgccttcgggaactctgagacag<br>gtgctgcatggctgtcgtcagctcgtgttgtgaaatgttgggttaagtcccgcaacgagcgcaacccttatcctttgttgccagcacgtaatggt<br>gggaactcaaaggagactgccggtgataaaccggaggaaggtggggatgacgtcaagtcatcattgcccttacgagtagggctacacacgtgcta<br>caatggcatatacaaagagaagcgaactcgcgagagcaagcggacctcataaagtatgtcgtagtccggattggagtctgcaactcgactccatg<br>aagtcggaatcgctagtaatcgtagatcagaatgctacggtgaatacgttcccgggccttgtacacaccgcccgtcacaccatgggagtgggttgc<br>aaaagaagtaggtagcttaaccttcgggagggcgcttaccactttgtgattcatgactggggtgaagtcgtaacaaggtaaccgtaggggaacct<br>gcggttggatcacctcctt |
| 278 | attgaagagtttgatcatggctcagattgaacgctggcggcaggcctaacacatgcaagtcgagcggcatcgggaagtagcttgctactttgccg<br>gcgagcggcggacgggtgagtaatgtctgggaaactgcctgatggaggggataactactggaaacggtagctaataccgcatgacctcgaaaga<br>gcaaagtgggggatcttcggacctcacgccatcggatgtgcccagatgggattagctagtaggtgaggtaatggctnacctaggcgacgatccct<br>agctggtctgagaggatgaccagccacactggaactgagacacggtccagactcctacgggaggcagcagtgggaatattgcacaatcggcgca<br>agcctgatgcagccatgccgcgtgtgaagaaggccttagggggttaaagcactttcagcgaggaggaaggcatcatacttaatacgtgtggta<br>ttgacgttactcgcagaagaagcaccggctaactccgtgccagcagacgggtaatacggagggtgcaagcgttaatcggaattactgggcgtaaa<br>gcgcacgcaggcggtttgttaagtcagatgtgaaatccccgagcttaacttgggaactgcatttgaaactggcaagctagagtcttgtagagggg<br>gtagaattccaggtgtagggtgaaatgcgtagagatctggaggaataccggtggcgaaggcggcccctggacaaagtctgacgctcaggtgcg<br>aaagcgtggggagcaaacaggattagataccctggtagtccacgctgtaaacgatgtcgacttggaggttgtgcccttgaggcgtggcttccgga<br>gctaacgcgttaagtcgaccgcctggggagtacggccgcaaggttaaaactcaaatgaattgacgggggcccgcacaagcggtggagcatggt<br>ttaattcgatgcaacgcgaagaaccttacctactcttgacatccagagaatttgccagagatggcgaagtgccttcgggaactctgagacaggtg<br>ctgcatggctgtcgtcagctcgtgttgtgaaatgttgggttaagtcccgcaacgagcgcaacccttatcctttgttgccagcacgtgatggtggg<br>aactcaaaggagactgccggtgataaaccggaggaaggtggggatgacgtcaagtcatcatggcccttacgagtagggctacacacgtgctacaa<br>tggcatatacaaagagaagcgaactcgcgagagcaagcggacctcataaagtatgtcgtagtccggattggagtctgcaactcgactccatgaagt<br>cggaatcgctagtaatcgtagatcagaatgctacggtgaatacgttcccgggccttgtacacaccgcccgtcacaccatgggagtgggtttgcaaa<br>agaagtaggtagcttaaccttcgggagggcgcttaccactttgtgattcatgactggggtgaagtcgtaacaaggtaaccgtaggggaacctgcg<br>gttggatcacctcctt |
| 279 | attgaagagtttgatcatggctcagattgaacgctggcggcaggcctaacacatgcaagtcgagcggcaggggaagtagcttgctactttgccgg<br>cgagcggcggacgggtgagtaatgtctgggaaactgcctgatggaggggataactactggaaacggtagctaataccgcatgacctcgaaagag<br>caaagtgggggatcttcggacctcacgccatcggatgtgcccagatgggattagctagtaggtgaggttaatggctcacctaggcgacgatccc<br>tagctggtctgagaggatgaccagccacactgaactgagacacggtccagactcctacgggaggcagcagtgggaatattgcacaatgggcgc<br>aagcctgatgcagccatgccgcgtgtgaagaaggccttagggttgtaaagcactttcagcgaggaggaaggcancatacttaatacgtgtggt<br>gattgacgttactcgcagaagaaccggctaactccgtgccagcagccgcggtaatacggagggtgcaagcgttaatcggaattactgggcgt<br>aaagcgcacgcaggcggtttgttaagtcagatgtgaaatccccgagcttaacttgggaactgcatttgaaactggcaagctagagtcttgtagag<br>gggggtagaattccaggtgtagcggtgaaatgcgtagagatctggaggaataccggtggcgaaggcggcccctggacaaagactgacgctcagg<br>tgcgaaaggcgtggggagcaaacaggattagataccctggtagtccacgctgtaaacgatgtcgacttggaggttgtgcccttgaggcgtggctt<br>ccggagctaacgcgttaagtcgaccgcctggggagtacggccgcaaggttaaactcaaatgaattgacgggggcccgcacaagcggtggagcatg<br>tggtttaattcgatgcaacgcgaagaaccttacctactcttgacatccagagaatttgccagagatggcgaagtgccttcgggaactctgagaca<br>ggtgctgcatggctgtcgtcagctcgtgttgtgaaatgttgggttaagtcccgcaacgagcgcaacccttatcctttgttgccagcacgtgatggt<br>gggaactcaaaggagactgccggtgataaaccggaggaaggtggggatgacgtcaagtcatcatggcccttacgagtagggctacacacgtgcta<br>caatggcatatacaaagagaagcgaactcgcgagagcaagcggacctcataaagtatgtcgtagtccggattggagtagcaactcgactccatga<br>agtcggaatcgctagtaatcgtagatcagaatgctacggtgaatacgttcccgggccttgtacacaccgcccgtcacaccatgggagtgggttgc<br>aaaagaagtaggtagcttaaccttcgggagggcgcttaccactttgtgattcatgactggggtgaagtcgtaacaaggtaaccgtaggggaacct<br>gcggttggatcacctcctt |

TABLE H-continued

| SEQ ID NO: | Sequence |
|---|---|
| 280 | attgaagagtttgatcatggctcagattgaacgctggcggcaggcctaacacatgcaagtcgagcgacancgggaagtagcttgctactttgccg gcgagcggcggacgggtgagtaatgtctgggaaactgcctgatggaggggggataactactggaaacggtagctaataccgcatgacctcgaaaga gcaaagtgggggatcttcggacctcacgccatcggatgtgcctagatgggattagctagtaggtgaggtaatggcttacctaggcgacgatccct agctggctgagaggatgaccagccacactggaactgagacacggtccagactcctacgggaggcagcaggggaatattgcacaatgggcgcaag cctgatgcagccatgccgcgtgtgtgaagaaggccttagggttgtaaagcactttcagcgaggaggaagcatcacacttaatacgtgggtgatt gacgttactcgcagaagaagcaccggctaactccgtgccagcagccgcggtaatacggagggtgcaagcgttaatcggaattactgggcgtaaag cgcacgcaggcggtttgttaagtcagatgtgaaatccccgagcttaacttgggaactgcatttgaaactggcaagctagagtcttgtagaggggg tgagaattccaggtgtagcggtgaaatgcgtagagatctggaggaataccggtggcgaaggcggccccctggacaaagactgacgctcaggtgcg aaagcgtggggagcaaacaggattagataccctggtagtccacgctgtaaacgatgtcgacttggaggttgtgcccttgaggcgtggcttccgga gctaacgcgttaagtcgaccgactggggagtacggccgaaaggtttaaaactcaaatgaattgacgggggcccgcacaagcggtggagcatgtgg tttaattcgatgcaacgcgaagaaccttacctactcttgacatccagagaatttgccagagatggcgaaggccttcgggaactctgagacaggtg ctgcatggctgtcgtcagctcgtgttgtgaaatgttgggttaagtcccgcaacgagcgcaacccttatcctttgttgccagcacgtgatggtggg aactcaaaggagactgccggtgataaaccggaggaaggtggggatgacgtcaagtcatcatggcccttacgagtagggctacacacgtgctacaat ggcatatacaaagagaagcgaactcgcgagagcaagcggacctcataaagtatgtcgtagtccggattggagtctgcaactcgactccatgaagt cggaatcgctagtaatcgtagatcagaatgctactgtgaatacgttcccgggccttgtacacaccgcccgtcacaccatgggagtgggttgcaaa agaagtaggtagcttaaccttcgggagggcgcttaccactttgtgattcatgactggggtgaagtcgtaacaaggtaaccgtaggggaacctgcg gttggatcacctcctt |
| 281 | attgaagagtttgatcatggctcagattgaacgctggcggcaggcctaacacatgcaagtcgagcggcagcgggaagaagcttgctactttgccg gcgagcggcggacgggtgagtaatgtctgggaaactgcctgatggagggggataactactggaaacggtagctaataccgcatgacctcgaaaga gcaaagtgggggatcttcggacctcacgccatcggatgtgccagatgggattagctagtagaggtgaggtaatggtcacctaggcgacgatcccta gctggtctgagaggatgaccagccacactggaactgagacacggtccagactcctacgggaggcagcagtggggaatattgcacaatgggcgcaa gcctgatgcagccatgccgcgtgtgtgaagaaggccttagggttgtaaagcactttcagcgaggaggaaggcatcacacttaatacgtgtgttga ttgacgttactcgcagaagaagcaccggctaactccgtgccagcagccgcggtaatacggagggtgcaagcgttaatcggaattactgggcgta aagcgcacgcaggcggtttgttaagtcagatgtgaaatccccgagcttaacttgggaactgcatttgaaactggcaagctagagtcttgtagagg ggggtagaattccaggtgtagcggtgaaatgcgtagagatctggaggaataccggtggcgaaggcggccccctggacaaagactgacgctcaggt gctgaaagcgtggggagcaaacaggattagataccctggtagtccacgctgtaaacgatgtcgacttggaggttgtgcccttgaggcgtggcttcc ggagctaacgcgttaagtcgaccgcctggggagtacggccgcaaggttaaaactcaaatgaattgacgggggcccgcacaagcggtggagcatgt ggtttaattcgatgcaacgcgaagaaccttacctactcttgacatccagagaatttgccagagatggcgaagtgccttcgggaactctgagacag gtgctgcatggctgtcgtcagctcgtgttgtgaaatgttgggttaagtcccgcaacgagcgcaacccttatcctttgttgccagcacgtgatgtg ggaactcaaaggagactgccggtgataaaccggaggaaggtggggatgacgtcaagtcatcatggcccttacgagtagggctacacacgtgctac aatggcatatacaaagagaagcgaactcgcgagagcaagcggacctcataaagtatgtcgtagtccggattggagtctgcaactcgactccatga gtcggaatcgctagtaatcgtagatcagaatgctacggtgaatacgttcccgggccttgtacacaccgcccgtcacaccatgggagtgggttgc aaaagaagtaggtagcttaaccttcgggagggcgcttaccactttgtgattcatgactggggtgaagtcgtaacaaggtaaccgtaggggaacct gcggttggatcacctcctt |
| 282 | gtagctaataccgcatgacctcgaaagagcaaagtgggggatcttcggacctcacgccatcggatgtgcccagatgggattagctagtaggtgag gtaatggctcacctaggcgacgatccctagctggtctgagaggatgaccacactggaacacggtccagactcctacgggaggcagcagtgggga atattgcacaatgggcgcaagcctgatgcagccatgccgcgtgtgtgaagaaggccttagggttgtaaagcactttcagcggag gaaggcatcanacttaatacgtgtgntgattgacgttactcgcagaagaagcaccggctaactccgtgccagcagccgcggtaatacggagggtg caagcgttaatcggaattactgcgcgtaaagcgcacgcaggcggtttgttaagtcagatgtgaaatccccgagcttaacttgggaactgcatttg aaactggcaagctagagtcttgtagagggggtagaattccaggtgtagcggtgaaatgcgtagagatctggaggaataccggtggcgaaggcgg ccccctggacaaagactgacgctcaggtgcgaaagcgtggggagcaaacaggattagataccctggtagtccacgctaaacgatgtcgacttggag gttgtgcccttgaggcgtggcttccggagctaacgcgttaagtcgaccgcctggggagtacggccgcaaggttaaaactcaaatgaattgacggg ggcccgcacaagcggtggagcatgtggtttaattcgatgcaacgcgaagaaccttacctactcttgacatccagagaatttgccagagatggcga agtgccttcgggaactctgagacaggtgctgcatggctgtcgtcagctcgtgttgtgaaatgttgggttaagtcccgcaacgagcgcaaccctta tcctttgttgccagcacgtnatggtgggaactcaaaggagactgccggtgataaac |
| 283 | attgaagagtttgatcatggctcagattgaacgctggcggcaggcctaacacatgaagtcgagcggcagcgggaagtagcttgctactttgccgg cgagcggcggacgggtgagtaatgtcctgatggagggggataactactggaacggtagctaataccgcacctcgaaagagcaaagtgggggatctt cggacctcacgccatcggatgtgccagatgggattagctagtaggtgaggtaatggtcacctaggcgacgatccctagctggtctgagaggat gaccagccacactggaactgagacacggtccagactcctacgggaggcagcagtggggaatattgcacaatgggcgcaagcctgatgcagccatg ccgcgtgtgtgaagaaggccttagggttctaaagcactttcagcgagcaggaaggcatcatacttaatacgtgtggtgattgacgttactcgcag aagaagcaccggctaactccgtgccagcagccgcggtaatacggagggtgcaagcttaatcggaattactgggcgtaaagcgcacgcaggcggtt gttaagtcagatgtgaaatccccgagcttaacttgggaactgcatttgaaactggcaagctagagtcttgtttgaggggggtagaattccaggtg tagcggtgaaatgcgtagagatctggaggaataccggtggcgaaggcggccccctggacaaagactgacgctcaggtgcgaaagcggggagcaa acaggattaatacccctggtagtccacgctgtaacgatgtcgacttggaggttgtgcccctgaggcgtggcttccggagctaacgcgttaagtcgac cgcctggggagtacggccgcaaggttaaaactcaaatgaattgacggggccccgcacaagcggtggagcatgtggtttaattcgatgcaacgcgaa gaaccttacctactcttgacatccagagaatttgccagagatggcgaagtgccttcgggaactctgagacaggtgctgcatggctgtcgtcagct cgtgttgtgaaatgttgggttaagtcccgcaacgagcgcaacccttatcctttgttgccagcacgtaatggtgggaactcaaaggagactgccgg tgataaaccggaggaaggtggggatgacgtcaagtcatcatggcccttacgagtagggctacacacgtgctacaatggcatatacaaagagaagc gaactcgcgagagcaagcggacctcataaagtatgtcgtagtccggattggagtctgcgactcgactccatgaagtcggaatcgctagaatcgta gatcagaatgctacggtgaatacgttcccgggccttgtacacaccgcccgtcacaccatgggagtgggttgcaaaagaagtaggtagcttaacct tcgggagggcgcttaccactttgtgattcatgactggggtgaagtcgtaacaaggtaaccgtaggggaacctgcggttggatcacctcctt |
| 284 | atgaccatgcgtcaatgcgctatctacggtaaaggcggtatcggtaaatccaccaccacccagaatctcgtcgcggccctcgccgagatgggtaa gaaagtgatgatcgtcgctgacgatccgaaagcggatctgccacccgtctgatcctccacgctaaagcccagaacacatcatggagatggcgg aagtgggctcggtcgaggatctggagctcgaagacgttctgcaaatcggctatggcgatgtccgttgcgccgaatccggcggcccggagccaggc gtcggctcgcgccggacgcgggtgatcaccgccatcaacttcctcgaggaaggcgcctatgaagaagatttggatttcgtcttctatgacgtcct cggcgacgtggtctcgcggcggcttcgctatgccgatccgcgaaaacaaagcccaggagatctacatcgtctgctccggcgagatgatggcgatgt atgccgccaacaatatctccaaagggatcgtgaagctgtccaagaacccgcaagggtcgcctccgccggcctgatcgtgtaactcgcgcaaaaccgac cgggaagacgaactgatcatcgccctggcggagaagctggcacgcaaggatcctccacttcgttccccgcgacaacattgtgcagcgcgcggagat ccgccggatgacggtgatcgagtacgacccgacctgtcagcaggcgaggaatatcgtcaactgcgcagaagatcgtcaataacaccaaaaagt ggtgccgacgccgtgcaccatggacgagctggaatcgctgctgatggagttcggcatcatggaagaagaagacaccagcatcattggtaaaaccg ccgctgaagaaaacgcgggcctga |

TABLE H-continued

| SEQ ID NO: | Sequence |
|---|---|
| 285 | atggttaggaaaagtagaagtaaaaatacaaatatagaactaactgaacatgaccatttattaataagtcaaataaaaaagcttaaaacacaaac cacttgcttttttaataataaaggagggggttgggaagactacattagtagcaaatttaggagcagagctatcaataaactttagtgcaaaagttc ttattgtggatgccgaccctcaatgtaatctcacgcagtatgtattaagtgatgaagaaactcaggacttatatgggcaagaaaatccagatagt atttatacagtaataagaccactatcctttggtaaaggatatgaaagtgaccccctataaggcatgtagagaatttcggttttgacataattgt cggtgaccctagacttgctttacaggaagacctttttagctggagactggcgagatgccaaaggcggtgggatgcgaggaattaggacaacttttg tatttgcagagttaattaagaaaagctcgtgagctaaattatgattttgtttctttgacatgggaccatcattaggcgcaatcaacagggcagta ttactggcaatggaattcttttgtcgtcccaatttcaatcgatgtattttcactatgggctattaaaaatattggctccacggtttcaatatggaa aaaagaattagacacagggattcggctctcagaggaacctagcgaattatcacaattatcttcctcaaggaaaactaaagtttctcggttacgtc acccaacaacataaagaacgctctggatacgatacaattcagcttgagaatactgaggaagaaataaaatcgaaacgtcgggtaaaggcgtatga agacattggagaggtgtttccttctaaaattactgagcatcttctaaactttatgatcaaaagatatgaacccacaccttggagatatacgtca tttaggtagtttagctccgaaatcacaatcacaacacgttccgatgatatcagtgtctggtacaggaaattacaccagacttagaaaaagcgcgc gtgaactttatcgagatattgcaagaagatacttagagaacattcagactgctaatgacgtgagaaatag |
| 286 | atgaagggaaaggaaattctggcgctgctggacgaacccgcctgcgagcacaaccagaagcaaaaatccggctgcagcgcccctaagcccggcgc taccgccggcggttgcgccttcgacggcgcgcagataacgctcctgcccatcgccgacgtcgcgcaccctggtgcacggccccatcggctgcgcgg gcagctcgtgggataaccgcggcagcgtcagcgccggcccggccctcaaccggctcggctttaccaccgatcttaacgaacaggatgtgattatg ggccgcggcgaacgccgcctgttccacgccgtgcgtcacatcgtcgaccgctatcatccggcggcggtcttatctacaacacctgcgtaccggc gatggagggcgatgacatcgaggcggtctgccaggccgcacagaccgccacccggcgtcccggtcatcgctattgacgccgccggttctacggca gtaaaaatcttggcaaccgaatggcgggcgacgtgatgctcaggcaggtgattggccagcgcgaaccggcccgttggccagacaacacgccctt gccccggccagcgccacgatatcggcctgattggcgaattcaatatcgcggcgagttctggcaggtccagccgctgacgacgagctggggatc cgcgtcctcggcagcctctccggcgacggccgctttgccgagatccagaccctgcaccgggcgcaggccaatatgctggtgtgctcgcgcgcgct gatcaacgtcgccggggggctggagctgcgctacggcacgccgccgcgcgtggtttgaaggcagctctacgggatccgcgccacctccgacgcttgcgc agctggcgacgctgctgggggatgacgacctgccgccgccaccgaggcgctgatcgcccgcgaagagcaggcggcggagcaggctcttgcgccg tggcgtgagcagctccgcgggcgcaaatgctgctctataccggcggctgaaatcctggtcggtggtatcggcctgcaggatctcggcatgacc gtggtggccaccggcacgcgcaaatccaccgaggaggacaaacagcggatccgtgagctgatgggcgacgaggcggtgatgcttgaggagggcaa tgcccgcaccctgctcgacgtggtgtaccgctatcaggccgacctgatgatcgccggcggacgcaatatgtacaccgcctggaaagcccggctgc cgtttctcgatatcaatcaggagcgcgagcacgcctacgccggcgctatcagggcatcatcaccctcgcccgccagctctgtctgaccctcgccagc cccgtctggccgcaaacgcatacccgcgcccgtggcgctag |
| 287 | atgaccaacgcaacaggcgaacgtaaccttgcgctcatccaggaagtcctggaggtgtttcccgaaaccgcgcgcaaagagcgcagaaagcacat gatgatcagcgatccgagatggagagcgtcggcaagtgcattatctcgaaccgtaaatcgcagcccggggtgatgaccgtgcggcgctgcgccta tgcgggctcgaaaggggtggtgtttgggccaatcaaagacatggcccatatctcgcacgcccatcggctgcgccagtattcccgcgccggac ggcgcaactactataccggcgtcagcggtgtcgacagcttcggcacccctgaacttcacctctgattttcaggagcgcgatattgttttcggcggc gataaaaagctgaccaaactgatcgaagagatggagagctgttcccgctgaccaaagggatcaccatccagtcggagtgcccggtgggcctgatc ggcgatgacatcagcgccgtagccaacgccagcagcaaggcgctggataaaaccggtgatcccggtgcgtcgcgaaggctttcgcggcgtatcgca atcgctgggccaccatatcgccaacgacgtggtgcgcgactgggtgctgaacaatcgcgaaggcagccgtttgccagcacccgtacgatgttg ccatcattggcgattacaacatcggcggcgacgctgggcctcgcgcattctgctggaagagatggggcgtgcgcgtagtggcgcagtggtccggc gacggcaccctggtggagatggagagcacccattcgttaagcttaacctcgtccactgctaccgttcgatgaactatatcgcccgccatatgga ggagaaacatcagatccccatggatggaatataacttcttcggcccgaccaaaatcgctgccgaagatcgccgatcaatttgatgaca ccattcgcgccaatgcggaagcggtgatcgccaaatatgaggggcagatggcggccatcatcgccaaatatcgcccgcggctggagggggcgcaaa gtgctgctgtacatgggggggctgaggccgcgccacgtcatcggcgcctatgaggatctcggggatggagatcatcgccgccggctacgagtttgc ccataacgatgattacgaccgcaccctgacggacctgaaagagggcaccctgctgtttgacgatgccagcagatatgagctggaggccttcgtca aagcgctgaaacctgacctcatcggctccgggatcaaagagaaatatatcttccagaaaatgggggtgcgttccgccagatgcactcctggact attccggcccctatcacgctatgacggcttcgccatcttgcccgcgatatggatatgaccctgaacaatccggcgtggaacgaactgactgcc ccgtggctgaagtctgcgtga |
| 288 | atggcagatattatccgcagtgaaaaaccgctggcggtgagcccgattaaaaccgggcaaccgctcggggcgatcctcgccagcctcgggctggc ccaggccatcccgctggccacggcgcccagggctgcagcgccttcgccaaagtttttctttattcagcatttccatgaccggtgccgctgcagtc gacggccatggatccgaccgccacgatcatgggggccgacggcaatatcttcaccgcgctcgacaccctctgccagcgccacagcccgcaggca tcgtgctgctcagcaccggtctggcggaagcgcagggcagcgatatcgcccgggtggtgcgccagtttcgcgaggcgcatccgcgccataacggc gtggcgatcctcaccgtcaatacccggattttttttggctctatggaaaacgctacagcgcggtgatcgagagcgtgatcgagaagtgggtcgc gccgacgccgcgtccgggcagcgcccgggtcaacctgctggtcagcacctctgttcgccagggatatcgaatggctgggcgctgcgt ggaggcctttggcctgcagccggtgatcctgccggaccctcgcagtcaatggatggccacctcggtgaaggggatttttacgcccctgacccagg gcggcgcctcgctgcgccagattgcccagatgggccagagtagggcagcttcgccattggcgtgtcgctcagagggcggcatcgatcctgaccc aacgcagccgcggcgacgtgatcgccctgccgatctgatgaccctcgaccattgcgataccttatccatcagctggcgaagatgtccggacgcc gcgtaccggcctggattgagcgccagcgtggccagctgcaggatgccgatgctgactgccatatgtggctcaggggcagcatgggcatggcg gcggagggcgacctgctggcggcgtggtgtgatttcgcccgcagccagggggatgcagcccggcccgctggtcgccccaccagcaccccagcct gcgccagctgccggtcgagcaagtcgtgccgggggatcttgaggatctgcagcagctgctgagccaccaacccgccgatctgctggtggctaact ctcacgcccgcgatctggcggagcagtttgccctgccgctgatccgcgtcggttttcccctcttcgacggctcggtgagtttcgtcgagtccgc caggggtacgccggtatgcgagatacgctgtttgaactggccaatctgctgcgcgaccgccatcaccacaccgccctctaccgctcgccgcttcg ccagggcgccgaccccagccggcttcaggagacgcttatgccgcccattaa |
| 289 | atgagccaaacgatcgataaaattcacagctgttatccgatatttgaacaggatgaataccagaccctgttccagaataaaaagacccttgaaga ggcgcacgacgcggacgtgtgcaggaggttttgcctggaccaccaccgccgagtcatgcaagctgaacttccagcgcgaggcgctgaccgtcg acccggcaaagcctgccagccgtcggcgccgtactctgcgcgtcggggttcgccggcaccctgcctacgtgcacggctcccagggctgcgtc gcctatttcgcacctactttaaccgccattttaaagagccggtcgcctgcgtctccgactccatgaccgaggacgcggcgttcggcgcaac aacaacatgaatctgggcctgcacaatgccagcgcgctgtataaacccgagattatcgccgtctccaccacctgtatggccgaggtgatcggcga cgatctgcaggcgttttatcgccaacgccaaaaaaagagggattttgttgacgacgcatcgccattccttacgccccatacccccagcttttatcggca gccatgtcaccgagctgggacaatatgttcgaagggttcgcgaagaccttttaccgctacgccggagcgggcaaacagaaaaagctcaat ctggtgaccggatttgagacctatctcggcaacttccgcgtgctgaagcagtgatgatgcgcagatggatgtccctgcagcctgctctccgaccc atcagaggtgctcgacacccccgccgacggccattaccggatgtacgccggcggcaccagccagcaggagatcaaaaccgcgccgacgccattg acacccctgctgctgcagccgtgacgatggtgaaaagcaaaaaggtggttcaggagatcgtgaacccagcccgccaccgaggtggccgttccgctg ggcctgacgccaccgacgcgctgctgatgaccgtcagtcagtcgaccggcaaaccgatcgccgacgctctgaccctggagagagcggcgtggt cgacatgatgctggattccacacctggctgcatgcaaaaaattcggcctctacggcgatccggatttcgtgatgggctgacgcgcttcctgc tggagctgggctgcgagccgacggtgatcctcagtcataacgccaataaacgctggcaaaaagcgatgaagaaatgctcgatgcctcgccgtac ggtcaggaaagcgaagtgttcatcaactgcgaccctgtggcacttccggtcgctgatgttcaccgtcagccggactttatgatcggtaactccta cggcaagtttatccagcgcgatacctggcaaagggcaaagccttcgaagtgccgatgatccgtctgggcttccgctgttcgaccgccatcatc |

TABLE H-continued

| SEQ ID NO: | Sequence |
|---|---|
| | tgcaccgccagaccacctggggctatgaaggcgcaatgaacatcgtcacgacgctggtgaacgccgtgctggaaaaactggaccacgacaccagc<br>cagttgggcaaaaccgattacagcttcgacctcgttcgttaa |
| 290 | atgatgccgctttctccgcaattacagcagcactggcagacggtcgctgaccgtctgccagaggattttcccattgccgaactgagcccacaggc<br>caggtcggtcatggcgttcagcgattttgtcgaacagagtgtgatcgcccagccgggctggctgaatgagcttgaggactcctcgccggaggcgg<br>aagagtggcggcattacgaggcctggctgcaggatcgcctgccaggccgtcactgacgaaggggggttgatgcgagagctgcgtctcttccgccgcc<br>agatgatggtccgcatcgcctgggcgcaggcgctgtcgctggtgagcgaagaagagactctgcagcagctgagcgtcctggccggagaccctgatt<br>gtcgccgcccgcgactggctgtacgccgctgctgtaaggagtggggaacgccatgcaatgccgagggccagccgcagccgctgctgatcctcgg<br>gatgggaaagctgggcggcggcgagctgaacttctcttcccgatatcgatctgatctttgcctggcctgagcatggcgccacccgcggcggccgcc<br>gcgagctggataacgcccagttcttacccgtctggggcagcggctgatcaaggcccttgaccagccgacgcaggacggcttttgtctatcgggtt<br>gacatgcgcctgcgccgtttggcgacagtgggccgctggtactcagttttgcggcgctggaagattattaccaggagaagggtcgggactggga<br>acgctatgcgatggtgaaagcgcggatcatggccgataacgacggcgtgtacgccagcgacttgcgcgcgatgctccgtcctttcgtcttccgcc<br>gttatatcgacttcagcgtgatccagtcgctgcgtaacatgaaaggcatgatcgcccgcgaagtgcggcgtcgcgggctgaaagacaacatcaag<br>ctcggcgccggcgggatccgtgaaattgagtttatcgttcaggctttcaactgatccgcggtggtccgaacctgcactgcagcagcgcgccctg<br>ctgccgacgctggcggcggcgattgatgagctacatctgctgccggaaggcgacgcggcgctgctgcgcgaggcctatctgttcctgcgccggctgga<br>aaacctgctgcaaagcatcaacgatgagcagacccagaccctgccgcaggatgaacttaaccgcgccaggctggcgtggggatgcataccgaag<br>actgggagacgctgagcgcgcagctggcgagccagatggccaacgtgcggcgagtgtttaatgaactgatcggcgatgatgaggatcagtccccg<br>gatgagcaactggccgagtactggcgcgagctgtggcagcatcgcgctggagaagatgacgccagccggcgctggcgcattaaacgatacga<br>ccgccgtagcgtgctggcgctgattgccgattttcgtaaagagctggatcggcgcaccatcgccccgccggccgcaggtgctggatcagcttg<br>atgccgcatctgctgagcgaaatctgctcgcgcgccgatgcgccgctgcctctggcgcggatcacgccgctgttgaccgggatcgtcaccgtac<br>cacctatcttgagctgctgagcgaattcccggcgcgctgaagcacctgatcacgctctgcgcggcgtcgccgatggtcgccagccagctggcgc<br>gccaccgctgctgctggatgagctgctggatccaaccaccctctatcagccgacggcgaccgatgcctatcgcgacgagctgcgccagtacctg<br>ctgccgcgtgccggaagaggatgaagagcagcagatgaaggcgtttgcgcccagtttaagcaggcgcagcagctgcatatcgcggcgggatatcgc<br>tggtaccctgccggtgatgaaggtcagcgatcacttaacctggcttgccgaagcgatcctcgacgcggtggtgcagcaggcatgggggcagatgg<br>tcgctcgctacgccagccgacccacctgcacgatcgccagggtcgcggcttcgccgtcgtcggctacgctaagcttggcggctgggagctgggc<br>tacagctccgatctcgatctggtgttcctccatgactgcccggcggaggtgatgaccgacggcgagcgggagattgacggccgtcagttctacct<br>gcggctgcccagccggatcatgcacctgttcagcaccgccacctcgtccggtattctctacgaagttgacgcccggagcgccttctggcgcggcg<br>gggatgctggtcaccaccgccgacgcgttgctgactatcagcagaacgaagcaggacgtgggaacatcaggcgctggtgcgcgcccgcgtggtc<br>tatggcgaccggcgctgcaggcgcgctttgacgccattcgtcgcgatatcctgaccaccccgcgggaggggatgaccctgcagaccgaggttcg<br>cgagatgcgcgagaagatgcgcgcccaccttggcaacaaacatcccgatcgttttgatatcaaagccgatgccggcgggatcaccgatattgaat<br>ttattactcagtctggtcctacgctatgccagtgacaagccgaagctgacccgctggtctgacaacgtgcgtattcttgagctgctggcgcag<br>aacgacatcatggaggaggaggaggcgcgcgccttaacgcatgcgtacaccaccttgcgtgatgcgctccatcacctggccctgcaggagcagcc<br>gggacacgtggcgccagaggccttcagccgggagcgtcagcaggtcagcgccagctggcagaagtggctcgatggcttaa |
| 291 | agtctgaactcatcctgcgcagtcggtgagacgtattttttgaccaaagagtgatctacatcacggaattttgtggttgttgctgcttaaaaggg<br>caaatctacccttagaatcaactgttatatcaggggggattcagagagatattaggaatttgcacaagcgcacaatttaaccacatcatgataacg<br>ccatgtaaaacaaagataaaaaaacaaaatgcagtgacttacatcgcaagcaaggcattttcttatccaattgctcaaagtttggcctttcatat<br>cgcaacgaaaatgcgtaatatacgcgcccttgcggacatcagtatggtcattcctagttcatgcgcatcggacaccaccagcttacaaattgcct<br>gattgcggccccgatggccggtatcactgaccgaccatttcgtgccttatgtcatgcgatgggggctgg |
| 292 | tgaacatcactgatgcacaagctacctatgacgaagaattaactaaaaaactgcaagatgaggcattcgcgttaaagccgacttgagaaatgaga<br>agattggctttaaaattcgcgaacacacgctacgccgtgttcatatatgttagtttgtggcgataaagaggtcgaagcaggcaaagttgctgttc<br>gtacccgccgcggcaaagacttaggaagcatggatgttagcgaagtcgttgacaaactgctgcagcgagaaatccgcagcgagatcttcatcaactg<br>gaggaataaagtattaaaggcggaaaacgagttcaaccggcgcgtcctcaatcgcattaacaaagagattcgccgcgcaagaagttcgcctcacagg<br>cgtcgatggcgagcagattggtattgtcagtagaatgaagctcttgaaaaagctgaggaaggggcgtcgatttagtagaaatcagtccgaatgcc<br>gagccgccagtttgtcgaatc |
| 293 | tacagtagcgcctctcaaaaatagataaaacggctcatgtacgtgggccgtttattttttctacctataatcgggaaccggtgttataatgccgcg<br>ccctcatattgtggggattcttaatgaccctatcctgggtcctaaagttgtagttgacattagcggagcactaac |
| 294 | aatttttttttcacaaagcgtagcgttattgaatcgcacattttaaactgttggccgctgtggaagcgaatattcgtgaaagtgcggttttaaggc<br>cttttcttttgactctctgtcgttacaaagttaatatgcgcgccct |
| 295 | ttaaaaacgtgaccacgagcattaataaacgccacgaaatgtggcgtttattttattcaaaaagtatctctttcataaaaagtgctaaatgcagta<br>gcagcaaaatgggataagtcccatggaatacggctgttttcgctgcaattttttaacttttttcgtaaaaaagatgttcttttgagcgaacgatc<br>aaaatatagcgttaaccggcaaaaaattattctcattagaaaatagtttgtgtaatacttgtaacgctacatggagattaacttaatctagaggg<br>ttttata |
| 296 | atggcgctcaaacagttaatccgtctgtgtgccgcctcgccgatggtcgcgacacaacttgcacgtcatcctttattgctcgatgaactgctcga<br>cccgcgcacgctttaccagccgattgagcgggcgcttaccgcgacgaactgcgtcagtatctgatggcgggtgccaacagaagacgaagaacagc<br>agcttgaagccgtgcgccagttcaaacaggccagcatttgcgtatcgcagccggggatatttccggggcattgccggtgatgaaagtcagtgac<br>catttaacctaccttgccgaggccattctcgatgtcgtggtgcagcatgcgtgggaacaaatggtcgtaaaatacgggcagcccgcgcatcttca<br>gcaccgtgaggggcgcggttttgccgtggtcggttacgggaaactcggtggctgggagctggttatagctcagatctggatctggtcttcctgct<br>cgattgcgcgccggaggtgatgacggccgaaccgcagcatcgacggacgtcagttttatcttcggctggcgcagcgcattatgcacttattca<br>gcacccggacatcgtcaggcattctttacgaggttgatccgcgtctgcgacctttccgcgcatccatgctggtcagtaccattgaagcgttt<br>gcagattatcaggccaatgaagcctggacgtgggagcatcaggcgctggtcgcgcgcgtggtttacggggatccgcaactgacacagcaatt<br>taacgccacgcgtcgcgacattctttgccgccagcgcgatggcgacggcctgcgtaaggaggtccgtgaaatgcgcgagaaatgtatgcccatc<br>tggggagtaaaaaagcccacgagtttgactgaaagccgatccgggtggcatcacggatattgaattcattgcacaatacctggttctgcgtttcg<br>cgcatgatgagccgagctgacgcgctggtctgataacgtcggattttttgaactgatggcacgatatgacatcatgccggaagaggaagcgcgcc<br>atctgacgcaggcttatgtgacgctgcgcgatgaaattcatcctggcgttgcaggaacacagcgggaaagtggccgcggacagctttgctact<br>gagcgcgcgcagatccgtgccagctgggcgaagtggctcggctga |
| 297 | cggtactggaacagaaatcggcggatgcgcaggaaatttgttatgacacggcctgtctgaagtgcaagttagtgcttacttcctggctggcaacc<br>tcaggctggacgcgtttattgatgataaatctgcgaagaaactggacgcttccttcaaacgttttgctgacatcatgctcggtcgtaccgcagc<br>ggatctgaaagaagcctttgcgcagccactgacggaagaaggttatcgcgatcagctggcgcgcctgaaacgccagatcattaccttccatttga<br>tgccggtgcttaccctgaaaaagacgtcgatgcgtatattgccggctgggtggacctgcaacaggccatcgttcagcagcaacacgcctgggagg<br>attcggcccgtctcacgcggtgatgatggatgctttctggtttaaacgggcaacctcgttaactgactgactagcctgggcaaactgccccgggctt |

TABLE H-continued

| SEQ ID NO: | Sequence |
|---|---|
| | tttttttgcaaggaatctgatttcatggcgctcaaacagttaatccgtctgtgtgccgcctcgccgatggtcgcgacacaacttgcacgtcatcct<br>ttattgctcgatgaactgctcgacccgcgcacgctttaccagccgattgagccgggcgcttaccgcgacgaactgcgtcagtatctgatgcgggt<br>gccaacagaagacgaagaacagcagcttgaagccgtgcgccagttcaaacaggcccagcatttgcgtatcgcagccggggatatttccggggcat<br>tgccggtgatgaaagtcagtgaccatttaacctaccttgccgaggccattctcgatgtcgggtgcagcatgctgtgggaacaaatggtcgtaaaa<br>tacgggcagcccgcgcatcttcagcaccgtgaggggcgcggttttgccgtggtcggttacgggaaactcggtggctgggagctgggttatagctc<br>agatctggatctggtcttcctgctcgattgcgcgccggaggtgatgacggacggcgaacgcagcatcgacggacgtcagttttatcttcggctgg<br>cgcagcgcattatgcacttattcagcacccggacatcgtcaggcattctttacgaggttgatccgcgtctgcgaccttccggcgcatccggcatg<br>ctggtcagtaccattgaagcgtttgcagattatcaggccaatgaagcttgacgtgggagcatcaggcgctggttcgcgcgcgcgtggtttacggg<br>ggatccgcaactgacacagcaatttaacgccacgcgtcgcgacattctttgccgccagcgcgatggcgacggcctgcgtaaggaggtccgtgaaa<br>tgccgcgagaaaatgtatgcccatctggggagtaaaaaagcccacgagtttgatagaaagccgatccgggtggcatcacggatattgaattcattg<br>cacaatacctggttctgcgtttcgcgcatgatgagccgaagctgacgcgctggtctgataacgtcgcggattttttgaactgatgcacgatatgac<br>atcatgccggaagaggaagcgcgccatctgacgcaggcttatgtgacgctgcgcgatgaaattcatcatctggcgttgcaggaacacagcgggaa<br>agtggccgcggacagctttgctactgagcgcgcgcagatccgtgccagctgggcaaagtggctcggctgagggttttattcggctaacaggcgc<br>ttgtgatattatccggcgcattgtatttacccgatttgatttatctgtttggagtcttgggatgaaagtgacttttgcagattttcaccgcgcag<br>gtgtgctggttgtcggtgacgtaatgttagaccgttactggtatggcccgaccaatcgtatttctccggaagctccggtgccggtggtgaaggtc<br>agtaccattgaagagcggcctggcggtgcagctaacgtggcgatgaacatttcatctctgggcgcctcttcctgtctgatcggcctgaccggcgt<br>agacgacgctgcgcgtgccctcagtgagcgtctggcagaagtgaaagttaactgcgttttcgtcgcactatccacacatcctaccatcaccaaac<br>tgcgaattttgtcccgtaaccagcaactgatccgcctcgactttgaggaaggttttgaaggcgttgatctcgagccgatgctgaccaaaatga |
| 298 | atgagcatcacgcgcgttatcagcatcatttcctgaggggaatatcgccagccgcttgtcgctgcaacatccttcactgttttataccgtggttga<br>acaatcttcggtggcgatttcgctgaccgatccgcaggcgcgcatttgttatgccaatccggcattctgccgccagacgggttttgcacttgaga<br>cacttttgggcgagaaccaccgtctgctggagtctgaactcatcctgcgatggggctgggccgtctctgaagctctcggtgaacattgttgcga<br>ggcaggatgcgagctggttgtgttttgacattaccgataatgtgccgcgtgaacggtgcgttatgcccgcccggaagggcgttttcccgtccgg<br>ggaatggcatggagctgcgccttatccagacgctgatcgcccatcatcgcggttctttagatctctcggtccgccctgatggcggcaccttgctg<br>acgttacgcctgccggtacagcaggttatcaccggaggcttaaaatga |
| 299 | tgtttcgtctcgaggccgggcaactgagcggccccgttgaaaccgacctgggctggcatctgttgttgtgcgaacaaattcgcctgccgcaacctt<br>gccgaaagcccaagccttaacgcgggtgcgtcagcaactgattgcccggcaacagaaacattatcagcgccagtggctgcaacaactgatcaacg<br>cctgagcctgttctccttcttgttgatgcagacgggttaatgcccgttttgcacgaaaaatgcacataaattgcctgcgttgccttataacaggc<br>agggaaatcctgcctccggccttgtgccacaccgcgctttgcctggttgtggtaaaaactggcccgctttgcatcctgatgcttaaaacacccc<br>gttcagatcaaccttgggcagataagcccgcgaaacgcctgcaaattgcacggttattccgggtgagtatatgtctgtgatttgggttccggcatt<br>gcgcaataaaggggagaaagacatgagcatcacgcgcgttatcagcatcatttcctgacgggaatatcgccagccgcttgtcgctgcaacatcctt<br>cactgttttataccgtggttgaacaatcttcggtggcgatttcgctgaccgatccgcaggcgcgcatttgttatgccaatccggcattctgccgc<br>cagacgggttttgcacttgagacacttttgggcgagaaccaccgtctgctggagtctgaactcatcctgcgatggggctgggccgtctctgaag<br>ctctcggtgaacattgttgcgaggcaggatgcgagctggttgtgttttcacattaccgataatgtgccgcgtgaacggtgcgttatgcccgccc<br>ggaagcggcgttttcccgtccggggaatggcatggagctgcgccttatccagacgctgatcgcccatcatcgcggttctttagatctctcggtcc<br>gccctgatggcggcaccttgctgacgttacgcctgccggtacagcaggttatcaccggaggcttaaaatgacccagttacctaccgcgcgcccgg<br>ttatccggcgctttgatatgtctgcccagtttacggcgctttatcgcatcagcgtggcgctgagtcaggaaagcaacaccgggcgcgcactggcg<br>gcgatcctcgaagtgcttcacgatcatgcatttatgcaatacggcatggtgtgtctgtttgataagaacgcaatgcactctttgtggaatccct<br>gcatggcatcgacggcgaaaggaaaaaagagacccgccatgtccgttaccgcatggggggaaggcgtgatcggcgcggtgatgagccagcgtcagg<br>cgctggtgttaccgcgcattttcagacgatcagcgttttctcgacccgcctgaatatttacgattacagcctgccgttgattggcgtgccgatcccc<br>ggtgcggataatcagccatcgggcgtgctggtggcacagccgatggcgttgcacgaagaccggctgactgccagtacgcggttttttagaaatggt<br>c |
| 300 | atgagcatcacgcgcgttatcagcatcatttcctgaggggaatatcgccagccgcttgtcgctgcaacatccttcactgttttataccgtggttga<br>acaatcttcggtggcgatttcgctgaccgatccgcaggcgcgcatttgttatgccaatccggcattctgccgccagacgggttttgcacttgaga<br>cacttttgggcgagaaccaccgtctgctggttaaagcctgccggtacagcaggttatcaccggaggcttaaaatga |
| 301 | tgtttcgtctcgaggccgggcaactgagcggccccgttgaaaccgacctgggctggcatctgttgttgtgcgaacaaattcgcctgccgcaaccc<br>ttgccgaaagccgaagccttaacgcgggtgcgtcagcaactgattgcccggcaacagaaacattatcagcgccagtggagcaacaactgatcaac<br>gcctgagcctgttctccttcttgttgatgcagacgggttaatgcccgttttgcacgaaaaatgcacataaattgcctgcgttgccttataacac<br>gcagggaaatcctgcctccggccttgtgccacaccgcgctttgcctggtttgtggtaaaaactggcccgctttgcatcctgatgcttaaaacac<br>cccgttcagatcaaccttgggcagataagcccgcgaaaggcctgcaaattgcacggttattccgggtgagtatctgtgatttgggttccggc<br>attgcgcaataaaggggagaaagacatgagcatcacgcgcgttatcagcatcatttcctgaggggaatatcgccagccgcttgtcgctgcaacatc<br>cttcactgttttataccgtggttgaacaatcttcggtggcgatttcgctgaccgatccgcaggcgcgcatttgttatgccaatccggcattctg<br>ccgccagacgggttttgcacttgagacacttttgggcgagaaccaccgtctgctggttaaagcctgccggtacagcaggttatcaccggaggctt<br>aaaatgacccagttacctaccgcgcgcccggttatccggcgctttgatatgtctgcccagtttacggcgctttatcgcatcagcgtggcgctgag<br>tcaggaaagcaacaccgggcgcgcactggcggcgatcctcgaagtgcttcacgatcatgcatttatgcaatacggcatggtgtgtctgtttgata<br>agaacgcaatgcactctttgtggaatccctgcatggcatcgacggcgaaaggaaaaaagagacccgccatgtccgttaccgcatggggaaggc<br>gtgatcggcgcggtgatgagccagcgtcaggcgctggtgttaccgcgcattttcagacgatcagcgttttctcgaccgcctgaatatttacgatta<br>cagcctgccgttgattggcgtgccgatccccggtgcggataatcagccatcgggcgtgctggtggcacagccgatggcgttgcacgaagaccggc<br>tgactgccagtacgcggttttttagaaatggtc |
| 302 | atgagcatcacgcgcgttatcagcatcatttcctgaggggaatatcgccagccgcttgtcgctgcaacatccttcactgttttataccgtggttga<br>acaatcttcggtggcgatttcgctgaccgatccgcaggcgcgcatttgttatgccaatccggcattctgccgccagacgggttttgcacttgaga<br>cacttttgggcgagaaccaccgtctgctggagtctgaactcatcctgcgggcagtcggtgagacgtatttttgaccaaagagtgatctacatcacg<br>gaatttttgtggttgttgctgcttaaagggcaaatctacccttagaatcaactgttatatcagggggattcagagagatattaggaatttgcaca<br>agcgcacaatttaaccacatcatgataacgccatgtaaaacaaagataaaaaacaaaatgcagtgacttacatcgcaagcaaggcatttcttat<br>ccaattgctcaaagtttggccttcatatgcaacgaaaatgcgtaatatacgcgccttgcggacactgacgtatgtgcattcctagttcatgcat<br>catcggacaccaccagcttacaaattgcctgattgcggccccgatggccggtatcactgaccgaccatttcgtgccttatgtcatgcgatgggg<br>ctggcccgtctctgaagctctcggtgaacattgttgcgaggcaggatgcgagctggttgtgttttgacattaccgataatgtgccgcgtgaacgg<br>gtgcgttatgcccgcccggaagggcgttttcccgtccggggaatggcatggagctgcgccttatccagacgctgatcgcccatcatcgcggttct<br>ttagatctctcggtccgccctgatggcggcaccttgctgacgttacgcctgccggtacagcaggttatcaccggaggcttaaaatga |
| 303 | tgtttcgtctcgaggccgggcaactgagcggccccgttgaaaccgacctgggctggcatctgttgttgtgcgaacaaattcgcctgccgcaaccc<br>ttgccgaaagccgaagccttaacgcgggtgcgtcagcaactgattgcccggcaacagaaacattatcagcgccagtggctgcaacaactgatcaa<br>cgcctgagcctgttctccttcttgttgatgagacgggttaatgcccgttttgcacggaaaatgcacataaattgcctgcgttgccttataacagc |

TABLE H-continued

| SEQ ID NO: | Sequence |
|---|---|
| | gcagggaaatcctgcctccggccttgtgccacaccgcgctttgcctggtttgtggtaaaaactggcccgctttgcatcctgatgcttaaaacacc<br>ccgttcagatcaacctttgggcagataagcccgcgaaaggcctgcaaattgcacggttattccgggtgagtatatgtgtcatttgggttccgcca<br>ttgcgcaataaaggggagaaagacatgagcatcacggcgttatcagcatcatttcctgaggggaatatcgccagccgcttgtcgctgcaacatcc<br>ttcactgttttataccgtggttgaacaatcttcggtggcgatttcgctgaccgatccgcaggcgcgcatttgttatgccaatccggcattctgcc<br>cccagacgggttttgcacttgagacacttttgggcgagaaccaccgtctgctggagtctgaactcatcctgcggcagtcggtgagacgtattttt<br>gaccaaagagtgatctacatcacggaattttgtggttgttgctgcttaaaagggcaaatctacccttagaatcaactgttatatcagggggattc<br>agagagatattaggaatttgcacaagcgcacaattaaccacatcatgataacgccatgtaaaacaaagataaaaaaacaaaatgcagtgactta<br>catcgcaagcaaggcattttcttatccaattgctcaaagtttggcctttcatatcgcaacgaaaatgcgtaatatacgcgccttgcggacatca<br>gtatggtcattcctagttcatgcgcatcggacaccaccagcttacaaattgcctgattgcggcccgatggccggtatcactgaccgaccatttc<br>gtgccttatgtcatgcgatgggggctgggccgtctctgaagctctcggtgaacattgttgcgaggcaggatgcgagctggttgtgttttgacatt<br>accgataatgtgccgcgtgaacgggtgcgttatgcccgcccggaagcggcgttttcccgtccggggaatggcatggagctgcgccttatccagac<br>gctgatcgcccatcatcgcggttctttagatctctcggtccgccctgatggcggcacctgctgacgttacgcctgccggtacagcaggttatca<br>ccggaggcttaaaatgacccagttacctaccgcgggcccggttatccggcgctttgatatgtctgcccagtttacggcgctttatcgcatcagcg<br>tggcgctgagtcacgaaagcaaccaccgggcgcgcactggcgccgatcctcgaagtgcttcacgatcatgcatttatgcaatacggcatggtgtgc<br>tgtttgataaagaacgcaatgcactctttgtggaatccctgcatggcatcgacggcgaaaggaaaaaagagacccgccatgtccgttaccgcatg<br>ggggaaggcgtgatcggcgcggtgatgagccagcgtcaggcgctggtgttaccgcgcatttcagacgatcagcgttttctcgaccgcctgaatat<br>atttacgattacagcctgccgttgattggcgtgccgatccccggtgcggataatcagccatcgggcgtgctggtggcacagccgatggcgttgca<br>cgaagaccggctgactgccagtacgcggtttttagaaatggtc |

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

CLAUSES

1. A method of increasing nitrogen fixation in a non-leguminous plant, comprising:
   a. applying to the plant a plurality of non-intergeneric bacteria, said plurality comprising non-intergeneric bacteria that:
      i. have an average colonization ability per unit of plant root tissue of at least about $1.0 \times 10^4$ bacterial cells per gram of fresh weight of plant root tissue, and/or
      ii. produce fixed N of at least about $1 \times 10^{-17}$ mmol N per bacterial cell per hour, and
      wherein the plurality of non-intergeneric bacteria, in planta, produce 1% or more of the fixed nitrogen in the plant, and
      wherein each member of the plurality of non-intergeneric bacteria comprises at least one genetic variation introduced into at least one gene, or non-coding polynucleotide, of the nitrogen fixation or assimilation genetic regulatory network, such that the non-intergeneric bacteria are capable of fixing atmospheric nitrogen in the presence of exogenous nitrogen.

2. The method according to clause 1, wherein the plurality of non-intergeneric bacteria comprise bacteria that: have an average colonization ability per unit of plant root tissue of at least about $1.0 \times 10^4$ bacterial cells per gram of fresh weight of plant root tissue.

3. The method according to clause 1, wherein the plurality of non-intergeneric bacteria comprise bacteria that: produce fixed N of at least about $1 \times 10^{-17}$ mmol N per bacterial cell per hour.

4. The method according to clause 1, wherein the plurality of non-intergeneric bacteria comprise bacteria that: have an average colonization ability per unit of plant root tissue of at least about $1.0 \times 10^4$ bacterial cells per gram of fresh weight of plant root tissue and produce fixed N of at least about $1 \times 10^{-17}$ mmol N per bacterial cell per hour.

5. The method according to clause 1, wherein the at least one genetic variation comprises an introduced control sequence operably linked to the at least one gene of the nitrogen fixation or assimilation genetic regulatory network.

6. The method according to clause 1, wherein the at least one genetic variation comprises a promoter operably linked to the at least one gene of the nitrogen fixation or assimilation genetic regulatory network.

7. The method according to clause 1, wherein the at least one genetic variation comprises an inducible promoter operably linked to the at least one gene of the nitrogen fixation or assimilation genetic regulatory network.

8. The method according to clause 1, wherein the plurality of non-intergeneric bacteria do not comprise a constitutive promoter operably linked to a gene of the nitrogen fixation or assimilation genetic regulatory network.

9. The method according to clause 1, wherein the plurality of non-intergeneric bacteria do not comprise a constitutive promoter operably linked to a gene in the nif gene cluster.

10. The method according to clause 1, wherein the plurality of non-intergeneric bacteria, in planta, excrete nitrogen-containing products of nitrogen fixation.

11. The method according to clause 1, wherein the plurality of non-intergeneric bacteria applied to the plant do not stimulate an increase in the uptake of exogenous non-atmospheric nitrogen.

12. The method according to clause 1, wherein the plant is grown in soil from a field which has been administered at least about 50 lbs of nitrogen-containing fertilizer per acre, and wherein the nitrogen-containing fertilizer comprises at least about 5% nitrogen by weight.
13. The method according to clause 1, wherein the plant is grown in soil from a field which has been administered at least about 50 lbs of nitrogen-containing fertilizer per acre, and wherein the nitrogen-containing fertilizer comprises at least about 5% nitrogen by weight, and wherein the nitrogen-containing fertilizer comprises ammonium or an ammonium containing molecule.
14. The method according to clause 1, wherein the exogenous nitrogen is selected from fertilizer comprising one or more of: glutamine, ammonia, ammonium, urea, nitrate, nitrite, ammonium-containing molecules, nitrate-containing molecules, and nitrite-containing molecules.
15. The method according to clause 1, wherein the plurality of non-intergeneric bacteria, in planta, produce 5% or more of the fixed nitrogen in the plant.
16. The method according to clause 1, wherein the plurality of non-intergeneric bacteria, in planta, produce 10% or more of the fixed nitrogen in the plant.
17. The method according to clause 1, wherein the plurality of non-intergeneric bacteria, in planta, fix atmospheric nitrogen in non-nitrogen-limiting conditions.
18. The method according to clause 1, wherein the plurality of non-intergeneric bacteria, in planta, excrete nitrogen-containing products of nitrogen fixation.
19. The method according to clause 1, wherein the fixed nitrogen produced by the plurality of non-intergeneric bacteria is measured through dilution of enriched fertilizer by atmospheric $N_2$ gas in plant tissue.
20. The method according to clause 1, wherein the at least one gene, or non-coding polynucleotide, of the nitrogen fixation or assimilation genetic regulatory network are selected from the group consisting of: nifA, nifL, ntrB, ntrC, polynucleotide encoding glutamine synthetase, glnA, glnB, glnK, drat, amtB, polynucleotide encoding glutaminase, glnD, glnE, nifJ, nifH, nifD, nifK, nifY, nifE, nifN, nifU, nifS, nifV, nifW, nifZ, nifM, nifF, nifB, nifQ, and a gene associated with biosynthesis of a nitrogenase enzyme.
21. The method according to clause 1, wherein the at least one genetic variation is a mutation that results in one or more of: increased expression or activity of NifA or glutaminase; decreased expression or activity of NifL, NtrB, glutamine synthetase, GlnB, GlnK, DraT, AmtB; decreased adenylyl-removing activity of GlnE; or decreased uridylyl-removing activity of GlnD.
22. The method according to clause 1, wherein the at least one genetic variation is selected from: (A) a knock-out mutation; (B) alters or abolishes a regulatory sequence of a target gene; (C) comprises the insertion of a heterologous regulatory sequence; or (D) a domain deletion.
23. The method according to clause 1, wherein the at least one genetic variation is a mutated nifL gene that has been altered to comprise a heterologous promoter inserted into said nifL gene.
24. The method according to clause 1, wherein the at least one genetic variation is a mutated glnE gene that results in a truncated GlnE protein lacking an adenylyl-removing (AR) domain.
25. The method according to clause 1, wherein the at least one genetic variation is a mutated amtB gene that results in the lack of expression of said amtB gene.
26. The method according to clause 1, wherein the at least one genetic variation is selected from: a mutated nifL gene that has been altered to comprise a heterologous promoter inserted into said nifL gene; a mutated glnE gene that results in a truncated GlnE protein lacking an adenylyl-removing (AR) domain; a mutated amtB gene that results in the lack of expression of said amtB gene; and combinations thereof.
27. The method according to clause 1, wherein the at least one genetic variation is a mutated nifL gene that has been altered to comprise a heterologous promoter inserted into said nifL gene and a mutated glnE gene that results in a truncated GlnE protein lacking an adenylyl-removing (AR) domain.
28. The method according to clause 1, wherein the at least one genetic variation is a mutated nifL gene that has been altered to comprise a heterologous promoter inserted into said nifL gene and a mutated glnE gene that results in a truncated GlnE protein lacking an adenylyl-removing (AR) domain and a mutated amtB gene that results in the lack of expression of said amtB gene.
29. The method according to clause 1, wherein the plant comprises the seed, stalk, flower, fruit, leaves, or rhizome.
30. The method according to clause 1, wherein the plurality of non-intergeneric bacteria are formulated into a composition.
31. The method according to clause 1, wherein the plurality of non-intergeneric bacteria are formulated into a composition comprising an agriculturally acceptable carrier.
32. The method according to clause 1, wherein the plurality of non-intergeneric bacteria are applied into furrows in which seeds of said plant are planted.
33. The method according to clause 1, wherein the plurality of non-intergeneric bacteria are formulated into a liquid in-furrow composition comprising bacteria at a concentration of about $1 \times 10^7$ to about $1 \times 10^{10}$ cfu per milliliter.
34. The method according to clause 1, wherein the plurality of non-intergeneric bacteria are applied onto a seed of said plant.
35. The method according to clause 1, wherein the plurality of non-intergeneric bacteria are formulated into a seed coating and are applied onto a seed of said plant.
36. The method according to clause 1, wherein the plurality of non-intergeneric bacteria are formulated into a seed coating and are applied onto a seed of said plant, at a concentration of about $1 \times 10^5$ to about $1 \times 10^7$ cfu per seed.
37. The method according to clause 1, wherein the plant is a cereal crop.
38. The method according to clause 1, wherein the plant is selected from the group consisting of: corn, rice, wheat, barley, *sorghum*, millet, oat, rye, and triticale.
39. The method according to clause 1, wherein the plant is corn.
40. The method according to clause 1, wherein the plant is an agricultural crop plant.
41. The method according to clause 1, wherein the plant is a genetically modified organism.
42. The method according to clause 1, wherein the plant is not a genetically modified organism.
43. The method according to clause 1, wherein the plant has been genetically engineered or bred for efficient nitrogen use.
44. The method according to clause 1, wherein the plurality of non-intergeneric bacteria comprise at least two different species of bacteria.

45. The method according to clause 1, wherein the plurality of non-intergeneric bacteria comprise at least two different strains of the same species of bacteria.

46. The method according to clause 1, wherein the plurality of non-intergeneric bacteria comprise bacteria selected from: *Rahnella aquatilis, Klebsiella variicola, Achromobacter spiritinus, Achromobacter marplatensis, Aficrobacterium murale, Kluvvera intermedia, Kosakonia pseudosacchari, Enterobacter* sp., *Azospirillum lipoferum, Kosakonia sacchari*, and combinations thereof.

47. The method according to clause 1, wherein the plurality of non-intergeneric bacteria are endophytic, epiphytic, or rhizospheric.

48. The method according to clause 1, wherein the plurality of non-intergeneric bacteria comprise bacteria selected from: a bacteria deposited as PTA-122293, a bacteria deposited as PTA-122294, a bacteria deposited as NCMA 201701002, a bacteria deposited as NCMA 201708004, a bacteria deposited as NCMA 201708003, a bacteria deposited as NCMA 201708002, a bacteria deposited as NCMA 201712001, a bacteria deposited as NCMA 201712002, and combinations thereof.

49. A bacterial composition, comprising: at least one genetically engineered bacterial strain that fixes atmospheric nitrogen in an agricultural system that has been fertilized with more than 20 lbs of Nitrogen per acre.

50. A bacterial composition, comprising: at least one bacterial strain that has been bred to fix atmospheric nitrogen in an agricultural system that has been fertilized with more than 20 lbs of Nitrogen per acre.

51. The bacterial composition of clause 49 or clause 50, wherein said fertilizer is a chemical fertilizer selected from the group consisting of anhydrous ammonia, ammonia sulfate, urea, diammonium phosphate, urea-form, UAN (urea ammonium nitrate) monoammonium phosphate, ammonium nitrate, nitrogen solutions, calcium nitrate, potassium nitrate, and sodium nitrate.

52. A bacterial composition, comprising: at least one genetically engineered bacterial strain that fixes atmospheric nitrogen, the at least one genetically engineered bacterial strain comprising exogenously added DNA wherein said exogenously added DNA shares at least 80% identity to a corresponding native bacterial strain.

53. The bacterial composition of clause 52, wherein said exogenously added DNA shares at least 85% identity to a corresponding native bacterial strain.

54. The bacterial composition of clause 52, wherein said exogenously added DNA shares at least 90% identity to a corresponding native bacterial strain.

55. The bacterial composition of clause 52, wherein said exogenously added DNA shares at least 95% identity to a corresponding native bacterial strain.

56. The bacterial composition of clause 52, wherein said exogenously added DNA shares at least 99% identity to a corresponding native bacterial strain.

57. The bacterial composition of clause 52, wherein said exogenously added DNA is derived from a same bacterial strain as said corresponding native bacterial strain.

58. The bacterial composition of any of the preceding clauses, wherein said bacterial composition is a fertilizing composition.

59. The bacterial composition of any of the preceding clauses, wherein said at least one genetically engineered bacterial strain comprises at least one variation in a gene or intergenic region within 10,000 bp of a gene selected from the group consisting of: nifA, nifL, ntrB, ntrC, glnA, glnB, glnK, draT, amtB, glnD, glnE, nifJ, nifH, nifD, nifK, nifY, nifE, nifN, nifU, nifS, nifV, nifW, nifZ, nifM, nifF, nifB, and nifQ.

60. The bacterial composition of any of the preceding clauses, further comprising at least one additional component selected from the group consisting of a tackifier, a microbial stabilizer, a fungicide, an antibacterial agent, a preservative, a stabilizer, a surfactant, an anti-complex agent, an herbicide, a nematicide, an insecticide, a plant growth regulator, a fertilizer, a rodenticide, a desiccant, a bactericide, and a nutrient.

61. The bacterial composition of any of the preceding clauses, further comprising at least one additional component selected from the group consisting of a colorant, primer, pellet, disinfectant, plant growth regulator, safener, and a nematicide.

62. The bacterial composition of any of the preceding clauses, wherein said bacterial composition is formulated to be applied to a field.

63. The bacterial composition of clause 62, wherein said bacterial composition is formulated to be applied in-furrow.

64. The bacterial composition of clause 62, wherein said bacterial composition is formulated to be applied as a seed coating, seed dressing, or seed treatment.

65. The bacterial composition of clause 61 or clause 62, wherein said bacterial composition is formulated to be applied at, prior to, or post planting of the seed.

66. A seed composition comprising a seed of a plant that is inoculated with a bacterial composition of any of the preceding clauses.

67. A method of growing a crop using a plurality of seeds having a seed composition of clause 66.

68. The method of clause 67, further comprising harvesting said crop.

69. A method of applying a bacterial composition of any of the preceding clauses to a field.

70. The method of clause 69, wherein said bacterial composition is applied to said field in a form selected from the group consisting of a liquid form, a dry form, a granule, a powder, and a pellet.

71. The method of clause 69, wherein said bacterial composition is applied to said field as a seed coating, seed dressing, or seed treatment.

72. The method of clause 69, wherein said bacterial composition is applied to said field as an in-furrow treatment.

73. The method of clause 69, wherein said bacterial composition is applied to said field at, prior to, or post planting of the seed.

74. A fertilizer composition comprising a bacterial composition of any of the preceding clauses.

75. The fertilizer composition of clause 74, wherein said fertilizer composition is a seed coating, seed dressing, or seed treatment composition.

76. The fertilizer composition of clause 74, wherein said fertilizer composition is an in-furrow composition.

77. The fertilizer composition of clause 74, wherein said fertilizer composition is provided to a crop at, prior to, or post planting.

78. The fertilizer composition of clause 74, further comprising a porous carrier.

79. The fertilizer composition of clause 74, further comprising an additional synergistic component that, when combined with said bacterial composition, increases a fertilizing benefit of said fertilizer composition to a crop that is beyond a cumulative benefit of its individual components.

80. A method of maintaining soil nitrogen levels, comprising: planting, in soil of a field, a crop inoculated by a genetically engineered bacterium that fixes atmospheric nitrogen; and harvesting said crop, wherein no more than 90% of a nitrogen dose required for producing said crop is administered to said soil of said field between planting and harvesting.
81. The method of clause 80, wherein no more than 80% of a nitrogen dose required for producing said crop is administered to said soil of said field between planting and harvesting.
82. The method of clause 80, wherein no more than 70% of a nitrogen dose required for producing said crop is administered to said soil of said field between planting and harvesting.
83. The method of clause 80, wherein no more than 60% of a nitrogen dose required for producing said crop is administered to said soil of said field between planting and harvesting.
84. The method of clause 80, wherein no more than 50% of a nitrogen dose required for producing said crop is administered to said soil of said field between planting and harvesting.
85. The method of clause 80, wherein no more than 40% of a nitrogen dose required for producing said crop is administered to said soil of said field between planting and harvesting.
86. The method of clause 80, wherein said genetically engineered bacterium comprises a bacterial composition of any of the preceding clauses.
87. The method of clause 80, wherein said genetically engineered bacterium consists of a bacterial composition of any of the preceding clauses.
88. A method of delivering a probiotic supplement to a crop plant, comprising: coating a crop seed with a seed coating, seed treatment, or seed dressing, wherein said seed coating, seed dressing, or seed treatment comprises living representatives of said probiotic; and applying, in soil of a field, said crop seeds.
89. The method of clause 88, wherein said seed coating, seed dressing, or seed treatment is applied in a single layer to said crop seed.
90. The method of clause 88, wherein said seed coating is applied in multiple layers to said crop seed.
91. The method of clause 88, wherein said seed coating is applied in a blend to said crop seed.
92. The method of clause 88, wherein said crop seed is non-modulating.
93. The method of clause 88, wherein said seed coating comprises a bacterial composition of any of the preceding clauses.
94. The method of any of the proceeding clauses, wherein the genetically engineered bacterial strain is a genetically engineered Gram-positive bacterial strain.
95. The method of clause 94, wherein the genetically engineered Gram-positive bacterial strain has an altered expression level of a regulator of a Nif cluster.
96. The method of clause 94, wherein the genetically engineered Gram-positive bacterial strain expresses a decreased amount of a negative regulator of a Nif cluster.
97. The method of clause 94, wherein the genetically engineered bacterial strain expresses a decreased amount of GlR.
98. The method of any one of the proceeding clauses, wherein the genome of the genetically engineered bacterial strain encodes a polypeptide with at least 75% identity to a sequence from the Zehr lab NifH database.
99. The method of any one of the proceeding clauses, wherein the genome of the genetically engineered bacterial strain encodes a polypeptide with at least 85% identity to a sequence from the Zehr lab NifH database.
100. The method of any one of the proceeding clauses, wherein the genome of the genetically engineered bacterial strain encodes a polypeptide with at least 75% identity to a sequence from the Buckley lab NifH database.
101. The method of any one of the proceeding clauses, wherein the genome of the genetically engineered bacterial strain encodes a polypeptide with at least 85% identity to a sequence from the Buckley lab NifH database.
102. A method of breeding microbial strains to improve specific traits of agronomic relevance, comprising:
providing a plurality of microbial strains that have the ability to colonize a desired crop;
improving regulatory networks influencing the trait through intragenomic rearrangement;
assessing microbial strains within the plurality of microbial strains to determine a measure of the trait; and
selecting one or more microbial strains of the plurality of microbial strains that generate an improvement in the trait in the presence of the desired crop.
103. The method of clause 102, wherein the specific trait which is improved is the ability of the microbial strain to fix nitrogen.
104. The method of clause 103, wherein the specific trait which is improved is the ability of the microbial strain to fix atmospheric nitrogen in the presence of N-fertilized growing conditions.
105. A method of breeding microbial strains to improve specific traits of agronomic relevance, comprising:
providing a plurality of microbial strains that have the ability to colonize a desired crop;
introducing genetic diversity into the plurality of microbial strains;
assessing microbial strains within the plurality of microbial strains to determine a measure of the trait; and
selecting one or more microbial strains of the plurality of microbial strains that generate an improvement in the trait in the presence of the desired crop.
106. The method of clause 105, wherein the specific trait which is improved is the ability of the microbial strain to fix nitrogen.
107. The method of clause 106, wherein the specific trait which is improved is the ability of the microbial strain to fix atmospheric nitrogen in the presence of N-fertilized growing conditions.
108. A method of increasing the amount of atmospheric derived nitrogen in a non-leguminous plant, comprising:
exposing said non-leguminous plant to engineered non-intergeneric microbes, said engineered non-intergeneric microbes comprising at least one genetic variation introduced into a nitrogen fixation genetic regulatory network or at least one genetic variation introduced into a nitrogen assimilation genetic regulatory network.
109. The method of clause 108, wherein said engineered non-intergeneric microbes comprise at least one genetic variation introduced into said nitrogen fixation genetic regulatory network.
110. The method of clause 108, wherein said engineered non-intergeneric microbes comprise at least one genetic variation introduced into said nitrogen assimilation genetic regulatory network.
111. The method of clause 108, wherein said engineered non-intergeneric microbes comprise at least one genetic variation introduced into said nitrogen fixation genetic regulatory network and at least one genetic variation introduced into said nitrogen assimilation genetic regulatory network.

112. The method of clause 108, wherein said engineered non-intergeneric microbes are applied into furrows in which seeds of said non-leguminous plant are planted.

113. The method of clause 108, wherein said engineered non-intergeneric microbes are coated onto a seed of said non-leguminous plant.

114. The method of clause 108, wherein said non-leguminous plant is a non-leguminous agricultural crop plant selected from the group consisting of *sorghum*, canola, tomato, strawberry, barley, rice, corn, wheat, potato, millet, cereals, grains, and maize.

115. The method of clause 108, wherein said engineered non-intergeneric microbes colonize at least a root of said non-leguminous plant such that said engineered non-intergeneric microbes are present in said non-leguminous plant in an amount of at least $10^5$ colony forming units per gram fresh weight of tissue.

116. The method of clause 108, wherein said engineered non-intergeneric microbes are capable of fixing atmospheric nitrogen in non-nitrogen-limiting conditions.

117. The method of clause 108, wherein said engineered non-intergeneric microbes, in planta, excrete nitrogen-containing products of nitrogen fixation.

118. The method of clause 108, wherein said at least one genetic variation is introduced into a gene selected from the group consisting of nifA, nifL, ntrB, ntrC, polynucleotide encoding glutamine synthetase, glnA, glnB, glnK, drat, amtB, polynucleotide encoding glutaminase, glnD, glnE, nifJ, nifH, nifD, nifK, nifY, nifE, nifN, nifU, nifS, nifV, nifW, nifZ, nifM, nifF, nifB, nifQ, and a gene associated with biosynthesis of a nitrogenase enzyme.

119. The method of clause 108, wherein said engineered non-intergeneric microbes, in planta, produce at least 1% of fixed nitrogen in said non-leguminous plant.

120. The method of clause 119, wherein said fixed nitrogen in said non-leguminous plant produced by said engineered non-intergeneric microbes is measured by dilution of 15N in crops grown in fields treated with fertilizer containing 1.2% 15N.

121. The method of clause 119, wherein said engineered non-intergeneric microbes, in planta, produce 5% or more of the fixed nitrogen in said non-leguminous plant.

122. The method of clause 108, wherein said non-intergeneric microbes are engineered using at least one type of engineering selected from the group consisting of directed mutagenesis, random mutagenesis, and directed evolution.

123. A method of increasing an amount of atmospheric derived nitrogen in a corn plant, comprising
exposing said corn plant to engineered non-intergeneric microbes comprising engineered genetic variations within at least two genes selected from the group consisting of nifL, glnB, glnE, and amtB.

124. The method of clause 123, wherein said engineered non-intergeneric microbes, in planta, excrete nitrogen-containing products of nitrogen fixation.

125. The method of clause 123, wherein said engineered non-intergeneric microbes are applied into furrows in which seeds of said corn plant are planted.

126. The method of clause 123, wherein said engineered non-intergeneric microbes are coated onto a seed of said corn plant.

127. A method of increasing an amount of atmospheric derived nitrogen in a corn plant, comprising:
exposing said corn plant to engineered non-intergeneric microbes comprising at least one genetic variation introduced into a nitrogen fixation genetic regulatory network and at least one genetic variation introduced into a nitrogen assimilation genetic regulatory network, wherein said engineered non-intergeneric microbes, in planta, produce at least 5% of fixed nitrogen in said corn plant as measured by dilution of 15N in crops grown in fields treated with fertilizer containing 1.2% 15N.

128. A method of increasing nitrogen fixation in a non-leguminous plant, comprising:
a. applying to the plant a plurality of non-intergeneric bacteria, said plurality comprising non-intergeneric bacteria that:
i. have an average colonization ability per unit of plant root tissue of at least about $1.0 \times 10^4$ bacterial cells per gram of fresh weight of plant root tissue; and
ii. produce fixed N of at least about $1 \times 10^{-17}$ mmol N per bacterial cell per hour, and
wherein the product of (i) the average colonization ability per unit of plant root tissue and (ii) produced fixed N per bacterial cell per hour, is at least about $2.5 \times 10^{-8}$ mmol N per gram of fresh weight of plant root tissue per hour, and
wherein the plurality of non-intergeneric bacteria, in planta, produce 1% or more of the fixed nitrogen in the plant, and
wherein each member of the plurality of non-intergeneric bacteria comprises at least one genetic variation introduced into at least one gene, or non-coding polynucleotide, of the nitrogen fixation or assimilation genetic regulatory network, such that the non-intergeneric bacteria are capable of fixing atmospheric nitrogen in the presence of exogenous nitrogen.

129. The method according to clause 128, wherein the at least one genetic variation comprises an introduced control sequence operably linked to the at least one gene of the nitrogen fixation or assimilation genetic regulatory network.

130. The method according to clause 128, wherein the at least one genetic variation comprises a promoter operably linked to the at least one gene of the nitrogen fixation or assimilation genetic regulatory network.

131. The method according to clause 128, wherein the at least one genetic variation comprises an inducible promoter operably linked to the at least one gene of the nitrogen fixation or assimilation genetic regulatory network.

132. The method according to clause 128, wherein the plurality of non-intergeneric bacteria do not comprise a constitutive promoter operably linked to a gene of the nitrogen fixation or assimilation genetic regulatory network.

133. The method according to clause 128, wherein the plurality of non-intergeneric bacteria do not comprise a constitutive promoter operably linked to a gene in the nif gene cluster.

134. The method according to clause 128, wherein the plurality of non-intergeneric bacteria, in planta, excrete the nitrogen-containing products of nitrogen fixation.

135. The method according to clause 128, wherein the plurality of non-intergeneric bacteria applied to the plant do not stimulate an increase in the uptake of exogenous non-atmospheric nitrogen.

136. The method according to clause 128, wherein the plant is grown in soil from a field which has been administered at least about 50 lbs of nitrogen-containing fertilizer per acre, and wherein the nitrogen-containing fertilizer comprises at least about 5% nitrogen by weight.

137. The method according to clause 128, wherein the plant is grown in soil from a field which has been administered at least about 50 lbs of nitrogen-containing fertilizer per acre, and wherein the nitrogen-containing fertilizer comprises at least about 5% nitrogen by weight, and wherein the nitrogen-containing fertilizer comprises ammonium or an ammonium containing molecule.

138. The method according to clause 128, wherein the exogenous nitrogen is selected from fertilizer comprising one or more of: glutamine, ammonia, ammonium, urea, nitrate, nitrite, ammonium-containing molecules, nitrate-containing molecules, and nitrite-containing molecules.

139. The method according to clause 128, wherein the plurality of non-intergeneric bacteria, in planta, produce 5% or more of the fixed nitrogen in the plant.

140. The method according to clause 128, wherein the plurality of non-intergeneric bacteria, in planta, produce 10% or more of the fixed nitrogen in the plant.

141. The method according to clause 128, wherein the plurality of non-intergeneric bacteria, in planta, fix atmospheric nitrogen in non-nitrogen-limiting conditions.

142. The method according to clause 128, wherein the plurality of non-intergeneric bacteria, in planta, excrete nitrogen-containing products of nitrogen fixation.

143. The method according to clause 128, wherein the fixed nitrogen produced by the plurality of non-intergeneric bacteria is measured through dilution of enriched fertilizer by atmospheric $N_2$ gas in plant tissue.

144. The method according to clause 128, wherein the at least one gene, or non-coding polynucleotide, of the nitrogen fixation or assimilation genetic regulatory network are selected from the group consisting of: nifA, nifL, ntrB, ntrC, polynucleotide encoding glutamine synthetase, glnA, glnB, glnK, drat, amtB, polynucleotide encoding glutaminase, glnD, glnE, nifJ, nifH, nifD, nifK, nifY, nifE, nifN, nifU, nifS, nifV, nifW, nifZ, nifM, nifF, nifB, nifQ, and a gene associated with biosynthesis of a nitrogenase enzyme.

145. The method according to clause 128, wherein the at least one genetic variation is a mutation that results in one or more of: increased expression or activity of NifA or glutaminase; decreased expression or activity of NifL, NtrB, glutamine synthetase, GlnB, GlnK, DraT, AmtB; decreased adenylyl-removing activity of GlnE; or decreased uridylyl-removing activity of GlnD.

146. The method according to clause 128, wherein the at least one genetic variation is selected from: (A) a knockout mutation; (B) alters or abolishes a regulatory sequence of a target gene; (C) comprises the insertion of a heterologous regulatory sequence; or (D) a domain deletion.

147. The method according to clause 128, wherein the at least one genetic variation is a mutated nifL gene that has been altered to comprise a heterologous promoter inserted into said nifL gene.

148. The method according to clause 128, wherein the at least one genetic variation is a mutated glnE gene that results in a truncated GlnE protein lacking an adenylyl-removing (AR) domain.

149. The method according to clause 128, wherein the at least one genetic variation is a mutated amtB gene that results in the lack of expression of said amtB gene.

150. The method according to clause 128, wherein the at least one genetic variation is selected from: a mutated nifL gene that has been altered to comprise a heterologous promoter inserted into said nifL gene; a mutated glnE gene that results in a truncated GlnE protein lacking an adenylyl-removing (AR) domain; a mutated amtB gene that results in the lack of expression of said amtB gene; and combinations thereof.

151. The method according to clause 128, wherein the at least one genetic variation is a mutated nifL gene that has been altered to comprise a heterologous promoter inserted into said nifL gene and a mutated glnE gene that results in a truncated GlnE protein lacking an adenylyl-removing (AR) domain.

152. The method according to clause 128, wherein the at least one genetic variation is a mutated nifL gene that has been altered to comprise a heterologous promoter inserted into said nifL gene and a mutated glnE gene that results in a truncated GlnE protein lacking an adenylyl-removing (AR) domain and a mutated amtB gene that results in the lack of expression of said amtB gene.

153. The method according to clause 128, wherein the plant comprises the seed, stalk, flower, fruit, leaves, or rhizome.

154. The method according to clause 128, wherein the plurality of non-intergeneric bacteria are formulated into a composition.

155. The method according to clause 128, wherein the plurality of non-intergeneric bacteria are formulated into a composition comprising an agriculturally acceptable carrier.

156. The method according to clause 128, wherein the plurality of non-intergeneric bacteria are applied into furrows in which seeds of said plant are planted.

157. The method according to clause 128, wherein the plurality of non-intergeneric bacteria are formulated into a liquid in-furrow composition comprising bacteria at a concentration of about $1 \times 10^7$ to about $1 \times 10^{10}$ cfu per milliliter.

158. The method according to clause 128, wherein the plurality of non-intergeneric bacteria are applied onto a seed of said plant.

159. The method according to clause 128, wherein the plurality of non-intergeneric bacteria are formulated into a seed coating and are applied onto a seed of said plant.

160. The method according to clause 128, wherein the plurality of non-intergeneric bacteria are formulated into a seed coating and are applied onto a seed of said plant, at a concentration of about $1 \times 10^5$ to about $1 \times 10^7$ cfu per seed.

161. The method according to clause 128, wherein the plant is a cereal crop.

162. The method according to clause 128, wherein the plant is selected from the group consisting of: corn, rice, wheat, barley, *sorghum*, millet, oat, rye, and triticale.

163. The method according to clause 128, wherein the plant is corn.

164. The method according to clause 128, wherein the plant is an agricultural crop plant.

165. The method according to clause 128, wherein the plant is a genetically modified organism.

166. The method according to clause 128, wherein the plant is not a genetically modified organism.

167. The method according to clause 128, wherein the plant has been genetically engineered or bred for efficient nitrogen use.
168. The method according to clause 128, wherein the plurality of non-intergeneric bacteria comprise at least two different species of bacteria.
169. The method according to clause 128, wherein the plurality of non-intergeneric bacteria comprise at least two different strains of the same species of bacteria.
170. The method according to clause 128, wherein the plurality of non-intergeneric bacteria comprise bacteria selected from: *Rahnella aquatilis, Klebsiella variicola, Achromobacter spiritinus, Achromobacter marplatensis, Microbacterium murale, Kluyvera intermedia, Kosakonia pseudosacchari, Enterobacter* sp., *Azospirillum lipoferum, Kosakonia sacchari*, and combinations thereof.
171. The method according to clause 128, wherein the plurality of non-intergeneric bacteria are endophytic, epiphytic, or rhizospheric.
172. The method according to clause 128, wherein the plurality of non-intergeneric bacteria comprise bacteria selected from: a bacteria deposited as PTA-122293, a bacteria deposited as PTA-122294, a bacteria deposited as NCMA 201701002, a bacteria deposited as NCMA 201708004, a bacteria deposited as NCMA 201708003, a bacteria deposited as NCMA 201708002, a bacteria deposited as NCMA 201712001, a bacteria deposited as NCMA 201712002, and combinations thereof.
173. A method of increasing nitrogen fixation in a non-leguminous plant, comprising:
  a. applying to the plant a plurality of bacteria, said plurality comprising bacteria that:
    i. have an average colonization ability per unit of plant root tissue of at least about $1.0 \times 10^4$ bacterial cells per gram of fresh weight of plant root tissue, and/or
    ii. produce fixed N of at least about $1 \times 10^{-17}$ mmol N per bacterial cell per hour, and
    wherein the plurality of bacteria, in planta, produce 1% or more of the fixed nitrogen in the plant.
174. The method according to clause 173, wherein the plurality of bacteria comprise bacteria that: have an average colonization ability per unit of plant root tissue of at least about $1.0 \times 10^4$ bacterial cells per gram of fresh weight of plant root tissue.
175. The method according to clause 173, wherein the plurality of bacteria comprise bacteria that: produce fixed N of at least about $173 \times 10^{-17}$ mmol N per bacterial cell per hour.
176. The method according to clause 173, wherein the plurality of bacteria comprise bacteria that: have an average colonization ability per unit of plant root tissue of at least about $1.0 \times 10^4$ bacterial cells per gram of fresh weight of plant root tissue and produce fixed N of at least about $1 \times 10^{-17}$ mmol N per bacterial cell per hour.
177. The method according to clause 173, wherein the plurality of bacteria comprise bacteria that: have an average colonization ability per unit of plant root tissue of at least about $1.0 \times 10^4$ bacterial cells per gram of fresh weight of plant root tissue and produce fixed N of at least about $1 \times 10^{-17}$ mmol N per bacterial cell per hour, and wherein the product of (i) the average colonization ability per unit of plant root tissue and (ii) produced fixed N per bacterial cell per hour, is at least about $2.5 \times 10^{-8}$ mmol N per gram of fresh weight of plant root tissue per hour.
178. The method according to clause 173, wherein the plurality of bacteria, in planta, excrete the nitrogen-containing products of nitrogen fixation.
179. The method according to clause 173, wherein the plurality of bacteria applied to the plant do not stimulate an increase in the uptake of exogenous non-atmospheric nitrogen.
180. The method according to clause 173, wherein the plant comprises the seed, stalk, flower, fruit, leaves, or rhizome.
181. The method according to clause 173, wherein the plurality of bacteria are formulated into a composition.
182. The method according to clause 173, wherein the plurality of bacteria are formulated into a composition comprising an agriculturally acceptable carrier.
183. The method according to clause 173, wherein the plurality of bacteria are applied into furrows in which seeds of said plant are planted.
184. The method according to clause 173, wherein the plurality of bacteria are formulated into a liquid in-furrow composition comprising bacteria at a concentration of about $1 \times 10^7$ to about $1 \times 10^{10}$ cfu per milliliter.
185. The method according to clause 173, wherein the plurality of bacteria are applied onto a seed of said plant.
186. The method according to clause 173, wherein the plurality of bacteria are formulated into a seed coating and are applied onto a seed of said plant.
187. The method according to clause 173, wherein the plurality of bacteria are formulated into a seed coating and are applied onto a seed of said plant, at a concentration of about $1 \times 10^5$ to about $1 \times 10^7$ cfu per seed.
188. The method according to clause 173, wherein the plant is a cereal crop.
189. The method according to clause 173, wherein the plant is selected from the group consisting of: corn, rice, wheat, barley, *sorghum*, millet, oat, rye, and triticale.
190. The method according to clause 173, wherein the plant is corn.
191. The method according to clause 173, wherein the plant is an agricultural crop plant.
192. The method according to clause 173, wherein the plant is a genetically modified organism.
193. The method according to clause 173, wherein the plant is not a genetically modified organism.
194. The method according to clause 173, wherein the plant has been genetically engineered or bred for efficient nitrogen use.
195. The method according to clause 173, wherein the plurality of bacteria comprise at least two different species of bacteria.
196. The method according to clause 173, wherein the plurality of bacteria comprise at least two different strains of the same species of bacteria.
197. The method according to clause 173, wherein the plurality of bacteria comprise bacteria selected from: *Rahnella aquatilis, Klebsiella variicola, Achromobacter spiritinus, Achromobacter marplatensis, Microbacterium murale, Kluyvera intermedia, Kosakonia pseudosacchari, Enterobacter* sp., *Azospirillum lipoferum, Kosakonia sacchari*, and combinations thereof.
198. The method according to clause 173, wherein the plurality of bacteria are endophytic, epiphytic, or rhizospheric.
199. The method according to clause 173, wherein the plurality of bacteria are selected from: a bacteria deposited as NCMA 201701003, a bacteria deposited as NCMA 201701001, and a bacteria deposited as NCMA 201708001.

200. A non-intergeneric bacterial population capable of increasing nitrogen fixation in a non-leguminous plant, comprising:
   a. a plurality of non-intergeneric bacteria, that:
      i. have an average colonization ability per unit of plant root tissue of at least about $1.0 \times 10^4$ bacterial cells per gram of fresh weight of plant root tissue; and/or
      ii. produce fixed N of at least about $1 \times 10^{-17}$ mmol N per bacterial cell per hour, and
   wherein the plurality of non-intergeneric bacteria, in planta, produce 1% or more of the fixed nitrogen in a plant grown in the presence of the plurality of non-intergeneric bacteria, and
   wherein each member of the plurality of non-intergeneric bacteria comprises at least one genetic variation introduced into at least one gene, or non-coding polynucleotide, of the nitrogen fixation or assimilation genetic regulatory network, such that the non-intergeneric bacteria are capable of fixing atmospheric nitrogen in the presence of exogenous nitrogen.

201. The non-intergeneric bacterial population according to clause 200, wherein the plurality of non-intergeneric bacteria comprise bacteria that: have an average colonization ability per unit of plant root tissue of at least about $1.0 \times 10^4$ bacterial cells per gram of fresh weight of plant root tissue.

202. The non-intergeneric bacterial population according to clause 200, wherein the plurality of non-intergeneric bacteria comprise bacteria that: produce fixed N of at least about $1 \times 10^{-17}$ mmol N per bacterial cell per hour.

203. The non-intergeneric bacterial population according to clause 200, wherein the plurality of non-intergeneric bacteria comprise bacteria that: have an average colonization ability per unit of plant root tissue of at least about $1.0 \times 10^4$ bacterial cells per gram of fresh weight of plant root tissue and produce fixed N of at least about $1 \times 10^{-17}$ mmol N per bacterial cell per hour.

204. The non-intergeneric bacterial population according to clause 200, wherein the at least one genetic variation comprises an introduced control sequence operably linked to the at least one gene of the nitrogen fixation or assimilation genetic regulatory network.

205. The non-intergeneric bacterial population according to clause 200, wherein the at least one genetic variation comprises a promoter operably linked to the at least one gene of the nitrogen fixation or assimilation genetic regulatory network.

206. The non-intergeneric bacterial population according to clause 200, wherein the at least one genetic variation comprises an inducible promoter operably linked to the at least one gene of the nitrogen fixation or assimilation genetic regulatory network.

207. The non-intergeneric bacterial population according to clause 200, wherein the plurality of non-intergeneric bacteria do not comprise a constitutive promoter operably linked to a gene of the nitrogen fixation or assimilation genetic regulatory network.

208. The non-intergeneric bacterial population according to clause 200, wherein the plurality of non-intergeneric bacteria do not comprise a constitutive promoter operably linked to a gene in the nif gene cluster.

209. The non-intergeneric bacterial population according to clause 200, wherein the plurality of non-intergeneric bacteria, in planta, excrete nitrogen-containing products of nitrogen fixation.

210. The non-intergeneric bacterial population according to clause 200, wherein the plurality of non-intergeneric bacteria applied to the plant do not stimulate an increase in the uptake of exogenous non-atmospheric nitrogen.

211. The non-intergeneric bacterial population according to clause 200, wherein the plant is grown in soil from a field which has been administered at least about 50 lbs of nitrogen-containing fertilizer per acre, and wherein the nitrogen-containing fertilizer comprises at least about 5% nitrogen by weight.

212. The non-intergeneric bacterial population according to clause 200, wherein the plant is grown in soil from a field which has been administered at least about 50 lbs of nitrogen-containing fertilizer per acre, and wherein the nitrogen-containing fertilizer comprises at least about 5% nitrogen by weight, and wherein the nitrogen-containing fertilizer comprises ammonium or an ammonium containing molecule.

213. The non-intergeneric bacterial population according to clause 200, wherein the exogenous nitrogen is selected from fertilizer comprising one or more of: glutamine, ammonia, ammonium, urea, nitrate, nitrite, ammonium-containing molecules, nitrate-containing molecules, and nitrite-containing molecules.

214. The non-intergeneric bacterial population according to clause 200, wherein the plurality of non-intergeneric bacteria, in planta, produce 5% or more of the fixed nitrogen in the plant.

215. The non-intergeneric bacterial population according to clause 200, wherein the plurality of non-intergeneric bacteria, in planta, produce 10% or more of the fixed nitrogen in the plant.

216. The non-intergeneric bacterial population according to clause 200, wherein the plurality of non-intergeneric bacteria, in planta, fix atmospheric nitrogen in non-nitrogen-limiting conditions.

217. The non-intergeneric bacterial population according to clause 200, wherein the plurality of non-intergeneric bacteria, in planta, excrete nitrogen-containing products of nitrogen fixation.

218. The non-intergeneric bacterial population according to clause 200, wherein the fixed nitrogen produced by the plurality of non-intergeneric bacteria is measured through dilution of enriched fertilizer by atmospheric $N_2$ gas in plant tissue.

219. The non-intergeneric bacterial population according to clause 200, wherein the at least one gene, or non-coding polynucleotide, of the nitrogen fixation or assimilation genetic regulatory network are selected from the group consisting of: nifA, nifL, ntrB, ntrC, polynucleotide encoding glutamine synthetase, glnA, glnB, glnK, drat, amtB, polynucleotide encoding glutaminase, glnD, glnE, nifJ, nifH, nifD, nifK, nifY, nifE, nifN, nifU, nifS, nifV, nifW, nifZ, nifM, nifF, nifB, nifQ, and a gene associated with biosynthesis of a nitrogenase enzyme.

220. The non-intergeneric bacterial population according to clause 200, wherein the at least one genetic variation is a mutation that results in one or more of: increased expression or activity of NifA or glutaminase; decreased expression or activity of NifL, NtrB, glutamine synthetase, GlnB, GlnK, DraT, AmtB, decreased adenylyl-removing activity of GlnE; or decreased uridylyl-removing activity of GlnD.

221. The non-intergeneric bacterial population according to clause 200, wherein the at least one genetic variation is selected from: (A) a knock-out mutation; (B) alters or abolishes a regulatory sequence of a target gene; (C)

comprises the insertion of a heterologous regulatory sequence; or (D) a domain deletion.
222. The non-intergeneric bacterial population according to clause 200, wherein the at least one genetic variation is a mutated nifL gene that has been altered to comprise a heterologous promoter inserted into said nifL gene.
223. The non-intergeneric bacterial population according to clause 200, wherein the at least one genetic variation is a mutated glnE gene that results in a truncated GlnE protein lacking an adenylyl-removing (AR) domain.
224. The non-intergeneric bacterial population according to clause 200, wherein the at least one genetic variation is a mutated amtB gene that results in the lack of expression of said amtB gene.
225. The non-intergeneric bacterial population according to clause 200, wherein the at least one genetic variation is selected from: a mutated nifL gene that has been altered to comprise a heterologous promoter inserted into said nifL gene; a mutated glnE gene that results in a truncated GlnE protein lacking an adenylyl-removing (AR) domain; a mutated am/B gene that results in the lack of expression of said amtB gene; and combinations thereof.
226. The non-intergeneric bacterial population according to clause 200, wherein the at least one genetic variation is a mutated nifL gene that has been altered to comprise a heterologous promoter inserted into said nifL gene and a mutated glnE gene that results in a truncated GlnE protein lacking an adenylyl-removing (AR) domain.
227. The non-intergeneric bacterial population according to clause 200, wherein the at least one genetic variation is a mutated nifL gene that has been altered to comprise a heterologous promoter inserted into said nifL gene and a mutated glnE gene that results in a truncated GlnE protein lacking an adenylyl-removing (AR) domain and a mutated amtB gene that results in the lack of expression of said amtB gene.
228. The non-intergeneric bacterial population according to clause 200, wherein the plant comprises the seed, stalk, flower, fruit, leaves, or rhizome.
229. The non-intergeneric bacterial population according to clause 200, wherein the plurality of non-intergeneric bacteria are formulated into a composition.
230. The non-intergeneric bacterial population according to clause 200, wherein the plurality of non-intergeneric bacteria are formulated into a composition comprising an agriculturally acceptable carrier.
231. The non-intergeneric bacterial population according to clause 200, wherein the plurality of non-intergeneric bacteria are formulated into a liquid in-furrow composition comprising bacteria at a concentration of about $1\times10^7$ to about $1\times10^{10}$ cfu per milliliter.
232. The non-intergeneric bacterial population according to clause 200, wherein the plurality of non-intergeneric bacteria are formulated into a seed coating.
233. The non-intergeneric bacterial population according to clause 200, wherein the plant is a cereal crop.
234. The non-intergeneric bacterial population according to clause 200, wherein the plant is selected from the group consisting of: corn, rice, wheat, barley, *sorghum*, millet, oat, rye, and triticale.
235. The non-intergeneric bacterial population according to clause 200, wherein the plant is corn.
236. The non-intergeneric bacterial population according to clause 200, wherein the plant is an agricultural crop plant.
237. The non-intergeneric bacterial population according to clause 200, wherein the plant is a genetically modified organism.
238. The non-intergeneric bacterial population according to clause 200, wherein the plant is not a genetically modified organism.
239. The non-intergeneric bacterial population according to clause 200, wherein the plant has been genetically engineered or bred for efficient nitrogen use.
240. The non-intergeneric bacterial population according to clause 200, wherein the plurality of non-intergeneric bacteria comprise at least two different species of bacteria.
241. The non-intergeneric bacterial population according to clause 200, wherein the plurality of non-intergeneric bacteria comprise at least two different strains of the same species of bacteria.
242. The non-intergeneric bacterial population according to clause 200, wherein the plurality of non-intergeneric bacteria comprise bacteria selected from: *Rahnella aquatilis, Klebsiella variicola, Achromobacter spiritinus, Achromobacter marplatensis, Microbacterium murale, Kluyvera intermedia, Kosakonia pseudosacchari, Enterobacter sp., Azospirillum lipoferum, Kosakonia sacchari*, and combinations thereof.
243. The non-intergeneric bacterial population according to clause 200, wherein the plurality of non-intergeneric bacteria are endophytic, epiphytic, or rhizospheric.
244. The non-intergeneric bacterial population according to clause 200, wherein the plurality of non-intergeneric bacteria comprise bacteria selected from: a bacteria deposited as PTA-122293, a bacteria deposited as PTA-122294, a bacteria deposited as NCMA 201701002, a bacteria deposited as NCMA 201708004, a bacteria deposited as NCMA 201708003, a bacteria deposited as NCMA 201708002, a bacteria deposited as NCMA 201712001, a bacteria deposited as NCMA 201712002, and combinations thereof.
245. A bacterial population capable of increasing nitrogen fixation in a non-leguminous plant, comprising:
  a. a plurality of bacteria, that:
    i. have an average colonization ability per unit of plant root tissue of at least about $1.0\times10^4$ bacterial cells per gram of fresh weight of plant root tissue; and/or
    ii. produce fixed N of at least about $1\times10^{-17}$ mmol N per bacterial cell per hour, and
    wherein the plurality of bacteria, in planta, produce 1% or more of the fixed nitrogen in the plant.
246. The bacterial population according to clause 245, wherein the plurality of bacteria comprise bacteria that: have an average colonization ability per unit of plant root tissue of at least about $1.0\times10^4$ bacterial cells per gram of fresh weight of plant root tissue.
247. The bacterial population according to clause 245, wherein the plurality of bacteria comprise bacteria that: produce fixed N of at least about $245\times10^{-17}$ mmol N per bacterial cell per hour.
248. The bacterial population according to clause 245, wherein the plurality of bacteria comprise bacteria that: have an average colonization ability per unit of plant root tissue of at least about $1.0\times10^4$ bacterial cells per gram of fresh weight of plant root tissue and produce fixed N of at least about $1\times10^{-17}$ mmol N per bacterial cell per hour.
249. The bacterial population according to clause 245, wherein the plurality of bacteria comprise bacteria that: have an average colonization ability per unit of plant root tissue of at least about $1.0\times10^4$ bacterial cells per gram of fresh weight of plant root tissue and produce fixed N of at least about $1\times10^{-17}$ mmol N per bacterial cell per hour, and wherein the product of (i) the average colonization ability per unit of plant root tissue and (ii) produced fixed N per bacterial cell per hour, is at least about $2.5 \times 10^{-8}$ mmol N per gram of fresh weight of plant root tissue per hour.

250. The bacterial population according to clause 245, wherein the plurality of bacteria, in planta, excrete the nitrogen-containing products of nitrogen fixation.
251. The bacterial population according to clause 245, wherein the plurality of bacteria applied to the plant do not stimulate an increase in the uptake of exogenous non-atmospheric nitrogen.
252. The bacterial population according to clause 245, wherein the plant comprises the seed, stalk, flower, fruit, leaves, or rhizome.
253. The bacterial population according to clause 245, wherein the plurality of bacteria are formulated into a composition.
254. The bacterial population according to clause 245, wherein the plurality of bacteria are formulated into a composition comprising an agriculturally acceptable carrier.
255. The bacterial population according to clause 245, wherein the plurality of bacteria are applied into furrows in which seeds of said plant are planted.
256. The bacterial population according to clause 245, wherein the plurality of bacteria are formulated into a liquid in-furrow composition comprising bacteria at a concentration of about $1 \times 10^7$ to about $1 \times 10^{10}$ cfu per milliliter.
257. The bacterial population according to clause 245, wherein the plurality of bacteria are applied onto a seed of said plant.
258. The bacterial population according to clause 245, wherein the plurality of bacteria are formulated into a seed coating and are applied onto a seed of said plant.
259. The bacterial population according to clause 245, wherein the plurality of bacteria are formulated into a seed coating and are applied onto a seed of said plant, at a concentration of about $1 \times 10^5$ to about $1 \times 10^7$ cfu per seed.
260. The bacterial population according to clause 245, wherein the plant is a cereal crop.
261. The bacterial population according to clause 245, wherein the plant is selected from the group consisting of: corn, rice, wheat, barley, *sorghum*, millet, oat, rye, and triticale.
262. The bacterial population according to clause 245, wherein the plant is corn.
263. The bacterial population according to clause 245, wherein the plant is an agricultural crop plant.
264. The bacterial population according to clause 245, wherein the plant is a genetically modified organism.
265. The bacterial population according to clause 245, wherein the plant is not a genetically modified organism.
266. The bacterial population according to clause 245, wherein the plant has been genetically engineered or bred for efficient nitrogen use.
267. The bacterial population according to clause 245, wherein the plurality of bacteria comprise at least two different species of bacteria.
268. The bacterial population according to clause 245, wherein the plurality of bacteria comprise at least two different strains of the same species of bacteria.
269. The bacterial population according to clause 245, wherein the plurality of bacteria comprise bacteria selected from: *Rahnella aquatilis, Klebsiella variicola, Achromobacter spiritinus, Achromobacter marplatensis, Aficrobacterium murale, Kluyvera intermedia, Kosakonia pseudosacchari, Enterobacter* sp., *Azospirillum lipoferum, Kosakonia sacchari*, and combinations thereof.
270. The bacterial population according to clause 245, wherein the plurality of bacteria are endophytic, epiphytic, or rhizospheric.
271. The bacterial population according to clause 245, wherein the plurality of bacteria are selected from: a bacteria deposited as NCMA 201701003, a bacteria deposited as NCMA 201701001, and a bacteria deposited as NCMA 201708001.
272. A bacterium that:
   i. has an average colonization ability per unit of plant root tissue of at least about $1.0 \times 10^4$ bacterial cells per gram of fresh weight of plant root tissue; and/or
   ii. produces fixed N of at least about $1 \times 10^{-17}$ mmol N per bacterial cell per hour.
273. A non-intergeneric bacterium, comprising: at least one genetic variation introduced into at least one gene, or non-coding polynucleotide, of the nitrogen fixation or assimilation genetic regulatory network, such that the non-intergeneric bacterium is capable of fixing atmospheric nitrogen in the presence of exogenous nitrogen, and wherein said bacterium:
   i. has an average colonization ability per unit of plant root tissue of at least about $1.0 \times 10^4$ bacterial cells per gram of fresh weight of plant root tissue; and/or
   ii. produces fixed N of at least about $1 \times 10^{-17}$ mmol N per bacterial cell per hour.
274. The non-intergeneric bacterium according to clause 273, wherein the bacterium has an average colonization ability per unit of plant root tissue of at least about $1.0 \times 10^4$ bacterial cells per gram of fresh weight of plant root tissue.
275. The non-intergeneric bacterium according to clause 273, wherein the bacterium produces fixed N of at least about $1 \times 10^{-17}$ mmol N per bacterial cell per hour.
276. The non-intergeneric bacterium according to clause 273, wherein the bacterium has an average colonization ability per unit of plant root tissue of at least about $1.0 \times 10^4$ bacterial cells per gram of fresh weight of plant root tissue and produces fixed N of at least about $1 \times 10^{-17}$ mmol N per bacterial cell per hour.
277. The non-intergeneric bacterium according to clause 273, wherein the bacterium has an average colonization ability per unit of plant root tissue of at least about $1.0 \times 10^4$ bacterial cells per gram of fresh weight of plant root tissue and produces fixed N of at least about $1 \times 10^{-17}$ mmol N per bacterial cell per hour, and wherein the product of (i) the average colonization ability per unit of plant root tissue and (ii) produced fixed N per bacterial cell per hour, is at least about $2.5 \times 10^{-8}$ mmol N per gram of fresh weight of plant root tissue per hour.
278. The non-intergeneric bacterium according to clause 273, wherein the at least one genetic variation comprises an introduced control sequence operably linked to the at least one gene of the nitrogen fixation or assimilation genetic regulatory network.
279. The non-intergeneric bacterium according to clause 273, wherein the at least one genetic variation comprises a promoter operably linked to the at least one gene of the nitrogen fixation or assimilation genetic regulatory network.
280. The non-intergeneric bacterium according to clause 273, wherein the at least one genetic variation comprises an inducible promoter operably linked to the at least one gene of the nitrogen fixation or assimilation genetic regulatory network.

281. The non-intergeneric bacterium according to clause 273, wherein the bacterium does not comprise a constitutive promoter operably linked to a gene of the nitrogen fixation or assimilation genetic regulatory network.

282. The non-intergeneric bacterium according to clause 273, wherein the bacterium does not comprise a constitutive promoter operably linked to a gene in the nif gene cluster.

283. The non-intergeneric bacterium according to clause 273, wherein the bacterium, in planta, excretes the nitrogen-containing products of nitrogen fixation.

284. The non-intergeneric bacterium according to clause 273, wherein the at least one gene, or non-coding polynucleotide, of the nitrogen fixation or assimilation genetic regulatory network are selected from the group consisting of: nifA, nifL, ntrB, ntrC, polynucleotide encoding glutamine synthetase, glnA, glnB, glnK, drat, amtB, polynucleotide encoding glutaminase, glnD, glnE, nifJ, nifH, nifD, nifK, nif, nifE, nifN, nifU, nifS, nifV, nifW, nifZ, nifM, nifF, nifB, nifQ, and a gene associated with biosynthesis of a nitrogenase enzyme.

285. The non-intergeneric bacterium according to clause 273, wherein the at least one genetic variation is a mutation that results in one or more of: increased expression or activity of NifA or glutaminase; decreased expression or activity of NifL, NtrB, glutamine synthetase, GlnB, GlnK, DraT, AmtB; decreased adenylyl-removing activity of GlnE; or decreased uridylyl-removing activity of GlnD.

286. The non-intergeneric bacterium according to clause 273, wherein the at least one genetic variation is selected from: (A) a knock-out mutation; (B) alters or abolishes a regulatory sequence of a target gene; (C) comprises the insertion of a heterologous regulatory sequence; or (D) a domain deletion.

287. The non-intergeneric bacterium according to clause 273, wherein the at least one genetic variation is a mutated nifL gene that has been altered to comprise a heterologous promoter inserted into said nifL gene.

288. The non-intergeneric bacterium according to clause 273, wherein the at least one genetic variation is a mutated glnE gene that results in a truncated GlnE protein lacking an adenylyl-removing (AR) domain.

289. The non-intergeneric bacterium according to clause 273, wherein the at least one genetic variation is a mutated amtB gene that results in the lack of expression of said amtB gene.

290. The non-intergeneric bacterium according to clause 273, wherein the at least one genetic variation is selected from: a mutated nifL gene that has been altered to comprise a heterologous promoter inserted into said nifL gene; a mutated glnE gene that results in a truncated GlnE protein lacking an adenylyl-removing (AR) domain; a mutated amtB gene that results in the lack of expression of said amtB gene; and combinations thereof.

291. The non-intergeneric bacterium according to clause 273, wherein the at least one genetic variation is a mutated nifL gene that has been altered to comprise a heterologous promoter inserted into said nifL gene and a mutated glnE gene that results in a truncated GlnE protein lacking an adenylyl-removing (AR) domain.

292. The non-intergeneric bacterium according to clause 273, wherein the at least one genetic variation is a mutated nifL gene that has been altered to comprise a heterologous promoter inserted into said nifL gene and a mutated glnE gene that results in a truncated GlnE protein lacking an adenylyl-removing (AR) domain and a mutated amtB gene that results in the lack of expression of said amtB gene.

293. The non-intergeneric bacterium according to clause 273, formulated into a composition.

294. The non-intergeneric bacterium according to clause 273, formulated into a composition comprising an agriculturally acceptable carrier.

295. The non-intergeneric bacterium according to clause 273, formulated into a liquid in-furrow composition.

296. The non-intergeneric bacterium according to clause 273, formulated into a seed coating.

297. The non-intergeneric bacterium according to clause 273, wherein said bacterium is selected from: *Rahnella aquatilis, Klebsiella variicola, Achromobacter spiritinus, Achromobacter marplatensis, Microbacterium murale, Kluyvera intermedia, Kosakonia pseudosacchari, Enterobacter* sp., *Azospirillum lipoferum, Kosakonia sacchari*, and combinations thereof.

298. The non-intergeneric bacterium according to clause 273, wherein said bacterium is endophytic, epiphytic, or rhizospheric.

299. The non-intergeneric bacterium according to clause 273, wherein said bacterium is selected from: a bacteria deposited as PTA-122293, a bacteria deposited as PTA-122294, a bacteria deposited as NCMA 201701002, a bacteria deposited as NCMA 201708004, a bacteria deposited as NCMA 201708003, a bacteria deposited as NCMA 201708002, a bacteria deposited as NCMA 201712001, a bacteria deposited as NCMA 201712002, and combinations thereof.

300. A method of increasing nitrogen fixation in a plant, comprising administering to the plant an effective amount of a composition comprising:
  i. a purified population of bacteria that comprises bacteria with a 16S nucleic acid sequence that is at least about 97% identical to a nucleic acid sequence selected from SEQ ID NOs: 85, 96, 111, 121, 122, 123, 124, 136, 149, 157, 167, 261, 262, 269, 277-283;
  ii. a purified population of bacteria that comprises bacteria with a nucleic acid sequence that is at least about 90% identical to a nucleic acid sequence selected from SEQ ID NOs: 86-95, 97-110, 112-120, 125-135, 137-148, 150-156, 158-166, 168-176, 263-268, 270-274, 275, 276, 284-295; and/or
  iii. a purified population of bacteria that comprises bacteria with a nucleic acid sequence that is at least about 90% identical to a nucleic acid sequence selected from SEQ ID NOs: 177-260, 296-303; and
  wherein the plant administered the effective amount of the composition exhibits an increase in nitrogen fixation, as compared to a plant not having been administered the composition.

301. The method of clause 300, wherein the composition comprises: a purified population of bacteria that comprises bacteria with a 16S nucleic acid sequence that is at least about 97% identical to a nucleic acid sequence selected from SEQ ID NOs: 85, 96, 111, 121, 122, 123, 124, 136, 149, 157, 167, 261, 262, 269, and 277-283.

302. The method of clause 300, wherein the composition comprises: a purified population of bacteria that comprises bacteria with a 16S nucleic acid sequence that is at least about 99% identical to a nucleic acid sequence selected from SEQ ID NOs: 85, 96, 111, 121, 122, 123, 124, 136, 149, 157, 167, 261, 262, 269, and 277-283.

303. The method of clause 300, wherein the composition comprises: a purified population of bacteria that comprises bacteria with a 16S nucleic acid sequence selected from SEQ ID NOs: 85, 96, 111, 121, 122, 123, 124, 136, 149, 157, 167, 261, 262, 269, and 277-283.

304. The method of clause 300, wherein the composition comprises: a purified population of bacteria that comprises bacteria with a nucleic acid sequence that is at least about 90% identical to a nucleic acid sequence selected from SEQ ID NOs: 86-95, 97-110, 112-120, 125-135, 137-148, 150-156, 158-166, 168-176, 263-268, 270-274, 275, 276, and 284-295.

305. The method of clause 300, wherein the composition comprises: a purified population of bacteria that comprises bacteria with a nucleic acid sequence that is at least about 95% identical to a nucleic acid sequence selected from SEQ ID NOs: 86-95, 97-110, 112-120, 125-135, 137-148, 150-156, 158-166, 168-176, 263-268, 270-274, 275, 276, and 284-295.

306. The method of clause 300, wherein the composition comprises: a purified population of bacteria that comprises bacteria with a nucleic acid sequence that is at least about 99% identical to a nucleic acid sequence selected from SEQ ID NOs: 86-95, 97-110, 112-120, 125-135, 137-148, 150-156, 158-166, 168-176, 263-268, 270-274, 275, 276, and 284-295.

307. The method of clause 300, wherein the composition comprises: a purified population of bacteria that comprises bacteria with a nucleic acid sequence selected from SEQ ID NOs: 86-95, 97-110, 112-120, 125-135, 137-148, 150-156, 158-166, 168-176, 263-268, 270-274, 275, 276, and 284-295.

308. The method of clause 300, wherein the composition comprises: a purified population of bacteria that comprises bacteria with a nucleic acid sequence that is at least about 90% identical to a nucleic acid sequence selected from SEQ ID NOs: 177-260 and 296-303.

309. The method of clause 300, wherein the composition comprises: a purified population of bacteria that comprises bacteria with a nucleic acid sequence that is at least about 95% identical to a nucleic acid sequence selected from SEQ ID NOs: 177-260 and 296-303.

310. The method of clause 300, wherein the composition comprises: a purified population of bacteria that comprises bacteria with a nucleic acid sequence that is at least about 99% identical to a nucleic acid sequence selected from SEQ ID NOs: 177-260 and 296-303.

311. The method of clause 300, wherein the composition comprises: a purified population of bacteria that comprises bacteria with a nucleic acid sequence selected from SEQ ID NOs: 177-260 and 296-303.

312. The method of clause 300, wherein the composition comprises: a purified population of bacteria that comprise bacteria with at least one genetic variation introduced into a gene selected from the group consisting of nifA, nifL, ntrB, ntrC, polynucleotide encoding glutamine synthetase, glnA, glnB, glnK, drat, amtB, polynucleotide encoding glutaminase, glnD, glnE, nifJ, nifH, nifD, nifK, nifY, nifE, nifN, nifU, nifS, nifV, nifW, nifZ, nifM, nifF, nifB, nifQ, and a gene associated with biosynthesis of a nitrogenase enzyme.

313. The method of clause 300, wherein the composition comprises: a purified population of bacteria that comprise bacteria with at least one genetic variation introduced into a gene selected from the group consisting of nifA, nifL, ntrB, nifC, polynucleotide encoding glutamine synthetase, glnA, glnB, glnK, drat, amtB, polynucleotide encoding glutaminase, glnD, glnE, nifJ, nifH, nifD, nifK, nifY, nifE, nifN, nifU, nifS, nifV, nifW, nifZ, nifM, nifF, nifB, nifQ, and a gene associated with biosynthesis of a nitrogenase enzyme, wherein the genetic variation (A) is a knock-out mutation; (B) alters or abolishes a regulatory sequence of a target gene; (C) comprises the insertion of a heterologous regulatory sequence; or (D) a domain deletion.

314. The method of clause 300, wherein the composition comprises: a purified population of bacteria that comprise bacteria with at least one mutation that results in one or more of: increased expression or activity of NifA or glutaminase; decreased expression or activity of NifL, NtrB, glutamine synthetase, GlnB, GlnK, DraT, or AmtB; decreased adenylyl-removing activity of GlnE; or decreased uridylyl-removing activity of GlnD.

315. The method of clause 300, wherein the composition comprises: a purified population of bacteria that comprise bacteria with a mutated nifL gene that has been altered to comprise a heterologous promoter inserted into said nifL gene.

316. The method of clause 300, wherein the composition comprises: a purified population of bacteria that comprise bacteria with a mutated glnE gene that results in a truncated GlnE protein lacking an adenylyl-removing (AR) domain.

317. The method of clause 300, wherein the composition comprises: a purified population of bacteria that comprise bacteria with a mutated amtB gene that results in the lack of expression of said amtB gene.

318. The method of clause 300, wherein the composition comprises: a purified population of bacteria that comprise bacteria with at least one of the following genetic alterations: a mutated nif gene that has been altered to comprise a heterologous promoter inserted into said nifL gene; a mutated glnE gene that results in a truncated GlnE protein lacking an adenylyl-removing (AR) domain; a mutated amtB gene that results in the lack of expression of said amtB gene; and combinations thereof.

319. The method of clause 300, wherein the composition comprises: a purified population of bacteria that comprise bacteria with a mutated nifL gene that has been altered to comprise a heterologous promoter inserted into said nifL gene and a mutated glnE gene that results in a truncated GlnE protein lacking an adenylyl-removing (AR) domain.

320. The method of clause 300, wherein the composition comprises: a purified population of bacteria that comprise bacteria with a mutated nifL gene that has been altered to comprise a heterologous promoter inserted into said nm/L gene and a mutated glnE gene that results in a truncated GlnE protein lacking an adenylyl-removing (AR) domain and a mutated amtB gene that results in the lack of expression of said amtB gene.

321. The method of clause 300, wherein the composition comprises: a purified population of bacteria that comprise bacteria with a nifL modification that expresses a NifL protein at less than about 50% of a bacteria lacking the nifL modification.

322. The method of clause 300, wherein the composition comprises: a purified population of bacteria that comprise bacteria with a nifL modification that expresses a NifL protein at less than about 50% of a bacteria lacking the nifL modification, wherein the modification is a disruption, knockout, or truncation.

323. The method of clause 300, wherein the composition comprises: a purified population of bacteria that comprise bacteria with a nifL modification that expresses a NifL protein at less than about 50% of a bacteria lacking the nifL modification, and wherein the bacteria further comprise a promoter operably linked to a nifA sequence.

324. The method of clause 300, wherein the composition comprises: a purified population of bacteria that comprise bacteria with a nifL modification that expresses a NifL protein at less than about 50% of a bacteria lacking the nifL modification, and wherein the bacteria lack a nifL homolog.

325. The method of clause 300, wherein the composition comprises: a purified population of bacteria that comprise bacteria with a glnE modification that expresses a GlnE protein at less than about 50% of a bacteria lacking the glnE modification.

326. The method of clause 300, wherein the composition comprises: a purified population of bacteria that comprise bacteria with a glnE modification that expresses a GlnE protein at less than about 50% of a bacteria lacking the glnE modification, wherein the modification is a disruption, knockout, or a truncation.

327. The method of clause 300, wherein the composition comprises: a purified population of bacteria that comprise bacteria with a glnE modification that expresses a GlnE protein at less than about 50% of a bacteria lacking the glnE modification, and wherein the GlnE protein sequence lacks an adenylyl removing (AR) domain.

328. The method of clause 300, wherein the composition comprises: a purified population of bacteria that comprise bacteria with a glnE modification that expresses a GlnE protein at less than about 50% of a bacteria lacking the glnE modification, and wherein the GlnE protein sequence lacks adenylyl removing (AR) activity.

329. The method of clause 300, wherein the purified population of bacteria, in planta, provide at least 1% of fixed nitrogen to the plant.

330. The method of clause 300, wherein the purified population of bacteria, in planta, provide at least 5% of fixed nitrogen to the plant.

331. The method of clause 300, wherein the purified population of bacteria, in planta, provide at least 10% of fixed nitrogen to the plant.

332. The method of clause 300, wherein the purified population of bacteria are capable of fixing atmospheric nitrogen in non-nitrogen-limiting conditions.

333. The method of clause 300, wherein the purified population of bacteria, in planta, excrete nitrogen-containing products of nitrogen fixation.

334. The method of clause 300, wherein the purified population of bacteria, in planta, provide at least 1% of fixed nitrogen to the plant, and wherein said fixed nitrogen is measured through dilution of enriched fertilizer by atmospheric $N_2$ gas in plant tissue.

335. The method of clause 300, wherein the purified population of bacteria colonize a root of said plant and are present in an amount of at least about $1.0 \times 10^4$ bacterial cells per gram of fresh weight of plant root tissue.

336. The method of clause 300, wherein the plant comprises the seed, stalk, flower, fruit, leaves, or rhizome.

337. The method of clause 300, wherein the composition comprises: an agriculturally acceptable carrier.

338. The method of clause 300, wherein the composition comprising the purified population of bacteria is administered into furrows in which seeds of said plant are planted.

339. The method of clause 300, wherein the composition comprising the purified population of bacteria is formulated as a liquid in-furrow composition comprising bacteria at a concentration of about $1 \times 10^7$ to about $1 \times 10^{10}$ cfu per milliliter.

340. The method of clause 300, wherein the composition comprising the purified population of bacteria is administered onto a seed of said plant.

341. The method of clause 300, wherein the composition comprising the purified population of bacteria is formulated as a seed coating and is administered onto a seed of said plant.

342. The method of clause 300, wherein the composition comprising the purified population of bacteria is formulated as a seed coating and is administered onto a seed of said plant, at a concentration of about $1 \times 10^5$ to about $1 \times 10^7$ cfu per seed.

343. The method of clause 300, wherein the plant is non-leguminous.

344. The method of clause 300, wherein the plant is a cereal crop.

345. The method of clause 300, wherein the plant is selected from the group consisting of: corn, rice, wheat, barley, sorghum, millet, oat, rye, and triticale.

346. The method of clause 300, wherein the plant is corn.

347. The method of clause 300, wherein the plant is a legume.

348. The method of clause 300, wherein the plant is a grain crop.

349. The method of clause 300, wherein the purified population of bacteria comprise bacteria selected from: Rahnella aquatilis, Klebsiella variicola, Achromobacter spiritinus, Achromobacter marplatensis, Microbacterium murale, Kluyvera intermedia, Kosakonia pseudosacchari, Enterobacter sp., Azospirillum lipoferum, Kosakonia sacchari, and combinations thereof.

350. The method of clause 300, wherein the purified population of bacteria comprise a bacteria of genus Rahnella.

351. The method of clause 300, wherein the purified population of bacteria comprise a bacteria of species Rahnella aquatilis.

352. The method of clause 300, wherein the purified population of bacteria comprise a bacteria deposited as PTA-122293.

353. The method of clause 300, wherein the purified population of bacteria comprise a bacteria deposited as NCMA 201701003.

354. The method of clause 300, wherein the purified population of bacteria comprise a bacteria of genus Kosakonia.

355. The method of clause 300, wherein the purified population of bacteria comprise a bacteria of species Kosakonia sacchari.

356. The method of clause 300, wherein the purified population of bacteria comprise a bacteria deposited as PTA-122294.

357. The method of clause 300, wherein the purified population of bacteria comprise a bacteria deposited as NCMA 201701001.

358. The method of clause 300, wherein the purified population of bacteria comprise a bacteria deposited as NCMA 201701002.

359. The method of clause 300, wherein the purified population of bacteria comprise a bacteria deposited as NCMA 201708004.

360. The method of clause 300, wherein the purified population of bacteria comprise a bacteria deposited as NCMA 201708003.

361. The method of clause 300, wherein the purified population of bacteria comprise a bacteria deposited as NCMA 201708002.
362. The method of clause 300, wherein the purified population of bacteria comprise a bacteria of genus *Klebsiella*.
363. The method of clause 300, wherein the purified population of bacteria comprise a bacteria of species *Klebsiella variicola*.
364. The method of clause 300, wherein the purified population of bacteria comprise a bacteria deposited as NCMA 201708001.
365. The method of clause 300, wherein the purified population of bacteria comprise a bacteria deposited as NCMA 201712001.
366. The method of clause 300, wherein the purified population of bacteria comprise a bacteria deposited as NCMA 201712002.
367. An isolated bacteria, comprising:
   i. a 16S nucleic acid sequence that is at least about 97% identical to a nucleic acid sequence selected from SEQ ID NOs: 85, 96, 111, 121, 122, 123, 124, 136, 149, 157, 167, 261, 262, 269, 277-283;
   ii. a nucleic acid sequence that is at least about 90% identical to a nucleic acid sequence selected from SEQ ID NOs: 86-95, 97-110, 112-120, 125-135, 137-148, 150-156, 158-166, 168-176, 263-268, 270-274, 275, 276, 284-295; and/or
   iii. a nucleic acid sequence that is at least about 90% identical to a nucleic acid sequence selected from SEQ ID NOs: 177-260, 296-303.
368. The isolated bacteria of clause 367, comprising: a 16S nucleic acid sequence that is at least about 97% identical to a nucleic acid sequence selected from SEQ ID NOs: 85, 96, 111, 121, 122, 123, 124, 136, 149, 157, 167, 261, 262, 269, and 277-283.
369. The isolated bacteria of clause 367, comprising: a 16S nucleic acid sequence that is at least about 99% identical to a nucleic acid sequence selected from SEQ ID NOs: 85, 96, 111, 121, 122, 123, 124, 136, 149, 157, 167, 261, 262, 269, and 277-283.
370. The isolated bacteria of clause 367, comprising: a 16S nucleic acid sequence selected from SEQ ID NOs: 85, 96, 111, 121, 122, 123, 124, 136, 149, 157, 167, 261, 262, 269, and 277-283.
371. The isolated bacteria of clause 367, comprising: a nucleic acid sequence that is at least about 90% identical to a nucleic acid sequence selected from SEQ ID NOs: 86-95, 97-110, 112-120, 125-135, 137-148, 150-156, 158-166, 168-176, 263-268, 270-274, 275, 276, and 284-295.
372. The isolated bacteria of clause 367, comprising: a nucleic acid sequence that is at least about 95% identical to a nucleic acid sequence selected from SEQ ID NOs: 86-95, 97-110, 112-120, 125-135, 137-148, 150-156, 158-166, 168-176, 263-268, 270-274, 275, 276, and 284-295.
373. The isolated bacteria of clause 367, comprising: a nucleic acid sequence that is at least about 99% identical to a nucleic acid sequence selected from SEQ ID NOs: 86-95, 97-110, 112-120, 125-135, 137-148, 150-156, 158-166, 168-176, 263-268, 270-274, 275, 276, and 284-295.
374. The isolated bacteria of clause 367, comprising: a nucleic acid sequence selected from SEQ ID NOs: 86-95, 97-110, 112-120, 125-135, 137-148, 150-156, 158-166, 168-176, 263-268, 270-274, 275, 276, and 284-295.
375. The isolated bacteria of clause 367, comprising: a nucleic acid sequence that is at least about 90% identical to a nucleic acid sequence selected from SEQ ID NOs: 177-260 and 296-303.
376. The isolated bacteria of clause 367, comprising: a nucleic acid sequence that is at least about 95% identical to a nucleic acid sequence selected from SEQ ID NOs: 177-260 and 296-303.
377. The isolated bacteria of clause 367, comprising: a nucleic acid sequence that is at least about 99% identical to a nucleic acid sequence selected from SEQ ID NOs: 177-260 and 296-303.
378. The isolated bacteria of clause 367, comprising: a nucleic acid sequence selected from SEQ ID NOs: 177-260 and 296-303.
379. The isolated bacteria of clause 367, comprising: at least one genetic variation introduced into a gene selected from the group consisting of nifA, nifL, ntrB, ntrC, polynucleotide encoding glutamine synthetase, glnA, glnB, glnK, drat, amtB, polynucleotide encoding glutaminase, glnD, glnE, nifJ, nifH, nifD, nifK, nifY, nifE, nifN, nifU, nifS, nifV, nifW, nifZ, nifM, nifF, nifB, nifQ, and a gene associated with biosynthesis of a nitrogenase enzyme.
380. The isolated bacteria of clause 367, comprising: at least one genetic variation introduced into a gene selected from the group consisting of nifA, nifL, ntrB, ntrC, polynucleotide encoding glutamine synthetase, glnA, glnB, glnK, drat, amtB, polynucleotide encoding glutaminase, glnD, glnE, nifJ, nifH, nifD, nifK, nifY, nifE, nifN, nifU, nifS, nifV, nifW, nifZ, nifM, nifF, nifB, nifQ, and a gene associated with biosynthesis of a nitrogenase enzyme, wherein the genetic variation (A) is a knock-out mutation; (B) alters or abolishes a regulatory sequence of a target gene; (C) comprises the insertion of a heterologous regulatory sequence; or (D) a domain deletion.
381. The isolated bacteria of clause 367, comprising: at least one mutation that results in one or more of: increased expression or activity of NifA or glutaminase; decreased expression or activity of NifL, NtrB, glutamine synthetase, GlnB, GlnK, DraT, or AmtB; decreased adenylyl-removing activity of GlnE; or decreased uridylyl-removing activity of GlnD.
382. The isolated bacteria of clause 367, comprising: a mutated nifL gene that has been altered to comprise a heterologous promoter inserted into said nifL gene.
383. The isolated bacteria of clause 367, comprising: a mutated glnE gene that results in a truncated GlnE protein lacking an adenylyl-removing (AR) domain.
384. The isolated bacteria of clause 367, comprising: a mutated amtB gene that results in the lack of expression of said amtB gene.
385. The isolated bacteria of clause 367, comprising: at least one of the following genetic alterations: a mutated nifL gene that has been altered to comprise a heterologous promoter inserted into said nifL gene; a mutated glnE gene that results in a truncated GlnE protein lacking an adenylyl-removing (AR) domain; a mutated amtB gene that results in the lack of expression of said amtB gene; and combinations thereof.
386. The isolated bacteria of clause 367, comprising: a mutated nifL gene that has been altered to comprise a heterologous promoter inserted into said nifL gene and a mutated glnE gene that results in a truncated GlnE protein lacking an adenylyl-removing (AR) domain.
387. The isolated bacteria of clause 367, comprising: a mutated nifL gene that has been altered to comprise a heterologous promoter inserted into said nifL gene and a mutated glnE gene that results in a truncated GlnE protein lacking an adenylyl-removing (AR) domain and a mutated amtB gene that results in the lack of expression of said amtB gene.

388. The isolated bacteria of clause 367, comprising: a nifL modification that expresses a NifL protein at less than about 50% of a bacteria lacking the nifL modification.
389. The isolated bacteria of clause 367, comprising: a nifL modification that expresses a NifL protein at less than about 50% of a bacteria lacking the nifL modification, wherein the modification is a disruption, knockout, or truncation.
390. The isolated bacteria of clause 367, comprising: a nifL modification that expresses a NifL protein at less than about 50% of a bacteria lacking the nifL modification, and wherein the bacteria further comprise a promoter operably linked to a nifA sequence.
391. The isolated bacteria of clause 367, comprising: a nit modification that expresses a NifL protein at less than about 50% of a bacteria lacking the nifL modification, and wherein the bacteria lack a nifL homolog.
392. The isolated bacteria of clause 367, comprising: a glnE modification that expresses a GlnE protein at less than about 50% of a bacteria lacking the glnE modification.
393. The isolated bacteria of clause 367, comprising: a glnE modification that expresses a GlnE protein at less than about 50% of a bacteria lacking the glnE modification, wherein the modification is a disruption, knockout, or a truncation.
394. The isolated bacteria of clause 367, comprising: a glnE modification that expresses a GlnE protein at less than about 50% of a bacteria lacking the glnE modification, and wherein the GlnE protein sequence lacks an adenylyl removing (AR) domain.
395. The isolated bacteria of clause 367, comprising: a glnE modification that expresses a GlnE protein at less than about 50% of a bacteria lacking the glnE modification, and wherein the GlnE protein sequence lacks adenylyl removing (AR) activity.
396. The isolated bacteria of clause 367, wherein the bacteria, in planta, provide at least 1% of fixed nitrogen to a plant exposed to said bacteria.
397. The isolated bacteria of clause 367, wherein the bacteria, in planta, provide at least 5% of fixed nitrogen to a plant exposed to said bacteria.
398. The isolated bacteria of clause 367, wherein the bacteria, in planta, provide at least 10% of fixed nitrogen to a plant exposed to said bacteria.
399. The isolated bacteria of clause 367, wherein the bacteria is capable of fixing atmospheric nitrogen in non-nitrogen-limiting conditions.
400. The isolated bacteria of clause 367, wherein the bacteria, in planta, excretes nitrogen-containing products of nitrogen fixation.
401. The isolated bacteria of clause 367, wherein the bacteria, in planta, provide at least 1% of fixed nitrogen to a plant exposed to said bacteria, and wherein said fixed nitrogen is measured through dilution of enriched fertilizer by atmospheric $N_2$ gas in plant tissue.
402. The isolated bacteria of clause 367, wherein the bacteria colonize a root of a plant exposed to said bacteria to a concentration of at least about $1.0 \times 10^4$ bacterial cells per gram of fresh weight of plant root tissue.
403. The isolated bacteria of clause 367, formulated into an agricultural composition.
404. The isolated bacteria of clause 367, formulated into an in-furrow composition.
405. The isolated bacteria of clause 367, formulated as a liquid in-furrow composition that comprises bacteria at a concentration of about $1 \times 10^7$ to about $1 \times 10^{10}$ cfu per milliliter.
406. The isolated bacteria of clause 367, formulated as a seed treatment or seed coating.
407. The isolated bacteria of clause 367, formulated as a seed treatment or seed coating that comprises bacteria at a concentration of about $1 \times 10^5$ to about $1 \times 10^7$ cfu per seed.
408. The isolated bacteria of clause 367, wherein the bacteria is in contact with a plant and increases nitrogen fixation in the plant.
409. The isolated bacteria of clause 367, disposed on a non-leguminous plant.
410. The isolated bacteria of clause 367, disposed on a cereal crop.
411. The isolated bacteria of clause 367, disposed on a plant selected from the group consisting of: corn, rice, wheat, barley, *sorghum*, millet, oat, rye, and triticale.
412. The isolated bacteria of clause 367, disposed on corn.
413. The isolated bacteria of clause 367, disposed on a legume.
414. The isolated bacteria of clause 367, disposed on a grain crop.
415. The isolated bacteria of clause 367, selected from: *Rahnella aquatilis, Klebsiella variicola, Achromobacter spiritinus, Achromobacter marplatensis, Microbacterium murale, Kluyvera intermedia, Kosakonia pseudosacchari, Enterobacter* sp., *Azospirillum lipoferum, Kosakonia sacchari*, and combinations thereof.
416. The isolated bacteria of clause 367, wherein the bacteria is of the genus *Rahnella*.
417. The isolated bacteria of clause 367, wherein the bacteria is of the species *Rahnella aquatilis*.
418. The isolated bacteria of clause 367, deposited as PTA-122293.
419. The isolated bacteria of clause 367, deposited as NCMA 201701003.
420. The isolated bacteria of clause 367, wherein the bacteria is of the genus *Kosakonia*.
421. The isolated bacteria of clause 367, wherein the bacteria is of the species *Kosakonia sacchari*.
422. The isolated bacteria of clause 367, deposited as PTA-122294.
423. The isolated bacteria of clause 367, deposited as NCMA 201701001.
424. The isolated bacteria of clause 367, deposited as NCMA 201701002.
425. The isolated bacteria of clause 367, deposited as NCMA 201708004.
426. The isolated bacteria of clause 367, deposited as NCMA 201708003.
427. The isolated bacteria of clause 367, deposited as NCMA 201708002.
428. The isolated bacteria of clause 367, wherein the bacteria is of the genus *Klebsiella*.
429. The isolated bacteria of clause 367, wherein the bacteria is of the species *Klebsiella variicola*.
430. The isolated bacteria of clause 367, deposited as NCMA 201708001.
431. The isolated bacteria of clause 367, deposited as NCMA 201712001.
432. The isolated bacteria of clause 367, deposited as NCMA 201712002.
433. A composition comprising any one or more bacteria of clauses 415 to 432.
434. A method of detecting a non-native junction sequence, comprising: amplifying a nucleotide sequence that shares at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%,%, 950, 96%, 97%, 98%, 99%, or 100% sequence identity to SEQ ID NOs: 372-405.
435. The method according to clause 434, wherein said amplifying is by conducting a polymerase chain reaction.
436. The method according to clause 434, wherein said amplifying is by conducting a quantitative polymerase chain reaction.
437. A method of detecting a non-native junction sequence, comprising: amplifying a nucleotide sequence that shares at least about 70%, 71%, 72%, 73%, 74%, 75%, 76%, 77%, 780%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to at least a 10 contiguous base pair fragment contained in SEQ ID NOs: 372-405, said contiguous base pair fragment being comprised of nucleotides at the intersection of: an upstream sequence comprising SEQ ID NOs: 304-337 and downstream sequence comprising SEQ ID NOs: 338-371.
438. The method according to clause 437, wherein said amplifying is by conducting a polymerase chain reaction.
439. The method according to clause 437, wherein said amplifying is by conducting a quantitative polymerase chain reaction.
440. A non-native junction sequence, comprising: a nucleotide sequence that shares at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NOs: 372-405.
441. A non-native junction sequence, comprising: a nucleotide sequence that shares at least about 70%, 71%, 72%, 73%, 74%, 75%, 76%, 770%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to at least a 10 contiguous base pair fragment contained in SEQ ID NOs: 372-405, said contiguous base pair fragment being comprised of nucleotides at the intersection of: an upstream sequence comprising SEQ ID NOs: 304-337 and downstream sequence comprising SEQ ID NOs: 338-371.
442. A bacterial composition, comprising:
at least one remodeled bacterial strain that fixes atmospheric nitrogen, the at least one remodeled bacterial strain comprising exogenously added DNA wherein said exogenously added DNA shares at least 8% identity to a corresponding native bacterial strain.
443. A method of maintaining soil nitrogen levels, comprising:
planting, in soil of a field, a crop inoculated by a remodeled bacterium that fixes atmospheric nitrogen; and
harvesting said crop, wherein no more than 90% of a nitrogen dose required for producing said crop is administered to said soil of said field between planting and harvesting.
444. A method of delivering a probiotic supplement to a crop plant, comprising:
coating a crop seed with a seed coating, seed treatment, or seed dressing, wherein said seed coating, seed dressing, or seed treatment comprising living representatives of said probiotic; and
applying in soil of a field, said crop seeds.
445. A method of increasing the amount of atmospheric derived nitrogen in a non-leguminous plant, comprising:
exposing said non-leguminous plant to remodeled non-intergeneric microbes, said remodeled non-intergeneric microbes comprising at least one genetic variation introduced into a nitrogen fixation genetic regulatory network or at least one genetic variation introduced into a nitrogen assimilation genetic regulatory network.
446. A method of increasing an amount of atmospheric derived nitrogen in a corn plant, comprising:
exposing said corn plant to remodeled non-intergeneric microbes comprising remodeled genetic variations within at least two genes selected from the group consisting of nifL, glnB, glnE, and amtB.
447. A method of increasing an amount of atmospheric derived nitrogen in a corn plant, comprising:
exposing said corn plant to remodeled non-intergeneric microbes comprising at least one genetic variation introduced into a nitrogen fixation genetic regulatory network and at least one genetic variation introduced into a nitrogen assimilation genetic regulatory network, wherein said remodeled non-intergeneric microbes, in planta, produce at least 5% of fixed nitrogen in said corn plant as measured by dilution of 15N in crops grown in fields treated with fertilizer containing 1.2% 15N.
448. The method of any of the previous clauses, wherein the bacterium produces fixed N of at least about $1 \times 10^{-17}$ mmol N per bacterial cell per hour when in the presence of exogenous nitrogen.
449. The bacterium of any of the previous clauses, wherein the bacterium produces fixed N of at least about $1 \times 10^{-17}$ mmol N per bacterial cell per hour when in the presence of exogenous nitrogen.
450. The bacterial population of any of the previous clauses, wherein the bacterium produces fixed N of at least about $1 \times 10^{-17}$ mmol N per bacterial cell per hour when in the presence of exogenous nitrogen.
451. The isolated bacteria of any of the previous clauses, wherein the bacterium produces fixed N of at least about $1 \times 10^{-17}$ mmol N per bacterial cell per hour when in the presence of exogenous nitrogen.
452. The non-intergeneric bacterial population of any of the previous clauses, wherein the bacterium produces fixed N of at least about $1 \times 10^{-17}$ mmol N per bacterial cell per hour when in the presence of exogenous nitrogen.
453. The non-intergeneric bacterium of any of the previous clauses, wherein the bacterium produces fixed N of at least about $1 \times 10^{-17}$ mmol N per bacterial cell per hour when in the presence of exogenous nitrogen.
454. The method of any of the previous clauses, wherein the plurality of bacteria, in planta, produce 5% or more of the fixed nitrogen in the plant.
455. The method of any of the previous clauses, wherein the plurality of non-intergeneric bacteria, in planta, produce 5% or more of the fixed nitrogen in the plant.
456. The bacterium of any of the previous clauses, wherein the plurality of bacteria, in planta, produce 5% or more of the fixed nitrogen in the plant.
457. The bacterial population of any of the previous clauses, wherein the plurality of bacteria, in planta, produce 5% or more of the fixed nitrogen in the plant.
458. The isolated bacteria of any of the previous clauses, wherein the plurality of bacteria, in planta, produce 5% or more of the fixed nitrogen in the plant.
459. The non-intergeneric bacterial population of any of the previous clauses, wherein the plurality of non-intergeneric bacteria, in planta, produce 5% or more of the fixed nitrogen in the plant.

460. The non-intergeneric bacterium of any of the previous clauses, wherein the plurality of non-intergeneric bacteria, in planta, produce 5% or more of the fixed nitrogen in the plant.
461. The method of any of the previous clauses, wherein the plurality of bacteria, in planta, produce 10% or more of the fixed nitrogen in the plant.
462. The method of any of the previous clauses, wherein the plurality of non-intergeneric bacteria, in planta, produce 10% or more of the fixed nitrogen in the plant.
463. The bacterium of any of the previous clauses, wherein the plurality of bacteria, in planta, produce 10% or more of the fixed nitrogen in the plant.
464. The bacterial population of any of the previous clauses, wherein the plurality of bacteria, in planta, produce 10% or more of the fixed nitrogen in the plant.
465. The isolated bacteria of any of the previous clauses, wherein the plurality of bacteria, in planta, produce 10% or more of the fixed nitrogen in the plant.
466. The non-intergeneric bacterial population of any of the previous clauses, wherein the plurality of non-intergeneric bacteria, in planta, produce 10% or more of the fixed nitrogen in the plant.
467. The non-intergeneric bacterium of any of the previous clauses, wherein the plurality of non-intergeneric bacteria, in planta, produce 10% or more of the fixed nitrogen in the plant.
468. The method of any of the previous clauses, wherein the plurality of bacteria, in planta, produce 15% or more of the fixed nitrogen in the plant.
469. The method of any of the previous clauses, wherein the plurality of non-intergeneric bacteria, in planta, produce 15% or more of the fixed nitrogen in the plant.
470. The bacterium of any of the previous clauses, wherein the plurality of bacteria, in planta, produce 15% or more of the fixed nitrogen in the plant.
471. The bacterial population of any of the previous clauses, wherein the plurality of bacteria, in planta, produce 15% or more of the fixed nitrogen in the plant.
472. The isolated bacteria of any of the previous clauses, wherein the plurality of bacteria, in planta, produce 15% or more of the fixed nitrogen in the plant.
473. The non-intergeneric bacterial population of any of the previous clauses, wherein the plurality of non-intergeneric bacteria, in planta, produce 15% or more of the fixed nitrogen in the plant.
474. The non-intergeneric bacterium of any of the previous clauses, wherein the plurality of non-intergeneric bacteria, in planta, produce 15% or more of the fixed nitrogen in the plant.
475. The method of any of the previous clauses, wherein the plurality of bacteria, in planta, produce 20% or more of the fixed nitrogen in the plant.
476. The method of any of the previous clauses, wherein the plurality of non-intergeneric bacteria, in planta, produce 20% or more of the fixed nitrogen in the plant.
477. The bacterium of any of the previous clauses, wherein the plurality of bacteria, in planta, produce 20% or more of the fixed nitrogen in the plant.
478. The bacterial population of any of the previous clauses, wherein the plurality of bacteria, in planta, produce 20% or more of the fixed nitrogen in the plant.
479. The isolated bacteria of any of the previous clauses, wherein the plurality of bacteria, in planta, produce 20% or more of the fixed nitrogen in the plant.
480. The non-intergeneric bacterial population of any of the previous clauses, wherein the plurality of non-intergeneric bacteria, in planta, produce 20% or more of the fixed nitrogen in the plant.
481. The non-intergeneric bacterium of any of the previous clauses, wherein the plurality of non-intergeneric bacteria, in planta, produce 20% or more of the fixed nitrogen in the plant.
482. The method of any of the previous clauses, wherein the product of (i) the average colonization ability per unit of plant root tissue and (ii) produced fixed N per bacterial cell per hour, is at least about $2.0 \times 10^{-7}$ mmol N per gram of fresh weight of plant root tissue per hour.
483. The bacterium of any of the previous clauses, wherein the product of (i) the average colonization ability per unit of plant root tissue and (ii) produced fixed N per bacterial cell per hour, is at least about $2.0 \times 10^{-7}$ mmol N per gram of fresh weight of plant root tissue per hour.
484. The bacterial population of any of the previous clauses, wherein the product of (i) the average colonization ability per unit of plant root tissue and (ii) produced fixed N per bacterial cell per hour, is at least about $2.0 \times 10^{-7}$ mmol N per gram of fresh weight of plant root tissue per hour.
485. The isolated bacteria of any of the previous clauses, wherein the product of (i) the average colonization ability per unit of plant root tissue and (ii) produced fixed N per bacterial cell per hour, is at least about $2.0 \times 10^{-7}$ mmol N per gram of fresh weight of plant root tissue per hour.
486. The non-intergeneric bacterial population of any of the previous clauses, wherein the product of (i) the average colonization ability per unit of plant root tissue and (ii) produced fixed N per bacterial cell per hour, is at least about $2.0 \times 10^{-7}$ mmol N per gram of fresh weight of plant root tissue per hour.
487. The non-intergeneric bacterium of any of the previous clauses, wherein the product of (i) the average colonization ability per unit of plant root tissue and (ii) produced fixed N per bacterial cell per hour, is at least about $2.0 \times 10^{-7}$ mmol N per gram of fresh weight of plant root tissue per hour.
488. The method of any of the previous clauses, wherein the product of (i) the average colonization ability per unit of plant root tissue and (ii) produced fixed N per bacterial cell per hour, is at least about $2.0 \times 10^{-6}$ mmol N per gram of fresh weight of plant root tissue per hour.
489. The bacterium of any of the previous clauses, wherein the product of (i) the average colonization ability per unit of plant root tissue and (ii) produced fixed N per bacterial cell per hour, is at least about $2.0 \times 10^{-6}$ mmol N per gram of fresh weight of plant root tissue per hour.
490. The bacterial population of any of the previous clauses, wherein the product of (i) the average colonization ability per unit of plant root tissue and (ii) produced fixed N per bacterial cell per hour, is at least about $2.0 \times 10^{-6}$ mmol N per gram of fresh weight of plant root tissue per hour.
491. The isolated bacteria of any of the previous clauses, wherein the product of (i) the average colonization ability per unit of plant root tissue and (ii) produced fixed N per bacterial cell per hour, is at least about $2.0 \times 10^{-6}$ mmol N per gram of fresh weight of plant root tissue per hour.
492. The non-intergeneric bacterial population of any of the previous clauses, wherein the product of (i) the average colonization ability per unit of plant root tissue and (ii) produced fixed N per bacterial cell per hour, is at least about $2.0 \times 10^{-6}$ mmol N per gram of fresh weight of plant root tissue per hour.

493. The non-intergeneric bacterium of any of the previous clauses, wherein the product of (i) the average colonization ability per unit of plant root tissue and (ii) produced fixed N per bacterial cell per hour, is at least about $2.0 \times 10^{-6}$ mmol N per gram of fresh weight of plant root tissue per hour.

494. The method of any of the previous clauses, wherein the plant has been remodeled or bred for efficient nitrogen use.

495. The bacterial composition of any of the previous clauses, wherein said at least one remodeled bacterial strain comprises at least one variation in a gene or intergenic region within 10,000 bp of a gene selected from the group consisting of: nifA, nifL, ntrB, ntrC, glnA, glnB, glnK, draT, amtB, glnD, glnE, nifJ, nifH, nifD, nifK, nifY, nifE, nifN, nifU, nifS, nifV, nifW, nifZ, nifM, nifF, nifB, and nifQ.

496. The method of any of the previous clauses, wherein said remodeled bacterium comprises a bacterial composition of any of the preceding clauses.

497. The method of any of the previous clauses, wherein said remodeled bacterium consists of a bacterial composition of any of the preceding clauses.

498. The method of any of the previous clauses, wherein the remodeled bacterial strain is a remodeled Gram-positive bacterial strain.

499. The method of any of the previous clauses, wherein the remodeled Gram-positive bacterial strain has an altered expression level of a regulator of a Nif cluster.

500. The method of any of the previous clauses, wherein the remodeled Gram-positive bacterial strain expresses a decreased amount of a negative regulator of a Nif cluster.

501. The method of any of the previous clauses, wherein the remodeled bacterial strain expresses a decreased amount of GlnR.

502. The method of any of the previous clauses, wherein the genome of the remodeled bacterial strain encodes a polypeptide with at least 75% identity to a sequence from the Zehr lab NifH database.

503. The method of any of the previous clauses, wherein the genome of the remodeled bacterial strain encodes a polypeptide with at least 85% identity to a sequence from the Zehr lab NifH database.

504. The method of any of the previous clauses, wherein the genome of the remodeled bacterial strain encodes a polypeptide with at least 75% identity to a sequence from the Buckley lab NifH database.

505. The method of any of the previous clauses, wherein the genome of the remodeled bacterial strain encodes a polypeptide with at least 85% identity to a sequence from the Buckley lab NifH database.

506. The method of any of the previous clauses, wherein said remodeled non-intergeneric microbes comprise at least one genetic variation introduced into said nitrogen fixation genetic regulatory network.

507. The method of any of the previous clauses, wherein said remodeled non-intergeneric microbes comprise at least one genetic variation introduced into said nitrogen assimilation genetic regulatory network.

508. The method of any of the previous clauses, wherein said remodeled non-intergeneric microbes comprise at least one genetic variation introduced into said nitrogen fixation genetic regulatory network and at least one genetic variation introduced into said nitrogen assimilation genetic regulatory network.

509. The method of any of the previous clauses, wherein said remodeled non-intergeneric microbes are applied into furrows in which seeds of said non-leguminous plant are planted.

510. The method of any of the previous clauses, wherein said remodeled non-intergeneric microbes are coated onto a seed of said non-leguminous plant.

511. The method of any of the previous clauses, wherein said remodeled non-intergeneric microbes colonize at least a root of said non-leguminous plant such that said remodeled non-intergeneric microbes are present in said non-leguminous plant in an amount of at least $10^5$ colony forming units per gram fresh weight of tissue.

512. The method of any of the previous clauses, wherein said remodeled non-intergeneric microbes are capable of fixing atmospheric nitrogen in non-nitrogen-limiting conditions.

513. The method of any of the previous clauses, wherein said remodeled non-intergeneric microbes, in planta, excrete nitrogen-containing products of nitrogen fixation.

514. The method of any of the previous clauses, wherein said remodeled non-intergeneric microbes, in planta, produce at least 1% of fixed nitrogen in said non-leguminous plant.

515. The method of any of the previous clauses, wherein said fixed nitrogen in said non-leguminous plant produced by said remodeled non-intergeneric microbes is measured by dilution of 15N in crops grown in fields treated with fertilizer containing 1.2% 15N.

516. The method of any of the previous clauses, wherein said remodeled non-intergeneric microbes, in planta, produce 5% or more of the fixed nitrogen in said non-leguminous plant.

517. The method of any of the previous clauses, wherein said non-intergeneric microbes are remodeled using at least one type of engineering selected from the group consisting of directed mutagenesis, random mutagenesis, and directed evolution.

518. The method of any of the previous clauses, wherein said remodeled non-intergeneric microbes, in planta, excrete nitrogen-containing products of nitrogen fixation.

519. The method of any of the previous clauses, wherein said remodeled non-intergeneric microbes are applied into furrows in which seeds of said corn plant are planted.

520. The method of any of the previous clauses, wherein said remodeled non-intergeneric microbes are coated onto a seed of said corn plant.

521. The method of any of the previous clauses, wherein said remodeled non-intergeneric microbes comprise at least one genetic variation introduced into a nitrogen fixation genetic regulatory network and at least one genetic variation introduced into a nitrogen assimilation genetic regulatory network.

522. The method of any of the previous clauses, wherein said non-intergeneric microbes comprise at least one genetic variation introduced into a nitrogen fixation genetic regulatory network and at least one genetic variation introduced into a nitrogen assimilation genetic regulatory network.

523. The method of any of the previous clauses, wherein said genetically engineered non-intergeneric microbes comprise at least one genetic variation introduced into a nitrogen fixation genetic regulatory network and at least one genetic variation introduced into a nitrogen assimilation genetic regulatory network.

524. The method of any of the previous clauses, wherein said remodeled non-intergeneric bacteria comprise at least one genetic variation introduced into a nitrogen fixation genetic regulatory network and at least one genetic variation introduced into a nitrogen assimilation genetic regulatory network.
525. The method of any of the previous clauses, wherein said non-intergeneric bacteria comprise at least one genetic variation introduced into a nitrogen fixation genetic regulatory network and at least one genetic variation introduced into a nitrogen assimilation genetic regulatory network.
526. The method of any of the previous clauses, wherein said genetically engineered non-intergeneric bacteria comprise at least one genetic variation introduced into a nitrogen fixation genetic regulatory network and at least one genetic variation introduced into a nitrogen assimilation genetic regulatory network.
527. The bacterium of any of the previous clauses, wherein said bacterium comprise at least one genetic variation introduced into a nitrogen fixation genetic regulatory network and at least one genetic variation introduced into a nitrogen assimilation genetic regulatory network.
528. The bacterial population of any of the previous clauses, wherein bacteria within said bacterial population comprise at least one genetic variation introduced into a nitrogen fixation genetic regulatory network and at least one genetic variation introduced into a nitrogen assimilation genetic regulatory network.
529. The isolated bacteria of any of the previous clauses, wherein said isolated bacteria comprise at least one genetic variation introduced into a nitrogen fixation genetic regulatory network and at least one genetic variation introduced into a nitrogen assimilation genetic regulatory network.
530. The non-intergeneric bacterial population of any of the previous clauses, wherein non-intergeneric bacteria within said non-intergeneric bacterial population comprise at least one genetic variation introduced into a nitrogen fixation genetic regulatory network and at least one genetic variation introduced into a nitrogen assimilation genetic regulatory network.
531. The non-intergeneric bacterium of any of the previous clauses, wherein said non-intergeneric bacterium comprises at least one genetic variation introduced into a nitrogen fixation genetic regulatory network and at least one genetic variation introduced into a nitrogen assimilation genetic regulatory network.
532. A composition comprising any one or more bacteria of any of the previous clauses.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The invention claimed is:

1. A method of decreasing an amount of nitrogen-containing fertilizer required for producing a yield of a crop, the method comprising:
   a) inoculating soil of a field with a plurality of genetically engineered bacteria that fix atmospheric nitrogen, wherein the genetically engineered bacteria comprise at least one genetic variation introduced into at least one gene, or non-coding polynucleotide, of a nitrogen fixation or assimilation genetic regulatory network, such that the genetically engineered bacteria are capable of fixing atmospheric nitrogen in the presence of exogenous nitrogen, wherein said plurality of genetically engineered bacteria:
      i. have an average colonization ability per unit of plant root tissue of at least about $1.0 \times 10^4$ bacterial cells per gram of fresh weight of plant root tissue; and
      ii. produce fixed N at a rate of at least about $1 \times 10^{-17}$ mmol N per bacterial cell per hour,
   b) planting a crop in said inoculated soil; and
   c) applying a nitrogen-containing fertilizer, wherein the applied nitrogen-containing fertilizer corresponds to no more than 90% of a dose of said nitrogen-containing fertilizer, wherein said yield of said crop is the same as if 100% of the dose of nitrogen-containing fertilizer is applied under similar conditions between planting and harvesting said crop in the absence of said plurality of genetically engineered bacteria.

2. The method of claim 1, wherein no more than 80% of said dose of said nitrogen-containing fertilizer required for producing said crop is applied to said soil of said field between planting and harvesting.

3. The method of claim 1, wherein no more than 70% of said dose of said nitrogen-containing fertilizer required for producing said crop is applied to said soil of said field between planting and harvesting.

4. The method of claim 1, wherein no more than 60% of said dose of said nitrogen-containing fertilizer required for producing said crop is applied to said soil of said field between planting and harvesting.

5. The method of claim 1, wherein no more than 50% of said dose of said nitrogen-containing fertilizer required for producing said crop is applied to said soil of said field between planting and harvesting.

6. The method of claim 1, wherein no more than 40% of said dose of said nitrogen-containing fertilizer required for producing said crop is applied to said soil of said field between planting and harvesting.

7. The method of claim 1, wherein the genetically engineered bacteria comprise an introduced control sequence operably linked to at least one gene of a nitrogen fixation or assimilation genetic regulatory network.

8. The method of claim 1, wherein the genetically engineered bacteria comprise a promoter operably linked to at least one gene of a nitrogen fixation or assimilation genetic regulatory network.

9. The method of claim 1, wherein the genetically engineered bacteria comprise an inducible promoter operably linked to at least one gene of a nitrogen fixation or assimilation genetic regulatory network.

10. The method of claim 1, wherein said plurality of genetically engineered bacteria are applied into a furrow in which seeds of said crop are planted.

11. The method of claim 1, wherein said plurality of genetically engineered bacteria are selected from the group consisting of: Proteobacteria, Firmicutes, and Actinobacteria.

12. The method of claim 1, wherein said plurality of genetically engineered bacteria are from a genus selected from the group consisting of *Rahnella, Enterobacter, Kosakonia*, and *Klebsiella*.

13. The method of claim 11, wherein the genetically engineered bacteria comprise a negative regulator of nitrogen fixation.

14. The method of claim 13, wherein said negative regulator of nitrogen fixation is selected from the group consisting of NifL and GlnR.

* * * * *

UNITED STATES PATENT AND TRADEMARK OFFICE
CERTIFICATE OF CORRECTION

| | |
|---|---|
| PATENT NO. | : 11,565,979 B2 |
| APPLICATION NO. | : 16/192738 |
| DATED | : January 31, 2023 |
| INVENTOR(S) | : Karsten Temme et al. |

It is certified that error appears in the above-identified patent and that said Letters Patent is hereby corrected as shown below:

On the Title Page

Column 1 Item (72) (Inventors), Line 5, please delete "Milbrae, CA (US)" and insert -- Millbrae, CA (US) --, therefor.

Signed and Sealed this
Twentieth Day of August, 2024

Katherine Kelly Vidal
*Director of the United States Patent and Trademark Office*

SEQUENCE LISTING

```
<160> NUMBER OF SEQ ID NOS: 424

<210> SEQ ID NO 1
<211> LENGTH: 9
<212> TYPE: PRT
<213> ORGANISM: Unknown
<220> FEATURE:
<223> OTHER INFORMATION: Description of Unknown:
      "LAGLIDADG" family peptide motif sequence

<400> SEQUENCE: 1

Leu Ala Gly Leu Ile Asp Ala Asp Gly
1               5

<210> SEQ ID NO 2
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gttgatcaga ccgatgttcg gaccttccaa ggtttcgatc ggacatacgc gaccgtagtg      60
ggtcgggtgt acgtctcgaa cttcaaagcc                                      90

<210> SEQ ID NO 3
<211> LENGTH: 257
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 3

```
gcctctcggg gcgctttttt ttattccggc actagccgct attaataaaa atgcaaatcg      60
gaatttacta tttaacgcga gattatctaa gatgaatccg atggaagcgc gctgttttca     120
ctcgcctttt taaagttacg tgatgatttc gatgcttctt tgagcgaacg atcaaaaata     180
agcgtattca ggtaaaaaaa tattctcatc acaaaaaagt ttgtgtaata cttgtaacgc     240
tacatggaga ttaactc                                                    257
```

<210> SEQ ID NO 4
<211> LENGTH: 260
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4

```
ggttcacata aacataatta tcgccacggc gatagccgta cgcttttttgc gtcacaacat      60 ccatggtgaa gccggctttt tcaagaacac gcgccacctc atcgggtctt aaatacatac     120
tcattcctca ttatctttta ccgcacgtta accttacctt attcattaaa ggcaacgctt     180
tcggaatatt ccataaaggg ctatttacag cataattcaa aatcttgtcc tacacttata     240
gactcaatgg aattaaggga                                                 260
```

<210> SEQ ID NO 5
<211> LENGTH: 260
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5

```
gcgcggaaaa tcgacgcata gcgcattctc agaagccggc ctggtctcgg tggaaaagcg      60
aatctttccc acgaccgccg ggcctttaac aaaagaatca atgacctgat taatgtcgct     120
atccattctc tctccgcgta atgcgatctt ttttcatcat acctaacaaa ctggcagagg     180
gaaaagccgc gcggttttttc tgcgaagtgt attgtaagat ttgtttgata tgttatatcg     240
taacatatta ttgcaaacat                                                 260
```

<210> SEQ ID NO 6
<211> LENGTH: 259
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6

```
ctgacgaagc gagttacatc accggtgaaa ctctgcacgt caacggcgga atgtatatgg      60
tctgaccgag atttgcgcaa aacgctcagg aaccgcgcag tctgtgcggt tcactgtaat     120
gttttgtaca aaatgatttg cgttatgagg gcaaacagcc gcaaaatagc gtaaaatcgt     180
ggtaagacct gccgggattt agttgcaaat ttttcaacat tttatacact acgaaaacca     240
tcgcgaaagc gagttttga                                                  259
```

<210> SEQ ID NO 7
<211> LENGTH: 260

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7

| | | | | | |
|---|---|---|---|---|---|
| acgcctgggg | cgccgaccag | cgggaagagt | gatttggcca | acgaggcgcc | gctctgaatg | 60 |
| gaaatcatgg | cgattaaaat | aaccagtatc | ggcaaccatg | ccgtacctt | acgagacgag | 120 |
| ccgggcatcc | tttctcctgt | caattttgtc | aaatgcggta | aaggttccag | tgtaattgaa | 180 |
| ttaccccgcg | ccggttgagc | taatgttgaa | aaaagggtc | ttaaaagcag | tacaataggg | 240 |
| cgggtctgaa | gataatttca | | | | | 260 |

<210> SEQ ID NO 8
<211> LENGTH: 260
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8

| | | | | | |
|---|---|---|---|---|---|
| tctgattcct | gatgaaaata | aacgcgacct | tgaagaaatt | ccggataacg | ttatcgccga | 60 |
| tttagatatc | catccggtga | aacgaatcga | ggaagttctg | gcacttgcgc | tacagaacga | 120 |
| accgtttgga | atggaagtcg | tcacggcaaa | atagtgattt | cgcgcaaata | gcgctaagaa | 180 |
| aaatagggct | ggtaagtaaa | ttcgtacttg | ccagccttt | tttgtgtagc | taacttagat | 240 |
| cgctggcagg | ggggtcaatt | | | | | 260 |

<210> SEQ ID NO 9
<211> LENGTH: 259
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9

| | | | | | |
|---|---|---|---|---|---|
| gtaagaaagt | cggcctgcgt | aaagcacgtc | gtcgtcctca | gttctccaaa | cgttaattgt | 60 |
| tttctgctca | cgcagaacaa | tttgcgaaaa | aacccgcttc | ggcgggtttt | tttatggata | 120 |
| aatttgccat | tttccctcta | caaacgcccc | attgttacca | cttttttcagc | atttccagaa | 180 |
| tccctcacc | acaacgtctt | caaaatctgg | taaactatca | tccaattttc | tgcccaaatg | 240 |
| caggtgattg | ttcattttt | | | | | 259 |

<210> SEQ ID NO 10
<211> LENGTH: 260
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10

| | | | | | |
|---|---|---|---|---|---|
| gtcaaagccg | tattatcgac | cccttaggga | caacgcttgc | cggggcggga | gagcggccgc | 60 |
| agttgatttt | tgccgaactt | tcagctgatt | atattcagca | ggtacgcgag | cgcctgccgg | 120 |
| tgttgcgcaa | tcgccgcttt | gcgccaccgc | aattattatg | acgttttttt | aaacaaggct | 180 | tgattcacct tgttacagat tgctattgtg tccgcgcgtc aaatagccgt taattgtatg      240 cgtgtatgat ggcgtattcg                                                  260

<210> SEQ ID NO 11
<211> LENGTH: 260
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
gaggcggtgg ttgaccgtat cggtcccgag catcatgagc tttcggggcg agcgaaagat      60
atgggatcgg cggcggtact gctggcgatt atcatcgcgc tgatcgcgtg gggaacgctg      120
ctgtgggcga actaccgcta agtcttgtcg tagctgctcg caaaacggaa agaaactcct      180 gattttgtg tgaaatgtgg ttccaaaatc accgttagct gtatatactc acagcataac      240
tgtatataca cccagggggc                                                  260

<210> SEQ ID NO 12
<211> LENGTH: 260
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
taagaaaagc ggcctgtacg aagacggcgt acgtaaagac aggctggata acgacgatat      60
gatcgatcag ctggaagcgc gtattcgcgc taaagcatcg atgctggatg aggcgcgtcg      120
tatcgatatc cagcaggttg aagcgaaata acgtgttggg aagcgatacg cttcccgtgt      180
atgattgaac ctgcgggcgc gaggcgccgg ggttcatttt tgtatatata aagagaataa      240
acgtggcaaa gaacattcaa                                                  260

<210> SEQ ID NO 13
<211> LENGTH: 237
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
atgaatcgta ctaaactggt actgggcgcg gtaatcctgg gttctactct gctggctggt      60
tgctccagca atgctaaaat cgatcagctg tcttctgacg ttcagactct gaacgctaaa      120
gttgaccagc tgagcaacga cgtgaacgca atgcgttccg acgttcaggc tgctaaagat      180
gacgcagctc gcgctaacca gcgtctggac aacgcagcta ctaaataccg taagtaa        237

<210> SEQ ID NO 14
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide

```
<400> SEQUENCE: 14
atggccaacc gagcaaaccg caacaacgta gaagagagcg ctgaagatat ccataacgat      60
gtcagccaat tagcggatac gctggaagag gtgctgaaat cgtggggcag cgacgccaaa     120
gacgaagcgg aggccgcgcg caaaaaagcg caggcgctgc tgaaagagac ccgcgcccgg     180
cttaacggca caaccgcgt ccagcaggcg gcgtgcgacg ccatgggctg cgctgacagc      240
tacgtgcgcg acaaaccgtg gcaaagcgtc ggcgccgcag cagccgttgg ggtatttatt     300
ggcgtattac tgaatttacg tcgataa                                         327

<210> SEQ ID NO 15
<211> LENGTH: 648
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
atgaccaaaa agatttccgc cctagcgttt ggcattggca tggtaatggc gagcagccag      60
gcttttgccc acggtcacca tagtcatggc ccggcgctga ccgaagcgga acaaaaggcg     120
agtgaaggca ttttgctga ccaggacgta aaggacaggg cgctgagcga ctgggagggg      180
atctggcagt cggttaaccc ctatctgctg aacggggatt tagatccggt tctggagcag     240
aaggccaaaa aggccggtaa aagcgtggcg gaatatcggg aatattataa gaagggctac     300
gctaccgatg tcgaccagat tggtatcgag gataacgtca tggagtttca cgtcgggaaa     360
accgtcaacg cctgtaagta cagctattcc ggttacaaaa ttctgaccta cgcatccggt     420
aaaaaaggcg tgcgctacct gttcgaatgc agcaggcgg attcaaaagc gccgaagttt      480
gttcagttta gcgatcacac catcgcgcca cgcaagtccc agcatttcca catctttatg     540
ggcaatgagt cccaggaagc gctgctgaaa gagatggata ctggccaac ctactatcct      600 tatgcgctgc ataagagca gattgtcgac gaaatgctgc accactaa                  648

<210> SEQ ID NO 16
<211> LENGTH: 237
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
atgagcacta tcgaagaacg cgttaagaaa attatcggcg aacagctggg cgttaagcag      60
gaagaagtta ccaacaatgc ttccttcgtt gaagacctgg cgctgattc tcttgacacc      120 gttgagctgg taatggctct ggaagaagag tttgatactg agattccgga cgaagaagct     180
gagaaaatca ctactgttca ggctgccatt gattacatca acggccacca ggcgtaa       237

<210> SEQ ID NO 17
<211> LENGTH: 513
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 17

```
atgaataaaa ttgcacgttt ttcagcactg gccgttgttc tggctgcatc cgtaggtacc      60
actgctttcg ctgcgacttc taccgttacc ggtggctacg cgcagagcga catgcagggt     120
gaagcgaaca aagctggcgg tttcaacctg aagtaccgct acgagcaaga caacaacccg     180
ctgggtgtta tcggttcttt cacctacacc gaaaaagatc gttctgaatc tggcgtttac     240
aaaaaaggcc agtactacgg catcaccgca ggtccggctt accgtctgaa cgactgggct     300
agcatctacg gcgtagtggg tgttggttac ggtaaattcc aggacaacag ctacccgaac     360
aaatctgata tgagcgacta cggtttctct tacggcgctg gtctgcagtt caacccgatc     420
gaaaacgttg ccctggactt ctcctacgag cagtctcgca ttcgtaacgt tgacgttggc     480
acctggattg ctggcgtagg ttaccgcttc taa                                  513
```

<210> SEQ ID NO 18
<211> LENGTH: 273
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18

```
gtgaataaat ctcaactgat tgacaaaatt gctgccggtg cggacatttc taaagccgca      60
gctggacgtg cgttagatgc tttaatcgct tctgttactg aatctctgca ggctggagat     120
gacgttgcgc tggtagggtt tggtactttt gctgttaaag agcgcgctgc ccgtactggt     180
cgcaatccgc aaacaggcaa agaaatcacc attgctgctg ctaaagttcc gggtttccgc     240
gcaggtaaag cgctgaaaga cgcggtaaac tga                                  273
```

<210> SEQ ID NO 19
<211> LENGTH: 639
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19

```
atggctgtcg ctgccaacaa acgttcggta atgacgctgt tttctggtcc tactgacatc      60
tatagccatc aggtccgcat cgtgctggcc gaaaaaggtg ttagttttga gatagagcac     120
gtggagaagg acaacccgcc tcaggatctg attgacctca acccgaatca aagcgtaccg     180
acgcttgtgg atcgtgagct cactctgtgg gaatctcgca tcattatgga atatctggat     240
gagcgtttcc cgcatccgcc gctcatgccg gtttacccgg tggcgcgtgg ggaaagccgt     300
ctgtatatgc agcgtatcga aaaggactgg tattcgttga tgaataccat tcagaccggt     360
accgctgcgc aggctgatac tgcgcgtaag cagctgcgtg aagaactaca ggcgattgcg     420
ccagttttca cccagaagcc ctacttcctg agcgatgagt tcagcctggt ggactgctac     480
ctggcaccac tgctgtggcg tctgccggtt ctcggcgtag agctggtcgg cgctggcgcg     540
aaagagctta aaggctatat gactcgcgta tttgagcgcg actctttcct cgcttcttta     600
actgaagccg aacgtgaaat gcgtctcggt cggggctaa                            639
```

<210> SEQ ID NO 20
<211> LENGTH: 204
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 20

```
atgggtgaga ttagtattac caaactgctg gtagtcgcag cgctgattat cctggtgttt      60
ggtaccaaaa agttacgcac gctgggtgga gacctgggct cggctatcaa aggctttaaa     120
aaagccatga gcgatgacga tgacagtgcg aagaagacca gtgctgaaga agcgccggca     180
cagaagctct ctcataaaga gtaa                                            204
```

<210> SEQ ID NO 21
<211> LENGTH: 609
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 21

```
atgaaagcgt taacgaccag gcagcaagag gtgtttgatc tcattcggga tcatatcagc      60
cagacgggca tgccgccgac gcgtgcggag attgctcagc gcttgggggtt tcgctcccca    120
aacgcggcgg aagagcatct gaaagcgctg gcgcgtaaag gcgcaatcga gatcgtttcc    180
ggcgcctccc gcggtattcg tctgctgacg gaagaagaaa ccggtctgcc gcttattggc    240
cgcgtcgcgg caggtgagcc gctgctagcg cagcagcaca ttgaaggcca ctaccaggtg    300
gacccggcca tgtttaagcc gaacgccgat tttctgctgc gtgttagcgg tatgtcgatg    360
aaggatatcg gtattctcga tggcgacctg ctggctgtcc ataaaacgca ggatgtgcgc    420
aatggtcagg tggttgtggc gcgtatcgac gaagaagtga ccgtgaagcg tctgaaaaaa    480
cagggtaacg tcgtggaatt gctgccggaa acagcgaat tctcgccgat cgtggtcgac    540
cttcgcgaac aaagctttac tattgaaggc ctggccgtcg cgttatccg caacggcaac    600
tggcaataa                                                            609
```

<210> SEQ ID NO 22
<211> LENGTH: 1245
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 22

```
atgaacgatt atctgccggg cgaaaccgct ctctggcagc gcattgaagg ctcactgaag      60
caggtgcttg gtagctacgg ttacagcgaa atccgtttgc cgattgtaga gcagaccccg     120
ttattcaaac gcgctatcgg cgaagtgacc gacgtggttg aaaaagagat gtacaccttt     180
gaggaccgta acggcgatag cctgactcta cgtccggaag gcacggctgg ctgcgtacgc     240
gccggtatcg aacatggtct cctgtacaat caagaacagc gcctgtggta cattgggccg     300
atgttccgcc acgaacgtcc gcaaaaaggc cgctaccgtc agttccacca gattggcgcc     360
gaagcgtttg gcctgcaggg gccggatatc gatgccgagc tgattatgct gaccgcccgc     420
tggtggcgcg agctgggcat ctccggccac gttgcgctgg agctgaactc tatcggttcg     480
ctggaggctc gcgctaacta tcgcgacgcg ctggtggcct atcttgagca gtttaaagat     540
aagctggacg aagactgcaa acgccgcatg tacaccaacc cgctgcgcgt gctggattct     600
```

| aaaaacccgg acgtccaggc gctgctgaac gacgccccga cgctgggcga ctatcttgat | 660 |
| gaagagtcca aaacgcattt tgccgggctg tgcgcgctgc tggatgatgc cggtattcgc | 720 |
| tataccgtga atcagcgtct ggtacgcggt ctcgactact acaaccgcac cgtgtttgag | 780 |
| tgggtcacca ccagcctcgg ttcccagggc accgtctgcg ccggaggccg ttacgatggt | 840 |
| ctggttgagc agcttggcgg tcgcgctacc cctggcgtcg gctttgcgat ggggctggaa | 900 |
| cgtcttgttt tactggttca ggcagtgaat ccggaattta agccgatcc tgttgtcgat | 960 |
| atatacctgg tagcctccgg aactgacacc cagtccgcag caatgcgtct ggctgaacag | 1020 |
| gtacgcgatg cgttacccgg cgttaagctg atgaccaacc atggcggcgg caactttaag | 1080 |
| aagcagtttg cgcgcgctga taaatggggc gctcgcgttg cgctggtgct gggcgaatca | 1140 |
| gaaatcgccg acggaaacgt ggtagtgaaa gatttacgct caggtgagca aactaccgta | 1200 |
| acgcaggata gcgttgctgc gcatttgcgc acacttctgg gttaa | 1245 |

<210> SEQ ID NO 23
<211> LENGTH: 1413
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23

| atgaaaaaga ccaaaattgt ttgcaccatc ggtccgaaaa ccgaatccga agagatgttg | 60 |
| accaaaatgc tggacgcggg catgaacgtt atgcgtctga acttctctca cggtgactat | 120 |
| gcggaacacg gtcagcgcat ccagaatctg cgcaatgtga tgagtaaaac cggtaagaaa | 180 |
| gcggcaatcc tgctggacac caaaggtccg gaaatccgta ccattaagct ggaaggcggc | 240 |
| aacgacgtct ccctgaaagc gggccagacc ttcacctcc ccaccgataa atccgttgtc | 300 |
| ggtaataacg aaatcgttgc ggtgacctat gaaggcttca ccagcgacct gagcgttggc | 360 |
| aacacggtac tggttgacga tggtctgatc ggtatggaag tgaccgctat cgaaggcaac | 420 |
| aaagttgttt gtaaagtgct gaacaacggc gacctcggcg agaacaaagg cgttaacctg | 480 |
| ccgggcgtat ctatcgcgct gccggcgctg gctgaaaaag acaaacagga tctgatcttc | 540 |
| ggttgcgaac agggcgttga ctttgttgcg gcatccttta tccgtaagcg ttctgacgtt | 600 |
| gttgaaatcc gtgagcacct gaaagcccac ggcggcgaga agatccagat catctccaaa | 660 |
| atcgaaaacc aggaaggcct gaacaacttc gacgaaatcc tcgaagcctc tgacggcatc | 720 |
| atggtagccc gtggcgacct gggcgttgaa atcccggttg aagaagttat cttcgcgcag | 780 |
| aagatgatga tcgagaaatg tatccgcgcg cgtaaagtcg ttatcaccgc gacccagatg | 840 |
| ctggattcca tgatcaaaaa cccgcgtccg acccgtgcgg aagcaggcga cgtggccaac | 900 |
| gccatcctcg acggcaccga cgcagttatg ctgtccggcg aatccgcgaa aggtaaatac | 960 |
| ccgctggaag cggtcaccat catggcgacc atctgcgaac gtaccgaccg cgtcatgacc | 1020 |
| agccgtcttg agtacaacaa cgacaaccgt aagctgcgca tcaccgaagc ggtgtgccgc | 1080 |
| ggtgcggtag aaacggctga aaactggaa gcgccgctga tcgttgtggc aacccagggc | 1140 |
| ggtaaatccg cgcgcgccgt acgtaaatac ttcccggatg ccactatcct ggcgctgacc | 1200 |
| accaacgaaa ccaccgcgcg tcagctggtg ctgagcaaag cgttgtggc acagctggtt | 1260 |

```
gaagatatct cctctaccga tgcgttctac atccagggta aagaactggc gctgcagagc    1320
ggtctggcgc gtaaaggcga cgtggttgtt atggtttccg gcgcgttagt cccgagcgga    1380
accaccaata ccgcttccgt gcacgtgctg taa                                 1413

<210> SEQ ID NO 24
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24
atgtatttaa gacccgatga ggtggcgcgt gttcttgaaa aagccggctt caccatggat    60
gttgtgacgc aaaaagcgta cggctatcgc cgtggcgata attatgttta tgtgaaccgt    120
gaagctcgta tggggcgtac cgcgttaatt attcatccgg ctttaaaaga gcgcagcaca    180
acgcttgcgg agcccgcgtc ggatatcaaa acctgcgatc attatgagca gttcccgctc    240
tatttagcgg gggatgctca acagcattat ggtattccac acgggttcag ttcgcgaatg    300
gcgcttgagc gttttctgag tggcctgttt ggcgaaacgc agtatagctg a            351

<210> SEQ ID NO 25
<211> LENGTH: 864
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
atggatagcg acattaatca ggtcattgat tcttttgtta aaggcccggc ggtcgtggga    60
aagattcgct tttccaccga gaccaggccg gcttctgaga atgcgctatg cgtcgatttt    120
ccgcgcctcg aaatcatgct tgcgggtcag cttcacgatc cggcgattaa agccgatcgc    180
gcccagctca tgccgcacga tgtgctgtat attcccgctg gcggatggaa tgacccgcaa    240
tggctggcgc cctccactct gctcactatc ttatttggta acagcagct ggaattcgtc    300 ctgcgccact gggacggcag cgcgcttaac gtgctggata acagcaggt tccgcgccgc    360 ggtccccggg tcggctcttt tctgctgcag gcgctgaatg aaatgcagat gcagccgcgg    420
gagcagcaca cggcccgctt tattgtcacc agcctgctca gccactgtgc cgatctgctg    480
ggcagccagg tacaaacctc atcgcgcagc caggcgcttt ttgaagcgat tcgtaagcat    540
attgacgccc actttgccga cccgttaacc cgggagtcgg tggcgcaggc gttttacctc    600
tcgccaaact atctatccca cctgttccag aaatgcgggc caatgggctt aacgagtat    660 ctgaatcaca tccgcctgga gcaggccaga atgctgttaa aaggccacga tatgaaagtg    720
aaagatatcg cccacgcctg cggtttcgcc gacagcaact acttctgccg cctgtttcgc    780
aaaaacaccg aacgctcgcc gtcggagtat cgccgtcaat atcacagcca gctgacggaa    840
aaaacagccc cggcaaaaaa ctag                                           864

<210> SEQ ID NO 26
<211> LENGTH: 735
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 26

```
atgagttttg aaggaaaaat cgcgctggtt accggtgcaa gtcgcgggat tggccgcgca    60
atcgctgaaa cgctcgttgc ccgtggcgcg aaagttatcg ggactgcgac cagcgaaagc   120
ggcgcgcagg cgatcagcga ttatttaggt gctaacggta aaggtctgct gctgaatgtg   180
accgatcctg catctattga atctgttctg gaaatattc gcgcagaatt tggtgaagtt    240
gatatcctgg tgaacaatgc cgggatcact cgtgataacc tgttaatgcg catgaaagat   300
gatgagtgga acgatattat cgaaaccaac ctgtcatctg ttttccgtct gtcaaaagcg   360
gtaatgcgcg ctatgatgaa aaagcgtcat ggacgtatta tcactatcgg ttctgtggtt   420
ggtaccatgg gaaatgcggg tcaggccaac tacgctgcgg cgaaagcggg tctgattggc   480
ttcagtaaat cactggctcg cgaagttgcg tcccgcggta ttactgtaaa cgttgttgct   540
ccgggcttta ttgaaacgga catgacgcgt gcgctgaccg atgagcagcg tgcgggtacg   600
ctggcggcag ttcctgcggg gcgcctcggc tctccaaatg aaatcgccag tgcggtggca   660
ttttagcct ctgacgaagc gagttacatc accggtgaaa ctctgcacgt caacggcgga   720
atgtatatgg tctga                                                    735
```

<210> SEQ ID NO 27
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27

```
atgcccggct cgtctcgtaa ggtaccggca tggttgccga tactggttat tttaatcgcc    60
atgatttcca t                                                        71
```

<210> SEQ ID NO 28
<211> LENGTH: 2355
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28

```
atgaatcctg agcgttctga acgcattgaa atccccgtat tgccgttgcg cgatgtggtg    60
gtttatccgc acatggtcat acccctgttt gtagggcggg aaaaatctat ccgttgtctc   120
gaagcagcca tggaccatga taaaaaaatc atgctggttg cgcagaaaga agcctcgacg   180
gatgagccgg tgtaaacga tcttttcacc gtcgggaccg tggcgtctat tttgcaaatg   240
ctgaagctac cggacggtac tgttaaagtg ctggtcgaag gtttgcagcg cgcgcgcatc   300
tctgcgctgt ctgataatgg cgaacatttt tcggcgaagg cggaatacct tgaatcgccg   360
gcgattgacg aacgcgagca ggaagtgctg gttcgtaccg ctatcagcca gtttgaaggc   420
tacatcaagc tgaacaaaaa aatccctccg gaagtgctga cgtcgctgaa tagcatcgac   480
gatccggcgc gtctggcgga taccatcgct gcgcatatgc cgctgaagct ggcggacaaa   540
cagtccgtgc tggagatgtc cgacgttaac gagcgtctgg aatatctgat ggcgatgatg   600
gagtcggaaa tcgatctgct gcaggtggag aagcgtattc gcaaccgcgt gaaaaagcag   660
atggagaaat ctcagcgcga gtactatctg aatgagcaaa tgaaagccat tcaaaaagag   720
```

| | |
|---|---|
| ctcggcgaga tggacgacgc cccggacgag aacgaagcgc tgaagcgtaa gatcgacgcg | 780 |
| gcgaaaatgc cgaaagaggc aaaagagaaa accgaagcgg aactgcaaaa actgaaaatg | 840 |
| atgtccccga tgtcggcgga agcgaccgtc gttcgcggct acatcgactg gatggtgcag | 900 |
| gtaccgtgga acgctcgcag caaggttaaa aaagacctgc gtcaggctca ggagatcctc | 960 |
| gataccgatc actacggcct tgagcgcgtg aaggatcgca ttcttgagta cctcgcggtg | 1020 |
| cagagccgtg ttaacaagct caaagggccg atcctgtgcc tggttgggcc tccggggggta | 1080 |
| ggtaaaacct ctctcggcca atccatcgcc aaagcaactg gacgcaaata tgtgcgtatg | 1140 |
| gcgctgggcg gcgtgcgtga tgaagcggaa atccgcggtc accgccgtac ctatattggc | 1200 |
| tcaatgccgg gcaaactgat ccagaaaatg gctaaagtgg gcgttaaaaa cccgctgttc | 1260 |
| ttgctggatg agatcgacaa gatgtcttct gacatgcgcg gcgatccggc ctcggcgctg | 1320 |
| ctggaggtgt tggatccgga acagaacgtg gcctttaacg accactatct ggaagtggat | 1380 |
| tacgatctca gcgacgtgat gttcgttgcg acctctaact ccatgaacat cccggcgccg | 1440 |
| ctgctggatc gtatggaagt gatccgcctc tccggctata ccgaagatga gaagctaaac | 1500 |
| atcgccaaac gccatctgct gtcaaaacag attgagcgta acgcgctcaa gaaaggcgag | 1560 |
| ctgacggtgg atgacagcgc gattatcggc atcattcgct actacacccg tgaagcaggc | 1620 |
| gtgcgtggtc tggagcgtga aatctcgaaa ctgtgccgca aagcggtgaa acagctgctg | 1680 |
| ctggataagt cgctgaaaca catcgagatt aacggcgaca acctgcacga tttccttggc | 1740 |
| gtgcagcgct acgactatgg tcgtgcggat agcgaaaaac cgcgtaggtca ggtgaccgga | 1800 |
| ctggcgtgga cggaagtggg cggcgatctg ctgaccattg aaaccgcctg cgttccgggt | 1860 |
| aaaggcaaac tgacctacac cggttcactg ggtgaagtca tgcaggaatc catccaggcg | 1920 |
| gcgctgacgg tggttcgttc acgtgcggat aagctgggta ttaactcaga cttttacgaa | 1980 |
| aaacgtgata ttcacgttca cgtgccggaa ggcgcgacgc cgaaggatgg tccaagcgcc | 2040 |
| ggtatcgcga tgtgcaccgc gctggttttcc tgtctgacgg gtaatccggt acgcgccgac | 2100 |
| gtggcgatga ccggtgagat taccctccgt ggccaggtat tgccgattgg tggtctgaag | 2160 |
| gaaaaactgt tggccgcgca tcgcggcggc attaagactg ttctgattcc tgatgaaaat | 2220 |
| aaacgcgacc ttgaagaaat tccggataac gttatcgccg atttagatat ccatccggtg | 2280 |
| aaacgaatcg aggaagttct ggcacttgcg ctacagaacg aaccgtttgg aatggaagtc | 2340 |
| gtcacggcaa aatag | 2355 |

<210> SEQ ID NO 29
<211> LENGTH: 393
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29

| | |
|---|---|
| atggctgaaa atcaatacta cggcaccggt cgccgcaaaa gttccgcagc tcgcgttttc | 60 |
| atcaaaccgg gcaacggtaa aatcgttatc aaccagcgtt ctctggaaca gtacttcggt | 120 |
| cgtgaaactg cccgcatggt agttcgtcag ccgctggaac tggtcgacat ggttgagaaa | 180 |
| ttagatctgt acatcaccgt taaaggtggt ggtatctctg gtcaggctgg tgcgatccgt | 240 |

```
cacggtatca cccgcgctct gatggagtac gacgagtccc tgcgtggcga actgcgtaaa    300
gctggtttcg ttactcgtga tgctcgtcag gttgaacgta agaaagtcgg cctgcgtaaa    360
gcacgtcgtc gtcctcagtt ctccaaacgt taa                                 393
```

<210> SEQ ID NO 30
<211> LENGTH: 789
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30

```
atgtttgttg ctgccggaca atttgccgta acgccggact ggacgggaaa cgcgcagacc     60
tgcgtcagca tgatgcgcca ggccgcggag cgggggggcgt cgcttctggt tctgcctgag   120
gcgttgctgg cgcgagacga taacgatgcg gatttatcgg ttaaatccgc ccagcagctg    180
gatggcggct tcttacagct cttgctggcg gagagcgaaa acagcgcttt gacgacggtg    240
ctgaccctgc atatcccttc cggcgaaggt cgagcgacga atacgctggt ggccctgcgt    300
caggggaaga ttgtggcgca atatcagaaa ctgcatctct atgatgcgtt caatatccag    360
gaatccaggc tggtcgatgc cgggcggcaa attccgccgc tgatcgaagt cgacgggatg    420
cgcgtcgggc tgatgacctg ctacgattta cgtttccctg agctggcgct gtcgttagcg    480
ctcagcggcg cgcagctcat agtgttgcct gccgcgtggg taaaagggcc gctgaaggaa    540
catcactggg cgacgctgct ggcggcgcgg gcgctggata caacctgcta tattgtcgcc    600
gcaggagagt gcgggacgcg taatatcggt caaagccgta ttatcgaccc cttagggaca    660
acgcttgccg gggcgggaga gcggccgcag ttgattttg ccgaactttc agctgattat    720
attcagcagg tacgcgagcg cctgccggtg ttgcgcaatc gccgctttgc gccaccgcaa    780
ttattatga                                                            789
```

<210> SEQ ID NO 31
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31

```
atggccaata ataccactgg gttaacccga attattaaag cggccgggta ttcctggaaa     60
ggattccgtg cggcgtgggt caatgaggcc gcatttcgtc aggaaggcat cgcggccgtt    120
attgccgtgg cgatcgcctg ctggttggac gtcgatgcca tcacgcgggt gctgctcatt    180
agctcggtcc tgttagtgat gatagttgaa attatcaata gcgcgattga ggcggtggtt    240
gaccgtatcg gtcccgagca tcatgagctt tcggggcgag cgaaagatat gggatcggcg    300
gcggtactgc tggcgattat catcgcgctg atcgcgtggg gaacgctgct gtgggcgaac    360
taccgctaa                                                             369
```

<210> SEQ ID NO 32
<211> LENGTH: 1122
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32

```
atgcataacc aggctccgat tcaacgtaga aaatcaaaac gaatttacgt tgggaatgtg      60
ccgattggcg atggcgcccc catcgccgta cagtcgatga caaacacgcg caccaccgat     120
gtggcggcga cggtaaatca aattaaagcc ctcgagcgcg ttggcgcgga tatcgtgcgc     180
gtttcggtgc cgacgatgga tgcggcggaa gcgttcaaac ttatcaaaca gcaggttaac     240
gtcccgctgg ttgccgatat ccacttcgat taccgcattg cgctgaaggt agcggaatac     300
ggcgttgatt gcctgcgtat taacccgggc aatatcggca acgaagagcg tatccgcatg     360
gtggtggact cgcgctcgcga taaaaatatt cctatccgta tcggggtaaa cgccggttct     420
ctggaaaaag atctccagga aaaatacggc gaaccgactc cgcaggcgct gctggaatcg     480
gcaatgcgcc atgttgatca tctcgatcgt ctcaacttcg atcagtttaa agtcagcgta     540
aaagcctccg atgtgttcct cgcggttgaa tcctatcgcc tgttggcgaa acagatcgat     600
cagcctctgc acctcgggat caccgaagcg ggcggcgcgc gcagcggcgc ggtgaagtcc     660
gcgatcggcc tcggcctgct gctgtctgaa gggattggcg atacgctgcg cgtctctctg     720
gcggcggatc ccgttgaaga gatcaaagtg ggcttcgata ttctcaagtc gctgcgtatt     780
cgctctcgcg ggatcaactt tattgcctgc ccgacctgtt cacgtcagga gtttgacgtt     840
atcggtaccg ttaacgcgct ggagcagcgc ctggaagata tcattacgcc gatggatatt     900
tcgatcattg gctgcgtggt aaacggtccc ggcgaggcgc tggtttccac cctcggcgta     960
accggcggca ataagaaaag cggcctgtac gaagacggcg tacgtaaaga caggctggat    1020
aacgacgata tgatcgatca gctggaagcg cgtattcgcg ctaaagcatc gatgctggat    1080
gaggcgcgtc gtatcgatat ccagcaggtt gaagcgaaat aa                       1122
```

<210> SEQ ID NO 33
<211> LENGTH: 876
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 33

```
atgagccata ttcaacggga aacgtcttgc tccaggccgc gattaaattc caacatggat      60
gctgatttat atgggtataa atgggctcgc gataatgtcg ggcaatcagg tgcgacaatc     120
tatcgattgt atgggaagcc cgatgcgcca gagttgtttc tgaaacatgg caaaggtagc     180
gttgccaatg atgttacaga tgagatggtc agactaaact ggctgacgga atttatgcct     240
cttccgacca tcaagcattt tatccgtact cctgatgatg catggttact caccactgcg     300
atccccggga aaacagcatt ccaggtatta gaagaatatc ctgattcagg tgaaaatatt     360
gttgatgcgc tggcagtgtt cctgcgccgg ttgcattcga ttcctgtttg taattgtcct     420
tttaacagcg atcgcgtatt tcgtctcgct caggcgcaat cacgaatgaa taacggtttg     480
gttgatgcga gtgattttga tgacgagcgt aatggctggc ctgttgaaca gtctggaaa     540 gaaatgcata agcttttgcc attctcaccg gattcagtcg tcactcatgg tgatttctca     600
cttgataacc ttattttga cgaggggaaa ttaataggtt gtattgatgt tggacgagtc     660
ggaatcgcag accgatacca ggatcttgcc atcctatgga actgcctcgg tgagttttct     720
ccttcattac agaaacggct ttttcaaaaa tatggtattg ataatcctga tatgaataaa     780
```

```
ttgcagtttc atttgatgct cgatgagttt ttctaataag cctgcctggt tctgcgtttc    840
ccgctcttta ataccctgac cggaggtgag caatga                               876
```

<210> SEQ ID NO 34
<211> LENGTH: 1491
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 34

```
atgagcatca cggcgttatc agcatcattt cctgagggga atatcgccag ccgcttgtcg     60
ctgcaacatc cttcactgtt ttataccgtg gttgaacaat cttcggtggc gagcgtgttg    120
agtcatcctg actagctgag atgagggctc gcccctcgt cccgacactt ccagatcgcc    180
atagcgcaca gcgcctcgag cggtggtaac ggcgcagtgg cggttttcat ggcttgttat    240
gactgttttt ttggggtaca gtctatgcct cgggcatcca agcagcaagc gcgttacgcc    300
gtgggtcgat gtttgatgtt atggagcagc aacgatgtta cgcagcaggg cagtcgccct    360
aaaacaaagt taaacatcat gagggaagcg gtgatcgccg aagtatcgac tcaactatca    420
gaggtagttg gcgtcatcga gcgccatctc gaaccgacgt tgctggccgt acatttgtac    480
ggctccgcag tggatggcgg cctgaagcca cacagtgata ttgatttgct ggttacggtg    540
accgtaaggc ttgatgaaac aacgcggcga gctttgatca cgacctttt ggaaacttcg    600
gcttcccctg gagagagcga gattctccgc gctgtagaag tcaccattgt tgtgcacgac    660
gacatcattc cgtggcgtta tccagctaag cgcgaactgc aatttggaga atggcagcgc    720
aatgacattc ttgcaggtat cttcgagcca gccacgatcg acattgatct ggctatcttg    780
ctgacaaaag caagagaaca tagcgttgcc ttggtaggtc cagcggcgga ggaactcttt    840
gatccggttc ctgaacagga tctatttgag gcgctaaatg aaaccttaac gctatggaac    900
tcgccgcccg actgggctgg cgatgagcga aatgtagtgc ttacgttgtc ccgcatttgg    960
tacagcgcag taaccggcaa aatcgcgccg aaggatgtcg ctgccgactg ggcaatggag   1020
cgcctgccgg cccagtatca gcccgtcata cttgaagcta gacaggctta tcttggacaa   1080
gaagaagatc gcttggcctc gcgcgcagat cagttggaag aatttgtcca ctacgtgaaa   1140
ggcgagatca ccaaggtagt cggcaaataa tgtctaacaa ttcgttcaag ccgacgccgc   1200
ttcgcggcgc ggcttaactc aagcgttaga tgcactaagc acataattgc tcacagccaa   1260
actatcaggt caagtctgct tttattattt ttaagcgtgc ataataagcc ctacacaaat   1320
ggtacccgac cggtggtgaa tttaatctcg ctgacgtgta gacattccct tatccagacg   1380
ctgatcgccc atcatcgcgg ttctttagat ctctcggtcc gccctgatgg cggcaccttg   1440
ctgacgttac gcctgccggt acagcaggtt atcaccggag cttaaaatg a             1491
```

<210> SEQ ID NO 35
<211> LENGTH: 1021
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 35

```
ctgatccttc aactcagcaa aagttcgatt tattcaacaa agccacgttg tgtctcaaaa         60
tctctgatgt tacattgcac aagataaaaa tatatcatca tgaacaataa aactgtctgc        120
ttacataaac agtaatacaa ggggtgttat gagccatatt caacgggaaa cgtcttgctc        180
caggccgcga ttaaattcca acatggatgc tgatttatat gggtataaat gggctcgcga        240
taatgtcggg caatcaggtg cgacaatcta tcgattgtat gggaagcccg atgcgccaga        300
gttgtttctg aaacatggca aaggtagcgt tgccaatgat gttacagatg agatggtcag        360
actaaactgg ctgacggaat ttatgcctct tccgaccatc aagcatttta tccgtactcc        420
tgatgatgca tggttactca ccactgcgat ccccgggaaa acagcattcc aggtattaga        480
agaatatcct gattcaggtg aaaatattgt tgatgcgctg gcagtgttcc tgcgccggtt        540
gcattcgatt cctgtttgta attgtccttt taacagcgat cgcgtatttc gtctcgctca        600
ggcgcaatca cgaatgaata acggtttggt tgatgcgagt gattttgatg acgagcgtaa        660
tggctggcct gttgaacaag tctggaaaga atgcataag ctttgccat tctcaccgga         720
ttcagtcgtc actcatggtg atttctcact tgataacctt attttgacg aggggaaatt         780
aataggttgt attgatgttg acgagtcgg aatcgcagac cgataccagg atcttgccat         840
cctatggaac tgcctcggtg agttttctcc ttcattacag aaacggcttt ttcaaaaata        900
tggtattgat aatcctgata tgaataaatt gcagtttcat ttgatgctcg atgagttttt        960
ctaataagcc ttgaccctac gattcccgct atttcattca ctgaccggag gttcaaaatg       1020
a                                                                       1021
```

<210> SEQ ID NO 36
<211> LENGTH: 1071
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 36

```
atgaagatag caacaatgaa aacaggtctg ggagcgttgg ctcttcttcc ctgatccttc         60
aactcagcaa aagttcgatt tattcaacaa agccacgttg tgtctcaaaa tctctgatgt        120
tacattgcac aagataaaaa tatatcatca tgaacaataa aactgtctgc ttacataaac        180
agtaatacaa ggggtgttat gagccatatt caacgggaaa cgtcttgctc cgtccgcgc         240
ttaaactcca acatggacgc tgatttatat gggtataaat gggctcgcga taatgtcggg        300
caatcaggtg cgacaatcta tcgcttgtat gggaagcccg atgcgccaga gttgtttctg        360
aaacatggca aaggtagcgt tgccaatgat gttacagatg agatggtccg tctcaactgg        420
ctgacggagt ttatgcctct cccgaccatc aagcatttta tccgtactcc tgatgatgcg        480
tggttactca ccaccgcgat tcctgggaaa acagccttcc aggtattaga agaatatcct        540
gattcaggtg aaaatattgt tgatgcgctg gccgtgttcc tgcgccggtt acattcgatt        600
cctgtttgta attgtccttt taacagcgat cgtgtatttc gtcttgctca ggcgcaatca        660
cgcatgaata acggtttggt tgatgcgagt gattttgatg acgagcgtaa tggctggcct        720
gttgaacaag tctggaaaga atgcacaag ctcttgccat tctcaccgga ttcagtcgtc         780
actcatggtg atttctcact tgataacctt attttgacg aggggaaatt aataggttgt         840
attgatgttg acgggtcgg aatcgcagac cgttaccagg accttgccat tctttggaac        900
```

| | |
|---|---|
| tgcctcggtg agttttctcc ttcattacag aaacggcttt ttcaaaaata tggtattgat | 960 |
| aatcctgata tgaataaatt gcagtttcat ttgatgctcg atgagttttt ctaataagcc | 1020 |
| tgtgaagggc tggacgtaaa cagccacggc gaaaacgcct acaacgcctg a | 1071 |

<210> SEQ ID NO 37
<211> LENGTH: 1071
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 37

| | |
|---|---|
| atgaccctga atatgatgct cgataacgcc gtacccgagg cgattgccgg ctgatccttc | 60 |
| aactcagcaa aagttcgatt tattcaacaa agccacgttg tgtctcaaaa tctctgatgt | 120 |
| tacattgcac aagataaaaa tatatcatca tgaacaataa aactgtctgc ttacataaac | 180 |
| agtaatacaa ggggtgttat gagccatatt caacgggaaa cgtcttgctc ccgtccgcgc | 240 |
| ttaaactcca acatggacgc tgatttatat gggtataaat gggctcgcga taatgtcggg | 300 |
| caatcaggtg cgacaatcta tcgcttgtat gggaagcccg atgcgccaga gttgtttctg | 360 |
| aaacatggca aaggtagcgt tgccaatgat gttacagatg agatggtccg tctcaactgg | 420 |
| ctgacggagt ttatgcctct cccgaccatc aagcatttta tccgtactcc tgatgatgcg | 480 |
| tggttactca ccaccgcgat tcctgggaaa acagccttcc aggtattaga agaatatcct | 540 |
| gattcaggtg aaaatattgt tgatgcgctg gccgtgttcc tgcgccggtt acattcgatt | 600 |
| cctgtttgta attgtccttt taacagcgat cgtgtatttc gtcttgctca ggcgcaatca | 660 |
| cgcatgaata acggtttggt tgatgcgagt gattttgatg acgagcgtaa tggctggcct | 720 |
| gttgaacaag tctggaaaga atgcacaaag ctcttgccat tctcaccgga ttcagtcgtc | 780 |
| actcatggtg atttctcact tgataacctt atttttgacg aggggaaatt aataggttgt | 840 |
| attgatgttg gacgggtcgg aatcgcagac cgttaccagg accttgccat tctttggaac | 900 |
| tgcctcggtg agttttctcc ttcattacag aaacggcttt ttcaaaaata tggtattgat | 960 |
| aatcctgata tgaataaatt gcagtttcat ttgatgctcg atgagttttt ctaataagcc | 1020 |
| ttggttctgc gtttcccgct ctttaatacc ctgaccggag gtgagcaatg a | 1071 |

<210> SEQ ID NO 38
<211> LENGTH: 426
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 38

| | |
|---|---|
| atgaccctga atatgatgat ggatgccggc ggacatcatc gcgacaaaca atattaatac | 60 |
| cggcaaccac accggcaatt tacgagactg cgcaggcatc ctttctcccg tcaatttctg | 120 |
| tcaaataaag taaagaggc agtctacttg aattaccccc ggctggttga gcgtttgttg | 180 |
| aaaaaaagta actgaaaaat ccgtagaata gcgccactct gatggttaat taacctattc | 240 |
| aattaagaat tatctggatg aatgtgccat taaatgcgca gcataatggt gcgttgtgcg | 300 |

```
ggaaaactgc ttttttttga aagggttggt cagtagcgga acaactcac ttcacacccc      360 gaaggggggaa gttgcctgac cctacgattc ccgctatttc attcactgac cggaggttca    420
aaatga                                                                 426

<210> SEQ ID NO 39
<211> LENGTH: 446
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39
atgaccctga atatgatgat ggatgccggc tcaccacggc gataaccata ggttttcggc      60
gtggccacat ccatggtgaa tcccactttt tccagcacgc gcgccacttc atcgggtctt     120
aaatacatag attttcctcg tcatctttcc aaagcctcgc caccttacat gactgagcat     180
ggaccgtgac tcagaaaatt ccacaaacga acctgaaagg cgtgattgcc gtctggcctt     240
aaaaattatg gtctaaacta aaatttacat cgaaaacgag ggaggatcct atgtttaaca     300
aaccgaatcg ccgtgacgta gatgaaggtg ttgaggatat taaccacgat gttaaccagc     360
tcgaactcac ttcacacccc gaaggggggaa gttgcctgac cctacgattc ccgctatttc    420
attcactgac cggaggttca aaatga                                          446

<210> SEQ ID NO 40
<211> LENGTH: 452
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40
atgaccctga atatgatgat ggatgccggc tgacgaggca ggttacatca ctggtgaaac      60
cctgcacgtc aatggcggaa tgtatatggt ttaaccacga tgaaaattat ttgcgttatt     120
agggcgaaag gcctcaaaat agcgtaaaat cgtggtaaga actgccggga tttagttgca     180 aattttttcaa catttttatac actacgaaaa ccatcgcgaa agcgagttt gataggaaat     240 ttaagagtat gagcactatc gaagaacgcg ttaagaaaat tatcggcgaa cagctgggcg     300
ttaagcagga agaagttacc aacaatgctt ccttcgttga agacctgggc gctgattctc     360
ttgacaccga actcacttca cacccgaag ggggaagttg cctgacccta cgattcccgc     420
tatttcattc actgaccgga ggttcaaaat ga                                   452

<210> SEQ ID NO 41
<211> LENGTH: 461
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
atgaccctga atatgatgat ggatgccggc cgtcctgtaa aataaccgg acaattcgga      60 ctgattaaaa aagcgccctt gtggcgcttt ttttatattc ccgcctccat ttaaaataaa     120
aaatccaatc ggatttcact atttaaactg gccattatct aagatgaatc cgatggaagc     180
tcgctgtttt aacacgcgtt ttttaacctt ttattgaaag tcggtgcttc tttgagcgaa     240
```

```
cgatcaaatt taagtggatt cccatcaaaa aaatattctc aacctaaaaa agtttgtgta    300
atacttgtaa cgctacatgg agattaactc aatctagagg gtattaataa tgaatcgtac    360
taaactggta ctgggcgcaa ctcacttcac accccgaagg gggaagttgc ctgaccctac    420
gattcccgct atttcattca ctgaccggag gttcaaaatg a                        461
```

<210> SEQ ID NO 42
<211> LENGTH: 463
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42

```
atgaccctga atatgatgat ggatgccggc atattgacac catgacgcgc gtaatgctga     60
ttggttctgt gacgctggta atgattgtcg aaattctgaa cagtgccatc gaagccgtag    120
tagaccgtat tggtgcagaa ttccatgaac tttccgggcg gcgaaggat atggggtcgg    180 cggcggtgct gatgtccatc ctgctggcga tgtttacctg gatcgcatta ctctggtcac    240
attttcgata acgcttccag aattcgataa cgccctggtt ttttgcttaa atttggttcc    300
aaaatcgcct ttagctgtat atactcacag cataactgta tatacaccca ggggggcggga   360 tgaaagcatt aacggccagg aactcacttc acaccccgaa gggggaagtt gcctgaccct    420
acgattcccg ctatttcatt cactgaccgg aggttcaaaa tga                      463
```

<210> SEQ ID NO 43
<211> LENGTH: 428
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43

```
atgaccctga atatgatgat ggatgccggc atcatattgc gctccctggt tatcatttgt     60
tactaaatga aatgttataa tataacaatt ataaatacca catcgctttc aattcaccag    120
ccaaatgaga ggagcgccgt ctgacatagc cagcgctata aaacatagca ttatctatat    180
gtttatgatt aataactgat ttttgcgttt tggatttggc tgtggcatcc ttgccgctct    240
tttcgcagcg tctgcgtttt tgccctccgg tcagggcatt taagggtcag caatgagttt    300
ttacgcaatt acgattcttg ccttcggcat gtcgatggca gctttaactc acttcacacc    360
ccgaaggggg aagttgcctg accctacgat tcccgctatt tcattcactg accggaggtt    420
caaaatga                                                             428
```

<210> SEQ ID NO 44
<211> LENGTH: 452
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44

```
atgaccctga atatgatgat ggatgccggc cgcgtcaggt tgaacgtaaa aaagtcggtc     60
tgcgcaaagc acgtcgtcgt ccgcagttct ccaaacgtta attggtttct gcttcggcag    120
aacgattggc gaaaaaaccc ggtgcgaacc gggttttttt atggataaag atcgtgttat    180
```

```
ccacagcaat ccattgatta tctcttcttt ttcagcattt ccagaatccc ctcaccacaa    240
agcccgcaaa atctggtaaa ctatcatcca attttctgcc caaatggctg ggattgttca    300
ttttttgttt gccttacaac gagagtgaca gtacgcgcgg gtagttaact caacatctga    360
ccggtcgata actcacttca caccccgaag ggggaagttg cctgaccta cgattcccgc     420 tatttcattc actgaccgga ggttcaaaat ga                                  452
```

<210> SEQ ID NO 45
<211> LENGTH: 410
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 45

```
atgaccctga atatgatgat ggatgccggc cctgtatgaa gatggcgtgc gcaaagatcg     60
cctggataac agcgatatga ttagccagct tgaagcccgc attcgcgcga aagcgtcaat    120
gctggacgaa gcgcgtcgta tcgatgtgca acaggtagaa aaataaggtt gctgggaagc    180
ggcaggcttc ccgtgtatga tgaacccgcc cggcgcgacc cgttgttcgt cgcggccccg    240
agggttcatt ttttgtatta ataaagagaa taaacgtggc aaaaaatatt caagccattc    300
gcggcatgaa cgattatctg cctggcgaac tcacttcaca ccccgaaggg ggaagttgcc    360
tgaccctacg attcccgcta tttcattcac tgaccggagg ttcaaaatga              410
```

<210> SEQ ID NO 46
<211> LENGTH: 1071
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 46

```
atgaaaaaga ttgatgcgat tattaaacct ttcaaactgg atgacgtgcg ctgatccttc     60
aactcagcaa aagttcgatt tattcaacaa agccacgttg tgtctcaaaa tctctgatgt    120
tacattgcac aagataaaaa tatatcatca tgaacaataa aactgtctgc ttacataaac    180
agtaatacaa ggggtgttat gagccatatt caacgggaaa cgtcttgctc ccgtccgcgc    240
ttaaactcca acatggacgc tgatttatat gggtataaat gggctcgcga taatgtcggg    300
caatcaggtg cgacaatcta tcgcttgtat gggaagcccg atgcgccaga gttgtttctg    360
aaacatggca aaggtagcgt tgccaatgat gttacagatg atggtccg tctcaactgg     420 ctgacggagt ttatgcctct cccgaccatc aagcatttta tccgtactcc tgatgatgcg    480
tggttactca ccaccgcgat tcctgggaaa acagccttcc aggtattaga agaatatcct    540
gattcaggtg aaaatattgt tgatgcgctg gccgtgttcc tgcgccggtt acattcgatt    600
cctgtttgta attgtccttt taacagcgat cgtgtatttc gtcttgctca ggcgcaatca    660
cgcatgaata acggtttggt tgatgcgagt gattttgatg acgagcgtaa tggctggcct    720
gttgaacaag tctggaaaga atgcacaag ctcttgccat tctcaccgga ttcagtcgtc     780
actcatggtg atttctcact tgataacctt attttgacg aggggaaatt aataggttgt    840
attgatgttg acgggtcgg aatcgcagac cgttaccagg accttgccat tctttggaac    900
tgcctcggtg agttttctcc ttcattacag aaacggcttt ttcaaaaata tggtattgat    960
```

```
aatcctgata tgaataaatt gcagtttcat ttgatgctcg atgagttttt ctaataagcc    1020
tcgcgcgtga ttcgtatccg caccggcgaa gaagacgacg cggcgattta a             1071
```

<210> SEQ ID NO 47
<211> LENGTH: 1295
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 47

```
atgaccatga acctgatgac ggatgtcgtc tcagccaccg ggatcgccgg gttgctttca      60
cgacaacacc cgacgctgtt ttttacacta attgaacagg cccccgtggc gatcacgctg     120
acggataccg ctgcccgcat tgtctatgcc aacccgggcg tgttgagtca tcctgactag     180
ctgagatgag ggctcgcctg atccttcaac tcagcaaaag ttcgatttat tcaacaaagc     240
cacgttgtgt ctcaaaatct ctgatgttac attgcacaag ataaaaatat atcatcatga     300
acaataaaac tgtctgctta cataaacagt aatacaaggg gtgttatgag ccatattcaa     360
cgggaaacgt cttgctccag gccgcgatta aattccaaca tggatgctga tttatatggg     420
tataaatggg ctcgcgataa tgtcgggcaa tcaggtgcga caatctatcg attgtatggg     480
aagcccgatg cgccagagtt gtttctgaaa catggcaaag gtagcgttgc caatgatgtt     540
acagatgaga tggtcagact aaactggctg acggaattta tgcctcttcc gaccatcaag     600
cattttatcc gtactcctga tgatgcatgg ttactcacca ctgcgatccc cgggaaaaca     660
gcattccagg tattagaaga atatcctgat tcaggtgaaa atattgttga tgcgctggca     720
gtgttcctgc gccggttgca ttcgattcct gtttgtaatt gtcctttttaa cagcgatcgc     780 gtatttcgtc tcgctcaggc gcaatcacga atgaataacg gtttggttga tgcgagtgat     840
tttgatgacg agcgtaatgg ctggcctgtt gaacaagtct ggaaagaaat gcataagctt     900
ttgccattct caccggattc agtcgtcact catggtgatt tctcacttga taaccttatt     960
tttgacgagg ggaaattaat aggttgtatt gatgttggac gagtcggaat cgcagaccga    1020
taccaggatc ttgccatcct atggaactgc ctcggtgagt tttctccttc attacagaaa    1080 cggcttttc aaaaatatgg tattgataat cctgatatga ataaattgca gtttcatttg    1140
atgctcgatg agttttctta taagcctga ccggtggtga atttaatctc gctgacgtgt    1200
agacattcat cgatctgcat ccacggtccg gcggcggtac ctgcctgacg ctacgtttac    1260
cgctctttta tgaactgacc ggaggcccaa gatga                               1295
```

<210> SEQ ID NO 48
<211> LENGTH: 1491
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 48

```
atgagcatca cggcgttatc agcatcattt cctgagggga atatcgccag ccgcttgtcg      60
ctgcaacatc cttcactgtt ttataccgtg gttgaacaat cttcggtggc gagcgtgttg     120
agtcatcctg actagctgag atgagggctc gccccctcgt cccgacactt ccagatcgcc     180
atagcgcaca gcgcctcgag cggtggtaac ggcgcagtgg cggttttcat ggcttgttat     240
gactgttttt ttggggtaca gtctatgcct cgggcatcca agcagcaagc gcgttacgcc     300
```

```
gtgggtcgat gtttgatgtt atggagcagc aacgatgtta cgcagcaggg cagtcgccct      360
aaaacaaagt taaacatcat gagggaagcg gtgatcgccg aagtatcgac tcaactatca      420
gaggtagttg gcgtcatcga gcgccatctc gaaccgacgt tgctggccgt acatttgtac      480
ggctccgcag tggatggcgg cctgaagcca cacagtgata ttgatttgct ggttacggtg      540
accgtaaggc ttgatgaaac aacgcggcga gctttgatca cgacctttt ggaaacttcg       600 gcttccctg gagagagcga gattctccgc gctgtagaag tcaccattgt tgtgcacgac       660
gacatcattc cgtggcgtta tccagctaag cgcgaactgc aatttggaga atggcagcgc      720
aatgacattc ttgcaggtat cttcgagcca gccacgatcg acattgatct ggctatcttg      780
ctgacaaaag caagagaaca tagcgttgcc ttggtaggtc cagcggcgga ggaactcttt      840
gatccggttc ctgaacagga tctatttgag gcgctaaatg aaaccttaac gctatggaac      900
tcgccgcccg actgggctgg cgatgagcga aatgtagtgc ttacgttgtc ccgcatttgg      960
tacagcgcag taaccggcaa aatcgcgccg aaggatgtcg ctgccgactg ggcaatggag     1020
cgcctgccgg cccagtatca gcccgtcata cttgaagcta gacaggctta tcttggacaa     1080
gaagaagatc gcttggcctc gcgcgcagat cagttggaag aatttgtcca ctacgtgaaa     1140
ggcgagatca ccaaggtagt cggcaaataa tgtctaacaa ttcgttcaag ccgacgccgc     1200
ttcgcggcgc ggcttaactc aagcgttaga tgcactaagc acataattgc tcacagccaa     1260
actatcaggt caagtctgct tttattattt ttaagcgtgc ataataagcc ctacacaaat     1320
ggtacccgac cggtggtgaa tttaatctcg ctgacgtgta gacattccct tatccagacg     1380
ctgatcgccc atcatcgcgg ttctttagat ctctcggtcc gccctgatgg cggcaccttg     1440
ctgacgttac gcctgccggt acagcaggtt atcaccggag gcttaaaatg a              1491

<210> SEQ ID NO 49
<211> LENGTH: 1021
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49
ctgatccttc aactcagcaa aagttcgatt tattcaacaa agccacgttg tgtctcaaaa       60
tctctgatgt tacattgcac aagataaaaa tatatcatca tgaacaataa aactgtctgc      120
ttacataaac agtaatacaa ggggtgttat gagccatatt caacgggaaa cgtcttgctc      180
caggccgcga ttaaattcca acatggatgc tgatttatat gggtataaat gggctcgcga      240
taatgtcggg caatcaggtg cgacaatcta tcgattgtat gggaagcccg atgcgccaga      300
gttgtttctg aaacatggca aaggtagcgt tgccaatgat gttacagatg agatggtcag      360
actaaactgg ctgacggaat ttatgcctct tccgaccatc aagcatttta tccgtactcc      420
tgatgatgca tggttactca ccactgcgat ccccgggaaa acagcattcc aggtattaga      480
agaatatcct gattcaggtg aaaatattgt tgatgcgctg gcagtgttcc tgcgccggtt      540
gcattcgatt cctgtttgta attgtccttt taacagcgat cgcgtatttc gtctcgctca      600
ggcgcaatca cgaatgaata acggtttggt tgatgcgagt gattttgatg acgagcgtaa      660
tggctggcct gttgaacaag tctggaaaga aatgcataag cttttgccat tctcaccgga      720
ttcagtcgtc actcatggtg atttctcact tgataacctt attttgacg aggggaaatt       780 aataggttgt attgatgttg gacgagtcgg aatcgcagac cgataccagg atcttgccat      840
```

```
cctatggaac tgcctcggtg agttttctcc ttcattacag aaacggcttt ttcaaaaata    900
tggtattgat aatcctgata tgaataaatt gcagtttcat ttgatgctcg atgagttttt    960
ctaataagcc ttgaccctac gattcccgct atttcattca ctgaccggag gttcaaaatg   1020
a                                                                   1021
```

<210> SEQ ID NO 50
<211> LENGTH: 1071
<212> TYPE: DNA
<213> ORGANISM: Artificial Sequence
<220> FEATURE:
<223> OTHER INFORMATION: Description of Artificial Sequence: Synthetic
       polynucleotide

<400> SEQUENCE: 50

```
atgaccctga atatgatgct cgataacgcc gtacccgagg cgattgccgg ctgatccttc     60
aactcagcaa agttcgatt tattcaacaa agccacgttg tgtctcaaaa tctctgatgt    120
tacattgcac aagataaaaa tatatcatca tgaacaataa aactgtctgc ttacataaac    180
agtaatacaa ggggtgttat gagccatatt caacgggaaa cgtcttgctc ccgtccgcgc    240
ttaaactcca acatggacgc tgatttatat gggtataaat gggctcgcga taatgtcggg    300
caatcaggtg cgacaatcta tcgcttgtat gggaagcccg atgcgccaga gttgtttctg    360
aaacatggca aaggtagcgt tgccaatgat gttacagatg agatggtccg tctcaactgg    420
ctgacggagt ttatgcctct cccgaccatc aagcatttta tccgtactcc tgatgatgcg    480
tggttactca ccaccgcgat tcctgggaaa acagccttcc aggtattaga gaatatcct    540 gattcaggtg aaaatattgt tgatgcgctg gccgtgttcc tgcgccggtt acattcgatt    600
cctgtttgta attgtccttt taacagcgat cgtgtatttc gtcttgctca ggcgcaatca    660
cgcatgaata acggtttggt tgatgcgagt gattttgatg acgagcgtaa tggctggcct    720
gttgaacaag tctggaaaga atgcacaag ctcttgccat tctcaccgga ttcagtcgtc    780
actcatggtg atttctcact tgataacctt atttttgacg aggggaaatt aataggttgt    840
attgatgttg gacgggtcgg aatcgcagac cgttaccagg accttgccat tctttggaac    900
tgcctcggtg agttttctcc ttcattacag aaacggcttt ttcaaaaata tggtattgat    960
aatcctgata tgaataaatt gcagtttcat ttgatgctcg atgagttttt ctaataagcc   1020
ttggttctgc gtttcccgct ctttaatacc ctgaccggag gtgagcaatg a            1071
```

<210> SEQ ID NO 51
<211> LENGTH: 461
<212> TYPE: DNA
<213> ORGANISM: Artificial Sequence
<220> FEATURE:
<223> OTHER INFORMATION: Description of Artificial Sequence: Synthetic
       polynucleotide

<400> SEQUENCE: 51

```
atgaccctga atatgatgat ggatgccggc cgtcctgtaa taataaccgg acaattcgga     60
ctgattaaaa aagcgccctt gtggcgcttt ttttatattc ccgcctccat ttaaaataaa    120
aaatccaatc ggatttcact atttaaactg gccattatct aagatgaatc cgatggaagc    180
tcgctgtttt aacacgcgtt ttttaacctt ttattgaaag tcggtgcttc tttgagcgaa    240
cgatcaaatt taagtggatt cccatcaaaa aaatattctc aacctaaaaa agtttgtgta    300
atacttgtaa cgctacatgg agattaactc aatctagagg gtattaataa tgaatcgtac    360
```

```
taaactggta ctgggcgcaa ctcacttcac accccgaagg gggaagttgc ctgaccctac      420
gattcccgct atttcattca ctgaccggag gttcaaaatg a                          461
```

<210> SEQ ID NO 52
<211> LENGTH: 426
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52

```
atgaccctga atatgatgat ggatgccggc ggacatcatc gcgacaaaca atattaatac      60
cggcaaccac accggcaatt tacgagactg cgcaggcatc ctttctcccg tcaatttctg     120
tcaaataaag taaagaggc agtctacttg aattacccc ggctggttga gcgtttgttg      180
aaaaaaagta actgaaaaat ccgtagaata gcgccactct gatggttaat taacctattc    240
aattaagaat tatctggatg aatgtgccat taaatgcgca gcataatggt gcgttgtgcg    300
ggaaaactgc ttttttttga aagggttggt cagtagcgga aacaactcac ttcacacccc    360 gaaggggggaa gttgcctgac cctacgattc ccgctatttc attcactgac cggaggttca    420
aaatga                                                                426
```

<210> SEQ ID NO 53
<211> LENGTH: 452
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53

```
atgaccctga atatgatgat ggatgccggc tgacgaggca ggttacatca ctggtgaaac      60
cctgcacgtc aatggcggaa tgtatatggt ttaaccacga tgaaaattat ttgcgttatt    120
agggcgaaag gcctcaaaat agcgtaaaat cgtggtaaga actgccggga tttagttgca    180 aattttttcaa catttttatac actacgaaaa ccatcgcgaa agcgagtttt gataggaaat    240
ttaagagtat gagcactatc gaagaacgcg ttaagaaaat tatcggcgaa cagctgggcg    300
ttaagcagga agaagttacc aacaatgctt ccttcgttga agacctgggc gctgattctc    360
ttgacaccga actcacttca caccccgaag ggggaagttg cctgaccta cgattcccgc    420 tatttcattc actgaccgga ggttcaaaat ga                                  452
```

<210> SEQ ID NO 54
<211> LENGTH: 426
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54

```
atgaccctga atatgatgat ggatgccggc ggacatcatc gcgacaaaca atattaatac      60
cggcaaccac accggcaatt tacgagactg cgcaggcatc ctttctcccg tcaatttctg    120
tcaaataaag taaagaggc agtctacttg aattacccc ggctggttga gcgtttgttg     180
aaaaaaagta actgaaaaat ccgtagaata gcgccactct gatggttaat taacctattc    240
aattaagaat tatctggatg aatgtgccat taaatgcgca gcataatggt gcgttgtgcg    300
```

| | |
|---|---|
| ggaaaactgc tttttttga aagggttggt cagtagcgga acaactcac ttcacacccc | 360 |
| gaaggggaa gttgcctgac cctacgattc ccgctatttc attcactgac cggaggttca | 420 |
| aaatga | 426 |

<210> SEQ ID NO 55
<211> LENGTH: 461
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 55

| | |
|---|---|
| atgaccctga atatgatgat ggatgccggc cgtcctgtaa aataaccgg acaattcgga | 60 |
| ctgattaaaa aagcgcccctt gtggcgcttt ttttatattc ccgcctccat ttaaaataaa | 120 |
| aaatccaatc ggatttcact atttaaactg gccattatct aagatgaatc cgatggaagc | 180 |
| tcgctgtttt aacacgcgtt ttttaacctt ttattgaaag tcggtgcttc tttgagcgaa | 240 |
| cgatcaaatt taagtggatt cccatcaaaa aaatattctc aacctaaaaa agtttgtgta | 300 |
| atacttgtaa cgctacatgg agattaactc aatctagagg gtattaataa tgaatcgtac | 360 |
| taaactggta ctgggcgcaa ctcacttcac accccgaagg gggaagttgc ctgaccctac | 420 |
| gattcccgct atttcattca ctgaccggag gttcaaaatg a | 461 |

<210> SEQ ID NO 56
<211> LENGTH: 1491
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 56

| | |
|---|---|
| atgagcatca cggcgttatc agcatcattt cctgagggga atatcgccag ccgcttgtcg | 60 |
| ctgcaacatc cttcactgtt ttataccgtg gttgaacaat cttcggtggc gagcgtgttg | 120 |
| agtcatcctg actagctgag atgagggctc gccccctcgt cccgacactt ccagatcgcc | 180 |
| atagcgcaca gcgcctcgag cggtggtaac ggcgcagtgg cggttttcat ggcttgttat | 240 |
| gactgttttt ttggggtaca gtctatgcct cgggcatcca agcagcaagc gcgttacgcc | 300 |
| gtgggtcgat gttttgatgtt atggagcagc aacgatgtta cgcagcaggg cagtcgccct | 360 |
| aaaacaaagt taaacatcat gagggaagcg gtgatcgccg aagtatcgac tcaactatca | 420 |
| gaggtagttg gcgtcatcga gcgccatctc gaaccgacgt tgctggccgt acatttgtac | 480 |
| ggctccgcag tggatggcgg cctgaagcca cacagtgata ttgatttgct ggttacggtg | 540 |
| accgtaaggc ttgatgaaac aacgcggcga gctttgatca cgacctttt ggaaacttcg | 600 |
| gcttcccctg gagagagcga gattctccgc gctgtagaag tcaccattgt tgtgcacgac | 660 |
| gacatcattc cgtggcgtta tccagctaag cgcgaactgc aatttggaga atggcagcgc | 720 |
| aatgacattc ttgcaggtat cttcgagcca gccacgatcg acattgatct ggctatcttg | 780 |
| ctgacaaaag caagagaaca tagcgttgcc ttggtaggtc cagcggcgga ggaactcttt | 840 |
| gatccggttc ctgaacagga tctatttgag gcgctaaatg aaaccttaac gctatggaac | 900 |
| tcgccgcccg actgggctgg cgatgagcga aatgtagtgc ttacgttgtc ccgcatttgg | 960 |
| tacagcgcag taaccggcaa aatcgcgccg aaggatgtcg ctgccgactg ggcaatggag | 1020 |
| cgcctgccgg cccagtatca gcccgtcata cttgaagcta gacaggctta tcttggacaa | 1080 |

```
gaagaagatc gcttggcctc gcgcgcagat cagttggaag aatttgtcca ctacgtgaaa    1140
ggcgagatca ccaaggtagt cggcaaataa tgtctaacaa ttcgttcaag ccgacgccgc    1200
ttcgcggcgc ggcttaactc aagcgttaga tgcactaagc acataattgc tcacagccaa    1260
actatcaggt caagtctgct tttattattt ttaagcgtgc ataataagcc ctacacaaat    1320
ggtacccgac cggtggtgaa tttaatctcg ctgacgtgta gacattccct tatccagacg    1380
ctgatcgccc atcatcgcgg ttctttagat ctctcggtcc gccctgatgg cggcaccttg    1440
ctgacgttac gcctgccggt acagcaggtt atcaccggag gcttaaaatg a             1491

<210> SEQ ID NO 57
<211> LENGTH: 1491
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57
atgagcatca cggcgttatc agcatcattt cctgagggga atatcgccag ccgcttgtcg      60
ctgcaacatc cttcactgtt ttataccgtg gttaacaat cttcggtggc gagcgtgttg     120
agtcatcctg actagctgag atgagggctc gcccctcgt cccgacactt ccagatcgcc     180
atagcgcaca gcgcctcgag cggtggtaac ggcgcagtgg cggttttcat ggcttgttat    240
gactgttttt ttggggtaca gtctatgcct cgggcatcca agcagcaagc gcgttacgcc    300
gtgggtcgat gtttgatgtt atggagcagc aacgatgtta cgcagcaggg cagtcgccct    360
aaaacaaagt taaacatcat gagggaagcg gtgatcgccg aagtatcgac tcaactatca    420
gaggtagttg gcgtcatcga cgccatctc gaaccgacgt tgctggccgt acatttgtac    480
ggctccgcag tggatggcgg cctgaagcca cacagtgata ttgatttgct ggttacggtg    540
accgtaaggc ttgatgaaac aacgcggcga gctttgatca cgaccttttt ggaaacttcg    600
gcttcccctg gagagagcga gattctccgc gctgtagaag tcaccattgt tgtgcacgac    660
gacatcattc cgtggcgtta ccagctaag cgcgaactgc aatttggaga atggcagcgc    720
aatgacattc ttgcaggtat cttcgagcca gccacgatcg acattgatct ggctatcttg    780
ctgacaaaag caagagaaca tagcgttgcc ttggtaggtc cagcggcgga ggaactcttt    840
gatccggttc ctgaacagga tctatttgag gcgctaaatg aaaccttaac gctatggaac    900
tcgccgcccg actgggctgg cgatgagcga aatgtagtgc ttacgttgtc ccgcatttgg    960
tacagcgcag taaccggcaa atcgcgccg aaggatgtcg ctgccgactg gcaatggag     1020 cgcctgccgg cccagtatca gcccgtcata cttgaagcta gacaggctta tcttggacaa   1080
gaagaagatc gcttggcctc gcgcgcagat cagttggaag aatttgtcca ctacgtgaaa   1140
ggcgagatca ccaaggtagt cggcaaataa tgtctaacaa ttcgttcaag ccgacgccgc   1200
ttcgcggcgc ggcttaactc aagcgttaga tgcactaagc acataattgc tcacagccaa   1260
actatcaggt caagtctgct tttattattt ttaagcgtgc ataataagcc ctacacaaat   1320
ggtacccgac cggtggtgaa tttaatctcg ctgacgtgta gacattccct tatccagacg   1380
ctgatcgccc atcatcgcgg ttctttagat ctctcggtcc gccctgatgg cggcaccttg   1440
ctgacgttac gcctgccggt acagcaggtt atcaccggag gcttaaaatg a             1491

<210> SEQ ID NO 58
<211> LENGTH: 1021
```

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58

| | |
|---|---|
| ctgatccttc aactcagcaa aagttcgatt tattcaacaa agccacgttg tgtctcaaaa | 60 |
| tctctgatgt tacattgcac aagataaaaa tatatcatca tgaacaataa aactgtctgc | 120 |
| ttacataaac agtaatacaa ggggtgttat gagccatatt caacgggaaa cgtcttgctc | 180 |
| caggccgcga ttaaattcca acatggatgc tgatttatat gggtataaat gggctcgcga | 240 |
| taatgtcggg caatcaggtg cgacaatcta tcgattgtat gggaagcccg atgcgccaga | 300 |
| gttgtttctg aaacatggca aaggtagcgt tgccaatgat gttacagatg agatggtcag | 360 |
| actaaactgg ctgacggaat ttatgcctct tccgaccatc aagcatttta tccgtactcc | 420 |
| tgatgatgca tggttactca ccactgcgat ccccgggaaa acagcattcc aggtattaga | 480 |
| agaatatcct gattcaggtg aaaatattgt tgatgcgctg gcagtgttcc tgcgccggtt | 540 |
| gcattcgatt cctgtttgta attgtccttt taacagcgat cgcgtatttc gtctcgctca | 600 |
| ggcgcaatca cgaatgaata acggtttggt tgatgcgagt gattttgatg acgagcgtaa | 660 |
| tggctggcct gttgaacaag tctggaaaga atgcataag cttttgccat tctcaccgga | 720 |
| ttcagtcgtc actcatggtg atttctcact tgataacctt atttttgacg aggggaaatt | 780 |
| aataggttgt attgatgttg acgagtcgg aatcgcagac cgataccagg atcttgccat | 840 |
| cctatggaac tgcctcggtg agttttctcc ttcattacag aaacggcttt ttcaaaaata | 900 |
| tggtattgat aatcctgata tgaataaatt gcagtttcat ttgatgctcg atgagttttt | 960 |
| ctaataagcc ttgaccctac gattcccgct atttcattca ctgaccggag gttcaaaatg | 1020 |
| a | 1021 |

<210> SEQ ID NO 59
<211> LENGTH: 1491
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59

| | |
|---|---|
| atgagcatca cggcgttatc agcatcattt cctgagggga atatcgccag ccgcttgtcg | 60 |
| ctgcaacatc cttcactgtt ttataccgtg gttaacaat cttcggtggc gagcgtgttg | 120 |
| agtcatcctg actagctgag atgagggctc gccccctcgt cccgacactt ccagatcgcc | 180 |
| atagcgcaca gcgcctcgag cggtggtaac ggcgcagtgg cggttttcat ggcttgttat | 240 |
| gactgttttt ttggggtaca gtctatgcct cgggcatcca agcagcaagc gcgttacgcc | 300 |
| gtgggtcgat gtttgatgtt atggagcagc aacgatgtta cgcagcaggg cagtcgccct | 360 |
| aaaacaaagt taaacatcat gagggaagcg gtgatcgccg aagtatcgac tcaactatca | 420 |
| gaggtagttg gcgtcatcga gcgccatctc gaaccgacgt tgctggccgt acatttgtac | 480 |
| ggctccgcag tggatggcgg cctgaagcca cacagtgata ttgatttgct ggttacggtg | 540 |
| accgtaaggc ttgatgaaac aacgcggcga gctttgatca cgaccttttt ggaaacttcg | 600 |
| gcttcccctg gagagagcga gattctccgc gctgtagaag tcaccattgt tgtgcacgac | 660 |
| gacatcattc cgtggcgtta tccagctaag cgcgaactgc aatttggaga atggcagcgc | 720 |

```
aatgacattc ttgcaggtat cttcgagcca gccacgatcg acattgatct ggctatcttg    780
ctgacaaaag caagagaaca tagcgttgcc ttggtaggtc cagcggcgga ggaactcttt    840
gatccggttc ctgaacagga tctatttgag gcgctaaatg aaaccttaac gctatggaac    900
tcgccgcccg actgggctgg cgatgagcga aatgtagtgc ttacgttgtc ccgcatttgg    960
tacagcgcag taaccggcaa aatcgcgccg aaggatgtcg ctgccgactg gcaatggag   1020 cgcctgccgg cccagtatca gcccgtcata cttgaagcta gacaggctta tcttggacaa  1080
gaagaagatc gcttggcctc gcgcgcagat cagttggaag aatttgtcca ctacgtgaaa  1140
ggcgagatca ccaaggtagt cggcaaataa tgtctaacaa ttcgttcaag ccgacgccgc  1200
ttcgcggcgc ggcttaactc aagcgttaga tgcactaagc acataattgc tcacagccaa  1260
actatcaggt caagtctgct tttattattt ttaagcgtgc ataataagcc ctacacaaat   1320
ggtacccgac cggtggtgaa tttaatctcg ctgacgtgta gacattccct tatccagacg  1380
ctgatcgccc atcatcgcgg ttctttagat ctctcggtcc gccctgatgg cggcaccttg   1440
ctgacgttac gcctgccggt acagcaggtt atcaccggag gcttaaaatg a             1491
```

<210> SEQ ID NO 60
<211> LENGTH: 1491
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60

```
atgagcatca cggcgttatc agcatcattt cctgagggga atatcgccag ccgcttgtcg     60
ctgcaacatc cttcactgtt ttataccgtg gttgaacaat cttcggtggc gagcgtgttg    120
agtcatcctg actagctgag atgagggctc gccccctcgt cccgacactt ccagatcgcc    180
atagcgcaca gcgcctcgag cggtggtaac ggcgcagtgg cggttttcat ggcttgttat   240
gactgttttt ttggggtaca gtctatgcct cgggcatcca agcagcaagc gcgttacgcc   300
gtgggtcgat gtttgatgtt atggagcagc aacgatgtta cgcagcaggg cagtcgccct   360
aaaacaaagt taaacatcat gagggaagcg gtgatcgccg aagtatcgac tcaactatca   420
gaggtagttg gcgtcatcga gcgccatctc gaaccgacgt tgctggccgt acatttgtac   480
ggctccgcag tggatggcgg cctgaagcca cacagtgata ttgatttgct ggttacggtg   540
accgtaaggc ttgatgaaac aacgcggcga gctttgatca cgacctttt ggaaacttcg    600 gcttcccctg gagagagcga gattctccgc gctgtagaag tcaccattgt tgtgcacgac   660
gacatcattc cgtggcgtta tccagctaag cgcgaactgc aatttggaga atggcagcgc  720
aatgacattc ttgcaggtat cttcgagcca gccacgatcg acattgatct ggctatcttg    780
ctgacaaaag caagagaaca tagcgttgcc ttggtaggtc cagcggcgga ggaactcttt    840
gatccggttc ctgaacagga tctatttgag gcgctaaatg aaaccttaac gctatggaac   900
tcgccgcccg actgggctgg cgatgagcga aatgtagtgc ttacgttgtc ccgcatttgg   960
tacagcgcag taaccggcaa aatcgcgccg aaggatgtcg ctgccgactg gcaatggag   1020 cgcctgccgg cccagtatca gcccgtcata cttgaagcta gacaggctta tcttggacaa  1080
gaagaagatc gcttggcctc gcgcgcagat cagttggaag aatttgtcca ctacgtgaaa  1140
ggcgagatca ccaaggtagt cggcaaataa tgtctaacaa ttcgttcaag ccgacgccgc  1200
ttcgcggcgc ggcttaactc aagcgttaga tgcactaagc acataattgc tcacagccaa  1260
```

```
actatcaggt caagtctgct tttattattt ttaagcgtgc ataataagcc ctacacaaat    1320
ggtacccgac cggtggtgaa tttaatctcg ctgacgtgta gacattccct tatccagacg    1380
ctgatcgccc atcatcgcgg ttctttagat ctctcggtcc gccctgatgg cggcaccttg    1440
ctgacgttac gcctgccggt acagcaggtt atcaccggag gcttaaaatg a             1491
```

<210> SEQ ID NO 61
<211> LENGTH: 1563
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61

```
atgtttaacg atctgattgg cgatgatgaa acggattcgc cggaagatgc gctttctgag      60
agctggcgcg aattgtggca ggatgcgttg caggaggagg attccacgcc cgtgctggcg    120
catctctcag aggacgatcg ccgccgcgtg gtggcgctga ttgccgattt tcgcaaagag    180
ttggataaac gcaccattgg cccgcgaggg cggcaggtac tcgatcactt aatgccgcat    240
ctgctcagcg atgtatgctc gcgcgacgat gcgccagtac cgctgtcacg cctgacgccg    300
ctgctcaccg gaattattac ccgcaccact taccttgagc tgctaagtga atttcccggc    360 gcactgaaaac acctcatttc cctgtgtgcc gcgtcgccga tggttgccag tcagctggcg    420
cgctacccga tcctgcttga tgaattgctc gacccgaata cgctctatca accgacggcg    480
atgaatgcct atcgcgatga gctgcgccaa tacctgctgc gcgtgccgga agatgatgaa    540
gagcaacagc ttgaggcgct gcggcagttt aagcaggcgc agttgctgcg cgtggcggcg    600
gcggatattg ccggtacgtt gccagtaatg aaagtgagcg atcacttaac ctggctggcg    660
gaagcgatta ttgatgcggt ggtgcagcaa gcctggggc agatggtggc gcgttatggc    720
cagccaacgc atctgcacga tcgcgaaggg cgcggttttg cggtggtcgg ttatggcaag    780
ctgggcggct gggagctggg ttacagctcc gatctggatc tggtattcct gcacgactgc    840
ccgatggatg tgatgaccga tggcgagcgt gaaatcgatg gtcgccagtt ctatttgcgt    900
ctcgcgcagc gcgtgatgca cctgtttagc acgcgcacgt cgtccggcat cctttatgaa    960
gttgatgcgc gtctgcgtcc atctggcgct gcggggatgc tggtcactac tacggaatcg   1020
ttcgccgatt accagcaaaa cgaagcctgg acgtgggaac atcaggcgct ggcccgtgcg   1080
cgcgtggtgt acggcgatcc gcaactgacc gccgaatttg acgccattcg ccgcgatatt   1140
ctgatgacgc ctcgcgacgg cgcaacgctg caaaccgacg tgcgagaaat gcgcgagaaa   1200
atgcgtgccc atcttggcaa caagcataaa gaccgcttcg atctgaaagc cgatgaaggc   1260
ggtatcaccg acatcgagtt tatcgcccaa tatctggtgc tgcgctttgc ccatgacaag   1320
ccgaaactga cgcgctggtc ggataatgtg cgcattctcg aagggctggc gcaaaacggc   1380
atcatggagg agcaggaagc gcaggcattg acgctggcgt acaccacatt gcgtgatgag   1440
ctgcaccacc tggcgctgca agagttgccg ggacatgtgg cgctctcctg ttttgtcgcc   1500
gagcgtgcgc ttattaaaac cagctgggac aagtggctgg tggaaccgtg cgccccggcg   1560
taa                                                                   1563
```

<210> SEQ ID NO 62
<211> LENGTH: 1536
<212> TYPE: DNA
<213> ORGANISM: Kosakonia sacchari
<220> FEATURE:

<223> OTHER INFORMATION: 16S rDNA - contig 5, strain CI006

<400> SEQUENCE: 62

```
ttgaagagtt tgatcatggc tcagattgaa cgctggcggc aggcctaaca catgcaagtc    60
gaacggtagc acagagagct tgctctcggg tgacgagtgg cggacgggtg agtaatgtct   120
gggaaactgc ctgatggagg gggataacta ctggaaacgg tagctaatac cgcataacgt   180
cgcaagacca agagggggga ccttcgggcc tcttgccatc agatgtgccc agatgggatt   240
agctagtagg tggggtaacg gctcacctag gcgacgatcc ctagctggtc tgagaggatg   300
accagccaca ctggaactga gacacggtcc agactcctac gggaggcagc agtggggaat   360
attgcacaat gggcgcaagc ctgatgcagc catgccgcgt gtgtgaagaa ggccttcggg   420
ttgtaaagca ctttcagcgg ggaggaaggg agtaaggtta ataaccttat tcattgacgt   480
tacccgcaga agaagcaccg gctaactccg tgccagcagc cgcggtaata cggagggtgc   540
aagcgttaat cggaattact gggcgtaaag cgcacgcagg cggtctgtca gtcggatgt   600
gaaatccccg ggctcaacct gggaactgca tccgaaactg gcaggcttga gtctcgtaga   660
gggaggtaga attccaggtg tagcggtgaa atgcgtagag atctggagga ataccggtgg   720
cgaaggcggc ctcctggacg aagactgacg ctcaggtgcg aaagcgtggg gagcaaacag   780
gattagatac cctggtagtc cacgccgtaa acgatgtcta tttggaggtt gtgcccttga   840
ggcgtggctt ccggagctaa cgcgttaaat agaccgcctg gggagtacgg ccgcaaggtt   900
aaaactcaaa tgaattgacg ggggcccgca caagcggtgg agcatgtggt ttaattcgat   960
gcaacgcgaa gaaccttacc tggtcttgac atccacagaa ctttccagag atggattggt  1020
gccttcggga actgtgagac aggtgctgca tggctgtcgt cagctcgtgt tgtgaaatgt  1080
tgggttaagt cccgcaacga gcgcaaccct tatcctttgt tgccagcggt ccggccggga  1140
actcaaagga gactgccagt gataaactgg aggaaggtgg ggatgacgtc aagtcatcat  1200
ggcccttacg accagggcta cacacgtgct acaatggcgc atacaaagag aagcgacctc  1260
gcgagagtaa gcggacctca taaagtgcgt cgtagtccgg attggagtct gcaactcgac  1320
tccatgaagt cggaatcgct agtaatcgtg gatcagaatg ccacggtgaa tacgttcccg  1380
ggccttgtac acaccgcccg tcacaccatg ggagtgggtt gcaaagaag taggtagctt  1440
aaccttcggg agggcgctta ccactttgtg attcatgact ggggtgaagt cgtaacaagg  1500
taaccgtagg ggaacctgcg gttggatcac ctcctt                            1536
```

<210> SEQ ID NO 63
<211> LENGTH: 1537
<212> TYPE: DNA
<213> ORGANISM: Kosakonia sacchari
<220> FEATURE:
<223> OTHER INFORMATION: 16S rDNA - contig 8, strain CI006
<220> FEATURE:
<221> NAME/KEY: modified_base
<222> LOCATION: (450)..(450)
<223> OTHER INFORMATION: a, c, g, or t
<220> FEATURE:
<221> NAME/KEY: modified_base
<222> LOCATION: (452)..(452)
<223> OTHER INFORMATION: a, c, g, or t
<220> FEATURE:
<221> NAME/KEY: modified_base
<222> LOCATION: (455)..(455)
<223> OTHER INFORMATION: a, c, g, or t
<220> FEATURE:
<221> NAME/KEY: modified_base
<222> LOCATION: (473)..(473)
<223> OTHER INFORMATION: a, c, g, or t

<400> SEQUENCE: 63

```
ttgaagagtt tgatcatggc tcagattgaa cgctggcggc aggcctaaca catgcaagtc      60
gaacggtagc acagagagct tgctctcggg tgacgagtgg cggacgggtg agtaatgtct     120
gggaaactgc ctgatggagg gggataacta ctggaaacgg tagctaatac cgcataacgt     180
cgcaagacca agaggggga ccttcgggcc tcttgccatc agatgtgccc agatgggatt     240
agctagtagg tggggtaacg gctcacctag gcgacgatcc ctagctggtc tgagaggatg     300
accagccaca ctgaactga gacacggtcc agactcctac gggaggcagc agtggggaat     360
attgcacaat gggcgcaagc ctgatgcagc catgccgcgt gtgtgaagaa ggccttcggg     420
ttgtaaagca ctttcagcgg ggaggaaggn antanggtta ataacctgtg ttnattgacg     480
ttacccgcag aagaagcacc ggctaactcc gtgccagcag ccgcggtaat acggagggtg     540
caagcgttaa tcggaattac tgggcgtaaa gcgcacgcag gcggtctgtc aagtcggatg     600
tgaaatcccc gggctcaacc tgggaactgc atccgaaact gcaggcttg agtctcgtag     660
agggaggtag aattccaggt gtagcggtga atgcgtaga gatctggagg aataccggtg     720
gcgaaggcgg cctcctggac gaagactgac gctcaggtgc gaaagcgtgg ggagcaaaca     780
ggattagata ccctggtagt ccacgccgta acgatgtct atttggaggt tgtgcccttg     840
aggcgtggct tccggagcta acgcgttaaa tagaccgcct ggggagtacg gccgcaaggt     900
taaaactcaa atgaattgac ggggggcccgc acaagcggtg gagcatgtgg tttaattcga     960
tgcaacgcga agaaccttac ctggtcttga catccacaga acttagcaga gatgctttgg    1020
tgccttcggg aactgtgaga caggtgctgc atggctgtcg tcagctcgtg ttgtgaaatg    1080
ttgggttaag tcccgcaacg agcgcaaccc ttatcctttg ttgccagcgg ttaggccggg    1140
aactcaaagg agactgccag tgataaactg gaggaaggtg gggatgacgt caagtcatca    1200
tggcccttac gaccagggct acacacgtgc tacaatggcg catacaaaga gaagcgacct    1260
cgcgagagta agcggacctc ataaagtgcg tcgtagtccg gattggagtc tgcaactcga    1320
ctccatgaag tcggaatcgc tagtaatcgt ggatcagaat gccacggtga atacgttccc    1380
gggccttgta cacaccgccc gtcacaccat gggagtgggt tgcaaaagaa gtaggtagct    1440
taaccttcgg gagggcgctt accactttgt gattcatgac tggggtgaag tcgtaacaag    1500
gtaaccgtag gggaacctgc ggttggatca cctcctt                             1537
```

<210> SEQ ID NO 64
<211> LENGTH: 1540
<212> TYPE: DNA
<213> ORGANISM: Rahnella sp.
<220> FEATURE:
<223> OTHER INFORMATION: 16S rDNA, strain CI019
<220> FEATURE:
<221> NAME/KEY: modified_base
<222> LOCATION: (70)..(70)
<223> OTHER INFORMATION: a, c, g, or t
<220> FEATURE:
<221> NAME/KEY: modified_base
<222> LOCATION: (267)..(267)
<223> OTHER INFORMATION: a, c, g, or t
<220> FEATURE:
<221> NAME/KEY: modified_base
<222> LOCATION: (455)..(455)
<223> OTHER INFORMATION: a, c, g, or t
<220> FEATURE:
<221> NAME/KEY: modified_base
<222> LOCATION: (458)..(458)
<223> OTHER INFORMATION: a, c, g, or t
<220> FEATURE:

<221> NAME/KEY: modified_base
<222> LOCATION: (473)..(473)
<223> OTHER INFORMATION: a, c, g, or t
<220> FEATURE:
<221> NAME/KEY: modified_base
<222> LOCATION: (1135)..(1135)
<223> OTHER INFORMATION: a, c, g, or t

<400> SEQUENCE: 64

```
attgaagagt ttgatcatgg ctcagattga acgctggcgg caggcctaac acatgcaagt    60
cgagcggcan cgggaagtag cttgctactt tgccggcgag cggcggacgg gtgagtaatg   120
tctgggaaac tgcctgatgg aggggggataa ctactggaaa cggtagctaa taccgcatga   180
cctcgaaaga gcaaagtggg ggatcttcgg acctcacgcc atcggatgtg cccagatggg   240
attagctagt aggtgaggta atggctnacc taggcgacga tccctagctg gtctgagagg   300
atgaccagcc acactggaac tgagacacgg tccagactcc tacgggaggc agcagtgggg   360
aatattgcac aatgggcgca agcctgatgc agccatgccg cgtgtgtgaa gaaggcctta   420
gggttgtaaa gcactttcag cgaggaggaa ggcancanac ttaatacgtg tgntgattga   480
cgttactcgc agaagaagca ccggctaact ccgtgccagc agccgcggta atacggaggg   540
tgcaagcgtt aatcggaatt actgggcgta aagcgcacgc aggcggtttg ttaagtcaga   600
tgtgaaatcc ccgagcttaa cttgggaact gcatttgaaa ctggcaagct agagtcttgt   660
agaggggggt agaattccag gtgtagcggt gaaatgcgta gagatctgga ggaataccgg   720
tggcgaaggc ggccccctgg acaaagactg acgctcaggt gcgaaagcgt ggggagcaaa   780
caggattaga taccctggta gtccacgctg taaacgatgt cgacttggag gttgtgccct   840
tgaggcgtgg cttccggagc taacgcgtta agtcgaccgc ctgggagta cggccgcaag   900
gttaaaactc aaatgaattg acgggggccc gcacaagcgg tggagcatgt ggtttaattc   960
gatgcaacgc gaagaacctt acctactctt gacatccaga gaatttgcca gagatggcga  1020
agtgccttcg ggaactctga gacaggtgct gcatggctgt cgtcagctcg tgttgtgaaa  1080
tgttgggtta agtcccgcaa cgagcgcaac ccttatcctt tgttgccagc acgtnatggt  1140
gggaactcaa aggagactgc cggtgataaa ccggaggaag gtggggatga cgtcaagtca  1200
tcatggccct tacgagtagg gctacacacg tgctacaatg gcatatacaa agagaagcga  1260
actcgcgaga gcaagcggac ctcataaagt atgtcgtagt ccggattgga gtctgcaact  1320
cgactccatg aagtcggaat cgctagtaat cgtagatcag aatgctacgg tgaatacgtt  1380
cccgggcctt gtacacaccg cccgtcacac catgggagtg ggttgcaaaa gaagtaggta  1440
gcttaacctt cgggagggcg cttaccactt tgtgattcat gactggggtg aagtcgtaac  1500
aaggtaaccg tagggaacc tgcggttgga tcacctcctt                         1540
```

<210> SEQ ID NO 65
<211> LENGTH: 882
<212> TYPE: DNA
<213> ORGANISM: Kosakonia sacchari
<220> FEATURE:
<223> OTHER INFORMATION: nifH, strain CI006

<400> SEQUENCE: 65

```
atgaccatgc gtcaatgcgc catttacggc aaaggtggga tcggcaaatc gaccaccaca    60
cagaacctgg tcgccgcgct ggcggagatg ggtaaaaaag tcatgattgt cggctgtgac   120
ccgaaagccg attccacgcg tttgatcctg catgcgaaag cgcagaacac cattatggag   180
atggctgctg aagtcggctc cgtggaagac ctggagttag aagacgtgct gcaaatcggt   240
```

```
tacggcggcg tgcgctgcgc agagtccggc ggcccggagc caggcgtggg ctgtgccggt    300
cgcggggtga tcaccgcgat taacttcctc gaagaagaag gcgcttacgt gccggatctc    360
gattttgttt tctacgacgt gctgggcgac gtggtatgcg gtggtttcgc catgccgatt    420
cgtgaaaaca aagcgcagga gatctacatc gtttgctctg cgaaatgat ggcgatgtac     480 gccgccaaca acatctccaa aggcatcgtg aaatacgcca aatccggtaa agtgcgcctc    540
ggcgggctga tttgtaactc gcgccagacc gaccgtgaag atgaactgat cattgcgctg    600
gcagaaaaac tcggcacgca gatgatccac tttgttcccc gcgacaacat tgtgcagcgt    660
gcggaaatcc gccgtatgac ggttatcgaa tatgacccga cctgcaatca ggcgaacgaa    720
tatcgcagcc ttgccagcaa aatcgtcaac aacaccaaaa tggtggtgcc caccccctgc    780
accatggatg aactggaaga actgctgatg gagttcggca ttatggatgt ggaagacacc    840
agcatcattg gtaaaaccgc cgccgaagaa aacgccgtct ga                       882
```

<210> SEQ ID NO 66
<211> LENGTH: 1449
<212> TYPE: DNA
<213> ORGANISM: Kosakonia sacchari
<220> FEATURE:
<223> OTHER INFORMATION: NifD, strain CI006

<400> SEQUENCE: 66

```
atgagcaatg caacaggcga acgcaacctg gagataatcg agcaggtgct cgaggttttc    60
ccggagaaga cgcgcaaaga acgcagaaaa cacatgatgg tgacggaccc ggagcaggaa   120
agcgtcggta agtgcatcat ctctaaccgc aaatcgcagc caggcgtgat gaccgtgcgc   180
ggctgctcgt atgccggttc gaaagggtg gtatttgggc caatcaagga tatggcgcat   240
atctcgcatg gcccaatcgg ctgcggccaa tactcccgcg ccgggcggcg gaactactac   300
accggcgtca gcggcgtgga cagcttcggc acgctcaact tcacctccga ttttcaggag   360
cgcgacatcg tgtttggcgg cgataaaaag ctcgccaaac tgattgaaga gctggaagag   420
ctgttcccgc tgaccaaagg catttcgatt cagtcggaat gcccggtcgg cctgattggc   480
gatgacattg aggccgtcgc gaacgccagc cgcaaagcca tcaacaaacc ggttattccg   540
gtgcgttgcg aaggctttcg cggcgtgtcg caatccctcg gtcaccatat tgccaacgat   600
gtgatccgcg actgggtgct ggataaccgc gaaggcaaac cgttcgaatc cacccccttac   660 gatgtggcga tcatcggcga ttacaacatc ggcggcgatg cctgggcttc gcgcattttg   720
ctcgaagaga tgggcttgcg ggtggtggca cagtggtctg cgacggtac gctggtggag   780 atggaaaaca cgccgttcgt caaactgaac ctggtgcatt gttaccgctc aatgaactac   840
atctcgcgcc atatggagga gaagcacggt attccgtgga tggaatacaa cttctttggt   900
ccgacgaaaa tcgcggaatc gctgcgcaaa atcgccgacc agtttgacga caccattcgc    960
gccaacgccg aagcggtgat cgccagatac caggcgcaaa acgacgccat tatcgccaaa   1020
tatcgcccgc gtctggaggg cgcaaagtg ctgctttata tgggcgggct gcgtccgcgc   1080
catgtgattg cgcctatga agacctggga atggagatca tcgctgccgg ttatgagttc   1140
ggtcataacg atgattacga ccgcaccttg ccggatctga agagggcac gctgctgttt   1200 gatgatgcca gcagttatga gctggaggcg ttcgtcaacg cgctgaaacc ggatctcatc   1260
ggttccggca tcaaagagaa gtacatcttt cagaaaatgg cgtgccgtt cgccagatg   1320 cactcctggg attactccgg cccgtaccac ggctatgacg gcttcgccat cttcgcccgc   1380
```

```
gatatggata tgacgctcaa caaccccgcg tggggccagt tgaccgcgcc gtggctgaaa    1440
tccgcctga                                                           1449
```

<210> SEQ ID NO 67
<211> LENGTH: 1563
<212> TYPE: DNA
<213> ORGANISM: Kosakonia sacchari
<220> FEATURE:
<223> OTHER INFORMATION: nifK, strain CI006

<400> SEQUENCE: 67

```
atgagccaga ctgctgagaa aatacagaat tgccatcccc tgtttgaaca ggatgcttac      60
cagacgctgt tgccggtaa acgggcactc gaagaggcgc actcgccgga gcgggtgcag     120
gaagtgtttc aatggaccac taccccggaa tatgaagcgc tgaactttaa acgcgaagcg     180
ctgactatcg acccggcaaa agcctgccag ccgctgggcg cggtgctctg ttcgctgggg     240
tttgccaata ccctaccgta tgtgcacggt tcacagggtt gcgtggccta tttccgcacg     300
tactttaacc gccactttaa agaaccggtg gcctgcgtgt cggattcaat gacgaaagac     360
gcggcggtgt tcggcgggaa taacaacctc aacaccggct acaaaacgc cagcgcgctg      420 tataaaccgg agattatcgc cgtctctacc acctgtatgg cggaagtgat cggtgatgat     480
ttgcaggcct ttatcgccaa cgccaaaaaa gatggttttc tcgatgccgc catccccgtg     540
ccctacgcgc acacccccag ttttatcggc agccatatca ccggctggga taacatgttt     600
gaaggttttg cccggacctt tacgcagac catgaagctc agcccggcaa actttcacgc      660
atcaacctgg tgaccgggtt tgaaacctat ctcggcaatt ccgcgtgct gaaacgcatg      720 atggaacaaa tggaggtgcc ggcgagtgtg ctctccgatc cgtcggaagt gctggatact     780
cccgccaacg ggcattacca gatgtacgcg ggcgggacga cgcagcaaga gatgcgcgag     840
gcgccggatg ctatcgacac cctgttgctg cagccctggc aactggtgaa agcaaaaaaa    900
gtggtgcagg agatgtggaa tcagcccgcc accgaggttt ctgttcccgt tgggctggca    960
ggaacagacg aactgttgat ggcgattagc cagttaaccg gcaaggccat tcccgattca   1020
ctggcgctgg agcgcgggcg gctggtcgat atgatgctcg attcccacac ctggttgcac   1080
ggtaaaaaat tcggcctgtt tggcgatccg gattttgtca tgggattgac ccgtttcctg   1140
ctggagctgg gctgcgaacc gaccgttatc ctctgccaca acggtaacaa cgctggcag    1200 aaagcaatga gaaaaatgct tgacgcctcg ccgtacggcc aggagagcga agtgtttatc   1260
aactgcgatt tgtggcattt ccgctcgctg atgtttaccc gccagccgga ttttatgatt   1320
ggcaactcgt acggcaagtt cattcagcgc gacaccttag ccaaaggcga gcagtttgaa   1380
gttccgctga tccgctcgg tttccccctg ttcgaccgcc accatctgca ccgccagacc   1440
acctggggct acgagggcgc catgagcatt ctcactaccc ttgtgaatgc ggtactggag   1500
aaagtggaca aagagaccat caagctcggc aaaaccgact acagcttcga tcttatccgt   1560
taa                                                                 1563
```

<210> SEQ ID NO 68
<211> LENGTH: 1488
<212> TYPE: DNA
<213> ORGANISM: Kosakonia sacchari
<220> FEATURE:
<223> OTHER INFORMATION: nifL, strain CI006

<400> SEQUENCE: 68

```
atgaccctga atatgatgat ggatgccggc gcgcccgagg caatcgccgg tgcgctttcg      60
cgacaccatc ctgggctgtt ttttaccatc gttgaagaag cgcccgtcgc catttcgctg     120
actgatgccg acgcacgcat tgtctatgcc aacccggctt tctgccgcca gaccggctat     180
gaactagaag cgttgttgca gcaaaatccc cgcctgcttg caagtcgcca aaccccacgg     240
gaaatctatc aggatatgtg gcacaccttg ttacaacgcc gaccgtggcg cgggcaattg     300
attaaccgcc accgcgacgg cagcctgtat ctggtcgaga tcgatatcac cccggtgatt     360
aacccgtttg cgaactgga acactacctg gcaatgcagc gcgatatcag cgccagttat     420
gcgctggagc agcggttgcg caatcacatg acgctgaccg aagcggtgct gaataacatt     480
ccggcggcgt tggttgtagt ggatgaacgc gatcatgtgg ttatggataa ccttgcctac     540
aaaacgttct gtgccgactg cggcggaaaa gagctcctga gcgaactcaa tttttcagcc     600
cgaaaagcgg agctggcaaa cggccaggtc ttaccggtgg tgctgcgcgg tgaggtgcgc     660
tggttgtcgg tgacctgctg ggcgctgccg ggcgtcagcg aagaagccag tcgctacttt     720
attgataaca ggctgacgcg cacgctggtg gtgatcaccg acgaccccca acaacgccag     780
cagcaggaac agggccgact tgaccgcctt aaacagcaga tgaccaacgg caaactactg     840
gcagcgatcc gcgaagcgct tgacgccgcg ctgatccagc ttaactgccc catcaatatg     900
ctggcggcgg cgcgacgttt aaacggcagt gataacaaca atgtggcgct cgacgccgcg     960
tggcgcgaag gtgaagaggc gatggcgcgg ctgaaacgtt gccgcccgtc gctggaactg    1020
gaaagtgcgg ccgtctggcc gctgcaaccc ttttttgacg atctgcgcgc gctttatcac    1080
acccgctacg agcaggggaa aaatttgcag gtcacgctgg attcccatca tctggtggga    1140
tttggtcagc gtacgcaact gttagcctgc ctgagtctgt ggctcgatcg cacgctggat    1200
attgccgccg ggctgggtga tttcaccgcg caaacgcaga tttacgcccg cgaagaagag    1260
ggctggctct ctttgtatat cactgacaat gtgccgctga tcccgctgcg ccacacccac    1320
tcgccggatg cgcttaacgc tccgggaaaa ggcatggagc tgcgcctgat ccagacgctg    1380
gtggcacacc accacggcgc aatagaactc acttcacacc ccgaaggggg aagttgcctg    1440
accctacgat tcccgctatt tcattcactg accggaggtt caaaatga               1488
```

<210> SEQ ID NO 69
<211> LENGTH: 1575
<212> TYPE: DNA
<213> ORGANISM: Kosakonia sacchari
<220> FEATURE:
<223> OTHER INFORMATION: nifA, strain CI006

<400> SEQUENCE: 69

```
atgacccagc gaaccgagtc gggtaatacc gtctggcgct tcgatttgtc ccagcagttc      60
actgcgatgc agcgcataag cgtggtactc agccgggcga ccgaggtcga tcagacgctc     120
cagcaagtgc tgtgcgtatt gcacaatgac gcctttttgc agcacggcat gatctgtctg     180
tacgacagcc agcaggcgat tttgaatatt gaagcgttgc aggaagccga tcagcagtta     240
atccccggca gctcgcaaat ccgctatcgt ccgggcgaag gctggtcgg acggtgctt      300
tcgcagggcc aatcattagt gctggcgcgc gttgctgacg atcagcgctt tcttgaccgg     360
ctcgggttgt atgattacaa cctgccgttt atcgccgtgc cgctgatagg ccagatgcg      420
cagactttcg gtgtgctgac ggcacaaccc atggcgcgtt acgaagagcg attacccgcc     480
```

```
tgcacccgct ttctggaaac ggtcgctaac ctggtcgcgc aaaccgtgcg tttgatggca      540
ccaccggcag tgcgcccttc cccgcgcgcc gccataacac aggccgccag cccgaaatcc      600
tgcacggcct cacgcgcatt tggttttgaa aatatggtcg gtaacagtcc ggcgatgcgc      660
cagaccatgg agattatccg tcaggtttcg cgctgggaca ccaccgttct ggtacgcggc      720
gagagtggca ccggcaagga gctgattgcc aacgccatcc accaccattc gccgcgtgcc      780
ggtgcgccat ttgtgaaatt caactgtgcg gcgctgccgg acacactgct ggaaagcgaa      840
ttgttcggtc acgagaaagg ggcatttacc ggcgcggtac gccagcgtaa aggccgtttt      900
gagctggccg atggcggcac gctgtttctt gacgagatcg gcgagagtag cgcctcgttt      960
caggctaagc tgctgcgcat tttgcaggaa ggcgaaatgg aacgcgtcgg cggcgacgag     1020
acattgcaag tgaatgtgcg cattattgcc gcgacgaacc gcaatcttga agatgaagtc     1080
cggctggggc actttcgcga agatctctat tatcgcctga atgtgatgcc catcgccctg     1140
ccgccactac gcgaacgcca ggaggacatt gccgagctgg cgcactttct ggtgcgtaaa     1200
atcgcccata accagagccg tacgctgcgc attagcgagg gcgctatccg cctgctgatg     1260
agctacaact ggcccggtaa tgtgcgcgaa ctggaaaaact gccttgagcg ctcagcggtg     1320
atgtcggaga acggtctgat cgatcgggat gtgattttgt ttaatcatcg cgaccagcca     1380
gccaaaccgc cagttatcag cgtctcgcat gatgataact ggctcgataa caaccttgac     1440
gagcgccagc ggctgattgc ggcgctggaa aaagcgggat gggtacaagc caaagccgcg     1500
cgcttgctgg ggatgacgcc gcgccaggtc gcctatcgta ttcagacgat ggatataacc     1560
ctgccaaggc tataa                                                     1575

<210> SEQ ID NO 70
<211> LENGTH: 876
<212> TYPE: DNA
<213> ORGANISM: Rahnella sp.
<220> FEATURE:
<223> OTHER INFORMATION: nifH, strain CI019

<400> SEQUENCE: 70
atggcaatgc gtcaatgtgc aatctacggg aaaggggggta ttggtaaatc caccactacc       60
caaaaccttg tagcggctct ggccgaaatg aataagaagg tcatgatcgt cggctgtgac      120
cctaaggctg attcaacccg cctcattctg catgcgaaag cacagaacac catcatggaa      180
atggccgctg aagtgggctc cgtggaagat ctggagctgg aagatgtgat gcaaatcggc      240
tatgcgggcg tgcgctgtgc ggaatcaggc ggccctgagc ctggtgtggg ttgtgccgga      300
cgcggggtga tcaccgccat caacttcctc gaagaagaag gcgcgtatgt gccggatctg      360
gatttcgtgt tttacgacgt attgggcgat gtggtctgtg gcggtttcgc gatgccaatt      420
cgcgaaaaca aagcgcagga aatctacatc gtatgctccg gtgaaatgat ggcgatgtat      480
gccgccaaca catttccaa aggcatcgtg aaatacgcga atcgggcaa agttcgcctg      540
gccgggctga tctgtaactc ccgccagacg gatcgcgaag atgaactgat catcgcgctg      600
gctgaaaaac ttggcacgca aatgatccac ttcgtgccgc gtgacaacat tgtgcaacgc      660
gctgaaatcc gccgcatgac ggtcatcgaa tacgacccga cttgtgcgca ggcagatcag      720
tatcgtgcac tggcgaacaa aatcgtcaac aacaccaaaa tggtggtgcc gacaccggtc      780
accatggatg agctggaagc cctgttaatg gaatttggca ttatggaaga agaagacctg      840
accatcgtcg gtcgtaccgc cgccgaagag gcgtga                              876
```

```
<210> SEQ ID NO 71
<211> LENGTH: 1449
<212> TYPE: DNA
<213> ORGANISM: Rahnella sp.
<220> FEATURE:
<223> OTHER INFORMATION: nifD, strain CI019

<400> SEQUENCE: 71
atgaccagtg aaacacgcga acgtaacgag gcattgatcc aggaagtgct ggagatcttc      60
cccgagaagg cgcttaaaga tcgtaagaaa cacatgatga ccaccgaccc ggcgatggaa     120
tctgtcggca agtgtattgt ctcaaaccgc aaatcacagc cgggcgtgat gaccgtgcga     180
ggctgcgctt acgccggttc caaaggcgtg gtctttggcc cgatcaaaga catggcgcat     240
atctcccacg gccggttgg ttgcggccag tattctcgtg ccggacgccg taactattac     300
accggctgga gcgcgtgaa cagctttggc accctcaact tcaccagtga ttttcaggaa     360
cgggacatcg tatttggcgg cgataaaaag ctcgacaaac tgatcgacga actggagatg     420
ttgttcccgc tgaccaaagg catttcggta cagtcggaat gtccggtcgg tctgatcggc     480
gatgacattt ctgccgtcgc caaagccagc agcgccaaaa tcggtaagcc ggtcgtgccg     540
gtacgctgcg aggggttccg cggtgtgtcg caatcgctcg gccatcacat tgctaacgat     600
gtcatccgcg actgggtgct ggataaccgc gaaggcaatg aatttgaaac cacgccttac     660
gacgtggcga ttatcggcga ctacaacatc ggcggtgacg cctgggcctc acgtattctg     720
ctcgaagaaa tggggctgcg tgtggtggcg cagtggtccg gcgacggcac gctggtggag     780
atggaaaaca ccccgaaagt cgcactcaat ctggtgcact gctaccgctc gatgaactac     840
atctcccgtc atatggaaga aaaacacggc attccgtgga tggaatacaa cttctttggc     900
ccgaccaaaa ttgcggaatc tctgcgcgaa atcgcggcgc gttttgacga taccatccgg     960
aaaaacgccg aagcggtgat tgaaaaatat caggcgcaaa cgcaggcggt gatcgacaaa    1020
taccgtccgc gtctggaagg caaaaaggtg ctgttgtatc tcggcggttt acgtccgcgc    1080
cacatcatcg gggcgtatga agatctggga atggaaatca tcggtaccgg ctatgaattc    1140
ggtcataacg atgattacga ccgcacctta ccgatgctca agaaggcac gttgctgttc    1200
gatgacctga gcagttatga gctggaagcg ttcgttaaag cgctgaaacc ggatcttgtc    1260
gggtcaggca tcaaagaaaa atacattttc cagaaaatgg cgtgccgtt ccgccagatg    1320
cactcctggg attattccgg cccttatcac ggctacgacg tttcggcat tttgcccgt     1380
gacatggaca tgacgctgaa caatccgggc tggagtcagc tgaccgcccc ctggttgaaa    1440
tcggcctga                                                           1449

<210> SEQ ID NO 72
<211> LENGTH: 1569
<212> TYPE: DNA
<213> ORGANISM: Rahnella sp.
<220> FEATURE:
<223> OTHER INFORMATION: nifK, strain CI019

<400> SEQUENCE: 72
atgagtcaag atcttggcac cccaaaatcc tgtttcccgc tgttcgagca ggatgaatac      60
cagagtatgt ttacccacaa acgcgcgctg aagaagcaca cggcgaggc gaaagtgcgg     120
gaagtgtttg aatggaccac cacgcaggaa tatcaggatc tgaacttctc gcgtgaagcg     180
ctgaccgtcg acccggcgaa agcctgccag ccgttaggcg cggtactttg cgcgctgggt     240
tttgccaaca cgttgccgta tgtccacggt tcacaaggct gtgtggcgta tttccgtacc     300
```

```
tattttaatc gtcatttcaa agagccggtg gcctgtgttt ccgactcaat gaccgaagat    360
gccgccgttt ttggcggaaa taacaacatg aatgtcggtc tggaaaacgc cagcgcgctg    420
tacaagccgg aaattattgc tgtctccacc acctgtatgg cggaagtgat cggtgatgac    480
ctgcaggctt ttatcgccaa cgccaaaaaa gacggatttg tggatgccgg tatgccaatc    540
ccgtatgccc ataccgag ttttctgggc agtcatgtca ccggctggga caacatgttt    600
gaaggcttcg cccgtacctt taccaccgac gccacgcggg aatatcagcc gggcaaactt    660
gccaaactga acgtggtgac cggttttgaa acttatctcg gcaactaccg ggttattcac    720
cgcatgatga ccagatggg ggtcgaatgc agcgtcttgt ccgatccgtc tgaagtgctc    780
gacaccccgg ctgacggcca ataccgcatg tatgccggcg gcaccacgca aaccgaaatg    840
cgtgatgcac cggatgccat cgacaccttg ctgctgcaac cgtggcaatt gcagaaaacc    900
aaaaaagtgg tgcagggcga ctggaatcag ccgggcaccg aagtcagtgt accgattggc    960
ctggcggcga ccgatgcctt gctgatgacg gtaagcgaac tgaccggcaa accgatagct   1020
gacacgctgg cgactgaacg tggccgtctg gtggacatga tgctcgattc ccacacctgg   1080
ctgcatggca agcgtttcgg tctctacggt gacccggatt tgtgatggg catgaccgca   1140 ttcctgctgg aactgggctg tgaaccgacc accattctca gccataacgg caacaaacgc   1200
tggcagaaag ccatgaagaa aatgctggct gattcgcctt acgggcagga cagcgaagtg   1260
tatgtgaact gcgatctgtg gcatttccgc tcgctgatgt ttacccgtaa ccggactttt   1320
atgatcggca actcttacgg aaaattcatt cagcgtgaca cgctggccaa aggcgaacag   1380
ttcgaagtgc cgctgatccg catcggtttt ccgattttttg accggcacca tttgcaccgt   1440
cagaccacct ggggatacga aggggcgatg agcatactga cgcaactggt gaatgcggta   1500
cttgaacaac tggatcgcga aaccatgaag ctcggcaaaa ccgactacaa cttcgacctg   1560
atccgctaa                                                           1569
```

<210> SEQ ID NO 73
<211> LENGTH: 1488
<212> TYPE: DNA
<213> ORGANISM: Rahnella sp.
<220> FEATURE:
<223> OTHER INFORMATION: nifL, strain CI019

<400> SEQUENCE: 73

```
atgagcatca cggcgttatc agcatcattt cctgagggga atatcgccag ccgcttgtcg     60
ctgcaacatc cttcactgtt ttataccgtg gttgaacaat cttcggtggc gatttcgctg    120
accgatccgc aggcgcgcat ttgttatgcc aatccggcat tctgccgcca gacgggtttt    180
gcacttgaga cacttttggg cgagaaccac cgtctgctgg ccagccagca gacgccgaaa    240
catatctatg acgaaatgtg gcgcactttg ttgcagggca atcctggaa cggccaactg    300 atcaaccggc gtaataaccg ttcgctttat ctggcggatg tcactatcac gcctgtttta    360
ggcgcggacg ggcaggtgga gcattacctc ggcatgcaca aagatatcag cgagaaatac    420
gcgctggaac agcggttgcg caaccacatc accttgttca cggaggtgct gaacaatatt    480
cccgccgccg tggtggtggt ggatgagcag gacaatgtgg tgatggacaa tctggcctac    540
aaaacccttt gcgcggactg cggcggcaaa gagctgctgg ctgaaatggg ctatccgcaa    600
ctcaaagaga tgctcaacag tggcgaaccg gtgccggttt ccatgcgcgg caacgtacgc    660 tggttttcttt tcggtcaatg gttattgcag ggcgttaatg aagaggccag ccgctttttt    720
accggcatta ccgcgccggg aaaactgatt gttctgaccg actgcaccga tcagcatcac    780
```

```
cggcagcagc agggttatct tgaccggctt aagcaaaaac tcaccaacgg caaattattg    840
gcggccatcc gtgagtcgct cgatgccgcg cttatccagc tcaacgggcc aatcaatatg    900
ctggcggctg cgcgtcgtct taacggcgaa gaaggcaaca acatggcgct ggaattcgcc    960
tggcgcgaag cgagcaggc ggtgagtcgc ttacaggcct gccgtccgtc gctggatttt   1020
gagccgcagg cagaatggcc ggtcagtgaa ttctttgacg atctgagcgc gctgtacgac   1080
agccattttc tcagtgacgg tgaattgcgt tacgtggtca tgccatctga tctgcacgct   1140
gtcgggcaac gaacgcaaat ccttaccgcg ctgagcttat ggattgatca cacgctgtca   1200
caggcgcagg ccatgccgtc tctgaagctc tcggtgaaca ttgttgcgag caggatgcg    1260 agctggttgt gttttgacat taccgataat gtgccgcgtg aacgggtgcg ttatgcccgc   1320
ccggaagcgg cgttttcccg tccggggaat ggcatggagc tgcgccttat ccagacgctg   1380
atcgcccatc atcgcggttc tttagatctc tcggtccgcc ctgatggcgg caccttgctg   1440
acgttacgcc tgccggtaca gcaggttatc accggaggct aaaatga                1488
```

<210> SEQ ID NO 74
<211> LENGTH: 1557
<212> TYPE: DNA
<213> ORGANISM: Rahnella sp.
<220> FEATURE:
<223> OTHER INFORMATION: nifA, strain CI019

<400> SEQUENCE: 74

```
atgacccagt tacctaccgc gggcccggtt atccggcgct ttgatatgtc tgcccagttt     60
acggcgcttt atcgcatcag cgtggcgctg agtcaggaaa gcaacaccgg gcgcgcactg    120
gcggcgatcc tcgaagtgct tcacgatcat gcatttatgc aatacggcat ggtgtgtctg    180
tttgataaag aacgcaatgc actctttgtg gaatccctgc atggcatcga cggcgaaagg    240
aaaaaagaga cccgccatgt ccgttaccgc atggggaag gcgtgatcgg cgcggtgatg     300
agccagcgtc aggcgctggt gttaccgcgc atttcagacg atcagcgtt tctcgaccgc     360 ctgaatattt acgattacag cctgccgttg attggcgtgc gatccccgg tgcggataat     420 cagccatcgg gcgtgctggt ggcacagccg atggcgttgc acgaagaccg gctgactgcc    480
agtacgcggt tttagaaat ggtcgccaat ctcatcagcc agccactgcg ttctgccacg     540 ccccggaat cattgcctgc tcaaacgccg gtccggtgca gtgttccgcg ccagtttggt     600
ttcgagcaga tggtcgggaa aagtcaggcg atgcgccaga cgatggacat tttacggcag    660
gtttccaaat gggataccac ggttctggtg cgtggtgaaa gcggcaccgg caaggaactt    720
atcgccaatg ccattcatta caactcaccc cgtgcggccg cgccatttgt gaaattcaac    780
tgcgccgcgc tgccggataa cctgctggaa agcgaactgt tcggtcatga aaaggggcc    840 ttcaccggcg ctatccgtac ccgtaaaggc cgctttgaac tggcggacgg gggcacgtta    900
ttcctcgatg aaatcggcga atcgagcgcg tcgtttcagg ccaaattgct cgcatttgt    960 caggaaggtg aaatggaacg ggtcggcggc gataccacgc tgaaagttga tgtgcgcatt   1020
attgctgcca ccaaccgtaa tcttgaagag gaagtgcgtg ccgggaattt tcgcgaagac   1080
ctgtattatc gcctgaacgt gatgccggtt tcgctgcctg cactgcgtga aaggctggat   1140
gatatcgccg atctggcgcc gtttctggtc aaaaagattg cgctgcgtca ggggcgggaa   1200
ctgcgcatca gcgacggtgc ggtgcgtctg ctgatgacct acagctggcc aggcaacgtg   1260
cgtgaactgg aaaactgtct cgaacgggcg tcggtaatga ccgatgaagg gctgatcgac   1320
```

```
cgcgacgtga tcctgttcaa tcaccatgaa tccccggcgc tgtccgtcaa acccggcctg  1380
ccgctcgcga cagatgaaag ctggctggat caggaactcg acgaacgcca gcgggtgatt  1440
gccgcactgg agaaaaccgg ctgggtgcag gccaaagcgg cccgactgct gggcatgaca  1500
ccgcgccaga ttgcctaccg tatccagatt atggacatca acatgcaccg tatctga     1557
```

<210> SEQ ID NO 75
<211> LENGTH: 1314
<212> TYPE: DNA
<213> ORGANISM: Kosakonia sacchari
<220> FEATURE:
<223> OTHER INFORMATION: Prm5 with 500bp flanking regions, strain CI006

<400> SEQUENCE: 75

```
aaaactaccg ccgcaattaa tgaacccaac gctactgttg ccgggccatg ctcttccccg   60
gcgcgctgcc cggaaaggat atagattgcc cagcacgcgc cagcaccaag cgcgaacgcc  120
gcgccagtga gatcaacatg tgaaacattt tcgcccagcg gcagcagata caagaggcca  180
agtaccgcca ggatcaccca gatgaaatcc accggcggc gtgaggcaaa aagcgccacc   240
gccagcgggc cggtaaattc cagcgccacc gcaacgccga gcggtatcgt ctggatcgat  300
aaatagaaca tatagttcat ggcgccgagc gacaggccat aaaacagcag tggcaggcgt  360
tgttcacggg taaaatgtaa acgccagggc ttgaacacta cgaccaaaat aagggtgcca  420
agtgcgagac gcagcgcggt gacgccgggt gcgccaacaa tcggaaacag tgatttcgcc  480
agcgacgcgc ctccctgaat ggacatcatc gcgacaaaca atattaatac cggcaaccac  540
accggcaatt tacgagactg cgcaggcatc ctttctcccg tcaatttctg tcaaataaag  600 taaagaggc agtctacttg aattacccccc ggctggttga gcgtttgttg aaaaaaagta  660
actgaaaaat ccgtagaata gcgccactct gatggttaat taacctattc aattaagaat  720
tatctggatg aatgtgccat taaatgcgca gcataatggt gcgttgtgcg ggaaaactgc  780 tttttttga aagggttggt cagtagcgga aactttctgt tacatcaaat ggcgctttag  840
accccaattc ccgcaaagag tttcttaact aattttgata tatttaaacg cgtaggacgt  900
aggatttact tgaagcacat ttgaggtgga ttatgaaaaa aattgcatgt ctttcagcac  960
tggccgcact tctggcggtt tctgcaggtt ccgcagtagc agcaacttca accgtaactg 1020
gcggctacgc tcagagcgac gctcagggta ttgctaacaa aactaacggt ttcaacctga 1080
aatatcgcta cgagcaggac aacaacccgc tgggtgttat cggttccttt acttacactg 1140
aaaaagatcg caccgaaagc agcgtttata acaaagcgca gtactacggc atcaccgcag 1200
gcccggctta ccgcatcaac gactgggcga gcatctacgg tgttgtgggt gtaggttacg 1260
gtaaattcca gcagactgta gacaccgcta aagtgtctga caccagcgac tacg        1314
```

<210> SEQ ID NO 76
<211> LENGTH: 3413
<212> TYPE: DNA
<213> ORGANISM: Kosakonia sacchari
<220> FEATURE:
<223> OTHER INFORMATION: nifLA operon - upstream intergenic region plus
     nifL and nifA CDSs, strain CI006

<400> SEQUENCE: 76

```
aacacacgct cctgttgaaa aagagatccc gccgggaaat gcggtgaacg tgtctgatat   60
tgcgaagagt gtgccagttt tggtcgcggg caaaacctgc accagtttgg ttattaatgc  120
accagtctgg cgcttttttt cgccgagttt ctcctcgcta atgcccgcca ggcgcggctt  180
```

| | |
|---|---|
| tggcgctgat agcgcgctga ataccgatct ggatcaaggt tttgtcgggt tatcagccaa | 240 |
| aaggtgcact ctttgcatgg ttatacgtgc ctgacatgtt gtccgggcga caaacggcct | 300 |
| ggtggcacaa attgtcagaa ctacgacacg actaactgac cgcaggagtg tgcgatgacc | 360 |
| ctgaatatga tgatggatgc cggcgcgccc gaggcaatcg ccggtgcgct ttcgcgacac | 420 |
| catcctgggc tgttttttac catcgttgaa gaagcgcccg tcgccatttc gctgactgat | 480 |
| gccgacgcac gcattgtcta tgccaacccg gctttctgcc gccagaccgg ctatgaacta | 540 |
| gaagcgttgt tgcagcaaaa tccccgcctg cttgcaagtc gccaaacccc acgggaaatc | 600 |
| tatcaggata tgtggcacac cttgttacaa cgccgaccgt ggcgcgggca attgattaac | 660 |
| cgccaccgcg acggcagcct gtatctggtc gagatcgata tcaccccggt gattaacccg | 720 |
| tttggcgaac tggaacacta cctgcaatg cagcgcgata tcagcgccag ttatgcgctg | 780 |
| gagcagcggt tgcgcaatca catgacgctg accgaagcgg tgctgaataa cattccggcg | 840 |
| gcggtggttg tagtggatga acgcgatcat gtggttatgg ataaccttgc ctacaaaacg | 900 |
| ttctgtgccg actgcggcgg aaaagagctc ctgagcgaac tcaattttc agcccgaaaa | 960 |
| gcggagctgg caaacggcca ggtcttaccg gtggtgctgc gcggtgaggt gcgctggttg | 1020 |
| tcggtgacct gctgggcgct gccgggcgtc agcgaagaag ccagtcgcta ctttattgat | 1080 |
| aacaggctga cgcgcacgct ggtggtgatc accgacgaca cccaacaacg ccagcagcag | 1140 |
| gaacagggcc gacttgaccg ccttaaacag cagatgacca acggcaaact actggcagcg | 1200 |
| atccgcgaag cgcttgacgc cgcgctgatc cagcttaact gccccatcaa tatgctggcg | 1260 |
| gcggcgcgac gtttaaacgg cagtgataac aacaatgtgg cgctcgacgc cgcgtggcgc | 1320 |
| gaaggtgaag aggcgatggc gcggctgaaa cgttgccgcc cgtcgctgga actggaaagt | 1380 |
| gcggccgtct ggccgctgca accctttttt gacgatctgc gcgcgcttta tcacacccgc | 1440 |
| tacgagcagg ggaaaaattt gcaggtcacg ctggattccc atcatctggt gggatttggt | 1500 |
| cagcgtacgc aactgttagc ctgcctgagt ctgtggctcg atcgcacgct ggatattgcc | 1560 |
| gccgggctgg gtgatttcac cgcgcaaacg cagatttacg cccgcgaaga gagggctgg | 1620 |
| ctctctttgt atatcactga caatgtgccg ctgatcccgc tgcgccacac ccactcgccg | 1680 |
| gatgcgctta acgctccggg aaaaggcatg gagctgcgcc tgatccagac gctggtggca | 1740 |
| caccaccacg gcgcaataga actcacttca cacccccgaag ggggaagttg cctgaccta | 1800 |
| cgattcccgc tatttcattc actgaccgga ggttcaaaat gacccagcga accgagtcgg | 1860 |
| gtaataccgt ctggcgcttc gatttgtccc agcagttcac tgcgatgcag cgcataagcg | 1920 |
| tggtactcag ccgggcgacc gaggtcgatc agacgctcca gcaagtgctg tgcgtattgc | 1980 |
| acaatgacgc cttttttgcag cacggcatga tctgtctgta cgacagccag caggcgattt | 2040 |
| tgaatattga agcgttgcag gaagccgatc agcagttaat ccccggcagc tcgcaaatcc | 2100 |
| gctatcgtcc gggcgaaggg ctggtcggga cggtgctttc gcagggccaa tcattagtgc | 2160 |
| tggcgcgcgt tgctgacgat cagcgctttc ttgaccggct cgggttgtat gattacaacc | 2220 |
| tgccgtttat cgccgtgccg ctgatagggc cagatgcgca actttcggt gtgctgacgg | 2280 |
| cacaacccat ggcgcgttac gaagagcgat taccgcctg cacccgctt ctggaaacgg | 2340 |
| tcgctaacct ggtcgcgcaa accgtgcgtt tgatggcacc accggcagtg cgcccttccc | 2400 |
| cgcgcgccgc cataacacag gccgccagcc cgaaatcctg cacggcctca cgcgcatttg | 2460 |
| gttttgaaaa tatggtcggt aacagtccgg cgatgcgcca gaccatggag attatccgtc | 2520 |
| aggtttcgcg ctgggacacc accgttctgg tacgcggcga gagtggcacc ggcaaggagc | 2580 |

```
tgattgccaa cgccatccac caccattcgc cgcgtgccgg tgcgccattt gtgaaattca   2640
actgtgcggc gctgccggac acactgctgg aaagcgaatt gttcggtcac gagaaagggg   2700
catttaccgg cgcggtacgc cagcgtaaag gccgttttga gctggccgat ggcggcacgc   2760
tgtttcttga cgagatcggc gagagtagcg cctcgtttca ggctaagctg ctgcgcattt   2820
tgcaggaagg cgaaatggaa cgcgtcggcg gcgacgagac attgcaagtg aatgtgcgca   2880
ttattgccgc gacgaaccgc aatcttgaag atgaagtccg gctggggcac tttcgcgaag   2940
atctctatta tcgcctgaat gtgatgccca tcgccctgcc gccactacgc gaacgccagg   3000
aggacattgc cgagctggcg cactttctgg tgcgtaaaat cgcccataac cagagccgta   3060
cgctgcgcat tagcgagggc gctatccgcc tgctgatgag ctacaactgg cccggtaatg   3120
tgcgcgaact ggaaaactgc cttgagcgct cagcggtgat gtcggagaac ggtctgatcg   3180
atcgggatgt gattttgttt aatcatcgcg accagccagc caaaccgcca gttatcagcg   3240
tctcgcatga tgataactgg ctcgataaca accttgacga cgccagcgg ctgattgcgg   3300 cgctggaaaa agcgggatgg gtacaagcca aagccgcgcg cttgctgggg atgacgccgc   3360
gccaggtcgc ctatcgtatt cagacgatgg atataaccct gccaaggcta taa           3413
```

<210> SEQ ID NO 77
<211> LENGTH: 495
<212> TYPE: PRT
<213> ORGANISM: Kosakonia sacchari
<220> FEATURE:
<223> OTHER INFORMATION: NifL, strain CI006

<400> SEQUENCE: 77

```
Met Thr Leu Asn Met Met Asp Ala Gly Ala Pro Glu Ala Ile Ala
1               5                   10                  15

Gly Ala Leu Ser Arg His His Pro Gly Leu Phe Phe Thr Ile Val Glu
                20                  25                  30

Glu Ala Pro Val Ala Ile Ser Leu Thr Asp Ala Asp Ala Arg Ile Val
            35                  40                  45

Tyr Ala Asn Pro Ala Phe Cys Arg Gln Thr Gly Tyr Glu Leu Glu Ala
        50                  55                  60

Leu Leu Gln Gln Asn Pro Arg Leu Leu Ala Ser Arg Gln Thr Pro Arg
65                  70                  75                  80

Glu Ile Tyr Gln Asp Met Trp His Thr Leu Leu Gln Arg Arg Pro Trp
                85                  90                  95

Arg Gly Gln Leu Ile Asn Arg His Arg Asp Gly Ser Leu Tyr Leu Val
            100                 105                 110

Glu Ile Asp Ile Thr Pro Val Ile Asn Pro Phe Gly Glu Leu Glu His
        115                 120                 125

Tyr Leu Ala Met Gln Arg Asp Ile Ser Ala Ser Tyr Ala Leu Glu Gln
    130                 135                 140

Arg Leu Arg Asn His Met Thr Leu Thr Glu Ala Val Leu Asn Asn Ile
145                 150                 155                 160

Pro Ala Ala Val Val Val Asp Glu Arg Asp His Val Val Met Asp
                165                 170                 175

Asn Leu Ala Tyr Lys Thr Phe Cys Ala Asp Cys Gly Gly Lys Glu Leu
            180                 185                 190

Leu Ser Glu Leu Asn Phe Ser Ala Arg Lys Ala Glu Leu Ala Asn Gly
        195                 200                 205
```

```
Gln Val Leu Pro Val Leu Arg Gly Glu Val Arg Trp Leu Ser Val
    210                 215                 220

Thr Cys Trp Ala Leu Pro Gly Val Ser Glu Ala Ser Arg Tyr Phe
225                 230                 235                 240

Ile Asp Asn Arg Leu Thr Arg Thr Leu Val Val Ile Thr Asp Asp Thr
                245                 250                 255

Gln Gln Arg Gln Gln Glu Gln Gly Arg Leu Asp Arg Leu Lys Gln
            260                 265                 270

Gln Met Thr Asn Gly Lys Leu Leu Ala Ala Ile Arg Glu Ala Leu Asp
        275                 280                 285

Ala Ala Leu Ile Gln Leu Asn Cys Pro Ile Asn Met Leu Ala Ala Ala
    290                 295                 300

Arg Arg Leu Asn Gly Ser Asp Asn Asn Asn Val Ala Leu Asp Ala Ala
305                 310                 315                 320

Trp Arg Glu Gly Glu Glu Ala Met Ala Arg Leu Lys Arg Cys Arg Pro
                325                 330                 335

Ser Leu Glu Leu Glu Ser Ala Ala Val Trp Pro Leu Gln Pro Phe Phe
            340                 345                 350

Asp Asp Leu Arg Ala Leu Tyr His Thr Arg Tyr Glu Gln Gly Lys Asn
        355                 360                 365

Leu Gln Val Thr Leu Asp Ser His His Leu Val Gly Phe Gly Gln Arg
    370                 375                 380

Thr Gln Leu Leu Ala Cys Leu Ser Leu Trp Leu Asp Arg Thr Leu Asp
385                 390                 395                 400

Ile Ala Ala Gly Leu Gly Asp Phe Thr Ala Gln Thr Gln Ile Tyr Ala
                405                 410                 415

Arg Glu Glu Glu Gly Trp Leu Ser Leu Tyr Ile Thr Asp Asn Val Pro
            420                 425                 430

Leu Ile Pro Leu Arg His Thr His Ser Pro Asp Ala Leu Asn Ala Pro
        435                 440                 445

Gly Lys Gly Met Glu Leu Arg Leu Ile Gln Thr Leu Val Ala His His
    450                 455                 460

His Gly Ala Ile Glu Leu Thr Ser His Pro Glu Gly Gly Ser Cys Leu
465                 470                 475                 480

Thr Leu Arg Phe Pro Leu Phe His Ser Leu Thr Gly Gly Ser Lys
                485                 490                 495

<210> SEQ ID NO 78
<211> LENGTH: 524
<212> TYPE: PRT
<213> ORGANISM: Kosakonia sacchari
<220> FEATURE:
<223> OTHER INFORMATION: NifA, strain CI006

<400> SEQUENCE: 78

Met Thr Gln Arg Thr Glu Ser Gly Asn Thr Val Trp Arg Phe Asp Leu
1               5                   10                  15

Ser Gln Gln Phe Thr Ala Met Gln Arg Ile Ser Val Val Leu Ser Arg
            20                  25                  30

Ala Thr Glu Val Asp Gln Thr Leu Gln Gln Val Leu Cys Val Leu His
        35                  40                  45

Asn Asp Ala Phe Leu Gln His Gly Met Ile Cys Leu Tyr Asp Ser Gln
    50                  55                  60

Gln Ala Ile Leu Asn Ile Glu Ala Leu Gln Glu Ala Asp Gln Gln Leu
65                  70                  75                  80
```

```
Ile Pro Gly Ser Ser Gln Ile Arg Tyr Arg Pro Glu Gly Leu Val
                85                  90                  95

Gly Thr Val Leu Ser Gln Gly Gln Ser Leu Val Leu Ala Arg Val Ala
            100                 105                 110

Asp Asp Gln Arg Phe Leu Asp Arg Leu Gly Leu Tyr Asp Tyr Asn Leu
            115                 120                 125

Pro Phe Ile Ala Val Pro Leu Ile Gly Pro Asp Ala Gln Thr Phe Gly
            130                 135                 140

Val Leu Thr Ala Gln Pro Met Ala Arg Tyr Glu Glu Arg Leu Pro Ala
145                 150                 155                 160

Cys Thr Arg Phe Leu Glu Thr Val Ala Asn Leu Val Ala Gln Thr Val
                165                 170                 175

Arg Leu Met Ala Pro Pro Ala Val Arg Pro Ser Pro Arg Ala Ala Ile
            180                 185                 190

Thr Gln Ala Ala Ser Pro Lys Ser Cys Thr Ala Ser Arg Ala Phe Gly
            195                 200                 205

Phe Glu Asn Met Val Gly Asn Ser Pro Ala Met Arg Gln Thr Met Glu
            210                 215                 220

Ile Ile Arg Gln Val Ser Arg Trp Asp Thr Thr Val Leu Val Arg Gly
225                 230                 235                 240

Glu Ser Gly Thr Gly Lys Glu Leu Ile Ala Asn Ala Ile His His His
                245                 250                 255

Ser Pro Arg Ala Gly Ala Pro Phe Val Lys Phe Asn Cys Ala Ala Leu
            260                 265                 270

Pro Asp Thr Leu Leu Glu Ser Glu Leu Phe Gly His Glu Lys Gly Ala
            275                 280                 285

Phe Thr Gly Ala Val Arg Gln Arg Lys Gly Arg Phe Glu Leu Ala Asp
            290                 295                 300

Gly Gly Thr Leu Phe Leu Asp Glu Ile Gly Glu Ser Ser Ala Ser Phe
305                 310                 315                 320

Gln Ala Lys Leu Leu Arg Ile Leu Gln Glu Gly Glu Met Glu Arg Val
            325                 330                 335

Gly Gly Asp Glu Thr Leu Gln Val Asn Val Arg Ile Ile Ala Ala Thr
            340                 345                 350

Asn Arg Asn Leu Glu Asp Glu Val Arg Leu Gly His Phe Arg Glu Asp
            355                 360                 365

Leu Tyr Tyr Arg Leu Asn Val Met Pro Ile Ala Leu Pro Pro Leu Arg
            370                 375                 380

Glu Arg Gln Glu Asp Ile Ala Glu Leu Ala His Phe Leu Val Arg Lys
385                 390                 395                 400

Ile Ala His Asn Gln Ser Arg Thr Leu Arg Ile Ser Glu Gly Ala Ile
            405                 410                 415

Arg Leu Leu Met Ser Tyr Asn Trp Pro Gly Asn Val Arg Glu Leu Glu
            420                 425                 430

Asn Cys Leu Glu Arg Ser Ala Val Met Ser Glu Asn Gly Leu Ile Asp
            435                 440                 445

Arg Asp Val Ile Leu Phe Asn His Arg Asp Gln Pro Ala Lys Pro Pro
            450                 455                 460

Val Ile Ser Val Ser His Asp Asp Asn Trp Leu Asp Asn Asn Leu Asp
465                 470                 475                 480

Glu Arg Gln Arg Leu Ile Ala Ala Leu Glu Lys Ala Gly Trp Val Gln
            485                 490                 495
```

Ala Lys Ala Ala Arg Leu Leu Gly Met Thr Pro Arg Gln Val Ala Tyr
            500                 505                 510

Arg Ile Gln Thr Met Asp Ile Thr Leu Pro Arg Leu
            515                 520

<210> SEQ ID NO 79
<211> LENGTH: 2850
<212> TYPE: DNA
<213> ORGANISM: Kosakonia sacchari
<220> FEATURE:
<223> OTHER INFORMATION: glnE, strain CI006

<400> SEQUENCE: 79

| | |
|---|---|
| atgccgcacc acgcaggatt gtcgcagcac tggcaaacgg tattttctcg tctgccggaa | 60 |
| tcgctcaccg cgcagccatt gagcgcgcag gcgcagtcag tgctcacttt tagtgatttt | 120 |
| gttcaggaca gcatcatcgc gcatcctgag tggctggcag agcttgaaag cgcgccgccg | 180 |
| cctgcgaacg aatggcaaca ctatgcgcaa tggctgcaag cggcgctgga tggcgtcacc | 240 |
| gatgaagcct cgctgatgcg cgcgctgcgg ctgtttcgcc gtcgcatcat ggtgcgcatc | 300 |
| gcctggagcc aggcgttaca gttggtggcg gaagaagata tcctgcaaca gcttagcgtg | 360 |
| ctggcggaaa ccctgatcgt cgccgcgcgc gactggcttt atgaggcctg ctgccgtgag | 420 |
| tggggaacgc cgagcaatcc acaaggcgtg gcgcagccga tgctggtact cggcatgggc | 480 |
| aaactgggtg gcggcgaact caatttctca tccgatatcg atttgatttt cgcctggccg | 540 |
| gaaaatggcg caacgcgcgg tggacgccgt gagctggata cgcgcaatt tttcactcgc | 600 |
| cttggtcaac ggctgattaa agtcctcgac cagccaacgc aggatggctt tgtctaccgc | 660 |
| gtcgatatgc gcttgcgccc gtttggcgac agcggcccgc tggtgctgag ctttgccgcg | 720 |
| ctggaagatt actaccagga gcaggggcgc gattgggaac gctacgcgat ggtgaaagcg | 780 |
| cgcattatgg gcgataacga cggcgaccat gcgcgggagt gcgcgcaat gctgcgcccg | 840 |
| tttgttttcc gccgttatat cgacttcagc gtgattcagt ccctgcgtaa catgaaaggc | 900 |
| atgattgccc gcgaagtgcg tcgccgtggc ctgaaggaca acattaagct cggcgcgggc | 960 |
| gggatccgcg aaatagaatt tatcgtccag gttttccagc tgattcgcgg cggtcgcgag | 1020 |
| cctgcactgc aatcgcgttc actgttgccg acgcttgctg ccatagatca actgcatctg | 1080 |
| ctgccggatg gcgacgcaac ccggctgcgc gaggcgtatt tgtggctgcg acggctggag | 1140 |
| aacctgctgc aaagcatcaa tgacgaacag acacagacgc tgccgggcga tgaactgaat | 1200 |
| cgcgcgcgcc tcgcctgggg aatgggcaaa gatagctggg aagcgctctg cgaaacgctg | 1260 |
| gaagcgcata tgtcggcggt gcgtcagata tttaacgatc tgattggcga tgatgaaacg | 1320 |
| gattcgccgg aagatgcgct ttctgagagc tggcgcgaat gtggcaggα tgcgttgcag | 1380 |
| gaggaggatt ccacgcccgt gctggcgcat ctctcagagg acgatcgccg ccgcgtggtg | 1440 |
| gcgctgattg ccgatttcg caaagagttg gataaacgca ccattggccc gcgagggcgg | 1500 |
| caggtactcg atcacttaat gccgcatctg ctcagcgatg tatgctcgcg cgacgatgcg | 1560 |
| ccagtaccgc tgtcacgcct gacgccgctg ctcaccggaa ttattacccg caccacttac | 1620 |
| cttgagctgc taagtgaatt tccggcgca ctgaaacacc tcatttccct gtgtgccgcg | 1680 |
| tcgccgatgg ttgccagtca gctggcgcgc tacccgatcc tgcttgatga attgctcgac | 1740 |
| ccgaatacgc tctatcaacc gacggcgatg aatgcctatc gcgatgagct gcgccaatac | 1800 |
| ctgctgcgcg tgccggaaga tgatgaagag caacagcttg aggcgctgcg gcagtttaag | 1860 |
| caggcgcagt tgctgcgcgt ggcggcggcg gatattgccg gtacgttgcc agtaatgaaa | 1920 |

-continued

```
gtgagcgatc acttaacctg gctggcggaa gcgattattg atgcggtggt gcagcaagcc    1980
tgggggcaga tggtggcgcg ttatggccag ccaacgcatc tgcacgatcg cgaagggcgc    2040
ggttttgcgg tggtcggtta tggcaagctg ggcggctggg agctgggtta cagctccgat    2100
ctggatctgt tattcctgca cgactgcccg atggatgtga tgaccgatgg cgagcgtgaa    2160
atcgatggtc gccagttcta tttgcgtctc gcgcagcgcg tgatgcacct gtttagcacg    2220
cgcacgtcgt ccggcatcct ttatgaagtt gatgcgcgtc tgcgtccatc tggcgctgcg    2280
gggatgctgg tcactactac ggaatcgttc gccgattacc agcaaaacga agcctggacg    2340
tgggaacatc aggcgctggc ccgtgcgcgc gtggtgtacg gcgatccgca actgaccgcc    2400
gaatttgacg ccattcgccg cgatattctg atgacgcctc gcgacggcgc aacgctgcaa    2460
accgacgtgc gagaaatgcg cgagaaaatg cgtgcccatc ttggcaacaa gcataaagac    2520
cgcttcgatc tgaaagccga tgaaggcggt atcaccgaca tcgagtttat cgcccaatat    2580
ctggtgctgc gctttgccca tgacaagccg aaactgacgc gctggtcgga taatgtgcgc    2640
attctcgaag ggctggcgca aaacggcatc atggaggagc aggaagcgca ggcattgacg    2700
ctggcgtaca ccacattgcg tgatgagctg caccacctgg cgctgcaaga gttgccggga    2760
catgtggcgc tctcctgttt tgtcgccgag cgtgcgctta ttaaaaccag ctgggacaag    2820
tggctggtgg aaccgtgcgc cccggcgtaa                                    2850
```

<210> SEQ ID NO 80
<211> LENGTH: 1563
<212> TYPE: DNA
<213> ORGANISM: Kosakonia sacchari
<220> FEATURE:
<223> OTHER INFORMATION: glnE_KO1, strain CI006

<400> SEQUENCE: 80

```
atgtttaacg atctgattgg cgatgatgaa acggattcgc cggaagatgc gctttctgag      60
agctggcgcg aattgtggca ggatgcgttg caggaggagg attccacgcc cgtgctggcg     120
catctctcag aggacgatcg ccgccgcgtg gtggcgctga ttgccgattt tcgcaaagag     180
ttggataaac gcaccattgg cccgcgaggg cggcaggtac tcgatcactt aatgccgcat     240
ctgctcagcg atgtatgctc gcgcgacgat gcgccagtac cgctgtcacg cctgacgccg     300
ctgctcaccg gaattattac ccgcaccact taccttgagc tgctaagtga atttcccggc     360
gcactgaaaac acctcatttc cctgtgtgcc gcgtcgccga tggttgccag tcagctggcg     420
cgctacccga tcctgcttga tgaattgctc gacccgaata cgctctatca accgacggcg     480
atgaatgcct atcgcgatga gctgcgccaa tacctgctgc gcgtgccgga agatgatgaa     540
gagcaacagc ttgaggcgct gcggcagttt aagcaggcgc agttgctgcg cgtggcggcg     600
gcggatattg ccggtacgtt gccagtaatg aaagtgagcg atcacttaac ctggctggcg     660
gaagcgatta ttgatgcggt ggtgcagcaa gcctgggggc agatggtggc gcgttatggc     720
cagccaacgc atctgcacga tcgcgaaggg cgcggttttg cggtggtcgg ttatggcaag     780
ctgggcggct gggagctggg ttacagctcc gatctggatc tggtattcct gcacgactgc     840
ccgatggatg tgatgaccga tggcgagcgt gaaatcgatg gtcgccagtt ctatttgcgt     900
ctcgcgcagc gcgtgatgca cctgtttagc acgcgcacgt cgtccggcat cctttatgaa     960
gttgatgcgc gtctgcgtcc atctggcgct gcggggatgc tggtcactac tacggaatcg    1020
ttcgccgatt accagcaaaa cgaagcctgg acgtgggaac atcaggcgct ggcccgtgcg    1080
```

```
cgcgtggtgt acggcgatcc gcaactgacc gccgaatttg acgccattcg ccgcgatatt    1140
ctgatgacgc ctcgcgacgg cgcaacgctg caaaccgacg tgcgagaaat gcgcgagaaa    1200
atgcgtgccc atcttggcaa caagcataaa gaccgcttcg atctgaaagc cgatgaaggc    1260
ggtatcaccg acatcgagtt tatcgcccaa tatctggtgc tgcgctttgc ccatgacaag    1320
ccgaaactga cgcgctggtc ggataatgtg cgcattctcg aagggctggc gcaaaacggc    1380
atcatggagg agcaggaagc gcaggcattg acgctggcgt acaccacatt gcgtgatgag    1440
ctgcaccacc tggcgctgca agagttgccg ggacatgtgg cgctctcctg ttttgtcgcc    1500
gagcgtgcgc ttattaaaac cagctgggac aagtggctgg tggaaccgtg cgccccggcg    1560
taa                                                                  1563
```

<210> SEQ ID NO 81
<211> LENGTH: 949
<212> TYPE: PRT
<213> ORGANISM: Kosakonia sacchari
<220> FEATURE:
<223> OTHER INFORMATION: glnE, strain CI006

<400> SEQUENCE: 81

```
Met Pro His His Ala Gly Leu Ser Gln His Trp Gln Thr Val Phe Ser
1               5                   10                  15

Arg Leu Pro Glu Ser Leu Thr Ala Gln Pro Leu Ser Ala Gln Ala Gln
            20                  25                  30

Ser Val Leu Thr Phe Ser Asp Phe Val Gln Asp Ser Ile Ile Ala His
        35                  40                  45

Pro Glu Trp Leu Ala Glu Leu Glu Ser Ala Pro Pro Ala Asn Glu
    50                  55                  60

Trp Gln His Tyr Ala Gln Trp Leu Gln Ala Ala Leu Asp Gly Val Thr
65                  70                  75                  80

Asp Glu Ala Ser Leu Met Arg Ala Leu Arg Leu Phe Arg Arg Ile
                85                  90                  95

Met Val Arg Ile Ala Trp Ser Gln Ala Leu Gln Leu Val Ala Glu Glu
            100                 105                 110

Asp Ile Leu Gln Gln Leu Ser Val Leu Ala Glu Thr Leu Ile Val Ala
        115                 120                 125

Ala Arg Asp Trp Leu Tyr Glu Ala Cys Cys Arg Glu Trp Gly Thr Pro
    130                 135                 140

Ser Asn Pro Gln Gly Val Ala Gln Pro Met Leu Val Leu Gly Met Gly
145                 150                 155                 160

Lys Leu Gly Gly Gly Glu Leu Asn Phe Ser Ser Asp Ile Asp Leu Ile
                165                 170                 175

Phe Ala Trp Pro Glu Asn Gly Ala Thr Arg Gly Gly Arg Arg Glu Leu
            180                 185                 190

Asp Asn Ala Gln Phe Phe Thr Arg Leu Gly Gln Arg Leu Ile Lys Val
        195                 200                 205

Leu Asp Gln Pro Thr Gln Asp Gly Phe Val Tyr Arg Val Asp Met Arg
    210                 215                 220

Leu Arg Pro Phe Gly Asp Ser Gly Pro Leu Val Leu Ser Phe Ala Ala
225                 230                 235                 240

Leu Glu Asp Tyr Tyr Gln Glu Gln Gly Arg Asp Trp Glu Arg Tyr Ala
                245                 250                 255

Met Val Lys Ala Arg Ile Met Gly Asp Asn Asp Gly Asp His Ala Arg
            260                 265                 270
```

```
Glu Leu Arg Ala Met Leu Arg Pro Phe Val Phe Arg Tyr Ile Asp
            275                 280                 285
Phe Ser Val Ile Gln Ser Leu Arg Asn Met Lys Gly Met Ile Ala Arg
290                 295                 300
Glu Val Arg Arg Gly Leu Lys Asp Asn Ile Lys Leu Gly Ala Gly
305                 310                 315                 320
Gly Ile Arg Glu Ile Glu Phe Ile Val Gln Val Phe Gln Leu Ile Arg
            325                 330                 335
Gly Gly Arg Glu Pro Ala Leu Gln Ser Arg Ser Leu Leu Pro Thr Leu
            340                 345                 350
Ala Ala Ile Asp Gln Leu His Leu Leu Pro Asp Gly Asp Ala Thr Arg
            355                 360                 365
Leu Arg Glu Ala Tyr Leu Trp Leu Arg Arg Leu Glu Asn Leu Leu Gln
370                 375                 380
Ser Ile Asn Asp Glu Gln Thr Gln Thr Leu Pro Gly Asp Glu Leu Asn
385                 390                 395                 400
Arg Ala Arg Leu Ala Trp Gly Met Gly Lys Asp Ser Trp Glu Ala Leu
                405                 410                 415
Cys Glu Thr Leu Glu Ala His Met Ser Ala Val Arg Gln Ile Phe Asn
            420                 425                 430
Asp Leu Ile Gly Asp Asp Glu Thr Asp Ser Pro Glu Asp Ala Leu Ser
            435                 440                 445
Glu Ser Trp Arg Glu Leu Trp Gln Asp Ala Leu Gln Glu Glu Asp Ser
450                 455                 460
Thr Pro Val Leu Ala His Leu Ser Glu Asp Asp Arg Arg Val Val
465                 470                 475                 480
Ala Leu Ile Ala Asp Phe Arg Lys Glu Leu Asp Lys Arg Thr Ile Gly
                485                 490                 495
Pro Arg Gly Arg Gln Val Leu Asp His Leu Met Pro His Leu Leu Ser
                500                 505                 510
Asp Val Cys Ser Arg Asp Asp Ala Pro Val Pro Leu Ser Arg Leu Thr
            515                 520                 525
Pro Leu Leu Thr Gly Ile Ile Thr Arg Thr Thr Tyr Leu Glu Leu Leu
            530                 535                 540
Ser Glu Phe Pro Gly Ala Leu Lys His Leu Ile Ser Leu Cys Ala Ala
545                 550                 555                 560
Ser Pro Met Val Ala Ser Gln Leu Ala Arg Tyr Pro Ile Leu Leu Asp
                565                 570                 575
Glu Leu Leu Asp Pro Asn Thr Leu Tyr Gln Pro Thr Ala Met Asn Ala
            580                 585                 590
Tyr Arg Asp Glu Leu Arg Gln Tyr Leu Leu Arg Val Pro Glu Asp Asp
            595                 600                 605
Glu Glu Gln Gln Leu Glu Ala Leu Arg Gln Phe Lys Gln Ala Gln Leu
610                 615                 620
Leu Arg Val Ala Ala Ala Asp Ile Ala Gly Thr Leu Pro Val Met Lys
625                 630                 635                 640
Val Ser Asp His Leu Thr Trp Leu Ala Glu Ala Ile Ile Asp Ala Val
                645                 650                 655
Val Gln Gln Ala Trp Gly Gln Met Val Ala Arg Tyr Gly Gln Pro Thr
            660                 665                 670
His Leu His Asp Arg Glu Gly Arg Gly Phe Ala Val Val Gly Tyr Gly
            675                 680                 685
```

```
Lys Leu Gly Gly Trp Glu Leu Gly Tyr Ser Ser Asp Leu Asp Leu Val
        690                 695                 700

Phe Leu His Asp Cys Pro Met Asp Val Met Thr Asp Gly Glu Arg Glu
705                 710                 715                 720

Ile Asp Gly Arg Gln Phe Tyr Leu Arg Leu Ala Gln Arg Val Met His
                725                 730                 735

Leu Phe Ser Thr Arg Thr Ser Ser Gly Ile Leu Tyr Glu Val Asp Ala
            740                 745                 750

Arg Leu Arg Pro Ser Gly Ala Ala Gly Met Leu Val Thr Thr Thr Glu
        755                 760                 765

Ser Phe Ala Asp Tyr Gln Gln Asn Glu Ala Trp Thr Trp Glu His Gln
770                 775                 780

Ala Leu Ala Arg Ala Arg Val Val Tyr Gly Asp Pro Gln Leu Thr Ala
785                 790                 795                 800

Glu Phe Asp Ala Ile Arg Arg Asp Ile Leu Met Thr Pro Arg Asp Gly
                805                 810                 815

Ala Thr Leu Gln Thr Asp Val Arg Glu Met Arg Lys Met Arg Ala
            820                 825                 830

His Leu Gly Asn Lys His Lys Asp Arg Phe Asp Leu Lys Ala Asp Glu
        835                 840                 845

Gly Gly Ile Thr Asp Ile Glu Phe Ile Ala Gln Tyr Leu Val Leu Arg
850                 855                 860

Phe Ala His Asp Lys Pro Lys Leu Thr Arg Trp Ser Asp Asn Val Arg
865                 870                 875                 880

Ile Leu Glu Gly Leu Ala Gln Asn Gly Ile Met Glu Gln Glu Ala
                885                 890                 895

Gln Ala Leu Thr Leu Ala Tyr Thr Thr Leu Arg Asp Glu Leu His His
            900                 905                 910

Leu Ala Leu Gln Glu Leu Pro Gly His Val Ala Leu Ser Cys Phe Val
        915                 920                 925

Ala Glu Arg Ala Leu Ile Lys Thr Ser Trp Asp Lys Trp Leu Val Glu
930                 935                 940

Pro Cys Ala Pro Ala
945

<210> SEQ ID NO 82
<211> LENGTH: 520
<212> TYPE: PRT
<213> ORGANISM: Kosakonia sacchari
<220> FEATURE:
<223> OTHER INFORMATION: GlnE_KO1, strain CI006

<400> SEQUENCE: 82

Met Phe Asn Asp Leu Ile Gly Asp Asp Glu Thr Asp Ser Pro Glu Asp
1               5                   10                  15

Ala Leu Ser Glu Ser Trp Arg Glu Leu Trp Gln Asp Ala Leu Gln Glu
            20                  25                  30

Glu Asp Ser Thr Pro Val Leu Ala His Leu Ser Glu Asp Asp Arg Arg
        35                  40                  45

Arg Val Val Ala Leu Ile Ala Asp Phe Arg Lys Glu Leu Asp Lys Arg
    50                  55                  60

Thr Ile Gly Pro Arg Gly Arg Gln Val Leu Asp His Leu Met Pro His
65                  70                  75                  80

Leu Leu Ser Asp Val Cys Ser Arg Asp Asp Ala Pro Val Pro Leu Ser
                85                  90                  95
```

```
Arg Leu Thr Pro Leu Leu Thr Gly Ile Ile Thr Arg Thr Thr Tyr Leu
            100                 105                 110

Glu Leu Leu Ser Glu Phe Pro Gly Ala Leu Lys His Leu Ile Ser Leu
            115                 120                 125

Cys Ala Ala Ser Pro Met Val Ala Ser Gln Leu Ala Arg Tyr Pro Ile
130             135                 140

Leu Leu Asp Glu Leu Leu Asp Pro Asn Thr Leu Tyr Gln Pro Thr Ala
145             150                 155                 160

Met Asn Ala Tyr Arg Asp Glu Leu Arg Gln Tyr Leu Leu Arg Val Pro
                165                 170                 175

Glu Asp Asp Glu Glu Gln Gln Leu Glu Ala Leu Arg Gln Phe Lys Gln
            180                 185                 190

Ala Gln Leu Leu Arg Val Ala Ala Asp Ile Ala Gly Thr Leu Pro
            195                 200                 205

Val Met Lys Val Ser Asp His Leu Thr Trp Leu Ala Glu Ala Ile Ile
            210                 215                 220

Asp Ala Val Val Gln Gln Ala Trp Gly Gln Met Val Ala Arg Tyr Gly
225                 230                 235                 240

Gln Pro Thr His Leu His Asp Arg Glu Gly Arg Gly Phe Ala Val Val
                245                 250                 255

Gly Tyr Gly Lys Leu Gly Gly Trp Glu Leu Gly Tyr Ser Ser Asp Leu
            260                 265                 270

Asp Leu Val Phe Leu His Asp Cys Pro Met Asp Val Met Thr Asp Gly
            275                 280                 285

Glu Arg Glu Ile Asp Gly Arg Gln Phe Tyr Leu Arg Leu Ala Gln Arg
            290                 295                 300

Val Met His Leu Phe Ser Thr Arg Thr Ser Ser Gly Ile Leu Tyr Glu
305                 310                 315                 320

Val Asp Ala Arg Leu Arg Pro Ser Gly Ala Ala Gly Met Leu Val Thr
                325                 330                 335

Thr Thr Glu Ser Phe Ala Asp Tyr Gln Gln Asn Glu Ala Trp Thr Trp
            340                 345                 350

Glu His Gln Ala Leu Ala Arg Ala Arg Val Val Tyr Gly Asp Pro Gln
            355                 360                 365

Leu Thr Ala Glu Phe Asp Ala Ile Arg Arg Asp Ile Leu Met Thr Pro
370                 375                 380

Arg Asp Gly Ala Thr Leu Gln Thr Asp Val Arg Glu Met Arg Glu Lys
385                 390                 395                 400

Met Arg Ala His Leu Gly Asn Lys His Lys Asp Arg Phe Asp Leu Lys
                405                 410                 415

Ala Asp Glu Gly Gly Ile Thr Asp Ile Glu Phe Ile Ala Gln Tyr Leu
            420                 425                 430

Val Leu Arg Phe Ala His Asp Lys Pro Lys Leu Thr Arg Trp Ser Asp
            435                 440                 445

Asn Val Arg Ile Leu Glu Gly Leu Ala Gln Asn Gly Ile Met Glu Glu
            450                 455                 460

Gln Glu Ala Gln Ala Leu Thr Leu Ala Tyr Thr Thr Leu Arg Asp Glu
465                 470                 475                 480

Leu His His Leu Ala Leu Gln Glu Leu Pro Gly His Val Ala Leu Ser
                485                 490                 495

Cys Phe Val Ala Glu Arg Ala Leu Ile Lys Thr Ser Trp Asp Lys Trp
            500                 505                 510
```

```
Leu Val Glu Pro Cys Ala Pro Ala
        515                 520
```

<210> SEQ ID NO 83
<211> LENGTH: 341
<212> TYPE: PRT
<213> ORGANISM: Kosakonia sacchari
<220> FEATURE:
<223> OTHER INFORMATION: GlnE ATase domain, strain CI006

<400> SEQUENCE: 83

```
Glu Glu Gln Gln Leu Glu Ala Leu Arg Gln Phe Lys Gln Ala Gln Leu
1               5                   10                  15

Leu Arg Val Ala Ala Ala Asp Ile Ala Gly Thr Leu Pro Val Met Lys
            20                  25                  30

Val Ser Asp His Leu Thr Trp Leu Ala Glu Ala Ile Ile Asp Ala Val
        35                  40                  45

Val Gln Gln Ala Trp Gly Gln Met Val Ala Arg Tyr Gly Gln Pro Thr
    50                  55                  60

His Leu His Asp Arg Glu Gly Arg Gly Phe Ala Val Val Gly Tyr Gly
65                  70                  75                  80

Lys Leu Gly Gly Trp Glu Leu Gly Tyr Ser Ser Asp Leu Asp Leu Val
                85                  90                  95

Phe Leu His Asp Cys Pro Met Asp Val Met Thr Asp Gly Glu Arg Glu
            100                 105                 110

Ile Asp Gly Arg Gln Phe Tyr Leu Arg Leu Ala Gln Arg Val Met His
        115                 120                 125

Leu Phe Ser Thr Arg Thr Ser Ser Gly Ile Leu Tyr Glu Val Asp Ala
130                 135                 140

Arg Leu Arg Pro Ser Gly Ala Ala Gly Met Leu Val Thr Thr Thr Glu
145                 150                 155                 160

Ser Phe Ala Asp Tyr Gln Gln Asn Glu Ala Trp Thr Trp Glu His Gln
                165                 170                 175

Ala Leu Ala Arg Ala Arg Val Val Tyr Gly Asp Pro Gln Leu Thr Ala
            180                 185                 190

Glu Phe Asp Ala Ile Arg Arg Asp Ile Leu Met Thr Pro Arg Asp Gly
        195                 200                 205

Ala Thr Leu Gln Thr Asp Val Arg Glu Met Arg Glu Lys Met Arg Ala
    210                 215                 220

His Leu Gly Asn Lys His Lys Asp Arg Phe Asp Leu Lys Ala Asp Glu
225                 230                 235                 240

Gly Gly Ile Thr Asp Ile Glu Phe Ile Ala Gln Tyr Leu Val Leu Arg
                245                 250                 255

Phe Ala His Asp Lys Pro Lys Leu Thr Arg Trp Ser Asp Asn Val Arg
            260                 265                 270

Ile Leu Glu Gly Leu Ala Gln Asn Gly Ile Met Glu Glu Gln Glu Ala
        275                 280                 285

Gln Ala Leu Thr Leu Ala Tyr Thr Thr Leu Arg Asp Glu Leu His His
    290                 295                 300

Leu Ala Leu Gln Glu Leu Pro Gly His Val Ala Leu Ser Cys Phe Val
305                 310                 315                 320

Ala Glu Arg Ala Leu Ile Lys Thr Ser Trp Asp Lys Trp Leu Val Glu
                325                 330                 335

Pro Cys Ala Pro Ala
            340
```

<210> SEQ ID NO 84
<211> LENGTH: 1342
<212> TYPE: DNA
<213> ORGANISM: Kosakonia sacchari
<220> FEATURE:
<223> OTHER INFORMATION: Prm5 inserted into nifL region, strain CI006, now strain CM029

<400> SEQUENCE: 84

| | | |
|---|---|---|
| ccgagcgtcg gggtgcctaa tatcagcacc ggatacgaga gaaaagtgtc tacatcggtt | 60 |
| cggttgatat tgaccggcgc atccgccagc ccgcccagtt tctggtggat ctgtttggcg | 120 |
| attttgcggg tcttgccggt gtcggtgccg aaaaaaatac caatatttgc cataacacac | 180 |
| gctcctgttg aaaagagat cccgccggga aatgcggtga acgtgtctga tattgcgaag | 240 |
| agtgtgccag ttttggtcgc gggcaaaacc tgcaccagtt tggttattaa tgcaccagtc | 300 |
| tggcgctttt tttcgccgag tttctcctcg ctaatgcccg ccaggcgcgg ctttggcgct | 360 |
| gatagcgcgc tgaataccga tctggatcaa ggttttgtcg ggttatcagc caaaggtgc | 420 |
| actctttgca tggttatacg tgcctgacat gttgtccggg cgacaaacgg cctggtggca | 480 |
| caaattgtca gaactacgac acgactaact gaccgcagga gtgtgcgatg accctgaata | 540 |
| tgatgatgga tgccggcgga catcatcgcg acaaacaata ttaataccgg caaccacacc | 600 |
| ggcaatttac gagactgcgc aggcatcctt tctcccgtca atttctgtca aataaagtaa | 660 |
| aagaggcagt ctacttgaat tacccccggc tggttgagcg tttgttgaaa aaaagtaact | 720 |
| gaaaaatccg tagaatagcg ccactctgat ggttaattaa cctattcaat taagaattat | 780 |
| ctggatgaat gtgccattaa atgcgcagca taatggtgcg ttgtgcggga aaactgcttt | 840 |
| tttttgaaag ggttggtcag tagcggaaac aactcacttc acaccccgaa gggggaagtt | 900 |
| gcctgaccct acgattcccg ctatttcatt cactgaccgg aggttcaaaa tgacccagcg | 960 |
| aaccgagtcg ggtaataccg tctggcgctt cgatttgtcc cagcagttca ctgcgatgca | 1020 |
| gcgcataagc gtggtactca gccgggcgac cgaggtcgat cagacgctcc agcaagtgct | 1080 |
| gtgcgtattg cacaatgacg ccttttttgca gcacggcatg atctgtctgt acgacagcca | 1140 |
| gcaggcgatt ttgaatattg aagcgttgca ggaagccgat cagcagttaa tccccggcag | 1200 |
| ctcgcaaatc cgctatcgtc cgggcgaagg gctggtcggg acggtgcttt cgcagggcca | 1260 |
| atcattagtg ctggcgcgcg ttgctgacga tcagcgcttt cttgaccggc tcgggttgta | 1320 |
| tgattacaac ctgccgttta tc | 1342 |

<210> SEQ ID NO 85
<211> LENGTH: 1270
<212> TYPE: DNA
<213> ORGANISM: Rahnella aquatilis
<220> FEATURE:
<223> OTHER INFORMATION: 16S
<220> FEATURE:
<221> NAME/KEY: modified_base
<222> LOCATION: (186)..(186)
<223> OTHER INFORMATION: a, c, t, g, unknown or other
<220> FEATURE:
<221> NAME/KEY: modified_base
<222> LOCATION: (458)..(458)
<223> OTHER INFORMATION: a, c, t, g, unknown or other
<220> FEATURE:
<221> NAME/KEY: modified_base
<222> LOCATION: (1041)..(1041)
<223> OTHER INFORMATION: a, c, t, g, unknown or other
<220> FEATURE:
<221> NAME/KEY: modified_base
<222> LOCATION: (1131)..(1132)

```
<223> OTHER INFORMATION: a, c, t, g, unknown or other
<220> FEATURE:
<221> NAME/KEY: modified_base
<222> LOCATION: (1135)..(1135)
<223> OTHER INFORMATION: a, c, t, g, unknown or other
<220> FEATURE:
<221> NAME/KEY: modified_base
<222> LOCATION: (1139)..(1140)
<223> OTHER INFORMATION: a, c, t, g, unknown or other

<400> SEQUENCE: 85
attgaagagt ttgatcatgg ctcagattga acgctggcgg caggcctaac acatgcaagt      60
cgagcggcag cgggaagtag cttgctactt tgccggcgag cggcggacgg gtgagtaatg     120
tctgggaaac tgcctgatgg aggggggataa ctactggaaa cggtagctaa taccgcatga   180
cctcgnaaga gcaaagtggg ggatcttcgg acctcacgcc atcggatgtg cccagatggg    240
attagctagt aggtgaggta atggctcacc taggcgacga tccctagctg gtctgagagg    300
atgaccagcc acactggaac tgagacacgg tccagactcc tacggaggc agcagtgggg     360
aatattgcac aatgggcgca agcctgatgc agccatgccg cgtgtgtgaa gaaggcctta    420
gggttgtaaa gcactttcag cgaggaggaa ggcatcanac ttaatacgtg tggtgattga    480
cgttactcgc agaagaagca ccggctaact ccgtgccagc agccgcggta atacggaggg    540
tgcaagcgtt aatcggaatt actgggcgta aagcgcacgc aggcggtttg ttaagtcaga    600
tgtgaaatcc ccgcgcttaa cgtgggaact gcatttgaaa ctggcaagct agagtcttgt    660
agaggggggt agaattccag gtgtagcggt gaaatgcgta gagatctgga ggaataccgg    720
tggcgaaggc ggccccctgg acaaagactg acgctcaggt gcgaaagcgt ggggagcaaa    780
caggattaga taccctggta gtccacgctg taaacgatgt cgacttggag gttgtgccct    840
tgaggcgtgg cttccggagc taacgcgtta agtcgaccgc ctgggagta cggccgcaag    900
gttaaaactc aaatgaattg acggggggccc gcacaagcgg tggagcatgt ggtttaattc    960
gatgcaacgc gaagaacctt acctactctt gacatccacg gaattcgcca gagatggctt   1020
agtgccttcg ggaaccgtga nacaggtgct gcatggctgt cgtcagctcg tgttgtgaaa   1080
tgttgggtta gtcccgcaa cgagcgcaac ccttatcctt tgttgccagc nngtnatgnn   1140
gggaactcaa aggagactgc cggtgataaa ccggaggaag gtggggatga cgtcaagtca   1200
tcatggccct tacgagtagg gctacacacg tgctacaatg gcatatacaa agagaagcga   1260
actcgcgagg                                                           1270

<210> SEQ ID NO 86
<211> LENGTH: 876
<212> TYPE: DNA
<213> ORGANISM: Rahnella aquatilis
<220> FEATURE:
<223> OTHER INFORMATION: nifH

<400> SEQUENCE: 86
atggcaatgc gtcaatgcgc aatctacggg aaaggggta ttgggaaatc caccactacc      60
caaaaccttg tagcggctct ggccgaaatg aataagaagg tcatgatcgt cggctgtgac    120
cctaaggctg attcaacccg cctcattctg catgcgaaag cacagaacac catcatggaa    180
atggccgctg aagtgggctc cgtggaagat ctggagctgg aagatgtgat gcaaatcggc    240
tatggcggcg tgcgctgtgc ggaatcaggc ggccctgagc ctggtgtggg ttgtgccgga    300
cgcggggtga tcaccgccat caacttcctc gaagaagaag gcgcgtatgt gccggatctg    360
gattttgtgt tttacgacgt attgggcgat gtggtctgtg gcggtttcgc gatgccaatt    420
```

```
cgcgaaaaca aagcgcagga aatctacatc gtgtgctccg gtgaaatgat ggcgatgtat      480
gccgccaaca acatttccaa aggcatcgtg aaatacgcga atcgggcaa agttcgcctg       540 gccgggctga tctgtaactc ccgccagacg atcgcgaag atgaactgat catcgcgctg       600
gctgaaaaac ttggcacgca aatgatccac ttcgtgccgc gtgacaacat tgtgcaacgc     660
gctgaaatcc gccgcatgac ggtcatcgaa tacgacccga cttgtgcgca ggcagatcag     720
tatcgtgcac tggcgaacaa aatcgtcaac aacaccaaaa tggtggtgcc gacaccggtc     780
accatggatg agctggaagc cctgttaatg gaatttggca ttatggaaga agaagacctg     840
gccatcgtcg gtcgtaccgc cgccgaagag gcgtga                               876

<210> SEQ ID NO 87
<211> LENGTH: 1374
<212> TYPE: DNA
<213> ORGANISM: Rahnella aquatilis
<220> FEATURE:
<223> OTHER INFORMATION: nifD1

<400> SEQUENCE: 87
atgaaggcaa aagagattct ggcgctgatt gatgagccag cctgtgagca taaccacaag      60
cagaagtcgg gttgcagcct gccgaaaccg ggcgcgacgg caggcggttg tgcgtttgat     120
ggcgcgcaga ttgcgctgct gccggtcgcg gacgtcgcgc atctggtgca cggcccgatt     180
ggctgtaccg gcagttcatg ggacaaccgt ggcagccgca gttccgggcc ttccatcaac     240
cgcatgggct tcaccaccga catgagcgag caggatgtga ttatggggcg cggcgagcga     300
cgcttatttc acgccgtgca gcacatcgtc agccattacc atccggtggc ggtctttatt     360 tacaacaccct gcgtacccgc gatggaaggg gatgacgttg aagccgtgtg tcgcgccgca    420
tcggccgctg ccggtgtgcc ggttatttca gtcgatgccg ccggtttcta cggcagcaaa    480
aatctcggta accgcattgc cggggacgtg atggtcaaaa aggtgatcgg ccagcgcgaa    540
cccgcgccgt ggccggaaaa ctcaccgatc cccgccggac accgccacag catcagcctg    600
attggcgaat tcaatattgc cggcgagttc tggcacgttc tgccgctgct cgatgagctc    660
gggatccgcg tgctgtgcag cctttccggg gattcccgtt ttgctgaaat ccagactatg    720
caccgtggcg aagccaacat gctggtgtgc tcgcgggcgc tgatcaacgt cgcccgaaaa    780
atggaagagc gttaccagat cccatggttt gaaggcagtt tttatggcct gcgttccatg    840
gctgattccc tgcgcacgat cgccgtgctg ctcaaagacc cggatttaca ggcgcgcaca    900
gaacgtctga ttgagcgcga ggaggcggcg acacatcttg cgcttgcgcc ttaccgtgcg    960
cggctcagcg ggcgcaaggc gctgctgtat accggtggcg tgaaatcctg gtcggtggtc   1020
tcggcgttac aggatttagg catcacggtg gtggcgaccg gcacccgaaa atcaaccgaa    1080
gaagacaagc agcgtattcg cgaactgatg ggtgaagacg tgctgatgct cgacgaaggc    1140
aatgccagaa ccttgctcga caccctctat cgtttcggcg cgacatcat gatcgccggg     1200 ggccgcaaca tgtataccgc gtacaaagcc cgcctgccgt tcctggatat caatcaggag    1260
cgcgagcatg cgtttgccgg atatcacggg ctggtaaatc tggccgaaca gttgtgtatc    1320
accctggaaa gcccggtctg ggcgcaggtc aaccgtctgg cgccgtggcg ctaa          1374

<210> SEQ ID NO 88
<211> LENGTH: 1449
<212> TYPE: DNA
<213> ORGANISM: Rahnella aquatilis
<220> FEATURE:
```

<223> OTHER INFORMATION: nifD2

<400> SEQUENCE: 88

```
atgaccagtg aaacacgcga acgtaacgag gcattgatcc aggaagtgct ggagatcttc      60
cccgagaagg cgcttaaaga tcgtaagaaa cacatgatga ccaccgaccc ggcgatggaa     120
tctgtcggca agtgtattgt ctcaaaccgc aaatcacagc cgggcgtgat gaccgtgcga     180
ggctgcgctt acgccggttc caaaggcgtg gtctttggcc cgatcaaaga catgcgcat      240
atctcccacg gcccggttgg ttgcggccag tattcccgtg ccggacgccg taactattac     300
accggctgga gcggcgtgaa cagctttggc accctcaact tcaccagtga ttttcaggaa     360
cgggacatcg tatttggcgg cgataaaaag ctcgacaaat tgatcgatga actggagatg     420
ttgttcccgc tgagcaaagg catttcggtg cagtcggaat gtccggtcgg tctgatcggc     480
gatgacattt ctgccgtcgc caaagccagc agcgccaaaa tcggtaagcc ggtcgtgccg     540
gtacgctgcg aggggttccg cggtgtgtcg caatcgctcg gccatcacat tgctaacgat     600
gtcatccgcg actgggtgct ggataaccgc gaaggcaatg aatttgaaac cacgccttac     660
gacgtggcga ttatcggcga ctacaacatc ggcggtgacg cctgggcctc acgtattctg     720
ctcgaagaaa tggggctgcg cgtggtggcg cagtggtccg cgacggcac gctggtggag      780
atggaaaaca ccccgaaagt cgcgctcaat ctggtgcact gctaccgctc gatgaactac     840
atctcccgtc atatgaaga aaaacacggc attccgtgga tggaatacaa cttctttggc      900
ccgaccaaaa ttgcggaatc tctgcgcgaa atcgcggcgc gttttgacga taccatccgg     960
aaaaacgccg aagcggtgat tgaaaaatat caggcgcaaa cgcaggcggt gatcgacaaa    1020
taccgtccgc gtctggaagg caaaaaggtg ctgttgtatc tcggcggttt acgtccgcgc    1080
cacatcatcg gggcgtatga agatctggga atggaaatca tcggtaccgg ctatgaattc    1140
ggtcataacg atgattacga ccgcaccttt acgatgctca agaaggcac gttgctgttc      1200
gatgacctga gcagttatga gctggaagcg ttcgttaaag cgctgaaacc ggatcttgtc    1260
gggtcaggta tcaaagaaaa atacattttc cagaaaatgg gcgtgccgtt ccgccagatg    1320
cactcctggg attattccgg cccttatcac ggctacgacg tttcggcat tttgcccgt      1380
gacatggaca tgacgctgaa caatccgggc tggagtcagc tgaccgcccc ctggttgaaa    1440
acggcctga                                                             1449
```

<210> SEQ ID NO 89
<211> LENGTH: 1386
<212> TYPE: DNA
<213> ORGANISM: Rahnella aquatilis
<220> FEATURE:
<223> OTHER INFORMATION: nifK1

<400> SEQUENCE: 89

```
atggctcaaa ttctgcgtaa tgccaagccg cttgccacca cgcctgtcaa aagcgggcaa      60
ccgctcgggg cgatcctggc cagtcagggg ctggaaaatt gcatcccgct ggttcacggc     120
gcgcaaggtt gtagcgcgtt cgccaaagtt ttcttcatcc agcattttca cgatccgatc     180
ccgttgcagt ccacgcgcat ggaatcgacc acgactatca tgggctcgga tggcaacgtc     240
agtactgcgt tgaccacgtt gtgtcagcgc agtaatccaa aagccattgt gattttgagc     300
accggactgt cagaagcgca gggcagtgat ttgtcgatgg cgctgcgtga gtttcgcgac     360
aaagaaccgc gctttaatgc catcgctatt ctgaccgtta acacgccgga ttttacggc     420
tcgctggaaa acggctacag cgcgctgatg gaaagcgtga tcactcagtg ggtgccggaa    480
```

```
aagccgccga ccggcatgcg taacaagcgc gtgaacctgc tggtgagcca tctgctgacg    540 ccggggatc tggaattact gcgcagctat gtcgaagcct ttggcctgca accggtgatc     600
ctgccggatt tatcacagtc gctggacgga catctggcga atggcgattt caatccggtc    660
acgcagggcg gcacgtcgca acgccagatt gaacaaatgg ggcagagcct gaccaccatt    720
accattggca gttcgctcaa ctgcgccgcc agtctgatgg cgatgcgcag ccgtggcatg    780
gcgctgaacc tgccgcacct gatgacgctg aaaacatgg acagtctgat ccgccatctg    840
catcaggtgt caggccgcga ggtaccggca tggattgagc ccagcgcgg gcaactgctg     900 gacgccatga tcgactgcca tacctggctg cagtcacagc gtattgcgct ggcggcagaa    960
gcggatttgc tggtggcgtg gtgcgatttc gctcagagcc agggaatgcg cgtcgggccg   1020
gtgattgcgc cggttaatca gcagtcactg gccgggctgc cggtcgaaca ggtggtgatc   1080
ggcgatctgg aagatttaca aacccggctc gacagctacc cggtttcact gctggtggcg   1140
aactcccacg ctgcaccact ggcggaaaaa aacggtatcg cgctggtacg tgccggtttc   1200
ccgctttacg accgtctcgg ggaatttcgc cgcgtgcggc agggctatgc gggtattcgc   1260
gacaccttgt tcgaactcgc gaacctgatg caggcgcgcc atcacatgct gacggcgtat   1320
cactcaccgc ttaggcaggt gttcggcctg agcccggtac cggaggccag tcatgaggcg   1380
cgctaa                                                              1386

<210> SEQ ID NO 90
<211> LENGTH: 1569
<212> TYPE: DNA
<213> ORGANISM: Rahnella aquatilis
<220> FEATURE:
<223> OTHER INFORMATION: nifK2

<400> SEQUENCE: 90
atgagtcaag atcttggcac cccaaaatcc tgtttcccgc tgttcgagca ggatgaatac      60
cagaatatgt ttacccacaa acgcgcgctg gaagaagcac acggcgaggc gaaagtgcgg     120
gaagtgtttg aatggaccac cacgcaggaa tatcaggatc tgaacttctc gcgtgaagcg     180
ctgaccgtcg acccggcgaa agcctgccag ccgttaggcg cggtactttg cgcgctgggt     240
tttaccaaca cgttgccgta tgtccatggt tcacaaggct gtgtggcgta tttccgtacc     300
tattttaatc gtcatttcaa agagccggtg gcctgtgttt ccgactcaat gaccgaagat     360
gccgccgttt ttggcggaaa taacaacatg aatgtcggtc tggaaaacgc cagcgcgctg     420
tacaagccgg aaattattgc ggtctccacc acctgtatgg cggaagtgat cggtgatgac     480
ctgcaggctt ttatcgccaa cgccaaaaaa gacggatttg tggatgccgg tatgccaatc     540
ccgtatgccc atacaccgag ttttctgggc agtcatgtca ccggctggga caacatgttt     600
gaaggcttcg cccgtacctt taccaccgac gccacgcggg aatatcagcc gggcaaactt     660
gccaaactga acgtggtgac cggttttgaa acttatctcg caactaccg ggttattcac     720 cgcatgatga gccagatggg ggtcgaatgc agcgtcttgt ccgatccgtc tgaagtgctc     780
gacaccccgg ctgacggcca ataccgcatg tatgccggcg gcaccacgca aaccgaaatg     840
cgtgatgcac cggatgccat cgacaccttg ctgctgcaac gtggcaatt acagaaaacc     900 aaaaaggtgg tgcagggcga ctggaatcag ccgggcaccg aagtcagtgt accgattggc     960
ctggcggcga ccgatgcctt gctgatgacg gtaagcgaac tgaccggcaa accgatagct    1020
gacgcgctgg cgactgaacg tggccgtctg gtggacatga tgctcgattc tcacacctgg    1080
```

-continued

```
ctgcacggca agcgtttcgg tctctacggt gacccggatt ttgtgatggg catgaccgca    1140
ttcctgctgg aactgggctg tgaaccgacc accattctca gccataacgg caacaaacgc    1200
tggcagaaag ccatgaagaa aatgctggct gattcgcctt acggacagga cagcgaagtg    1260
tatgtgaact gcgatctgtg gcatttccgc tcgctgatgt ttacccgtaa accggacttt    1320
atgatcggca actcttacgg aaaattcatt cagcgtgaca cgctggccaa aggcgaacag    1380
ttcgaagtgc cgctgatccg tatcggattc ccgattttg accggcacca tttgcaccgt     1440
cagaccacct ggggatacga gggcgcgatg agcatcctga cgcaactggt gaatgcggtg    1500
ctcgaacagc tggatcgcga aaccatgaag ctcggcaaaa ccgactacaa cttcgatctg    1560
atccgctaa                                                            1569
```

<210> SEQ ID NO 91
<211> LENGTH: 1488
<212> TYPE: DNA
<213> ORGANISM: Rahnella aquatilis
<220> FEATURE:
<223> OTHER INFORMATION: nifL

<400> SEQUENCE: 91

```
atgagcatca cggcgttatc agcatcattt cctgaggga atatcgccag ccgcttgtcg      60
ctgcaacatc cttcactgtt ttataccgtg gttgaacaat catcggtggc gatttcgctg    120
accgatccgc aggcgcgcat ttgttatgcc aatccgcat tctgccgcca gacgggtttt     180
gcacttgaga cacttttggg cgagaaccac cgtctgctgg ccagccagca gacgccgaaa    240
catatctatg cgaaatgtg gcgcactttg ttgcaggca atcctggaa cggccaactg       300
atcaaccggc gtaataaccg ttcgctttat ctggcggatg tcactatcac gcctgtttta    360
ggcgcggacg ggcaggtgga gcattacctc ggcatgcaca aagatatcag cgagaaatac    420
gcgctggagc agcggttgcg caaccacatc accttgttca cggaggtgct gaacaatatt    480
cccgccgccg tggtggtggt ggatgagcag gacaatgtgg tgatggacaa tctgcctac    540
aaaaccctgt gcgctgactg cggcggaaaa gagctgttgg ccgaaatggg ctatccgcaa    600
ctcaaagaga tgctcaacag tggcgaaccg gtgccggttt ccatgcgcgg caacgtacgc    660
tggtttcc tccggtcagtg gtcattgcag ggcgttaatg aagaggccag ccgcttttt      720
accggcatta ccgcgccggg aaaactgatt gttctcaccg actgcaccga tcagcatcac    780
cggcagcagc agggttatct tgaccggctc aagcaaaaac ttaccaacgg caaattgctg    840
gcagccatcc gcgagtcgct tgatgccgcg ctgattcagc tcaacgggcc aattaatatg    900
ctggcggctg cgcgtcgtct taacggcgaa gaaggcaaca acatggcgct ggaattcgcc    960
tggcgcgaag cgagcaggc ggtgagtcgc ttacaggcct gccgtccgtc gctggatttt    1020
gagccgcagg cagaatggcc ggtcagtgaa ttcttcgacg atctgagcgc gctgtacgac    1080
agccattttc tcagtgacgg tgaattgcgt tacgtggtca tgccatctga tctgcacgct    1140
gtcgggcaac gaacgcaaat ccttaccgcg ctgagcttat ggattgatca cacgctgtca    1200
caggcgcagg ccatgccgtc tctgaagctc tcggtgaaca ttgttgcgaa gcaggatgcg    1260
agctggttgt gttttgacat taccgataat gtgccgcgtg aacgggtgcg ttatgcccgc    1320
ccggaagcgg cgttttcccg tccggggaat ggcatggagc tgcgccttat ccagacgctg    1380
atcgcccatc atcgcggttc tttagatctc tcggtccgcc ctgatggcgg caccttgctg    1440
acgttacgcc tgccggtaca gcaggttatc accggaggct taaaatga                 1488
```

-continued

<210> SEQ ID NO 92
<211> LENGTH: 1557
<212> TYPE: DNA
<213> ORGANISM: Rahnella aquatilis
<220> FEATURE:
<223> OTHER INFORMATION: nifA

<400> SEQUENCE: 92

```
atgacccagt tacctaccgc gggcccggtt atccggcgct ttgatatgtc tgcccagttt      60
acggcgcttt atcgcatcag cgtggcgctg agtcaggaaa gcaataccgc gcgcgcactg     120
gcggcgatcc tcgaagtgct tcacgatcat gcatttatgc aatacggcat ggtgtgtctg     180
ttcgataaag aacgcaatgc actgtttgtg aatccctgc atggcatcga cggcgaaagg      240
aaaaaagaga cccgccatgt ccgttaccgc atggggaag gcgtgatcgg cgcggtgatg      300
agccagcgtc aggcgctggt gttaccgcgc atttcagacg atcagcgttt tctcgaccgc     360
ctgaatattt acgattacag cctgccgctg attggtgtgc cgatccccgg tgcggataat     420
cagcctgcgg gtgtgctggt ggcacagccg atggcgttgc acgaagaccg gctggctgcc     480
agtacgcggt ttttagaaat ggtcgccaat ctcatcagcc agccactgcg ttctgccacg     540
ccccccggaat cattgcctgc tcaaacgccg gtccggtgca gtgttccgcg ccagtttggt     600
tttgagcaga tggtcgggaa aagtcaggcg atgcgccaga cgatggacat tttacggcag     660
gtttccaaat gggataccac ggttctggtg cgtggtgaaa gcggcaccgg caaggaactt     720
atcgccaatg ccattcatta caactcaccc cgtgcggccg cgccatttgt gaaattcaac     780
tgcgccgcgc tgccggataa cctgctggaa agcgaactgt tcggtcatga aaaaggggcc     840
ttcaccggcg ctatacgcac ccgaaaaggc cgctttgaac tggcggacgg gggcacgtta     900
ttcctcgatg aaatcggcga atcgagcgcg tcgtttcagg ccaaattgct gcgcattttg     960
caggaaggtg aaatggaacg ggtcggcggc gataccacgc tgaaagttga tgtgcgcatt    1020
attgctgcca ccaaccgtaa tcttgaggag gaagtgcgtg ccgggaattt tcgcgaagac    1080
ctgtattatc gcctgaacgt gatgccggtt tcgctgcctg cactgcgtga aaggctggat    1140
gatatcgccg atctggcgcc gtttctggtc aaaaagattg cgctgcgtca ggggcgggaa    1200
ctgcgcatca gtgatggtgc ggtgcgtctg ctgatgacct acagctggcc aggcaacgtg    1260
cgtgaactgg aaaactgcct cgaacgggcg tcggtaatga ccgatgaagg gctgatcgac    1320
cgcgacgtga tcctgttcaa tcaccatgag tccccgcgc tgtccgtcaa acccggtctg    1380
ccgctggcga cagatgaaag ctggctggat caggaactcg acgaacgcca gcgggtgatt    1440
gctgcactga gaaaaccgg ctgggtgcag gccaaagcgg cccgactgct gggcatgaca    1500
ccgcgccaga ttgcctaccg tatccagatt atggacatca acatgcaccg tatctga       1557
```

<210> SEQ ID NO 93
<211> LENGTH: 2838
<212> TYPE: DNA
<213> ORGANISM: Rahnella aquatilis
<220> FEATURE:
<223> OTHER INFORMATION: glnE

<400> SEQUENCE: 93

```
atgttgccac tttcttctgt tttgcaaagc cacgcgcaga gtttgcctga acgctggcat      60
gaacatcctg aaaacctgcc cctccccgat gatgaacagc tggctgtgct gagcagcagt     120
gaattcatga cggacagttt gctggctttt ccgcagtggt ggcatgaaat tgtccaaaat     180
cccccctcagg cgcaggagtg gcaactttac cgtcagtggc tggatgaatc gctgacgcag     240
```

```
gtgactgacg aagccgggtt aatgaaagct ttgcgtctgt tccgccgccg tattctgacc    300
cgcattgcgt ggtcacagtc cgcgcaaacc agcgaagcaa aagatacgct tcaccagctg    360
agtgaactgg cggaattatt gattgtcagc gcccgtgact ggctgtatgc cgcttgctgt    420
cgcgagttcg gtacgccggt caatgccgca ggggaaccgc agagaatgct gatcctcggg    480
atgggcaaac tcggcggtgg cgagctgaat ttctcatcgg acatcgacct gattttttgct    540 tatccggaaa atggccagac acgcggcggt cggcgtgaac tggataacgc acaatttttc    600
acccggctcg gccagcgtct gatcaaagcg ctggatcagc ccactatcga cggttttgtc    660
tatcgcgtgg acatgcgttt gcgtccgttc ggcgacagtg gcccgctggt gatgagcttc    720
ccggcactgg aagattatta tcaggaacag gggcgcgact gggaacgcta cgcaatggtg    780
aaagcgcgtc tgatgggcgg cgcggaggac atcagcagtc aggaattgcg taaaatgctg    840
atgccttttg tcttccgccg ttatatcgat ttcagtgtga tccagtccct gcgtaacatg    900
aaaggcatga tcgcccgcga agtacgccgc cgtggtctga agacaacat caaactcggc    960 gcaggcggta ttcgtgaaat tgaatttatc gtgcaggtat ttcagctgat ccgtggcggt    1020
cgtgaaccgg cattgcagca gcgtgcgttg ttgccaacgc ttcaggcgct ggaaaatctg    1080
gggctgctgc cggtagagca ggtgttgcag ttgcgtaaca gctatctgtt cctgcgacgt    1140
ctggaaaacc tgttgcaggc cattgctgac gagcaaacgc aaaccttacc gtccgatgag    1200
ctgaatcagg cgcgtctggc gtgggggatg aattacgctg gctggccgca gcttctggat    1260
gcagtgaatg ctcacatgca ggccgtacgc gcggtattta acgatctgat tggcgatgac    1320
acgccagatg ccgaagatga cgtgcaactc tcccggttca gcagtttatg gattgatacg    1380
cttgagcctg acgagctggc tccgctggtg ccgcaacttg acgaaaatgc gcaacggcat    1440
gttttacatc agattgctga ttttcgccgt gacgtggata aacgcacgat agggccacgt    1500
gggcgtgatc agttggattt gctgatgccg cgtttactgg cccaggtctg cacctataaa    1560 aatgcgcgatg tgacgttaca gcgcctgatg cagttgctgc tcaatatcgt cacgcgcacg    1620
acgtatatcg agctgctggt ggaatatccc ggtgcgctca acagttaat acgtctgtgc    1680 gctgcctcgc cgatggtggc gacgcaactt gcgcgtcatc ctttattgct cgacgaactg    1740
ctcgacccgc gcacgcttta ccagccgatt gagccgggcg cgtaccgtga tgaactgcgg    1800
caatatctga tgcgggtgcc aaccgaagac gaagaacaac agcttgaagc cgtgcgccag    1860
ttcaaacagg cacagcattt acgtattgcg gccggggata tttccggtgc gttgccggtg    1920
atgaaagtca gtgaccattt aacctaccct cgggaggcca ttctcgacgt tgtggtgcaa    1980
caggcgtggg aacaaatggt cgtaaaatac ggtcagccaa cccatcttca gcaccgtaaa    2040
gggcgcggtt ttgccgtggt gggttacgga aaactcggtg gctgggagct gggttacagc    2100
tcggatctgg atctggtctt cctgctcgat tgcgcgccgg aagtcatgac cgacggcgaa    2160
cgcagcattg acgggcgtca gttttatctg cggctggcgc agcgcatcat gcatttattc    2220
agcacccgta cgtcgtcagg cattctttat gaggttgacc cgcgtctgcg gccttccggt    2280
gcttccggca tgctggtcag caccatcgaa gcttttgcgg attatcaggc caacgaagcc    2340
tggacatggg agcatcaggc gctggttcgc gcgcgtgtgg tttatggtga tccgcaactg    2400
acgcagcaat ttaatgccac gcgtcgcgac attctttgcc gccagcgcga tgccgacggc    2460
ttgcgtaagg aagtccgtga atgcgcgag aaaatgtatg cccatctggg cagcaaaaga    2520
gccgacgagt tgatctgaa agccgatccg ggtggcataa cggatattga attcatcgca    2580
caatatctgg ttctgcgttt cgcgcatgat gagccgaagc tgacccgctg gtctgataac    2640
```

| | |
|---|---|
| gtgcggattt tcgaactgat ggcgcgacat gacatcatgc cggaagagga agcacgccat | 2700 |
| ctgacgcagg cttacgtgac attgcgcgat gaaattcatc atctggcgtt gcaggaacac | 2760 |
| agcgggaaag tggccgcaga cagctttgcc actgagcgcg cgcaaatccg cgccagctgg | 2820 |
| gcaaactggc ttggctga | 2838 |

```
<210> SEQ ID NO 94
<211> LENGTH: 1290
<212> TYPE: DNA
<213> ORGANISM: Rahnella aquatilis
<220> FEATURE:
<223> OTHER INFORMATION: amtB

<400> SEQUENCE: 94
```

| | |
|---|---|
| atgaaaaaac ttttatccat gatggggctt ggtgcagtgg ctttgctacc ttcgcttgcc | 60 |
| atggcagcag caccagcagc ggcaaacggt gctgataacg cctttatgat gatttgtacc | 120 |
| gcgctggtat tgttcatgac cgtacccggt gtggcgttgt tctacggcgg cttactgcgt | 180 |
| tctaaaaacg ttttgtccat gctgactcag gttattgtta cctttgctct ggtctgcgtc | 240 |
| ctgtggatcc tctacggtta cagccttgcc ttcagtgaag gtaacgcgtt cttcggtggt | 300 |
| ttcagcaacg taatgatgaa aggcattggc ctggattctg tgactggcac cttctcgcag | 360 |
| atgatccacg ttgcattcca gtgttcattt gcctgcatca ctgtagcgct gatcgtaggt | 420 |
| ggtattgctg aacgtgtgcg tttctcagca gttctgattt tcactgtgat ctggctgact | 480 |
| ttctcttata ttccgatggc tcacatggta tgggcaggcg gtttcctggc tgctgacggt | 540 |
| gcgctggact ttgccggtgg taccgttgtt catatcaatg ccgcaattgc tggcctggta | 600 |
| ggggcttatc tgctgggtaa acgcgccggt tttggcaaag aagctttcaa accacacaac | 660 |
| ctgccaatgg tcttcactgg cgcctcaatc ctgtatgtgg gctggttcgg cttcaatgcg | 720 |
| ggttcagcaa gtgccgcaag ctctgttgcc gcgctggctt tcctgaacac tgtcattgct | 780 |
| actgctggcg caatcctgtc ctggacgctg gttgagtgga tggtgcgcgg taagccctca | 840 |
| ctgctgggcg caagctccgg tgctatcgca ggtctggtgg ctatcacgcc tgcatgtggt | 900 |
| acggtcggcg taggtggtgc tctgattatc ggtctgtag cggtatcac tggtctgtgg | 960 |
| ggggttgtta ccctgaaaaa atggctgcgt gttgatgaca cctgtgatgt gttcggtgtt | 1020 |
| catggcgtgt gcggtatcgt aggttgtctg ctgacgggtg tattcacgtc cagttcactt | 1080 |
| ggcggcgtgg gctacgcaga aggcgtgacc atgggccatc aggtttgggt gcagttcttc | 1140 |
| agcgtgtgcg taacattggt ctggtcaggc gttgttgcct tcatcggtta caaagtggct | 1200 |
| gacatgatcg taggtctgcg tgttcctgaa gaacaagaac gcgaaggtct ggacgttaac | 1260 |
| agccacggcg aaaacgctta caaccaataa | 1290 |

```
<210> SEQ ID NO 95
<211> LENGTH: 500
<212> TYPE: DNA
<213> ORGANISM: Rahnella aquatilis
<220> FEATURE:
<223> OTHER INFORMATION: PinfC

<400> SEQUENCE: 95
```

| | |
|---|---|
| tgaatatcac tgactcacaa gctacctatg tcgaagaatt aactaaaaaa ctgcaagatg | 60 |
| caggcattcg cgttaaagcc gacttgagaa atgagaagat tggctttaaa attgcgaac | 120 |
| acacgctacg ccgtgttcct tatatgttag tttgtggcga taaagaggtc gaagcaggca | 180 |

```
aagttgctgt tcgtactcgt cgcggcaaag acttaggaag catggatgtt agcgaagtcg    240
ttgacaaact gctggcggaa atccgcagca gaagtcatca tcaactggag gaataaagta    300
ttaaaggcgg aaaacgagtt caaccggcgc gtcctaatcg cattaacaaa gagattcgcg    360
cgcaagaagt tcgcctcacc ggcgtcgatg gcgagcagat tggtattgtc agtctgaatg    420
aagctcttga aaaagctgag gaagcgggcg tcgatttagt agaaatcagt ccgaatgccg    480
agccgccagt tgtcgaatc                                                 500

<210> SEQ ID NO 96
<211> LENGTH: 1085
<212> TYPE: DNA
<213> ORGANISM: Klebsiella variicola
<220> FEATURE:
<223> OTHER INFORMATION: 16S

<400> SEQUENCE: 96
attgaagagt ttgatcatgg ctcagattga acgctggcgg caggcctaac acatgcaagt     60
cgagcggtag cacagagagc ttgctctcgg gtgacgagcg gcggacgggt gagtaatgtc    120
tgggaaactg cctgatggag ggggataact actggaaacg gtagctaata ccgcataacg    180
tcgcaagacc aaagtggggg accttcgggc ctcatgccat cagatgtgcc cagatgggat    240
tagctagtag gtggggtaac ggctcaccta ggcgacgatc cctagctggt ctgagaggat    300
gaccagccac actggaactg agacacggtc cagactccta cgggaggcag cagtggggaa    360
tattgcacaa tgggcgcaag cctgatgcag ccatgccgcg tgtgtgaaga aggccttcgg    420
gttgtaaagc actttcagcg gggaggaagg cggtgaggtt aataacctca ccgattgacg    480
ttacccgcag aagaagcacc ggctaactcc gtgccagcag ccgcggtaat acggagggtg    540
caagcgttaa tcggaattac tgggcgtaaa gcgcacgcag gcggtctgtc aagtcggatg    600
tgaaatcccc gggctcaacc tgggaactgc attcgaaact ggcaggctag agtcttgtag    660 agggggtag aattccaggt gtagcggtga atgcgtaga gatctggagg aataccggtg    720
gcgaaggcgg ccccctggac aaagactgac gctcaggtgc gaaagcgtgg ggagcaaaca    780
ggattagata ccctggtagt ccacgctgta aacgatgtcg atttggaggt tgtgcccttg    840
aggcgtggct tccggagcta acgcgttaaa tcgaccgcct ggggagtacg gccgcaaggt    900
taaaactcaa atgaattgac gggggcccgc acaagcggtg agcatgtgg tttaattcga    960 tgcaacgcga agaaccttac ctggtcttga catccacaga actttccaga gatggattgg   1020
tgccttcggg aactgtgaga caggtgctgc atggctgtcg tcagctcgtg ttgtgaaatg   1080
ttggg                                                               1085

<210> SEQ ID NO 97
<211> LENGTH: 882
<212> TYPE: DNA
<213> ORGANISM: Klebsiella variicola
<220> FEATURE:
<223> OTHER INFORMATION: nifH1

<400> SEQUENCE: 97
atgaccatgc gtcaatgcgc tatctacggt aaaggcggta tcggtaaatc caccaccacc    60
cagaatctcg tcgcggccct cgccgagatg ggtaagaaag tgatgatcgt cggctgcgat    120
ccgaaagcgg attccacccg tctgatcctc cacgctaaag cccagaacac catcatggag    180 atggcggcg aagtgggctc ggtcgaggat ctggagctcg aagacgttct gcaaatcggc    240
tatggcgatg tccgttgcgc cgaatccggc ggcccggagc caggcgtcgg ctgcgccgga    300
```

```
cgcggggtga tcaccgccat caacttcctc gaggaagaag gcgcctatga agaagatttg    360
gatttcgtct tctatgacgt cctcggcgac gtggtctgcg gcggcttcgc tatgccgatc    420
cgcgaaaaca aagcccagga gatctacatc gtctgctccg gcgagatgat ggcgatgtat    480
gccgccaaca atatctccaa agggatcgtg aagtacgcca atccggcaa ggtgcgcctc     540 ggcggcctga tctgtaactc gcgcaaaacc gaccgggaag acgaactgat catcgccctg    600
gcggagaagc ttggcacgca gatgatccac ttcgttcccc gcacaacat tgtgcagcgc     660 gcggagatcc gccggatgac ggtgatcgag tacgacccga cctgtcagca ggcgaatgaa    720
tatcgtcaac tggcgcagaa gatcgtcaat aacaccaaaa agtggtgcc gacgccgtgc     780 accatggacg agctggaatc gctgctgatg gagttcggca tcatggaaga agaagacacc    840
agcatcattg gtaaaaccgc cgctgaagaa aacgcggcct ga                       882
```

<210> SEQ ID NO 98
<211> LENGTH: 1113
<212> TYPE: DNA
<213> ORGANISM: Klebsiella variicola
<220> FEATURE:
<223> OTHER INFORMATION: nifH2

<400> SEQUENCE: 98

```
atggttagga aaagtagaag taaaaataca aatatagaac taactgaaca tgaccattta     60
ttaataagtc aaataaaaaa gcttaaaaca caaaccactt gcttttttaa taataaagga    120
ggggttggga agactacatt agtagcaaat ttaggagcag agctatcaat aaactttagt    180
gcaaaagttc ttattgtgga tgccgaccct caatgtaatc tcacgcagta tgtattaagt    240
gatgaagaaa ctcaggactt atatgggcaa gaaaatccag atagtattta tacagtaata    300
agaccactat cctttggtaa aggatatgaa agtgacctcc ctataaggca tgtagagaat    360
ttcggttttg acataattgt cggtgaccct agacttgctt tacaggaaga ccttttagct    420
ggagactggc gagatgccaa aggcggtggg atgcgaggaa ttaggacaac ttttgtattt    480
gcagagttaa ttaagaaagc tcgtgagcta aattatgatt ttgttttctt tgacatggga    540
ccatcattag gcgcaatcaa caggcagta ttactggcaa tggaattctt tgtcgtccca    600
atgtcaatcg atgtattttc actatgggct attaaaaata ttggctccac ggtttcaata    660
tggaaaaaag aattagacac agggattcgg ctctcagagg aacctagcga attatcacaa    720
ttatcacctc aaggaaaact aaagtttctc ggttacgtca cccaacaaca taaagaacgc    780
tctggatacg atacaattca gcttgagaat actgaggaag aaataaaatc gaaacgtcgg    840
gtaaaggcgt atgaagacat tggagaggtg tttccttcta aaattactga gcatcttttct   900 aaactttatg catcaaaaga tatgaaccca caccttggag atatacgtca tttaggtagt    960
ttagctccga aatcacaatc acaacacgtt ccgatgatat cagtgtctgg tacaggaaat   1020
tacaccagac ttagaaaaag cgcgcgtgaa ctttatcgag atattgcaag aagatactta   1080
gagaacattc agactgctaa tggcgagaaa tag                                1113
```

<210> SEQ ID NO 99
<211> LENGTH: 1374
<212> TYPE: DNA
<213> ORGANISM: Klebsiella variicola
<220> FEATURE:
<223> OTHER INFORMATION: nifD1

<400> SEQUENCE: 99

```
atgaaggaa aggaaattct ggcgctgctg gacgaacccg cctgcgagca caaccagaag      60
caaaaatccg gctgcagcgc ccctaagccc ggcgctaccg ccggcggttg cgccttcgac     120
ggcgcgcaga taacgctcct gcccatcgcc gacgtcgcgc acctggtgca cggccccatc     180
ggctgcgcgg gcagctcgtg ggataaccgc ggcagcgtca cgccggccc ggccctcaac      240
cggctcggct ttaccaccga tcttaacgaa caggatgtga ttatgggccg cggcgaacgc     300
cgcctgttcc acgccgtgcg tcacatcgtc gaccgctatc atccggcggc ggtctttatc     360
tacaacacct gcgtaccggc gatggagggc gatgacatcg aggcggtctg ccaggccgca     420
cagaccgcca ccggcgtccc ggtcatcgct attgacgccg ccggtttcta cggcagtaaa     480
aatcttggca accgaatggc gggcgacgtg atgctcaggc aggtgattgg ccagcgcgaa     540
ccggccccgt ggccagacaa cacgcccttt gccccggccc agcgccacga tatcggcctg     600
attggcgaat caatatcgc cggcgagttc tggcaggtcc agccgctgct cgacgagctg     660
gggatccgcg tcctcggcag cctctccggc gacggccgct tgccgagat ccagaccctg     720
caccgggcgc aggccaatat gctggtgtgc tcgcgcgcgc tgatcaacgt cgcccggggg     780
ctggagctgc gctacggcac gccgtggttt gaaggcagct tctacgggat ccgcgccacc     840
tccgacgcct tgcgccagct ggcgacgctg ctggggatg acgacctgcg ccgccgcacc     900
gaggcgctga tcgcccgcga agagcaggcg gcggagcagg ctcttgcgcc gtggcgtgag     960
cagctccgcg ggcgcaaagt gctgctctat accggcggcg tgaaatcctg gtcggtggta    1020
tcggccctgc aggatctcgg catgaccgtg gtggccaccg gcacgcgcaa atccaccgag    1080
gaggacaaac agcggatccg tgagctgatg ggcgacgagg cggtgatgct tgaggagggc    1140
aatgcccgca ccctgctcga cgtggtgtac cgctatcagg ccgacctgat gatcgccggc    1200
ggacgcaata tgtacaccgc ctggaaagcc cggctgccgt ttctcgatat caatcaggag    1260
cgcgagcacg cctacgccgg ctatcagggc atcatcaccc tcgcccgcca gctctgtctg    1320
accctcgcca gccccgtctg gccgcaaacg catacccgcg ccccgtggcg ctag           1374
```

<210> SEQ ID NO 100
<211> LENGTH: 1449
<212> TYPE: DNA
<213> ORGANISM: Klebsiella variicola
<220> FEATURE:
<223> OTHER INFORMATION: nifD2

<400> SEQUENCE: 100

```
atgaccaacg caacaggcga acgtaacctt gcgctcatcc aggaagtcct ggaggtgttt      60
cccgaaaccg cgcgcaaaga gcgcagaaag cacatgatga tcagcgatcc gcagatggag     120
agcgtcggca agtgcattat ctcgaaccgt aaatcgcagc ccggggtgat gaccgtgcgc     180
ggctgcgcct atgcgggctc gaaaggggtg gtgtttgggc caatcaaaga catgcccat      240
atctcgcacg gccccatcgg ctgcggccag tattcccgcg ccggacggcg caactactat     300
accggcgtca gcgtgtcga cagcttcggc accctgaact tcacctctga ttttcaggag     360
cgcgatattg ttttcggcgg cgataaaaag ctgaccaaac tgatcgaaga gatggagctg     420
ctgttcccgc tgaccaaagg gatcaccatc cagtcggagt gcccggtggg cctgatcggc     480
gatgacatca gcgccgtagc caacgccagc agcaaggcgc tggataaacc ggtgatcccg     540
gtgcgctgcg aaggctttcg cggcgtatcg caatcgctgg ccaccatat cgccaacgac     600
```

```
gtggtgcgcg actgggtgct gaacaatcgc gaagggcagc cgtttgccag caccccgtac    660
gatgttgcca tcattggcga ttacaacatc ggcggcgacg cctgggcctc gcgcattctg    720
ctggaagaga tggggctgcg cgtagtggcg cagtggtccg gcgacggcac cctggtggag    780
atggagaaca ccccattcgt taagcttaac ctcgtccact gctaccgttc gatgaactat    840
atcgcccgcc atatggagga gaaacatcag atcccatgga tggaatataa cttcttcggc    900
ccgaccaaaa tcgccgaatc gctgcgcaag atcgccgatc aatttgatga caccattcgc    960
gccaatgcgg aagcggtgat cgccaaatat gaggggcaga tggcggccat catcgccaaa   1020
tatcgcccgc ggctggaggg cgcaaagtg ctgctgtaca tgggggggct gcggccgcgc    1080
cacgtcatcg gcgcctatga ggatctcggg atggagatca tcgccgccgg ctacgagttt   1140
gcccataacg atgattacga ccgcaccctg ccggacctga agagggcac cctgctgttt    1200 gacgatgcca gcagctatga gctggaggcc ttcgtcaaag cgctgaaacc tgacctcatc   1260
ggctccggga tcaaagagaa atatatcttc agaaaatggg ggtgccgtt ccgccagatg    1320 cactcctggg actattccgg ccctatcac ggctatgacg cttcgccat cttgcccgc     1380 gatatggata tgaccctgaa caatccggcg tggaacgaac tgactgcccc gtggctgaag   1440
tctgcgtga                                                            1449

<210> SEQ ID NO 101
<211> LENGTH: 1386
<212> TYPE: DNA
<213> ORGANISM: Klebsiella variicola
<220> FEATURE:
<223> OTHER INFORMATION: nifK1

<400> SEQUENCE: 101
atggcagata ttatccgcag tgaaaaaccg ctggcggtga gcccgattaa aaccgggcaa      60
ccgctcgggg cgatcctcgc cagcctcggg ctggcccagg ccatcccgct ggtccacggc    120
gcccagggct gcagcgcctt cgccaaagtt ttctttattc agcatttcca tgacccggtg    180
ccgctgcagt cgacggccat ggatccgacc gccacgatca tggggggcga cggcaatatc    240
ttcaccgcgc tcgacaccct ctgccagcgc acagcccgc aggccatcgt gctgctcagc    300
accggtctgg cggaagcgca gggcagcgat atcgcccggg tggtgcgcca gtttcgcgag    360
gcgcatccgc gccataacgg cgtggcgatc ctcaccgtca ataccccgga ttttttttggc    420 tctatggaaa acggctacag cgcggtgatc gagagcgtga tcgagcagtg ggtcgcgccg    480
acgccgcgtc cggggcagcg gccccggcgg gtcaacctgc tggtcagcca cctctgttcg    540 ccagggata tcgaatggct gggccgctgc gtggaggcct ttggcctgca gccggtgatc    600
ctgccggacc tctcgcagtc aatggatggc cacctcggtg aagggattt tacgcccctg    660 acccagggcg cgcctcgct cgccagatt gcccagatgg ccagagtct gggcagcttc    720 gccattggcg tgtcgctcca gcgggcggca tcgctcctga cccaacgcag ccgcggcgac    780
gtgatcgccc tgccgcatct gatgacctc gaccattgcg ataccttttat ccatcagctg    840 gcgaagatgt ccggacgccg cgtaccggcc tggattgagc ccagcgtgg ccagctgcag    900 gatgcgatga tcgactgcca tatgtggctt caggccagc gcatggcgat ggcggcggag    960
ggcgacctgc tggcggcgtg gtgtgatttc gcccgcagcc aggggatgca gcccggcccg   1020
ctggtgcgcc ccaccagcca ccccagcctg cgccagctgc ggtcagcaga gtcgtgccg    1080 ggggatcttg aggatctgca gcagctgctg agccaccaac ccgccgatct gctggtggct   1140
aactctcacg cccgcgatct ggcggagcag tttgccctgc cgctgatccg cgtcggtttt   1200
```

```
ccctcttcg accggctcgg tgagtttcgt cgcgtccgcc aggggtacgc cggtatgcga    1260
gatacgctgt ttgaactggc caatctgctg cgcgaccgcc atcaccacac cgccctctac    1320
cgctcgccgc ttcgccaggg cgccgacccc cagccggctt caggagacgc ttatgccgcc    1380
cattaa                                                              1386

<210> SEQ ID NO 102
<211> LENGTH: 1563
<212> TYPE: DNA
<213> ORGANISM: Klebsiella variicola
<220> FEATURE:
<223> OTHER INFORMATION: nifK2

<400> SEQUENCE: 102
atgagccaaa cgatcgataa aattcacagc tgttatccgc tgtttgaaca ggatgaatac      60
cagaccctgt tccagaataa aaagacccct gaagaggcgc acgacgcgca gcgtgtgcag    120 gaggttttg cctggaccac caccgccgag tatgaagcgc tgaacttcca gcgcgaggcg    180
ctgaccgtcg acccggccaa agcctgccag ccgctcggcg ccgtactctg cgcgctgggg    240
ttcgccggca ccctgcccta cgtgcacggc tcccagggct cgtcgccta ttttcgcacc    300 tactttaacc gccattttaa agagccggtc gcctgcgtct ccgactccat gaccgaggac    360
gcggcggtgt cggcggcaa caacaacatg aatctgggcc tgcagaatgc cagcgcgctg    420
tataaacccg agattatcgc cgtctccacc acctgtatgg ccgaggtgat cggcgacgat    480
ctgcaggcgt ttatcgccaa cgccaaaaaa gagggatttg ttgacgaccg catcgccatt    540
ccttacgccc ataccccag ctttatcggc agccatgtca ccggctggga caatatgttc    600
gaagggttcg cgaagacctt taccgctgac tacgccgggc agccgggcaa acagcaaaag    660
ctcaatctgg tgaccggatt tgagacctat ctcggcaact tccgcgtgct gaagcggatg    720
atggcgcaga tggatgtccc gtgcagcctg ctctccgacc catcagaggt gctcgacacc    780
cccgccgacg gccattaccg gatgtacgcc ggcggcacca gccagcagga gatcaaaacc    840
gcgccggacg ccattgacac cctgctgctg cagccgtggc agctggtgaa agcaaaaaag    900
gtggttcagg agatgtggaa ccagcccgcc accgaggtgg ccgttccgct gggcctggcc    960
gccaccgacg cgctgctgat gaccgtcagt cagctgaccg gcaaaccgat cgccgacgct   1020 ctgacctgg agcgcggccg gctggtcgac atgatgctgg attccacac ctggctgcat   1080 ggcaaaaaat tcggcctcta cggcgatccg gatttcgtga tggggctgac gcgcttcctg    1140
ctggagctgg gctgcgagcc gacggtgatc ctcagtcata cgccaataa acgctggcaa    1200 aaagcgatga agaaaatgct cgatgcctcg ccgtacggtc aggaaagcga agtgttcatc    1260
aactgcgacc tgtggcactt ccggtcgctg atgttcaccc gtcagccgga ctttatgatc    1320
ggtaactcct acggcaagtt tatccagcgc gatacctgg caagggcaa agccttcgaa    1380 gtgccgctga tccgtctggg cttttcgctg ttcgaccgcc atcatctgca ccgccagacc    1440
acctggggct atgaaggcgc aatgaacatc gtcacgacgc tggtgaacgc cgtgctggaa    1500
aaactggacc acgacaccag ccagttgggc aaaaccgatt acagcttcga cctcgttcgt    1560
taa                                                                   1563

<210> SEQ ID NO 103
<211> LENGTH: 1485
<212> TYPE: DNA
<213> ORGANISM: Klebsiella variicola
<220> FEATURE:
```

<223> OTHER INFORMATION: nifL

<400> SEQUENCE: 103

| | | | | | |
|---|---|---|---|---|---|
| atgaccctga | atatgatgct | cgataacgcc | gcgccggagg | ccatcgccgg | cgcgctgact | 60 |
| caacaacatc | cggggctgtt | ttttaccatg | gtggaacagg | cctcggtggc | catctccctc | 120 |
| accgatgcca | gcgccaggat | catttacgcc | aacccggcgt | tttgccgcca | gaccggctat | 180 |
| tcgctggcgc | aattgttaaa | ccagaacccg | cgcctgctgg | ccagcagcca | gacgccgcgc | 240 |
| gagatctatc | aggagatgtg | gcataccctg | ctccagcgtc | agccctggcg | cggtcagctg | 300 |
| attaatcagc | gtcgggacgg | cggcctgtac | ctggtggaga | ttgacatcac | cccggtgctt | 360 |
| agcccgcaag | gggaactgga | gcattatctg | gcgatgcagc | gggatatcag | cgtcagctac | 420 |
| accctcgaac | agcggctgcg | caaccatatg | accctgatgg | aggcggtgct | gaataatatc | 480 |
| cccgccgccg | tggtagtggt | ggacgagcag | gatcgggtgg | tgatggacaa | cctcgcctac | 540 |
| aaaaccttct | gcgctgactg | cggcggccgg | gagctgctca | ccgagctgca | ggtctcccct | 600 |
| ggccggatga | cgcccggcgt | ggaggcgatc | ctgccggtgg | cgctgcgcgg | ggccgcgcgc | 660 |
| tggctgtcgg | taacctgctg | gccgttgccc | ggcgtcagtg | aagaggccag | ccgctacttt | 720 |
| atcgacagcg | cgctggcgcg | gaccctggtg | gtgatcgccg | actgtaccca | gcagcgtcag | 780 |
| cagcaggagc | aagggcgcct | tgaccggctg | aagcagcaaa | tgaccgccgg | caagctgctg | 840 |
| gcggcgatcc | gcgagtcgct | ggacgccgcg | ctgatccagc | tgaactgccc | gattaatatg | 900 |
| ctggcggcag | cccgtcggct | gaacggcgag | ggaagcggga | atgtggcgct | ggaggccgcc | 960 |
| tggcgtgaag | gggaagaggc | gatggcgcgg | ctccagcgct | gtcgcccatc | gctggaactc | 1020 |
| gaaaaccccg | ccgtctggcc | gctgcagccc | tttttcgacg | atctgtgcgc | cctctaccgt | 1080 |
| acacgcttcg | atcccgacgg | gctgcaggtc | gacatggcct | caccgcatct | gatcggcttt | 1140 |
| ggccagcgca | ccccactgct | ggcgtgctta | agcctgtggc | tcgatcgcac | cctggccctc | 1200 |
| gccgccgaac | tcccctccgt | gccgctggcg | atgcagctct | acgccgagga | gaacgacggc | 1260 |
| tggctgtcgc | tgtatctgac | tgacaacgta | ccgctgctgc | aggtgcgcta | cgctcactcc | 1320 |
| cccgacgcgc | tgaactcgcc | gggcaaaggc | atggagctgc | ggctgatcca | gaccctggtg | 1380 |
| gcgcaccatc | gcggggccat | tgagctggct | tcccgaccgc | agggcggcac | ctgcctgacc | 1440 |
| ctgcgtttcc | cgctgtttaa | caccctgacc | ggaggtgaag | catga | | 1485 |

<210> SEQ ID NO 104
<211> LENGTH: 1575
<212> TYPE: DNA
<213> ORGANISM: Klebsiella variicola
<220> FEATURE:
<223> OTHER INFORMATION: nifA

<400> SEQUENCE: 104

| | | | | | |
|---|---|---|---|---|---|
| atgatccctg | aatccgaccc | ggacaccacc | gtcagacgct | tcgacctctc | tcagcagttc | 60 |
| accgccatgc | agcggataag | cgtggtgctg | agccgggcca | ccgaggccag | caaaacgctg | 120 |
| caggaggtgc | tcagcgtatt | acacaacgat | gcctttatgc | agcacgggat | gatctgcctg | 180 |
| tacgacagcg | agcaggagat | cctcagtatc | gaagcgctgc | agcaaaccgg | ccagcagccc | 240 |
| ctccccggca | gcacgcagat | ccgctatcgc | cccggcgagg | gactggtggg | gaccgtgctg | 300 |
| gcccagggggc | agtcgctggt | gctgcccccgg | gtcgccgacg | atcagcgttt | tctcgaccgc | 360 |
| ctgagcctct | acgattacga | tctgccgttt | atcgccgtac | cgttgatggg | gcccaacgcc | 420 |
| cggccaatag | gggtgctggc | ggcccagccg | atggcgcgcc | aggaagagcg | gctgccggcc | 480 |

```
tgcacccgtt ttctcgaaac cgtcgccaac ctcgtcgccc agaccatccg gctgatgatc    540
cttccggcct cacccgccct gtcgagccgc cagccgccga aggtggaacg gccgccggcc    600
tgctcgtcgt cgcgcggcgt gggccttgac aatatggtcg gcaagagccc ggcgatgcgc    660
cagatcgtgg aggtgatccg tcaggtttcg cgctgggaca ccaccgtgct ggtacgcggc    720
gaaagcggca ccgggaaaga gctgatcgcc aacgccatcc atcaccattc gccacgggct    780
ggcgccgcct tcgtcaaatt taactgcgcg gcgctgccgg acaccctgct ggaaagcgaa    840
ctgttcggcc atgagaaagg cgcctttacc ggggcggtgc gtcagcgtaa aggacgtttt    900 gagctggcg atggcggcac cctgttcctc gatgagattg tgaaagcag cgcctcgttc    960 caggccaagc tgctgcgtat cctccaggag ggggagatgg agcgggtcgg cggcgatgag   1020
accctgcggg tgaatgtccg catcatcgcc gccaccaacc gtcacctgga ggaggaggtc   1080
cggctgggcc atttccgcga ggatctctac tatcgtctga acgtgatgcc catcgccctg   1140
cccccgctgc gcgagcgtca ggaggacatc gccgagctgg cgcacttcct ggtgcgcaaa   1200
atcggccagc atcaggggcg cacgctgcgg atcagcgagg gcgcgatccg cctgctgatg   1260
gagtacagct ggccgggtaa cgttcgcgaa ctggagaact gcctcgaacg atcgcggtg   1320 atgtcggaga gtggcctgat cgatcgcgac gtgatcctct tcactcacca ggatcgtccc   1380
gccaaagccc tgcctgccag cgggccagcg gaagacagct ggctgacaa cagcctggac   1440 gaacgtcagc gactgatcgc cgcgctggaa aaagccggct gggtgcaggc caaggcggca   1500
cggctgctgg ggatgacgcc gcgccaggtc gcttatcgga tccagatcat ggatatcacc   1560
ctgccgcgtc tgtag                                                    1575

<210> SEQ ID NO 105
<211> LENGTH: 2838
<212> TYPE: DNA
<213> ORGANISM: Klebsiella variicola
<220> FEATURE:
<223> OTHER INFORMATION: glnE

<400> SEQUENCE: 105
atgatgccgc tttctccgca attacagcag cactggcaga cggtcgctga ccgtctgcca     60
gcggattttc ccattgccga actgagccca caggccaggt cggtcatggc gttcagcgat    120
tttgtcgaac agagtgtgat cgcccagccg ggctggctga atgagcttgc ggactcctcg    180
ccggaggcgg aagagtggcg gcattacgag gcctggctgc aggatcgcct gcaggccgtc    240
actgacgaag cggggttgat gcgagagctg cgtctcttcc gccgccagat gatggtccgc    300
atcgcctggg cgcaggcgct gtcgctggtg agcgaagaag agactctgca gcagctgagc    360 gtcctggcg agaccctgat tgtcgccgcc gcgactggc tgtacgccgc tgctgtaag    420 gagtggggaa cgccatgcaa tgccgagggc cagccgcagc cgctgctgat cctcgggatg    480
ggaaagctgg gcgcggcga gctgaacttc tcttccgata tcgatctgat ctttgcctgg    540
cctgagcatg gcgccacccg cggcggccgc cgcgagctgg ataacgccca gttctttacc    600
cgtctggggc agcggctgat caaggcccctt gaccagccga gcaggacgg ctttgtctat    660 cgggttgaca tgcgcctgcg gccgtttggc gacagtgggc gctggtact cagttttgcg    720 gcgctggaag attattacca ggagcagggt cgggactggg aacgctatgc gatggtgaaa    780
gcgcggatca tggcgataa cgacggcgtg tacgccagcg agttgcgcgc gatgctccgt    840
cctttcgtct tccgccgtta tatcgacttc agcgtgatcc agtcgctgcg taacatgaaa    900
```

```
ggcatgatcg cccgcgaagt gcggcgtcgc gggctgaaag acaacatcaa gctcggcgcc    960
ggcgggatcc gtgaaattga gtttatcgtt caggtctttc aactgatccg cggtggtcgc   1020
gaacctgcac tgcagcagcg cgccctgctg ccgacgctgg cggcgattga tgagctacat   1080
ctgctgccgg aaggcgacgc ggcgctgctg cgcgaggcct atctgttcct gcgccggctg   1140
gaaaacctgc tgcaaagcat caacgatgag cagacccaga ccctgccgca ggatgaactt   1200
aaccgcgcca ggctggcgtg ggggatgcat accgaagact gggagacgct gagcgcgcag   1260
ctggcgagcc agatggccaa cgtgcggcga gtgtttaatg aactgatcgg cgatgatgag   1320
gatcagtccc cggatgagca actggccgag tactggcgcg agctgtggca ggatgcgctg   1380
gaagaagatg acgccagccc ggcgctggcg catttaaacg ataccgaccg ccgtagcgtg   1440
ctggcgctga ttgccgattt tcgtaaagag ctggatcggc gcaccatcgg cccgcgcggc   1500
cgccaggtgc tggatcagct gatgccgcat ctgctgagcg aaatctgctc gcgcgccgat   1560
gcgccgctgc ctctggcgcg gatcacgccc ctgttgaccg gatcgtcac ccgtaccacc    1620
tatcttgagc tgctgagcga attccccggc gcgctgaagc acctgatcac gctctgcgcg   1680
gcgtcgccga tggtcgccag ccagctggcg cgccacccgc tgctgctgga tgagctgctg   1740
gatcccaaca ccctctatca gccgacgcg accgatgcct atcgcgacga gctgcgccag    1800
tacctgctgc gcgtgccgga agaggatgaa gagcagcagc tggaggcgtt gcgccagttt   1860
aagcaggcgc agcagctgca tatcgcgcg gcggatatcg ctggtaccct gccggtgatg    1920
aaggtcagcg atcacttaac ctggcttgcc gaagcgatcc tcgacgcggt ggtgcagcag   1980
gcatgggggc agatggtcgc tcgctacggc cagccgaccc acctgcacga tcgccagggt   2040
cgcggcttcg ccgtcgtcgg ctacggtaag cttggcggct gggagctggg ctacagctcc   2100
gatctcgatc tggtgttcct ccatgactgc ccggcggagg tgatgaccga cggcgagcgg   2160
gagattgacg gccgtcagtt ctacctgcgg ctggcccagc ggatcatgca cctgttcagc   2220
acccgcacct cgtccggtat tctctacgaa gtggacgccc ggctgcgtcc ttctggcgcg   2280
gcggggatgc tggtcaccac cgccgacgcg tttgctgact atcagcagaa cgaagcctgg   2340
acgtgggaac atcaggcgct ggtgcgcgcc cgcgtggtct atggcgaccc ggcgctgcag   2400
gcgcgctttg acgccattcg tcgcgatatc ctgaccaccc cgcgggaggg gatgaccctg   2460
cagaccgagg ttcgcgagat gcgcgagaag atgcgcgccc accttggcaa caaacatccc   2520
gatcgttttg atatcaaagc cgatgccggc gggatcaccg atattgaatt tattactcag   2580
tatctggtcc tacgctatgc cagtgacaag ccgaagctga cccgctggtc tgacaacgtg   2640
cgtattcttg agctgctggc gcagaacgac atcatggacg aggaggaggc gcgcgcctta   2700
acgcatgcgt acaccacctt gcgtgatgcg ctccatcacc tggccctgca ggagcagccg   2760
ggacacgtgg cgccagaggc cttcagccgg gagcgtcagc aggtcagcgc cagctggcag   2820
aagtggctga tggcttaa                                                 2838
```

<210> SEQ ID NO 106
<211> LENGTH: 500
<212> TYPE: DNA
<213> ORGANISM: Klebsiella variicola
<220> FEATURE:
<223> OTHER INFORMATION: PinfC

<400> SEQUENCE: 106

```
agcgtcaggt accggtcatg attcaccgtg cgattctcgg ttccctggag cgcttcattg     60
gcatcctgac cgaagagttc gctggcttct tcccaacctg gattgcacca gtgcaggtag    120
```

| | |
|---|---|
| tggtcatgaa tattaccgat tctcaggctg aatacgttaa cgaattgacg cgtaaactac | 180 |
| aaaatgcggg cattcgtgta aaagcagact tgagaaatga aagattggc tttaaaatcc | 240 |
| gcgagcacac tttacgtcgt gtcccgtata tgttggtctg tggcgacaaa gaagtcgaag | 300 |
| ccggcaaagt ggccgtgcgc acccgtcgcg ggaaagacct cggcagcatg gacgtaagtg | 360 |
| aagtgattga aagctgcaa caagagattc gcagccgcag tcttcaacaa ctggaggaat | 420 |
| aaggtattaa aggcggaaaa cgagttcaaa cggcacgtcc gaatcgtatc aatggcgaga | 480 |
| ttcgcgcccct ggaagttcgc | 500 |

<210> SEQ ID NO 107
<211> LENGTH: 1287
<212> TYPE: DNA
<213> ORGANISM: Klebsiella variicola
<220> FEATURE:
<223> OTHER INFORMATION: amtB

<400> SEQUENCE: 107

| | |
|---|---|
| atgaaaatgg caacaatgaa atcgggtctg ggggcattag cccttcttcc gggactggca | 60 |
| atggccgcgc ccgcagtggc ggacaaagcc gataacgcgt ttatgatgat ttgcaccgcg | 120 |
| ctggttctgt ttatgaccat cccgggggatc gcgctgtttt acggcggcct gatccgcggc | 180 |
| aaaaacgtcc tttccatgct gactcaggtg attgtgacct ttggcctggt ctgcgtactg | 240 |
| tgggtgattt atggctatac cctggccttc ggcaccggcg gcagcttctt cggtagtttt | 300 |
| gactgggtga tgctgaaaaa tattgaactg aaagcgctga tggcacctt ctatcagtac | 360 |
| atccacgtgg ccttccaggg ctcgttcgcc tgtatcaccg tcgggctgat cgtggggcg | 420 |
| ctggctgagc gtattcgttt ctccgccgtg ctgatttttg tggtggtgtg gatgacgctc | 480 |
| tcttatgttc cgattgcgca catggtctgg ggcggcggtc tgctggcgac ccacggcgcg | 540 |
| ctggacttcg cgggcggcac cgttgtacac atcaacgccg cggttgccgg gctggtgggt | 600 |
| gcgtacatga tgggcaaacg tgtgggcttc ggcaagaag cgttcaaacc gcacaatctg | 660 |
| ccgatggtgt tcaccggaac cgccatcctc tacgtgggct ggttcggctt caacgccggc | 720 |
| tccgccagcg cagcgaacga aattgccgca ttggctttcg tcaacaccgt cgtcgccaca | 780 |
| gcggctgcca tcctggcgtg gacctttggc gaatgggccc tgcgcggtaa accttcactg | 840 |
| ctgggcgcct gctccggggc gattgccggt ctggttggcg tcacaccagc ctgtgggtat | 900 |
| atcggtgtcg gtggggcgtt gattgtgggt atcgcatctg gtctggcggg catctggggc | 960 |
| gtaacgcgc tgaaacgctg gctgcgggtt gatgaccctt gcgacgtctt cggcgtccac | 1020 |
| ggcgtctgcg gcatcgtcgg ctgtatcctg accggtatct tcgcggccac ctctctgggc | 1080 |
| ggcgtgggtt atgcagaagg cgtcaccatg ggccatcagc tgctggtgca actcgagagt | 1140 |
| atcgcgatta ccatcgtctg gtcgggcgtt gtcgcttttca ttggctacaa agtggcggac | 1200 |
| atgaccgtgg ggctgcgcgt accagaagag caggagcgcg aaggactgga cgtcaacagc | 1260 |
| catggcgaaa acgcctacaa cgcctga | 1287 |

<210> SEQ ID NO 108
<211> LENGTH: 299
<212> TYPE: DNA
<213> ORGANISM: Klebsiella variicola
<220> FEATURE:
<223> OTHER INFORMATION: Prm8.2

<400> SEQUENCE: 108

```
cgccgtcctc gcagtaccat tgcaaccgac tttacagcaa gaagtgattc tggcacgcat      60
ggaacaaatt cttgccagtc gggctttatc cgatgacgaa cgcgcacagc ttttatatga     120
gcgcggagtg ttgtatgata gtctcggtct gagggcatta gcgcgaaatg attttttcaca    180 agcgctggca atccgacccg atatgcctga agtattcaat tacttaggca tttacttaac    240
gcaggcaggc aattttgatg ctgcctatga agcgtttgat tctgtacttg agcttgatc      299
```

<210> SEQ ID NO 109
<211> LENGTH: 300
<212> TYPE: DNA
<213> ORGANISM: Klebsiella variicola
<220> FEATURE:
<223> OTHER INFORMATION: Prm6.2

<400> SEQUENCE: 109

```
gctaaagttc tcggctaatc gctgataaca tttgacgcaa tgcgcaataa aagggcatca     60
tttgatgccc tttttgcacg ctttcatacc agaacctggc tcatcagtga ttttttttgt    120
cataatcatt gctgagacag gctctgaaga gggcgtttat acaccaaacc attcgagcgg    180
tagcgcgacg gcaagtcagc gttctccttt gcaatagcag ggaagaggcg ccagaaccgc    240
cagcgttgaa gcagtttgaa cgcgttcagt gtataatccg aaacttaatt tcggtttgga    300
```

<210> SEQ ID NO 110
<211> LENGTH: 400
<212> TYPE: DNA
<213> ORGANISM: Klebsiella variicola
<220> FEATURE:
<223> OTHER INFORMATION: Prm1.2

<400> SEQUENCE: 110

```
gcccgctgac cgaccagaac ttccaccttg gactcggcta tacccttggc gtgacggcgc     60
gcgataactg ggactacatc cccattccgg tgatcttacc attggcgtca ataggttacg    120
gtccggcgac tttccagatg acctatattc ccggcaccta caataacggt aacgtttact    180
tcgcctgggc tcgtatacag ttttaattcg ctaagtctta gcaataaatg agataagcgg    240
tgtgtcttgt ggaaaaacaa ggactaaagc gttacccact aaaaaagata gcgactttta    300 tcactttta gcaaagttgc actggacaaa aggtaccaca attggtgtac tgatactcga    360
cacagcatta gtgtcgattt ttcatataaa ggtaattttg                          400
```

<210> SEQ ID NO 111
<211> LENGTH: 1536
<212> TYPE: DNA
<213> ORGANISM: Klebsiella variicola
<220> FEATURE:
<223> OTHER INFORMATION: 16S
<220> FEATURE:
<221> NAME/KEY: modified_base
<222> LOCATION: (245)..(245)
<223> OTHER INFORMATION: a, c, t, g, unknown or other
<220> FEATURE:
<221> NAME/KEY: modified_base
<222> LOCATION: (452)..(452)
<223> OTHER INFORMATION: a, c, t, g, unknown or other
<220> FEATURE:
<221> NAME/KEY: modified_base
<222> LOCATION: (454)..(454)
<223> OTHER INFORMATION: a, c, t, g, unknown or other
<220> FEATURE:
<221> NAME/KEY: modified_base
<222> LOCATION: (1131)..(1132)

<223> OTHER INFORMATION: a, c, t, g, unknown or other

<400> SEQUENCE: 111

```
ttgaagagtt tgatcatggc tcagattgaa cgctggcggc aggcctaaca catgcaagtc      60
gagcggtagc acagagagct tgctctcggg tgacgagcgg cggacgggtg agtaatgtct     120
gggaaactgc ctgatggagg gggataacta ctggaaacgg tagctaatac cgcataacgt     180
cgcaagacca aagtgggggg accttcgggc ctcatgccat cagatgtgcccc agatgggatt     240
agctngtagg tggggtaacg gctcacctag gcgacgatcc ctagctggtc tgagaggatg     300
accagccaca ctggaactga gacacggtcc agactcctac gggaggcagc agtggggaat     360
attgcacaat gggcgcaagc ctgatgcagc catgccgcgt gtgtgaagaa ggccttcggg     420
ttgtaaagca ctttcagcgg ggaggaaggc gntnaggtta ataaccttgt cgattgacgt     480
tacccgcaga agaagcaccg gctaactccg tgccagcagc cgcggtaata cggagggtgc     540
aagcgttaat cggaattact gggcgtaaag cgcacgcagg cggtctgtca agtcggatgt     600
gaaatccccg ggctcaacct gggaactgca ttcgaaactg gcaggctaga gtcttgtaga     660
gggggggtaga attccaggtg tagcggtgaa atgcgtagag atctggagga ataccggtgg     720
cgaaggcggc cccctggaca aagactacgg ctcaggtgcg aaagcgtggg gagcaaacag     780
gattagatac cctggtagtc cacgctgtaa acgatgtcga tttggaggtt gtgcccttga     840
ggcgtggctt ccggagctaa cgcgttaaat cgaccgcctg ggagtacggc cgcaaggtt     900
aaaactcaaa tgaattgacg ggggcccgca caagcggtgg agcatgtggt ttaattcgat     960
gcaacgcgaa gaaccttacc tggtcttgac atccacagaa ctttccagag atggattggt    1020
gccttcggga actgtgagac aggtgctgca tggctgtcgt cagctcgtgt tgtgaaatgt    1080
tgggttaagt cccgcaacga gcgcaaccct tatcctttgt tgccagcggt nnggccggga    1140
actcaaagga gactgccagt gataaactgg aggaaggtgg ggatgacgtc aagtcatcat    1200
ggcccttacg accagggcta cacacgtgct acaatggcat atacaaagag aagcgacctc    1260
gcgagagcaa gcggacctca taaagtatgt cgtagtccgg attggagtct gcaactcgac    1320
tccatgaagt cggaatcgct agtaatcgta gatcagaatg ctacggtgaa tacgttcccg    1380
ggccttgtac acaccgcccg tcacaccatg ggagtgggtt gcaaaagaag taggtagctt    1440
aaccttcggg agggcgctta ccactttgtg attcatgact ggggtgaagt cgtaacaagg    1500
taaccgtagg ggaacctgcg gttggatcac ctcctt                              1536
```

<210> SEQ ID NO 112
<211> LENGTH: 882
<212> TYPE: DNA
<213> ORGANISM: Klebsiella variicola
<220> FEATURE:
<223> OTHER INFORMATION: nifH

<400> SEQUENCE: 112

```
atgaccatgc gtcaatgcgc tatctacggt aaaggcggta tcggtaaatc caccaccacc      60
cagaatctcg tcgcggccct cgccgagatg ggtaagaaag tgatgatcgt cggctgcgat     120
ccgaaagcgg actccacccg tctgatcctt cacgctaaag cccagaacac catcatggag     180
atggcggcgg aagtgggctc ggtcgaggat ctggagctcg aagacgttct gcaaatcggc     240
tatggcgatg tccgttgcgc cgaatccggc ggccccgagc caggcgtcgg ctgcgccgga     300
cgcggggtga tcaccgccat caacttcctc gaggaagaag cgccatatga ggaagatttg     360
gatttcgtct tctatgacgt cctcggcgac gtagtctgcg gcggcttcgc catgccgatc     420
```

```
cgcgaaaaca aagcccagga gatctacatc gtctgctccg gcgagatgat ggcgatgtat      480
gccgccaaca atatctccaa ggggatcgtg aagtacgcga aatctggcaa ggtgcgcctc      540
ggcggcctga tctgtaactc gcgcaaaacc gaccgggaag acgaactgat catcgccctg      600
gcggagaagc ttggcacgca gatgatccac ttcgttcccc gcgacaacat tgtgcagcgc      660
gcggagatcc gccggatgac ggtgatcgag tacgacccga cctgtcagca ggcgaatgaa      720
tatcgtcaac tggcgcagaa gatcgtcaat aacaccaaaa agtggtgcc aacgccgtgc       780 accatggacg agctggaatc gctgctgatg gagttcggca tcatggaaga agaagacacc      840
agcatcattg gtaaaaccgc cgctgaagaa acgcggcct ga                          882
```

<210> SEQ ID NO 113
<211> LENGTH: 1449
<212> TYPE: DNA
<213> ORGANISM: Klebsiella variicola
<220> FEATURE:
<223> OTHER INFORMATION: nifD1

<400> SEQUENCE: 113

```
atgaccaacg caacaggcga acgtaacctt gcgctcatcc aggaagtcct ggaggtgttt       60
cccgaaaccg cgcgcaaaga gcgcagaaag cacatgatga tcagcgatcc gcagatggag      120
agcgtcggca agtgcattat ctcgaaccgt aaatcgcagc ccggggtgat gaccgtgcgt      180
ggctgcgcct atgcgggctc gaaaggggtg gtgtttgggc aatcaaaga catggcccat       240 atctcgcacg gccccatcgg ctgcggccag tactcgcgcg ccggacggcg caactactat      300
accggcgtca gcggtgtcga cagcttcggc accctgaact tcacctctga ttttcaggag      360
cgcgatattg ttttcggcgg cgataaaaag ctgaccaaac tgatcgaaga gatggagctg      420
ctgttcccgc tgaccaaagg gatcaccatc cagtcggagt gcccggtggg cctgatcggc      480
gatgacatca gcgccgtggc caacgccagc agcaaggcgc tggataaacc ggtgatcccg      540
gtgcgctgcg aaggctttcg cggcgtatcg caatcgctgg ccaccatat cgccaacgac      600 gtggtgcgcg actgggtgct gaacaatcgc gaagggcagc cgtttgccag cacccccgtat      660 gatgttgcca tcattggcga ttacaacatc ggcggcgacg cctgggcctc gcgcattctg      720
ctggaagaga tggggctgcg cgtagtggcg cagtggtccg gcgacggcac cctggtggag      780
atggagaaca cccccattcgt taagcttaac ctcgtccact gctaccgttc gatgaactat      840
atcgcccgcc atatggagga gaaacatcag atcccgtgga tggaatataa cttcttcggc      900
ccgaccaaaa tcgccgaatc gctgcgcaag atcgccgatc aatttgatga caccattcgc      960
gccaatgcgg aagcggtgat cgccaaatat gaggggcaga tggcggccat catcgccaaa     1020
tatcgcccgc ggctggaggg gcgcaaagtg ctgctgtaca tggggggggct gcggccgcgc     1080 cacgtcatcg gcgcctatga ggatctcggg atggagatca tcgccgccgg ctacgagttt     1140
gcccataacg atgattacga ccgcacccct ccggacctga agagggcac cctgctgttt      1200 gacgatgcca gcagctatga gctggaggcc ttcgtcaaag cgctgaaacc tgacctcatc     1260
ggctccggga tcaaagagaa atatatcttc cagaaaatgg gggtgccgtt ccgccagatg     1320
cactcctggg actattccgg ccccatcac ggctatgacg cttcgccat cttttgcccgc     1380 gatatggata tgaccctgaa caatccggcg tggaacgaac tgactgcccc gtggctgaag    1440
tctgcgtga                                                              1449
```

<210> SEQ ID NO 114

<211> LENGTH: 1374
<212> TYPE: DNA
<213> ORGANISM: Klebsiella variicola
<220> FEATURE:
<223> OTHER INFORMATION: nifD2

<400> SEQUENCE: 114

| | | | | | |
|---|---|---|---|---|---|
| atgaaggaa | aggaaattct | ggcgctgctg | gacgaacccg | cctgcgagca | caaccagaag | 60 |
| caaaaatccg | gctgcagcgc | tcctaagccc | ggcgcaaccg | ccggcggctg | cgccttcgac | 120 |
| ggcgcgcaga | taacgctcct | gcccatcgcc | gacgtcgcgc | acctggtgca | cggccccatc | 180 |
| ggctgcgcgg | gcagctcgtg | ggataaccgc | ggcagcgtca | cgccggccc | ggccctcaac | 240 |
| cggctcggct | ttaccaccga | tcttaacgaa | caggatgtga | ttatgggccg | cggcgaacgc | 300 |
| cgcctgttcc | acgccgtccg | tcacatcgtc | gaccgctatc | atccggcggc | ggtctttatc | 360 |
| tacaacacct | gcgtaccggc | gatggagggg | gatgacctgg | aggccgtctg | ccaggccgca | 420 |
| cagaccgcca | ccggcgtccc | ggtcatcgcc | attgacgccg | ccggtttcta | cggcagtaaa | 480 |
| aatcttggca | accgaatggc | gggcgacgtg | atgctcaggc | aggtgattgg | ccagcgcgaa | 540 |
| ccggccccgt | ggccagacaa | cacgcccttt | gccccggccc | agcgccacga | tatcggcctg | 600 |
| attggcgaat | caatatcgc | cggcgagttc | tggcaggtcc | agccgctgct | cgacgagctg | 660 |
| gggatccgcg | tcctcggcag | cctctccggc | gacggccgct | tgccgagat | ccagaccctg | 720 |
| caccgggcgc | aggccaatat | gctggtgtgc | tcgcgcgcgc | tgatcaacgt | cgcccggggg | 780 |
| ctggagctgc | gctacggcac | gccgtggttt | gaaggcagct | tctacgggat | ccgcgccacc | 840 |
| tccgacgcct | tgcgccagct | ggcggcgctg | ctggggatg | acgacctgtg | ccgccgcacc | 900 |
| gaggcgctga | tcgcccgcga | agagcaggcg | gcggagcagg | cgctggcgcc | gtggcgcgag | 960 |
| cagctccgtg | ggcgcaaagt | gttgctctac | accggcggcg | tgaaatcctg | gtcggtggta | 1020 |
| tcagccctgc | aggatctcgg | catgaccgtg | gtggccaccg | gcacgcggaa | atccaccgag | 1080 |
| gaggacaaac | agcggatccg | tgagctgatg | gcgacgagg | cggtgatgct | tgaggagggc | 1140 |
| aatgcccgca | ccctgctcga | cgtggtgtac | cgctatcagg | ccgacctgat | gatcgccggc | 1200 |
| ggacgcaata | tgtacaccgc | ctggaaagcc | cggctgccgt | ttctcgatat | caatcaggag | 1260 |
| cgcgagcacg | cctacgccgg | ctatcagggc | atcatcaccc | tcgcccgcca | gctctgtctg | 1320 |
| accctcgcca | gtcccgtctg | gccgcaaacg | catacccgcg | ccccgtggcg | ctag | 1374 |

<210> SEQ ID NO 115
<211> LENGTH: 1386
<212> TYPE: DNA
<213> ORGANISM: Klebsiella variicola
<220> FEATURE:
<223> OTHER INFORMATION: nifK1

<400> SEQUENCE: 115

| | | | | | |
|---|---|---|---|---|---|
| atggcagaca | ttatccgcag | tgaaaaaccg | ctggcggtga | gcccgattaa | aaccgggcaa | 60 |
| ccgctcgggg | cgatcctcgc | cagcctcggg | ctggcccagg | ccatcccgct | ggtccacggc | 120 |
| gcccagggct | gcagcgcctt | cgccaaagtt | ttctttattc | agcatttcca | tgacccggtg | 180 |
| ccgctgcagt | cgacggccat | ggatccgacc | gccacgatca | tgggggccga | cggcaatatc | 240 |
| ttcaccgcgc | tcgacaccct | ctgccagcgc | cacagcccgc | aggccatcgt | gctgctcagc | 300 |
| accggtctgg | cggaagcgca | gggcagcgat | atcgcccggg | tggtgcgcca | gtttcgtgag | 360 |
| gcgcatccgc | gccataacgg | cgtggcgatc | ctcaccgtca | taccccgga | ttttttggc | 420 |
| tcgatggaaa | acggctacag | cgcggtgatc | gagagcgtga | tcgagcagtg | ggtcgcgccg | 480 |

```
acgccgcgtc cggggcagcg gccccggcgg gtcaacctgc tggtcagcca cctctgttcg    540 ccagggata tcgaatggct gggccgctgc gtggaggcct ttggcctgca gccggtgatc     600
ctgccggacc tctcgcagtc aatggatggc cacctcggtg aagggatttt acgcccctg    660 acccagggcg gcgcctcgct gcgccagatt gcccagatgg ccagagtct gggcagcttc    720 gccattggcg tgtcgctcca gcgggcggca tcgctcctga cccaacgcag ccgcggcgac   780
gtgatcgccc tgccgcatct gatgaccctc gaccattgcg atacctttat ccatcagctg   840
gcgaagatgt ccggacgccg cgtaccggcc tggattgagc gccagcgcgg ccagctgcag   900
gatgcgatga tcgactgcca tatgtggctt cagggccagc gcatggcgat ggcggcggag   960
ggcgacctgc tggcggcgtg tgtgatttc gcccgcagcc aggggatgca gcccggcccg   1020
ctggtcgccc ccaccagcca ccccagcctg cgccagctgc cggtcgatca ggtcgtgccg   1080
ggggatcttg aggatctgca gcagctgctg agccaccaac ccgccgatct gctggtggct   1140
aactctcacg cccgcgatct ggcggagcag tttgccctgc cgctgatccg cgtcggtttt   1200
cccctcttcg accggctcgg tgagtttcgt cgcgtccgcc aggggtacgc cggtatgcga   1260
gatacgctgt ttgagctggc caatctgctg cgcgaccgcc atcaccacac cgccctctac   1320
cgctcgccgc ttcgccaggg cgccgacccc ctgccggctt caggagacgc ttatgccgcc   1380
cattaa                                                              1386

<210> SEQ ID NO 116
<211> LENGTH: 183
<212> TYPE: DNA
<213> ORGANISM: Klebsiella variicola
<220> FEATURE:
<223> OTHER INFORMATION: nifK2

<400> SEQUENCE: 116
gtgccgctga tccgtctggg ctttccgctg ttcgaccgcc atcatctgca ccgccagacc     60
acctggggct atgaaggcgc aatgaacatc gtcacgacgc tggtgaacgc cgtgctggaa    120
aaactggacc acgacaccag ccagttgggc aaaaccgatt acagcttcga cctcgttcgt    180
taa                                                                  183

<210> SEQ ID NO 117
<211> LENGTH: 1485
<212> TYPE: DNA
<213> ORGANISM: Klebsiella variicola
<220> FEATURE:
<223> OTHER INFORMATION: nifL

<400> SEQUENCE: 117
atgaccctga atatgatgct cgataacgcc gcaccggagg ccatcgccgg cgcgctgact     60
caacaacatc cggggctgtt ttttaccatg gtggaacagg cctcggtggc catatccctc    120
accgatgcca gcgccaggat catttacgcc aacccagcgt tttgccgcca gaccggctat    180
tcgctggcgc aattgttaaa ccagaacccg cgcctgctgg ccagcagcca gacgccgcgc    240
gcgatctatc aggagatgtg gcataccctg ctccagcgtc agccctggcg cggtcagctg    300
attaatcagc gtcgggacgg cggcctgtgc ctggtggaga ttgacatcac cccggtgctt    360
agcccgcaag gggaactgga gcattatctg gcgatgcagc gggatatcag cgtcagctac    420
accctcgaac aacggctgcg caaccatatg accctgatgg aggcggtgct gaataatatc    480
cccgccgccg tggtggtggt ggacgagcag gatcgggtgg tgatggacaa cctcgcctac    540
```

| | |
|---|---|
| aaaaccttct gcgctgactg cggcggccgg gagctgctca ccgagctgca ggtctcccct | 600 |
| ggccggatga cgcccggcgt ggaggcgatc ctgccggtag cgctgcgcgg ggccgcgcgc | 660 |
| tggctgtcgg taacctgctg gccgttgccc ggcgtcagtg aagaggccag ccgctacttt | 720 |
| atcgacagcg cgctggcgcg gaccctggtg gtgatcgccg actgtaccca gcagcgtcag | 780 |
| cagcaggagc aaggacgcct tgaccggctg aagcagcaaa tgaccgccgg caagctgctg | 840 |
| gcggcgatcc gcgagtcgct ggacgccgcg ctgatccagc tgaactgccc gattaatatg | 900 |
| ctggcggcag cccgtcggct gaacggcgag ggaagcggga atgtggcgct ggaggccgcc | 960 |
| tggcgtgaag gggaagaggc gatggcgcgg ctccagcgct gtcgcccatc gctggaactc | 1020 |
| gaaaaccccg ccgtctggcc gctgcagccc tttttcgacg atctgtgcgc cctctaccgt | 1080 |
| acccgcttcg atcccgacgg gctgcaggtc gacatggcct caccgcatct gatcggcttt | 1140 |
| ggccagcgca ccccgctgct ggcgtgctta agcctgtggc tcgaccgcac cctggccctc | 1200 |
| gccgccgaat tgccctccgt gccgctggcg atgcagctct atgccgagga gaacgacggc | 1260 |
| tggctgtcgc tgtacctgac tgataacgta ccgctgttgc aggtgcgcta cgcccactcc | 1320 |
| cccgacgcgc tgaactcgcc gggtaaaggc atggagctgc ggctgatcca gaccctggtg | 1380 |
| gcgcaccatc gcggggccat tgagctggct tcccgaccgc agggcggcac ctgcctgacc | 1440 |
| ctgcgtttcc cgctgtttaa caccctgacc ggaggtgaag catga | 1485 |

<210> SEQ ID NO 118
<211> LENGTH: 1575
<212> TYPE: DNA
<213> ORGANISM: Klebsiella variicola
<220> FEATURE:
<223> OTHER INFORMATION: nifA

<400> SEQUENCE: 118

| | |
|---|---|
| atgatccctg aatccgaccc ggacaccacc gtcagacgct tcgacctctc tcagcagttc | 60 |
| accgccatgc agcggataag cgtggtgctg agccgggcca ccgaggccag caaaacgctg | 120 |
| caggaggtac tcactgtatt gcacaacgat gcctttatgc agcacgggat gatctgcctg | 180 |
| tacgacagcg agcaggagat cctcagtatc gaagcgctgc agcaaaccgg ccagcagccc | 240 |
| ctccccggca gcacgcagat ccgctatcgc cccggcgagg gactggtggg gaccgtgctg | 300 |
| gcccaggggc agtcgctggt gctgccccgg gtcgccgacg atcagcgttt tctcgaccgc | 360 |
| ctgagcctct acgattacga tctgccgttt atcgccgtac cgttgatggg gcccaacgcc | 420 |
| cggccaatag gggtgctggc ggcccagccg atggcgcgcc aggaagagcg gctgccggcc | 480 |
| tgcacccgtt ttctcgaaac cgtcgccaac ctcgtcgccc agaccatccg gctgatgatc | 540 |
| cttccggcct cacccgccct gtcgagccgc cagccgccga aggtggaacg gccgccggcc | 600 |
| tgctcgtcgt cgcgcggcgt gggccttgac aatatggtcg gcaagagccc ggcgatgcgc | 660 |
| cagatcgtgg aggtgatccg tcaggtttcg cgctgggaca ccaccgtgct ggtgcgcggt | 720 |
| gaaagcggca ccgggaaaga gctgatcgcc aacgccatcc atcaccattc gccacgggct | 780 |
| ggcgccgcct tcgtcaaatt taactgcgcg gcgctgccgg acaccctgct ggaaagcgaa | 840 |
| ctgttcggcc atgagaaagg cgcctttacc ggggcggtgc gtcagcgtaa aggacgtttt | 900 |
| gagctggcgg atggcggcac cctgttcctc gatgagattg gtgaaagcag cgcctcgttc | 960 |
| caggccaagc tgctgcgtat cctccaggag ggggagatgg agcgggtcgg cggcgatgag | 1020 |
| accctgcggg tgaatgtccg catcatcgcc gccaccaacc gtcacctgga ggaggaggtc | 1080 |
| cggctgggcc atttccgcga ggatctctat tatcgtctga acgtgatgcc catcgccctg | 1140 |

| | |
|---|---|
| cccccgctgc gcgagcgtca ggaggacatc gccgagctgg cgcacttcct ggtgcgcaaa | 1200 |
| atcggccagc atcaggggcg cacgctgcgg atcagcgagg gcgcgatccg cctgctgatg | 1260 |
| gagtacagct ggccgggtaa cgttcgcgaa ctggagaact gcctcgaacg atcggcggtg | 1320 |
| atgtcggaga gtggcctgat cgatcgcgac gtgatcctct tcactcacca ggatcgtccc | 1380 |
| gccaaagccc tgcctgccag cgggccagcg aagacagct ggctggacaa cagcctggac | 1440 |
| gaacgtcagc gactgatcgc cgcgctgaaa aagccggct gggtgcaggc caaggcggca | 1500 |
| cggctgctgg ggatgacgcc gcgccaggtc gcttaccgga tccagatcat ggatatcacc | 1560 |
| ctgccgcgtc tgtag | 1575 |

<210> SEQ ID NO 119
<211> LENGTH: 2838
<212> TYPE: DNA
<213> ORGANISM: Klebsiella variicola
<220> FEATURE:
<223> OTHER INFORMATION: glnE

<400> SEQUENCE: 119

| | |
|---|---|
| atgatgccgc tttctccgca attacagcag cactggcaga cggtcgctga ccgtctgcca | 60 |
| gcggattttc ccattgcaga actgagccca caggccaggt cggtcatggc gttcagcgat | 120 |
| tttgtcgaac agagtgtgat cgcccagccg ggctggctga atgagcttgc ggactcctcg | 180 |
| ccggaggcgg aagagtggcg gcattacgag gcctggctgc aggatcgcct gcaggccgtc | 240 |
| actgacgaag cggggttgat gcgagagctg cgtctcttcc gccgccagat gatggtccgc | 300 |
| atcgcctggg cgcaggcgct gtcgctggtg agcgaagaag agaccctgca gcagctgagc | 360 |
| gccctgcgg agaccctgat tgtcgccgcc cgcgactggc tctacgccgc tgctgtaag | 420 |
| gagtggggaa cgccatgcaa tgccgagggc cagccgcagc cgctgctgat cctcgggatg | 480 |
| ggaaagctgg gcgcggcga gctgaacttc tcttccgata tcgatctgat cttttgcctgg | 540 |
| cctgagcatg gcgccacccg cggcggccgc cgcgagctga taacgcccca gttctttacc | 600 |
| cgtctggggc agcggctgat caaggcccctt gaccagccga gcaggacgg cttttgtctat | 660 |
| cgggttgaca tgcgcctgcg gccgtttggc gacagtgggc cgctggtact cagctttgcg | 720 |
| gcactggaag attattacca ggagcagggt cgggactggg aacgctatgc gatggtgaaa | 780 |
| gcgcggatca tgggcgataa cgacggcgtg tacgccagcg agttgcgcgc gatgctccgt | 840 |
| cctttcgtct ccgccgttta tatcgacttc agcgtgatcc agtcgctgcg taacatgaaa | 900 |
| ggcatgatcg cccgcgaagt gcggcgtcgc gggctgaaag acaacatcaa gctcggcgcc | 960 |
| ggcgggatcc gtgaaattga gtttatcgtt caggtctttc agctgatccg cggtggtcgc | 1020 |
| gaacctgcac tgcagcagcg cgccctgctg ccgacgctgg cggcgattga tgagctacat | 1080 |
| ctgctgccgg aaggcgacgc ggcgctgctg cgcgaggcct atctgttcct gcgccggctg | 1140 |
| gaaaacctgc tgcaaagcat caacgatgaa cagacccaga ccctgccgca ggatgaactt | 1200 |
| aaccgcgcca ggctggcgtg ggggatgcat accgaagact gggagacgct gagcgcgcag | 1260 |
| ctggcgagcc agatggccaa cgtgcggcga gtgtttaatg aactgatcgg cgatgatgag | 1320 |
| gatcagtccc cggatgagca actggccgag tactggcgcg agctgtggca ggatgcgctg | 1380 |
| gaagaagatg acgccagccc ggcgctggcg catttaaacg ataccgaccg ccgtagcgtg | 1440 |
| ctggcgctga ttgccgattt tcgtaaagag ctggatcggc gcaccatcgg cccgcgcggc | 1500 |
| cgccaggtgc tggatcagct gatgccgcat ctgctgagcg aaatctgctc gcgtgccgat | 1560 |

```
gcgccgctgc ctctggcgcg gatcacgccg ctgttgaccg ggatcgtcac ccgtaccacc    1620
tatcttgagc tgctgagcga attccccggc gcgctgaagc acctgatcac gctctgcgcg    1680
gcgtcgccga tggtcgccag ccagctggcg cgccacccgc tgctgctgga tgagctgctg    1740
gatcccaaca ccctctatca gccgacggcg accgatgcct atcgcgacga gctgcgccag    1800
tacctgctgc gcgtgccgga agaggatgaa gagcagcagc tggaggcgtt cgccagtttt    1860
aagcaggcgc agcagctgca tatcgcggcg gcggatatcg ctggtaccct gccggtgatg    1920
aaggtcagcg atcacttaac ctggcttgcc gaagcgatcc tcgacgcggt ggtgcagcag    1980
gcatgggggc agatggtcgc tcgctacggt cagccgaccc acctgcacga tcgccagggt    2040
cgcggcttcg ccgttgtcgg ctacggtaag ctcggcggct gggagctggg ctacagctcc    2100
gatctcgatc tggtgttcct ccatgactgc ccggcggagg tgatgaccga cggcgagcgg    2160
gagattgacg gccgtcagtt ctacctgcgg ctggcccagc ggatcatgca cctgttcagc    2220
acccgcacct cgtccggtat tctctacgaa gtggacgccc ggctgcgtcc ttctggcgcg    2280
gcggggatgc tggtcaccac cgccgacgcg tttgctgact atcagcagaa cgaagcctgg    2340
acgtgggaac atcaggcgct ggtgcgcgcc cgcgtggtct atggcgaccc ggcgctgcag    2400
gcgcgctttg acgccattcg tcgcgatatc ctgaccaccc gcggggaggg gacgaccctg    2460
cagaccgagg ttcgcgagat gcgcgagaag atgcgcgccc accttggcaa caaacatccc    2520
gatcgttttg atatcaaagc cgatgccggc gggatcaccg atattgaatt tattactcag    2580
tatctggtcc tacgctatgc cagtgacaag ccgaagctga cccgctggtc tgacaacgtg    2640
cgtattcttg agctgctggc gcagaacgac atcatggacg aggaggaggc gcgcgcctta    2700
acgcatgcat acaccacctt gcgtgatgcg ctccatcacc tggccctgca ggagcagccg    2760
ggacacgtgg cgccagaggc cttcagccgg gagcgtcagc aggtcagcgc cagctggcag    2820
aagtggctga tggcttaa                                                  2838
```

<210> SEQ ID NO 120
<211> LENGTH: 1287
<212> TYPE: DNA
<213> ORGANISM: Klebsiella variicola
<220> FEATURE:
<223> OTHER INFORMATION: amtB

<400> SEQUENCE: 120

```
atgaaaatgg caacaatgaa atcgggtctg ggggcattag ccccttcttcc gggactggca      60 atggccgcgc ccgcagtggc ggacaaagcc gataacgcgt ttatgatgat ttgcaccgcg     120
ctggttctgt ttatgaccat cccggggatc gcgctgtttt acggcggcct gatccgcggc     180
aaaaacgtcc tttccatgct gactcaggtg attgtgacct ttggcctggt ctgcgtactg     240
tgggtgattt atggctatac cctggccttc ggcaccggcg gcagcttctt cggtagcttt     300
gactgggtga tgctgaaaaa tattgaactg aaagcgctga tgggcaccct ctatcagtac     360
atccacgtgg ccttccaggg ctcgttcgcc tgtatcaccg tcgggctgat cgtggggcg     420 ctggctgagc gtattcgttt ctccgccgtg ctgatttttcg tggtggtgtg gatgacgctc     480
tcttatgttc cgattgcgca catggtctgg ggcggcggtc tgctggcgac ccacggcgcg     540
ctggacttcg cgggcggcac cgttgtacac atcaacgccg cggttgccgg gctggtgggt     600
gcgtatatga tgggcaaacg tgtgggcttc ggcaagaag cgttcaaacc gcacaatctg     660
ccgatggtgt tcaccggaac cgccatcctc tacgtgggct ggttcggctt caacgccggc     720
tccgccagcg cagcgaacga aattgccgca ctggctttcg tcaacaccgt cgtcgccaca     780
```

```
gcggcagcca tcctggcctg gacctttggc gaatgggctc tgcgcggcaa accttcactg    840
ctgggcgcct gctccggggc gattgccggt ctggttggcg tcacaccagc ctgtgggtat    900
atcggtgtcg gtggggcgtt gattgtgggt atcgcatctg gtctggcggg catctggggc    960
gtaacggcgc tgaaacgctg gctgcgggtt gatgacccct tcgacgtctt cggcgtccac   1020
ggcgtctgcg gcatcgtcgg ctgtatcctg accggtatct tcgcggccac ctctctgggc   1080 ggcgtggggtt atgcagaagg cgtcaccatg gccatcagc tgctggtgca actcgagagt   1140
atcgcgatta ccatcgtctg gtcgggcgtt gtcgctttca ttggctacaa agtggcggac   1200
atgaccgtgg ggctgcgcgt accagaagag caggagcgcg aaggactcga cgtcaacagc   1260
catggcgaaa acgcctacaa cgcctga                                       1287

<210> SEQ ID NO 121
<211> LENGTH: 1435
<212> TYPE: DNA
<213> ORGANISM: Achromobacter spiritinus
<220> FEATURE:
<223> OTHER INFORMATION: 16S
<220> FEATURE:
<221> NAME/KEY: modified_base
<222> LOCATION: (255)..(255)
<223> OTHER INFORMATION: a, c, t, g, unknown or other
<220> FEATURE:
<221> NAME/KEY: modified_base
<222> LOCATION: (454)..(454)
<223> OTHER INFORMATION: a, c, t, g, unknown or other

<400> SEQUENCE: 121
ctgaagagtt tgatcctggc tcagattgaa cgctagcggg atgccttaca catgcaagtc     60
gaacggcagc acggacttcg gtctggtggc gagtggcgaa cgggtgagta atgtatcgga    120
acgtgcctag tagcggggga taactacgcg aaagcgtagc taataccgca tacgccctac    180
gggggaaagc aggggatcgc aagaccttgc actattagag cggccgatat cggattagct    240
agttggtggg gtaanggctc accaaggcga cgatccgtag ctggtttgag aggacgacca    300
gccacactgg gactgagaca cggcccagac tcctacggga ggcagcagtg gggaattttg    360
gacaatgggg gaaaccctga tccagccatc ccgcgtgtgc gatgaaggcc ttcgggttgt    420
aaagcacttt tggcaggaaa gaaacgtcat gggntaatac cccgtgaaac tgacggtacc    480
tgcagaataa gcaccggcta actacgtgcc agcagccgcg gtaatacgta gggtgcaagc    540
gttaatcgga attactgggc gtaaagcgtg cgcaggcggt tcggaaagaa agatgtgaaa    600
tcccagagct taactttgga actgcatttt taactaccgg ctagagtgt gtcagaggga    660 ggtggaattc cgcgtgtagc agtgaaatgc gtagatatgc ggaggaacac cgatggcgaa    720
ggcagcctcc tgggataaca ctgacgctca tgcacgaaag cgtggggagc aaacaggatt    780
agataccctg gtagtccacg ccctaaacga tgtcaactag ctgttgggc cttcgggcct    840 tagtagcgca gctaacgcgt gaagttgacc gcctggggag tacggtcgca agattaaaac    900
tcaaaggaat tgacggggac ccgcacaagc ggtggatgat gtggattaat tcgatgcaac    960
gcgaaaaacc ttacctaccc ttgacatgtc tggaattctg aagagattcg aagtgctcg   1020 caagagaacc ggaacacagg tgctgcatgg ctgtcgtcag ctcgtgtcgt gagatgttgg   1080
gttaagtccc gcaacgagcg caacccttgt cattagttgc tacgaaaggg cactctaatg   1140
agactgccgg tgcaaaaccg gaggaaggtg gggatgacgt caagtcctca tggcccttat   1200
gggtagggct tcacacgtca tacaatggtc gggacagagg gtcgccaacc cgcgaggggg   1260
```

| | |
|---|---|
| agccaatccc agaaacccga tcgtagtccg gatcgcagtc tgcaactcga ctgcgtgaag | 1320 |
| tcggaatcgc tagtaatcgc ggatcagcat gtcgcggtga atacgttccc gggtcttgta | 1380 |
| cacaccgccc gtcacaccat gggagtgggt tttaccagaa gtagttagcc taacc | 1435 |

<210> SEQ ID NO 122
<211> LENGTH: 1528
<212> TYPE: DNA
<213> ORGANISM: Achromobacter marplatensis
<220> FEATURE:
<223> OTHER INFORMATION: 16S
<220> FEATURE:
<221> NAME/KEY: modified_base
<222> LOCATION: (255)..(255)
<223> OTHER INFORMATION: a, c, t, g, unknown or other
<220> FEATURE:
<221> NAME/KEY: modified_base
<222> LOCATION: (999)..(999)
<223> OTHER INFORMATION: a, c, t, g, unknown or other
<220> FEATURE:
<221> NAME/KEY: modified_base
<222> LOCATION: (1009)..(1009)
<223> OTHER INFORMATION: a, c, t, g, unknown or other
<220> FEATURE:
<221> NAME/KEY: modified_base
<222> LOCATION: (1437)..(1437)
<223> OTHER INFORMATION: a, c, t, g, unknown or other

<400> SEQUENCE: 122

| | |
|---|---|
| ctgaagagtt tgatcctggc tcagattgaa cgctagcggg atgccttaca catgcaagtc | 60 |
| gaacggcagc acggacttcg gtctggtggc gagtggcgaa cgggtgagta atgtatcgga | 120 |
| acgtgcctag tagcggggga taactacgcg aaagcgtagc taataccgca tacgccctac | 180 |
| gggggaaagc aggggatcgc aagaccttgc actattagag cggccgatat cggattagct | 240 |
| agttggtggg gtaanggctc accaaggcga cgatccgtag ctggtttgag aggacgacca | 300 |
| gccacactgg gactgagaca cggcccagac tcctacggga ggcagcagtg gggaattttg | 360 |
| gacaatgggg gaaaccctga tccagccatc ccgcgtgtgc gatgaaggcc ttcgggttgt | 420 |
| aaagcacttt tggcaggaaa gaaacgtcat gggttaatac cccgtgaaac tgacggtacc | 480 |
| tgcagaataa gcaccggcta actacgtgcc agcagccgcg gtaatacgta gggtgcaagc | 540 |
| gttaatcgga attactgggc gtaaagcgtg cgcaggcggt tcggaagaa agatgtgaaa | 600 |
| tcccagagct taactttgga actgcatttt taactaccgg gctagagtgt gtcagaggga | 660 |
| ggtggaattc cgcgtgtagc agtgaaatgc gtagatatgc ggaggaacac cgatggcgaa | 720 |
| ggcagcctcc tgggataaca ctgacgctca tgcacgaaag cgtggggagc aaacaggatt | 780 |
| agataccctg gtagtccacg ccctaaacga tgtcaactag ctgttggggc cttcgggcct | 840 |
| tagtagcgca gctaacgcgt gaagttgacc gcctggggag tacggtcgca agattaaaac | 900 |
| tcaaaggaat tgacggggac ccgcacaagc ggtggatgat gtggattaat tcgatgcaac | 960 |
| gcgaaaaacc ttacctaccc ttgacatgtc tggaattcng aagagattng gaagtgctcg | 1020 |
| caagagaacc ggaacacagg tgctgcatgg ctgtcgtcag ctcgtgtcgt gagatgttgg | 1080 |
| gttaagtccc gcaacgagcg caacccttgt cattagttgc tacgaaaggg cactctaatg | 1140 |
| agactgccgg tgacaaaccg gaggaaggtg gggatgacgt caagtcctca tggcccttat | 1200 |
| gggtagggct tcacacgtca tacaatggtc gggacagagg gtcgccaacc cgcgaggggg | 1260 |
| agccaatccc agaaacccga tcgtagtccg gatcgcagtc tgcaactcga ctgcgtgaag | 1320 |
| tcggaatcgc tagtaatcgc ggatcagcat gtcgcggtga atacgttccc gggtcttgta | 1380 |
| cacaccgccc gtcacaccat gggagtgggt tttaccagaa gtagttagcc taaccgnaag | 1440 |

```
gggggcgatt accacggtag gattcatgac tggggtgaag tcgtaacaag gtagccgtat   1500
cggaaggtgc ggctggatca cctcctttt                                    1528

<210> SEQ ID NO 123
<211> LENGTH: 1522
<212> TYPE: DNA
<213> ORGANISM: Microbacterium murale
<220> FEATURE:
<223> OTHER INFORMATION: 16S

<400> SEQUENCE: 123
tacggagagt ttgatcctgg ctcaggatga acgctggcgg cgtgcttaac acatgcaagt     60
cgaacggtga acacggagct tgctctgtgg gatcagtggc gaacgggtga gtaacacgtg    120
agcaacctgc ccctgactct gggataagcg ctggaaacgg cgtctaatac tggatatgtg    180
acgtggccgc atggtctgcg tctggaaaga atttcggttg gggatgggct cgcggcctat    240
cagcttgttg gtgaggtaat ggctcaccaa ggcgtcgacg ggtagccggc ctgagagggt    300
gaccggccac actgggactg agacacggcc cagactccta cgggaggcag cagtggggaa    360
tattgcacaa tgggcgcaag cctgatgcag caacgccgcg tgagggatga cggccttcgg    420
gttgtaaacc tcttttagca gggaagaagc gaaagtgacg gtacctgcag aaaaagcgcc    480
ggctaactac gtgccagcag ccgcggtaat acgtagggcg caagcgttat ccggaattat    540
tgggcgtaaa gagctcgtag gcggtttgtc gcgtctgctg tgaaatccgg aggctcaacc    600
tccggcctgc agtgggtacg ggcagactag agtgcggtag gggagattgg aattcctggt    660
gtagcggtgg aatgcgcaga tatcaggagg aacaccgatg gcgaaggcag atctctgggc    720
cgtaactgac gctgaggagc gaaagggtgg ggagcaaaca ggcttagata ccctggtagt    780
ccaccccgta acgttggga actagttgtg gggtccattc cacggattcc gtgacgcagc    840
taacgcatta agttccccgc ctggggagta cggccgcaag gctaaaactc aaaggaattg    900
acggggaccc gcacaagcgg cggagcatgc ggattaattc gatgcaacgc gaagaacctt    960
accaaggctt gacatatacg agaacgggcc agaaatggtc aactctttgg acactcgtaa   1020
acaggtggtg catggttgtc gtcagctcgt gtcgtgagat gttgggttaa gtcccgcaac   1080
gagcgcaacc ctcgttctat gttgccagca cgtaatggtg ggaactcatg ggatactgcc   1140
ggggtcaact cggaggaagg tggggatgac gtcaaatcat catgcccctt atgtcttggg   1200
cttcacgcat gctacaatgg ccggtacaaa gggctgcaat accgcgaggt ggagcgaatc   1260
ccaaaaagcc ggtcccagtt cggattgagg tctgcaactc gacctcatga agtcggagtc   1320
gctagtaatc gcagatcagc aacgctgcgg tgaatacgtt cccgggtctt gtacacaccg   1380
cccgtcaagt catgaaagtc ggtaacacct gaagccggtg gcctaaccct tgtgaggga   1440 gccgtcgaag gtgggatcgg taattaggac taagtcgtaa caaggtagcc gtaccggaag   1500
gtgcggctgg atcacctcct tt                                           1522

<210> SEQ ID NO 124
<211> LENGTH: 1537
<212> TYPE: DNA
<213> ORGANISM: Kluyvera intermedia
<220> FEATURE:
<223> OTHER INFORMATION: 16S
<220> FEATURE:
<221> NAME/KEY: modified_base
<222> LOCATION: (455)..(455)
<223> OTHER INFORMATION: a, c, t, g, unknown or other
<220> FEATURE:
```

<221> NAME/KEY: modified_base
<222> LOCATION: (1004)..(1004)
<223> OTHER INFORMATION: a, c, t, g, unknown or other

<400> SEQUENCE: 124

```
attgaagagt tgatcatgg ctcagattga acgctggcgg caggcctaac acatgcaagt      60
cgaacggtag cacagagagc ttgctctcgg gtgacgagtg gcggacgggt gagtaatgtc     120
tgggaaactg cccgatggag ggggataact actggaaacg gtagctaata ccgcataatg     180
tcgcaagacc aaagagggg accttcgggc ctcttgccat cggatgtgcc cagatgggat     240
tagcttgttg gtgaggtaat ggctcaccaa ggcgacgatc cctagctggt ctgagaggat     300
gaccagccac actggaactg agacacggtc cagactccta cgggaggcag cagtggggaa     360
tattgcacaa tgggcgcaag cctgatgcag ccatgccgcg tgtgtgaaga aggccttcgg     420
gttgtaaagc actttcagcg gggaggaagg cgatncggtt aataaccgtg ttgattgacg     480
ttacccgcag aagaagcacc ggctaactcc gtgccagcag ccgcggtaat acggagggtg     540
caagcgttaa tcggaattac tgggcgtaaa gcgcacgcag gcggtctgtc aagtcggatg     600
tgaaatcccc gggctcaacc tgggaactgc attcgaaact ggcaggcttg agtcttgtag     660
agggggtag aattccaggt gtagcggtga atgcgtaga gatctggagg ataccggtg       720
gcgaaggcgg cccctggac aaagactgac gctcaggtgc gaaagcgtgg ggagcaaaca    780
ggattagata ccctggtagt ccacgccgta acgatgtcg acttggaggt tgtgcccttg     840
aggcgtggct tccggagcta acgcgttaag tcgaccgcct ggggagtacg gccgcaaggt    900
taaaactcaa atgaattgac ggggggcccgc acaagcggtg gagcatgtgg tttaattcga    960
tgcaacgcga agaaccttac ctggtcttga catccacgga attggcaga gatgccttag    1020
tgccttcggg aaccgtgaga caggtgctgc atggctgtcg tcagctcgtg ttgtgaaatg    1080
ttgggttaag tcccgcaacg agcgcaaccc ttatcctttg ttgccagcgg tccggccggg    1140
aactcaaagg agactgccag tgataaactg gaggaaggtg gggatgacgt caagtcatca    1200
tggcccttac gaccagggct acacacgtgc tacaatggca tatacaaaga gaagcgacct    1260
cgcgagagca agcggacctc ataaagtatg tcgtagtccg gattggagtc tgcaactcga    1320
ctccatgaag tcggaatcgc tagtaatcgt ggatcagaat gccacggtga atacgttccc    1380
gggccttgta cacaccgccc gtcacaccat gggagtgggt tgcaaaagaa gtaggtagct    1440
taaccttcgg gagggcgctt accactttgt gattcatgac tggggtgaag tcgtaacaag    1500
gtaaccgtag gggaacctgc ggttggatca cctcctt                            1537
```

<210> SEQ ID NO 125
<211> LENGTH: 882
<212> TYPE: DNA
<213> ORGANISM: Kluyvera intermedia
<220> FEATURE:
<223> OTHER INFORMATION: nifH

<400> SEQUENCE: 125

```
atgaccatgc gtcaatgcgc catttatggc aaaggtggga tcggcaaatc caccaccacg      60
caaaacctcg tcgccgctct cgcggaaatg ggtaaaaaag tgatgatcgt cggctgcgac     120
ccgaaagcgg actccacccg tctgatcctg catgcgaaag cacagaacac cattatggag     180
atggccgccg aagtgggttc agtggaagac cttgaactgg aagatgtgct gcaaatcggt     240
tacggcggcg tgcgttgtgc agaatccggc ggcccggagc aggcgtgggt tgtgcaggc      300
cgcggcgtta ttaccgccat taacttcctt gaagaagaag gcgcctatgt cagcgacctc     360
```

```
gactttgtct tctatgacgt cctcggtgac gtggtctgcg gcgggttcgc catgccgatt    420
cgtgaaaaca aagcgcaaga gatctatatc gtctgctccg gggaaatgat ggcgatgtat    480
gccgctaaca acatctccaa aggcatcgtg aaatacgcta atccggcaa ggtgcgcctg     540 ggcgggctga tttgtaactc ccgtcagacc gaccgcgaag atgaactgat catcgcgctg    600
gcagaaaaac tgggcaccca gatgattcac tttgtgccac gcgacaacat cgtccagcgc    660
gcggaaattc gccgtatgac ggttatcgaa atgacccga aatgcaacca ggccgacgaa      720
taccgcgcgc tggcgaacaa gatcgtcaac aacaccctga tggtcgtccc gacccccttgc   780 accatggatg aactggaaga gctgctgatg aattcggca ttatggatgt ggaagacgcc      840
agcatcatcg gtaaaaccgc cgccgaagaa aacgcggcct ga                       882
```

<210> SEQ ID NO 126
<211> LENGTH: 660
<212> TYPE: DNA
<213> ORGANISM: Kluyvera intermedia
<220> FEATURE:
<223> OTHER INFORMATION: Dinitrogenase iron-molybdenum cofactor CDS

<400> SEQUENCE: 126

```
atgaacgata acgatgtcct tttctggcgc atgctggcgc tatttcagtg tctgccggaa    60
ctgcaacccg cgcagatcct ggcctggctg acaggagaac gcgacgacgc cttaaccccg    120
gcgtacctcg ataagcttaa cgtccgcgaa ctggaagcga ccttcccgtc tgaaacggcg    180
atgatgtcgc ccgcacgctg gagccgcgtt aacgcgtgcc ttcacggtac gctgcccgca    240
cacctgcagg taaaaagcac cactcgtcag gggcaattac gggtagcctt tgttcacag    300 gatggattgc tgatcaatgg tcattttggt caggggcggc tgttttttat ctacgccttt    360
gatgaacagg gcggatggct acacgcgtta cgccgtcttc cctcggcccc gcaaacccag    420
gagccgaatg aagttcgcgc gcagctcctg agtgattgcc acctgctgtt ttgtgaagcc    480
attggcggcc ctgcggcggc ccggctgatt cgtcacaata tccacccgat gaaagtgtcg    540
ccagggatgt ccattgccgc ccagtgtgat gccattaccg cactgctgag cggacgtctg    600
ccaccgtggc tggcaaaacg tcttgagaaa gccaacccgc tggaagagcg ggtgttttaa   660
```

<210> SEQ ID NO 127
<211> LENGTH: 1374
<212> TYPE: DNA
<213> ORGANISM: Kluyvera intermedia
<220> FEATURE:
<223> OTHER INFORMATION: nifD1

<400> SEQUENCE: 127

```
atgaagggaa atgacattct cgcgctgctg atgaacccg cctgcgaaca caatcacaaa     60
cagaaatccg gctgtagcgc ccctaaaccc ggtgccacgg cggcggttg cgcgttcgac    120 ggcgcgcaaa tcaccctgtt gccgctgtcg gatgtggcgc acctggtcca cggaccgatt    180
ggctgcacgg gaagctcctg ggataaccgg gcagtatga gctccggccc cagtctcaac    240
cggctcggct ttaccaccga cctgaacgag caggatgtca ttatggggcg cggcgaacgg    300
cggcttttcc acgcggtgcg tcatatcgtc aaccgttatc accctgccgc cgtgtttatc    360
tataacacct gcgttccggc gatggagggt gatgatattg acgccgtctg tcaggcggcg    420
gaaaccgcca ccgcgtgcc agtgattgcc gttgatgccg ccgggttcta tggcagcaaa    480
aaccttggca accgtctcgc gggtgaagtg atggttaaca aggtcattgg acggcgcccg    540
```

| | |
|---|---|
| cccgccccct ggccggacga tacccccttc gcgccggaac accgccacga tatcggcctg | 600 |
| attggcgaat ttaatatcgc cggggagttc tggcacgttc agccgctgct cgatgagctg | 660 |
| ggtattcgcg tgctgggcag cctttccggg gatggccgtt ttagtgaaat ccagaccctg | 720 |
| caccacgcgc aggtcaatat gctggtctgc tcaagagcgc tgatcaatgt tgcccgcacc | 780 |
| ctggaacagc gctatggcac cccctggttt gagggcagtt tttacggcgt gcgcgctacc | 840 |
| tccgatgccc tgcgtcaact ggcatccctg cttggcgaca cgatctgat tgcccgcacc | 900 |
| gaagccgtta ttgcccgcga agaagccacg gcaaatcagg cgctcgcccc gtggcgcgaa | 960 |
| cggctacagg gtcgcaaagt gctgctctat accggtgggg tgaaatcctg gtcggtggtc | 1020 |
| tccgcattgc aggatttagg gatgaccgtc gtggcgactg gcacccgcaa atctaccgaa | 1080 |
| gaagataagc agcgtattcg cgaattaatg ggcgatgacg cgctaatgct ggaagaaggc | 1140 |
| aacgcccgca ccctgctgga tgtggtgtac cgctatcagg cggatttgat gatcgctggg | 1200 |
| gggcgtaaca tgtataccgc gtacaaagcg cggctgccgt ttctggatat caaccaggag | 1260 |
| cgtgaacacg cctttgcggg ttatcgcggc atcgtcaccc tcgcccaaca gctttgccag | 1320 |
| actattgaaa gccccgtctg gccgcaaaca cacgcccgcg cgccgtggca ataa | 1374 |

<210> SEQ ID NO 128
<211> LENGTH: 1449
<212> TYPE: DNA
<213> ORGANISM: Kluyvera intermedia
<220> FEATURE:
<223> OTHER INFORMATION: nifD2

<400> SEQUENCE: 128

| | |
|---|---|
| atgagcaatg caacaggcga acgtaatctg gaaattatcc aggaagtgct ggagatcttt | 60 |
| cccgaaaaaa cgcgcaaaga acgcagaaag cacatgatgg tgaccgaccc ggagatggaa | 120 |
| agcgtcggga aatgcatcat ctctaaccgc aaatcgcagc cgggtgtgat gactgtccgc | 180 |
| ggctgctcct acgccgggtc gaaaggcgtg gtttttgggc cgattaaaga tatgccccac | 240 |
| atctcccacg cccgatcgg ctgtgggcag tactcccgtg ccgggcggcg caactactac | 300 |
| accggggtca gcgcgttga ttccttcggg acgctgaact ttacctctga ttttcaggag | 360 |
| cgcgatatcg tcttcggcgg cgataaaaag ctcaccaaac tgattgagga gatggaggaa | 420 |
| ctgttcccgc tgaccaaagg catctccatt cagtcggagt gcccggtagg tttaatcggt | 480 |
| gacgatatcg aagcggtggc gaatgccagt aaaaaagcgc tcaacaagcc ggtgatcccg | 540 |
| gtgcgttgcg aaggctttcg cggcgtgtcg cagtcgctcg tcaccatat cgccaacgac | 600 |
| gttatccgcg actgggtgct ggataaccgc gaagggaagc cttcgaatc taccccctat | 660 |
| gacgtggcca tcatcggcga ttacaacatc ggggggggatg cctgggcgtc gcgcattctg | 720 |
| cttgaagaga tgggggттacg cgtggtggcg cagtggtccg gtgacggcac gctggtagag | 780 |
| atggaaaaca ccccgttcgt caagctgaac ctggtgcact gctaccgctc tatgaactac | 840 |
| atctctcgcc atatggaaga gaaacacggt atcccgtgga tggagtacaa cttcttcggc | 900 |
| ccgaccaaaa tcgccgaatc gctgcgtaag atcgccgatc aatttgacga caccatccgc | 960 |
| gccaatgcgg aagcggtgat cgccaaatat caggcgcaaa cgatgcgat tatcgccaaa | 1020 |
| taccgcccgc gtctcgaagg ccgcaaggtg ctgctctata tgggtggcct gcgtcctcgc | 1080 |
| cacgtgattg gcgcgtatga ggatttgggc atgagattg tcgccgcgg gtatgaattt | 1140 |
| gcccataacg acgattacga ccgcaccctg ccggacctca agagggcac gctgttgttc | 1200 |
| gacgatgcca gcagttatga actggaagcc ttcgtgaagg cgattaagcc ggacctcatt | 1260 |

```
ggctcaggca tcaaggaaaa atacattttc cagaaaatgg gggtaccgtt tcgccagatg      1320
cactcctggg attactccgg cccgtatcac ggctatgacg ctttgccat ctttgcccgc       1380 gatatggaca tgacgctcaa caatcccgcc tggggcgagt tgaccgcacc ctggctgaaa      1440
tcagcctga                                                              1449
```

<210> SEQ ID NO 129
<211> LENGTH: 1383
<212> TYPE: DNA
<213> ORGANISM: Kluyvera intermedia
<220> FEATURE:
<223> OTHER INFORMATION: nifK1

<400> SEQUENCE: 129

```
atggcagata tcatccgtaa tcagaaaccg ctggcggtaa gcccggtaaa aagcggccag        60
ccgttaggcg ccattctggc gagcctcggc tttgagcaca gtattccact ggtgcacggt       120
gcgcagggat gcagcgcgtt cgccaaagtg tttttttatcc aacatttttca tgacccctatt    180 ccgctgcaat ccacggcgat ggaccccacc tcaacggtca tggggggcgga cggcaatatc     240 cttgccgcgc tcaatacgct gtgccagcgc aacaccccga agctatcgt cctgttgagt       300 accggcctgt ctgaggcgca gggcagcgat atcagccgcg tggtacgtca gtttcgtgag      360
gattttcccc gccacaaaaa tatcgccctc ctgacggtca cacccccgga tttttacggc     420
acgctggaga acggctttag tgcggtggtg gaaagcgtca tcgaacagtg ggtgccggaa     480
aagcctcagc atggcctgcg taaccggcgg gtcaacttgt tgttaagtca cctgctgacg     540
cccggtgatg ttgagttgct gcgcagctac gtggaggctt ttggcctgca accggtgatc     600
gtgccggatc tttcacagtc gctggatggt cacctggcaa gcggtgattt ttcgccggtc     660 actcagggg gaacgcccct gcgcattatc gaacagatgg gacagagcct gtgcacgttt      720
gctattggcg tgtcgctgtc ccgtgcggca tcgctgctgg cacagcgtag ccgtggcgag    780
gtgatcgtgc ttccccatct gatgaccatg aacattgcg accgttttat tcatcaactg    840
aagatcattt ccgggcgcga ggttcccgcc tggattgagc gccagcgcgg acaattgcag    900
gatgcgatga tcgattgtca tatgtggttg caggataccc ggctcgcgct ggccgccgag    960
ggcgatctgc tggcgggctg gtgtgatttc gcccgtagcc agggcatgct ccccggcccc   1020
gttgtggcgc cggtcagcca gccgggcctg caacagcttc ccgtggagaa agtggtcatt   1080
ggcgatctgg aagatatgca ggatttactc tgcgctatgc ctgctgacct gctggtcgcc   1140
aactcccatg ccgcagacct ggccgaacaa ttctccatcc cgctgatccg cgccgggttc   1200
cctatcttcg acaggcttgg cgaatttcgt cgcgtgcgtc agggatacccc cggcattcgc   1260 gacacgctgt ttgagctggc gaacctgatg cgcgaacgtc atcaccacct gcccgtctac   1320
cgctcccccc tgcgccagca atttgcccag gacgctgacg gaggccgcta tgcaacatgt   1380
taa                                                                 1383
```

<210> SEQ ID NO 130
<211> LENGTH: 1563
<212> TYPE: DNA
<213> ORGANISM: Kluyvera intermedia
<220> FEATURE:
<223> OTHER INFORMATION: nifK2

<400> SEQUENCE: 130

```
atgagccaaa ctgctgagaa aattgtcacc tgtcatccgc tgtttgaaca ggacgaatac      60
cagacgctgt ttcgcaataa gcgcggtctg gaagaggcgc acgacccgca gcgcgtgcaa     120
gaggttttg aatggaccac cacggcggag tatgaagcgc tgaactttaa gcgtgaagcg     180
ttaaccgtcg atccggcaaa ggcctgccag cctttaggat cggtactctg ctcgctgggt     240
tttgccaata cgctgcctta tgtgcacggt tcccagggct gtgtggccta tttccgcacc     300
tattttaacc gtcatttcaa agagccgatc gcttgcgttt ccgactctat gacagaggat     360
gcggcggtct tcggcggcaa caacaacctt aacaccgggt tgcaaaatgc cagcgccctg     420
tacaaaccgg aaattgtcgc tgtctccact acctgtatgg cggaggtcat cggcgatgac     480
ctgcaggcct ttatcgccaa cgccaaaaag gacgggttta ttgatgccgc cattccggtg     540
ccctacgccc atacgccaag ttttatcggt agccacatca ccggctggga caacatgttt     600
gaaggtttcg cccgggcatt taccgccgat acgtgcgc aaccgggcaa actggcgaag     660
ctaaacctgg tgaccggttt tgaaacctat cttggcaatt accgcgtgct caaacgcatg     720
atggcccaga tggaggtgcc ctgtagcctg ctgtctgacc cgtctgaggt gttagatacg     780
ccagccgacg gccactatcg catgtatgcg ggcggcacaa cgcaacaaga gatgcgcgac     840
gcccccgatg ctatcgacac cctgctgctg caaccctggc atctggtgaa gagtaaaaaa     900
gtggtgcagg agtcctgggg ccagcccgcc acagaagtgt ccatcccaat gggactgacc     960
gggaccgacg aactgctgat ggcagtcagt cagttaaccg gcaaaccggt ggccgatgaa    1020
ctgacgctgg agcgtgggcg cctggtggat atgattctcg attcacacac ctggctgcac    1080
ggtaagaaat tcggtctcta cggcgatccg gattttgtga tggggctgac gcgtttcctg    1140
ctggaactgg gctgcgagcc gacggttatc ctctgtcata acggtagcaa gcgctggcag    1200
aaagcgatga agaaaatgct tgaggcatcg ccctacggtc aggagagcga agtgttcatc    1260
aactgcgatc tgtggcattt ccgctcgctg atgtttaccc gcaaaccgga ctttatgatc    1320
ggcaactcgt acgccaaatt catccagcgt gacacgctgg cgaaaggcga acagtttgaa    1380
gttccgctga tccgtcttgg cttcccgttg ttcgaccgcc accacctgca tcgccagacc    1440
acatggggtt atgaaggggc gatgaatatc gtcaccaccc tggtcaacgc cgtgctggaa    1500
aaagtcgacc gcgataccat caaactgggc aaaacggact acagcttcga ccttgtccgc    1560
taa                                                                 1563
```

<210> SEQ ID NO 131
<211> LENGTH: 1488
<212> TYPE: DNA
<213> ORGANISM: Kluyvera intermedia
<220> FEATURE:
<223> OTHER INFORMATION: nifL

<400> SEQUENCE: 131

```
atgacccttta atatgatgct ggagaccagc gcaccgcagc acattgcggg caacctctca      60
cttcaacatc ccggactgtt ttccacgatg gttgaacagg ctccgatcgc gatttcgctg     120
accgaccccgg acgcgaggat tctgtacgct aatccggcct tttgtcgcca gaccggttat     180
agcctggaag agctgctcaa ccagaaccat cgcatactgg caagccaaca gacgccgcgc     240
agcatttatc aggaactgtg gcaaacgctg ctgcaacaga tgcccctggcg cggtcagctc     300
atcaatcgcc gtcgggatgg cagcctttat ctggctgagg tcgatatcac cccggtcgtc     360
```

```
aacaaacagg gcgaactgga acactacctc gccatgcaac gtgatatcag cgccagctat      420
gcgctcgaac agcgattgcg caatcacacc accatgagcg aggcggtgct gaacaacatt      480
cctgccgccg tggtggtggt caacgagcag gaccaggtag tcatggacaa cctcgcctac      540
aaaaccttct gtgccgactg cggtggcaag gagctgctca ccgaactgga tttctcccgg      600
cgcaaaagcg atctctatgc cgggcaaata ctgcctgtgg tgctgcgcgg cgccgtgcgc      660
tggctctctg tcacctgctg gaccttgccg ggggtgagcg aagaagccag ccgctacttt      720
attgataccg cgctgccccg caccctggtg gtgatcaccg actgcaccca gcaacaacaa      780
caggccgaac agggccgtct cgatcgtctc aaacaggaga tgaccaccgg gaagctgctg      840
gccgcgatcc gtgaatcgtt ggatgccgcg ctggttcagc taaactgccc catcaatatg      900
ctggcggcgg cgcgacgtct caacggtgaa gataaccata cgtggcgct ggatgccgcg      960 tggcgcgagg gggaagaggc gctggcccgc ctgcaacgct gccgcccttc tctcgatctg     1020
gaagagagcg cgctgtggcc tctgcaaccg ctgtttgacg acctgcgcgc cctttaccat     1080
acccgctata caatggcga aaatctgcac gttgaaatgg cctctccgca tctggcgggg     1140
tttggtcagc gcacgcagat ccttgcctgt ctcagtttgt ggctcgaccg tacgctggcc     1200
ctcgccgccg cgctaccgga cagaacgctg catacccagc tttacgcccg tgaagaagat     1260
ggctggctgt ccatttggct gacagataat gtgccgctca tccatgtgcg atacgcccac     1320
tcccccgatg ccctgaacgc ccccggcaaa gggatggagc tgcgattgat tcaaaccctg     1380
gttgcccatc atcgcggcgc aatagaacta actacccgcc tgaaggcgg tacctgcctg     1440 accctgcgat tcccgttatt tcattcactg accggaggcc cacgatga                  1488

<210> SEQ ID NO 132
<211> LENGTH: 1572
<212> TYPE: DNA
<213> ORGANISM: Kluyvera intermedia
<220> FEATURE:
<223> OTHER INFORMATION: nifA

<400> SEQUENCE: 132
atgacccagc gacccgagtc gggcaccacc gtctggcgtt ttgatctctc acagcaattt       60
accgccatgc agcgcatcag cgtggtgttg agtcgcgcaa ccgagataag ccagacgctg      120
caggaggtgc tgtgtgttct gcataatgac gcatttatgc aacacggcat gctgtgtctg      180
tatgacaacc agcaggaaat tctgagtatt gaagccttgc aggaggcaga ccaacatctg      240
atccccggca gctcgcaaat tcgctatcgc cctggcgaag ggctggtagg agccgtactg      300
tcccagggac aatctcttgt gctgccgcgt gtcgccgacg atcaacgctt tctcgacagg      360
cttggcatct atgattacaa cctgccgttt atcgccgtcc ccttaatggg gccaggcgcg      420
cagacgattg gcgtgctcgc cgcgcagccg atggcgcgtc tggaggagcg gcttccttcc      480
tgtacgcgct ttctggaaac cgtcgccaat ctggtcgcac agacagtccg gctgatgacc      540
ccgcctgccg ccgccacacc gcgcgccgcg attgcccaga ccgaacgcca gcgcaactgt      600
ggcactcctc gcccttcgg ctttgagaat atggtgggca aaagcccggc catgcagcag      660
acaatggaca ttatccgcca ggtttcgcgc tgggatacca cggtactggt gcgcggcgaa      720
agcggcaccg gtaaagaact tatcgccaat gctattcatc acaactcccc tcgcgccgcc      780
gcgccctttg tgaaatttaa ctgcgcggcg ctaccggata cgctactgga gagcgaattg      840
ttcggccatg aaaaaggggc gttcaccggc gcggttcgcc agcgtaaagg acgttttgaa      900
ctggccgatg gcggcacact gtttcttgat gaaattggcg aaagcagcgc ctcgttccag      960
```

```
gccaaactgc tgcgtatttt gcaggagggt gaaatggagc gcgttggcgg cgacgaaacc    1020
ctgcgcgtca atgtgcgtat catcgccgcc accaaccgga atctggaaga agaggtgcgg    1080
atgggcaatt ccgcgagga tctctattat cgcctcaacg taatgcccat ctccctgccc    1140
ccgctgcgtg aacgtcagga ggacattgcc gagctggcgc actttctggt gcgcaaaatc    1200
gcccataacc aggggcgtac gctgcgcatc agtgatggcg ccatccgtct gctgatgggt    1260
tacaactggc ccgtaacgt gcgtgagctg aaaaattgcc tggaacgttc ggcagtgatg    1320
tcagaaaacg gcctgatcga ccgcgatgtg gtgctcttta accaccgtga aacacgcca    1380 aaactcgcta tcgccgccgc gccaaaagag gatagctggc ttgatcaaac gctggatgaa    1440
cgtcaacggc tgattgccgc gctggaaaaa gccgggtggg tgcaggccaa agcggcgcgt    1500
ctgctgggta tgacgccccg tcaggtcgcc tatcggatac aaattatgga tatcagcatg    1560
cccaggatgt ga                                                        1572

<210> SEQ ID NO 133
<211> LENGTH: 2853
<212> TYPE: DNA
<213> ORGANISM: Kluyvera intermedia
<220> FEATURE:
<223> OTHER INFORMATION: glnE

<400> SEQUENCE: 133
atgatgccgc actctccaca gctacagcag cactggcaaa ctgtactggc ccgcttgcct      60
gagtcattca gtgaaacacc gcttagtgaa caagcgcagt tagtgcttac tttcagtgat     120
tttgtgcagg atagccttgc cgcgcatcct gactggctgg ctgagctgga aagcgcaccg     180
ccacaggcgg acgagtggaa gcagtatgcg caaaccctttc gcgaatcgct ggaaggtgtg     240
ggagatgagg catcattaat gcgtgcgctg cgcctgttcc gtcgccatat gatggtgcgc     300
attgcctggg cgcagtcgct ggcgctggtg gcagaagatg agacgttgca gcagttgagc     360
gtactggcgg agaccctgat cgtcgctgca cgcgactggc tttacgatgc ctgctgtcgc     420
gagtggggaa cgccgtgcaa tcagcagggg gaaccgcagc cgttgctgat cctgggcatg     480
ggcaagctgg gtggcgggga gcttaacttt tcgtccgata tcgatctgat ttttgcctgg     540
ccggaaaacg gttcaacgcg cggtgggcga cgcgaacttg ataacgccca gttttttact     600
cgcttgggac agcgcctgat caaagtgctc gaccagccga cgcaggatgg ctttgtctat     660
cgcgtggata tgcggctgcg cccgtttggc gacagcggtc cgctggtgct gagttttgcc     720
gcgctggaag attattatca ggagcagggg cgcgactggg aacgttatgc gatggtgaaa     780
gcccgcatta tgggcgataa ggacgatgtt tacgctggcg aattacgggc catgctgcgg     840
ccgttcgtct tccgtcgcta tatcgatttc agcgttattc agtctctgcg taacatgaaa     900
gggatgattg cccgcgaagt gcgccgccgt ggtctgaaag ataacattaa gctgggcgcg     960
ggcggcatcc gtgagattga gtttatcgtt caggtgttcc agttgatacg cggtgggcgc    1020
gagccgtcgt tgcagtcccg ttcactgtta ccgacgctgg acgctatcga taagctgggt    1080
ttgctgccgc ctggcgatgc accggcgtta cgccaggcct atttgtatct gcgccgtctg    1140
gaaaacctgc tgcaaagcat taacgacgaa caaacgcaga cgctgccgac agatgaactc    1200
aatcgcgcgc gtctggcctg ggggatgcgg gtcgcagact gggaaaccct gaccgctgag    1260
cttgaaaagc agatgtctgc cgtacgaggg atattcaaca ccctgattgg cgatgacgaa    1320
gccgaagagc aggggggatgc gctctgcggg caatggagtg agttgtggca ggatgcgttt    1380
```

```
caggaagatg acagcacgcc tgtgctggcg cacctttctg acgatgatcg ccgccgcgtg    1440
gtcgcgatga ttgctgattt tcgcaaagag ctggataaac gcaccattgg cccacgcggc    1500
cgccaggtgc tcgaccatct gatgccgcat ctgttgagtg atgtctgctc ccgtgaggat    1560
gcccctgtac cgttgtctcg cgtgacgccg ctgttaacgg aattgtcac gcgtacgacg     1620
tatcttgagc tgctcagcga gtttcctggt gcgcgtaagc atctgatttc actctgtgcc    1680
gcctcgccga tggtggccag taagctggcg cgctatccgt tattgctgga tgagttgctc    1740
gatccgaata ccctttatca gcccacggcg atgaatgcct accgggatga gctacgtcag    1800
tatctgctgc gtgtgccgga tgacgatgaa gagcagcaac tggaggcgtt acgccagttt    1860
aaacaggctc aattgttgcg tgtggcggca gcagatctgg caggcacact ccccgtgatg    1920
aaagtgagcg atcacttaac atggcttgcc gaagccatca ttgaagccgt ggtacaacag    1980
gcgtggagcc tgatggtatc gcgttatggg cagccgaaac acttacgcga ccgtgaaggc    2040
cgtgggtttg cagtggtcgg ttacggcaaa ctgggcggtt gggagctggg ctatagttcc    2100
gatctggatt tgattttcct tcatgactgt ccggtgacg tgatgactga cggcgagcgg     2160
gaaatcgatg gccgccaatt ttatctgcgc cttgcccagc gcgtgatgca cctgttcagt    2220
acgcgcacct catccgggat cctgtatgag gtagacgcgc gcttgcgccc gtccggtgcg    2280
gcgggaatgc tggtgacctc aaccgaatcc tttgccgact accagcgcac cgaagcctgg    2340
acctgggaac atcaggcgct ggttcgcgcc cgcgttgtct atggcgatcc acaattaaac    2400
gcgcaatttg atgccatccg ccgcgatatc accatgaccg tgcgtaatgg tgcaacgtta    2460
caaaccgagg tgcgcgagat gcgcgaaaaa atgcgcgccc acttgagcaa taagcacaag    2520
gatcgctttg atattaaagc cgatgagggt ggaattaccg atatcgaatt tatcacccag    2580
tatctggtgc tgcgttatgc ccatgccaaa ccgaaactga cgcgctggtc ggacaatgtc    2640
cgcattctgg aagggctggc gcaaaacggc attatggaag agcaggaagc gcaggcactt    2700
accaccgcct atacaacgtt gcgtgatgag ctgcatcacc tggcgctaca ggagctgcca    2760
ggacatgttc cggaggcatg ttttgtcgct gaacgcgcga tggtgcgagc ctgctggaac    2820
aagtggttgg tggagccgtg cgaggacgcg taa                                 2853
```

<210> SEQ ID NO 134  
<211> LENGTH: 1290  
<212> TYPE: DNA  
<213> ORGANISM: Kluyvera intermedia  
<220> FEATURE:  
<223> OTHER INFORMATION: amtB

<400> SEQUENCE: 134

```
atgaagaaag cactattaaa agcgggtctg gcctcgctgg cattactgcc gtgtctggct      60
atggcagccg atccggttgt cgtcgataaa gccgacaatg cctttatgat gatttgcacc     120
gcgctggtgc tgtttatgtc aattccgggc atcgccctgt tctatggtgg tttaatccgc    180
ggtaaaaacg tcctttctat gctgacacag gttgcggtta cgttcgcact ggtgtgcgtg    240
ctgtgggtgg tttacggcta ctctctggcc tttggcactg gcggcagctt cttcggtagc    300
ttcgactggg tgatgctgaa aaatattgag ctgaaagcgc tgatgggcac catctatcag    360
tacattcacg ttgcgttcca gggctcgttt gcctgtatta ccgtcggcct gattgtcggt    420
gcgctggcag aacgtatccg tttctccgca gtactgattt tcgtcgtggt atggctgacg    480
ctgtcctacg tgccgatcgc acacatggtc tgggcggcg gtctgctggc aacccatggc    540
gccatggatt ttgcgggcgg tacagtcgtt cacatcaacg cagccgttgc aggcctggtg    600
```

-continued

```
ggtgcttacc tgattggcaa acgtgtcggt ttcggtaaag aagcgtttaa accgcacaac    660
ctgccgatgg tgtttaccgg tacggcaatc ctctactttg gctggttcgg attcaacgcg    720
ggttctgcaa gcgcggcgaa cgaaattgcg ggtctggctt ttgttaacac cgtcgtggca    780
acagcgggtg caatcctctc ctgggtcttc ggtgagtggg cgctgcgcgg caaaccgtct    840
ctgttgggtg cctgttctgg tgcgattgct ggcctcgtgg gtatcacccc ggcgtgtggt    900
tacgttggtg tgggtggcgc gctgatcgtg ggcatcgttg caggcctggc gggtctgtgg    960
ggcgttaccg cgctgaaacg ctggctgcgt gttgacgacc cgtgtgatgt cttcggtgtt   1020 cacgcgtgt gcggtatcgt aggttgtatc atgacaggta tcttcgcagc cacttcactg    1080
ggcggcgtgg gttatgccga aggcgtgacc atgggccatc aggttctggt acaactggaa   1140
agtatcgcca ttactatcgt atggtctggt atcgtcgcct ttatcggtta caaactggct   1200
gatatgacag tgggtctgcg tgttccggaa gatcaggaac gcgaagggct ggacgtcaac   1260
agccacggcg agaacgccta caacgcctga                                    1290
```

<210> SEQ ID NO 135
<211> LENGTH: 498
<212> TYPE: DNA
<213> ORGANISM: Kluyvera intermedia
<220> FEATURE:
<223> OTHER INFORMATION: PinfC

<400> SEQUENCE: 135

```
ctggggtcac tggagcgctt tatcggcatc ctgaccgaag aatttgccgg tttcttcccg    60
acctggctgg cccctgttca ggttgtggtg atgaatatca ctgattctca agctgaatat   120
gtcaacgaat tgaccctgtaa attgcaaaat gcgggcattc gtgtaaaagc ggacttgaga   180
aacgagaaga ttggctttaa aatccgcgag cacactttac gtcgtgtccc ttatatgttg   240
gtctgtggtg ataaagaggt ggaagcaggc aaagtggccg ttcgcacccg ccgcggtaaa   300
gacctgggca gcctggacgt aagtgaagtg attgagaagc tgcaacaaga gattcgcagc   360
cgcagtcttc aacaactgga ggaataaggt attaaggcg gaaaacgagt tcaaacggca   420
cgtccgaatc gtatcaatgg cgagattcgc gcccaggaag ttcgcttaac tggtctggaa   480
ggtgagcagc tgggtatt                                                 498
```

<210> SEQ ID NO 136
<211> LENGTH: 1537
<212> TYPE: DNA
<213> ORGANISM: Kosakonia pseudosacchari
<220> FEATURE:
<223> OTHER INFORMATION: 16S
<220> FEATURE:
<221> NAME/KEY: modified_base
<222> LOCATION: (454)..(454)
<223> OTHER INFORMATION: a, c, t, g, unknown or other

<400> SEQUENCE: 136

```
attgaagagt ttgatcatgg ctcagattga acgctggcgg caggcctaac acatgcaagt    60
cgaacggtag cacagagagc ttgctctcgg gtgacgagtg cggacgggt gagtaatgtc    120 tgggaaactg cctgatggag ggggataact actggaaacg gtagctaata ccgcataacg   180
tcgcaagacc aaagaggggg accttcgggc ctcttgccat cagatgtgcc cagatgggat   240
tagctagtag gtggggtaac ggctcaccta ggcgacgatc cctagctggt ctgagaggat   300
gaccagccac actggaactg agacacggtc cagactccta cgggaggcag cagtggggaa   360
```

```
tattgcacaa tgggcgcaag cctgatgcag ccatgccgcg tgtatgaaga aggccttcgg    420
gttgtaaagt actttcagcg gggaggaagg cganacggtt aataaccgtg ttgattgacg    480
ttacccgcag aagaagcacc ggctaactcc gtgccagcag ccgcggtaat acggagggtg    540
caagcgttaa tcggaattac tgggcgtaaa gcgcacgcag gcggtctgtc aagtcggatg    600
tgaaatcccc gggctcaacc tgggaactgc atccgaaact ggcaggcttg agtctcgtag    660
agggaggtag aattccaggt gtagcggtga atgcgtaga gatctggagg aataccggtg    720
gcgaaggcgg cctcctggac aagactgac gctcaggtgc gaaagcgtgg ggagcaaaca    780
ggattagata ccctggtagt ccacgccgta acgatgtct atttggaggt tgtgcccttg    840
aggcgtggct tccggagcta acgcgttaaa tagaccgcct ggggagtacg gccgcaaggt    900
taaaactcaa atgaattgac gggggcccgc acaagcggtg gagcatgtgg tttaattcga    960
tgcaacgcga agaaccttac ctggtcttga catccacaga acttgccaga gatggcttgg   1020
tgccttcggg aactgtgaga caggtgctgc atggctgtcg tcagctcgtg ttgtgaaatg   1080
ttgggttaag tcccgcaacg agcgcaaccc ttatcctttg ttgccagcgg tccggccggg   1140
aactcaaagg agactgccag tgataaactg gaggaaggtg gggatgacgt caagtcatca   1200
tggcccttac gaccagggct acacacgtgc tacaatggcg catacaaaga gaagcgacct   1260
cgcgagagca agcggacctc ataaagtgcg tcgtagtccg gattggagtc tgcaactcga   1320
ctccatgaag tcggaatcgc tagtaatcgt ggatcagaat gccacggtga atacgttccc   1380
gggccttgta cacaccgccc gtcacaccat gggagtgggt tgcaaaagaa gtaggtagct   1440
taaccttcgg gagggcgctt accactttgt gattcatgac tggggtgaag tcgtaacaag   1500
gtaaccgtag gggaacctgc ggttggatca cctcctt                            1537
```

<210> SEQ ID NO 137
<211> LENGTH: 882
<212> TYPE: DNA
<213> ORGANISM: Kosakonia pseudosacchari
<220> FEATURE:
<223> OTHER INFORMATION: nifH

<400> SEQUENCE: 137

```
atgaccatgc gtcaatgcgc catttacggc aaaggtggga tcggtaaatc gaccaccaca     60
cagaacctgg tcgccgcgct ggcggagatg ggtaagaaag tcatgatcgt cggctgcgat    120
ccgaaagccg actccacgcg tttgatcctg catgcgaaag cgcagaacac cattatggag    180
atggccgccg aagtcggctc cgtcgaagac ctggaattag aagacgtgct gcaaatcggt    240
tacggcggcg tgcgctgcgc ggaatccggt ggcccggagc aggtgtggg ttgtgccggt    300 cgtggcgtga tcaccgcgat taacttcctc gaagaagaag gcgcttacgt gccggatctg    360
gattttgttt tctacgacgt gctgggcgac gtggtatgcg gtggtttcgc catgccgatt    420
cgtgaaaaca aagcgcagga gatctacatc gtttgctctg gcgaaatgat ggcgatgtac    480
gccgccaata acatctccaa aggcatcgtg aaatatgcca atccggtaa agtgcgcctc    540 ggcgggctga tttgtaactc gcgccagacc gaccgcgaag atgaactcat cattgcgctg    600
gcggaaaaac tcggcacgca aatgatccac tttgttcccc gcgacaacat tgtgcagcgt    660
gcggaaatcc gccgtatgac ggttatcgaa tatgacccga cctgcaatca ggccaacgaa    720
tatcgcagcc ttgccagcaa aatcgtcaac aacaccaaaa tggtggtacc aacccctgc   780 accatggatg aactggaaga actgctgatg gagttcggca ttatgatgt ggaagacgcc    840 agcatcattg gtaaaaccgc cgccgaagaa aacgccgtct ga                      882
```

<210> SEQ ID NO 138
<211> LENGTH: 1449
<212> TYPE: DNA
<213> ORGANISM: Kosakonia pseudosacchari
<220> FEATURE:
<223> OTHER INFORMATION: nifD1

<400> SEQUENCE: 138

| | | | | | |
|---|---|---|---|---|---|
| atgagcaatg | caacaggcga | acgtaacctg | gaaatcatcg | agcaggtgct | ggaggttttc | 60 |
| ccggaaaaga | cgcgcaaaga | gcgcagaaaa | cacatgatgg | tgacggaccc | ggagcaggag | 120 |
| agcgtcggca | agtgcatcat | ctctaaccgc | aaatcgcagc | cggcgtgat | gaccgtgcgt | 180 |
| ggctgctcgt | atgccggatc | aaaaggggtg | gtatttgggc | caatcaaaga | tatggcgcat | 240 |
| atctcccacg | gcccgatcgg | ctgcgggcag | tactcccgcg | ccgggcggcg | taactactat | 300 |
| accggcgtca | gcggcgtgga | cagtttcggc | acgctcaact | tcacctccga | tttccaggag | 360 |
| cgcgacatcg | tgtttggcgg | cgacaaaaag | ctcgccaaac | tgattgaaga | gctggaagaa | 420 |
| ctgtttccgc | tgaccaaagg | catttcgatt | cagtcggaat | gcccggtcgg | cctgattggc | 480 |
| gatgatattg | aagccgtggc | gaacgccagc | cgcaaagcga | tcaacaaacc | ggttattccg | 540 |
| gtgcgttgcg | aaggctttcg | cggcgtgtcg | caatccctcg | gtcaccatat | gccaacgat | 600 |
| gtgatccgcg | actgggtact | ggataaccgc | gaaggcaaac | cgtttgaatc | cacccttac | 660 |
| gatgtggcga | tcatcggcga | ttacaacatc | ggtggcgacg | cctgggcctc | gcgcattttg | 720 |
| ctcgaagaga | tggggttgcg | ggtggtcgcg | cagtggtccg | gcgacggtac | gctggtggag | 780 |
| atggaaaaca | cgccgttcgt | caaactgaac | ctggtgcact | gctaccgctc | gatgaactac | 840 |
| atctcgcgcc | atatggagga | gaagcacggt | attccgtgga | tggaatacaa | cttctttggc | 900 |
| ccgacgaaaa | tcgcggaatc | gctgcgcaaa | atcgccgacc | tgttcgacga | caccattcgc | 960 |
| gccaacgccg | aagcggtgat | cgcccgatac | caggcgcaga | acgacgccat | tatcgccaaa | 1020 |
| tatcgcccac | gtctggaggg | tcgcaaagtg | ttgctctata | tgggcgggct | gcgtccgcgc | 1080 |
| catgtgattg | cgccctatga | agatctggga | atggagatca | tcgccgccgg | ttatgagttt | 1140 |
| ggtcataacg | acgattacga | ccgcacccctg | ccggatctga | agagggcac | gctgctgttt | 1200 |
| gatgacgcca | gcagctatga | gctggaggcg | tttgtcaacg | cgctgaaacc | ggatctcatc | 1260 |
| ggttccggca | tcaaagagaa | gtacatcttt | cagaaaatgg | gcgtgccgtt | cgccagatg | 1320 |
| cactcctggg | attactccgg | cccgtaccac | ggctatgacg | gcttcgccat | cttcgcccgc | 1380 |
| gatatggata | tgacgctcaa | caaccccgcc | tggggtcagt | tgaccgcgcc | gtggcttaaa | 1440 |
| tccgcctga | | | | | | 1449 |

<210> SEQ ID NO 139
<211> LENGTH: 1374
<212> TYPE: DNA
<213> ORGANISM: Kosakonia pseudosacchari
<220> FEATURE:
<223> OTHER INFORMATION: nifD2

<400> SEQUENCE: 139

| | | | | | |
|---|---|---|---|---|---|
| atgaagggga | acgacatcct | ggctctgctc | gatgaaccag | cctgcgagca | taaccataaa | 60 |
| cagaaaaccg | gctgtagcgc | gccaaaaccc | ggcgccaccg | ccggaggctg | cgccttcgac | 120 |
| ggcgcacaga | tcaccctgct | gccacttttcc | gatgtgcgc | atctggtaca | tggcccgatt | 180 |
| ggctgcgccg | gcagctcatg | ggataaccgt | ggcagcctga | gttctggccc | gctgattaac | 240 |

```
cgactcggat tcaccactga tttgaacgaa caggatgtca tcatggggcg cggcgagcgg    300
cggttgtttc acgcggtgcg ccatattgtc gagcgctatc acccggcggc ggtatttatt    360
tacaacacct gcgttccggc tatggaaggc gatgacattg acgcggtctg ccaggccgcc    420
gcgaccgcca ccggtgtgcc cgtgattgcc gtagatgtgg ccggttttta cggtagcaaa    480
aacctgggta accgcctcgc gggcgaggtg atggtgaaaa aagttatcgg cgggcgcgaa    540
cccgcgccgt ggccggacaa tacaccttt gccccggcgc accgccatga cataggcctg     600
attggcgaat taacatcgc cggcgagttc tggcatatcc agccgctgct tgatgagctg      660
ggtattcgcg tccttggctc cctttccggc gacgggcgct tgccgagat ccagacgttg      720 caccgcgcgc aggtcaatat gctggtgtgc tccagggcgc tgattaatgt cgccagatcg    780
cttgaacaac gttatggcac accctggttt gaaggcagtt tttatggcgt tcgcgccacc    840
tccgatgccc tgcgccagct ggcaacactc accggcgata gcgatttaat ggcgcgaacc    900
gaacggctga tcgcacgtga agagcaagcc acagaacagg cgctagcacc gctgcgtgaa    960
cggttacacg gccggaaagt gctgctctat accggtggct gaaatcctg gtcggtggtt    1020 tcggcgctgc aggatctcgg catgacggtc gttgctaccg gaacgcgcaa atccaccgaa   1080
gaggataaac aacgcatccg tgaactgatg gcgatgacg ccatcatgct ggatgaaggc     1140
aatgcccgcg ccttgctgga tgtggtctat cgctacaaag ccgacatgat gatcgcgggc    1200
gggcgcaaca tgtacaccgc ctataaagcc cgtctgccct ttctggatat caaccaggag   1260
cgtgaacacg cgtttgccgg ttatcgcggc atcatcacgc ttgccgaaca actttgtcag   1320
acgctggaaa gcccggtctg gccgcaaaca catgcccgcg ccccgtggca ataa         1374
```

<210> SEQ ID NO 140
<211> LENGTH: 1563
<212> TYPE: DNA
<213> ORGANISM: Kosakonia pseudosacchari
<220> FEATURE:
<223> OTHER INFORMATION: nifK1

<400> SEQUENCE: 140

```
atgagccaga ctgctgagaa atacagaat tgccatcccc tgtttgaaca ggacgcctac     60
cagacactat ttgccggtaa acgggcactc gaagaggctc actcgccgga gcgggtgcag   120
gaagtgtttc aatggaccac cacccccgaa tacgaagcgc tgaacttcaa acgcgaagcg   180
ctgactatcg acccggcaaa agcctgccag ccgctggggg cggtgctctg ttcgctgggg   240
tttgccaaca ccctgccgta tgtgcacggt tcacagggtt gtgtggccta tttccgtacg    300
tactttaacc gccacttcaa agaaccggtg gcctgcgtgt cggattcgat gacggaagac   360
gcggccgtgt cggcgggaa taacaacctc aacaccgggt tacaaaacgc cagcgcactg    420
tataaaccgg agattatcgc cgtctctacc acctgtatgg cggaagtgat cggtgatgat   480
ttacaggcgt ttatcgccaa cgccaaaaaa gatggttttc tcgatgccgc catcccgtg     540 ccctacgccc acacccccag ttttatcggt agccatatca ccggctggga caacatgttt     600
gaaggttttg cccgtacctt taccgcaaac catcagccac agcccggtaa actttcacgc    660
ctgaacctgg tgaccgggtt tgaaacctat ctcggcaatt tccgcgtgct gaaacgcatg   720
atggaacaaa tggaggtgca ggcgagtgtg ctctccgatc cgtcggaggt gctggacacc   780
cccgccaatg ccattacca gatgtacgcg ggcggtacga cgcagcaaga gatgcgcgag    840
gcaccggatg ccatcgacac cctgctgctg caaccgtggc agctggtgaa aagcaaaaaa    900
gtggtgcagg agatgtggaa tcagcccgcc accgaggttg ccattcccgt cgggctggca   960
```

```
ggcacagacg aactgttgat ggcgattagc cagttaaccg gcaaagccat tcccgattcg    1020
ctggcgctgg agcgcgggcg gctggtcgat atgatgctcg actcccacac ctggttacac    1080
ggtaaaaaat tcggtctgtt tggcgatccg gattttgtca tgggattgac ccgcttcctg    1140
ctggaactgg gctgtgaacc tgccgtcatc ctctgccata acggtaacaa acgctggcaa    1200
aaagcgatga agaaaatgct cgatgcttca ccgtacggcc aggagagcga agtgtttatc    1260
aactgcgact tgtggcattt ccgctcgctg atgttcaccc gccagccgga ttttatgatt    1320
ggcaactcgt acgccaagtt tattcagcgc gacaccttag ccaagggcga acagtttgaa    1380
gtcccgctga tccgcctcgg ttttccgctg ttcgaccgtc accatctgca ccgccagacc    1440
acctggggct acgagggcgc gatgagcatt ctcacgacgc tggtgaatgc ggtactggag    1500
aaagtggaca aagagaccat caagctcggc aaaaccgact acagcttcga tcttatccgt    1560
taa                                                                  1563

<210> SEQ ID NO 141
<211> LENGTH: 1386
<212> TYPE: DNA
<213> ORGANISM: Kosakonia pseudosacchari
<220> FEATURE:
<223> OTHER INFORMATION: nifK2

<400> SEQUENCE: 141
atggctgata ttgttcgtag taaaaaaccg ctggcggtga gcccgataaa aagcggccag      60
ccgctggggg cgatcctggc aagcctgggt ttcgaacagt gcataccgct ggtacacggc     120
gctcaggggt gcagcgcgtt cgcgaaagtg ttctttattc aacattttca cgacccgatc     180
ccgctgcaat cgacggcgat ggacccgact tccaccatta tgggcgccga tgaaaacatt     240
tttaccgcgc tcaatgttct ctgccagcgc aacgccgcga agccatcgt gctgctcagc      300 accgggctgt cagaagccca gggcagcgat atttcacgag tggtgcgcca gtttcgtgat     360
gactttccgc ggcataaaaa cgtggcgctg ctcaccgtca acaccccgga tttctacggc     420
tcgctggaaa acggctacag cgccgtgctg gaaagcatga ttgaacagtg ggtgcccgcg     480
cagcccgccg ccagcctgcg caaccgtcgc gtcaacctgc tggtcagcca tttactgacg     540
ccgggcgata tcgaactgtt acgcagttat gtggaagcat tcggtctgca accggtgatt     600
gtgccggatc tatcgcagtc gctggacgga catctggcca acggtgattt tcgcccgtc     660 acccaggggg gaacaccgct gcgcatgatt gaacagatgg ggcaaaacct ggccactttt     720
gtgattggcc actcgctggg gcgggcggcg gcgttactgg cgcagcgcag ccgtggcgag     780
gtgatcgccc tgccgcatct gatgacgctt gatgcgtgcg acacctttat ccatcgcctg     840
aaaaccctct ccgggcgcga cgtgcccgcg tggattgagc ccagcgcgg gcaagtgcag     900 gatgcgatga tcgattgcca tatgtggttg cagggcgcgg ctatcgccat ggccgcagaa     960
ggcgatcacc tggcggcatg gtgcgatttc gcccgcagcc agggcatgat ccccggcccg    1020
gttgtcgcgc cggtcagcca gccggggttg caaaatctgc cggttgaaat ggtggtcatc    1080
ggcgatctgg aagatatgca ggatcggctt tgcgcgacgc ccgccgcgtt actggtggcc    1140
aattctcatg ccgccgatct cgccacgcag tttgatatgt cgcttatccg cgccgggttt    1200
ccggtgtatg accggctggg ggaatttcgt cggctgcgcc aggggtatag cggcattcgt    1260
```

```
gacacgctgt tgagctggc gaatgtgatg cgcgaacgcc attgcccgct tgcaacctac   1320
cgctcgccgc tgcgtcagcg cttcggcgac aacgttacgc caggagatcg gtatgccgca   1380
tgttaa                                                              1386

<210> SEQ ID NO 142
<211> LENGTH: 1488
<212> TYPE: DNA
<213> ORGANISM: Kosakonia pseudosacchari
<220> FEATURE:
<223> OTHER INFORMATION: nifL

<400> SEQUENCE: 142
atgaccctga atatgatgat ggatgccagc gcgcccgagg ccatcgccgg tgcgctttcg     60
caacaacatc ctgggctgtt ttttaccatc gttgaagaag ccccgtcgc tatttcacta    120 accgatgccg aggcacgtat tgtctatgcc aacccggcat tctgccgcca gaccggctat    180
gagcttgagg agttgttgca gcaaaatccc cgcctgcttg ccagtcagca gaccccacgg    240
gaaatctacc aggatatgtg gcacaccctg ttacaacgtc gaccatggcg cgggcaattg    300
atcaaccgcc accgtgacgg cagcctttt ctggttgaga tcgatatcac cccggtgatt    360
aacccgtttg gcgaactgga acactacctg gccatgcagc gcgatatcag cgccggttat    420
gcgctggagc agcggttgcg taatcacatg gcgctgaccg aagcggtgct gaataacatt    480
ccggcggcgg tggtcgtggt cgatgaacgc gatcgtgtgg ttatggataa cctcgcctat    540
aaaactttct gtgctgattg cggcggaaaa gagctactga gcgaactcca ttttcagcc     600 cgtaaagcgg agctggcaaa cggccaggtc ttaccggtgg tgctgcgcgg cgcggtgcgc    660
tggttgtcgg tcacctgctg ggcgctgcca ggcgtcagcg aagaagccag tcgctacttt    720
attgataata ccttgacgcg cacgctggtg gtcatcaccg acgacaccca gcagcgccag    780
cagcaagagc aaggacggct tgaccgcctt aaacagcaga tgaccagcgg caaactgctg    840
gcggcgatcc gcgaagcgct tgacgccgcg ctgatccagc ttaactgccc catcaatatg    900
ctggcggcgg cgcggcgttt aaacggcagt gataacagca acgtagcgct ggacgccgcg    960
tggcgcgaag gtgaagaagc gatggcgcgg ctgaaacggt gccgcccgtc gctggagctg   1020
gaaagtgccg ccgtctggcc gctgcaaccc tttttgacg acttgcgcgc gctttatcac   1080
acccgctacg agcagggtaa aaatttgcag gtcacgctgg attcgacgca tctggtggga   1140
tttggtcagc gaacccaact gctggcctgc ctgagtctgt ggctcgatcg cacgctggat   1200
attgccgtcg ggctgcgtga tttcaccgcc caaacgcaga tttacgcccg ggaagaagcg   1260
ggctggctct cgttgtatat cactgacaat gtgccgttga ttccgctgcg ccatacccat   1320
tcgccggatg cgcttaacgc accgggaaaa ggtatggagt tgcggctgat ccagacgctg   1380
gtagcgcatc acaacggcgc gatagaactc acttcacgcc ccgaagggg aagctgcctg   1440 accctacgat tcccgctatt tcattcactg accggaggtt caaaatga              1488

<210> SEQ ID NO 143
<211> LENGTH: 1575
<212> TYPE: DNA
<213> ORGANISM: Kosakonia pseudosacchari
<220> FEATURE:
<223> OTHER INFORMATION: nifA
```

<400> SEQUENCE: 143

```
atgacccagc gaaccgagtc gggtaatacc gtctggcgct tcgatttatc ccagcagttc       60
accgcgatgc agcggataag cgtggttctc agccgggcga ccgaggttga acagacactc      120
cagcaggtgt tgtgcgtatt gcacaatgac gccttttttgc agcacggcat gatctgtctg     180
tacgacagcc agcaggcgat tttgactatt gaagcgttgc aggaagccga tcagcagttg     240
atccccggca gctcgcaaat tcgctaccgt ccgggtgaag ggctggtcgg acggtgctt       300
tcgcaggggc aatcgttagt gctggcgcgt gtggctgacg atcagcgctt tcttgaccgc     360
ctgggactgt atgattacaa cctgccgttt atcgccgtgc cgctgatagg gccggatgcg     420
cagactttg gcgtgctgac ggcgcaaccg atggcgcgtt acgaagagcg gttacccgcc      480
tgcacccgct ttctggaaac ggtcgcgaat ctggtggcgc agaccgtgcg tttgatgacg     540
ccgccggctg cacgcccttc cccacgcgct gccatcacgc caaccgccag cccgaaatcg     600
tgcagtactt cacgcgcgtt cggcttcgaa aatatggtcg gcaacagccc ggcaatgcgc     660
cagaccatgg agattatccg tcaggtttcg cgctgggata ccaccgttct ggtgcgcggc     720
gagagcggca ccggcaagga actgattgcc aacgccatcc atcacaattc gccgcgcgcc     780
agtgcgccat ttgtgaaatt caactgtgcg gcgctgccgg acacattgct gaaagcgaa      840
ttatttggtc atgaaaaagg cgcctttacc ggcgcggtac gccagcgtaa aggccgtttt     900
gagctggccg atggcggcac gctgtttctt gacgaaattg gggaaagcag cgcctcgttt     960
caggctaagc tgctgcgtat tttgcaggag ggcgaaatgg aacgcgtcgg tggtgacgag    1020
acattgcaag tgaatgtgcg catcattgcc gcgacgaacc gcaaccttga agatgaagta   1080
cgcctgggac atttttcgcga agatctctat taccgcctga atgtgatgcc catcgccctg   1140
ccgccgctgc gcgaacgcca ggacgacatc gccgaactgg cacattttct ggtgcgtaaa   1200
atcgcccaca accagaaccg cacgctgcgc attagcgagg gcgctatccg cctgctgatg   1260
agctacagct ggcccggcaa tgtgcgcgaa ctggaaaact gccttgagcg ctctgcggtg   1320
atgtcggaaa acggtctgat cgatcggac gtgattttat ttaatcatcg cgaccagcca    1380
gccaaaccgc cggttatcag cgtcacgccc gacgataact ggctcgataa caccttgac    1440
gagcgccagc ggctgattgc cgcgctggaa aaagcgggat gggtacaagc caaagccgcc   1500
cgcttgctgg ggatgacgcc gcgccaggtc gcttatcgta ttcagaccat ggatatcacc   1560
ctgccaaggc tataa                                                   1575
```

<210> SEQ ID NO 144
<211> LENGTH: 2850
<212> TYPE: DNA
<213> ORGANISM: Kosakonia pseudosacchari
<220> FEATURE:
<223> OTHER INFORMATION: glnE

<400> SEQUENCE: 144

```
atgccgcacc acgcaggatt gtcgcagcac tggcaaacgg ttttttctcg tctgccggaa       60
gcgctcaccg cgcaaccatt gagcgcgcag gcgcagtcag tgctcacttt tagtgatttt      120
gttcaggaca gcatcatcgt gcatcctgag tggctggcag agcttgaaag cgcaccgccg     180
ccagcgaacg agtggcaaca ctacgcgcaa tggctgcaag cggcgctgga gggcgtcacc    240
gatgaaacct cgctgatgcg cacgctgcgg ctgtttcgcc gtcgcattat ggtgcgcatc     300
gcctggagtc aggcgctaca gttggtggcg gaagaggata tcctgcaaca gctcagcgtg    360
```

```
ctggcggaaa ctctgatcgt cgccgcgcgc gactggctct atgacgcctg ctgccgtgag      420
tggggaacgc cgtgcaatcc gcaaggcgtc gcgcagccga tgctggtgct cggcatgggc      480
aaacttggcg gcggcgaact caatttctca tccgatatcg atttgatttt tgcctggccg      540
gaaaatggca ccacgcgcgg cggacgccgt gaactggata cgcgcagtt ttttacccgc       600 cttggtcaac ggctaattaa agtcctcgac cagcccacgc aggatggctt tgtctaccgc      660
gtcgatatgc gcttgcgtcc ctttggcgac agcggcccgc tggtgctgag ttttgccgcg      720
ctggaagatt actaccagga gcaggggcgc gactgggaac gatacgcgat ggtgaaagcg      780
cgcattatgg gggacaacga cggcgaccat cgcgcagagt gcgcgccat gctgcgcccg       840 ttcgttttcc gccgctatat cgacttcagc gtgatccagt ctctgcgcaa catgaaaggc      900
atgattgccc gcgaagtgcg gcgtcgcggc ctgaaggaca acataaaact cggcgcgggc      960
ggtattcgcg aaatagagtt tatcgtgcag gtttttccagt tgattcgcgg cggtcgcgag     1020
cctgcgctgc aatcgcgttc gctgttgccg acgcttgctg ccattgatca actacatctg     1080
ctgccggatg gtgatgcacc ccggctgcgc gaggcgtatt tgtggctgcg acggctggaa     1140
aacttgctgc aaagcattaa tgacgaacag acacagacgc tgccggccga tgatttgaat     1200
cgcgcgcgcc tcgcctgggg aatgggcaaa gagagctggg aagcgctctg cgaaacgctg     1260
gaagcgcata tgtcggcggt gcggcagatt ttcaacgatc tgattggcga tgatgaaacg     1320
gattcgccga aagatgcgct ttctgagggc tggcgcgaat tgtggcagga tgcgttgcag     1380
gaagaggact ctacgcccgt gctggcgcat cttttccgagg acgatcgccg ccgcgtggtg     1440
gcgctgattg ctgattttcg caaagagctg ataaacgca ccattggccc gcgcgggcga      1500
caggtactcg atcacttaat gccgcatctg ctcagcgatg tatgctcgcg tgacgatgcg     1560
ccagtgccgc tgtcgcgtct gacgccgctg ctcaccggta ttattacgcg caccacttac     1620
cttgagctgc tgagtgaatt ccccggtgcg ctgaaacacc tcatttccct gtgcgccgcg     1680
tcgccgatgt tggccagcca actggcgcgc tacccgatcc tgctcgatga actgctcgac     1740
ccgaacacgc tctatcaacc gacggcgatg aacgcctatc gcgatgaact gcgacaatac     1800
ctgttgcgcg tgccggaaga ggatgaagag cagcaactgg aggcgctacg gcagtttaag     1860
caggcgcagt tgttgcgcgt agcggcggcg gatatcgccg gtacgttacc cgtcatgaaa     1920
gtgagcgatc acttaacctg gctggcggaa gcgattatcg atgcggtggt gcagcaagcc     1980
tggaaccaga tggtggcgcg ttacggccag ccgacgcatc tgcacgatcg cgaagggcgc     2040
ggtttcgccg tggtcggtta cggcaaactt ggcggctggg aattaggtta cagctccgat     2100
ctggatctgg tgttcctgca cgactgcccc atggatgtga tgaccgatgg cgagcgtgaa     2160
atcgatggcc gccagttcta tttgcgcctc gcgcagcgcg tgatgcacct gttcagcacg     2220
cgcacgtcgt ccggcattct ttatgaagtc gatgcgcgtt tgcgcccgtc cggcgcggcc     2280
ggaatgctgg tgaccactgc ggaagcgttc gccgattatc aaaaaaatga agcctggaca     2340
tgggagcatc aggcgctggc gcgtgcgcgc gtggtgtacg cgatccgca actgaccgcc      2400 gaatttgacg ccattcgccc cgatatcctg atgacctccc gcgatgccgc taccctgcaa     2460
accgaagtgc gggaaatgcg tgagaaaatg cgcgcccatc ttggtaacaa gcacaaagac     2520
cgtttcgatc tgaaagccga tgaaggcggt atcaccgata ttgagtttat cgctcagtat     2580
ctggtgctgc gcttgcccca tgagaagccc aaactgacgc gctggtcgga taatgtgcgc     2640
atcctcgaag gctggcgcca aaacggcatc atggatgagc aggaagcgca ggcattgacg     2700
ctggcgtaca ccacgttgcg tgatgagctg caccacctgg cgctgcaaga gctgccagga     2760
```

| | |
|---|---|
| catgtggcgc tctcctgttt tgtcgccgag cgtgcgctta tcaaaaccag ctgggacaag | 2820 |
| tggctggtgg aaccgtgcgc cccggcgtaa | 2850 |

<210> SEQ ID NO 145
<211> LENGTH: 1287
<212> TYPE: DNA
<213> ORGANISM: Kosakonia pseudosacchari
<220> FEATURE:
<223> OTHER INFORMATION: amtB

<400> SEQUENCE: 145

| | |
|---|---|
| atgaaaaaca caacattaaa aacggctctt gcttcgctgg cgttgctgcc aggcctggcg | 60 |
| atggcggctc ccgctgtggc ggataaagcc gacaacggct ttatgatgat ttgcaccgcg | 120 |
| ctggtgctgt ttatgaccat tccgggcatt gcgctgttct acggcggttt gatccgcggt | 180 |
| aaaaacgtgc tgtcgatgct gacgcaggtt gccgtcacct cgctctggt gtgcatcctg | 240 |
| tgggtggttt acggctactc tctggcattt ggcgagggca acagcttctt cggcagtttc | 300 |
| aactgggcga tgttgaaaaa catcgaattg aaagccgtga tgggcagcat ttatcagtac | 360 |
| atccacgtgg cgttccaggg ctcctttgct tgtatcaccg ttggcctgat tgtcggtgcg | 420 |
| ctggctgagc gtattcgctt ctctgcggtg ctgattttg tggtggtatg gctgacgctt | 480 |
| tcttatgtgc cgattgcgca catggtctgg ggtggcggtc tgctggcaac ccacggcgcg | 540 |
| ctggatttcg cgggcggtac ggttgttcac atcaacgccg cgatcgcagg tctggtgggg | 600 |
| gcttacctga ttggcaaacg cgtgggcttt ggcaaagaag cgttcaaacc gcataacctg | 660 |
| ccgatggtct tcaccggcac cgcgatcctc tatgttggct ggtttggctt caacgccggc | 720 |
| tctgcaagct cggcgaacga aatcgctgcg ctggctttcg tgaacacggt tgttgccact | 780 |
| gcggccgcta ttctggcgtg ggtatttggc gagtgggcaa tgcgcggtaa gccgtctctg | 840 |
| ctcggtgcct gttctggtgc catcgcgggt ctggttggta tcaccccggc gtgcggttat | 900 |
| gtgggtgtcg gcggcgcgct gattgtgggt ctgattgccg gtctggcagg gctgtggggc | 960 |
| gttactgcac tgaaacgtat gttgcgtgtt gatgacccat gcgatgtctt cggtgtgcac | 1020 |
| ggcgtgtgcg gcatcgtggg ttgtatcctg accggtatct tcgcgtctac gtcgctgggc | 1080 |
| ggtgtcggtt tcgctgaagg ggtgaccatg ggccatcagg tactggtaca gctggaaagc | 1140 |
| gttgccatca ctatcgtgtg gtctggcgtg gtggccttta tcggttacaa actggcggat | 1200 |
| atgacggtag gcctgcgcgt accggaagag caagagcgtg aagggctgga tgtgaacagc | 1260 |
| cacggcgaaa atgcgtataa cgcctga | 1287 |

<210> SEQ ID NO 146
<211> LENGTH: 500
<212> TYPE: DNA
<213> ORGANISM: Kosakonia pseudosacchari
<220> FEATURE:
<223> OTHER INFORMATION: PinfC

<400> SEQUENCE: 146

| | |
|---|---|
| ttcttggttc tctggagcgc tttatcggca tcctgactga agaatttgca ggcttcttcc | 60 |
| caacctggct tgcacccgtg caggtagttg tgatgaacat cactgattcg caggctgaat | 120 |
| acgttaacga attgacccgt aaactgcaaa atgcgggcat tcgtgtaaaa gcagacttga | 180 |
| gaaacgagaa gattggcttt aaaatccgcg agcacacttt acgtcgtgtc ccttatatgc | 240 |
| tggtttgtgg tgacaaagag gtcgaagccg gcaaagttgc tgtgcgtacc cgtcgcggta | 300 |

```
aagacctggg tagcctggac gtaaatgatg ttatcgagaa gctgcaacaa gagattcgca      360
gccgcagtct tcaacaactg gaggaataag gtattaaagg cggaaaacga gttcaaacgg      420
cgcgtcccaa tcgtattaat ggcgagattc gcgccacgga agttcgctta acaggtctgg      480
aaggcgagca gcttggtatt                                                 500

<210> SEQ ID NO 147
<211> LENGTH: 348
<212> TYPE: DNA
<213> ORGANISM: Kosakonia pseudosacchari
<220> FEATURE:
<223> OTHER INFORMATION: Prm1

<400> SEQUENCE: 147
cgttctgtaa taataaccgg acaattcgga ctgattaaaa aagcgccctc gcggcgcttt      60
ttttatattc tcgactccat ttaaaataaa aaatccaatc ggatttcact atttaaactg     120
gccattatct aagatgaatc cgatggaagc tcgctgtttt aacacgcgtt ttttaacctt     180
ttattgaaag tcggtgcttc tttgagcgaa cgatcaaatt taagtggatt cccatcaaaa     240
aaatattctc aacctaaaaa agtttgtgta atacttgtaa cgctacatgg agattaactc     300
aatctagagg gtattaataa tgaatcgtac taaactggta ctgggcgc                 348

<210> SEQ ID NO 148
<211> LENGTH: 339
<212> TYPE: DNA
<213> ORGANISM: Kosakonia pseudosacchari
<220> FEATURE:
<223> OTHER INFORMATION: Prm7

<400> SEQUENCE: 148
cgcgtcaggt tgaacgtaaa aaagtcggtc tgcgcaaagc acgtcgtcgt ccgcagttct      60
ccaaacgtta attggtttct gcttcggcag aacgattggc gaaaaaaccc ggtgcgaacc     120
gggttttttt atggataaag atcgtgttat ccacagcaat ccattgatta tctcttcttt     180
ttcagcattt ccagaatccc ctcaccacaa agcccgcaaa atctggtaaa ctatcatcca     240
attttctgcc caaatggctg ggattgttca tttttgttt gccttacaac gagagtgaca     300
gtacgcgcgg gtagttaact caacatctga ccggtcgat                          339

<210> SEQ ID NO 149
<211> LENGTH: 1538
<212> TYPE: DNA
<213> ORGANISM: Enterobacter sp.
<220> FEATURE:
<223> OTHER INFORMATION: 16S
<220> FEATURE:
<221> NAME/KEY: modified_base
<222> LOCATION: (62)..(62)
<223> OTHER INFORMATION: a, c, t, g, unknown or other
<220> FEATURE:
<221> NAME/KEY: modified_base
<222> LOCATION: (265)..(265)
<223> OTHER INFORMATION: a, c, t, g, unknown or other
<220> FEATURE:
<221> NAME/KEY: modified_base
<222> LOCATION: (457)..(457)
<223> OTHER INFORMATION: a, c, t, g, unknown or other
<220> FEATURE:
<221> NAME/KEY: modified_base
<222> LOCATION: (469)..(469)
<223> OTHER INFORMATION: a, c, t, g, unknown or other
<220> FEATURE:
<221> NAME/KEY: modified_base
<222> LOCATION: (539)..(539)
<223> OTHER INFORMATION: a, c, t, g, unknown or other
```

-continued

```
<220> FEATURE:
<221> NAME/KEY: modified_base
<222> LOCATION: (551)..(552)
<223> OTHER INFORMATION: a, c, t, g, unknown or other
<220> FEATURE:
<221> NAME/KEY: modified_base
<222> LOCATION: (559)..(559)
<223> OTHER INFORMATION: a, c, t, g, unknown or other
<220> FEATURE:
<221> NAME/KEY: modified_base
<222> LOCATION: (561)..(561)
<223> OTHER INFORMATION: a, c, t, g, unknown or other
<220> FEATURE:
<221> NAME/KEY: modified_base
<222> LOCATION: (576)..(576)
<223> OTHER INFORMATION: a, c, t, g, unknown or other
<220> FEATURE:
<221> NAME/KEY: modified_base
<222> LOCATION: (587)..(587)
<223> OTHER INFORMATION: a, c, t, g, unknown or other
<220> FEATURE:
<221> NAME/KEY: modified_base
<222> LOCATION: (591)..(591)
<223> OTHER INFORMATION: a, c, t, g, unknown or other
<220> FEATURE:
<221> NAME/KEY: modified_base
<222> LOCATION: (655)..(657)
<223> OTHER INFORMATION: a, c, t, g, unknown or other
<220> FEATURE:
<221> NAME/KEY: modified_base
<222> LOCATION: (665)..(665)
<223> OTHER INFORMATION: a, c, t, g, unknown or other
<220> FEATURE:
<221> NAME/KEY: modified_base
<222> LOCATION: (678)..(678)
<223> OTHER INFORMATION: a, c, t, g, unknown or other
<220> FEATURE:
<221> NAME/KEY: modified_base
<222> LOCATION: (706)..(706)
<223> OTHER INFORMATION: a, c, t, g, unknown or other
<220> FEATURE:
<221> NAME/KEY: modified_base
<222> LOCATION: (710)..(710)
<223> OTHER INFORMATION: a, c, t, g, unknown or other
<220> FEATURE:
<221> NAME/KEY: modified_base
<222> LOCATION: (714)..(714)
<223> OTHER INFORMATION: a, c, t, g, unknown or other
<220> FEATURE:
<221> NAME/KEY: modified_base
<222> LOCATION: (718)..(718)
<223> OTHER INFORMATION: a, c, t, g, unknown or other
<220> FEATURE:
<221> NAME/KEY: modified_base
<222> LOCATION: (735)..(735)
<223> OTHER INFORMATION: a, c, t, g, unknown or other
<220> FEATURE:
<221> NAME/KEY: modified_base
<222> LOCATION: (755)..(755)
<223> OTHER INFORMATION: a, c, t, g, unknown or other
<220> FEATURE:
<221> NAME/KEY: modified_base
<222> LOCATION: (759)..(759)
<223> OTHER INFORMATION: a, c, t, g, unknown or other
<220> FEATURE:
<221> NAME/KEY: modified_base
<222> LOCATION: (796)..(796)
<223> OTHER INFORMATION: a, c, t, g, unknown or other
<220> FEATURE:
<221> NAME/KEY: modified_base
<222> LOCATION: (1006)..(1007)
<223> OTHER INFORMATION: a, c, t, g, unknown or other
<220> FEATURE:
<221> NAME/KEY: modified_base
<222> LOCATION: (1016)..(1017)
<223> OTHER INFORMATION: a, c, t, g, unknown or other
<220> FEATURE:
<221> NAME/KEY: modified_base
<222> LOCATION: (1133)..(1133)
```

<223> OTHER INFORMATION: a, c, t, g, unknown or other

<400> SEQUENCE: 149

```
ttgaagagtt tgatcatggc tcagattgaa cgctggcggc aggcctaaca catgcaagtc      60
gngcggaagc acaggagagc ttgctctctg ggtgacgagc ggcggacggg tgagtaatgt     120
ctgggaaact gcctgatgga gggggataac tactggaaac ggtagctaat accgcataac     180
gtcgcaagac caaagagggg gaccttcggg cctcttgcca tcagatgtgc ccagatggga     240
ttagctagta ggtggggtaa cggcncacct aggcgacgat ccctagctgg tctgagagga     300
tgaccagcca cactggaact gagacacggt ccagactcct acgggaggca gcagtgggga     360
atattgcaca atgggcgcaa gcctgatgca gccatgccgc gtgtatgaag aaggccttcg     420
ggttgtaaag tactttcagc ggggaggaag gtgttgnggt taataaccnc agcaattgac     480
gttacccgca gaagaagcac cggctaactc cgtgccagca gccgcggtaa tacggaggnt     540
gcaagcgtta nncggaatna ntgggcgtaa agcgtncgca ggcggtntgt naagtcggat     600
gtgaaatccc cgggctcaac ctgggaactg cattcgaaac tggcaggcta gagtnnngta     660
gaggngggta gaattccngg tgtagcggtg aaatgcgtag agatcnggan gaanaccngt     720
ggcgaaggcg gccnctgga caaagactga cgctnaggng cgaaagcgtg gggagcaaac     780
aggattagat accctngtag tccacgccgt aaacgatgtc gacttggagg ttgtgccctt     840
gaggcgtggc ttccggagct aacgcgttaa gtcgaccgcc tggggagtac ggccgcaagg     900
ttaaaactca aatgaattga cgggggcccg cacaagcggt ggagcatgtg gtttaattcg     960
atgcaacgcg aagaacctta cctactcttg acatccagag aacttnncag agatgnnttg    1020
gtgccttcgg gaactctgag acaggtgctg catggctgtc gtcagctcgt gttgtgaaat    1080
gttgggttaa gtcccgcaac gagcgcaacc cttatccttt gttgccagcg gtncggccgg    1140
gaactcaaag gagactgcca gtgataaact ggaggaaggt ggggatgacg tcaagtcatc    1200
atggccctta cgagtagggc tacacacgtg ctacaatggc gcatacaaag agaagcgacc    1260
tcgcgagagc aagcggacct cataaagtgc gtcgtagtcc ggattggagt ctgcaactcg    1320
actccatgaa gtcggaatcg ctagtaatcg tagatcagaa tgctacggtg aatacgttcc    1380
cgggccttgt acacaccgcc cgtcacacca tgggagtggg ttgcaaaaga agtaggtagc    1440
ttaaccttcg ggagggcgct taccactttg tgattcatga ctggggtgaa gtcgtaacaa    1500
ggtaaccgta ggggaacctg cggttggatc acctcctt                            1538
```

<210> SEQ ID NO 150
<211> LENGTH: 882
<212> TYPE: DNA
<213> ORGANISM: Enterobacter sp.
<220> FEATURE:
<223> OTHER INFORMATION: nifH

<400> SEQUENCE: 150

```
atgaccatgc gtcaatgtgc catttacggc aaaggtggta tcggtaaatc cactaccacg      60
caaaacctgg tcgccgcgct ggcggagatg ggcaagaaag taatgatcgt cggctgcgac     120
ccgaaagcag actccactcg tctgatcctg catgcgaaag cgcagaacac cattatggag     180
atggcggctg aagtcggctc cgtggaagac cttgaactgg aagatgtgct gcaaatcggt     240
tacggcgacg tacgctgcgc agaatccggc ggcccggaac caggcgttgg ctgtgctggt     300
cgcggggtaa ttaccgccat caacttcctg gaagaagaag cgccctatgt tcccgacctc     360
gatttcgtct tttacgacgt gttgggcgac gtggtgtgcg gggggttcgc catgccgatt     420
```

```
cgcgaaaaca aagcgcagga gatctacatc gtctgctccg gcgaaatgat ggcgatgtac    480
gccgccaaca acatctctaa aggcatcgtg aaatacgcca atccggcaa agtgcgcctt    540 ggcgggctga tctgtaactc ccgtcagacc gaccgcgaag atgagctgat catagcgctg    600
gcggaaaaac tcggcaccca gatgatccac ttcgtgccgc gcgacaacat cgtgcaacgc    660
gctgaaatcc gccgtatgac ggtgattgag tacgatccga aatgcaacca ggccaatgaa    720
taccgcacgc tggcgaacaa gatcgtcaac aacaccaaaa tggtcgtgcc aacgcccatc    780
accatggacg aactggaaga gctgttgatg gaattcggca ttatggatgt ggaagacacc    840
agcattatcg gtaaaaccgc cgcagaagaa aacgcggttt ga                      882
```

<210> SEQ ID NO 151
<211> LENGTH: 1449
<212> TYPE: DNA
<213> ORGANISM: Enterobacter sp.
<220> FEATURE:
<223> OTHER INFORMATION: nifD1

<400> SEQUENCE: 151

```
atgagcaatg caacaggcga acgtaatctg gagatcatcc aggaagtgct ggagatcttt     60
ccggaaaaaa cgcgcaaaga acgcagaaag cacatgatgg tgagcgaccc ggagatggaa    120
agcgtcggga aatgcatcat ctccaaccgt aagtcgcagc ccggcgtaat gaccgtgcgc    180
ggttgctctt acgccggttc taaaggggtg gtattcgggc cgatcaaaga tatggcccat    240
atttcccacg gccggtcgg ctgccggtcag tactcccgcg ccgggcggcg taactactac    300
accggcgtca gcggtgtgga tagcttcggt acgctcaact ttacctccga ttttcaggag    360
cgcgatatcg tgtttggcgg cgataaaaag ctgaccaaac tgattgaaga gatggagacg    420
ctgttcccgc tgaccaaagg gatctccatt cagtccgaat gcccggtcgg cctgattggc    480
gacgacattg aagccgttgc caacgccagc cgcaaagcca tcaataaacc ggtcattccg    540
gtgcgctgcg aaggttttcg cggcgtttcc cagtcactcg gtcaccacat tgccaacgac    600
gtgatccgcg actgggtact ggataaccgc gaaggcaagc cgtttgaggc cggtccttat    660
gacgtggcga tcatcggcga ttacaacatc ggcgcgatg cctgggcgtc gcgcattttg    720
ctcgaagaga tgggcctgcg cgtggtggcg cagtggtccg gcgacggcac gctggttgag    780
atggagaaca cgccgttcgt caaactcaac cttgtgcact gctaccgctc aatgaactat    840
atctcccgcc atatggagga gaaacacggt attccgtgga tggagtacaa cttcttcggt    900
ccgaccaaag tcgccgaatc gttgcgcaaa atcgccgata tgtttgatga caccattcgc    960
gccaacgccg aagcggtgat cgccaaatat caggcgcaga acgacgccat catcgccaaa   1020
taccgtccgc gtctggaagg ccgcaaagtg ctgctgtata tgggcggttt acgtcctcgc   1080
catgtgattg cgcttatga agatctgggg atggaaatta cgctgcggg ttatgaattc   1140 gcccacaacg atgactacga ccgcacccct ccggatctga agaaggcac cttgctgttc   1200 gacgatgcca gcagttatga actggaagcc tttgtcaaag cgctgaagcc ggatctgatc   1260
ggctccggca ttaaagagaa gtacatcttc cagaaaatgg gcgtgccgtt tcgccagatg   1320
cactcctggg attactccgg ccctatcac ggttatgacg ctttgccat cttcgcccgc   1380 gatatggata tgacgatcaa caaccccgcg tgggccagt tgaccgcgcc gtggctgaaa   1440
tccgcctga                                                         1449
```

<210> SEQ ID NO 152

```
<211> LENGTH: 1092
<212> TYPE: DNA
<213> ORGANISM: Enterobacter sp.
<220> FEATURE:
<223> OTHER INFORMATION: nifD2
<220> FEATURE:
<221> NAME/KEY: modified_base
<222> LOCATION: (709)..(709)
<223> OTHER INFORMATION: a, c, t, g, unknown or other

<400> SEQUENCE: 152
atgggacgcg gcgagcgccg cctgttccat gccgtgcgcc acatcgtcaa ccgctaccac      60
ccggccgccg tctttatcta taacacctgc gttcccgcga tggagggcga cgatatcgaa     120
gccgtctgcc aggcggcaga aaccgccatc ggcgtaccgg tgattgccgt tgatgtcgcc     180
gggttttacg gcagcaaaaa tctcggcaac cggttggccg gtgaagtgat ggtgaaaaag     240
gtgattggcg gcgtgaacc cgcgccgtgg ccggaagata cccttttgc cccggcgcac      300
cgccacgata tcgggctgat tggcgaattc aatattgccg agagttctg gcatattcag      360
ccgctgctcg atgagctggg tattcgcgtg ctcggcagcc tctccggcga cgggcgcttc     420
agtgaaatcc agacgctgca ccgggcgcag gtcaatatgc tggtctgctc cagggcgctg     480
atcaacgtcg cccgctcgct ggagcagcgc tacggcacgc cgtggtttga aggcagtttt     540
tatggtgttc gcgccacctc tgacgccctg cgccaactgg cggcgctgac cggagaccgc     600
gatctgatgc agcgcaccga acagctcatt gcccgcgaag agcagcaaac agagcaggcg     660
ctggccccgc tgcgcgagcg cctgcgcggg cgcaaagcgc tgctctatnc cggcggcgtg     720
aaatcctggt cggtggtttc ggcgcttcag gatctgggca tggaagtggt ggcgaccggc     780
acgcgcaaat ccaccgaaga ggataaacag cgcatccgcg aactgatggg cgccgacgcg     840
ctgatgcttg atgaaggtaa cgcccgctcg ctgctggacg tggtttaccg ctacaaggcg     900
gacatgatga tcgccggggg acgcaatatg tacaccgcct acaaagcgcg gctgccgttc     960
ctcgatatca atcaggagcg cgagcacgcc tttgccggct accgcggcat tgtcaccctg    1020
gccgaacagc tctgcctgac catggaaagc ccggtctggc gcaaacccca ttcccgcgca    1080
ccgtggcaat aa                                                        1092

<210> SEQ ID NO 153
<211> LENGTH: 846
<212> TYPE: DNA
<213> ORGANISM: Enterobacter sp.
<220> FEATURE:
<223> OTHER INFORMATION: nifK

<400> SEQUENCE: 153
atgatggagc aaatggacgt gccgtgcagc ctgctttccg atccctccga agtgctggat      60
accccggctg acgggcatta ccacatgtat gcgggcggta cgacccagca ggagatgcgc     120
gaagcgcctg acgctatcga cacccctgctg ctgcaaccct ggcaactggt gaaaaccaaa     180
aaagtggtgc aggaaagctg gaaccagccc gctaccgagg tgcaaatccc aatgggggctg     240
gccggaaccg acgagctgct gatgacggta agccagttaa ccggcaaagc cattccggat     300
agcttagcgc tggaacgcgg tcggctggtg gatatgatgc tcgactccca cacctggctg     360
cacggcaaga aattcggcct gttcggtgac ccggattttg tcatggggct gacccgcttc     420
ctgctggaac tgggctgcga accgacggtg attctgtgcc ataacggcag caagcgctgg     480
cagaaagcga tgaagaaaat gcttgaagcc tcgccgtacg ggaaagagag cgaagtcttt     540
atcaactgcg atttgtggca tttccgctcg ctgatgttta cccgtcagcc ggactttatg     600
```

-continued

```
atcggcaact cctacgccaa gtttatccag cgcgatacgc tggcgaaggg tgagcagttt      660
gaagtgccgc tgatccgcct ggggttcccg ctgttcgatc gccaccatct gcaccgccag      720
accacctggg gttacgaagg ggccatgagt atcctcacca cgctggttaa tgcggtgctg      780
gagaaagtcg acagagagac catcaagctc ggcaaaaccg actacagctt cgatcttatc      840
cgttaa                                                                 846
```

<210> SEQ ID NO 154
<211> LENGTH: 1095
<212> TYPE: DNA
<213> ORGANISM: Enterobacter sp.
<220> FEATURE:
<223> OTHER INFORMATION: nifL
<220> FEATURE:
<221> NAME/KEY: modified_base
<222> LOCATION: (942)..(942)
<223> OTHER INFORMATION: a, c, t, g, unknown or other

<400> SEQUENCE: 154

```
atgcagcgcg acatcagcac cagctacgcg ctggaacaac ggctgcgcaa tcatatgacg       60
ctgaccgaag ccgtcttgaa taacattccg gcggcggttg tagtggtgga tgaacgcgat      120
cgggtggtga tggataacct cgcctacaaa accttttgcg ccgattgcgg cggtaaagaa      180
ctactcaccg aaatcaactt ttccgcccat aaggcggagc tggcgcaggg cctggtactg      240
ccggtagtgc tgcgcggcac cgtgcgctgg ttgtccgtta cctgttgggc gctgccgggc      300
gtcagcgaag aagcaggccg ctactttatt gatagcgccg tgccgcgcac gctggtggtg      360
atcaccgata atactcagca gcagcaacaa caggagcagg ggcgtcttga tcgtctgaag      420
cagcagataa ccagcggtaa aattgctggc gcgatccgcg aatcgctgga cgccgcgctg      480
gtacaactca attgcccaat taatatgctg ccgccgcac gccgcttaaa tggcgacgag      540
catagcaatc tggcgctgga tgccgcatgg cgtgaaggcg aagaagcgat ggcgcggttg      600
cagcgctgcc gccgtcgct ggaactggaa agcccggcag tctggccgct ccagccgttc       660
cttgacgatc tgcgtgccct gtatcacacc cgatataacc agggcgaaaa cctgcaaatt      720
gagctggaat ccccgacct ggtgggcttt ggccagcgaa cacaactgct tgcctgcctg      780
agcctgtggc tcgacagaac cctggatatt gccgcggagc tacgtgattt cacggtacag      840
actcaacttt acgcccgcga agagagcggc tggctgtcgt tctatttaaa cgacaatgtg      900
ccgctgattc aggtgcgcta cacccattca cccgatgcac tnaatgcgcc cggtaaaggc      960
atggagctgc ggctgatcca gacgctggtc gcccaccatc gaggcgcaat agaactgacc     1020
tcacgccctc agggaggcac ctgtctgatc ctgcgtttcc cattatttta ctcgctgaca     1080
ggaggctcac tatga                                                     1095
```

<210> SEQ ID NO 155
<211> LENGTH: 219
<212> TYPE: DNA
<213> ORGANISM: Enterobacter sp.
<220> FEATURE:
<223> OTHER INFORMATION: nifA partial gene

<400> SEQUENCE: 155

```
atgactcagc gaaccgagtc gggtacaacc gtctggcgct tgacctctc ccaacagttt      60
acagccatgc agcgtatcag tgtggtgtta agccgcgcga cggagatcgg gcagacgcta    120
caggaagtgc tgtgcgtgct gcacaacgat gcctttatgc agcacgggat gatctgtccg    180
tacgcgcggg tgcgcgtctt cgcgagcgta tggctttga                            219
```

<210> SEQ ID NO 156
<211> LENGTH: 1635
<212> TYPE: DNA
<213> ORGANISM: Enterobacter sp.
<220> FEATURE:
<223> OTHER INFORMATION: glnE
<220> FEATURE:
<221> NAME/KEY: modified_base
<222> LOCATION: (234)..(234)
<223> OTHER INFORMATION: a, c, t, g, unknown or other
<220> FEATURE:
<221> NAME/KEY: modified_base
<222> LOCATION: (274)..(274)
<223> OTHER INFORMATION: a, c, t, g, unknown or other
<220> FEATURE:
<221> NAME/KEY: modified_base
<222> LOCATION: (1535)..(1535)
<223> OTHER INFORMATION: a, c, t, g, unknown or other

<400> SEQUENCE: 156

```
atgcgcgtgg aagactggtc aacgctgacc gaacggctcg atgcccatat ggcaggcgtg      60
cgccgaatct ttaacgaact gatcggtgat gacgaaagtg agtcgcagga cgatgcgctc    120
tccgagcact ggcgcgagct gtggcaggac gcgcttcagg aagatgacac cacgccggtg    180
ctgacgcact taaccgacga cgcgcgccat cgcgtggtgg cgctgatcgc tganttccgt    240
cttgagctga acaaacgcgc catcggcccg cgtngtcgcc aggtgctgga tcacctgatg    300
ccgcacctgc tgagcgaagt ctgctcgcgt gccgatgcgc cggtgccgct gtcgcggatg    360
atgcccctgc tgagcgggat tatcacccgt actacctacc ttgaactcct gagcgagttc    420
cctggcgcgc ttaagcacct gatttcactc tgcgccgcgt cgccgatggt ggccaacaag    480
ctggcgcgtt acccgctgct gctggatgag ctgctcgatc gaataccct ttatcaaccg    540
acggcgaccg acgcctaccg ggacgaactg cgtcagtatc tgctgcgcgt gccggaagaa    600
gacgaagagc aacagctgga ggcgctgcgt cagtttaagc aggcccagat gctgcgcgtg    660
gcggccgcag atattgccgg aacgctgccg gtgatgaaag tgagcgatca cttaacctgg    720
cttgcggaag cgattatcga cgcggtggtg catcaggcct gggtgcagat ggtggcgcgc    780
tatggccagc cgaaacatct ggctgaccgt gatggtcgcg gcttcgcggt ggtgggttac    840
ggtaagctcg gcgttggga gctgggctat agctccgatc tggatttaat cttcctccac    900
gactgcccgg ttgatgtgat gaccgacggc gagcgcgaga ttgacgggcg tcagttctac    960
ctgcgcctgg cgcagcgcat catgcacctg ttcagcaccc gcacctcgtc gggcatttg   1020
tatgaagtgg atgcccgtct gcgcccgtcc ggcgcggcgg gcatgctggt cacctcgacg   1080
gagtccttcg ctgattacca gaagaatgaa gcctggacgt gggagcatca ggcgctggtg   1140
cgcgcccgtg tggtgtatgg cgatccgctg ctgaaaacgc agtttgacgt gattcgtaag   1200
gaagtcatga ccaccgtgcg cgatggcagc acgctgcaaa cggaagtgcg cgaaatgcgc   1260
gagaaaatgc gcgcgcactt aggcaataaa catcgcgatc gctttgatat taaagccgat   1320
gagggcggta ttaccgatat tgagtttatt acccagtatc tggtgttgct gcacgcgcat   1380
```

| | | |
|---|---|---|
| gacaagccga agctgacgcg ctggtcggat aacgtgcgca ttctggaact gctggcgcaa | 1440 | |
| aacgacatta tggacgagca ggaggcgcag gccttaaccc gtgcctatac aacgcttcgc | 1500 | |
| gatgagctcc atcatctggc gttgcaggag cagcnggac acgtggcgct ggactgtttc | 1560 | |
| accgctgaac gcgctcaggt aacggccagc tggcagaagt ggctggtgga accgtgcgta | 1620 | |
| acaaatcaag tgtga | 1635 | |

<210> SEQ ID NO 157
<211> LENGTH: 1316
<212> TYPE: DNA
<213> ORGANISM: Enterobacter sp.
<220> FEATURE:
<223> OTHER INFORMATION: 16S
<220> FEATURE:
<221> NAME/KEY: modified_base
<222> LOCATION: (43)..(43)
<223> OTHER INFORMATION: a, c, t, g, unknown or other
<220> FEATURE:
<221> NAME/KEY: modified_base
<222> LOCATION: (247)..(247)
<223> OTHER INFORMATION: a, c, t, g, unknown or other
<220> FEATURE:
<221> NAME/KEY: modified_base
<222> LOCATION: (784)..(785)
<223> OTHER INFORMATION: a, c, t, g, unknown or other
<220> FEATURE:
<221> NAME/KEY: modified_base
<222> LOCATION: (794)..(795)
<223> OTHER INFORMATION: a, c, t, g, unknown or other

<400> SEQUENCE: 157

| | | |
|---|---|---|
| agatgtgccc agatgggatt agctagtagg tggggtaacg gcncacctag gcgacgatcc | 60 | |
| ctagctggtc tgagaggatg accagccaca ctggaactga dacacggtcc agactcctac | 120 | |
| gggaggcagc agtggggaat attgcacaat gggcgcaagc ctgatgcagc catgccgcgt | 180 | |
| gtatgaagaa ggccttcggg ttgtaaagta ctttcagcgg ggaggaaggt gttgtggtta | 240 | |
| ataaccncag caattgacgt tacccgcaga agaagcaccg gctaactccg tgccagcagc | 300 | |
| cgcggtaata cggagggtgc aagcgttaat cggaattact gggcgtaaag cgcacgcagg | 360 | |
| cggtctgtca agtcggatgt gaaatccccg ggctcaacct gggaactgca ttcgaaactg | 420 | |
| gcaggctaga gtcttgtaga ggggggtaga attccaggtg tagcggtgaa atgcgtagag | 480 | |
| atctggagga ataccggtgg cgaaggcggc cccctggaca aagactgacg ctcaggtgcg | 540 | |
| aaagcgtggg gagcaaacag gattagatac cctggtagtc cacgccgtaa acgatgtcga | 600 | |
| cttggaggtt gtgcccttga ggcgtggctt ccggagctaa cgcgttaagt cgaccgcctg | 660 | |
| gggagtacgg ccgcaaggtt aaaactcaaa tgaattgacg ggggcccgca caagcggtgg | 720 | |
| agcatgtggt ttaattcgat gcaacgcgaa gaaccttacc tactcttgac atccagagaa | 780 | |
| cttnncagag atgnnttggt gccttcggga actctgagac aggtgctgca tggctgtcgt | 840 | |
| cagctcgtgt tgtgaaatgt tgggttaagt cccgcaacga gcgcaaccct tatcctttgt | 900 | |
| tgccagcggt ccggccggga actcaaagga gactgccagt gataaactgg aggaaggtgg | 960 | |
| ggatgacgtc aagtcatcat ggcccttacg agtagggcta cacacgtgct acaatggcgc | 1020 | |
| atacaaagag aagcgacctc gcgagagcaa gcggacctca taaagtgcgt cgtagtccgg | 1080 | |
| attggagtct gcaactcgac tccatgaagt cggaatcgct agtaatcgta gatcagaatg | 1140 | |
| ctacggtgaa tacgttcccg ggccttgtac acaccgcccg tcacaccatg ggagtgggtt | 1200 | |
| gcaaaagaag taggtagctt aaccttcggg agggcgctta ccactttgtg attcatgact | 1260 | |
| ggggtgaagt cgtaacaagg taaccgtagg ggaacctgcg gttggatcac ctcctt | 1316 | |

-continued

<210> SEQ ID NO 158
<211> LENGTH: 882
<212> TYPE: DNA
<213> ORGANISM: Enterobacter sp.
<220> FEATURE:
<223> OTHER INFORMATION: nifH

<400> SEQUENCE: 158

| | | | | | |
|---|---|---|---|---|---|
| atgaccatgc | gtcaatgtgc | catttacggc | aaaggtggta | tcggtaaatc | cactaccacg | 60 |
| caaaacctgg | tcgccgcgct | ggcggagatg | ggcaagaaag | taatgatcgt | cggctgcgac | 120 |
| ccgaaagcag | actccactcg | tctgatcctg | catgcgaaag | cgcagaacac | cattatggag | 180 |
| atggcggctg | aagtcggctc | cgtggaagac | cttgaactgg | aagatgtgct | gcaaatcggt | 240 |
| tacggcgacg | tacgctgcgc | agaatccggc | ggcccggaac | caggcgttgg | ctgtgctggt | 300 |
| cgcggggtaa | ttaccgccat | caacttcctg | aagaagaag | gcgcctatgt | tcccgacctc | 360 |
| gatttcgtct | tttacgacgt | gttgggcgac | gtggtgtgcg | ggggttcgc | catgccgatt | 420 |
| cgcgaaaaca | aagcgcagga | gatctacatc | gtctgctccg | gcgaaatgat | ggcgatgtac | 480 |
| gccgccaaca | acatctctaa | aggcatcgtg | aaatacgcca | atccggcaa | agtgcgcctt | 540 |
| ggcgggctga | tctgtaactc | ccgtcagacc | gaccgcgaag | atgagctgat | catagcgctg | 600 |
| gcggaaaaac | tcggcaccca | gatgatccac | ttcgtgccgc | gcgacaacat | cgtgcaacgc | 660 |
| gctgaaatcc | gccgtatgac | ggtgattgag | tacgatccga | aatgcaacca | ggccaatgaa | 720 |
| taccgcacgc | tggcgaacaa | gatcgtcaac | aacaccaaaa | tggtcgtgcc | aacgcccatc | 780 |
| accatggacg | aactggaaga | gctgttgatg | gaattcggca | ttatggatgt | ggaagacacc | 840 |
| agcattatcg | gtaaaaccgc | cgcagaagaa | aacgcggttt | ga | | 882 |

<210> SEQ ID NO 159
<211> LENGTH: 1449
<212> TYPE: DNA
<213> ORGANISM: Enterobacter sp.
<220> FEATURE:
<223> OTHER INFORMATION: nifD1

<400> SEQUENCE: 159

| | | | | | |
|---|---|---|---|---|---|
| atgagcaatg | caacaggcga | acgtaatctg | gagatcatcc | aggaagtgct | ggagatcttt | 60 |
| ccggaaaaaa | cgcgcaaaga | acgcagaaag | cacatgatgg | tgagcgaccc | ggagatggaa | 120 |
| agcgtcggga | aatgcatcat | ctccaaccgt | aagtcgcagc | ccggcgtaat | gaccgtgcgc | 180 |
| ggttgctctt | acgccggttc | taaagggtg | gtattcgggc | cgatcaaaga | tatgcccat | 240 |
| atttcccacg | gcccggtcgg | ctgcggtcag | tactcccgcg | ccgggcggcg | taactactac | 300 |
| accggcgtca | gcgtgtggga | tagcttcggt | acgctcaact | ttacctccga | ttttcaggag | 360 |
| cgcgatatcg | tgtttggcgg | cgataaaaag | ctgaccaaac | tgattgaaga | gatggagacg | 420 |
| ctgttcccgc | tgaccaaagg | gatctccatt | cagtccgaat | gcccggtcgg | cctgattggc | 480 |
| gacgacattg | aagccgttgc | caacgccagc | cgcaaagcca | tcaataaacc | ggtcattccg | 540 |
| gtgcgctgcg | aaggtttcg | cggcgtttcc | cagtcactcg | gtcaccacat | tgccaacgac | 600 |
| gtgatccgcg | actgggtact | ggataaccgc | gaaggcaagc | cgtttgaggc | cggtccttat | 660 |
| gacgtggcga | tcatcggcga | ttacaacatc | ggcggcgatg | cctgggcgtc | gcgcattttg | 720 |
| ctcgaagaga | tgggcctgcg | cgtggtggcg | cagtggtccg | gcgacggcac | gctggttgag | 780 |
| atggagaaca | cgccgttcgt | caaactcaac | cttgtgcact | gctaccgctc | aatgaactat | 840 |

| | |
|---|---|
| atctcccgcc atatggagga gaaacacggt attccgtgga tggagtacaa cttcttcggt | 900 |
| ccgaccaaag tcgccgaatc gttgcgcaaa atcgccgata tgtttgatga caccattcgc | 960 |
| gccaacgccg aagcggtgat cgccaaatat caggcgcaga acgacgccat catcgccaaa | 1020 |
| taccgtccgc gtctggaagg ccgcaaagtg ctgctgtata tgggcggttt acgtcctcgc | 1080 |
| catgtgattg gcgcttatga agatctgggg atggaaatta tcgctgcggg ttatgaattc | 1140 |
| gcccacaacg atgactacga ccgcaccctg ccggatctga agaaggcac cttgctgttc | 1200 |
| gacgatgcca gcagttatga actggaagcc tttgtcaaag cgctgaagcc ggatctgatc | 1260 |
| ggctccggca ttaaagagaa gtacatcttc cagaaaatgg gcgtgccgtt cgccagatg | 1320 |
| cactcctggg attactccgg ccctatcac ggttatgacg gctttgccat cttcgcccgc | 1380 |
| gatatggata tgacgatcaa caaccccgcg tggggccagt tgaccgcgcc gtggctgaaa | 1440 |
| tccgcctga | 1449 |

<210> SEQ ID NO 160
<211> LENGTH: 1374
<212> TYPE: DNA
<213> ORGANISM: Enterobacter sp.
<220> FEATURE:
<223> OTHER INFORMATION: nifD2

<400> SEQUENCE: 160

| | |
|---|---|
| atgaagggga acgagatcct ggctttgctc gatgaacctg cctgcgagca caaccataaa | 60 |
| cagaaatccg gctgcagcgc gccgaaaccc ggcgcgacag cgggcggctg cgcctttgac | 120 |
| ggtgcgcaga tcaccctgct gccactctcc gatgttgccc acctggtaca cggccccatt | 180 |
| ggttgtaccg gtagctcatg ggataaccgt ggcagcttca gttccggccc gacgatcaac | 240 |
| cggctgggtt ttaccaccga tctgagcgaa caggatgtga tcatgggacg cggcgagcgc | 300 |
| cgcctgttcc atgccgtgcg ccacatcgtc aaccgctacc accggccgc cgtctttatc | 360 |
| tataacacct gcgttcccgc gatggagggc gacgatatcg aagccgtctg ccaggcggca | 420 |
| gaaaccgcca tcggcgtacc ggtgattgcc gttgatgtcg ccgggtttta cggcagcaaa | 480 |
| aatctcggca accggttggc cggtgaagtg atggtgaaaa aggtgattgg cgggcgtgaa | 540 |
| cccgcgccgt ggccggaaga taccccttttt gccccggcgc accgccacga tatcgggctg | 600 |
| attggcgaat tcaatattgc cggagagttc tggcatattc agccgctgct cgatgagctg | 660 |
| ggtattcgcg tgctcggcag cctctccggc gacgggcgct tcagtgaaat ccagacgctg | 720 |
| caccgggcgc aggtcaatat gctggtctgc tccaggcgc tgatcaacgt cgcccgctcg | 780 |
| ctggagcagc gctacggcac gccgtggttt gaaggcagtt tttatggtgt cgcgccacc | 840 |
| tctgacgccc tgcgccaact ggcggcgctg accggagacc gcgatctgat gcagcgcacc | 900 |
| gaacagctca ttgcccgcga agagcagcaa acagagcagg cgctggcccc gctgcgcgag | 960 |
| cgcctgcgcg ggcgcaaagc gctgctctat accggcggcg tgaaatcctg gtcggtggtt | 1020 |
| tcggcgcttc aggatctggg catggaagtg gtggcgaccg gcacgcgcaa atccaccgaa | 1080 |
| gaggataaac agcgcatccg cgaactgatg ggcgccgacg cgctgatgct tgatgaaggt | 1140 |
| aacgcccgct cgctgctgga cgtggtttac cgctacaagg cggacatgat gatcgccggg | 1200 |
| ggacgcaata tgtacaccgc ctacaaagcg cggctgccgt tcctcgatat caatcaggag | 1260 |
| cgcgagcacg cctttgccgg ctaccgcggc attgtcaccc tggccgaaca gctctgcctg | 1320 |
| accatggaaa gccggtctg gccgcaaacc cattcccgcg caccgtggca ataa | 1374 |

<210> SEQ ID NO 161
<211> LENGTH: 1563
<212> TYPE: DNA
<213> ORGANISM: Enterobacter sp.
<220> FEATURE:
<223> OTHER INFORMATION: nifK1

<400> SEQUENCE: 161

```
atgagccaaa gtgctgagaa aattcaaaac tgtcatccgc tgtttgaaca ggatgcgtac      60
cagatgctgt ttaaagataa acggcaactg gaagaggccc acgatccggc gcgcgtgcag     120
gaggtctttc aatggaccac caccgccgag tatgaagcgc ttaactttca acgcgaagcg     180
ctgactatcg atccggccaa agcctgccag ccgctgggtg cggtactgtg ctcgctgggc     240
tttgccaata ccctgcccta tgttcacggc tcccaggggt gcgtggccta tttccgcacc     300
tattttaacc gtcactttaa agagccgatt gcctgtgttt ctgactcgat gacgaagat      360
gcggcagtat tcggcggcaa caacaacctg aacaccgggt tgcagaacgc cagcgccctc     420
tacaagccgg aaatcattgc cgtctccacc acctgtatgg cggaggtcat cggcgacgac     480
ctgcaggcgt ttattgctaa cgccaaaaaa gacggcttta tcgacgcggc gatcccggtg     540
ccttacgcgc acacgccaag ctttatcggc agccatatca ccggctggga caatatgttt     600
gagggcttcg cccgtacctt taccgccgat tacagcggac aaccgggcaa attaccgcgt     660
atcaatctgg tcagcggatt tgaaacctat ctcggtaatt tccgcgtgct gaaacgcatg     720
atggagcaaa tggacgtgcc gtgcagcctg ctttccgatc cctccgaagt gctggatacc     780
ccggctgacg gcattaccca catgtatgcg ggcggtacga cccagcagga gatgcgcgaa     840
gcgcctgacg ctatcgacac cctgctgctg caaccctggc aactggtgaa aaccaaaaaa     900
gtggtgcagg aaagctggaa ccagcccgct accgaggtgc aaatcccaat ggggctggcc     960
ggaaccgacg agctgctgat gacggtaagc cagttaaccg gcaaagccat tccggatagc    1020
ttagcgctgg aacgcggtcg gctggtggat atgatgctcg actccacac ctggctgcac     1080
ggcaagaaat tcggcctgtt cggtgacccg gattttgtca tggggctgac ccgcttcctg    1140
ctggaactgg gctgcgaacc gacggtgatt ctgtgccata acggcagcaa gcgctggcag    1200
aaagcgatga agaaaatgct tgaagcctcg ccgtacggga agagagcga agtctttatc     1260
aactgcgatt tgtggcattt ccgctcgctg atgtttaccc gtcagccgga ctttatgatc    1320
ggcaactcct acgccaagtt tatccagcgc gatacgctgg cgaagggtga gcagtttgaa    1380
gtgccgctga tccgcctggg gttcccgctg ttcgatcgcc accatctgca ccgccagacc    1440
acctggggtt acgaagggc catgagtatc ctcaccacgc tggttaatgc ggtgctggag    1500
aaagtcgaca gagagaccat caagctcggc aaaaccgact acagcttcga tcttatccgt    1560
taa                                                                   1563
```

<210> SEQ ID NO 162
<211> LENGTH: 1386
<212> TYPE: DNA
<213> ORGANISM: Enterobacter sp.
<220> FEATURE:
<223> OTHER INFORMATION: nifK2

<400> SEQUENCE: 162

```
atggcagaaa ttatccgtag taaaaagccg ctggccgtca gcccggtaaa aagtggccag      60
ccgctgggcg cgattctggc gagcatgggc tttgaacaga gcattccgct ggttcatggc     120
gctcagggt gcagcgccctt cgcgaaggtc ttttttatcc agcattttca cgatccgatc     180
```

```
ccgctgcaat cgacggcaat ggacccgaca tcgaccatta tgggtgccga tgagaacatc    240
tttaccgcgc tgaatgtgct gtgttcacgc aacaacccga aagcgattgt tctgctgagc    300
actggccttt ccgaggcgca gggcagcgat atttcgcgcg tggtgcgcca gttccgcgat    360
gaatatccgc gccataaagg ggtggcgctg ctgaccgtca acacgccgga tttttacggc    420
agcctggaaa acggctacag cgcggtgctg gagagcatgg ttgaacagtg ggtgccggaa    480
aaaccgcagc cgggcgtgcg caatcgccgc gtgaacctgc tgctcagcca tttgcttacg    540
ccgggcgaca ttgagctgct gcgaagttat gtcgaggcat ttggcctgca gccggtgatg    600
gtgccggatc tttcccagtc gctggatggc catctcgcca gcggggattt ctcgccaatt    660
acccagggcg gcagcagcct gcggctgatt gaacagatgg gacagagtct tggcacgttc    720
gccattggcg tatccctctc ccgcgccgcg caattgctgg cgcagcgcag ccatgcggaa    780
gtggtcaccc tgccgcatct gatgaccatg agccagtgcg atacgtttat tcatcaactg    840
aagcgcctct ccgggcgcga tgttccggcg tggatcgaac gccagcgcgg gcaactgcag    900
gatgcgatga tcgattgtca tatgtggttg cagggcgcgc tgtcgcgct ggccgccgag     960 ggcgatctgc tcgccgcctg gtgcgatttc gcctgcgata tgggcatggt gcccggcccg   1020
gtggtggcgc cggtgagcca gaaagggttg caggatctgc cggtcgaaaa agtcattatc   1080
ggcgatctgg aggatatgca ggatctgttg tgtgaaacgc ctgcatcgct gctcgtctct   1140
aattctcacg ccgctgattt ggccgggcag ttcgacattc gctggtgcg cgccggtttc    1200 cccctgttcg accgtctggg cgagtttcgc cgcgtgcgcc agggttacgc cgggatgcgc   1260
gacaccttgt ttgagctggc gaatgcgctg cgcgatcgcc atcatcatct tgccgcttat   1320
cactcgccgc tgcgccagcg tttttacgaa cccgcatctt cgggaggtga ctatgcaaca   1380
tgttaa                                                              1386
```

<210> SEQ ID NO 163
<211> LENGTH: 1488
<212> TYPE: DNA
<213> ORGANISM: Enterobacter sp.
<220> FEATURE:
<223> OTHER INFORMATION: nifL

<400> SEQUENCE: 163

```
atgaccctga atatgatgat ggacgccacc gcgcccgccg agatcgccgg agcgctctca     60
caacagcatc ccgggttgtt tttcaccatg gttgaacagg cgcccgtcgc gatttcactg    120
accgatgccg atgcccacat tctctacgcc aaccccgcgt tttgtcgcca gtcggggtat    180
gaactggaag agttgttgca gcaaaacccg cgcctgcttg ccagtaagca gacgccgcgt    240
gaaatctacc aggaaatgtg gcacaccctg ctgcaacacc gtccgtggcg cggacaactg    300
atcaaccgtc gccgcgacgg cagcctgttt ctggtggaaa tcgacatcac cccactgttt    360
gatgcgttcg gcaaactcga acattacctg gccatgcagc gcgacatcag caccagctac    420
gcgctggaac aacggctgcg caatcatatg acgctgaccg aagccgtctt gaataacatt    480
ccggcggcgg ttgtagtggt ggatgaacgc gatcgggtgg tgatggataa cctcgcctac    540 aaaaccttt gcgccgattg cggcggtaaa gaactactca ccgaaatcaa cttttccgcc     600
cataaggcgg agctggcgca gggcctggta ctgccggtag tgctgcgcgg caccgtgcgc    660
tggttgtccg ttacctgttg ggcgctgccg ggcgtcagcg aagaagcagg ccgctacttt    720
attgatagcg ccgtgccgcg cacgctggtg gtgatcaccg ataatactca gcagcagcaa    780
caacaggagc aggggcgtct tgatcgtctg aagcagcaga taaccagcgg taaattgctg    840
```

```
gcggcgatcc gcgaatcgct ggacgccgcg ctggtacaac tcaattgccc aattaatatg      900
ctggccgccg cacgccgctt aaatggcgac gagcatagca atctggcgct ggatgccgca      960
tggcgtgaag gcgaagaagc gatggcgcg  ttgcagcgct gccgcccgtc gctggaactg     1020
gaaagcccgg cagtctggcc gctccagccg ttccttgacg atctgcgtgc cctgtatcac     1080
acccgatata accagggcga aaacctgcaa attgagctgg aatccccga cctggtgggc      1140 tttggccagc gaacacaact gcttgcctgc ctgagcctgt ggctcgacag aaccctggat     1200
attgccgcgg agctacgtga tttcacggta cagactcaac tttacgcccg cgaagagagc     1260
ggctggctgt cgttctattt aaacgacaat gtgccgctga ttcaggtgcg ctacacccat     1320
tcacccgatg cactcaatgc gcccggtaaa ggcatggagc tgcggctgat ccagacgctg     1380
gtcgcccacc atcgaggcgc aatagaactg acctcacgcc ctcagggagg cacctgtctg     1440
atcctgcgtt tcccattatt ttactcgctg acaggaggct cactatga               1488

<210> SEQ ID NO 164
<211> LENGTH: 1575
<212> TYPE: DNA
<213> ORGANISM: Enterobacter sp.
<220> FEATURE:
<223> OTHER INFORMATION: nifA

<400> SEQUENCE: 164
atgactcagc gaaccgagtc gggtacaacc gtctggcgct ttgacctctc ccaacagttt       60
acagccatgc agcgtatcag tgtggtgtta agccgcgcga cggagatcgg gcagacgcta      120
caggaagtgc tgtgcgtgct gcacaacgat gcctttatgc agcacgggat gatctgtctg      180
tacgacagta agcaagcgat cctttccatt gaagccttgc atgaggccga tcagcagtta      240
attcccggca gttcacagat tcgctaccgt ccgggcgaag ggctggtagg cacggtgctt      300
tcacagggac agtcgctggt actgcccgt  gtctccgacg atcggcgttt tctcgatcgc      360
ctgggattgt atgattacag cttgccgttt atcgccgtgc cgctgatggg gccaaactcg      420
cagcctatcg gcgtgctggc cgcccagcct atggcgcgtt acgaggagcg gctgccgcc       480 tgcacgcgtt ttcttgaaac cgtcgccaat ctggtggcg  aaaccgttcg cctgatgaca      540
ccgcccagcg tcgcgtctcc accccgtgct gctgccgcgc agattgccag ccagcgcggg      600
tgcgcgtctt cgcgagcgta tggctttgaa aacatggtcg gtaaaagcgc ggctatgcgt      660
cagacgctgg aaattattcg ccaggtatca cgctgggaca ccaccgtgct ggtgcgtggc      720
gaaagcggaa ccgtaaaga  gttgatagcc aacgctatcc accacaattc accgcgcgcc      780
gccgcgccgt tgtcaaatt  caactgcgcg gcgctgcccg atacgctgct ggagagtgaa      840
ctcttcggtc atgaaaaagg cgcgtttacc ggcgcggtgc cgcagcgcaa aggccgtttc      900
gaactggcgg atggcggtac gctgtttctt gatgagatcg gcgaaagtag cgcctcgttt      960
caggcgaaat tgctgcgtat cttgcaggaa ggcgaaatgg aacgcgtcgg cggcgacgaa     1020
acgctgcggg tgaatgtacg gatcattgcc gccaccaacc gcaatctgga agaggaagtg     1080
cggctgggta tttttcgcga agatctctac tatcgcctta atgtgatgcc gatctccctg     1140
cccccgctcc gcgagcgtca ggaggacatc gtcgagctgg cgcattttct ggtgcgcaaa     1200
atcgcgcaaa accagaaccg cacgctgcgc atcagcgatg gcgcgatccg tttgttgatg     1260
agctatagct ggcctggaaa cgtgcgtgag ctggaaaact gccttgagcg atcgcggtg      1320 atgtcggaaa acgggctgat cgatcgcgac gtgattttgt ttcaccacag ggaaaatctg     1380
```

| | |
|---|---|
| ccaaaaacgc cacagaccag tgcgccgcgc aagagagct ggctcgatca gaacctcgat | 1440 |
| gagcgacaaa gattgatcgc cgcgctggag aaagccggtt gggtacaggc aaaagccgcg | 1500 |
| cgcctgctgg gaatgacccc gcgccaggtg gcctatcgta ttcagacgat ggacattgcc | 1560 |
| atgccgagat tgtag | 1575 |

<210> SEQ ID NO 165
<211> LENGTH: 2856
<212> TYPE: DNA
<213> ORGANISM: Enterobacter sp.
<220> FEATURE:
<223> OTHER INFORMATION: glnE

<400> SEQUENCE: 165

| | |
|---|---|
| atgccgcttt cttcgcagtt acagcagcag tggcagaccg tttgcgaacg tctgcctgag | 60 |
| tcattaccgg cgtcatcgtt aagcgagcag gcaaagagcg tgctcgtctt cagtgatttt | 120 |
| gtgcaggaaa gtatcaccgc caacccgaac tggctggcgg aacttgagaa cgcaccaccg | 180 |
| caggcagaag agtggcggca ctatgctggc tggctgcaaa ctgtactcga agacgttacg | 240 |
| gatgaggcca cgctgatgcg cgtcctgcgc cagttccgtc gtcgggtgat ggtgcgcatt | 300 |
| gcctgggctc aggcgctgga actggtgagc gaagagagta cgctgcagca gttaagcgag | 360 |
| ctggcgcaaa cgttgattgt cgccgcgcga gactggctct atgccgcctg ctgtaaagag | 420 |
| tggggcacgc cgtgcagcga ggaagggggtt cctcagccgc tgttgattct ggggatggga | 480 |
| aagctgggcg gctgcgagct gaacttctcc tctgatatcg acctgatttt tgcctggccg | 540 |
| gagaacggct ccacgcgcgg aggccgccgc gagctggaca cgcgcagtt ctttacccgt | 600 |
| ctcggccagc gcctgattaa agcgctggat cagcccacgc aggacggttt tgtttaccgc | 660 |
| gtggacatgc gcctgcgtcc gtttggcgac agcgggccgc tggtgctgag cttttgcggcg | 720 |
| ctggaagatt attaccagga gcaaggtcgc gactgggagc gttacgcgat ggtcaaagcg | 780 |
| cggatcatgg gcgacagcga cgacgcttat gccaacgagc tgcgcgccat gctgcgtccg | 840 |
| ttcgtgttcc gtcgctatat cgacttcagc gtcatccagt ccctgcgaaa tatgaaaggg | 900 |
| atgattgccc gcgaggtgcg ccgccgtggg ctgaaagaca atatcaagct cggtgcgggc | 960 |
| ggcatccgcg aaatcgaatt tatcgtccag gtcttccagc ttattcgcgg cggacgcgag | 1020 |
| ccgtcgctgc agtcccgttc cttattaccg acgctgagcg ccattgcgca gctgcatctc | 1080 |
| ctgccggacg gcgacgcgca aaccctgcgc gaggcctatc ttttcctgcg tcgtctggaa | 1140 |
| aacctgctgc aaagcattaa tgacgaacag acccaaaccc tgccgggcga cgaccttaac | 1200 |
| cgggcgcgtc tggcctgggg aatgcgcgtg aagactggt caacgctgac cgaacggctc | 1260 |
| gatgcccata tggcaggcgt gcgccgaatc tttaacgaac tgatcggtga tgacgaaagt | 1320 |
| gagtcgcagg acgatgcgct ctccgagcac tggcgcgagc tgtggcagga cgcgcttcag | 1380 |
| gaagatgaca ccacgccggt gctgacgcac ttaaccgacg acgcgcgcca tcgcgtggtg | 1440 |
| gcgctgatcg ctgatttccg tcttgagctg aacaaacgcg ccatcggccc gcgtggtcgc | 1500 |
| caggtgctgg atcacctgat gccgcacctg ctgagcgaag tctgctcgcg tgccgatgcg | 1560 |
| ccggtgccgc tgtcgcggat gatgcccctg ctgagcggga ttatcacccg tactacctac | 1620 |
| cttgaactcc tgagcgagtt ccctggcgcg cttaagcacc tgatttcact ctgcgccgcg | 1680 |
| tcgccgatgg tggccaacaa gctggcgcgt taccgctgc tgctggatga gctgctcgat | 1740 |
| ccgaataccc tttatcaacc gacggcgacc gacgcctacc gggacgaact gcgtcagtat | 1800 |
| ctgctgcgcg tgccggaaga agacgaagag caacagctgg aggcgctgcg tcagtttaag | 1860 |

| | |
|---|---|
| caggcccaga tgctgcgcgt ggcggccgca gatattgccg gaacgctgcc ggtgatgaaa | 1920 |
| gtgagcgatc acttaacctg gcttgcggaa gcgattatcg acgcggtggt gcatcaggcc | 1980 |
| tgggtgcaga tggtggcgcg ctatggccag ccgaaacatc tggctgaccg tgatggtcgc | 2040 |
| ggcttcgcgg tggtgggtta cggtaagctc ggcggttggg agctgggcta tagctccgat | 2100 |
| ctggatttaa tcttcctcca cgactgcccg gttgatgtga tgaccgacgg cgagcgcgag | 2160 |
| attgacgggc gtcagttcta cctgcgcctg gcgcagcgca tcatgcacct gttcagcacc | 2220 |
| cgcacctcgt cgggcatttt gtatgaagtg gatgcccgtc tgcgcccgtc cggcgcggcg | 2280 |
| ggcatgctgg tcacctcgac ggagtccttc gctgattacc agaagaatga agcctggacg | 2340 |
| tgggagcatc aggcgctggt gcgcgcccgt gtggtgtatg gcgatccgct gctgaaaacg | 2400 |
| cagtttgacg tgattcgtaa ggaagtcatg accaccgtgc gcgatggcag cacgctgcaa | 2460 |
| acggaagtgc gcgaaatgcg cgagaaaatg cgcgcgcact taggcaataa acatcgcgat | 2520 |
| cgctttgata ttaaagccga tgagggcggt attaccgata ttgagtttat tacccagtat | 2580 |
| ctggtgttgc tgcacgcgca tgacaagccg aagctgacgc gctggtcgga taacgtgcgc | 2640 |
| attctggaac tgctggcgca aaacgacatt atggacgagc aggaggcgca ggccttaacc | 2700 |
| cgtgcctata caacgcttcg cgatgagctc catcatctgg cgttgcagga gcagccggga | 2760 |
| cacgtggcgc tggactgttt caccgctgaa cgcgctcagg taacggccag ctggcagaag | 2820 |
| tggctggtgg aaccgtgcgt aacaaatcaa gtgtga | 2856 |

<210> SEQ ID NO 166
<211> LENGTH: 1290
<212> TYPE: DNA
<213> ORGANISM: Enterobacter sp.
<220> FEATURE:
<223> OTHER INFORMATION: amtB

<400> SEQUENCE: 166

| | |
|---|---|
| atgaagatag caacacttaa aacgggtctg ggttcgctgg cactgctgcc gggcctggcg | 60 |
| ctggctgctg cacctgcggt ggcagacaaa gccgataacg cctttatgat gatcagcacc | 120 |
| gcgctggtgc tgttcatgtc cattccgggc attgcgctgt tctatggcgg cctgatccgt | 180 |
| ggcaaaaacg ttctctccat gctgacgcag gttgccgtaa cgttcgcgct ggtctgcgta | 240 |
| ctgtgggtgg tttacggtta ctcgctggct ttcggcacgg gcaacgcgtt ctttggtaac | 300 |
| ttcgactggg tgatgctgaa aaatattgaa ctgaccgcgc tgatgggcag tttctaccag | 360 |
| tatattcacg ttgcttttcca gggctcgttc gcctgcatta ccgtcgggct gattgtaggc | 420 |
| gcgcttgccg agcgtattcg tttctctgcg gtcctgatct tcgtggtggt ctggctgacg | 480 |
| ctctcctatg tgccgattgc gcacatggtc tggggtggcg gtctgctggc gacgcatggc | 540 |
| gcgctggact cgcgggcgg taccgttgtg cacattaacg ccgcggtagc gggtctggtt | 600 |
| ggcgcatacc tgattggcaa acgcgtgggc ttcggtaaag aagcgttcaa accgcacaac | 660 |
| ctgccgatgg tcttcaccgg taccgcgatc ctctactttg gctggtttgg tttcaacgcc | 720 |
| ggctcagcaa gtgccgcgaa cgaaatcgcc gcgctggcct tcgtgaatac cgttgtggcc | 780 |
| acggcaggtg caatcctctc ctgggtctttt ggcgagtggg ctgtgcgcgg taaaccttct | 840 |
| ctgctgggtg cctgttcggg ggcgattgct ggtctggtcg gtatcacccc agcatgtggt | 900 |
| tatgtcggtg tgggtggcgc gctgctggtc ggccggtgt caggtctggc gggtctgtgg | 960 |
| ggcgtgacgg cgctgaaacg tattctgcgc gttgatgacc cttgcgatgt gtttggcgtg | 1020 |

-continued

```
cacggcgtgt gcggcatcgt cggctgtatc atgaccggta tctttgcagc gaaatcgctg    1080
ggtggcgtgg gctacgcaga aggcgtcacc atggcccatc aggtgctggt gcagctggaa    1140
agtattgctg tcaccgtggt gtggtctgcc gttgtcgctt tcattggcta caaactggcg    1200
gacatgacgg ttggtctgcg cgtgccggaa gagcaggaac gcgaaggtct ggacgtcaac    1260
agccacggcg agaatgcgta taacgcatga                                     1290

<210> SEQ ID NO 167
<211> LENGTH: 1299
<212> TYPE: DNA
<213> ORGANISM: Azospirillum lipoferum
<220> FEATURE:
<223> OTHER INFORMATION: 16S
<220> FEATURE:
<221> NAME/KEY: modified_base
<222> LOCATION: (294)..(294)
<223> OTHER INFORMATION: a, c, t, g, unknown or other
<220> FEATURE:
<221> NAME/KEY: modified_base
<222> LOCATION: (299)..(299)
<223> OTHER INFORMATION: a, c, t, g, unknown or other
<220> FEATURE:
<221> NAME/KEY: modified_base
<222> LOCATION: (302)..(302)
<223> OTHER INFORMATION: a, c, t, g, unknown or other
<220> FEATURE:
<221> NAME/KEY: modified_base
<222> LOCATION: (309)..(310)
<223> OTHER INFORMATION: a, c, t, g, unknown or other
<220> FEATURE:
<221> NAME/KEY: modified_base
<222> LOCATION: (332)..(332)
<223> OTHER INFORMATION: a, c, t, g, unknown or other
<220> FEATURE:
<221> NAME/KEY: modified_base
<222> LOCATION: (346)..(346)
<223> OTHER INFORMATION: a, c, t, g, unknown or other
<220> FEATURE:
<221> NAME/KEY: modified_base
<222> LOCATION: (351)..(351)
<223> OTHER INFORMATION: a, c, t, g, unknown or other
<220> FEATURE:
<221> NAME/KEY: modified_base
<222> LOCATION: (438)..(438)
<223> OTHER INFORMATION: a, c, t, g, unknown or other
<220> FEATURE:
<221> NAME/KEY: modified_base
<222> LOCATION: (445)..(445)
<223> OTHER INFORMATION: a, c, t, g, unknown or other
<220> FEATURE:
<221> NAME/KEY: modified_base
<222> LOCATION: (454)..(454)
<223> OTHER INFORMATION: a, c, t, g, unknown or other
<220> FEATURE:
<221> NAME/KEY: modified_base
<222> LOCATION: (469)..(469)
<223> OTHER INFORMATION: a, c, t, g, unknown or other
<220> FEATURE:
<221> NAME/KEY: modified_base
<222> LOCATION: (477)..(477)
<223> OTHER INFORMATION: a, c, t, g, unknown or other
<220> FEATURE:
<221> NAME/KEY: modified_base
<222> LOCATION: (492)..(492)
<223> OTHER INFORMATION: a, c, t, g, unknown or other
<220> FEATURE:
<221> NAME/KEY: modified_base
<222> LOCATION: (504)..(504)
<223> OTHER INFORMATION: a, c, t, g, unknown or other
<220> FEATURE:
<221> NAME/KEY: modified_base
<222> LOCATION: (555)..(555)
<223> OTHER INFORMATION: a, c, t, g, unknown or other
<220> FEATURE:
<221> NAME/KEY: modified_base
```

<222> LOCATION: (775)..(775)
<223> OTHER INFORMATION: a, c, t, g, unknown or other

<400> SEQUENCE: 167

```
gccgagagag gggcccgcgt cggattaggt agttggtgag gtaatggctc accaagcctt     60
cgatccgtag ctggtctgag aggatgatca gccacactgg gactgagaca cggcccagac    120
tcctacggga ggcagcagtg gggaatattg gacaatgggc gcaagcctga tccagcaatg    180
ccgcgtgagt gatgaaggcc ttagggttgt aaagctcttt cgcacgcgac gatgatgacg    240
gtagcgtgag aagaagcccc ggctaacttc gtgccagcag ccgcggtaat acgnagggng    300
cnagcgttnn tcggaattac tgggcgtaaa gngcgcgtag gcggcntgtt nagtcagaag    360
tgaaagcccc gggctcaacc tgggaatagc ttttgatact ggcaggcttg agttccggag    420
aggatggtgg aattcccngt gtagnggtga aatncgtaga tattgggang aacaccngtg    480
gcgaaggcgg cnatctggac gganactgac gctgaggcgc gaaagcgtgg ggagcaaaca    540
ggattagata ccctngtagt ccacgccgta acgatgaat gctagacgtc ggggtgcatg    600
cacttcggtg tcgccgctaa cgcattaagc attccgcctg gggagtacgg ccgcaaggtt    660
aaaactcaaa ggaattgacg ggggcccgca caagcggtgg agcatgtggt ttaattcgaa    720
gcaacgcgca gaaccttacc aacccttgac atgtccactt tgggctcgag agatngggtc    780
cttcagttcg gctgggtgga acacaggtgc tgcatggctg tcgtcagctc gtgtcgtgag    840
atgttgggtt aagtcccgca acgagcgcaa ccctaccgt cagttgccat cattcagttg    900
ggcactctgg tggaaccgcc ggtgacaagc cggaggaagg cggggatgac gtcaagtcct    960
catggccctt atgggttggg ctacacacgt gctacaatgg cggtgacagt gggaagcgaa   1020
gtcgcgagat ggagcaaatc cccaaaagcc gtctcagttc ggatcgcact ctgcaactcg   1080
agtgcgtgaa gttggaatcg ctagtaatcg cggatcagca cgccgcggtg aatacgttcc   1140
cgggccttgt acacaccgcc cgtcacacca tgggagttgg ttttacccga aggtggtgcg   1200
ctaaccgcaa ggaggcagcc aaccacggta aggtcagcga ctggggtgaa gtcgtaacaa   1260
ggtagccgta ggggaacctg cggctggatc acctcctttt                         1299
```

<210> SEQ ID NO 168
<211> LENGTH: 897
<212> TYPE: DNA
<213> ORGANISM: Azospirillum lipoferum
<220> FEATURE:
<223> OTHER INFORMATION: nifH

<400> SEQUENCE: 168

```
atggccaaag cgcctctgcg tcagatcgcc ttttacggca agggcggtat cggcaagtcc     60
accacctctc agaacacgct ggccgcgctg gtcgagctgg atcagaggat cctgatcgtc    120
ggctgcgacc cgaaggccga ctcgacccgc ctgatcctgc acgcaaaggc ccaggacacc    180
gtcctgcatc tggccgccga ggccggctcg gtcgaggatc tggagctcga ggacgttctc    240
aagatcggct acaagaacat caagtgcgtc gagtccggcg gtccggagcc ggggggtcggc    300
tgcgccggcc gcggcgtcat cacctcgatc aacttcctgg aagagaacgg cgcctacgac    360
gacgtggact atgtgtccta cgacgtgctg ggcgacgtgg tctgcggcgg cttcgccatg    420
ccgatccgcg agaacaaggc ccaggaaatc tacatcgtca tgtccggcga gatgatggcg    480
ctgtacgccg ccaacaacat cgccaagggc atcctgaagt acgcgcacag cggcggcgtc    540
cgtctcggcg gcctgatctg caacgagcgc cagaccgaca aggaatggga tctggccgac    600
```

-continued

```
gcgctggcca agcgcctggg ctccaagctg atccacttcg tgccgcgcga caacatcgtc     660
cagcacgccg agctgcgccg catgacggtc atcgagtacg ccccggacag caagcaggcc     720
ggcgaatacc gcgcgctcgc caacaagatc catgcgaact ccggccaggg ttgcatcccg     780
accccgatca ccatggaaga gctggaagag atgctgatgg acttcggcat catgaagacc     840
gaggagcagc agctcgccga gctcgccgcc aaggaagcgg cgaaggccgg cgcctga        897

<210> SEQ ID NO 169
<211> LENGTH: 1440
<212> TYPE: DNA
<213> ORGANISM: Azospirillum lipoferum
<220> FEATURE:
<223> OTHER INFORMATION: nifD1

<400> SEQUENCE: 169
atgagcctgt ccgagaacac cacggtcgac gtcaagaacc tcgtcaacga agtcctcgaa      60
gcctatcccg aaaaatcccg caagcgccgc gccaagcacc tgaacgtgct ggaggccgag     120
gccaaggact gcggcgtcaa gtcgaacgtc aagtccatcc ccggcgtcat gaccatccgc     180
ggctgcgcct atgccggctc aagggcgtg gtgtggggtc cgatcaagga catgatccac     240
atctcccacg tccggtcgg ctgccggctac tactcctggt ccggccgccg caactactac     300
atcggcgaca ccggtgtgga cagctgggc acgatgcact caccteega cttccaggag      360 aaggacatcg tcttcggcgg cgacaagaag ctgcacaagg tcatcgagga aatcaacgag     420
ctgttcccgc tggtgaacgg catctcgatc cagtcggaat gcccgatcgg cctgatcggc     480
gacgacatcg aggctgtcgc ccgcgccaag tcggcggaaa tcggcaagcc ggtcatcccc     540
gtgcgctgcg aaggcttccg cggcgtgtcc cagtcgctgg ccaccacat cgccaacgac     600 gccatccgag actgggtgtt cgagaagacg gaacccaagg ccggcttcgt ctccaccccc     660
tatgacgtca ccatcatcgg cgactacaac atcgcggcg acgcctggtc gtcccgcatc     720
ctgctggagg agatcggcct gcgcgtgatc gcccagtggt cgggcgacgg cacgctcgcc     780
gaactggaga acacgccgaa ggccaaggtc aacctgatcc actgctaccg ctcgatgaac     840
tacatcgcgc gccacatgga agagaagttc aacattcctt ggatggaata caacttcttc     900
ggcccgagcc agatcgccga atccctgcgc aagatcgccg ctctcttcga cgacaagatc     960
aaggagaacg ccgagaaggt catcgcccgc taccagccga tggtcgatgc ggtcatcgcc    1020
aagtacaagc gcggctcga aggcaagaag tcatgatct acgtcggcgg cctgcgtccc    1080
cgccacgtcg tcgatgccta ccatgacctc ggcatggaga tcaccggcac cggctacgag    1140
ttcgcccaca cgacgacta tcagcgcacg cagcactacg tgaaggaagg cacgctgatc    1200
tacgacgacg tcaccgcgtt cgaactggag aagttcgtcg aggcgatgcg tcccgacctc    1260
gtcgcgtcgg gcatcaagga aaagtacgtg ttccagaaga tgggcctgcc gttccgccag    1320
atgcacagct gggactactc cggcccgtac cacggctatg acggcttcgc gatcttcgcc    1380
cgcgacatgg acctggccat caacaacccc gtctggggcg tgatgaaggc cccgttctga    1440

<210> SEQ ID NO 170
<211> LENGTH: 1419
<212> TYPE: DNA
<213> ORGANISM: Azospirillum lipoferum
<220> FEATURE:
<223> OTHER INFORMATION: nifD2
```

<400> SEQUENCE: 170

```
atgctccagg acaagatcca ggatgtcttc aacgaaccgg gctgcgcgac caaccaagcc      60
aaatcggcca aggagaagaa gaagggctgc accaagtcgc tgaaaccggg ggcggcagcc     120
ggcggctgcg cctatgacgg ggcgatgatc gtgctccagc cgatcgccga cgccgcccat     180
ctggtccatg gccccatcgc ctgcctcgga aacagttggg acaaccgcgg ctccaaatcc     240
tccggctcgc agctctaccg caccggcttc accaccgatc tgtcggaact ggacgtcatc     300
ggcggcggcg agaagaagct ctaccgcgcc atcaaggaga tcgttcagca atacgacccg     360
ccggccgtct tcgtctatca gacctgcgtg cccgccatga ccggcgacga catcgccgcg     420
gtctgcaagt cgccacgca gaagctgggc aagccggtga tcccggtgga ctcgccgggc     480
ttcgtcgggt cgaagaatct cggcaacaag ctggccggcg aagccctgct ggagcatgtc     540
atcggcacgg tcgaaccgga ctacaccacc ccgaccgacg tctgcatcat cggcgaatac     600
aaccttgccg cgagctgtg gctggtcaag ccgctgctgg acgagatcgg catccgcctc     660
ctgtcctgca tttccggcga cggccgctac cgggaggtgg cgcaggccca ccgcgcccgc     720
gtcaccatga tggtgtgcag ccaggcgctg gtgaatgtcg ggcgcaagat ggaggagcgc     780
tacggcatcc cctatttcga ggggtccttc tacggcgtgt ccgacatgtc ggacaccctg     840
cgcaccatga cccgcatgct ggtggagcgc ggcgccgaca agggcctgat cgaccgggcg     900
gagggcgtga tcgcgcggga ggaaagccgg gtctggcgcc ggctggaacc ctacaagccg     960
cgcttcgacg gcaagcgcgt ccttctcttc accggcggcg tcaagagctg gtcgatggtc    1020
agcgcgctgg agggtgcggg gctgaccatc ctcggcacct ccaccaagaa atcgaccagg    1080
gaggacaagg agcgcatcaa gaagatgaag ggcgaagagt tccaccagtg ggacgatttg    1140
aagccgcgcg acatctacag gatgctggcc gacgatcagg ccgacatcat gatgtccggc    1200
ggccgctcgc agttcatctc gctgaaggcc aaggttccct ggctcgacat caaccaggag    1260
cgccaccacg cctatgccgg ctatgacggc atcgtcaatc tctgcgagga gatcgacaaa    1320
acgctgtcga atccgatctg gcgtcaggtg cgtcagccgg caccgtggga gtccggcgcg    1380
tcctccaccc ttctggcttc ctcgatggcg gcggagtga                           1419
```

<210> SEQ ID NO 171
<211> LENGTH: 1383
<212> TYPE: DNA
<213> ORGANISM: Azospirillum lipoferum
<220> FEATURE:
<223> OTHER INFORMATION: nifK

<400> SEQUENCE: 171

```
atgtcccaca tccagcgctt cccctccgcc gccaaggccg cctccaccaa cccgctgaag      60
atgagccagc cgctgggtgc ggctctggcc tatctcggcg tcgaccgctg cctgccgctg     120
ttccatggct cgcagggctg caccgccttc gggctggtcc tgctggtgcg ccatttccgc     180
gaggcgatcc cgctccagac cacggcgatg gatcaggtcg ccaccatcct cggcggctac     240
gacaatctgg agcaggcgat ccgcaccatc gtcgagcgca accagcccgc catgatcggc     300
gtcgccacca ccggcgtcac cgagaccaag ggcgaggata tggccggaca gtacacgctg     360
ttccgccagc gcaaccccga cttggccgac acggccctgg tcttcgccaa caccccgac     420
ttcgccggcg gcttcgagga cggcttcgcc gccgcggtca ccgcgatggt cgagcggttg     480
gtcgaaccgt cgccggtgcg catcccgacc caggtcaacg tgctggccgg ctgccatctg     540
```

```
tcccccggcg acgtggagga actgcgcgac atcatcgaag gcttcggcct gtcgccgatc    600
ttcctgcccg acctgtcgct gtcgatggcg ggccgccagc cggccgactt caccgccacc    660
tcgctgggcg gcgtgaccgt cgatcagatc cgcgccatgg gcgcttcggc cctcaccatc    720
gtggtcggtg agcatatgcg ggtggccggt aacgcgctgg agctgaagac cgacgtgccc    780
agccatttct tcaaccgcct gaccgggctg gaggcgacgg acaagctggt ccggctgctg    840
atggagttgt cgggcaagcc ggcgcccgcc cggctgcggc gccagcgcga aagcctggtc    900
gatgccatgc tcgacgggca tttcttctac agccgcaagc gcatcgccgt cgcgctggag    960
cccgacctgc tctatgccgt caccggcttc ctcgccgaca tggggggccga ggtgatcgcc   1020 gcggtgtccc cgacgcagag cccggtgctg gagcggttga aggccgccac catcatggtc   1080
ggcgatcatt ccgacgtgga gacgctggcc cgcgacgccg acctgatcgt ctccaactcg   1140
cacgggcggc agggagccgc gcggatcggc gtggctctgc accgcatggg cctgccgctg   1200
ttcgaccggc tgggggccgg cctgcgcgtc caggtcggct accgcggcac gcgggaactg   1260
ctgtgcgaca tcggcaacct gttcctcgcc cgcgagatgg accacgagca cgggcacgag   1320
agccacgacc acggggaatc ccacggctgc ggaggcggat catgcggatg caacgccgtc   1380
tga                                                                 1383
```

<210> SEQ ID NO 172
<211> LENGTH: 1560
<212> TYPE: DNA
<213> ORGANISM: Azospirillum lipoferum
<220> FEATURE:
<223> OTHER INFORMATION: nifK1

<400> SEQUENCE: 172

```
atgaccgaca gctttcgca gagcgccgac aaggtcctcg accactacac cctcttccgg     60
cagcccgaat acgcggcgat gttcgagaag aagaagaccg agttcgagta cggccattcg    120
gacgaggaag tcgcccgcgt gtccgaatgg accaagtccg aggactacaa ggcgaagaac    180
ttcgcccgtg aagcggtcgt catcaacccg accaaggcct gccagccgat cggcgcaatg    240
ttcgccgccc agggcttcga aggcaccctg cccttcgtcc acggctccca gggctgcgtc    300
gcctattacc gcacccacct gacccgtcac ttcaaggagc cgaacagcgc ggtctcctcg    360
tcgatgacgg aggacgcggc ggtgttcggc ggcctgaaca acatgatcga cggcctggcg    420
aacgcctatg cgctctacaa gccgaagatg atcgcggtga tgaccacctg catggccgaa    480
gtcatcggcg acgatttgca gggcttcatc gccaatgcga agaccaagga cagcgtcccg    540
gccgacttcc cggtccccta cgcccacacc ccggccttcg tcggcagcca catcgtcggc    600
tacgacaaca tgatcaaggg gatcctgacc aacttctggg gtacgtcgga gaatttcgac    660
acacccaaga ccgagcagat caacctgatc ccgggcttcg acggcttcgc cgtcggcaac    720
aaccgcgaac tgaagcgcat cgccggcgaa ttcggcgtga agctgcaaat cctgtccgac    780
gtgtccgaca atttcgacac gccgatggat ggcgagtacc gcatgtatga cggcggcacc    840
accatcgagg agaccaagga ggccctgcac gccaaggcca ccatctccat gcaggagtac    900
aacacgaccc agaccctgca attctgcaag gagaagggtc aggaagtcgc caagttcaac    960
tacccgatgg gcgtcaccgg caccgacgag ctgctgctga gctcgccga actgtcgggc   1020 aagccggtcc cggccagcct gaagctggag cgcggccgtc tggtcgacgc catcgccgac   1080
agccacaccc acatgcacgg caagcgcttc gccgtctatg cgaccccgga cttctgcctg   1140
ggcatgtcca agttcctgct ggagctgggt gcggagccgg tgcacatcct gtcgacgtcg   1200
```

```
ggctccaaga agtgggagaa gcaggtccag aaggtgctgg acggctcgcc cttcggcgcc      1260
tcgggcaagg cccatggcgg caaggatctg tggcacctgc gttcgctgat cttcaccgac      1320
aaggtggact acatcatcgg caacagctac ggcaagtatc tggagcgcga caccaaggtt      1380
ccgctgatcc gcctgaccta cccgatcttc gaccgccacc accaccaccg ctacccgacc      1440
tggggctacc agggcgcgct gaacgtgctg gtacggatcc tggaccggat cttcgaggac      1500
atcgacgcca acaccaacat cgtcggccag accgactact cgttcgacct gatccgctga      1560
```

<210> SEQ ID NO 173
<211> LENGTH: 1530
<212> TYPE: DNA
<213> ORGANISM: Azospirillum lipoferum
<220> FEATURE:
<223> OTHER INFORMATION: nifA

<400> SEQUENCE: 173

```
atgttgacct ctgatattgt tggcaaattg cgctgcatcg cagcagaccc caaagcgggc       60
atcgcaaggg gcctcgacac cggacgacg aagatcggtc ccgtttggga gggtgacgtg       120
ggcgacaccg tggatttcga agcgctgcgc cagcgggcgg tccactccct gttcgaacat      180
ctggaatcca tgtgcgtcgg cgccgtcgcc gtcgaccaca ccggccgcat cgcctggatg      240
gacgagaagt acaaggctct gctgggcgtt cccgacgacc cgcgcggccg gcaggtggag      300
gacgtcatcc ccaacagcca gctgcgccgg gtgatcgaca gcggccagcc gcagccgctg      360
gacatcatgg agttcgacga ccggtccttc gtggtgacgc ggatgccgct gttcggcacc      420
gacggttcga tcatcggcgc catcggcttc gtgctgttcg accgcgccga atatctccgc      480
ccgctggtcc gcaaatacga gaagatgcag gaggagctgg cccgcaccca gcaggagctg      540
gcgcatgagc gccgcgccaa atactccttc tcgcagttcc tgggcgccag cgaatcgatc      600
cgcgagatca gcggctgggg gcgccgcgcc gcccagatgg attcgaccgt cctgctgctg      660
ggcgaaaccg ggaccggcaa ggagctgctg gcccaggcca tccattccgc cagcccgcgg      720
gcgtccaagc ccttcgtcgg cgtcaatgtc gccgccattc cggaaaccct gctggaggcg      780
gagttcttcg gcgtcgcccc cggcgccttc accgcgcc accgccgcca ccgcgacggc      840
aagttccagc tcgccaacgg cggcacccctg ttcctcgacg agatcggcga catgccgctg      900
ccggtgcagg ccaagcttct gcgcgtgctg caggagcggg agatcgagcc gctcggctcc      960
aacaaggtgg tgcgggtcga tgtccgcatc atccgcgcca ccagccgtga cctgcacgcc      1020
ctggtgcgtg agaagcagtt ccgcgccgac ctctattacc ggctgaatgt ggtgccgatc      1080
accctgccgc cgctgcgcga ccggccggag gacatcgaga gcatcgccga ccgcatcctg      1140
gaacagctgg cgatccagca gggcacgccg ccgcgcgagc tgctggaatc ggcggtgcag      1200
gtgctgcgcg actatgactg gcccggcaat gtgcgcgagc tttacaacac gctggaacgg      1260
gtggtggcgc tgaccgatgc gccgatcctg accgcgccgc acatccgcag cgtgctgccc      1320
ggccagcatc cggccggcgc gtcggccctg ccgctggcgg ccggcgcgcg gccgttgcag      1380
gaggtgctgc acgccgccga gcgccacgcc atcgccgcgg cgcttgagga ggcgaacggc      1440
gtcaaggcgc gggcggcgaa gctgctgggc atttcgcgcg cgtcgctgta cgaacgcatg      1500
gtgacgctgg ggttgggggc gacgcagtag                                       1530
```

<210> SEQ ID NO 174
<211> LENGTH: 3030
<212> TYPE: DNA

<213> ORGANISM: Azospirillum lipoferum
<220> FEATURE:
<223> OTHER INFORMATION: glnE

<400> SEQUENCE: 174

```
atgccgagtc ccatcgcgtt ctcaagcccc ttgccgaagc ctttcgacag cgcgcaggcg      60
gcgctgggga tggagcgctg cgccagcag gccgccgcgg cggagccgga gacccgcgcc     120
tgggcggaag ccttcgccga ttcggagacc ggccgggcgc tgatcggggc ggtgtgcggc     180
aacagcccgt atctcggcca cagcctgacg cgggagttgc ccttcgtcgc ccgtacagtg     240
caggacggct tcgacgacac cttcgccgcg ctgatcgccg ctctccatgc cgagcatggc     300
gaggagaaat cgatggaccg gctgatggcc ggcctgcggg tggcgaagcg gcgggcggcg     360
ctgctgatcg cgctggccga catcgccggc gcgtggccgc tgttccgcgt caccggcgcc     420
ctgtcggagc tggcggagac ggggtgcag ctggccgcga atttcctgct cgccgcgcc       480
agggaggcgg ggacgctgac gctgccggat ccgcagcgac cgtgggtcgg ttcgggcctg     540
atcgttttgg gcatgggtaa gcttggcggg cgcgaactca actattccag cgacatcgac     600
ctgatcgtcc tgtatgacga cgctgttgtg cagacgcccc agccggacaa cctcgcgcga     660
accttcatca ggctcgcacg cgatcttgtc cgcattatgg atgaacggac caaggacggc     720
tacgtcttcc gcaccgacct tcggcttagg cccgatcccg cgccacgcc gctggcggtt      780
tccgtctccg cagccgaaat ttattacggc agcgtcggtc agaactggga acgcgcggcg     840
atgatcaagg cccgtcccat cgccggcgat ctggaggcgg cgcctccttt gtccgcttc      900
ctggagcccct tcgtctggcg ccgcaacctg gatttcgccg ccatccagga catccattcg     960
atcaaacgcc agatcaacgc ccacaagggc caccgcgagg tgacggtcaa cggccacgac    1020
atcaaggtcg gccgcggcgg catccgcgag atcgagttct tcgcccagac ccagcagctg    1080
atcttcggcg ggcgcgaccc cgcgcgtgcga atcgctccga ccctgatggc gaacgaggcg    1140
ctgcgcgacg tcgccgcgt gccgccgcag acggtggaag agcttgccgg ggcctatcat    1200
ttcctgcgcc gtgtcgaaca tcgcatccag atgatcgacg accagcagac ccatcgtatt    1260
cccgccgacg atgccggggt ggcgcatttg gccaccttcc tcggctatga cgaccccgcc    1320
gccttccggg cggaactgct ggcgacgctg gggcaggtgg aggaccgcta tgccgagctg    1380
ttcgaggagg cgccgtcgct ttccggcccc ggcaatctgg tcttcaccgg caccgacccc    1440
gatccgggca cgatggagac gctgaagggc atgggcttcg ccgatccggc ccgcgtcatc    1500
agcgtggtgt cggcctggca tcgcggccgc taccgcgcca cccggtcggg ccgggcgcgg    1560
gagctgctga cggagctgac gccggccctg ctgagtgcgc tgaccaagac cccggccccc    1620
gattcggcgc tgatgaactt cgacgatttc ctcggcaagc tgccggccgg cgtcggtctg    1680
ttctcgctgt tcgtcgccaa tccctggctc ctggagctgg tggcggagat catgggcatc    1740
gcgccgcaga tggcgcagac gctgtcgcgc aacccgtcgc tgctcgacgc cgtgctgtcg    1800
ccggacttct tcgacccgct gccgggcaag gaggacgggc tggccgacga ccacgcccgc    1860
gtgatggcgc cggcccgcga tttcgaggat gcgctgaccc tgtcgcggcg ctggaccaac    1920
gaccagcgct tccgcgccgg ggtgcatatc ctgcgcggca tcaccgatgg cgaccgctgc    1980
ggcgccttcc tggccgatct ggccgacatc gtcgtccccg accttgcccg ccgggtggag    2040
gaggagttcg cccagcgcca cggccatatt cccggcggcg cctgggtggt ggtggcgatg    2100
ggcaagctcg gcagccggca gctgaccatc acgtccgaca tcgacctgat cgtcatctac    2160
gatgtggcgc cgggccaagg gggcgggggc ggtccccgct tgtcggatgg tgccaagccg    2220
```

```
ctgtcgccca acgagtatta catcaagctg actcagcgtc tgaccaacgc cattaccgcg    2280
ccgatgggcg acggccggct ctacgaggtc gacatgcggc tgcgcccgtc gggcaacgcc    2340
gggccgctcg ccacctcgct ggacgctttc ctgaaatatc aggcgaccga tgcctggacc    2400
tgggagcata tggccctgac ccgcgcccgg gtgatcggcg tgatgcgga gctggccggg    2460 cgggtgtcgg cagcgatccg ctcggtgctg acggcgccgc gcgatgccga ccggctgctg    2520
tgggacgtgg ccgacatgcg gcggcggatc gagaaggagt tcgggacgac caatgtctgg    2580
aacgtcaaat acgcccgcgg cggcctgatc gacatcgagt tcatcgccca gtacctgcaa    2640
ctgccgccat ggtcacgagcg gccggacatc ctgcacatcg gcaccgccaa ggcgctgggc    2700
tgcgccgccc ggacgggcgc gctggcgccg gaggtggcgg aggatctgga gacgacgctg    2760
cggctgtggc ggcgggtgca gggctttctg cggttgacca ccgccggggt gctcgatccc    2820
aatcaggtgt cgcccagcct gctggccggg ctggtccgcg ccgcctttcc tgctgacttt    2880
cagggcgagc gtgagcctgg cactgttgac ttccccgaac tggaccacaa aatccgtgcc    2940
gtcgccgccc gcgcccatgg tcatttcaag accctggtcg aggaaccggc gggccgtctg    3000
gccccacccg ccaccacgcc tccagcctga                                    3030

<210> SEQ ID NO 175
<211> LENGTH: 1440
<212> TYPE: DNA
<213> ORGANISM: Azospirillum lipoferum
<220> FEATURE:
<223> OTHER INFORMATION: amtB1

<400> SEQUENCE: 175
atgaaccgtc tgttccttat ggccgcaccg atgatggcgg ttgctctggg cgcggtcggc      60
atgccggccg cagcccttgc ccaggatccg gcggctgccg ccgctgccgc ggctgcggct     120
gcggctgccg ccgctgctgc cgcaccggcg gctccggcgc tgaatggcgg cgacaccgcc     180
tggatgctca tctccaccgc gctggtgctg atgatgacca tccccggcct ggcgctgttc     240
tacggcggca tggtccgcaa gatgaacgtg ctgtcgacgg tgatgcagag cttcgccatc     300
acctgcctga tcagcgtcct gtggtacgtc atcggctaca gcctggcctt caccggcacc     360
ggtgcctatg tcggcggtct cgaccggctg ttcctcaacg ggctcgactt cacgaaggcc     420
ttcgtgctgg gcgaggcgac cgggtcgggc gtcccgacga ccatccccga gccggtcttc     480
atgatgttcc agatgacctt tgcgatcatc accccggccc tgatcaccgg cgccttcgcc     540
gaccgcatga agttctcctc cctgctggtc ttcaccgcgc tgtggtcgat cgtggtctat     600
gcgccgatcg cccactgggt ctggtacccg tcgggcttcc tgttcggcct gggcgtgctg     660
gacttcgccg gcggcacggt cgtgcacatc aacgccggcg tcgccggcct ggtcgccgcg     720
ctggtgatcg gcaagcgcaa gggctacccg aaggaagcct tcatgccgca aacctggtg     780 ctgtcgctga tcgcgcctc gctgctgtgg gtcggctggt tcggcttcaa cgccggttcg     840
gccctgaccg ccggtccgcg tgccggcatg gcgctggccg ccacgcacat cgccaccgcc     900
ggtgccgcca tgggctggct gttcgcggag tggatcgtca agggcaagcc gtcgatcctc     960
ggcatcatct ccgcgccgt cgccggcctg gtcgcggtga ccccggccgc cggcttcgtc    1020
gacccgacgg gcgccatcgt catcggcatc gtcgccggcg tggtctgctt ctggtcggcc    1080
accagcctca agcacatgct gggctatgac gacagcctgg acgccttcgg cgtgcacggc    1140
gtcggcggcc tgatcggcgc catcctgacc ggcgtcttcg ccaagatgtc ggtgtccaac    1200
```

```
agcgaaggcg gcttcgcctc cgtcctgcag gccgacccga aggccacgct gggcctgctg   1260
gaaggcaacg ccgccgccgt ctggatccag gtccagggcg tcctctacac catggtctgg   1320
tgcgccatcg ccaccttcgt cctgctgaag atcgtcgatg tggtcatggg cctgcgcgtc   1380
gaagaggatg tggagcgcga cggtctcgac ctcgccctgc atggcgagag catccactaa   1440
```

<210> SEQ ID NO 176
<211> LENGTH: 1227
<212> TYPE: DNA
<213> ORGANISM: Azospirillum lipoferum
<220> FEATURE:
<223> OTHER INFORMATION: amtB2

<400> SEQUENCE: 176

```
atggatgcgg caaagacggg tggcgacgtc cttttcgtgc tgatgggcgc ggtgatggtg     60
ctggcgatgc attgcggctt cgccctgctg gaggtcggga cggtccggcg caagaatcag    120
gtcaacgcgc tggtgaagat cctgtcggac ttcgccatgt cgaccatcgc ctattttttc    180
gtcggttatg ccgtggccta cggcatcgac ttcttcgccg acgccacaca gctggtcggc    240
aagggaagcg gcgggttcgc ggcctatggc tacgatctgg tgaagttctt cttcctggcg    300
accttcgccg ccgcggtgcc ggccatcgtc tcgggcggca tcgccgagcg tgctaggttc    360
tggccgcagg ccgccgccac gctggcgctg atcgcgctgt tctatccatt gctggaaggc    420
acggtctggg gcacccgctt cggcctgcaa agctggatgg ccgcgacctt cggccagcct    480
ttccacgact cgccggatc tgtggtggtg catgccttcg gcggctgggt ggcgctgggt    540
gccgtgctga acctcggcaa ccgccgcggc cgctaccgtc cgaacggctc gctgatcgcc    600
attccgccgt cgaacatccc cttcctggcg ctgggcgcct gggtgctgtg cgtggggtgg    660
ttcggcttca acgtgatgag cgcccaggtg ctggatggcg tgacgggtct ggtggcgctg    720
aactcgctga tggcgatggt cggcggcatc gtcacctcgc tggtgatcag ccgcaccgat    780
cccggcttcg tccacaacgg cgcgctgccc ggtctggtgg cggtctgcgc cgggtccgac    840
gtgatgcacc cgctgggcgc gctggtcacc ggcggcatcg ccgggctgct gttcgtctgg    900
gccttcaaca aatgccagat cgactggaag atcgacgacg tgctgggcgt ctggccgctg    960
cacggtctgt gcggcctgac cggcggcctg ctggccggcg tcttcgggca ggaggcactg   1020
ggcggccttg gcggcgtgtc gatcctcagc cagatcgtcg gcacggcaag cggcgccagc   1080
ttcggattcg tctcgggtct ggcggtctac ggcctgctgc gcgtcaccgt cggcatccgc   1140
ctcgatcccg agcaggagta caagggcgcc gacttgtcgt tgcaccatat caccgcgtac   1200
ccggaagagg acgcgccgac cctgtaa                                         1227
```

<210> SEQ ID NO 177
<211> LENGTH: 613
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::PinfC

<400> SEQUENCE: 177

```
atgaccctga atatgatgat ggattccttgg ttctctggag cgctttatcg gcatcctgac    60
tgaagaattt gcaggcttct tcccaacctg gcttgcaccc gtgcaggtag ttgtgatgaa   120
catcactgat tcgcaggctg aatacgttaa cgaattgacc cgtaaactgc aaaatgcggg   180
```

| | |
|---|---|
| cattcgtgta aaagcagact tgagaaacga gaagattggc tttaaaatcc gcgagcacac | 240 |
| tttacgtcgt gtcccttata tgctggtttg tggtgacaaa gaggtcgaag ccggcaaagt | 300 |
| tgctgtgcgt acccgtcgcg gtaaagacct gggtagcctg gacgtaaatg atgttatcga | 360 |
| gaagctgcaa caagagattc gcagccgcag tcttcaacaa ctggaggaat aaggtattaa | 420 |
| aggcggaaaa cgagttcaaa cggcgcgtcc caatcgtatt aatggcgaga ttcgcgccac | 480 |
| ggaagttcgc ttaacaggtc tggaaggcga gcagcttggt attgcgatag aactcacttc | 540 |
| acgccccgaa gggggaagct gcctgaccct acgattcccg ctatttcatt cactgaccgg | 600 |
| aggttcaaaa tga | 613 |

<210> SEQ ID NO 178
<211> LENGTH: 1613
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: delta-nifL::PinfC with 500bp flank

<400> SEQUENCE: 178

| | |
|---|---|
| accggataag agagaaaagt gtcgacgtcg gtccggttga tattgaccgg cgcatccgcc | 60 |
| agctcgccca gttttggtg gatctgtttg gcgattttgc gggtcttgcc ggtgtcggtg | 120 |
| ccgaaaaaaa taccaatatt tgccataaca cacgctcctg ttgaaaaaga gatcccgcgg | 180 |
| ggaaaatgcg gtgaacatgt cagctattgc gaagagtgtg ccagttttgc tcacgggcaa | 240 |
| aagctgcacc agaatgggta ttaatgcacc agcctggcgc ttttttttcgc ggcacgtccc | 300 |
| ctcgctaatg cccgtctggc gcggctttga cgctgataag gcgctgaata ccgatctgga | 360 |
| tcaaggtttt gtcgggttat cgtccaaaag gtgcactctt tgcatggtta taagtgcctg | 420 |
| acatggtgtc cgggcgaacg tcgccaggtg gcacaaattg tcagaactac gacacgacta | 480 |
| accgaccgca ggagtgtgcg atgaccctga atatgatgat ggattcttgg ttctctggag | 540 |
| cgctttatcg gcatcctgac tgaagaattt gcaggcttct tcccaacctg gcttgcaccc | 600 |
| gtgcaggtag ttgtgatgaa catcactgat tcgcaggctg aatacgttaa cgaattgacc | 660 |
| cgtaaactgc aaaatgcggg cattcgtgta aaagcagact tgagaaacga gaagattggc | 720 |
| tttaaaatcc gcgagcacac tttacgtcgt gtcccttata tgctggtttg tggtgacaaa | 780 |
| gaggtcgaag ccggcaaagt tgctgtgcgt acccgtcgcg gtaaagacct gggtagcctg | 840 |
| gacgtaaatg atgttatcga gaagctgcaa caagagattc gcagccgcag tcttcaacaa | 900 |
| ctggaggaat aaggtattaa aggcggaaaa cgagttcaaa cggcgcgtcc caatcgtatt | 960 |
| aatggcgaga ttcgcgccac ggaagttcgc ttaacaggtc tggaaggcga gcagcttggt | 1020 |
| attgcgatag aactcacttc acgccccgaa gggggaagct gcctgaccct acgattcccg | 1080 |
| ctatttcatt cactgaccgg aggttcaaaa tgacccagcg aaccgagtcg gtaataccg | 1140 |
| tctggcgctt cgatttatcc cagcagttca ccgcgatgca gcggataagc gtggttctca | 1200 |
| gccgggcgac cgaggttgaa cagacactcc agcaggtgct gtgcgtattg cacaatgacg | 1260 |
| cctttttgca gcacggcatg atctgtctgt acgacagcca gcaggcgatt ttgactattg | 1320 |
| aagcgttgca ggaagccgat cagcagttga tccccggcag ctcgcaaatt cgctaccgtc | 1380 |
| cgggtgaagg gctggtcggg acggtgcttt cgcaggggca atcgttagtg ctggcgcgtg | 1440 |
| tggctgacga tcagcgcttt cttgaccgcc tgggactgta tgattacaac ctgccgttta | 1500 | tcgccgtgcc gctgataggg ccggatgcgc agacttttgg cgtgctgacg gcgcaaccga    1560 tggcgcgtta cgaagagcgg ttacccgcct gcaccgcttt ctggaaacg gtc           1613

<210> SEQ ID NO 179
<211> LENGTH: 1185
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: glnE-delta-AR-2

<400> SEQUENCE: 179
tccctgtgcg ccgcgtcgcc gatggtggcc agccaactgg cgcgctaccc gatcctgctc     60
gatgaactgc tcgacccgaa cacgctctat caaccgacgg cgatgaacgc ctatcgcgat    120
gaactgcgac aatacctgtt gcgcgtgccg gaagaggatg aagagcagca actggaggcg    180
ctacggcagt ttaagcaggc gcagttgttg cgcgtagcgg cggcggatat cgccggtacg    240
ttacccgtca tgaaagtgag cgatcactta acctggctgg cggaagcgat tatcgatgcg    300
gtggtgcagc aagcctggaa ccagatggtg gcgcgttacg ccagccgac gcatctgcac     360 gatcgcgaag ggcgcggttt cgccgtggtc ggttacggca acttggcgg ctgggaatta     420 ggttacagct ccgatctgga tctggtgttc ctgcacgact gccccatgga tgtgatgacc    480
gatggcgagc gtgaaatcga tggccgccag ttctatttgc gcctcgcgca gcgcgtgatg    540
cacctgttca gcacgcgcac gtcgtccggc attctttatg aagtcgatgc gcgtttgcgc    600
ccgtccggcg cggccggaat gctggtgacc actgcgaag cgttcgccga ttatcaaaaa     660
aatgaagcct ggacatggga gcatcaggcg ctggcgcgtg cgcgcgtggt gtacggcgat    720
ccgcaactga ccgccgaatt tgacgccatt cgccgcgata tcctgatgac ctcccgcgat    780
gccgctaccc tgcaaaccga agtgcgggaa atgcgtgaga aatgcgcgc ccatcttggt     840 aacaagcaca aagaccgttt cgatctgaaa gccgatgaag gcggtatcac cgatattgag    900
tttatcgctc agtatctggt gctgcgcttt gcccatgaga agccgaaact gacgcgctgg    960
tcggataatg tgcgcatcct cgaagggctg gcgcaaaacg gcatcatgga tgagcaggaa    1020
gcgcaggcat tgacgctggc gtacaccacg ttgcgtgatg agctgcacca cctggcgctg    1080
caagagctgc aggacatgt ggcgctctcc tgttttgtcg ccgagcgtgc gcttatcaaa    1140
accagctggg acaagtggct ggtggaaccg tgcgccccgg cgtaa                    1185

<210> SEQ ID NO 180
<211> LENGTH: 2085
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: glnE-delta-AR-2 with 500bp flank

<400> SEQUENCE: 180
taaagcgagc gctcacttac gtgatctgtt gacgcagtcc gaagcgacca ttacttcagc     60
cgtttcagca gatacggcgg tgtggagtgc gcaatcagcc ctggcgaaac tggtgctcac    120
cgagtggtta gtgacgcagg gctggcgaac cttccttgat gaaaaagcgc aggctaagtt    180
tgccgactcc tttaaacgct tgctgacgt tcatctgtca cgcagcgccg ccgagctgaa     240
aaaagccttt gcccagccgc tgggcgacag ctatcgcgac cagttaccgc ggctggcgcg    300

```
tgatatcgac agcgcgttat tgctggccgg acattacgat cgcgcgcgcg ccgtggagtg    360
gctggaaaac tggcaggggc ttcagcacgc tattgaaacg cgccagagag ttgaaatcga    420
acatttccgt aataccgcca ttacccagga gccgttctgg ttgcacagcg aaaacgtta     480 acgaaaggat atttcgcatg tccctgtgcg ccgcgtcgcc gatggtggcc agccaactgg    540
cgcgctaccc gatcctgctc gatgaactgc tcgacccgaa cacgctctat caaccgacgg    600
cgatgaacgc ctatcgcgat gaactgcgac aatacctgtt cgcgcgtgcc gaagaggatg    660
aagagcagca actggaggcg ctacggcagt ttaagcaggc gcagttgttg cgcgtagcgg    720
cggcggatat cgccggtacg ttacccgtca tgaaagtgag cgatcactta acctggctgg    780
cggaagcgat tatcgatgcg gtggtgcagc aagcctggaa ccagatggtg gcgcgttacg    840
gccagccgac gcatctgcac gatcgcgaag ggcgcggttt cgccgtggtc ggttacggca    900
aacttggcgg ctgggaatta ggttacagct ccgatctgga tctggtgttc ctgcacgact    960
gccccatgga tgtgatgacc gatggcgagc gtgaaatcga tggccgccag ttctatttgc   1020
gcctcgcgca gcgcgtgatg cacctgttca gcacgcgcac gtcgtccggc attctttatg   1080
aagtcgatgc gcgtttgcgc ccgtccggcg cggccggaat gctggtgacc actgcggaag   1140
cgttcgccga ttatcaaaaa aatgaagcct ggacatggga gcatcaggcg ctggcgcgtg   1200
cgcgcgtggt gtacggcgat ccgcaactga ccgccgaatt tgacgccatt cgccgcgata   1260
tcctgatgac ctcccgcgat gccgctaccc tgcaaaccga agtgcgggaa atgcgtgaga   1320
aaatgcgcgc ccatcttggt aacaagcaca aagaccgttt cgatctgaaa gccgatgaag   1380
gcggtatcac cgatattgag tttatcgctc agtatctggt gctgcgcttt gcccatgaga   1440
agccgaaact gacgcgctgg tcggataatg tgcgcatcct cgaagggctg cgcaaaacg    1500 gcatcatgga tgagcaggaa gcgcaggcat tgacgctggc gtacaccacg ttgcgtgatg   1560
agctgcacca cctggcgctg caagagctgc caggacatgt ggcgctctcc tgttttgtcg   1620
ccgagcgtgc gcttatcaaa accagctggg acaagtggct ggtggaaccg tgcgcccgg    1680 cgtaagtgtg gtatcatcgc gcgcaaattt tgtatctctc aggagacagg aatgaaagtt   1740
acgctgccag agttcaatca agccggtgtc atggtggtgg gtgatgtgat gctggatcgc   1800
tactggtacg gcccaaccag ccgcatttct ccggaagcgc cagttccggt tgttaaagtc   1860
gatactattg aagagcgacc gggcggtgcg gcaaacgtgg cgatgaacat tgcctcgctg   1920
ggcgcaacgg cgcgtctggt tggcctgact ggcattgatg atgcggcgcg cgcgctgagc   1980
aaagcgctgg cggatgttaa tgttaaatgt gacttcgttt ctgttccgac tcaccccacc   2040
atcactaagc tgcgcgtgct gtcgcgtaac cagcaactga ttcgc                  2085
```

<210> SEQ ID NO 181
<211> LENGTH: 461
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::Prm1

<400> SEQUENCE: 181

```
atgaccctga atatgatgat ggatgccagc cgttctgtaa taataaccgg acaattcgga    60
ctgattaaaa aagcgccctc gcggcgcttt ttttatattc tcgactccat ttaaaataaa   120
aaatccaatc ggatttcact atttaaactg gccattatct aagatgaatc cgatggaagc   180
```

-continued

```
tcgctgtttt aacacgcgtt ttttaacctt ttattgaaag tcggtgcttc tttgagcgaa      240
cgatcaaatt taagtggatt cccatcaaaa aaatattctc aacctaaaaa agtttgtgta      300
atacttgtaa cgctacatgg agattaactc aatctagagg gtattaataa tgaatcgtac      360
taaactggta ctgggcgcaa ctcacttcac gccccgaagg gggaagctgc ctgaccctac      420
gattcccgct atttcattca ctgaccggag gttcaaaatg a                         461
```

<210> SEQ ID NO 182
<211> LENGTH: 1461
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: delta-nifL::Prm1 with 500bp flank

<400> SEQUENCE: 182

```
accggataag agagaaaagt gtcgacgtcg gtccggttga tattgaccgg cgcatccgcc      60
agctcgccca gttttggtg gatctgtttg gcgattttgc gggtcttgcc ggtgtcggtg      120
ccgaaaaaaa taccaatatt tgccataaca cacgctcctg ttgaaaaaga gatcccgcgg      180
ggaaaatgcg gtgaacatgt cagctattgc gaagagtgtg ccagttttgc tcacgggcaa      240
aagctgcacc agaatgggta ttaatgcacc agctggcgc ttttttttcgc ggcacgtccc      300 ctcgctaatg cccgtctggc gcggctttga cgctgataag gcgctgaata ccgatctgga      360
tcaaggtttt gtcgggttat cgtccaaaag gtgcactctt tgcatggtta taagtgcctg      420
acatggtgtc cgggcgaacg tcgccaggtg gcacaaattg tcagaactac gacacgacta      480
accgaccgca ggagtgtgcg atgaccctga atatgatgat ggatgccagc cgttctgtaa      540
taataaccgg acaattcgga ctgattaaaa aagcgccctc gcggcgcttt ttttatattc      600
tcgactccat ttaaaataaa aaatccaatc ggatttcact atttaaactg gccattatct      660
aagatgaatc cgatggaagc tcgctgtttt aacacgcgtt ttttaacctt ttattgaaag      720
tcggtgcttc tttgagcgaa cgatcaaatt taagtggatt cccatcaaaa aaatattctc      780
aacctaaaaa agtttgtgta atacttgtaa cgctacatgg agattaactc aatctagagg      840
gtattaataa tgaatcgtac taaactggta ctgggcgcaa ctcacttcac gccccgaagg      900
gggaagctgc ctgaccctac gattcccgct atttcattca ctgaccggag gttcaaaatg      960
acccagcgaa ccgagtcggg taataccgtc tggcgcttcg atttatccca gcagttcacc     1020
gcgatgcagc ggataagcgt ggttctcagc cgggcgaccg aggttgaaca gacactccag     1080
caggtgctgt gcgtattgca caatgacgcc tttttgcagc acggcatgat ctgtctgtac     1140
gacagccagc aggcgatttt gactattgaa gcgttgcagg aagccgatca gcagttgatc     1200
cccggcagct cgcaaattcg ctaccgtccg ggtgaagggc tggtcgggac ggtgcttccg     1260 cagggcaat cgttagtgct ggcgcgtgtg gctgacgatc agcgctttct tgaccgcctg     1320
ggactgtatg attacaacct gccgtttatc gccgtgccgc tgatagggcc ggatgcgcag     1380
acttttggcg tgctgacggc gcaaccgatg gcgcgttacg aagagcggtt acccgcctgc     1440
acccgctttc tggaaacggt c                                              1461
```

<210> SEQ ID NO 183
<211> LENGTH: 1185
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: glnE-delta-AR-2

<400> SEQUENCE: 183

| | | | | | | |
|---|---|---|---|---|---|---|
| tccctgtgcg | ccgcgtcgcc | gatggtggcc | agccaactgg | cgcgctaccc | gatcctgctc | 60 |
| gatgaactgc | tcgacccgaa | cacgctctat | caaccgacgg | cgatgaacgc | ctatcgcgat | 120 |
| gaactgcgac | aatacctgtt | gcgcgtgccg | gaagaggatg | aagagcagca | actggaggcg | 180 |
| ctacggcagt | ttaagcaggc | gcagttgttg | cgcgtagcgg | cggcggatat | cgccggtacg | 240 |
| ttacccgtca | tgaaagtgag | cgatcactta | acctggctgg | cggaagcgat | tatcgatgcg | 300 |
| gtggtgcagc | aagcctggaa | ccagatggtg | gcgcgttacg | gccagccgac | gcatctgcac | 360 |
| gatcgcgaag | ggcgcggttt | cgccgtggtc | ggttacggca | acttggcgg | ctgggaatta | 420 |
| ggttacagct | ccgatctgga | tctggtgttc | ctgcacgact | gccccatgga | tgtgatgacc | 480 |
| gatggcgagc | gtgaaatcga | tggccgccag | ttctatttgc | gcctcgcgca | gcgcgtgatg | 540 |
| cacctgttca | gcacgcgcac | gtcgtccggc | attctttatg | aagtcgatgc | gcgtttgcgc | 600 |
| ccgtccggcg | cggccggaat | gctggtgacc | actgcggaag | cgttcgccga | ttatcaaaaa | 660 |
| aatgaagcct | ggacatggga | gcatcaggcg | ctggcgcgtg | cgcgcgtggt | gtacggcgat | 720 |
| ccgcaactga | ccgccgaatt | tgacgccatt | cgccgcgata | tcctgatgac | ctcccgcgat | 780 |
| gccgctaccc | tgcaaaccga | agtgcgggaa | atgcgtgaga | aaatgcgcgc | ccatcttggt | 840 |
| aacaagcaca | aagaccgttt | cgatctgaaa | gccgatgaag | gcggtatcac | cgatattgag | 900 |
| tttatcgctc | agtatctggt | gctgcgcttt | gcccatgaga | agccgaaact | gacgcgctgg | 960 |
| tcggataatg | tgcgcatcct | cgaagggctg | gcgcaaaacg | gcatcatgga | tgagcaggaa | 1020 |
| gcgcaggcat | tgacgctggc | gtacaccacg | ttgcgtgatg | agctgcacca | cctggcgctg | 1080 |
| caagagctgc | aggacatgt | ggcgctctcc | tgttttgtcg | ccgagcgtgc | gcttatcaaa | 1140 |
| accagctggg | acaagtggct | ggtggaaccg | tgcgccccgg | cgtaa | | 1185 |

<210> SEQ ID NO 184
<211> LENGTH: 2085
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: glnE-delta-AR-2 with 500bp flank

<400> SEQUENCE: 184

| | | | | | | |
|---|---|---|---|---|---|---|
| taaagcgagc | gctcacttac | gtgatctgtt | gacgcagtcc | gaagcgacca | ttacttcagc | 60 |
| cgtttcagca | gatacggcgg | tgtggagtgc | gcaatcagcc | ctggcgaaac | tggtgctcac | 120 |
| cgagtggtta | gtgacgcagg | gctggcgaac | cttccttgat | gaaaaagcgc | aggctaagtt | 180 |
| tgccgactcc | tttaaacgct | tgctgacgt | tcatctgtca | cgcagcgccg | ccgagctgaa | 240 |
| aaaagccttt | gcccagccgc | tgggcgacag | ctatcgcgac | cagttaccgc | ggctggcgcg | 300 |
| tgatatcgac | agcgcgttat | tgctggccgg | acattacgat | cgcgcgcgcg | ccgtggagtg | 360 |
| gctggaaaac | tggcaggggc | ttcagcacgc | tattgaaacg | cgccagagag | ttgaaatcga | 420 |
| acatttccgt | aataccgcca | ttacccagga | gccgttctgg | ttgcacagcg | gaaaacgtta | 480 |
| acgaaaggat | atttcgcatg | tccctgtgcg | ccgcgtcgcc | gatggtggcc | agccaactgg | 540 |

```
cgcgctaccc gatcctgctc gatgaactgc tcgacccgaa cacgctctat caaccgacgg    600
cgatgaacgc ctatcgcgat gaactgcgac aatacctgtt gcgcgtgccg gaagaggatg    660
aagagcagca actggaggcg ctacggcagt ttaagcaggc gcagttgttg cgcgtagcgg    720
cggcggatat cgccggtacg ttacccgtca tgaaagtgag cgatcactta acctggctgg    780
cggaagcgat tatcgatgcg gtggtgcagc aagcctggaa ccagatggtg gcgcgttacg    840
gccagccgac gcatctgcac gatcgcgaag ggcgcggttt cgccgtggtc ggttacggca    900
aacttggcgg ctgggaatta ggttacagct ccgatctgga tctggtgttc ctgcacgact    960
gccccatgga tgtgatgacc gatggcgagc gtgaaatcga tggccgccag ttctatttgc   1020
gcctcgcgca gcgcgtgatg cacctgttca gcacgcgcac gtcgtccggc attctttatg   1080
aagtcgatgc gcgtttgcgc ccgtccggcg cggccggaat gctggtgacc actgcggaag   1140
cgttcgccga ttatcaaaaa aatgaagcct ggacatggga gcatcaggcg ctggcgcgtg   1200
cgcgcgtggt gtacggcgat ccgcaactga ccgccgaatt tgacgccatt cgccgcgata   1260
tcctgatgac ctcccgcgat gccgctaccc tgcaaaccga agtgcgggaa atgcgtgaga   1320
aaatgcgcgc ccatcttggt aacaagcaca aagaccgttt cgatctgaaa gccgatgaag   1380
gcggtatcac cgatattgag tttatcgctc agtatctggt gctgcgcttt gcccatgaga   1440
agccgaaact gacgcgctgg tcggataatg tgcgcatcct cgaagggctg cgcaaaacg    1500 gcatcatgga tgagcaggaa gcgcaggcat tgacgctggc gtacaccacg ttgcgtgatg   1560
agctgcacca cctggcgctg caagagctgc aggacatgt ggcgctctcc tgttttgtcg    1620
ccgagcgtgc gcttatcaaa accagctggg acaagtggct ggtggaaccg tgcgccccgg   1680
cgtaagtgtg gtatcatcgc gcgcaaattt tgtatctctc aggagacagg aatgaaagtt   1740
acgctgccag agttcaatca agccggtgtc atggtggtgg gtgatgtgat gctggatcgc   1800
tactggtacg gcccaaccag ccgcatttct ccggaagcgc cagttccggt tgttaaagtc   1860
gatactattg aagagcgacc gggcggtgcg gcaaacgtgg cgatgaacat tgcctcgctg   1920
ggcgcaacgg cgcgtctggt tggcctgact ggcattgatg atgcggcgcg cgcgctgagc   1980
aaagcgctgg cggatgttaa tgttaaatgt gacttcgttt ctgttccgac tcaccccacc   2040
atcactaagc tgcgcgtgct gtcgcgtaac cagcaactga ttcgc               2085
```

<210> SEQ ID NO 185
<211> LENGTH: 461
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::Prm1

<400> SEQUENCE: 185

```
atgaccctga atatgatgat ggatgccagc cgttctgtaa taataaccgg acaattcgga     60
ctgattaaaa aagcgccctc gcggcgcttt ttttatattc tcgactccat ttaaaataaa    120
aaatccaatc ggatttcact atttaaactg gccattatct aagatgaatc cgatggaagc    180
tcgctgtttt aacacgcgtt ttttaacctt ttattgaaag tcggtgcttc tttgagcgaa    240
cgatcaaatt taagtggatt cccatcaaaa aaatattctc aacctaaaaa agtttgtgta    300
```

```
atacttgtaa cgctacatgg agattaactc aatctagagg gtattaataa tgaatcgtac    360
taaactggta ctgggcgcaa ctcacttcac gccccgaagg gggaagctgc ctgaccctac    420
gattcccgct atttcattca ctgaccggag gttcaaaatg a                       461
```

<210> SEQ ID NO 186
<211> LENGTH: 1461
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::Prm1 with 500bp flank

<400> SEQUENCE: 186

```
accggataag agagaaaagt gtcgacgtcg gtccggttga tattgaccgg cgcatccgcc     60
agctcgccca gttttggtg gatctgtttg gcgattttgc gggtcttgcc ggtgtcggtg    120
ccgaaaaaaa taccaatatt tgccataaca cacgctcctg ttgaaaaaga gatcccgcgg    180
ggaaaatgcg gtgaacatgt cagctattgc gaagagtgtg ccagttttgc tcacgggcaa    240
aagctgcacc agaatgggta ttaatgcacc agcctggcgc ttttttttcgc ggcacgtccc    300 ctcgctaatg cccgtctggc gcggctttga cgctgataag gcgctgaata ccgatctgga    360
tcaaggtttt gtcgggttat cgtccaaaag gtgcactctt tgcatggtta taagtgcctg    420
acatggtgtc cgggcgaacg tcgccaggtg gcacaaattg tcagaactac gacacgacta    480
accgaccgca ggagtgtgcg atgaccctga atatgatgat ggatgccagc cgttctgtaa    540
taataaccgg acaattcgga ctgattaaaa aagcgccctc gcggcgcttt ttttatattc    600
tcgactccat ttaaaataaa aaatccaatc ggatttcact atttaaactg gccattatct    660
aagatgaatc cgatggaagc tcgctgtttt aacacgcgtt ttttaacctt ttattgaaag    720
tcggtgcttt tttgagcgaa cgatcaaatt taagtggatt cccatcaaaa aaatattctc    780
aacctaaaaa agtttgtgta atacttgtaa cgctacatgg agattaactc aatctagagg    840
gtattaataa tgaatcgtac taaactggta ctgggcgcaa ctcacttcac gccccgaagg    900
gggaagctgc ctgaccctac gattcccgct atttcattca ctgaccggag gttcaaaatg    960
acccagcgaa ccgagtcggg taataccgtc tggcgcttcg atttatccca gcagttcacc    1020
gcgatgcagc ggataagcgt ggttctcagc cgggcgaccg aggttgaaca gacactccag    1080
caggtgctgt gcgtattgca caatgacgcc ttttttgcagc acggcatgat ctgtctgtac    1140
gacagccagc aggcgatttt gactattgaa gcgttgcagg aagccgatca gcagttgatc    1200
cccggcagct cgcaaaattcg ctaccgtccg ggtgaagggc tggtcgggac ggtgctttcg    1260
caggggcaat cgttagtgct ggcgcgtgtg gctgacgatc agcgctttct tgaccgcctg    1320
ggactgtatg attacaacct gccgtttatc gccgtgccgc tgatagggcc ggatgcgcag    1380
acttttggcg tgctgacggc gcaaccgatg gcgcgttacg aagagcggtt acccgcctgc    1440
acccgctttc tggaaacggt c                                              1461
```

<210> SEQ ID NO 187
<211> LENGTH: 1185
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:

<223> OTHER INFORMATION: glnE-delta-AR-2

<400> SEQUENCE: 187

```
tccctgtgcg ccgcgtcgcc gatggtggcc agccaactgg cgcgctaccc gatcctgctc      60
gatgaactgc tcgacccgaa cacgctctat caaccgacgg cgatgaacgc ctatcgcgat     120
gaactgcgac aatacctgtt gcgcgtgccg gaagaggatg aagagcagca actggaggcg     180
ctacggcagt ttaagcaggc gcagttgttg cgcgtagcgg cggcggatat cgccggtacg     240
ttacccgtca tgaaagtgag cgatcactta acctggctgg cggaagcgat tatcgatgcg     300
gtggtgcagc aagcctggaa ccagatggtg gcgcgttacg gccagccgac gcatctgcac     360
gatcgcgaag ggcgcggttt cgccgtggtc ggttacggca acttggcgg ctgggaatta     420
ggttacagct ccgatctgga tctggtgttc ctgcacgact gccccatgga tgtgatgacc     480
gatggcgagc gtgaaatcga tggccgccag ttctatttgc gcctcgcgca gcgcgtgatg     540
cacctgttca gcacgcgcac gtcgtccggc attctttatg aagtcgatgc gcgtttgcgc     600
ccgtccggcg cggccggaat gctggtgacc actgcggaag cgttcgccga ttatcaaaaa     660
aatgaagcct ggacatggga gcatcaggcg ctggcgcgtg cgcgcgtggt gtacggcgat     720
ccgcaactga ccgccgaatt tgacgccatt cgccgcgata tcctgatgac ctcccgcgat     780
gccgctaccc tgcaaaccga agtgcgggaa atgcgtgaga aaatgcgcgc ccatcttggt     840
aacaagcaca aagaccgttt cgatctgaaa gccgatgaag gcggtatcac cgatattgag     900
tttatcgctc agtatctggt gctgcgcttt gcccatgaga agccgaaact gacgcgctgg     960
tcggataatg tgcgcatcct cgaagggctg gcgcaaaacg gcatcatgga tgagcaggaa    1020
gcgcaggcat tgacgctggc gtacaccacg ttgcgtgatg agctgcacca cctggcgctg    1080
caagagctgc aggacatgt ggcgctctcc tgttttgtcg ccgagcgtgc gcttatcaaa    1140
accagctggg acaagtggct ggtggaaccg tgcgccccgg cgtaa              1185
```

<210> SEQ ID NO 188
<211> LENGTH: 2085
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: glnE-delta-AR-2 with 500bp flank

<400> SEQUENCE: 188

```
taaagcgagc gctcacttac gtgatctgtt gacgcagtcc gaagcgacca ttacttcagc      60
cgtttcagca gatacggcgg tgtggagtgc gcaatcagcc ctggcgaaac tggtgctcac     120
cgagtggtta gtgacgcagg gctggcgaac cttccttgat gaaaaagcgc aggctaagtt     180
tgccgactcc tttaaacgct tgctgacgt tcatctgtca cgcagcgccg ccgagctgaa     240
aaagcctttt gccagccgc tgggcgacag ctatcgcgac cagttaccgc ggctggcgcg     300
tgatatcgac agcgcgttat tgctggccgg acattacgat cgcgcgcgcg ccgtggagtg     360
gctggaaaac tggcagggc ttcagcacgc tattgaaacg cgccagagag ttgaaatcga     420
acatttccgt aataccgcca ttacccagga gccgttctgg ttgcacagcg gaaaacgtta     480
acgaaaggat atttcgcatg tccctgtgcg ccgcgtcgcc gatggtggcc agccaactgg     540
cgcgctaccc gatcctgctc gatgaactgc tcgacccgaa cacgctctat caaccgacgg     600
cgatgaacgc ctatcgcgat gaactgcgac aatacctgtt gcgcgtgccg gaagaggatg     660
```

```
aagagcagca actggaggcg ctacggcagt ttaagcaggc gcagttgttg cgcgtagcgg    720
cggcggatat cgccggtacg ttacccgtca tgaaagtgag cgatcactta acctggctgg    780
cggaagcgat tatcgatgcg gtggtgcagc aagcctggaa ccagatggtg gcgcgttacg    840
gccagccgac gcatctgcac gatcgcgaag ggcgcggttt cgccgtggtc ggttacggca    900
aacttggcgg ctgggaatta ggttacagct ccgatctgga tctggtgttc ctgcacgact    960
gccccatgga tgtgatgacc gatggcgagc gtgaaatcga tggccgccag ttctatttgc   1020
gcctcgcgca gcgcgtgatg cacctgttca gcacgcgcac gtcgtccggc attctttatg   1080
aagtcgatgc gcgtttgcgc ccgtccggcg cggccggaat gctggtgacc actgcggaag   1140
cgttcgccga ttatcaaaaa aatgaagcct ggacatggga gcatcaggcg ctggcgcgtg   1200
cgcgcgtggt gtacggcgat ccgcaactga ccgccgaatt tgacgccatt cgccgcgata   1260
tcctgatgac ctcccgcgat gccgctaccc tgcaaaccga agtgcgggaa atgcgtgaga   1320
aaatgcgcgc ccatcttggt aacaagcaca agaccgtttc gatctgaaa gccgatgaag   1380 gcggtatcac cgatattgag tttatcgctc agtatctggt gctgcgcttt gcccatgaga   1440
agccgaaact gacgcgctgg tcggataatg tgcgcatcct cgaagggctg gcgcaaaacg   1500
gcatcatgga tgagcaggaa gcgcaggcat tgacgctggc gtacaccacg ttgcgtgatg   1560
agctgcacca cctggcgctg caagagctgc caggacatgt ggcgctctcc tgttttgtcg   1620
ccgagcgtgc gcttatcaaa accagctggg acaagtggcg ggtggaaccg tgcgccccgg   1680
cgtaagtgtg gtatcatcgc gcgcaaattt tgtatctctc aggagacagg aatgaaagtt   1740
acgctgccag agttcaatca agccggtgtc atggtggtgg gtgatgtgat gctggatcgc   1800
tactggtacg gcccaaccag ccgcatttct ccggaagcgc cagttccggt tgttaaagtc   1860
gatactattg aagagcgacc gggcggtgcg gcaaacgtgg cgatgaacat tgcctcgctg   1920
ggcgcaacgg cgcgtctggt tggcctgact ggcattgatg atgcggcgcg cgcgctgagc   1980
aaagcgctgg cggatgttaa tgttaaatgt gacttcgttt ctgttccgac tcaccccacc   2040
atcactaagc tgcgcgtgct gtcgcgtaac cagcaactga ttcgc              2085
```

<210> SEQ ID NO 189
<211> LENGTH: 452
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: delta-nifL::Prm7

<400> SEQUENCE: 189

```
atgaccctga atatgatgat ggatgccagc cgcgtcaggt tgaacgtaaa aaagtcggtc     60
tgcgcaaagc acgtcgtcgt ccgcagttct ccaaacgtta attggtttct gcttcggcag    120
aacgattggc gaaaaaaccc ggtgcgaacc gggtttttt atggataaag atcgtgttat    180
ccacagcaat ccattgatta tctcttcttt ttcagcattt ccagaatccc ctcaccacaa    240
agcccgcaaa atctggtaaa ctatcatcca attttctgcc caaatggctg ggattgttca    300
ttttttgttt gccttacaac gagagtgaca gtacgcgcgg gtagttaact caacatctga    360
ccggtcgata actcacttca cgccccgaag ggggaagctg cctgacccta cgattcccgc    420
tatttcattc actgaccgga ggttcaaaat ga                                   452
```

<210> SEQ ID NO 190

```
<211> LENGTH: 1451
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::Prm7 with 500bp flank

<400> SEQUENCE: 190
accggataag agagaaaagt gtcgacgtcg gtccggttga tattgaccgg cgcatccgcc        60
agctcgccca gttttggtg  gatctgtttg gcgattttgc gggtcttgcc ggtgtcggtg      120
ccgaaaaaaa taccaatatt tgccataaca cacgctcctg ttgaaaaaga gatcccgcgg      180
ggaaaatgcg gtgaacatgt cagctattgc gaagagtgtg ccagttttgc tcacgggcaa     240
aagctgcacc agaatgggta ttaatgcacc agcctggcgc ttttttttcgc ggcacgtccc    300
ctcgctaatg cccgtctggc gcggctttga cgctgataag gcgctgaata ccgatctgga    360
tcaaggtttt gtcgggttat cgtccaaaag gtgcactctt tgcatggtta taagtgcctg    420
acatggtgtc cgggcgaacg tcgccaggtg gcacaaattg tcagaactac gacacgacta    480
accgaccgca ggagtgtgcg atgaccctga atatgatgat ggatgccagc cgcgtcaggt    540
tgaacgtaaa aaagtcggtc tgcgcaaagc acgtcgtcgt ccgcagttct ccaaacgtta    600
attggtttct gcttcggcag aacgattggc gaaaaaccc  ggtgcgaacc gggttttttt    660
atggataaag atcgtgttat ccacagcaat ccattgatta tctcttcttt ttcagcattt    720
ccagaatccc ctcaccacaa agcccgcaaa atctggtaaa ctatcatcca attttctgcc    780
caaatggctg ggattgttca tttttttgttt gccttacaac gagagtgaca gtacgcgcgg    840
gtagttaact caacatctga ccggtcgata actcacttca cgccccgaag ggggaagctg    900
cctgacccta cgattcccgc tatttcattc actgaccgga ggttcaaaat gacccagcga    960
accgagtcgg gtaataccgt ctggcgcttc gatttatccc agcagttcac cgcgatgcag   1020
cggataagcg tggttctcag ccgggcgacc gaggttgaac agacactcca gcaggtgctg   1080
tgcgtattgc acaatgacgc cttttttgcag cacggcatga tctgtctgta cgacagccag   1140
caggcgattt tgactattga agcgttgcag gaagccgatc agcagttgat ccccggcagc   1200
tcgcaaattc gctaccgtcc gggtgaaggg ctggtcggga cggtgctttc gcaggggcaa   1260
tcgttagtgc tggcgcgtgt ggctgacgat cagcgctttc ttgaccgcct gggactgtat   1320
gattacaacc tgccgtttat cgccgtgccg ctgatagggc cggatgcgca gacttttggc   1380
gtgctgacgg cgcaaccgat ggcgcgttac gaagagcggt tacccgcctg cacccgcttt   1440
ctggaaacgg t                                                         1451

<210> SEQ ID NO 191
<211> LENGTH: 1191
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: glnE-delta-AR-2

<400> SEQUENCE: 191
atggcgctga agcacctgat cacgctctgc gcggcgtcgc cgatggtcgc cagccagctg       60
gcgcgccacc cgctgctgct ggatgagctg ctggatccca acaccctcta tcagccgacg      120
gcgaccgatg cctatcgcga cgagctgcgc cagtacctgc tgcgcgtgcc ggaagaggat      180
```

```
gaagagcagc agctggaggc gttgcgccag tttaagcagg cgcagcagct gcatatcgcg    240
gcggcggata tcgctggtac cctgccggtg atgaaggtca gcgatcactt aacctggctt    300
gccgaagcga tcctcgacgc ggtggtgcag caggcatggg ggcagatggt cgctcgctac    360
ggccagccga cccacctgca cgatcgccag ggtcgcggct tcgccgtcgt cggctacggt    420
aagcttggcg gctgggagct gggctacagc tccgatctcg atctggtgtt cctccatgac    480
tgcccggcgc aggtgatgac cgacggcgag cgggagattg acggccgtca gttctacctg    540
cggctggccc agcggatcat gcacctgttc agcacccgca cctcgtccgg tattctctac    600
gaagtggacg cccggctgcg tccttctggc gcggcgggga tgctggtcac caccgccgac    660
gcgtttgctg actatcagca gaacgaagcc tggacgtggg aacatcaggc gctggtgcgc    720
gcccgcgtgg tctatggcga cccggcgctg caggcgcgct ttgacgccat cgtcgcgat     780 atcctgacca ccccgcggga ggggatgacc ctgcagaccg aggttcgcga gatgcgcgag    840
aagatgcgcg cccaccttgg caacaaacat cccgatcgtt ttgatatcaa agccgatgcc    900
ggcgggatca ccgatattga atttattact cagtatctgg tcctacgcta tgccagtgac    960
aagccgaagc tgacccgctg gtctgacaac gtgcgtattc ttgagctgct ggcgcagaac   1020
gacatcatgg acgaggagga ggcgcgcgcc ttaacgcatg cgtacaccac cttgcgtgat   1080
gcgctccatc acctggccct gcaggagcag ccgggacacg tggcgccaga ggccttcagc   1140
cgggagcgtc agcaggtcag cgccagctgg cagaagtggc tgatggctta a            1191

<210> SEQ ID NO 192
<211> LENGTH: 2191
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: glnE-delta-AR-2 with 500bp flank

<400> SEQUENCE: 192
cgtaaggcga ccacccagct ccgcgcgttg ctgaacgacg ctgaagccgt tctgctggcc     60
gcggacaccg ccgacgaggc gttattccgc accgaggtcg tcggcgccaa actggccctg    120
actgaatggc tggtccagcg cggctggcgt ccgttcctca acgaggcagg agagaaaaaa    180
atagccggat cgttcaaacg gtttgccgat attaacctct cgcgggtggc ggccgagctg    240
cgcagcgccg tgcagcatct ggcggttgaa gatgccgccg accagttgcc gaagctgtcc    300
cgcgacatcg acagcgtcca gctgctggcg ggcgcctatg gcgacgccgt cgcgccgtgg    360
ctggagaact ggcaggagct tcaccgtgca atagcacatg acgatcgcag cgtcttttgaa   420 tatttccgtc gccaggcgct ggctgccgag ccgttctggc tgcatagtgg aaaacgataa    480
tttcaggcca gggagccctt atggcgctga agcacctgat cacgctctgc gcggcgtcgc    540
cgatggtcgc cagccagctg gcgcgccacc cgctgctgct ggatgagctg ctggatccca    600
acaccctcta tcagccgacg gcgaccgatg cctatcgcga cgagctgcgc cagtacctgc    660
tgcgcgtgcc ggaagaggat gaagagcagc agctggaggc gttgcgccag tttaagcagg    720
cgcagcagct gcatatcgcg gcggcggata tcgctggtac cctgccggtg atgaaggtca    780
gcgatcactt aacctggctt gccgaagcga tcctcgacgc ggtggtgcag caggcatggg    840
ggcagatggt cgctcgctac ggccagccga cccacctgca cgatcgccag ggtcgcggct    900
tcgccgtcgt cggctacggt aagcttggcg gctgggagct gggctacagc tccgatctcg    960
```

```
atctggtgtt cctccatgac tgcccggcgg aggtgatgac cgacggcgag cgggagattg    1020
acggccgtca gttctacctg cggctggccc agcggatcat gcacctgttc agcacccgca    1080
cctcgtccgg tattctctac gaagtggacg cccggctgcg tccttctggc gcggcgggga    1140
tgctggtcac caccgccgac gcgtttgctg actatcagca gaacgaagcc tggacgtggg    1200
aacatcaggc gctggtgcgc gcccgcgtgg tctatggcga cccggcgctg caggcgcgct    1260
ttgacgccat tcgtcgcgat atcctgacca ccccgcggga ggggatgacc ctgcagaccg    1320
aggttcgcga gatgcgcgag aagatgcgcg cccaccttgg caacaaacat cccgatcgtt    1380
ttgatatcaa agccgatgcc ggcgggatca ccgatattga atttattact cagtatctgg    1440
tcctacgcta tgccagtgac aagccgaagc tgacccgctg gtctgacaac gtgcgtattc    1500
ttgagctgct ggcgcagaac gacatcatgg acgaggagga ggcgcgcgcc ttaacgcatg    1560
cgtacaccac cttgcgtgat gcgctccatc acctggccct gcaggagcag ccgggacacg    1620
tggcgccaga ggccttcagc cgggagcgtc agcaggtcag cgccagctgg cagaagtggc    1680
tgatggctta actataaaat cgggtgtgct attatcgcgc gcaaagtttg cgtctcgcag    1740
gagagagtca tgaaagtaac gctgccggag tttgaacgtg caggagtgtt ggtggtgggt    1800
gatgtgatgc tggaccgcta ctggtacggc cccaccagtc gtatttcccc ggaagccccg    1860
gtgccggtgg tgaaggtgga aaatatcgaa gaacgtcctg cggcgcggc aaacgtagcg    1920 atgaacatcg cctccctggg ggcaacgtcg cgcctggtgg gattgaccgg gattgatgac    1980
gctgcccgcg cgctgagcca ggcgctggcc aatgtgaatg tgaagtgcga cttcgtctcc    2040
gtcccgactc acccgaccat caccaagctg cgggtgctgt cgcgcaatca gcagctgatc    2100
cgcctcgact ttgaagaggg cttctccggc gtggatccgc agccgatgca tgagcgcatt    2160
cagcaggcgc tgggagccat ggcgcactg g                                    2191
```

<210> SEQ ID NO 193
<211> LENGTH: 613
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::PinfC

<400> SEQUENCE: 193

```
atgaccctga atatgatgct agaagcgtca ggtaccggtc atgattcacc gtgcgattct     60
cggttccctg gagcgcttca ttggcatcct gaccgaagag ttcgctggct tcttcccaac    120
ctggattgca ccagtgcagg tagtggtcat gaatattacc gattctcagg ctgaatacgt    180
taacgaattg acgcgtaaac tacaaaatgc gggcattcgt gtaaaagcag acttgagaaa    240
tgagaagatt ggctttaaaa tccgcgagca cactttacgt cgtgtcccgt atatgttggt    300
ctgtggcgac aaagaagtcg aagccggcaa agtggccgtg cgcacccgtc gcgggaaaga    360
cctcggcagc atggacgtaa gtgaagtgat tgagaagctg caacaagaga ttcgcagccg    420
cagtcttcaa caactggagg aataaggtat taaaggcgga aaacgagttc aaacggcacg    480
tccgaatcgt atcaatggcg agattcgcgc cctggaagtt cgcgccattg agctggcttc    540
ccgaccgcag ggcggcacct gcctgaccct gcgtttcccg ctgtttaaca ccctgaccgg    600
aggtgaagca tga                                                       613
```

<210> SEQ ID NO 194
<211> LENGTH: 1613
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: delta-nifL::PinfC with 500bp flank

<400> SEQUENCE: 194

```
ggccgtcgcc cagcgtcggc gtccccaaca gcagggccgg gtaggccagc aggtccgcca      60
gcgtggcgcg gttaatattg accggggcgg cggcggcctc ccccagctgc ttgtggatca     120
ttttcgcgat cttgcgggtt ttaccggtat cggtaccaaa gaaaatgcca atgttcgcca     180
tagtacgctc ctgtcggaat ggtgttgaaa aaggaatga cgacagaggt attgcgaagg      240
ctgtgccagg ttgccctgca ccgcgacggc ccatccctgc ccatcagga tcgcttcgca      300
tcacgatgcc gcgcgccaaa ggcgcacccg gcggggcgaa aggtaaaaat ccgtgaattt     360
tccccctgtc ggatcaatgt ttcgcgtggt cgttccgata agggcgcaca cttgcatgg     420
ttatccgggt tcggcttacc ccgccgcgtt ttgcgcacgg tgtcggacaa tttgtcataa     480
ctgcgacaca ggagtttgcg atgaccctga atatgatgct agaagcgtca ggtaccggtc     540
atgattcacc gtgcgattct cggttccctg gagcgcttca ttggcatcct gaccgaagag     600
ttcgctggct tcttcccaac ctggattgca ccagtgcagg tagtggtcat gaatattacc     660
gattctcagg ctgaatacgt taacgaattg acgcgtaaac tacaaaatgc gggcattcgt     720
gtaaaagcag acttgagaaa tgagaagatt ggctttaaaa tccgcgagca cactttacgt     780
cgtgtcccgt atatgttggt ctgtggcgac aaagaagtcg aagccggcaa agtggccgtg     840
cgcacccgtc gcgggaaaga cctcggcagc atggacgtaa gtgaagtgat tgagaagctg     900
caacaagaga ttcgcagccg cagtcttcaa caactggagg aataaggtat taaaggcgga     960
aaacgagttc aaacggcacg tccgaatcgt atcaatggcg agattcgcgc cctggaagtt    1020
cgcgccattg agctggcttc ccgaccgcag ggcggcacct gcctgaccct gcgtttcccg    1080
ctgtttaaca ccctgaccgg aggtgaagca tgatccctga atccgacccg gacaccaccg    1140
tcagacgctt cgacctctct cagcagttca ccgccatgca gcggataagc gtggtgctga    1200
gccgggccac cgaggccagc aaaacgctgc aggaggtgct cagcgtatta cacaacgatg    1260
cctttatgca gcacgggatg atctgcctgt acgacagcga gcaggagatc ctcagtatcg    1320
aagcgctgca gcaaaccggc cagcagcccc tccccggcag cacgcagatc cgctatcgcc    1380
ccggcgaggg actggtgggg accgtgctgg cccaggggca gtcgctggtg ctgccccggg    1440
tcgccgacga tcagcgtttt ctcgaccgcc tgagcctcta cgattacgat ctgccgttta    1500
tcgccgtacc gttgatgggg cccaacgccc ggccaatagg ggtgctggcg gcccagccga    1560
tggcgcgcca ggaagagcgg ctgccggcct gcacccgttt tctcgaaacc gtc          1613
```

<210> SEQ ID NO 195
<211> LENGTH: 1155
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: glnE-delta-AR-2 36bp deletion

<400> SEQUENCE: 195

```
atggcgctga agcacctgat cacgctctgc gcggcgtcgc cgatggtcgc cagccagctg      60
gcgcgccacc cgctgctgct ggatgagctg ctggatccca acaccctcta tcagccgacg     120
gcgaccgatg cctatcgcga cgagctgcgc cagtacctgc tgcgcgtgcc ggaagaggat     180
gaagagcagc agctgcatat cgcggcggcg gatatcgctg gtaccctgcc ggtgatgaag     240
gtcagcgatc acttaacctg gcttgccgaa gcgatcctcg acgcggtggt gcagcaggca     300
tgggggcaga tggtcgctcg ctacggccag ccgacccacc tgcacgatcg ccagggtcgc     360
ggcttcgccg tcgtcggcta cggtaagctt ggcggctggg agctgggcta cagctccgat     420
ctcgatctgg tgttcctcca tgactgcccg gcggaggtga tgaccgacgg cgagcgggag     480
attgacggcc gtcagttcta cctgcggctg gcccagcgga tcatgcacct gttcagcacc     540
cgcacctcgt ccggtattct ctacgaagtg gacgcccggc tgcgtccttc tggcgcggcg     600
gggatgctgg tcaccaccgc cgacgcgttt gctgactatc agcagaacga agcctggacg     660
tgggaacatc aggcgctggt gcgcgcccgc gtggtctatg cgacccggc gctgcaggcg      720
cgctttgacg ccattcgtcg cgatatcctg accaccccgc ggggagggga taccctgcag     780
accgaggttc gcgagatgcg cgagaagatg cgcgcccacc ttggcaacaa acatcccgat     840
cgttttgata tcaaagccga tgccggcggg atcaccgata ttgaatttat tactcagtat     900
ctggtcctac gctatgccag tgacaagccg aagctgaccc gctggtctga caacgtgcgt     960
attcttgagc tgctggcgca aacgacatc atggacgagg aggaggcgcg cgccttaacg     1020
catgcgtaca ccaccttgcg tgatgcgctc catcacctgg ccctgcagga gcagccggga    1080
cacgtggcgc cagaggcctt cagccgggag cgtcagcagg tcagcgccag ctggcagaag    1140
tggctgatgg cttaa                                                     1155
```

<210> SEQ ID NO 196
<211> LENGTH: 2155
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: glnE-delta-AR-2 36bp deletion

<400> SEQUENCE: 196

```
cgtaaggcga ccacccagct ccgcgcgttg ctgaacgacg ctgaagccgt tctgctggcc      60
gcggacaccg ccgacgaggc gttattccgc accgaggtcg tcggcgccaa actggccctg     120
actgaatggc tggtccagcg cggctggcgt ccgttcctca acgaggcagg agagaaaaaa     180
atagccggat cgttcaaacg gtttgccgat attaacctct cgcgggtggc ggccgagctg     240
cgcagcgccg tgcagcatct ggcggttgaa gatgccgccg accagttgcc gaagctgtcc     300
cgcgacatcg acagcgtcca gctgctggcg ggcgcctatg cgacgccgt cgcgccgtgg      360
ctggagaact ggcaggagct tcaccgtgca atagcacatg acgatcgcag cgtctttgaa     420
tatttccgtc gccaggcgct ggctgccgag ccgttctggc tgcatagtgg aaaacgataa     480
tttcaggcca gggagcccct tatggcgctg aagcacctga tcacgctctg cgcggcgtcgc    540
cgatggtcgc cagccagctg gcgcgccacc cgctgctgct ggatgagctg ctggatccca    600
acaccctcta tcagccgacg gcgaccgatg cctatcgcga cgagctgcgc cagtacctgc    660
tgcgcgtgcc ggaagaggat gaagagcagc agctgcatat cgcggcggcg gatatcgctg    720
```

```
gtaccctgcc ggtgatgaag gtcagcgatc acttaacctg gcttgccgaa gcgatcctcg    780
acgcggtggt gcagcaggca tgggggcaga tggtcgctcg ctacgccag ccgacccacc     840
tgcacgatcg ccagggtcgc ggcttcgccg tcgtcggcta cggtaagctt ggcggctggg    900
agctgggcta cagctccgat ctcgatctgg tgttcctcca tgactgcccg gcggaggtga    960
tgaccgacgg cgagcgggag attgacggcc gtcagttcta cctgcggctg cccagcgga   1020
tcatgcacct gttcagcacc cgcacctcgt ccggtattct ctacgaagtg gacgcccggc   1080
tgcgtccttc tggcgcggcg gggatgctgg tcaccaccgc cgacgcgttt gctgactatc   1140
agcagaacga agcctggacg tgggaacatc aggcgctggt gcgcgcccgc gtggtctatg   1200
gcgacccggc gctgcaggcg cgctttgacg ccattcgtcg cgatatcctg accaccccgc   1260
gggaggggat gaccctgcag accgaggttc gcgagatgcg cgagaagatg cgcgcccacc   1320
ttggcaacaa acatcccgat cgttttgata tcaaagccga tgccggcggg atcaccgata   1380
ttgaatttat tactcagtat ctggtcctac gctatgccag tgacaagccg aagctgaccc   1440
gctggtctga caacgtgcgt attcttgagc tgctggcgca gaacgacatc atggacgagg   1500
aggaggcgcg cgccttaacg catgcgtaca ccaccttgcg tgatgcgctc catcacctgg   1560
ccctgcagga gcagccggga cacgtggcgc cagaggcctt cagccgggag cgtcagcagg   1620
tcagcgccag ctggcagaag tggctgatgg cttaactata aaatcgggtg tgctattatc   1680
gcgcgcaaag tttgcgtctc gcaggagaga gtcatgaaag taacgctgcc ggagtttgaa   1740
cgtgcaggag tgttggtggt gggtgatgtg atgctggacc gctactggta cggccccacc   1800
agtcgtatttt ccccggaagc cccggtgccg gtggtgaagg tggaaaatat cgaagaacgt   1860
cctggcggcg cggcaaacgt agcgatgaac atcgcctccc tggggcaac gtcgcgcctg    1920
gtgggattga ccgggattga tgacgctgcc cgcgcgctga ccaggcgct ggccaatgtg    1980
aatgtgaagt gcgacttcgt ctccgtcccg actcacccga ccatcaccaa gctgcgggtg   2040
ctgtcgcgca atcagcagct gatccgcctc gactttgaag agggcttctc cggcgtggat   2100
ccgcagccga tgcatgagcg cattcagcag gcgctgggag ccattggcgc actgg         2155
```

<210> SEQ ID NO 197
<211> LENGTH: 412
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::Prm8.2

<400> SEQUENCE: 197

```
atgaccctga atatgatgct cgacgccgtc ctcgcagtac cattgcaacc gactttacag     60
caagaagtga ttctggcacg catggaacaa attcttgcca gtcgggcttt atccgatgac   120
gaacgcgcac agcttttata tgagcgcgga gtgttgtatg atagtctcgg tctgagggca   180
ttagcgcgaa atgattttc acaagcgctg gcaatccgac ccgatatgcc tgaagtattc    240
aattacttag gcatttactt aacgcaggca ggcaattttg atgctgccta tgaagcgttt   300
gattctgtac ttgagcttga tcgccattga gctggcttcc cgaccgcagg gcggcaccctg  360
cctgaccctg cgtttcccgc tgtttaacac cctgaccgga ggtgaagcat ga             412
```

<210> SEQ ID NO 198
<211> LENGTH: 1389

```
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::Prm8.2 with 500bp flank

<400> SEQUENCE: 198
cccaacagca gggccgggta ggccagcagg tccgccagcg tggcgcggtt aatattgacc      60
ggggcggcgg cggcctcccc cagctgcttg tggatcattt tcgcgatctt gcgggtttta    120
ccggtatcgg taccaaagaa aatgccaatg ttcgccatag tacgctcctg tcggaatggt    180
gttgaaaaaa ggaatgacga cagaggtatt gcgaaggctg tgccaggttg ccctgcaccg    240
cgacggccca tccctgcccc atcaggatcg cttcgcatca cgatgccgcg cgccaaaggc    300
gcacccggcg gggcgaaagg taaaaatccg tgaattttcc ccctgtcgga tcaatgtttc    360
gcgtggtcgt tccgataagg gcgcacactt tgcatggtta tccgggttcg gcttaccccg    420
ccgcgttttg cgcacggtgt cggacaattt gtcataactg cgacacagga gtttgcgatg    480
accctgaata tgatgctcga cgccgtcctc gcagtaccat tgcaaccgac tttacagcaa    540
gaagtgattc tggcacgcat ggaacaaatt cttgccagtc gggctttatc cgatgacgaa    600
cgcgcacagc ttttatatga gcgcggagtg ttgtatgata gtctcggtct gagggcatta    660
gcgcgaaatg attttttcaca agcgctggca atccgacccg atatgcctga agtattcaat    720
tacttaggca tttacttaac gcaggcaggc aatttttgatg ctgcctatga agcgtttgat    780
tctgtacttg agcttgatcg ccattgagct ggcttcccga ccgcagggcg gcacctgcct    840
gaccctgcgt ttcccgctgt ttaacaccct gaccggaggt gaagcatgat ccctgaatcc    900
gacccggaca ccaccgtcag acgcttcgac ctctctcagc agttcaccgc catgcagcgg    960
ataagcgtgg tgctgagccg ggccaccgag gccagcaaaa cgctgcagga ggtgctcagc   1020
gtattacaca acgatgcctt tatgcagcac gggatgatct gcctgtacga cagcgagcag   1080
gagatcctca gtatcgaagc gctgcagcaa accggccagc agcccctccc cggcagcacg   1140
cagatccgct atcgcccggg cgagggactg gtggggaccg tgctggccca ggggcagtcg   1200
ctggtgctgc cccgggtcgc cgacgatcag cgttttctcg accgcctgag cctctacgat   1260
tacgatctgc cgtttatcgc cgtaccgttg atggggccca acgcccggcc aatagggtgt   1320
ctggcggccc agccgatggc gcgccaggaa gagcggctgc cggcctgcac ccgttttctc   1380
gaaaccgtc                                                          1389

<210> SEQ ID NO 199
<211> LENGTH: 1155
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: glnE-delta-AR-2 36bp deletion

<400> SEQUENCE: 199
atggcgctga agcacctgat cacgctctgc gcggcgtcgc cgatggtcgc cagccagctg     60
gcgcgccacc cgctgctgct ggatgagctg ctggatccca acaccctcta tcagccgacg    120
gcgaccgatg cctatcgcga cgagctgcgc cagtacctgc tgcgcgtgcc ggaagaggat    180
gaagagcagc agctgcatat cgcggcggcg gatatcgctg gtaccctgcc ggtgatgaag    240
```

-continued

```
gtcagcgatc acttaacctg gcttgccgaa gcgatcctcg acgcggtggt gcagcaggca      300
tgggggcaga tggtcgctcg ctacggccag ccgacccacc tgcacgatcg ccagggtcgc      360
ggcttcgccg tcgtcggcta cggtaagctt ggcggctggg agctgggcta cagctccgat      420
ctcgatctgg tgttcctcca tgactgcccg gcggaggtga tgaccgacgg cgagcgggag      480
attgacggcc gtcagttcta cctgcggctg gcccagcgga tcatgcacct gttcagcacc      540
cgcacctcgt ccggtattct ctacgaagtg gacgcccggc tgcgtccttc tggcgcggcg      600
gggatgctgg tcaccaccgc cgacgcgttt gctgactatc agcagaacga agcctggacg      660
tgggaacatc aggcgctggt gcgcgcccgc gtggtctatg gcgacccggc gctgcaggcg      720
cgctttgacg ccattcgtcg cgatatcctg accaccccgc gggaggggat gaccctgcag      780
accgaggttc gcgagatgcg cgagaagatg cgcgcccacc ttggcaacaa acatcccgat      840
cgttttgata tcaaagccga tgccggcggg atcaccgata ttgaatttat tactcagtat      900
ctggtcctac gctatgccag tgacaagccg aagctgaccc gctggtctga caacgtgcgt      960
attcttgagc tgctggcgca gaacgacatc atggacgagg aggaggcgcg cgccttaacg     1020
catgcgtaca ccaccttgcg tgatgcgctc catcacctgg ccctgcagga gcagccggga     1080
cacgtggcgc cagaggcctt cagccgggag cgtcagcagg tcagcgccag ctggcagaag     1140
tggctgatgg cttaa                                                      1155
```

<210> SEQ ID NO 200
<211> LENGTH: 2155
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: glnE-delta-AR-2 36bp deletion

<400> SEQUENCE: 200

```
cgtaaggcga ccacccagct ccgcgcgttg ctgaacgacg ctgaagccgt tctgctggcc       60
gcggacaccg ccgacgaggc gttattccgc accgaggtcg tcggcgccaa actggccctg      120
actgaatggc tggtccagcg cggctggcgt ccgttcctca acgaggcagg agagaaaaaa      180
atagccggat cgttcaaacg gtttgccgat attaacctct cgcgggtggc ggccgagctg      240
cgcagcgccg tgcagcatct ggcggttgaa gatgccgccg accagttgcc gaagctgtcc      300
cgcgacatcg acagcgtcca gctgctggcg ggcgcctatg cgacgccgt cgcgccgtgg      360 ctggagaact ggcaggagct tcaccgtgca atagcacatg acgatcgcag cgtctttgaa      420
tatttccgtc gccaggcgct ggctgccgag ccgttctggc tgcatagtgg aaaacgataa      480
tttcaggcca gggagccctt atggcgctga agcacctgat cacgctctgc gcggcgtcgc      540
cgatggtcgc cagccagctg gcgcgccacc cgctgctgct ggatgagctg ctggatccca      600
acaccctcta tcagccgacg gcgaccgatg cctatcgcga cgagctgcgc cagtacctgc      660
tgcgcgtgcc ggaagaggat gaagagcagc agctgcatat cgcggcggcg gatatcgctg      720
gtaccctgcc ggtgatgaag gtcagcgatc acttaacctg gcttgccgaa gcgatcctcg      780
acgcggtggt gcagcaggca tgggggcaga tggtcgctcg ctacggccag ccgacccacc      840
tgcacgatcg ccagggtcgc ggcttcgccg tcgtcggcta cggtaagctt ggcggctggg      900
agctgggcta cagctccgat ctcgatctgg tgttcctcca tgactgcccg gcggaggtga      960
tgaccgacgg cgagcgggag attgacggcc gtcagttcta cctgcggctg gcccagcgga     1020
```

```
tcatgcacct gttcagcacc cgcacctcgt ccggtattct ctacgaagtg gacgcccggc      1080
tgcgtccttc tggcgcggcg gggatgctgg tcaccaccgc cgacgcgttt gctgactatc      1140
agcagaacga agcctggacg tgggaacatc aggcgctggt gcgcgcccgc gtggtctatg      1200
gcgacccggc gctgcaggcg cgctttgacg ccattcgtcg cgatatcctg accaccccgc      1260
gggaggggat gaccctgcag accgaggttc gcgagatgcg cgagaagatg cgcgcccacc      1320
ttggcaacaa acatcccgat cgttttgata tcaaagccga tgccggcggg atcaccgata      1380
ttgaatttat tactcagtat ctggtcctac gctatgccag tgacaagccg aagctgaccc      1440
gctggtctga caacgtgcgt attcttgagc tgctggcgca gaacgacatc atggacgagg      1500
aggaggcgcg cgccttaacg catgcgtaca ccaccttgcg tgatgcgctc catcacctgg      1560
ccctgcagga gcagccggga cacgtggcgc cagaggcctt cagccgggag cgtcagcagg      1620
tcagcgccag ctggcagaag tggctgatgg cttaactata aaatcgggtg tgctattatc      1680
gcgcgcaaag tttgcgtctc gcaggagaga gtcatgaaag taacgctgcc ggagtttgaa      1740
cgtgcaggag tgttggtggt gggtgatgtg atgctggacc gctactggta cggccccacc      1800
agtcgtattt ccccggaagc cccggtgccg gtggtgaagg tggaaaatat cgaagaacgt      1860
cctggcggcg cggcaaacgt agcgatgaac atcgcctccc tgggggcaac gtcgcgcctg      1920
gtgggattga ccgggattga tgacgctgcc cgcgcgctga gccaggcgct ggccaatgtg      1980
aatgtgaagt gcgacttcgt ctccgtcccg actcacccga ccatcaccaa gctgcgggtg      2040
ctgtcgcgca atcagcagct gatccgcctc gactttgaag agggcttctc cggcgtggat      2100
ccgcagccga tgcatgagcg cattcagcag gcgctgggag ccattggcgc actgg           2155
```

<210> SEQ ID NO 201
<211> LENGTH: 413
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::Prm6.2

<400> SEQUENCE: 201

```
atgaccctga atatgatgct cgagctaaag ttctcggcta atcgctgata acatttgacg       60
caatgcgcaa taaagggca tcatttgatg ccctttttgc acgctttcat accagaacct      120
ggctcatcag tgattttttt tgtcataatc attgctgaga caggctctga agagggcgtt      180
tatacaccaa accattcgag cggtagcgcg acggcaagtc agcgttctcc tttgcaatag      240
cagggaagag gcgccagaac cgccagcgtt gaagcagttt gaacgcgttc agtgtataat      300
ccgaaactta atttcggttt ggagccattg agctggcttc ccgaccgcag gcggcacct      360 gcctgaccct gcgtttcccg ctgtttaaca ccctgaccgg aggtgaagca tga           413
```

<210> SEQ ID NO 202
<211> LENGTH: 1413
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::Prm6.2 with 500bp flank

<400> SEQUENCE: 202

```
ggccgtcgcc cagcgtcggc gtccccaaca gcagggccgg gtaggccagc aggtccgcca      60
gcgtggcgcg gttaatattg accggggcgg cggcggcctc ccccagctgc ttgtggatca     120
ttttcgcgat cttgcgggtt ttaccggtat cggtaccaaa gaaaatgcca atgttcgcca     180
tagtacgctc ctgtcggaat ggtgttgaaa aaggaatga cgacagaggt attgcgaagg      240
ctgtgccagg ttgccctgca ccgcgacggc ccatccctgc ccatcagga tcgcttcgca      300
tcacgatgcc gcgcgccaaa ggcgcacccg gcggggcgaa aggtaaaaat ccgtgaattt     360
tcccctgtc ggatcaatgt ttcgcgtggt cgttccgata agggcgcaca ctttgcatgg      420
ttatccgggt tcggcttacc ccgccgcgtt ttgcgcacgg tgtcggacaa tttgtcataa     480
ctgcgacaca ggagtttgcg atgaccctga atatgatgct cgagctaaag ttctcggcta    540
atcgctgata acatttgacg caatgcgcaa taaagggca tcatttgatg ccctttttgc     600
acgctttcat accagaacct ggctcatcag tgattttttt tgtcataatc attgctgaga   660
caggctctga agagggcgtt tatacaccaa accattcgag cggtagcgcg acggcaagtc    720
agcgttctcc tttgcaatag cagggaagag gcgccagaac cgccagcgtt gaagcagttt    780
gaacgcgttc agtgtataat ccgaaactta atttcggttt ggagccattg agctggcttc   840
ccgaccgcag ggcggcacct gcctgaccct gcgtttcccg ctgtttaaca ccctgaccgg    900
aggtgaagca tgatccctga atccgacccg gacaccaccg tcagacgctt cgacctctct    960
cagcagttca ccgccatgca gcggataagc gtggtgctga gccgggccac cgaggccagc   1020
aaaacgctgc aggaggtgct cagcgtatta cacaacgatg cctttatgca gcacgggatg  1080
atctgcctgt acgacagcga gcaggagatc ctcagtatcg aagcgctgca gcaaaccggc   1140
cagcagcccc tccccggcag cacgcagatc cgctatcgcc ccggcgaggg actggtgggg    1200
accgtgctgg cccaggggca gtcgctggtg ctgccccggg tcgccgacga tcagcgtttt    1260
ctcgaccgcc tgagcctcta cgattacgat ctgccgttta tcgccgtacc gttgatgggg   1320
cccaacgccc ggccaatagg ggtgctggcg gcccagccga tggcgcgcca ggaagagcgg    1380
ctgccggcct gcaccgtttt tctcgaaacc gtc                                1413
```

<210> SEQ ID NO 203
<211> LENGTH: 513
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: delta-nifL::Prm1.2

<400> SEQUENCE: 203

```
atgaccctga atatgatgct cgagcccgct gaccgaccag aacttccacc ttggactcgg    60
ctataccctt ggcgtgacgg cgcgcgataa ctgggactac atccccattc cggtgatctt   120
accattggcg tcaataggtt acggtccggc gactttccag atgacctata ttcccggcac   180
ctacaataac ggtaacgttt acttcgcctg ggctcgtata cagttttaat tcgctaagtc    240
ttagcaataa atgagataag cggtgtgtct tgtggaaaaa caaggactaa agcgttaccc   300
actaaaaaag atagcgactt ttatcacttt ttagcaaagt tgcactggac aaaaggtacc    360
acaattggtg tactgatact cgacacagca ttagtgtcga ttttcatat aaaggtaatt    420
```

```
ttggccattg agctggcttc ccgaccgcag ggcggcacct gcctgaccct gcgtttcccg    480
ctgtttaaca ccctgaccgg aggtgaagca tga                                513
```

<210> SEQ ID NO 204
<211> LENGTH: 1513
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::Prm1.2 with 500bp flank

<400> SEQUENCE: 204

```
ggccgtcgcc cagcgtcggc gtccccaaca gcagggccgg gtaggccagc aggtccgcca     60
gcgtggcgcg gttaatattg accggggcgg cggcggcctc ccccagctgc ttgtggatca    120
ttttcgcgat cttgcgggtt ttaccggtat cggtaccaaa gaaatgcca atgttcgcca     180 tagtacgctc ctgtcggaat ggtgttgaaa aaaggaatga cgacagaggt attgcgaagg    240
ctgtgccagg ttgccctgca ccgcgacggc ccatccctgc ccatcagga tcgcttcgca     300 tcacgatgcc gcgcgccaaa ggcgcacccg gcggggcgaa aggtaaaaat ccgtgaattt    360 tcccccctgtc ggatcaatgt ttcgcgtggt cgttccgata agggcgcaca ctttgcatgg   420
ttatccgggt tcggcttacc ccgccgcgtt ttgcgcacgg tgtcgacaa tttgtcataa     480 ctgcgacaca ggagtttgcg atgaccctga atatgatgct cgagcccgct gaccgaccag    540
aacttccacc ttggactcgg ctataccctt ggcgtgacgg cgcgcgataa ctgggactac    600
atccccattc cggtgatctt accattggcg tcaataggtt acggtccggc gactttccag    660
atgacctata ttcccggcac ctacaataac ggtaacgttt acttcgcctg ggctcgtata    720
cagttttaat tcgctaagtc ttagcaataa atgagataag cggtgtgtct tgtggaaaaa    780
caaggactaa agcgttaccc actaaaaaag atagcgactt ttatcacttt ttagcaaagt    840
tgcactggac aaaaggtacc acaattggtg tactgatact cgacacagca ttagtgtcga    900
tttttcatat aaaggtaatt ttggccattg agctggcttc ccgaccgcag ggcggcacct    960
gcctgaccct gcgtttcccg ctgtttaaca ccctgaccgg aggtgaagca tgatccctga   1020
atccgacccg gacaccaccg tcagacgctt cgacctctct cagcagttca ccgccatgca   1080
gcggataagc gtggtgctga gccgggccac cgaggccagc aaaacgctgc aggaggtgct   1140
cagcgtatta cacaacgatg cctttatgca gcacgggatg atctgcctgt acgacagcga   1200
gcaggagatc ctcagtatcg aagcgctgca gcaaaccggc cagcagcccc tccccggcag   1260
cacgcagatc cgctatcgcc ccggcgaggg actggtgggg accgtgctgg cccaggggca   1320
gtcgctggtg ctgccccggg tcgccgacga tcagcgtttt ctcgaccgcc tgagcctcta   1380
cgattacgat ctgccgttta tcgccgtacc gttgatgggg cccaacgccc ggccaatagg   1440
ggtgctggcg gcccagccga tggcgcgcca ggaagagcgg ctgccggcct gcacccgttt   1500
tctcgaaacc gtc                                                     1513
```

<210> SEQ ID NO 205
<211> LENGTH: 1155
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:

<223> OTHER INFORMATION: glnE-delta-AR-2 36bp deletion

<400> SEQUENCE: 205

| | |
|---|---|
| atggcgctga agcacctgat cacgctctgc gcggcgtcgc cgatggtcgc cagccagctg | 60 |
| gcgcgccacc cgctgctgct ggatgagctg ctggatccca acaccctcta tcagccgacg | 120 |
| gcgaccgatg cctatcgcga cgagctgcgc cagtacctgc tgcgcgtgcc ggaagaggat | 180 |
| gaagagcagc agctgcatat cgcggcggcg gatatcgctg gtaccctgcc ggtgatgaag | 240 |
| gtcagcgatc acttaacctg gcttgccgaa gcgatcctcg acgcggtggt gcagcaggca | 300 |
| tgggggcaga tggtcgctcg ctacggccag ccgacccacc tgcacgatcg ccagggtcgc | 360 |
| ggcttcgccg tcgtcggcta cggtaagctt ggcggctggg agctgggcta cagctccgat | 420 |
| ctcgatctgg tgttcctcca tgactgcccg gcggaggtga tgaccgacgg cgagcgggag | 480 |
| attgacggcc gtcagttcta cctgcggctg gcccagcgga tcatgcacct gttcagcacc | 540 |
| cgcacctcgt ccggtattct ctacgaagtg acgcccggc tgcgtccttc tggcgcggcg | 600 |
| gggatgctgg tcaccaccgc cgacgcgttt gctgactatc agcagaacga agcctggacg | 660 |
| tgggaacatc aggcgctggt gcgcgcccgc gtggtctatg gcgacccggc gctgcaggcg | 720 |
| cgctttgacg ccattcgtcg cgatatcctg accaccccgc gggaggggat gaccctgcag | 780 |
| accgaggttc gcgagatgcg cgagaagatg cgcgcccacc ttggcaacaa acatcccgat | 840 |
| cgttttgata tcaaagccga tgccggcggg atcaccgata ttgaatttat tactcagtat | 900 |
| ctggtcctac gctatgccag tgacaagccg aagctgaccc gctggtctga caacgtgcgt | 960 |
| attcttgagc tgctggcgca gaacgacatc atggacgagg aggaggcgcg cgccttaacg | 1020 |
| catgcgtaca ccaccttgcg tgatgcgctc catcacctgg ccctgcagga gcagccggga | 1080 |
| cacgtggcgc cagaggcctt cagccgggag cgtcagcagg tcagcgccag ctggcagaag | 1140 |
| tggctgatgg cttaa | 1155 |

<210> SEQ ID NO 206
<211> LENGTH: 2155
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: glnE-delta-AR-2 36bp deletion

<400> SEQUENCE: 206

| | |
|---|---|
| cgtaaggcga ccacccagct ccgcgcgttg ctgaacgacg ctgaagccgt tctgctggcc | 60 |
| gcggacaccg ccgacgaggc gttattccgc accgaggtcg tcggcgccaa actggccctg | 120 |
| actgaatggc tggtccagcg cggctggcgt ccgttcctca acgaggcagg agagaaaaaa | 180 |
| atagccggat cgttcaaacg gtttgccgat attaacctct cgcgggtggc ggccgagctg | 240 |
| cgcagcgccg tgcagcatct ggcggttgaa gatgccgccg accagttgcc gaagctgtcc | 300 |
| cgcgacatcg acagcgtcca gctgctggcg ggcgcctatg gcgacgccgt cgcgccgtgg | 360 |
| ctggagaact ggcaggagct tcaccgtgca atagcacatg acgatcgcag cgtcttgaa | 420 |
| tatttccgtc gccaggcgct ggctgccgag ccgttctggc tgcatagtgg aaaacgataa | 480 |
| tttcaggcca gggagcccct atggcgctga agcacctgat cacgctctgc gcggcgtcgc | 540 |
| cgatggtcgc cagccagctg gcgcgccacc cgctgctgct ggatgagctg ctggatccca | 600 |
| acaccctcta tcagccgacg gcgaccgatg cctatcgcga cgagctgcgc cagtacctgc | 660 |

```
tgcgcgtgcc ggaagaggat gaagagcagc agctgcatat cgcggcggcg gatatcgctg      720
gtaccctgcc ggtgatgaag gtcagcgatc acttaacctg gcttgccgaa gcgatcctcg      780
acgcggtggt gcagcaggca tgggggcaga tggtcgctcg ctacggccag ccgacccacc      840
tgcacgatcg ccagggtcgc ggcttcgccg tcgtcggcta cggtaagctt ggcggctggg      900
agctgggcta cagctccgat ctcgatctgg tgttcctcca tgactgcccg gcggaggtga      960
tgaccgacgg cgagcgggag attgacggcc gtcagttcta cctgcggctg gcccagcgga     1020
tcatgcacct gttcagcacc cgcacctcgt ccggtattct ctacgaagtg gacgcccggc     1080
tgcgtccttc tggcgcggcg gggatgctgg tcaccaccgc cgacgcgttt gctgactatc     1140
agcagaacga agcctggacg tggaacatca aggcgctggt gcgcgcccgc gtggtctatg     1200
gcgaccccgc gctgcaggcg cgctttgacg ccattcgtcg cgatatcctg accaccccgc     1260
gggaggggat gaccctgcag accgaggttc gcgagatgcg cgagaagatg cgcgcccacc     1320
ttggcaacaa acatcccgat cgttttgata tcaaagccga tgccggcggg atcaccgata     1380
ttgaatttat tactcagtat ctggtcctac gctatgccag tgacaagccg aagctgaccc     1440
gctggtctga aacgtgcgt attcttgagc tgctggcgca gaacgacatc atggacgagg     1500
aggaggcgcg cgccttaacg catgcgtaca ccaccttgcg tgatgcgctc catcacctgg     1560
ccctgcagga gcagccggga cacgtggcgc cagaggcctt cagccgggag cgtcagcagg     1620
tcagcgccag ctggcagaag tggctgatgg cttaactata aaatcgggtg tgctattatc     1680
gcgcgcaaag tttgcgtctc gcaggagaga gtcatgaaag taacgctgcc ggagtttgaa     1740
cgtgcaggag tgttggtggt gggtgatgtg atgctggacc gctactggta cggccccacc     1800
agtcgtattt ccccggaagc cccggtgccg gtggtgaagg tggaaaatat cgaagaacgt     1860
cctggcggcg cggcaaacgt agcgatgaac atcgcctccc tgggggcaac gtcgcgcctg     1920
gtgggattga ccgggattga tgacgctgcc cgcgcgctga gccaggcgct ggccaatgtg     1980
aatgtgaagt gcgacttcgt ctccgtcccg actcacccga ccatcaccaa gctgcgggtg     2040
ctgtcgcgca atcagcagct gatccgcctc gactttgaag agggcttctc cggcgtggat     2100
ccgcagccga tgcatgagcg cattcagcag gcgctgggag ccattggcgc actgg        2155
```

<210> SEQ ID NO 207
<211> LENGTH: 613
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::PinfC

<400> SEQUENCE: 207

```
atgaccctga atatgatgct agaagcgtca ggtaccggtc atgattcacc gtgcgattct       60
cggttccctg gagcgcttca ttggcatcct gaccgaagag ttcgctggct tcttcccaac      120
ctggattgca ccagtgcagg tagtggtcat gaatattacc gattctcagg ctgaatacgt      180
taacgaattg acgcgtaaac tacaaaatgc gggcattcgt gtaaaagcag acttgagaaa      240
tgagaagatt ggctttaaaa tccgcgagca cactttacgt cgtgtcccgt atatgttggt      300
ctgtggcgac aaagaagtcg aagccggcaa agtggccgtg cgcacccgtc gcgggaaaga      360
cctcggcagc atggacgtaa gtgaagtgat tgagaagctg caacaagaga ttcgcagccg      420
cagtcttcaa caactggagg aataaggtat taaaggcgga aaacgagttc aaacggcacg      480
```

```
tccgaatcgt atcaatggcg agattcgcgc cctggaagtt cgcgccattg agctggcttc       540
ccgaccgcag ggcggcacct gcctgaccct gcgtttcccg ctgtttaaca ccctgaccgg       600
aggtgaagca tga                                                         613
```

<210> SEQ ID NO 208
<211> LENGTH: 1613
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: delta-nifL::PinfC with 500bp flank

<400> SEQUENCE: 208

```
ggccgtcgcc cagcgtcggc gtccccaaca gcagggccgg gtaggccagc aggtccgcca        60
gcgtggcgcg gttaatattg accggggcgg cggcggcctc ccccagctgc ttgtggatca       120
ttttcgcgat cttgcgggtt ttaccggtat cggtaccaaa gaaaatgcca atgttcgcca       180
tagtacgctc ctgtcggaat ggtgttgaaa aaaggaatga cgacagaggt attgcgaagg       240
ctgtgccagg ttgccctgca ccgcgacggc ccatccctgc ccatcagga tcgcttcgca       300 tcacgatgcc gcgcgccaaa ggcgcacccg gcggggcgaa aggtaaaaat ccgtgaattt       360
tccccctgtc ggatcaatgt ttcgcgtggt cgttccgata agggcgcaca ctttgcatgg       420
ttatccgggt tcggcttacc ccgccgcgtt ttgcgcacgg tgtcggacaa tttgtcataa       480
ctgcgacaca ggagtttgcg atgacccctga atatgatgct agaagcgtca ggtaccggtc       540
atgattcacc gtgcgattct cggttccctg gagcgcttca ttggcatcct gaccgaagag       600
ttcgctggct tcttcccaac ctggattgca ccagtgcagg tagtggtcat gaatattacc       660
gattctcagg ctgaatacgt taacgaattg acgcgtaaac tacaaaatgc gggcattcgt       720
gtaaaagcag acttgagaaa tgagaagatt ggctttaaaa tccgcgagca cactttacgt       780
cgtgtcccgt atatgttggt ctgtggcgac aaagaagtcg aagccggcaa agtggccgtg       840
cgcacccgtc gcgggaaaga cctcggcagc atggacgtaa gtgaagtgat tgagaagctg       900
caacaagaga ttcgcagccg cagtcttcaa caactggagg aataaggtat taaaggcgga       960
aaacgagttc aaacggcacg tccgaatcgt atcaatggcg agattcgcgc cctggaagtt      1020
cgcgccattg agctggcttc ccgaccgcag ggcggcacct gcctgaccct gcgtttcccg      1080
ctgtttaaca ccctgaccgg aggtgaagca tgatccctga atccgacccg gacaccaccg      1140
tcagacgctt cgacctctct cagcagttca ccgccatgca gcggataagc gtggtgctga      1200
gccgggccac cgaggccagc aaaacgctgc aggaggtgct cagcgtatta cacaacgatg      1260
cctttatgca gcacgggatg atctgcctgt acgacagcga gcaggagatc ctcagtatcg      1320
aagcgctgca gcaaaccggc cagcagcccc tccccggcag cacgcagatc cgctatcgcc      1380
ccggcgaggg actggtgggg accgtgctgg cccaggggca gtcgctggtg ctgccccggg      1440
tcgccgacga tcagcgtttt ctcgaccgcc tgagcctcta cgattacgat ctgccgttta      1500
tcgccgtacc gttgatgggg cccaacgccc ggccaatagg ggtgctggcg gcccagccga      1560
tggcgcgcca ggaagagcgg ctgccggcct gcacccgttt tctcgaaacc gtc            1613
```

<210> SEQ ID NO 209
<211> LENGTH: 1191
<212> TYPE: DNA
<213> ORGANISM: Artificial Sequence
<220> FEATURE:

<223> OTHER INFORMATION: Description of Artificial Sequence: Synthetic
polynucleotide
<220> FEATURE:
<223> OTHER INFORMATION: glnE-delta-AR-2

<400> SEQUENCE: 209

| | |
|---|---|
| atggcgctga agcacctgat cacgctctgc gcggcgtcgc cgatggtcgc cagccagctg | 60 |
| gcgcgccacc cgctgctgct ggatgagctg ctggatccca acaccctcta tcagccgacg | 120 |
| gcgaccgatg cctatcgcga cgagctgcgc cagtacctgc tgcgcgtgcc ggaagaggat | 180 |
| gaagagcagc agctggaggc gttgcgccag tttaagcagg cgcagcagct gcatatcgcg | 240 |
| gcggcggata tcgctggtac cctgccggtg atgaaggtca gcgatcactt aacctggctt | 300 |
| gccgaagcga tcctcgacgc ggtggtgcag caggcatggg ggcagatggt cgctcgctac | 360 |
| ggccagccga cccacctgca cgatcgccag ggtcgcggct cgccgtcgt cggctacggt | 420 |
| aagcttggcg gctgggagct gggctacagc tccgatctcg atctggtgtt cctccatgac | 480 |
| tgcccggcgg aggtgatgac cgacggcgag cgggagattg acggccgtca gttctacctg | 540 |
| cggctggccc agcggatcat gcacctgttc agcacccgca cctcgtccgg tattctctac | 600 |
| gaagtggacg cccggctgcg tccttctggc gcggcgggga tgctggtcac caccgccgac | 660 |
| gcgtttgctg actatcagca gaacgaagcc tggacgtggg aacatcaggc gctggtgcgc | 720 |
| gcccgcgtgg tctatggcga cccggcgctg caggcgcgct tgacgccat cgtcgcgat | 780 |
| atcctgacca ccccgcggga ggggatgacc ctgcagaccg aggttcgcga gatgcgcgag | 840 |
| aagatgcgcg cccaccttgg caacaaacat cccgatcgtt ttgatatcaa gccgatgcc | 900 |
| ggcgggatca ccgatattga atttattact cagtatctgg tcctacgcta tgccagtgac | 960 |
| aagccgaagc tgacccgctg gtctgacaac gtgcgtattc ttgagctgct ggcgcagaac | 1020 |
| gacatcatgg acgaggagga ggcgcgcgcc ttaacgcatg cgtacaccac cttgcgtgat | 1080 |
| gcgctccatc acctggccct gcaggagcag ccgggacacg tggcgccaga ggccttcagc | 1140 |
| cgggagcgtc agcaggtcag cgccagctgg cagaagtggc tgatggctta a | 1191 |

<210> SEQ ID NO 210
<211> LENGTH: 2191
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: glnE-delta-AR-2 with 500bp flank

<400> SEQUENCE: 210

| | |
|---|---|
| cgtaaggcga ccacccagct ccgcgcgttg ctgaacgacg ctgaagccgt tctgctggcc | 60 |
| gcggacaccg ccgacgaggc gttattccgc accgaggtcg tcggcgccaa actggccctg | 120 |
| actgaatggc tggtccagcg cggctggcgt ccgttcctca acgaggcagg agagaaaaaa | 180 |
| atagccggat cgttcaaacg gtttgccgat attaacctct cgcgggtggc ggccgagctg | 240 |
| cgcagcgccg tgcagcatct ggcggttgaa gatgccgccg accagttgcc gaagctgtcc | 300 |
| cgcgacatcg acagcgtcca gctgctgcg ggcgcctatg cgacgccgt cgcgccgtgg | 360 |
| ctggagaact ggcaggagct tcaccgtgca atagcacatg acgatcgcag cgtctttgaa | 420 |
| tatttccgtc gccaggcgct ggctgccgag ccgttctggc tgcatagtgg aaaacgataa | 480 |
| tttcaggcca gggagccctt atggcgctga agcacctgat cacgctctgc gcggcgtcgc | 540 |
| cgatggtcgc cagccagctg gcgcgccacc cgctgctgct ggatgagctg ctggatccca | 600 |

```
acaccctcta tcagccgacg gcgaccgatg cctatcgcga cgagctgcgc cagtacctgc    660
tgcgcgtgcc ggaagaggat gaagagcagc agctggaggc gttgcgccag tttaagcagg    720
cgcagcagct gcatatcgcg gcggcggata tcgctggtac cctgccggtg atgaaggtca    780
gcgatcactt aacctggctt gccgaagcga tcctcgacgc ggtggtgcag caggcatggg    840
ggcagatggt cgctcgctac ggccagccga cccacctgca cgatcgccag ggtcgcggct    900
tcgccgtcgt cggctacggt aagcttggcg gctgggagct gggctacagc tccgatctcg    960
atctggtgtt cctccatgac tgcccggcgg aggtgatgac cgacggcgag cgggagattg   1020
acggccgtca gttctacctg cggctggccc agcggatcat gcacctgttc agcacccgca   1080
cctcgtccgg tattctctac gaagtggacg cccggctgcg tccttctggc gcggcgggga   1140
tgctggtcac caccgccgac gcgtttgctg actatcagca gaacgaagcc tggacgtggg   1200
aacatcaggc gctggtgcgc gcccgcgtgg tctatggcga cccggcgctg caggcgcgct   1260
ttgacgccat tcgtcgcgat atcctgacca ccccgcggga ggggatgacc ctgcagaccg   1320
aggttcgcga gatgcgcgag aagatgcgcg cccaccttgg caacaaacat cccgatcgtt   1380
ttgatatcaa agccgatgcc ggcgggatca ccgatattga atttattact cagtatctgg   1440
tcctacgcta tgccagtgac aagccgaagc tgacccgctg gtctgacaac gtgcgtattc   1500
ttgagctgct ggcgcagaac gacatcatgg acgaggagga ggcgcgcgcc ttaacgcatg   1560
cgtacaccac cttgcgtgat gcgctccatc acctggccct gcaggagcag ccgggacacg   1620
tggcgccaga ggccttcagc cgggagcgtc agcaggtcag cgccagctgg cagaagtggc   1680
tgatggctta actataaaat cgggtgtgct attatcgcgc gcaaagtttg cgtctcgcag   1740
gagagagtca tgaaagtaac gctgccggag tttgaacgtg caggagtgtt ggtggtgggt   1800
gatgtgatgc tggaccgcta ctggtacggc cccaccagtc gtatttcccc ggaagccccg   1860
gtgccggtgg tgaaggtgga aaatatcgaa gaacgtcctg gcggcgcggc aaacgtagcg   1920
atgaacatcg cctccctggg ggcaacgtcg cgcctggtgg gattgaccgg gattgatgac   1980
gctgcccgcg cgctgagcca ggcgctggcc aatgtgaatg tgaagtgcga cttcgtctcc   2040
gtcccgactc acccgaccat caccaagctg cgggtgctgt cgcgcaatca gcagctgatc   2100
cgcctcgact ttgaagaggg cttctccggc gtggatccgc agccgatgca tgagcgcatt   2160
cagcaggcgc tgggagccat ggcgcactg g                                   2191
```

<210> SEQ ID NO 211
<211> LENGTH: 1188
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: glnE-delta-AR-2

<400> SEQUENCE: 211

```
atggcgctca acagttaat ccgtctgtgt gccgcctcgc cgatggtcgc gacacaactt      60
gcacgtcatc ctttattgct cgatgaactg ctcgacccgc gcacgcttta ccagccgatt    120
gagccgggcg cttaccgcga cgaactgcgt cagtatctga tgcgggtgcc aacagaagac    180
gaagaacagc agcttgaagc cgtgcgccag ttcaaacagg cccagcattt gcgtatcgca    240
gccggggata tttccgggc attgccggtg atgaaagtca gtgaccattt aacctacctt    300
gccgaggcca ttctcgatgt cgtggtgcag catgcgtggg aacaaatggt cgtaaaatac    360
```

```
gggcagcccg cgcatcttca gcaccgtgag gggcgcggtt ttgccgtggt cggttacggg     420
aaactcggtg gctgggagct gggttatagc tcagatctgg atctggtctt cctgctcgat     480
tgcgcgccgg aggtgatgac ggacggcgaa cgcagcatcg acggacgtca gttttatctt     540
cggctggcgc agcgcattat gcacttattc agcacccgga catcgtcagg cattctttac     600
gaggttgatc cgcgtctgcg accttccggc gcatccggca tgctggtcag taccattgaa     660
gcgtttgcag attatcaggc caatgaagcc tggacgtggg agcatcaggc gctggttcgc     720
gcgcgcgtgg tttacgggga tccgcaactg acacagcaat taacgccac cgtcgcgac      780 attctttgcc gccagcgcga tggcgacggc ctgcgtaagg aggtccgtga aatgcgcgag     840
aaaatgtatg cccatctggg gagtaaaaaa gcccacgagt ttgatctgaa agccgatccg     900
ggtggcatca cggatattga attcattgca caatacctgg ttctgcgttt cgcgcatgat     960
gagccgaagc tgacgcgctg gtctgataac gtgcggattt ttgaactgat ggcacgatat    1020
gacatcatgc cggaagagga agcgcgccat ctgacgcagg cttatgtgac gctgcgcgat    1080
gaaattcatc atctggcgtt gcaggaacac agcgggaaag tggccgcgga cagctttgct    1140
actgagcgcg cgcagatccg tgccagctgg gcaaagtggc tcggctga                1188

<210> SEQ ID NO 212
<211> LENGTH: 2188
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: glnE-delta-AR-2 with 500bp flank

<400> SEQUENCE: 212
cggtactgga acagaaatcg gcggatgcgc aggaaatttg ttatgacacg gcctgtctga      60
agtgcaagtt agtgcttact tcctggctgg caacctcagg ctggacgccg tttattgatg     120
ataaatctgc gaagaaactg gacgcttcct tcaaacgttt tgctgacatc atgctcggtc     180
gtaccgcagc ggatctgaaa gaagcctttg cgcagccact gacggaagaa ggttatcgcg     240
atcagctggc gcgcctgaaa cgccagatca ttaccttcca tttgcttgcc ggtgcttacc     300
ctgaaaaaga cgtcgatgcg tatattgccg gctgggtgga cctgcaacag gccatcgttc     360
agcagcaaca cgcctgggag gattcggccc gttctcacgc ggtgatgatg gatgcttttct    420 ggttaaacgg gcaacctcgt taactgactg actagcctgg gcaaactgcc cgggcttttt     480
tttgcaagga atctgatttc atggcgctca acagttaat ccgtctgtgt gccgcctcgc      540
cgatggtcgc gacacaactt gcacgtcatc ctttattgct cgatgaactg ctcgacccgc     600
gcacgcttta ccagccgatt gagccgggcg cttaccgcga cgaactgcgt cagtatctga     660
tgcgggtgcc aacagaagac gaagaacagc agcttgaagc cgtgcgccag ttcaaacagg     720
cccagcattt gcgtatcgca gccggggata tttccgggcc attgccggtg atgaaagtca     780
gtgaccattt aacctaccct tgccgaggcca ttctcgatgt cgtggtgcag catgcgtggg    840
aacaaatggt cgtaaaatac gggcagcccg cgcatcttca gcaccgtgag gggcgcggtt    900
ttgccgtggt cggttacggg aaactcggtg gctgggagct gggttatagc tcagatctgg    960
atctggtctt cctgctcgat tgcgcgccgg aggtgatgac ggacggcgaa cgcagcatcg   1020
acggacgtca gttttatctt cggctggcgc agcgcattat gcacttattc agcacccgga   1080
catcgtcagg cattctttac gaggttgatc cgcgtctgcg accttccggc gcatccggca   1140
```

```
tgctggtcag taccattgaa gcgtttgcag attatcaggc caatgaagcc tggacgtggg    1200
agcatcaggc gctggttcgc gcgcgcgtgg tttacgggga tccgcaactg acacagcaat    1260
ttaacgccac gcgtcgcgac attctttgcc gccagcgcga tggcgacggc ctgcgtaagg    1320
aggtccgtga aatgcgcgag aaaatgtatg cccatctggg gagtaaaaaa gcccacgagt    1380
ttgatctgaa agccgatccg ggtggcatca cggatattga attcattgca caatacctgg    1440
ttctgcgttt cgcgcatgat gagccgaagc tgacgcgctg gtctgataac gtgcggattt    1500
ttgaactgat ggcacgatat gacatcatgc cggaagagga agcgcgccat ctgacgcagg    1560
cttatgtgac gctgcgcgat gaaattcatc atctggcgtt gcaggaacac agcgggaaag    1620
tggccgcgga cagctttgct actgagcgcg cgcagatccg tgccagctgg gcaaagtggc    1680
tcggctgagg ttttttattc ggctaacagg cgcttgtgat attatccggc gcattgtatt    1740
tacccgattt gatttatctg ttttggagtc ttgggatgaa agtgactttg cctgattttc    1800
accgcgcagg tgtgctggtt gtcggtacgg taatgttaga ccgttactgg tatggcccga    1860
ccaatcgtat ttctccggaa gctccggtgc cggtggtgaa ggtcagtacc attgaagagc    1920
ggcctggcgg tgcagctaac gtggcgatga acatttcatc tctgggcgcc tcttcctgtc    1980
tgatcggcct gaccggcgta gacgacgctg cgcgtgccct cagtgagcgt ctggcagaag    2040
tgaaagttaa ctgcgatttc gtcgcactat ccacacatcc taccatcacc aaactgcgaa    2100
ttttgtcccg taaccagcaa ctgatccgcc tcgactttga ggaaggtttt gaaggcgttg    2160
atctcgagcc gatgctgacc aaaataga                                      2188
```

<210> SEQ ID NO 213
<211> LENGTH: 635
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::Prm6.1

<400> SEQUENCE: 213

```
atgagcatca cggcgttatc agcatcattt cctgagggga atatcgccag ccgcttgtcg    60
ctgcaacatc cttcactgtt ttataccgtg gttgaacaat cttcggtggc gatttcgctg    120
accgatccgc aggcgcgcat ttgttatgcc aatccggcat tctgccgcca gacgggtttt    180
gcacttgaga cacttttggg cgagaaccac cgtctgctgg aattttttttt cacaaagcgt    240 agcgttattg aatcgcacat tttaaactgt tggccgctgt ggaagcgaat attggtgaaa    300
ggtgcggttt taaggccttt ttctttgact ctctgtcgtt acaaagttaa tatgcgcgcc    360
ctccgtctct gaagctctcg gtgaacattg ttgcgaggca ggatgcgagc tggttgtgtt    420
ttgacattac cgataatgtg ccgcgtgaac gggtgcgtta tgcccgcccg gaagcggcgt    480
tttcccgtcc ggggaatggc atggagctgc gccttatcca gacgctgatc gcccatcatc    540
gcggttcttt agatctctcg gtccgccctg atggcggcac cttgctgacg ttacgcctgc    600
cggtacagca ggttatcacc ggaggcttaa aatga                               635
```

<210> SEQ ID NO 214
<211> LENGTH: 1635
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::Prm6.1 with 500bp flank

<400> SEQUENCE: 214

| | | | | | |
|---|---|---|---|---|---|
| tgtttcgtct | cgaggccggg | caactgagcg | gccccgttga | aaccgacctg | ggctggcatc | 60 |
| tgttgttgtg | cgaacaaatt | cgcctgccgc | aacccttgcc | gaaagccgaa | gccttaacgc | 120 |
| gggtgcgtca | gcaactgatt | gcccggcaac | agaaacatta | tcagcgccag | tggctgcaac | 180 |
| aactgatcaa | cgcctgagcc | tgttctcctt | cttgttgatg | cagacgggtt | aatgcccgtt | 240 |
| ttgcacgaaa | aatgcacata | aattgcctgc | gttgccttat | aacagcgcag | ggaaatcctg | 300 |
| cctccggcct | tgtgccacac | cgcgctttgc | ctggtttgtg | gtaaaaactg | gcccgctttg | 360 |
| catcctgatg | cttaaaacac | cccgttcaga | tcaacctttg | ggcagataag | cccgcgaaag | 420 |
| gcctgcaaat | tgcacggtta | ttccgggtga | gtatatgtgt | gatttgggtt | ccggcattgc | 480 |
| gcaataaagg | ggagaaagac | atgagcatca | cggcgttatc | agcatcattt | cctgagggga | 540 |
| atatcgccag | ccgcttgtcg | ctgcaacatc | cttcactgtt | ttataccgtg | gttgaacaat | 600 |
| cttcggtggc | gatttcgctg | accgatccgc | aggcgcgcat | ttgttatgcc | aatccggcat | 660 |
| tctgccgcca | gacgggtttt | gcacttgaga | cacttttggg | cgagaaccac | cgtctgctgg | 720 |
| aattttttt | cacaaagcgt | agcgttattg | aatcgcacat | tttaaactgt | tggccgctgt | 780 |
| ggaagcgaat | attggtgaaa | ggtgcggttt | taaggccttt | ttctttgact | ctctgtcgtt | 840 |
| acaaagttaa | tatgcgcgcc | ctccgtctct | gaagctctcg | gtgaacattg | ttgcgaggca | 900 |
| ggatgcgagc | tggttgtgtt | ttgacattac | cgataatgtg | ccgcgtgaac | gggtgcgtta | 960 |
| tgcccgcccg | gaagcggcgt | tttcccgtcc | ggggaatggc | atggagctgc | gccttatcca | 1020 |
| gacgctgatc | gcccatcatc | gcggttcttt | agatctctcg | gtccgccctg | atggcggcac | 1080 |
| cttgctgacg | ttacgcctgc | cggtacagca | ggttatcacc | ggaggcttaa | aatgacccag | 1140 |
| ttacctaccg | cgggcccggt | tatccggcgc | tttgatatgt | ctgcccagtt | tacggcgctt | 1200 |
| tatcgcatca | gcgtggcgct | gagtcaggaa | agcaacaccg | ggcgcgcact | ggcggcgatc | 1260 |
| ctcgaagtgc | ttcacgatca | tgcatttatg | caatacggca | tggtgtgtct | gtttgataaa | 1320 |
| gaacgcaatg | cactctttgt | ggaatccctg | catggcatcg | acggcgaaag | gaaaaaagag | 1380 |
| acccgccatg | tccgttaccg | catgggggaa | ggcgtgatcg | gcgcggtgat | gagccagcgt | 1440 |
| caggcgctgg | tgttaccgcg | catttcagac | gatcagcgtt | ttctcgaccg | cctgaatatt | 1500 |
| tacgattaca | gcctgccgtt | gattggcgtg | ccgatccccg | gtgcggataa | tcagccatcg | 1560 |
| ggcgtgctgg | tggcacagcc | gatggcgttg | cacgaagacc | ggctgactgc | cagtacgcgg | 1620 |
| ttttagaaa | tggtc | | | | | 1635 |

<210> SEQ ID NO 215
<211> LENGTH: 635
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::Prm6.1

<400> SEQUENCE: 215

```
atgagcatca cggcgttatc agcatcattt cctgagggga atatcgccag ccgcttgtcg    60
ctgcaacatc cttcactgtt ttataccgtg gttgaacaat cttcggtggc gatttcgctg   120
accgatccgc aggcgcgcat ttgttatgcc aatccggcat tctgccgcca gacgggtttt   180
gcacttgaga cacttttggg cgagaaccac cgtctgctgg aatttttttt cacaaagcgt   240
agcgttattg aatcgcacat tttaaactgt tggccgctgt ggaagcgaat attggtgaaa   300
ggtgcggttt taaggccttt ttctttgact ctctgtcgtt acaaagttaa tatgcgcgcc   360
ctccgtctct gaagctctcg gtgaacattg ttgcgaggca ggatgcgagc tggttgtgtt   420
ttgacattac cgataatgtg ccgcgtgaac gggtgcgtta tgcccgcccg aagcggcgt    480 tttcccgtcc ggggaatggc atggagctgc gccttatcca gacgctgatc gcccatcatc   540
gcggttcttt agatctctcg gtccgccctg atggcggcac cttgctgacg ttacgcctgc   600
cggtacagca ggttatcacc ggaggcttaa aatga                              635
```

<210> SEQ ID NO 216
<211> LENGTH: 1635
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: delta-nifL::Prm6.1 with 500bp flank

<400> SEQUENCE: 216

```
tgtttcgtct cgaggccggg caactgagcg gccccgttga aaccgacctg ggctggcatc    60
tgttgttgtg cgaacaaatt cgcctgccgc aaccccttgcc gaaagccgaa gccttaacgc   120
gggtgcgtca gcaactgatt gcccggcaac agaaacatta tcagcgccag tggctgcaac   180
aactgatcaa cgcctgagcc tgttctcctt cttgttgatg cagacgggtt aatgcccgtt   240 tgcacgaaa aatgcacata aattgcctgc gttgccttat aacagcgcag ggaaatcctg    300
cctccggcct tgtgccacac cgcgcttttgc ctggtttgtg gtaaaaactg gcccgctttg   360
catcctgatg cttaaaacac cccgttcaga tcaacctttg ggcagataag cccgcgaaag   420
gcctgcaaat tgcacggtta ttccgggtga gtatatgtgt gatttgggtt ccggcattgc   480
gcaataaagg ggagaaagac atgagcatca cggcgttatc agcatcattt cctgagggga   540
atatcgccag ccgcttgtcg ctgcaacatc cttcactgtt ttataccgtg gttgaacaat   600
cttcggtggc gatttcgctg accgatccgc aggcgcgcat ttgttatgcc aatccggcat   660
tctgccgcca gacgggtttt gcacttgaga cacttttggg cgagaaccac cgtctgctgg   720
aatttttttt cacaaagcgt agcgttattg aatcgcacat tttaaactgt tggccgctgt   780
ggaagcgaat attggtgaaa ggtgcggttt taaggccttt ttctttgact ctctgtcgtt   840
acaaagttaa tatgcgcgcc ctccgtctct gaagctctcg gtgaacattg ttgcgaggca   900
ggatgcgagc tggttgtgtt ttgacattac cgataatgtg ccgcgtgaac gggtgcgtta   960
tgcccgcccg aagcggcgt tttcccgtcc ggggaatggc atggagctgc gccttatcca   1020
gacgctgatc gcccatcatc gcggttcttt agatctctcg gtccgccctg atggcggcac   1080
cttgctgacg ttacgcctgc cggtacagca ggttatcacc ggaggcttaa aatgacccag   1140
ttacctaccg cgggccggt tatccggcgc tttgatatgt ctgcccagtt tacggcgctt   1200
tatcgcatca gcgtggcgct gagtcaggaa agcaacaccg ggcgcgcact ggcggcgatc   1260
```

```
ctcgaagtgc ttcacgatca tgcatttatg caatacggca tggtgtgtct gtttgataaa    1320
gaacgcaatg cactctttgt ggaatccctg catggcatcg acggcgaaag gaaaaaagag    1380
acccgccatg tccgttaccg catgggggaa ggcgtgatcg gcgcggtgat gagccagcgt    1440
caggcgctgg tgttaccgcg catttcagac gatcagcgtt ttctcgaccg cctgaatatt    1500
tacgattaca gcctgccgtt gattggcgtg ccgatccccg gtgcggataa tcagccatcg    1560
ggcgtgctgg tggcacagcc gatggcgttg cacgaagacc ggctgactgc cagtacgcgg    1620
tttttagaaa tggtc                                                    1635
```

<210> SEQ ID NO 217
<211> LENGTH: 786
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: delta-nifL::Prm7.1

<400> SEQUENCE: 217

```
atgagcatca cggcgttatc agcatcattt cctgagggga atatcgccag ccgcttgtcg    60
ctgcaacatc cttcactgtt ttataccgtg gttgaacaat cttcggtggc gatttcgctg    120
accgatccgc aggcgcgcat tgttatgcc aatccggcac tctgccgcca gacgggtttt    180
gcacttgaga cactttttggg cgagaaccac cgtctgctgg ttaaaaacgt gaccacgagc    240
attaataaac gccacgaaat gtggcgttta tttattcaaa aagtatcttc tttcataaaa    300
agtgctaaat gcagtagcag caaaattggg ataagtccca tggaatacgg ctgttttcgc    360
tgcaattttt aacttttttcg taaaaaaaga tgtttctttg agcgaacgat caaaatatag    420
cgttaaccgg caaaaaatta ttctcattag aaaatagttt gtgtaatact tgtaacgcta    480
catggagatt aacttaatct agagggtttt ataccgtctc tgaagctctc ggtgaacatt    540
gttgcgaggc aggatgcgag ctggttgtgt tttgacatta ccgataatgt gccgcgtgaa    600
cgggtgcgtt atgcccgccc ggaagcggcg ttttcccgtc cggggaatgg catgagctg    660 cgccttatcc agacgctgat cgcccatcat cgcggttctt tagatctctc ggtccgccct    720
gatggcggca ccttgctgac gttacgcctg ccggtacagc aggttatcac cggaggctta    780
aaatga                                                              786
```

<210> SEQ ID NO 218
<211> LENGTH: 1786
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: delta-nifL::Prm7.1 with 500bp flank

<400> SEQUENCE: 218

```
gtttcgtctc gaggccgggc aactgagcgg ccccgttgaa accgacctgg gctggcatct    60
gttgttgtgc gaacaaattc gcctgccgca acccttgccg aaagccgaag ccttaacgcg    120
ggtgcgtcag caactgattg cccggcaaca gaaacattat cagcgccagt ggctgcaaca    180
actgatcaac gcctgagcct gttctccttc ttgttgatgc agacgggtta atgcccgttt    240
tgcacgaaaa atgcacataa attgcctgcg ttgccttata acagcgcagg gaaatcctgc    300
```

```
ctccggcctt gtgccacacc gcgctttgcc tggtttgtgg taaaaactgg cccgctttgc    360
atcctgatgc ttaaaacacc ccgttcagat caacctttgg gcagataagc ccgcgaaagg    420
cctgcaaatt gcacggttat tccgggtgag tatatgtgtg atttgggttc cggcattgcg    480
caataaaggg gagaaagaca tgagcatcac ggcgttatca gcatcatttc ctgaggggaa    540
tatcgccagc cgcttgtcgc tgcaacatcc ttcactgttt tataccgtgg ttgaacaatc    600
ttcggtggcg atttcgctga ccgatccgca ggcgcgcatt tgttatgcca atccggcatt    660
ctgccgccag acgggttttg cacttgagac acttttgggc gagaaccacc gtctgctggt    720
taaaaacgtg accacgagca ttaataaacg ccacgaaatg tggcgtttat ttattcaaaa    780
agtatcttct ttcataaaaa gtgctaaatg cagtagcagc aaaattggga taagtcccat    840
ggaatacggc tgttttcgct gcaattttta acttttcgt aaaaaaagat gtttctttga    900
gcgaacgatc aaaatatagc gttaaccggc aaaaaattat tctcattaga aaatagtttg    960
tgtaatactt gtaacgctac atggagatta acttaatcta gagggtttta taccgtctct   1020
gaagctctcg gtgaacattg ttgcgaggca ggatgcgagc tggttgtgtt ttgacattac   1080
cgataatgtg ccgcgtgaac gggtgcgtta tgcccgcccg aagcggcgt tttcccgtcc   1140
ggggaatggc atggagctgc gccttatcca gacgctgatc gcccatcatc gcggttcttt   1200
agatctctcg gtccgccctg atggcggcac cttgctgacg ttacgcctgc cggtacagca   1260
ggttatcacc ggaggcttaa aatgacccag ttacctaccg cgggcccggt tatccggcgc   1320
tttgatatgt ctgcccagtt tacggcgctt tatcgcatca gcgtggcgct gagtcaggaa   1380
agcaacaccg ggcgcgcact ggcggcgatc ctcgaagtgc ttcacgatca tgcatttatg   1440
caatacggca tggtgtgtct gtttgataaa aacgcaatg cactctttgt ggaatccctg   1500
catggcatca acggcgaaag gaaaaagag acccgccatg tccgttaccg catggggaa    1560
ggcgtgatcg gcgcggtgat gagccagcgt caggcgctgg tgttaccgcg catttcagac   1620
gatcagcgtt ttctcgaccg cctgaatatt tacgattaca gcctgccgtt gattggcgtg   1680
ccgatccccg gtgcggataa tcagccatcg ggcgtgctgg tggcacagcc gatggcgttg   1740
cacgaagacc ggctgactgc cagtacgcgg tttttagaaa tggtcg               1786
```

<210> SEQ ID NO 219
<211> LENGTH: 993
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::Prm1.2

<400> SEQUENCE: 219

```
atgagcatca cggcgttatc agcatcattt cctgagggga atatcgccag ccgcttgtcg     60
ctgcaacatc cttcactgtt ttataccgtg gttgaacaat cttcggtggc gatttcgctg    120
accgatccgc aggcgcgcat ttgttatgcc aatccggcat tctgccgcca gacgggtttt    180
gcacttgaga cacttttggg cgagaaccac cgtctgctgg tgaacatcac tgatgcacaa    240
gctacctatg tcgaagaatt aactaaaaaa ctgcaagatg caggcattcg cgttaaagcc    300
gacttgagaa atgagaagat tggctttaaa attcgcgaac acacgctacg ccgtgttcct    360
tatatgttag tttgtggcga taaagaggtc gaagcaggca agttgctgt tcgtacccgc    420
cgcggcaaag acttaggaag catggatgtt agcgaagtcg ttgacaaact gctggcggaa    480
```

| | | | |
|---|---|---|---|
| atccgcagca | gaagtcttca | tcaactggag gaataaagta | ttaaaggcgg aaaacgagtt | 540 |
| caaccggcgc | gtcctaatcg | cattaacaaa gagattcgcg | cgcaagaagt tcgcctcaca | 600 |
| ggcgtcgatg | gcgagcagat | tggtattgtc agtctgaatg | aagctcttga aaaagctgag | 660 |
| gaagcgggcg | tcgatttagt | agaaatcagt ccgaatgccg | agccgccagt ttgtcgaatc | 720 |
| ccgtctctga | agctctcggt | gaacattgtt gcgaggcagg | atgcgagctg gttgtgtttt | 780 |
| gacattaccg | ataatgtgcc | gcgtgaacgg gtgcgttatg | cccgcccgga agcggcgttt | 840 |
| tcccgtccgg | ggaatggcat | ggagctgcgc cttatccaga | cgctgatcgc ccatcatcgc | 900 |
| ggttctttag | atctctcggt | ccgccctgat ggcggcacct | tgctgacgtt acgcctgccg | 960 |
| gtacagcagg | ttatcaccgg | aggcttaaaa tga | | 993 |

<210> SEQ ID NO 220
<211> LENGTH: 1993
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: delta-nifL::Prm1.2 with 500bp flank

<400> SEQUENCE: 220

| | | | |
|---|---|---|---|
| tgtttcgtct | cgaggccggg | caactgagcg gcccgttga | aaccgacctg ggctggcatc | 60 |
| tgttgttgtg | cgaacaaatt | cgcctgccgc aacccttgcc | gaaagccgaa gccttaacgc | 120 |
| gggtgcgtca | gcaactgatt | gcccggcaac agaaacatta | tcagcgccag tggctgcaac | 180 |
| aactgatcaa | cgcctgagcc | tgttctcctt cttgttgatg | cagacgggtt aatgcccgtt | 240 |
| ttgcacgaaa | aatgcacata | aattgcctgc gttgccttat | aacagcgcag ggaaatcctg | 300 |
| cctccggcct | tgtgccacac | cgcgctttgc ctggtttgtg | gtaaaaactg gcccgctttg | 360 |
| catcctgatg | cttaaaacac | cccgttcaga tcaacctttg | ggcagataag cccgcgaaag | 420 |
| gcctgcaaat | tgcacggtta | ttccgggtga gtatatgtgt | gatttgggtt ccggcattgc | 480 |
| gcaataaagg | ggagaaagac | atgagcatca cggcgttatc | agcatcattt cctgagggga | 540 |
| atatcgccag | ccgcttgtcg | ctgcaacatc cttcactgtt | ttataccgtg gttgaacaat | 600 |
| cttcggtggc | gatttcgctg | accgatccgc aggcgcgcat | ttgttatgcc aatccggcat | 660 |
| tctgccgcca | gacgggtttt | gcacttgaga cacttttggg | cgagaaccac cgtctgctgg | 720 |
| tgaacatcac | tgatgcacaa | gctacctatg tcgaagaatt | aactaaaaaa ctgcaagatg | 780 |
| caggcattcg | cgttaaagcc | gacttgagaa atgagaagat | tggctttaaa attcgcgaac | 840 |
| acacgctacg | ccgtgttcct | tatatgttag tttgtggcga | taagagggtc gaagcaggca | 900 |
| aagttgctgt | tcgtacccgc | cgcggcaaag acttaggaag | catggatgtt agcgaagtcg | 960 |
| ttgacaaaact | gctggcggaa | atccgcagca gaagtcttca | tcaactggag gaataaagta | 1020 |
| ttaaaggcgg | aaaacgagtt | caaccggcgc gtcctaatcg | cattaacaaa gagattcgcg | 1080 |
| cgcaagaagt | tcgcctcaca | ggcgtcgatg gcgagcagat | tggtattgtc agtctgaatg | 1140 |
| aagctcttga | aaaagctgag | gaagcgggcg tcgatttagt | agaaatcagt ccgaatgccg | 1200 |
| agccgccagt | ttgtcgaatc | ccgtctctga agctctcggt | gaacattgtt gcgaggcagg | 1260 |
| atgcgagctg | gttgtgtttt | gacattaccg ataatgtgcc | gcgtgaacgg gtgcgttatg | 1320 |
| cccgcccgga | agcggcgttt | tcccgtccgg ggaatggcat | ggagctgcgc cttatccaga | 1380 |
| cgctgatcgc | ccatcatcgc | ggttctttag atctctcggt | ccgccctgat ggcggcacct | 1440 |

```
tgctgacgtt acgcctgccg gtacagcagg ttatcaccgg aggcttaaaa tgacccagtt    1500
acctaccgcg ggcccggtta tccggcgctt tgatatgtct gcccagttta cggcgcttta    1560
tcgcatcagc gtggcgctga gtcaggaaag caacaccggg cgcgcactgg cggcgatcct    1620
cgaagtgctt cacgatcatg catttatgca atacggcatg gtgtgtctgt ttgataaaga    1680
acgcaatgca ctctttgtgg aatccctgca tggcatcgac ggcgaaagga aaaagagac    1740 ccgccatgtc cgttaccgca tggggggaagg cgtgatcggc gcggtgatga gccagcgtca    1800
ggcgctggtg ttaccgcgca tttcagacga tcagcgtttt ctcgaccgcc tgaatattta    1860
cgattacagc ctgccgttga ttggcgtgcc gatccccggt gcggataatc agccatcggg    1920
cgtgctggtg gcacagccga tggcgttgca cgaagaccgg ctgactgcca gtacgcggtt    1980
tttagaaatg gtc                                                       1993

<210> SEQ ID NO 221
<211> LENGTH: 993
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::Prm1.2

<400> SEQUENCE: 221
atgagcatca cggcgttatc agcatcattt cctgagggga atatcgccag ccgcttgtcg      60
ctgcaacatc cttcactgtt ttataccgtg gttgaacaat cttcggtggc gatttcgctg     120
accgatccgc aggcgcgcat ttgttatgcc aatccggcat tctgccgcca gacgggtttt     180
gcacttgaga cacttttggg cgagaaccac cgtctgctgg tgaacatcac tgatgcacaa     240
gctacctatg tcgaagaatt aactaaaaaa ctgcaagatg caggcattcg cgttaaagcc     300
gacttgagaa atgagaagat tggctttaaa attcgcgaac acacgctacg ccgtgttcct     360
tatatgttag tttgtggcga taaagaggtc gaagcaggca agttgctgt tcgtacccgc     420 cgcggcaaag acttaggaag catggatgtt agcgaagtcg ttgacaaact gctggcggaa     480
atccgcagca gaagtcttca tcaactggag gaataaagta ttaaaggcgg aaaacgagtt     540
caaccggcgc gtcctaatcg cattaacaaa gagattcgcg cgcaagaagt tcgcctcaca     600
ggcgtcgatg gcgagcagat tggtattgtc agtctgaatg aagctcttga aaaagctgag     660
gaagcgggcg tcgatttagt agaaatcagt ccgaatgccg agccgccagt ttgtcgaatc     720
ccgtctctga agctctcggt gaacattgtt gcgaggcagg atgcgagctg gttgtgtttt     780
gacattaccg ataatgtgcc gcgtgaacgg gtgcgttatg cccgcccgga agcggcgttt     840
tcccgtccgg ggaatggcat ggagctgcgc cttatccaga cgctgatcgc ccatcatcgc     900
ggttctttag atctctcggt ccgccctgat ggcggcacct tgctgacgtt acgcctgccg     960
gtacagcagg ttatcaccgg aggcttaaaa tga                                  993

<210> SEQ ID NO 222
<211> LENGTH: 1993
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::Prm1.2 with 500bp flank
```

<400> SEQUENCE: 222

```
tgtttcgtct cgaggccggg caactgagcg gccccgttga aaccgacctg ggctggcatc      60
tgttgttgtg cgaacaaatt cgcctgccgc aacccttgcc gaaagccgaa gccttaacgc     120
gggtgcgtca gcaactgatt gcccggcaac agaaacatta tcagcgccag tggctgcaac     180
aactgatcaa cgcctgagcc tgttctcctt cttgttgatg cagacgggtt aatgcccgtt     240
ttgcacgaaa aatgcacata aattgcctgc gttgccttat aacagcgcag ggaaatcctg     300
cctccggcct tgtgccacac cgcgctttgc ctggtttgtg gtaaaaactg gcccgctttg     360
catcctgatg cttaaaacac cccgttcaga tcaacctttg ggcagataag cccgcgaaag     420
gcctgcaaat tgcacggtta ttccgggtga gtatatgtgt gatttgggtt ccggcattgc     480
gcaataaagg ggagaaagac atgagcatca cggcgttatc agcatcattt cctgagggga     540
atatcgccag ccgcttgtcg ctgcaacatc cttcactgtt ttataccgtg gttgaacaat     600
cttcggtggc gatttcgctg accgatccgc aggcgcgcat ttgttatgcc aatccggcat     660
tctgccgcca gacgggtttt gcacttgaga cacttttggg cgagaaccac cgtctgctgg     720
tgaacatcac tgatgcacaa gctacctatg tcgaagaatt aactaaaaaa ctgcaagatg     780
caggcattcg cgttaaagcc gacttgagaa atgagaagat tggctttaaa attcgcgaac     840
acacgctacg ccgtgttcct tatatgttag tttgtggcga taagaggtc gaagcaggca     900
aagttgctgt tcgtacccgc cgcggcaaag acttaggaag catggatgtt agcgaagtcg     960
ttgacaaact gctggcggaa atccgcagca gaagtcttca tcaactggag gaataaagta    1020
ttaaaggcgg aaaacgagtt caaccggcgc gtcctaatcg cattaacaaa gagattcgcg    1080
cgcaagaagt tcgcctcaca ggcgtcgatg gcgagcagat tggtattgtc agtctgaatg    1140
aagctcttga aaaagctgag gaagcgggcg tcgatttagt agaaatcagt ccgaatgccg    1200
agccgccagt ttgtcgaatc ccgtctctga gctctcggt gaacattgtt gcgaggcagg    1260
atgcgagctg gttgtgtttt gacattaccg ataatgtgcc gcgtgaacgg gtgcgttatg    1320
cccgcccgga agcggcgttt tcccgtccgg ggaatggcat ggagctgcgc cttatccaga    1380
cgctgatcgc ccatcatcgc ggttctttag atctctcggt ccgccctgat ggcggcacct    1440
tgctgacgtt acgcctgccg gtacagcagg ttatcaccgg aggcttaaaa tgacccagtt    1500
acctaccgcg ggcccggtta tccggcgctt tgatatgtct gcccagttta cggcgcttta    1560
tcgcatcagc gtggcgctga gtcaggaaag caacaccggg cgcgcactgg cggcgatcct    1620
cgaagtgctt cacgatcatg catttatgca atacggcatg gtgtgtctgt ttgataaaga    1680
acgcaatgca ctctttgtgg aatccctgca tggcatcgac ggcgaaagga aaaagagac    1740
ccgccatgtc cgttaccgca tggggaagg cgtgatcggc gcggtgatga ccagcgtca    1800
ggcgctggtg ttaccgcgca tttcagacga tcagcgtttt ctcgaccgcc tgaatattta    1860
cgattacagc ctgccgttga ttggcgtgcc gatccccggt gcggataatc agccatcggg    1920
cgtgctggtg gcacagccga tggcgttgca cgaagaccgg ctgactgcca gtacgcggtt    1980
tttagaaatg gtc                                                       1993
```

<210> SEQ ID NO 223
<211> LENGTH: 1188
<212> TYPE: DNA
<213> ORGANISM: Artificial Sequence
<220> FEATURE:
<223> OTHER INFORMATION: Description of Artificial Sequence: Synthetic polynucleotide -continued

```
<220> FEATURE:
<223> OTHER INFORMATION: glnE-delta-AR-2

<400> SEQUENCE: 223
atggcgctca aacagttaat ccgtctgtgt gccgcctcgc cgatggtcgc gacacaactt      60
gcacgtcatc ctttattgct cgatgaactg ctcgacccgc gcacgcttta ccagccgatt     120
gagccgggcg cttaccgcga cgaactgcgt cagtatctga tgcgggtgcc aacagaagac     180
gaagaacagc agcttgaagc cgtgcgccag ttcaaacagg cccagcattt gcgtatcgca     240
gccggggata tttccggggc attgccggtg atgaaagtca gtgaccattt aacctacctt     300
gccgaggcca ttctcgatgt cgtggtgcag catgcgtggg aacaaatggt cgtaaaatac     360
gggcagcccg cgcatcttca gcaccgtgag gggcgcggtt ttgccgtggt cggttacggg     420
aaactcggtg gctgggagct gggttatagc tcagatctgg atctggtctt cctgctcgat     480
tgcgcgccgg aggtgatgac ggacggcgaa cgcagcatcg acggacgtca gttttatctt     540
cggctggcgc agcgcattat gcacttattc agcacccgga catcgtcagg cattctttac     600
gaggttgatc cgcgtctgcg accttccggc gcatccggca tgctggtcag taccattgaa     660
gcgtttgcag attatcaggc caatgaagcc tggacgtggg agcatcaggc gctggttcgc     720
gcgcgcgtgg tttacgggga tccgcaactg acacagcaat taacgccac gcgtcgcgac      780 attctttgcc gccagcgcga tggcgacggc ctgcgtaagg aggtccgtga atgcgcgag      840 aaaatgtatg cccatctggg gagtaaaaaa gcccacgagt ttgatctgaa agccgatccg     900
ggtggcatca cggatattga attcattgca caatacctgg ttctgcgttt cgcgcatgat     960
gagccgaagc tgacgcgctg gtctgataac gtgcggattt ttgaactgat ggcacgatat    1020
gacatcatgc cggaagagga agcgcgccat ctgacgcagg cttatgtgac gctgcgcgat    1080
gaaattcatc atctggcgtt gcaggaacac agcgggaaag tggccgcgga cagctttgct    1140
actgagcgcg cgcagatccg tgccagctgg gcaaagtggc tcggctga                 1188

<210> SEQ ID NO 224
<211> LENGTH: 2188
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: glnE-delta-AR-2 with 500bp flank

<400> SEQUENCE: 224
cggtactgga acagaaatcg gcggatgcgc aggaaatttg ttatgacacg gcctgtctga     60
agtgcaagtt agtgcttact tcctggctgg caacctcagg ctggacgccg tttattgatg    120
ataaatctgc gaagaaactg gacgcttcct tcaaacgttt tgctgacatc atgctcggtc    180
gtaccgcagc ggatctgaaa gaagcctttg cgcagccact gacggaagaa ggttatcgcg    240
atcagctggc gcgcctgaaa cgccagatca ttaccttcca tttgcttgcc ggtgcttacc    300
ctgaaaaaga cgtcgatgcg tatattgccg gctgggtgga cctgcaacag gccatcgttc    360
agcagcaaca cgcctgggag gattcggccc gttctcacgc ggtgatgatg gatgctttct    420
ggttaaacgg gcaacctcgt taactgactg actagcctgg caaactgcc cgggcttttt     480 tttgcaagga atctgatttc atggcgctca aacagttaat ccgtctgtgt gccgcctcgc    540
cgatggtcgc gacacaactt gcacgtcatc ctttattgct cgatgaactg ctcgacccgc    600
gcacgcttta ccagccgatt gagccgggcg cttaccgcga cgaactgcgt cagtatctga    660
```

```
tgcgggtgcc aacagaagac gaagaacagc agcttgaagc cgtgcgccag ttcaaacagg      720
cccagcattt gcgtatcgca gccggggata tttccggggc attgccggtg atgaaagtca      780
gtgaccattt aacctacctt gccgaggcca ttctcgatgt cgtggtgcag catgcgtggg      840
aacaaatggt cgtaaaatac gggcagcccg cgcatcttca gcaccgtgag gggcgcggtt      900
ttgccgtggt cggttacggg aaactcggtg gctgggagct gggttatagc tcagatctgg      960
atctggtctt cctgctcgat tgcgcgccgg aggtgatgac ggacggcgaa cgcagcatcg     1020
acggacgtca gttttatctt cggctggcgc agcgcattat gcacttattc agcacccgga     1080
catcgtcagg cattctttac gaggttgatc gcgtctgcg acctccggc gcatccggca      1140 tgctggtcag taccattgaa gcgtttgcag attatcaggc caatgaagcc tggacgtggg     1200
agcatcaggc gctggttcgc gcgcgcgtgg tttacgggga tccgcaactg acacagcaat     1260
ttaacgccac gcgtcgcgac attctttgcc gccagcgcga tggcgacggc ctgcgtaagg     1320
aggtccgtga atgcgcgag aaaatgtatg cccatctggg gagtaaaaaa gcccacgagt      1380
ttgatctgaa agccgatccg ggtggcatca cggatattga attcattgca caatacctgg     1440
ttctgcgttt cgcgcatgat gagccgaagc tgacgcgctg gtctgataac gtgcggattt     1500
ttgaactgat ggcacgatat gacatcatgc cggaagagga agcgcgccat ctgacgcagg     1560
cttatgtgac gctgcgcgat gaaattcatc atctggcgtt gcaggaacac agcgggaaag     1620
tggccgcgga cagctttgct actgagcgcg cgcagatccg tgccagctgg gcaaagtggc     1680
tcggctgagg gtttttattc ggctaacagg cgcttgtgat attatccggc gcattgtatt     1740
tacccgattt gatttatctg ttttggagtc ttgggatgaa agtgactttg cctgattttc     1800
accgcgcagg tgtgctggtt gtcggtgacg taatgttaga ccgttactgg tatggcccga     1860
ccaatcgtat ttctccggaa gctccggtgc cggtggtgaa ggtcagtacc attgaagagc     1920
ggcctggcgg tgcagctaac gtggcgatga acatttcatc tctgggcgcc tcttcctgtc     1980
tgatcggcct gaccggcgta gacgacgctg cgcgtgccct cagtgagcgt ctggcagaag     2040
tgaaagttaa ctgcgatttc gtcgcactat ccacacatcc taccatcacc aaactgcgaa     2100
ttttgtcccg taaccagcaa ctgatccgcc tcgactttga ggaaggtttt gaaggcgttg     2160
atctcgagcc gatgctgacc aaaatag                                       2188
```

<210> SEQ ID NO 225
<211> LENGTH: 663
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: delta-nifL::Prm3.1

<400> SEQUENCE: 225

```
atgagcatca cggcgttatc agcatcattt cctgagggga atatcgccag ccgcttgtcg       60
ctgcaacatc cttcactgtt ttataccgtg gttgaacaat cttcggtggc gatttcgctg      120
accgatccgc aggcgcgcat ttgttatgcc aatccgcat tctgccgcca gacgggtttt      180
gcacttgaga cacttttggg cgagaaccac cgtctgctgg tacagtagcg cctctcaaaa      240
atagataaac ggctcatgta cgtgggccgt ttatttttc tacccataat cgggaaccgg      300
tgttataatg ccgcgccctc atattgtggg gatttcttaa tgacctatcc tgggtcctaa      360
agttgtagtt gacattagcg gagcactaac ccgtctctga agctctcggt gaacattgtt      420
```

```
gcgaggcagg atgcgagctg gttgtgtttt gacattaccg ataatgtgcc gcgtgaacgg    480
gtgcgttatg cccgcccgga agcggcgttt cccgtccgg ggaatggcat ggagctgcgc      540
cttatccaga cgctgatcgc ccatcatcgc ggttctttag atctctcggt ccgccctgat    600
ggcggcacct tgctgacgtt acgcctgccg gtacagcagg ttatcaccgg aggcttaaaa    660
tga                                                                  663
```

<210> SEQ ID NO 226
<211> LENGTH: 1663
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::Prm3.1 with 500bp flank

<400> SEQUENCE: 226

```
tgtttcgtct cgaggccggg caactgagcg gccccgttga aaccgacctg ggctggcatc     60
tgttgttgtg cgaacaaatt cgcctgccgc aacccttgcc gaaagccgaa gccttaacgc    120
gggtgcgtca gcaactgatt gcccggcaac agaaacatta tcagcgccag tggctgcaac    180
aactgatcaa cgcctgagcc tgttctcctt cttgttgatg cagacgggtt aatgcccgtt    240
ttgcacgaaa aatgcacata aattgcctgc gttgccttat aacagcgcag ggaaatcctg    300
cctccggcct tgtgccacac cgcgctttgc ctggtttgtg gtaaaaactg gcccgctttg    360
catcctgatg cttaaaacac cccgttcaga tcaacctttg ggcagataag cccgcgaaag    420
gcctgcaaat tgcacggtta ttccgggtga gtatatgtgt gatttgggtt ccggcattgc    480
gcaataaagg ggagaaagac atgagcatca cggcgttatc agcatcattt cctgagggga    540
atatcgccag ccgcttgtcg ctgcaacatc cttcactgtt ttataccgtg gttgaacaat    600
cttcggtggc gatttcgctg accgatccgc aggcgcgcat tgttatgcc aatccggcat      660 tctgccgcca gacgggtttt gcacttgaga cacttttggg cgagaaccac cgtctgctgg    720
tacagtagcg cctctcaaaa atagataaac ggctcatgta cgtgggccgt ttatttttc     780 tacccataat cgggaaccgg tgttataatg ccgcgccctc atattgtggg gatttcttaa    840
tgacctatcc tgggtcctaa agttgtagtt gacattagcg gagcactaac ccgtctctga    900
agctctcggt gaacattgtt gcgaggcagg atgcgagctg gttgtgtttt gacattaccg    960
ataatgtgcc gcgtgaacgg gtgcgttatg cccgcccgga agcggcgttt cccgtccgg     1020 ggaatggcat ggagctgcgc cttatccaga cgctgatcgc ccatcatcgc ggttctttag    1080
atctctcggt ccgccctgat ggcggcacct tgctgacgtt acgcctgccg gtacagcagg    1140
ttatcaccgg aggcttaaaa tgacccagtt acctaccgcg ggcccggtta tccggcgctt    1200
tgatatgtct gcccagttta cggcgcttta tcgcatcagc gtggcgctga gtcaggaaag    1260
caacaccggg cgcgcactgg cggcgatcct cgaagtgctt cacgatcatg catttatgca    1320
atacggcatg gtgtgtctgt ttgataaaga acgcaatgca ctctttgtgg aatccctgca    1380
tggcatcgac ggcgaaagga aaaaagagac ccgccatgtc cgttaccgca tgggggaagg    1440
cgtgatcggc gcggtgatga ccagcgtca ggcgctggtg ttaccgcgca tttcagacga     1500
tcagcgtttt ctcgaccgcc tgaatattta cgattacagc ctgccgttga ttggcgtgcc    1560 gatcccggt gcggataatc agccatcggg cgtgctggtg gcacagccga tggcgttgca     1620
cgaagaccgg ctgactgcca gtacgcggtt tttagaaatg gtc                      1663
```

<210> SEQ ID NO 227
<211> LENGTH: 1188
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: glnE-delta-AR-2

<400> SEQUENCE: 227

| | | | | | |
|---|---|---|---|---|---|
| atggcgctca | aacagttaat | ccgtctgtgt | gccgcctcgc | cgatggtcgc | gacacaactt | 60 |
| gcacgtcatc | ctttattgct | cgatgaactg | ctcgacccgc | gcacgcttta | ccagccgatt | 120 |
| gagccgggcg | cttaccgcga | cgaactgcgt | cagtatctga | tgcgggtgcc | aacagaagac | 180 |
| gaagaacagc | agcttgaagc | cgtgcgccag | ttcaaacagg | cccagcattt | gcgtatcgca | 240 |
| gccggggata | tttccggggc | attgccggtg | atgaaagtca | gtgaccattt | aacctacctt | 300 |
| gccgaggcca | ttctcgatgt | cgtggtgcag | catgcgtggg | aacaaatggt | cgtaaaatac | 360 |
| gggcagcccg | cgcatcttca | gcaccgtgag | gggcgcggtt | ttgccgtggt | cggttacggg | 420 |
| aaactcggtg | gctgggagct | gggttatagc | tcagatctgg | atctggtctt | cctgctcgat | 480 |
| tgcgcgccgg | aggtgatgac | ggacggcgaa | cgcagcatcg | acggacgtca | gttttatctt | 540 |
| cggctggcgc | agcgcattat | gcacttattc | agcacccgga | catcgtcagg | cattctttac | 600 |
| gaggttgatc | cgcgtctgcg | accttccggc | gcatccggca | tgctggtcag | taccattgaa | 660 |
| gcgtttgcag | attatcaggc | caatgaagcc | tggacgtggg | agcatcaggc | gctggttcgc | 720 |
| gcgcgcgtgg | tttacgggga | tccgcaactg | acacagcaat | taacgccac | cgtcgcgac | 780 |
| attctttgcc | gccagcgcga | tggcgacggc | ctgcgtaagg | aggtccgtga | atgcgcgag | 840 |
| aaaatgtatg | cccatctggg | gagtaaaaaa | gcccacgagt | ttgatctgaa | agccgatccg | 900 |
| ggtggcatca | cggatattga | attcattgca | caatacctgg | ttctgcgttt | cgcgcatgat | 960 |
| gagccgaagc | tgacgcgctg | gtctgataac | gtgcggattt | ttgaactgat | ggcacgatat | 1020 |
| gacatcatgc | cggaagagga | agcgcgccat | ctgacgcagg | cttatgtgac | gctgcgcgat | 1080 |
| gaaattcatc | atctggcgtt | gcaggaacac | agcgggaaag | tggccgcgga | cagctttgct | 1140 |
| actgagcgcg | cgcagatccg | tgccagctgg | gcaaagtggc | tcggctga | | 1188 |

<210> SEQ ID NO 228
<211> LENGTH: 2188
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: glnE-delta-AR-2 with 500bp flank

<400> SEQUENCE: 228

| | | | | | |
|---|---|---|---|---|---|
| cggtactgga | acagaaatcg | gcggatgcgc | aggaaatttg | ttatgacacg | gcctgtctga | 60 |
| agtgcaagtt | agtgcttact | tcctggctgg | caacctcagg | ctggacgccg | tttattgatg | 120 |
| ataaatctgc | gaagaaactg | gacgcttcct | tcaaacgttt | tgctgacatc | atgctcggtc | 180 |
| gtaccgcagc | ggatctgaaa | gaagcctttg | cgcagccact | gacggaagaa | ggttatcgcg | 240 |
| atcagctggc | gcgcctgaaa | cgccagatca | ttaccttcca | tttgcttgcc | ggtgcttacc | 300 |
| ctgaaaaaga | cgtcgatgcg | tatattgccg | gctgggtgga | cctgcaacag | gccatcgttc | 360 |

| | | |
|---|---|---|
| agcagcaaca cgcctgggag gattcggccc gttctcacgc ggtgatgatg gatgctttct | 420 | |
| ggttaaacgg gcaacctcgt taactgactg actagcctgg gcaaactgcc cgggcttttt | 480 | |
| tttgcaagga atctgatttc atggcgctca aacagttaat ccgtctgtgt gccgcctcgc | 540 | |
| cgatggtcgc gacacaactt gcacgtcatc ctttattgct cgatgaactg ctcgacccgc | 600 | |
| gcacgcttta ccagccgatt gagccgggcg cttaccgcga cgaactgcgt cagtatctga | 660 | |
| tgcgggtgcc aacagaagac gaagaacagc agcttgaagc cgtgcgccag ttcaaacagg | 720 | |
| cccagcattt gcgtatcgca gccggggata tttccgggc attgccggtg atgaaagtca | 780 | |
| gtgaccattt aacctacctt gccgaggcca ttctcgatgt cgtggtgcag catgcgtggg | 840 | |
| aacaaatggt cgtaaaatac gggcagcccg cgcatcttca gcaccgtgag gggcgcggtt | 900 | |
| ttgccgtggt cggttacggg aaactcggtg gctgggagct gggttatagc tcagatctgg | 960 | |
| atctggtctt cctgctcgat tgcgcgccgg aggtgatgac ggacggcgaa cgcagcatcg | 1020 | |
| acggacgtca gttttatctt cggctggcgc agcgcattat gcacttattc agcacccgga | 1080 | |
| catcgtcagg cattctttac gaggttgatc cgcgtctgcg accttccggc gcatccggca | 1140 | |
| tgctggtcag taccattgaa gcgtttgcag attatcaggc caatgaagcc tggacgtggg | 1200 | |
| agcatcaggc gctggttcgc gcgcgcgtgg tttacgggga tccgcaactg acacagcaat | 1260 | |
| ttaacgccac gcgtcgcgac attctttgcc gccagcgcga tggcgacggc ctgcgtaagg | 1320 | |
| aggtccgtga aatgcgcgag aaaatgtatg cccatctggg gagtaaaaaa gcccacgagt | 1380 | |
| tgatctgaa agccgatccg ggtggcatca cggatattga attcattgca caatacctgg | 1440 | |
| ttctgcgttt cgcgcatgat gagccgaagc tgacgcgctg gtctgataac gtgcggattt | 1500 | |
| tgaactgat ggcacgatat gacatcatgc cggaagagga agcgcgccat ctgacgcagg | 1560 | |
| cttatgtgac gctgcgcgat gaaattcatc atctggcgtt gcaggaacac agcgggaaag | 1620 | |
| tggccgcgga cagctttgct actgagcgcg cgcagatccg tgccagctgg gcaaagtggc | 1680 | |
| tcggctgagg gttttattc ggctaacagg cgcttgtgat attatccggc gcattgtatt | 1740 | |
| tacccgattt gatttatctg ttttggagtc ttgggatgaa agtgactttg cctgattttc | 1800 | |
| accgcgcagg tgtgctggtt gtcggtgacg taatgttaga ccgttactgg tatggcccga | 1860 | |
| ccaatcgtat ttctccggaa gctccggtgc cggtggtgaa ggtcagtacc attgaagagc | 1920 | |
| ggcctggcg tgcagctaac gtggcgatga acatttcatc tctgggcgcc tcttcctgtc | 1980 | |
| tgatcggcct gaccggcgta gacgacgctg cgcgtgccct cagtgagcgt ctggcagaag | 2040 | |
| tgaaagttaa ctgcgatttc gtcgcactat ccacacatcc taccatcacc aaactgcgaa | 2100 | |
| ttttgtcccg taaccagcaa ctgatccgcc tcgactttga ggaaggtttt gaaggcgttg | 2160 | |
| atctcgagcc gatgctgacc aaaataga | 2188 | |

<210> SEQ ID NO 229
<211> LENGTH: 613
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: delta-nifL::PinfC

<400> SEQUENCE: 229

| | | |
|---|---|---|
| atgagcatca cggcgttatc agctgaatat cactgactca caagctacct atgtcgaaga | 60 | |
| attaactaaa aaactgcaag atgcaggcat tcgcgttaaa gccgacttga gaaatgagaa | 120 | |

```
gattggcttt aaaattcgcg aacacacgct acgccgtgtt ccttatatgt tagtttgtgg    180
cgataaagag gtcgaagcag gcaaagttgc tgttcgtact cgtcgcggca aagacttagg    240
aagcatggat gttagcgaag tcgttgacaa actgctggcg gaaatccgca gcagaagtca    300
tcatcaactg gaggaataaa gtattaaagg cggaaaacga gttcaaccgg cgcgtcctaa    360
tcgcattaac aaagagattc gcgcgcaaga agttcgcctc accggcgtcg atggcgagca    420
gattggtatt gtcagtctga atgaagctct tgaaaaagct gaggaagcgg gcgtcgattt    480
agtagaaatc agtccgaatg ccgagccgcc agtttgtcga atctctttag atctctcggt    540 ccgcccctgat ggcggcacct tgctgacgtt acgcctgccg gtacagcagg ttatcaccgg    600
aggcttaaaa tga                                                      613

<210> SEQ ID NO 230
<211> LENGTH: 1613
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::PinfC with 500bp flank

<400> SEQUENCE: 230
tgtttcgtct cgaagccggg caactgagca gccccgttga aaccgaactg ggctggcatc     60
tgttgttgtg cgaacaaatt cgcctgccgc aacccttgcc gaaagccgag gccttaacgc    120
gggtgcgtca gcaactgatt gcccggcaac agaatcatta tcagcgccag tggctgcaac    180
aactgatcaa cgcctgagcc tgttctcctt cttgttggtg cagacgggtt aatgcccgtt    240
ttgcacgaaa aatgcacata aactgccttc gctgccttat aacagcgcat ggaaatcctg    300
cctcctgcct tgtgccacgc cgcgctttgc ctggtttgtg gtaaaaactg gcccgctttg    360
catcctgatg tttaaaacac cccgttcaga tcaacctttg ggcagataag cccgcgaaag    420
gcctgcaaat tgcacggtta ttccgggtga gtatatgtgt gatttgggtt ccggcattgc    480
gcaataaagg ggagaaagac atgagcatca cggcgttatc agctgaatat cactgactca    540
caagctacct atgtcgaaga attaactaaa aaactgcaag atgcaggcat tcgcgttaaa    600
gccgacttga gaatgagaa gattggcttt aaaattcgcg aacacacgct acgccgtgtt    660
ccttatatgt tagtttgtgg cgataaagag gtcgaagcag gcaaagttgc tgttcgtact    720
cgtcgcggca aagacttagg aagcatggat gttagcgaag tcgttgacaa actgctggcg    780
gaaatccgca gcagaagtca tcatcaactg gaggaataaa gtattaaagg cggaaaacga    840
gttcaaccgg cgcgtcctaa tcgcattaac aaagagattc gcgcgcaaga agttcgcctc    900
accggcgtcg atggcgagca gattggtatt gtcagtctga atgaagctct tgaaaaagct    960
gaggaagcgg gcgtcgattt agtagaaatc agtccgaatg ccgagccgcc agtttgtcga   1020
atctctttag atctctcggt ccgcccctgat ggcggcacct tgctgacgtt acgcctgccg   1080
gtacagcagg ttatcaccgg aggcttaaaa tgacccagtt acctaccgcg ggcccggtta   1140
tccggcgctt tgatatgtct gcccagtttta cggcgcttta tcgcatcagc gtggcgctga   1200
gtcaggaaag caataccgcg cgcgcactgg cggcgatcct cgaagtgctt cacgatcatg   1260
catttatgca atacggcatg gtgtgtctgt tcgataaaga acgcaatgca ctgtttgtgg   1320
aatccctgca tggcatcgac ggcgaaagga aaaagaaac cgccatgtc cgttaccgca    1380 tgggggaagg cgtgatcggc gcggtgatga gccagcgtca ggcgctggtg ttaccgcgca   1440
```

```
tttcagacga tcagcgtttt ctcgaccgcc tgaatattta cgattacagc ctgccgctga    1500
ttggtgtgcc gatccccggt gcggataatc agcctgcggg tgtgctggtg cacagccga     1560 tggcgttgca cgaagaccgg ctggctgcca gtacgcggtt tttagaaatg gtc           1613

<210> SEQ ID NO 231
<211> LENGTH: 426
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::Prm5

<400> SEQUENCE: 231
atgaccctga atatgatgat ggatgccggc ggacatcatc gcgacaaaca atattaatac     60
cggcaaccac accggcaatt tacgagactg cgcaggcatc ctttctcccg tcaatttctg    120
tcaaataaag taaagaggc agtctacttg aattaccccc ggctggttga gcgtttgttg    180
aaaaaaagta actgaaaaat ccgtagaata gcgccactct gatggttaat taacctattc    240
aattaagaat tatctggatg aatgtgccat taaatgcgca gcataatggt gcgttgtgcg    300
ggaaaactgc ttttttttga aagggttggt cagtagcgga aacaactcac ttcacacccc    360 gaaggggggaa gttgcctgac cctacgattc ccgctatttc attcactgac cggaggttca    420
aaatga                                                                426

<210> SEQ ID NO 232
<211> LENGTH: 1426
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::Prm5 with 500bp flank

<400> SEQUENCE: 232
accggatacg agagaaaagt gtctacatcg gttcggttga tattgaccgg cgcatccgcc     60
agcccgccca gtttctggtg gatctgtttg gcgattttgc gggtcttgcc ggtgtcggtg    120
ccgaaaaaaa taccaatatt tgccataaca cacgctcctg ttgaaaaaga gatcccgccg    180
ggaaatgcgg tgaacgtgtc tgatattgcg aagagtgtgc cagttttggt cgcgggcaaa    240
acctgcacca gtttggttat taatgcacca gtctggcgct ttttttcgcc gagtttctcc    300
tcgctaatgc ccgccaggcg cggctttggc gctgatagcg cgctgaatac cgatctggat    360
caaggttttg tcgggttatc agccaaaagg tgcactcttt gcatggttat acgtgcctga    420
catgttgtcc gggcgacaaa cggcctggtg gcacaaattg tcagaactac gacacgacta    480
actgaccgca ggagtgtgcg atgaccctga atatgatgat ggatgccggc ggacatcatc    540
gcgacaaaca atattaatac cggcaaccac accggcaatt tacgagactg cgcaggcatc    600
ctttctcccg tcaatttctg tcaaataaag taaagaggc agtctacttg aattaccccc    660
ggctggttga gcgtttgttg aaaaaaagta actgaaaaat ccgtagaata gcgccactct    720
gatggttaat taacctattc aattaagaat tatctggatg aatgtgccat taaatgcgca    780
gcataatggt gcgttgtgcg ggaaaactgc ttttttttga aagggttggt cagtagcgga    840
aacaactcac ttcacacccc gaaggggggaa gttgcctgac cctacgattc ccgctatttc    900
attcactgac cggaggttca aaatgaccca gcgaaccgag tcgggtaata ccgtctggcg    960
```

```
cttcgatttg tcccagcagt tcactgcgat gcagcgcata agcgtggtac tcagccgggc    1020
gaccgaggtc gatcagacgc tccagcaagt gctgtgcgta ttgcacaatg acgcttttt    1080 gcagcacggc atgatctgtc tgtacgacag ccagcaggcg attttgaata ttgaagcgtt    1140
gcaggaagcc gatcagcagt taatccccgg cagctcgcaa atccgctatc gtccgggcga    1200
agggctggtc gggacggtgc tttcgcaggg ccaatcatta gtgctggcgc gcgttgctga    1260
cgatcagcgc tttcttgacc ggctcgggtt gtatgattac aacctgccgt ttatcgccgt    1320
gccgctgata gggccagatg cgcagacttt cggtgtgctg acggcacaac ccatggcgcg    1380
ttacgaagag cgattacccg cctgcacccg ctttctggaa acggtc                  1426
```

<210> SEQ ID NO 233
<211> LENGTH: 461
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::Prm1

<400> SEQUENCE: 233

```
atgaccctga atatgatgat ggatgccggc cgtcctgtaa taataaccgg acaattcgga     60
ctgattaaaa aagcgccctt gtggcgcttt ttttatattc ccgcctccat ttaaaataaa    120
aaatccaatc ggatttcact atttaaactg ccattatct aagatgaatc cgatggaagc    180
tcgctgtttt aacacgcgtt ttttaacctt ttattgaaag tcggtgcttc tttgagcgaa    240
cgatcaaatt taagtggatt cccatcaaaa aaatattctc aacctaaaaa agtttgtgta    300
atacttgtaa cgctacatgg agattaactc aatctagagg gtattaataa tgaatcgtac    360
taaactggta ctgggcgcaa ctcacttcac accccgaagg gggaagttgc ctgaccctac    420
gattcccgct atttcattca ctgaccggag gttcaaaatg a                       461
```

<210> SEQ ID NO 234
<211> LENGTH: 1461
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::Prm1 with 500bp flank

<400> SEQUENCE: 234

```
accggatacg agagaaaagt gtctacatcg gttcggttga tattgaccgg cgcatccgcc     60
agcccgccca gttctggtg gatctgtttg gcgattttgc gggtcttgcc ggtgtcggtg    120
ccgaaaaaaa taccaatatt tgccataaca cacgctcctg ttgaaaaaga tcccgccg    180 ggaaatgcgg tgaacgtgtc tgatattgcg aagagtgtgc cagttttggt cgcgggcaaa    240
acctgcacca gtttggttat taatgcacca gtctggcgct ttttttcgcc gagtttctcc    300
tcgctaatgc ccgccaggcg cggctttggc gctgatagcg cgctgaatac cgatctggat    360
caaggttttg tcgggttatc agccaaaagg tgcactcttt gcatggttat acgtgcctga    420
catgttgtcc gggcgacaaa cggcctggtg gcacaaattg tcagaactac gacacgacta    480
actgaccgca ggagtgtgcg atgaccctga atatgatgat ggatgccggc cgtcctgtaa    540
taataaccgg acaattcgga ctgattaaaa aagcgccctt gtggcgcttt ttttatattc    600
```

```
ccgcctccat ttaaaataaa aaatccaatc ggatttcact atttaaactg gccattatct      660
aagatgaatc cgatggaagc tcgctgtttt aacacgcgtt ttttaacctt ttattgaaag      720
tcggtgcttc tttgagcgaa cgatcaaatt taagtggatt cccatcaaaa aaatattctc      780
aacctaaaaa agtttgtgta atacttgtaa cgctacatgg agattaactc aatctagagg      840
gtattaataa tgaatcgtac taaactggta ctgggcgcaa ctcacttcac accccgaagg      900
gggaagttgc ctgaccctac gattcccgct atttcattca ctgaccggag gttcaaaatg      960
acccagcgaa ccgagtcggg taataccgtc tggcgcttcg atttgtccca gcagttcact     1020
gcgatgcagc gcataagcgt ggtactcagc cgggcgaccg aggtcgatca gacgctccag     1080
caagtgctgt gcgtattgca caatgacgcc ttttgcagc acggcatgat ctgtctgtac      1140
gacagccagc aggcgatttt gaatattgaa gcgttgcagg aagccgatca gcagttaatc     1200
cccggcagct cgcaaatccg ctatcgtccg ggcgaagggc tggtcgggac ggtgctttcg     1260
cagggccaat cattagtgct ggcgcgcgtt gctgacgatc agcgctttct tgaccggctc     1320
gggttgtatg attacaacct gccgtttatc gccgtgccgc tgatagggcc agatgcgcag     1380
actttcggtg tgctgacggc acaacccatg gcgcgttacg aagagcgatt acccgcctgc     1440
acccgctttc tggaaacggt c                                              1461

<210> SEQ ID NO 235
<211> LENGTH: 461
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::Prm1

<400> SEQUENCE: 235
atgaccctga atatgatgat ggatgccggc cgtcctgtaa taataaccgg acaattcgga       60
ctgattaaaa aagcgccctt gtggcgcttt ttttatattc ccgcctccat ttaaaataaa      120
aaatccaatc ggatttcact atttaaactg gccattatct aagatgaatc cgatggaagc      180
tcgctgtttt aacacgcgtt ttttaacctt ttattgaaag tcggtgcttc tttgagcgaa      240
cgatcaaatt taagtggatt cccatcaaaa aaatattctc aacctaaaaa agtttgtgta      300
atacttgtaa cgctacatgg agattaactc aatctagagg gtattaataa tgaatcgtac      360
taaactggta ctgggcgcaa ctcacttcac accccgaagg gggaagttgc ctgaccctac      420
gattcccgct atttcattca ctgaccggag gttcaaaatg a                         461

<210> SEQ ID NO 236
<211> LENGTH: 1461
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::Prm1 with 500bp flank

<400> SEQUENCE: 236
accggatacg agagaaaagt gtctacatcg gttcggttga tattgaccgg cgcatccgcc       60
agcccgccca gtttctggtg gatctgtttg gcgattttgc gggtcttgcc ggtgtcggtg      120
ccgaaaaaaa taccaatatt tgccataaca cacgctcctg ttgaaaaaga gatcccgccg      180
ggaaatgcgg tgaacgtgtc tgatattgcg aagagtgtgc cagttttggt cgcgggcaaa      240
```

```
acctgcacca gtttggttat taatgcacca gtctggcgct ttttttcgcc gagtttctcc      300
tcgctaatgc ccgccaggcg cggctttggc gctgatagcg cgctgaatac cgatctggat      360
caaggttttg tcgggttatc agccaaaagg tgcactcttt gcatggttat acgtgcctga      420
catgttgtcc gggcgacaaa cggcctggtg gcacaaattg tcagaactac gacacgacta      480
actgaccgca ggagtgtgcg atgaccctga atatgatgat ggatgccggc cgtcctgtaa      540
taataaccgg acaattcgga ctgattaaaa agcgccctt gtggcgcttt ttttatattc       600
ccgcctccat ttaaaataaa aaatccaatc ggatttcact atttaaactg gccattatct      660
aagatgaatc cgatggaagc tcgctgtttt aacacgcgtt ttttaacctt ttattgaaag      720
tcggtgcttc tttgagcgaa cgatcaaatt taagtggatt cccatcaaaa aaatattctc      780
aacctaaaaa agtttgtgta atacttgtaa cgctacatgg agattaactc aatctagagg      840
gtattaataa tgaatcgtac taaactggta ctgggcgcaa ctcacttcac accccgaagg      900
gggaagttgc ctgaccctac gattcccgct atttcattca ctgaccggag gttcaaaatg      960
acccagcgaa ccgagtcggg taataccgtc tggcgcttcg atttgtccca gcagttcact     1020
gcgatgcagc gcataagcgt ggtactcagc cgggcgaccg aggtcgatca gacgctccag     1080
caagtgctgt gcgtattgca caatgacgcc ttttgcagc acggcatgat ctgtctgtac      1140
gacagccagc aggcgatttt gaatattgaa gcgttcagg aagccgatca gcagttaatc      1200
cccggcagct cgcaaatccg ctatcgtccg ggcgaagggc tggtcgggac ggtgctttcg     1260
cagggccaat cattagtgct ggcgcgcgtt gctgacgatc agcgctttct tgaccggctc     1320
gggttgtatg attacaacct gccgtttatc gccgtgccgc tgatagggcc agatgcgcag     1380
actttcggtg tgctgacggc acaacccatg gcgcgttacg aagagcgatt acccgcctgc     1440
acccgctttc tggaaacggt c                                               1461
```

<210> SEQ ID NO 237
<211> LENGTH: 1188
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: glnE-delta-AR-2

<400> SEQUENCE: 237

```
atggcactga acacctcat ttccctgtgt gccgcgtcgc cgatggttgc cagtcagctg       60
gcgcgctacc cgatcctgct tgatgaattg ctcgacccga atacgctcta tcaaccgacg      120
gcgatgaatg cctatcgcga tgagctgcgc caatacctgc tgcgcgtgcc ggaagatgat      180
gaagagcaac agcttgaggc gctgcggcag tttaagcagg cgcagttgct cgcgcgtggcg    240 gcggcggata ttgccggtac gttgccagta atgaaagtga gcgatcactt aacctggctg     300
gcggaagcga ttattgatgc ggtggtgcag caagcctggg gcagatggt ggcgcgttat     360 ggccagccaa cgcatctgca cgatcgcgaa gggcgcggtt ttgcggtggt cggttatggc      420
aagctgggcg gctgggagct gggttacagc tccgatctgg atctggtatt cctgcacgac      480
tgcccgatgg atgtgatgac cgatggcgag cgtgaaatcg atggtcgcca gttctatttg      540
cgtctcgcgc agcgcgtgat gcacctgttt agcacgcgca cgtcgtccgg catcctttat      600
gaagttgatc gcgtctctcg tccatctggc gctgcgggga tgctggtcac tactacggaa      660
tcgttcgccg attaccagca aaacgaagcc tggacgtggg aacatcaggc gctggcccgt      720
```

```
gcgcgcgtgg tgtacggcga tccgcaactg accgccgaat ttgacgccat tcgccgcgat    780
attctgatga cgcctcgcga cggcgcaacg ctgcaaaccg acgtgcgaga atgcgcgag     840 aaaatgcgtg cccatcttgg caacaagcat aaagaccgct tcgatctgaa agccgatgaa    900
ggcggtatca ccgacatcga gtttatcgcc caatatctgg tgctgcgctt tgcccatgac    960
aagccgaaac tgacgcgctg gtcggataat gtgcgcattc tcgaagggct ggcgcaaaac   1020
ggcatcatgg aggagcagga agcgcaggca ttgacgctgg cgtacaccac attgcgtgat   1080
gagctgcacc acctggcgct gcaagagttg ccgggacatg tggcgctctc ctgttttgtc   1140
gccgagcgtg cgcttattaa aaccagctgg gacaagtggc tggtggaa                1188
```

<210> SEQ ID NO 238
<211> LENGTH: 2206
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: glnE-delta-AR-2 with 500bp flank

<400> SEQUENCE: 238

```
gcgcaaagcg agtgctcact tacgtgatct gttgacacaa tctgaagcga ccataacttc     60
tgccgtttca gcgaatacgg cggtgtggag cgcacaatca gccctggcga agctggtgct    120
caccgagtgg ctagtgacgc agggctggcg aaccttcctt gatgaaaaag cgcaggccaa    180
attcgccgac tcctttaaac gctttgctga catccatctg tcacgcagcg ccgccgagct    240 gaaaaagcc tttgcccaac cgctgggcga cagctatcgc gaccagttgc cgcgcctggc     300
gcgtgatatc gactgcgcgt tactgctggc cgggcattac gatcgcgcgc gcgccgtgga    360
atggctggaa aactggcagg gcttcagca cgccattgaa acgcgccaga gagtcgaaat     420
cgaacatttc cgtaataccg cgattaccca ggagccgttc tggttgcaca gcggaaaacg    480
ttaacgaaag atatttcgc atggcactga acacctcat ttccctgtgt gccgcgtcgc      540
cgatggttgc cagtcagctg gcgcgctacc cgatcctgct tgatgaattg ctcgacccga    600
atacgctcta tcaaccgacg gcgatgaatg cctatcgcga tgagctgcgc caatacctgc    660
tgcgcgtgcc ggaagatgat gaagagcaac agcttgaggc gctgcggcag tttaagcagg    720
cgcagttgct gcgcgtggcg gcggcggata ttgccggtac gttgccagta atgaaagtga    780
gcgatcactt aacctggctg gcggaagcga ttattgatgc ggtggtgcag caagcctggg    840
ggcagatggt ggcgcgttat ggccagccaa cgcatctgca cgatcgcgaa gggcgcggtt    900
ttgcggtggt cggttatggc aagctgggcg gctgggagct gggttacagc tccgatctgg    960
atctggtatt cctgcacgac tgcccgatgg atgtgatgac cgatggcgag cgtgaaatcg   1020
atggtcgcca gttctatttg cgtctccgcg agcgcgtgat gcacctgttt agcacgcgca   1080
cgtcgtccgg catcctttat gaagttgatg cgcgtctgcg tccatctggc gctgcgggga   1140
tgctggtcac tactacggaa tcgttcgccg attaccagca aaacgaagcc tggacgtggg   1200
aacatcaggc gctggcccgt gcgcgcgtgg tgtacggcga tccgcaactg accgccgaat   1260
ttgacgccat tcgccgcgat attctgatga cgcctcgcga cggcgcaacg ctgcaaaccg   1320
acgtgcgaga atgcgcgag aaaatgcgtg cccatcttgg caacaagcat aaagaccgct    1380
tcgatctgaa agccgatgaa ggcggtatca ccgacatcga gtttatcgcc caatatctgg   1440
tgctgcgctt tgcccatgac aagccgaaac tgacgcgctg gtcggataat gtgcgcattc   1500
```

```
tcgaagggct ggcgcaaaac ggcatcatgg aggagcagga agcgcaggca ttgacgctgg    1560
cgtacaccac attgcgtgat gagctgcacc acctggcgct gcaagagttg ccgggacatg    1620
tggcgctctc ctgttttgtc gccgagcgtg cgcttattaa aaccagctgg gacaagtggc    1680
tggtggaacc gtgcgccccg gcgtaagtgt ggtatcatcg cgcgcaaatt ttgtatctct    1740
caggagacag gaatgaaagt gacgctgcca gagtttaagc aagccggtgt aatggtggtg    1800
ggtgatgtga tgctggatcg ttactggtat ggcccaacca gccgtatctc tccggaagcg    1860
ccagtcccgg ttgttaaagt cgataccatt gaagagcgtc ctggcggcgc ggcaaacgtg    1920
gcgatgaata tcgcctcact gggcgccacg gcgcgtctgg ttggcctgac tggcattgac    1980
gatgcggcgc gcgcgctgag caaagcgctg gccgatgtta acgttaaatg tgacttcgtt    2040
tctgttccga cgcatcccac catcactaag ctgcgcgtgc tgtcgcgtaa ccagcagctg    2100
attcgcctgg actttgaaga gggttttgaa ggagtcgatc cgcaaccgat gcatgaacgc    2160
atcagccagg cgcttggtaa tattggcgcg ctggtgctgt cggatt          2206
```

<210> SEQ ID NO 239
<211> LENGTH: 1563
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: glnE-delta-AR-1

<400> SEQUENCE: 239

```
atgtttaacg atctgattgg cgatgatgaa acggattcgc cggaagatgc gctttctgag     60
agctggcgcg aattgtggca ggatgcgttg caggaggagg attccacgcc cgtgctggcg    120
catctctcag aggacgatcg ccgccgcgtg gtggcgctga ttgccgattt cgcaaagag    180 ttggataaac gcaccattgg cccgcgaggg cggcaggtac tcgatcactt aatgccgcat    240
ctgctcagcg atgtatgctc gcgcgacgat gcgccagtac cgctgtcacg cctgacgccg    300
ctgctcaccg gaattattac ccgcaccact taccttgagc tgctaagtga atttcccggc    360 gcactgaaaac acctcatttc cctgtgtgcc gcgtcgccga tggttgccag tcagctggcg    420
cgctacccga tcctgcttga tgaattgctc gacccgaata cgctctatca accgacggcg    480
atgaatgcct atcgcgatga gctgcgccaa tacctgctgc gcgtgccgga agatgatgaa    540
gagcaacagc ttgaggcgct gcggcagttt aagcaggcgc agttgctgcg cgtgcggcg    600 gcggatattg ccggtacgtt gccagtaatg aaagtgagcg atcacttaac ctggctggcg    660
gaagcgatta ttgatgcggt ggtgcagcaa gcctgggggc agatggtggc gcgttatggc    720
cagccaacgc atctgcacga tcgcgaaggg cgcggttttg cggtggtcgg ttatggcaag    780
ctgggcggct gggagctggg ttacagctcc gatctggatc tggtattcct gcacgactgc    840
ccgatggatg tgatgaccga tggcgagcgt gaaatcgatg tcgccagttt ctatttgcgt    900
ctcgcgcagc gcgtgatgca cctgtttagc acgcgcacgt cgtccggcat cctttatgaa    960
gttgatgcgc gtctgcgtcc atctggcgct gcggggatgc tggtcactac tacggaatcg   1020
ttcgccgatt accagcaaaa cgaagcctgg acgtgggaac atcaggcgct ggcccgtgcg   1080
cgcgtggtgt acggcgatcc gcaactgacc gccgaatttg acgccattcg ccgcgatatt   1140
ctgatgacgc tcgcgacgg cgcaacgctg caaaccgacg tgcgagaaat gcgcgagaaa   1200
atgcgtgccc atcttggcaa caagcataaa gaccgcttcg atctgaaagc cgatgaaggc   1260
```

```
ggtatcaccg acatcgagtt tatcgcccaa tatctggtgc tgcgctttgc ccatgacaag      1320
ccgaaactga cgcgctggtc ggataatgtg cgcattctcg aagggctggc gcaaaacggc      1380
atcatggagg agcaggaagc gcaggcattg acgctggcgt acaccacatt gcgtgatgag      1440
ctgcaccacc tggcgctgca agagttgccg ggacatgtgg cgctctcctg ttttgtcgcc      1500
gagcgtgcgc ttattaaaac cagctgggac aagtggctgg tggaaccgtg cgccccggcg      1560
taa                                                                   1563
```

<210> SEQ ID NO 240
<211> LENGTH: 461
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::Prm1

<400> SEQUENCE: 240

```
atgaccctga atatgatgat ggatgccggc cgtcctgtaa taataaccgg acaattcgga       60
ctgattaaaa aagcgcccett gtggcgcttt ttttatattc ccgcctccat ttaaaataaa      120
aaatccaatc ggatttcact atttaaactg gccattatct aagatgaatc cgatggaagc      180
tcgctgtttt aacacgcgtt ttttaacctt ttattgaaag tcggtgcttc tttgagcgaa      240
cgatcaaatt taagtggatt cccatcaaaa aaatattctc aacctaaaaa agtttgtgta      300
atacttgtaa cgctacatgg agattaactc aatctagagg gtattaataa tgaatcgtac      360
taaactggta ctgggcgcaa ctcacttcac accccgaagg gggaagttgc ctgaccctac      420
gattcccgct atttcattca ctgaccggag gttcaaaatg a                          461
```

<210> SEQ ID NO 241
<211> LENGTH: 1461
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::Prm1 with 500bp flank

<400> SEQUENCE: 241

```
accggatacg agagaaaagt gtctacatcg gttcggttga tattgaccgg cgcatccgcc       60
agcccgccca gttctggtg gatctgtttg gcgattttgc gggtcttgcc ggtgtcggtg       120
ccgaaaaaaa taccaatatt tgccataaca cacgctcctg ttgaaaaaga tcccgccg       180 ggaaatgcgg tgaacgtgtc tgatattgcg aagagtgtgc cagttttggt cgcgggcaaa      240
acctgcacca gtttggttat taatgcacca gtctggcgct ttttttcgcc gagtttctcc      300
tcgctaatgc ccgccaggcg cggctttggc gctgatagcg cgctgaatac cgatctggat      360
caaggttttg tcgggttatc agccaaaagg tgcactcttt gcatggttat acgtgcctga      420
catgttgtcc gggcgacaaa cggcctggtg gcacaaattg tcagaactac gacacgacta      480
actgaccgca ggagtgtgcg atgaccctga atatgatgat ggatgccggc cgtcctgtaa      540
taataaccgg acaattcgga ctgattaaaa aagcgccctt gtggcgcttt ttttatattc      600
ccgcctccat ttaaaataaa aaatccaatc ggatttcact atttaaactg gccattatct      660
aagatgaatc cgatggaagc tcgctgtttt aacacgcgtt ttttaacctt ttattgaaag      720
```

```
tcggtgcttc tttgagcgaa cgatcaaatt taagtggatt cccatcaaaa aaatattctc      780
aacctaaaaa agtttgtgta atacttgtaa cgctacatgg agattaactc aatctagagg      840
gtattaataa tgaatcgtac taaactggta ctgggcgcaa ctcacttcac accccgaagg      900
gggaagttgc ctgaccctac gattcccgct atttcattca ctgaccggag gttcaaaatg      960
acccagcgaa ccgagtcggg taataccgtc tggcgcttcg atttgtccca gcagttcact     1020
gcgatgcagc gcataagcgt ggtactcagc cgggcgaccg aggtcgatca gacgctccag     1080
caagtgctgt gcgtattgca caatgacgcc ttttgcagc acggcatgat ctgtctgtac      1140
gacagccagc aggcgatttt gaatattgaa gcgttgcagg aagccgatca gcagttaatc     1200
cccggcagct cgcaaatccg ctatcgtccg ggcgaagggc tggtcgggac ggtgctttcg     1260
cagggccaat cattagtgct ggcgcgcgtt gctgacgatc agcgcttcct tgaccggctc     1320
gggttgtatg attacaacct gccgtttatc gccgtgccgc tgatagggcc agatgcgcag     1380
actttcggtg tgctgacggc acaacccatg gcgcgttacg aagagcgatt acccgcctgc     1440
acccgctttc tggaaacggt c                                               1461
```

<210> SEQ ID NO 242
<211> LENGTH: 2563
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: glnE-delta-AR-1 with 500bp flank

<400> SEQUENCE: 242

```
gcgcaaagcg agtgctcact tacgtgatct gttgacacaa tctgaagcga ccataacttc       60
tgccgtttca gcgaatacgg cggtgtggag cgcacaatca gccctggcga agctggtgct      120
caccgagtgg ctagtgacgc agggctggcg aaccttcctt gatgaaaaag cgcaggccaa      180
attcgccgac tcctttaaac gctttgctga catccatctg tcacgcagcg ccgccgagct      240
gaaaaaagcc tttgcccaac cgctgggcga cagctatcgc gaccagttgc gcgcctggc      300 gcgtgatatc gactgcgcgt tactgctggc cgggcattac gatcgcgcgc gcgccgtgga      360
atggctggaa aactggcagg gcttcagca cgccattgaa acgcgccaga gagtcgaaat      420
cgaacatttc cgtaataccg cgattaccca ggagccgttc tggttgcaca gcggaaaacg      480
ttaacgaaag gatatttcgc atgtttaacg atctgattgg cgatgatgaa acggattcgc      540
cggaagatgc gctttctgag agctggcgcg aattgtggca ggatgcgttg caggaggagg      600
attccacgcc cgtgctggcg catctctcag aggacgatcg ccgccgcgtg gtggcgctga      660
ttgccgattt tcgcaaagag ttggataaac gcaccattgg cccgcgaggg cggcaggtac      720
tcgatcactt aatgccgcat ctgctcagcg atgtatgctc gcgcgacgat gcgccagtac      780
cgctgtcacg cctgacgccg ctgctcaccg gaattattac ccgcaccact taccttgagc      840
tgctaagtga atttcccggc gcactgaaac acctcatttc cctgtgtgcc gcgtcgccga      900
tggttgccag tcagctggcg cgctacccga tcctgcttga tgaattgctc gacccgaata      960
cgctctatca accgacggcg atgaatgcct atcgcgatga gctgcgccaa tacctgctgc     1020
gcgtgccgga agatgatgaa gagcaacagc ttgaggcgct gcggcagttt aagcaggcgc     1080
agttgctgcg cgtggcggcg gcggatattg ccggtacgtt gccagtaatg aaagtgagcg     1140
atcacttaac ctggctggcg gaagcgatta ttgatgcggt ggtgcagcaa gcctggggc     1200
```

-continued

```
agatggtggc gcgttatggc cagccaacgc atctgcacga tcgcgaaggg cgcggttttg      1260
cggtggtcgg ttatggcaag ctgggcggct gggagctggg ttacagctcc gatctggatc      1320
tggtattcct gcacgactgc ccgatggatg tgatgaccga tggcgagcgt gaaatcgatg      1380
gtcgccagtt ctatttgcgt ctcgcgcagc gcgtgatgca cctgtttagc acgcgcacgt      1440
cgtccggcat cctttatgaa gttgatgcgc gtctgcgtcc atctggcgct gcggggatgc      1500
tggtcactac tacggaatcg ttcgccgatt accagcaaaa cgaagcctgg acgtgggaac      1560
atcaggcgct ggcccgtgcg cgcgtggtgt acggcgatcc gcaactgacc gccgaatttg      1620
acgccattcg ccgcgatatt ctgatgacgc tcgcgacgg cgcaacgctg caaaccgacg       1680
tgcgagaaat gcgcgagaaa atgcgtgccc atcttggcaa caagcataaa gaccgcttcg      1740
atctgaaagc cgatgaaggc ggtatccacg acatcgagtt tatcgcccaa tatctggtgc      1800
tgcgctttgc ccatgacaag ccgaaactga cgcgctggtc ggataatgtg cgcattctcg      1860
aagggctggc gcaaaacggc atcatggagg gcaggaagc gcaggcattg acgctggcgt       1920
acaccacatt gcgtgatgag ctgcaccacc tggcgctgca agagttgccg ggacatgtgg      1980
cgctctcctg ttttgtcgcc gagcgtgcgc ttattaaaac cagctgggac aagtggctgg      2040
tggaaccgtg cgccccggcg taagtgtggt atcatcgcgc gcaaattttg tatctctcag      2100
gagacaggaa tgaaagtgac gctgccagag tttaagcaag ccggtgtaat ggtggtgggt      2160
gatgtgatgc tggatcgtta ctggtatggc ccaaccagcc gtatctctcc ggaagcgcca      2220
gtcccggttg ttaaagtcga taccattgaa gagcgtcctg gcggcgcggc aaacgtggcg      2280
atgaatatcg cctcactggg cgccacggcg cgtctggttg gcctgactgg cattgacgat      2340
gcggcgcgcg cgctgagcaa agcgctggcc gatgttaacg ttaaatgtga cttcgtttct      2400
gttccgacgc atcccaccat cactaagctg cgcgtgctgt cgcgtaacca gcagctgatt      2460
cgcctggact ttgaagaggg ttttgaagga gtcgatccgc aaccgatgca tgaacgcatc      2520
agccaggcgc ttggtaatat tggcgcgctg gtgctgtcgg att                       2563
```

<210> SEQ ID NO 243
<211> LENGTH: 1563
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: glnE-delta-AR-1

<400> SEQUENCE: 243

```
atgtttaacg atctgattgg cgatgatgaa acggattcgc cggaagatgc gctttctgag       60
agctggcgca aattgtggca ggatgcgttg caggaggagg attccacgcc cgtgctggcg      120
catctctcag aggacgatcg ccgccgcgtg gtggcgctga ttgccgattt cgcaaagag      180 ttggataaac gcaccattgg cccgcgaggg cggcaggtac tcgatcactt aatgccgcat      240
ctgctcagcg atgtatgctc gcgcgacgat gcgccagtac cgctgtcacg cctgacgccg      300
ctgctcaccg gaattattac ccgcaccact taccttgagc tgctaagtga atttcccggc      360
gcactgaaac acctcatttc cctgtgtgcc cgtcgccga tggttgccag tcagctggcg      420
cgctacccga tcctgcttga tgaattgctc gacccgaata cgctctatca accgacggcg      480
atgaatgcct atcgcgatga gctgcgccaa tacctgctgc gcgtgccgga agatgatgaa      540
gagcaacagc ttgaggcgct gcggcagttt aagcaggcgc agttgctgcg cgtggcggcg      600
```

-continued

```
gcggatattg ccggtacgtt gccagtaatg aaagtgagcg atcacttaac ctggctggcg      660
gaagcgatta ttgatgcggt ggtgcagcaa gcctggggc agatggtggc gcgttatggc       720
cagccaacgc atctgcacga tcgcgaaggg cgcggttttg cggtggtcgg ttatggcaag      780
ctgggcggct gggagctggg ttacagctcc gatctggatc tggtattcct gcacgactgc      840
ccgatggatg tgatgaccga tggcgagcgt gaaatcgatg gtcgccagtt ctatttgcgt      900
ctcgcgcagc gcgtgatgca cctgtttagc acgcgcacgt cgtccggcat cctttatgaa      960
gttgatgcgc gtctgcgtcc atctggcgct gcggggatgc tggtcactac tacggaatcg     1020
ttcgccgatt accagcaaaa cgaagcctgg acgtgggaac atcaggcgct ggcccgtgcg     1080
cgcgtggtgt acggcgatcc gcaactgacc gccgaatttg acgccattcg ccgcgatatt     1140
ctgatgacgc ctcgcgacgg cgcaacgctg caaaccgacg tgcgagaaat gcgcgagaaa     1200
atgcgtgccc atcttggcaa caagcataaa gaccgcttcg atctgaaagc cgatgaaggc     1260
ggtatcaccg acatcgagtt tatcgcccaa tatctggtgc tgcgctttgc ccatgacaag     1320
ccgaaactga cgcgctggtc ggataatgtg cgcattctcg aagggctggc gcaaaacggc     1380
atcatggagg agcaggaagc gcaggcattg acgctggcgt acaccacatt gcgtgatgag     1440
ctgcaccacc tggcgctgca agagttgccg ggacatgtgg cgctctcctg ttttgtcgcc     1500
gagcgtgcgc ttattaaaac cagctgggac aagtggctgg tggaaccgtg cgccccggcg     1560
taa                                                                   1563
```

<210> SEQ ID NO 244
<211> LENGTH: 2563
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: glnE-delta-AR-1 with 500bp flank

<400> SEQUENCE: 244

```
gcgcaaagcg agtgctcact tacgtgatct gttgacacaa tctgaagcga ccataacttc       60
tgccgtttca gcgaatacgg cggtgtggag cgcacaatca gccctggcga agctggtgct      120
caccgagtgg ctagtgacgc agggctggcg aaccttcctt gatgaaaaag cgcaggccaa      180
attcgccgac tcctttaaac gctttgctga catccatctg tcacgcagcg ccgccgagct      240
gaaaaaagcc tttgcccaac cgctgggcga cagctatcgc gaccagttgc gcgcgcctggc     300 gcgtgatatc gactgcgcgt tactgctggc cgggcattac gatcgcgcgc gcgccgtgga      360
atggctggaa aactggcagg ggcttcagca cgccattgaa acgcgccaga gagtcgaaat      420
cgaacatttc cgtaataccg cgattaccca ggagccgttc tggttgcaca gcggaaaacg      480
ttaacgaaag gatatttcgc atgtttaacg atctgattgg cgatgatgaa acggattcgc      540
cggaagatgc gctttctgag agctggcgcg aattgtggca ggatgcgttg caggaggagg      600
attccacgcc cgtgctggcg catctctcag aggacgatcg ccgccgcgtg gtggcgctga      660
ttgccgattt tcgcaaagag ttggataaac gcaccattgg cccgcgaggg cggcaggtac      720
tcgatcactt aatgccgcat ctgctcagcg atgtatgctc gcgcgacgat gcgccagtac      780
cgctgtcacg cctgacgccg ctgctcaccg gaattattac ccgcaccact taccttgagc      840
tgctaagtga atttcccggc gcactgaaac acctcatttc cctgtgtgcc gcgtcgccga      900
tggttgccag tcagctggcg cgctaccgga tcctgcttga tgaattgctc gacccgaata      960
```

```
cgctctatca accgacggcg atgaatgcct atcgcgatga gctgcgccaa tacctgctgc   1020
gcgtgccgga agatgatgaa gagcaacagc ttgaggcgct gcggcagttt aagcaggcgc   1080
agttgctgcg cgtggcggcg gcggatattg ccggtacgtt gccagtaatg aaagtgagcg   1140
atcacttaac ctggctggcg gaagcgatta ttgatgcggt ggtgcagcaa gcctggggc    1200 agatggtggc gcgttatggc cagccaacgc atctgcacga tcgcgaaggg cgcggttttg   1260
cggtggtcgg ttatggcaag ctgggcggct gggagctggg ttacagctcc gatctggatc   1320
tggtattcct gcacgactgc ccgatggatg tgatgaccga tggcgagcgt gaaatcgatg   1380
gtcgccagtt ctatttgcgt ctcgcgcagc gcgtgatgca cctgtttagc acgcgcacgt   1440
cgtccggcat cctttatgaa gttgatgcgc gtctgcgtcc atctggcgct gcggggatgc   1500
tggtcactac tacggaatcg ttcgccgatt accagcaaaa cgaagcctgg acgtgggaac   1560
atcaggcgct ggcccgtgcg cgcgtggtgt acggcgatcc gcaactgacc gccgaatttg   1620
acgccattcg ccgcgatatt ctgatgacgc ctcgcgacgg cgcaacgctg caaaccgacg   1680
tgcgagaaat gcgcgagaaa atgcgtgccc atcttggcaa caagcataaa gaccgcttcg   1740
atctgaaagc cgatgaaggc ggtatcaccg acatcgagtt tatcgcccaa tatctggtgc   1800
tgcgctttgc ccatgacaag ccgaaactga cgcgctggtc ggataatgtg cgcattctcg   1860
aagggctggc gcaaaacggc atcatggagg agcaggaagc gcaggcattg acgctggcgt   1920
acaccacatt gcgtgatgag ctgcaccacc tggcgctgca agagttgccg ggacatgtgg   1980
cgctctcctg ttttgtcgcc gagcgtgcgc ttattaaaac cagctgggac aagtggctgg   2040
tggaaccgtg cgccccggcg taagtgtggt atcatcgcgc gcaaattttg tatctctcag   2100
gagacaggaa tgaaagtgac gctgccagag tttaagcaag ccggtgtaat ggtggtgggt   2160
gatgtgatgc tggatcgtta ctggtatggc ccaaccagcc gtatctctcc ggaagcgcca   2220
gtcccggttg ttaaagtcga taccattgaa gagcgtcctg gcggcgcggc aaacgtggcg   2280
atgaatatcg cctcactggg cgccacggcg cgtctggttg gcctgactgg cattgacgat   2340
gcggcgcgcg cgctgagcaa agcgctggcc gatgttaacg ttaaatgtga cttcgtttct   2400
gttccgacgc atcccaccat cactaagctg cgcgtgctgt cgcgtaacca gcagctgatt   2460
cgcctggact ttgaagaggg ttttgaagga gtcgatccgc aaccgatgca tgaacgcatc   2520
agccaggcgc ttggtaatat tggcgcgctg gtgctgtcgg att                     2563
```

<210> SEQ ID NO 245
<211> LENGTH: 426
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: delta-nifL::Prm5

<400> SEQUENCE: 245

```
atgaccctga atatgatgat ggatgccggc ggacatcatc gcgacaaaca atattaatac    60
cggcaaccac accggcaatt tacgagactg cgcaggcatc ctttctcccg tcaatttctg   120
tcaaataaag taaagagggc agtctacttg aattaccccc ggctggttga gcgtttgttg   180
aaaaaaagta actgaaaaat ccgtagaata gcgccactct gatggttaat taacctattc   240
aattaagaat tatctggatg aatgtgccat taaatgcgca gcataatggt gcgttgtgcg   300
ggaaaactgc ttttttttga aagggttggt cagtagcgga acaactcac ttcacacccc    360
```

```
gaaggggaa gttgcctgac cctacgattc ccgctatttc attcactgac cggaggttca    420
aaatga                                                              426

<210> SEQ ID NO 246
<211> LENGTH: 1426
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::Prm5 with 500bp flank

<400> SEQUENCE: 246
accggatacg agagaaaagt gtctacatcg gttcggttga tattgaccgg cgcatccgcc     60
agcccgccca gtttctggtg gatctgtttg gcgattttgc gggtcttgcc ggtgtcggtg    120
ccgaaaaaaa taccaatatt tgccataaca cacgctcctg ttgaaaaaga gatcccgccg    180
ggaaatgcgg tgaacgtgtc tgatattgcg aagagtgtgc cagttttggt cgcgggcaaa    240
acctgcacca gtttggttat taatgcacca gtctggcgct ttttttcgcc gagtttctcc    300
tcgctaatgc ccgccaggcg cggctttggc gctgatagcg cgctgaatac cgatctggat    360
caaggttttg tcgggttatc agccaaaagg tgcactcttt gcatggttat acgtgcctga    420
catgttgtcc gggcgacaaa cggcctggtg gcacaaattg tcagaactac gacacgacta    480
actgaccgca ggagtgtgcg atgaccctga atatgatgat ggatgccggc ggacatcatc    540
gcgacaaaca atattaatac cggcaaccac accggcaatt tacgagactg cgcaggcatc    600
cttctctccg tcaatttctg tcaaataaag taaagaggc agtctacttg aattaccccc    660
ggctggttga gcgtttgttg aaaaaaagta actgaaaaat ccgtagaata gcgccactct    720
gatggttaat taacctattc aattaagaat tatctggatg aatgtgccat taaatgcgca    780
gcataatggt gcgttgtgcg ggaaaactgc tttttttga agggttggt cagtagcgga     840 aacaactcac ttcacacccc gaaggggaa gttgcctgac cctacgattc cgctatttc    900 attcactgac cggaggttca aaatgaccca gcgaaccgag tcgggtaata ccgtctggcg    960
cttcgatttg tcccagcagt tcactgcgat gcagcgcata agcgtggtac tcagcccggc   1020
gaccgaggtc gatcagacgc tccagcaagt gctgtgcgta ttgcacaatg acgccttttt   1080
gcagcacggc atgatctgtc tgtacgacag ccagcaggcg attttgaata ttgaagcgtt   1140
gcaggaagcc gatcagcagt taatccccgg cagctcgcaa atccgctatc gtccgggcga   1200
agggctggtc gggacggtgc tttcgcaggg ccaatcatta gtgctggcgc gcgttgctga   1260
cgatcagcgc tttcttgacc ggctcgggtt gtatgattac aacctgccgt ttatcgccgt   1320
gccgctgata gggccagatg cgcagacttt cggtgtgctg acggcacaac ccatggcgcg   1380
ttacgaagag cgattacccg cctgcacccg ctttctggaa acggtc                  1426

<210> SEQ ID NO 247
<211> LENGTH: 461
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::Prm1
```

<400> SEQUENCE: 247

```
atgaccctga atatgatgat ggatgccggc cgtcctgtaa taataaccgg acaattcgga      60
ctgattaaaa aagcgccctt gtggcgcttt ttttatattc ccgcctccat ttaaaataaa     120
aaatccaatc ggatttcact atttaaactg gccattatct aagatgaatc cgatggaagc     180
tcgctgtttt aacacgcgtt ttttaacctt ttattgaaag tcggtgcttc tttgagcgaa     240
cgatcaaatt taagtggatt cccatcaaaa aaatattctc aacctaaaaa agtttgtgta     300
atacttgtaa cgctacatgg agattaactc aatctagagg gtattaataa tgaatcgtac     360
taaactggta ctgggcgcaa ctcacttcac accccgaagg gggaagttgc ctgaccctac     420
gattcccgct atttcattca ctgaccggag gttcaaaatg a                         461
```

<210> SEQ ID NO 248
<211> LENGTH: 1461
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: delta-nifL::Prm1 with 500bp flank

<400> SEQUENCE: 248

```
accggatacg agagaaaagt gtctacatcg gttcggttga tattgaccgg cgcatccgcc      60
agcccgccca gtttctggtg gatctgtttg gcgattttgc gggtcttgcc ggtgtcggtg     120
ccgaaaaaaa taccaatatt tgccataaca cacgctcctg ttgaaaaaga gatcccgccg     180
ggaaatgcgg tgaacgtgtc tgatattgcg aagagtgtgc cagttttggt cgcgggcaaa     240
acctgcacca gtttggttat taatgcacca gtctggcgct ttttttcgcc gagtttctcc     300
tcgctaatgc ccgccaggcg cggctttggc gctgatagcg cgctgaatac cgatctggat     360
caaggttttg tcgggttatc agccaaaagg tgcactcttt gcatggttat acgtgcctga     420
catgttgtcc gggcgacaaa cggcctggtg gcacaaattg tcagaactac gacacgacta     480
actgaccgca ggagtgtgcg atgaccctga atatgatgat ggatgccggc cgtcctgtaa     540
taataaccgg acaattcgga ctgattaaaa aagcgccctt gtggcgcttt ttttatattc     600
ccgcctccat ttaaaataaa aaatccaatc ggatttcact atttaaactg gccattatct     660
aagatgaatc cgatggaagc tcgctgtttt aacacgcgtt ttttaacctt ttattgaaag     720
tcggtgcttc tttgagcgaa cgatcaaatt taagtggatt cccatcaaaa aaatattctc     780
aacctaaaaa agtttgtgta atacttgtaa cgctacatgg agattaactc aatctagagg     840
gtattaataa tgaatcgtac taaactggta ctgggcgcaa ctcacttcac accccgaagg     900
gggaagttgc ctgaccctac gattcccgct atttcattca ctgaccggag gttcaaaatg     960
acccagcgaa ccgagtcggg taataccgtc tggcgcttcg atttgtccca gcagttcact    1020
gcgatgcagc gcataagcgt ggtactcagc cgggcgaccg aggtcgatca gacgctccag    1080
caagtgctgt gcgtattgca caatgacgcc ttttttgcagc acggcatgat ctgtctgtac    1140
gacagccagc aggcgatttt gaatattgaa gcgttgcagg aagccgatca gcagttaatc    1200
cccggcagct cgcaaatccg ctatcgtccg ggcgaagggc tggtcgggac ggtgctttcg    1260
cagggccaat cattagtgct ggcgcgcgtt gctgacgatc agcgctttct tgaccggctc    1320
gggttgtatg attacaacct gccgtttatc gccgtgccgc tgataggggcc agatgcgcag    1380
```

```
actttcggtg tgctgacggc acaacccatg gcgcgttacg aagagcgatt acccgcctgc    1440
acccgctttc tggaaacggt c                                              1461
```

<210> SEQ ID NO 249
<211> LENGTH: 1188
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: glnE-delta-AR-2

<400> SEQUENCE: 249

```
atggcactga acacctcat ttccctgtgt gccgcgtcgc cgatggttgc cagtcagctg     60
gcgcgctacc cgatcctgct tgatgaattg ctcgacccga atacgctcta tcaaccgacg    120
gcgatgaatg cctatcgcga tgagctgcgc caatacctgc tgcgcgtgcc ggaagatgat    180
gaagagcaac agcttgaggc gctgcggcag tttaagcagg cgcagttgct cgcgcgtggcg   240 gcggcggata ttgccggtac gttgccagta atgaaagtga gcgatcactt aacctggctg    300
gcggaagcga ttattgatgc ggtggtgcag caagcctggg ggcagatggt ggcgcgttat    360
ggccagccaa cgcatctgca cgatcgcgaa gggcgcggtt ttgcggtggt cggttatggc    420
aagctgggcg gctgggagct gggttacagc tccgatctgg atctggtatt cctgcacgac    480
tgcccgatgg atgtgatgac cgatggcgag cgtgaaatcg atggtcgcca gttctatttg    540
cgtctcgcgc agcgcgtgat gcacctgttt agcacgcgca cgtcgtccgg catcctttat    600
gaagttgatg cgcgtctgcg tccatctggc gctgcgggga tgctggtcac tactacggaa    660
tcgttcgccg attaccagca aaacgaagcc tggacgtggg aacatcaggc gctggcccgt    720
gcgcgcgtgg tgtacggcga tccgcaactg accgccgaat ttgacgccat cgccgcgat    780 attctgatga cgcctcgcga cggcgcaacg ctgcaaaccg acgtgcgaga atgcgcgag    840 aaaatgcgtg cccatcttgg caacaagcat aaagaccgct tcgatctgaa agccgatgaa    900
ggcggtatca ccgacatcga gtttatcgcc caatatctgg tgctgcgctt tgcccatgac    960 aagccgaaaac tgacgcgctg gtcggataat gtgcgcattc tcgaagggct ggcgcaaaac   1020
ggcatcatgg aggagcagga agcgcaggca ttgacgctgg cgtacaccac attgcgtgat   1080
gagctgcacc acctggcgct gcaagagttg ccgggacatg tggcgctctc ctgttttgtc   1140
gccgagcgtg cgcttattaa aaccagctgg gacaagtggc tggtggaa                 1188
```

<210> SEQ ID NO 250
<211> LENGTH: 2206
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: glnE-delta-AR-2 with 500bp flank

<400> SEQUENCE: 250

```
gcgcaaagcg agtgctcact tacgtgatct gttgacacaa tctgaagcga ccataacttc     60
tgccgtttca gcgaatacgg cggtgtggag cgcacaatca gccctggcga agctggtgct    120
caccgagtgg ctagtgacgc agggctggcg aaccttcctt gatgaaaaag cgcaggccaa    180
attcgccgac tcctttaaac gctttgctga catccatctg tcacgcagcg ccgccgagct    240
```

```
gaaaaaagcc tttgcccaac cgctgggcga cagctatcgc gaccagttgc cgcgcctggc    300
gcgtgatatc gactgcgcgt tactgctggc cgggcattac gatcgcgcgc gcgccgtgga    360
atggctggaa aactggcagg ggcttcagca cgccattgaa acgcgccaga gagtcgaaat    420
cgaacatttc cgtaataccg cgattaccca ggagccgttc tggttgcaca gcggaaaacg    480
ttaacgaaag gatatttcgc atggcactga aacacctcat ttccctgtgt gccgcgtcgc    540
cgatggttgc cagtcagctg gcgcgctacc cgatcctgct tgatgaattg ctcgacccga    600
atacgctcta tcaaccgacg gcgatgaatg cctatcgcga tgagctgcgc caatacctgc    660
tgcgcgtgcc ggaagatgat gaagagcaac agcttgaggc gctgcggcag tttaagcagg    720
cgcagttgct gcgcgtggcg gcggcggata ttgccggtac gttgccagta atgaaagtga    780
gcgatcactt aacctggctg gcggaagcga ttattgatgc ggtggtgcag caagcctggg    840
ggcagatggt ggcgcgttat ggccagccaa cgcatctgca cgatcgcgaa gggcgcggtt    900
ttgcggtggt cggttatggc aagctgggcg gctgggagct gggttacagc tccgatctgg    960
atctggtatt cctgcacgac tgcccgatgg atgtgatgac cgatggcgag cgtgaaatcg   1020
atggtcgcca gttctatttg cgtctcgcgc agcgcgtgat gcacctgttt agcacgcgca   1080
cgtcgtccgg catcctttat gaagttgatg cgcgtctgcg tccatctggc gctgcgggga   1140
tgctggtcac tactacggaa tcgttcgccg attaccagca aaacgaagcc tggacgtggg   1200
aacatcaggc gctggcccgt gcgcgcgtgg tgtacggcga tccgcaactg accgccgaat   1260
ttgacgccat tcgccgcgat attctgatga cgcctcgcga cggcgcaacg ctgcaaaccg   1320
acgtgcgaga aatgcgcgag aaaatgcgtg cccatcttgg caacaagcat aaagaccgct   1380
tcgatctgaa agccgatgaa ggcggtatca ccgacatcga gtttatcgcc caatatctgg   1440
tgctgcgctt tgcccatgac aagccgaaac tgacgcgctg gtcggataat gtgcgcattc   1500
tcgaagggct ggcgcaaaac ggcatcatgg aggagcagga agcgcaggca ttgacgctgg   1560
cgtacaccac attgcgtgat gagctgcacc acctggcgct gcaagagttg ccgggacatg   1620
tggcgctctc ctgttttgtc gccgagcgtg cgcttattaa aaccagctgg acaagtggc   1680 tggtggaacc gtgcgccccg gcgtaagtgt ggtatcatcg cgcgcaaatt ttgtatctct   1740
caggagacag gaatgaaagt gacgctgcca gagtttaagc aagccggtgt aatggtggtg   1800
ggtgatgtga tgctggatcg ttactggtat ggcccaacca gccgtatctc tccggaagcg   1860
ccagtcccgg ttgttaaagt cgataccatt gaagagcgtc ctggcggcgc ggcaaacgtg   1920
gcgatgaata tcgcctcact gggcgccacg gcgcgtctgg ttggcctgac tggcattgac   1980
gatgcggcgc gcgcgctgag caaagcgctg gccgatgtta acgttaaatg tgacttcgtt   2040
tctgttccga cgcatcccac catcactaag ctgcgcgtgc tgtcgcgtaa ccagcagctg   2100
attcgcctgg actttgaaga gggttttgaa ggagtcgatc cgcaaccgat gcatgaacgc   2160
atcagccagg cgcttggtaa tattggcgcg ctggtgctgt cggatt              2206
```

<210> SEQ ID NO 251
<211> LENGTH: 199
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-amtB

<400> SEQUENCE: 251

```
tttcgctgaa ggtgtgacca tgggccatca ggtgctggtg cagctggaaa gtgttgccat      60
cactatcgtg tggtctggcg tggtggcctt tattggttac aaactggcgg acatgacggt     120
aggcctgcgc gtaccggaag aacaagaacg tgaaggctg gatgtaaaca gccacggcga     180
aaacgcctat aacgcctga                                                  199
```

<210> SEQ ID NO 252
<211> LENGTH: 1199
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: delta-amtB with 500bp flank

<400> SEQUENCE: 252

```
tttcctttct gactctgccc gtccgggcgc actaacggcc tgaaatactc cctcttttca      60
ttcctggcac aacgattgca atgtctgttg cgtgttagct gcggccatta tcgaattcga     120
ctggaggggg atctatgaag ctggttaccg tggtgattaa gccattcaaa cttgaagacg     180
tgcgtgaagc gctttcttct attggtattc aagggttgac cgtaactgaa gtgaaaggct     240
ttggccgtca aagggtcac gctgagctgt accgcggtgc ggaatatagc gttaatttcc     300
tgccgaaagt gaaaattgat gtggcgatcg ctgacgatca actcgatgaa gtaatcgatg     360
tgatcagcaa agcggcctac accggaaaaa ttggcgacgg caaaattttc gttgctgagc     420
tgcaacgcgt cattcgtatt cgtaccggcg aagccgacga agcggcactg taatacaaga     480
cacacagtga tggggatcgg tttcgctgaa ggtgtgacca tgggccatca ggtgctggtg     540
cagctggaaa gtgttgccat cactatcgtg tggtctggcg tggtggcctt tattggttac     600
aaactggcgg acatgacggt aggcctgcgc gtaccggaag aacaagaacg tgaaggctg     660 gatgtaaaca gccacggcga aaacgcctat aacgcctgat tgcgttgagt tatctcctga     720
gcataaaaaa gcctccattc ggaggctttt ctttttttaa gtttaaagcg cggttagttg     780
cgattgcgca tgacgccttc ctgcacgctg gacgcgacca gcacaccctc ttgcgtatag     840
aactcgccgc gcacaaaacc gcgagcgctg gaggctgacg tgctttccac actgtagagc     900
agccattcgt tcatattaaa cgggcgatgg aaccacatgg agtggtcaat ggtggcaacc     960
tgcataccgc gctcaaggaa gcccacgccg tgcggctgaa gtgcaaccgg caggaagtta    1020
aagtctgagg catatccaag cagatattga tgtacgcgaa aatcgtccgg caccgtgccg    1080
tttgcgcgga tccataccctg gcgggtggga tcggcaacgt ggcctttcag cgggttatga    1140
aactcaaccg ggcggatctc cagtggttta tcactaagaa acttctcttt ggcctgcgg    1199
```

<210> SEQ ID NO 253
<211> LENGTH: 1563
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: glnE-delta-AR-1

<400> SEQUENCE: 253

| | | | | | |
|---|---|---|---|---|---|
| atgtttaacg | atctgattgg | cgatgatgaa | acggattcgc | cggaagatgc | gctttctgag | 60 |
| agctggcgcg | aattgtggca | ggatgcgttg | caggaggagg | attccacgcc | cgtgctggcg | 120 |
| catctctcag | aggacgatcg | ccgccgcgtg | gtggcgctga | ttgccgattt | tcgcaaagag | 180 |
| ttggataaac | gcaccattgg | cccgcgaggg | cggcaggtac | tcgatcactt | aatgccgcat | 240 |
| ctgctcagcg | atgtatgctc | gcgcgacgat | gcgccagtac | cgctgtcacg | cctgacgccg | 300 |
| ctgctcaccg | gaattattac | ccgcaccact | taccttgagc | tgctaagtga | atttcccggc | 360 |
| gcactgaaac | acctcatttc | cctgtgtgcc | cgtcgccga | tggttgccag | tcagctggcg | 420 |
| cgctacccga | tcctgcttga | tgaattgctc | gacccgaata | cgctctatca | accgacggcg | 480 |
| atgaatgcct | atcgcgatga | gctgcgccaa | tacctgctgc | gcgtgccgga | agatgatgaa | 540 |
| gagcaacagc | ttgaggcgct | gcggcagttt | aagcaggcgc | agttgctgcg | cgtggcggcg | 600 |
| gcggatattg | ccggtacgtt | gccagtaatg | aaagtgagcg | atcacttaac | ctggctggcg | 660 |
| gaagcgatta | ttgatgcggt | ggtgcagcaa | gcctggggc | agatggtggc | gcgttatggc | 720 |
| cagccaacgc | atctgcacga | tcgcgaaggg | cgcggttttg | cggtggtcgg | ttatggcaag | 780 |
| ctgggcggct | gggagctggg | ttacagctcc | gatctggatc | tggtattcct | gcacgactgc | 840 |
| ccgatggatg | tgatgaccga | tggcgagcgt | gaaatcgatg | gtcgccagtt | ctatttgcgt | 900 |
| ctcgcgcagc | gcgtgatgca | cctgtttagc | acgcgcacgt | cgtccggcat | cctttatgaa | 960 |
| gttgatgcgc | gtctgcgtcc | atctggcgct | gcggggatgc | tggtcactac | tacggaatcg | 1020 |
| ttcgccgatt | accagcaaaa | cgaagcctgg | acgtgggaac | atcaggcgct | ggcccgtgcg | 1080 |
| cgcgtggtgt | acggcgatcc | gcaactgacc | gccgaatttg | acgccattcg | ccgcgatatt | 1140 |
| ctgatgacgc | ctcgcgacgg | cgcaacgctg | caaaccgacg | tgcgagaaat | gcgcgagaaa | 1200 |
| atgcgtgccc | atcttggcaa | caagcataaa | gaccgcttcg | atctgaaagc | cgatgaaggc | 1260 |
| ggtatcaccg | acatcgagtt | tatcgcccaa | tatctggtgc | tgcgctttgc | ccatgacaag | 1320 |
| ccgaaactga | cgcgctggtc | ggataatgtg | cgcattctcg | aagggctggc | gcaaaacggc | 1380 |
| atcatggagg | agcaggaagc | gcaggcattg | acgctggcgt | acaccacatt | gcgtgatgag | 1440 |
| ctgcaccacc | tggcgctgca | agagttgccg | ggacatgtgg | cgctctcctg | ttttgtcgcc | 1500 |
| gagcgtgcgc | ttattaaaac | cagctgggac | aagtggctgg | tggaaccgtg | cgccccggcg | 1560 |
| taa | | | | | | 1563 |

<210> SEQ ID NO 254
<211> LENGTH: 2563
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: glnE-delta-AR-1 with 500bp flank

<400> SEQUENCE: 254

| | | | | | |
|---|---|---|---|---|---|
| gcgcaaagcg | agtgctcact | tacgtgatct | gttgacacaa | tctgaagcga | ccataacttc | 60 |
| tgccgtttca | gcgaatacgg | cggtgtggag | cgcacaatca | gccctggcga | agctggtgct | 120 |
| caccgagtgg | ctagtgacgc | agggctggcg | aaccttcctt | gatgaaaaag | cgcaggccaa | 180 |
| attcgccgac | tcctttaaac | gctttgctga | catccatctg | tcacgcagcg | ccgccgagct | 240 |
| gaaaaaagcc | tttgcccaac | cgctgggcga | cagctatcgc | gaccagttgc | cgcgcctggc | 300 |

```
gcgtgatatc gactgcgcgt tactgctggc cgggcattac gatcgcgcgc gcgccgtgga    360
atggctggaa aactggcagg ggcttcagca cgccattgaa acgcgccaga gagtcgaaat    420
cgaacatttc cgtaataccg cgattaccca ggagccgttc tggttgcaca gcggaaaacg    480
ttaacgaaag gatatttcgc atgtttaacg atctgattgg cgatgatgaa acggattcgc    540
cggaagatgc gctttctgag agctggcgcg aattgtggca ggatgcgttg caggaggagg    600
attccacgcc cgtgctggcg catctctcag aggacgatcg ccgccgcgtg gtggcgctga    660
ttgccgattt tcgcaaagag ttggataaac gcaccattgg cccgcgaggg cggcaggtac    720
tcgatcactt aatgccgcat ctgctcagcg atgtatgctc gcgcgacgat gcgccagtac    780
cgctgtcacg cctgacgccg ctgctcaccg gaattattac ccgcaccact taccttgagc    840
tgctaagtga atttcccggc gcactgaaac acctcatttc cctgtgtgcc gcgtcgccga    900
tggttgccag tcagctggcg cgctacccga tcctgcttga tgaattgctc gacccgaata    960
cgctctatca accgacggcg atgaatgcct atcgcgatga gctgcgccaa tacctgctgc   1020
gcgtgccgga agatgatgaa gagcaacagc ttgaggcgct gcggcagttt aagcaggcgc   1080
agttgctgcg cgtggcggcg gcggatattg ccggtacgtt gccagtaatg aaagtgagcg   1140
atcacttaac ctggctggcg gaagcgatta ttgatgcggt ggtgcagcaa gcctgggggc   1200
agatggtggc gcgttatggc cagccaacgc atctgcacga tcgcgaaggg cgcggttttg   1260
cggtggtcgg ttatggcaag ctgggcggct gggagctggg ttacagctcc gatctggatc   1320
tggtattcct gcacgactgc ccgatggatg tgatgaccga tggcgagcgt gaaatcgatg   1380
gtcgccagtt ctatttgcgt ctcgcgcagc gcgtgatgca cctgtttagc acgcgcacgt   1440
cgtccggcat cctttatgaa gttgatgcgc gtctgcgtcc atctggcgct gcggggatgc   1500
tggtcactac tacggaatcg ttcgccgatt accagcaaaa cgaagcctgg acgtgggaac   1560
atcaggcgct ggcccgtgcg cgcgtggtgt acggcgatcc gcaactgacc gccgaatttg   1620
acgccattcg ccgcgatatt ctgatgacgc ctcgcgacgg cgcaacgctg caaaccgacg   1680
tgcgagaaat gcgcgagaaa atgcgtgccc atcttggcaa caagcataaa gaccgcttcg   1740
atctgaaagc cgatgaaggc ggtatcaccg acatcgagtt tatcgcccaa tatctggtgc   1800
tgcgcttgtc ccatgacaag ccgaaactga cgcgctggtc ggataatgtg cgcattctcg   1860
aagggctggc gcaaaacggc atcatggagg agcaggaagc gcaggcattg acgctggcgt   1920
acaccacatt gcgtgatgag ctgcaccacc tggcgctgca agagttgccg ggacatgtgg   1980
cgctctcctg ttttgtcgcc gagcgtgcgc ttattaaaac cagctgggac aagtggctgg   2040
tggaaccgtg cgccccggcg taagtgtggt atcatcgcgc gcaaattttg tatctctcag   2100
gagacaggaa tgaaagtgac gctgccagag tttaagcaag ccggtgtaat ggtggtgggt   2160
gatgtgatgc tggatcgtta ctggtatggc ccaaccagcc gtatctctcc ggaagcgcca   2220
gtcccggttg ttaaagtcga taccattgaa gagcgtcctg gcggcgcggc aaacgtggcg   2280
atgaatatcg cctcactggg cgccacggcg cgtctggttg gcctgactgg cattgacgat   2340
gcggcgcgcg cgctgagcaa agcgctggcc gatgttaacg ttaaatgtga cttcgtttct   2400
gttccgacgc atcccaccat cactaagctg cgcgtgctgt cgcgtaacca gcagctgatt   2460
cgcctggact ttgaagaggg ttttgaagga gtcgatccgc aaccgatgca tgaacgcatc   2520
agccaggcgc ttggtaatat tggcgcgctg gtgctgtcgg att                    2563
```

<210> SEQ ID NO 255

<211> LENGTH: 461
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: delta-nifL::Prm1

<400> SEQUENCE: 255

```
atgaccctga atatgatgat ggatgccggc cgtcctgtaa taataaccgg acaattcgga      60
ctgattaaaa aagcgcccct tgtggcgcttt ttttatattc ccgcctccat ttaaaataaa    120
aaatccaatc ggatttcact atttaaactg gccattatct aagatgaatc cgatggaagc    180
tcgctgtttt aacacgcgtt ttttaacctt ttattgaaag tcggtgcttc tttgagcgaa    240
cgatcaaatt taagtggatt cccatcaaaa aaatattctc aacctaaaaa agtttgtgta    300
atacttgtaa cgctacatgg agattaactc aatctagagg gtattaataa tgaatcgtac    360
taaactggta ctgggcgcaa ctcacttcac accccgaagg gggaagttgc ctgaccctac    420
gattcccgct atttcattca ctgaccggag gttcaaaatg a                        461
```

<210> SEQ ID NO 256
<211> LENGTH: 1461
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: delta-nifL::Prm1 with 500bp flank

<400> SEQUENCE: 256

```
accggatacg agagaaaagt gtctacatcg gttcggttga tattgaccgg cgcatccgcc      60
agcccgccca gtttctggtg gatctgtttg gcgattttgc gggtcttgcc ggtgtcggtg    120
ccgaaaaaaa taccaatatt tgccataaca cacgctcctg ttgaaaaaga gatcccgccg    180
ggaaatgcgg tgaacgtgtc tgatattgcg aagagtgtgc cagttttggt cgcgggcaaa    240
acctgcacca gtttggttat taatgcacca gtctggcgct ttttttcgcc gagtttctcc    300
tcgctaatgc ccgccaggcg cggctttggc gctgatagcg cgctgaatac cgatctggat    360
caaggttttg tcgggttatc agccaaaagg tgcactcttt gcatggttat acgtgcctga    420
catgttgtcc gggcgacaaa cggcctggtg gcacaaattg tcagaactac gacacgacta    480
actgaccgca ggagtgtgcg atgaccctga atatgatgat ggatgccggc cgtcctgtaa    540
taataaccgg acaattcgga ctgattaaaa aagcgcccct tgtggcgcttt ttttatattc    600
ccgcctccat ttaaaataaa aaatccaatc ggatttcact atttaaactg gccattatct    660
aagatgaatc cgatggaagc tcgctgtttt aacacgcgtt ttttaacctt ttattgaaag    720
tcggtgcttc tttgagcgaa cgatcaaatt taagtggatt cccatcaaaa aaatattctc    780
aacctaaaaa agtttgtgta atacttgtaa cgctacatgg agattaactc aatctagagg    840
gtattaataa tgaatcgtac taaactggta ctgggcgcaa ctcacttcac accccgaagg    900
gggaagttgc ctgaccctac gattcccgct atttcattca ctgaccggag gttcaaaatg    960
acccagcgaa ccgagtcggg taataccgtc tggcgcttcg atttgtccca gcagttcact  1020
gcgatgcagc gcataagcgt ggtactcagc cgggcgaccg aggtcgatca gacgctccag  1080
caagtgctgt gcgtattgca caatgacgcc ttttgcagc acggcatgat ctgtctgtac  1140
gacagccagc aggcgatttt gaatattgaa gcgttgcagg aagccgatca gcagttaatc  1200
```

```
cccggcagct cgcaaatccg ctatcgtccg ggcgaagggc tggtcggagc ggtgctttcg    1260
cagggccaat cattagtgct ggcgcgcgtt gctgacgatc agcgctttct tgaccggctc    1320
gggttgtatg attacaacct gccgtttatc gccgtgccgc tgatagggcc agatgcgcag    1380
actttcggtg tgctgacggc acaacccatg gcgcgttacg aagagcgatt acccgcctgc    1440
acccgctttc tggaaacggt c                                              1461

<210> SEQ ID NO 257
<211> LENGTH: 199
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-amtB

<400> SEQUENCE: 257
tttcgctgaa ggtgtgacca tgggccatca ggtgctggtg cagctggaaa gtgttgccat     60
cactatcgtg tggtctggcg tggtggcctt tattggttac aaactggcgg acatgacggt    120
aggcctgcgc gtaccggaag aacaagaacg tgaagggctg gatgtaaaca gccacggcga    180
aaacgcctat aacgcctga                                                 199

<210> SEQ ID NO 258
<211> LENGTH: 1199
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-amtB with 500bp flank

<400> SEQUENCE: 258
tttcctttct gactctgccc gtccgggcgc actaacggcc tgaaatactc cctcttttca     60
ttcctggcac aacgattgca atgtctgttg cgtgttagct gcggccatta tcgaattcga    120 ctggagggg  atctatgaag ctggttaccg tggtgattaa gccattcaaa cttgaagacg    180
tgcgtgaagc gctttcttct attggtattc aagggttgac cgtaactgaa gtgaaaggct    240
ttggccgtca gaagggtcac gctgagctgt accgcggtgc ggaatatagc gttaatttcc    300
tgccgaaagt gaaaattgat gtggcgatcg ctgacgatca actcgatgaa gtaatcgatg    360
tgatcagcaa agcggcctac accggaaaaa ttggcgacgg caaaattttc gttgctgagc    420
tgcaacgcgt cattcgtatt cgtaccggcg aagccgacga agcggcactg taatacaaga    480
cacacagtga tggggatcgg tttcgctgaa ggtgtgacca tgggccatca ggtgctggtg    540
cagctggaaa gtgttgccat cactatcgtg tggtctggcg tggtggcctt tattggttac    600
aaactggcgg acatgacggt aggcctgcgc gtaccggaag aacaagaacg tgaagggctg    660
gatgtaaaca gccacggcga aaacgcctat aacgcctgat gcgttgagt tatctcctga    720 gcataaaaaa gcctccattc ggaggctttt cttttttaa gtttaaagcg cggttagttg    780
cgattgcgca tgacgccttc ctgcacgctg acgcgacca gcacaccctc ttgcgtatag    840
aactcgccgc gcacaaaacc gcgagcgctg aggctgacg tgctttccac actgtagagc    900
agccattcgt tcatattaaa cgggcgatgg aaccacatgg agtggtcaat ggtggcaacc    960
tgcataccgc gctcaaggaa gcccacgccg tgcggctgaa gtgcaaccgg caggaagtta   1020
```

```
aagtctgagg catatccaag cagatattga tgtacgcgaa atcgtccgg caccgtgccg    1080 tttgcgcgga tccatacctg gcgggtggga tcggcaacgt ggcctttcag cgggttatga    1140
aactcaaccg ggcggatctc cagtggttta tcactaagaa acttctcttt ggcctgcgg    1199
```

<210> SEQ ID NO 259
<211> LENGTH: 607
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::PinfC

<400> SEQUENCE: 259

```
atgaccttta atatgatgcc tggggtcact ggagcgcttt atcggcatcc tgaccgaaga      60
atttgccggt ttcttcccga cctggctggc ccctgttcag gttgtggtga tgaatatcac     120
tgattctcaa gctgaatatg tcaacgaatt gacccgtaaa ttgcaaaatg cgggcattcg     180
tgtaaaagcg gacttgagaa acgagaagat tggctttaaa atccgcgagc acactttacg     240
tcgtgtccct tatatgttgg tctgtggtga taaagaggtg gaagcaggca aagtggccgt     300
tcgcacccgc cgcggtaaag acctgggcag cctggacgta agtgaagtga ttgagaagct     360
gcaacaagag attcgcagcc gcagtcttca acaactggag gaataaggta ttaaaggcgg     420
aaaacgagtt caaacggcac gtccgaatcg tatcaatggc gagattcgcg cccaggaagt     480
tcgcttaact ggtctggaag gtgagcagct gggtattgca atagaactaa ctacccgccc     540
tgaaggcggt acctgcctga ccctgcgatt cccgttattt cattcactga ccggaggccc     600
acgatga                                                               607
```

<210> SEQ ID NO 260
<211> LENGTH: 1607
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::PinfC with 500bp flank

<400> SEQUENCE: 260

```
ggtacgacaa aaacgtctcc agcgacgtgc ggttaatatt gactggcgca tccgccacat      60
cccccagttt ttgctggatc agtttggcga ttttgcgggt ttttcccgtg tcactgccaa     120
aaaaaatacc aatgttagcc atgtcgcgct cctgttgaga aagaataagg ccgcctgcaa     180
acggcggata tcccttctcc tgttgcgaag gctgtgccag gttttttttaa ggccttctgt     240 gcactgaaat gggtgaaaaa atgactcttt tttgtgcagg caccgtcctc tctccgctat     300
ccagacctgc tttgaaggcc tctgagggcc aaatcagggc caaaacacga atcaggatca     360
atgtttcggc gcgttacctg ttcgaaaggt gcactctttg catggttaat cacacccaat     420
cagggctgcg gatgtcgggc gtttcacaac acaaaatgtt gtaaatgcga cacagccggg     480 cctgaaaacca ggagcgtgtg atgaccttta atatgatgcc tggggtcact ggagcgcttt     540
atcggcatcc tgaccgaaga atttgccggt ttcttcccga cctggctggc ccctgttcag     600
gttgtggtga tgaatatcac tgattctcaa gctgaatatg tcaacgaatt gacccgtaaa     660
ttgcaaaatg cgggcattcg tgtaaaagcg gacttgagaa acgagaagat tggctttaaa     720
atccgcgagc acactttacg tcgtgtccct tatatgttgg tctgtggtga taaagaggtg     780
```

```
gaagcaggca aagtggccgt tcgcacccgc cgcggtaaag acctgggcag cctggacgta    840
agtgaagtga ttgagaagct gcaacaagag attcgcagcc gcagtcttca acaactggag    900
gaataaggta ttaaaggcgg aaaacgagtt caaacggcac gtccgaatcg tatcaatggc    960
gagattcgcg cccaggaagt tcgcttaact ggtctggaag gtgagcagct gggtattgca   1020
atagaactaa ctacccgccc tgaaggcggt acctgcctga ccctgcgatt cccgttattt   1080
cattcactga ccgagggccc acgatgaccc agcgacccga gtcgggcacc accgtctggc   1140
gttttgatct ctcacagcaa tttaccgcca tgcagcgcat cagcgtggtg ttgagtcgcg   1200
caaccgagat aagccagacg ctgcaggagg tgctgtgtgt tctgcataat gacgcattta   1260
tgcaacacgg catgctgtgt ctgtatgaca accagcagga aattctgagt attgaagcct   1320
tgcaggagga agaccaacat ctgatccccg gcagctcgca aattcgctat cgccctggcg   1380
aagggctggt aggagccgta ctgtcccagg acaatctct  tgtgctgccg cgtgtcgccg   1440
acgatcaacg ctttctcgac aggcttggca tctatgatta caacctgccg tttatcgccg   1500
tccccttaat ggggccaggc gcgcagacga ttggcgtgct cgccgcgcag ccgatggcgc   1560
gtctggagga gcggcttcct tcctgtacgc gctttctgga aaccgtc               1607
```

<210> SEQ ID NO 261
<211> LENGTH: 1536
<212> TYPE: DNA
<213> ORGANISM: Kosakonia sacchari
<220> FEATURE:
<223> OTHER INFORMATION: 16S-1

<400> SEQUENCE: 261

```
ttgaagagtt tgatcatggc tcagattgaa cgctggcggc aggcctaaca catgcaagtc     60
gaacggtagc acagagagct tgctctcggg tgacgagtgg cggacgggtg agtaatgtct    120
gggaaactgc ctgatggagg gggataacta ctggaaacgg tagctaatac cgcataacgt    180
cgcaagacca agaggggga  ccttcgggcc tcttgccatc agatgtgccc agatgggatt    240
agctagtagg tggggtaacg gctcacctag gcgacgatcc ctagctggtc tgagaggatg    300
accagccaca ctggaactga gacacggtcc agactcctac gggaggcagc agtggggaat    360
attgcacaat gggcgcaagc ctgatgcagc catgccgcgt gtgtgaagaa ggccttcggg    420
ttgtaaagca ctttcagcgg ggaggaaggg agtaaggtta ataaccttat tcattgacgt    480
tacccgcaga agaagcaccg gctaactccg tgccagcagc cgcggtaata cggagggtgc    540
aagcgttaat cggaattact gggcgtaaag cgcacgcagg cggtctgtca agtcggatgt    600
gaaatccccg gctcaacct  gggaactgca tccgaaactg gcaggcttga gtctcgtaga    660
gggaggtaga attccaggtg tagcggtgaa atgcgtagag atctggagga ataccggtgg    720
cgaaggcggc ctcctggacg aagactgacg ctcaggtgcg aaagcgtggg gagcaaacag    780
gattagatac cctggtagtc cacgccgtaa acgatgtcta tttggaggtt gtgcccttga    840
ggcgtggctt ccggagctaa cgcgttaaat agaccgcctg gggagtacgg ccgcaaggtt    900
aaaactcaaa tgaattgacg ggggcccgca caagcggtgg agcatgtggt ttaattcgat    960
gcaacgcgaa gaaccttacc tggtcttgac atccacagaa ctttccagag atggattggt   1020
gccttcggga actgtgagac aggtgctgca tggctgtcgt cagctcgtgt tgtgaaatgt   1080
tgggttaagt cccgcaacga gcgcaaccct tatcctttgt tgccagcggt ccggccggga   1140
actcaaagga gactgccagt gataaactgg aggaaggtgg ggatgacgtc aagtcatcat   1200
```

```
ggcccttacg accagggcta cacacgtgct acaatggcgc atacaaagag aagcgacctc    1260
gcgagagtaa gcggacctca taaagtgcgt cgtagtccgg attggagtct gcaactcgac    1320
tccatgaagt cggaatcgct agtaatcgtg gatcagaatg ccacggtgaa tacgttcccg    1380
ggccttgtac acaccgcccg tcacaccatg ggagtgggtt gcaaaagaag taggtagctt    1440
aaccttcggg agggcgctta ccactttgtg attcatgact ggggtgaagt cgtaacaagg    1500
taaccgtagg ggaacctgcg gttggatcac ctcctt                              1536
```

<210> SEQ ID NO 262
<211> LENGTH: 1537
<212> TYPE: DNA
<213> ORGANISM: Kosakonia sacchari
<220> FEATURE:
<223> OTHER INFORMATION: 16S-2
<220> FEATURE:
<221> NAME/KEY: modified_base
<222> LOCATION: (450)..(450)
<223> OTHER INFORMATION: a, c, t, g, unknown or other
<220> FEATURE:
<221> NAME/KEY: modified_base
<222> LOCATION: (452)..(452)
<223> OTHER INFORMATION: a, c, t, g, unknown or other
<220> FEATURE:
<221> NAME/KEY: modified_base
<222> LOCATION: (455)..(455)
<223> OTHER INFORMATION: a, c, t, g, unknown or other
<220> FEATURE:
<221> NAME/KEY: modified_base
<222> LOCATION: (473)..(473)
<223> OTHER INFORMATION: a, c, t, g, unknown or other

<400> SEQUENCE: 262

```
ttgaagagtt tgatcatggc tcagattgaa cgctggcggc aggcctaaca catgcaagtc     60
gaacggtagc acagagagct tgctctcggg tgacgagtgg cggacgggtg agtaatgtct    120
gggaaactgc ctgatggagg gggataacta ctggaaacgg tagctaatac cgcataacgt    180
cgcaagacca aagaggggga ccttcgggcc tcttgccatc agatgtgccc agatgggatt    240
agctagtagg tggggtaacg gctcacctag gcgacgatcc ctagctggtc tgagaggatg    300
accagccaca ctggaactga gacacggtcc agactcctac gggaggcagc agtggggaat    360
attgcacaat gggcgcaagc ctgatgcagc catgccgcgt gtgtgaagaa ggccttcggg    420
ttgtaaagca ctttcagcgg ggaggaaggn antanggtta ataacctgtg ttnattgacg    480
ttacccgcag aagaagcacc ggctaactcc gtgccagcag ccgcggtaat acggagggtg    540
caagcgttaa tcggaattac tgggcgtaaa gcgcacgcag gcggtctgtc aagtcggatg    600
tgaaatcccc gggctcaacc tgggaactgc atccgaaact ggcaggcttg agtctcgtag    660
agggaggtag aattccaggt gtagcggtga atgcgtaga gatctggagg aataccggtg    720
gcgaaggcgg cctcctggac gaagactgac gctcaggtgc gaaagcgtgg ggagcaaaca    780
ggattagata ccctggtagt ccacgccgta aacgatgtct atttggaggt tgtgcccttg    840
aggcgtggct tccggagcta acgcgttaaa tagaccgcct ggggagtacg gccgcaaggt    900
taaaactcaa atgaattgac ggggcccgc acaagcggtg gagcatgtgg tttaattcga    960
tgcaacgcga agaaccttac ctggtcttga catccacaga acttagcaga gatgctttgg   1020
tgccttcggg aactgtgaga caggtgctgc atggctgtcg tcagctcgtg ttgtgaaatg   1080
ttgggttaag tcccgcaacg agcgcaaccc ttatcctttg ttgccagcgg ttaggccggg   1140
aactcaaagg agactgccag tgataaactg gaggaaggtg gggatgacgt caagtcatca   1200
tggcccttac gaccagggct acacacgtgc tacaatggcg catacaaaga gaagcgacct   1260
```

```
cgcgagagta agcggacctc ataaagtgcg tcgtagtccg gattggagtc tgcaactcga    1320
ctccatgaag tcggaatcgc tagtaatcgt ggatcagaat gccacggtga atacgttccc    1380
gggccttgta cacaccgccc gtcacaccat gggagtgggt tgcaaaagaa gtaggtagct    1440
taaccttcgg gagggcgctt accactttgt gattcatgac tggggtgaag tcgtaacaag    1500
gtaaccgtag gggaacctgc ggttggatca cctcctt                             1537
```

<210> SEQ ID NO 263
<211> LENGTH: 882
<212> TYPE: DNA
<213> ORGANISM: Kosakonia sacchari
<220> FEATURE:
<223> OTHER INFORMATION: nifH

<400> SEQUENCE: 263

```
atgaccatgc gtcaatgcgc catttacggc aaaggtggga tcggcaaatc gaccaccaca     60
cagaacctgg tcgccgcgct ggcggagatg ggtaaaaaag tcatgattgt cggctgtgac    120
ccgaaagccg attccacgcg tttgatcctg catgcgaaag cgcagaacac cattatggag    180
atggctgctg aagtcggctc cgtggaagac ctggagttag aagacgtgct gcaaatcggt    240
tacggcggcg tgcgctgcgc agagtccggc ggcccggagc aggcgtgggc tgtgccggt     300 cgcggggtga tcaccgcgat taacttcctc gaagaagaag cgcttacgt gccggatctc     360 gattttgttt tctacgacgt gctgggcgac gtggtatgcg gtggtttcgc catgccgatt    420
cgtgaaaaca aagcgcagga gatctacatc gtttgctctg gcgaaatgat ggcgatgtac    480
gccgccaaca acatctccaa aggcatcgtg aaatacgcca atccggtaa agtgcgcctc     540 ggcgggctga tttgtaactc gcgccagacc gaccgtgaag atgaactgat cattgcgctg    600
gcagaaaaac tcggcacgca gatgatccac tttgttcccc gcgacaacat tgtgcagcgt    660
gcggaaatcc gccgtatgac ggttatcgaa tatgacccga cctgcaatca ggcgaacgaa    720
tatcgcagcc ttgccagcaa aatcgtcaac aacaccaaaa tggtggtgcc cacccctgc     780 accatggatg aactggaaga actgctgatg gagttcggca ttatggatgt ggaagacacc    840
agcatcattg gtaaaaccgc cgccgaagaa aacgccgtct ga                        882
```

<210> SEQ ID NO 264
<211> LENGTH: 1449
<212> TYPE: DNA
<213> ORGANISM: Kosakonia sacchari
<220> FEATURE:
<223> OTHER INFORMATION: nifD2

<400> SEQUENCE: 264

```
atgagcaatg caacaggcga acgcaacctg gagataatcg agcaggtgct cgaggttttc     60
ccggagaaga cgcgcaaaga acgcagaaaa cacatgatgg tgacggaccc ggagcaggaa    120
agcgtcggta agtgcatcat ctctaaccgc aaatcgcagc caggcgtgat gaccgtgcgc    180
ggctgctcgt atgccggttc gaaaggggtg gtatttgggc aatcaagga tatggcgcat    240 atctcgcatg gcccaatcgg ctgcggccaa tactcccgcg ccgggcggcg gaactactac    300
accggcgtca gcgcgtgga cagcttcggc acgctcaact tcacctccga ttttcaggag    360
cgcgacatcg tgtttggcgg cgataaaaag ctcgccaaac tgattgaaga gctggaagag    420
ctgttcccgc tgaccaaagg catttcgatt cagtcggaat gccgtcgg cctgattggc    480 gatgacattg aggccgtcgc gaacgccagc cgcaaagcca tcaacaaacc ggttattccg    540
```

```
gtgcgttgcg aaggctttcg cggcgtgtcg caatccctcg gtcaccatat tgccaacgat    600
gtgatccgcg actgggtgct ggataaccgc gaaggcaaac cgttcgaatc cacccccttac   660 gatgtggcga tcatcggcga ttacaacatc ggcggcgatg cctgggcttc gcgcattttg    720
ctcgaagaga tgggcttgcg ggtggtggca cagtggtctg cgacggtac gctggtggag     780 atggaaaaca cgccgttcgt caaactgaac ctggtgcatt gttaccgctc aatgaactac    840
atctcgcgcc atatggagga gaagcacggt attccgtgga tggaatacaa cttctttggt    900
ccgacgaaaa tcgcggaatc gctgcgcaaa atcgccgacc agtttgacga caccattcgc    960
gccaacgccg aagcggtgat cgccagatac caggcgcaaa acgacgccat tatcgccaaa   1020
tatcgcccgc gtctggaggg gcgcaaagtg ctctttata tgggcgggct gcgtccgcgc     1080
catgtgattg gcgcctatga agacctggga atggagatca tcgctgccgg ttatgagttc   1140
ggtcataacg atgattacga ccgcaccttg ccggatctga agagggcac gctgctgttt     1200 gatgatgcca gcagttatga gctggaggcg ttcgtcaacg cgctgaaacc ggatctcatc    1260
ggttccggca tcaaagagaa gtacatcttt cagaaaatgg gcgtgccgtt cgccagatg     1320 cactcctggg attactccgg cccgtaccac ggctatgacg gcttcgccat cttcgcccgc    1380
gatatggata tgacgctcaa caaccccgcg tggggccagt tgaccgcgcc gtggctgaaa   1440
tccgcctga                                                            1449

<210> SEQ ID NO 265
<211> LENGTH: 1563
<212> TYPE: DNA
<213> ORGANISM: Kosakonia sacchari
<220> FEATURE:
<223> OTHER INFORMATION: nifK2

<400> SEQUENCE: 265
atgagccaga ctgctgagaa aatacagaat tgccatcccc tgtttgaaca ggatgcttac     60
cagacgctgt ttgccggtaa acgggcactc gaagaggcgc actcgccgga gcgggtgcag    120
gaagtgtttc aatggaccac taccccggaa tatgaagcgc tgaactttaa acgcgaagcg    180
ctgactatcg acccggcaaa agcctgccag ccgctgggcg cggtgctctg ttcgctgggg    240
tttgccaata ccctaccgta tgtgcacggt tcacagggtt gcgtggccta tttccgcacg    300
tactttaacc gccactttaa agaaccggtg gcctgcgtgt cggattcaat gacgaaagac    360
gcggcggtgt tcggcgggaa taacaacctc aacaccggct acaaaacgc cagcgcgctg      420 tataaaccgg agattatcgc cgtctctacc acctgtatgg cggaagtgat cggtgatgat   480
ttgcaggcct ttatcgccaa cgccaaaaaa gatggttttc tcgatgccgc catccccgtg    540
ccctacgcgc acacccccag ttttatcggc agccatatca ccggctggga taacatgttt    600
gaaggttttg cccggacctt tacggcagac catgaagctc agcccggcaa actttcacgc   660
atcaacctgg tgaccgggtt tgaaacctat ctccggcaatt tccgcgtgct gaaacgcatg    720
atggaacaaa tggaggtgcc ggcgagtgtg ctctccgatc cgtcggaagt gctggatact   780
cccgccaacg ggcattacca gatgtacgcg ggcgggacga cgcagcaaga gatgcgcgag   840
gcgccggatg ctatcgacac cctgttgctg cagcccggc aactggtgaa aagcaaaaaa     900
gtggtgcagg agatgtggaa tcagcccgcc accgaggttt ctgttcccgt tgggctggca    960
ggaacagacg aactgttgat ggcgattagc cagttaaccg gcaaggccat tccgattca    1020 ctggcgctga gcgcggggcg gctggtcgat atgatgctcg attcccacac ctggttgcac   1080
ggtaaaaaat tcggcctgtt tggcgatccg gattttgtca tgggattgac ccgtttcctg    1140
```

-continued

```
ctggagctgg gctgcgaacc gaccgttatc ctctgccaca acggtaacaa acgctggcag    1200
aaagcaatga agaaaatgct tgacgcctcg ccgtacggcc aggagagcga agtgtttatc    1260
aactgcgatt tgtggcattt ccgctcgctg atgtttaccc gccagccgga ttttatgatt    1320
ggcaactcgt acggcaagtt cattcagcgc gacaccttag ccaaaggcga gcagtttgaa    1380
gttccgctga tccgcctcgg ttttcccctg ttcgaccgcc accatctgca ccgccagacc    1440
acctggggct acgagggcgc catgagcatt ctcactaccc ttgtgaatgc ggtactggag    1500
aaagtggaca agagaccat caagctcggc aaaaccgact acagcttcga tcttatccgt    1560
taa                                                                   1563
```

<210> SEQ ID NO 266
<211> LENGTH: 1488
<212> TYPE: DNA
<213> ORGANISM: Kosakonia sacchari
<220> FEATURE:
<223> OTHER INFORMATION: nifL

<400> SEQUENCE: 266

```
atgaccctga atatgatgat ggatgccggc gcgcccgagg caatcgccgg tgcgctttcg     60
cgacaccatc ctgggctgtt ttttaccatc gttgaagaag cgcccgtcgc catttcgctg    120
actgatgccg acgcacgcat tgtctatgcc aacccggctt tctgccgcca gaccggctat    180
gaactagaag cgttgttgca gcaaaatccc cgcctgcttg caagtcgcca aaccccacgg    240
gaaatctatc aggatatgtg gcacaccttg ttacaacgcc gaccgtggcg cgggcaattg    300
attaaccgcc accgcgacgg cagcctgtat ctggtcgaga tcgatatcac cccggtgatt    360
aacccgtttg gcgaactgga acactacctg gcaatgcagc gcgatatcag cgccagttat    420
gcgctggagc agcggttgcg caatcacatg acgctgaccg aagcggtgct gaataacatt    480
ccggcggcgg tggttgtagt ggatgaacgc gatcatgtgg ttatggataa ccttgcctac    540
aaaacgttct gtgccgactg cggcggaaaa gagctcctga gcgaactcaa tttttcagcc    600
cgaaaagcgg agctggcaaa cggccaggtc ttaccggtgg tgctgcgcgg tgaggtgcgc    660
tggttgtcgg tgacctgctg ggcgctgccg ggcgtcagcg aagaagccag tcgctacttt    720
attgataaca ggctgacgcg cacgctggtg gtgatcaccg acgacaccca acaacgccag    780
cagcaggaac agggccgact tgaccgcctt aaacagcaga tgaccaacgg caaactactg    840
gcagcgatcc gcgaagcgct tgacgccgcg ctgatccagc ttaactgccc catcaatatg    900 ctggcggcg cgcgacgttt aaacggcagt gataacaaca atgtggcgct cgacgccgcg    960
tggcgcgaag gtgaagaggc gatggcgcgg ctgaaacgtt gccgcccgtc gctggaactg   1020
gaaagtgcgc ccgtctggcc gctgcaaccc ttttttgacg atctgcgcgc gctttatcac   1080
acccgctacg agcaggggaa aaatttgcag gtcacgctgg attcccatca tctggtggga   1140
tttggtcagc gtacgcaact gttagcctgc ctgagtctgt ggctcgatcg cacgctggat   1200
attgccgccg ggctgggtga tttcaccgcg caaacgcaga tttacgcccg cgaagaagag   1260
ggctggctct ctttgtatat cactgacaat gtgccgctga tccgctgcg ccacaccccac   1320 tcgccggatg cgcttaacgc tccgggaaaa ggcatggagc tgcgcctgat ccagacgctg   1380
gtggcacacc accacggcgc aatagaactc acttcacacc ccgaaggggg aagttgcctg   1440
accctacgat tcccgctatt tcattcactg accggaggtt caaaatga               1488
```

<210> SEQ ID NO 267

<211> LENGTH: 1575
<212> TYPE: DNA
<213> ORGANISM: Kosakonia sacchari
<220> FEATURE:
<223> OTHER INFORMATION: nifA

<400> SEQUENCE: 267

| | |
|---|---:|
| atgacccagc gaaccgagtc gggtaatacc gtctggcgct tcgatttgtc ccagcagttc | 60 |
| actgcgatgc agcgcataag cgtggtactc agccgggcga ccgaggtcga tcagacgctc | 120 |
| cagcaagtgc tgtgcgtatt gcacaatgac gccttttgc agcacggcat gatctgtctg | 180 |
| tacgacagcc agcaggcgat tttgaatatt gaagcgttgc aggaagccga tcagcagtta | 240 |
| atccccggca gctcgcaaat ccgctatcgt ccgggcgaag ggctggtcgg gacggtgctt | 300 |
| tcgcagggcc aatcattagt gctggcgcgc gttgctgacg atcagcgctt tcttgaccgg | 360 |
| ctcgggttgt atgattacaa cctgccgttt atcgccgtgc cgctgatagg ccagatgcg | 420 |
| cagactttcg gtgtgctgac ggcacaaccc atggcgcgtt acgaagagcg attacccgcc | 480 |
| tgcacccgct ttctggaaac ggtcgctaac ctggtcgcgc aaaccgtgcg tttgatggca | 540 |
| ccaccggcag tgcgcccttc cccgcgcgcc gccataacac aggccgccag cccgaaatcc | 600 |
| tgcacggcct cacgcgcatt tggttttgaa aatatggtcg gtaacagtcc ggcgatgcgc | 660 |
| cagaccatgg agattatccg tcaggtttcg cgctgggaca ccaccgttct ggtacgcggc | 720 |
| gagagtggca ccggcaagga gctgattgcc aacgccatcc accaccattc gccgcgtgcc | 780 |
| ggtgcgccat ttgtgaaatt caactgtgcg gcgctgccgg acacactgct ggaaagcgaa | 840 |
| ttgttcggtc acgagaaagg ggcatttacc ggcgcggtac gccagcgtaa aggccgtttt | 900 |
| gagctggccg atggcggcac gctgtttctt gacgagatcg gcgagagtag cgcctcgttt | 960 |
| caggctaagc tgctgcgcat tttgcaggaa ggcgaaatgg aacgcgtcgg cggcgacgag | 1020 |
| acattgcaag tgaatgtgcg cattattgcc gcgacgaacc gcaatcttga gatgaagtc | 1080 |
| cggctggggc actttcgcga agatctctat tatcgcctga atgtgatgcc catcgccctg | 1140 |
| ccgccactac gcgaacgcca ggaggacatt gccgagctgg cgcactttct ggtgcgtaaa | 1200 |
| atcgcccata accagagccg tacgctgcgc attagcgagg cgctatccg cctgctgatg | 1260 |
| agctacaact ggcccggtaa tgtgcgcgaa ctggaaaact gccttgagcg ctcagcggtg | 1320 |
| atgtcggaga acggtctgat cgatcgggat gtgattttgt taatcatcg cgaccagcca | 1380 |
| gccaaaccgc cagttatcag cgtctcgcat gatgataact ggctcgataa caaccttgac | 1440 |
| gagcgccagc ggctgattgc ggcgctggaa aaagcgggat gggtacaagc caaagccgcg | 1500 |
| cgcttgctgg ggatgacgcc gcgccaggtc gcctatcgta ttcagacgat ggatataacc | 1560 |
| ctgccaaggc tataa | 1575 |

<210> SEQ ID NO 268
<211> LENGTH: 2850
<212> TYPE: DNA
<213> ORGANISM: Kosakonia sacchari
<220> FEATURE:
<223> OTHER INFORMATION: glnE

<400> SEQUENCE: 268

| | |
|---|---:|
| atgccgcacc acgcaggatt gtcgcagcac tggcaaacgg tattttctcg tctgccggaa | 60 |
| tcgctcaccg cgcagccatt gagcgcgcag gcgcagtcag tgctcacttt tagtgatttt | 120 |
| gttcaggaca gcatcatcgc gcatcctgag tggctggcag agcttgaaag cgcgccgccg | 180 |
| cctgcgaacg aatggcaaca ctatgcgcaa tggctgcaag cggcgctgga tggcgtcacc | 240 |

-continued

```
gatgaagcct cgctgatgcg cgcgctgcgg ctgtttcgcc gtcgcatcat ggtgcgcatc    300
gcctggagcc aggcgttaca gttggtggcg gaagaagata tcctgcaaca gcttagcgtg    360
ctggcggaaa ccctgatcgt cgccgcgcgc gactggcttt atgaggcctg ctgccgtgag    420
tggggaacgc cgagcaatcc acaaggcgtg gcgcagccga tgctggtact cggcatgggc    480
aaactgggtg gcggcgaact caatttctca tccgatatcg atttgatttt cgcctggccg    540
gaaaatggcg caacgcgcgg tggacgccgt gagctggata cgcgcaatt tttcactcgc    600 cttggtcaac ggctgattaa agtcctcgac cagccaacgc aggatggctt tgtctaccgc    660
gtcgatatgc gcttgcgccc gtttggcgac agcggcccgc tggtgctgag ctttgccgcg    720
ctggaagatt actaccagga gcaggggcgc gattgggaac gctacgcgat ggtgaaagcg    780
cgcattatgg gcgataacga cggcgaccat gcgcgggagt gcgcgcaat gctgcgcccg    840 tttgttttcc gccgttatat cgacttcagc gtgattcagt ccctgcgtaa catgaaaggc    900
atgattgccc gcgaagtgcg tcgccgtggc ctgaaggaca acattaagct cggcgcgggc    960
gggatccgcg aaatagaatt tatcgtccag ttttccagc tgattcgcgg cggtcgcgag   1020
cctgcactgc aatcgcgttc actgttgccg acgcttgctg ccatagatca actgcatctg   1080
ctgccggatg gcgacgcaac ccggctgcgc gaggcgtatt tgtggctgcg acggctggag   1140
aacctgctgc aaagcatcaa tgacgaacag acacagacgc tgccgggcga tgaactgaat   1200
cgcgcgcgcc tcgcctgggg aatgggcaaa gatagctggg aagcgctctg cgaaacgctg   1260
gaagcgcata tgtcggcggt gcgtcagata tttaacgatc tgattggcga tgatgaaacg   1320
gattcgccgg aagatgcgct ttctgagagc tggcgcgaat tgtggcagga tgcgttgcag   1380
gaggaggatt ccacgcccgt gctggcgcat ctctcagagg acgatcgccg ccgcgtggtg   1440
gcgctgattg ccgattttcg caaagagttg gataaacgca ccattggccc gcgagggcgg   1500
caggtactcg atcacttaat gccgcatctg ctcagcgatg tatgctcgcg cgacgatgcg   1560
ccagtaccgc tgtcacgcct gacgccgctg ctcaccggaa ttattacccg caccacttac   1620
cttgagctgc taagtgaatt tcccggcgca ctgaaacacc tcatttccct gtgtgccgcg   1680
tcgccgatgg ttgccagtca gctggcgcgc tacccgatcc tgcttgatga attgctcgac   1740
ccgaatacgc tctatcaacc gacggcgatg aatgcctatc gcgatgagct gcgccaatac   1800
ctgctgcgcg tgccggaaga tgatgaagag caacagcttg aggcgctgcg gcagtttaag   1860
caggcgcagt tgctgcgcgt ggcggcggcg gatattgccg gtacgttgcc agtaatgaaa   1920
gtgagcgatc acttaacctg gctggcggaa gcgattattg atgcggtggt gcagcaagcc   1980
tgggggcaga tggtggcgcg ttatggccag ccaacgcatc tgcacgatcg cgaagggcgc   2040
ggttttgcgg tggtcggtta tggcaagctg gcggctgggg agctgggtta cagctccgat   2100
ctggatctgg tattcctgca cgactgcccg atggatgtga tgaccgatgg cgagcgtgaa   2160
atcgatggtc gccagttcta tttgcgtctc gcgcagcgcg tgatgcacct gtttagcacg   2220
cgcacgtcgt ccggcatcct ttatgaagtt gatgcgcgtc tgcgtccatc tggcgctgcg   2280
gggatgctgg tcactactac ggaatcgttc gccgattacc agcaaaacga agcctggacg   2340
tgggaacatc aggcgctggc ccgtgcgcgc gtggtgtacg gcgatccgca actgaccgcc   2400
gaatttgacg ccattcgccg cgatattctg atgacgcctc gcgacggcgc aacgctgcaa   2460
accgacgtgc gagaaatgcg cgagaaaatg cgtgcccatc ttggcaacaa gcataaagac   2520
cgcttcgatc tgaaagccga tgaaggcggt atcaccgaca tcgagtttat cgcccaatat   2580
```

```
ctggtgctgc gctttgccca tgacaagccg aaactgacgc gctggtcgga taatgtgcgc    2640
attctcgaag ggctggcgca aaacggcatc atggaggagc aggaagcgca ggcattgacg    2700
ctggcgtaca ccacattgcg tgatgagctg caccacctgg cgctgcaaga gttgccggga    2760
catgtggcgc tctcctgttt tgtcgccgag cgtgcgctta ttaaaaccag ctgggacaag    2820
tggctggtgg aaccgtgcgc cccggcgtaa                                      2850
```

<210> SEQ ID NO 269
<211> LENGTH: 1536
<212> TYPE: DNA
<213> ORGANISM: Kosakonia sacchari
<220> FEATURE:
<223> OTHER INFORMATION: 16S-3
<220> FEATURE:
<221> NAME/KEY: modified_base
<222> LOCATION: (766)..(776)
<223> OTHER INFORMATION: a, c, t, g, unknown or other
<220> FEATURE:
<221> NAME/KEY: modified_base
<222> LOCATION: (905)..(905)
<223> OTHER INFORMATION: a, c, t, g, unknown or other

<400> SEQUENCE: 269

```
attgaagagt ttgatcatgg ctcagattga acgctggcgg caggcctaac acatgcaagt      60
cgaacggtag cacagagagc ttgctctcgg gtgacgagtg cggacgggt gagtaatgtc      120 tgggaaactg cctgatggag ggggataact actggaaacg gtagctaata ccgcataacg     180
tcgcaagacc aaagaggggg accttcgggc ctcttgccat cagatgtgcc cagatgggat    240
tagctagtag gtgggataac ggctcaccta ggcgacgatc cctagctggt ctgagaggat    300
gaccagccac actggaactg agacacggtc cagactccta cgggaggcag cagtggggaa    360
tattgcacaa tgggcgcaag cctgatgcag ccatgccgcg tgtgtgaaga aggccttcgg    420
gttgtaaagc actttcagcg gggaggaagg gagtaaggtt aataaccttg ctcattgacg    480
ttacccgcag aagaagcacc ggctaactcc gtgccagcag ccgcggtaat acggagggtg    540
caagcgttaa tcggaattac tgggcgtaaa gcgcacgcag gcggtctgtc aagtcggatg    600
tgaaatcccc gggctcaacc tgggaactgc atccgaaact ggcaggcttg agtctcgtag    660
agggaggtag aattccaggt gtagcggtga atgcgtaga gatctggagg aataccggtg    720
gcgaaggcgg cctcctggac gaagactgac gctcaggtgc gaaagnnnnn nnnnnnaaca    780
ggattagata ccctggtagt ccatgccgta aacgatgtct actagccgtt ggggcctttg    840
aggctttagt ggcgcagcta acgcgataag tagaccgcct ggggagtacg gtcgcaagac    900
taaanctcaa atgaattgac ggggccccgc acaagcggtg gagcatgtgg tttaattcga    960
tgcaacgcga agaaccttac ctggccttga catagtaaga ttttccaga gatggattgg    1020 tgccttcggg aacttacata caggtgctgc atggctgtcg tcagctcgtg tcgtgagatg    1080
ttgggttaag tcccgcaacg agcgcaaccc ttgtcattag ttgctacatt tagttgggca    1140
ctctaatgag actgccggtg acaaaccgga ggaaggtggg gatgacgtca agtcctcatg    1200
gcccttatag gtggggctac acacgtcata caatggctgg tacaaagggt tgccaacccg    1260 cgaggggag ctaatcccat aaaaccagtc gtagtccgga tcgcagtctg caactcgact    1320
gcgtgaagtc ggaatcgcta gtaatcgtgg atcagaatgt cacggtgaat acgttcccgg    1380
gtcttgtaca caccgcccgt cacaccatgg gagcgggttc tgccagaagt agttagctta    1440
accgcaagga gggcgattac cacggcaggg ttcgtgactg gggtgaagtc gtaacaaggt    1500
agccgtatcg gaaggtgcgg ctggatcacc tccttt                             1536
```

<210> SEQ ID NO 270
<211> LENGTH: 882
<212> TYPE: DNA
<213> ORGANISM: Kosakonia sacchari
<220> FEATURE:
<223> OTHER INFORMATION: nifD1

<400> SEQUENCE: 270

| | | | | | |
|---|---|---|---|---|---|
| atgaccatgc | gtcaatgcgc | catttacggc | aaaggtggga | tcggcaaatc | gaccaccaca | 60 |
| cagaacctgg | tcgccgcgct | ggcggagatg | ggtaaaaaag | tcatgattgt | cggctgtgac | 120 |
| ccgaaagccg | attccacgcg | tttgatcctg | catgcgaaag | cgcagaacac | cattatggag | 180 |
| atggctgctg | aagtcggctc | cgtggaagac | ctggagttag | aagacgtgct | gcaaatcggt | 240 |
| tacggcggcg | tgcgctgcgc | agagtccggc | ggcccggagc | caggcgtggg | ctgtgccggt | 300 |
| cgcggggtga | tcaccgcgat | taacttcctc | gaagaagaag | cgcttacgt | gccggatctc | 360 |
| gattttgttt | tctacgacgt | gctgggcgac | gtggtatgcg | gtggtttcgc | catgccgatt | 420 |
| cgtgaaaaca | agcgcagga | gatctacatc | gtttgctctg | cgaaatgat | ggcgatgtac | 480 |
| gccgccaaca | catctccaa | aggcatcgtg | aaatacgcca | atccggtaa | agtgcgcctc | 540 |
| ggcgggctga | tttgtaactc | gcgccagacc | gaccgtgaag | atgaactgat | cattgcgctg | 600 |
| gcagaaaaac | tcggcacgca | gatgatccac | tttgttcccc | gcgacaacat | tgtgcagcgt | 660 |
| gcggaaatcc | gccgtatgac | ggttatcgaa | tatgacccga | cctgcaatca | ggcgaacgaa | 720 |
| tatcgcagcc | ttgccagcaa | aatcgtcaac | aacaccaaaa | tggtggtgcc | cacccccctgc | 780 |
| accatggatg | aactggaaga | actgctgatg | gagttcggca | ttatggatgt | ggaagacacc | 840 |
| agcatcattg | gtaaaaccgc | cgccgaagaa | aacgccgtct | ga | | 882 |

<210> SEQ ID NO 271
<211> LENGTH: 1386
<212> TYPE: DNA
<213> ORGANISM: Kosakonia sacchari
<220> FEATURE:
<223> OTHER INFORMATION: nifK1

<400> SEQUENCE: 271

| | | | | | |
|---|---|---|---|---|---|
| atggccgaaa | ttctgcgcag | taaaaaaccg | ctggcggtca | gcccgataaa | aagcggccag | 60 |
| ccgctggggg | cgatcctcgc | aagcctgggt | gtcgaacagt | gcataccgct | ggtacacggc | 120 |
| gcacagggat | gtagcgcgtt | cgcgaaggtg | ttctttattc | aacattttca | cgatccgatc | 180 |
| ccgctgcaat | cgacggcgat | ggatccgact | tccaccatta | tgggcgccga | tgaaaacatt | 240 |
| tttaccgcgc | tcaatgtgct | ctgccagcgc | aacgccgcga | agccattgt | gctgctcagc | 300 |
| accgggcttt | cagaagccca | gggcagcgac | atttcgcggg | tggtgcgcca | gtttcgtgat | 360 |
| gattttcccc | ggcataaagg | cgttgcgctg | ctcaccgtca | acacacccga | tttctacggc | 420 |
| tcgctggaaa | acggctacag | cgccgtgctg | aaagcatga | ttgaacagtg | ggtaccgca | 480 |
| cagcccgccg | ccagcctgcg | caaccgccgt | gtcaacctgc | tggtcagcca | tttactgaca | 540 |
| ccaggcgata | tcgaactgtt | gcgcagttat | gttgaagcct | tcggcctgca | accggtgatt | 600 |
| gtgccggatc | tgtcgctgtc | gctggacggg | catctggcag | acggtgattt | tcgcctgtt | 660 |
| acccaagggg | gaacatcgct | gcgcatgatt | gaacagatgg | ggcaaaacct | ggccacctttt | 720 |
| gtgattggcg | cctcgctggg | ccgtgcggcg | cgttactgg | cgcagcgcag | ccgtggcgag | 780 |
| gtgatcgccc | tgccgcatct | gatgacgctt | gcagcctgcg | acacgtttat | tcatcgactg | 840 |

```
aaaaccctct ccgggcgcga tgtccccgcg tggattgagc gccagcgcgg ccaagttcag      900
gatgcgatga tcgattgcca tatgtggctg cagggtgcgg ctatcgccat ggcagcagaa      960
ggcgatcacc tggcggcatg gtgcgatttc gcccgcagcc agggcatgat ccccggcccg     1020
attgtcgcac cggtcagcca gccggggttg caaaatctgc cggttgaaac cgtggttatc     1080
ggcgatctgg aagatatgca ggatcggctt tgcgcgacgc ccgccgcgtt actggtggcc     1140
aattctcatg ccgccgatct cgccacgcag tttgatttgt cacttatccg cgccgggttc     1200
ccggtgtatg accggctggg ggaatttcgt cgcctgcgcc aggggtacag cggcattcgt     1260
gacacgctgt ttgagctggc gaatgtgatg cgcgagcgcc atcacccgct tgcaacctac     1320
cgctcgccgc tgcgccagca cgccgacgac aacgttacgc ctggagatct gtatgccgca     1380
tgttaa                                                                1386
```

<210> SEQ ID NO 272
<211> LENGTH: 1287
<212> TYPE: DNA
<213> ORGANISM: Kosakonia sacchari
<220> FEATURE:
<223> OTHER INFORMATION: amtB

<400> SEQUENCE: 272

```
atgaaaaaca caacattaaa aacagcgctt gcttcgctgg cgttactgcc tggcctggcg       60
atggcggctc ccgctgtggc ggataaagcc gacaacggct ttatgatgat ttgcaccgcg      120
ctggtgctgt ttatgaccat tccgggcatt gcgctgttct acggcggttt gatccgcggt      180
aaaaacgtgc tgtcgatgct gacgcaggtt gccgtcacct tcgcactggt gtgcattctg      240
tgggtggtgt atggctactc gctggcattt ggcgagggca acagcttctt cgggagtttt      300
aactgggcga tgttgaaaaa catcgaactg aaagccgtga tgggcagcat ttatcagtat      360
atccacgtgg cgttccaggg ttccttcgcc tgtatcaccg ttggcctgat tgtcggtgca      420
ctggctgagc gtattcgctt ctctgcgtg ctgattttg tggtggtatg gctgacgctt      480
tcttacgtgc cgattgcaca catggtgtgg ggcggcggtc tgctggcaac ccacggtgcg      540
ctggatttcg caggcggtac ggttgttcac atcaacgctg cgattgcagg tctggtgggg      600
gcttacctga ttggcaaacg cgtgggcttt ggcaaagaag cattcaaacc gcataacctg      660
ccgatggtct tcactggcac cgctatcctg tatgttggct ggtttggttt caacgccggc      720
tccgcaagct cggcgaacga aattgctgcg ctggccttcg tgaacactgt cgttgccact      780
gctgccgcta ttctggcgtg ggtatttggc gaatgggcaa tgcgcggcaa gccgtctctg      840
ctcggtgcct gttctggtgc catcgcgggt ctggttggta tcaccccgc ctgtggttat      900 gtgggtgtcg gcggtcgct gattgtgggt ctgattgccg gtctggctgg gctgtggggc      960
gttactgcgc tgaaacgtat gttgcgtgtc gatgacccgt gtgacgtatt cggtgtgcac     1020
ggcgtgtgcg gcatcgtggg ctgtatcctg acgggtatct tcgcctctac gtcgctgggt     1080
ggtgtcggtt tcgctgaagg tgtgaccatg gccatcagg tgctggtgca gctggaaagt     1140
gttgccatca ctatcgtgtg gtctggcgtg gtggccttta ttggttacaa actggcggac     1200
atgacggtag gcctgcgcgt accggaagaa caagaacgtg aagggctgga tgtaaacagc     1260
cacggcgaaa acgcctataa cgcctga                                         1287
```

<210> SEQ ID NO 273
<211> LENGTH: 348
<212> TYPE: DNA
<213> ORGANISM: Kosakonia sacchari

```
<220> FEATURE:
<223> OTHER INFORMATION: Prm1

<400> SEQUENCE: 273
cgtcctgtaa taataaccgg acaattcgga ctgattaaaa aagcgccctt gtggcgcttt      60
ttttatattc ccgcctccat ttaaaataaa aatccaatc ggatttcact atttaaactg     120
gccattatct aagatgaatc cgatggaagc tcgctgtttt aacacgcgtt ttttaacctt    180
ttattgaaag tcggtgcttc tttgagcgaa cgatcaaatt taagtggatt cccatcaaaa    240
aaatattctc aacctaaaaa agtttgtgta atacttgtaa cgctacatgg agattaactc    300
aatctagagg gtattaataa tgaatcgtac taaactggta ctgggcgc                 348

<210> SEQ ID NO 274
<211> LENGTH: 313
<212> TYPE: DNA
<213> ORGANISM: Kosakonia sacchari
<220> FEATURE:
<223> OTHER INFORMATION: Prm5

<400> SEQUENCE: 274
ggacatcatc gcgacaaaca atattaatac cggcaaccac accggcaatt tacgagactg     60
cgcaggcatc ctttctcccg tcaatttctg tcaaataaag taaagaggc agtctacttg    120 aattacccc ggctggttga gcgtttgttg aaaaaaagta actgaaaaat ccgtagaata    180
gcgccactct gatggttaat taacctattc aattaagaat tatctggatg aatgtgccat    240
taaatgcgca gcataatggt gcgttgtgcg ggaaaactgc ttttttttga aagggttggt    300
cagtagcgga aac                                                       313

<210> SEQ ID NO 275
<211> LENGTH: 1485
<212> TYPE: DNA
<213> ORGANISM: Rahnella aquatilis
<220> FEATURE:
<223> OTHER INFORMATION: nifL

<400> SEQUENCE: 275
atgaccctga atatgatgct cgataacgcc gcgccggagg ccatcgccgg cgcgctgact     60
caacaacatc cggggctgtt ttttaccatg gtggaacagg cctcggtggc catctccctc    120
accgatgcca gcgccaggat catttacgcc aacccggcgt tttgccgcca gaccggctat    180
tcgctggcgc aattgttaaa ccagaacccg cgcctgctgg ccagcagcca gacgccgcgc    240
gagatctatc aggagatgtg gcatacccctg ctccagcgtc agcccctggcg cggtcagctg    300 attaatcagc gtcgggacgg cggcctgtac ctggtggaga ttgacatcac cccggtgctt    360
agcccgcaag gggaactgga gcattatctg gcgatgcagc gggatatcag cgtcagctac    420
accctcgaac agcggctgcg caaccatatg accctgatgg aggcggtgct gaataatatc    480
cccgccgccg tggtagtggt ggacgagcag gatcgggtgg tgatgacaa cctcgcctac    540 aaaaccttct gcgctgactg cggcggccgg gagctgctca ccgagctgca ggtctcccct    600
ggccggatga cgcccggcgt ggaggcgatc ctgccggtgg cgctgcgcgg ggccgcgcgc    660
tggctgtcgg taacctgctg gccgttgccc ggcgtcagtg aagaggccag ccgctacttt    720
atcgacagcg cgctggcgcg gaccctggtg gtgatcgccg actgtaccca gcagcgtcag    780
cagcaggagc aagggcgcct tgaccggctg aagcagcaaa tgaccgccgg caagctgctg    840
gcggcgatcc gcgagtcgct ggacgccgcg ctgatccagc tgaactgccc gattaatatg    900
```

| | |
|---|---|
| ctggcggcag cccgtcggct gaacggcgag ggaagcggga atgtggcgct ggaggccgcc | 960 |
| tggcgtgaag gggaagaggc gatggcgcgg ctccagcgct gtcgcccatc gctggaactc | 1020 |
| gaaaaccccg ccgtctggcc gctgcagccc tttttcgacg atctgtgcgc cctctaccgt | 1080 |
| acacgcttcg atcccgacgg gctgcaggtc gacatggcct caccgcatct gatcggcttt | 1140 |
| ggccagcgca ccccactgct ggcgtgctta agcctgtggc tcgatcgcac cctggccctc | 1200 |
| gccgccgaac tcccctccgt gccgctggcg atgcagctct acgccgagga gaacgacggc | 1260 |
| tggctgtcgc tgtatctgac tgacaacgta ccgctgctgc aggtgcgcta cgctcactcc | 1320 |
| cccgacgcgc tgaactcgcc gggcaaaggc atggagctgc ggctgatcca gaccctggtg | 1380 |
| gcgcaccatc gcggggccat tgagctggct tcccgaccgc agggcggcac ctgcctgacc | 1440 |
| ctgcgtttcc cgctgtttaa caccctgacc ggaggtgaag catga | 1485 |

<210> SEQ ID NO 276
<211> LENGTH: 1575
<212> TYPE: DNA
<213> ORGANISM: Rahnella aquatilis
<220> FEATURE:
<223> OTHER INFORMATION: nifA

<400> SEQUENCE: 276

| | |
|---|---|
| atgatccctg aatccgaccc ggacaccacc gtcagacgct tcgacctctc tcagcagttc | 60 |
| accgccatgc agcggataag cgtggtgctg agccgggcca ccgaggccag caaaacgctg | 120 |
| caggaggtgc tcagcgtatt acacaacgat gcctttatgc agcacgggat gatctgcctg | 180 |
| tacgacagcg agcaggagat cctcagtatc gaagcgctgc agcaaaccgg ccagcagccc | 240 |
| ctccccggca gcacgcagat ccgctatcgc cccggcgagg gactggtggg gaccgtgctg | 300 |
| gcccaggggc agtcgctggt gctgccccgg gtcgccgacg atcagcgttt tctcgaccgc | 360 |
| ctgagcctct acgattacga tctgccgttt atcgccgtac cgttgatggg gcccaacgcc | 420 |
| cggccaatag gggtgctggc ggcccagccg atggcgcgcc aggaagagcg gctgccggcc | 480 |
| tgcacccgtt ttctcgaaac cgtcgccaac ctcgtcgccc agaccatccg gctgatgatc | 540 |
| cttccggcct cacccgccct gtcgagccgc cagccgccga aggtggaacg gccgccggcc | 600 |
| tgctcgtcgt cgcgcggcgt gggccttgac aatatggtcg gcaagagccc ggcgatgcgc | 660 |
| cagatcgtgg aggtgatccg tcaggtttcg cgctgggaca ccaccgtgct ggtacgcggc | 720 |
| gaaagcggca ccgggaaaga gctgatcgcc aacgccatcc atcaccattc gccacgggct | 780 |
| ggcgccgcct tcgtcaaatt taactgcgcg gcgctgccgg acaccctgct ggaaagcgaa | 840 |
| ctgttcggcc atgagaaagg cgcctttacc ggggcggtgc gtcagcgtaa aggacgtttt | 900 |
| gagctggcgg atggcggcac cctgttcctc gatgagattg tgaaagcag cgcctcgttc | 960 |
| caggccaagc tgctgcgtat cctccaggag ggggagatgg agcgggtcgg cggcgatgag | 1020 |
| accctgcggg tgaatgtccg catcatcgcc gccaccaacc gtcacctgga ggaggaggtc | 1080 |
| cggctgggcc atttccgcga ggatctctac tatcgtctga acgtgatgcc catcgccctg | 1140 |
| ccccccgctgc gcgagcgtca ggaggacatc gccgagctgg cgcacttcct ggtgcgcaaa | 1200 |
| atcggccagc atcaggggcg cacgctgcgg atcagcgagg cgcgatccg cctgctgatg | 1260 |
| gagtacagct ggccgggtaa cgttcgcgaa ctggagaact gcctcgaacg atcggcggtg | 1320 |
| atgtcggaga gtggcctgat cgatcgcgac gtgatcctct tcactcacca ggatcgtccc | 1380 |
| gccaaagccc tgcctgccag cgggccagcg gaagacagct ggctggacaa cagcctggac | 1440 |
| gaacgtcagc gactgatcgc cgcgctggaa aaagccggct gggtgcaggc caaggcggca | 1500 |

```
cggctgctgg ggatgacgcc gcgccaggtc gcttatcgga tccagatcat ggatatcacc    1560
ctgccgcgtc tgtag                                                      1575

<210> SEQ ID NO 277
<211> LENGTH: 1540
<212> TYPE: DNA
<213> ORGANISM: Rahnella aquatilis
<220> FEATURE:
<223> OTHER INFORMATION: 16S-1

<400> SEQUENCE: 277
attgaagagt tgatcatgg ctcagattga acgctggcgg caggcctaac acatgcaagt      60
cgagcggcag cgggaagtag cttgctactt tgccggcgag cggcggacgg gtgagtaatg    120
tctgggaaac tgcctgatgg aggggggataaa ctactggaaa cggtagctaa taccgcatga  180
cctcgaaaga gcaaagtggg ggatcttcgg acctcacgcc atcggatgtg cccagatggg   240
attagctagt aggtgaggta atggctcacc taggcgacga tccctagctg gtctgagagg   300
atgaccagcc acactggaac tgagacacgg tccagactcc tacgggaggc agcagtgggg   360
aatattgcac aatgggcgca agcctgatgc agccatgccg cgtgtgtgaa gaaggcctta   420
gggttgtaaa gcactttcag cgaggaggaa ggcatcatac ttaatacgtg tggtgattga   480
cgttactcgc agaagaagca ccggctaact ccgtgccagc agccgcggta atacggaggg   540
tgcaagcgtt aatcggaatt actgggcgta aagcgcacgc aggcggtttg ttaagtcaga   600
tgtgaaatcc ccgagcttaa cttgggaact gcatttgaaa ctggcaagct agagtcttgt   660 agagggggt agaattccag gtgtagcggt gaaatgcgta gagatctgga ggaataccgg    720
tggcgaaggc ggccccctgg acaaagactg acgctcaggt gcgaaagcgt ggggagcaaa   780
caggattaga taccctggta gtccacgctg taaacgatgt cgacttggag gttgtgccct   840
tgaggcgtgg cttccggagc taacgcgtta agtcgaccgc ctgggagta cggccgcaag    900 gttaaaactc aaatgaattg acgggggccc gcacaagcgg tggagcatgt ggtttaattc   960
gatgcaacgc gaagaacctt acctactctt gacatccaga gaatttgcca gagatggcga  1020
agtgccttcg ggaactctga gacaggtgct gcatggctgt cgtcagctcg tgttgtgaaa  1080
tgttgggtta agtcccgcaa cgagcgcaac ccttatcctt tgttgccagc acgtaatggt  1140
gggaactcaa aggagactgc cggtgataaa ccggaggaag gtgggggatga cgtcaagtca  1200 tcatggccct tacgagtagg gctacacacg tgctacaatg gcatatacaa agagaagcga  1260
actcgcgaga gcaagcggac ctcataaagt atgtcgtagt ccggattgga gtctgcaact  1320
cgactccatg aagtcggaat cgctagtaat cgtagatcag aatgctacgg tgaatacgtt  1380
cccgggcctt gtacacaccg cccgtcacac catgggagtg ggttgcaaaa gaagtaggta  1440
gcttaacctt cgggagggcg cttaccactt tgtgattcat gactggggtg aagtcgtaac  1500
aaggtaaccg tagggggaacc tgcggttgga tcacctcctt                        1540

<210> SEQ ID NO 278
<211> LENGTH: 1540
<212> TYPE: DNA
<213> ORGANISM: Rahnella aquatilis
<220> FEATURE:
<223> OTHER INFORMATION: 16S-2
<220> FEATURE:
<221> NAME/KEY: modified_base
<222> LOCATION: (267)..(267)
<223> OTHER INFORMATION: a, c, t, g, unknown or other
```

<400> SEQUENCE: 278

```
attgaagagt ttgatcatgg ctcagattga acgctggcgg caggcctaac acatgcaagt      60
cgagcggcat cgggaagtag cttgctactt tgccggcgag cggcggacgg gtgagtaatg     120
tctgggaaac tgcctgatgg aggggggataa ctactggaaa cggtagctaa taccgcatga    180
cctcgaaaga gcaaagtggg ggatcttcgg acctcacgcc atcggatgtg cccagatggg    240
attagctagt aggtgaggta atggctnacc taggcgacga tccctagctg gtctgagagg    300
atgaccagcc acactggaac tgagacacgg tccagactcc tacgggaggc agcagtgggg    360
aatattgcac aatgggcgca agcctgatgc agccatgccg cgtgtgtgaa gaaggcctta    420
gggttgtaaa gcactttcag cgaggaggaa ggcatcatac ttaatacgtg tggtgattga    480
cgttactcgc agaagaagca ccggctaact ccgtgccagc agccgcggta atacggaggg    540
tgcaagcgtt aatcggaatt actgggcgta aagcgcacgc aggcggtttg ttaagtcaga    600
tgtgaaatcc ccgagcttaa cttgggaact gcatttgaaa ctggcaagct agagtcttgt    660
agagggggggt agaattccag gtgtagcggt gaaatgcgta gagatctgga ggaataccgg    720
tggcgaaggc ggccccctgg acaaagactg acgctcaggt gcgaaagcgt ggggagcaaa    780
caggattaga taccctggta gtccacgctg taaacgatgt cgacttggag gttgtgccct    840
tgaggcgtgg cttccggagc taacgcgtta agtcgaccgc ctgggagta cggccgcaag    900
gttaaaactc aaatgaattg acggggggccc gcacaagcgg tggagcatgt ggtttaattc    960
gatgcaacgc gaagaacctt acctactctt gacatccaga gaatttgcca gagatggcga   1020
agtgccttcg ggaactctga cacaggtgct gcatggctgt cgtcagctcg tgttgtgaaa   1080
tgttgggtta agtcccgcaa cgagcgcaac ccttatcctt tgttgccagc acgtgatggt   1140
gggaactcaa aggagactgc cggtgataaa ccggaggaag gtgggggatga cgtcaagtca   1200
tcatggccct tacgagtagg gctacacacg tgctacaatg gcatatacaa agagaagcga   1260
actcgcgaga gcaagcggac ctcataaagt atgtcgtagt ccggattgga gtctgcaact   1320
cgactccatg aagtcggaat cgctagtaat cgtagatcag aatgctacgg tgaatacgtt   1380
cccgggcctt gtacacaccg cccgtcacac catgggagtg ggttgcaaaa gaagtaggta   1440
gcttaacctt cgggagggcg cttaccactt tgtgattcat gactgggggtg aagtcgtaac   1500
aaggtaaccg taggggaacc tgcggttgga tcacctcctt                          1540
```

<210> SEQ ID NO 279
<211> LENGTH: 1540
<212> TYPE: DNA
<213> ORGANISM: Rahnella aquatilis
<220> FEATURE:
<223> OTHER INFORMATION: 16S-3
<220> FEATURE:
<221> NAME/KEY: modified_base
<222> LOCATION: (455)..(455)
<223> OTHER INFORMATION: a, c, t, g, unknown or other

<400> SEQUENCE: 279

```
attgaagagt ttgatcatgg ctcagattga acgctggcgg caggcctaac acatgcaagt      60
cgagcggcag cgggaagtag cttgctactt tgccggcgag cggcggacgg gtgagtaatg    120
tctgggaaac tgcctgatgg aggggggataa ctactggaaa cggtagctaa taccgcatga    180
cctcgaaaga gcaaagtggg ggatcttcgg acctcacgcc atcggatgtg cccagatggg    240
attagctagt aggtgaggta atggctcacc taggcgacga tccctagctg gtctgagagg    300
atgaccagcc acactggaac tgagacacgg tccagactcc tacgggaggc agcagtgggg    360
```

```
aatattgcac aatgggcgca agcctgatgc agccatgccg cgtgtgtgaa gaaggcctta      420 ggggttgtaaa gcactttcag cgaggaggaa ggcancatac ttaatacgtg tggtgattga     480
cgttactcgc agaagaagca ccggctaact ccgtgccagc agccgcggta atacggaggg     540
tgcaagcgtt aatcggaatt actgggcgta aagcgcacgc aggcggtttg ttaagtcaga     600
tgtgaaatcc ccgagcttaa cttgggaact gcatttgaaa ctggcaagct agagtcttgt    660
agaggggggt agaattccag gtgtagcggt gaaatgcgta gagatctgga ggaataccgg    720
tggcgaaggc ggccccctgg acaaagactg acgctcaggt gcgaaagcgt ggggagcaaa    780
caggattaga taccctggta gtccacgctg taaacgatgt cgacttggag gttgtgccct    840
tgaggcgtgg cttccggagc taacgcgtta agtcgaccgc ctggggagta cggccgcaag    900
gttaaaactc aaatgaattg acgggggccc gcacaagcgg tggagcatgt ggtttaattc    960
gatgcaacgc gaagaacctt acctactctt gacatccaga gaatttgcca gagatggcga   1020
agtgccttcg ggaactctga cacaggtgct gcatggctgt cgtcagctcg tgttgtgaaa   1080
tgttgggtta agtcccgcaa cgagcgcaac ccttatcctt gttgccagc acgtgatggt    1140 gggaactcaa aggagactgc cggtgataaa ccggaggaag gtgggatga cgtcaagtca    1200 tcatggccct tacgagtagg gctacacacg tgctacaatg gcatatacaa agagaagcga   1260
actcgcgaga gcaagcggac ctcataaagt atgtcgtagt ccggattgga gtctgcaact   1320
cgactccatg aagtcggaat cgctagtaat cgtagatcag aatgctacgg tgaatacgtt   1380
cccgggcctt gtacacaccg cccgtcacac catgggagtg ggttgcaaaa gaagtaggta   1440
gcttaacctt cgggagggcg cttaccactt tgtgattcat gactggggtg aagtcgtaac   1500
aaggtaaccg tagggaacc tgcggttgga tcacctcctt                           1540

<210> SEQ ID NO 280
<211> LENGTH: 1540
<212> TYPE: DNA
<213> ORGANISM: Rahnella aquatilis
<220> FEATURE:
<223> OTHER INFORMATION: 16S-4
<220> FEATURE:
<221> NAME/KEY: modified_base
<222> LOCATION: (70)..(70)
<223> OTHER INFORMATION: a, c, t, g, unknown or other

<400> SEQUENCE: 280
attgaagagt ttgatcatgg ctcagattga acgctggcgg caggcctaac acatgcaagt    60
cgagcggcan cggaagtag cttgctactt tgccggcgag cggcggacgg gtgagtaatg    120
tctgggaaac tgcctgatgg aggggggataa ctactggaaa cggtagctaa taccgcatga   180
cctcgaaaga gcaaagtggg ggatcttcgg acctcacgcc atcggatgtg cccagatggg    240
attagctagt aggtgaggta atggcttacc taggcgacga tccctagctg gtctgagagg    300
atgaccagcc acactggaac tgagacacgg tccagactcc tacggaggc agcagtgggg    360 aatattgcac aatgggcgca agcctgatgc agccatgccg cgtgtgtgaa gaaggcctta    420
gggttgtaaa gcactttcag cgaggaggaa ggcatcacac ttaatacgtg tggtgattga    480
cgttactcgc agaagaagca ccggctaact ccgtgccagc agccgcggta atacggaggg    540
tgcaagcgtt aatcggaatt actgggcgta aagcgcacgc aggcggtttg ttaagtcaga    600
tgtgaaatcc ccgagcttaa cttgggaact gcatttgaaa ctggcaagct agagtcttgt    660
agaggggggt agaattccag gtgtagcggt gaaatgcgta gagatctgga ggaataccgg    720
```

```
tggcgaaggc ggccccctgg acaaagactg acgctcaggt gcgaaagcgt ggggagcaaa      780
caggattaga taccctggta gtccacgctg taaacgatgt cgacttggag gttgtgccct      840
tgaggcgtgg cttccggagc taacgcgtta agtcgaccgc ctggggagta cggccgcaag      900
gttaaaactc aaatgaattg acgggggccc gcacaagcgg tggagcatgt ggtttaattc      960
gatgcaacgc gaagaacctt acctactctt gacatccaga gaatttgcca gagatggcga     1020
agtgccttcg ggaactctga acaggtgctg catggctgtc gtcagctcgt gttgtgaaa      1080
tgttgggtta agtcccgcaa cgagcgcaac ccttatcctt gttgccagc acgtgatggt      1140
gggaactcaa aggagactgc cggtgataaa ccggaggaag gtgggga tga cgtcaagtca     1200
tcatggccct tacgagtagg gctacacacg tgctacaatg gcatatacaa agagaagcga     1260
actcgcgaga gcaagcggac ctcataaagt atgtcgtagt ccggattgga gtctgcaact     1320
cgactccatg aagtcggaat cgctagtaat cgtagatcag aatgctacgg tgaatacgtt     1380
cccgggcctt gtacacaccg cccgtcacac catgggagtg ggttgcaaaa gaagtaggta     1440
gcttaacctt cggagggcg cttaccactt tgtgattcat gactggggtg aagtcgtaac     1500
aaggtaaccg tagggaacc tgcggttgga tcacctcctt                            1540
```

<210> SEQ ID NO 281
<211> LENGTH: 1540
<212> TYPE: DNA
<213> ORGANISM: Rahnella aquatilis
<220> FEATURE:
<223> OTHER INFORMATION: 16S-5

<400> SEQUENCE: 281

```
attgaagagt ttgatcatgg ctcagattga acgctggcgg caggcctaac acatgcaagt       60
cgagcggcag cgggaagtag cttgctactt tgccggcgag cggcggacgg gtgagtaatg      120
tctgggaaac tgcctgatgg agggggataa ctactggaaa cggtagctaa taccgcatga      180
cctcgaaaga gcaaagtggg ggatcttcgg acctcacgcc atcggatgtg cccagatggg      240
attagctagt aggtgaggta atggctcacc taggcgacga tccctagctg gtctgagagg      300
atgaccagcc acactggaac tgagacacgg tccagactcc tacgggaggc agcagtgggg      360
aatattgcac aatgggcgca agcctgatgc agccatgccg cgtgtgtgaa gaaggcctta      420
gggttgtaaa gcactttcag cgaggaggaa ggcatcacac ttaatacgtg tgttgattga      480
cgttactcgc agaagaagca ccggctaact ccgtgccagc agccgcggta atacggaggg      540
tgcaagcgtt aatcggaatt actgggcgta aagcgcacgc aggcggtttg ttaagtcaga      600
tgtgaaatcc ccgagcttaa cttgggaact gcatttgaaa ctggcaagct agagtcttgt      660
agaggggggt agaattccag gtgtagcggt gaaatgcgta gagatctgga ggaataccgg      720
tggcgaaggc ggcccctgg acaaagactg acgctcaggt gcgaaagcgt ggggagcaaa      780
caggattaga taccctggta gtccacgctg taaacgatgt cgacttggag gttgtgccct      840
tgaggcgtgg cttccggagc taacgcgtta agtcgaccgc ctggggagta cggccgcaag      900
gttaaaactc aaatgaattg acgggggccc gcacaagcgg tggagcatgt ggtttaattc      960
gatgcaacgc gaagaacctt acctactctt gacatccaga gaatttgcca gagatggcga     1020
agtgccttcg ggaactctga acaggtgctg catggctgtc gtcagctcgt gttgtgaaa      1080
tgttgggtta agtcccgcaa cgagcgcaac ccttatcctt gttgccagc acgtgatggt      1140
gggaactcaa aggagactgc cggtgataaa ccggaggaag gtggggatga cgtcaagtca     1200
tcatggccct tacgagtagg gctacacacg tgctacaatg gcatatacaa agagaagcga     1260
```

-continued

```
actcgcgaga gcaagcggac ctcataaagt atgtcgtagt ccggattgga gtctgcaact    1320
cgactccatg aagtcggaat cgctagtaat cgtagatcag aatgctacgg tgaatacgtt    1380
cccgggcctt gtacacaccg cccgtcacac catgggagtg ggttgcaaaa gaagtaggta    1440
gcttaacctt cgggagggcg cttaccactt tgtgattcat gactggggtg aagtcgtaac    1500
aaggtaaccg tagggaacc tgcggttgga tcacctcctt                           1540
```

<210> SEQ ID NO 282
<211> LENGTH: 1009
<212> TYPE: DNA
<213> ORGANISM: Rahnella aquatilis
<220> FEATURE:
<223> OTHER INFORMATION: 16S-6
<220> FEATURE:
<221> NAME/KEY: modified_base
<222> LOCATION: (296)..(296)
<223> OTHER INFORMATION: a, c, t, g, unknown or other
<220> FEATURE:
<221> NAME/KEY: modified_base
<222> LOCATION: (311)..(311)
<223> OTHER INFORMATION: a, c, t, g, unknown or other
<220> FEATURE:
<221> NAME/KEY: modified_base
<222> LOCATION: (973)..(973)
<223> OTHER INFORMATION: a, c, t, g, unknown or other

<400> SEQUENCE: 282

```
gtagctaata ccgcatgacc tcgaaagagc aaagtggggg atcttcggac ctcacgccat      60
cggatgtgcc cagatgggat tagctagtag gtgaggtaat ggctcaccta ggcgacgatc     120
cctagctggt ctgagaggat gaccagccac actggaactg agacacggtc cagactccta     180
cgggaggcag cagtggggaa tattgcacaa tgggcgcaag cctgatgcag ccatgccgcg     240
tgtgtgaaga aggccttagg gttgtaaagc actttcagcg aggaggaagg catcanactt     300
aatacgtgtg ntgattgacg ttactcgcag aagaagcacc ggctaactcc gtgccagcag     360
ccgcggtaat acgagggtg caagcgttaa tcggaattac tgggcgtaaa gcgcacgcag     420
gcggtttgtt aagtcagatg tgaaatcccc gagcttaact tgggaactgc atttgaaact     480
ggcaagctag agtcttgtag aggggggtag aattccaggt gtagcggtga atgcgtaga     540 gatctggagg aataccggtg gcgaaggcgg cccctggac aaagactgac gctcaggtgc     600
gaaagcgtgg ggagcaaaca ggattagata ccctggtagt ccacgctgta acgatgtcg     660 acttggaggt tgtgcccttg aggcgtggct ccggagcta acgcgttaag tcgaccgcct     720
ggggagtacg gccgcaaggt taaaactcaa atgaattgac gggggcccgc acaagcggtg     780
gagcatgtgg tttaattcga tgcaacgcga agaaccttac ctactcttga catccagaga     840
atttgccaga gatggcgaag tgccttcggg aactctgaga caggtgctgc atggctgtcg     900
tcagctcgtg ttgtgaaatg ttgggttaag tcccgcaacg agcgcaaccc ttatcctttg     960
ttgccagcac gtnatggtgg gaactcaaag gagactgccg gtgataaac                  1009
```

<210> SEQ ID NO 283
<211> LENGTH: 1519
<212> TYPE: DNA
<213> ORGANISM: Rahnella aquatilis
<220> FEATURE:
<223> OTHER INFORMATION: 16S-7

<400> SEQUENCE: 283

```
attgaagagt ttgatcatgg ctcagattga acgctggcgg caggcctaac acatgcaagt      60
cgagcggcag cgggaagtag cttgctactt tgccggcgag cggcggacgg gtgagtaatg     120
tcctgatgga ggggataact actggaacgg tagctaatac cgcacctcga aagagcaaag     180
tgggggatct tcggacctca cgccatcgga tgtgcccaga tgggattagc tagtaggtga     240
ggtaatggct cacctaggcg acgatcccta gctggtctga gaggatgacc agccacactg     300
gaactgagac acggtccaga ctcctacggg aggcagcagt ggggaatatt gcacaatggg     360
cgcaagcctg atgcagccat gccgcgtgtg tgaagaaggc cttaggttg taaagcactt      420
tcagcgagga ggaaggcatc atacttaata cgtgtggtga ttgacgttac tcgcagaaga     480
agcaccggct aactccgtgc cagcagccgc ggtaatacgg agggtgcaag cttaatcgga     540
attactgggc gtaaagcgca cgcaggcggt tgttaagtca gatgtgaaat ccccgagctt     600
aacttgggaa ctgcatttga aactggcaag ctagagtctt gtagaggggg gtagaattcc     660
aggtgtagcg gtgaaatgcg tagagatctg gaggaatacc ggtggcgaag gcggccccct     720
ggacaaagac tgacgctcag gtgcgaaagc gtggggagca acaggatta ataccctggt      780
agtccacgct gtaacgatgt cgacttggag gttgtgccct gaggcgtggc ttccggagct     840
aacgcgttaa gtcgaccgcc tggggagtac ggccgcaagg ttaaaactca atgaattga      900
cggggggccg cacaagcggt ggagcatgtg gtttaattcg atgcaacgcg aagaaccttta    960
cctactcttg acatccagag aatttgccag agatggcgaa gtgccttcgg gaactctgag   1020
acaggtgctg catggctgtc gtcagctcgt gttgtgaaat gttgggttaa gtcccgcaac   1080
gagcgcaacc cttatccttt gttgccagca cgtaatggtg ggaactcaaa ggagactgcc   1140
ggtgataaac cggaggaagg tggggatgac gtcaagtcat catggccctt acgagtaggg   1200
ctacacacgt gctacaatgg catatacaaa gagaagcgaa ctcgcgagag caagcggacc   1260
tcataaagta tgtcgtagtc cggattggag tctgcaactc gactccatga agtcggaatc   1320
gctagtaatc gtagatcaga atgctacggt gaatacgttc ccgggccttg tacacaccgc   1380
ccgtcacacc atgggagtgg gttgcaaaag aagtaggtag cttaaccttc gggagggcgc   1440
ttaccacttt gtgattcatg actggggtga agtcgtaaca aggtaaccgt aggggaacct   1500
gcggttggat cacctcctt                                                1519
```

<210> SEQ ID NO 284
<211> LENGTH: 882
<212> TYPE: DNA
<213> ORGANISM: Rahnella aquatilis
<220> FEATURE:
<223> OTHER INFORMATION: nifH1

<400> SEQUENCE: 284

```
atgaccatgc gtcaatgcgc tatctacggt aaaggcggta tcggtaaatc caccaccacc      60
cagaatctcg tcgcggccct cgccgagatg ggtaagaaag tgatgatcgt cggctgcgat     120
ccgaaagcgg attccacccg tctgatcctc cacgctaaag cccagaacac catcatggag     180
atggcggcg aagtgggctc ggtcgaggat ctggagctcg aagacgttct gcaaatcggc     240
tatggcgatg tccgttgcgc cgaatccggc ggcccggagc caggcgtcgg ctgcgccgga     300
cgcggggtga tcaccgccat caacttcctc gaggaagaag cgccctatga agaagatttg     360
gatttcgtct tctatgacgt cctcggcgac gtggtctgcg gcggcttcgc tatgccgatc     420
```

```
cgcgaaaaca aagcccagga gatctacatc gtctgctccg gcgagatgat ggcgatgtat    480
gccgccaaca atatctccaa agggatcgtg aagtacgcca atccggcaa ggtgcgcctc     540 ggcggcctga tctgtaactc gcgcaaaacc gaccgggaag acgaactgat catcgccctg    600
gcggagaagc ttggcacgca gatgatccac ttcgttcccc gcgacaacat tgtgcagcgc    660
gcggagatcc gccggatgac ggtgatcgag tacgacccga cctgtcagca ggcgaatgaa    720
tatcgtcaac tggcgcagaa gatcgtcaat aacaccaaaa aagtggtgcc gacgccgtgc    780
accatggacg agctggaatc gctgctgatg gagttcggca tcatggaaga agaagacacc    840
agcatcattg gtaaaaccgc cgctgaagaa aacgcggcct ga                       882

<210> SEQ ID NO 285
<211> LENGTH: 1113
<212> TYPE: DNA
<213> ORGANISM: Rahnella aquatilis
<220> FEATURE:
<223> OTHER INFORMATION: nifH2

<400> SEQUENCE: 285
atggttagga aaagtagaag taaaaataca aatatagaac taactgaaca tgaccattta    60
ttaataagtc aaataaaaaa gcttaaaaca caaaccactt gcttttttaa taataaagga    120
ggggttggga agactacatt agtagcaaat ttaggagcag agctatcaat aaactttagt    180
gcaaaagttc ttattgtgga tgccgaccct caatgtaatc tcacgcagta tgtattaagt    240
gatgaagaaa ctcaggactt atatgggcaa gaaaatccag atagtattta tacagtaata    300
agaccactat cctttggtaa aggatatgaa agtgacctcc ctataaggca tgtagagaat    360
ttcggttttg acataattgt cggtgaccct agacttgctt tacaggaaga ccttttagct    420
ggagactggc gagatgccaa aggcggtggg atgcgaggaa ttaggacaac ttttgtattt    480
gcagagttaa ttaagaaagc tcgtgagcta aattatgatt ttgttttctt tgacatggga    540
ccatcattag gcgcaatcaa cagggcagta ttactggcaa tggaattctt tgtcgtccca    600
atgtcaatcg atgtattttc actatgggct attaaaaata ttggctccac ggtttcaata    660
tggaaaaaag aattagacac agggattcgg ctctcagagg aacctagcga attatcacaa    720
ttatcacctc aaggaaaact aaagtttctc ggttacgtca cccaacaaca taagaacgc     780 tctggatacg atacaattca gcttgagaat actgaggaag aaataaaatc gaaacgtcgg    840
gtaaaggcgt atgaagacat tggagaggtg tttccttcta aaattactga gcatctttct    900
aaactttatg catcaaaaga tatgaaccca caccttggag atatacgtca tttaggtagt    960
ttagctccga aatcacaatc acaacacgtt ccgatgatat cagtgtctgg tacaggaaat    1020
tacaccagac ttagaaaaag cgcgcgtgaa ctttatcgag atattgcaag aagatactta    1080
gagaacattc agactgctaa tggcgagaaa tag                                 1113

<210> SEQ ID NO 286
<211> LENGTH: 1374
<212> TYPE: DNA
<213> ORGANISM: Rahnella aquatilis
<220> FEATURE:
<223> OTHER INFORMATION: nifD1

<400> SEQUENCE: 286
atgaagggaa aggaaattct ggcgctgctg gacgaacccg cctgcgagca caaccagaag    60
caaaaatccg gctgcagcgc ccctaagccc ggcgctaccg ccggcggttg cgccttcgac    120
ggcgcgcaga taacgctcct gcccatcgcc gacgtcgcgc acctggtgca cggccccatc    180
```

-continued

| | |
|---|---|
| ggctgcgcgg gcagctcgtg ggataaccgc ggcagcgtca gcgccggccc ggccctcaac | 240 |
| cggctcggct ttaccaccga tcttaacgaa caggatgtga ttatgggccg cggcgaacgc | 300 |
| cgcctgttcc acgccgtgcg tcacatcgtc daccgctatc atccggcggc ggtctttatc | 360 |
| tacaacacct gcgtaccggc gatggagggc gatgacatcg aggcggtctg ccaggccgca | 420 |
| cagaccgcca ccggcgtccc ggtcatcgct attgacgccg ccggtttcta cggcagtaaa | 480 |
| aatcttggca accgaatggc gggcgacgtg atgctcaggc aggtgattgg ccagcgcgaa | 540 |
| ccggccccgt ggccagacaa cacgcccttt gccccggccc agcgccacga tatcggcctg | 600 |
| attggcgaat tcaatatcgc cggcgagttc tggcaggtcc agccgctgct cgacgagctg | 660 |
| gggatccgcg tcctcggcag cctctccggc gacggccgct tgccgagat ccagaccctg | 720 |
| caccgggcgc aggccaatat gctggtgtgc tcgcgcgcgc tgatcaacgt cgcccggggg | 780 |
| ctggagctgc gctacggcac gccgtggttt gaaggcagct tctacgggat ccgcgccacc | 840 |
| tccgacgcct tgcgccagct ggcgacgctg ctggggatg acgacctgcg ccgccgcacc | 900 |
| gaggcgctga tcgcccgcga agagcaggcg gcggagcagg ctcttgcgcc gtggcgtgag | 960 |
| cagctccgcg ggcgcaaagt gctgctctat accggcggcg tgaaatcctg gtcggtggta | 1020 |
| tcggccctgc aggatctcgg catgaccgtg gtggccaccg gcacgcgcaa atccaccgag | 1080 |
| gaggacaaac agcggatccg tgagctgatg ggcgacgagg cggtgatgct tgaggagggc | 1140 |
| aatgcccgca ccctgctcga cgtggtgtac cgctatcagg ccgacctgat gatcgccggc | 1200 |
| ggacgcaata tgtacaccgc ctggaaagcc cggctgccgt ttctcgatat caatcaggag | 1260 |
| cgcgagcacg cctacgccgg ctatcagggc atcatcaccc tcgcccgcca gctctgtctg | 1320 |
| accctcgcca gccccgtctg gccgcaaacg catacccgcg ccccgtggcg ctag | 1374 |

<210> SEQ ID NO 287
<211> LENGTH: 1449
<212> TYPE: DNA
<213> ORGANISM: Rahnella aquatilis
<220> FEATURE:
<223> OTHER INFORMATION: nifD2

<400> SEQUENCE: 287

| | |
|---|---|
| atgaccaacg caacaggcga acgtaacctt gcgctcatcc aggaagtcct ggaggtgttt | 60 |
| cccgaaaccg cgcgcaaaga gcgcagaaag cacatgatga tcagcgatcc gcagatggag | 120 |
| agcgtcggca agtgcattat ctcgaaccgt aaatcgcagc ccggggtgat gaccgtgcgc | 180 |
| ggctgcgcct atgcgggctc gaaaggggtg gtgtttgggc caatcaaaga catggcccat | 240 |
| atctcgcacg gccccatcgg ctgcggccag tattcccgcg ccggacggcg caactactat | 300 |
| accggcgtca gcggtgtcga cagcttcggc accctgaact tcacctctga tttttcagga | 360 |
| cgcgatattg ttttcggcgg cgataaaaag ctgaccaaac tgatcgaaga gatggagctg | 420 |
| ctgttcccgc tgaccaaagg gatcaccatc cagtcggagt gccccggtggg cctgatcggc | 480 |
| gatgacatca gcgccgtagc caacgccagc agcaaggcgc tggataaacc ggtgatcccg | 540 |
| gtgcgctgcg aaggctttcg cggcgtatcg caatcgctgg ccaccatat cgccaacgac | 600 |
| gtggtgcgca ctgggtgct gaacaatcgc gaagggcagc cgtttgccag caccccgtac | 660 |
| gatgttgcca tcattggcga ttacaacatc ggcggcgacg cctgggcctc gcgcattctg | 720 |
| ctggaagaga tggggctgcg cgtagtggcg cagtggtccg gcgacggcac cctggtggag | 780 |
| atggagaaca cccccattcgt taagcttaac ctcgtccact gctaccgttc gatgaactat | 840 |

| | |
|---|---|
| atcgcccgcc atatggagga gaaacatcag atcccatgga tggaatataa cttcttcggc | 900 |
| ccgaccaaaa tcgccgaatc gctgcgcaag atcgccgatc aatttgatga caccattcgc | 960 |
| gccaatgcgg aagcggtgat cgccaaatat gaggggcaga tggcggccat catcgccaaa | 1020 |
| tatcgcccgc ggctggaggg cgcaaagtg ctgctgtaca tggggggggct gcggccgcgc | 1080 |
| cacgtcatcg gcgcctatga ggatctcggg atggagatca tcgccgccgg ctacgagttt | 1140 |
| gcccataacg atgattacga ccgcaccctg ccggacctga agagggcac cctgctgttt | 1200 |
| gacgatgcca gcagctatga gctggaggcc ttcgtcaaag cgctgaaacc tgacctcatc | 1260 |
| ggctccggga tcaaagagaa atatatcttc cagaaaatgg gggtgccgtt ccgccagatg | 1320 |
| cactcctggg actattccgg cccctatcac ggctatgacg gcttcgccat cttgcccgc | 1380 |
| gatatggata tgaccctgaa caatccggcg tggaacgaac tgactgcccc gtggctgaag | 1440 |
| tctgcgtga | 1449 |

<210> SEQ ID NO 288
<211> LENGTH: 1386
<212> TYPE: DNA
<213> ORGANISM: Rahnella aquatilis
<220> FEATURE:
<223> OTHER INFORMATION: nifK1

<400> SEQUENCE: 288

| | |
|---|---|
| atggcagata ttatccgcag tgaaaaaccg ctggcggtga gcccgattaa aaccgggcaa | 60 |
| ccgctcgggg cgatcctcgc cagcctcggg ctggcccagg ccatcccgct ggtccacggc | 120 |
| gcccagggct gcagcgcctt cgccaaagtt ttctttattc agcatttcca tgacccggtg | 180 |
| ccgctgcagt cgacggccat ggatccgacc gccacgatca tgggggccga cggcaatatc | 240 |
| ttcaccgcgc tcgacaccct ctgccagcgc acagcccgc aggccatcgt gctgctcagc | 300 |
| accggtctgg cggaagcgca gggcagcgat atcgcccggg tggtgcgcca gtttcgcgag | 360 |
| gcgcatccgc gccataacgg cgtggcgatc ctcaccgtca ataccccgga ttttttggc | 420 |
| tctatggaaa acggctacag cgcggtgatc gagagcgtga tcgagcagtg ggtcgcgccg | 480 |
| acgccgcgtc cggggcagcg gccccggcgg gtcaacctgc tggtcagcca cctctgttcg | 540 |
| ccagggata tcgaatggct gggccgctgc gtggaggcct ttggcctgca gccggtgatc | 600 |
| ctgccggacc tctcgcagtc aatggatggc cacctcggtg aagggatttt acgcccctg | 660 |
| acccagggcg gcgcctcgct cgccagatt gcccagatgg gccagagtct gggcagcttc | 720 |
| gccattggcg tgtcgctcca gcgggcggca tcgctcctga cccaacgcag ccgcggcgac | 780 |
| gtgatcgccc tgccgcatct gatgaccctc gaccattgcg ataccttat ccatcagctg | 840 |
| gcgaagatgt ccggacgccg cgtaccggcc tggattgagc gccagcgtgg ccagctgcag | 900 |
| gatgcgatga tcgactgcca tatgtggctt cagggccagc gcatggcgat ggcggcggag | 960 |
| ggcgacctgc tggcggcgtg gtgtgatttc gcccgcagcc aggggatgca gcccggcccg | 1020 |
| ctggtcgccc ccaccagcca ccccagcctg cgccagctgc cggtcgagca agtcgtgccg | 1080 |
| ggggatcttg aggatctgca gcagctgctg agccaccaac ccgccgatct gctggtggct | 1140 |
| aactctcacg cccgcgatct ggcggagcag tttgccctgc cgctgatccg cgtcggtttt | 1200 |
| cccctcttcg accggctcgg tgagtttcgt cgcgtccgcc aggggtacgc cggtatgcga | 1260 |
| gatacgctgt ttgaactggc caatctgctg cgcgaccgcc atcaccacac cgccctctac | 1320 |
| cgctcgccgc ttcgccaggg cgccgacccc cagccggctt caggagacgc ttatgccgcc | 1380 |
| cattaa | 1386 |

<210> SEQ ID NO 289
<211> LENGTH: 1563
<212> TYPE: DNA
<213> ORGANISM: Rahnella aquatilis
<220> FEATURE:
<223> OTHER INFORMATION: nifK2

<400> SEQUENCE: 289

```
atgagccaaa cgatcgataa aattcacagc tgttatccgc tgtttgaaca ggatgaatac      60
cagaccctgt tccagaataa aaagacccct gaagaggcgc acgacgcgca gcgtgtgcag     120
gaggtttttg cctggaccac caccgccgag tatgaagcgc tgaacttcca gcgcgaggcg     180
ctgaccgtcg acccggccaa agcctgccag ccgctcggcg ccgtactctg cgcgctgggg     240
ttcgccggca ccctgcccta cgtgcacggc tcccagggct gcgtcgccta ttttcgcacc     300
tactttaacc gccattttaa agagccggtc gcctgcgtct ccgactccat gaccgaggac     360
gcggcggtgt tcggcggcaa caacaacatg aatctgggcc tgcagaatgc cagcgcgctg     420
tataaacccg agattatcgc cgtctccacc acctgtatgg ccgaggtgat cggcgacgat     480
ctgcaggcgt ttatcgccaa cgccaaaaaa gagggatttg ttgacgaccg catcgccatt     540
ccttacgccc atacccccag ctttatcggc agccatgtca ccggctggga caatatgttc     600
gaagggttcg cgaagacctt taccgctgac tacgccgggc agccgggcaa acagcaaaag     660
ctcaatctgg tgaccggatt tgagacctat ctcggcaact tccgcgtgct gaagcggatg     720
atggcgcaga tggatgtccc cgtgcagcct gctctccgac catcagaggt gctcgacacc     780
cccgccgacg gccattaccg gatgtacgcc ggcggcacca gccagcagga gatcaaaacc     840
gcgccgacg ccattgacac cctgctgctg cagccgtggc agctggtgaa agcaaaaag     900
gtggttcagg agatgtggaa ccagcccgcc accgaggtgg ccgttccgct gggcctggcc     960
gccaccgacg cgctgctgat gaccgtcagt cagctgaccg gcaaaccgat cgccgacgct    1020
ctgaccctgg agcgcggccg gctggtcgac atgatgctgg attcccacac ctggctgcat    1080
ggcaaaaaat tcggcctcta cggcgatccg gatttcgtga tggggctgac gcgcttcctg    1140
ctggagctgg gctgcgagcc gacggtgatc ctcagtcata cgccaataa acgctggcaa    1200
aaagcgatga agaaaatgct cgatgcctcg ccgtacggtc aggaaagcga agtgttcatc    1260
aactgcgacc tgtggcactt ccggtcgctg atgttcaccc gtcagccgga ctttatgatc    1320
ggtaactcct acggcaagtt tatccagcgc gataccctgg caagggcaa agccttcgaa    1380
gtgccgctga tccgtctggg cttttccgctg ttcgaccgcc atcatctgca ccgccagacc    1440
acctggggct atgaaggcgc aatgaacatc gtcacgacgc tggtgaacgc cgtgctggaa    1500
aaactggacc acgacaccag ccagttgggc aaaaccgatt acagcttcga cctcgttcgt    1560
taa                                                                  1563
```

<210> SEQ ID NO 290
<211> LENGTH: 2838
<212> TYPE: DNA
<213> ORGANISM: Rahnella aquatilis
<220> FEATURE:
<223> OTHER INFORMATION: glnE

<400> SEQUENCE: 290

```
atgatgccgc tttctccgca attacagcag cactggcaga cggtcgctga ccgtctgcca      60
gcggattttc ccattgccga actgagccca caggccaggt cggtcatggc gttcagcgat     120
```

```
tttgtcgaac agagtgtgat cgcccagccg ggctggctga atgagcttgc ggactcctcg      180
ccggaggcgg aagagtggcg gcattacgag gcctggctgc aggatcgcct gcaggccgtc      240
actgacgaag cggggttgat gcgagagctg cgtctcttcc gccgccagat gatggtccgc      300
atcgcctggg cgcaggcgct gtcgctggtg agcgaagaag agactctgca gcagctgagc      360
gtcctggcgg agaccctgat tgtcgccgcc cgcgactggc tgtacgccgc ctgctgtaag      420
gagtggggaa cgccatgcaa tgccgagggc cagccgcagc cgctgctgat cctcgggatg      480
ggaaagctgg gcggcggcga gctgaacttc tcttccgata tcgatctgat ctttgcctgg      540
cctgagcatg gcgccacccg cggcggccgc cgcgagctgg ataacgccca gttctttacc      600
cgtctggggc agcggctgat caaggccctt gaccagccga cgcaggacgg ctttgtctat      660
cgggttgaca tgcgcctgcg gccgtttggc gacagtgggc cgctggtact cagttttgcg      720
gcgctggaag attattacca ggagcagggt cgggactggg aacgctatgc gatggtgaaa      780
gcgcggatca tgggcgataa cgacggcgtg tacgccagcg agttgcgcgc gatgctccgt      840
cctttcgtct tccgccgtta tatcgacttc agcgtgatcc agtcgctgcg taacatgaaa      900
ggcatgatcg cccgcgaagt gcggcgtcgc gggctgaaag acaacatcaa gctcggcgcc      960
ggcgggatcc gtgaaattga gtttatcgtt caggtctttc aactgatccg cggtggtcgc     1020
gaacctgcac tgcagcagcg cgccctgctg ccgacgctgg cggcgattga tgagctacat     1080
ctgctgccga aggcgacgc ggcgctgctg cgcgaggcct atctgttcct gcgccggctg     1140
gaaaacctgc tgcaaagcat caacgatgag cagacccaga ccctgccgca ggatgaactt     1200
aaccgcgcca ggctggcgtg ggggatgcat accgaagact gggagacgct gagcgcgcag     1260
ctggcgagcc agatggccaa cgtgcggcga gtgtttaatg aactgatcgg cgatgatgag     1320
gatcagtccc cggatgagca actggccgag tactggcgcg agctgtggca ggatgcgctg     1380
gaagaagatg acgccagccc ggcgctggcg catttaaacg ataccgaccg ccgtagcgtg     1440
ctggcgctga ttgccgattt tcgtaaagag ctggatcggc gcaccatcgg cccgcgcggc     1500
cgccaggtgc tggatcagct gatgccgcat ctgctgagcg aaatctgctc gcgcgccgat     1560
gcgccgctgc ctctggcgcg gatcacgccg ctgttgaccg ggatcgtcac ccgtaccacc     1620
tatcttgagc tgctgagcga attccccggc gcgctgaagc acctgatcac gctctgcgcg     1680
gcgtcgccga tggtcgccag ccagctggcg cgccacccgc tgctgctgga tgagctgctg     1740
gatcccaaca ccctctatca gccgacggcg accgatgcct atcgcgacga gctgcgccag     1800
tacctgctgc gcgtgccgga agaggatgaa gagcagcagc tggaggcgtt gcgccagttt     1860
aagcaggcgc agcagctgca tatcgcggcg gcggatatcg ctggtaccct gccggtgatg     1920
aaggtcagcg atcacttaac ctggcttgcc gaagcgatcc tcgacgcggt ggtgcagcag     1980 gcatggggc agatggtcgc tcgctacggc cagccgaccc acctgcacga tcgccagggt     2040
cgcggcttcg ccgtcgtcgg ctacggtaag cttggcggct gggagctggg ctacagctcc     2100
gatctcgatc tggtgttcct ccatgactgc ccggcggagg tgatgaccga cggcgagcgg     2160
gagattgacg gccgtcagtt ctacctgcgg ctggcccagc ggatcatgca cctgttcagc     2220
acccgcacct cgtccggtat tctctacgaa gtgacgccc ggctgcgtcc ttctggcgcg     2280
gcggggatgc tggtcaccac cgccgacgcg tttgctgact atcagcagaa cgaagcctgg     2340
acgtgggaac atcaggcgct ggtgcgcgcc cgcgtggtct atggcgaccc ggcgctgcag     2400
gcgcgctttg acgccattcg tcgcgatatc ctgaccaccc cgcgggaggg gatgaccctg     2460
cagaccgagg ttcgcgagat gcgcgagaag atgcgcgccc accttggcaa caaacatccc     2520
```

```
gatcgttttg atatcaaagc cgatgccggc gggatcaccg atattgaatt tattactcag    2580
tatctggtcc tacgctatgc cagtgacaag ccgaagctga cccgctggtc tgacaacgtg    2640
cgtattcttg agctgctggc gcagaacgac atcatggacg aggaggaggc gcgcgcctta    2700
acgcatgcgt acaccacctt gcgtgatgcg ctccatcacc tggccctgca ggagcagccg    2760
ggacacgtgg cgccagaggc cttcagccgg gagcgtcagc aggtcagcgc cagctggcag    2820
aagtggctga tggcttaa                                                  2838

<210> SEQ ID NO 291
<211> LENGTH: 449
<212> TYPE: DNA
<213> ORGANISM: Rahnella aquatilis
<220> FEATURE:
<223> OTHER INFORMATION: Prm4

<400> SEQUENCE: 291
agtctgaact catcctgcgg cagtcggtga gacgtatttt tgaccaaaga gtgatctaca     60
tcacggaatt ttgtggttgt tgctgcttaa aagggcaaat ctaccccttag aatcaactgt    120 tatatcaggg ggattcagag agatattagg aatttgcaca agcgcacaat ttaaccacat    180
catgataacg ccatgtaaaa caaagataaa aaaacaaaat gcagtgactt acatcgcaag    240
caaggcattt tcttatccaa ttgctcaaag tttggccttt catatcgcaa cgaaaatgcg    300
taatatacgc gcccttgcgg acatcagtat ggtcattcct agttcatgcg catcggacac    360
caccagctta caaattgcct gattgcggcc ccgatggccg gtatcactga ccgaccattt    420
cgtgccttat gtcatgcgat gggggctgg                                      449

<210> SEQ ID NO 292
<211> LENGTH: 500
<212> TYPE: DNA
<213> ORGANISM: Rahnella aquatilis
<220> FEATURE:
<223> OTHER INFORMATION: Prm1.2

<400> SEQUENCE: 292
tgaacatcac tgatgcacaa gctacctatg tcgaagaatt aactaaaaaa ctgcaagatg     60
caggcattcg cgttaaagcc gacttgagaa atgagaagat tggctttaaa attcgcgaac    120
acacgctacg ccgtgttcct tatatgttag tttgtggcga taaagaggtc gaagcaggca    180
aagttgctgt tcgtacccgc cgcggcaaag acttaggaag catggatgtt agcgaagtcg    240
ttgacaaact gctggcggaa atccgcagca gaagtcttca tcaactggag gaataaagta    300
ttaaaggcgg aaaacgagtt caaccggcgc gtcctaatcg cattaacaaa gagattcgcg    360
cgcaagaagt tcgcctcaca ggcgtcgatg gcgagcagat tggtattgtc agtctgaatg    420
aagctcttga aaaagctgag gaagcgggcg tcgatttagt agaaatcagt ccgaatgccg    480
agccgccagt ttgtcgaatc                                                500

<210> SEQ ID NO 293
<211> LENGTH: 170
<212> TYPE: DNA
<213> ORGANISM: Rahnella aquatilis
<220> FEATURE:
<223> OTHER INFORMATION: Prm3.1
```

<400> SEQUENCE: 293

```
tacagtagcg cctctcaaaa atagataaac ggctcatgta cgtgggccgt ttattttttc     60
tacccataat cgggaaccgg tgttataatg ccgcgccctc atattgtggg gatttcttaa   120
tgacctatcc tgggtcctaa agttgtagtt gacattagcg gagcactaac              170
```

<210> SEQ ID NO 294
<211> LENGTH: 142
<212> TYPE: DNA
<213> ORGANISM: Rahnella aquatilis
<220> FEATURE:
<223> OTHER INFORMATION: Prm6.1

<400> SEQUENCE: 294

```
aatttttttt cacaaagcgt agcgttattg aatcgcacat tttaaactgt tggccgctgt     60
ggaagcgaat attggtgaaa ggtgcggttt taaggccttt ttctttgact ctctgtcgtt   120
acaaagttaa tatgcgcgcc ct                                             142
```

<210> SEQ ID NO 295
<211> LENGTH: 293
<212> TYPE: DNA
<213> ORGANISM: Rahnella aquatilis
<220> FEATURE:
<223> OTHER INFORMATION: Prm7.1

<400> SEQUENCE: 295

```
ttaaaaacgt gaccacgagc attaataaac gccacgaaat gtggcgttta tttattcaaa     60
aagtatcttc tttcataaaa agtgctaaat gcagtagcag caaaattggg ataagtccca   120
tggaatacgg ctgttttcgc tgcaatttttt aacttttttcg taaaaaaaga tgtttctttg   180
agcgaacgat caaaatatag cgttaaccgg caaaaaatta ttctcattag aaaatagttt   240
gtgtaatact tgtaacgcta catggagatt aacttaatct agagggtttt ata           293
```

<210> SEQ ID NO 296
<211> LENGTH: 1188
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: glnE-delta-AR-2

<400> SEQUENCE: 296

```
atggcgctca aacagttaat ccgtctgtgt gccgcctcgc cgatggtcgc gacacaactt     60
gcacgtcatc ctttattgct cgatgaactg ctcgacccgc gcacgcttta ccagccgatt   120
gagccgggcg cttaccgcga cgaactgcgt cagtatctga tgcgggtgcc aacagaagac   180
gaagaacagc agcttgaagc cgtgcgccag ttcaaacagg cccagcattt gcgtatcgca   240
gccggggata tttccggggc attgccggtg atgaaagtca gtgaccattt aacctacctt   300
gccgaggcca ttctcgatgt cgtggtgcag catgcgtggg aacaaatggt cgtaaaatac   360
gggcagcccg cgcatcttca gcaccgtgag gggcgcggtt ttgccgtggt cggttacggg   420
aaactcggtg gctgggagct gggttatagc tcagatctgg atctggtctt cctgctcgat   480
tgcgcgccgg aggtgatgac ggacggcgaa cgcagcatcg acggacgtca gttttatctt   540
cggctggcgc agcgcattat gcacttattc agcacccgga catcgtcagg cattctttac   600
gaggttgatc cgcgtctgcg accttccggc gcatccggca tgctggtcag taccattgaa   660
```

```
gcgtttgcag attatcaggc caatgaagcc tggacgtggg agcatcaggc gctggttcgc    720
gcgcgcgtgg tttacgggga tccgcaactg acacagcaat taacgccac gcgtcgcgac    780 attctttgcc gccagcgcga tggcgacggc ctgcgtaagg aggtccgtga aatgcgcgag    840
aaaatgtatg cccatctggg gagtaaaaaa gcccacgagt tgatctgaa agccgatccg    900 ggtggcatca cggatattga attcattgca caatacctgg ttctgcgttt cgcgcatgat    960
gagccgaagc tgacgcgctg gtctgataac gtgcggattt tgaactgat ggcacgatat    1020 gacatcatgc cggaagagga agcgcgccat ctgacgcagg cttatgtgac gctgcgcgat    1080
gaaattcatc atctggcgtt gcaggaacac agcgggaaag tggccgcgga cagctttgct    1140
actgagcgcg cgcagatccg tgccagctgg gcaaagtggc tcggctga                1188
```

<210> SEQ ID NO 297
<211> LENGTH: 2188
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: glnE-delta-AR-2 with 500bp flank

<400> SEQUENCE: 297

```
cggtactgga acagaaatcg gcggatgcgc aggaaatttg ttatgacacg gcctgtctga    60
agtgcaagtt agtgcttact tcctggctgg caacctcagg ctggacgccg tttattgatg    120
ataaatctgc gaagaaactg gacgcttcct tcaaacgttt tgctgacatc atgctcggtc    180
gtaccgcagc ggatctgaaa gaagcctttg cgcagccact gacggaagaa ggttatcgcg    240
atcagctggc gcgcctgaaa cgccagatca ttaccttcca tttgcttgcc ggtgcttacc    300
ctgaaaaaga cgtcgatgcg tatattgccg gctgggtgga cctgcaacag gccatcgttc    360
agcagcaaca cgcctgggag gattcggccc gttctcacgc ggtgatgatg gatgcttttct    420 ggttaaacgg gcaacctcgt taactgactg actagcctgg gcaaactgcc cgggcttttt    480
tttgcaagga atctgatttc atggcgctca aacagttaat ccgtctgtgt gccgcctcgc    540
cgatggtcgc gacacaactt gcacgtcatc ctttattgct cgatgaactg ctcgacccgc    600
gcacgcttta ccagccgatt gagccgggcg cttaccgcga cgaactgcgt cagtatctga    660
tgcgggtgcc aacagaagac gaagaacagc agcttgaagc cgtgcgccag ttcaaacagg    720
cccagcattt gcgtatcgca gccggggata tttccggggc attgccggtg atgaaagtca    780
gtgaccattt aacctacctt gccgaggcca ttctcgatgt cgtggtgcag catgcgtggg    840
aacaaatggt cgtaaaatac gggcagcccg cgcatcttca gcaccgtgag gggcgcggtt    900
ttgccgtggt cggttacggg aaactcggtg gctgggagct gggttatagc tcagatctgg    960
atctggtctt cctgctcgat tgcgcgccgg aggtgatgac ggacggcgaa cgcagcatcg    1020
acggacgtca gttttatctt cggctggcgc agcgcattat gcacttattc agcacccgga    1080
catcgtcagg cattctttac gaggttgatc gcgtctgcg accttccggc gcatccggca    1140
tgctggtcag taccattgaa gcgtttgcag attatcaggc caatgaagcc tggacgtggg    1200
agcatcaggc gctggttcgc gcgcgcgtgg tttacgggga tccgcaactg acacagcaat    1260
ttaacgccac gcgtcgcgac attctttgcc gccagcgcga tggcgacggc ctgcgtaagg    1320
aggtccgtga aatgcgcgag aaaatgtatg cccatctggg gagtaaaaaa gcccacgagt    1380 tgatctgaa agccgatccg ggtggcatca cggatattga attcattgca caatacctgg    1440
```

```
ttctgcgttt cgcgcatgat gagccgaagc tgacgcgctg gtctgataac gtgcggattt    1500
ttgaactgat ggcacgatat gacatcatgc cggaagagga agcgcgccat ctgacgcagg    1560
cttatgtgac gctgcgcgat gaaattcatc atctggcgtt gcaggaacac agcgggaaag    1620
tggccgcgga cagctttgct actgagcgcg cgcagatccg tgccagctgg gcaaagtggc    1680
tcggctgagg gttttattc ggctaacagg cgcttgtgat attatccggc gcattgtatt    1740
tacccgattt gatttatctg ttttggagtc ttgggatgaa agtgactttg cctgattttc    1800
accgcgcagg tgtgctggtt gtcggtgacg taatgttaga ccgttactgg tatggcccga    1860
ccaatcgtat ttctccggaa gctccggtgc cggtggtgaa ggtcagtacc attgaagagc    1920
ggcctggcgg tgcagctaac gtggcgatga catttcatc tctgggcgcc tcttcctgtc    1980
tgatcggcct gaccggcgta gacgacgctg cgcgtgccct cagtgagcgt ctggcagaag    2040
tgaaagttaa ctgcgatttc gtcgcactat ccacacatcc taccatcacc aaactgcgaa    2100
ttttgtcccg taaccagcaa ctgatccgcc tcgactttga ggaaggtttt gaaggcgttg    2160
atctcgagcc gatgctgacc aaaatga                                        2188
```

<210> SEQ ID NO 298
<211> LENGTH: 524
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::null-v1

<400> SEQUENCE: 298

```
atgagcatca cggcgttatc agcatcattt cctgagggga atatcgccag ccgcttgtcg     60
ctgcaacatc cttcactgtt ttataccgtg gttgaacaat cttcggtggc gatttcgctg    120
accgatccgc aggcgcgcat tgttatgcc aatccggcat tctgccgcca gacgggtttt    180
gcacttgaga cacttttggg cgagaaccac cgtctgctgg agtctgaact catcctgcga    240
tgggggctgg gccgtctctg aagctctcgg tgaacattgt tgcgaggcag gatgcgagct    300
ggttgtgttt tgacattacc gataatgtgc cgcgtgaacg ggtgcgttat gcccgcccgg    360
aagcggcgtt ttcccgtccg gggaatggca tggagctgcg ccttatccag acgctgatcg    420
cccatcatcg cggttcttta gatctctcgg tccgccctga tggcggcacc ttgctgacgt    480
tacgcctgcc ggtacagcag gttatcaccg gaggcttaaa atga                     524
```

<210> SEQ ID NO 299
<211> LENGTH: 1524
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::null-v1 with 500bp flank

<400> SEQUENCE: 299

```
tgtttcgtct cgaggccggg caactgagcg gccccgttga aaccgacctg ggctggcatc     60
tgttgttgtg cgaacaaatt cgcctgccgc aaccccttgcc gaaagccgaa gccttaacgc    120
gggtgcgtca gcaactgatt gcccggcaac agaaacatta tcagcgccag tggctgcaac    180
aactgatcaa cgcctgagcc tgttctcctt cttgttgatg cagacgggtt aatgcccgtt    240
```

```
ttgcacgaaa aatgcacata aattgcctgc gttgccttat aacagcgcag ggaaatcctg      300
cctccggcct tgtgccacac cgcgctttgc ctggtttgtg gtaaaaactg gcccgctttg      360
catcctgatg cttaaaacac cccgttcaga tcaacctttg ggcagataag cccgcgaaag      420
gcctgcaaat tgcacggtta ttccgggtga gtatatgtgt gatttgggtt ccggcattgc      480
gcaataaagg ggagaaagac atgagcatca cggcgttatc agcatcattt cctgagggga      540
atatcgccag ccgcttgtcg ctgcaacatc cttcactgtt ttataccgtg gttgaacaat      600
cttcggtggc gatttcgctg accgatccgc aggcgcgcat ttgttatgcc aatccggcat      660
tctgccgcca gacgggtttt gcacttgaga cacttttggg cgagaaccac cgtctgctgg      720
agtctgaact catcctgcga tgggggctgg gccgtctctg aagctctcgg tgaacattgt      780
tgcgaggcag gatgcgagct ggttgtgttt tgacattacc gataatgtgc cgcgtgaacg      840
ggtgcgttat gcccgcccgg aagcggcgtt ttcccgtccg gggaatggca tggagctgcg      900
ccttatccag acgctgatcg cccatcatcg cggttcttta gatctctcgg tccgccctga      960
tggcggcacc ttgctgacgt tacgcctgcc ggtacagcag gttatcaccg gaggcttaaa     1020
atgacccagt tacctaccgc gggcccggtt atccggcgct ttgatatgtc tgcccagttt     1080
acggcgcttt atcgcatcag cgtggcgctg agtcaggaaa gcaacaccgg gcgcgcactg     1140
gcggcgatcc tcgaagtgct tcacgatcat gcatttatgc aatacggcat ggtgtgtctg     1200
tttgataaag aacgcaatgc actctttgtg gaatccctgc atggcatcga cggcgaaagg     1260 aaaaagaga cccgccatgt ccgttaccgc atggggaag gcgtgatcgg cgcggtgatg       1320
agccagcgtc aggcgctggt gttaccgcgc atttcagacg atcagcgttt tctcgaccgc     1380
ctgaatattt acgattacag cctgccgttg attggcgtgc cgatccccgg tgcggataat     1440
cagccatcgg gcgtgctggt ggcacagccg atggcgttgc acgaagaccg gctgactgcc     1500
agtacgcggt ttttagaaat ggtc                                           1524

<210> SEQ ID NO 300
<211> LENGTH: 266
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::null-v2

<400> SEQUENCE: 300
atgagcatca cggcgttatc agcatcattt cctgagggga atatcgccag ccgcttgtcg       60
ctgcaacatc cttcactgtt ttataccgtg gttgaacaat cttcggtggc gatttcgctg      120
accgatccgc aggcgcgcat ttgttatgcc aatccggcat tctgccgcca gacgggtttt      180
gcacttgaga cacttttggg cgagaaccac cgtctgctgg ttaaagcctg ccggtacagc      240
aggttatcac cggaggctta aaatga                                           266

<210> SEQ ID NO 301
<211> LENGTH: 1266
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::null-v2 with 500bp flank
```

<400> SEQUENCE: 301

```
tgtttcgtct cgaggccggg caactgagcg gccccgttga aaccgacctg ggctggcatc    60
tgttgttgtg cgaacaaatt cgcctgccgc aacccttgcc gaaagccgaa gccttaacgc   120
gggtgcgtca gcaactgatt gcccggcaac agaaacatta tcagcgccag tggctgcaac   180
aactgatcaa cgcctgagcc tgttctcctt cttgttgatg cagacgggtt aatgcccgtt   240
ttgcacgaaa aatgcacata aattgcctgc gttgccttat aacagcgcag ggaaatcctg   300
cctccggcct tgtgccacac cgcgctttgc ctggtttgtg gtaaaaactg gcccgctttg   360
catcctgatg cttaaaacac cccgttcaga tcaacctttg ggcagataag cccgcgaaag   420
gcctgcaaat tgcacggtta ttccgggtga gtatatgtgt gatttgggtt ccggcattgc   480
gcaataaagg ggagaaagac atgagcatca cggcgttatc agcatcattt cctgagggga   540
atatcgccag ccgcttgtcg ctgcaacatc cttcactgtt ttataccgtg gttgaacaat   600
cttcggtggc gatttcgctg accgatccgc aggcgcgcat tgttatgcc aatccggcat    660
tctgccgcca gacgggtttt gcacttgaga cacttttggg cgagaaccac cgtctgctgg   720
ttaaagcctg ccggtacagc aggttatcac cggaggctta aaatgaccca gttacctacc   780
gcgggcccgg ttatccggcg cttttgatatg tctgcccagt ttacggcgct ttatcgcatc   840
agcgtggcgc tgagtcagga aagcaacacc gggcgcgcac tggcggcgat cctcgaagtg   900
cttcacgatc atgcatttat gcaatacggc atggtgtgtc tgtttgataa agaacgcaat   960
gcactctttg tggaatccct gcatggcatc gacggcgaaa ggaaaaaaga gacccgccat  1020
gtccgttacc gcatggggga aggcgtgatc ggcgcggtga tgagccagcg tcaggcgctg  1080
gtgttaccgc gcatttcaga cgatcagcgt tttctcgacc gcctgaatat ttacgattac  1140
agcctgccgt tgattggcgt gccgatcccc ggtgcggata tcagccatc gggcgtgctg   1200
gtggcacagc cgatggcgtt gcacgaagac cggctgactg ccagtacgcg gtttttagaa  1260
atggtc                                                            1266
```

<210> SEQ ID NO 302
<211> LENGTH: 943
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: delta-nifL::Prm4

<400> SEQUENCE: 302

```
atgagcatca cggcgttatc agcatcattt cctgagggga atatcgccag ccgcttgtcg    60
ctgcaacatc cttcactgtt ttataccgtg gttgaacaat cttcggtggc gatttcgctg   120
accgatccgc aggcgcgcat tgttatgcc aatccggcat tctgccgcca gacgggtttt    180
gcacttgaga cacttttggg cgagaaccac cgtctgctgg agtctgaact catcctgcgg   240
cagtcggtga gacgtatttt tgaccaaaga gtgatctaca tcacggaatt ttgtggttgt   300
tgctgcttaa agggcaaat ctaccccttag aatcaactgt tatatcaggg ggattcagag   360
agatattagg aatttgcaca agcgcacaat ttaaccacat catgataacg ccatgtaaaa   420
caaagataaa aaaacaaaat gcagtgactt acatcgcaag caaggcattt tcttatccaa   480
ttgctcaaag tttggccttt catatcgcaa cgaaaatgcg taatatacgc gcccttgcgg   540
acatcagtat ggtcattcct agttcatgcg catcggacac caccagctta caattgcct    600
```

```
gattgcggcc ccgatggccg gtatcactga ccgaccattt cgtgccttat gtcatgcgat      660
gggggctggg ccgtctctga agctctcggt gaacattgtt gcgaggcagg atgcgagctg      720
gttgtgtttt gacattaccg ataatgtgcc gcgtgaacgg gtgcgttatg cccgcccgga      780
agcggcgttt tcccgtccgg ggaatggcat ggagctgcgc cttatccaga cgctgatcgc      840
ccatcatcgc ggttctttag atctctcggt ccgccctgat ggcggcacct tgctgacgtt      900
acgcctgccg gtacagcagg ttatcaccgg aggcttaaaa tga                       943
```

<210> SEQ ID NO 303
<211> LENGTH: 1943
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: delta-nifL::Prm4 with 500bp flank

<400> SEQUENCE: 303

```
tgtttcgtct cgaggccggg caactgagcg gccccgttga aaccgacctg ggctggcatc       60
tgttgttgtg cgaacaaatt cgcctgccgc aacccttgcc gaaagccgaa gccttaacgc      120
gggtgcgtca gcaactgatt gcccggcaac agaaacatta tcagcgccag tggctgcaac      180
aactgatcaa cgcctgagcc tgttctcctt cttgttgatg cagacgggtt aatgcccgtt      240
ttgcacgaaa aatgcacata aattgcctgc gttgccttat aacagcgcag ggaaatcctg      300
cctccggcct tgtgccacac cgcgctttgc ctggtttgtg gtaaaaactg ccccgctttg      360
catcctgatg cttaaaacac cccgttcaga tcaacctttg ggcagataag cccgcgaaag      420
gcctgcaaat tgcacggtta ttccgggtga gtatatgtgt gatttgggtt ccggcattgc      480
gcaataaagg ggagaaagac atgagcatca cggcgttatc agcatcattt cctgagggga      540
atatcgccag ccgcttgtcg ctgcaacatc cttcactgtt ttataccgtg gttgaacaat      600
cttcggtggc gatttcgctg accgatccgc aggcgcgcat ttgttatgcc aatccggcat      660
tctgccgcca gacgggtttt gcacttgaga cacttttggg cgagaaccac cgtctgctgg      720
agtctgaact catcctgcgg cagtcggtga gacgtatttt tgaccaaaga gtgatctaca      780
tcacggaatt ttgtggttgt tgctgcttaa aagggcaaat ctacccttag aatcaactgt      840
tatatcaggg ggattcagag agatattagg aatttgcaca agcgcacaat ttaaccacat      900
catgataacg ccatgtaaaa caaagataaa aaacaaaat gcagtgactt acatcgcaag      960
caaggcattt tcttatccaa ttgctcaaag tttggccttt catatcgcaa cgaaaatgcg     1020
taatatacgc gcccttgcgg acatcagtat ggtcattcct agttcatgcg catcggacac     1080
caccagctta caaattgcct gattgcggcc ccgatggccg gtatcactga ccgaccattt     1140
cgtgccttat gtcatgcgat gggggctggg ccgtctctga agctctcggt gaacattgtt     1200
gcgaggcagg atgcgagctg gttgtgtttt gacattaccg ataatgtgcc gcgtgaacgg     1260
gtgcgttatg cccgcccgga agcggcgttt tcccgtccgg ggaatggcat ggagctgcgc     1320
cttatccaga cgctgatcgc ccatcatcgc ggttctttag atctctcggt ccgccctgat     1380
ggcggcacct tgctgacgtt acgcctgccg gtacagcagg ttatcaccgg aggcttaaaa     1440
tgacccagtt acctaccgcg ggcccggtta tccggcgctt tgatatgtct gcccagttta     1500
cggcgcttta tcgcatcagc gtggcgctga gtcaggaaag caacaccggg cgcgcactgg     1560
cggcgatcct cgaagtgctt cacgatcatg catttatgca atacggcatg gtgtgtctgt     1620
```

```
ttgataaaga acgcaatgca ctctttgtgg aatccctgca tggcatcgac ggcgaaagga    1680
aaaaagagac ccgccatgtc cgttaccgca tggggaagg cgtgatcggc gcggtgatga     1740
gccagcgtca ggcgctggtg ttaccgcgca tttcagacga tcagcgtttt ctcgaccgcc    1800
tgaatattta cgattacagc ctgccgttga ttggcgtgcc gatccccggt gcggataatc    1860
agccatcggg cgtgctggtg gcacagccga tggcgttgca cgaagaccgg ctgactgcca    1920
gtacgcggtt tttagaaatg gtc                                            1943
```

<210> SEQ ID NO 304
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp upstream of junction

<400> SEQUENCE: 304

```
tggtgtccgg gcgaacgtcg ccaggtggca caaattgtca gaactacgac acgactaacc    60
gaccgcagga gtgtgcgatg accctgaata tgatgatgga                          100
```

<210> SEQ ID NO 305
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp upstream of junction

<400> SEQUENCE: 305

```
cggaaaacga gttcaaacgg cgcgtcccaa tcgtattaat ggcgagattc gcgccacgga    60
agttcgctta acaggtctgg aaggcgagca gcttggtatt                          100
```

<210> SEQ ID NO 306
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp upstream of junction

<400> SEQUENCE: 306

```
cgccagagag ttgaaatcga acatttccgt aataccgcca ttacccagga gccgttctgg    60
ttgcacagcg gaaaacgtta acgaaaggat atttcgcatg                          100
```

<210> SEQ ID NO 307
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp upstream of junction

<400> SEQUENCE: 307
cgggcgaacg tcgccaggtg gcacaaattg tcagaactac gacacgacta accgaccgca    60
ggagtgtgcg atgaccctga atatgatgat ggatgccagc                          100

<210> SEQ ID NO 308
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp upstream of junction

<400> SEQUENCE: 308
tcaacctaaa aaagtttgtg taatacttgt aacgctacat ggagattaac tcaatctaga    60
gggtattaat aatgaatcgt actaaactgg tactgggcgc                          100

<210> SEQ ID NO 309
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp upstream of junction

<400> SEQUENCE: 309
cgggcgaacg tcgccaggtg gcacaaattg tcagaactac gacacgacta accgaccgca    60
ggagtgtgcg atgaccctga atatgatgat ggatgccagc                          100

<210> SEQ ID NO 310
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp upstream of junction

<400> SEQUENCE: 310
aattttctgc ccaaatggct gggattgttc atttttttgtt tgccttacaa cgagagtgac    60
agtacgcgcg ggtagttaac tcaacatctg accggtcgat                          100

<210> SEQ ID NO 311
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp upstream of junction

<400> SEQUENCE: 311
gtaaccaata aaggccacca cgccagacca cacgatagtg atggcaacac tttccagctg    60
caccagcacc tgatggccca tggtcacacc ttcagcgaaa                          100

<210> SEQ ID NO 312
<211> LENGTH: 100
<212> TYPE: DNA

```
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp upstream of junction

<400> SEQUENCE: 312
tggtattgtc agtctgaatg aagctcttga aaaagctgag gaagcgggcg tcgatttagt    60
agaaatcagt ccgaatgccg agccgccagt ttgtcgaatc                        100

<210> SEQ ID NO 313
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp upstream of junction

<400> SEQUENCE: 313
accgatccgc aggcgcgcat ttgttatgcc aatccggcat tctgccgcca gacgggtttt    60
gcacttgaga cacttttggg cgagaaccac cgtctgctgg                        100

<210> SEQ ID NO 314
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp upstream of junction

<400> SEQUENCE: 314
cgggaaccgg tgttataatg ccgcgccctc atattgtggg gatttcttaa tgacctatcc    60
tgggtcctaa agttgtagtt gacattagcg gagcactaac                        100

<210> SEQ ID NO 315
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp upstream of junction

<400> SEQUENCE: 315
accgatccgc aggcgcgcat ttgttatgcc aatccggcat tctgccgcca gacgggtttt    60
gcacttgaga cacttttggg cgagaaccac cgtctgctgg                        100

<210> SEQ ID NO 316
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp upstream of junction
```

<400> SEQUENCE: 316
tcaacctaaa aaagtttgtg taatacttgt aacgctacat ggagattaac tcaatctaga    60
gggtattaat aatgaatcgt actaaactgg tactgggcgc                         100

<210> SEQ ID NO 317
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp upstream of junction

<400> SEQUENCE: 317
gggcgacaaa cggcctggtg gcacaaattg tcagaactac gacacgacta actgaccgca    60
ggagtgtgcg atgaccctga atatgatgat ggatgccggc                         100

<210> SEQ ID NO 318
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp upstream of junction

<400> SEQUENCE: 318
gggcgacaaa cggcctggtg gcacaaattg tcagaactac gacacgacta actgaccgca    60
ggagtgtgcg atgaccctga atatgatgat ggatgccggc                         100

<210> SEQ ID NO 319
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp upstream of junction

<400> SEQUENCE: 319
taagaattat ctggatgaat gtgccattaa atgcgcagca taatggtgcg ttgtgcggga    60
aaactgcttt tttttgaaag ggttggtcag tagcggaaac                         100

<210> SEQ ID NO 320
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp upstream of junction

<400> SEQUENCE: 320
cgccagagag tcgaaatcga acatttccgt aataccgcga ttacccagga gccgttctgg    60
ttgcacagcg gaaaacgtta acgaaaggat atttcgcatg                         100

<210> SEQ ID NO 321
<211> LENGTH: 100
<212> TYPE: DNA

<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp upstream of junction

<400> SEQUENCE: 321
cgccagagag tcgaaatcga acatttccgt aataccgcga ttacccagga gccgttctgg    60
ttgcacagcg gaaaacgtta acgaaaggat atttcgcatg                         100

<210> SEQ ID NO 322
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp upstream of junction

<400> SEQUENCE: 322
gatgatggat gctttctggt taaacgggca acctcgttaa ctgactgact agcctgggca    60
aactgcccgg gcttttttttt gcaaggaatc tgatttcatg                        100

<210> SEQ ID NO 323
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp upstream of junction

<400> SEQUENCE: 323
accgatccgc aggcgcgcat ttgttatgcc aatccggcat tctgccgcca gacgggtttt    60
gcacttgaga cacttttggg cgagaaccac cgtctgctgg                         100

<210> SEQ ID NO 324
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp upstream of junction

<400> SEQUENCE: 324
catcggacac caccagctta caaattgcct gattgcggcc ccgatggccg gtatcactga    60
ccgaccattt cgtgccttat gtcatgcgat gggggctggg                         100

<210> SEQ ID NO 325
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp upstream of junction

<400> SEQUENCE: 325
tcttcaacaa ctggaggaat aaggtattaa aggcggaaaa cgagttcaaa cggcacgtcc    60
gaatcgtatc aatggcgaga ttcgcgccct ggaagttcgc                         100

<210> SEQ ID NO 326
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp upstream of junction

<400> SEQUENCE: 326
tccgggttcg gcttaccccg ccgcgttttg cgcacggtgt cggacaattt gtcataactg    60
cgacacagga gtttgcgatg accctgaata tgatgctcga                         100

<210> SEQ ID NO 327
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp upstream of junction

<400> SEQUENCE: 327
atcgcagcgt ctttgaatat ttccgtcgcc aggcgctggc tgccgagccg ttctggctgc    60
atagtggaaa acgataattt caggccaggg agcccttatg                         100

<210> SEQ ID NO 328
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp upstream of junction

<400> SEQUENCE: 328
tccgggttcg gcttaccccg ccgcgttttg cgcacggtgt cggacaattt gtcataactg    60
cgacacagga gtttgcgatg accctgaata tgatgctcga                         100

<210> SEQ ID NO 329
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp upstream of junction

<400> SEQUENCE: 329 tcactttta gcaaagttgc actggacaaa aggtaccaca attggtgtac tgatactcga     60
cacagcatta gtgtcgattt ttcatataaa ggtaattttg                         100

<210> SEQ ID NO 330
<211> LENGTH: 100
<212> TYPE: DNA

```
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp upstream of junction

<400> SEQUENCE: 330
tccgggttcg gcttaccccg ccgcgttttg cgcacggtgt cggacaattt gtcataactg    60
cgacacagga gtttgcgatg accctgaata tgatgctcga                        100

<210> SEQ ID NO 331
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp upstream of junction

<400> SEQUENCE: 331
gttctccttt gcaatagcag ggaagaggcg ccagaaccgc cagcgttgaa gcagtttgaa    60
cgcgttcagt gtataatccg aaacttaatt tcggtttgga                        100

<210> SEQ ID NO 332
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp upstream of junction

<400> SEQUENCE: 332
tccgggttcg gcttaccccg ccgcgttttg cgcacggtgt cggacaattt gtcataactg    60
cgacacagga gtttgcgatg accctgaata tgatgctcga                        100

<210> SEQ ID NO 333
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp upstream of junction

<400> SEQUENCE: 333
gatatgcctg aagtattcaa ttacttaggc atttacttaa cgcaggcagg caattttgat    60
gctgcctatg aagcgtttga ttctgtactt gagcttgatc                        100

<210> SEQ ID NO 334
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp upstream of junction
```

<400> SEQUENCE: 334
tggtattgtc agtctgaatg aagctcttga aaaagctgag gaagcgggcg tcgatttagt    60
agaaatcagt ccgaatgccg agccgccagt ttgtcgaatc                          100

<210> SEQ ID NO 335
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp upstream of junction

<400> SEQUENCE: 335
tgcaaattgc acggttattc cgggtgagta tatgtgtgat ttgggttccg gcattgcgca    60
ataaagggga gaaagacatg agcatcacgg cgttatcagc                          100

<210> SEQ ID NO 336
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp upstream of junction

<400> SEQUENCE: 336
tcagggctgc ggatgtcggg cgtttcacaa cacaaaatgt tgtaaatgcg acacagccgg    60
gcctgaaacc aggagcgtgt gatgaccttt aatatgatgc                          100

<210> SEQ ID NO 337
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp upstream of junction

<400> SEQUENCE: 337
cggaaaacga gttcaaacgg cacgtccgaa tcgtatcaat ggcgagattc gcgcccagga    60
agttcgctta actggtctgg aaggtgagca gctgggtatt                          100

<210> SEQ ID NO 338
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp downstream of junction

<400> SEQUENCE: 338
ttcttggttc tctggagcgc tttatcggca tcctgactga agaatttgca ggcttcttcc    60
caacctggct tgcacccgtg caggtagttg tgatgaacat                          100

<210> SEQ ID NO 339
<211> LENGTH: 100
<212> TYPE: DNA

<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp downstream of junction

<400> SEQUENCE: 339
gcgatagaac tcacttcacg ccccgaaggg ggaagctgcc tgaccctacg attcccgcta      60
tttcattcac tgaccggagg ttcaaaatga cccagcgaac                          100

<210> SEQ ID NO 340
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp downstream of junction

<400> SEQUENCE: 340
tccctgtgcg ccgcgtcgcc gatggtggcc agccaactgg cgcgctaccc gatcctgctc      60
gatgaactgc tcgacccgaa cacgctctat caaccgacgg                          100

<210> SEQ ID NO 341
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp downstream of junction

<400> SEQUENCE: 341
cgttctgtaa taataaccgg acaattcgga ctgattaaaa aagcgccctc gcggcgcttt      60
ttttatattc tcgactccat ttaaaataaa aaatccaatc                          100

<210> SEQ ID NO 342
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp downstream of junction

<400> SEQUENCE: 342
aactcacttc acgccccgaa gggggaagct gcctgaccct acgattcccg ctatttcatt      60
cactgaccgg aggttcaaaa tgacccagcg aaccgagtcg                          100

<210> SEQ ID NO 343
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp downstream of junction

<400> SEQUENCE: 343
cgcgtcaggt tgaacgtaaa aaagtcggtc tgcgcaaagc acgtcgtcgt ccgcagttct    60
ccaaacgtta attggtttct gcttcggcag aacgattggc                         100

<210> SEQ ID NO 344
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp downstream of junction

<400> SEQUENCE: 344
aactcacttc acgccccgaa gggggaagct gcctgaccct acgattcccg ctatttcatt    60
cactgaccgg aggttcaaaa tgacccagcg aaccgagtcg                         100

<210> SEQ ID NO 345
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp downstream of junction

<400> SEQUENCE: 345
ccgatcccca tcactgtgtg tcttgtatta cagtgccgct tcgtcggctt cgccggtacg    60
aatacgaatg acgcgttgca gctcagcaac gaaaattttg                         100

<210> SEQ ID NO 346
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp downstream of junction

<400> SEQUENCE: 346
ccgtctctga agctctcggt gaacattgtt gcgaggcagg atgcgagctg gttgtgtttt    60
gacattaccg ataatgtgcc gcgtgaacgg gtgcgttatg                         100

<210> SEQ ID NO 347
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp downstream of junction

<400> SEQUENCE: 347
tgaacatcac tgatgcacaa gctacctatg tcgaagaatt aactaaaaaa ctgcaagatg    60
caggcattcg cgttaaagcc gacttgagaa atgagaagat                         100

<210> SEQ ID NO 348
<211> LENGTH: 100
<212> TYPE: DNA

-continued

```
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp downstream of junction

<400> SEQUENCE: 348
ccgtctctga agctctcggt gaacattgtt gcgaggcagg atgcgagctg gttgtgtttt      60
gacattaccg ataatgtgcc gcgtgaacgg gtgcgttatg                           100

<210> SEQ ID NO 349
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp downstream of junction

<400> SEQUENCE: 349
tacagtagcg cctctcaaaa atagataaac ggctcatgta cgtgggccgt ttattttttc      60
tacccataat cgggaaccgg tgttataatg ccgcgccctc                           100

<210> SEQ ID NO 350
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp downstream of junction

<400> SEQUENCE: 350
aactcacttc acaccccgaa gggggaagtt gcctgaccct acgattcccg ctatttcatt      60
cactgaccgg aggttcaaaa tgacccagcg aaccgagtcg                           100

<210> SEQ ID NO 351
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp downstream of junction

<400> SEQUENCE: 351
cgtcctgtaa taataaccgg acaattcgga ctgattaaaa aagcgcccct gtggcgcttt      60
ttttatattc ccgcctccat ttaaaataaa aaatccaatc                           100

<210> SEQ ID NO 352
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp downstream of junction
```

```
<400> SEQUENCE: 352
ggacatcatc gcgacaaaca atattaatac cggcaaccac accggcaatt tacgagactg      60
cgcaggcatc ctttctcccg tcaatttctg tcaaataaag                           100

<210> SEQ ID NO 353
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp downstream of junction

<400> SEQUENCE: 353
aactcacttc acaccccgaa gggggaagtt gcctgaccct acgattcccg ctatttcatt      60
cactgaccgg aggttcaaaa tgacccagcg aaccgagtcg                           100

<210> SEQ ID NO 354
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp downstream of junction

<400> SEQUENCE: 354
tttaacgatc tgattggcga tgatgaaacg gattcgccgg aagatgcgct ttctgagagc      60
tggcgcgaat tgtggcagga tgcgttgcag gaggaggatt                           100

<210> SEQ ID NO 355
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp downstream of junction

<400> SEQUENCE: 355
gcactgaaac acctcatttc cctgtgtgcc gcgtcgccga tggttgccag tcagctggcg      60
cgctacccga tcctgcttga tgaattgctc gacccgaata                           100

<210> SEQ ID NO 356
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp downstream of junction

<400> SEQUENCE: 356
gcgctcaaac agttaatccg tctgtgtgcc gcctcgccga tggtcgcgac acaacttgca      60
cgtcatcctt tattgctcga tgaactgctc gacccgcgca                           100

<210> SEQ ID NO 357
<211> LENGTH: 100
<212> TYPE: DNA
```

```
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp downstream of junction

<400> SEQUENCE: 357
agtctgaact catcctgcgg cagtcggtga gacgtatttt tgaccaaaga gtgatctaca      60
tcacggaatt ttgtggttgt tgctgcttaa aagggcaaat                           100

<210> SEQ ID NO 358
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp downstream of junction

<400> SEQUENCE: 358
ccgtctctga agctctcggt gaacattgtt gcgaggcagg atgcgagctg gttgtgtttt      60
gacattaccg ataatgtgcc gcgtgaacgg gtgcgttatg                           100

<210> SEQ ID NO 359
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp downstream of junction

<400> SEQUENCE: 359
gccattgagc tggcttcccg accgcagggc ggcacctgcc tgaccctgcg tttcccgctg      60
tttaacaccc tgaccggagg tgaagcatga tccctgaatc                           100

<210> SEQ ID NO 360
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp downstream of junction

<400> SEQUENCE: 360
agcgtcaggt accggtcatg attcaccgtg cgattctcgg ttccctggag cgcttcattg      60
gcatcctgac cgaagagttc gctggcttct tcccaacctg                           100

<210> SEQ ID NO 361
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp downstream of junction
```

<400> SEQUENCE: 361
gcgctgaagc acctgatcac gctctgcgcg gcgtcgccga tggtcgccag ccagctggcg    60
cgccacccgc tgctgctgga tgagctgctg gatcccaaca                          100

<210> SEQ ID NO 362
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp downstream of junction

<400> SEQUENCE: 362
gcccgctgac cgaccagaac ttccaccttg gactcggcta taccettggc gtgacggcgc    60 gcgataactg ggactacatc cccattccgg tgatcttacc                          100

<210> SEQ ID NO 363
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp downstream of junction

<400> SEQUENCE: 363
gccattgagc tggcttcccg accgcagggc ggcacctgcc tgaccctgcg tttcccgctg    60
tttaacaccc tgaccggagg tgaagcatga tccctgaatc                          100

<210> SEQ ID NO 364
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp downstream of junction

<400> SEQUENCE: 364
gctaaagttc tcggctaatc gctgataaca tttgacgcaa tgcgcaataa aagggcatca    60
tttgatgccc tttttgcacg ctttcatacc agaacctggc                          100

<210> SEQ ID NO 365
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp downstream of junction

<400> SEQUENCE: 365
gccattgagc tggcttcccg accgcagggc ggcacctgcc tgaccctgcg tttcccgctg    60
tttaacaccc tgaccggagg tgaagcatga tccctgaatc                          100

<210> SEQ ID NO 366
<211> LENGTH: 100
<212> TYPE: DNA

```
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp downstream of junction

<400> SEQUENCE: 366
cgccgtcctc gcagtaccat tgcaaccgac tttacagcaa gaagtgattc tggcacgcat      60
ggaacaaatt cttgccagtc gggctttatc cgatgacgaa                          100

<210> SEQ ID NO 367
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp downstream of junction

<400> SEQUENCE: 367
gccattgagc tggcttcccg accgcagggc ggcacctgcc tgaccctgcg tttcccgctg      60
tttaacaccc tgaccggagg tgaagcatga tccctgaatc                          100

<210> SEQ ID NO 368
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp downstream of junction

<400> SEQUENCE: 368
tctttagatc tctcggtccg ccctgatggc ggcaccttgc tgacgttacg cctgccggta      60
cagcaggtta tcaccggagg cttaaaatga cccagttacc                          100

<210> SEQ ID NO 369
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp downstream of junction

<400> SEQUENCE: 369
tgaatatcac tgactcacaa gctacctatg tcgaagaatt aactaaaaaa ctgcaagatg      60
caggcattcg cgttaaagcc gacttgagaa atgagaagat                          100

<210> SEQ ID NO 370
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp downstream of junction
```

<400> SEQUENCE: 370

```
ctggggtcac tggagcgctt tatcggcatc ctgaccgaag aatttgccgg tttcttcccg      60
acctggctgg cccctgttca ggttgtggtg atgaatatca                           100
```

<210> SEQ ID NO 371
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 100 bp downstream of junction

<400> SEQUENCE: 371

```
gcaatagaac taactacccg ccctgaaggc ggtacctgcc tgaccctgcg attcccgtta      60
tttcattcac tgaccggagg cccacgatga cccagcgacc                           100
```

<210> SEQ ID NO 372
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: disrupted nifL gene / PinfC

<400> SEQUENCE: 372

```
tggtgtccgg gcgaacgtcg ccaggtggca caaattgtca gaactacgac acgactaacc      60
gaccgcagga gtgtgcgatg accctgaata tgatgatgga ttcttggttc tctggagcgc     120
tttatcggca tcctgactga agaatttgca ggcttcttcc caacctggct tgcacccgtg     180
caggtagttg tgatgaacat                                                 200
```

<210> SEQ ID NO 373
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: PinfC / disrupted nifL gene

<400> SEQUENCE: 373

```
cggaaaacga gttcaaacgg cgcgtcccaa tcgtattaat ggcgagattc gcgccacgga      60
agttcgctta acaggtctgg aaggcgagca gcttggtatt gcgatagaac tcacttcacg     120
ccccgaaggg ggaagctgcc tgaccctacg attcccgcta tttcattcac tgaccggagg     180
ttcaaaatga cccagcgaac                                                 200
```

<210> SEQ ID NO 374
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 5' UTR and ATG / truncated glnE gene

<400> SEQUENCE: 374

```
cgccagagag ttgaaatcga acatttccgt aataccgcca ttacccagga gccgttctgg    60
ttgcacagcg gaaaacgtta acgaaaggat atttcgcatg tccctgtgcg ccgcgtcgcc   120
gatggtggcc agccaactgg cgcgctaccc gatcctgctc gatgaactgc tcgacccgaa   180
cacgctctat caaccgacgg                                               200
```

<210> SEQ ID NO 375
<211> LENGTH: 200
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: disrupted nifL gene / Prm1

<400> SEQUENCE: 375

```
cgggcgaacg tcgccaggtg gcacaaattg tcagaactac gacacgacta accgaccgca    60
ggagtgtgcg atgaccctga atatgatgat ggatgccagc cgttctgtaa taataaccgg   120
acaattcgga ctgattaaaa aagcgccctc gcggcgcttt ttttatattc tcgactccat   180
ttaaaataaa aaatccaatc                                               200
```

<210> SEQ ID NO 376
<211> LENGTH: 200
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Prm1 / disrupted nifL gene

<400> SEQUENCE: 376

```
tcaacctaaa aaagtttgtg taatacttgt aacgctacat ggagattaac tcaatctaga    60
gggtattaat aatgaatcgt actaaactgg tactgggcgc aactcacttc acgccccgaa   120
gggggaagct gcctgaccct acgattcccg ctatttcatt cactgaccgg aggttcaaaa   180
tgacccagcg aaccgagtcg                                               200
```

<210> SEQ ID NO 377
<211> LENGTH: 200
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: disrupted nifL gene / Prm7

<400> SEQUENCE: 377

```
cgggcgaacg tcgccaggtg gcacaaattg tcagaactac gacacgacta accgaccgca    60
ggagtgtgcg atgaccctga atatgatgat ggatgccagc cgcgtcaggt tgaacgtaaa   120
aaagtcggtc tgcgcaaagc acgtcgtcgt ccgcagttct ccaaacgtta attggtttct   180
gcttcggcag aacgattggc                                               200
```

<210> SEQ ID NO 378
<211> LENGTH: 200
<212> TYPE: DNA
<213> ORGANISM: Artificial Sequence

```
<220> FEATURE:
<223> OTHER INFORMATION: Description of Artificial Sequence: Synthetic
      polynucleotide
<220> FEATURE:
<223> OTHER INFORMATION: Prm4 / disrupted nifL gene

<400> SEQUENCE: 378
aattttctgc ccaaatggct gggattgttc attttttgtt tgccttacaa cgagagtgac      60
agtacgcgcg ggtagttaac tcaacatctg accggtcgat aactcacttc acgccccgaa     120
gggggaagct gcctgaccct acgattcccg ctatttcatt cactgaccgg aggttcaaaa     180
tgacccagcg aaccgagtcg                                                 200

<210> SEQ ID NO 379
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 5' UTR up to ATG-4bp of amtB gene / disrupted
      amtB gene

<400> SEQUENCE: 379
gtaaccaata aaggccacca cgccagacca cacgatagtg atggcaacac tttccagctg      60
caccagcacc tgatggccca tggtcacacc ttcagcgaaa ccgatcccca tcactgtgtg     120
tcttgtatta cagtgccgct tcgtcggctt cgccggtacg aatacgaatg acgcgttgca     180
gctcagcaac gaaaattttg                                                 200

<210> SEQ ID NO 380
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Prm1.2 / disrupted nifL gene

<400> SEQUENCE: 380
tggtattgtc agtctgaatg aagctcttga aaaagctgag gaagcgggcg tcgatttagt      60
agaaatcagt ccgaatgccg agccgccagt ttgtcgaatc ccgtctctga agctctcggt     120
gaacattgtt gcgaggcagg atgcgagctg gttgtgtttt gacattaccg ataatgtgcc     180
gcgtgaacgg gtgcgttatg                                                 200

<210> SEQ ID NO 381
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: disrupted nifL gene / Prm1.2

<400> SEQUENCE: 381
accgatccgc aggcgcgcat ttgttatgcc aatccggcat tctgccgcca gacgggtttt      60
gcacttgaga cacttttggg cgagaaccac cgtctgctgg tgaacatcac tgatgcacaa     120
gctacctatg tcgaagaatt aactaaaaaa ctgcaagatg caggcattcg cgttaaagcc     180
gacttgagaa atgagaagat                                                 200
```

<210> SEQ ID NO 382
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Prm3.1 / disrupted nifL gene

<400> SEQUENCE: 382

```
cgggaaccgg tgttataatg ccgcgccctc atattgtggg gatttcttaa tgacctatcc    60
tgggtcctaa agttgtagtt gacattagcg gagcactaac ccgtctctga agctctcggt   120
gaacattgtt gcgaggcagg atgcgagctg gttgtgtttt gacattaccg ataatgtgcc   180
gcgtgaacgg gtgcgttatg                                               200
```

<210> SEQ ID NO 383
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: disrupted nifL gene / Prm3.1

<400> SEQUENCE: 383

```
accgatccgc aggcgcgcat ttgttatgcc aatccggcat tctgccgcca gacgggtttt    60
gcacttgaga cactttggg cgagaaccac cgtctgctgg tacagtagcg cctctcaaaa    120
atagataaac ggctcatgta cgtgggccgt ttatttttc tacccataat cgggaaccgg   180
tgttataatg ccgcgccctc                                               200
```

<210> SEQ ID NO 384
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Prm1 / disrupted nifL gene

<400> SEQUENCE: 384

```
tcaacctaaa aaagtttgtg taatacttgt aacgctacat ggagattaac tcaatctaga    60
gggtattaat aatgaatcgt actaaactgg tactgggcgc aactcacttc acaccccgaa   120
gggggaagtt gcctgaccct acgattcccg ctatttcatt cactgaccgg aggttcaaaa   180
tgacccagcg aaccgagtcg                                               200
```

<210> SEQ ID NO 385
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: disrupted nifL gene / Prm1

<400> SEQUENCE: 385

```
gggcgacaaa cggcctggtg gcacaaattg tcagaactac gacacgacta actgaccgca      60
ggagtgtgcg atgaccctga atatgatgat ggatgccggc cgtcctgtaa taataaccgg     120
acaattcgga ctgattaaaa aagcgccctt gtggcgcttt ttttatattc ccgcctccat     180
ttaaaataaa aaatccaatc                                                 200
```

<210> SEQ ID NO 386
<211> LENGTH: 200
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: disrupted nifL gene / Prm5

<400> SEQUENCE: 386

```
gggcgacaaa cggcctggtg gcacaaattg tcagaactac gacacgacta actgaccgca      60
ggagtgtgcg atgaccctga atatgatgat ggatgccggc ggacatcatc gcgacaaaca     120
atattaatac cggcaaccac accggcaatt tacgagactg cgcaggcatc ctttctcccg     180
tcaatttctg tcaaataaag                                                 200
```

<210> SEQ ID NO 387
<211> LENGTH: 200
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Prm5 / disrupted nifL gene

<400> SEQUENCE: 387

```
taagaattat ctggatgaat gtgccattaa atgcgcagca taatggtgcg ttgtgcggga      60
aaactgcttt ttttgaaag ggttggtcag tagcggaaac aactcacttc acaccccgaa      120
gggggaagtt gcctgaccct acgattcccg ctatttcatt cactgaccgg aggttcaaaa     180
tgacccagcg aaccgagtcg                                                 200
```

<210> SEQ ID NO 388
<211> LENGTH: 200
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: 5' UTR and ATG / truncated glnE gene

<400> SEQUENCE: 388

```
cgccagagag tcgaaatcga acatttccgt aataccgcga ttacccagga gccgttctgg      60
ttgcacagcg gaaaacgtta acgaaaggat atttcgcatg tttaacgatc tgattggcga     120
tgatgaaacg gattcgccgg aagatgcgct ttctgagagc tggcgcgaat tgtggcagga     180
tgcgttgcag gaggaggatt                                                 200
```

<210> SEQ ID NO 389
<211> LENGTH: 200
<212> TYPE: DNA
<213> ORGANISM: Artificial Sequence

```
<220> FEATURE:
<223> OTHER INFORMATION: Description of Artificial Sequence: Synthetic
      polynucleotide
<220> FEATURE:
<223> OTHER INFORMATION: 5' UTR and ATG / truncated glnE gene

<400> SEQUENCE: 389
cgccagagag tcgaaatcga acatttccgt aataccgcga ttacccagga gccgttctgg      60
ttgcacagcg gaaaacgtta acgaaaggat atttcgcatg gcactgaaac acctcatttc     120
cctgtgtgcc gcgtcgccga tggttgccag tcagctggcg cgctacccga tcctgcttga     180
tgaattgctc gacccgaata                                                 200

<210> SEQ ID NO 390
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 5' UTR and ATG / truncated glnE gene

<400> SEQUENCE: 390
gatgatggat gctttctggt taaacgggca acctcgttaa ctgactgact agcctgggca      60
aactgcccgg gcttttttt gcaaggaatc tgatttcatg gcgctcaaac agttaatccg      120
tctgtgtgcc gcctcgccga tggtcgcgac acaacttgca cgtcatcctt tattgctcga     180
tgaactgctc gacccgcgca                                                 200

<210> SEQ ID NO 391
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: disrupted nifL gene / Prm4

<400> SEQUENCE: 391
accgatccgc aggcgcgcat ttgttatgcc aatccggcat tctgccgcca gacgggtttt      60
gcacttgaga cacttttggg cgagaaccac cgtctgctgg agtctgaact catcctgcgg     120
cagtcggtga gacgtatttt tgaccaaaga gtgatctaca tcacggaatt ttgtggttgt     180
tgctgcttaa aagggcaaat                                                 200

<210> SEQ ID NO 392
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Prm4 / disrupted nifL gene

<400> SEQUENCE: 392
catcggacac caccagctta caaattgcct gattgcggcc ccgatggccg gtatcactga      60
ccgaccattt cgtgccttat gtcatgcgat gggggctggg ccgtctctga agctctcggt     120
gaacattgtt gcgaggcagg atgcgagctg gttgtgtttt gacattaccg ataatgtgcc     180
gcgtgaacgg gtgcgttatg                                                 200
```

<210> SEQ ID NO 393
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: PinfC / disrupted nifL gene

<400> SEQUENCE: 393

```
tcttcaacaa ctggaggaat aaggtattaa aggcggaaaa cgagttcaaa cggcacgtcc      60
gaatcgtatc aatggcgaga ttcgcgccct ggaagttcgc gccattgagc tggcttcccg     120
accgcagggc ggcacctgcc tgaccctgcg tttcccgctg tttaacaccc tgaccggagg     180
tgaagcatga tccctgaatc                                                 200
```

<210> SEQ ID NO 394
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: disrupted nifL gene / PinfC

<400> SEQUENCE: 394

```
tccgggttcg gcttaccccg ccgcgttttg cgcacggtgt cggacaattt gtcataactg      60
cgacacagga gtttgcgatg accctgaata tgatgctcga agcgtcaggt accggtcatg     120
attcaccgtg cgattctcgg ttccctggag cgcttcattg gcatcctgac cgaagagttc     180
gctggcttct tcccaacctg                                                 200
```

<210> SEQ ID NO 395
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 5' UTR and ATG / truncated glnE gene

<400> SEQUENCE: 395

```
atcgcagcgt ctttgaatat ttccgtcgcc aggcgctggc tgccgagccg ttctggctgc      60
atagtggaaa acgataattt caggccaggg agccctatg gcgctgaagc acctgatcac     120
gctctgcgcg gcgtcgccga tggtcgccag ccagctggcg cgccacccgc tgctgctgga     180
tgagctgctg gatcccaaca                                                 200
```

<210> SEQ ID NO 396
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: disrupted nifL gene / Prm1.2

<400> SEQUENCE: 396

```
tccgggttcg gcttaccccg ccgcgttttg cgcacggtgt cggacaattt gtcataactg      60
cgacacagga gtttgcgatg accctgaata tgatgctcga gcccgctgac cgaccagaac    120
```
ttccaccttg gactcggcta taccottggc gtgacggcgc gcgataactg ggactacatc    180
cccattccgg tgatcttacc                                               200

<210> SEQ ID NO 397
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Prm1.2 / disrupted nifL gene

<400> SEQUENCE: 397
tcacttttta gcaaagttgc actggacaaa aggtaccaca attggtgtac tgatactcga    60
cacagcatta gtgtcgattt tcatataaa ggtaattttg gccattgagc tggcttcccg     120
accgcagggc ggcacctgcc tgaccctgcg tttcccgctg tttaacaccc tgaccggagg    180
tgaagcatga tccctgaatc                                               200

<210> SEQ ID NO 398
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: disrupted nifL gene / Prm6.2

<400> SEQUENCE: 398
tccgggttcg gcttaccccg ccgcgttttg cgcacggtgt cggacaattt gtcataactg    60
cgacacagga gtttgcgatg accctgaata tgatgctcga gctaaagttc tcggctaatc    120
gctgataaca tttgacgcaa tgcgcaataa aagggcatca tttgatgccc tttttgcacg    180
ctttcatacc agaacctggc                                               200

<210> SEQ ID NO 399
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Prm6.2 / disrupted nifL gene

<400> SEQUENCE: 399
gttctccttt gcaatagcag ggaagaggcg ccagaaccgc cagcgttgaa gcagtttgaa    60
cgcgttcagt gtataatccg aaacttaatt tcggtttgga gccattgagc tggcttcccg    120
accgcagggc ggcacctgcc tgaccctgcg tttcccgctg tttaacaccc tgaccggagg    180
tgaagcatga tccctgaatc                                               200

<210> SEQ ID NO 400
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: disrupted nifL gene / Prm8.2

<400> SEQUENCE: 400

```
tccgggttcg gcttaccccg ccgcgttttg cgcacggtgt cggacaattt gtcataactg    60
cgacacagga gtttgcgatg accctgaata tgatgctcga cgccgtcctc gcagtaccat   120
tgcaaccgac tttacagcaa gaagtgattc tggcacgcat ggaacaaatt cttgccagtc   180
gggctttatc cgatgacgaa                                               200
```

<210> SEQ ID NO 401
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Prm8.2 / disrupted nifL gene

<400> SEQUENCE: 401

```
gatatgcctg aagtattcaa ttacttaggc atttacttaa cgcaggcagg caattttgat    60
gctgcctatg aagcgtttga ttctgtactt gagcttgatc gccattgagc tggcttcccg   120
accgcagggc ggcacctgcc tgaccctgcg tttcccgctg tttaacaccc tgaccggagg   180
tgaagcatga tccctgaatc                                               200
```

<210> SEQ ID NO 402
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: PinfC / disrupted nifL gene

<400> SEQUENCE: 402

```
tggtattgtc agtctgaatg aagctcttga aaaagctgag gaagcgggcg tcgatttagt    60
agaaatcagt ccgaatgccg agccgccagt ttgtcgaatc tctttagatc tctcggtccg   120
ccctgatggc ggcaccttgc tgacgttacg cctgccggta cagcaggtta tcaccggagg   180
cttaaaatga cccagttacc                                               200
```

<210> SEQ ID NO 403
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: disrupted nifL gene / PinfC

<400> SEQUENCE: 403

```
tgcaaattgc acggttattc cgggtgagta tatgtgtgat ttgggttccg gcattgcgca    60 ataagggga gaaagacatg agcatcacgg cgttatcagc tgaatatcac tgactcacaa   120
gctacctatg tcgaagaatt aactaaaaaa ctgcaagatg caggcattcg cgttaaagcc   180
gacttgagaa atgagaagat                                               200
```

<210> SEQ ID NO 404
<211> LENGTH: 200
<212> TYPE: DNA
<213> ORGANISM: Artificial Sequence
<220> FEATURE:

<223> OTHER INFORMATION: Description of Artificial Sequence: Synthetic
      polynucleotide
<220> FEATURE:
<223> OTHER INFORMATION: disrupted nifL gene / PinfC

<400> SEQUENCE: 404
tcagggctgc ggatgtcggg cgtttcacaa cacaaaatgt tgtaaatgcg acacagccgg    60
gcctgaaacc aggagcgtgt gatgaccttt aatatgatgc ctggggtcac tggagcgctt   120
tatcggcatc ctgaccgaag aatttgccgg tttcttcccg acctggctgg ccctgttca    180 ggttgtggtg atgaatatca                                               200

<210> SEQ ID NO 405
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: PinfC / disrupted nifL gene

<400> SEQUENCE: 405
cggaaaacga gttcaaacgg cacgtccgaa tcgtatcaat ggcgagattc gcgcccagga    60
agttcgctta actggtctgg aaggtgagca gctgggtatt gcaatagaac taactacccg   120
ccctgaaggc ggtacctgcc tgaccctgcg attcccgtta tttcattcac tgaccggagg   180
cccacgatga cccagcgacc                                               200

<210> SEQ ID NO 406
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 406
caagaagttc gcctcacagg                                                20

<210> SEQ ID NO 407
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 407
tgcctcgcaa caatgttcac                                                20

<210> SEQ ID NO 408
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 408
cgccctcata ttgtggggat                                                20

<210> SEQ ID NO 409
<211> LENGTH: 19
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 409
ggcataacgc acccgttca                                               19

<210> SEQ ID NO 410
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 410
tctgaagctc tcggt                                                   15

<210> SEQ ID NO 411
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 411
taaactggta ctgggcgcaa ct                                           22

<210> SEQ ID NO 412
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 412
caaatcgaag cgccagacgg tat                                          23

<210> SEQ ID NO 413
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 413
gaccctacga ttccc                                                   15

<210> SEQ ID NO 414
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 414
ggtgcactct ttgcatggtt                                              20

<210> SEQ ID NO 415
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 415
gcgcagtctc gtaaattgcc                                                    20

<210> SEQ ID NO 416
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 416
gcgatgaccc tgaat                                                         15

<210> SEQ ID NO 417
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 417
ctcggcagca tggacgtaa                                                     19

<210> SEQ ID NO 418
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 418
agggtgttaa acagcgggaa a                                                  21

<210> SEQ ID NO 419
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 419
tccgaatcgt atcaa                                                         15

<210> SEQ ID NO 420
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 420
gagccgttct ggctgcatag                                                    20

<210> SEQ ID NO 421
<211> LENGTH: 18
<212> TYPE: DNA
<213> ORGANISM: Artificial Sequence
<220> FEATURE:
```

-continued

```
<223> OTHER INFORMATION: Description of Artificial Sequence: Synthetic
      primer

<400> SEQUENCE: 421
gccgtcggct gatagagg                                                  18

<210> SEQ ID NO 422
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 422
tgaagcacct gatca                                                     15

<210> SEQ ID NO 423
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 423
ggaaaacgag ttcaaccggc                                                20

<210> SEQ ID NO 424
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 424
gggcggaccg agagatctaa                                                20
```